(12) United States Patent
Kim et al.

(10) Patent No.: US 10,580,998 B2
(45) Date of Patent: Mar. 3, 2020

(54) NITROGEN-CONTAINING CONDENSED CYCLIC COMPOUND AND ORGANIC LIGHT EMITTING DEVICE USING SAME

(71) Applicant: LG CHEM, LTD., Seoul (KR)

(72) Inventors: Minjun Kim, Daejeon (KR); Hyok Joon Kwon, Daejeon (KR); Wanpyo Hong, Daejeon (KR); Kongkyeom Kim, Daejeon (KR); Jungha Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/269,238

(22) Filed: Feb. 6, 2019

(65) Prior Publication Data

US 2019/0173022 A1 Jun. 6, 2019

Related U.S. Application Data

(63) Continuation of application No. 15/324,947, filed as application No. PCT/KR2016/005954 on Jun. 3, 2016.

(30) Foreign Application Priority Data

Jun. 3, 2015 (KR) ........................ 10-2015-0078801

(51) Int. Cl.
*H01L 51/00* (2006.01)
*H01L 51/50* (2006.01)
(Continued)

(52) U.S. Cl.
CPC ........ *H01L 51/0072* (2013.01); *C07D 487/16* (2013.01); *C07D 519/00* (2013.01); *C09K 11/025* (2013.01); *C09K 11/06* (2013.01); *H01L 51/0052* (2013.01); *H01L 51/0054* (2013.01); *H01L 51/0071* (2013.01); *H01L 51/50* (2013.01); *C09K 2211/1007* (2013.01); *C09K 2211/1044* (2013.01); *C09K 2211/1048* (2013.01); *C09K 2211/1051* (2013.01); *C09K 2211/1059* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| 2013/0026422 A1 | 1/2013 | Parham et al. |
| 2014/0319507 A1 | 10/2014 | Yamanoto et al. |
| 2016/0293853 A1 | 10/2016 | Zeng .................. H01L 51/0073 |

FOREIGN PATENT DOCUMENTS

| KR | 10-2000-0051826 A1 | 8/2000 |
| KR | 10-2014-0034710 | 3/2014 |

(Continued)

OTHER PUBLICATIONS

Machine English translation of Yu et al. (KR 10-2014-0034710). May 22, 2019.*

(Continued)

*Primary Examiner* — Jay Yang
(74) *Attorney, Agent, or Firm* — Dentons US LLP

(57) ABSTRACT

The present specification provides a nitrogen-containing condensed cyclic compound of chemical formula 1 and an organic light emitting device comprising the same.

5 Claims, 4 Drawing Sheets

(51) Int. Cl.
    *C07D 487/16*    (2006.01)
    *C07D 519/00*    (2006.01)
    *C09K 11/02*     (2006.01)
    *C09K 11/06*     (2006.01)

(56) References Cited

FOREIGN PATENT DOCUMENTS

| KR | 10-2014-0034710 A | 3/2014 |
| KR | 10-2014-0101411 A | 8/2014 |
| KR | 10-2014-0101807 A | 8/2014 |
| WO | 2011-128017 A1 | 10/2011 |

OTHER PUBLICATIONS

Machine English translation of Yu et al. (KR 10-2014-0034710). Jun. 12, 2018.
Rivoal, Morgane et al., "Substituted dibenzo[2,3:5,6]-pyrrolizino[1,7-bc]indolo[1,2,3-lm]carbazoles: a series of new plectron donors," Tetrahedron 2013, vol. 69, pp. 3302-3307.

\* cited by examiner

[Figure 1]
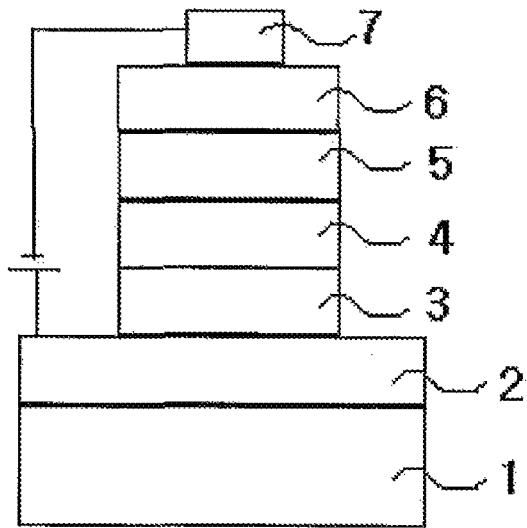
[Figure 2]
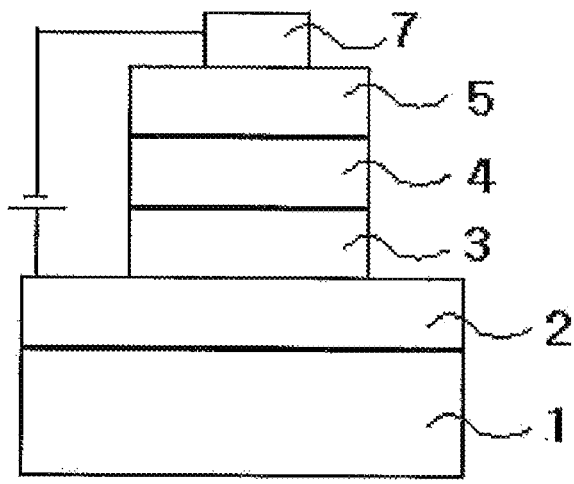

[Figure 3]
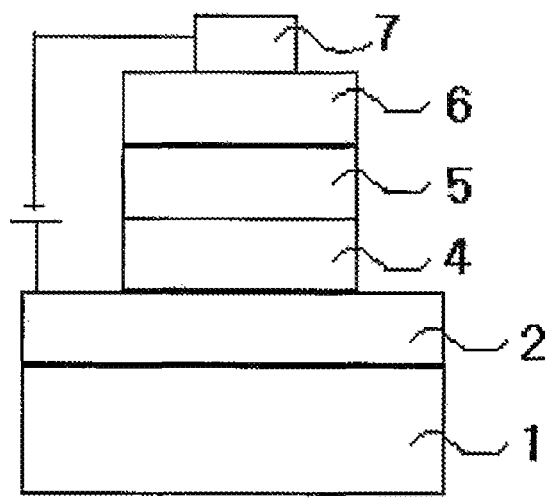
[Figure 4]
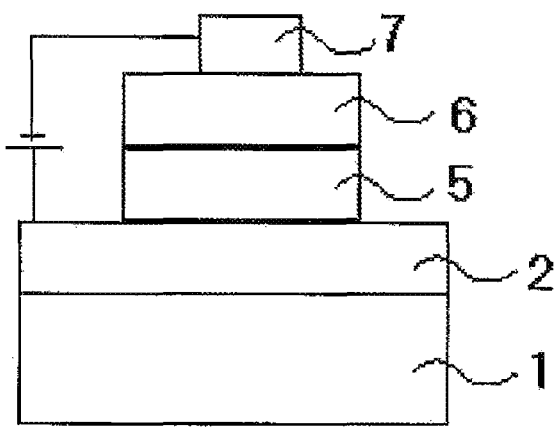

[Figure 5]
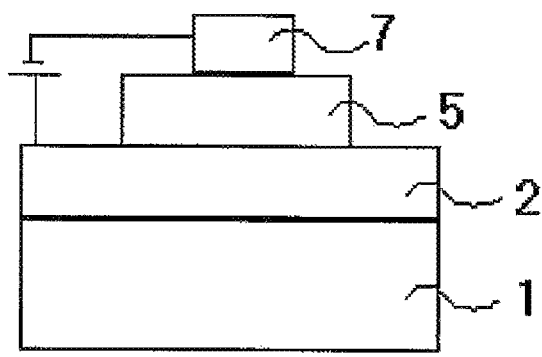
[Figure 6]
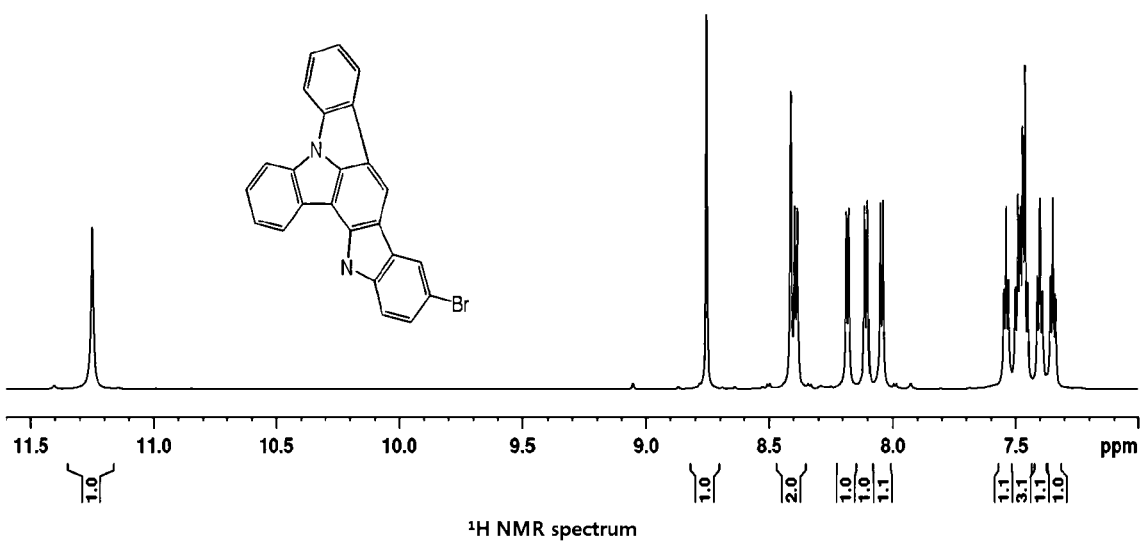
1H NMR spectrum

[Figure 7]
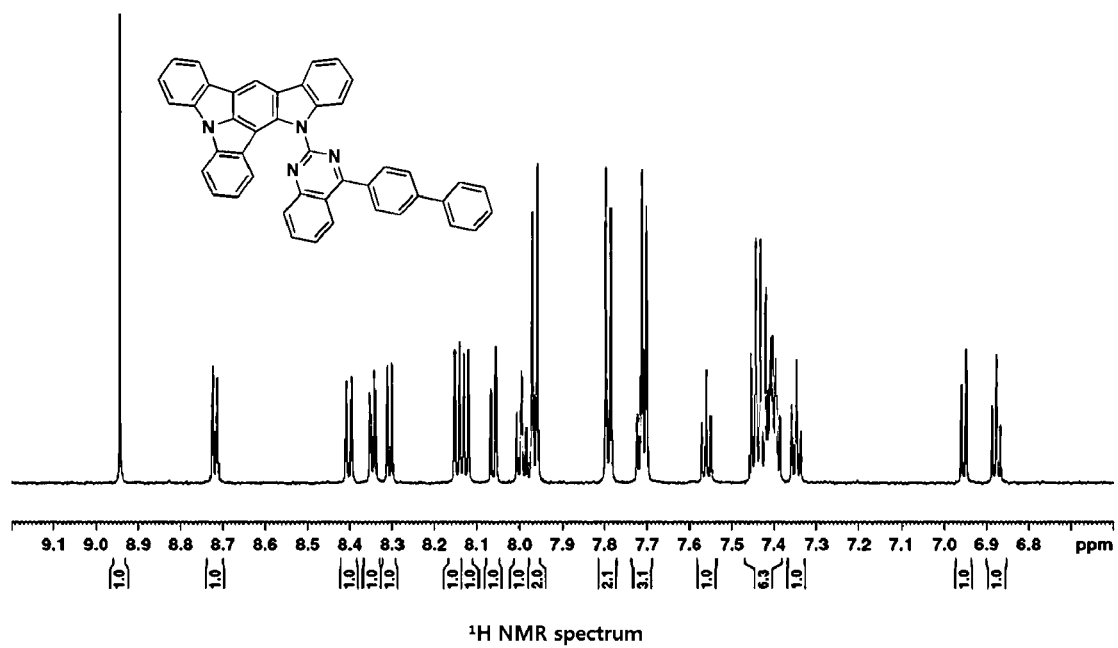
¹H NMR spectrum

NITROGEN-CONTAINING CONDENSED CYCLIC COMPOUND AND ORGANIC LIGHT EMITTING DEVICE USING SAME

TECHNICAL FIELD

This application is a Continuation of U.S. application Ser. No. 15/324,947, filed Jan. 9, 2017, which is a National Stage Application of PCT/KR2016/005954, filed Jun. 3, 2016 and claims priority to Korean Application Nos. 10-2015-0078801, filed on Jun. 3, 2015, all of which are hereby incorporated by reference in their entireties as if fully set forth herein.

The present specification relates to a fused cyclic compound including nitrogen and an organic light emitting device using the same.

BACKGROUND ART

An organic light emission phenomenon is one of the examples of converting current into visible rays through an internal process of a specific organic molecule. The principle of the organic light emission phenomenon is as follows. When an organic material layer is disposed between a positive electrode and a negative electrode, if voltage is applied between the two electrodes, electrons and holes are injected from the negative electrode and the positive electrode, respectively, into the organic material layer. The electrons and the holes which are injected into the organic material layer are recombined to form an exciton, and the exciton falls down again to the ground state to emit light. An organic light emitting device using this principle may be composed of a negative electrode, a positive electrode, and an organic material layer disposed therebetween, for example, an organic material layer including a hole injection layer, a hole transporting layer, a light emitting layer, and an electron transporting layer.

The materials used in the organic light emitting device are mostly pure organic materials or complex compounds in which organic materials and metals form a complex compound, and may be classified into a hole injection material, a hole transporting material, a light emitting material, an electron transporting material, an electron injection material, and the like according to the use thereof. Here, an organic material having a p-type property, that is, an organic material, which is easily oxidized and electrochemically stable when the material is oxidized, is usually used as the hole injection material or the hole transporting material. Meanwhile, an organic material having an n-type property, that is, an organic material, which is easily reduced and electrochemically stable when the material is reduced, is usually used as the electron injection material or the electron transporting material. As the light emitting layer material, a material having both p-type and n-type properties, that is, a material, which is stable during both the oxidation and reduction states, is preferred, and when an exciton is formed, a material having high light emitting efficiency for converting the exciton into light is preferred.

Therefore, there is a need for developing a new organic material in the art.

DISCLOSURE

Technical Problem

The present specification provides a fused cyclic compound and an organic light emitting device using the same.

Technical Solution

An exemplary embodiment of the present specification provides a compound represented by the following Chemical Formula 1:

[Chemical Formula 1]

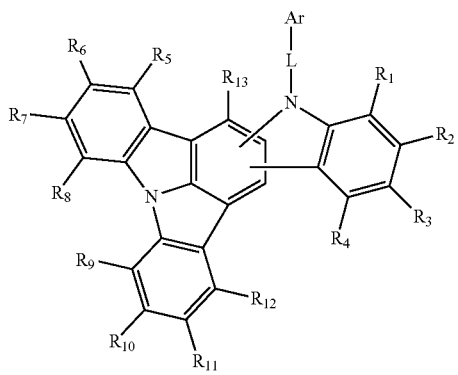

In Chemical Formula 1,

Ar is a substituted or unsubstituted bicyclic or more heterocyclic group,

L is a direct bond; a substituted or unsubstituted arylene group; or a substituted or unsubstituted heteroarylene group, $R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring. Another exemplary embodiment of the present specification provides an organic light emitting device including: a first electrode; a second electrode provided to face the first electrode; and one or more organic material layers including a light emitting layer provided between the first electrode and the second electrode, in which one or more layers of the organic material layers include the compound represented by Chemical Formula 1.

Advantageous Effects

A novel fused cyclic compound according to exemplary embodiments of the present specification has an appropriate energy level, and is excellent in electrochemical stability and thermal stability. Therefore, an organic light emitting device including the compound provides high efficiency and/or high driving stability and long service life effects.

DESCRIPTION OF DRAWINGS

FIGS. 1 to 5 are cross-sectional views illustrating the structure of an organic light emitting device according to an exemplary embodiment of the present specification.

FIGS. 6 and 7 illustrate 1H NMR spectra of the materials used and prepared in the Synthesis Examples.

MODE FOR INVENTION

Hereinafter, the present specification will be described in more detail.

An exemplary embodiment of the present specification provides the compound represented by Chemical Formula 1. A novel core structure represented by Chemical Formula 1 has flat structural characteristics and thus is excellent in thermal stability due to a higher glass transition temperature than the existing known structures, and the novel compounds may be used as a host material and/or a hole transporting material of an organic material layer, particularly, a light emitting layer of an organic light emitting device. Further, the novel compounds may serve as a hole injection material, an electron transporting material, an electron injection material, and the like.

Examples of the substituents will be described below, but are not limited thereto.

In the present specification,

means a moiety linked to another substituent.

In the present specification, the term "substituted or unsubstituted" means being unsubstituted or substituted with one or more substituents selected from the group consisting of deuterium; a nitrile group; an alkyl group; an alkenyl group; a cycloalkyl group; an aryl group; a heterocyclic group; an aralkyl group; an aralkenyl group; an alkylaryl group; an alkenylaryl group; an alkoxy group; an aryloxy group; an alkyl amine group; an aralkylamine group; an arylamine group; an alkylarylamine group; or a heteroarylamine group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 50. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group may be a monocyclic aryl group or a polycyclic aryl group. When the aryl group is a monocyclic aryl group, the number of carbon atoms thereof is not particularly limited, but is preferably 6 to 60. Specific examples of the monocyclic aryl group include a phenyl group, a biphenyl group, a terphenyl group, and the like, but are not limited thereto. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto. In the present specification, the fluorenyl group may be substituted, and two substituents may combine with each other to form a Spiro structure.

When the fluorenyl group is substituted, the group may be

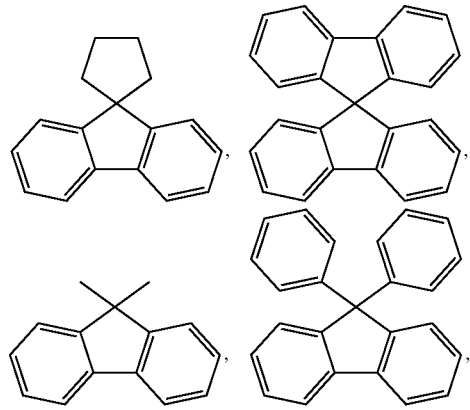

and the like. However, the group is not limited thereto.

In the present specification, a heterocyclic group is an aromatic or aliphatic heterocyclic group including one or more of O, N, and S as a hetero element, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridine group, a bipyridine group, a pyrimidine group, a triazine group, a triazole group, an acridine group, a pyridazine group, a pyrazine group, a qinoline group, a quinazoline group, a quinoxaline group, a phthalazine group, a pyridopyrimidinyl group, a pyridopyrazinyl group, a pyrazinopyrazinyl group, an isoquinoline group, an indole group, a carbazole group, a carboline group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the aryl group in the aryloxy group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, but are not limited thereto.

In the present specification, the alkylamine group, the aralkylamine group, the arylamine group, the alkylarylamine group, and the heteroarylamine group are amine groups substituted with an alkyl group, an aralkyl group, an aryl group, an alkylaryl group, and a heteroaryl group, respectively, and here, the above-described description on the alkyl group and the aryl group may be applied to alkyl and aryl, and the above-described description on the aromatic heterocyclic group in the heterocyclic group may be applied to the heteroaryl group. Specific examples of the amine group include a methylamine group, a dimethylamine group, an ethylamine group, a diethylamine group, a phenylamine group, a naphthylamine group, a biphenylamine group, an anthracenylamine group, 3-methyl-phenylamine, 4-methyl-naphthylamine, 2-methyl-biphenylamine, a 9-methyl-anthracenylamine group, a diphenylamine group, a phenylnaphthylamine group, a ditolylamine group, a phenyltolylamine group, a triphenylamine group, and the like, but are not limited thereto.

In the present specification, the arylene group means that there are two bonding positions in an aryl group, that is, a divalent group. The above-described description on the aryl group may be applied, except that the arylene groups are each a divalent group.

In the present specification, the heteroarylene group means that there are two bonding positions in a heteroaryl group, that is, a divalent group. The above-described description on the aromatic heterocyclic group may be applied, except that the heteroarylene groups are each a divalent group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; or a substituted or unsubstituted aromatic hetero ring.

In the present specification, the "adjacent group" may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as "an adjacent group" to each other.

In the present specification, the aliphatic hydrocarbon ring means a ring composed only of carbon and hydrogen atoms as a ring which is not an aromatic group. In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of N, O, or S atoms as a hetero atom.

In the present specification, the aromatic hetero ring means an aromatic ring including one or more of N, O, or S atoms as a hetero atom.

In the present specification, the aliphatic ring, the aromatic ring, the aliphatic hetero ring, and the aromatic hetero ring may be monocyclic or polycyclic.

In an exemplary embodiment of the present specification, the compound represented by Chemical Formula 1 may be represented by the following Chemical Formula 2 or 3.

[Chemical Formula 2]

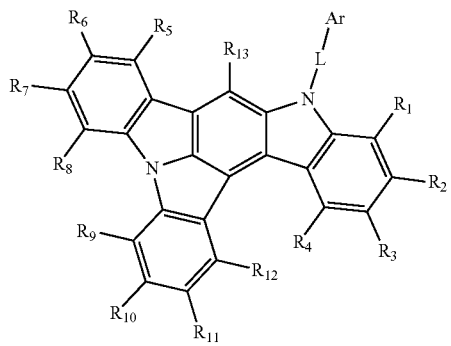

[Chemical Formula 3]

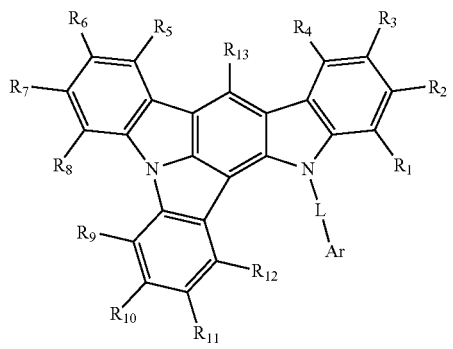

In Chemical Formulae 2 and 3, $R_1$ to $R_{13}$, Ar, and L are the same as those defined in Chemical Formula 1.

According to an exemplary embodiment of the present specification, Ar in Chemical Formulae 1 to 3 is a substituted or unsubstituted bicyclic or more heterocyclic group including N.

According to an exemplary embodiment of the present specification, Ar in Chemical Formulae 1 to 3 is a substituted or unsubstituted bicyclic or more heterocyclic group including two or more N's.

According to an exemplary embodiment of the present specification, Ar in Chemical Formulae 1 to 3 is an unsubstituted bicyclic or more heterocyclic group including two or more N's, which are unsubstituted or substituted with a nitrile group, an alkyl group, an aryl group, a heteroaryl group, an arylheteroaryl group, a heteroarylaryl group, and an aryl group which is substituted with a nitrile group.

According to an exemplary embodiment of the present specification, L in Chemical Formulae 1 to 3 is a direct bond; a substituted or unsubstituted phenylene group; or a substituted or unsubstituted monocyclic heteroarylene group.

According to an exemplary embodiment of the present specification, L in Chemical Formulae 1 to 3 is a direct bond; a substituted or unsubstituted phenylene group; or a substituted or unsubstituted monocyclic heteroarylene group.

According to an exemplary embodiment of the present specification, L in Chemical Formulae 1 to 3 is a direct bond; a substituted or unsubstituted phenylene group; or a substituted or unsubstituted monocyclic heteroarylene group including N.

According to an exemplary embodiment of the present specification, L in Chemical Formulae 1 to 3 is a direct bond; a substituted or unsubstituted phenylene group; a substituted or unsubstituted pyridine group; a substituted or unsubstituted pyrimidine group; or a substituted or unsubstituted triazine group.

According to an exemplary embodiment of the present specification, L in Chemical Formulae 1 to 3 is a direct bond; a phenylene group; a pyridine group; a pyrimidine group; or a triazine group.

According to an exemplary embodiment of the present specification, L in Chemical Formulae 1 to 3 is a direct bond; a phenylene group; or a pyridine group.

According to an exemplary embodiment of the present specification, the phenylene group may be represented by the following structure.

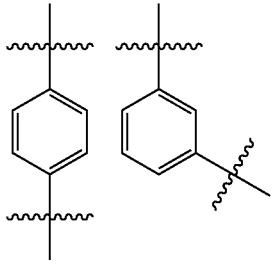

According to an exemplary embodiment of the present specification, Ar in Chemical Formulae 1 to 3 is represented by any one of the following Chemical Formulae A to F.

[Chemical Formula A]

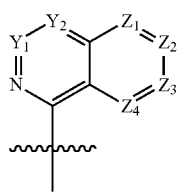

[Chemical Formula B]

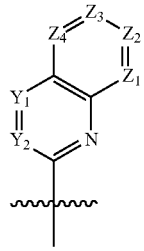

[Chemical Formula C]

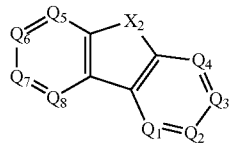

[Chemical Formula D]

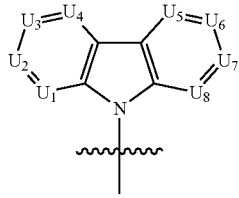

[Chemical Formula E]

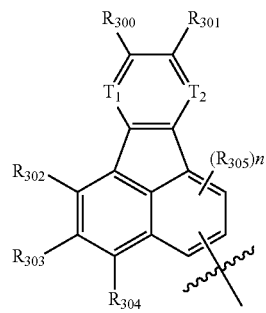

[Chemical Formula F]

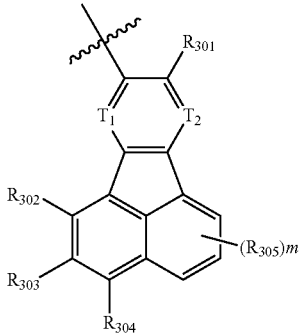

In Chemical Formulae A to F, $Y_1$, $Y_2$, $Z_1$ to $Z_4$, $Q_1$ to $Q_8$, $T_l$, $T_2$ and $U_1$ to $U_8$ are the same as or different from each other, and each independently N or CRd, provided that one of $Q_1$ to $Q_4$ is C linked to L, $X_2$ is $NAr_1$, S, or O, and $Ar_1$, Rd, and $R_{300}$ to $R_{305}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and when n is an integer of 0 to 2, m is an integer of 0 to 3, and n or m is 2, $R_{305}$'s are the same as or different from each other.

According to an exemplary embodiment of the present specification, Chemical Formula A may be represented by the following Chemical Formula A-1.

[Chemical Formula A-1]

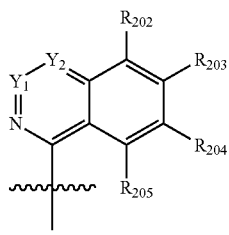

In Chemical Formula A-1, the definitions of $Y_1$ and $Y_2$ are the same as those described above, $R_{202}$ to $R_{205}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula B is represented by any one of the following Chemical Formulae B-1 to B-6-2.

[Chemical Formula B-1]

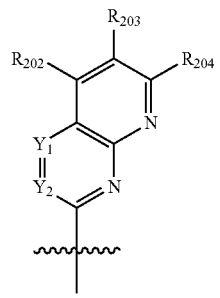

[Chemical Formula B-2]

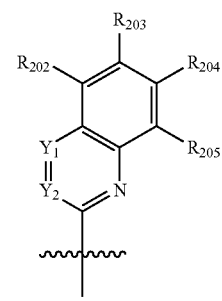

[Chemical Formula B-3]

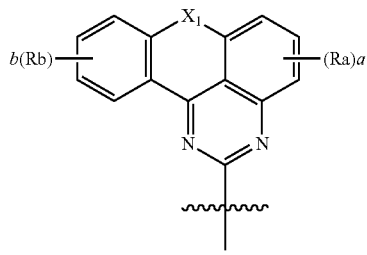

[Chemical Formula B-4]

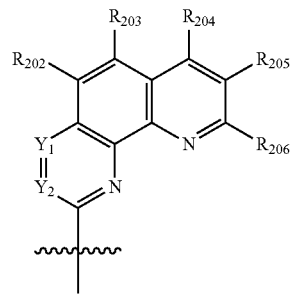

[Chemical Formula B-5]

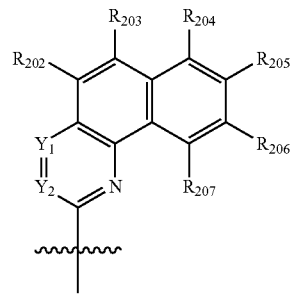

[Chemical Formula B-6-1]

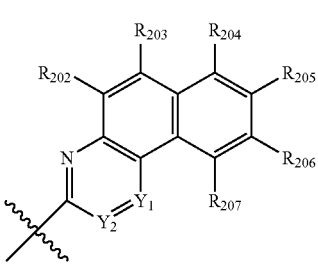

[Chemical Formula B-6-2]

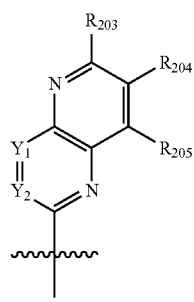

In Chemical Formulae B-1 to B-6-2, the definitions of $Y_1$ and $Y_2$ are the same as those described above, $X_1$ is a direct bond, $C(=O)$, or $CRR'$, and $R_{202}$ to $R_{207}$, R, R', Ra, and Rb are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and a is an integer of 0 to 3, and when a is 2 or more, Ra's are the same as or different from each other, and b is an integer of 0 to 4, and when b is 2 or more, Rb's are the same as or different from each other.

According to an exemplary embodiment of the present specification, in Chemical Formulae A-1, B-1, B-2, B-5, B-6-1, and B-6-2, at least one of $Y_1$ and $Y_2$ is N.

According to an exemplary embodiment of the present specification, in Chemical Formulae A-1, B-1, B-2, B-5, B-6-1, and B-6-2, one of $Y_1$ and $Y_2$ is N.

According to an exemplary embodiment of the present specification, at least one of $U_1$ to $U_8$ of Chemical Formula D is N.

According to an exemplary embodiment of the present specification, at least one of $Q_1$ to $Q_8$ of Chemical Formula C is N.

According to an exemplary embodiment of the present specification, at least one of $Q_1$ to $Q_4$ of Chemical Formula C is N.

According to an exemplary embodiment of the present specification, one of $Q_3$ and $Q_4$ of Chemical Formula C is N.

According to an exemplary embodiment of the present specification, one of $Q_3$ and $Q_4$ of Chemical Formula C is N, and $X_2$ is $NAr_1$.

According to an exemplary embodiment of the present specification, $Q_1$ and $Q_3$ of Chemical Formula C are N.

According to an exemplary embodiment of the present specification, Q1 and Q3 of Chemical Formula C are N, and $X_2$ is O or S.

According to an exemplary embodiment of the present specification, at least one of $U_1$ to $U_8$ of Chemical Formula D is N.

According to an exemplary embodiment of the present specification, Chemical Formula B-1 may be represented by the following Chemical Formula B-7 or B-8.

[Chemical Formula B-7]

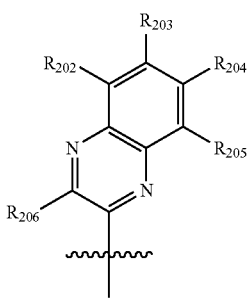

[Chemical Formula B-8]

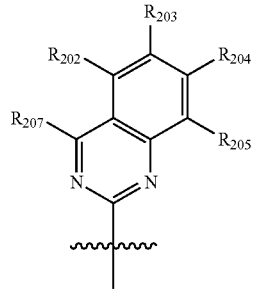

In Chemical Formulae B-7 and B-8, $R_{202}$ to $R_{207}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring. According to an exemplary embodiment of the present specification, Chemical Formulae B-2 and B-3 may be represented by the following Chemical Formula B-9 and B-10, respectively.

[Chemical Formula B-9]

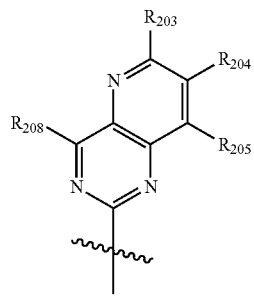

[Chemical Formula B-10]

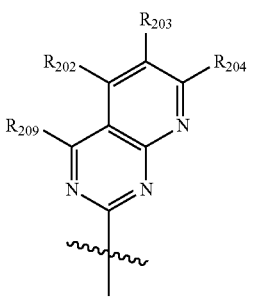

In Chemical Formulae B-9 and B-10, $R_{202}$ to $R_{205}$, $R_{208}$, and $R_{209}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula B-4 may be represented by any one of the following Chemical Formulae B-11 to B-13.

[Chemical Formula B-11]

[Chemical Formula B-12]

[Chemical Formula B-13]

In Chemical Formulae B-11 to B-13, $R_{210}$ to $R_{218}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula C may be represented by any one of the following Chemical Formulae C-1 to C-6.

[Chemical Formula C-1]

[Chemical Formula C-2]

[Chemical Formula C-3]

[Chemical Formula C-4]

[Chemical Formula C-5]

[Chemical Formula C-6]

In the chemical formulae, the definitions of X2 and Rd are the same as those described above, and q is an integer of 0 to 6, and when q is 2 or more, Rd's are the same as or different from each other.

According to an exemplary embodiment of the present specification, Chemical Formula C may be represented by any one of the following chemical formulae.

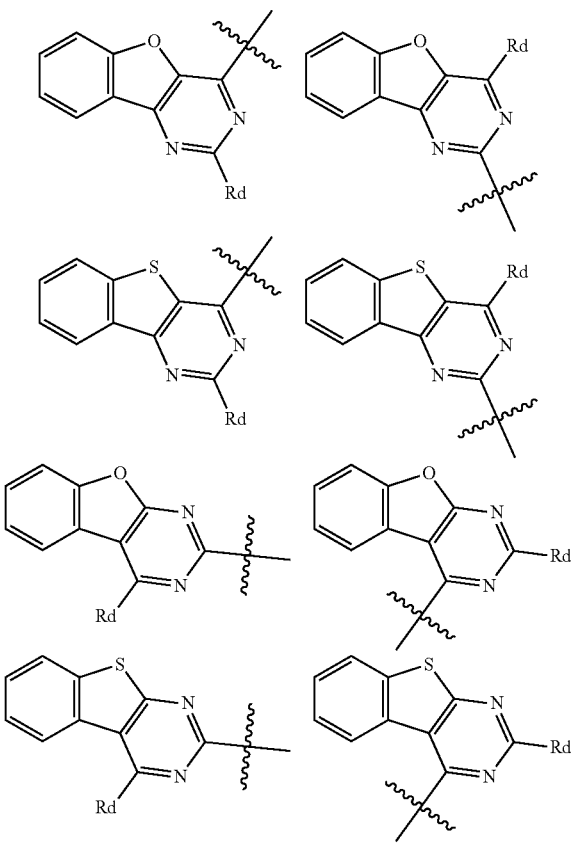

In the structural formulae, the definition of Rd is the same as that described above.

According to an exemplary embodiment of the present specification, Chemical Formula D may be represented by the following Chemical Formula D-1.

[Chemical Formula D-1]

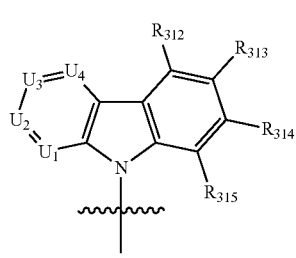

In Chemical Formula D-1, $U_1$ to $U_4$ are the same as those defined in Chemical Formula D, and $R_{312}$ to $R_{315}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, one or two or more of $U_1$ to $U_4$ of Chemical Formula D-1 is/are N.

According to an exemplary embodiment of the present specification, Chemical Formula D may be represented by the following Chemical Formula D-2 or D-3.

[Chemical Formula D-2]

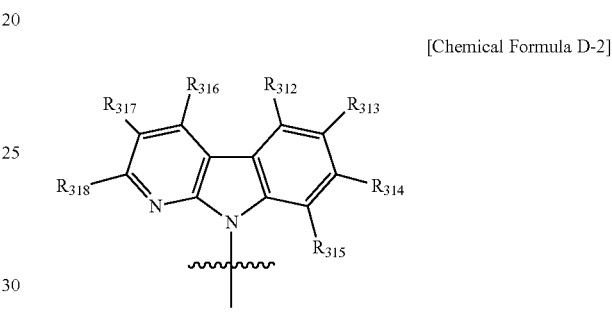

[Chemical Formula D-3]

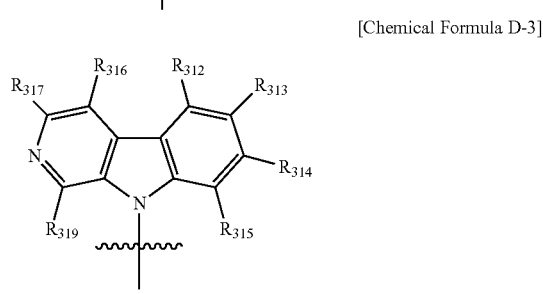

In Chemical Formulae D-2 and D-3, $R_{312}$ to $R_{319}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula E may be represented by the following Chemical Formula E-1.

[Chemical Formula E-1]

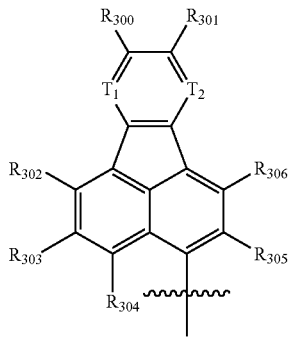

In Chemical Formula E-1, $T_1$ and $T_2$ are the same as those defined in Chemical Formula E, $R_{300}$ to $R_{306}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula E may be represented by any one of the following Chemical Formulae E-2 to E-4.

[Chemical Formula E-2]

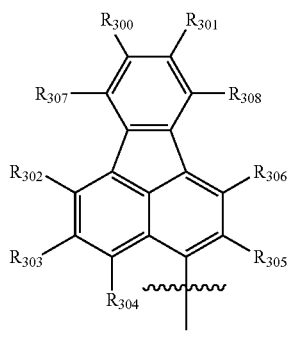

[Chemical Formula E-3]

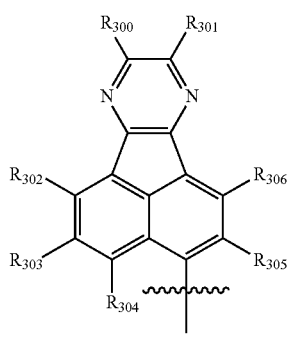

[Chemical Formula E-4]

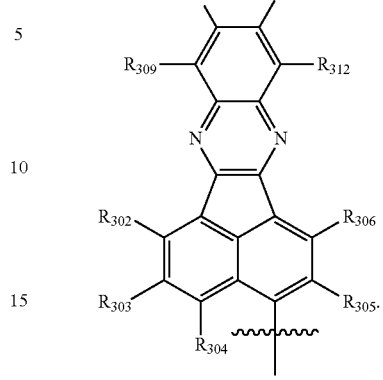

In Chemical Formulae E-2 to E-4, $R_{300}$ to $R_{312}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, adjacent two of $R_1$ to $R_4$ in Chemical Formulae 1 to 3 combine with each other to form a ring, for example, an aromatic ring.

According to an exemplary embodiment of the present specification, Chemical Formula 2 may be represented by any one of the following Chemical Formulae 6 to 8.

[Chemical Formula 6]

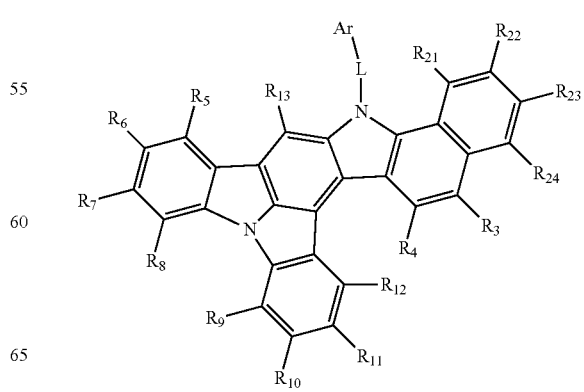

[Chemical Formula 7]

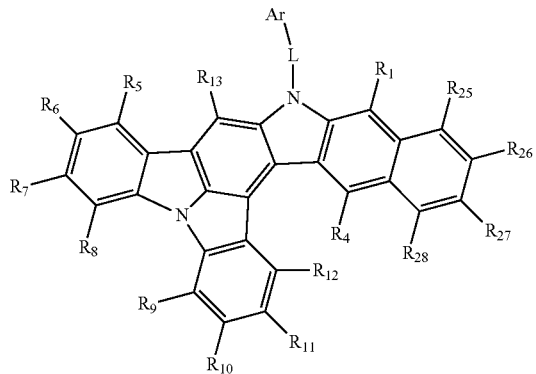

[Chemical Formula 9]

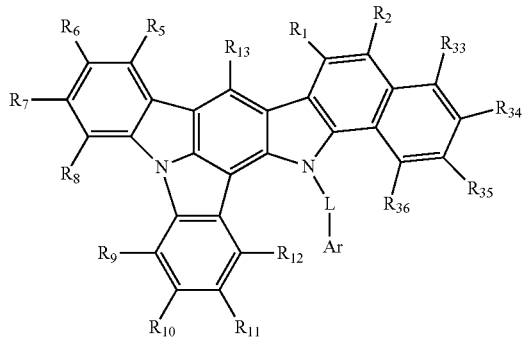

[Chemical Formula 10]

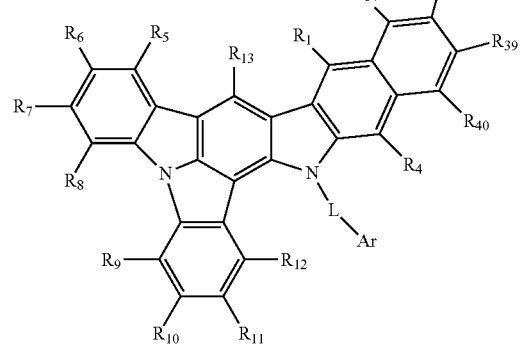

[Chemical Formula 8]

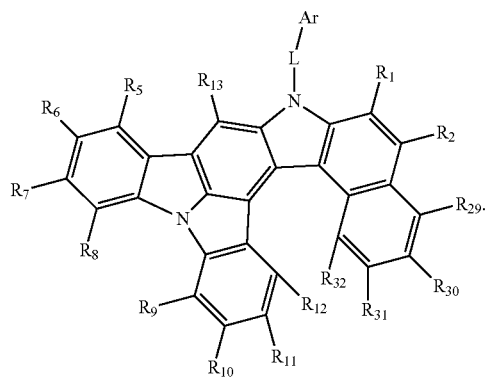

[Chemical Formula 11]

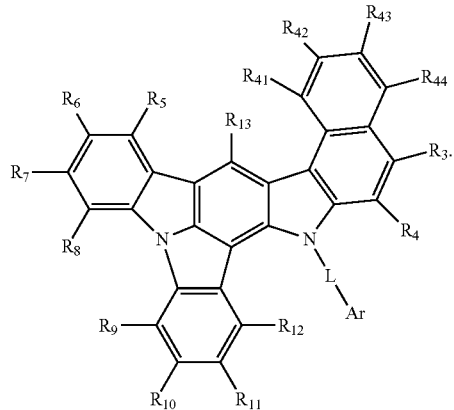

In Chemical Formulae 6 to 8, $R_1$ to $R_{13}$, L, and Ar are the same as those defined in Chemical Formula 1, and $R_{21}$ to $R_{32}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, Chemical Formula 3 may be represented by any one of the following Chemical Formulae 9 to 11.

In Chemical Formulae 9 to 11, $R_1$ to $R_{13}$, L, and Ar are the same as those defined in Chemical Formula 1, and $R_{33}$ to $R_{44}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

In an exemplary embodiment of the present specification, at least one of $R_3$, $R_6$, and $R_7$ of Chemical Formulae 1 to 3 is a substituted or unsubstituted phenyl group, a substituted or unsubstituted naphthyl group, or a substituted or unsubstituted biphenyl group.

In an exemplary embodiment of the present specification, Chemical Formula 1 is represented by the following Chemical Formula 12 or 13.

[Chemical Formula 12]

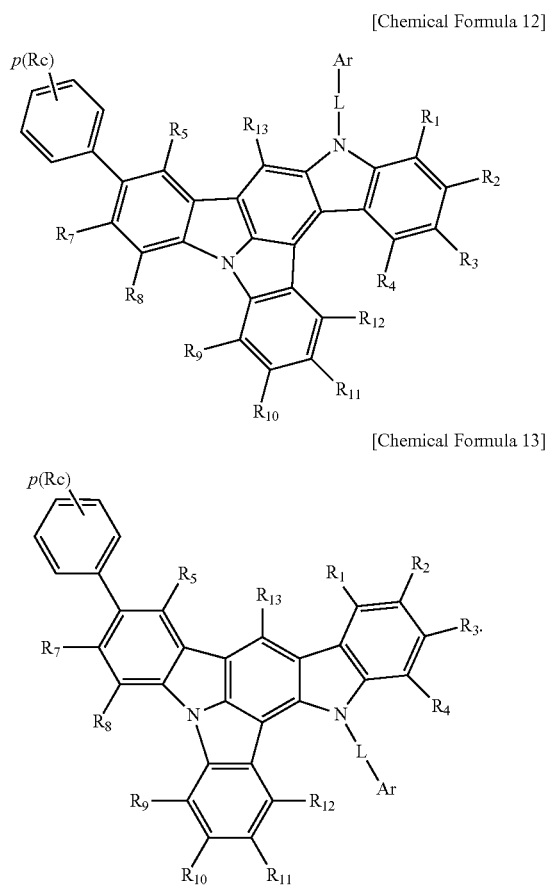

[Chemical Formula 13]

In Chemical Formulae 12 and 13, $R_1$ to $R_5$, $R_7$ to $R_{13}$, L, and Ar are the same as those defined in Chemical Formula 1, Rc is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and p is an integer of 1 to 5.

In an exemplary embodiment of the present specification, Chemical Formula 1 is represented by any one of the following Chemical Formulae 14 and 15.

[Chemical Formula 14]

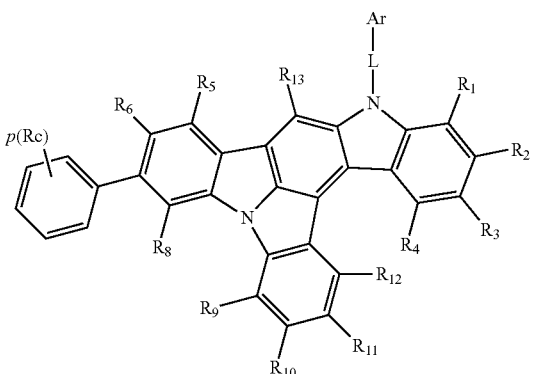

[Chemical Formula 15]

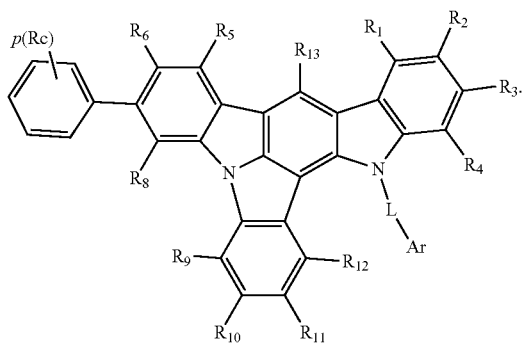

In Chemical Formulae 14 and 15, $R_1$ to $R_6$, $R_8$ to $R_{13}$, L, and Ar are the same as those defined in Chemical Formula 1, Rc is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring, and p is an integer of 1 to 5.

According to an exemplary embodiment of the present specification, adjacent two of $R_5$ to $R_8$ in Chemical Formulae 1 to 3 combine with each other to form a ring, for example, an aromatic ring.

According to an exemplary embodiment of the present specification, Chemical Formula 1 is represented by any one of the following Chemical Formulae 16 and 17.

[Chemical Formula 16]

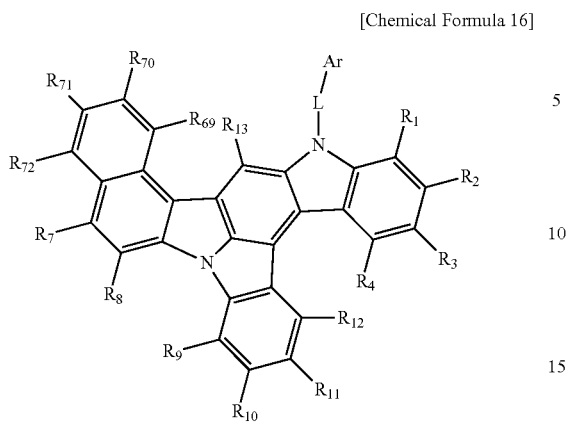

[Chemical Formula 18]

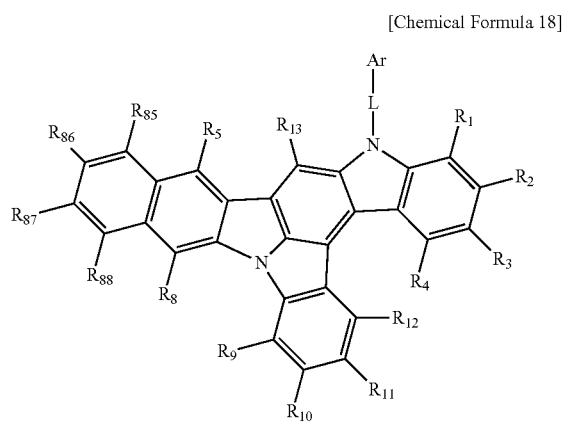

[Chemical Formula 17]

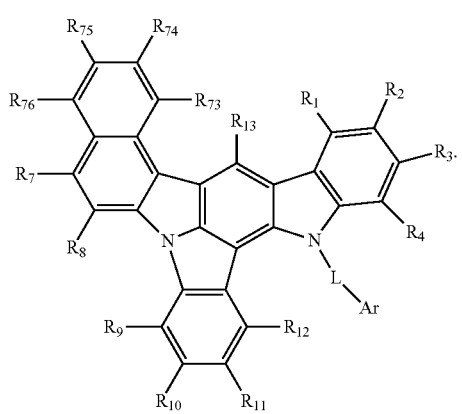

[Chemical Formula 19]

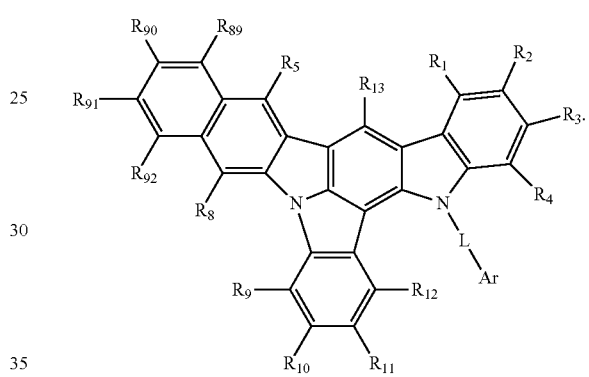

In Chemical Formulae 16 and 17, $R_1$ to R4, $R_7$ to $R_{13}$, L, and Ar are the same as those defined in Chemical Formula 1, and $R_{69}$ to $R_{76}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 18 and 19.

In Chemical Formulae 18 and 19, $R_1$ to $R_5$, $R_8$ to $R_{13}$, L, and Ar are the same as those defined in Chemical Formula 1, and $R_{85}$ to $R_{92}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 20 and 21.

[Chemical Formula 20]

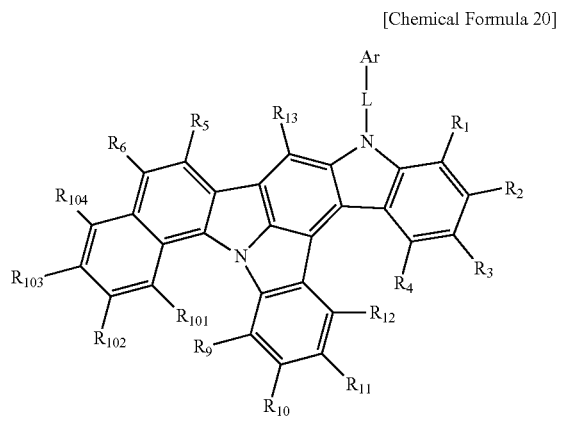

[Chemical Formula 21]

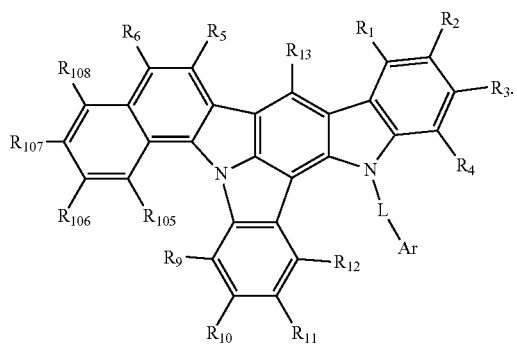

In Chemical Formulae 20 and 21, $R_1$ to $R_6$, $R_9$ to $R_{13}$, L, and Ar are the same as those defined in Chemical Formula 1, and $R_{101}$ to $R_{108}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, adjacent two of $R_9$ to $R_{12}$ in Chemical Formulae 1 to 3 combine with each other to form a ring, for example, an aromatic ring.

According to an exemplary embodiment of the present specification, Chemical Formula 1 is represented by any one of the following Chemical Formulae 22 and 23.

[Chemical Formula 22]

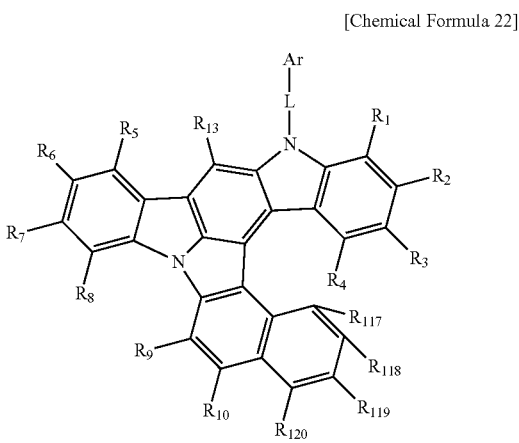

[Chemical Formula 23]

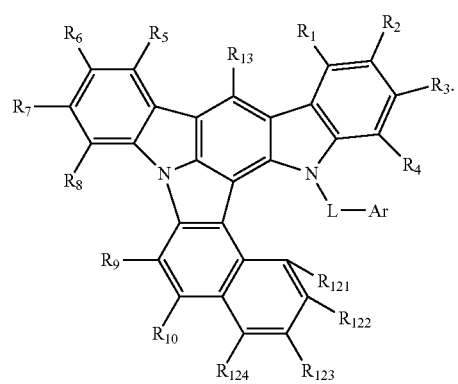

In Chemical Formulae 22 and 23, $R_1$ to $R_{10}$, $R_{13}$, L, and Ar are the same as those defined in Chemical Formula 1, and $R_{117}$ to $R_{124}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 24 and 25.

[Chemical Formula 24]

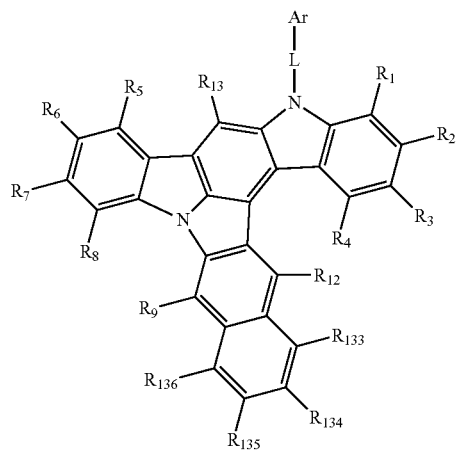

[Chemical Formula 25]

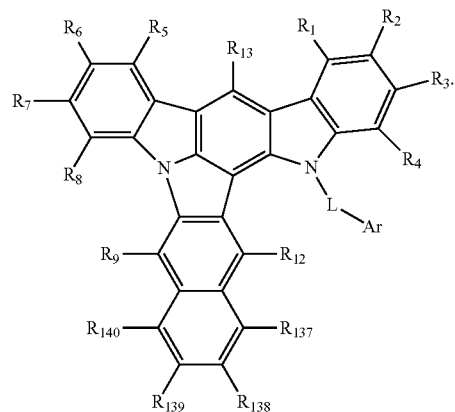

[Chemical Formula 26]

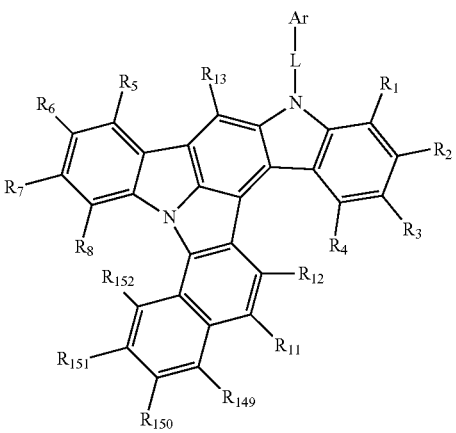

[Chemical Formula 27]

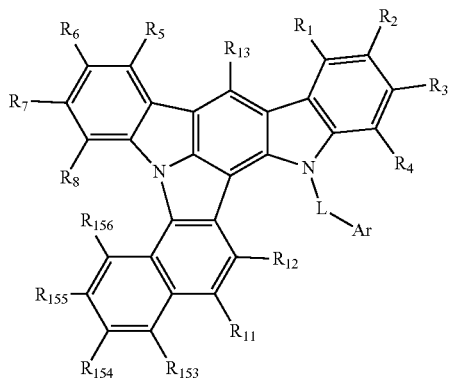

In Chemical Formulae 26 and 27, $R_1$ to $R_8$, $R_{11}$ to $R_{13}$, L, and Ar are the same as those defined in Chemical Formula 1, and $R_{149}$ to $R_{156}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, in Chemical Formula B-7, $R_{206}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-8, $R_{207}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-9, $R_{208}$ is hydrogen, a In Chemical Formulae 24 and 25, $R_1$ to $R_9$, $R_{12}$, $R_{13}$, L, and Ar are the same as those defined in Chemical Formula 1, and $R_{133}$ to $R_{140}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent substituent to form a ring.

According to an exemplary embodiment of the present specification, Chemical Formula 1 is represented by any one of the following Chemical Formulae 26 and 27.

substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B-10, $R_{209}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B, $Y_1$ is $CR_{219}$, $Y_2$ is N or $CR_{220}$, $R_{219}$ is hydrogen, a substituted or unsubstituted alkyl group, for example, a methyl group, or a substituted or unsubstituted aryl group, for example, a phenyl group, a biphenylyl group, or a naphthyl group, and $R_{220}$ is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group.

According to an exemplary embodiment of the present specification, in Chemical Formula B, $Y_1$ is $CR_{219}$, $Y_2$ is N, and $R_{219}$ is hydrogen, a substituted or unsubstituted alkyl group, for example, a methyl group, or a substituted or unsubstituted aryl group, for example, a phenyl group, a biphenylyl group, or a naphthyl group.

According to an exemplary embodiment of the present specification, in Chemical Formula B, $Y_1$ is $CR_{219}$, $Y_2$ is N, and $R_{219}$ is a substituted or unsubstituted aryl group, for example, a phenyl group, a biphenylyl group, or a naphthyl group.

According to an exemplary embodiment of the present specification, Ar may be a group represented by the following chemical formulae.

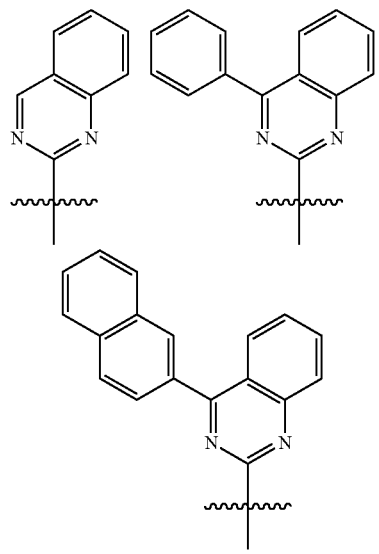

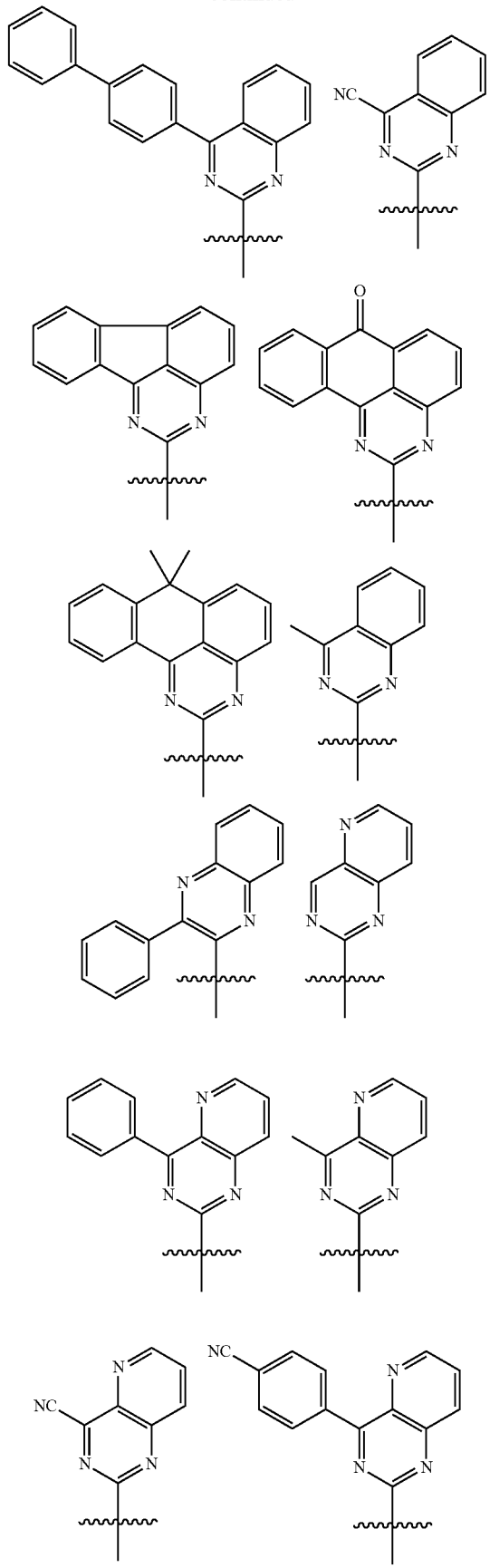

31
-continued
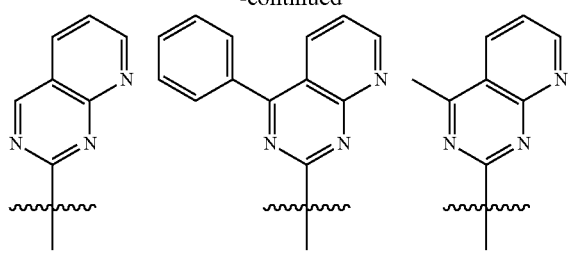
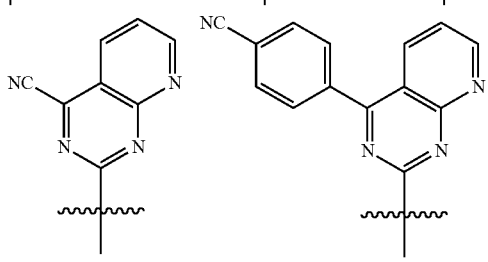
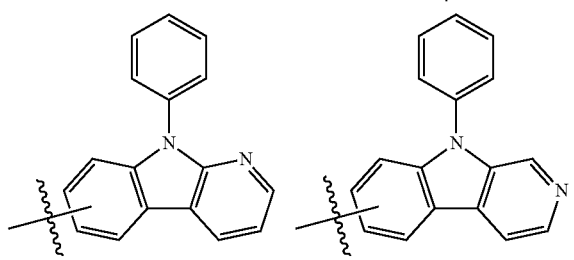
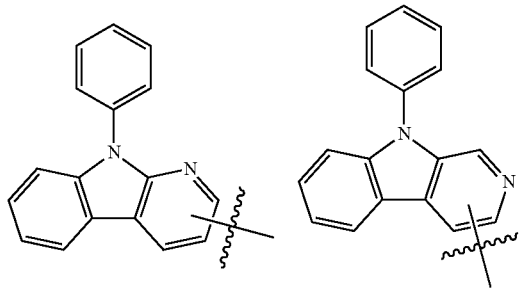
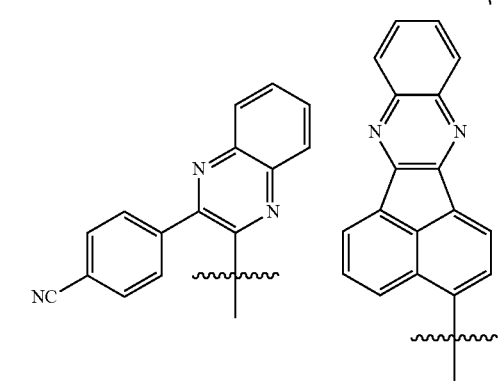
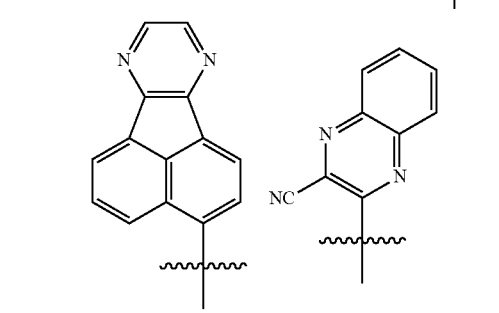
32
-continued
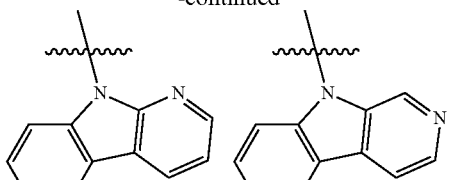
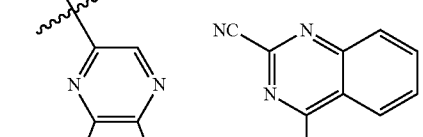
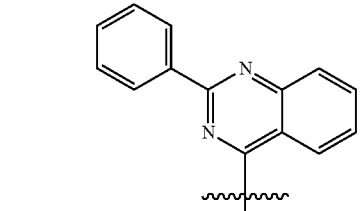
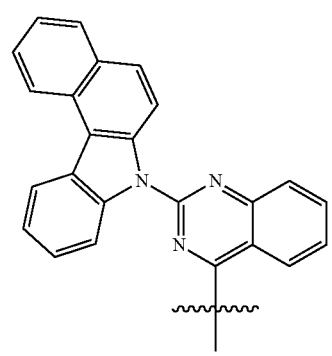
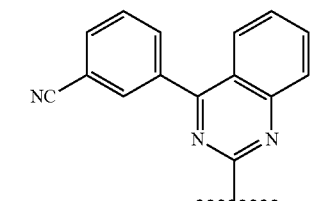
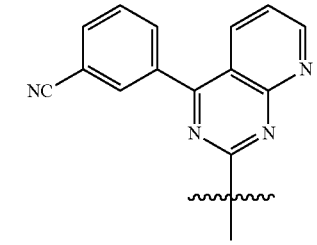

-continued
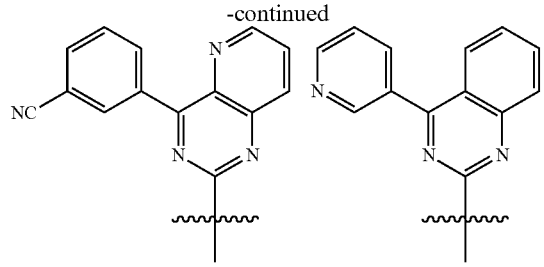
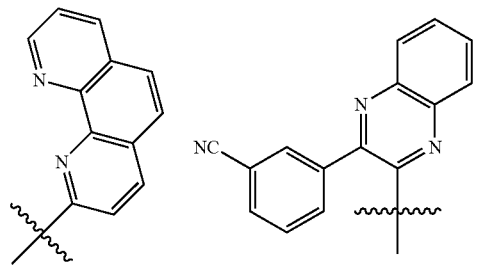
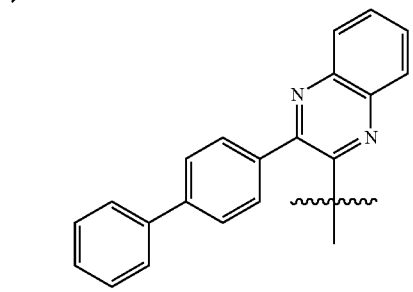
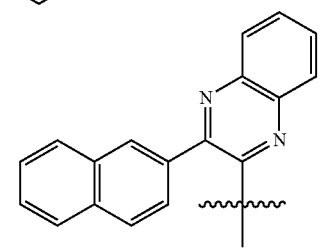
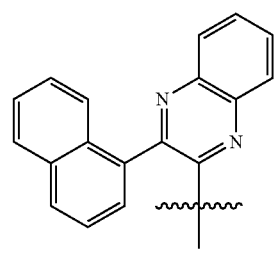
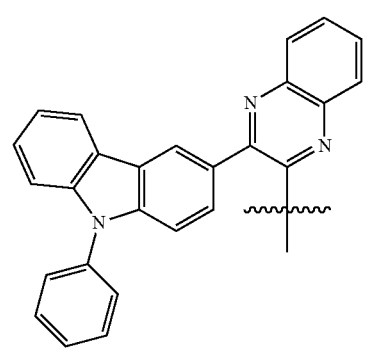
-continued
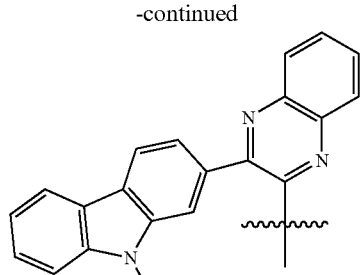
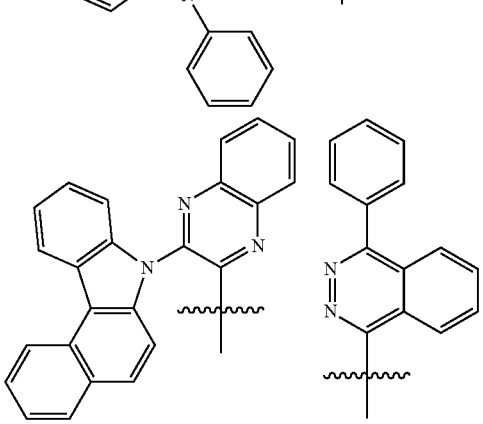
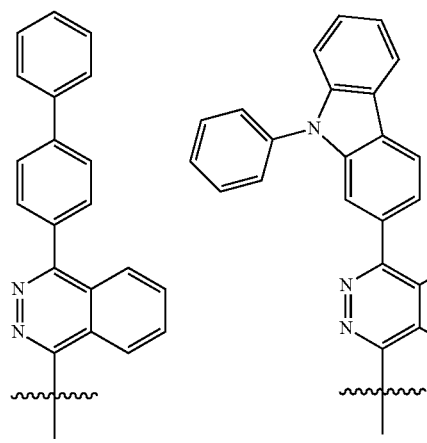
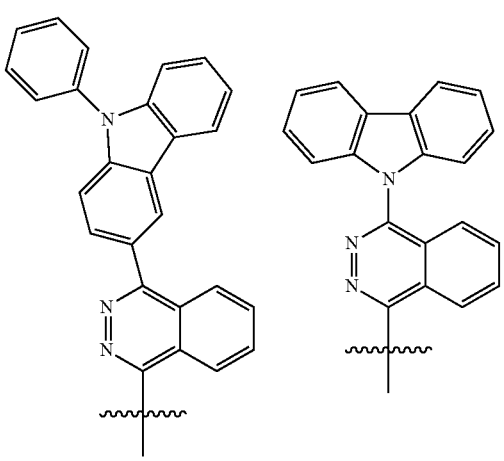

-continued
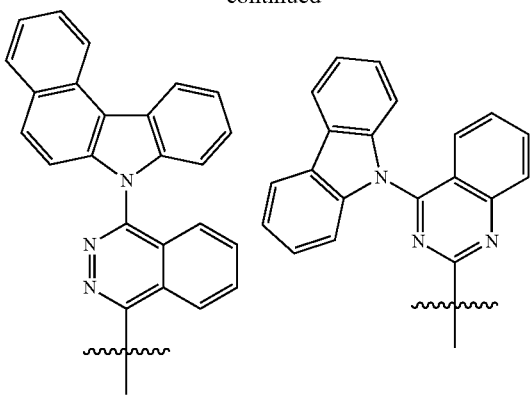
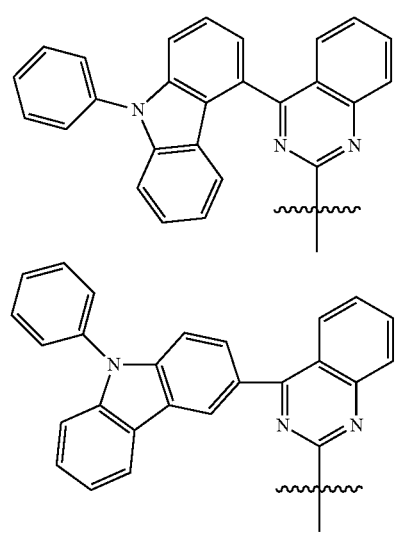
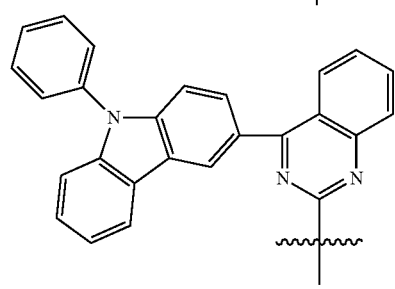
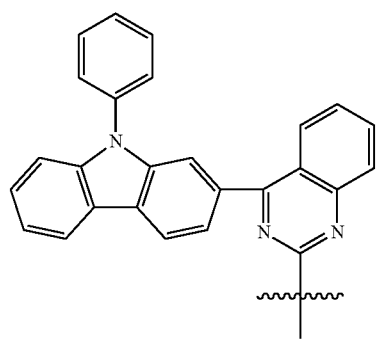
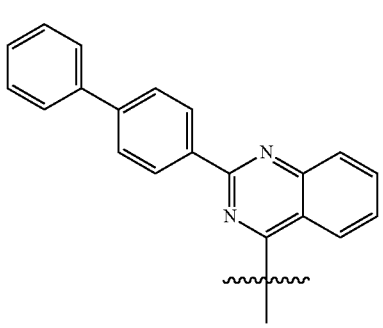
-continued
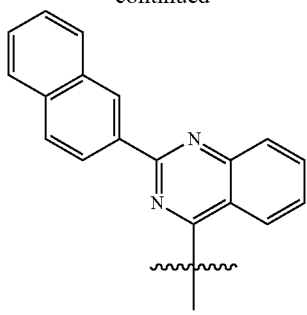
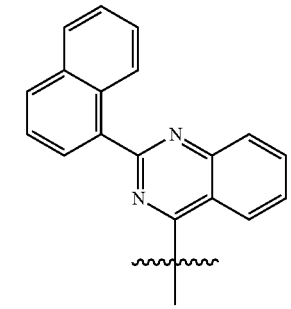
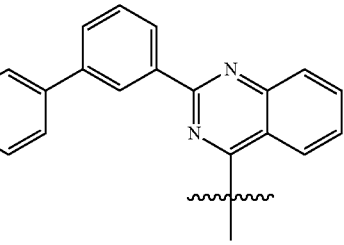
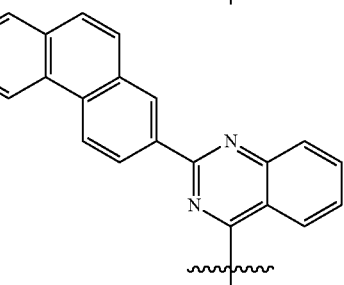
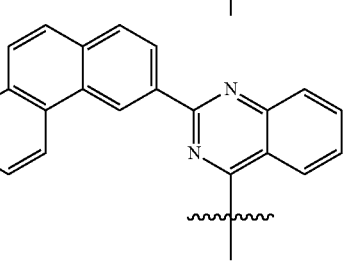
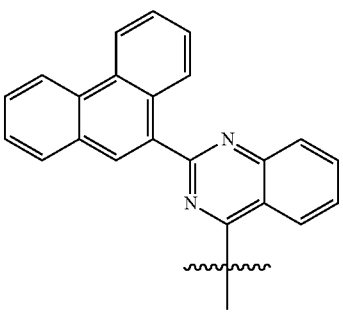

-continued
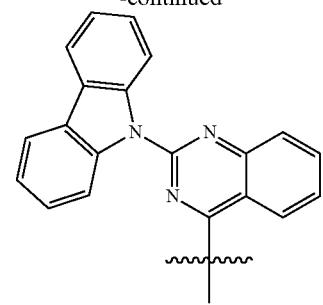
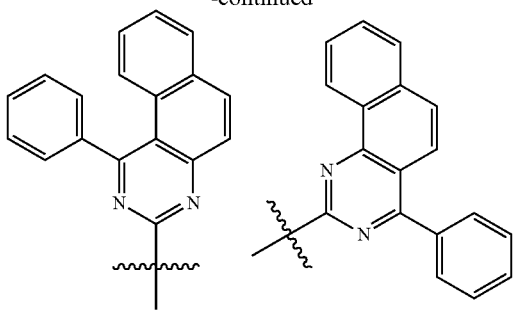
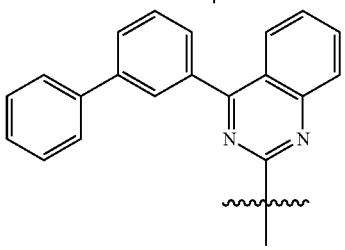
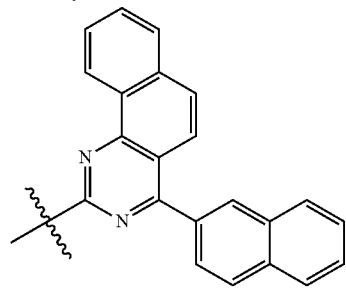
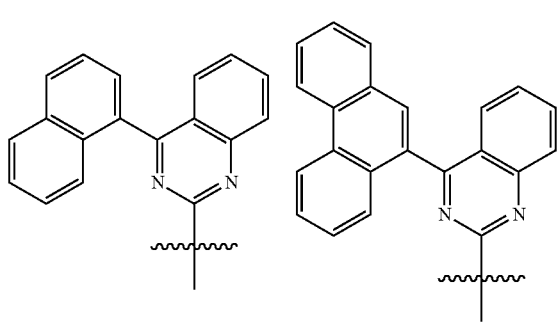
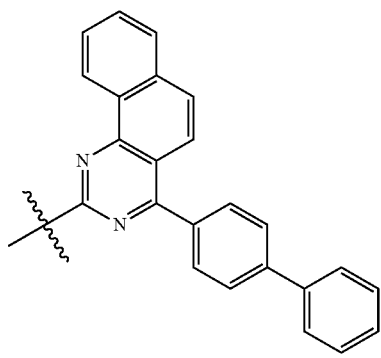
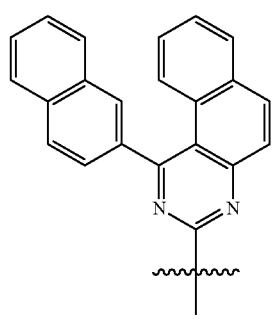
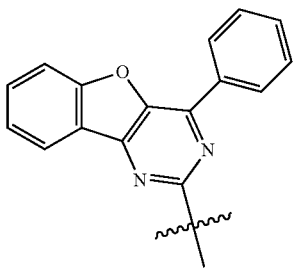
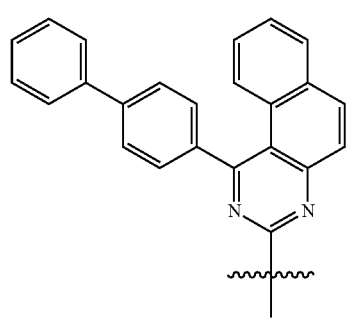
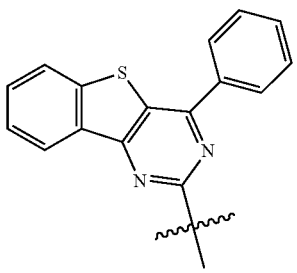

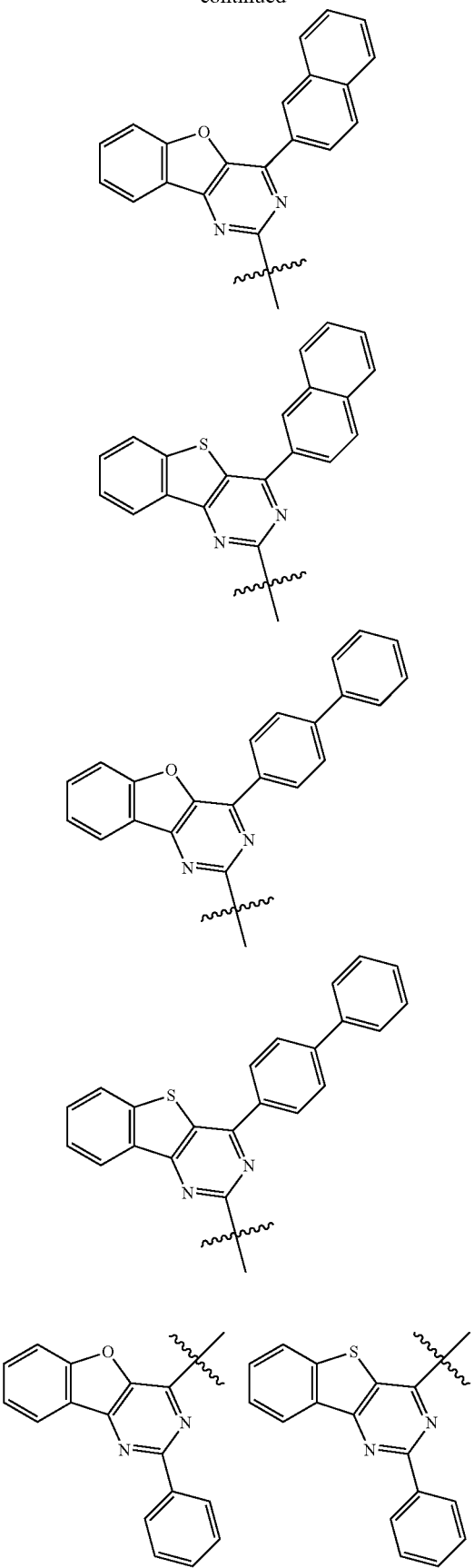
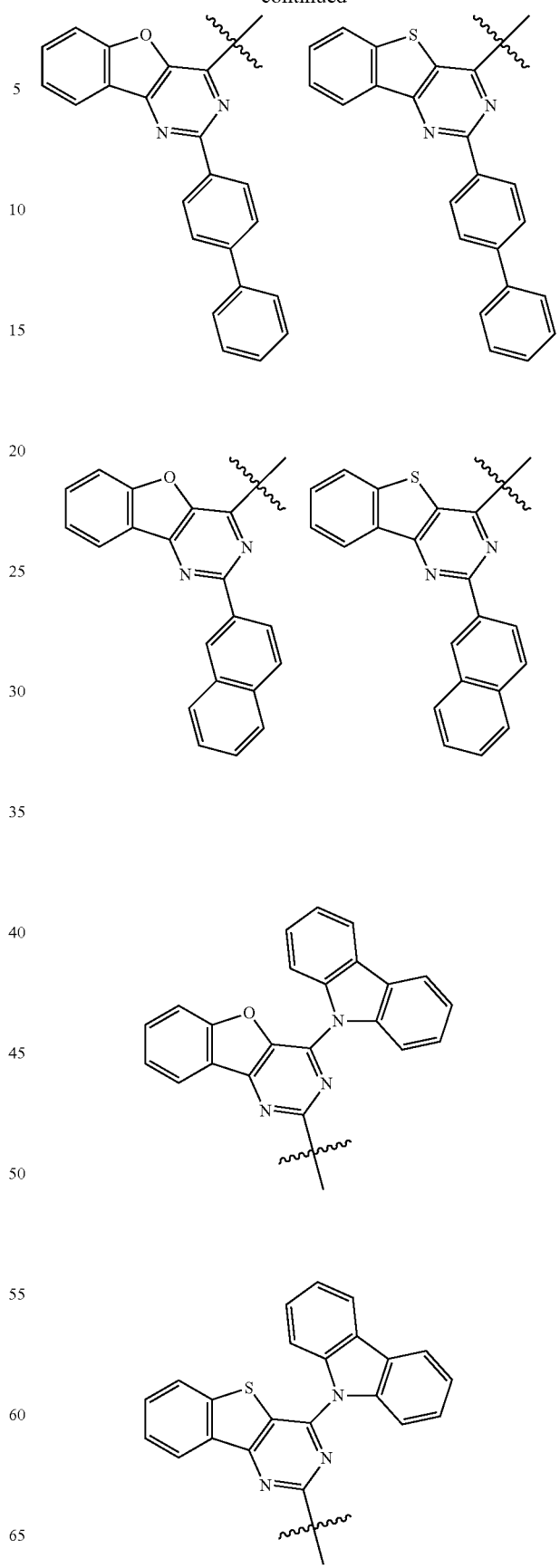

41
-continued
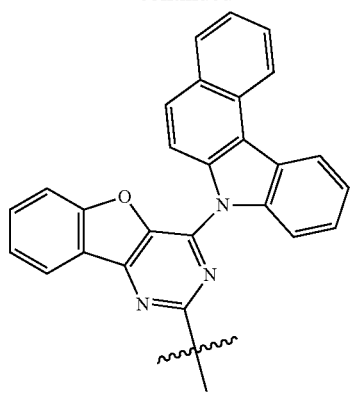
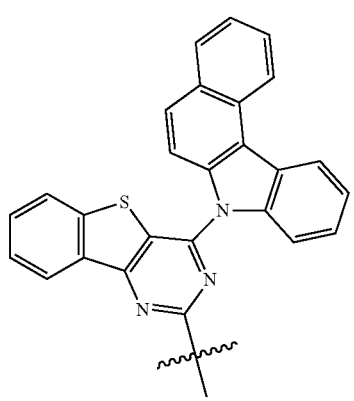
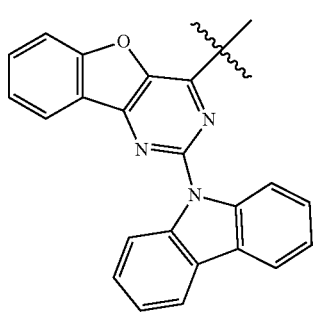
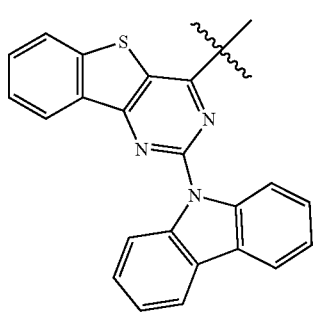
42
-continued
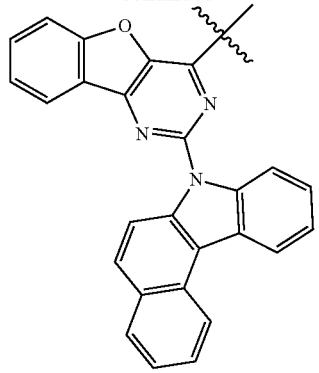
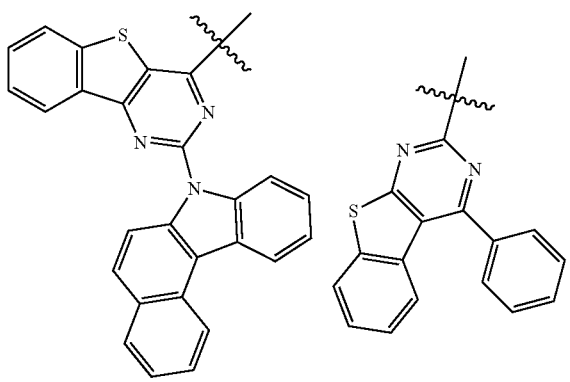
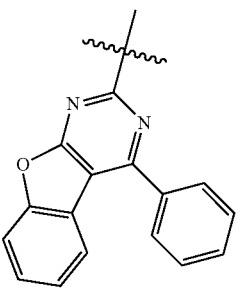
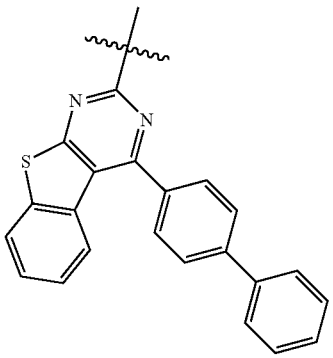

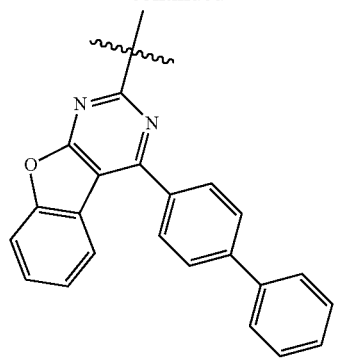
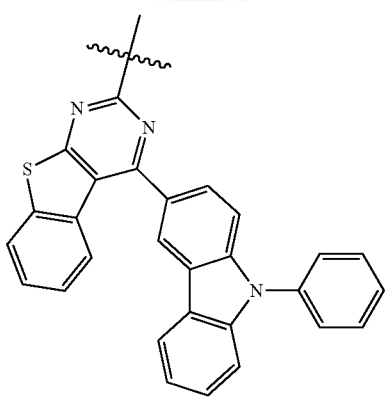
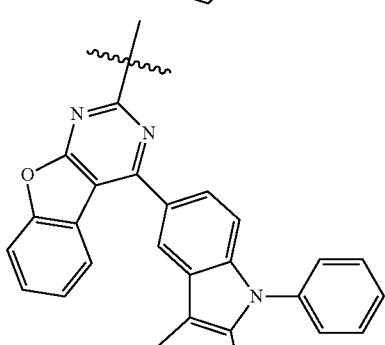
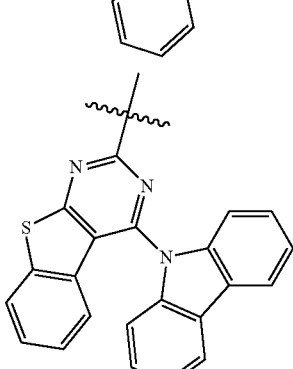
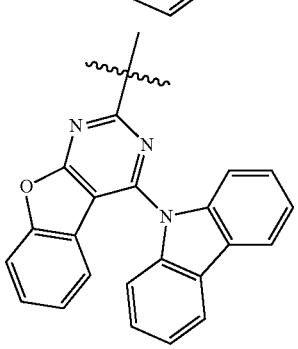
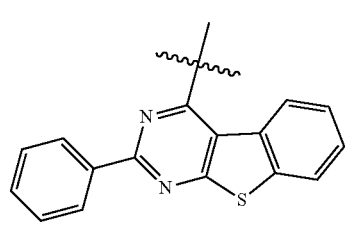

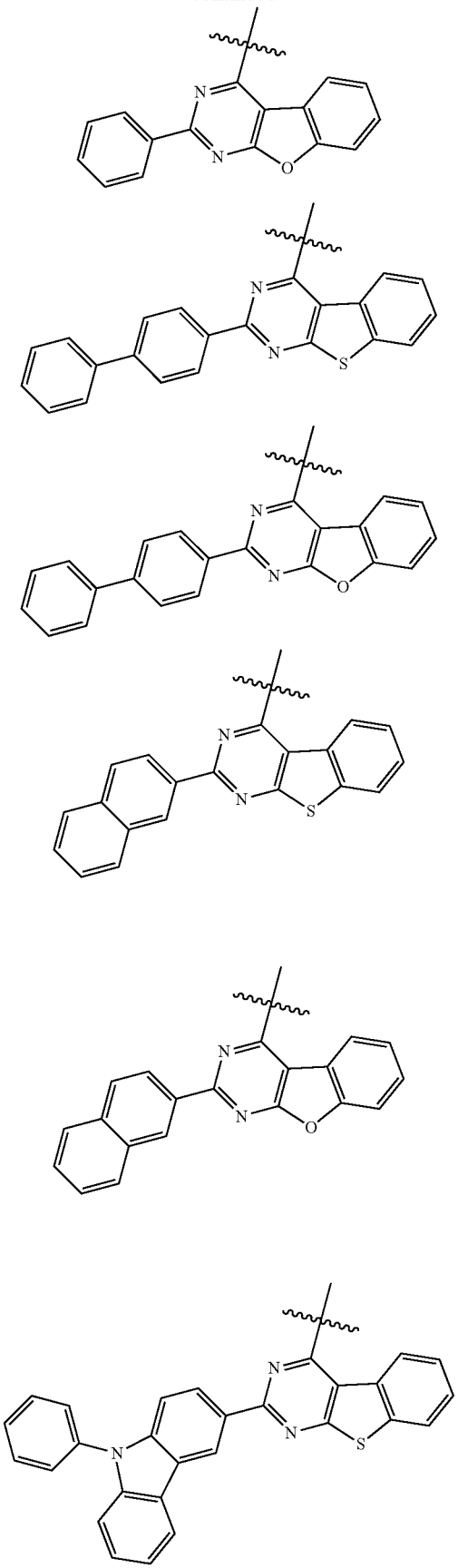
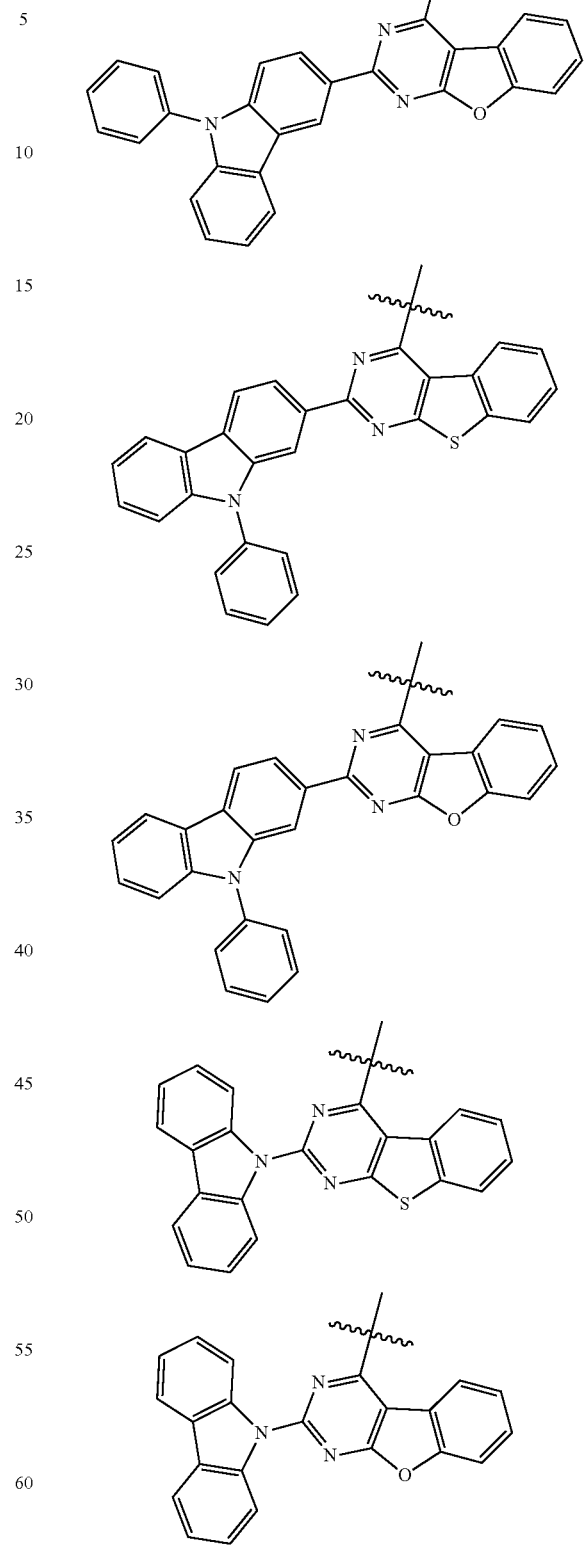
According to an exemplary embodiment of the present specification, Chemical Formula 1 is represented by any one of the following compounds.

47
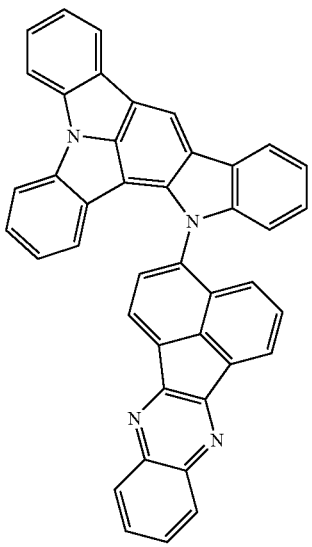
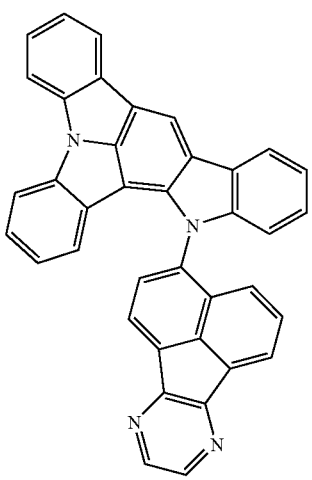
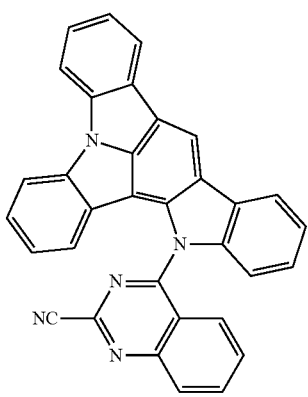
48
-continued
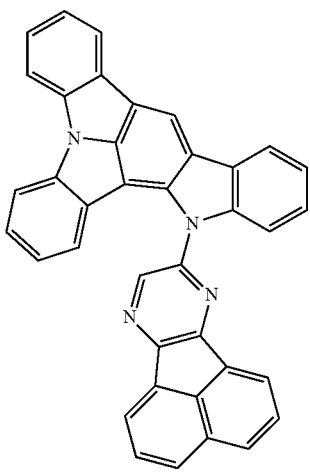
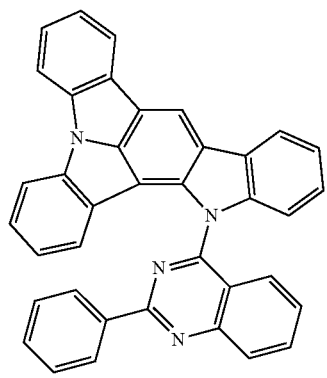
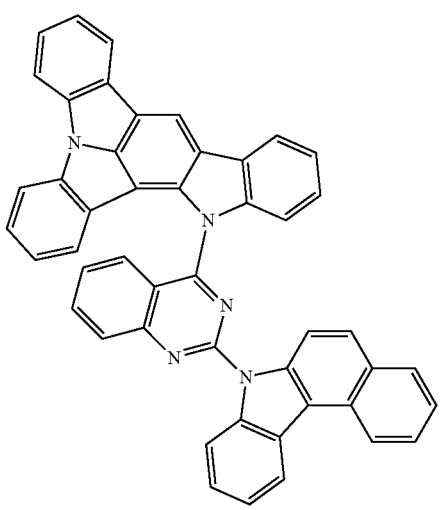

49
-continued
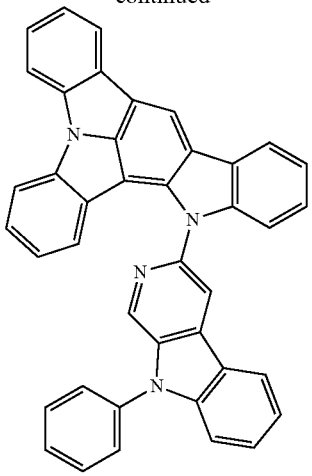
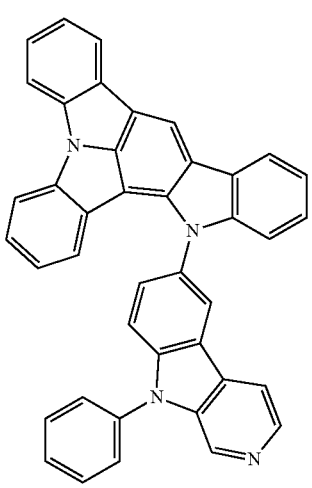
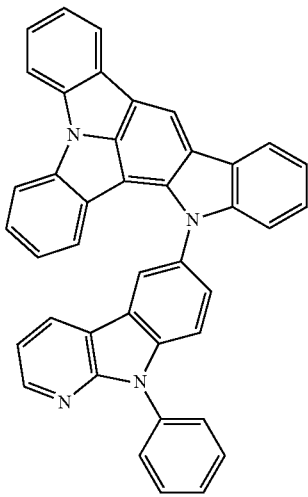
50
-continued
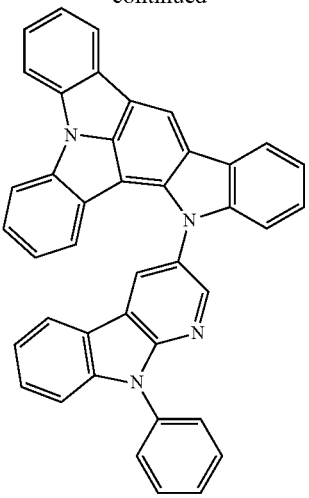
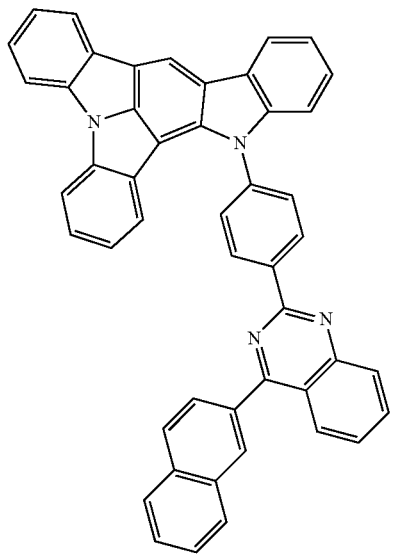
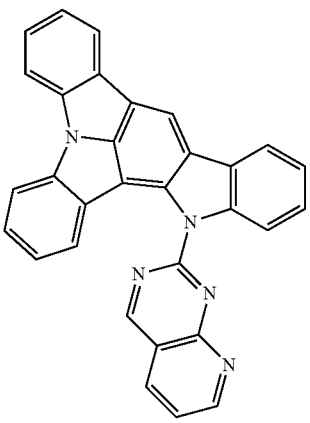

51
-continued
52
-continued
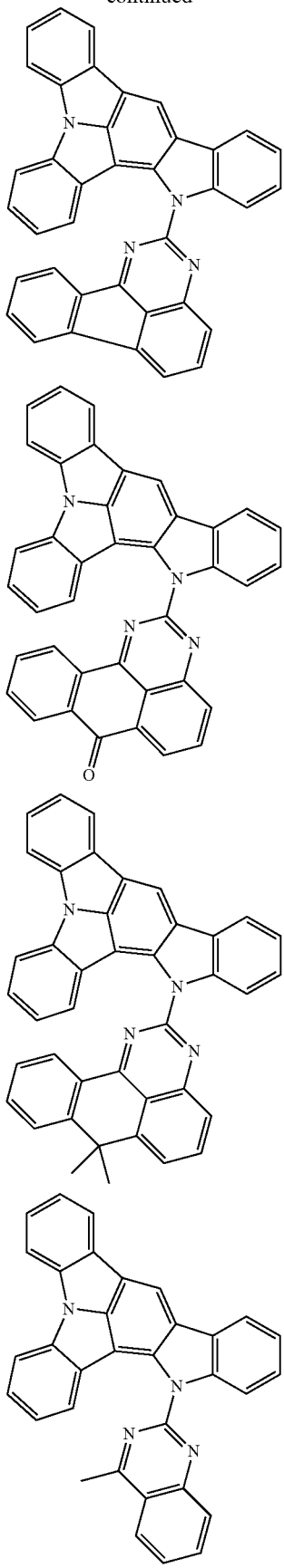
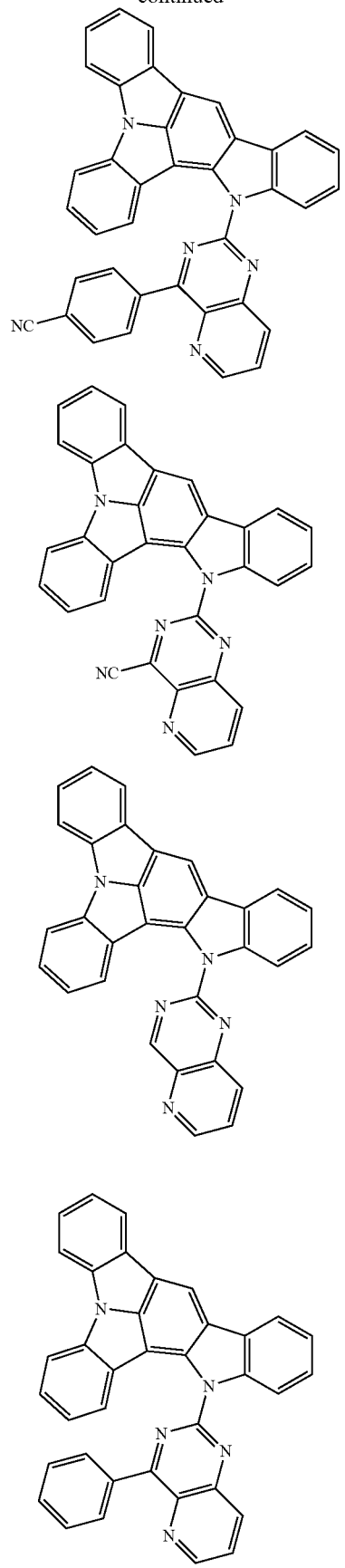

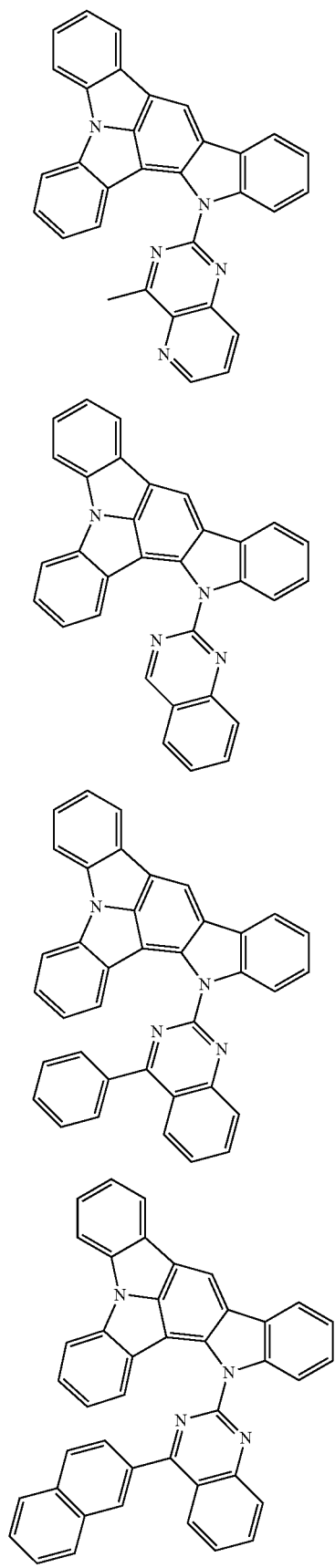
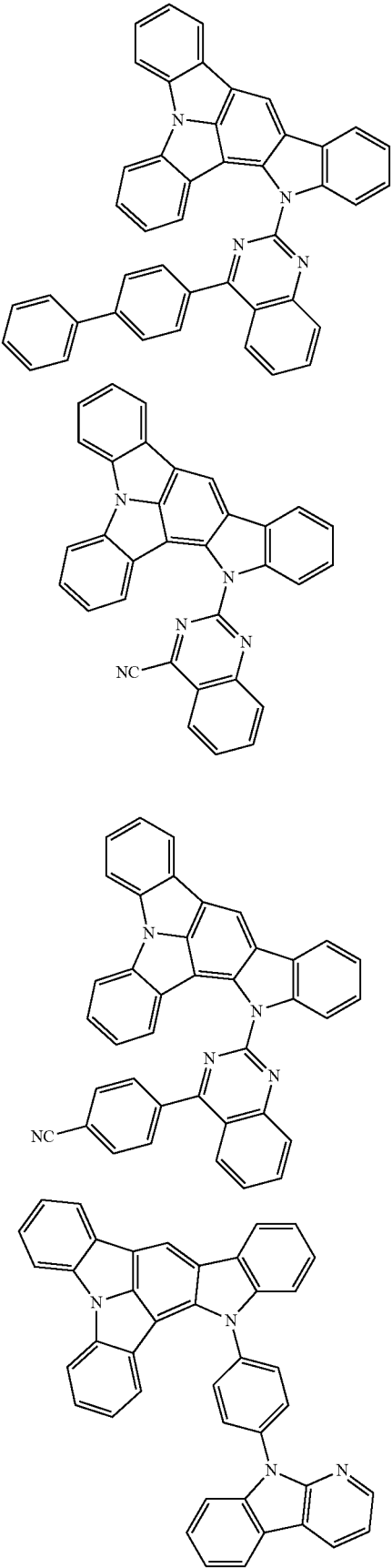

55
-continued
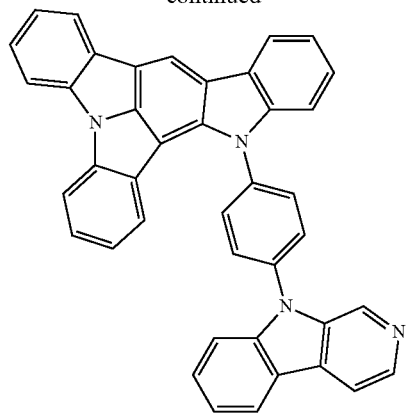
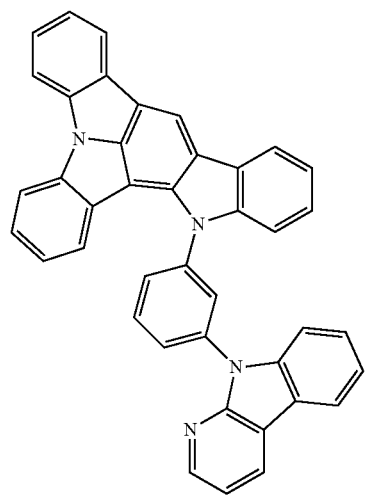
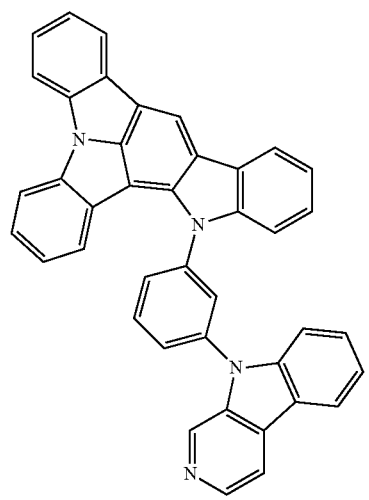
56
-continued
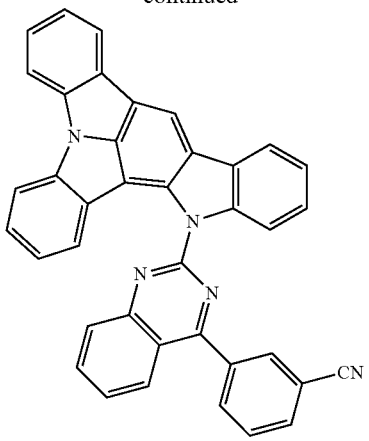
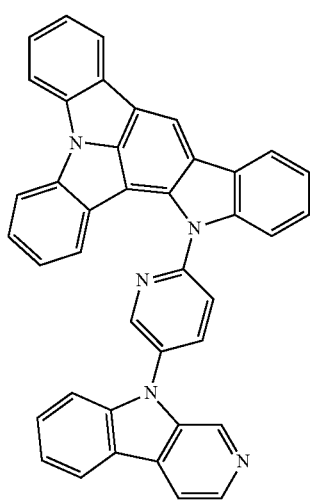
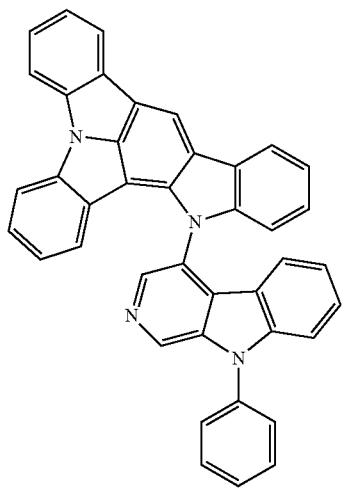

57
-continued

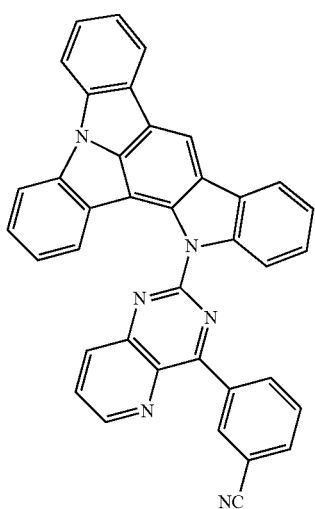
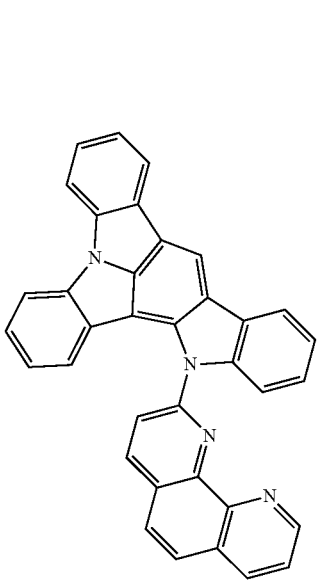
58
-continued
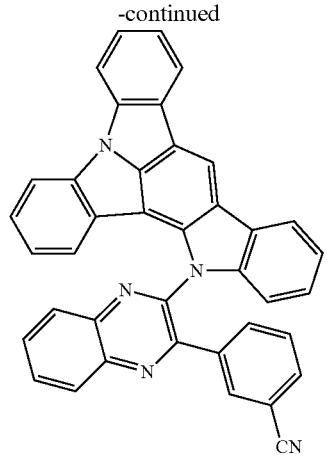
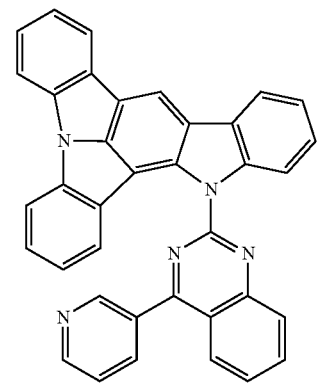
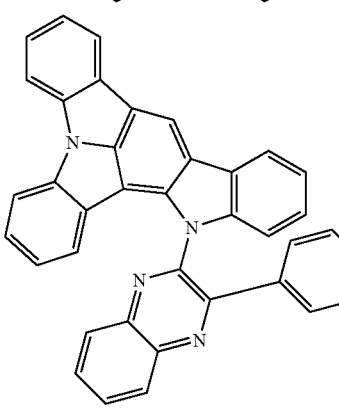

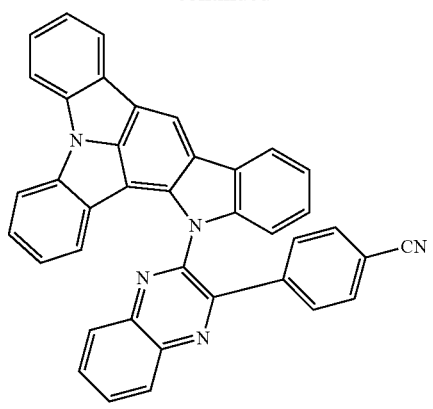
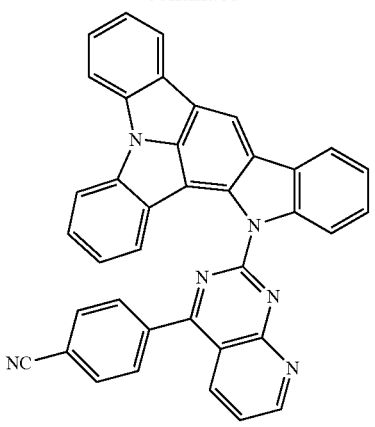
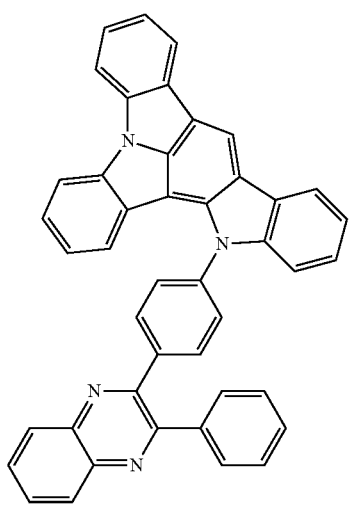
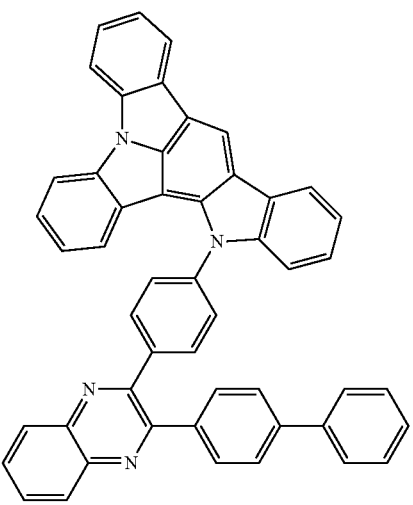

61
-continued
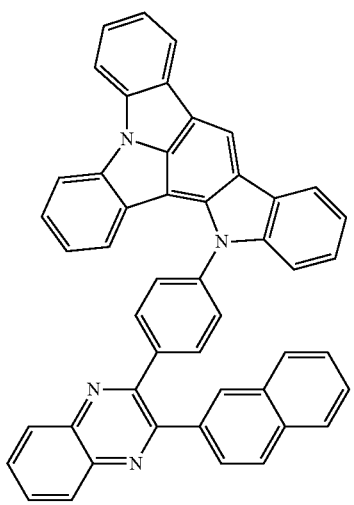
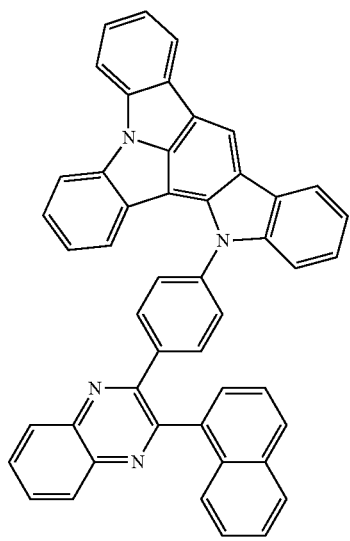
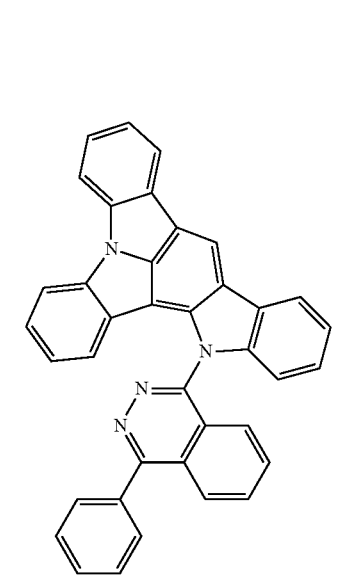
62
-continued
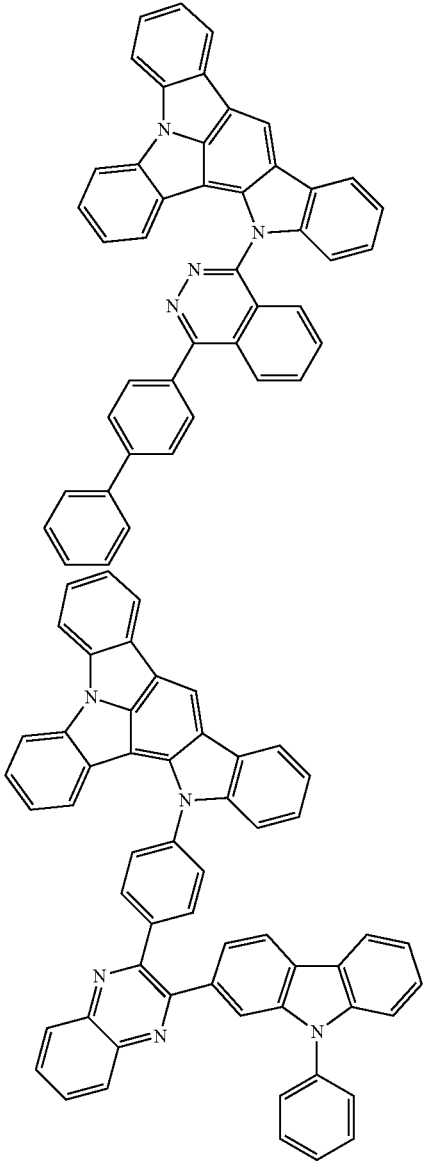
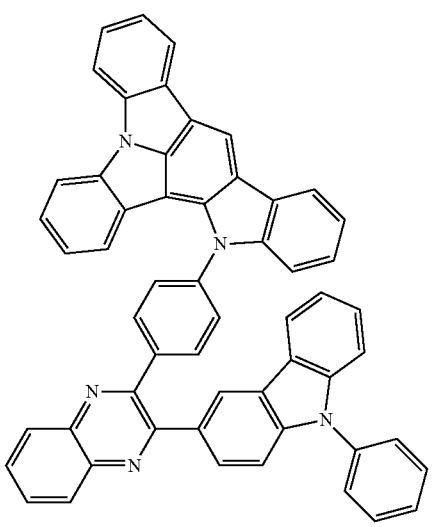

63
-continued
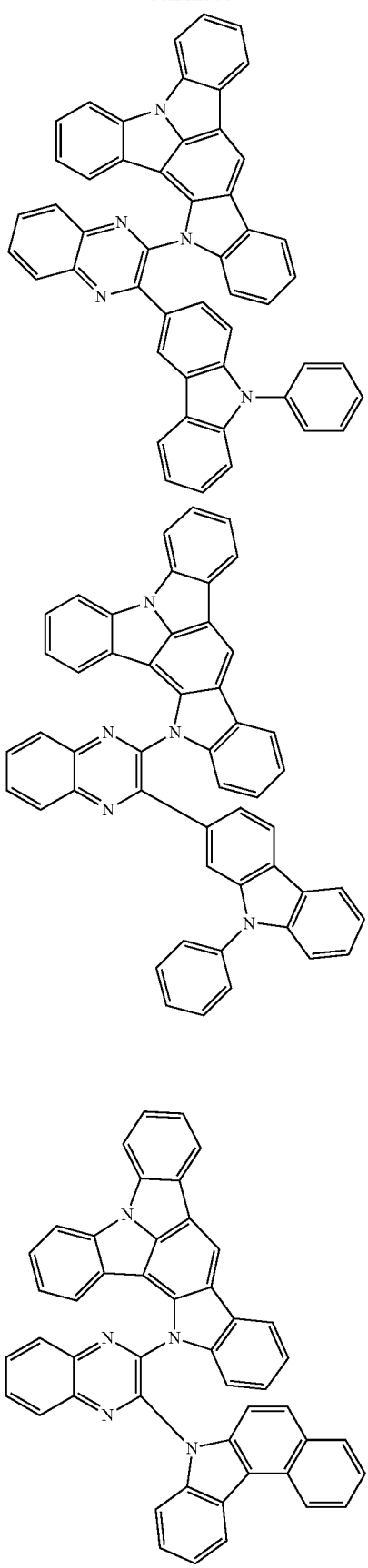
64
-continued
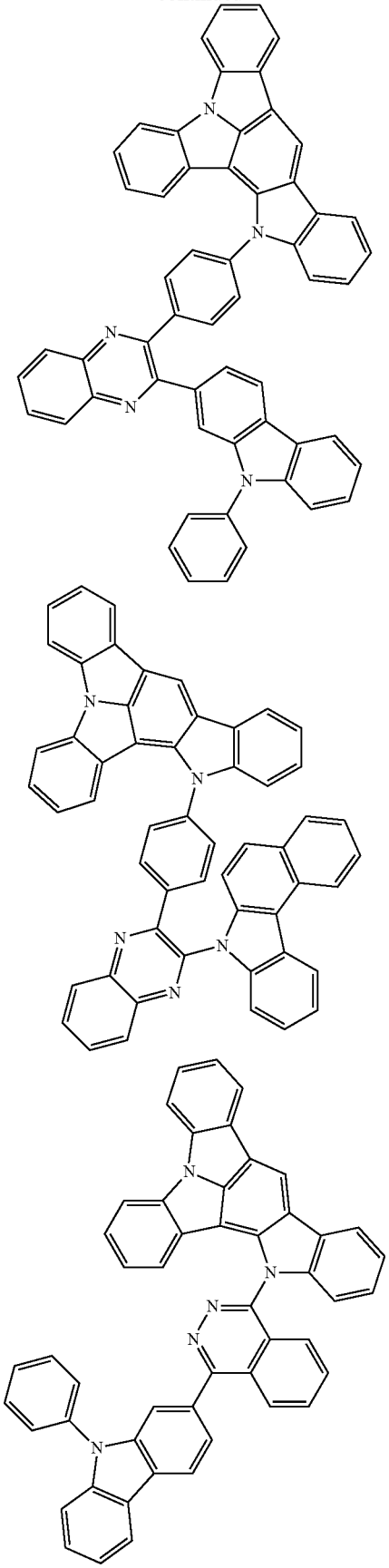

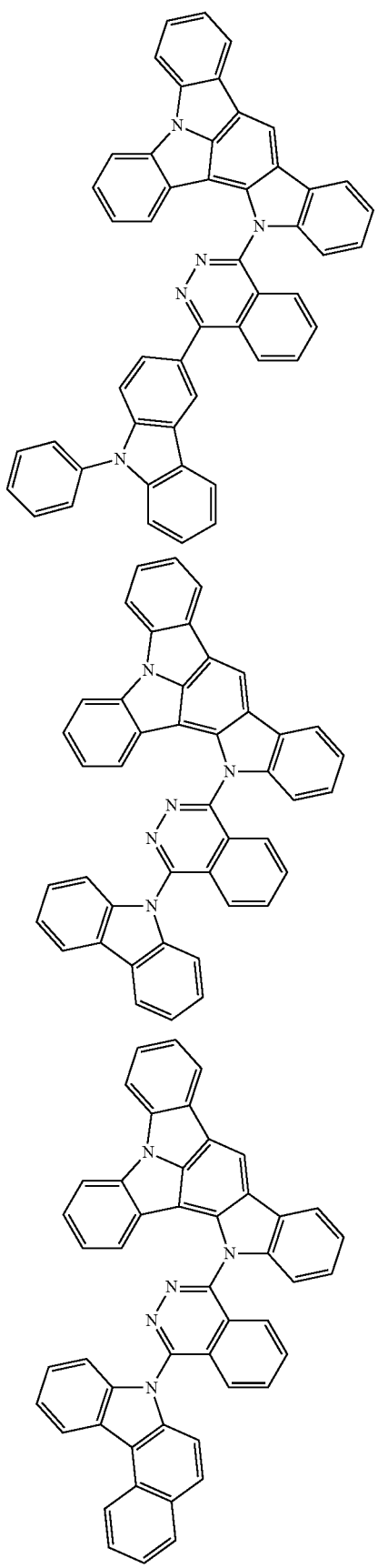
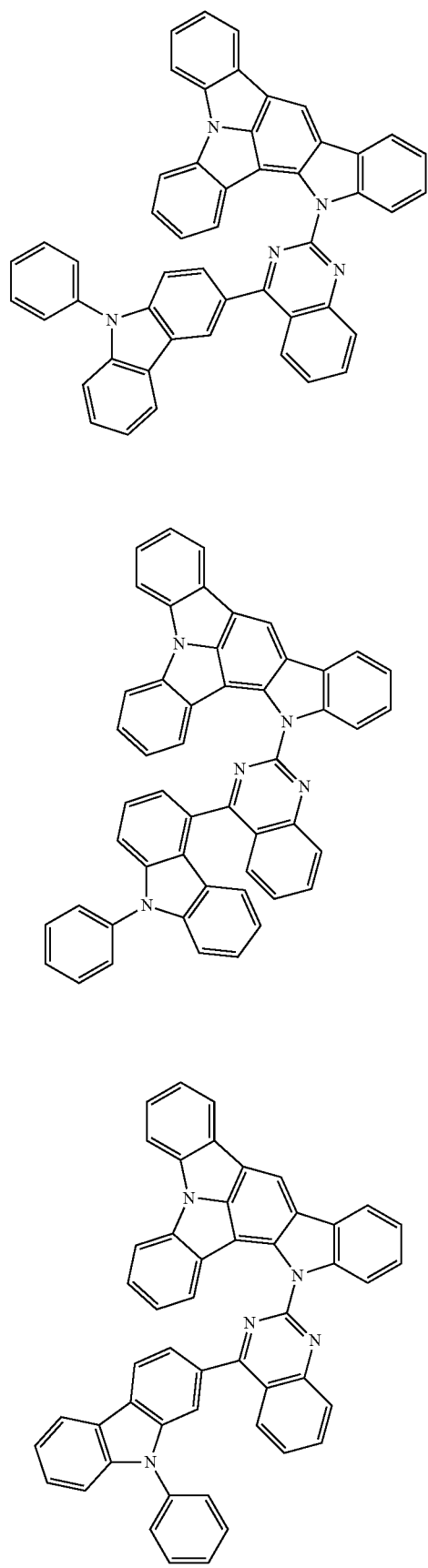

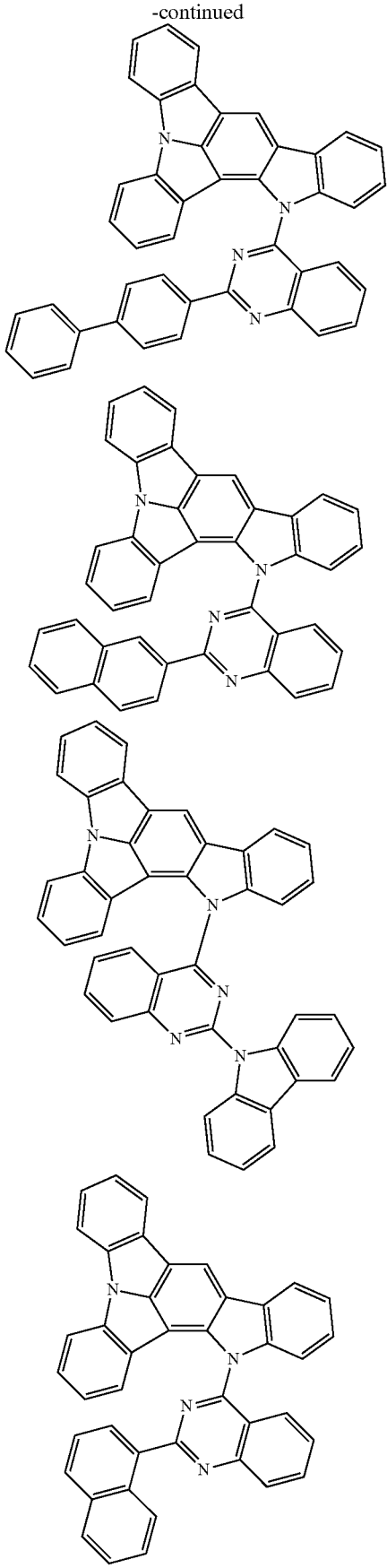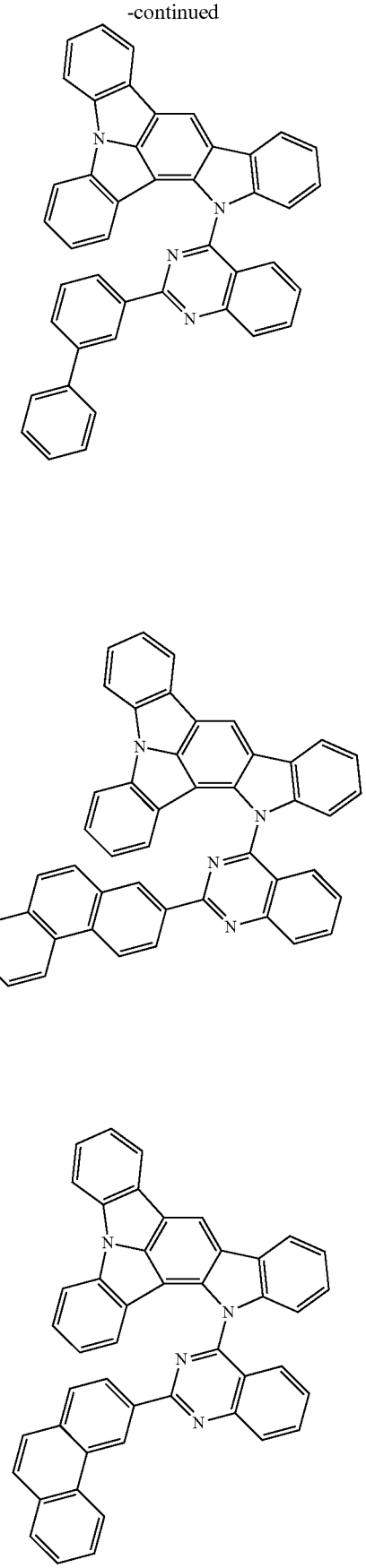

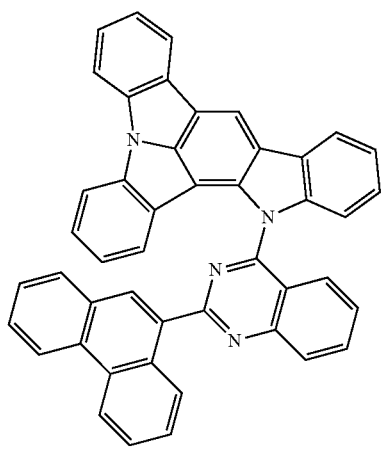
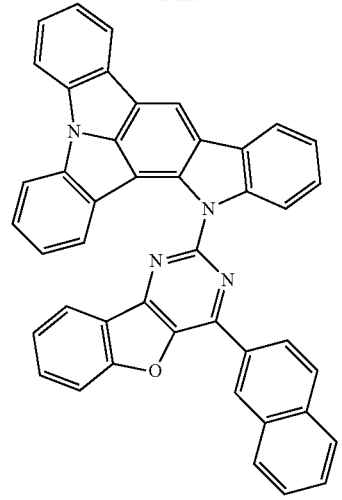
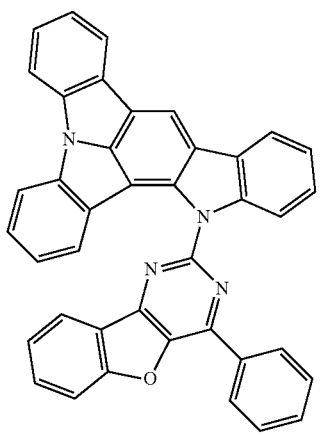
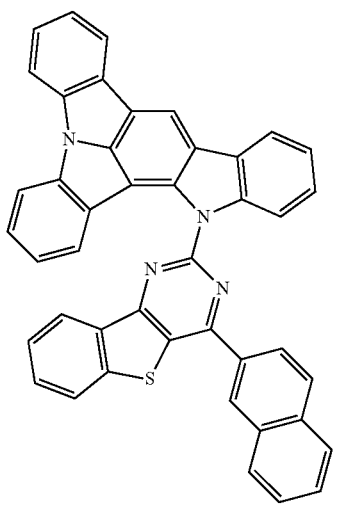
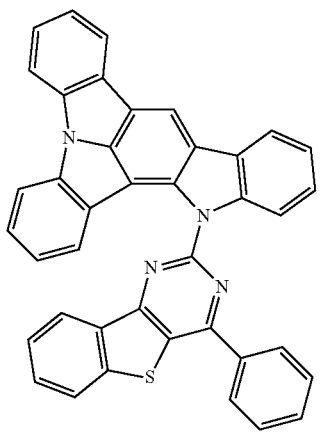
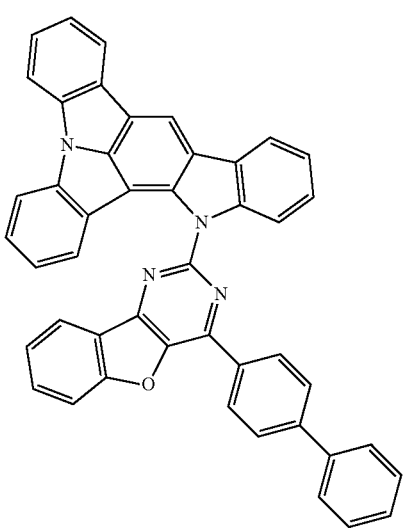

71
-continued
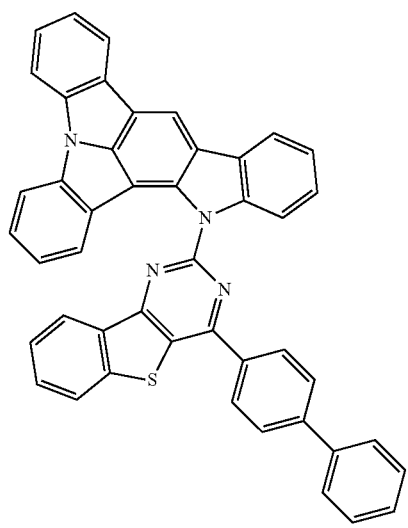
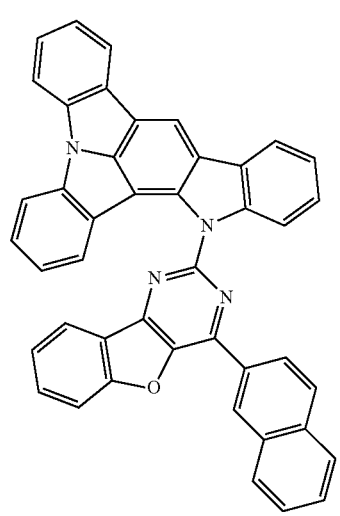
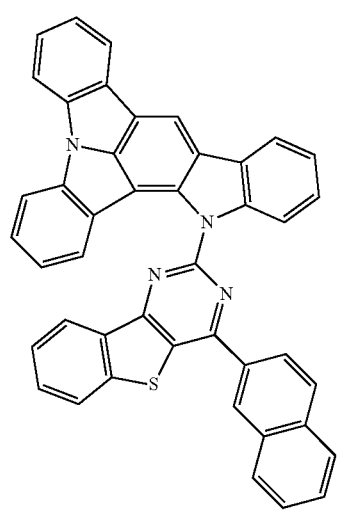
72
-continued
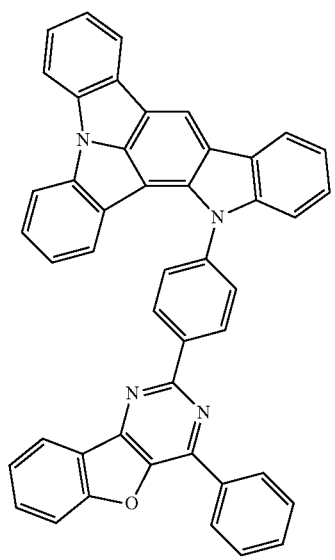
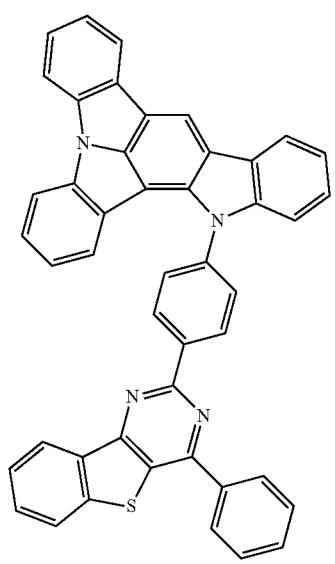

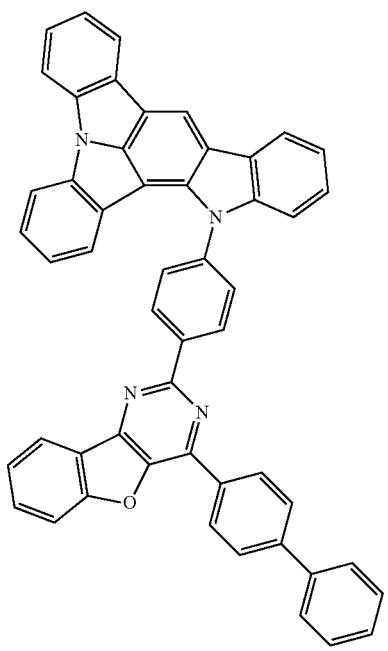
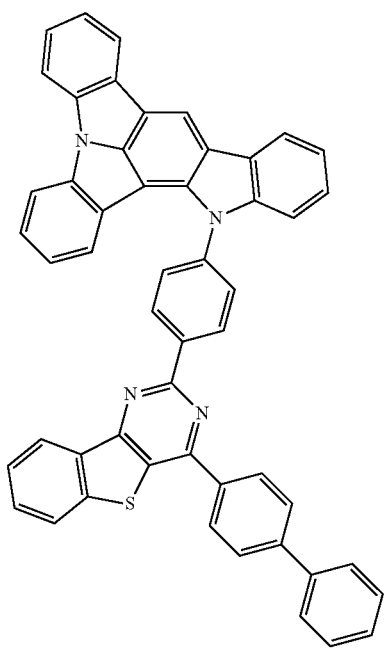
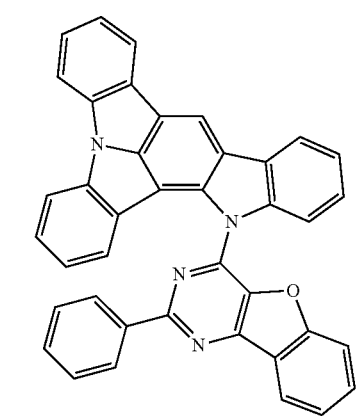
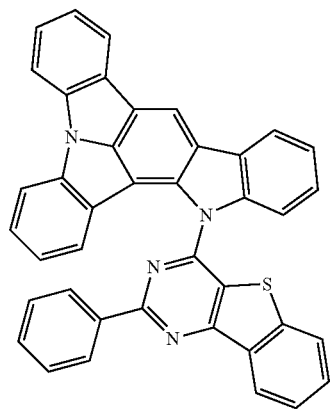
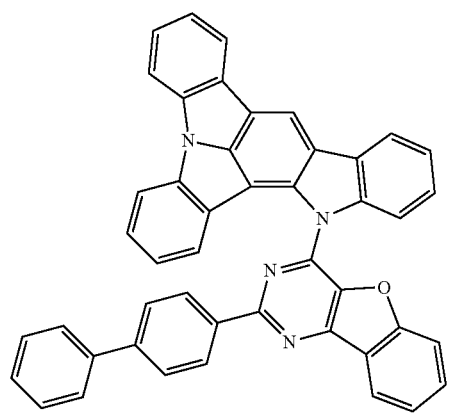
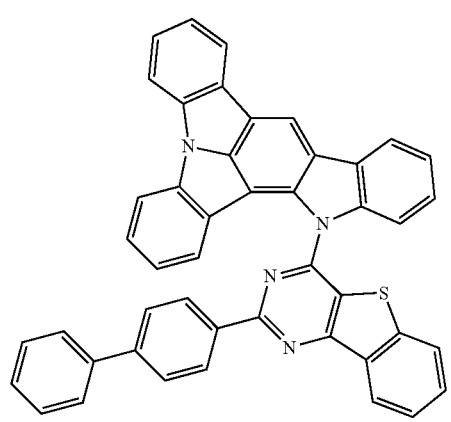

75
-continued
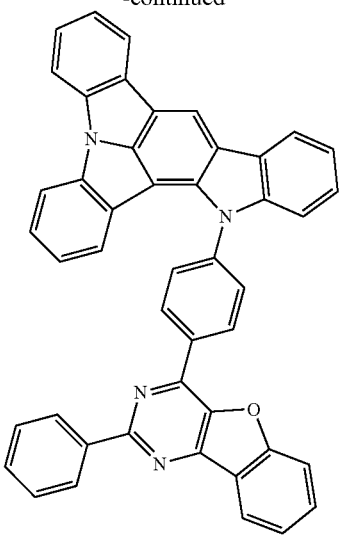
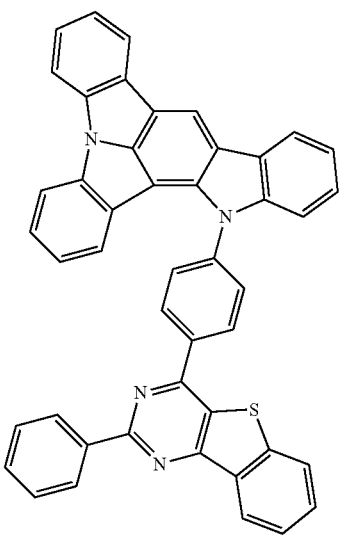
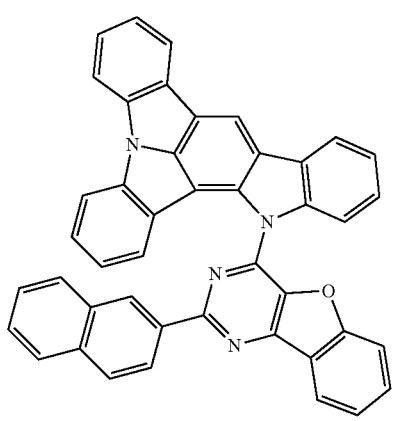
76
-continued
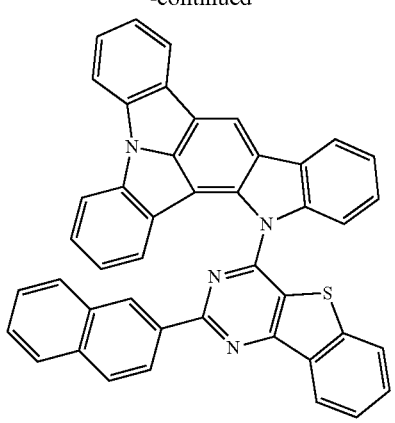
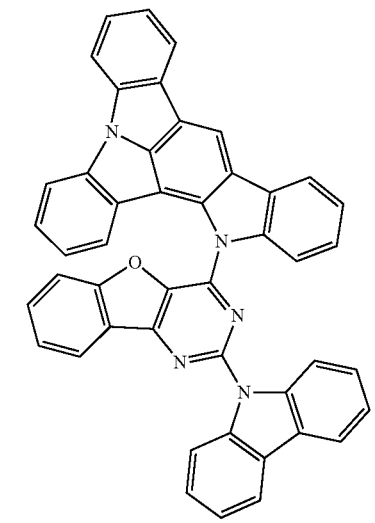
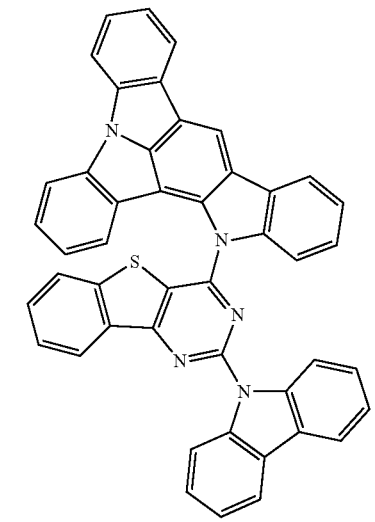

77
-continued
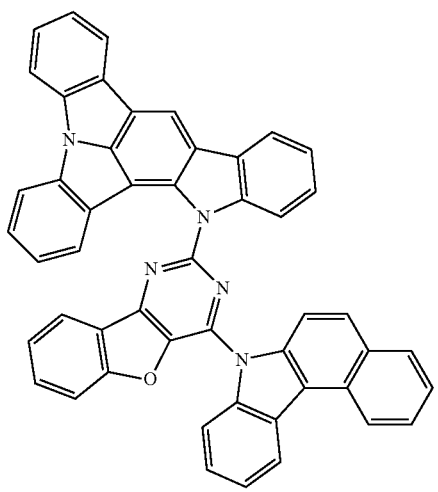
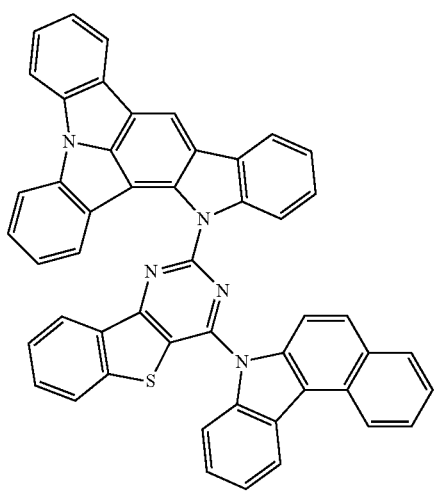
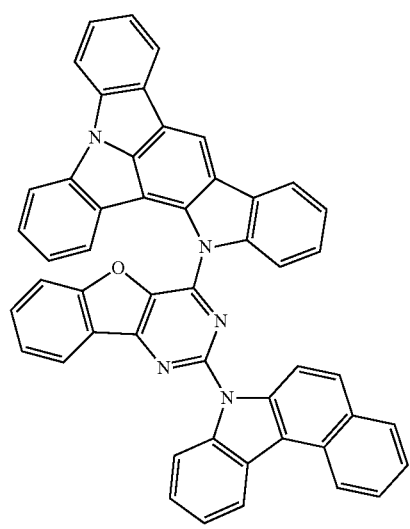
78
-continued
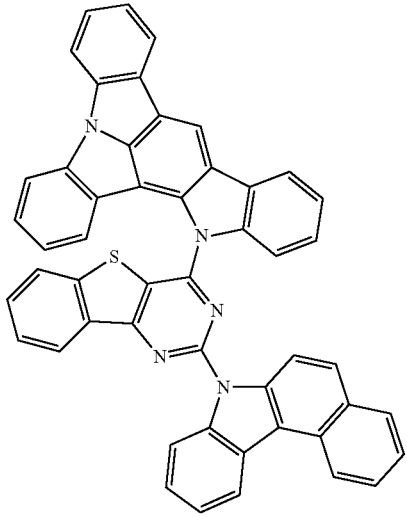
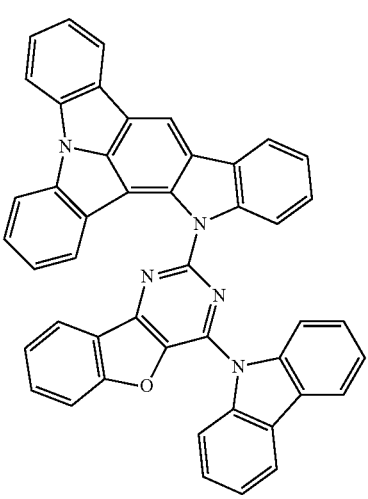

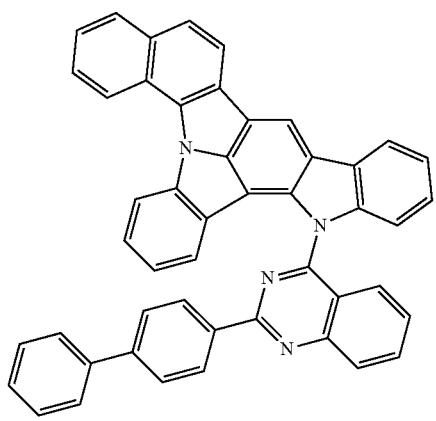
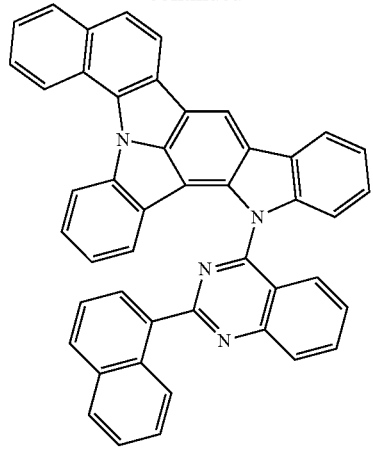
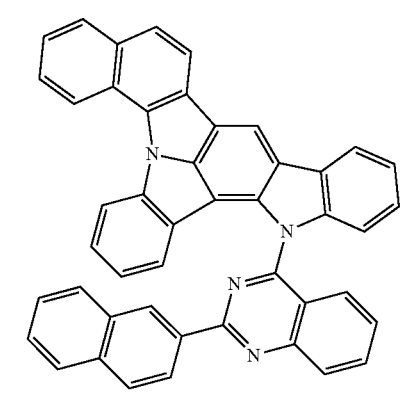
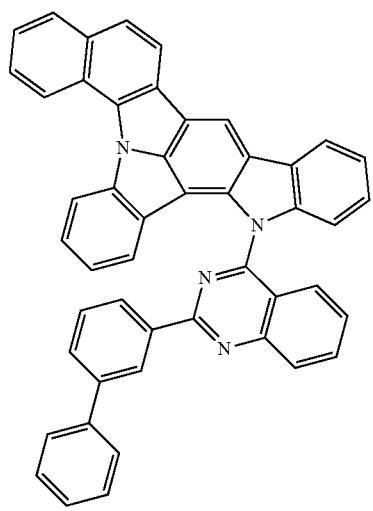
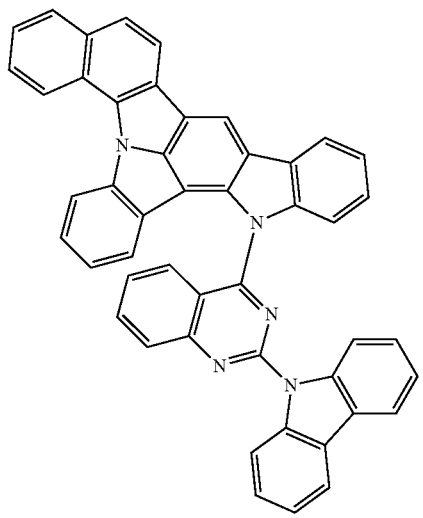
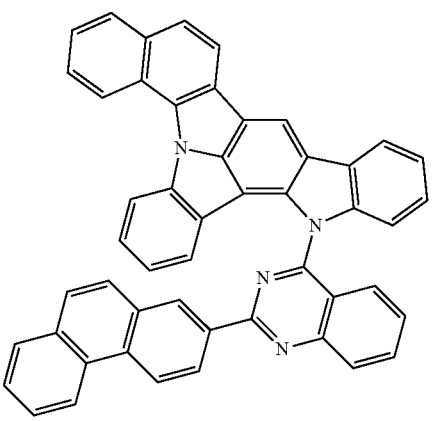

81
-continued
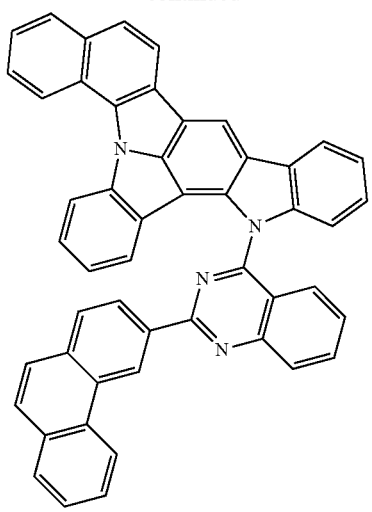
82
-continued
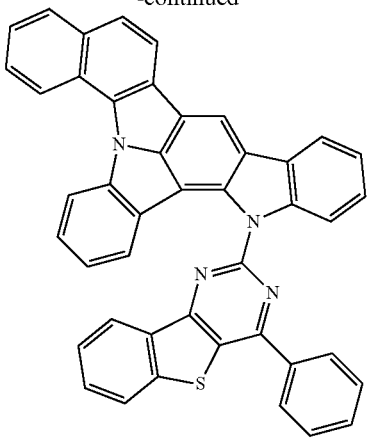
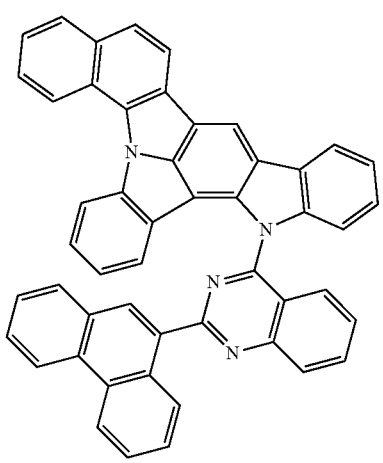
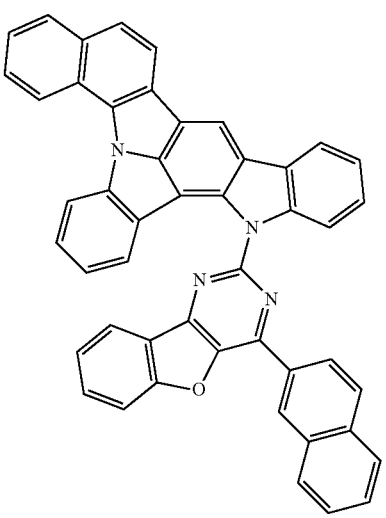
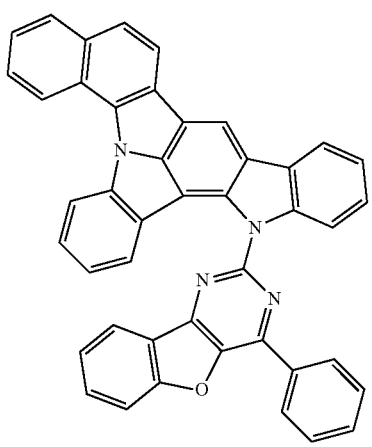
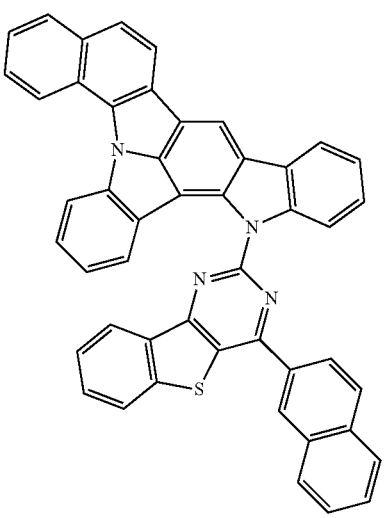

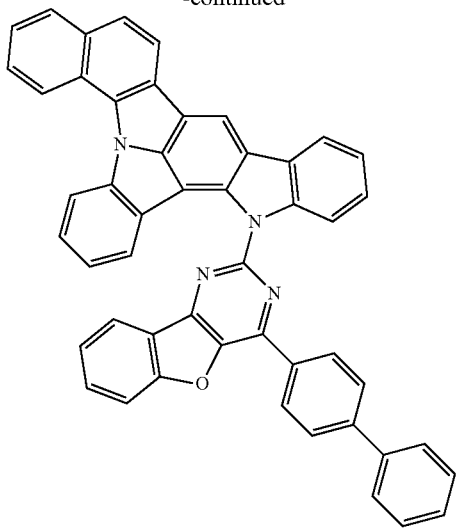
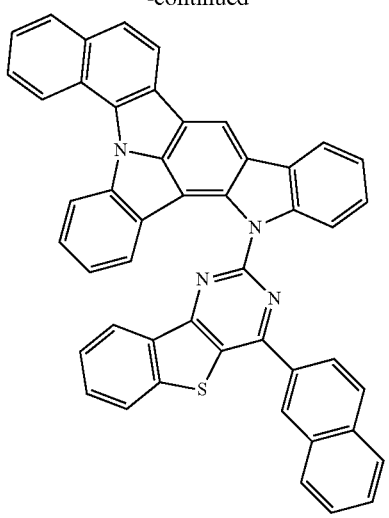
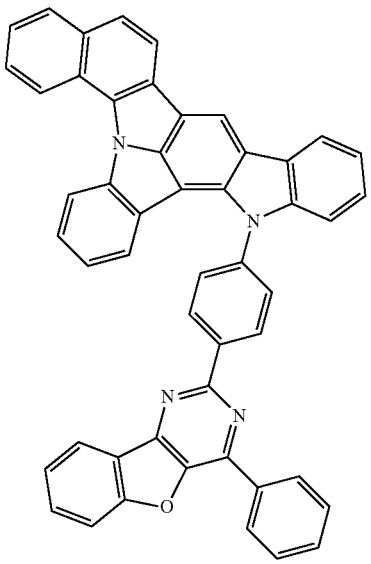
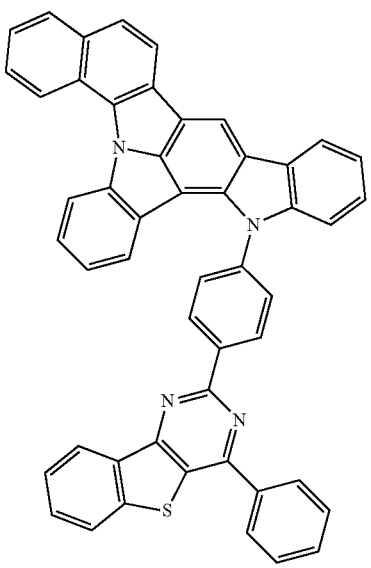

85
-continued

86
-continued

87
-continued
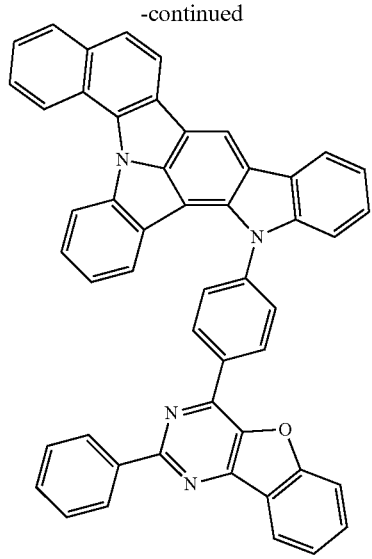
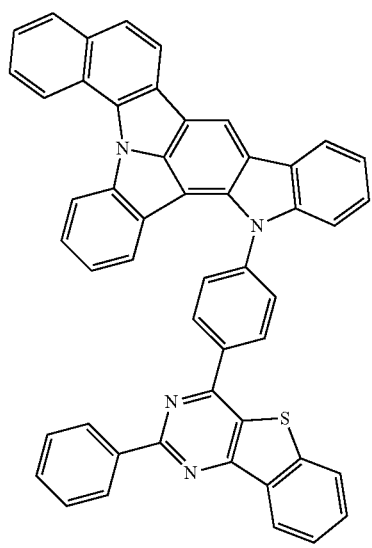
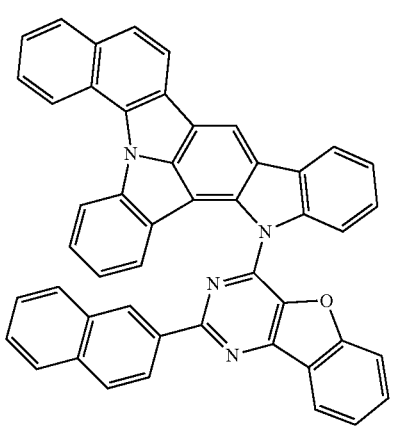
88
-continued
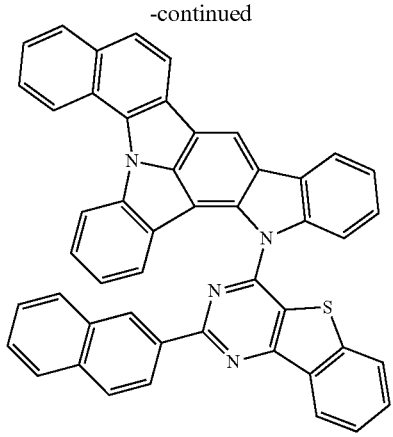
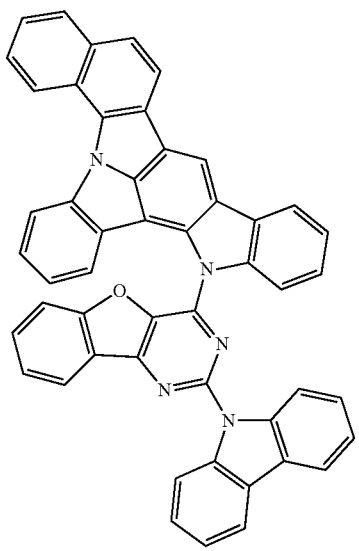
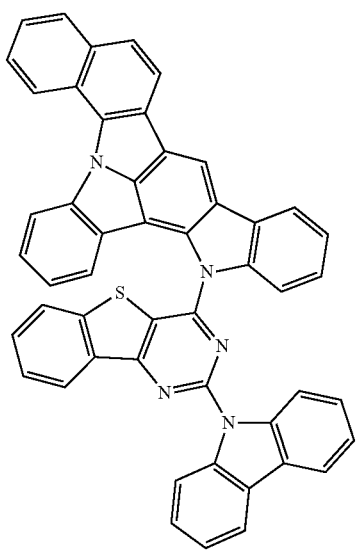

-continued
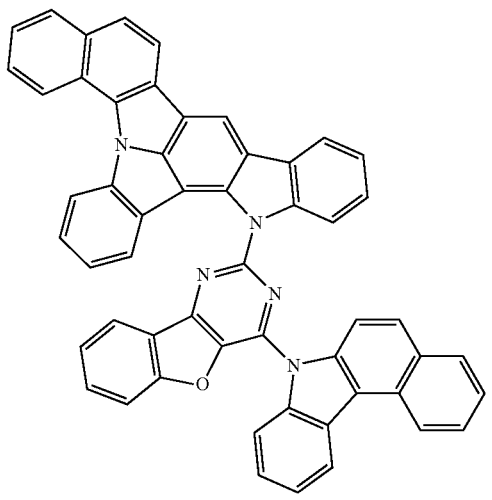
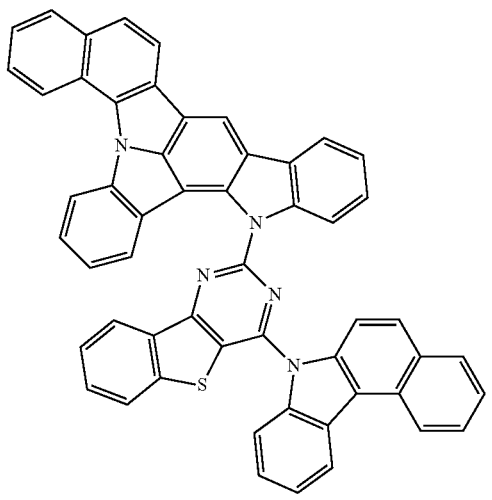
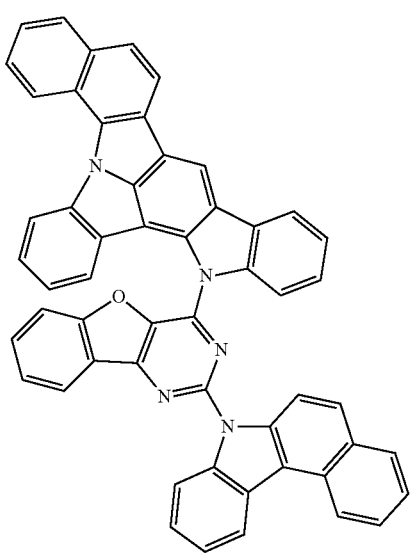
-continued
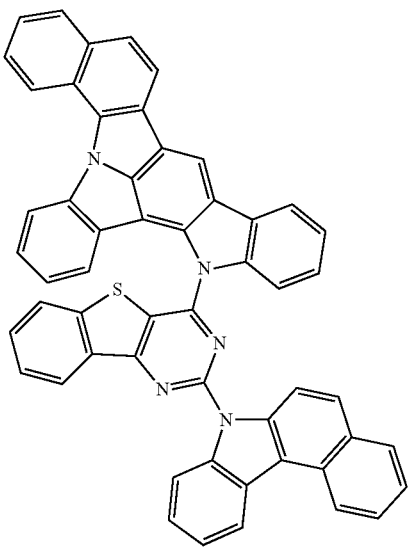
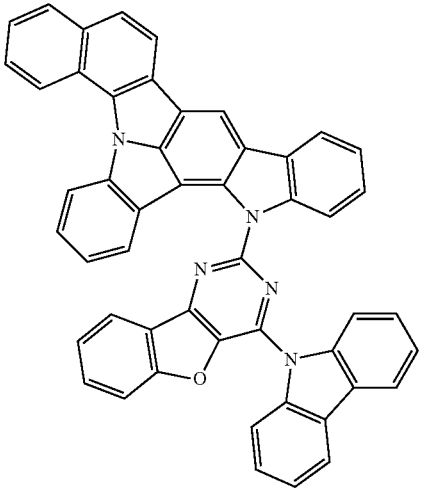
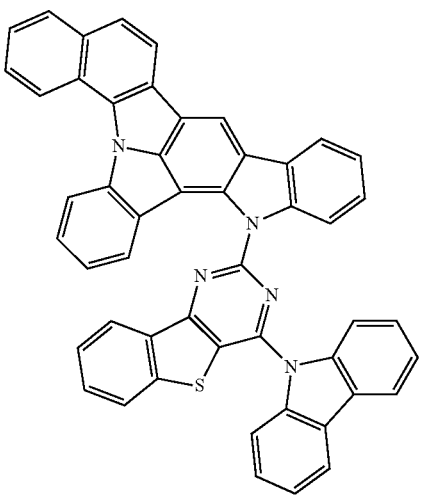

91
-continued
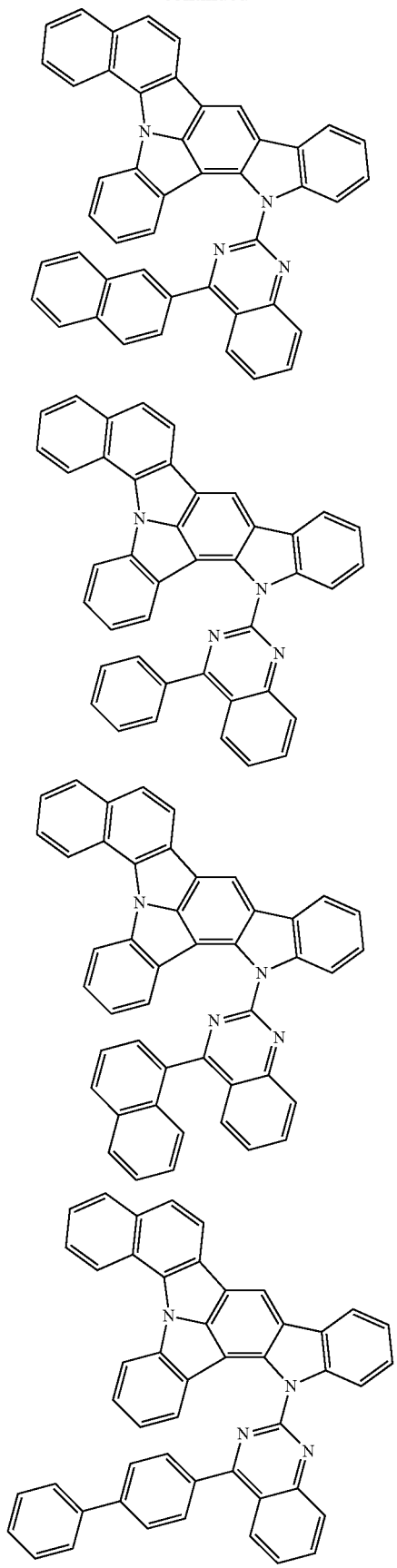
92
-continued
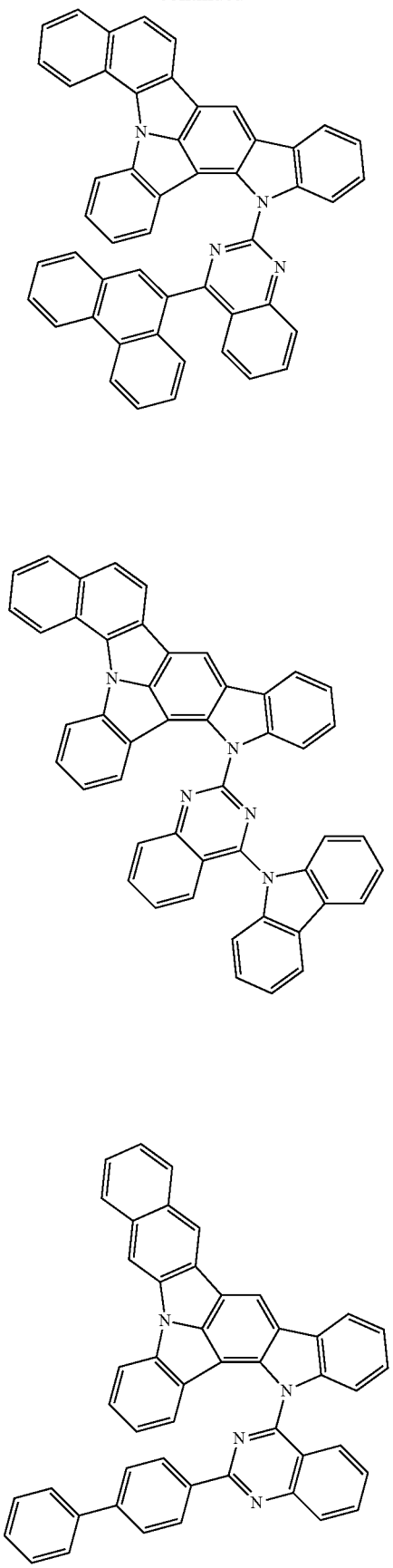

93
-continued
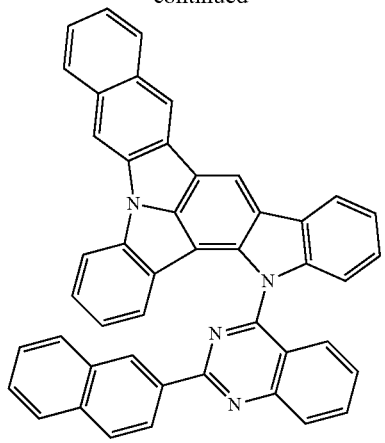
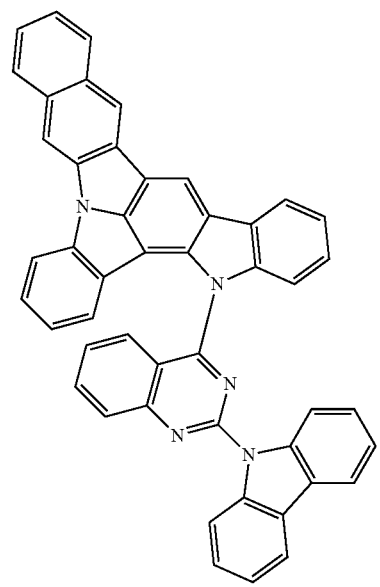
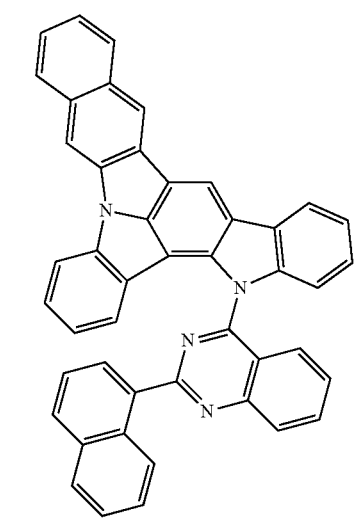
94
-continued
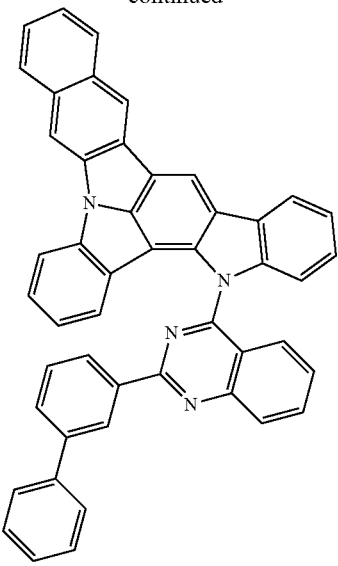
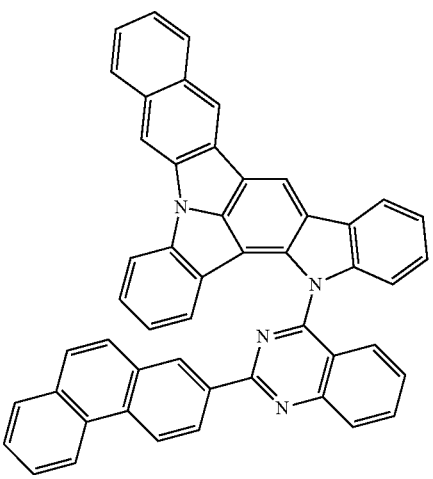
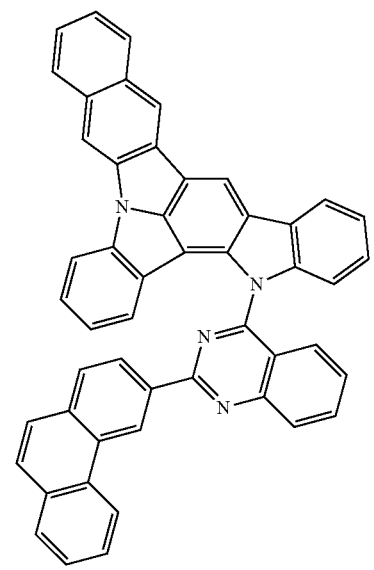

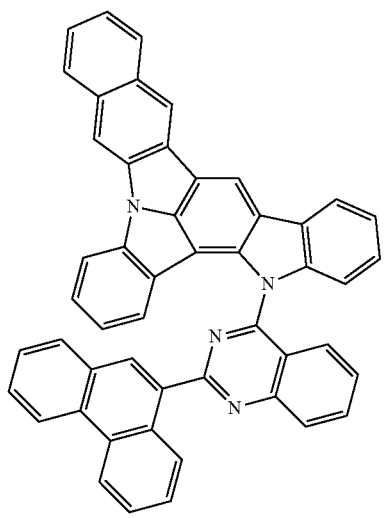
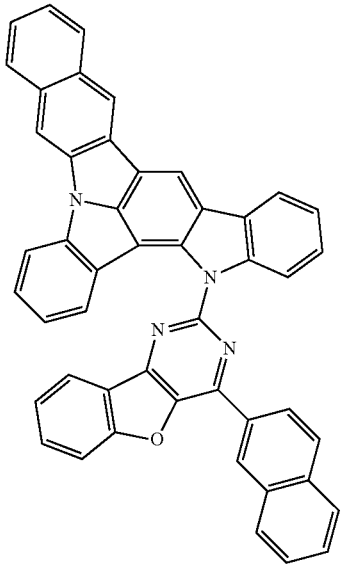
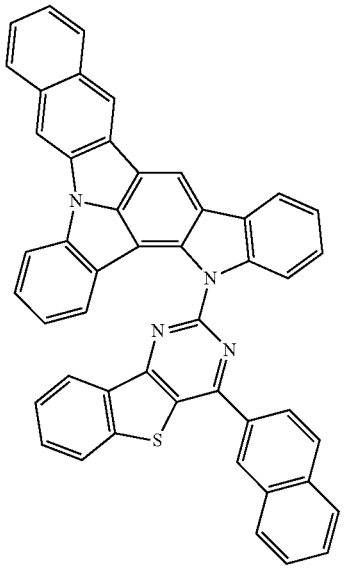
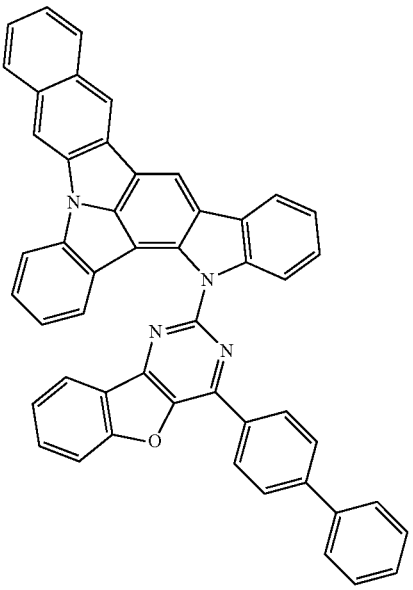

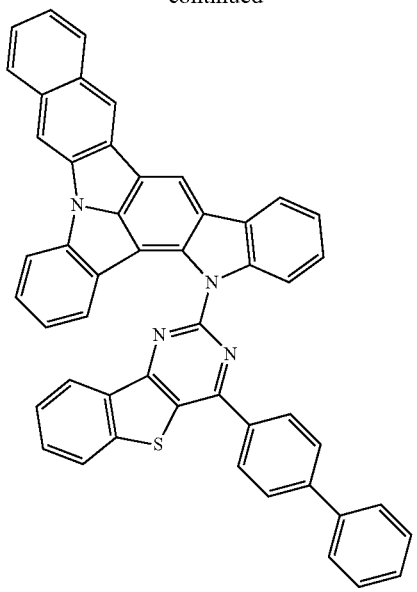
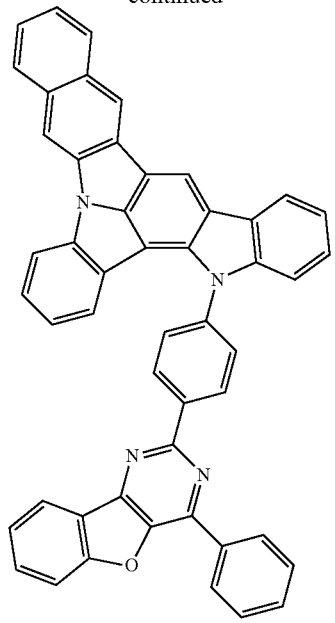

99
-continued
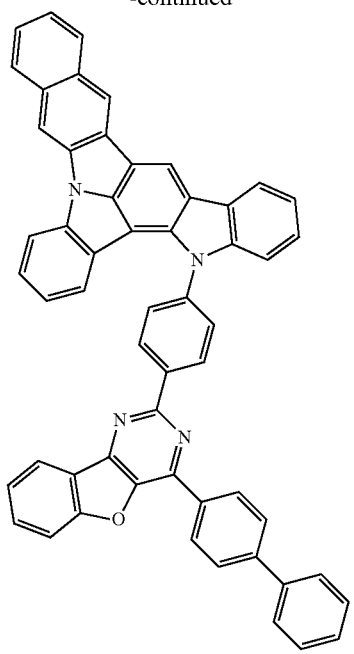
100
-continued
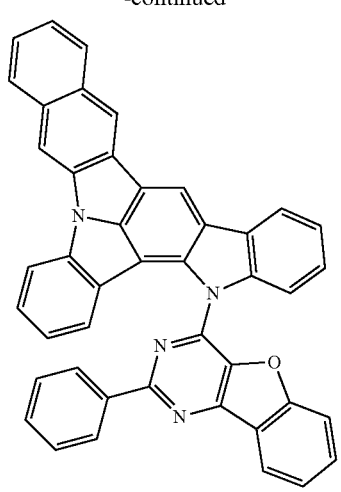
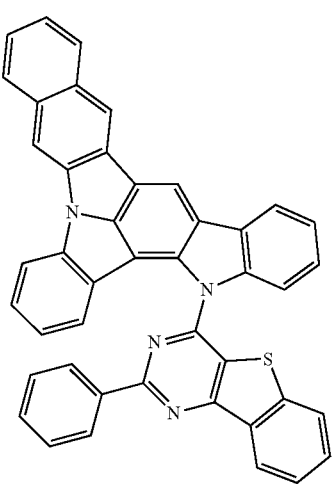
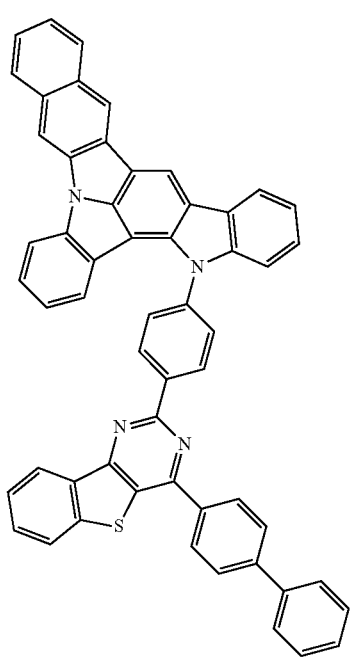
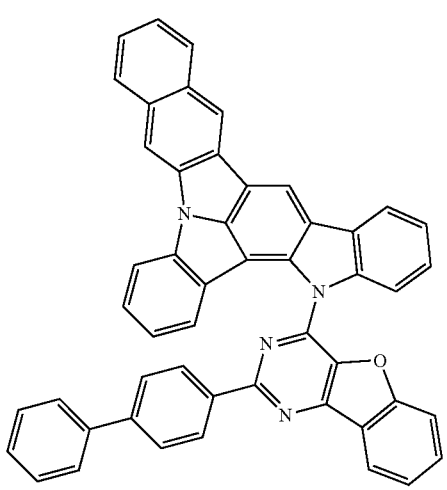

101
-continued
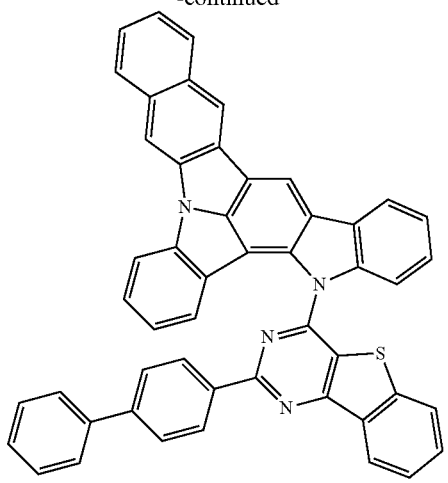
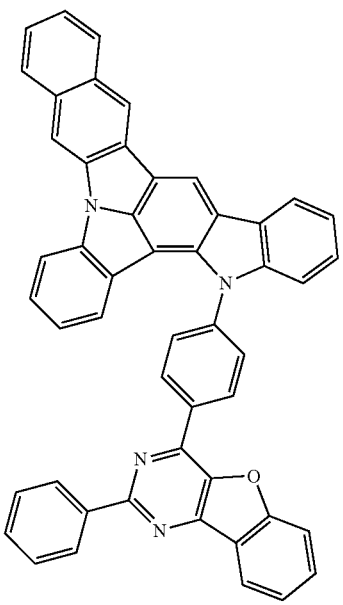
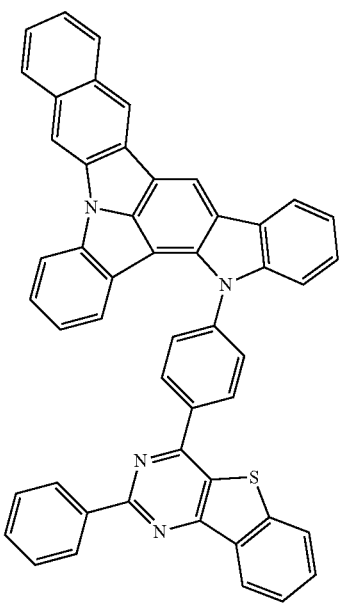
102
-continued
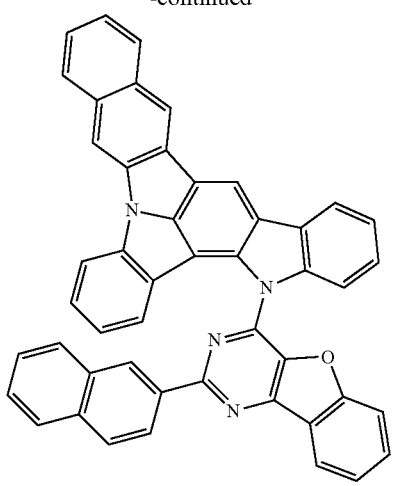
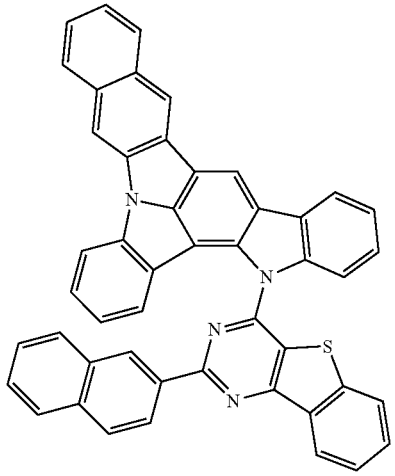
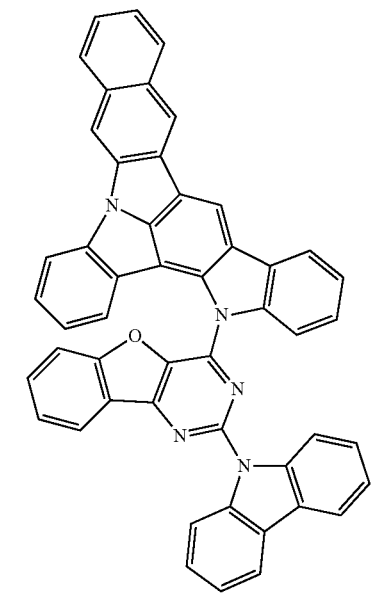

103
-continued
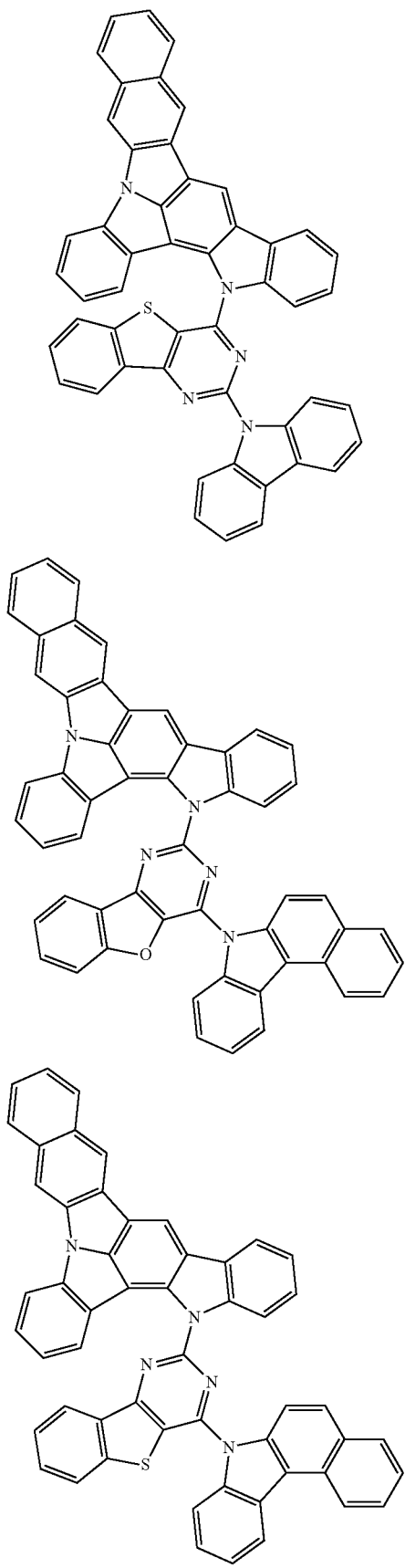
104
-continued
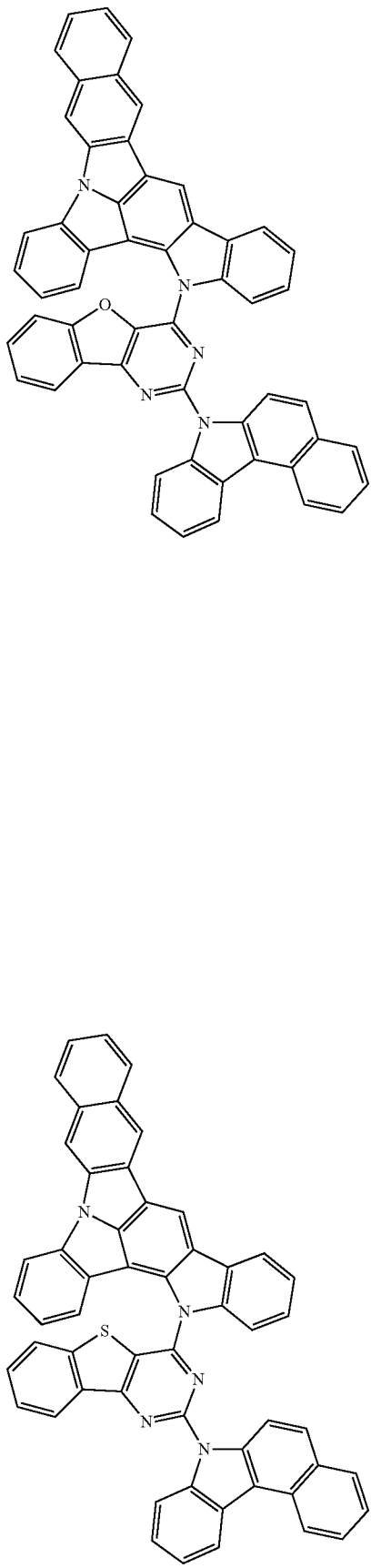

105
-continued
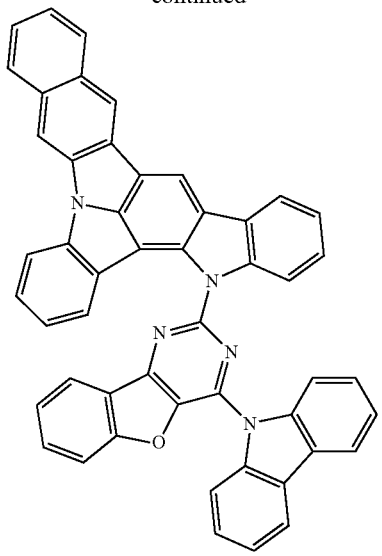
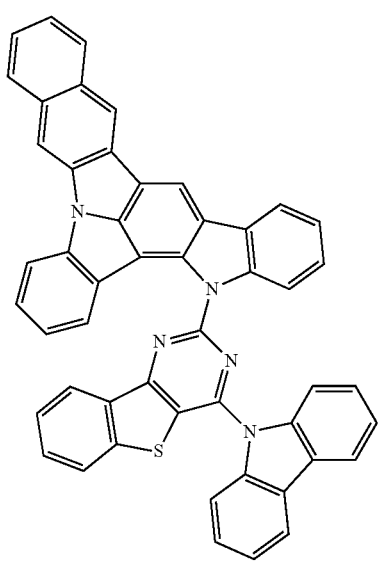
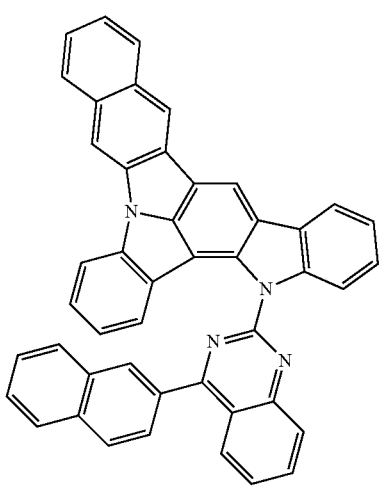
106
-continued
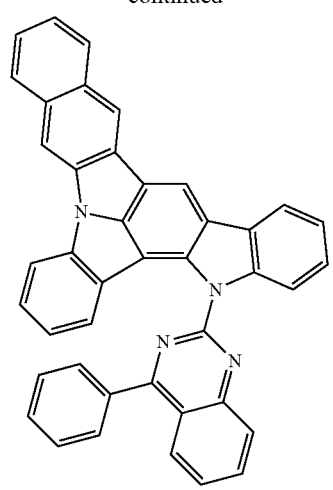
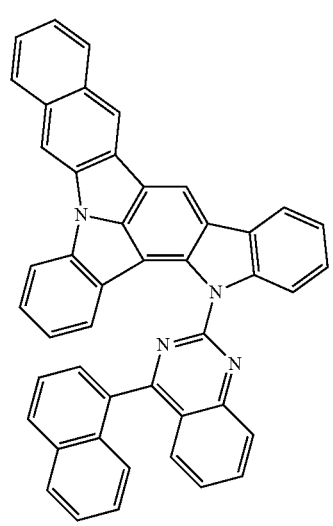
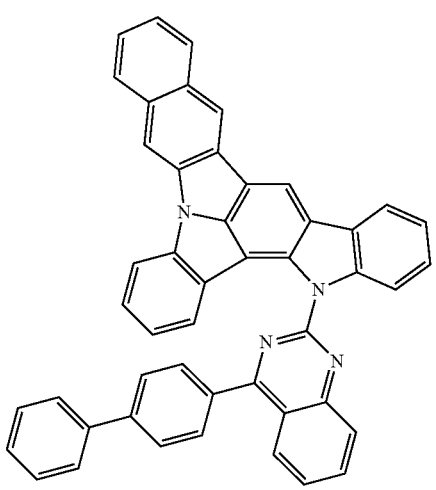

107
-continued
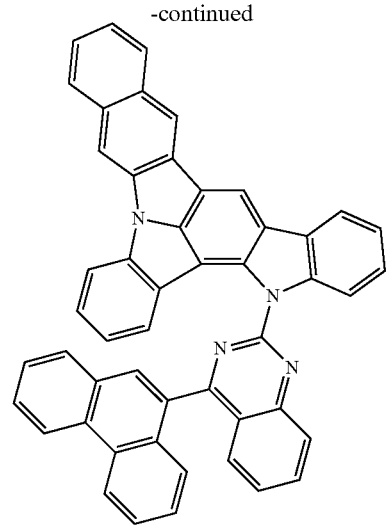
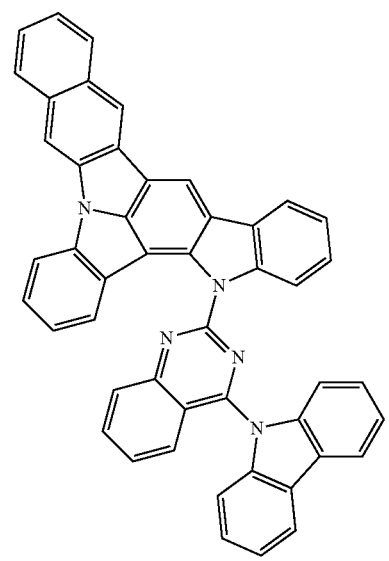 [SMILES: c1ccc2cc3c(cc2c1)c1cc2c4ccccc4n(-c4nc(-n5c6ccccc6c6ccccc65)c5ccccc5n4)c2c2c4ccccc4n3c12]
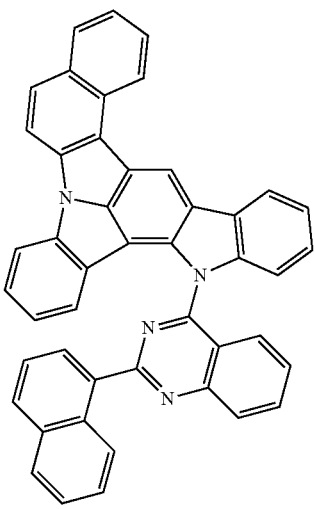
108
-continued
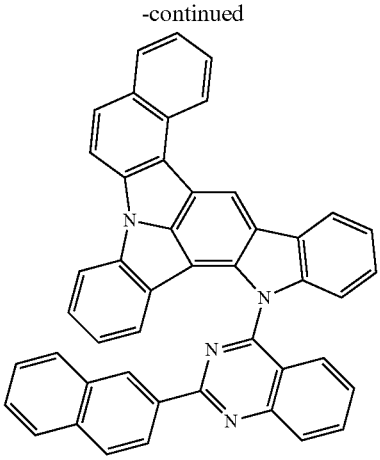
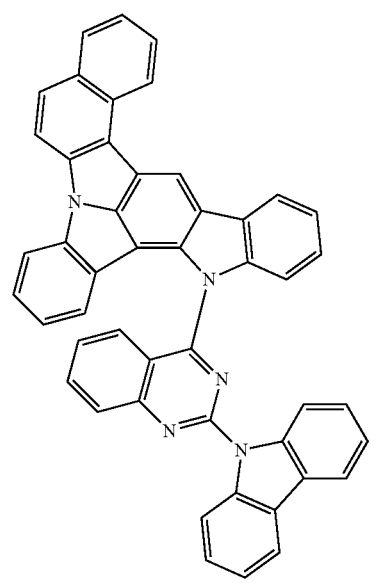

109
-continued
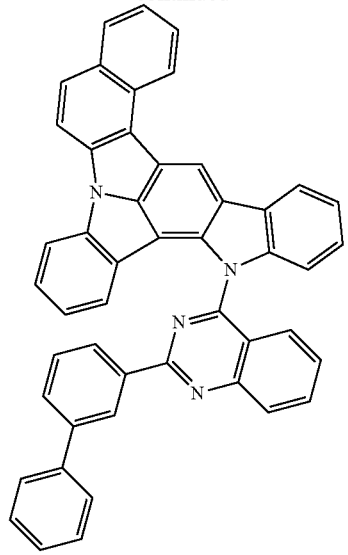
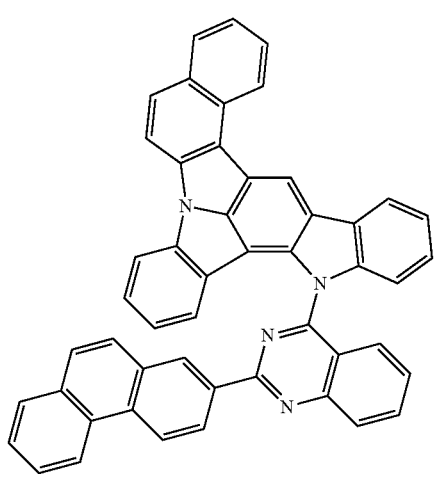
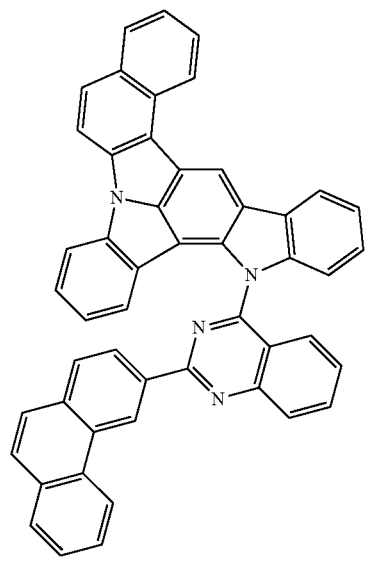
110
-continued
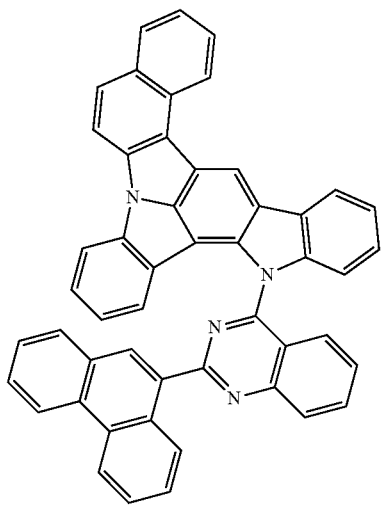
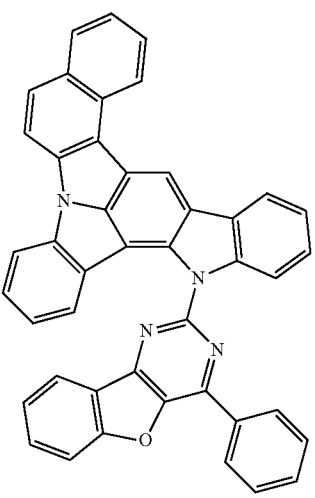
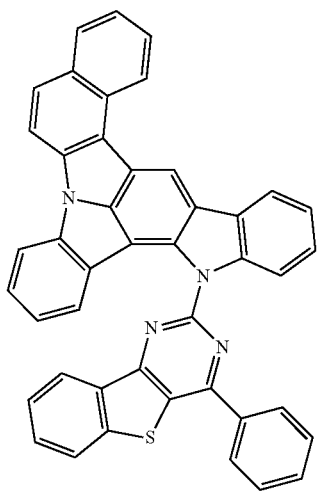

111
-continued
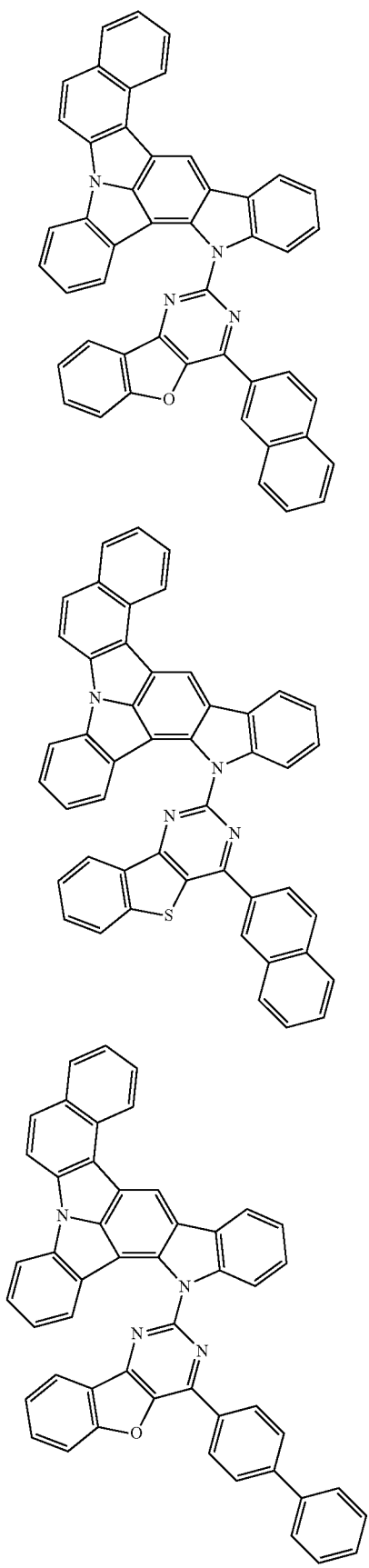
112
-continued
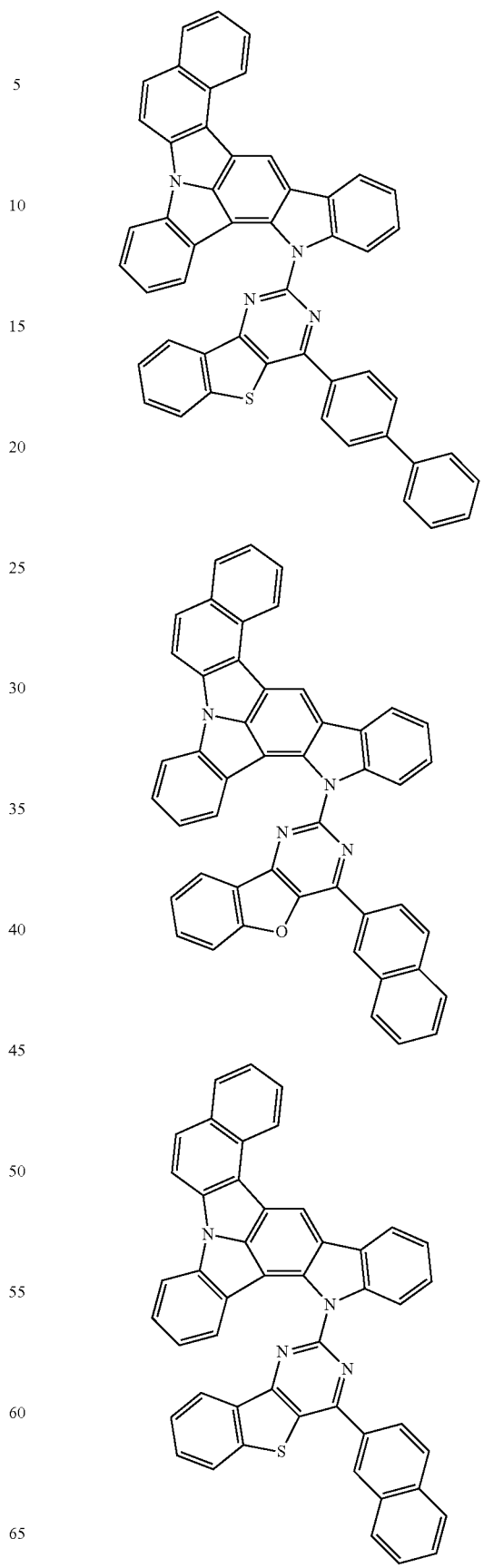

113
-continued
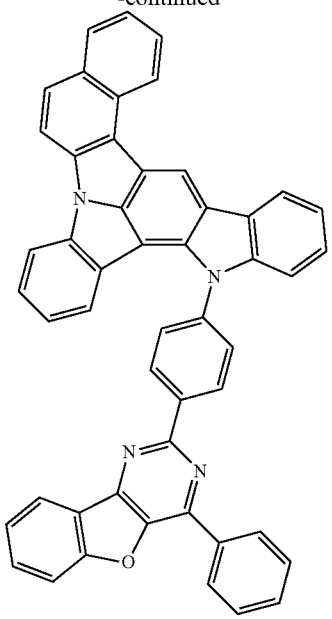
114
-continued
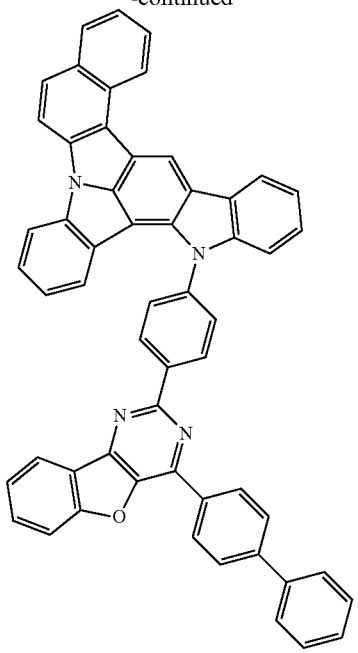
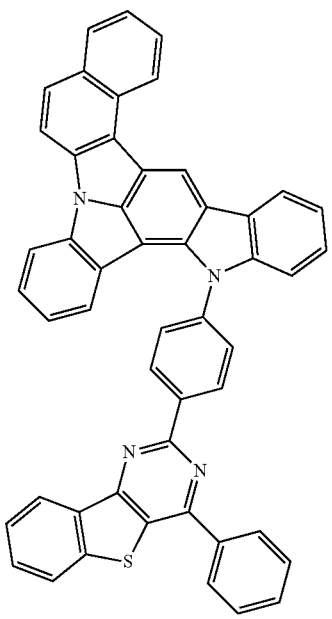
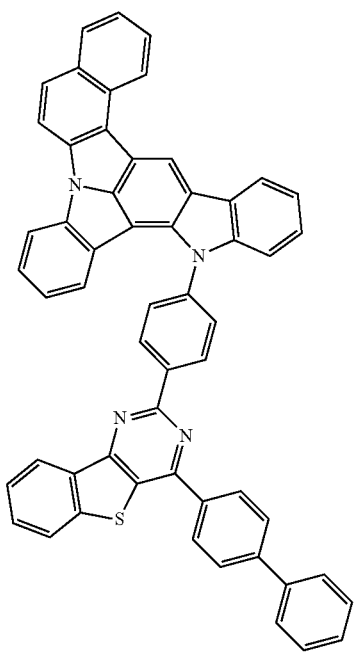

115
-continued
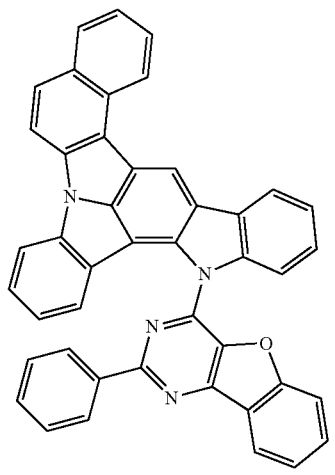
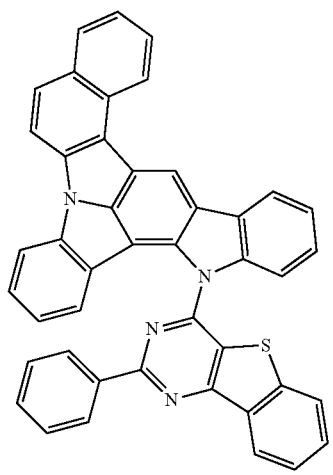
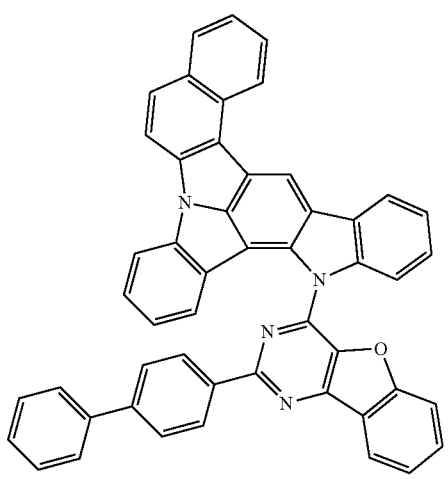
116
-continued
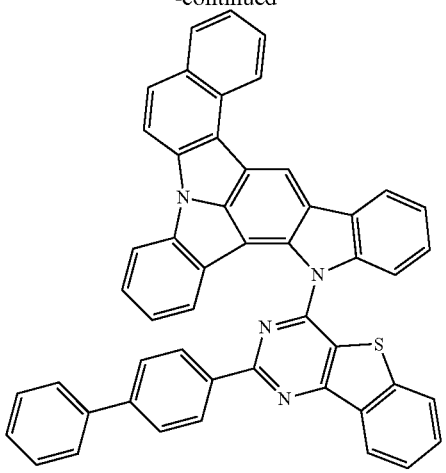
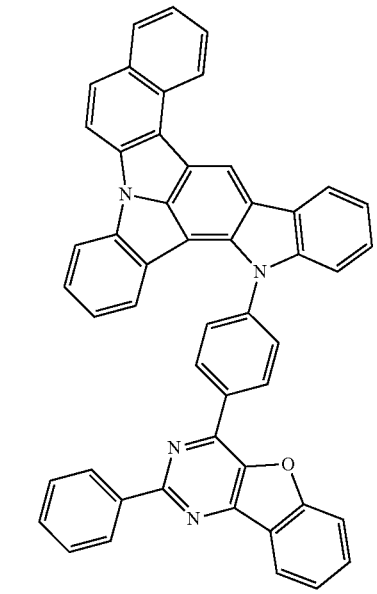
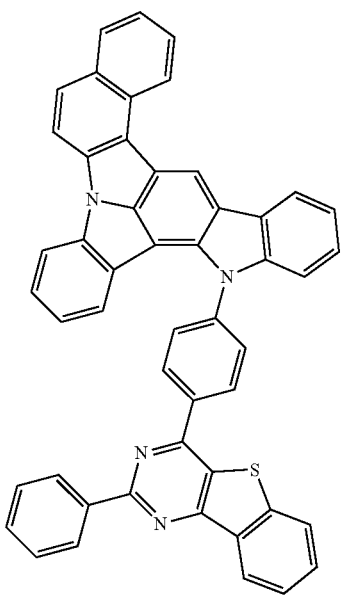

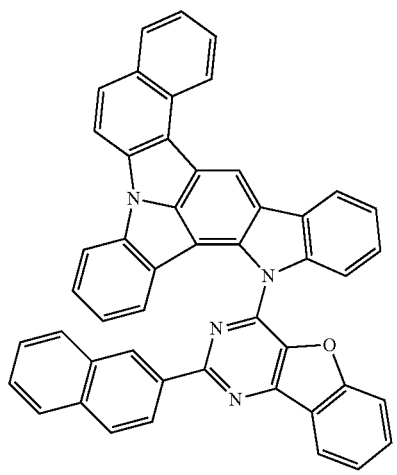
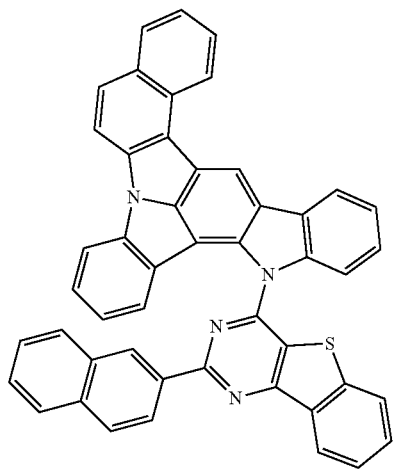
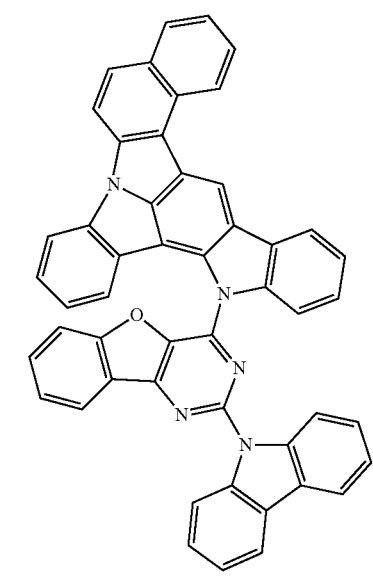
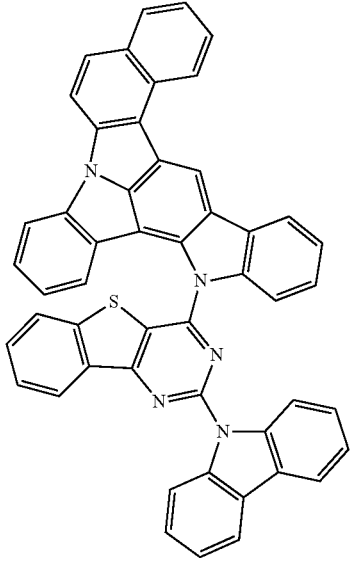
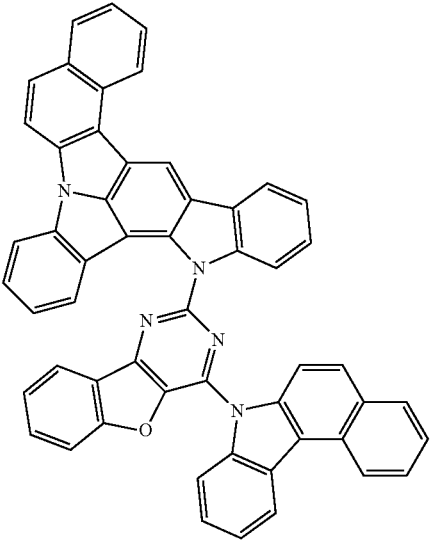
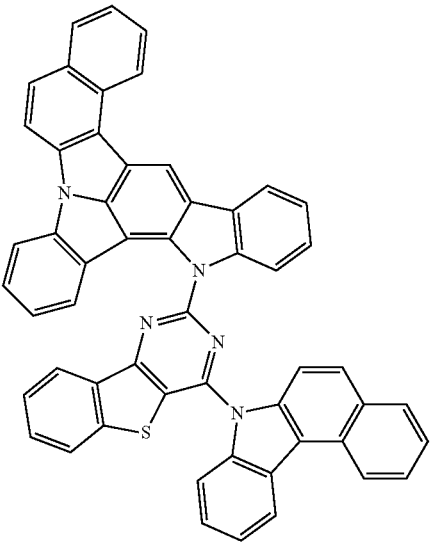

119
-continued

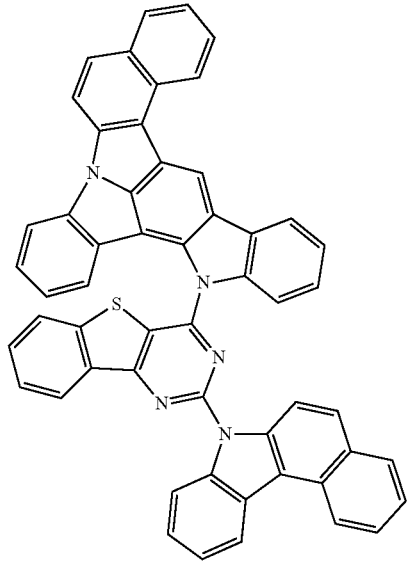
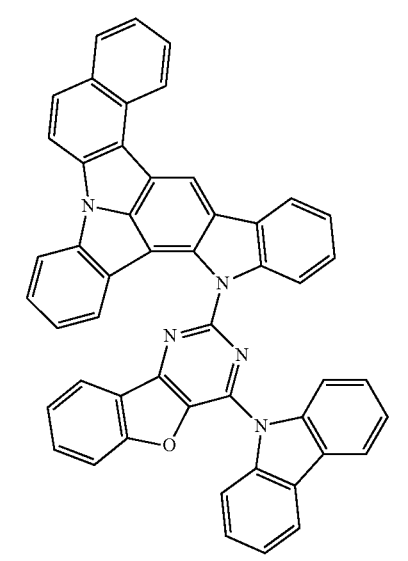
120
-continued
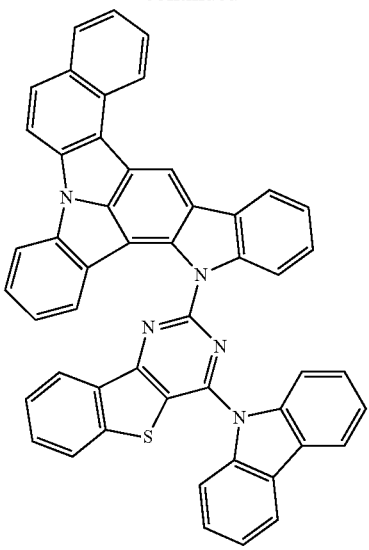
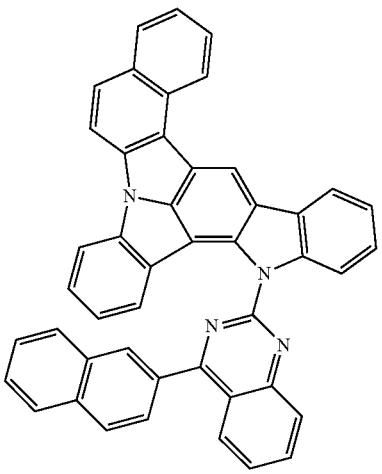
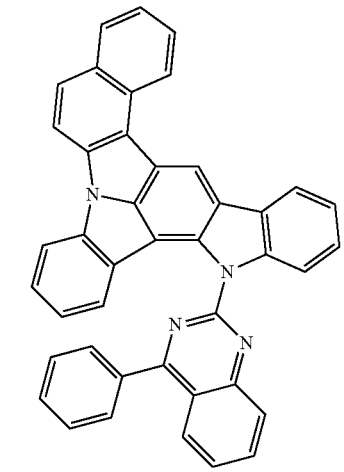

121
-continued
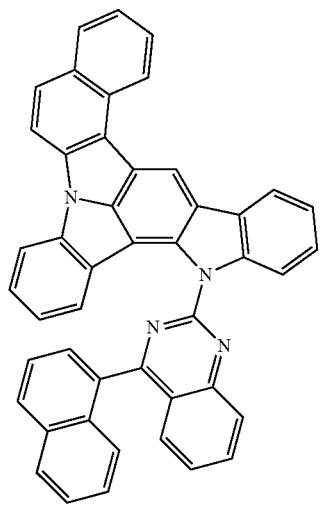
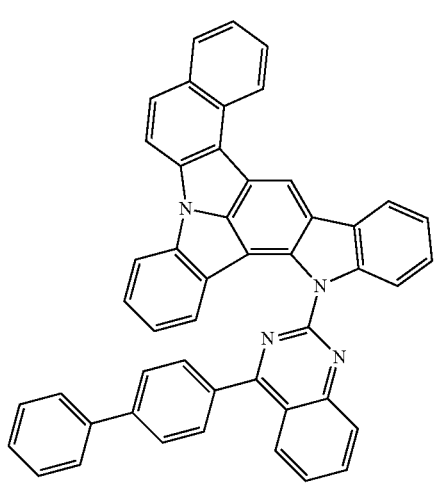
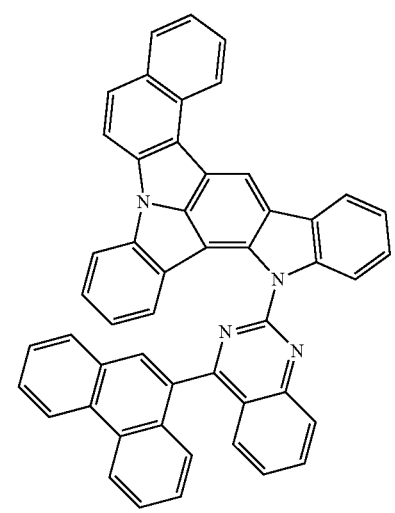
122
-continued
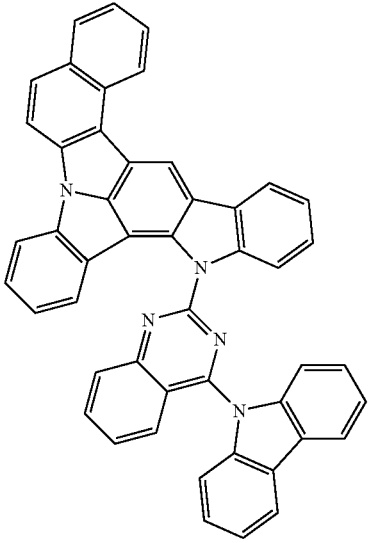
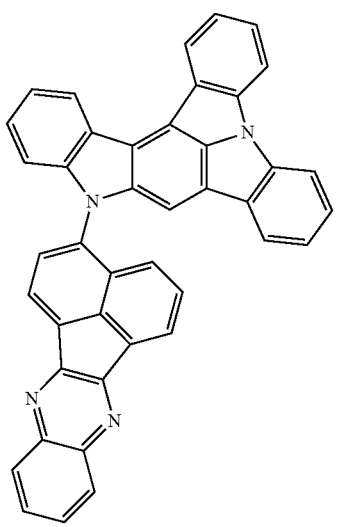
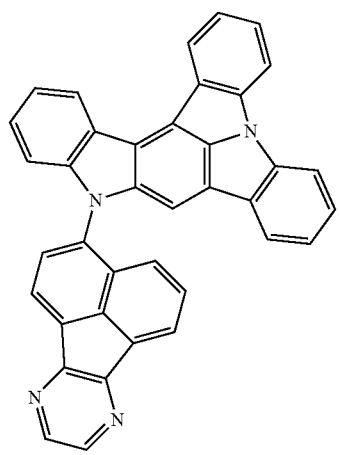

123
-continued
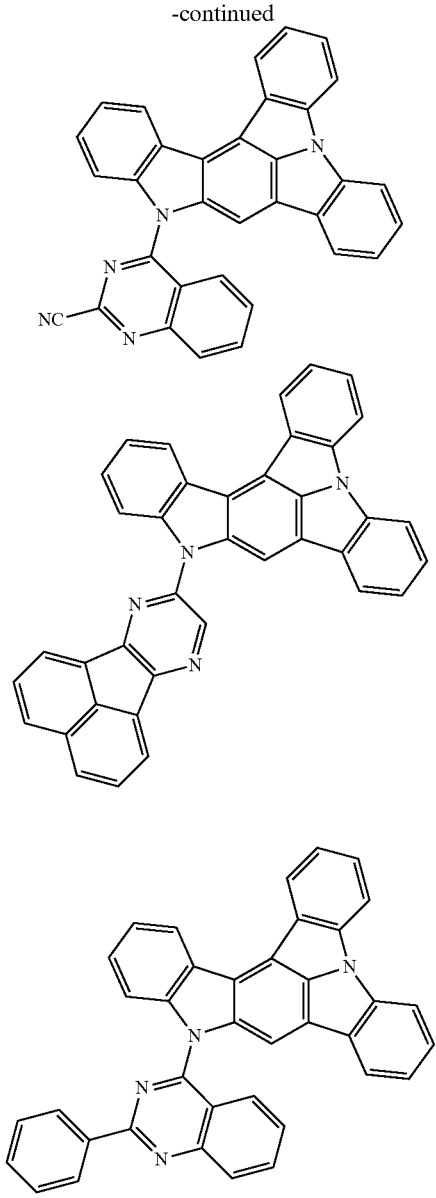
124
-continued
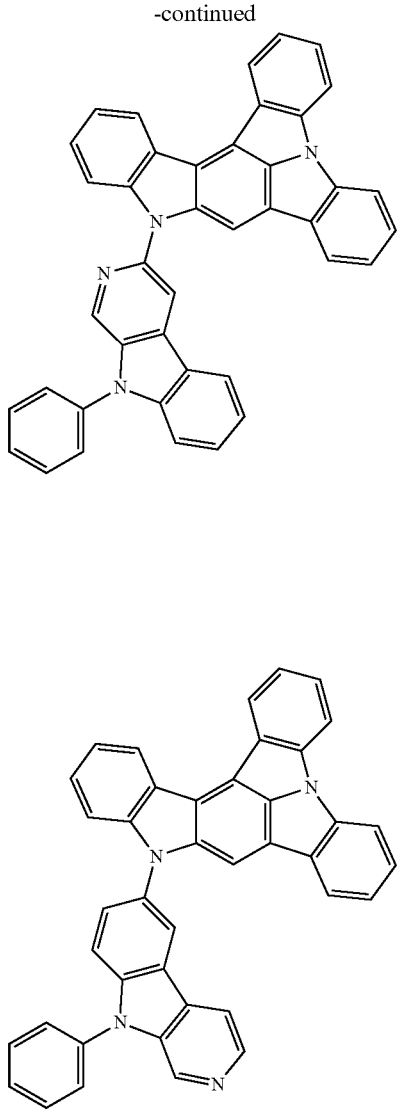
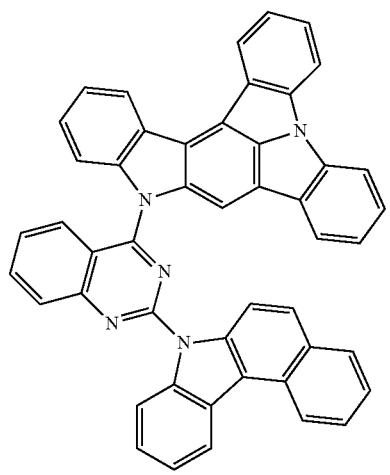
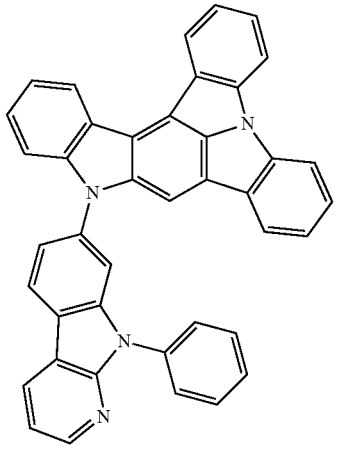

125
-continued
126
-continued
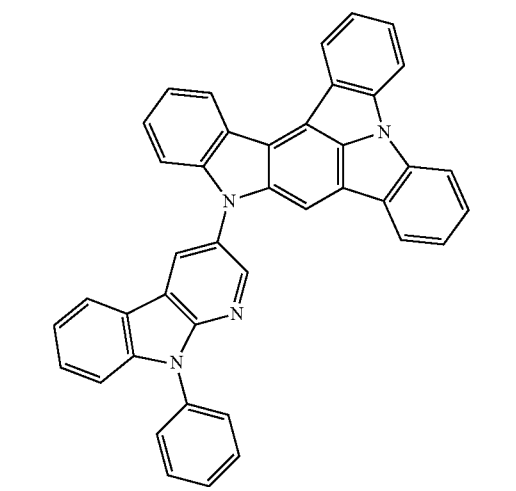
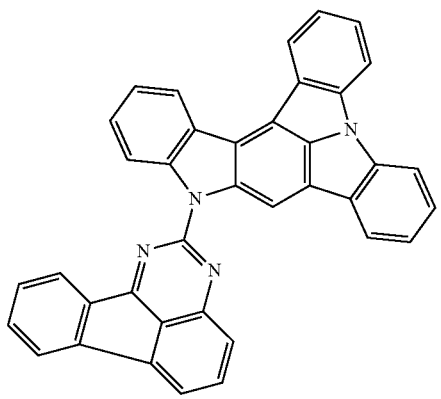
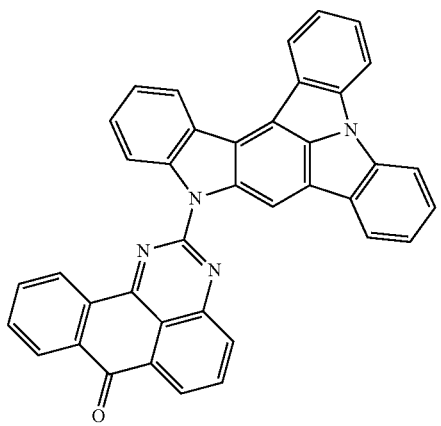
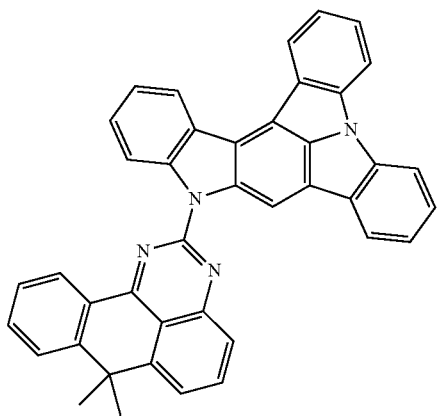
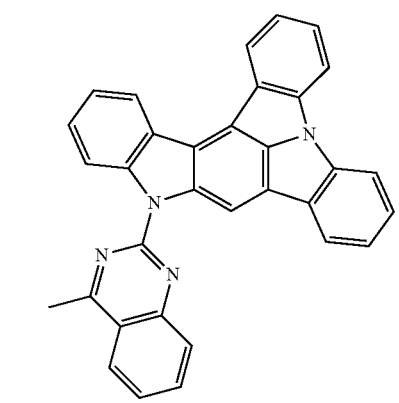

127
-continued
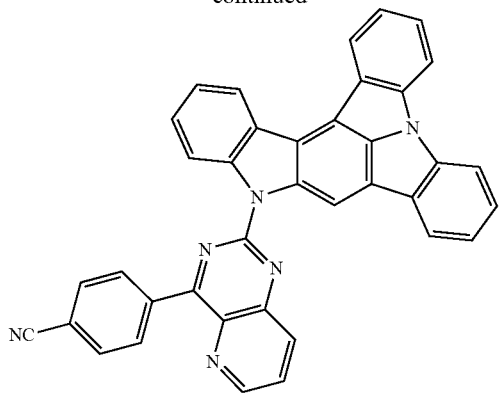
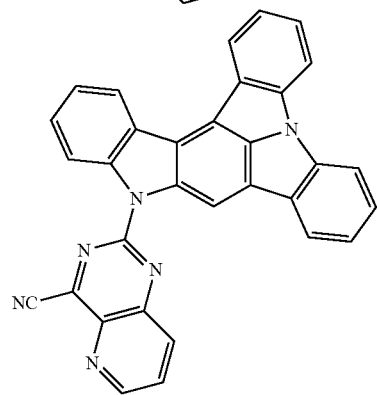
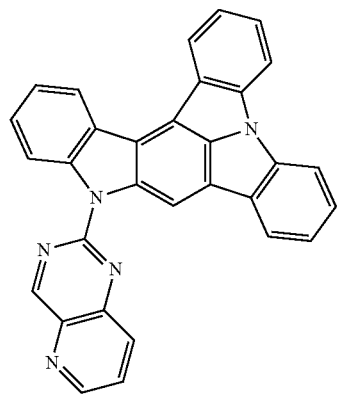
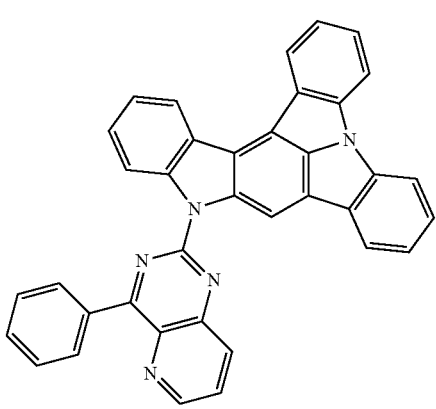
128
-continued
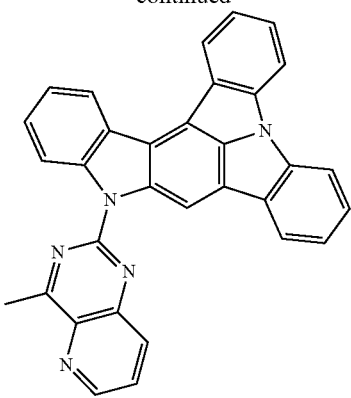
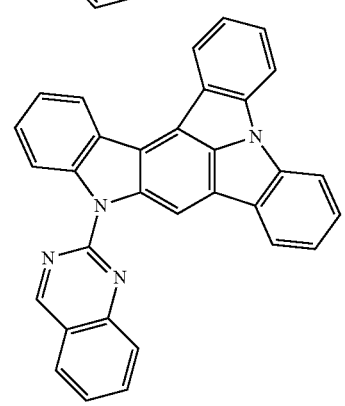
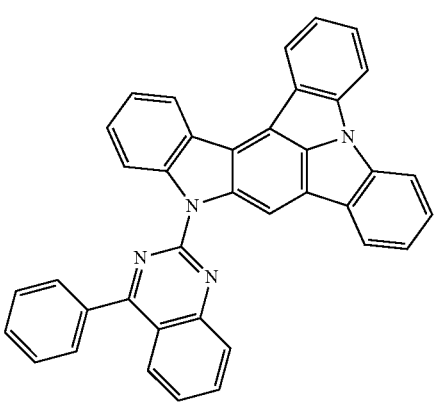
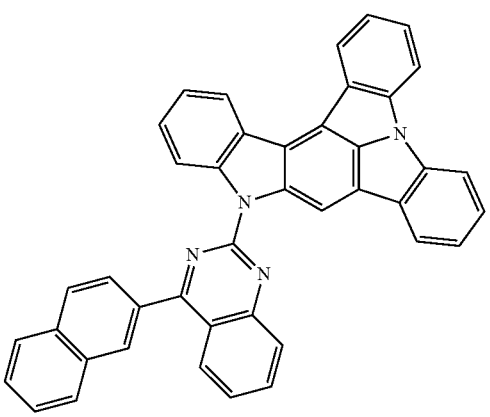

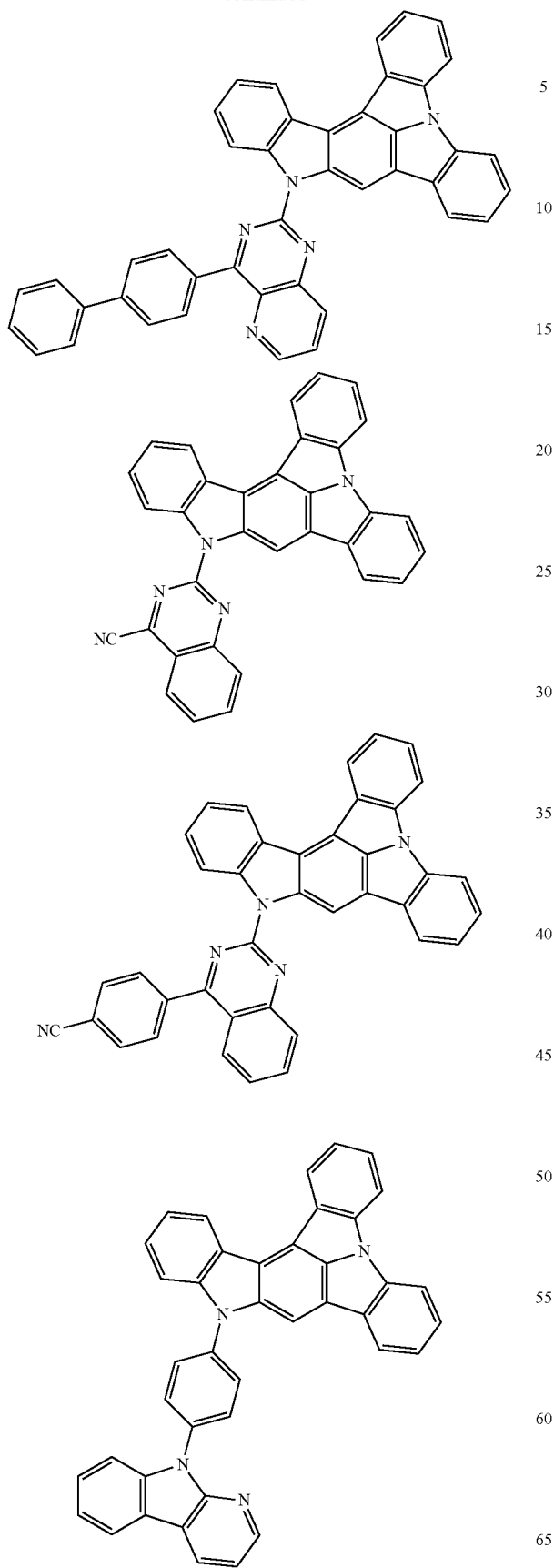

131
-continued
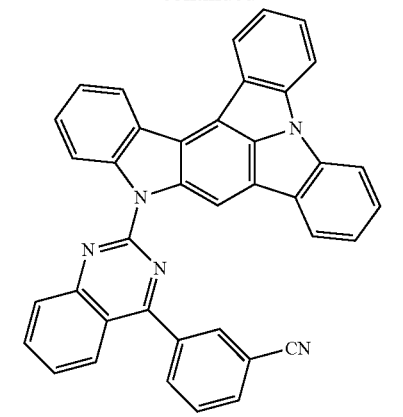
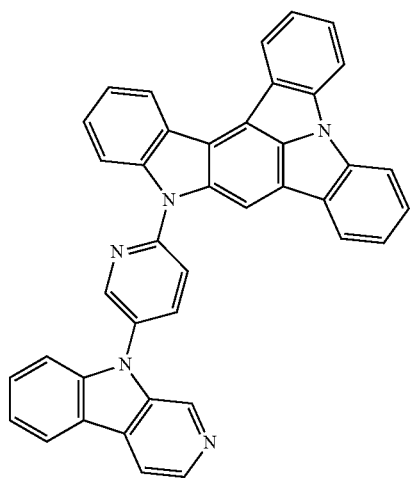
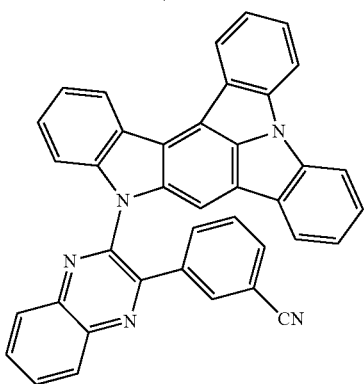
132
-continued
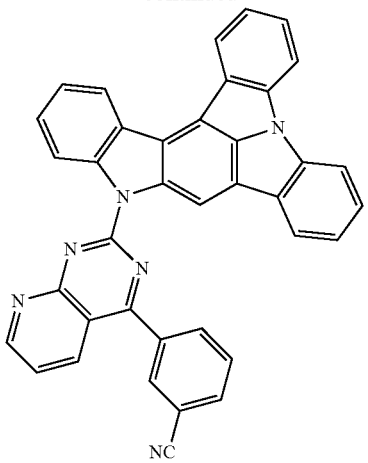
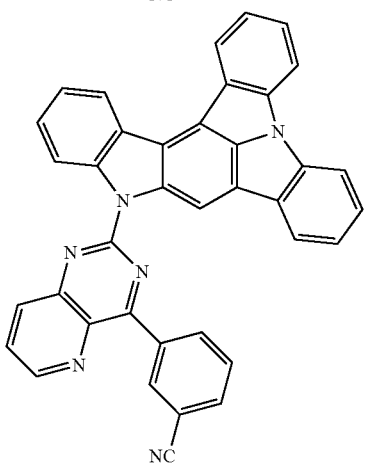
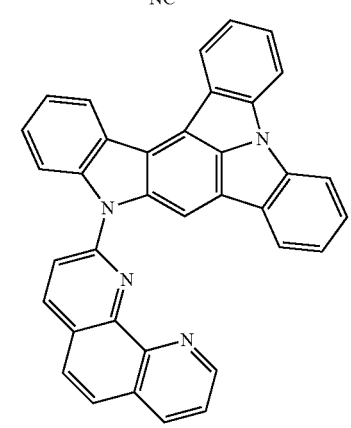
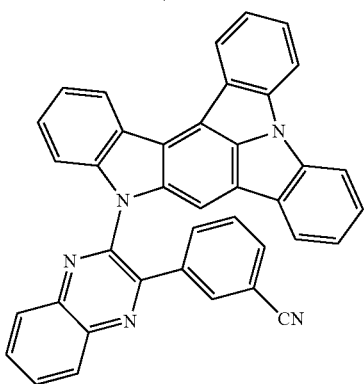

133
-continued
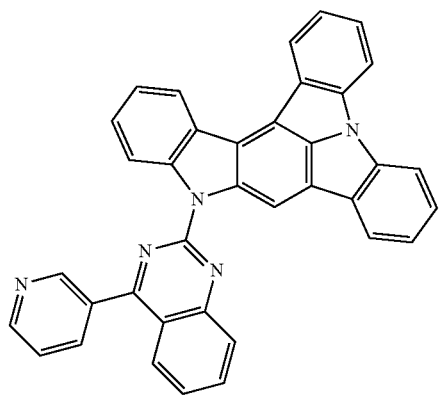
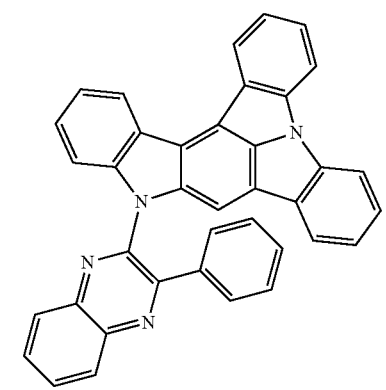
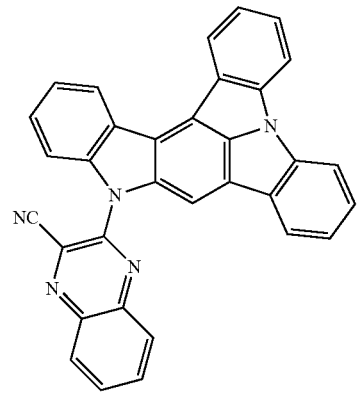
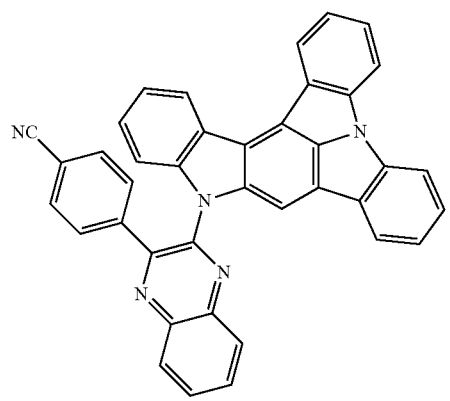
134
-continued
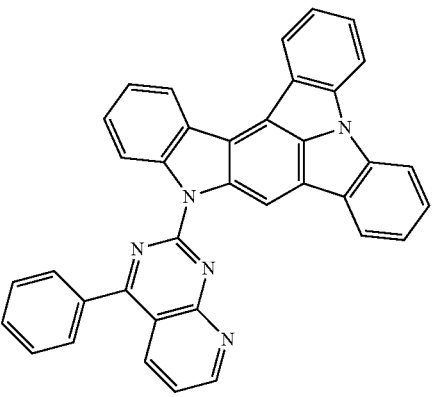
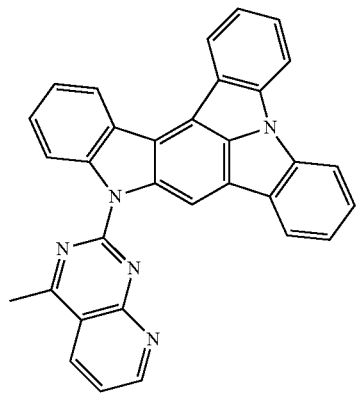
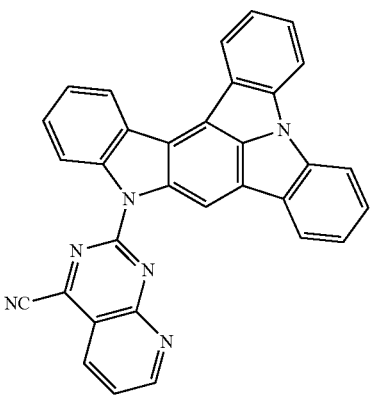
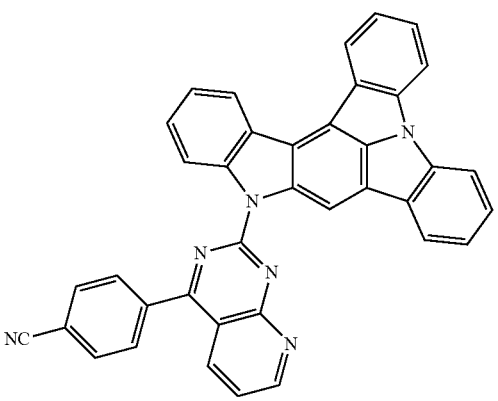

-continued
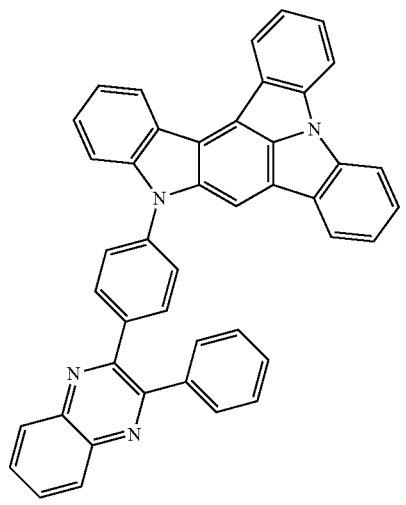
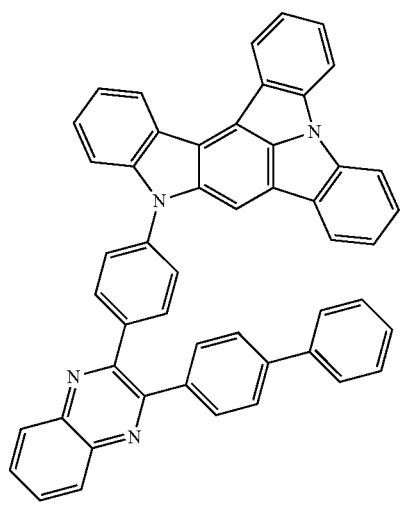
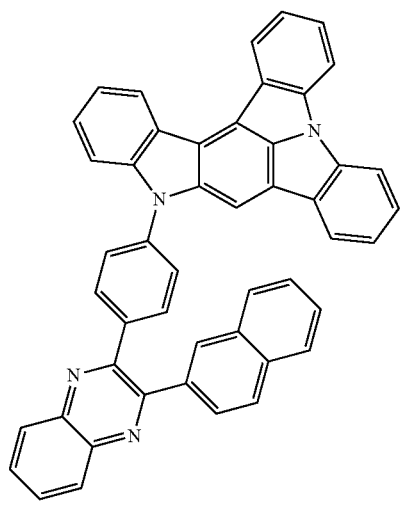
-continued
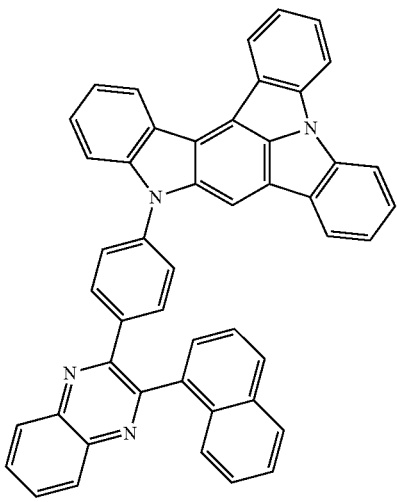
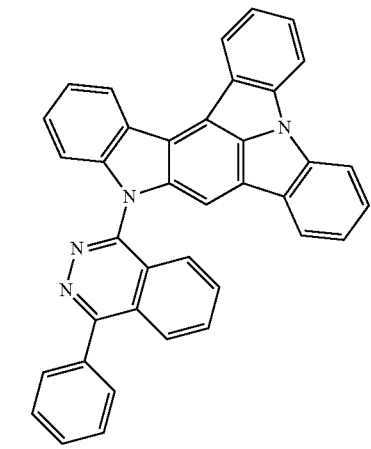
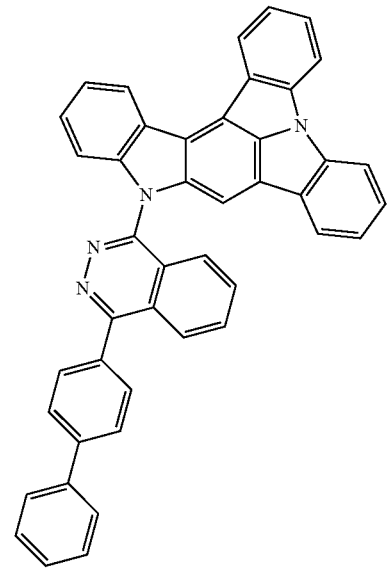

137
-continued
138
-continued
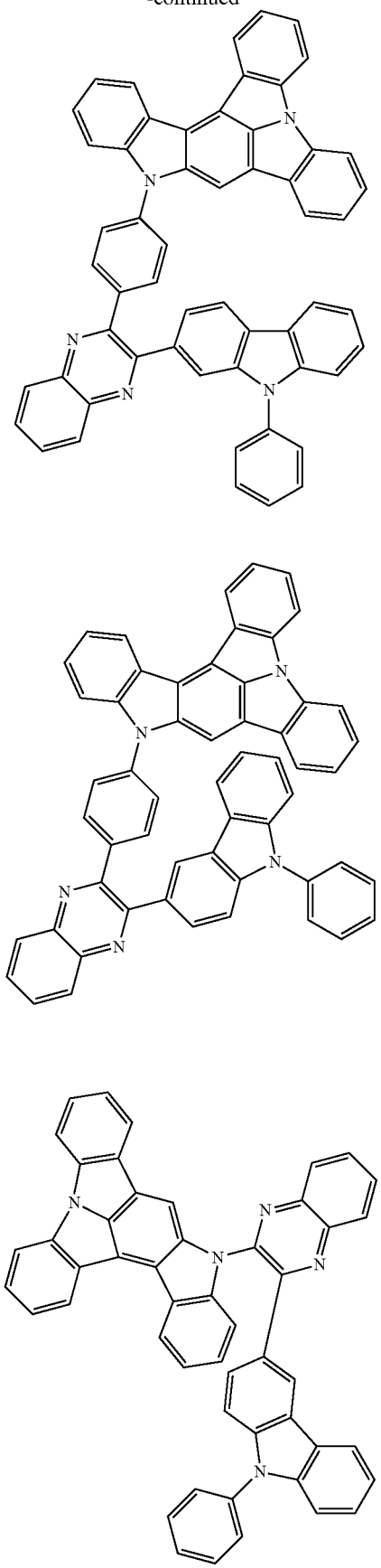
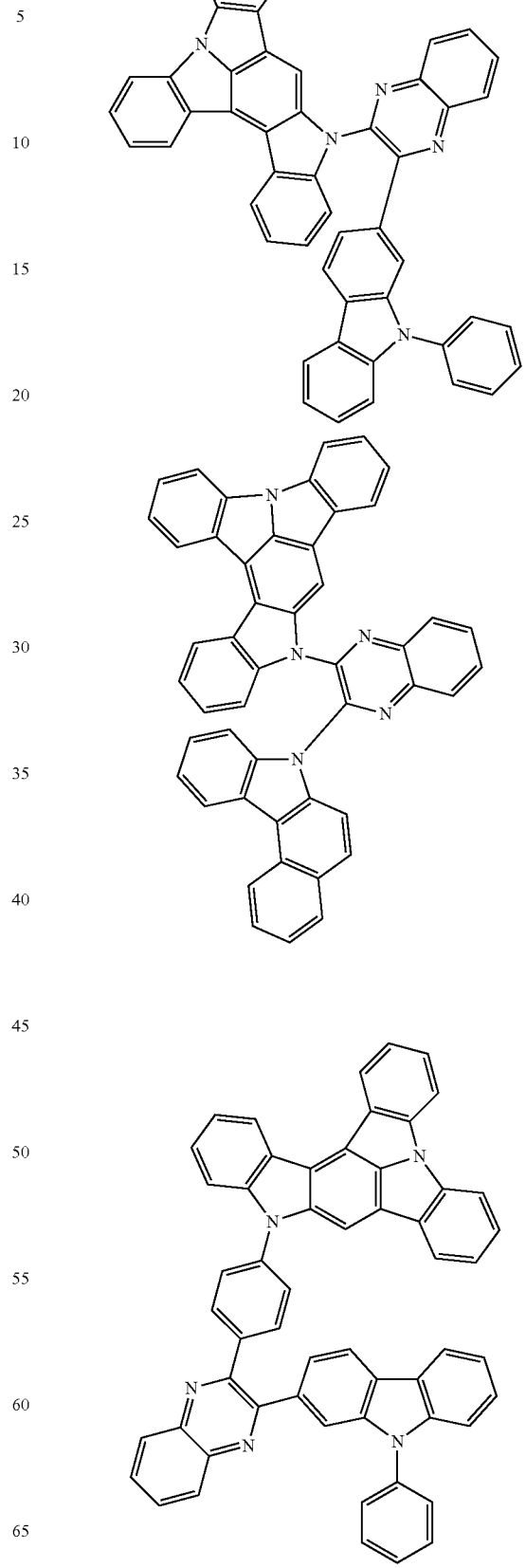

139
-continued
140
-continued
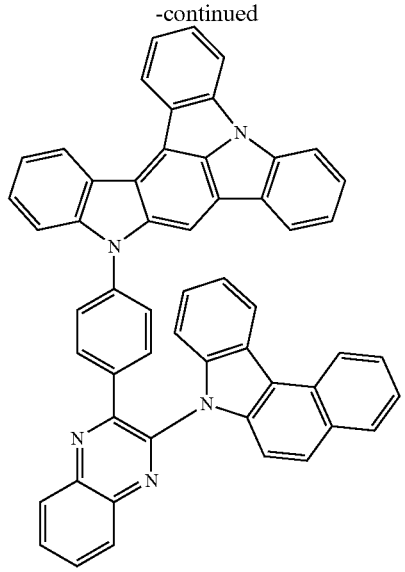
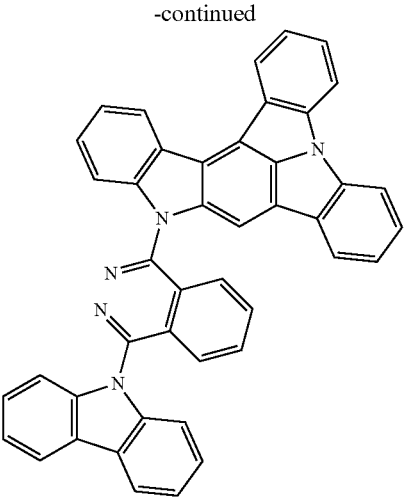
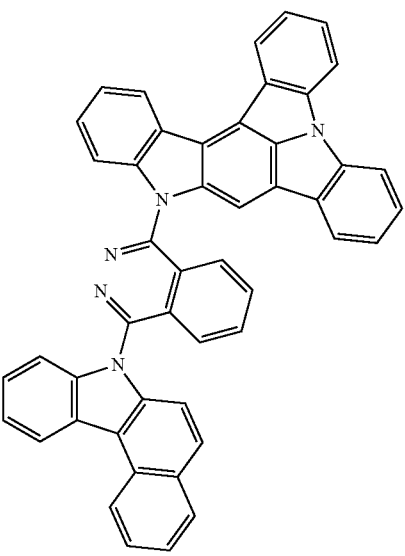
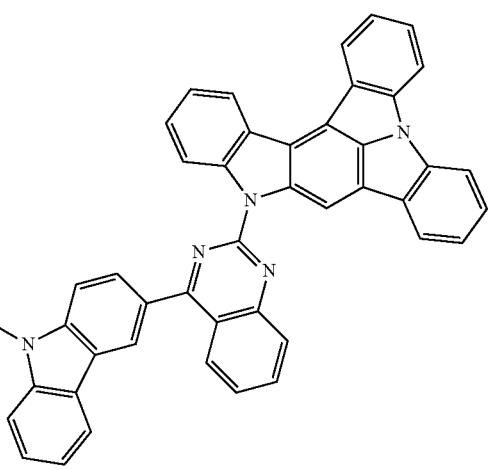

141
-continued
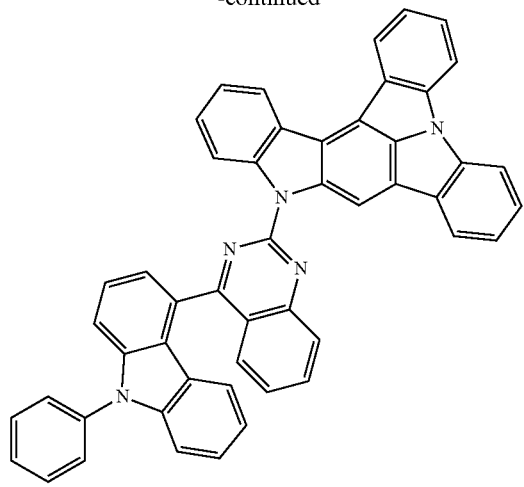

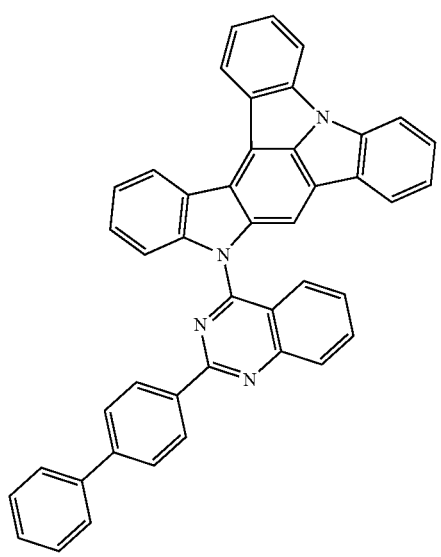
142
-continued
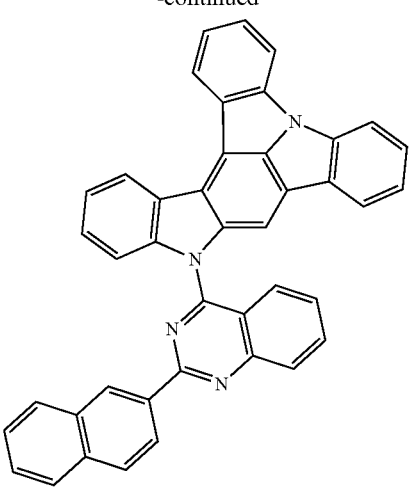
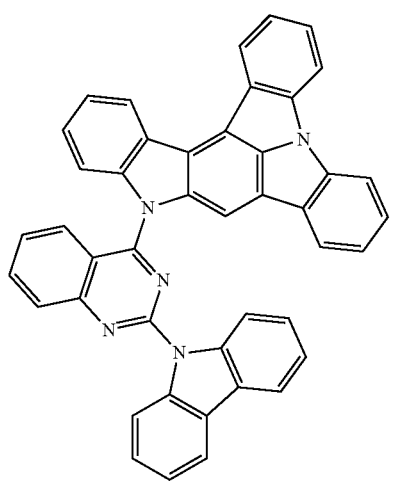
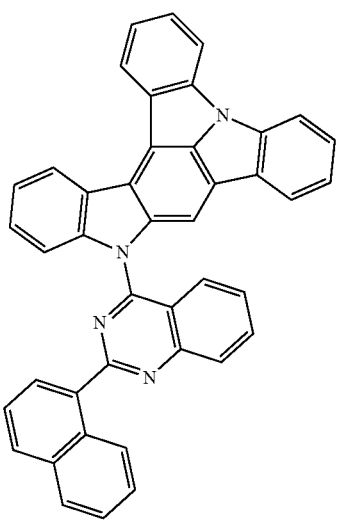

-continued
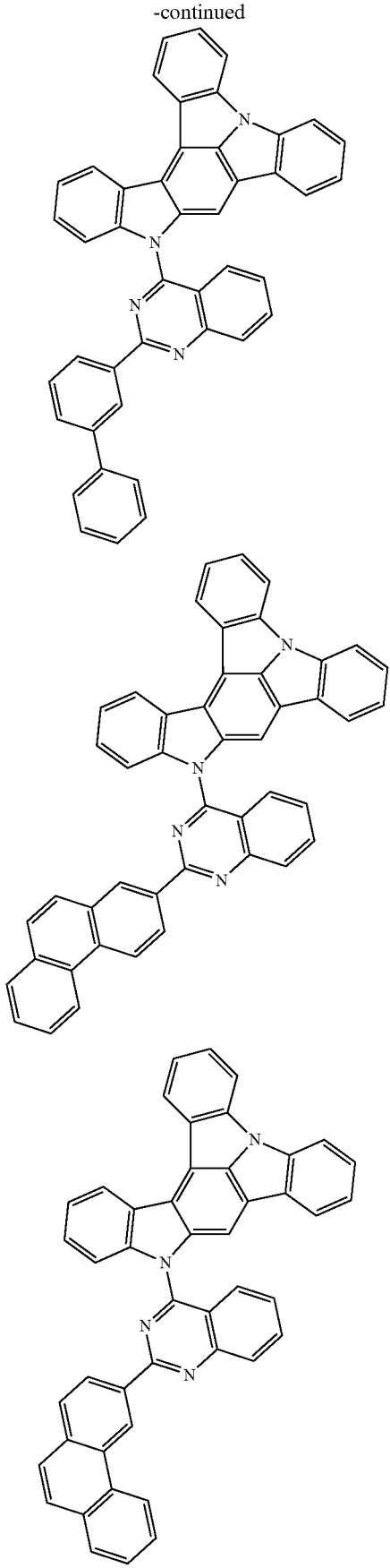
-continued
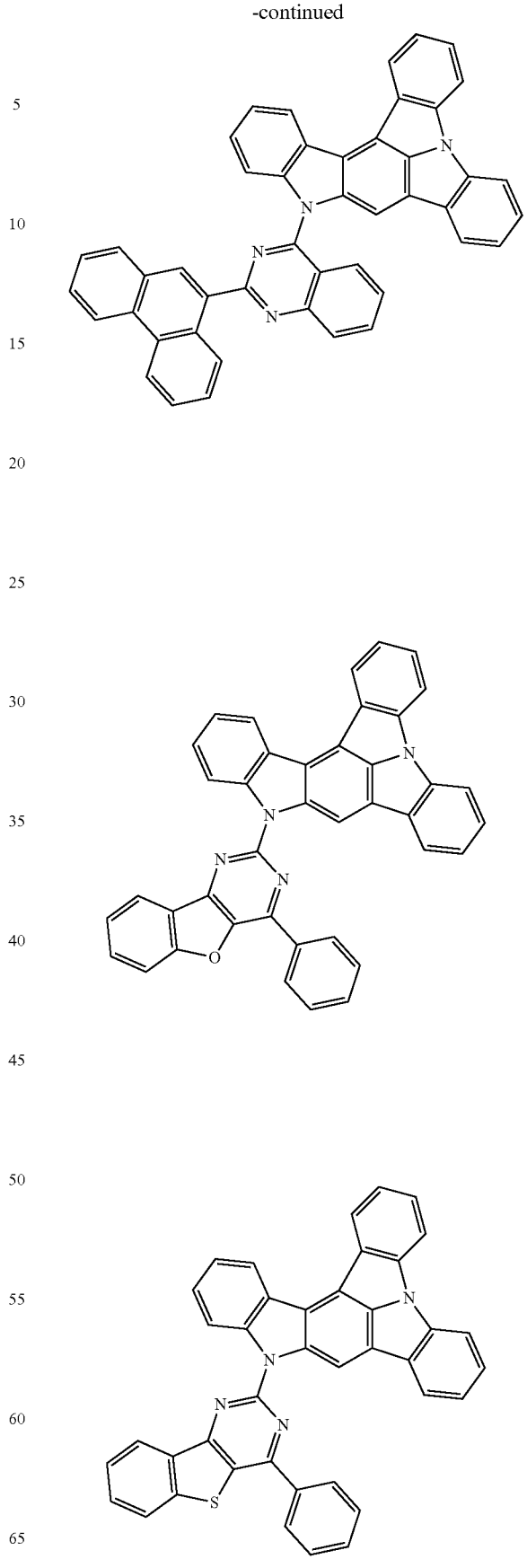

145
-continued
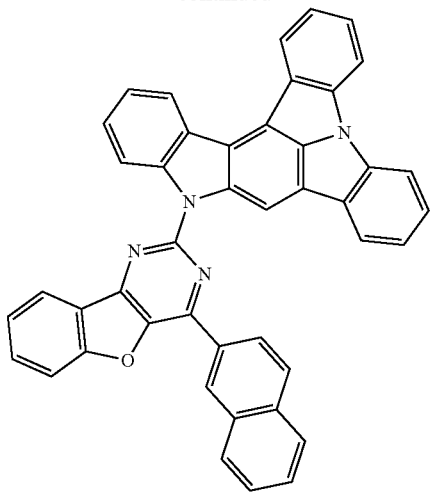
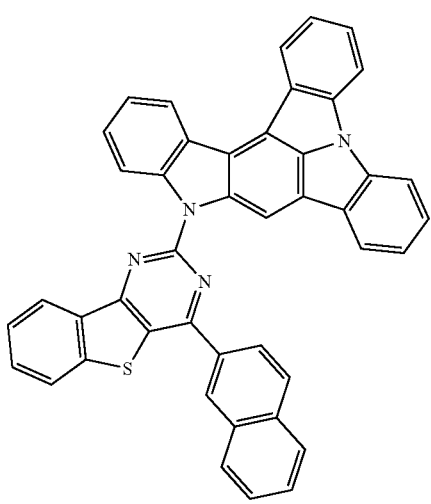
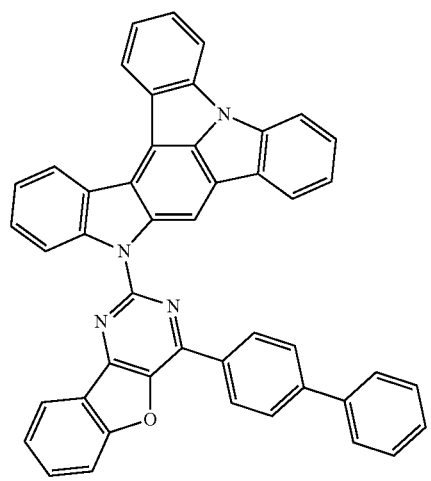
146
-continued
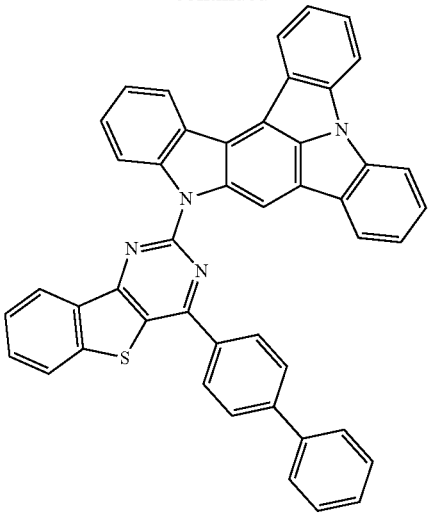
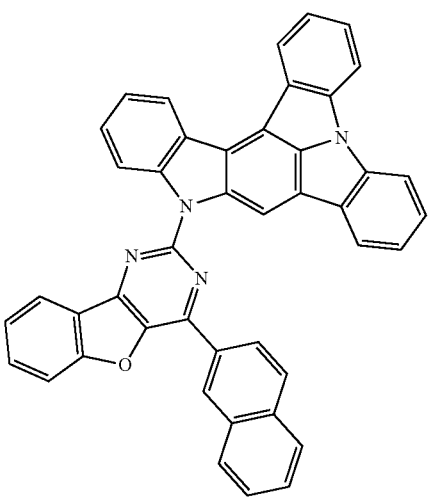
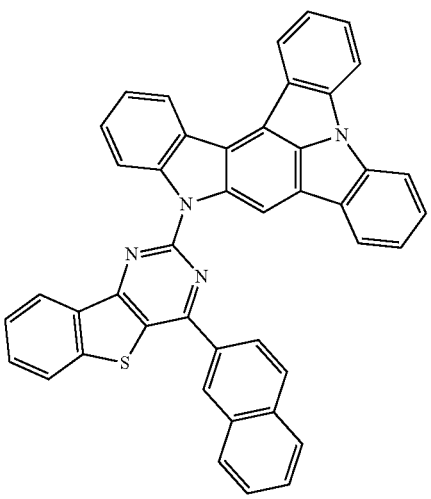

147
-continued
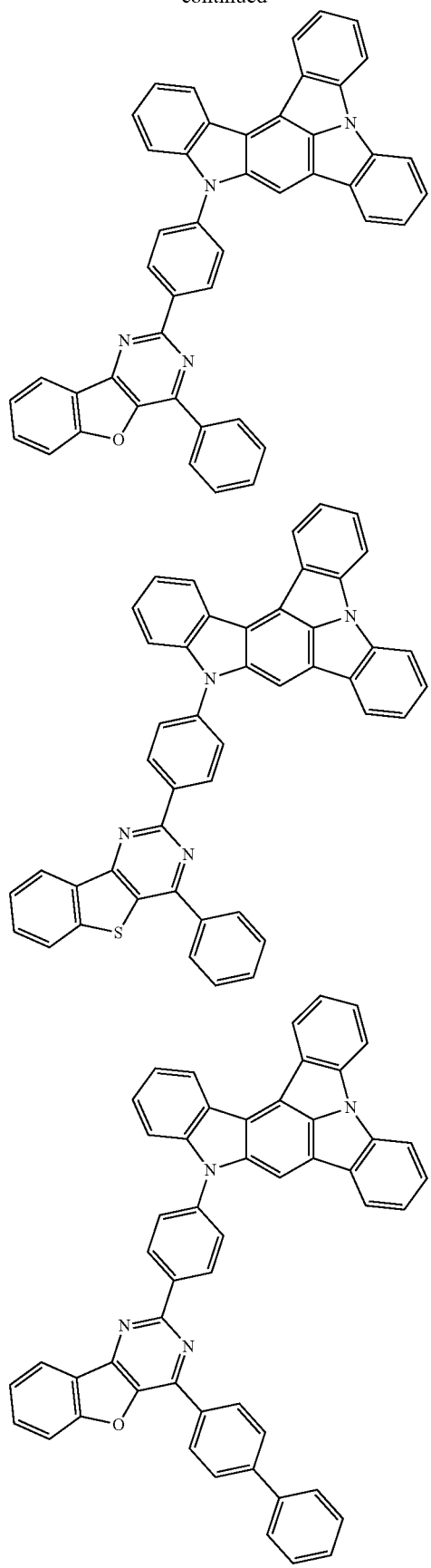 [SMILES: c1ccc(-c2nc(-c3ccc(-n4c5ccccc5c5c6c7ccccc7n7c8ccccc8c(cc54)c67)cc3)nc3c2oc2ccccc23)cc1 ; c1ccc(-c2nc(-c3ccc(-n4c5ccccc5c5c6c7ccccc7n7c8ccccc8c(cc54)c67)cc3)nc3c2sc2ccccc23)cc1 ; c1ccc(-c2ccc(-c3nc(-c4ccc(-n5c6ccccc6c6c7c8ccccc8n8c9ccccc9c(cc65)c78)cc4)nc4c3oc3ccccc34)cc2)cc1]
148
-continued
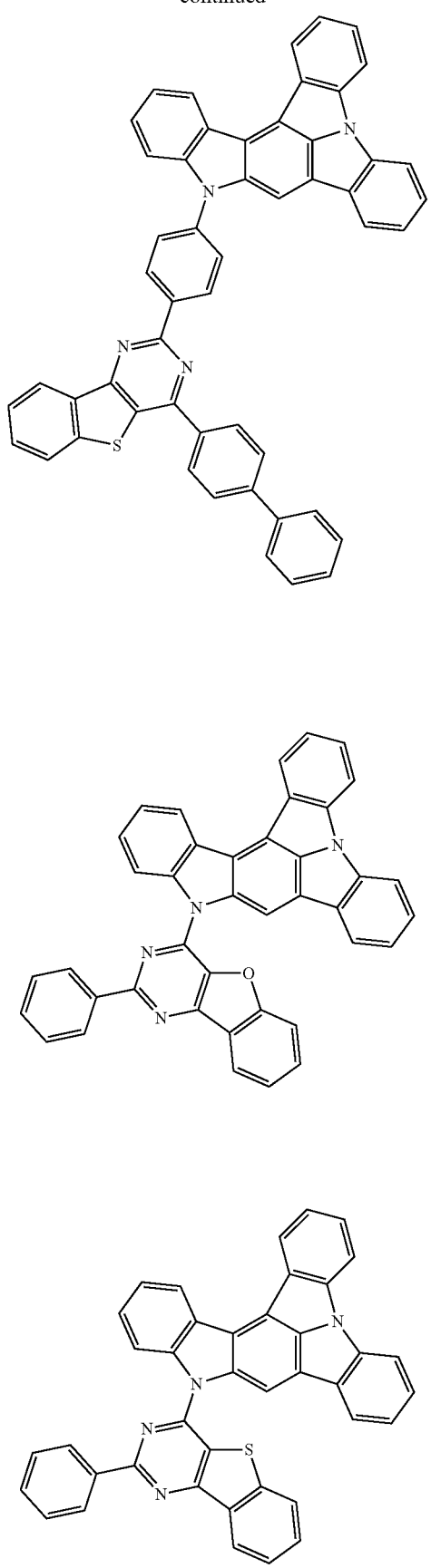

149
-continued
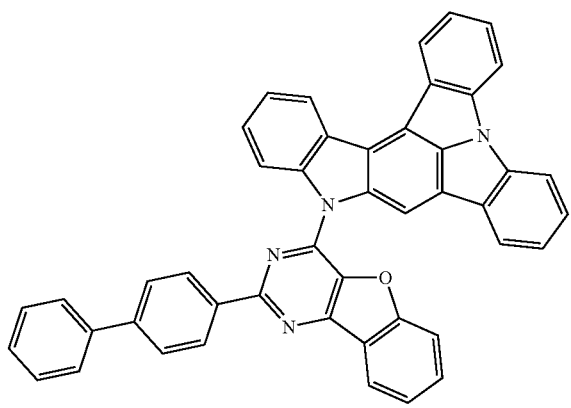
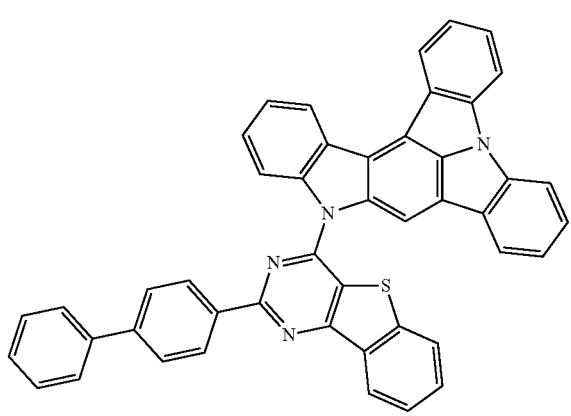
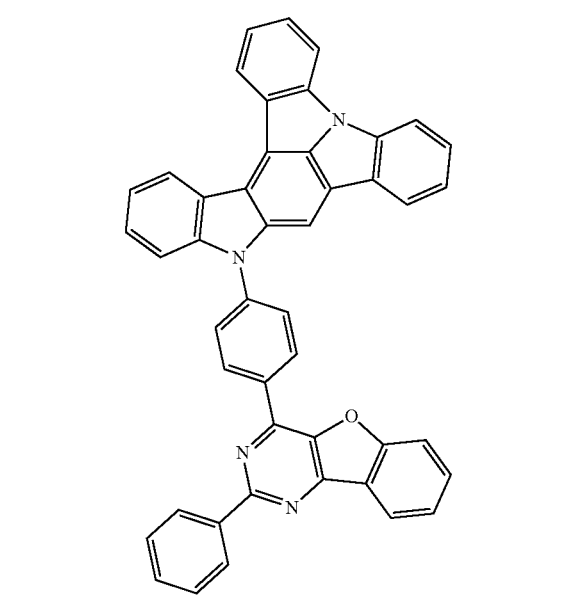
150
-continued
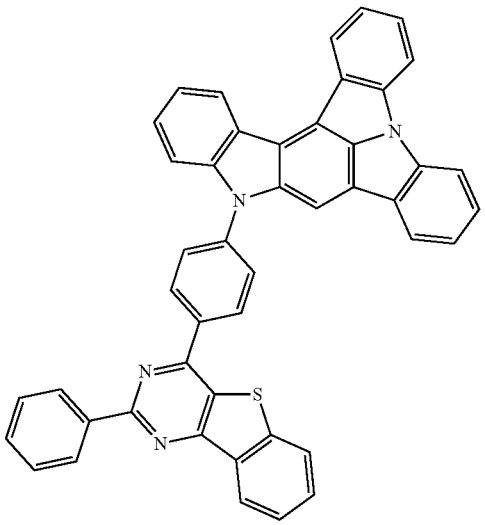
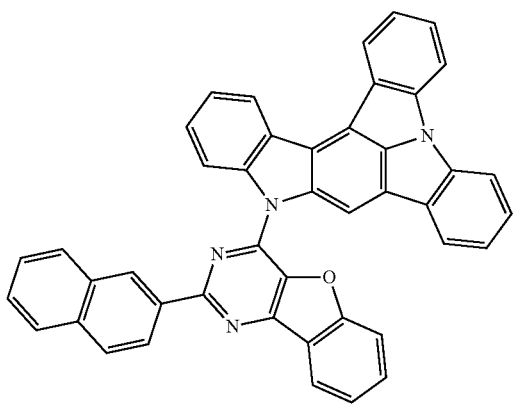
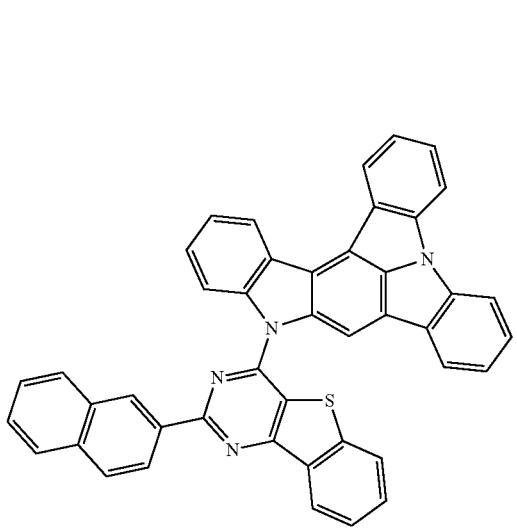

151
-continued
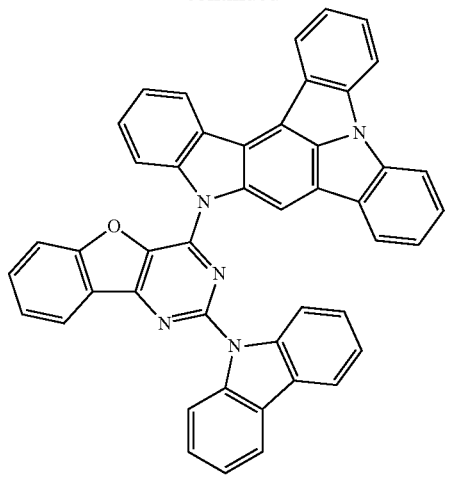
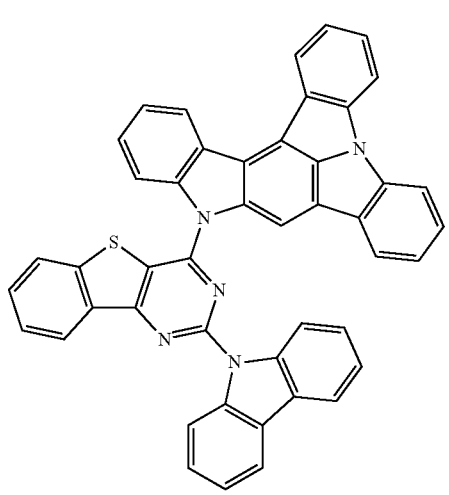
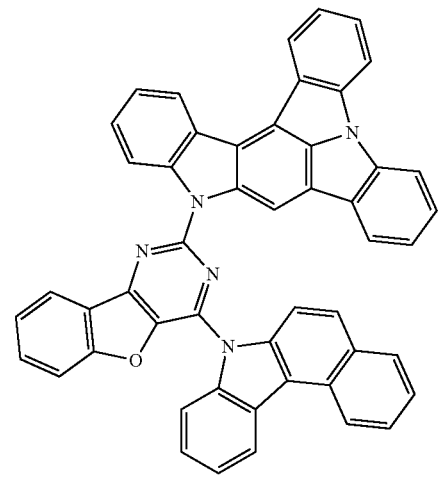
152
-continued
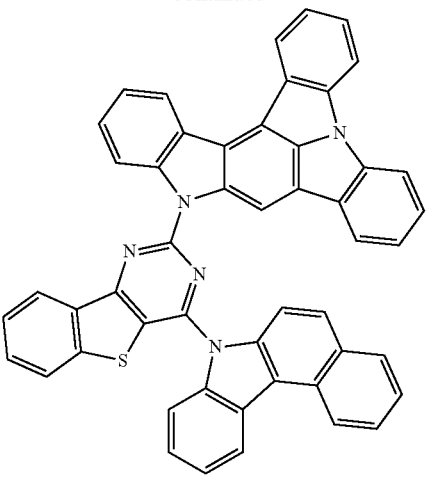
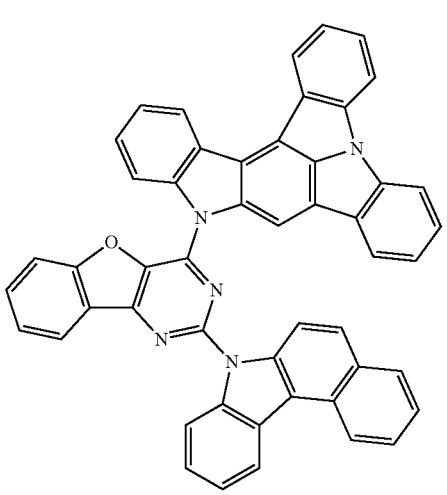
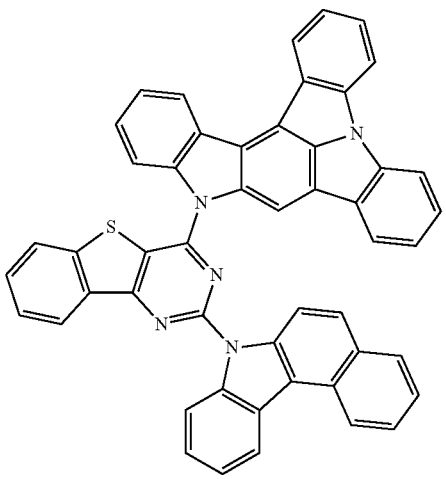

153
-continued
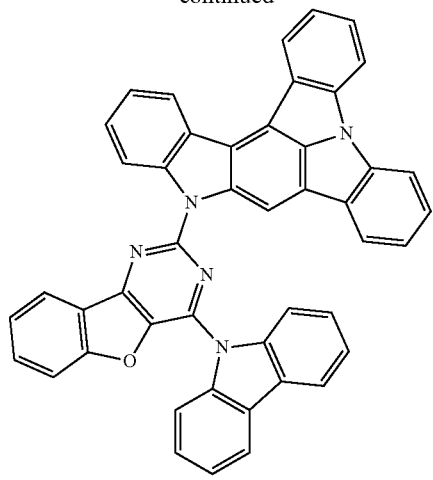
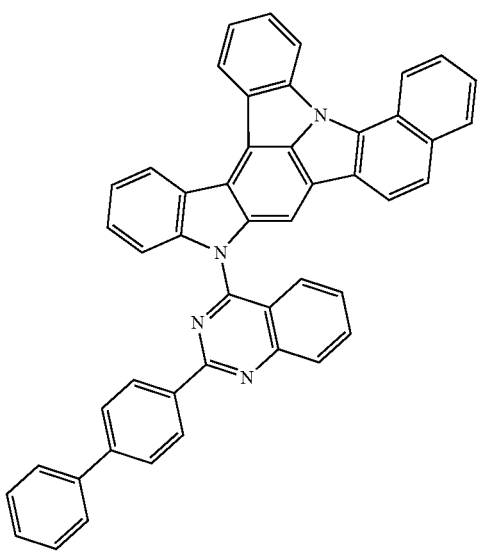
154
-continued
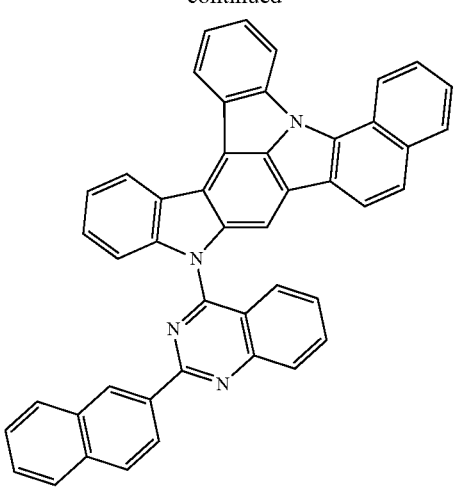
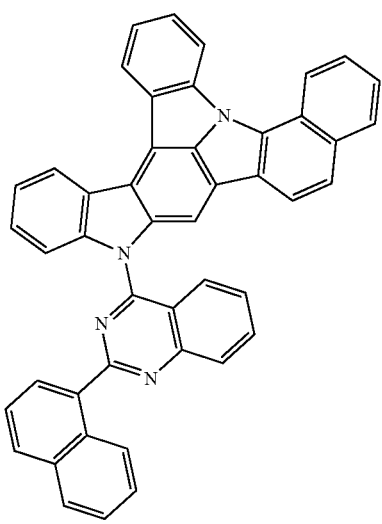

155
-continued
156
-continued
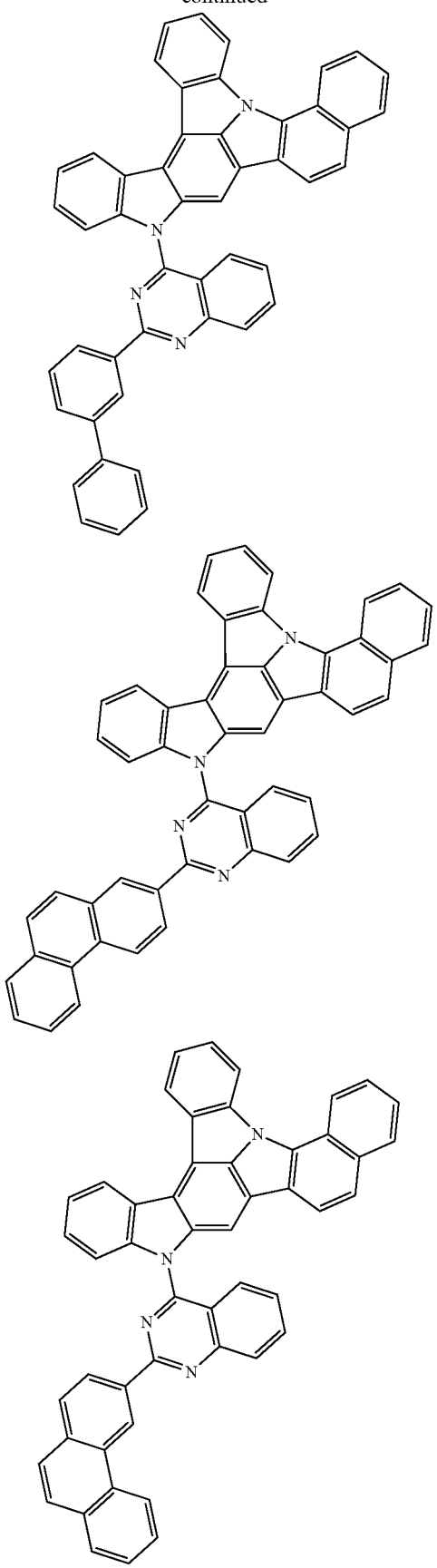
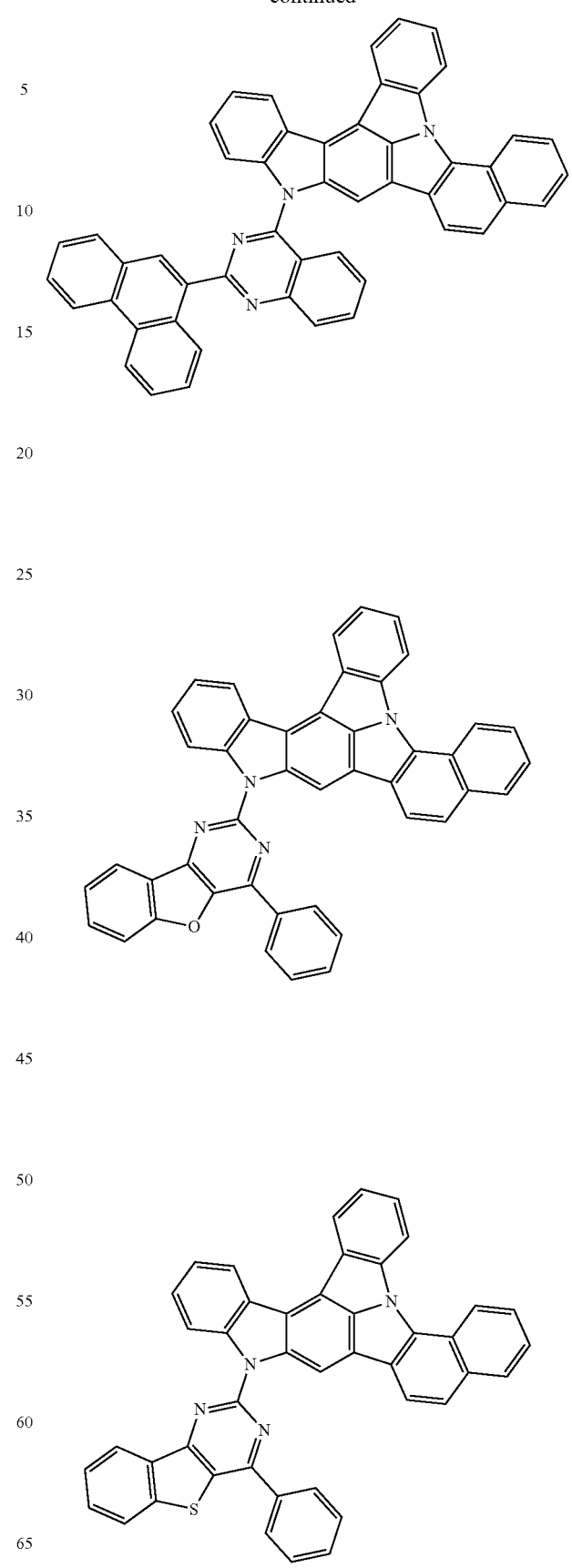

-continued
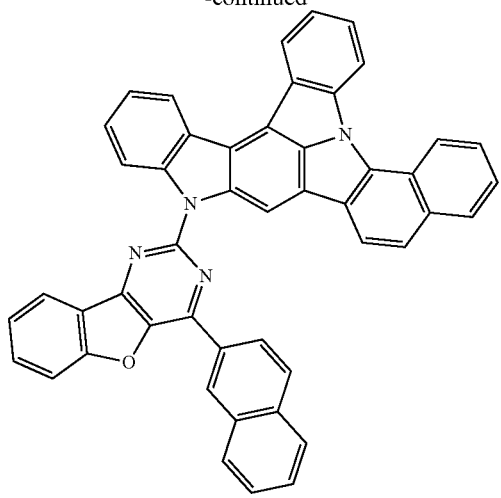
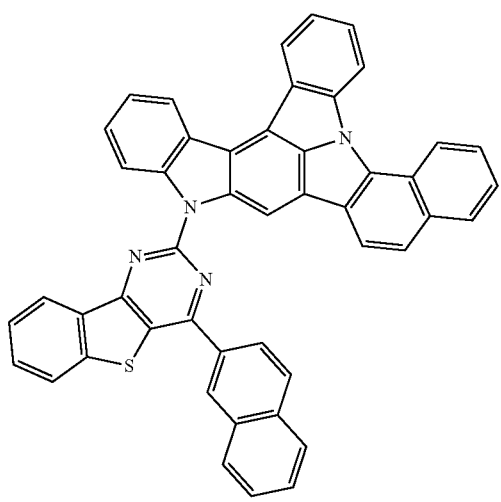
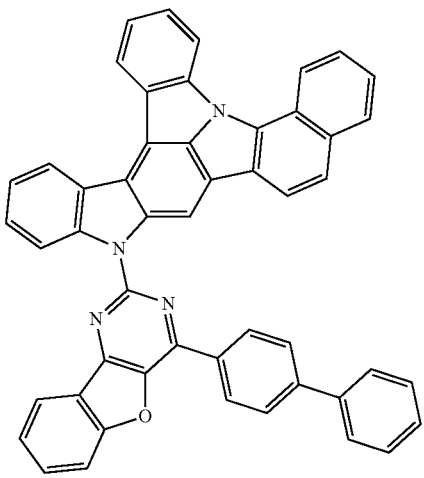
-continued
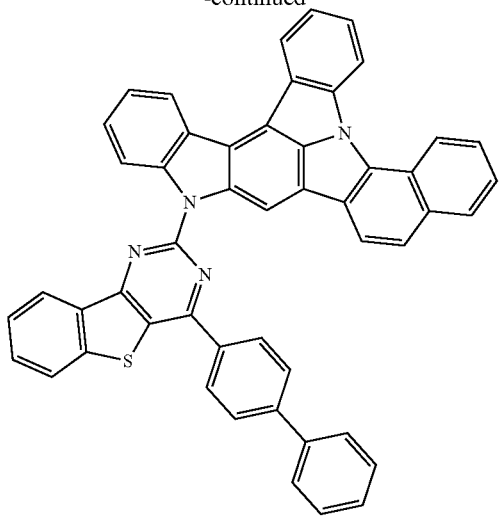
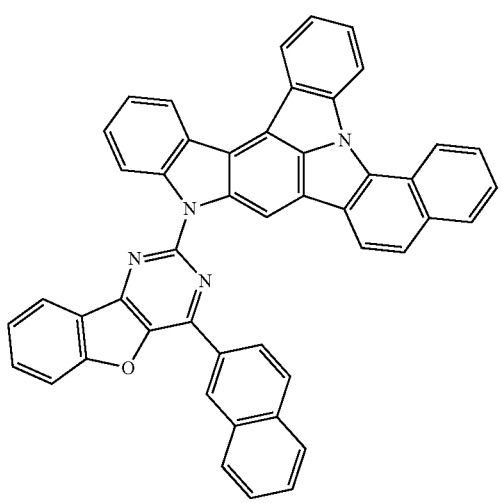
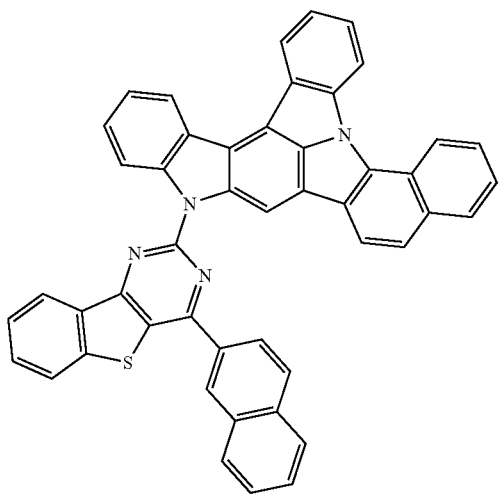

159
-continued
160
-continued
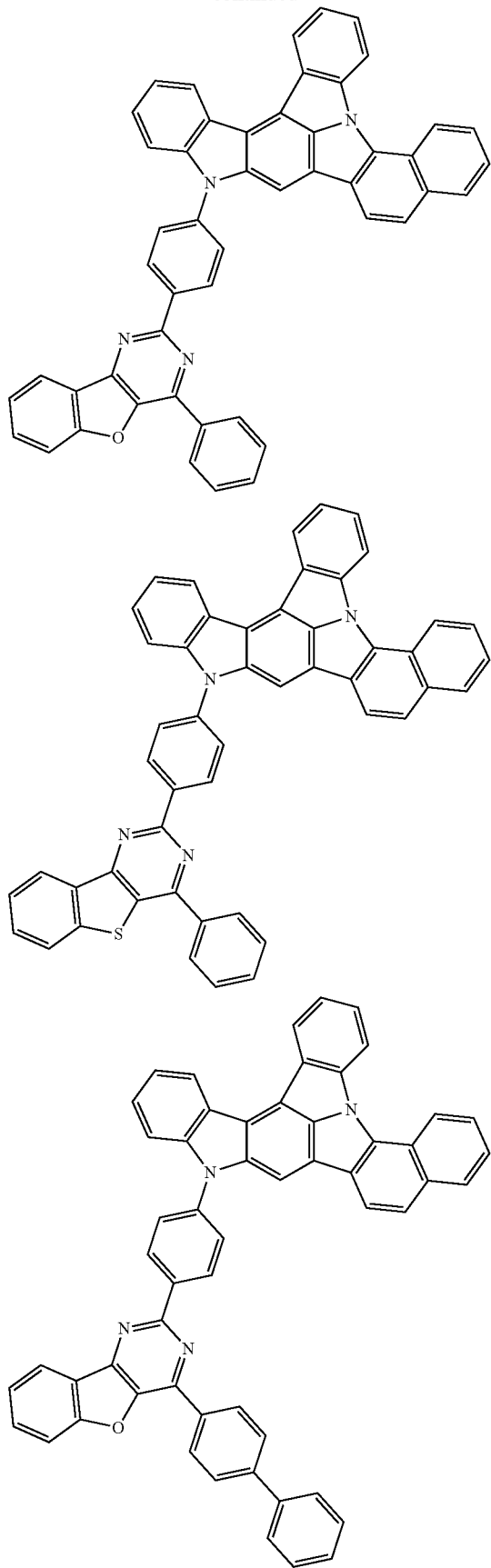
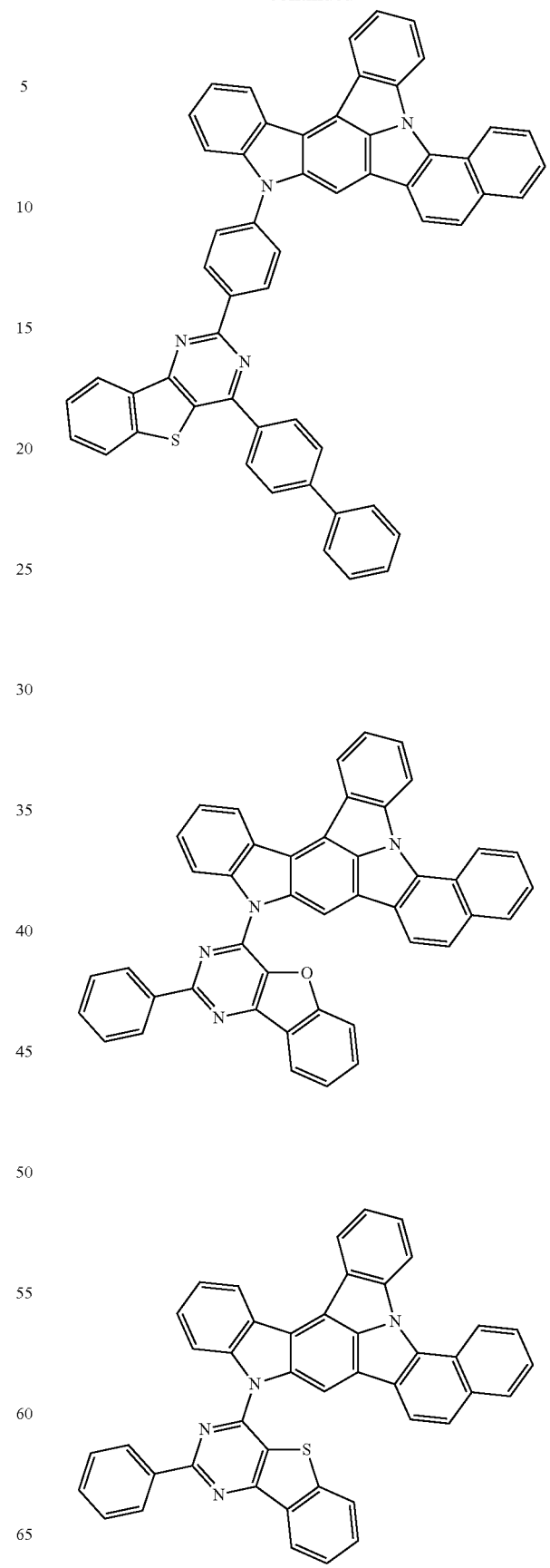

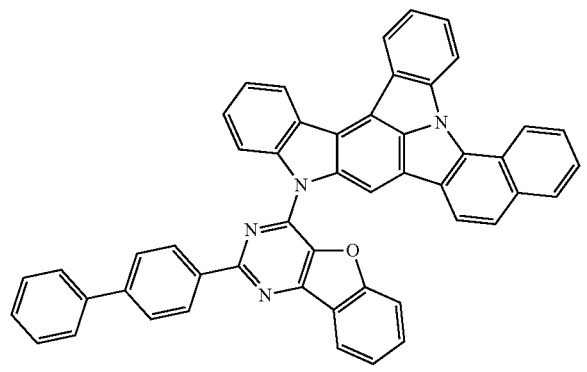
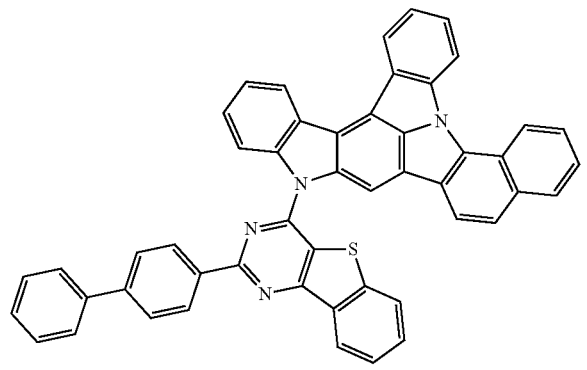
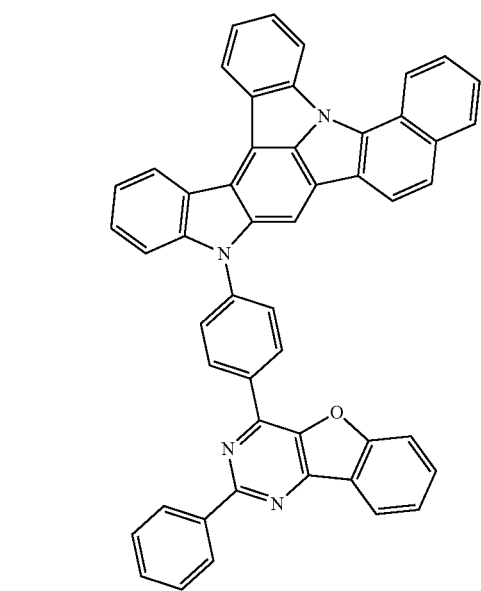
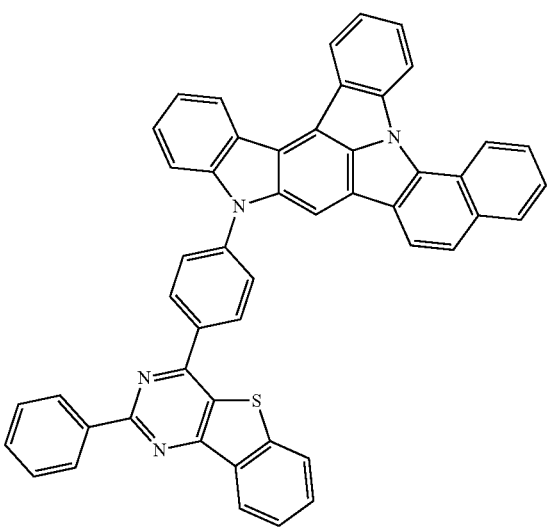
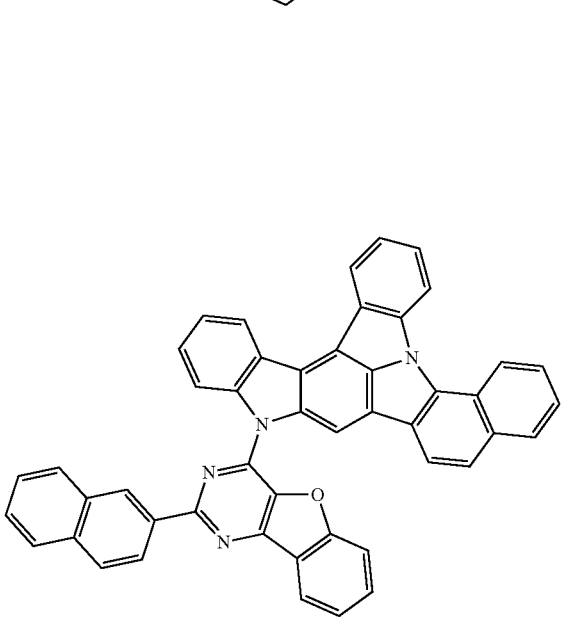

163
-continued
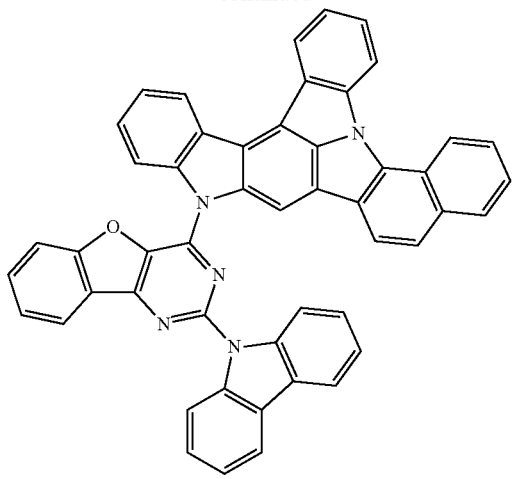
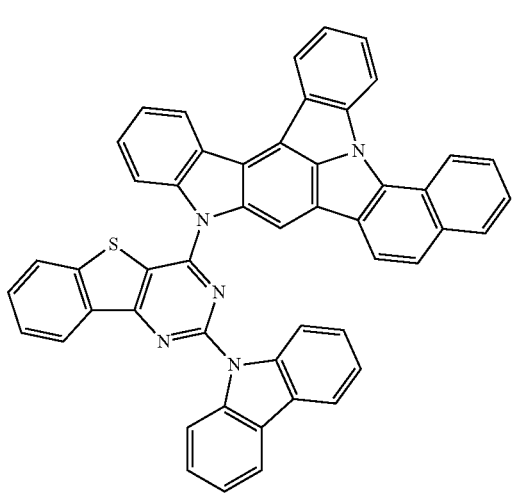
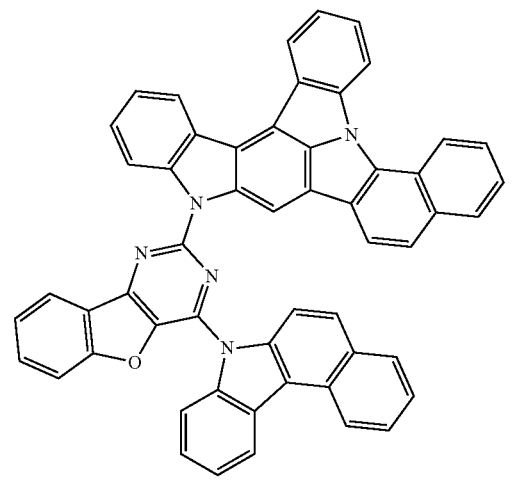
164
-continued
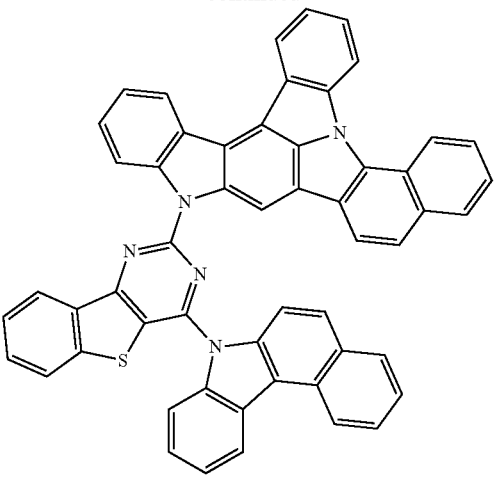
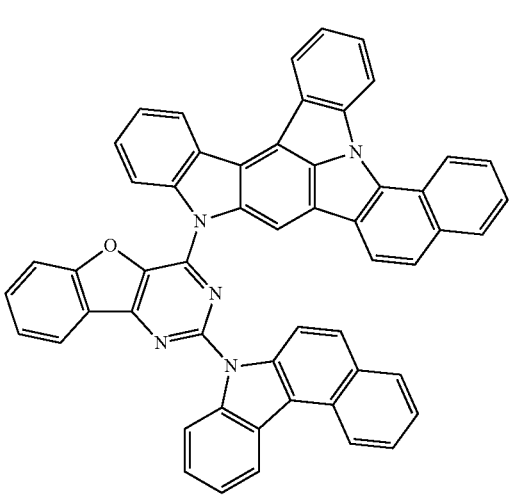
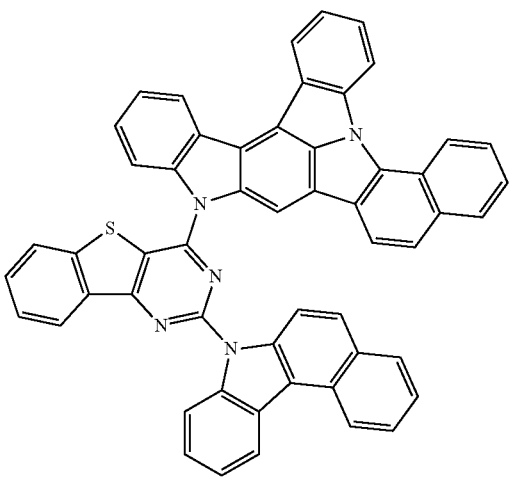

165
-continued
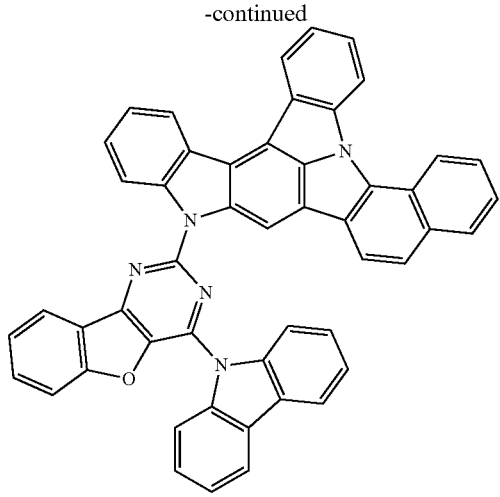
166
-continued
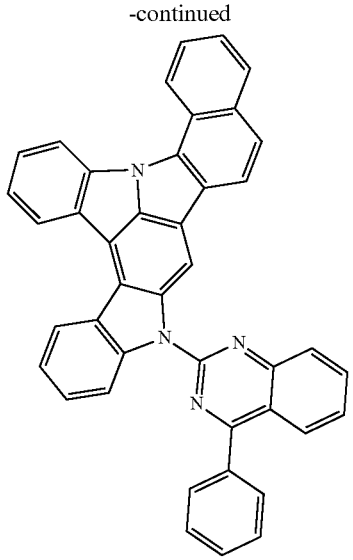
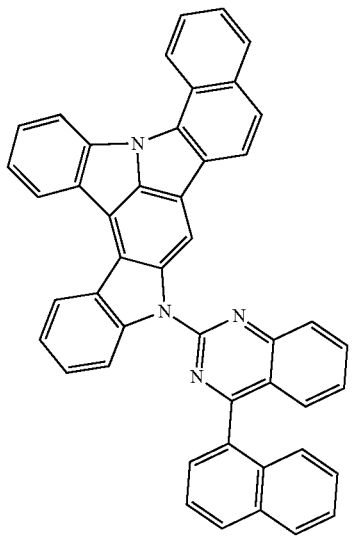
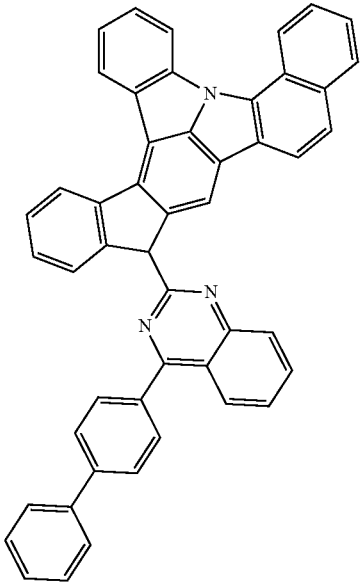

-continued
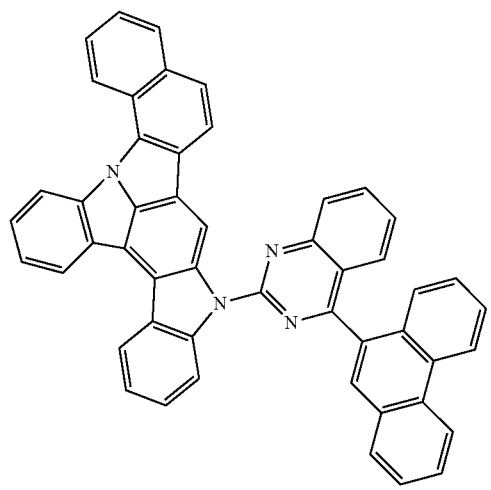
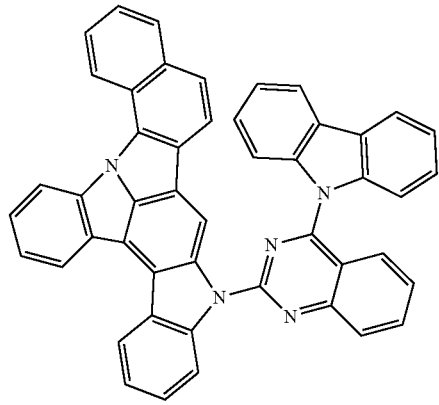
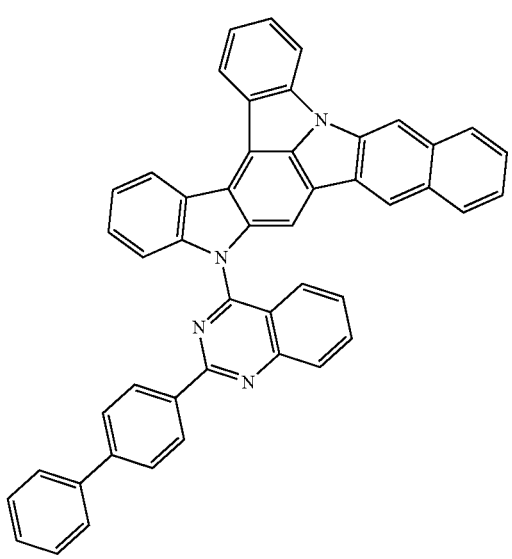
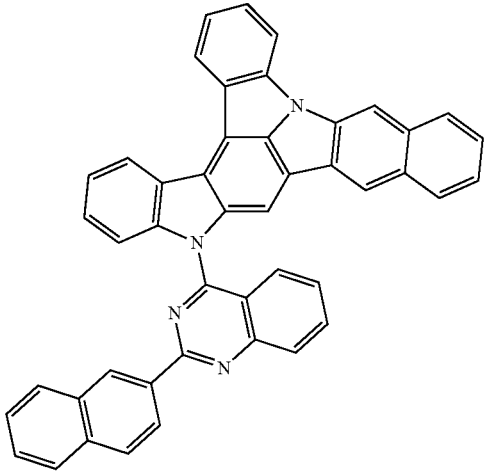
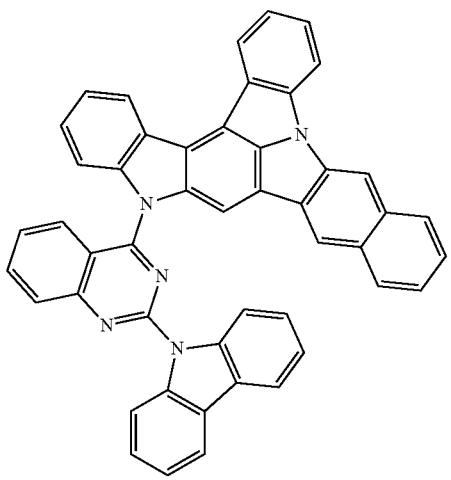
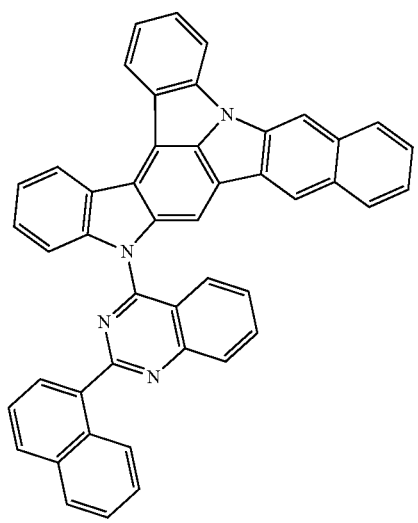

169
-continued
170
-continued
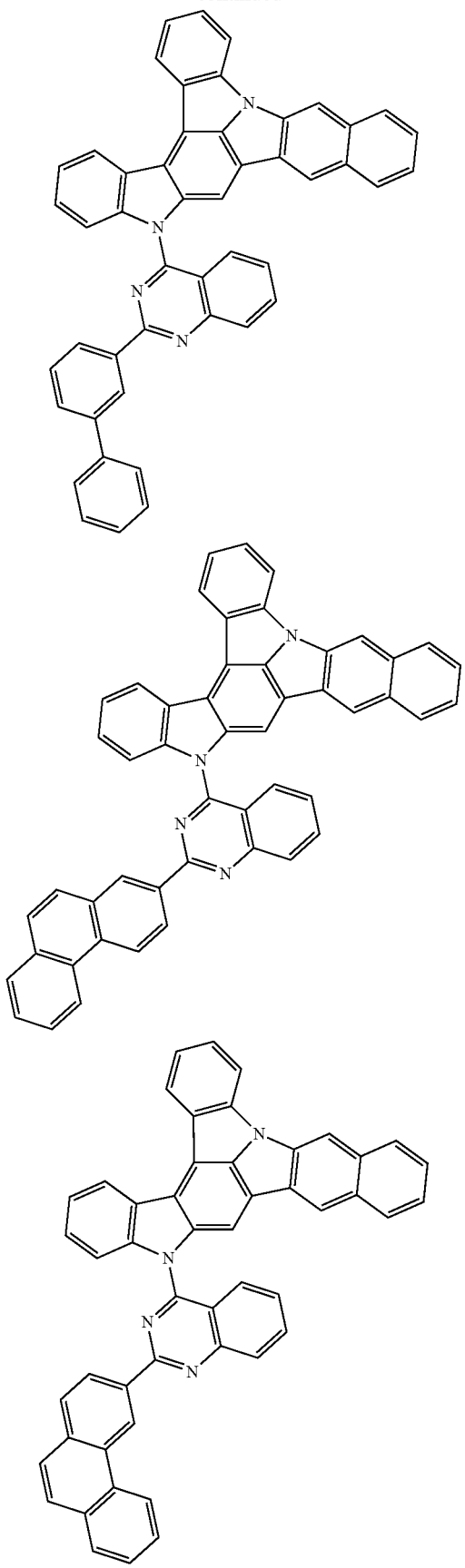 [SMILES: c1ccc(-c2cccc(-c3nc(-n4c5ccccc5c5c6c7ccccc7n7c8cc9ccccc9cc8c(cc54)c67)c4ccccc4n3)c2)cc1 ; c1ccc2cc3c(cc2c1)c1cc2c(c4ccccc4n2-c2nc(-c4ccc5c(ccc6ccccc65)c4)nc4ccccc24)c2c4ccccc4n3c12 ; c1ccc2cc3c(cc2c1)c1cc2c(c4ccccc4n2-c2nc(-c4ccc5ccc6ccccc6c5c4)nc4ccccc24)c2c4ccccc4n3c12]
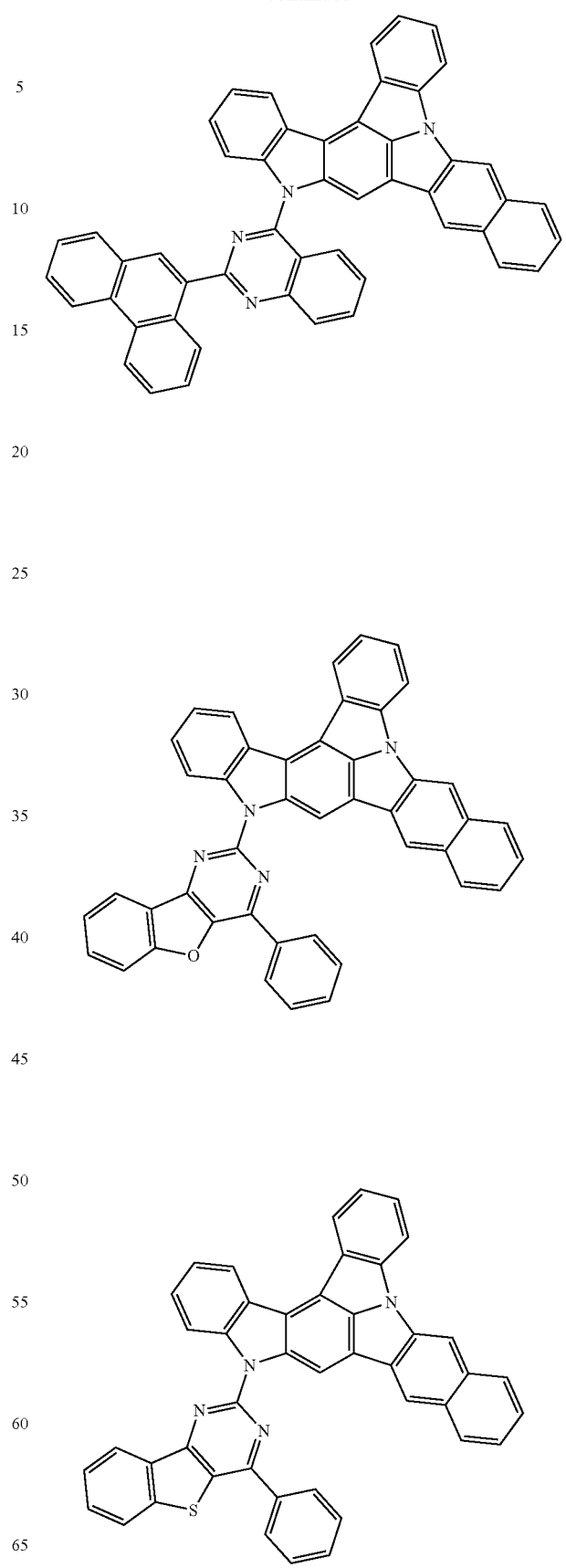

171
-continued
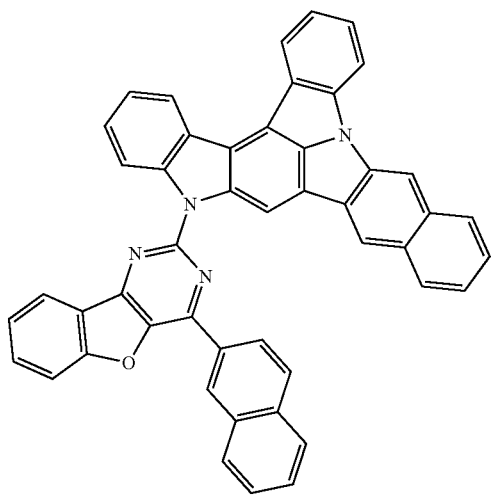
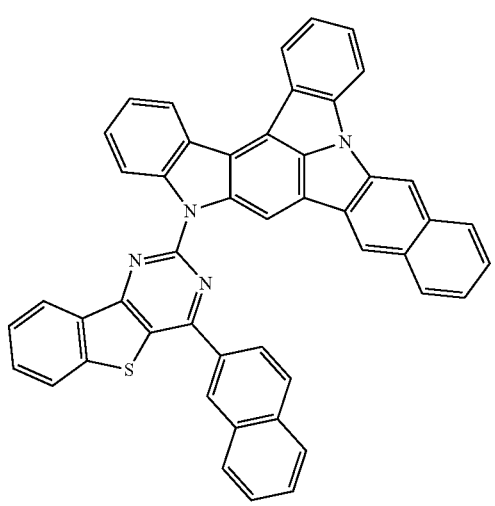
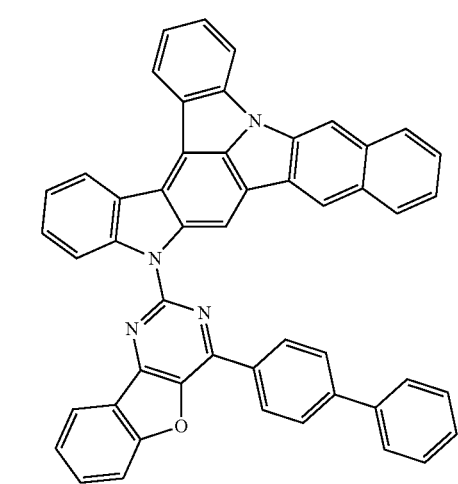
172
-continued
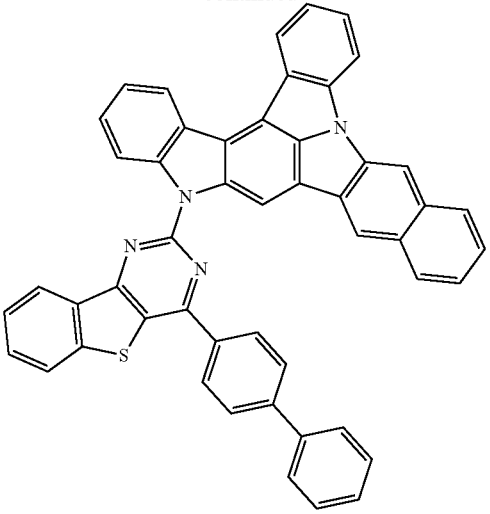
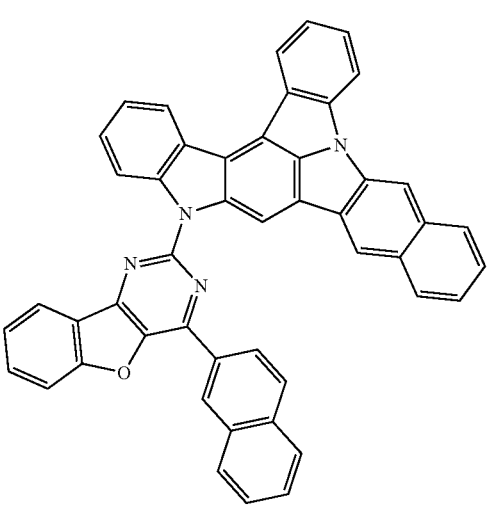
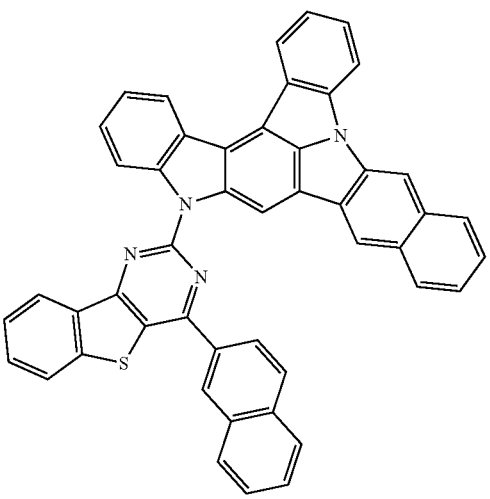

173
-continued
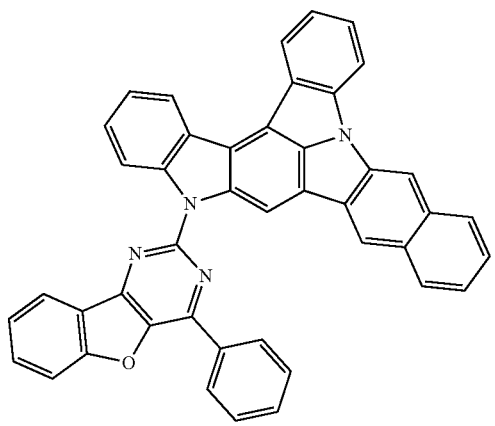
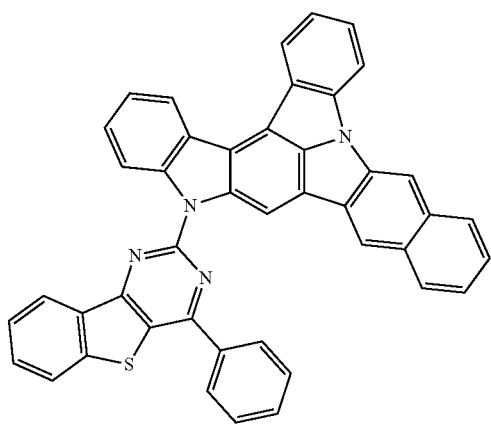
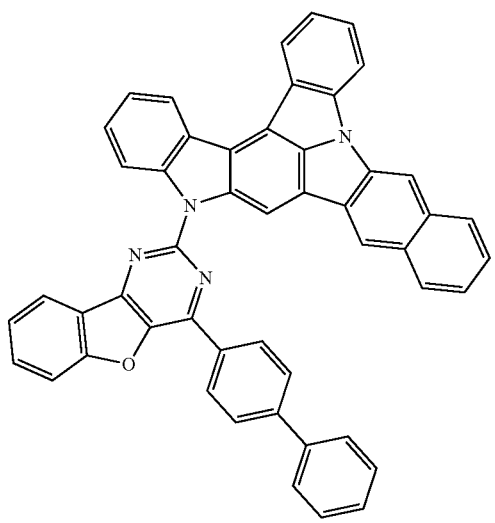
174
-continued
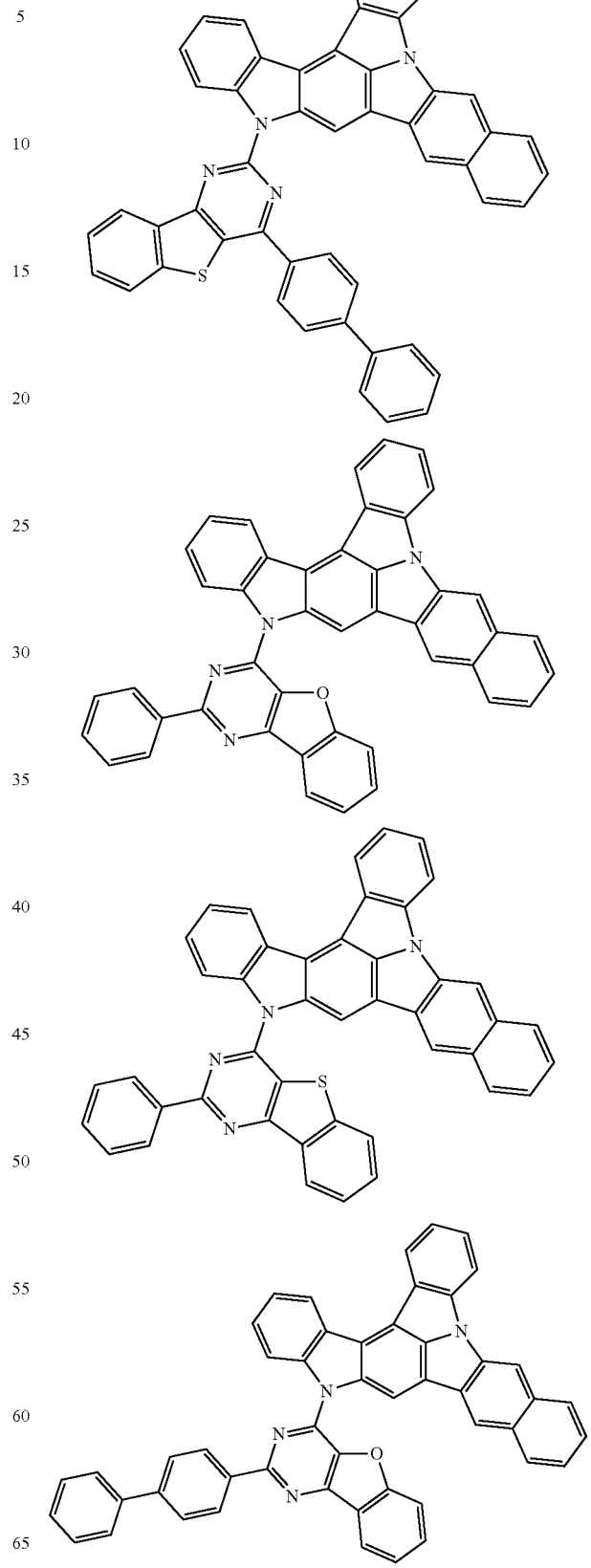

175
-continued
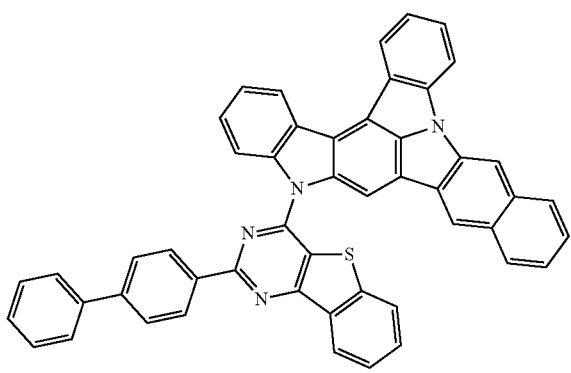
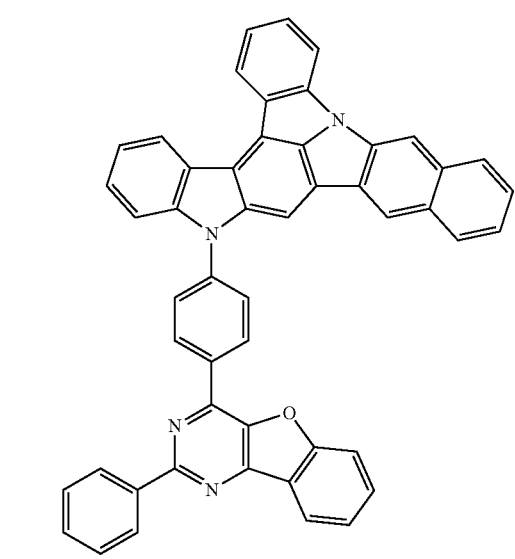
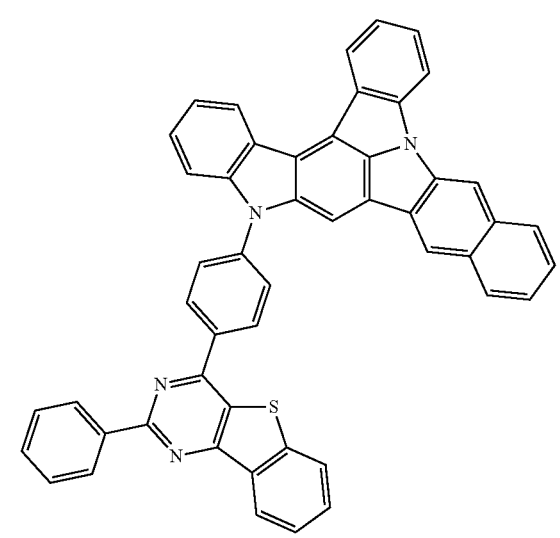
176
-continued
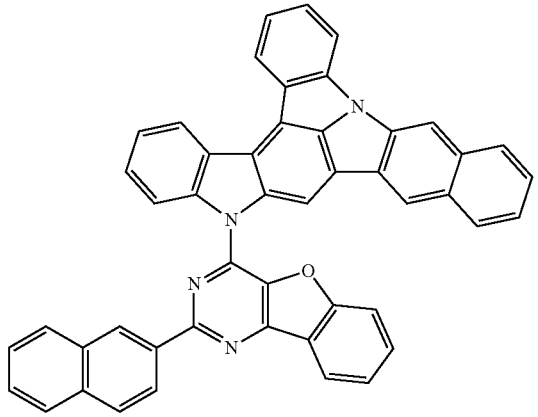
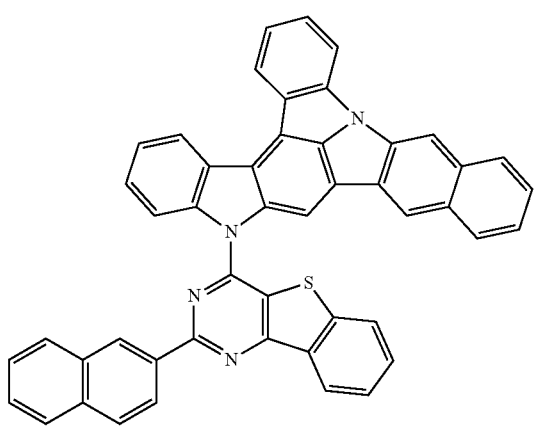
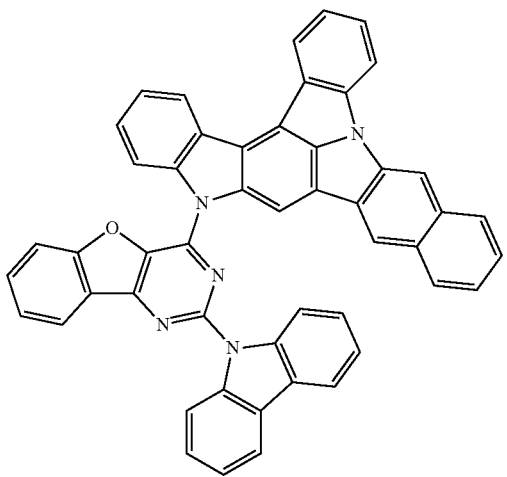

177
-continued
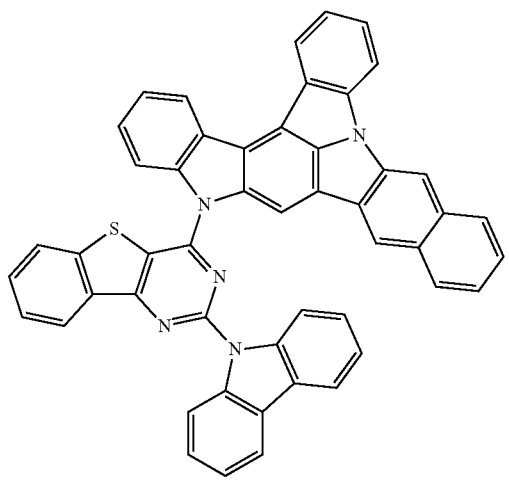
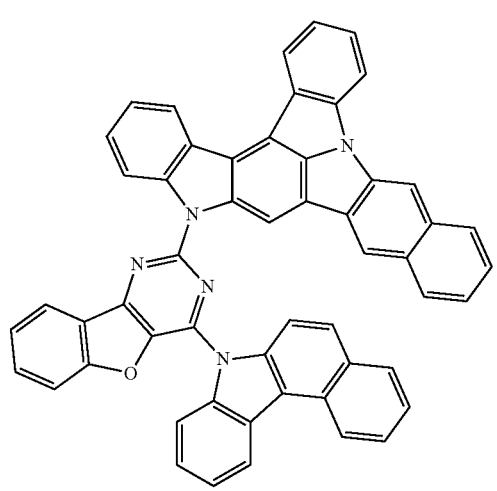
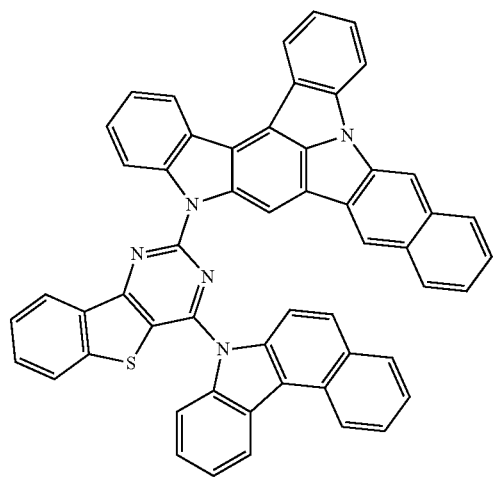
178
-continued
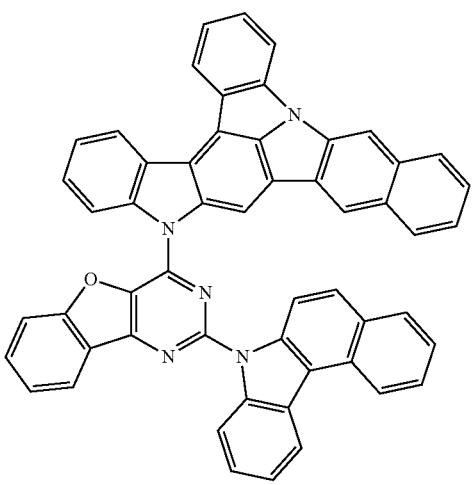
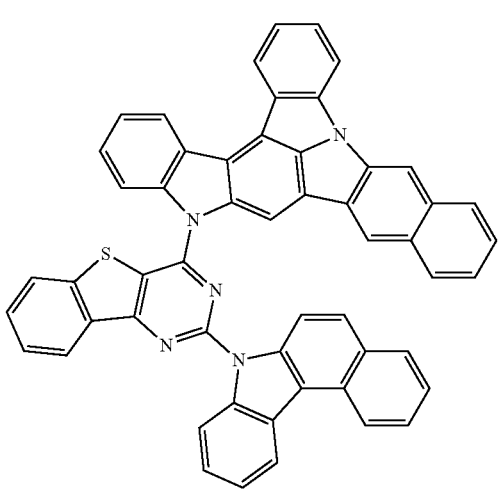
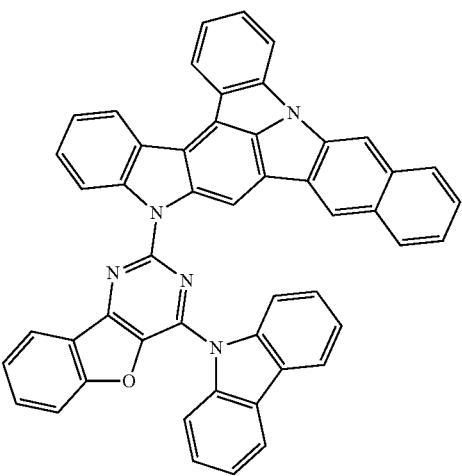

-continued
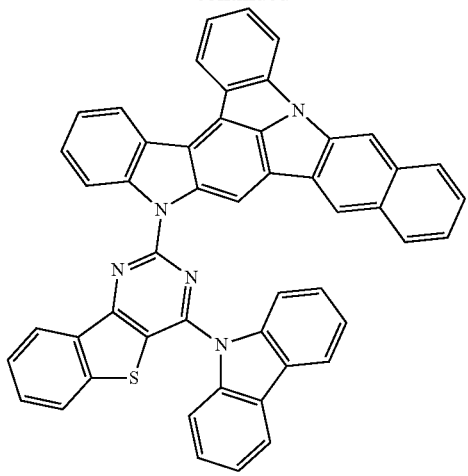
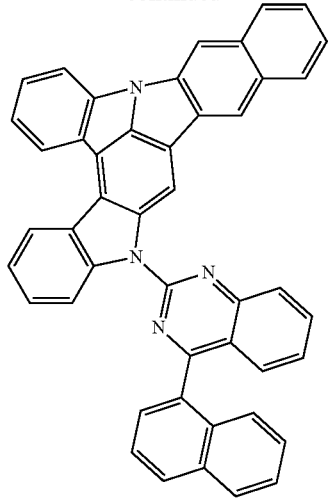
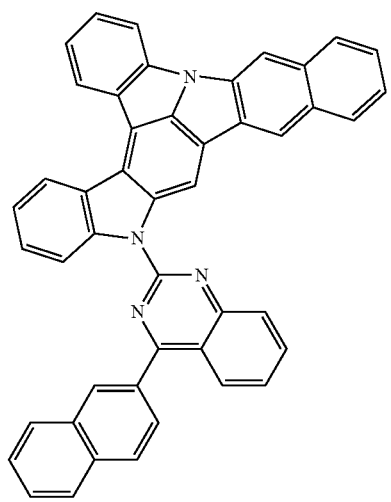
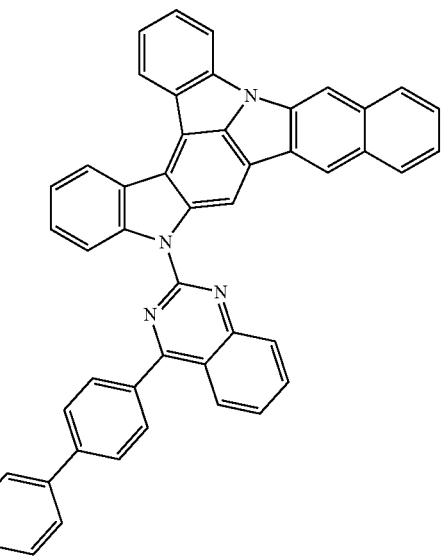
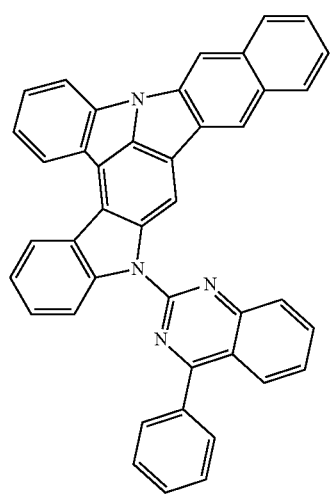
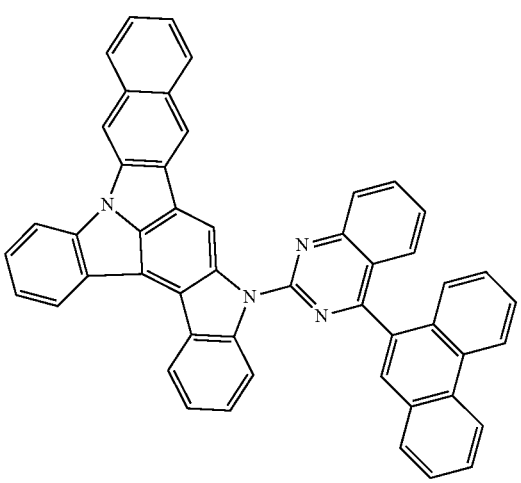

181
-continued
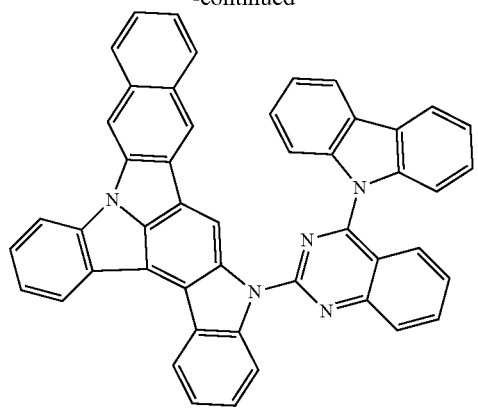
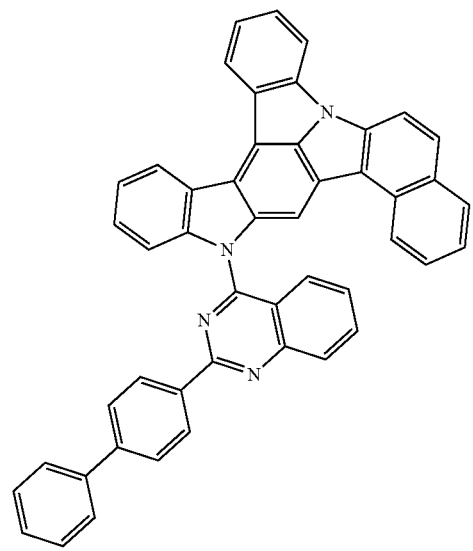
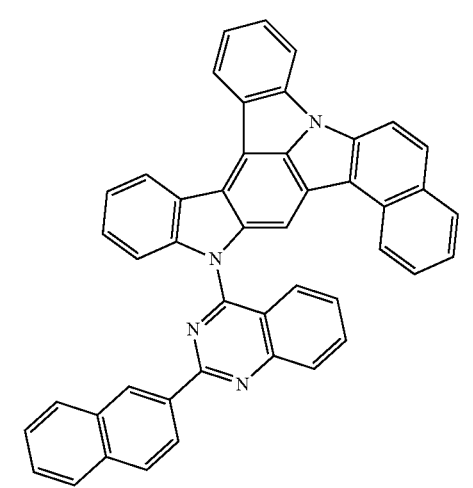
182
-continued
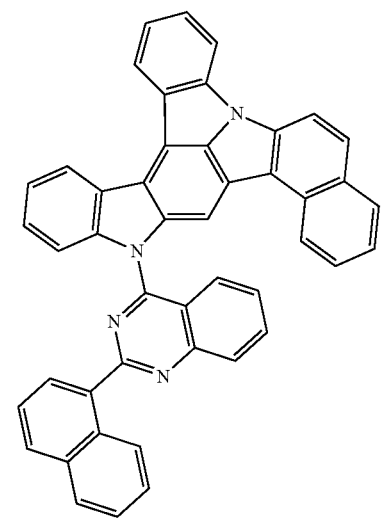
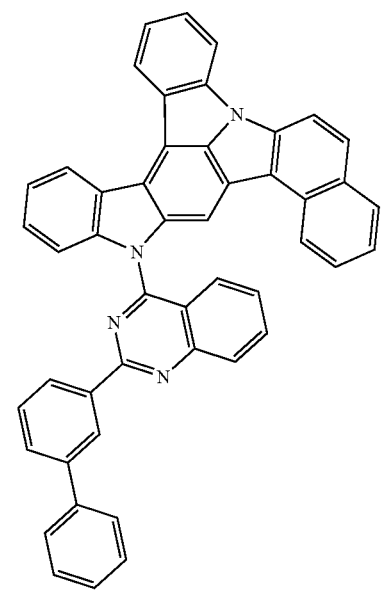

183
-continued
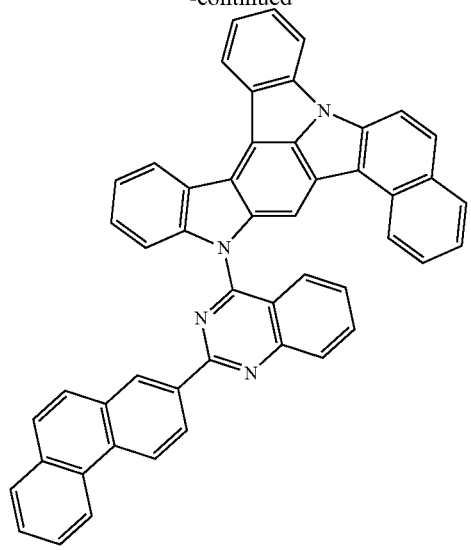
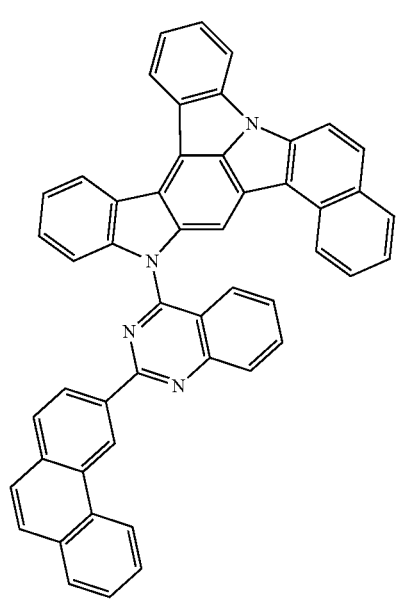
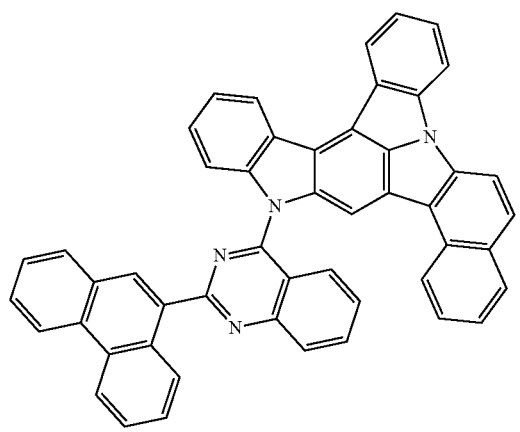
184
-continued
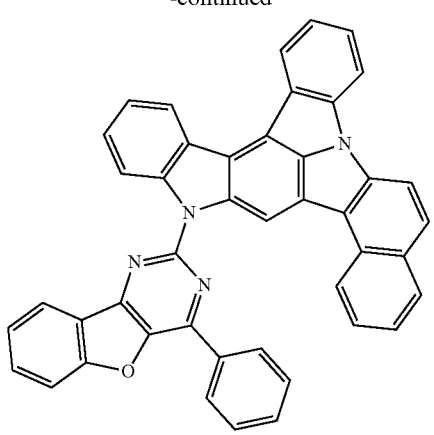
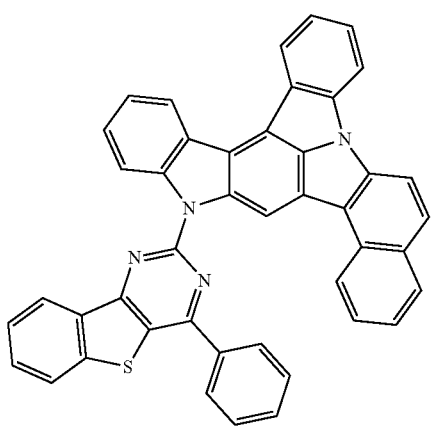
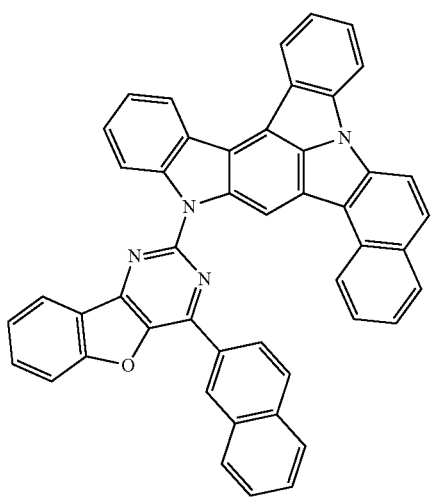

-continued
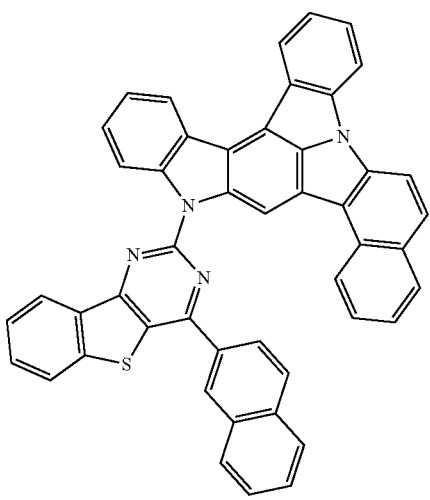
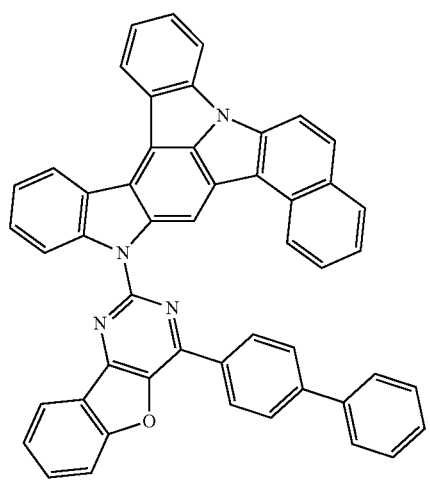
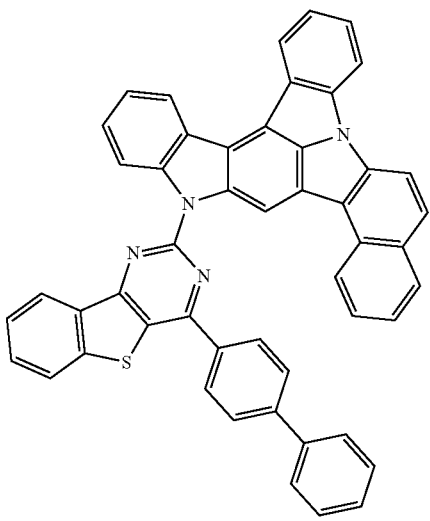
-continued
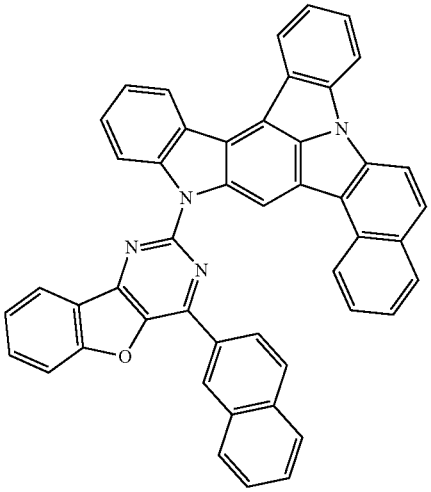
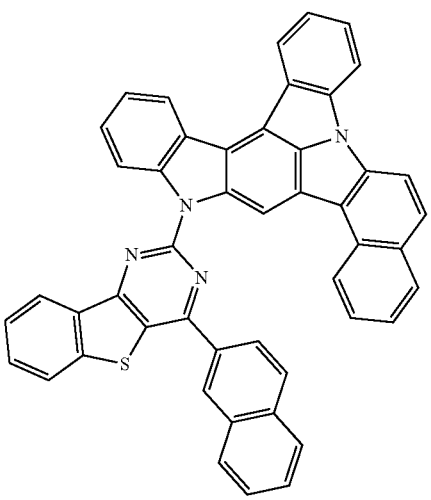
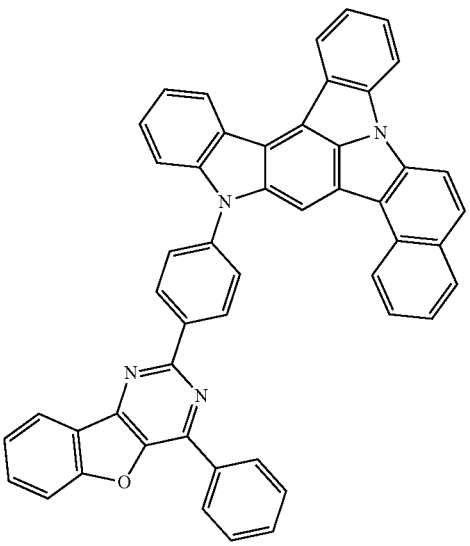

187
-continued
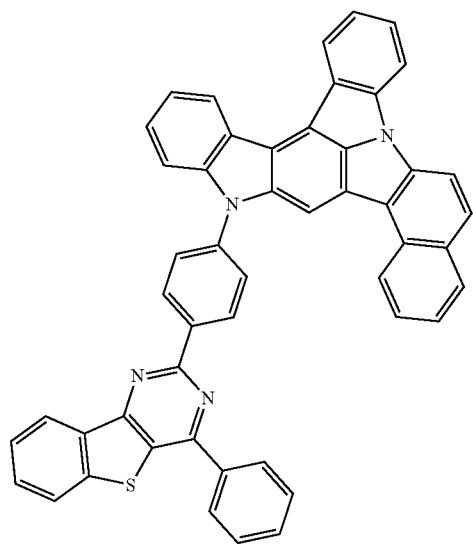
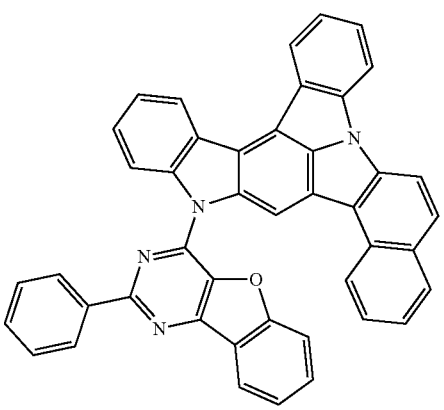
188
-continued
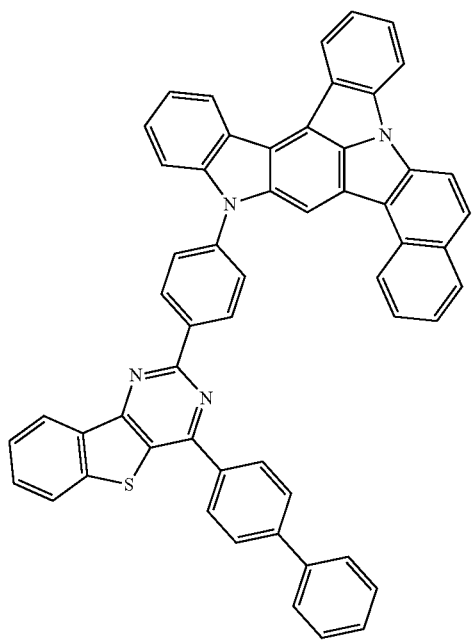
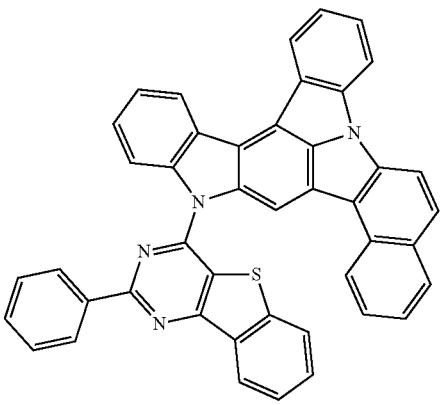

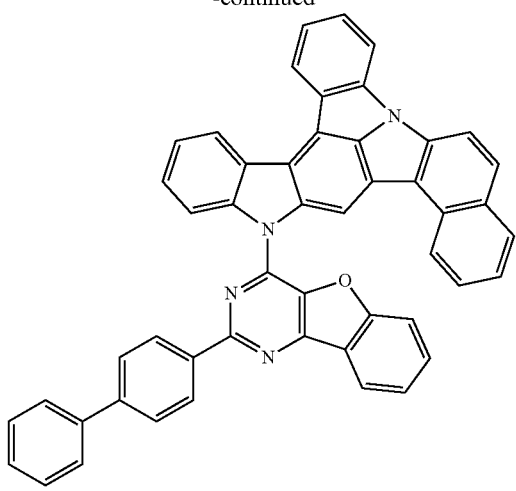
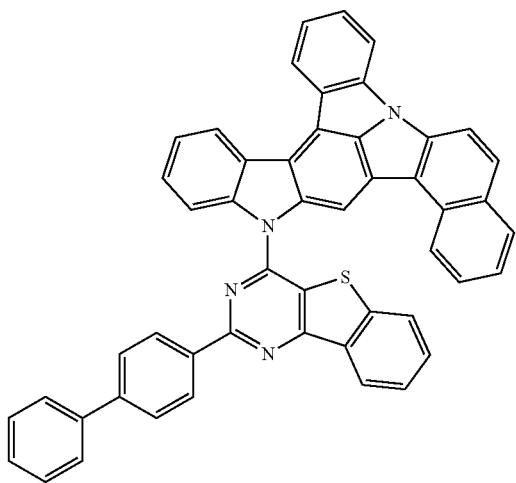
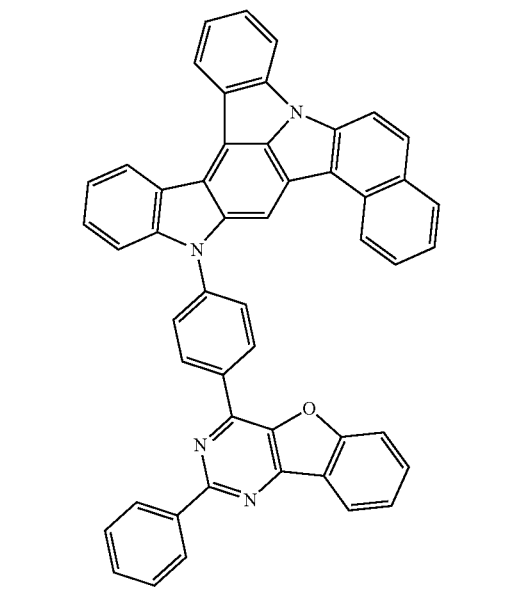
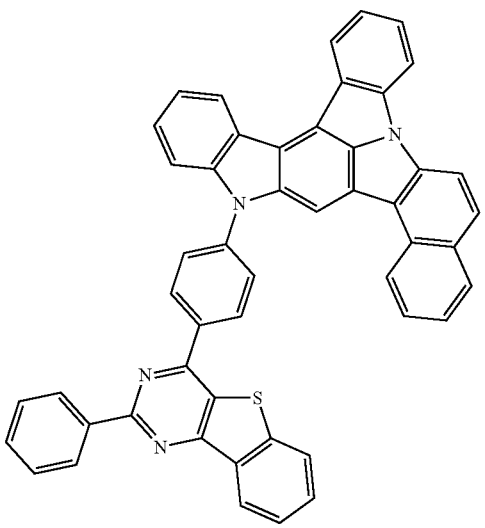
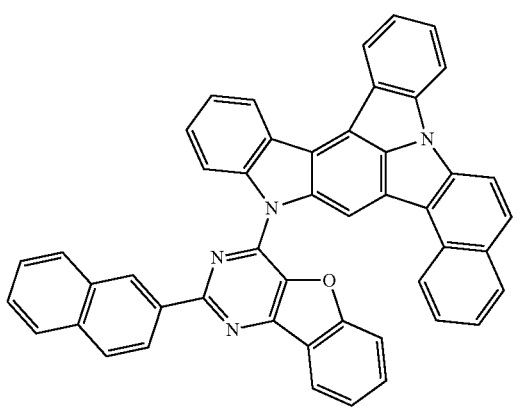
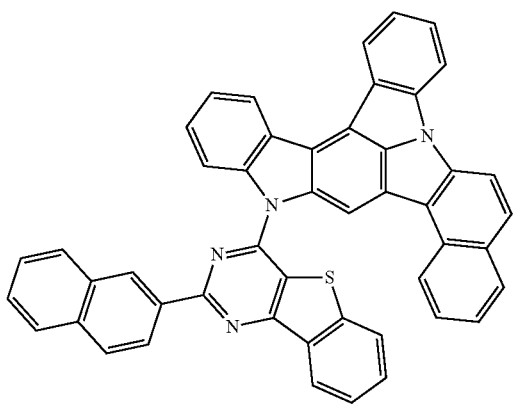

191
-continued
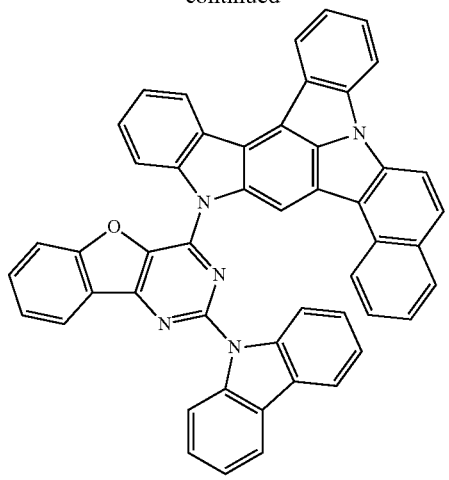
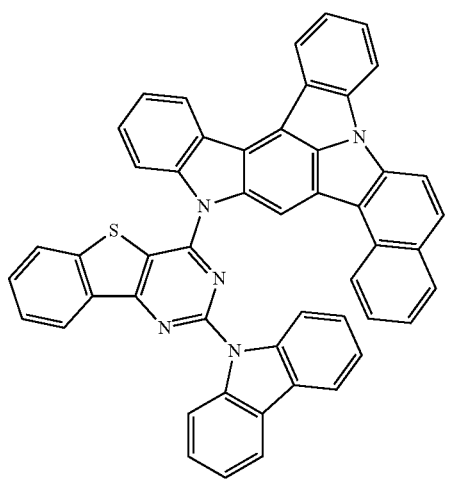
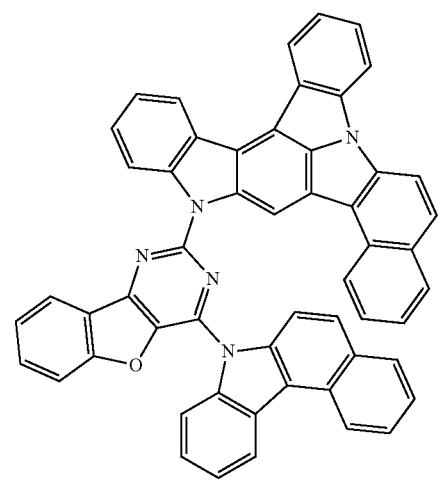
192
-continued
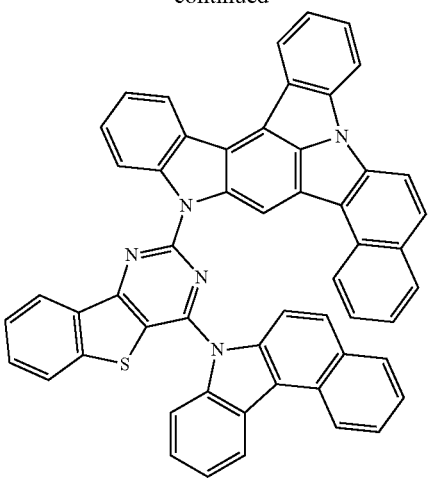
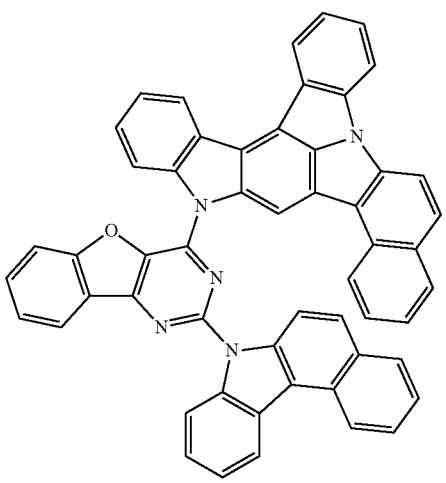
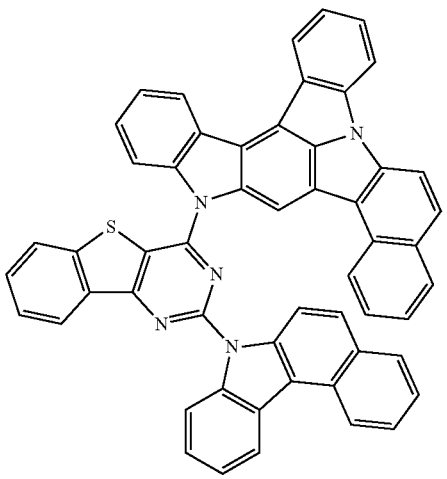

-continued
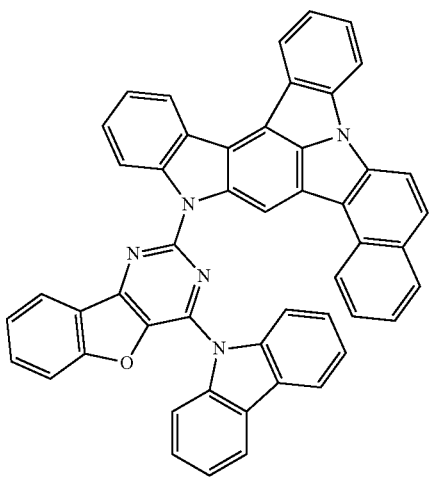
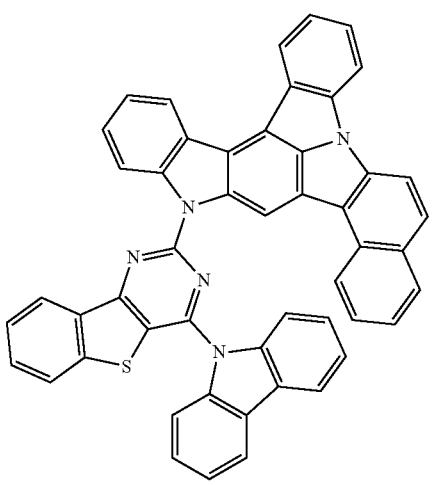
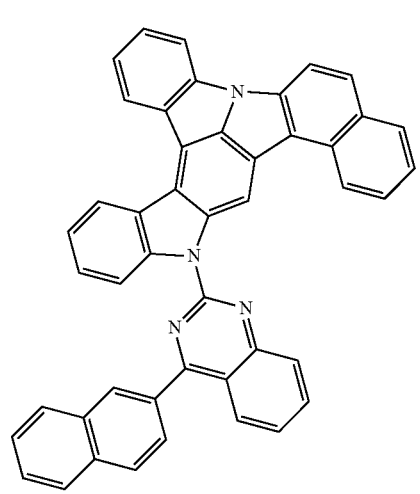
-continued
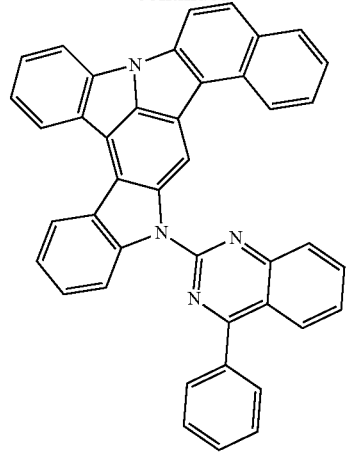
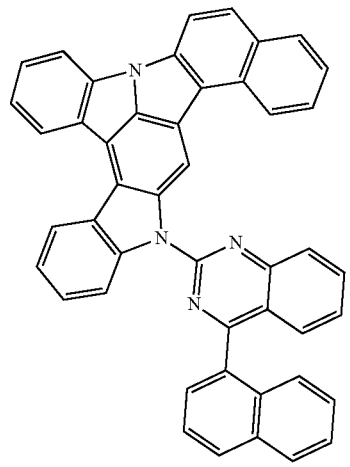
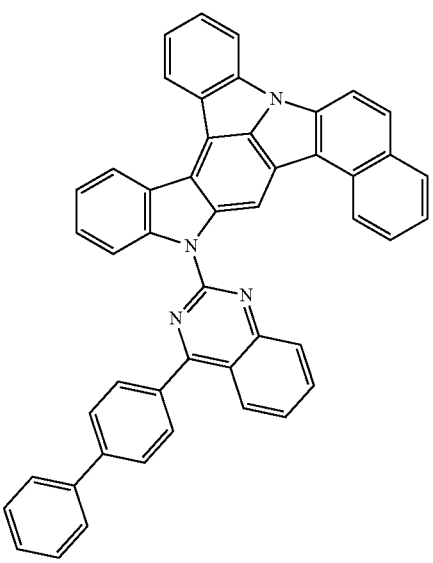

-continued
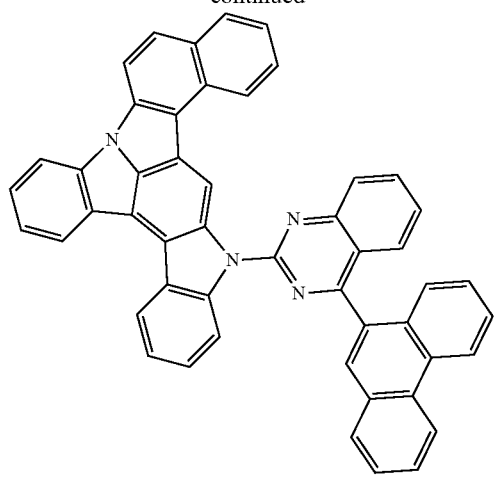
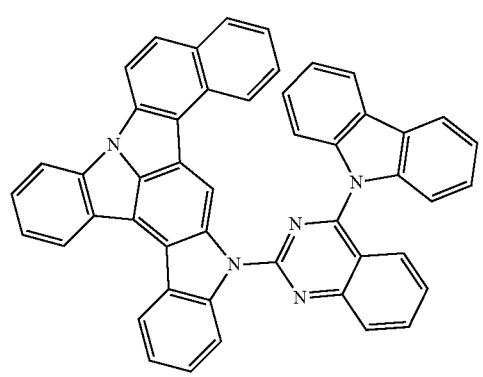
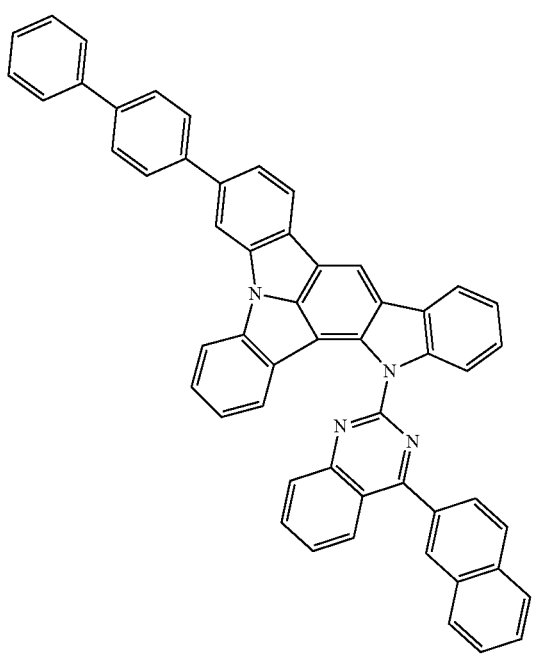
-continued
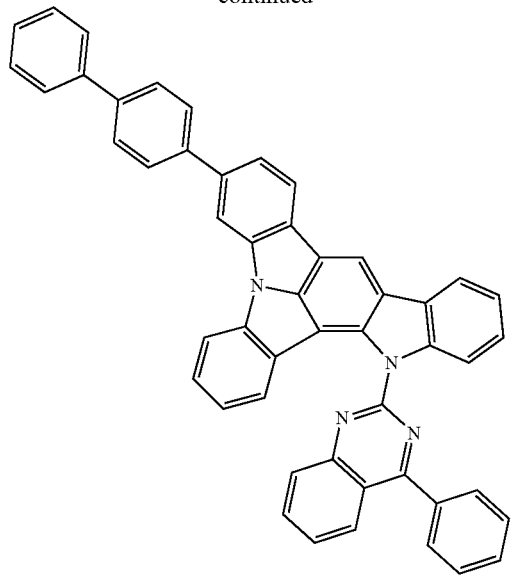
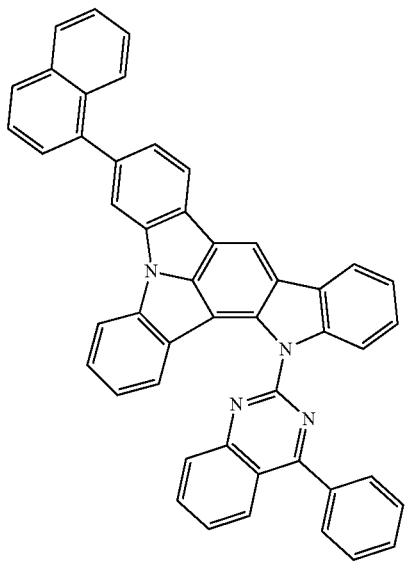
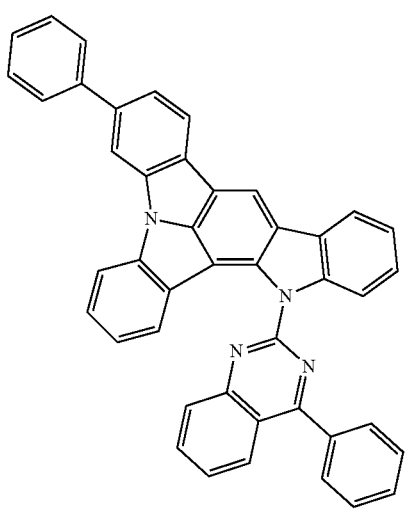

197
-continued
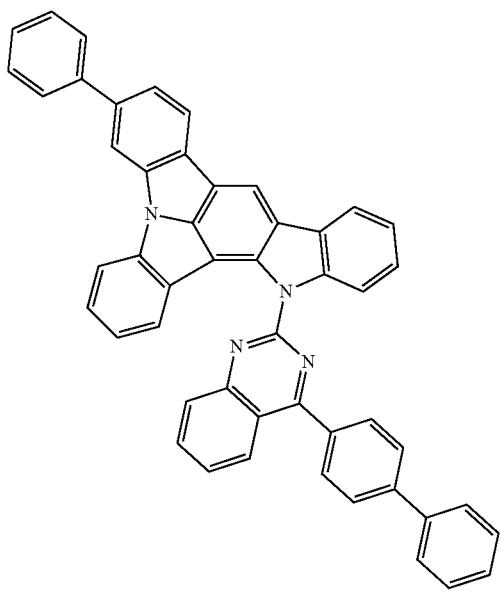
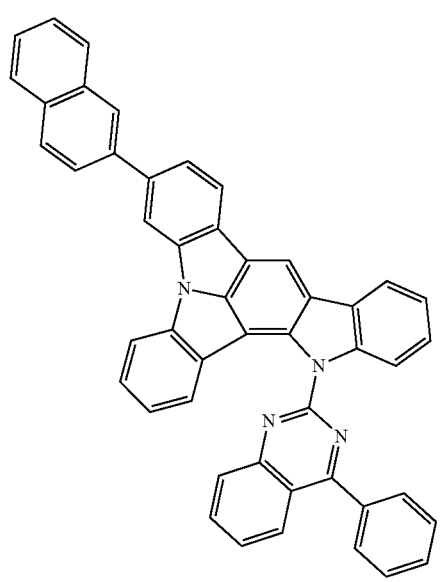
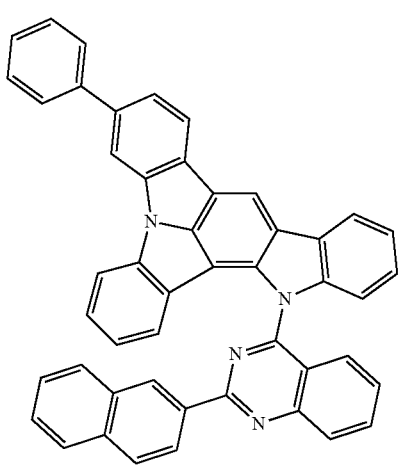
198
-continued
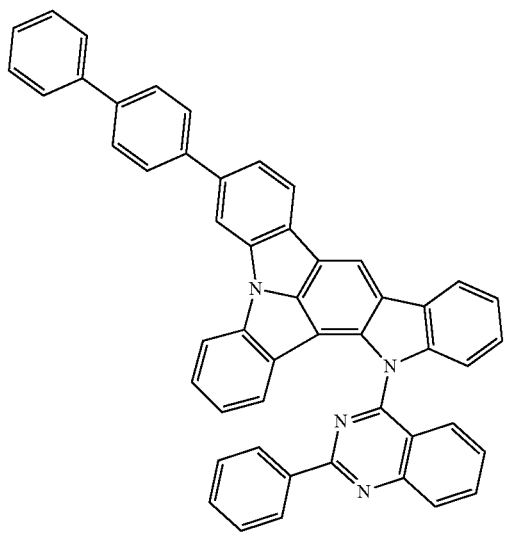
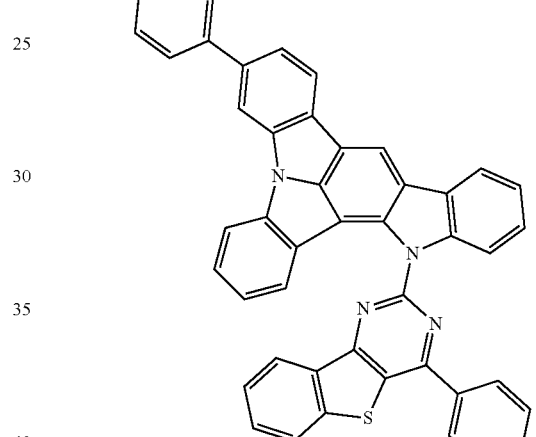
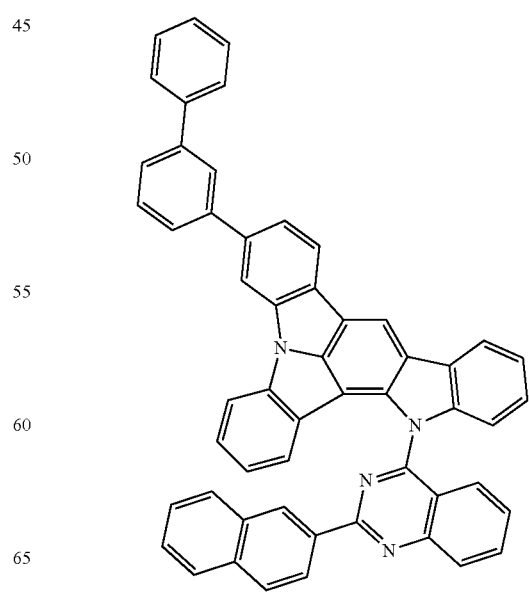

199
-continued
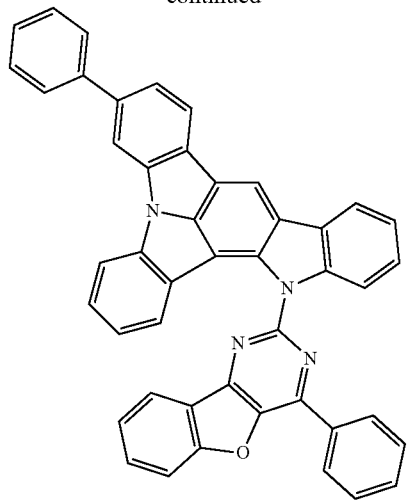
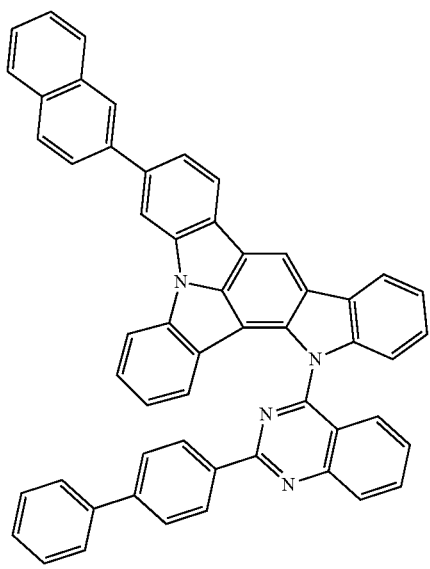
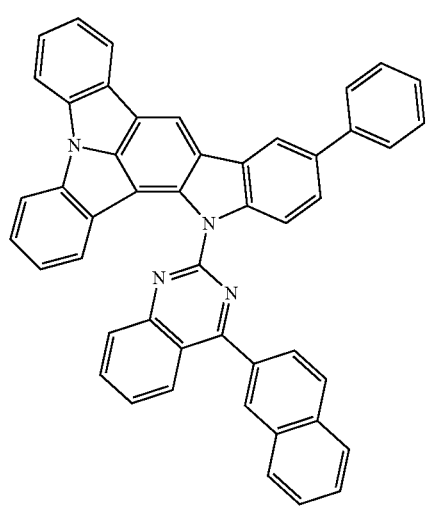
200
-continued
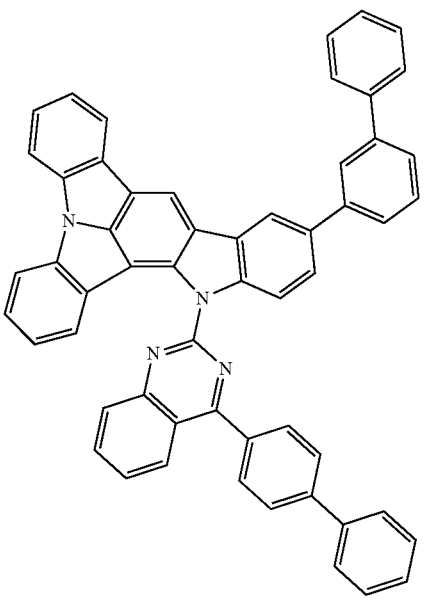
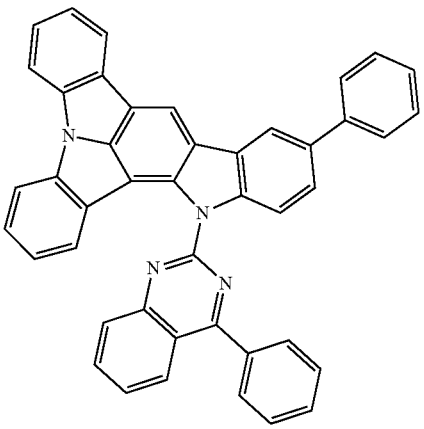
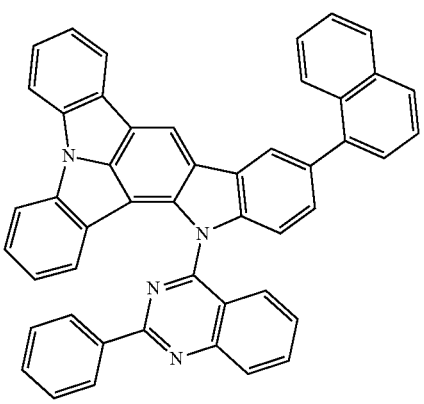

201
-continued
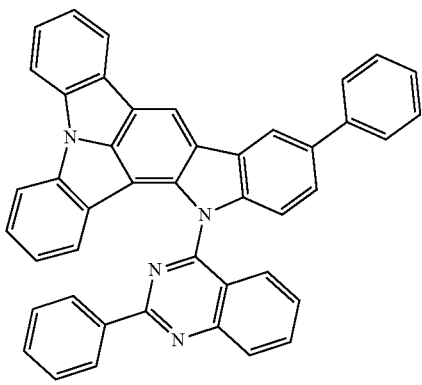
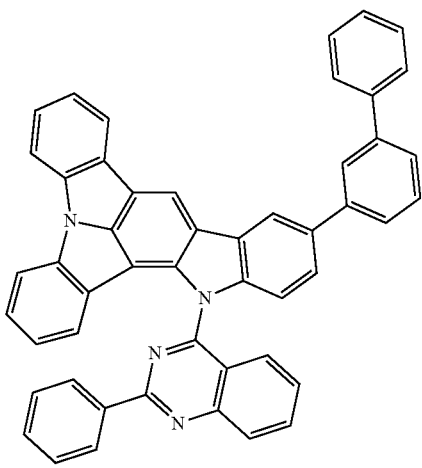
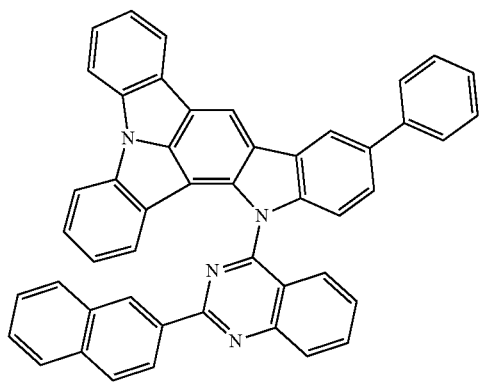
202
-continued
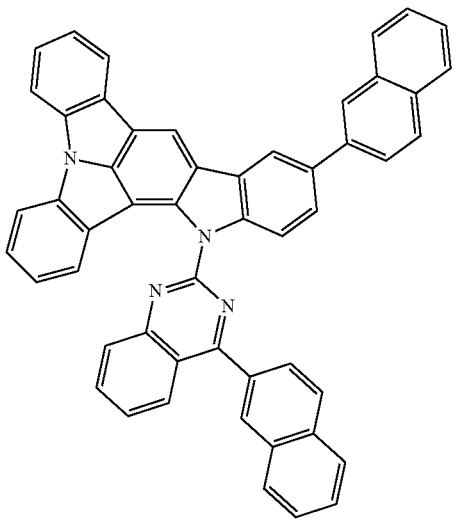
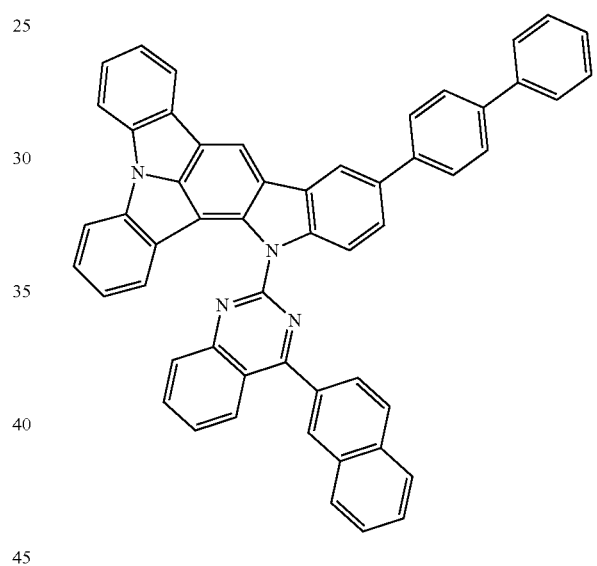
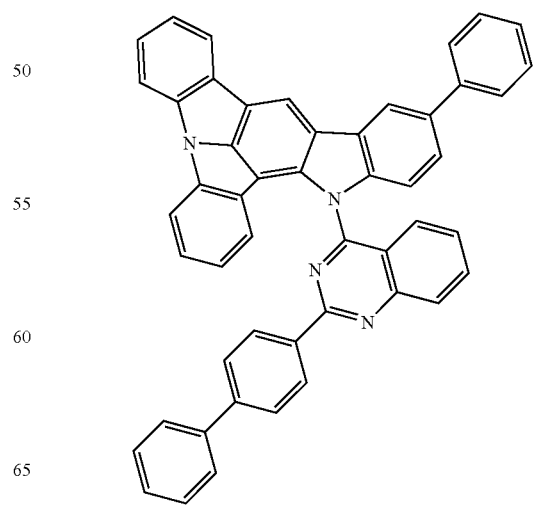

203
-continued
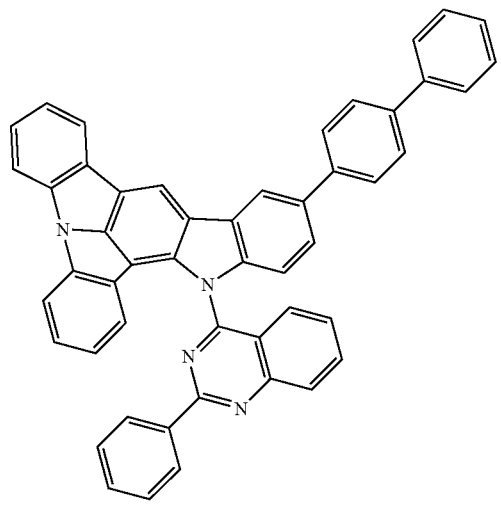
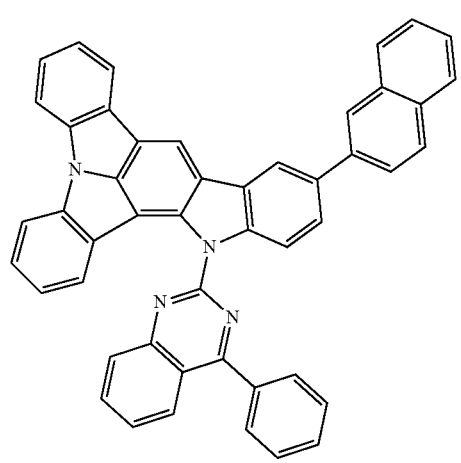
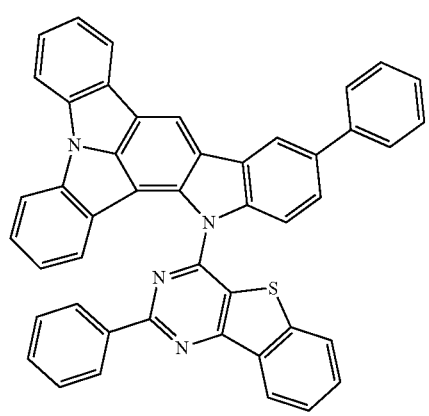
204
-continued
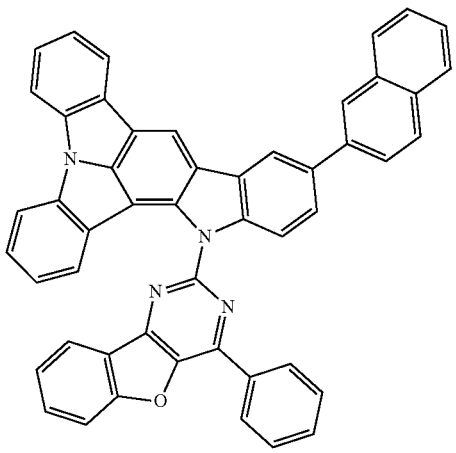
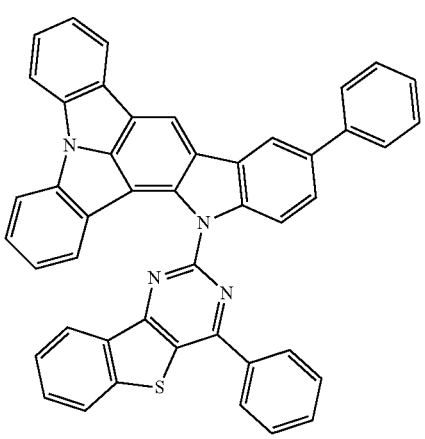
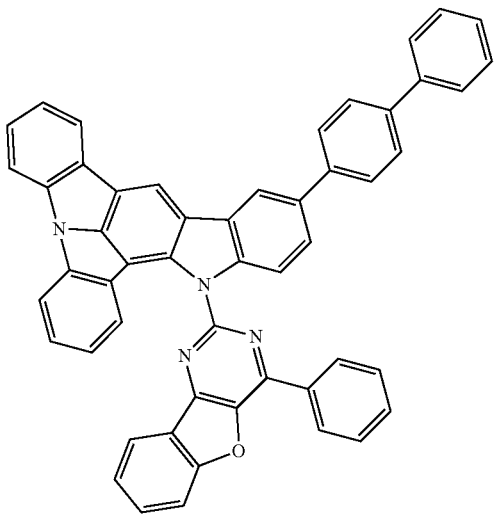

205
-continued
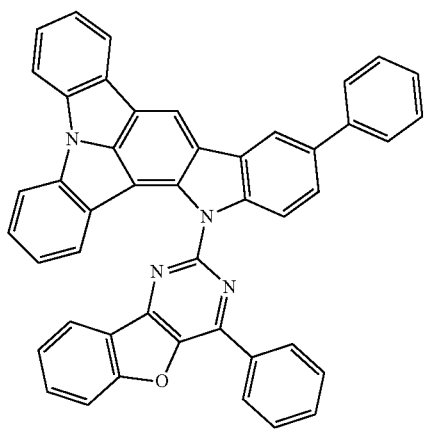
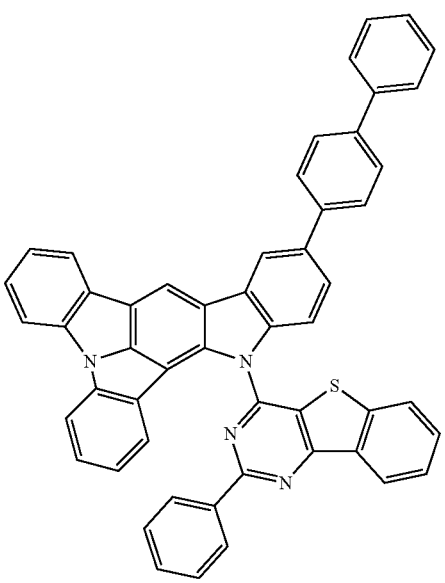
206
-continued
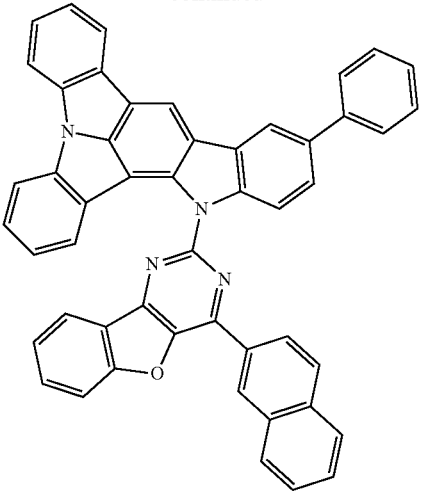
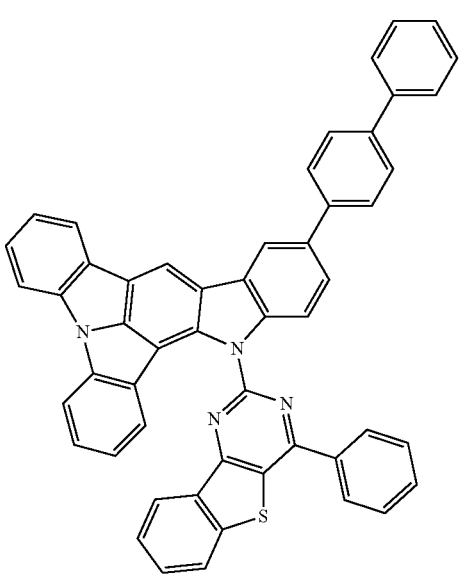
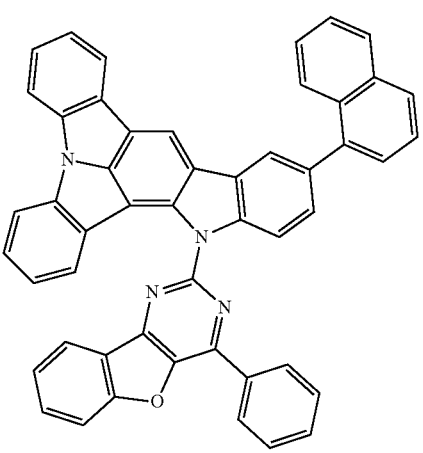

207
-continued
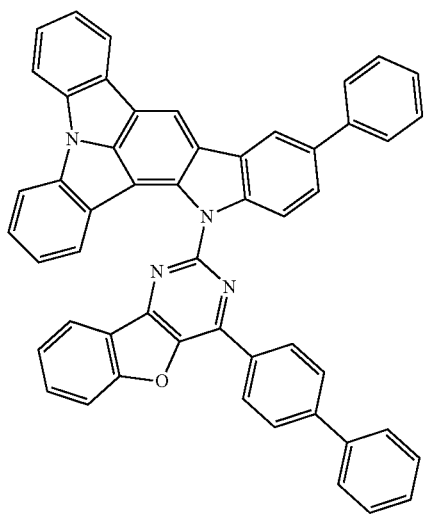
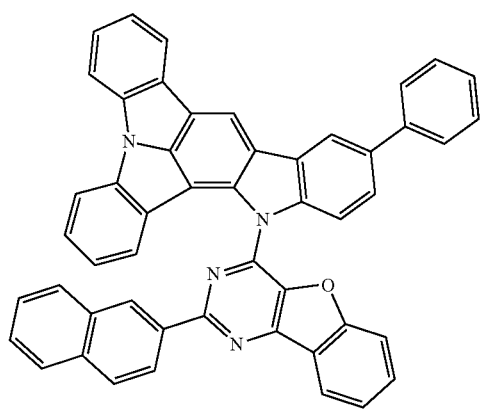
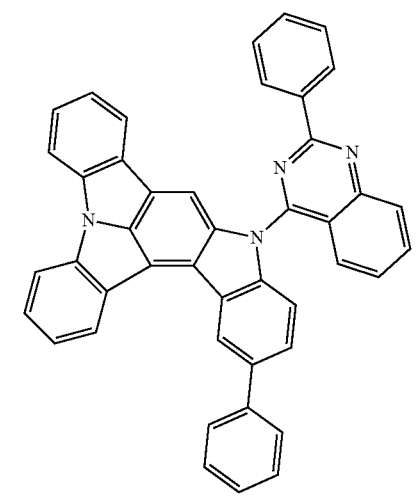
208
-continued
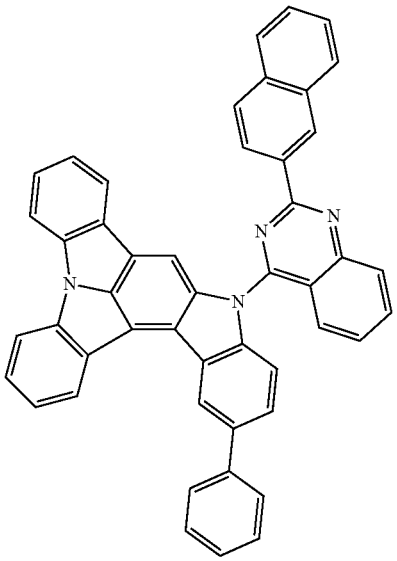
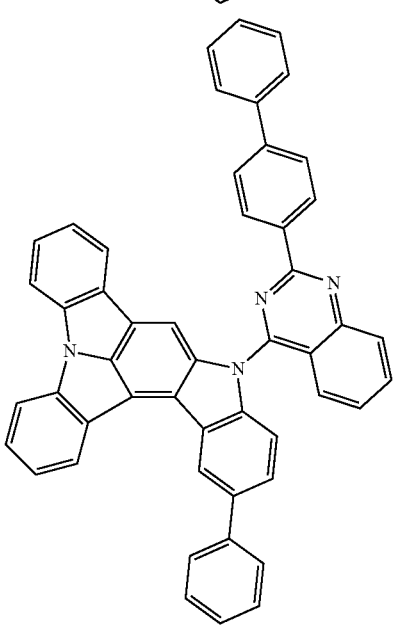
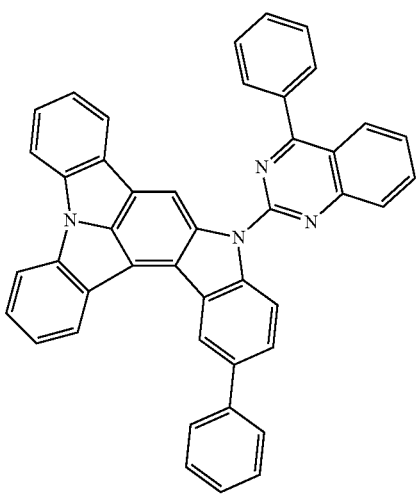

209
-continued
210
-continued
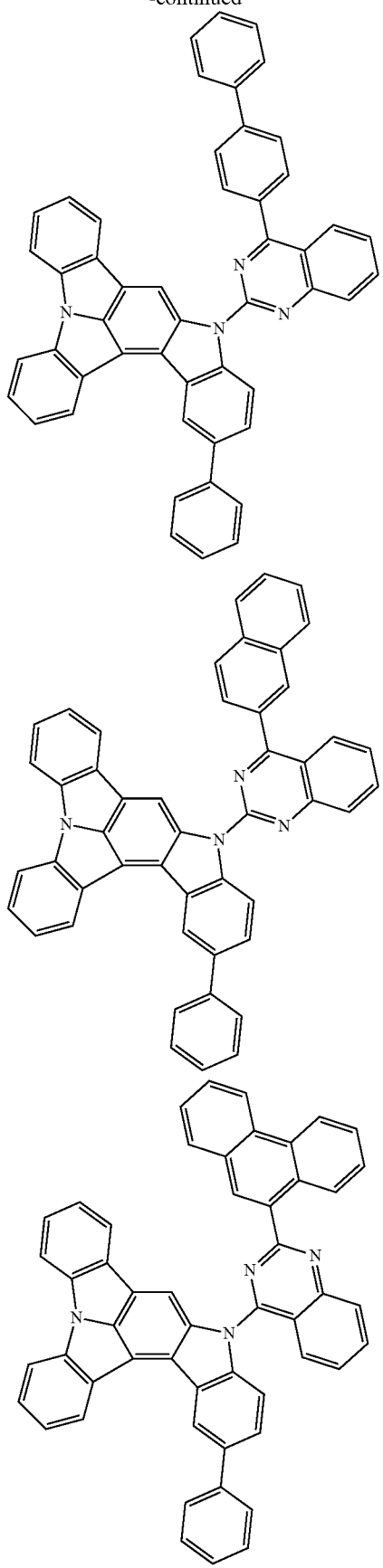
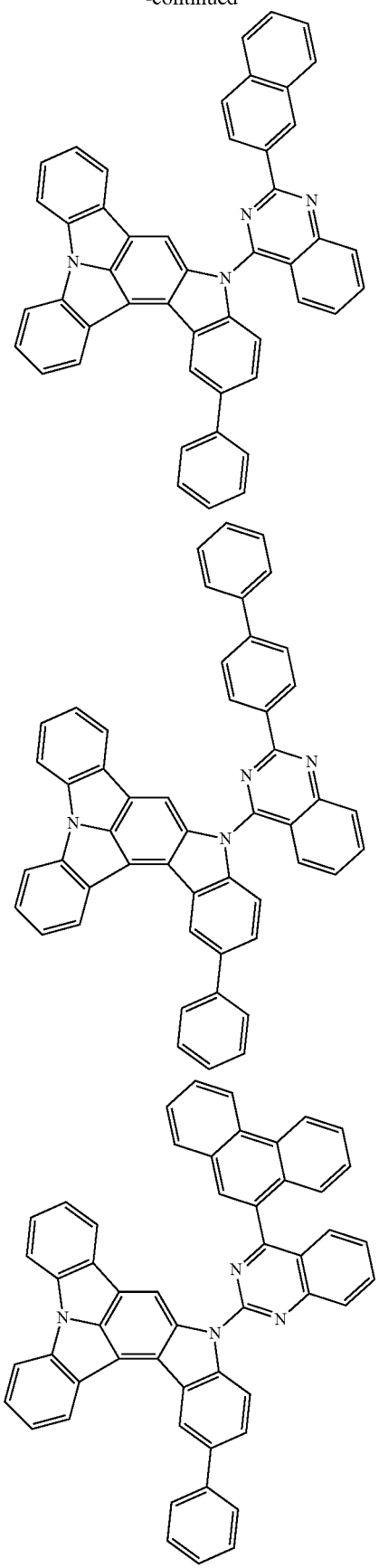

211
-continued
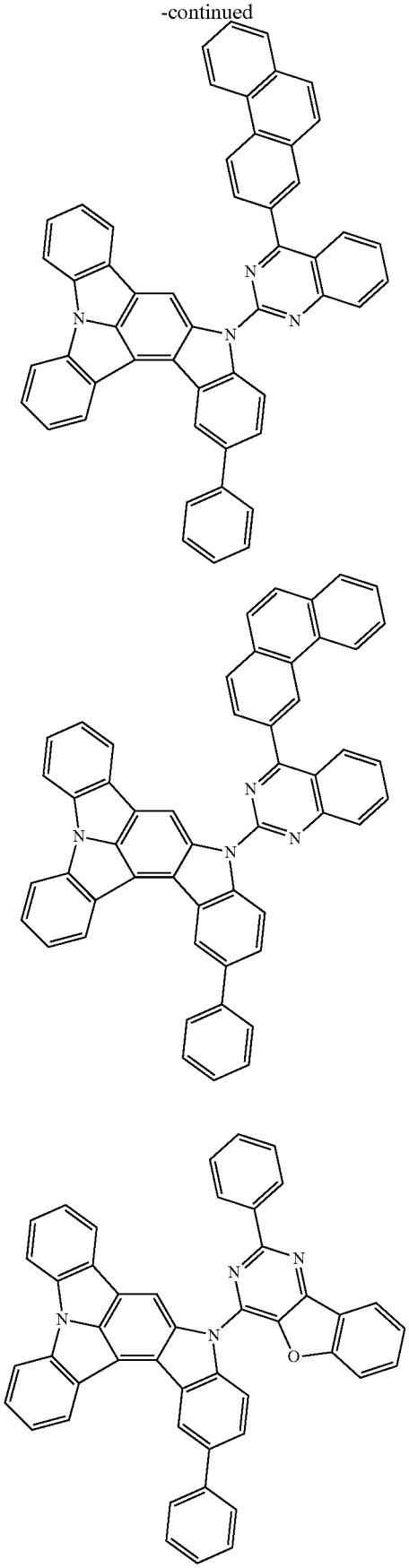
212
-continued
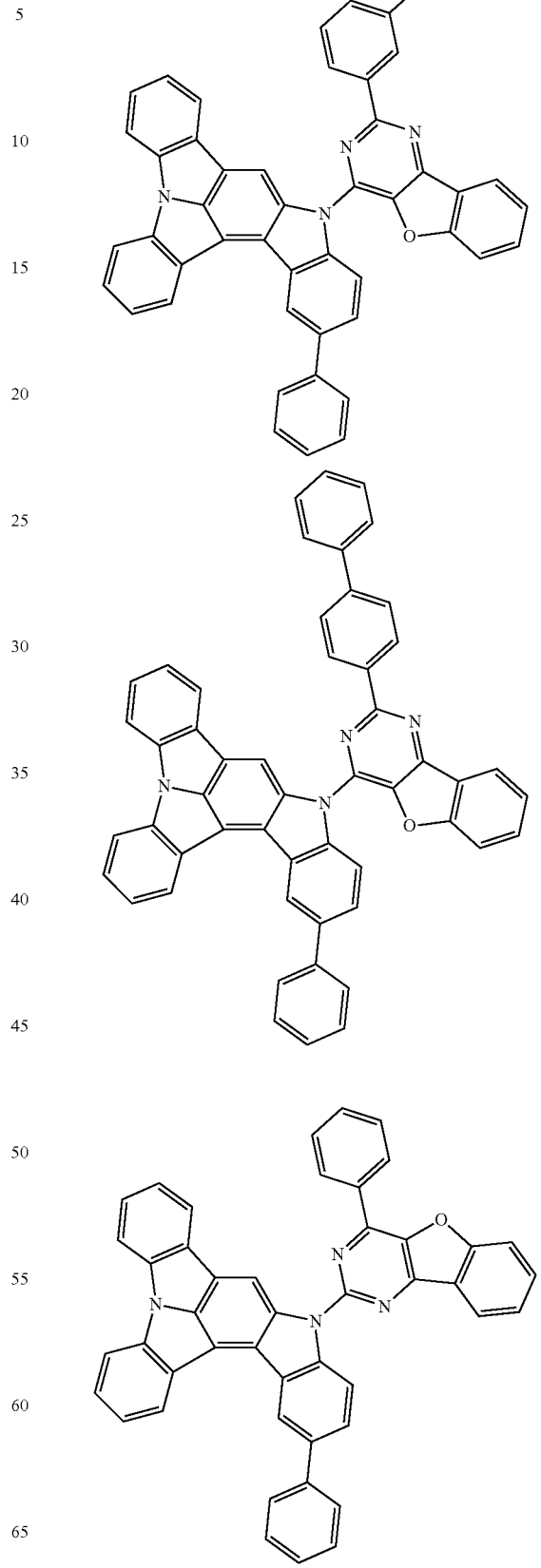

213
-continued
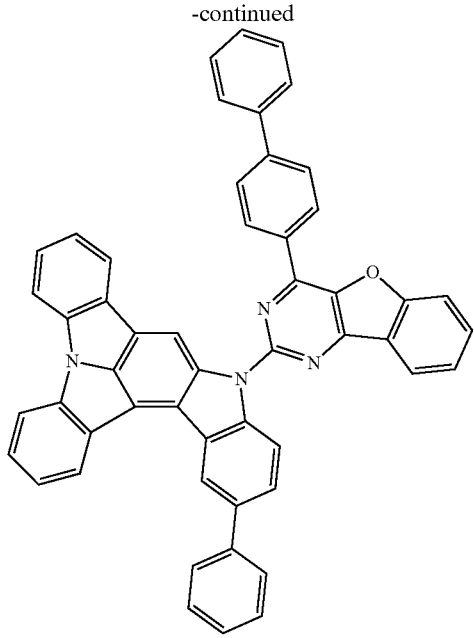
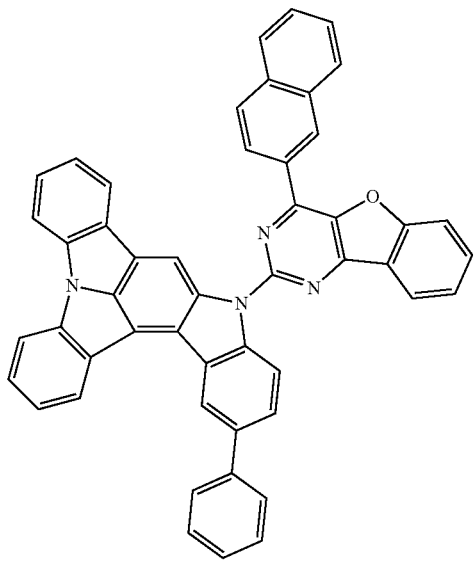
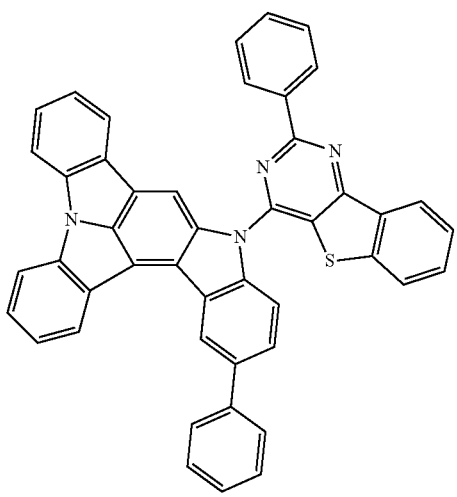
214
-continued
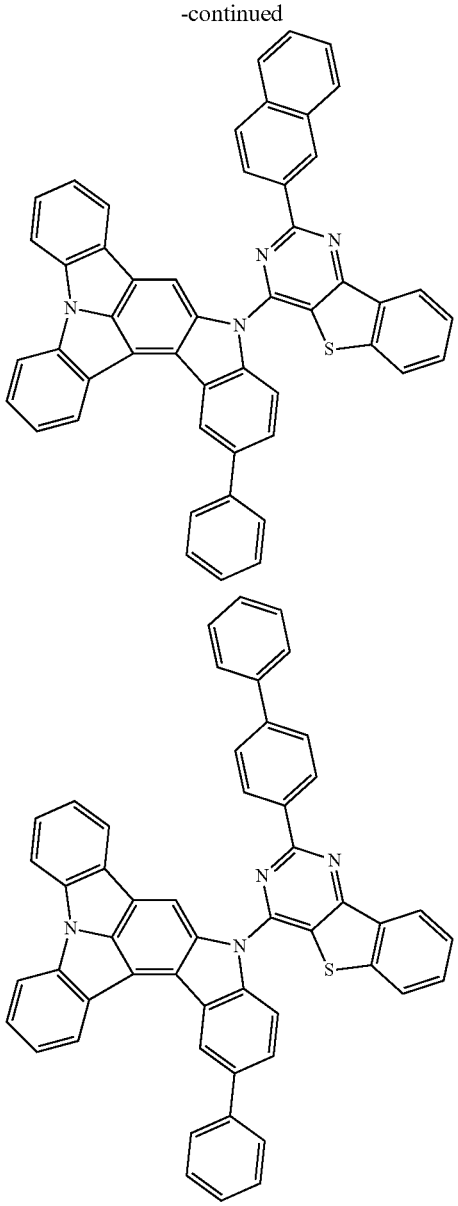
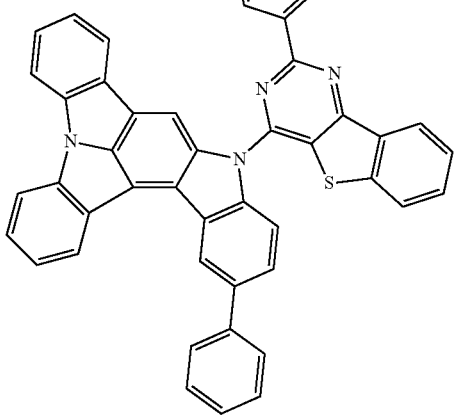
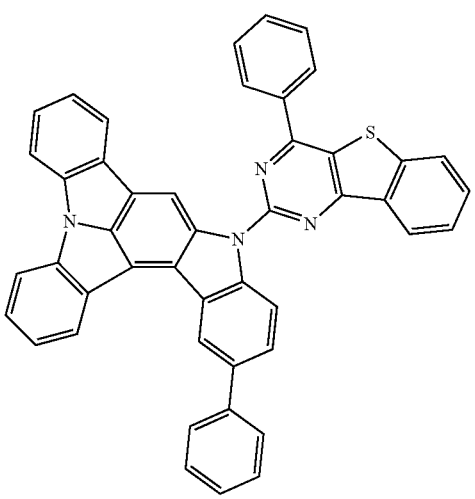

215
-continued
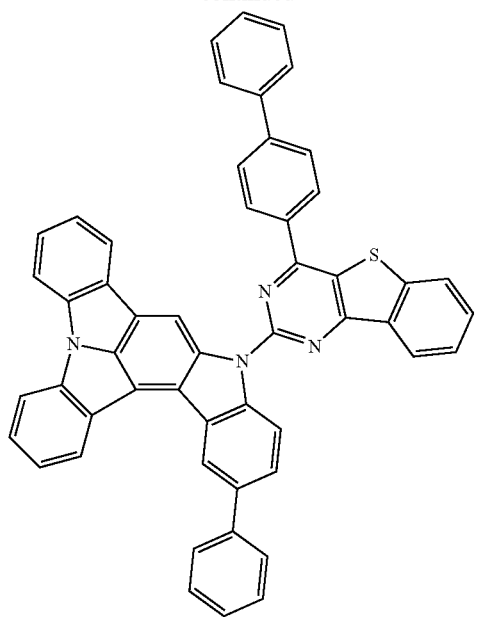
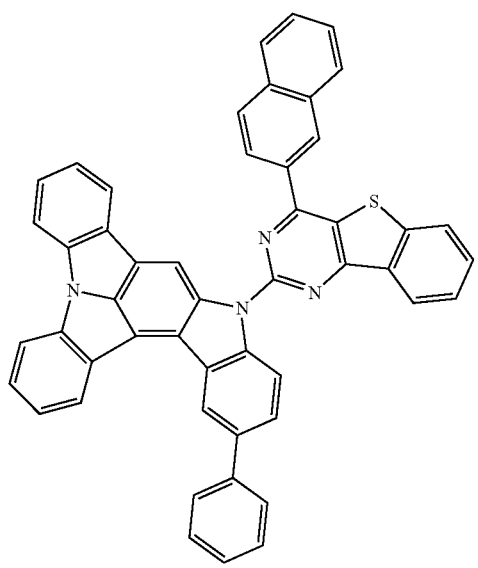
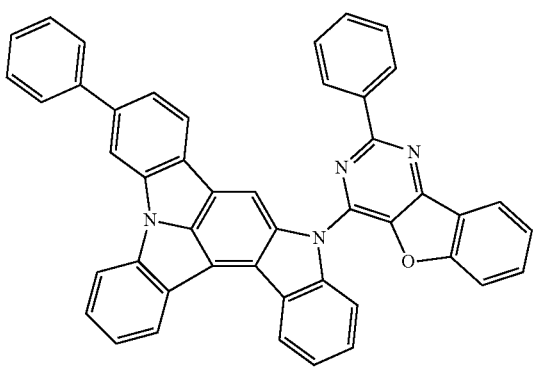
216
-continued
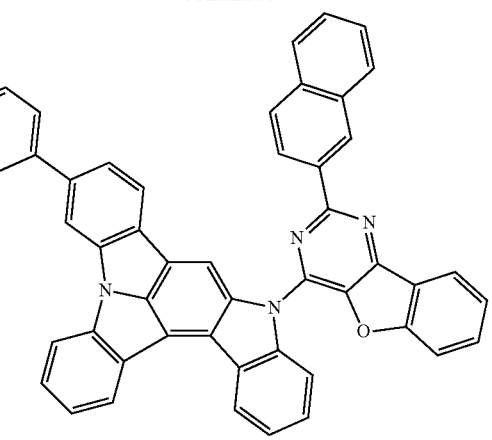
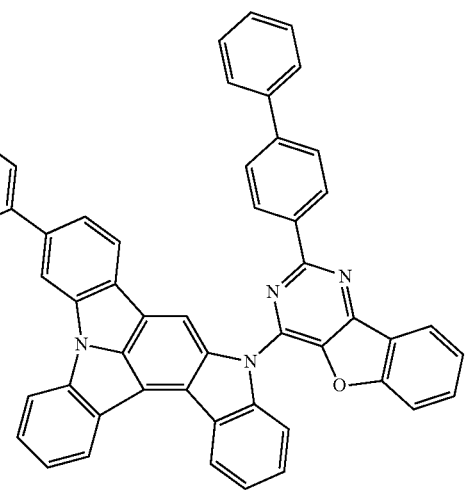
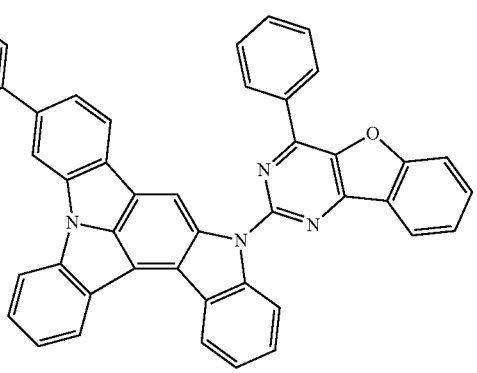

217
-continued
218
-continued
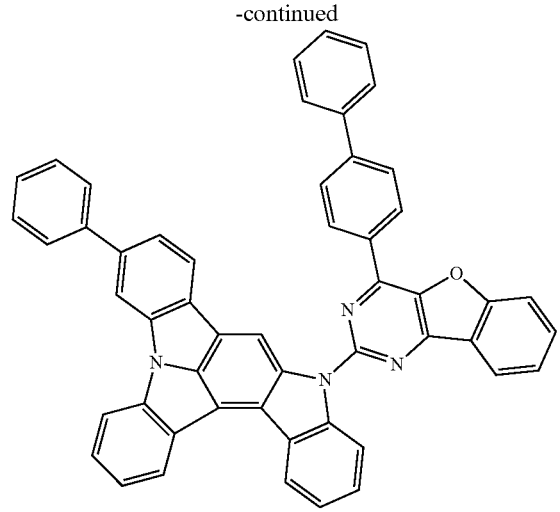
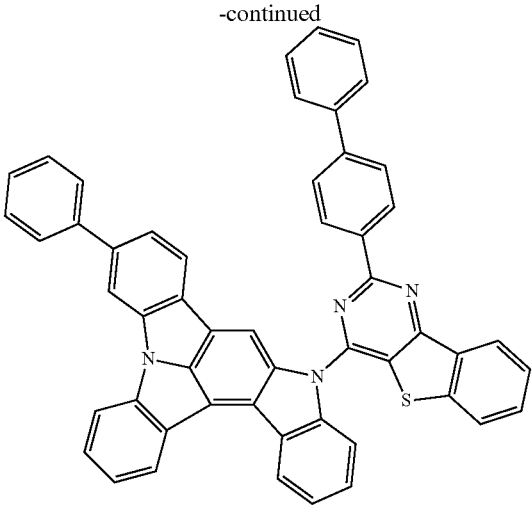

219
-continued
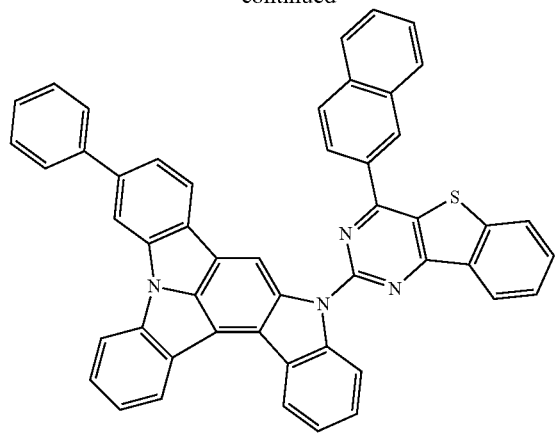
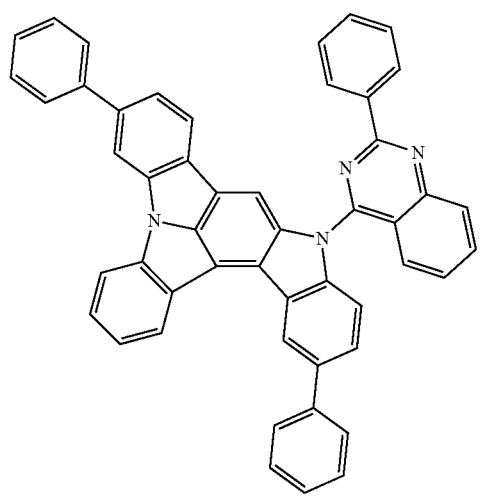
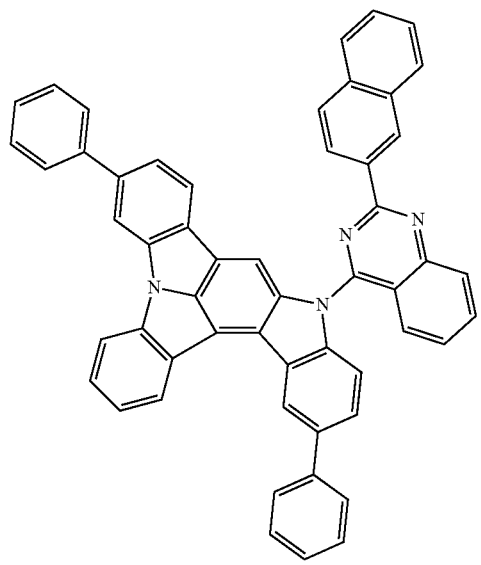
220
-continued
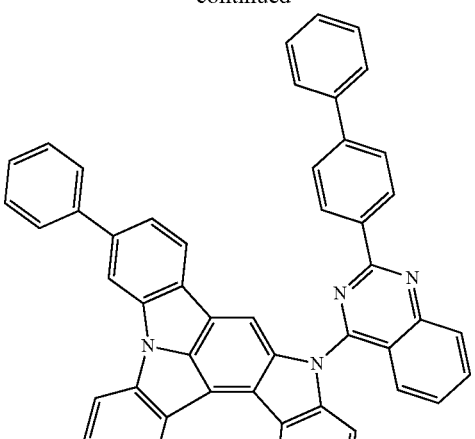
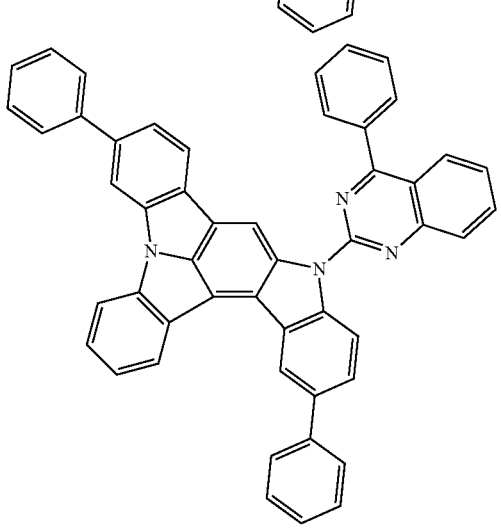
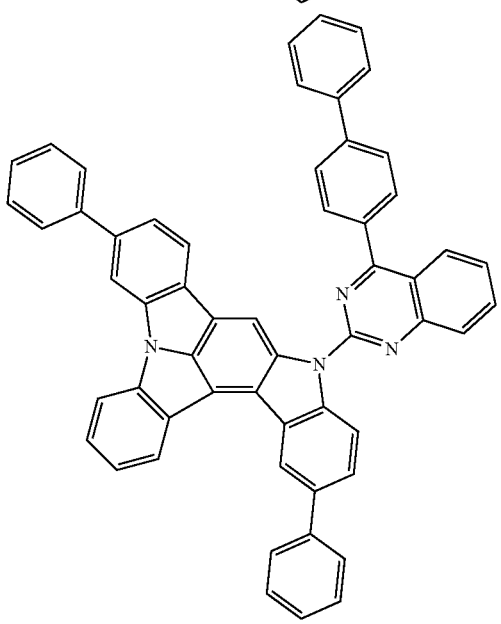

221
-continued
222
-continued
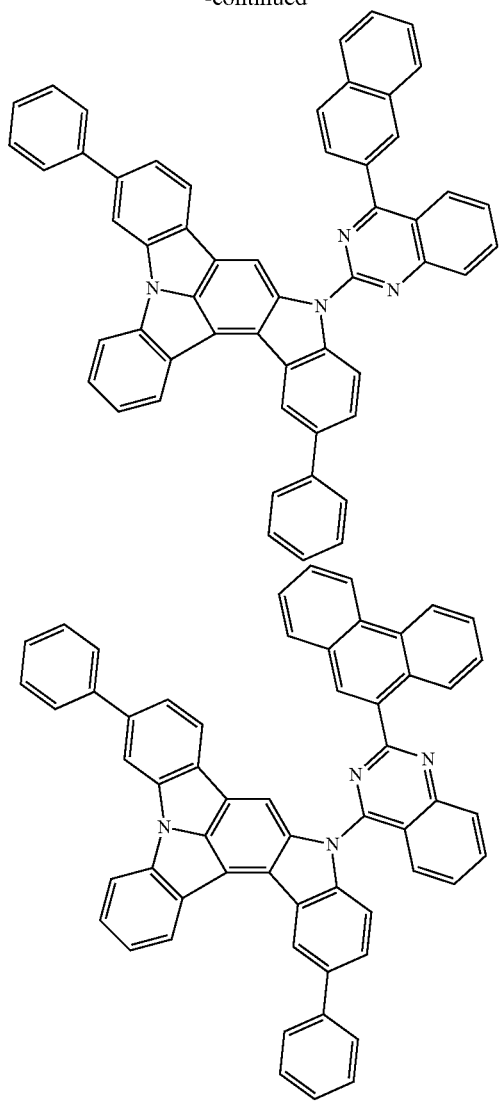
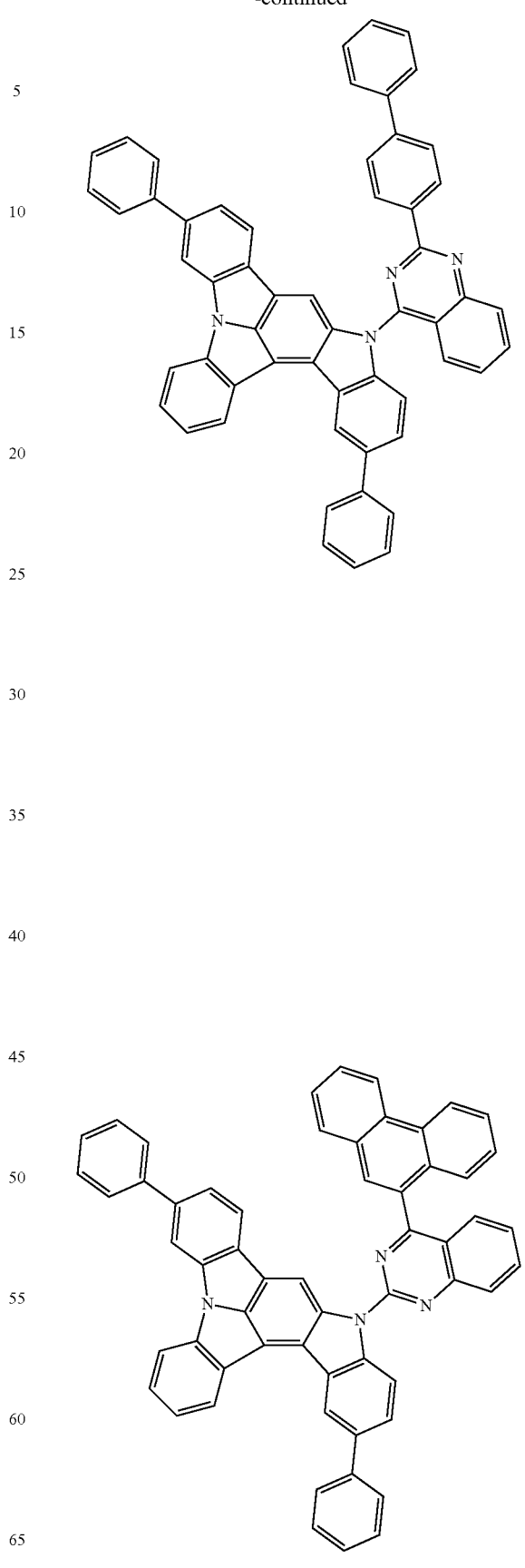

223
-continued
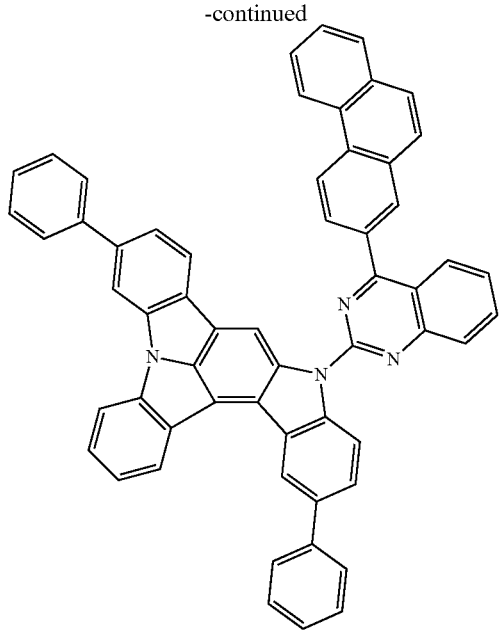
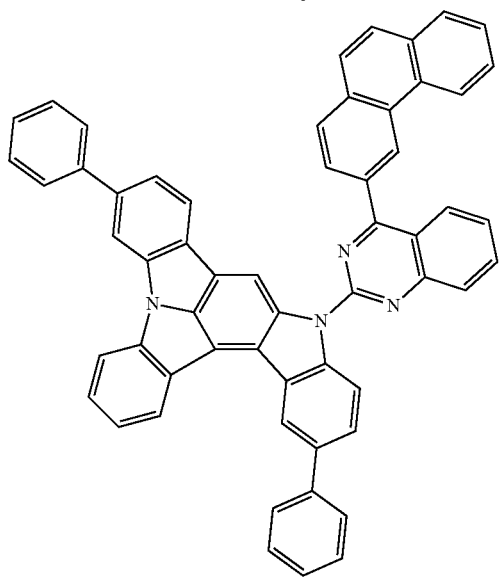
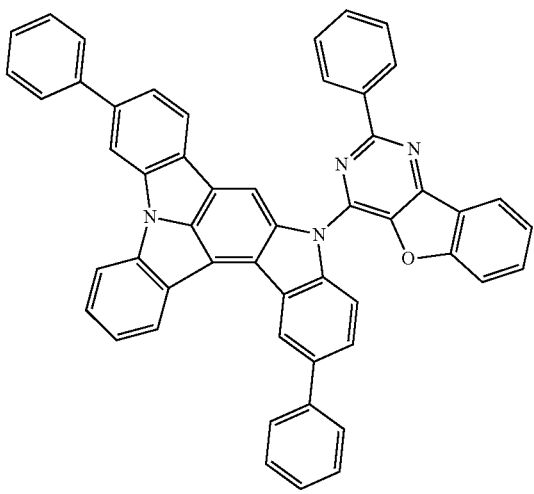
224
-continued
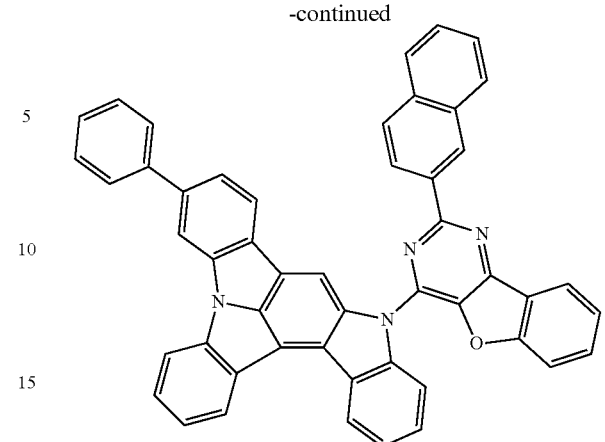
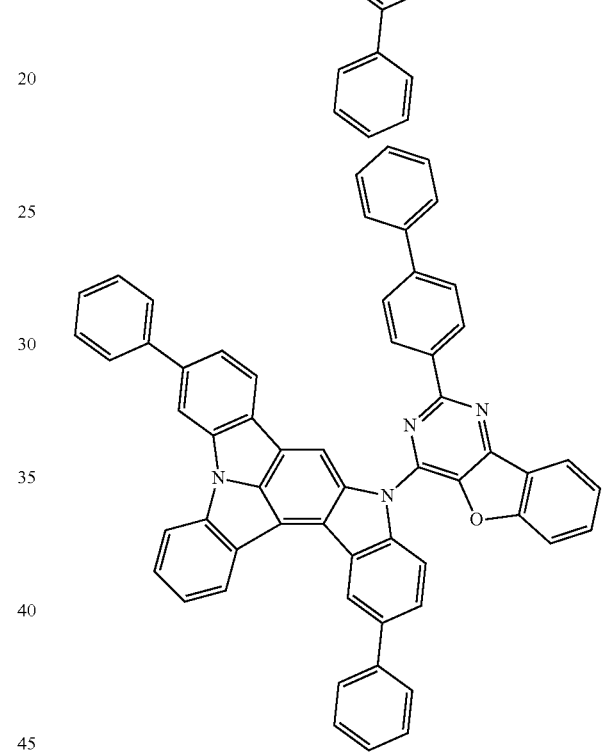
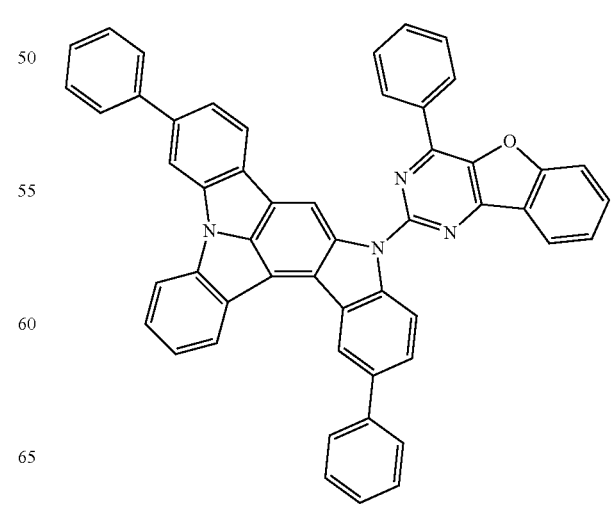

225
-continued
226
-continued
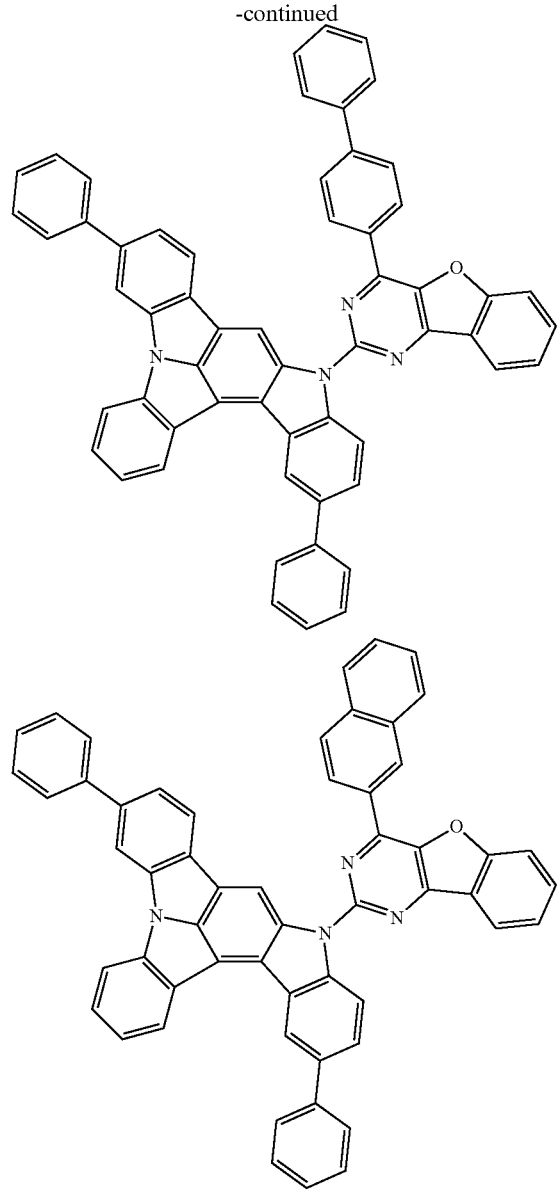
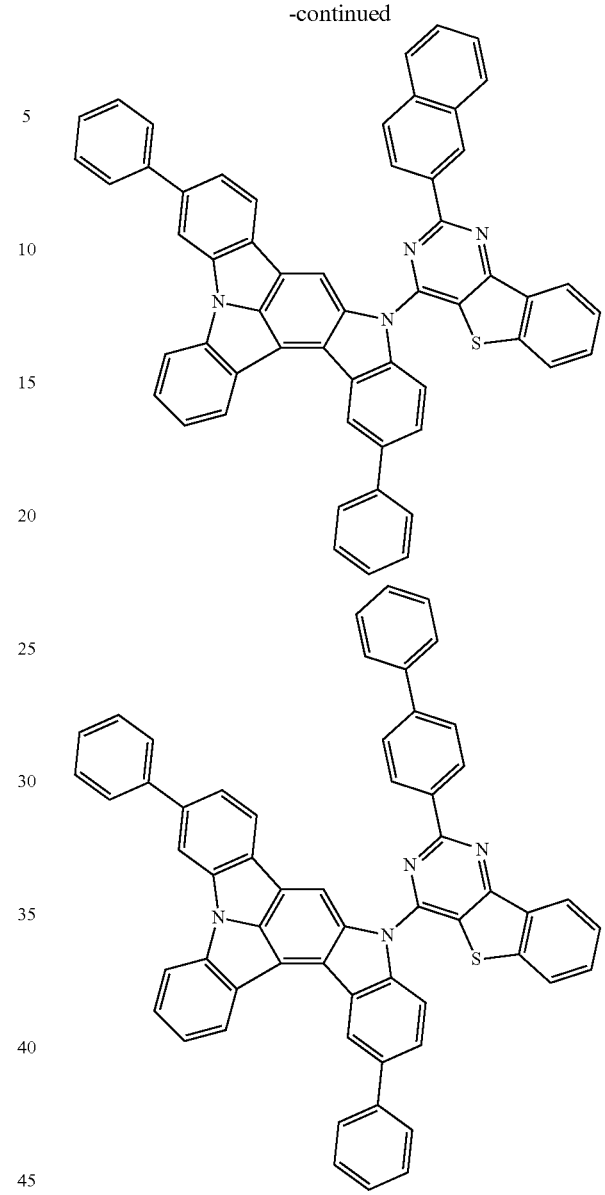
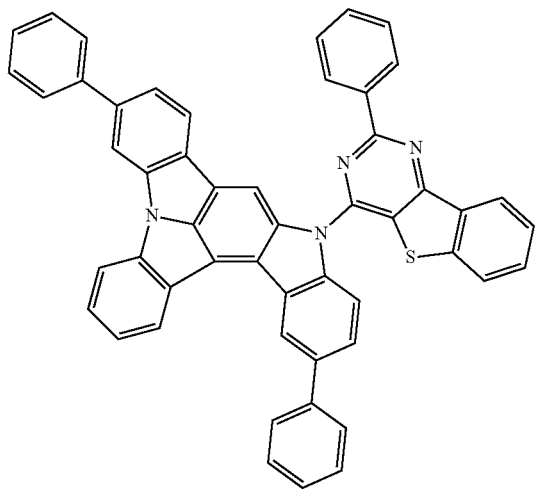

227
-continued
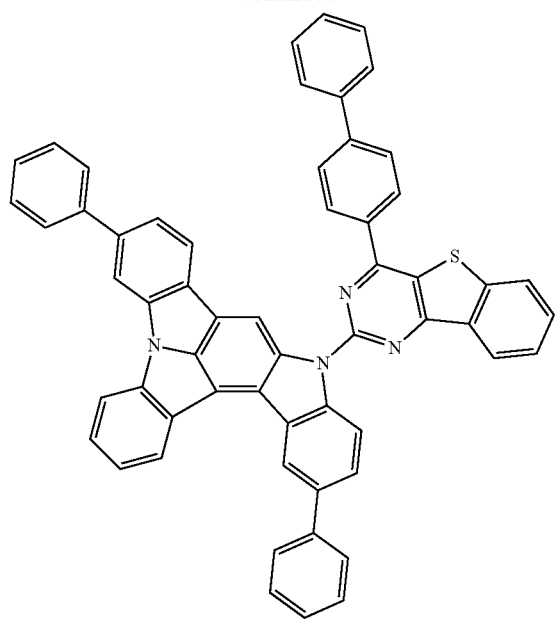
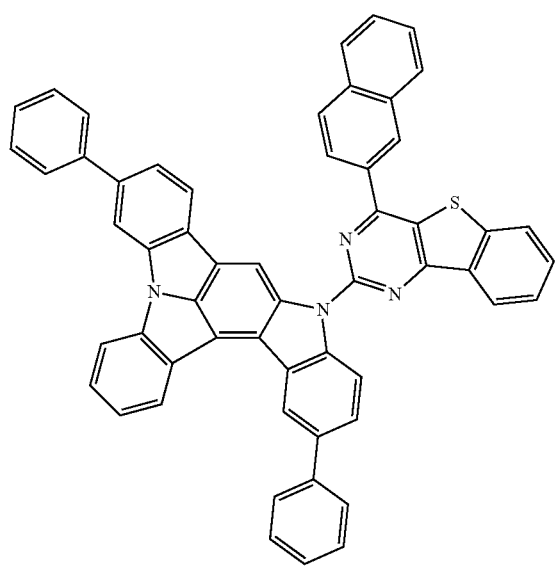
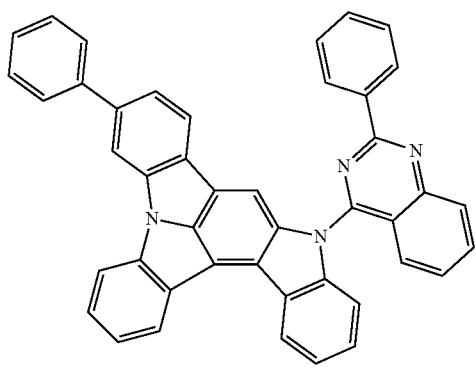
228
-continued
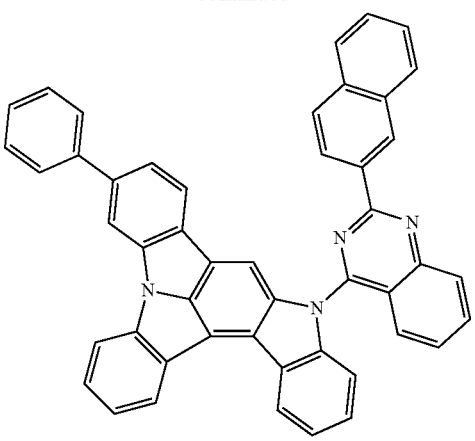
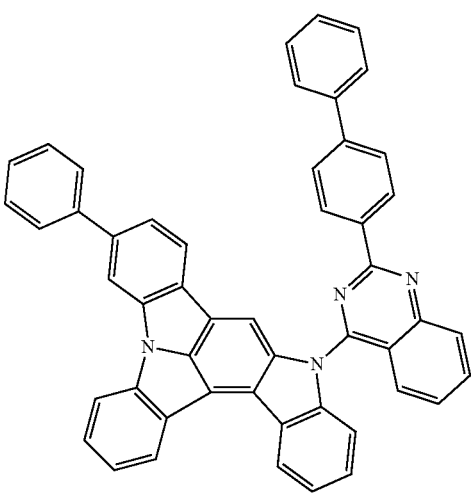
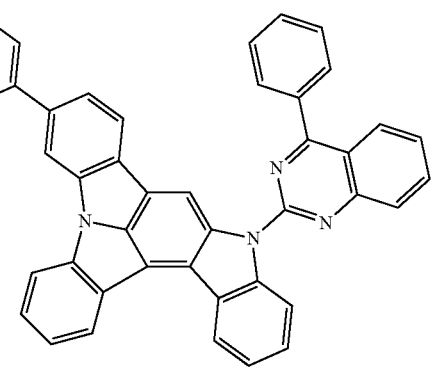

229
-continued
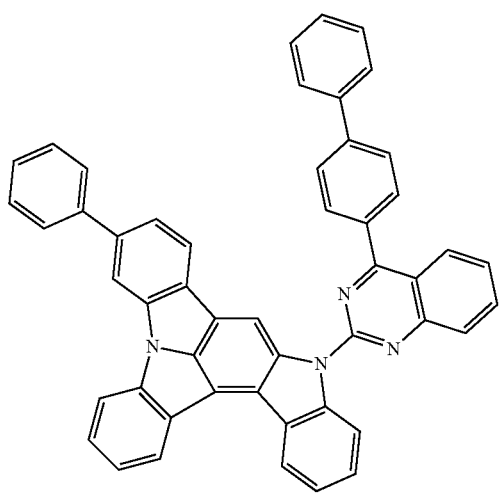
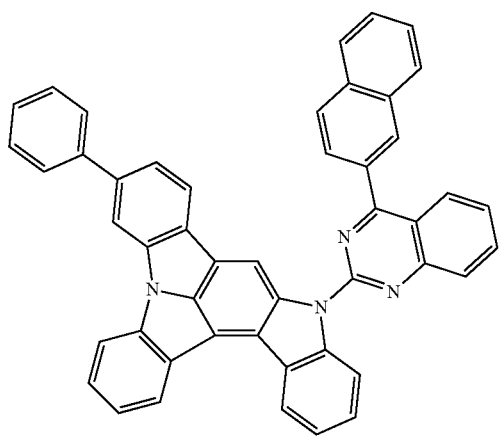
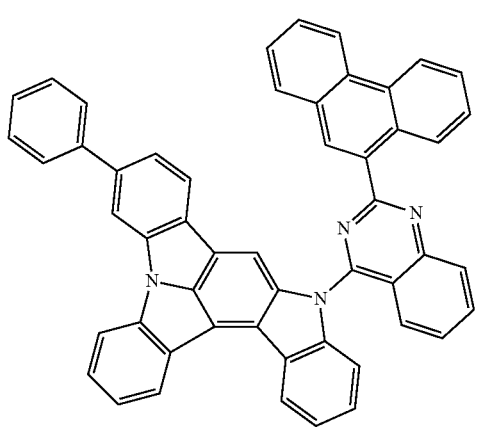
230
-continued
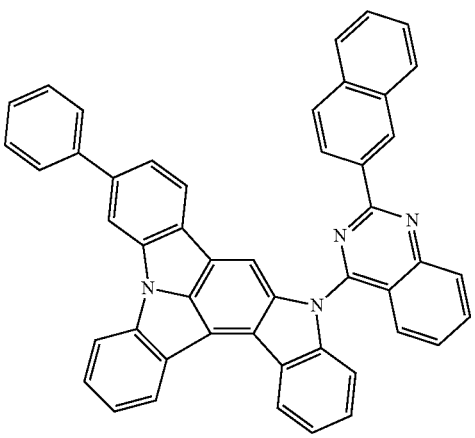
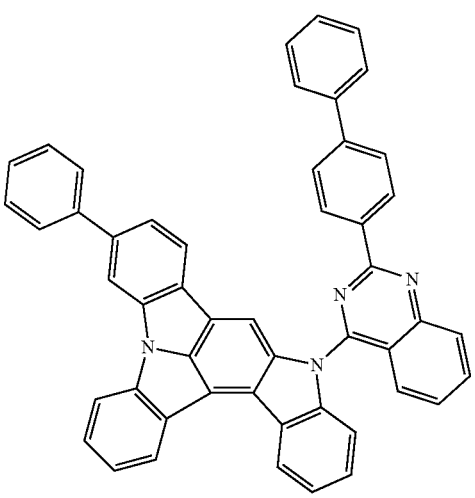
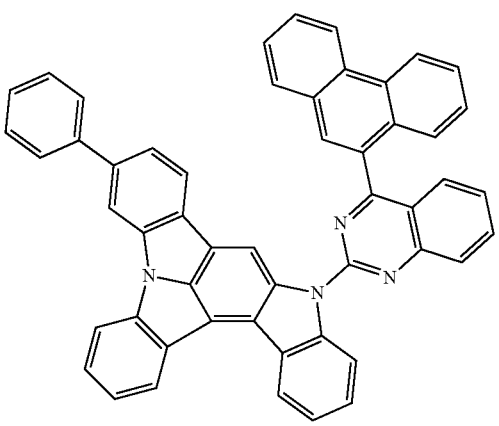

231
-continued
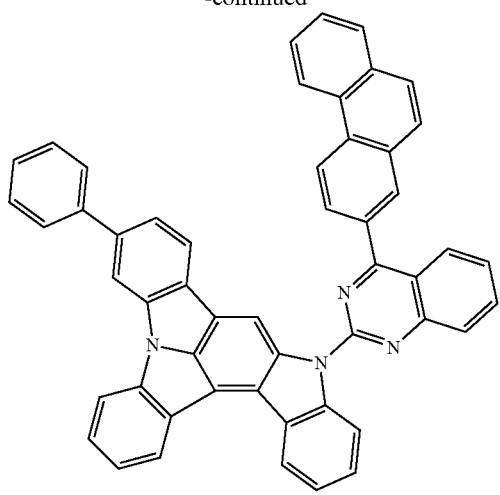
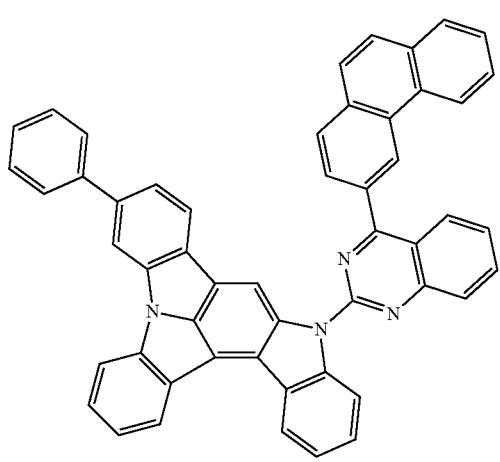
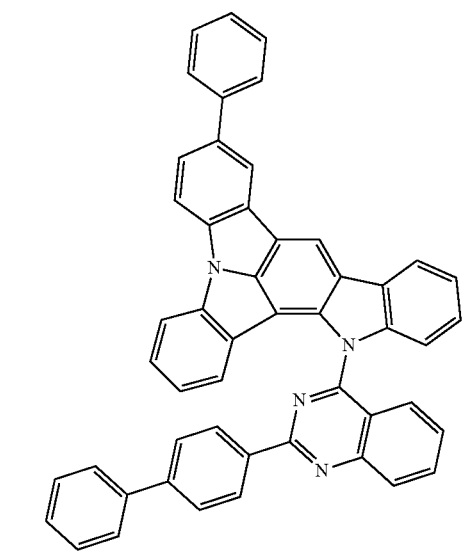
232
-continued
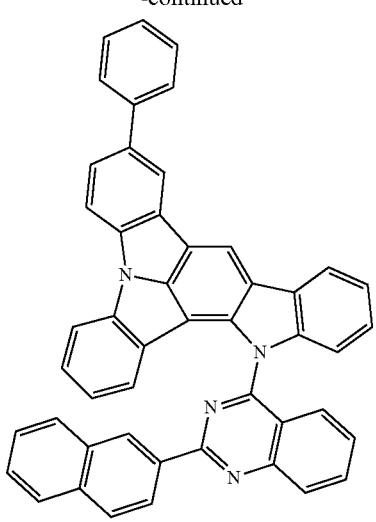
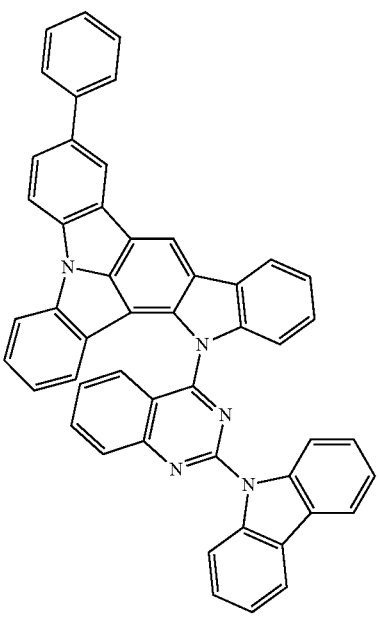
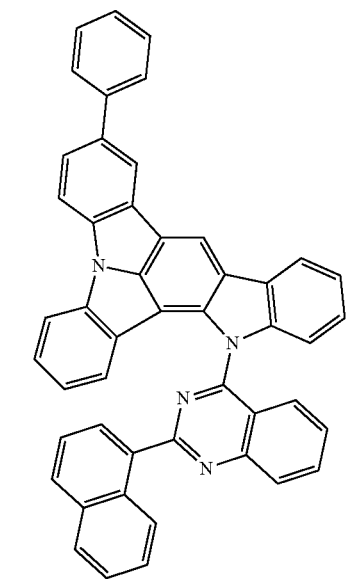

233
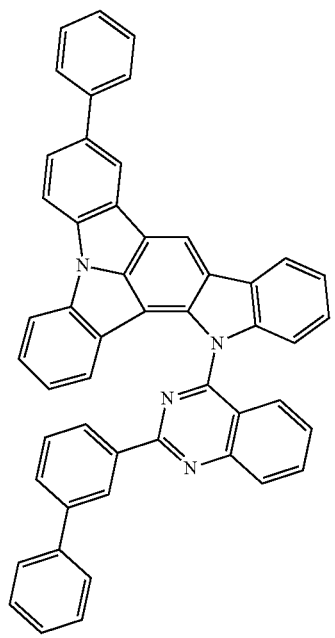
234
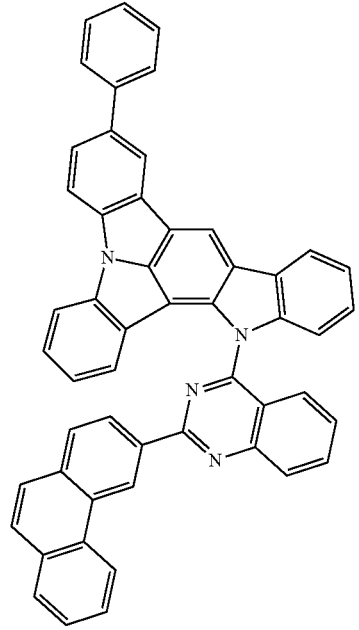
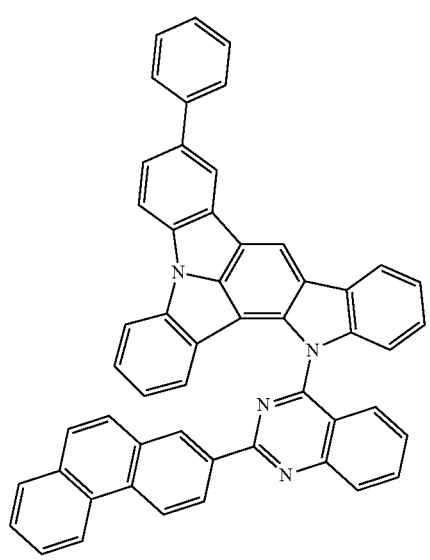
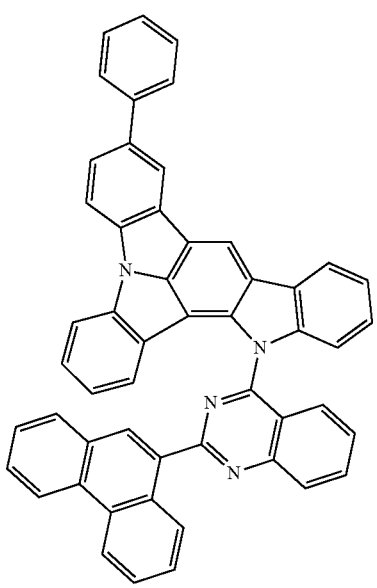

235
-continued
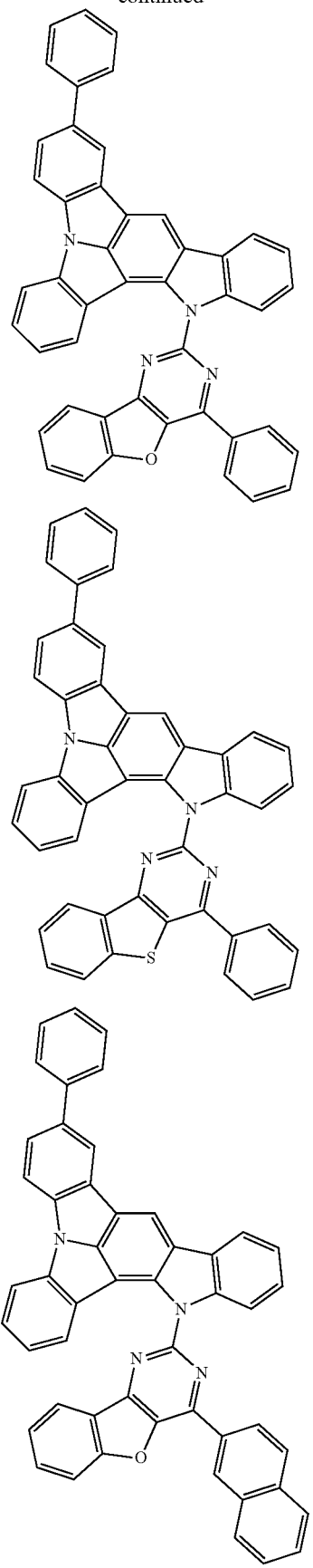
236
-continued

237
-continued
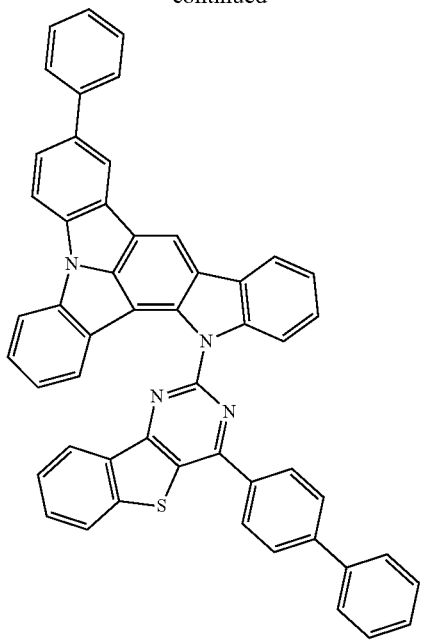
238
-continued
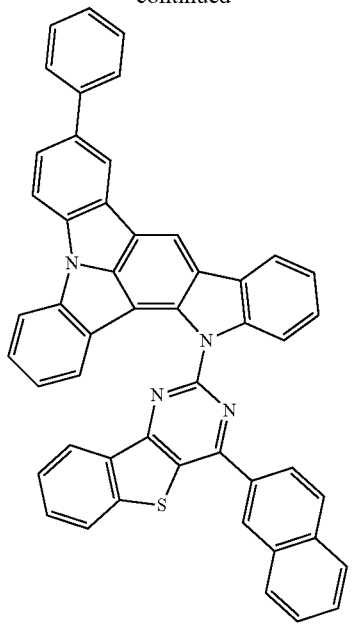
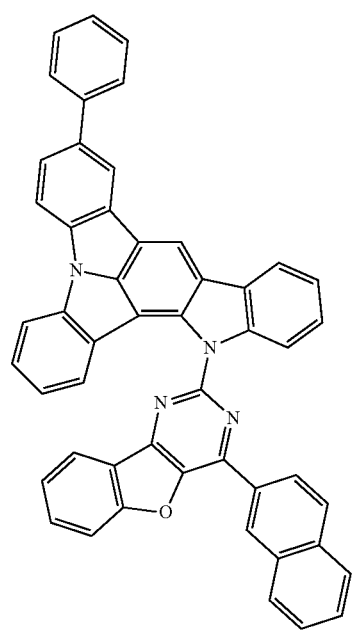
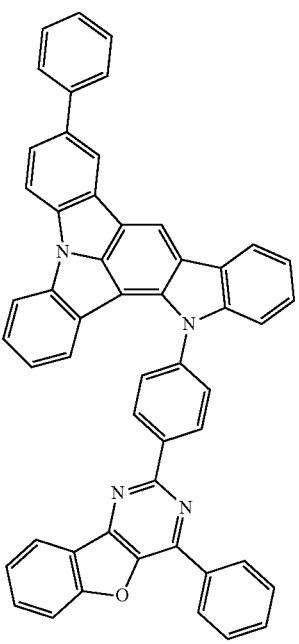

239
-continued
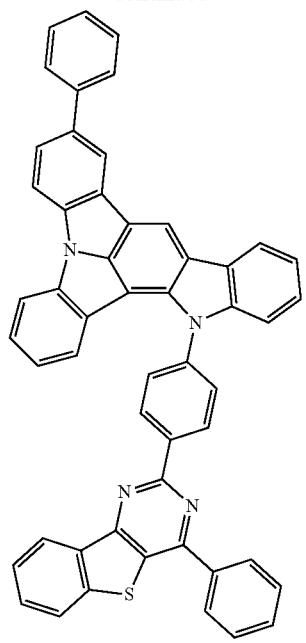
240
-continued
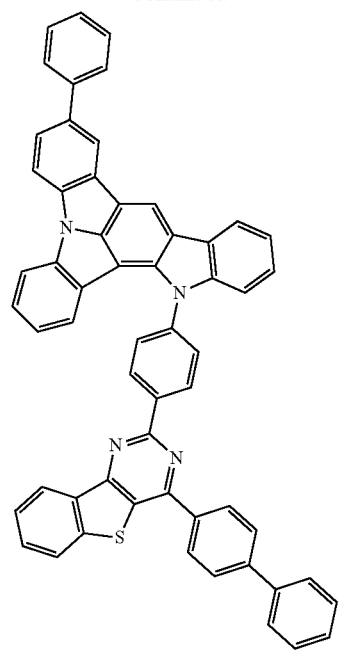
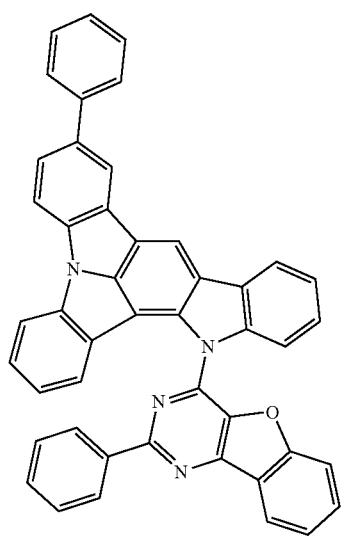
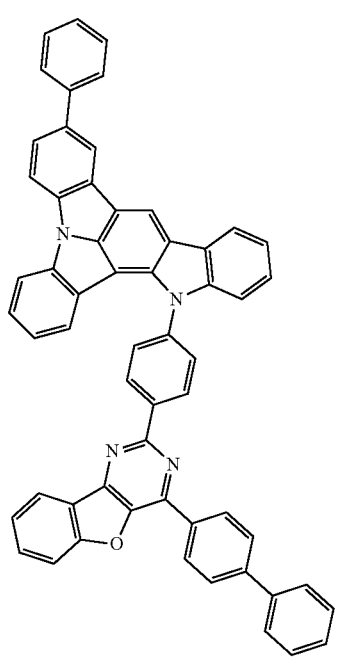

241
-continued
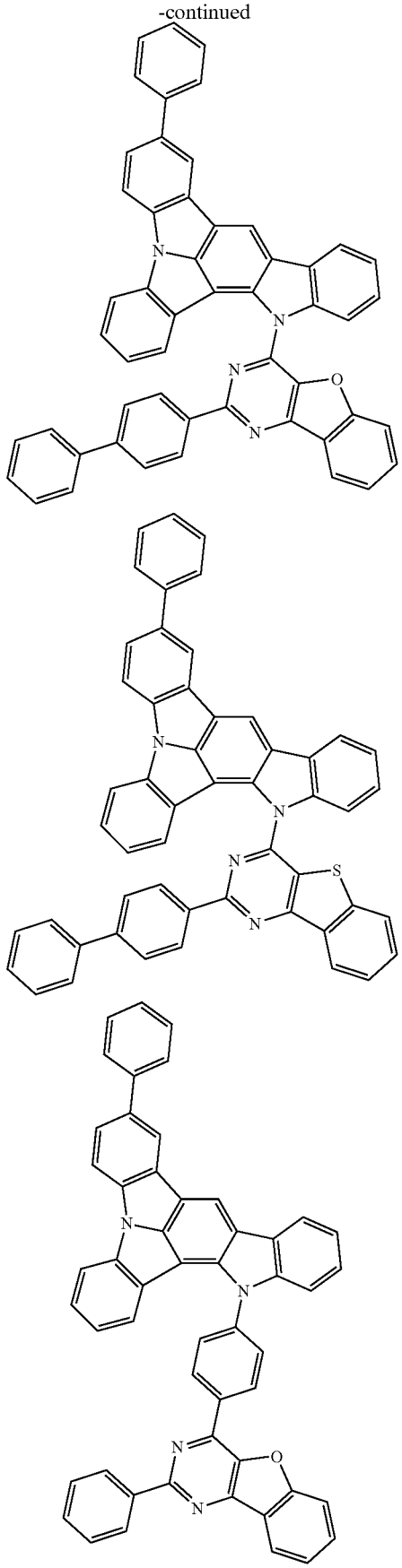
242
-continued
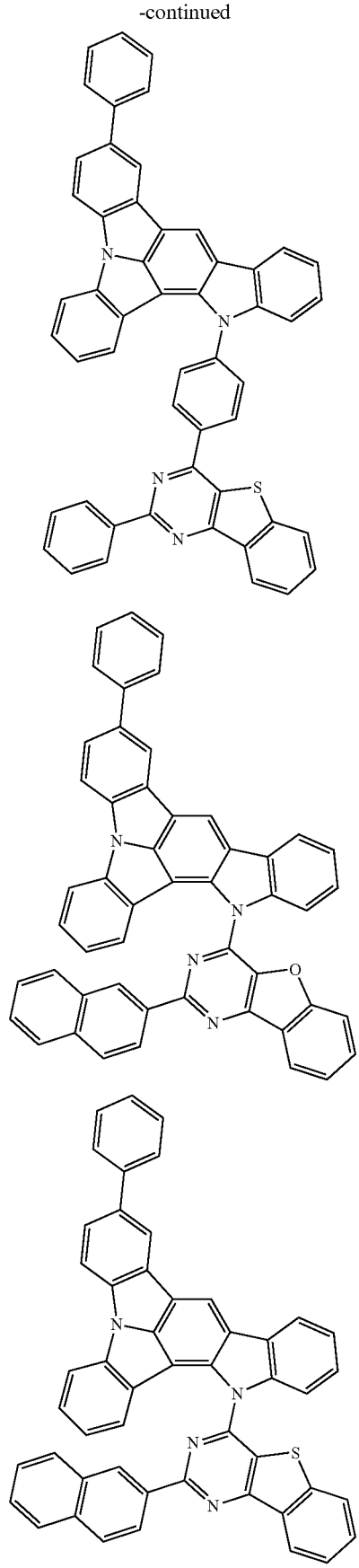

243
-continued
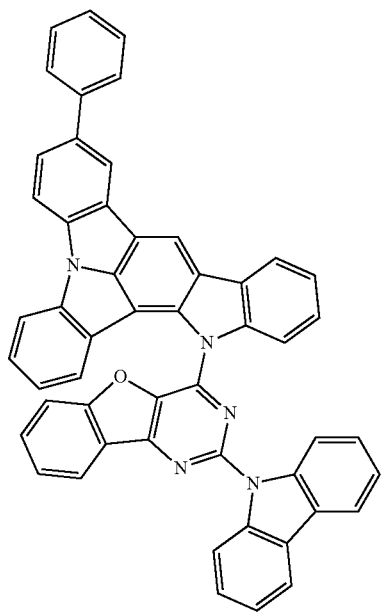
244
-continued
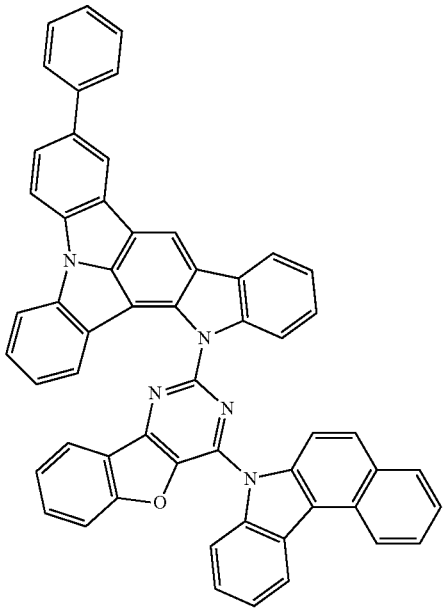
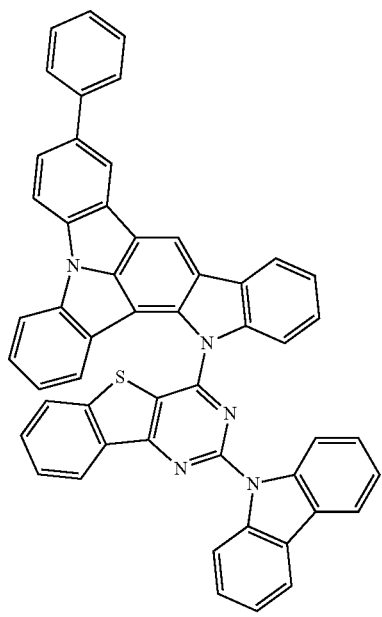
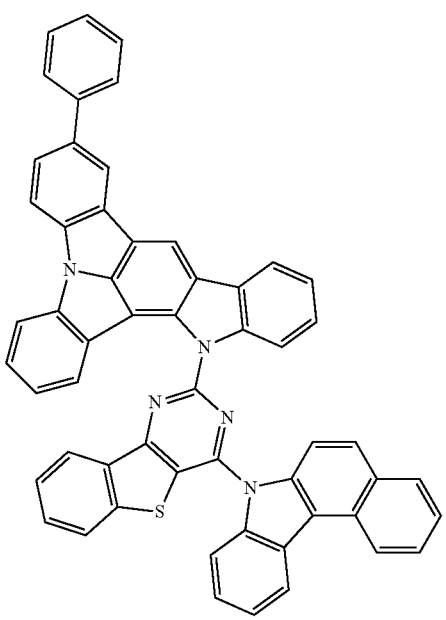

245
-continued
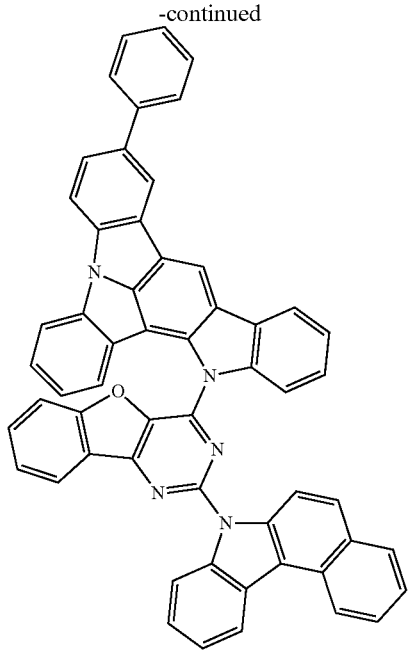
246
-continued
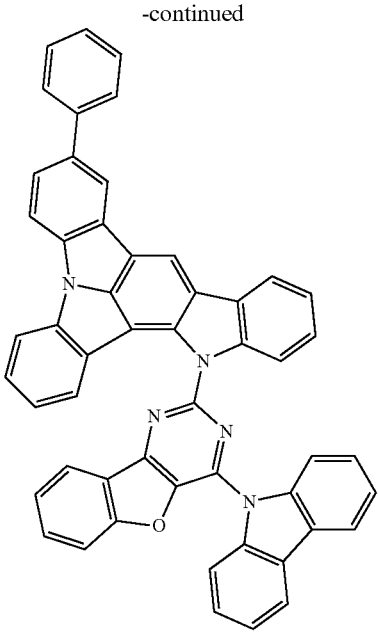
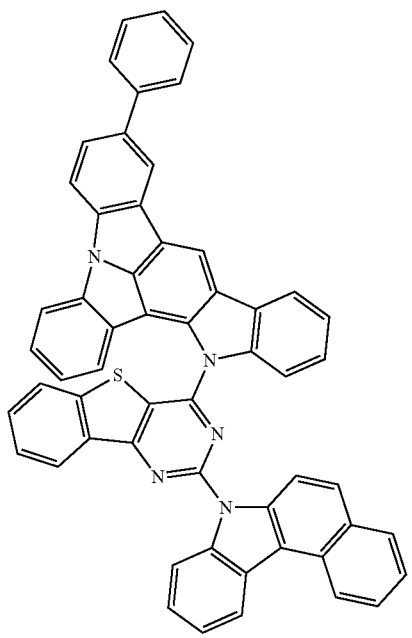

247
-continued
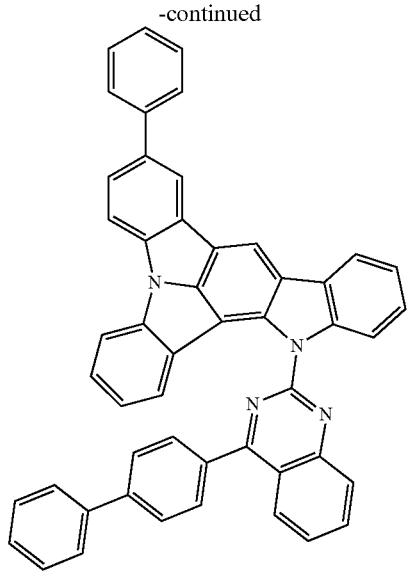
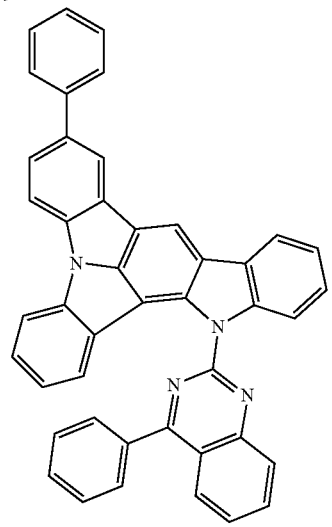
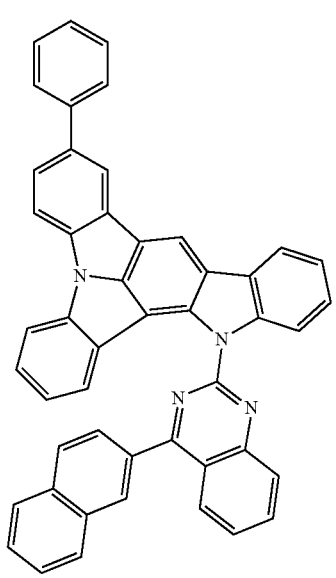
248
-continued
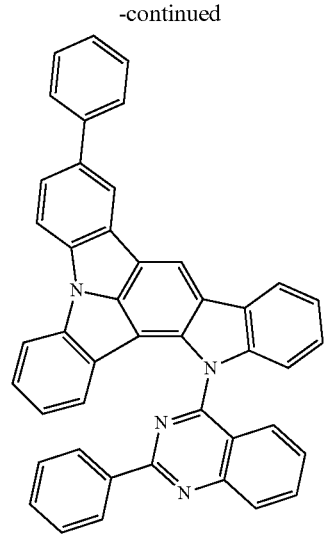
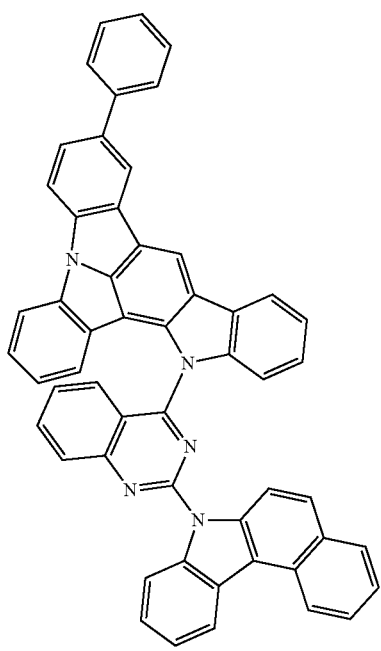

249
-continued
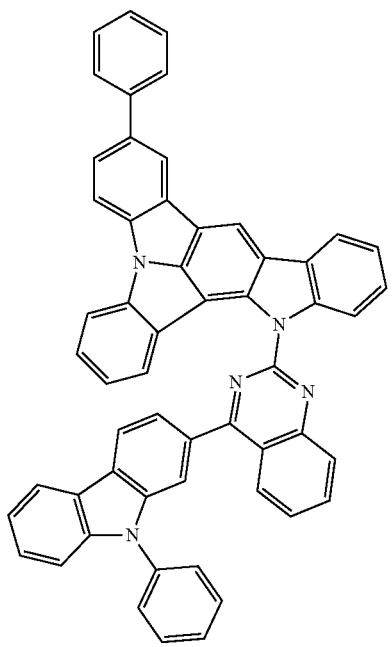 [SMILES: c1ccc(-c2ccc3c(c2)c2cc4c5ccccc5n(-c5nc(-c6ccc7c8ccccc8n(-c8ccccc8)c7c6)c6ccccc6n5)c4c4c5ccccc5n3c24)cc1]
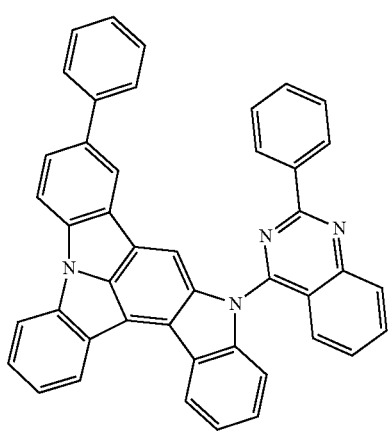
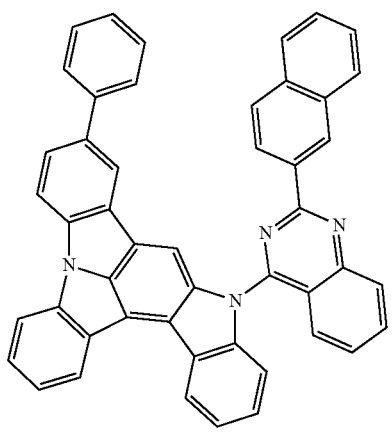
250
-continued
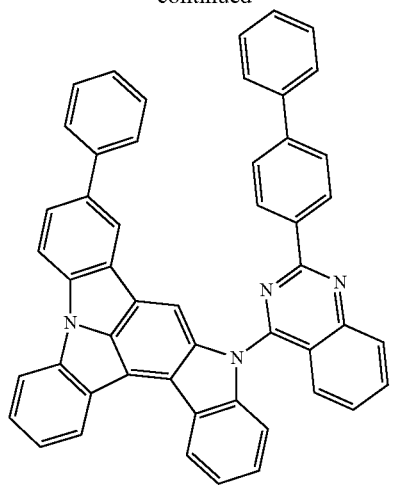
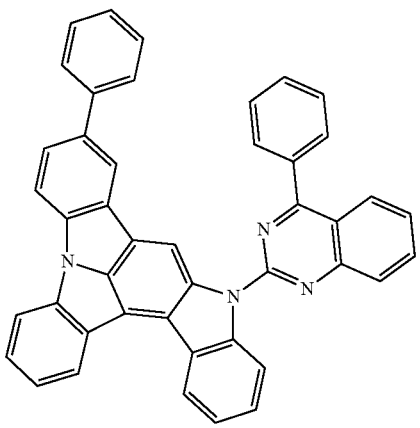 [SMILES: c1ccc(-c2ccc3c(c2)c2cc4c(c5ccccc5n4-c4nc(-c5ccccc5)c5ccccc5n4)c4c5ccccc5n3c24)cc1]
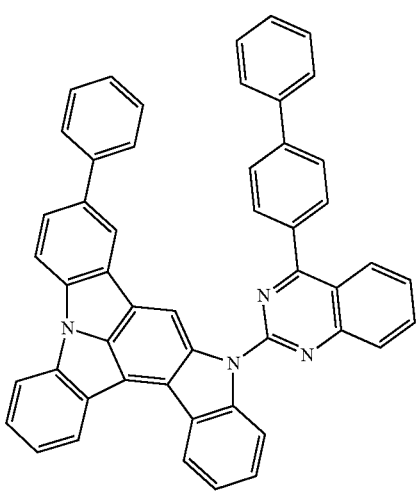

251
-continued
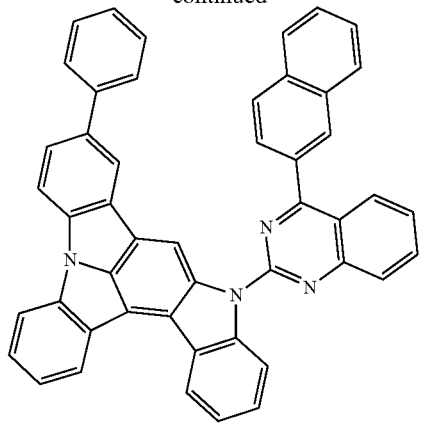
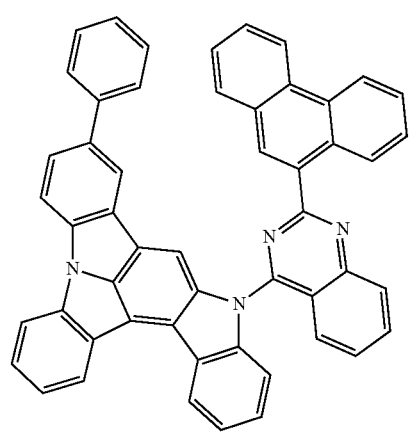
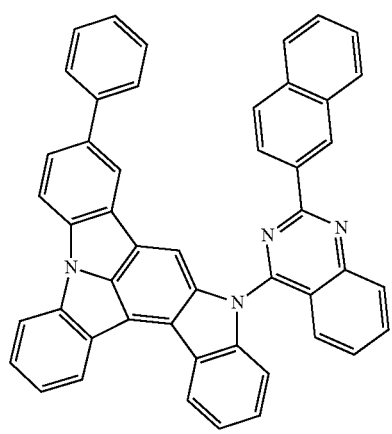
252
-continued
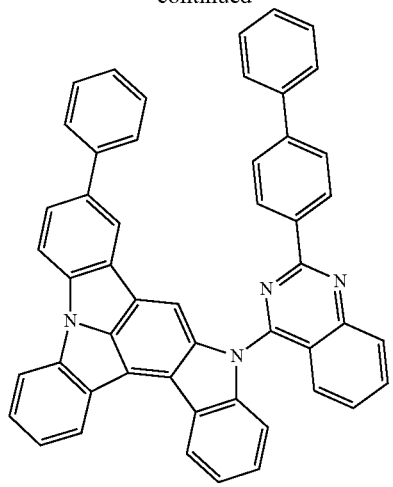
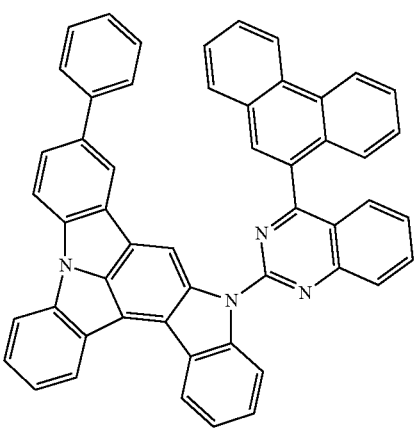
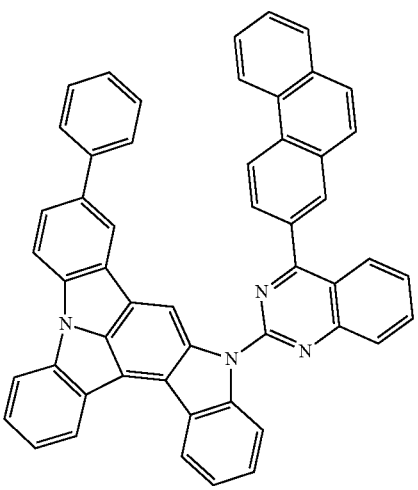

253
-continued
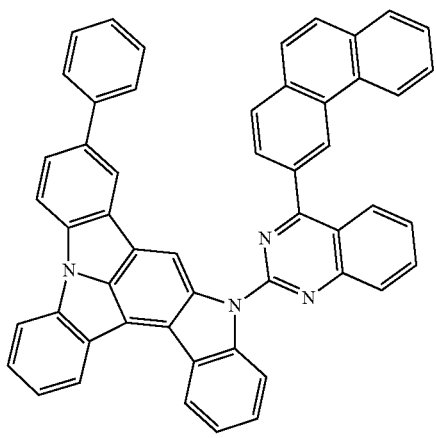
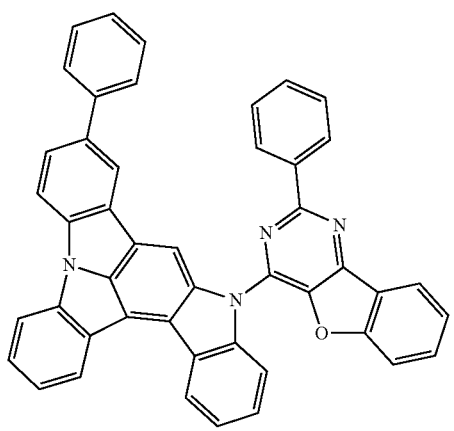
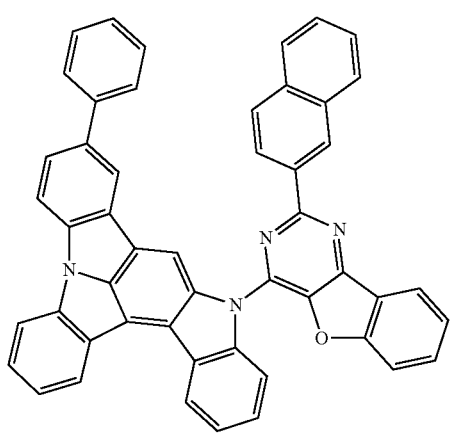
254
-continued
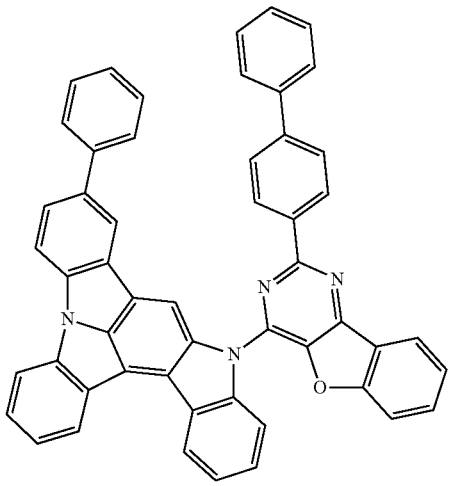
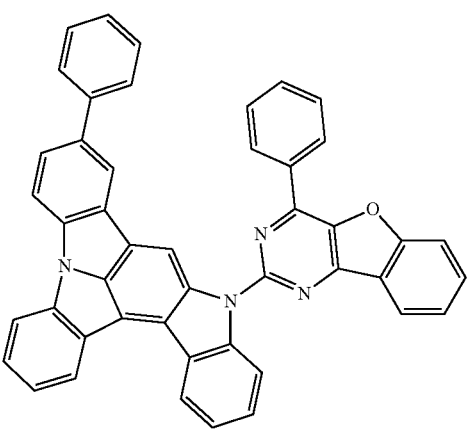
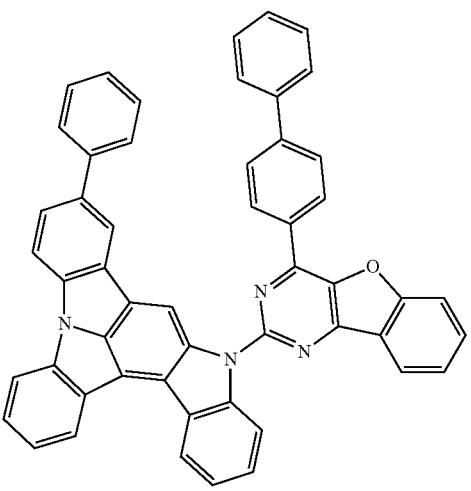

255
-continued
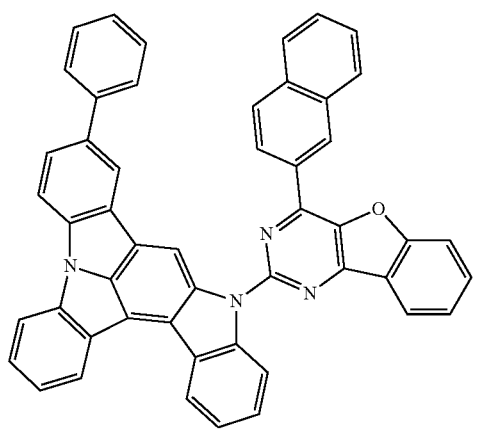
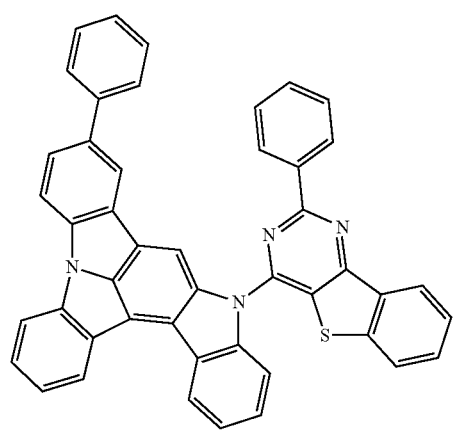
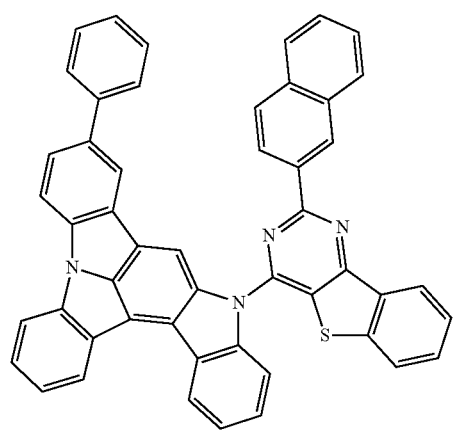
256
-continued
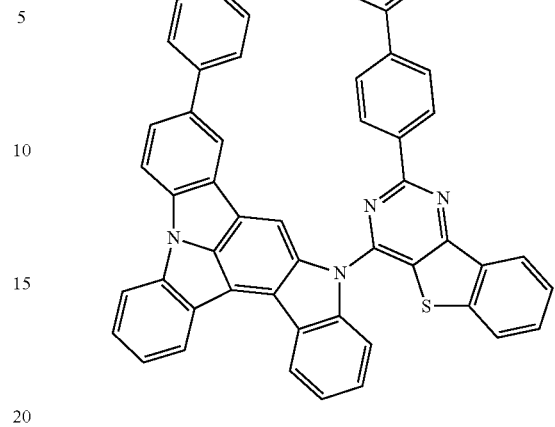
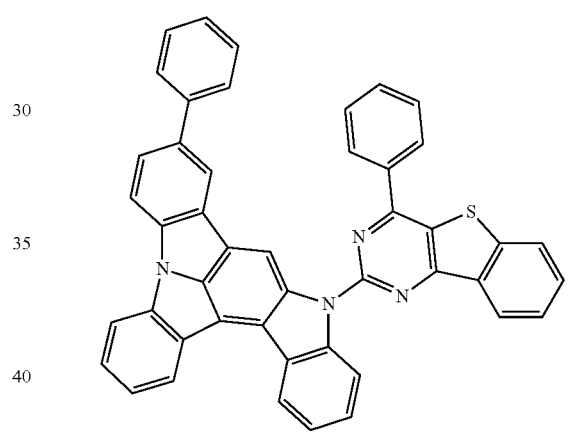
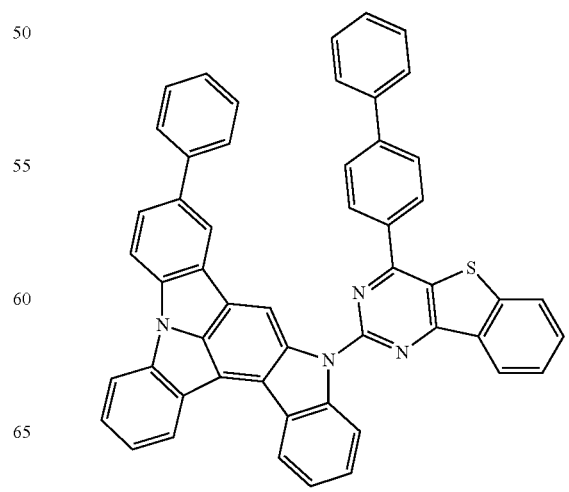

257
-continued
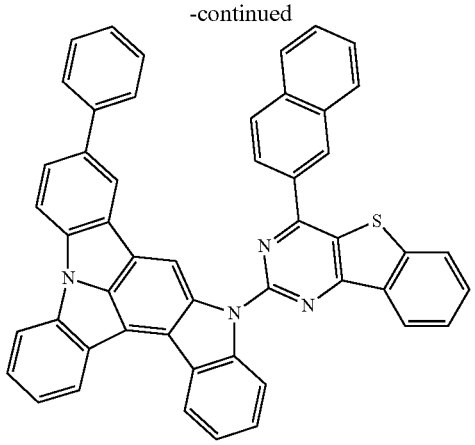
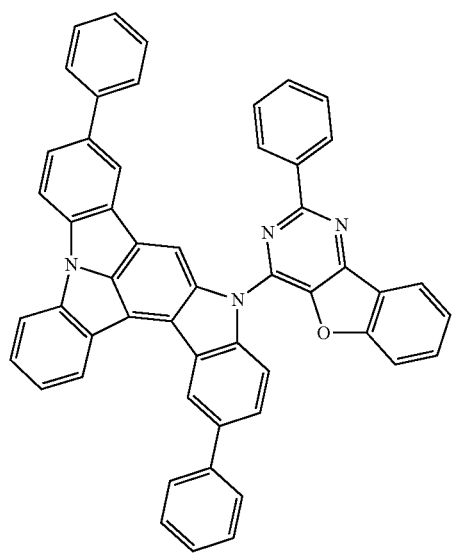
258
-continued
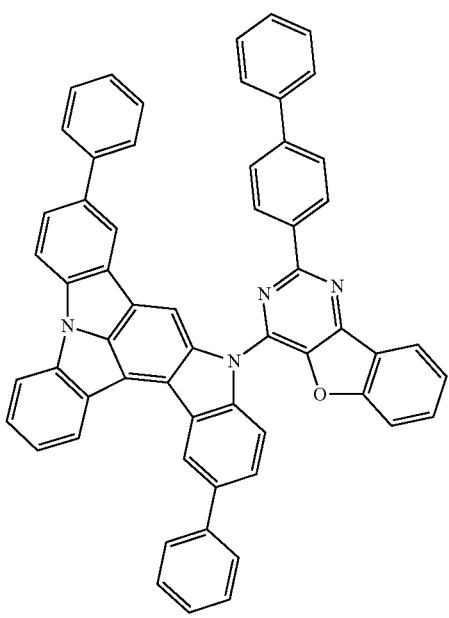
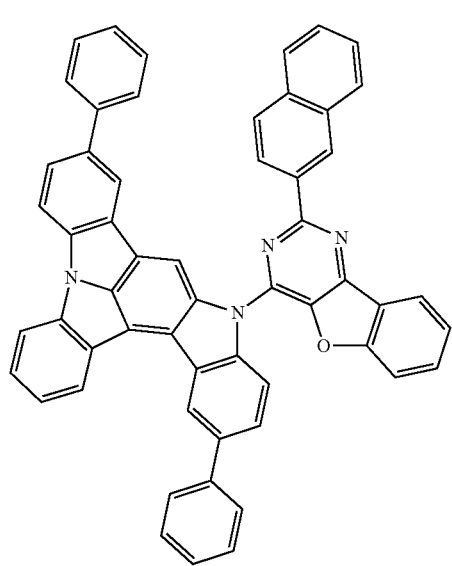

259
-continued
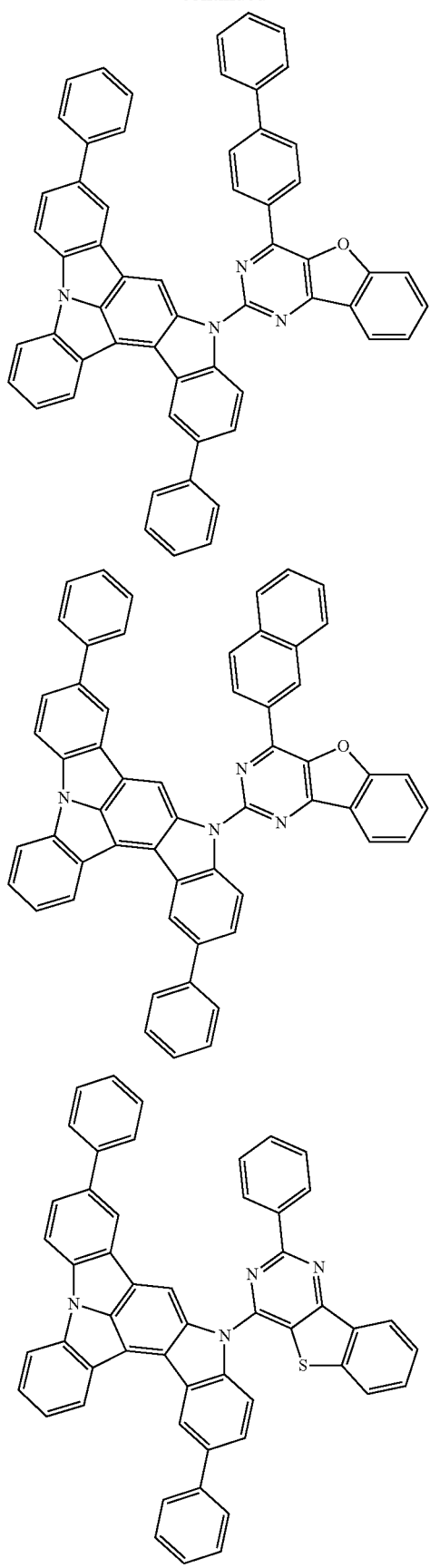
260
-continued
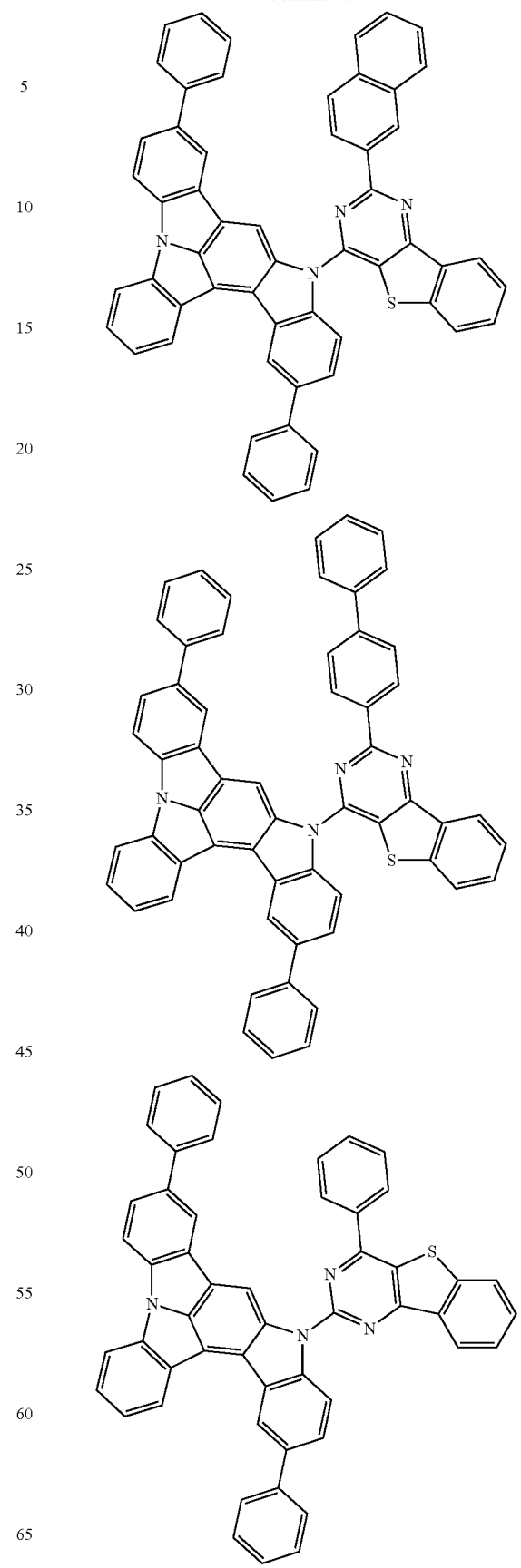

261
-continued
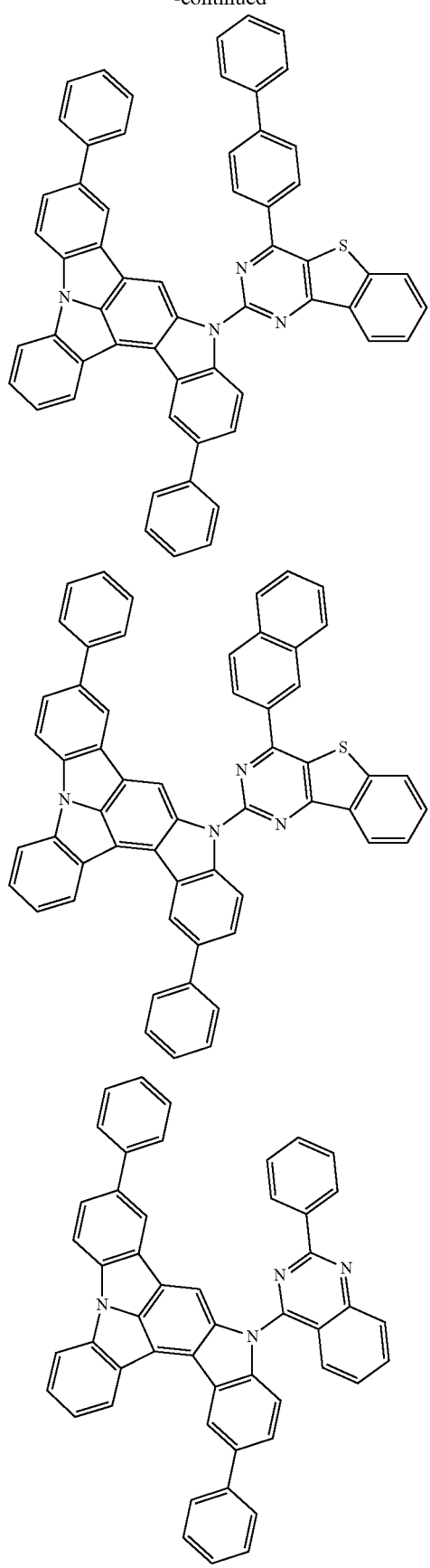
262
-continued
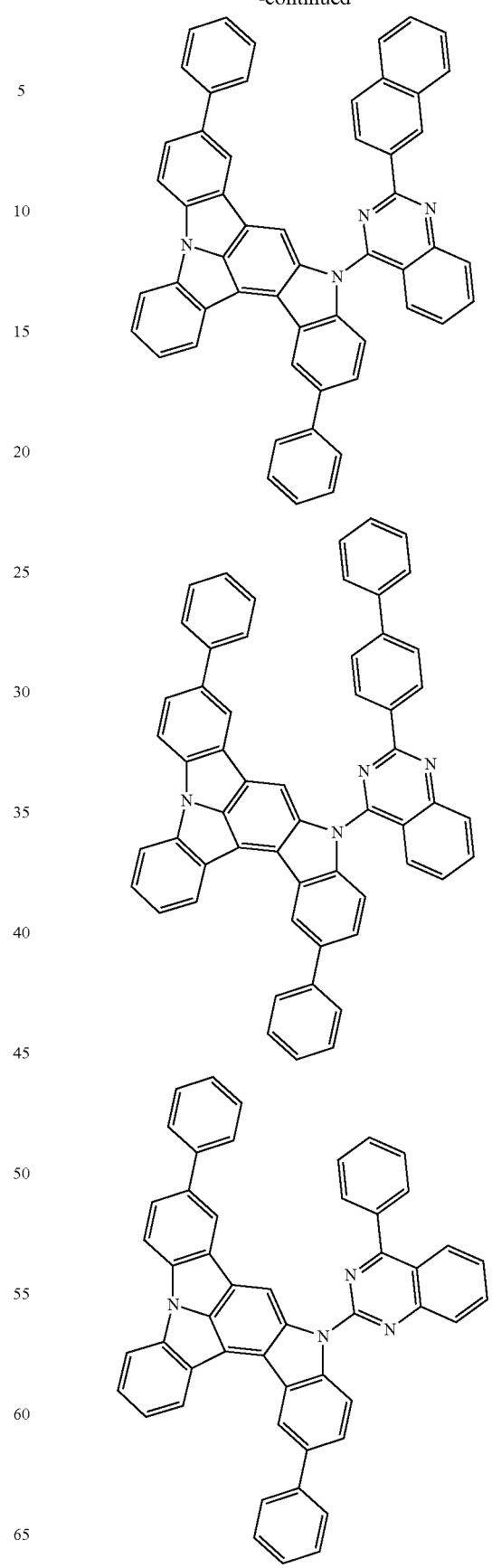

263
-continued
264
-continued
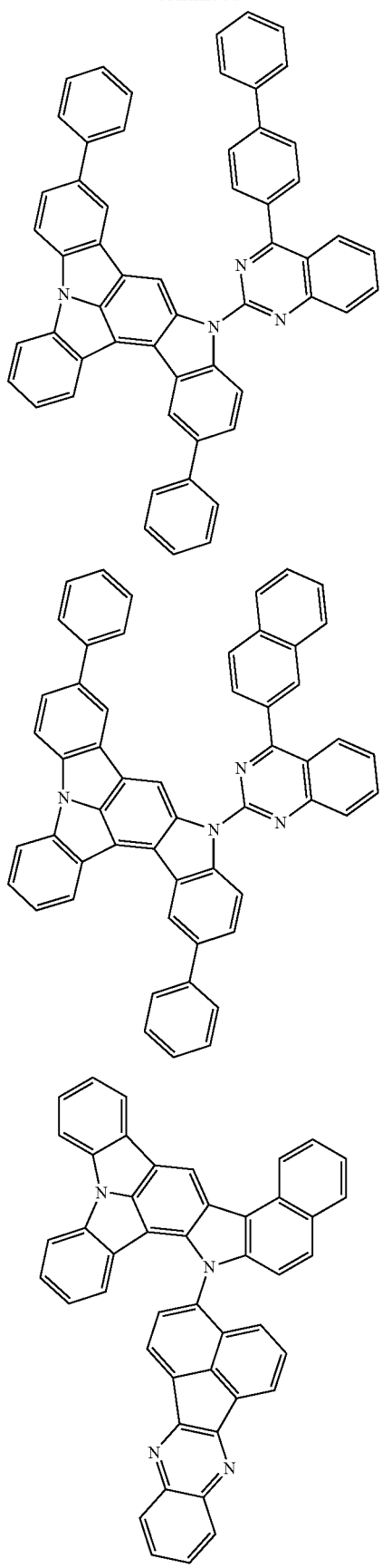
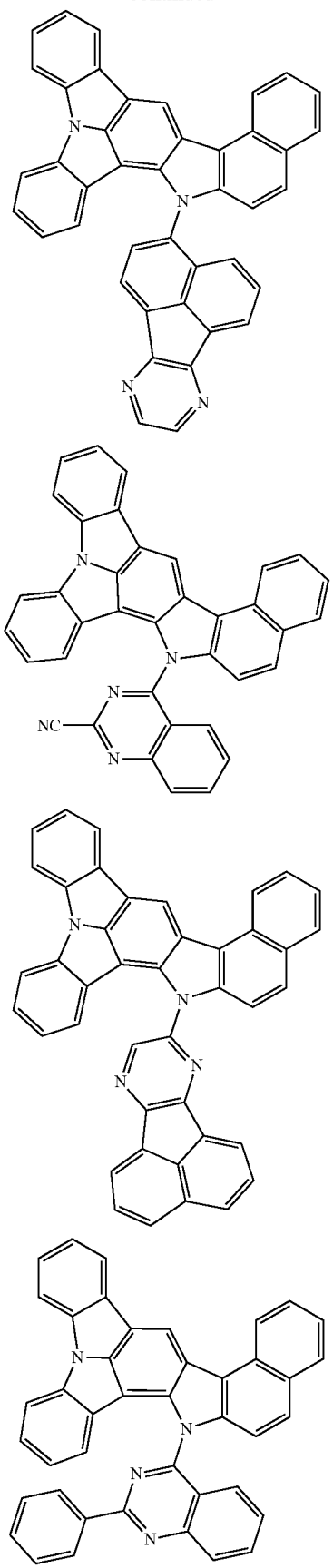

265
-continued
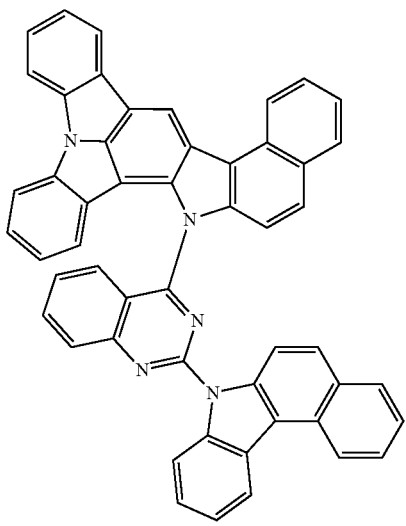
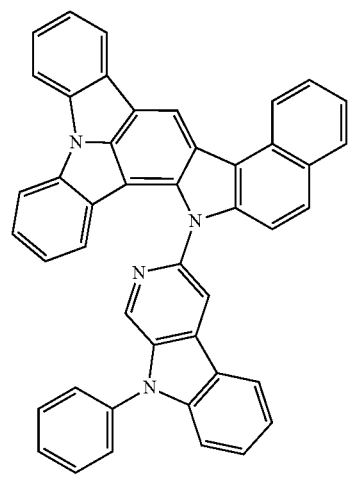
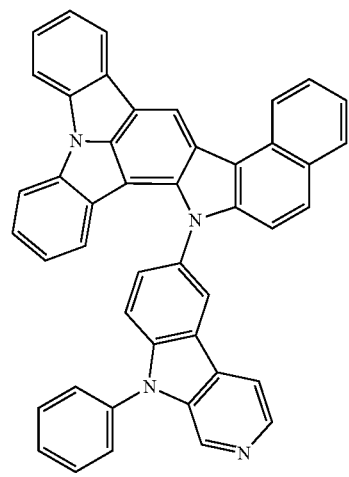
266
-continued
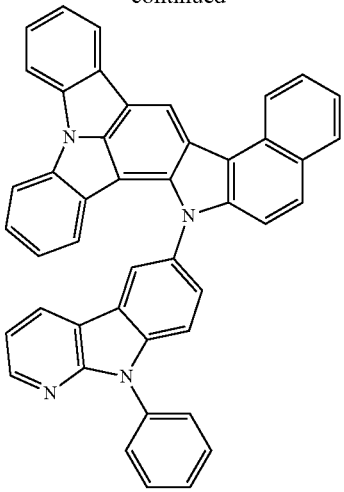
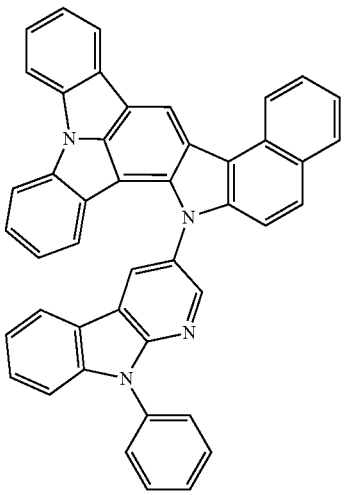
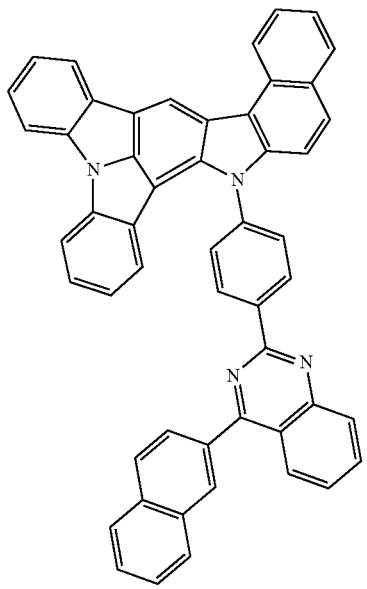

267
-continued
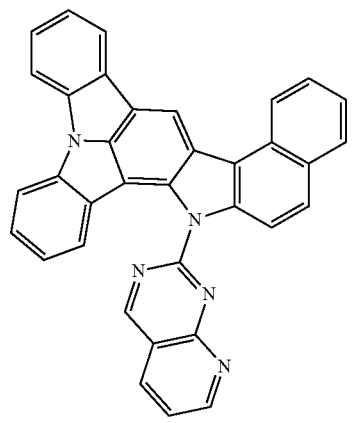
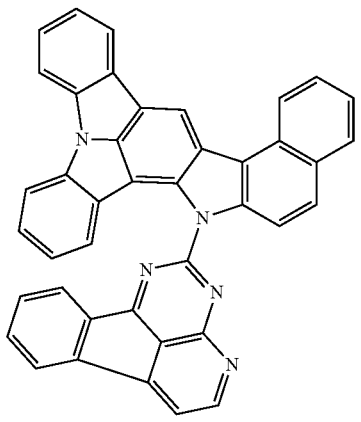
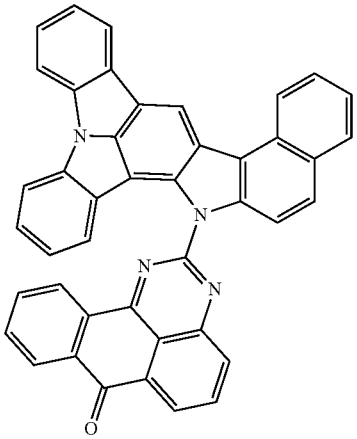
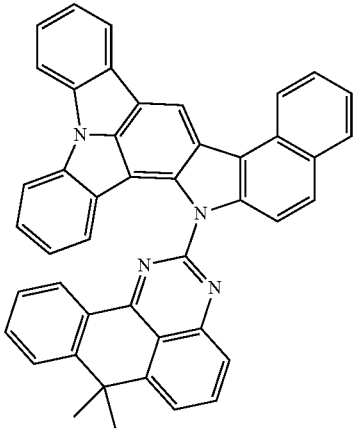
268
-continued
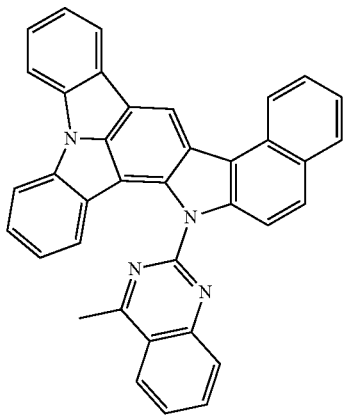
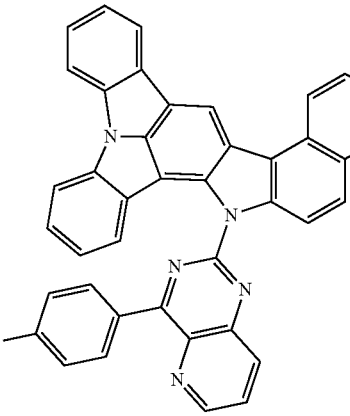
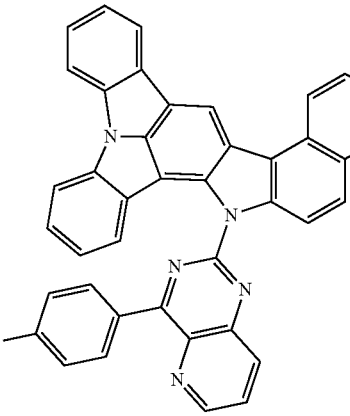
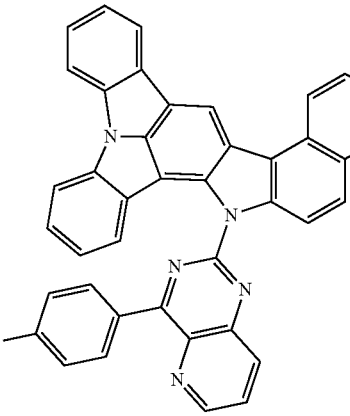

269
-continued
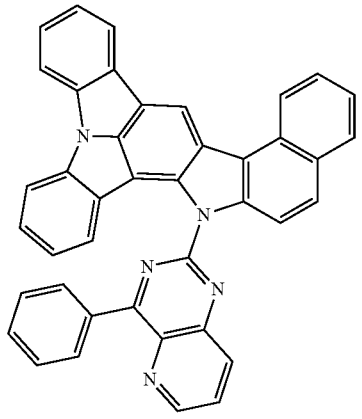
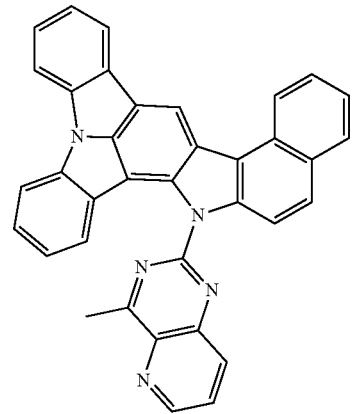
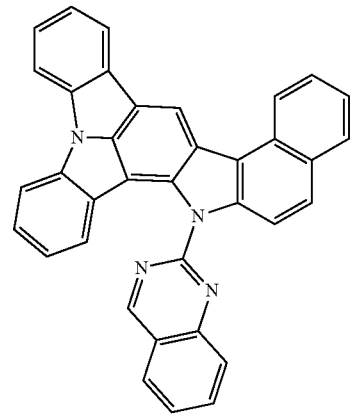
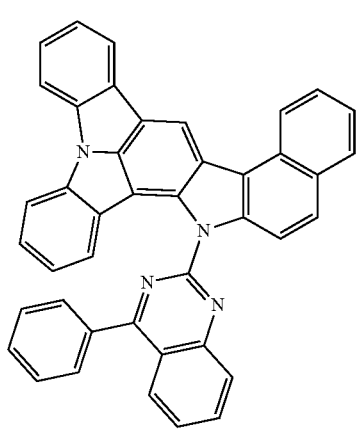
270
-continued
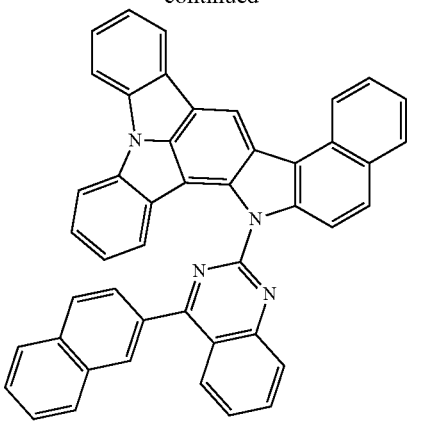
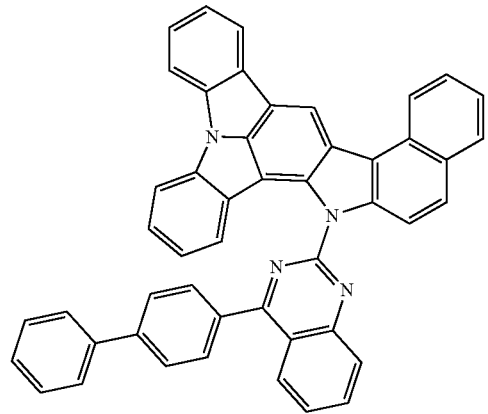
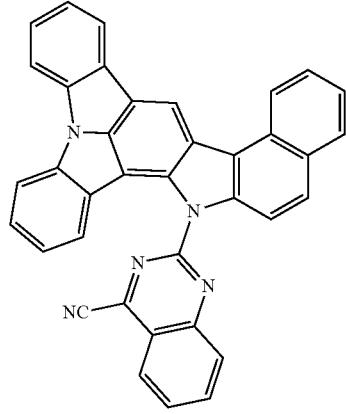
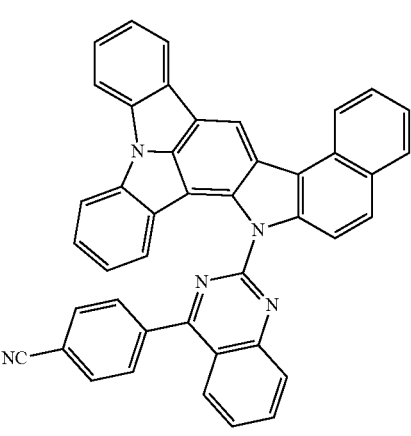

271
-continued
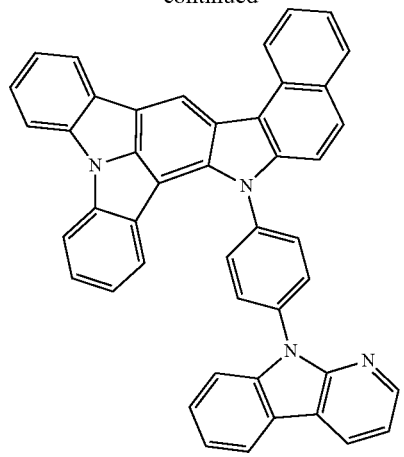
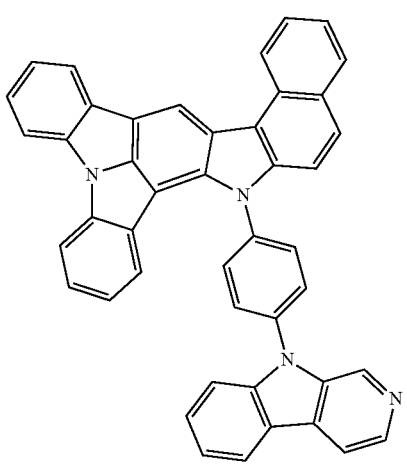
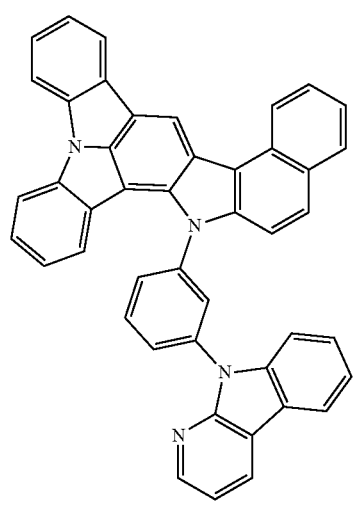
272
-continued
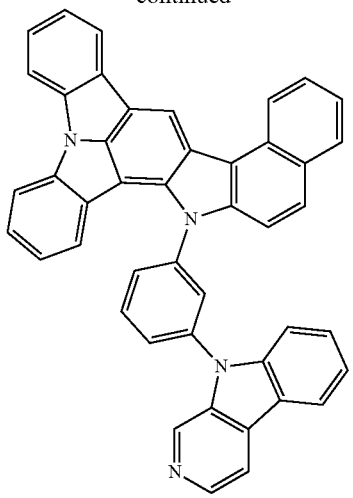
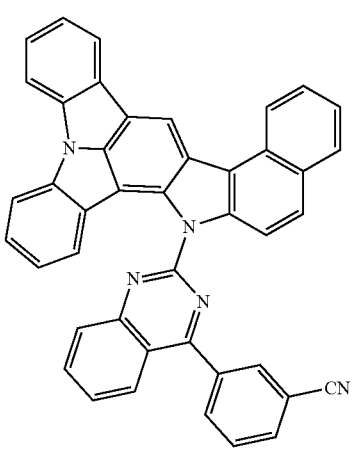
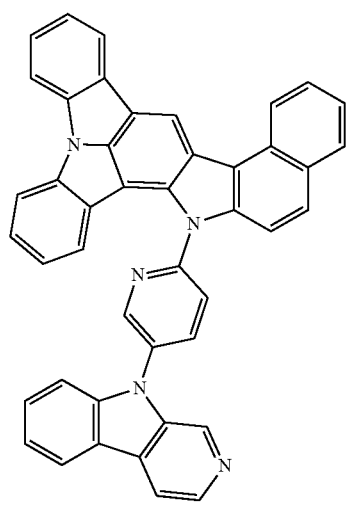

273
-continued
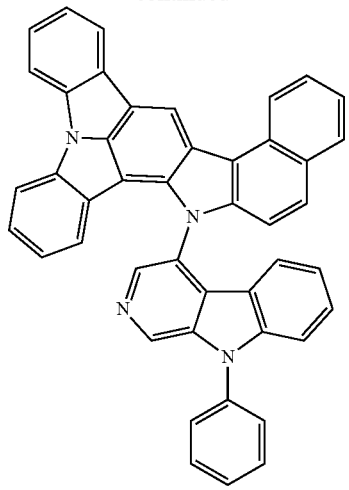
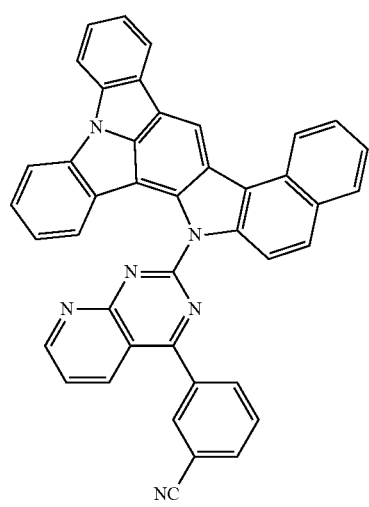
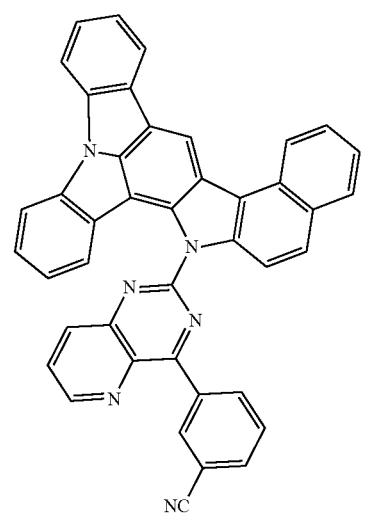
274
-continued
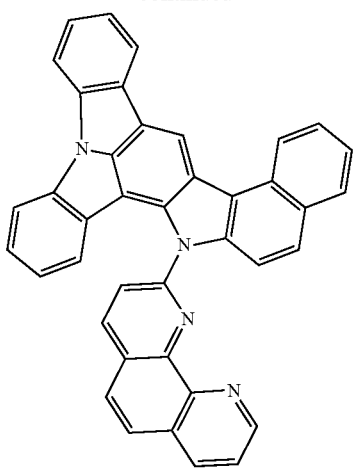
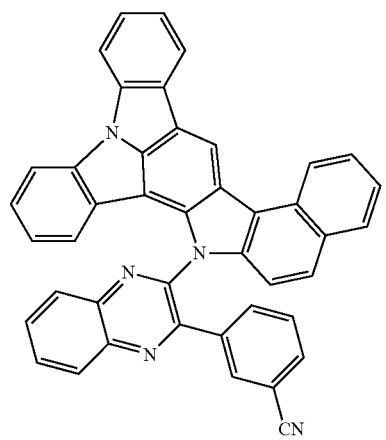
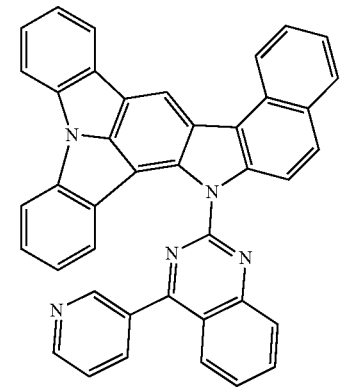
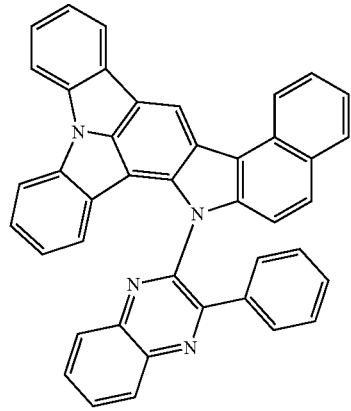

275
-continued
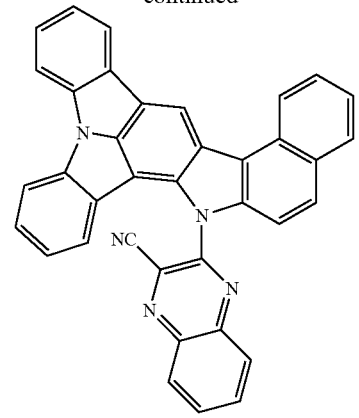
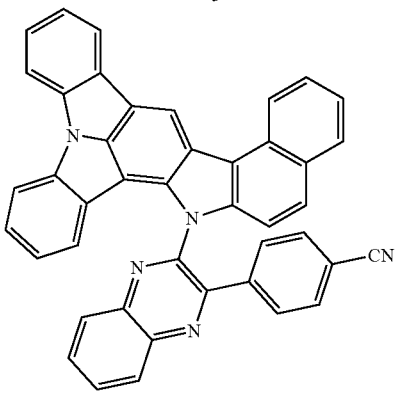
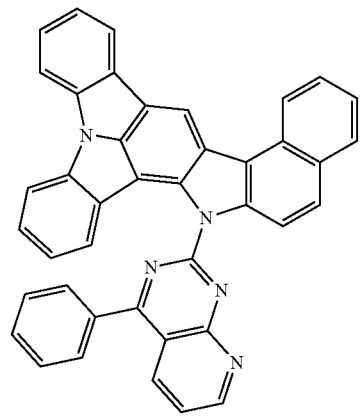
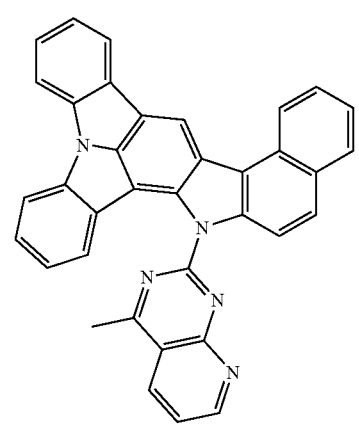
276
-continued
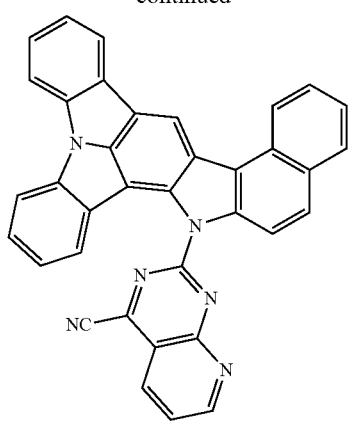
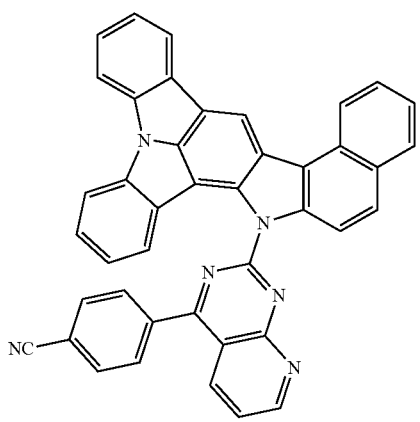
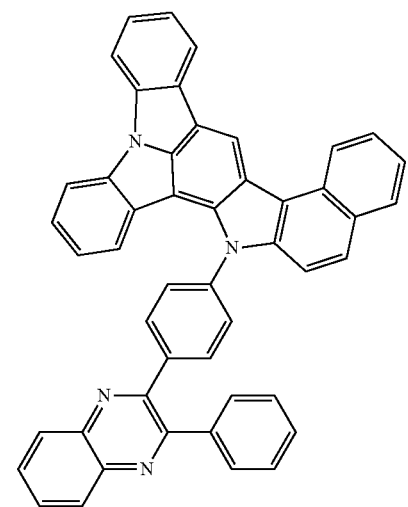

277
-continued
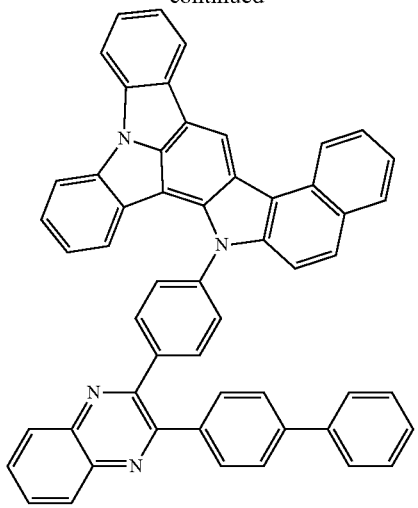
278
-continued
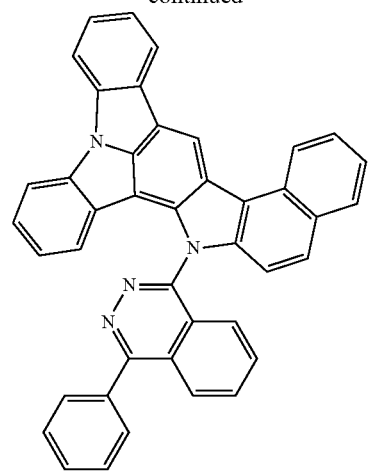
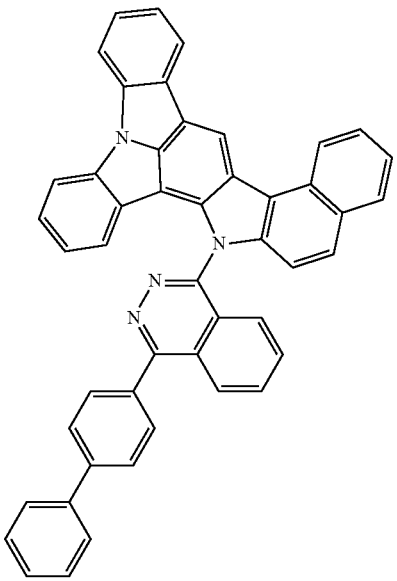
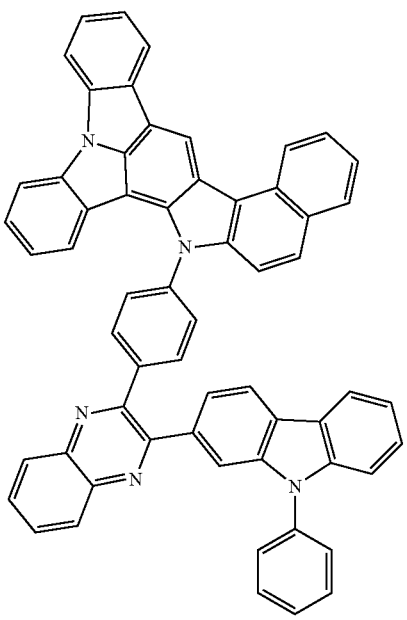

279
-continued
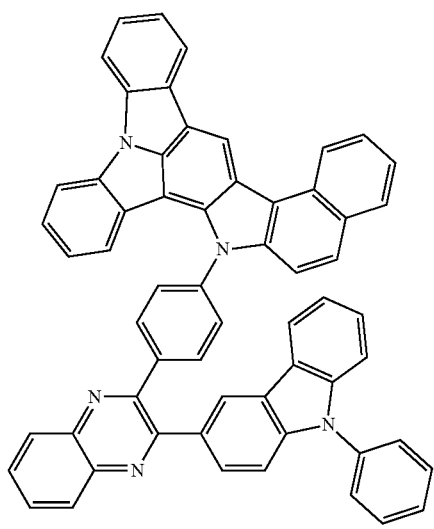
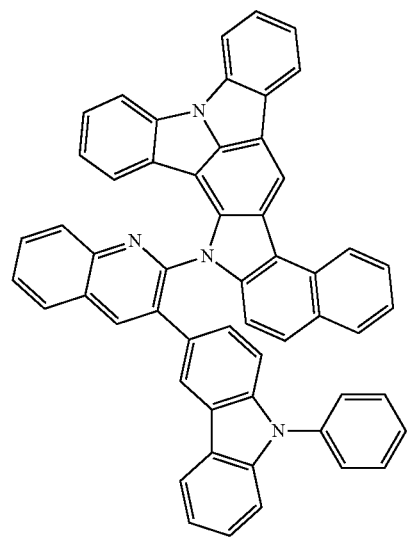
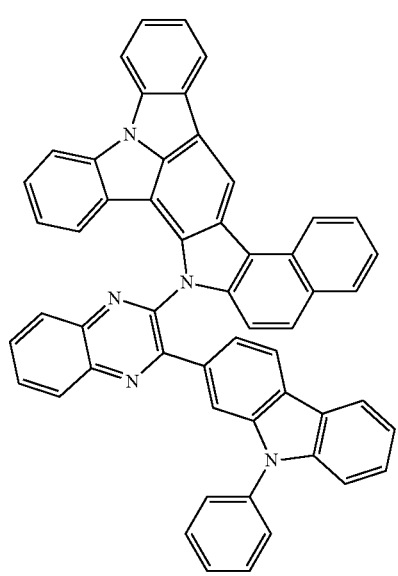
280
-continued
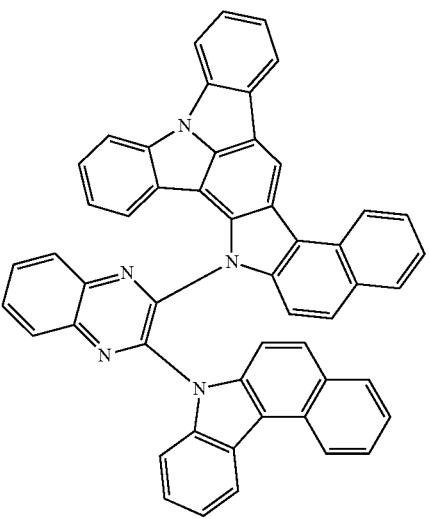
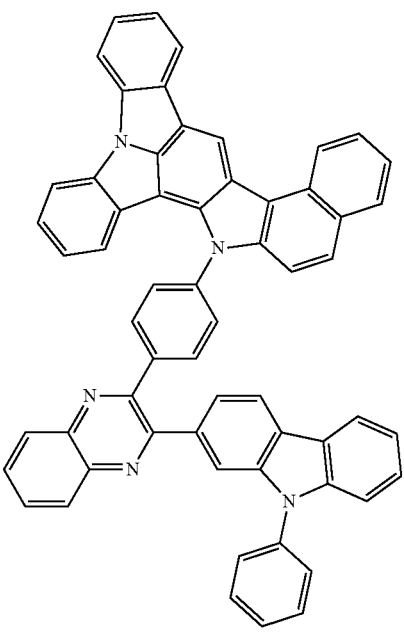
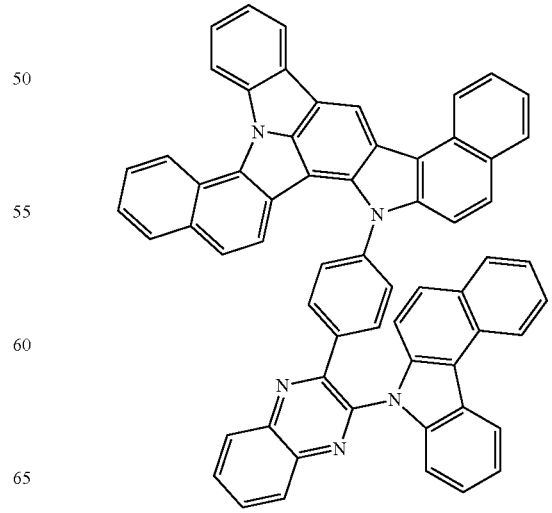

281
-continued
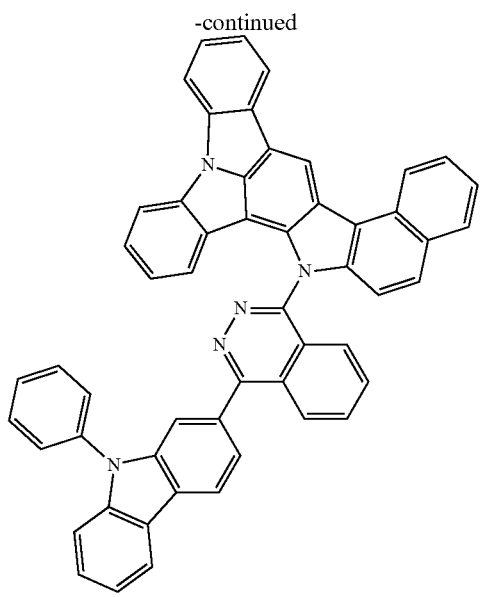
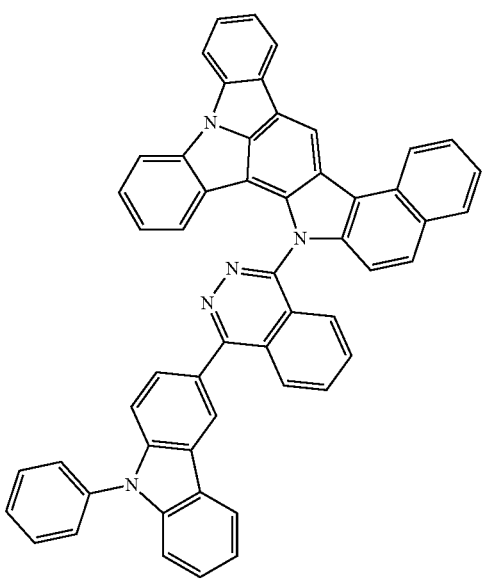
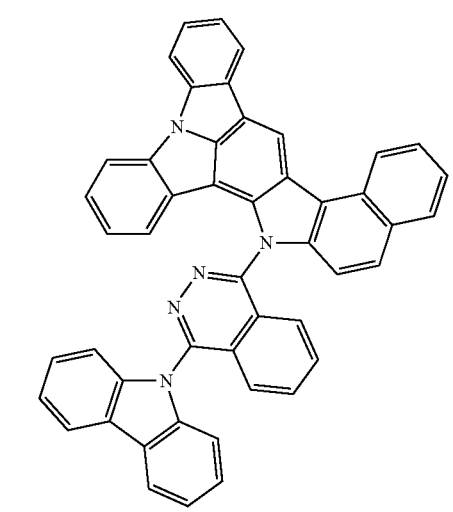
282
-continued
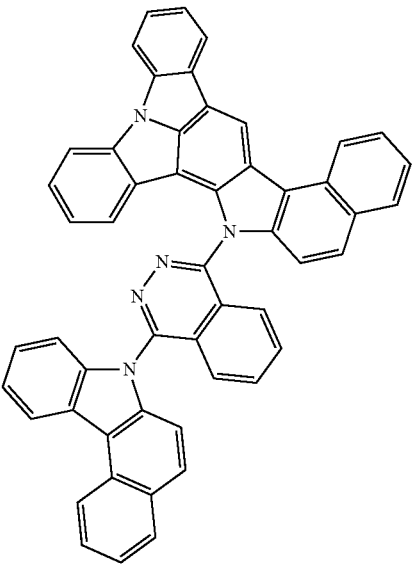 [SMILES: c1ccc2c(c1)ccc1c2c2ccccc2n1-c1nnc(-n2c3ccc4ccccc4c3c3cc4c5ccccc5n5c6ccccc6c(c32)c45)c2ccccc12]
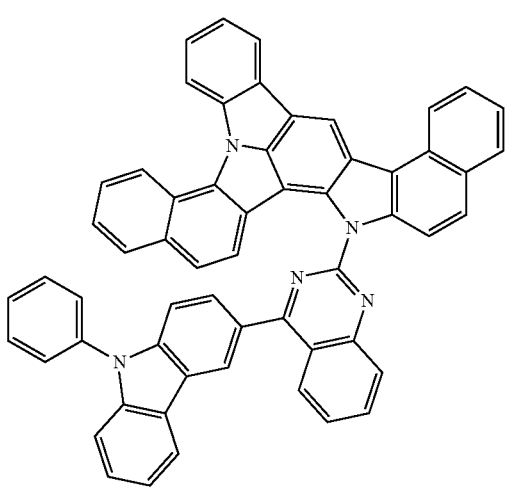
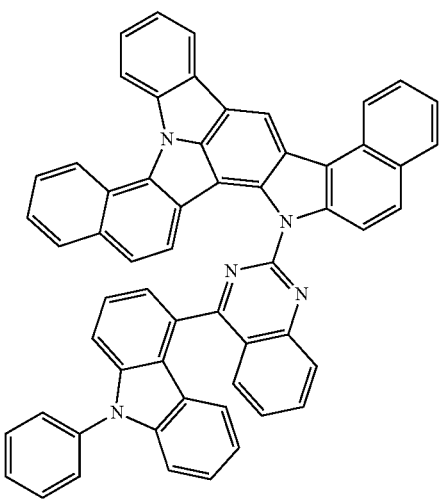

283
-continued
284
-continued
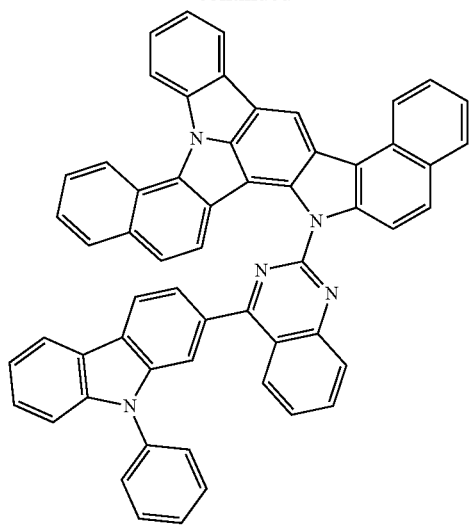
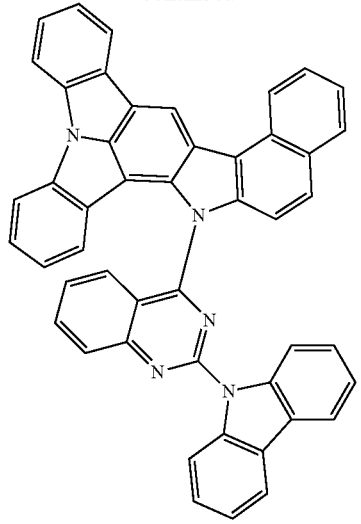
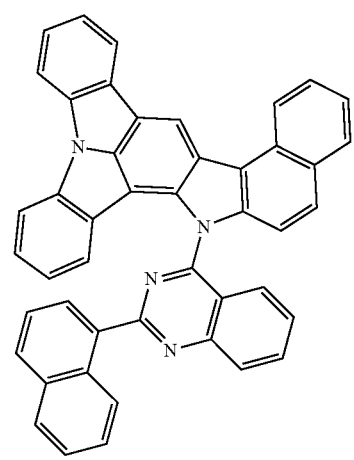
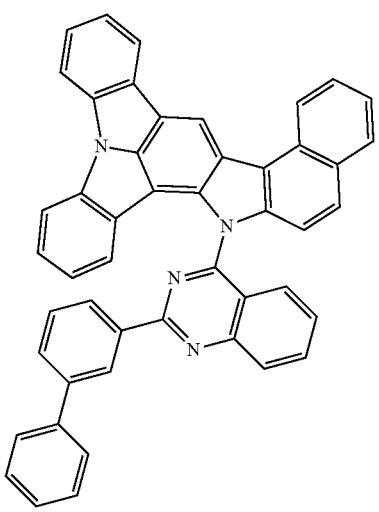

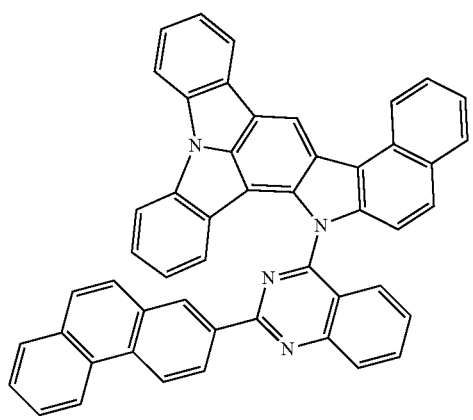
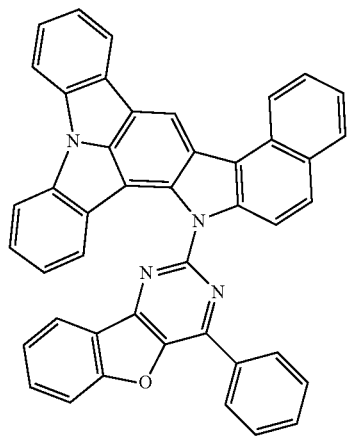
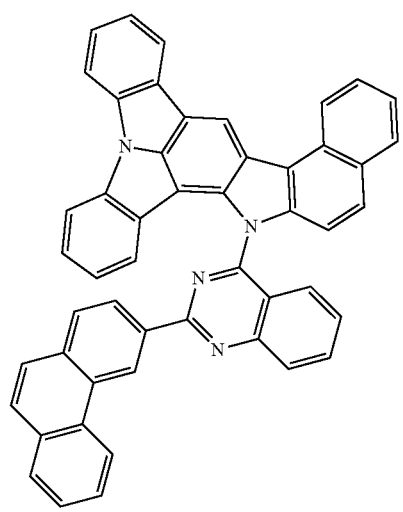
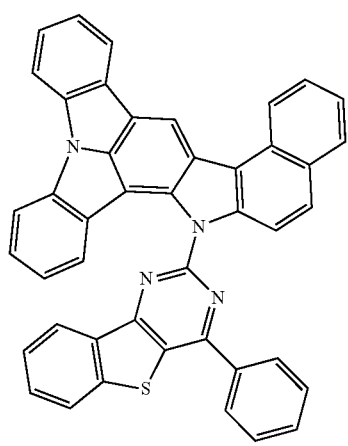
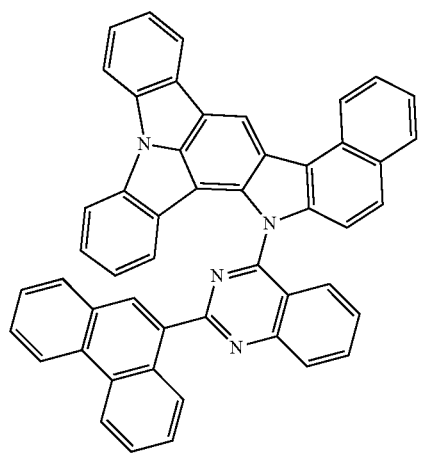
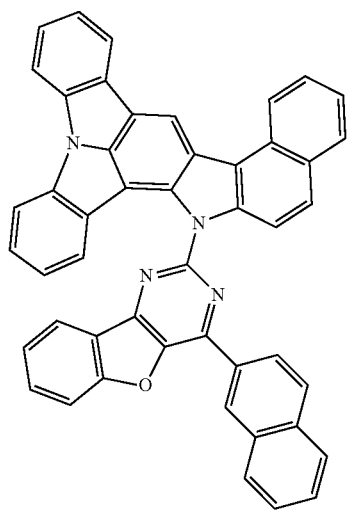

287
-continued
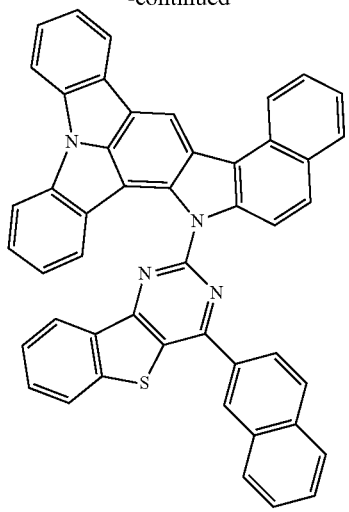
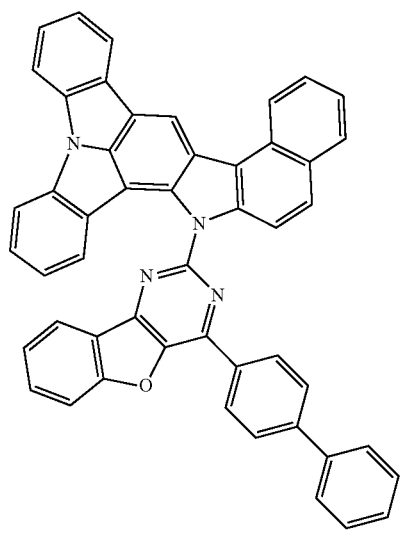
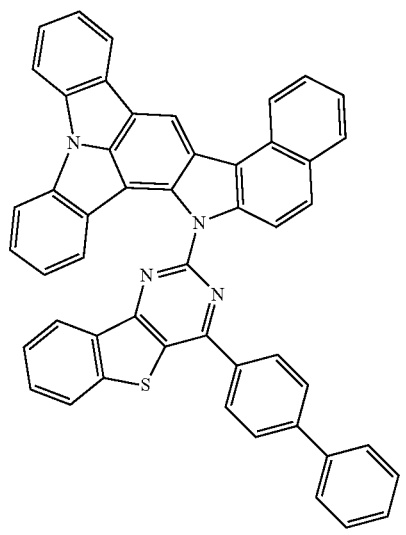
288
-continued
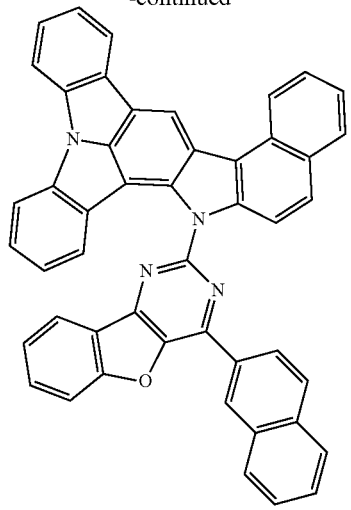
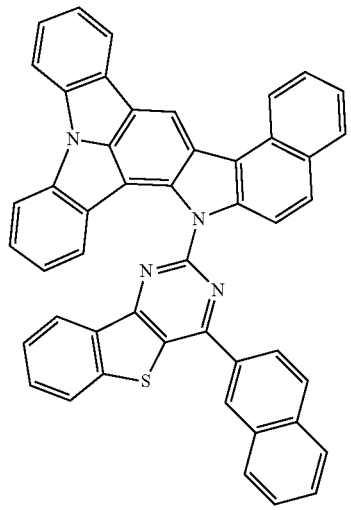
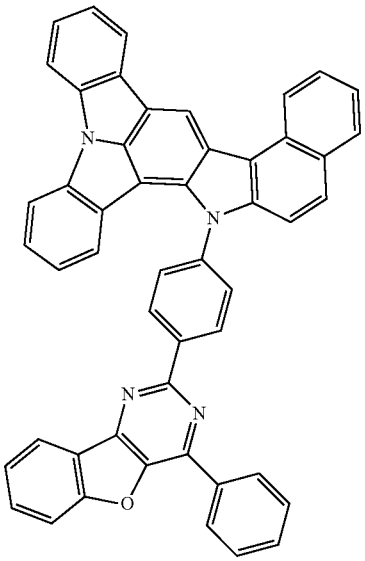

289
-continued
290
-continued
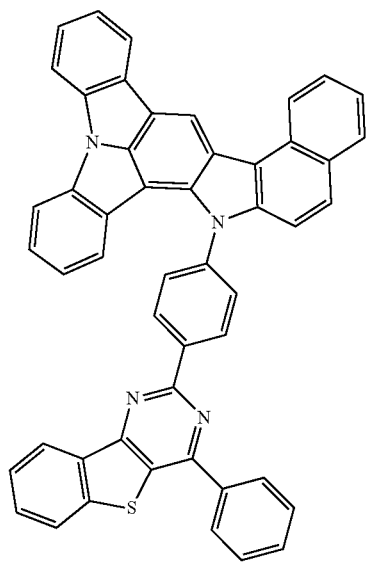
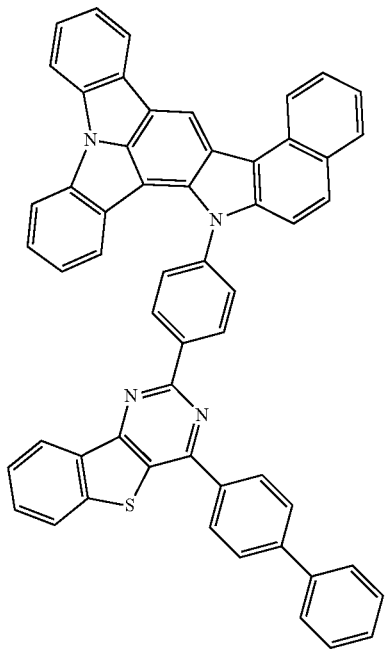
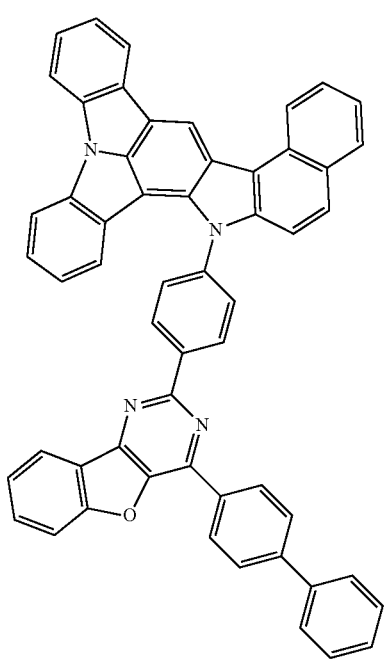
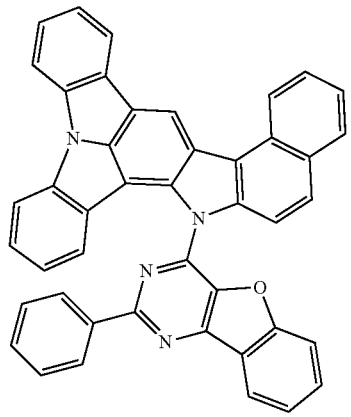

291
-continued
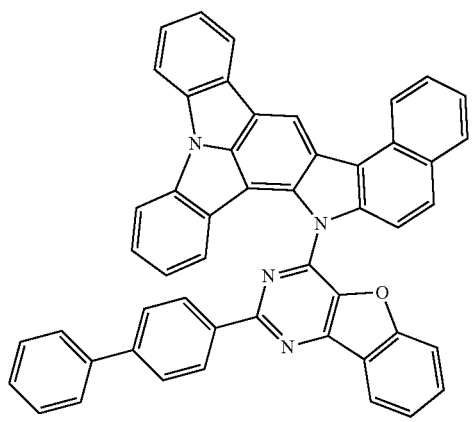
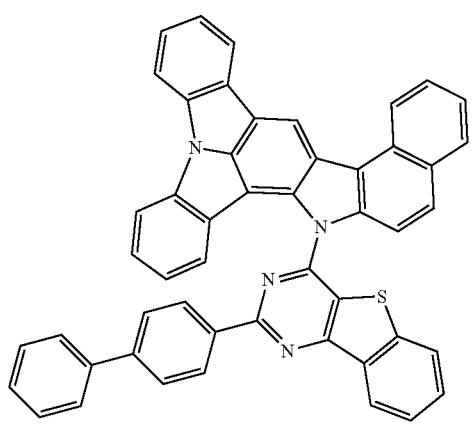
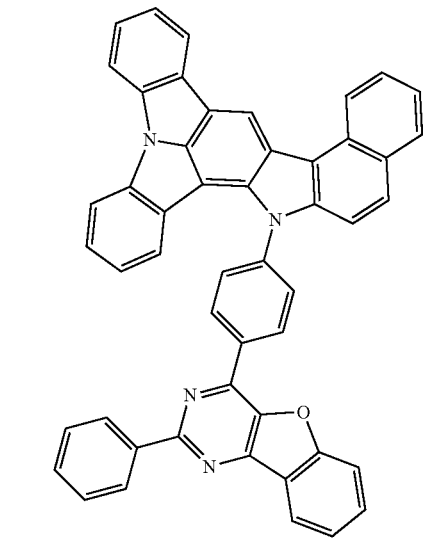
292
-continued
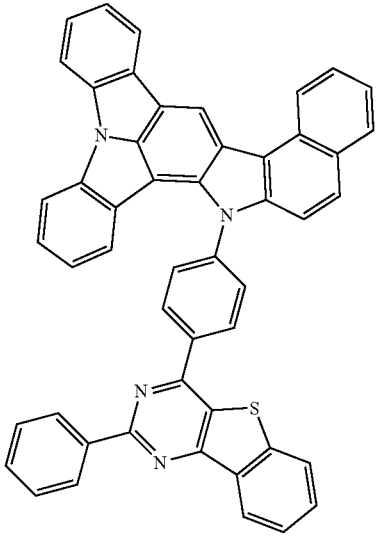
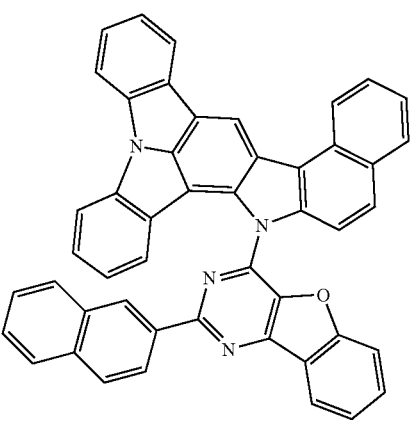
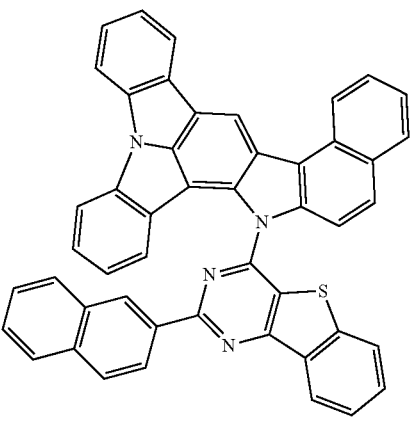

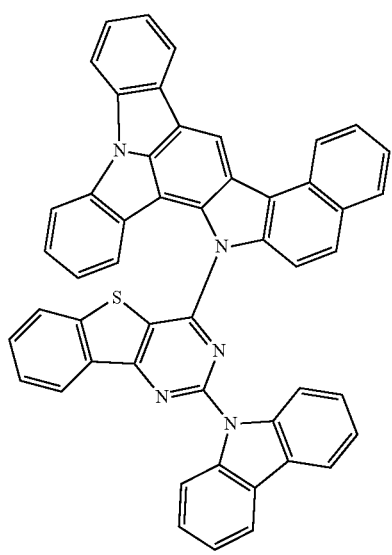
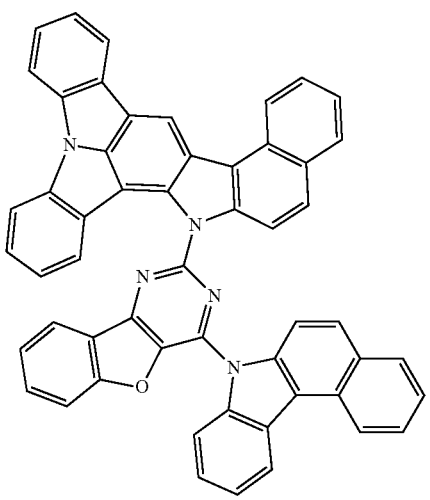
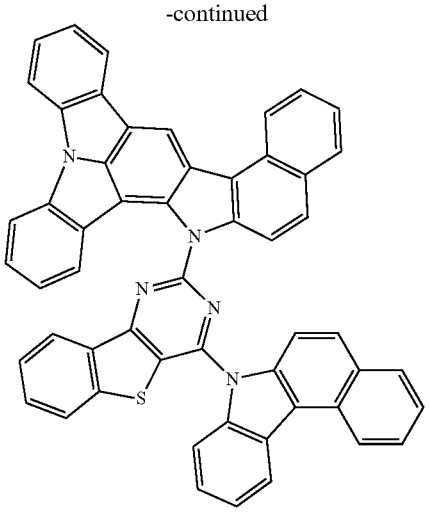
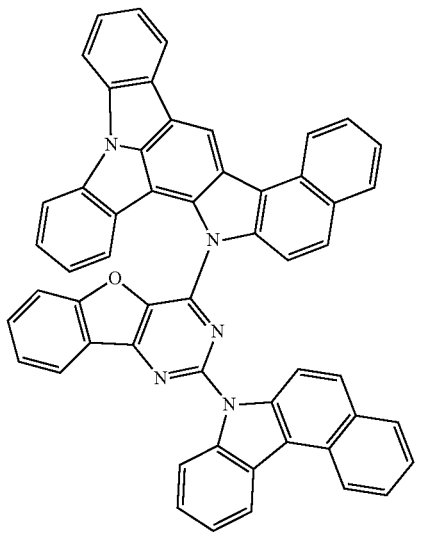
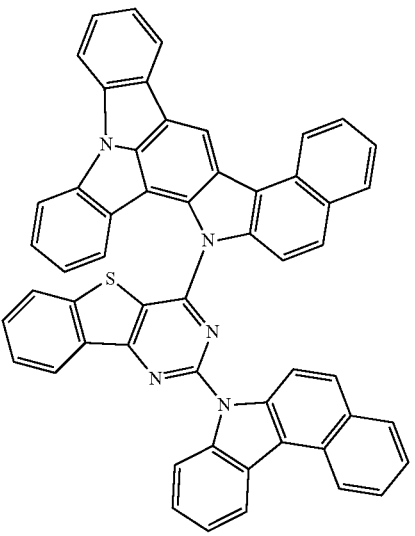

295
-continued
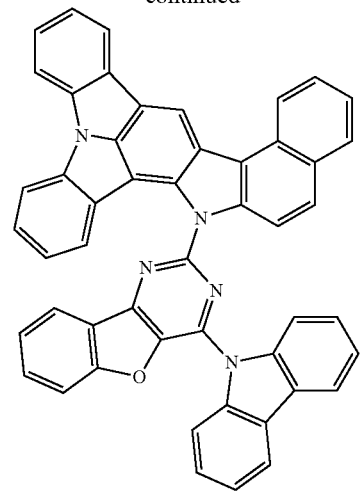
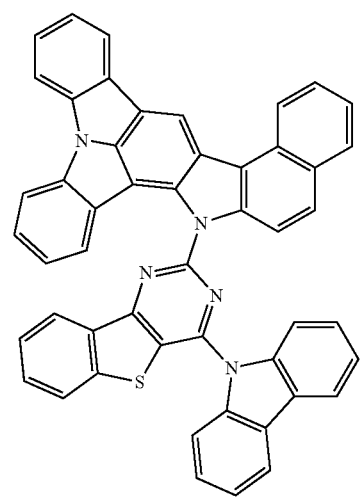
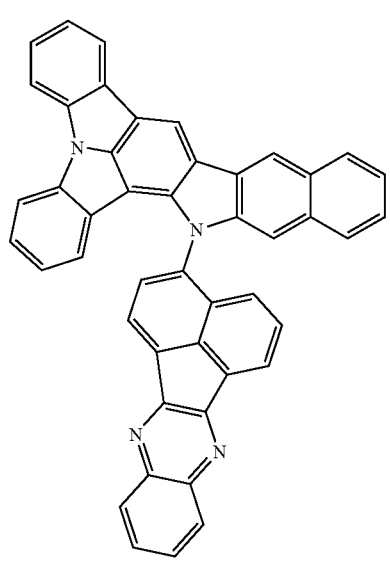
296
-continued
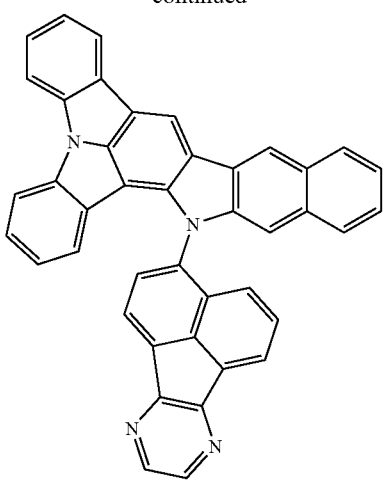
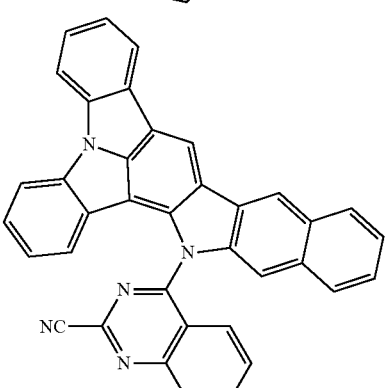
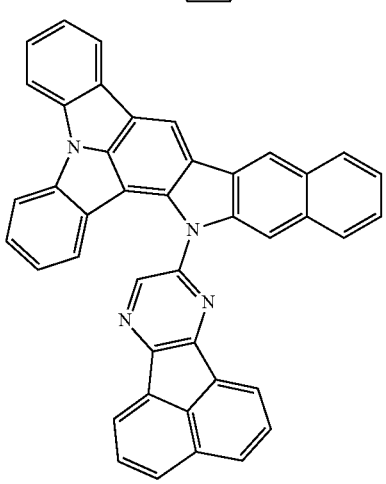

297
-continued
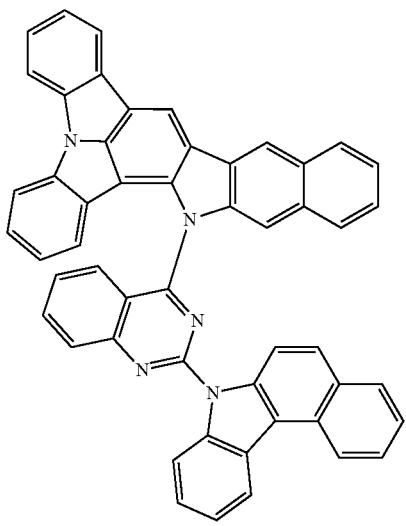
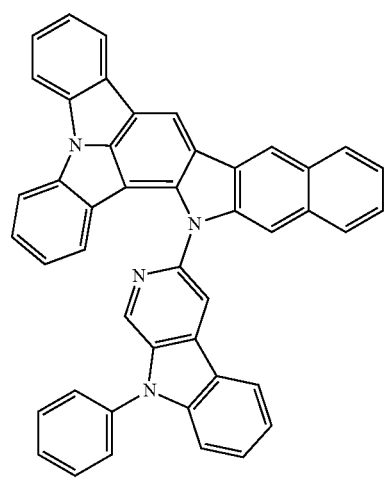
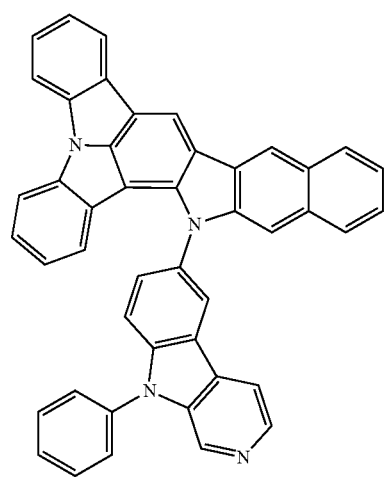
298
-continued
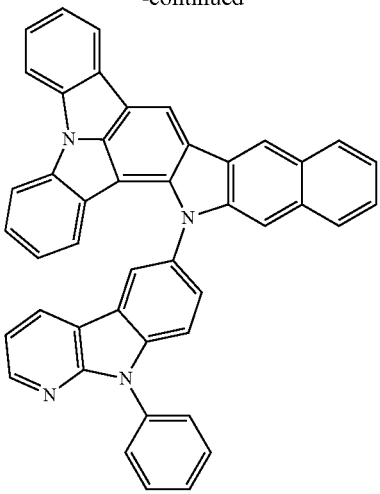
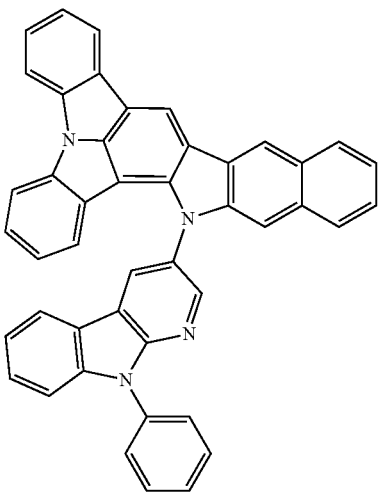
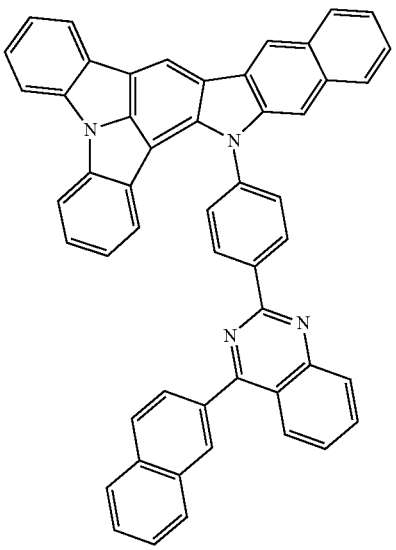

299
-continued
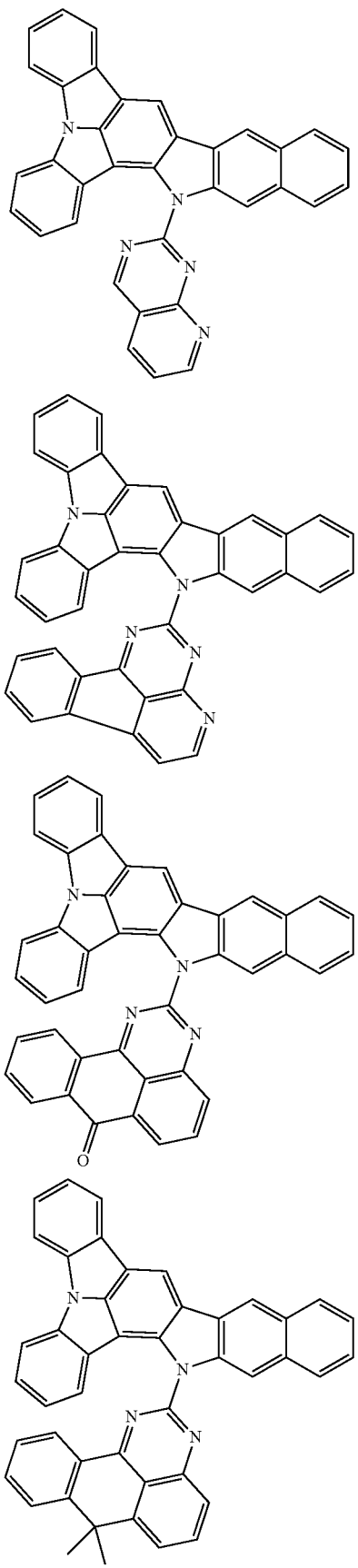
300
-continued
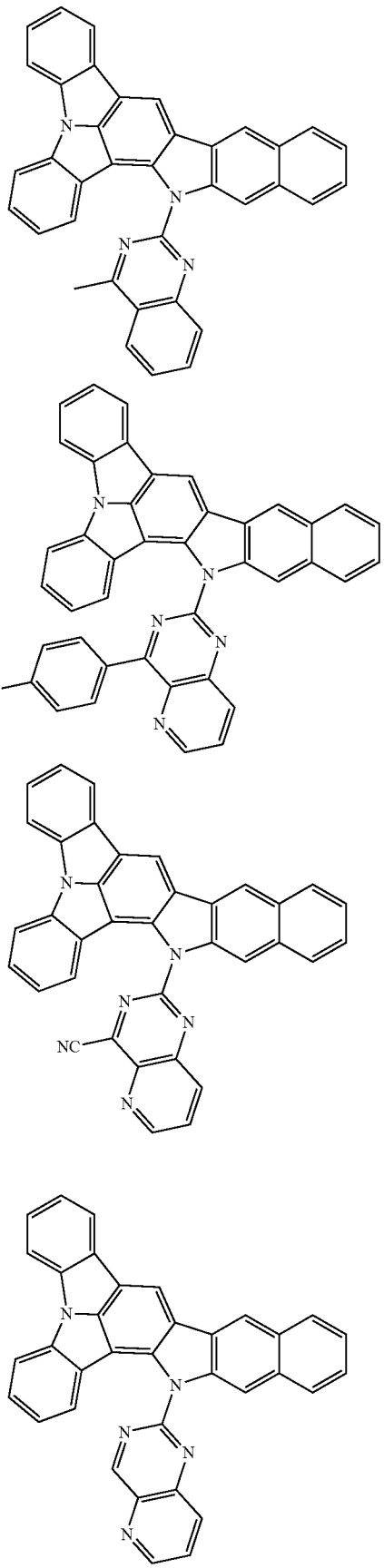

301
-continued
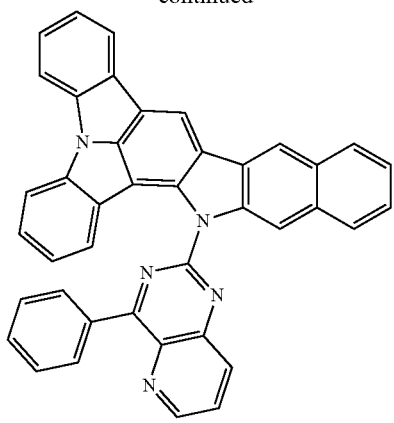
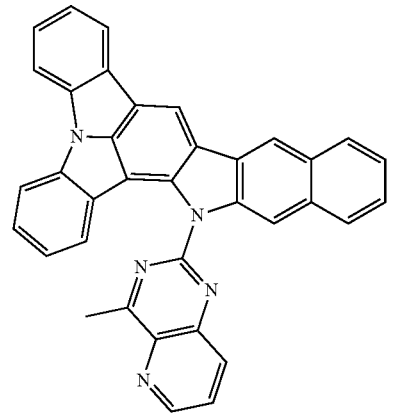
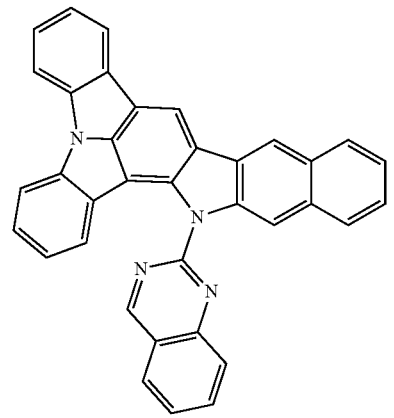
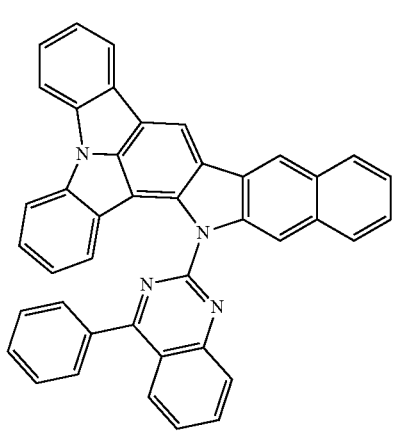
302
-continued
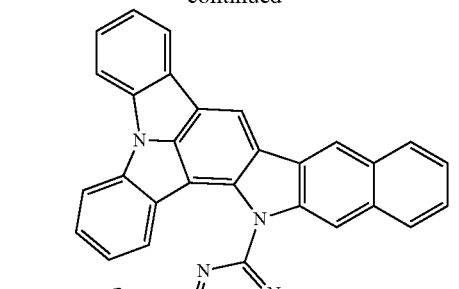

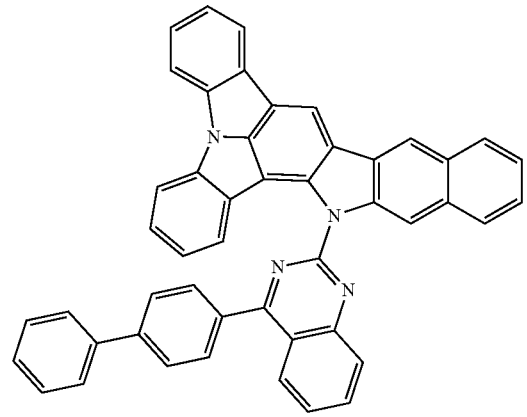
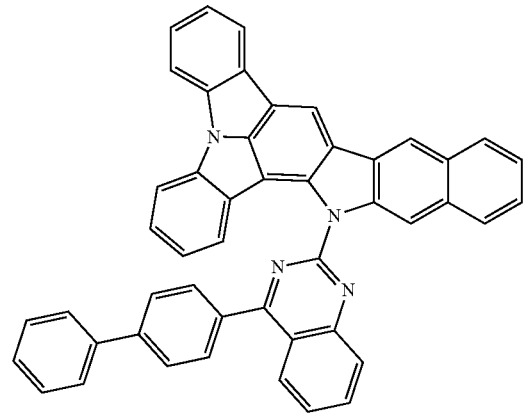

303
-continued
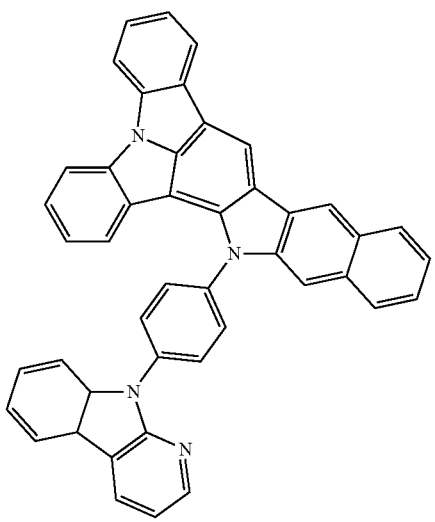
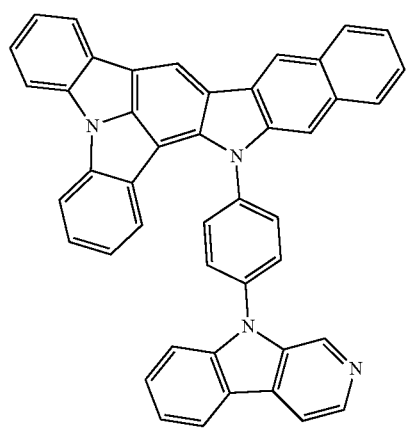
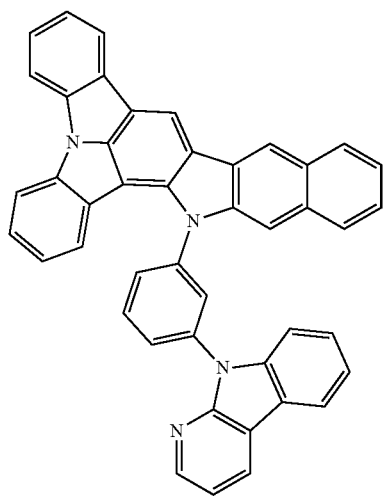
304
-continued
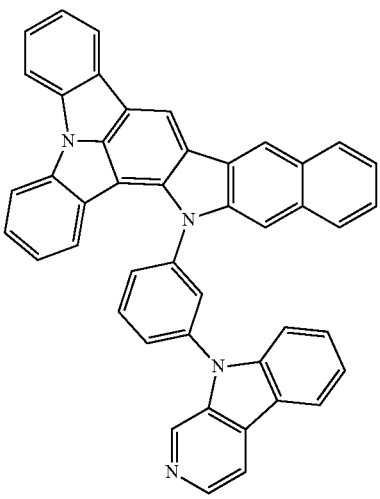
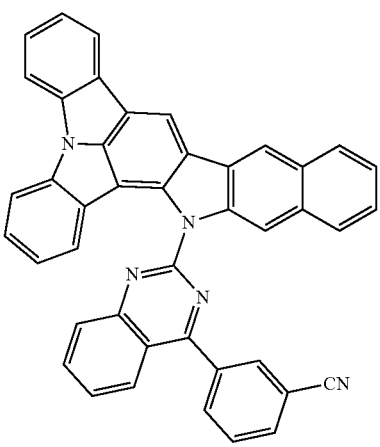
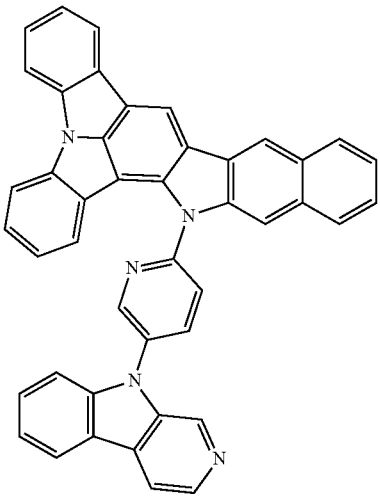

305
-continued
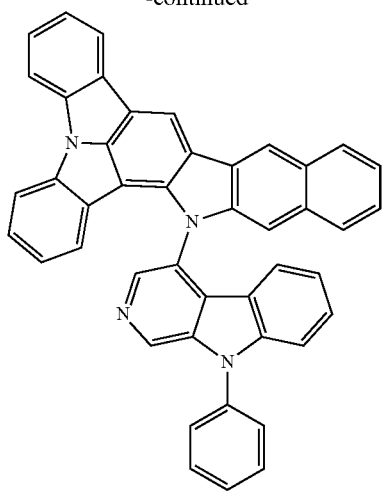
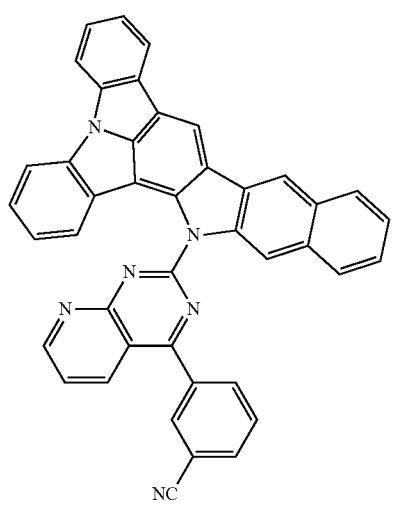
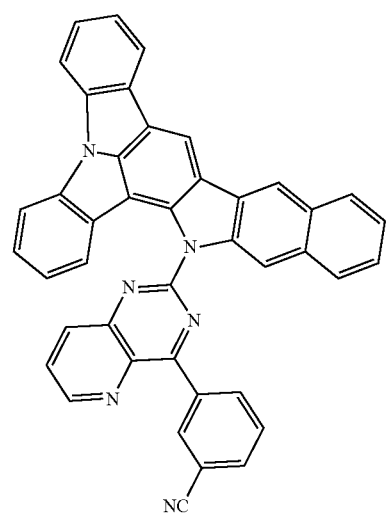
306
-continued
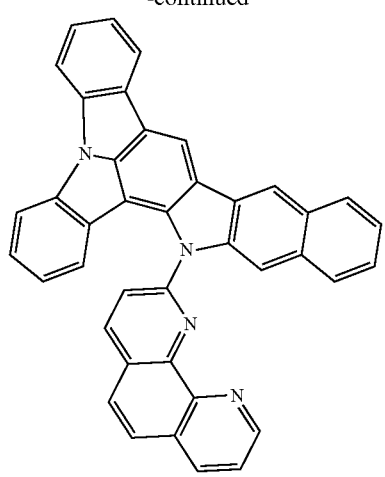
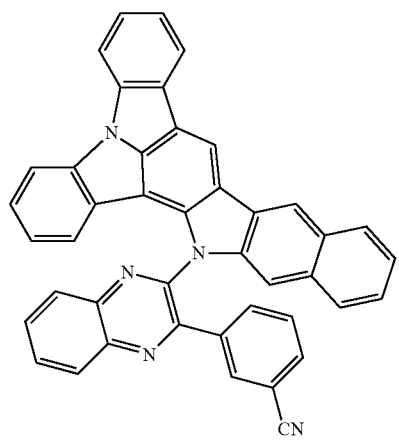
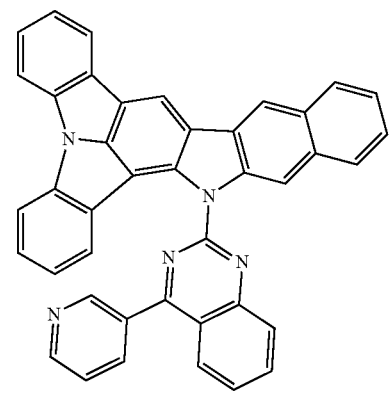
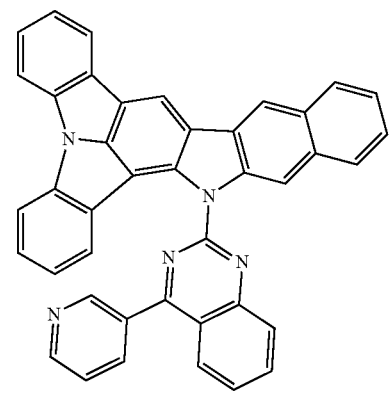

307
-continued
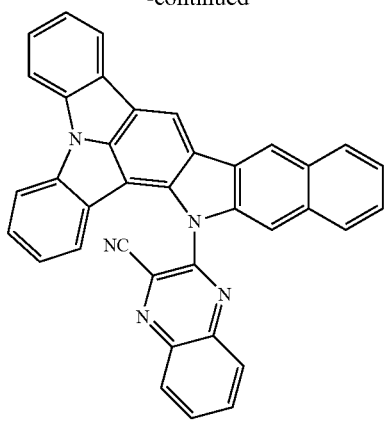
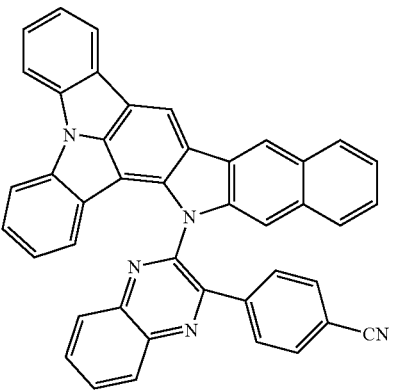
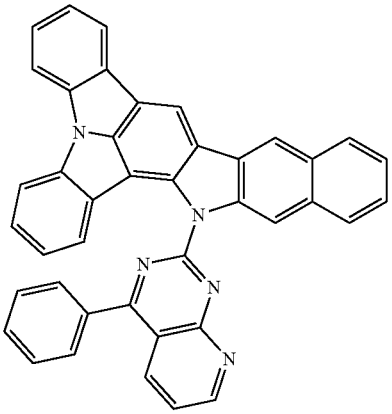
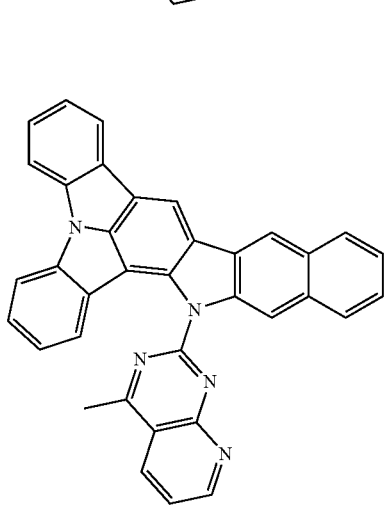
308
-continued
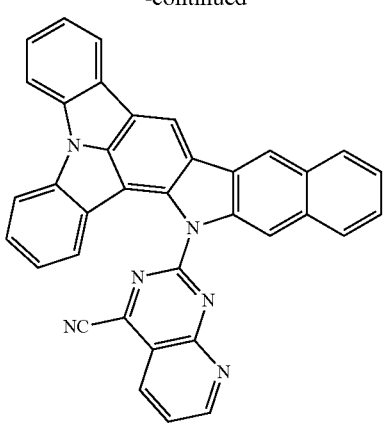
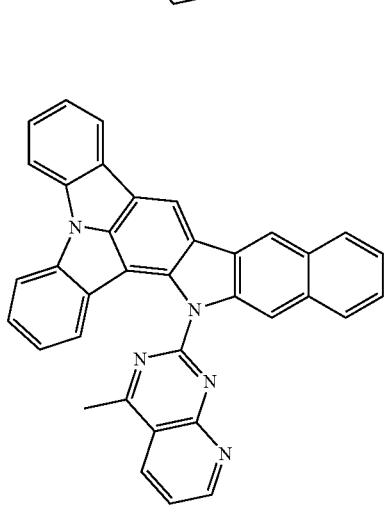
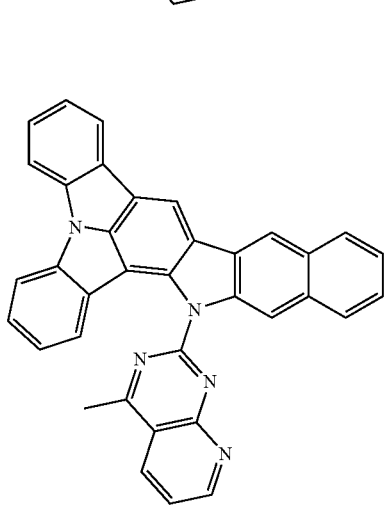

309
-continued

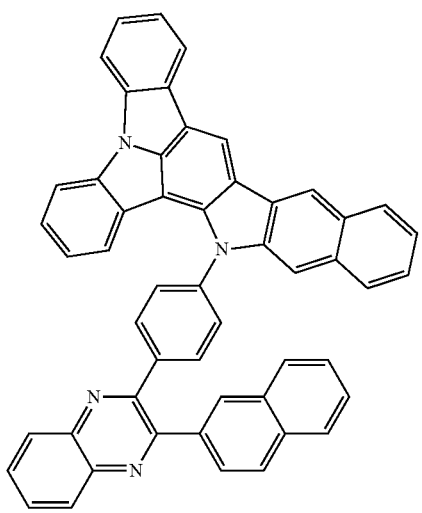
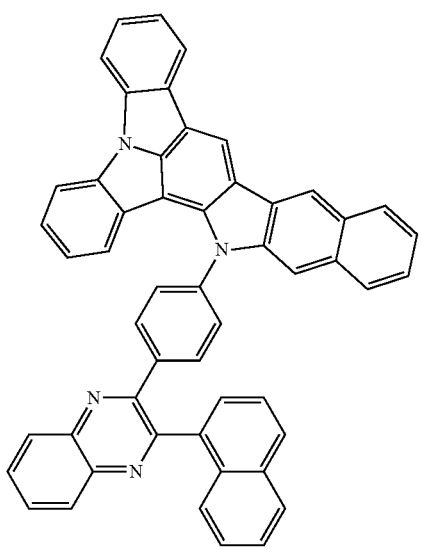
310
-continued
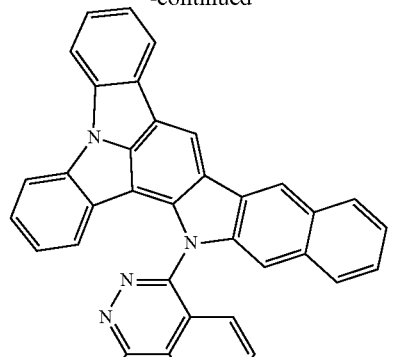
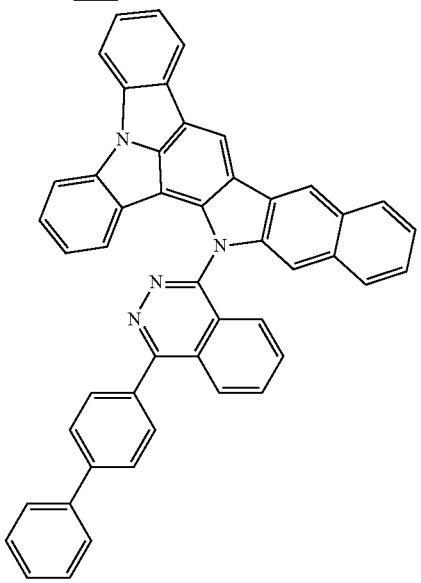
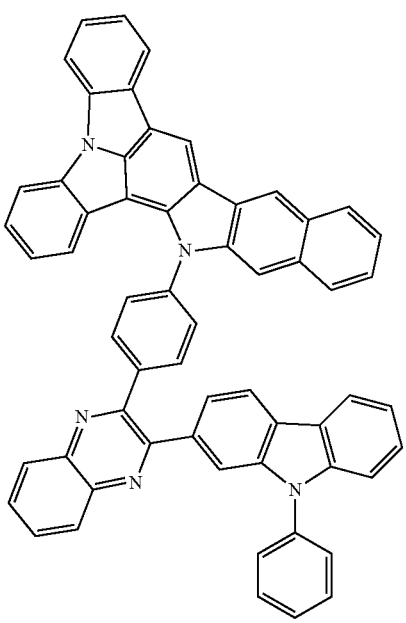

311
-continued
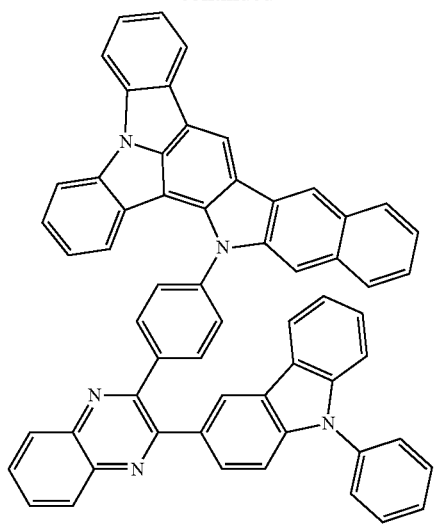
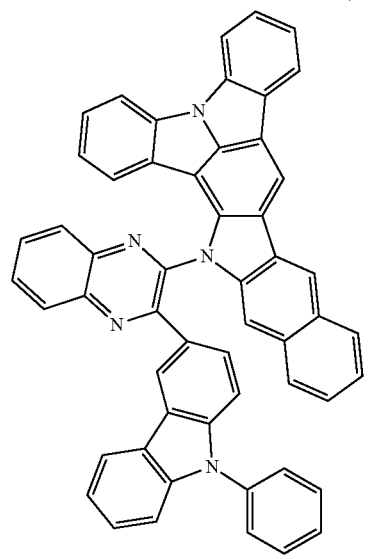
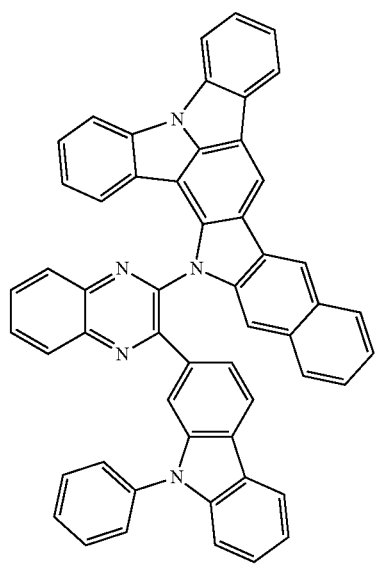
312
-continued
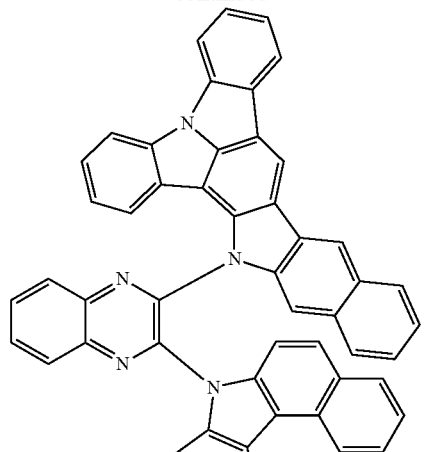
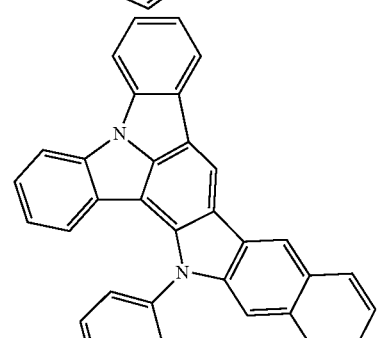
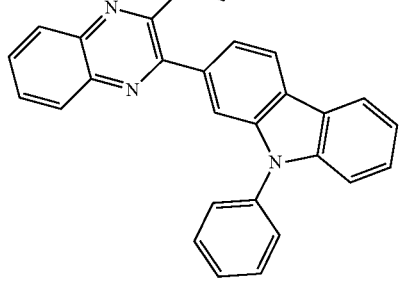
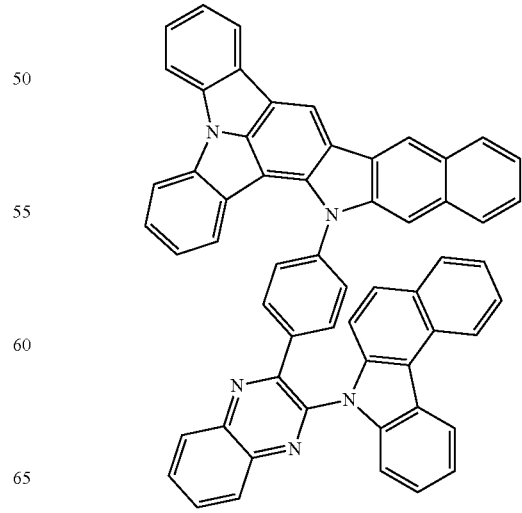

313
-continued
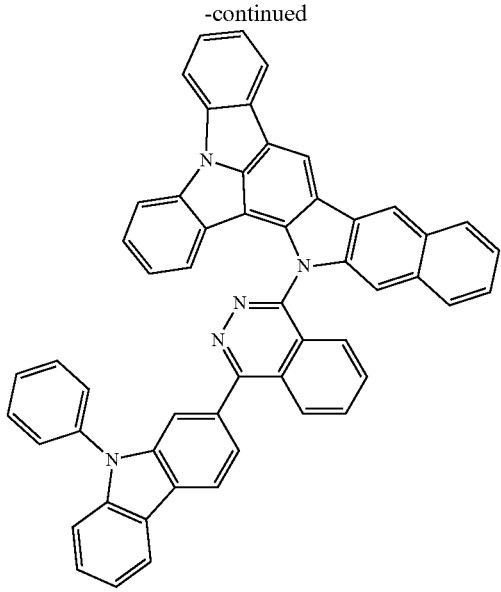
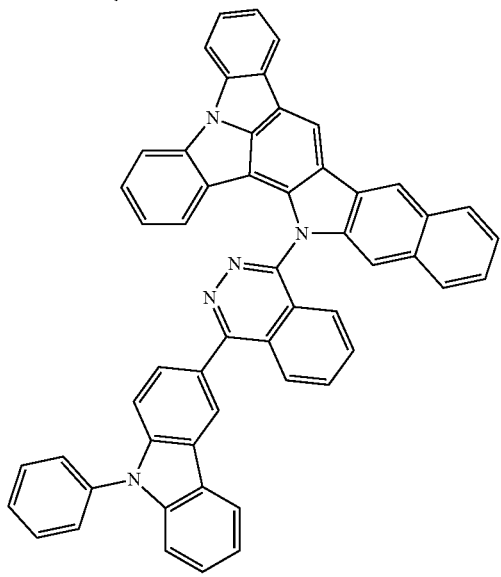
314
-continued
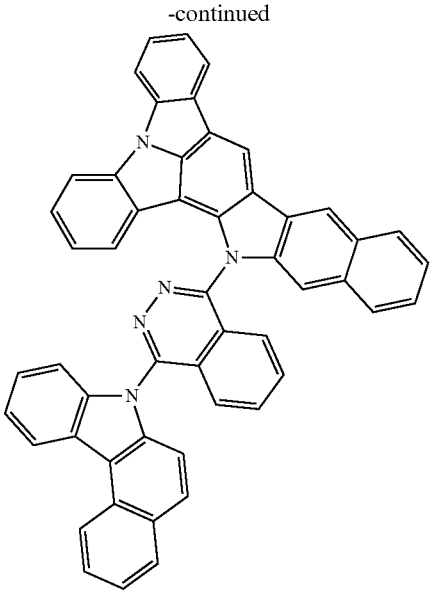
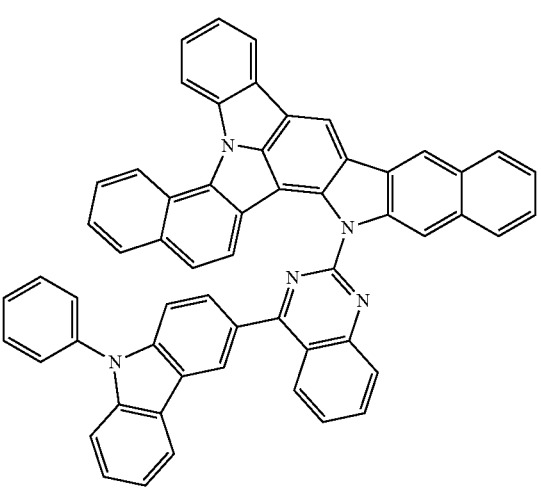
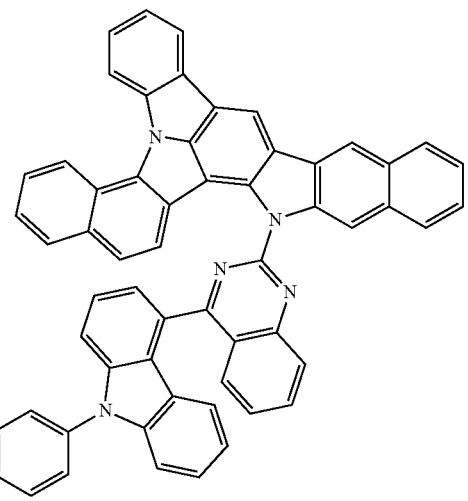

315
-continued
316
-continued
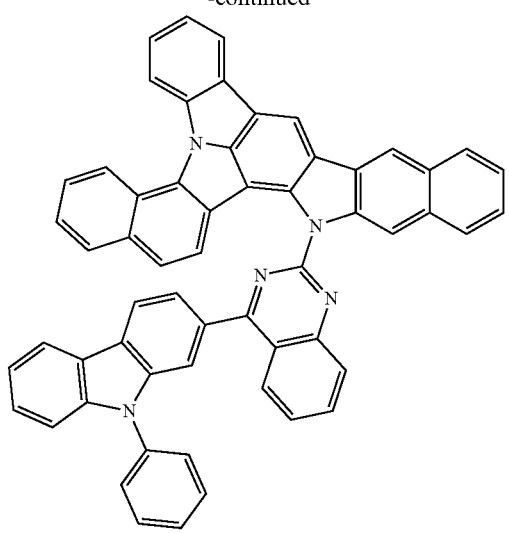
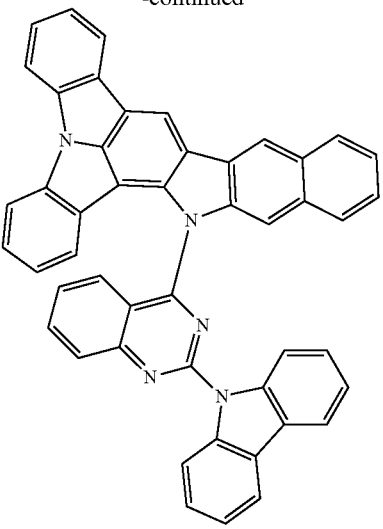

317
-continued
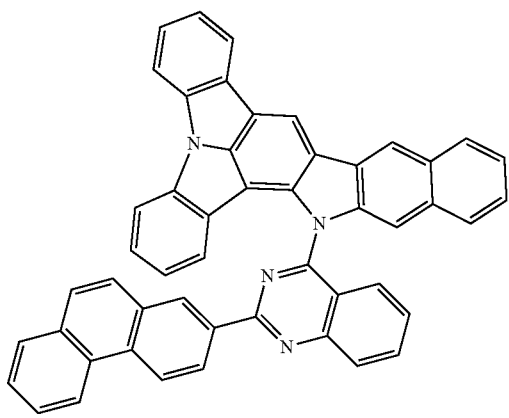
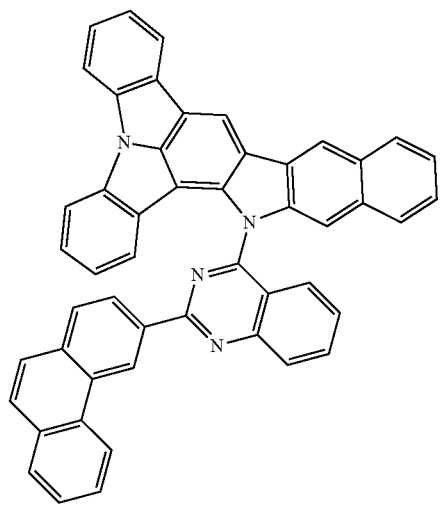
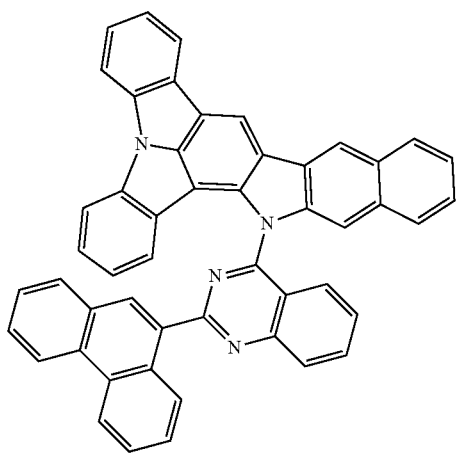
318
-continued
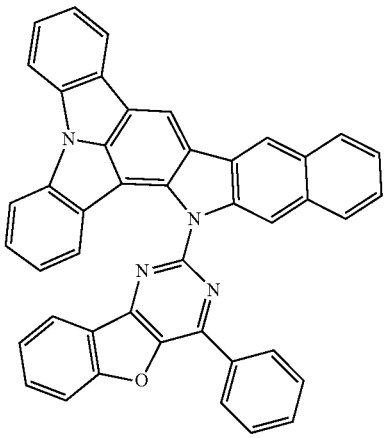
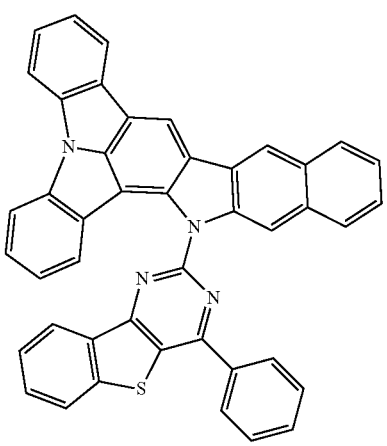
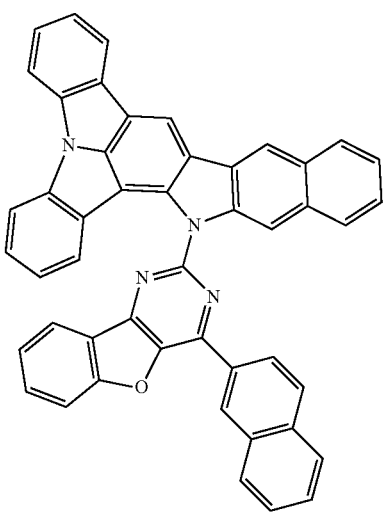

319
-continued
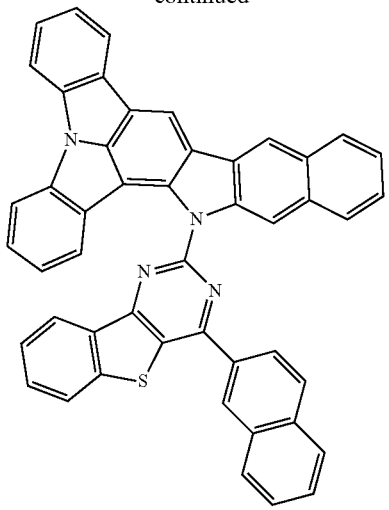
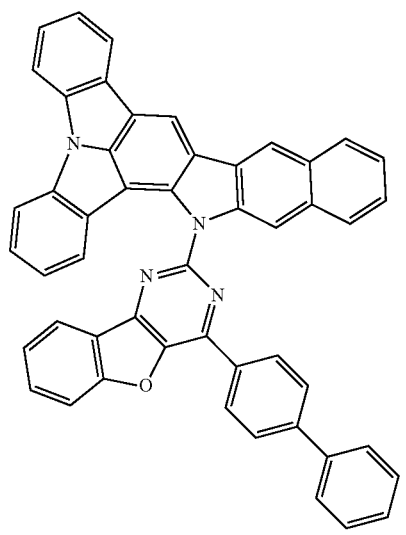
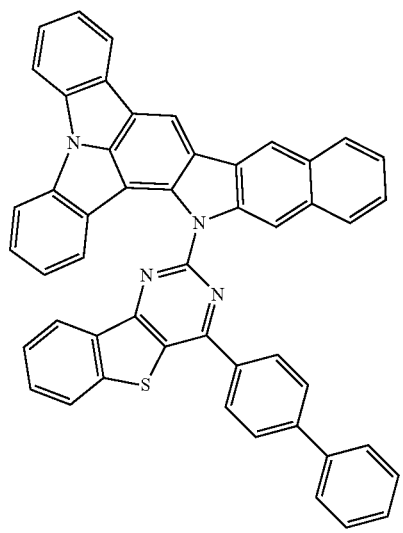
320
-continued
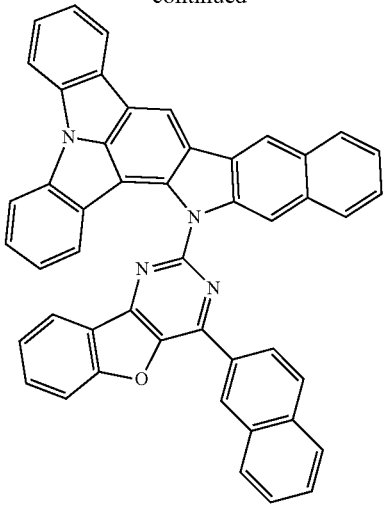
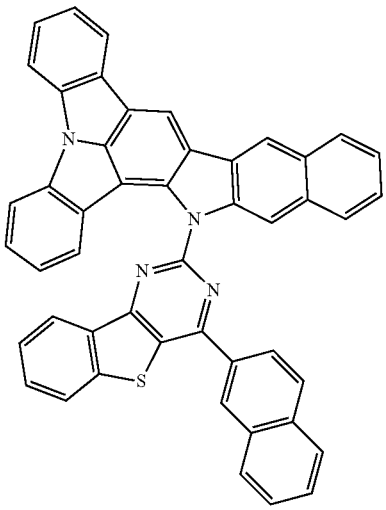
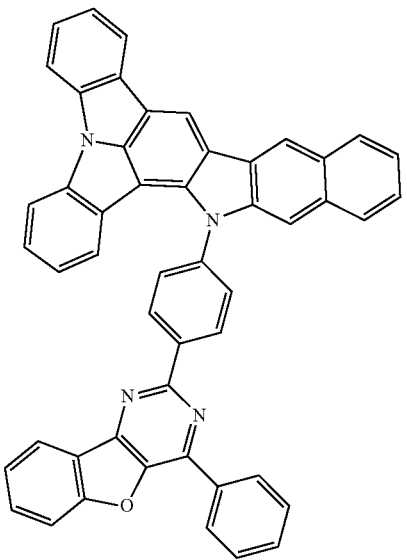

321
-continued
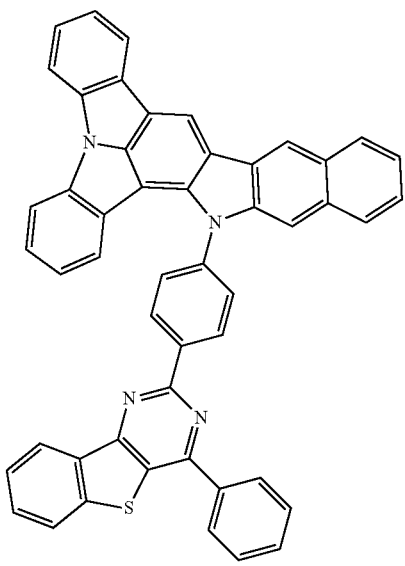
322
-continued
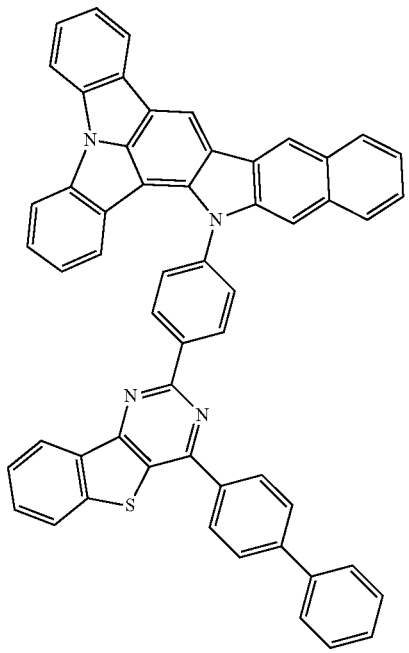
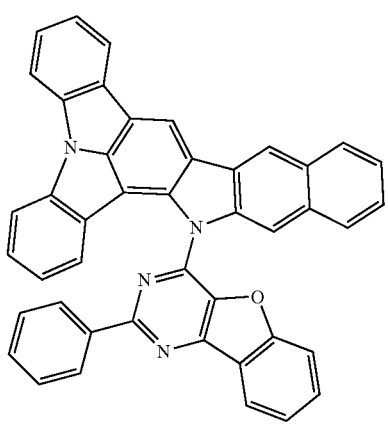
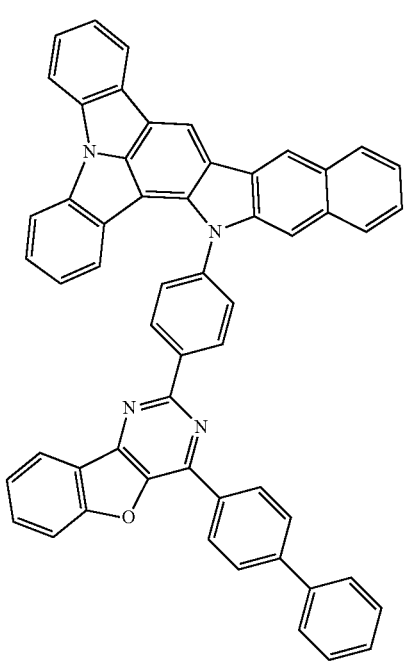
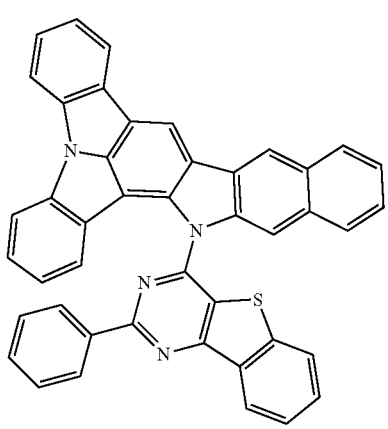

323
-continued
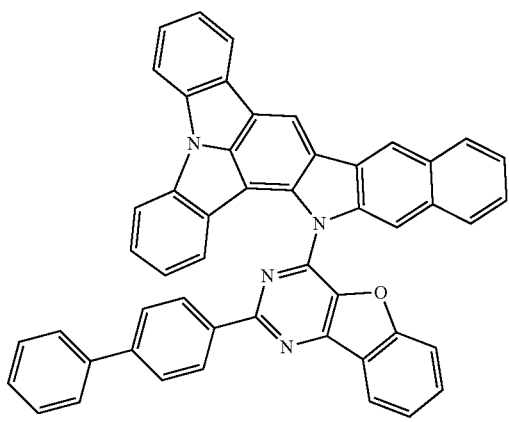
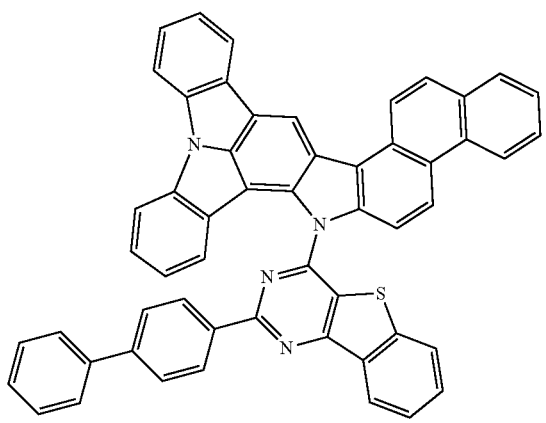
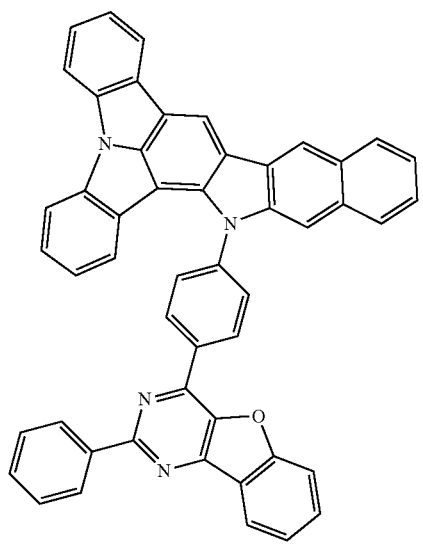
324
-continued
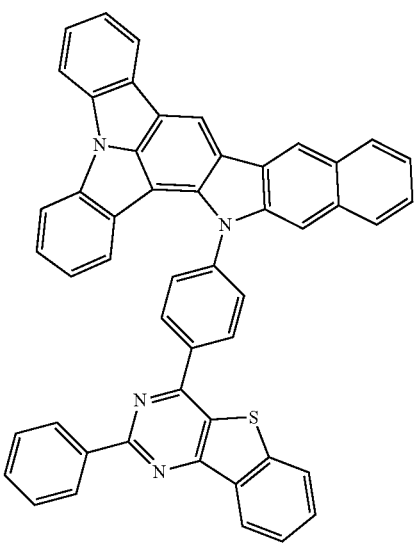
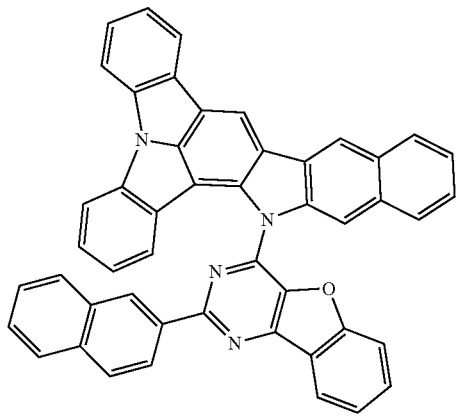
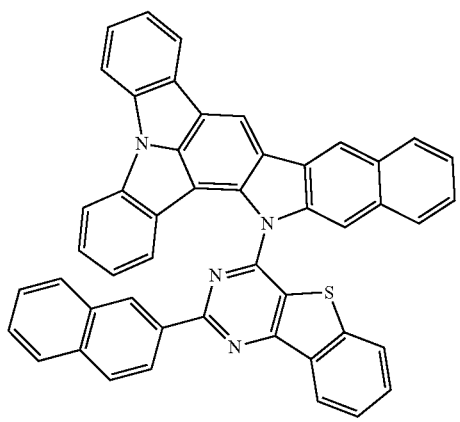

325
-continued
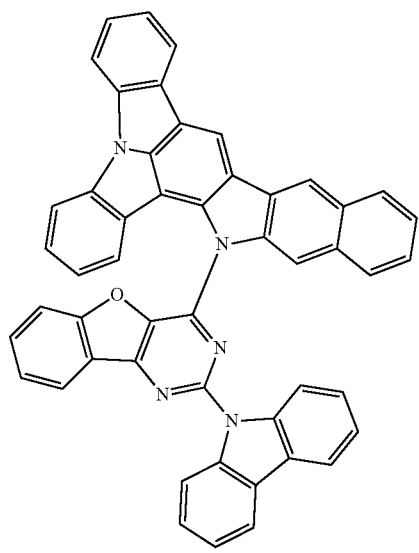
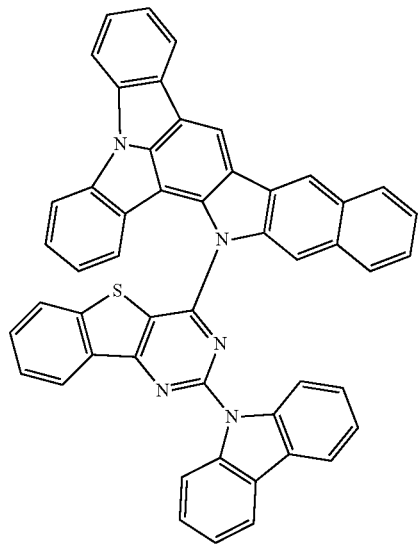
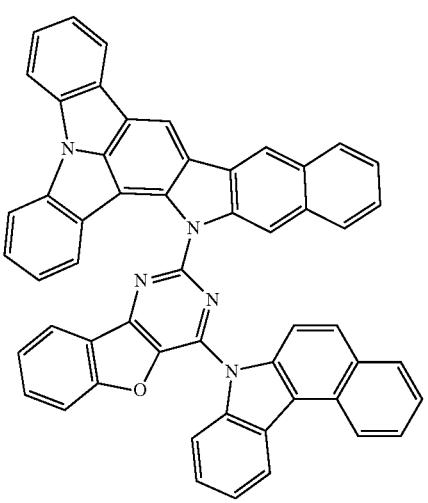
326
-continued
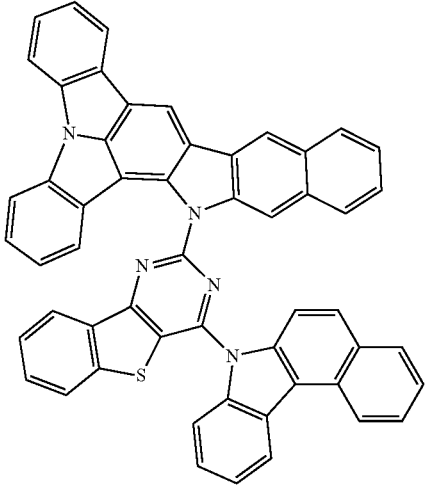
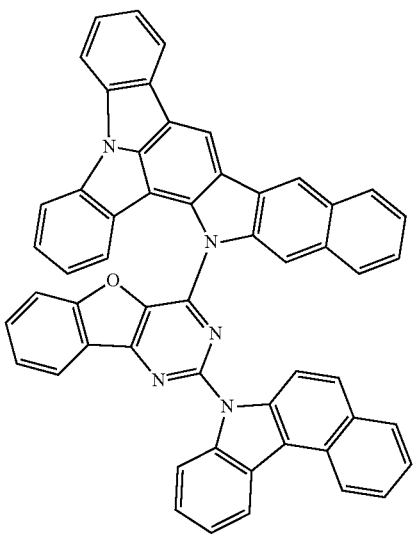
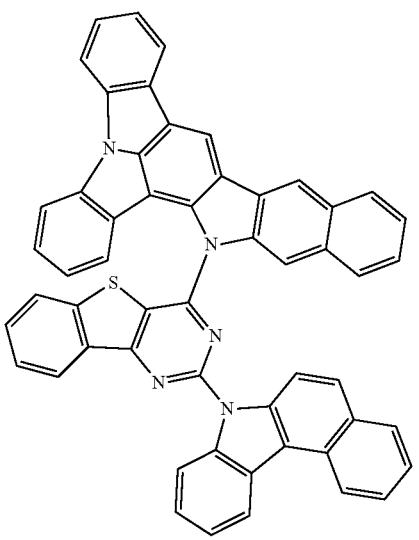

327
-continued
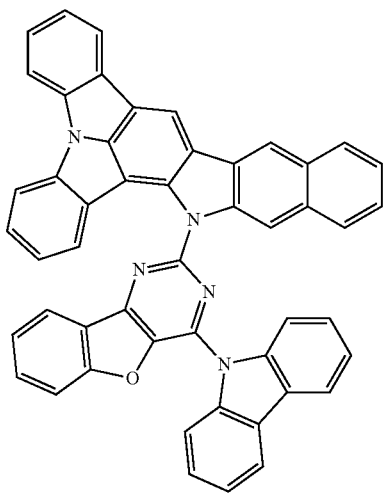
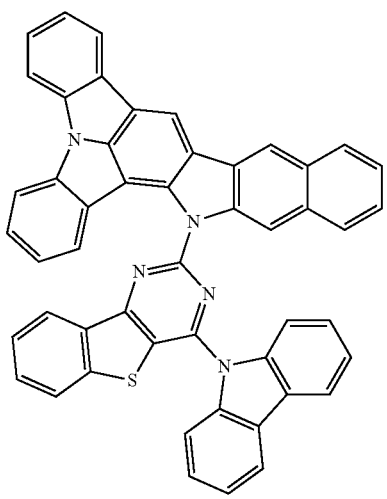
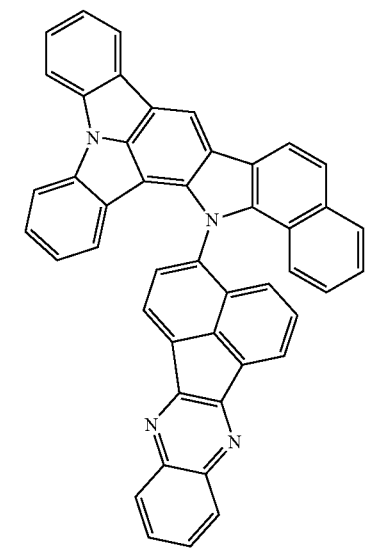
328
-continued
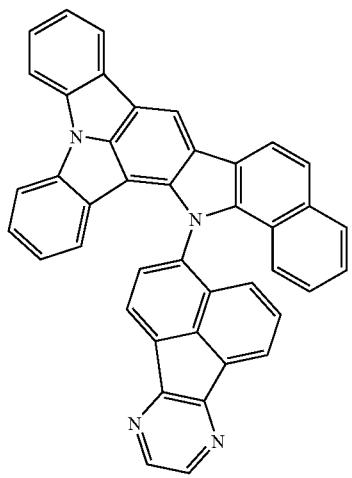
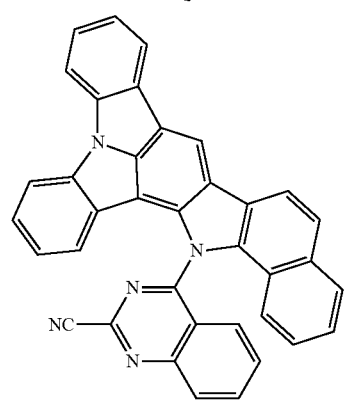
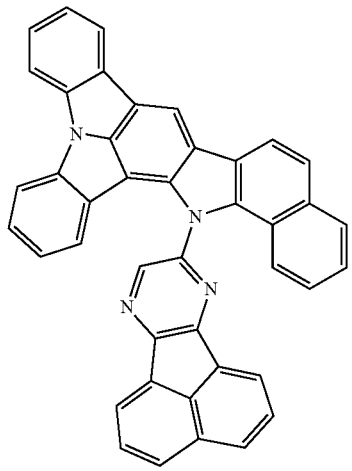
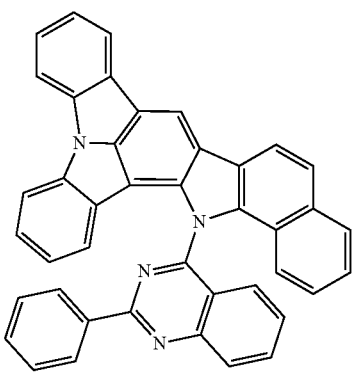

329
-continued
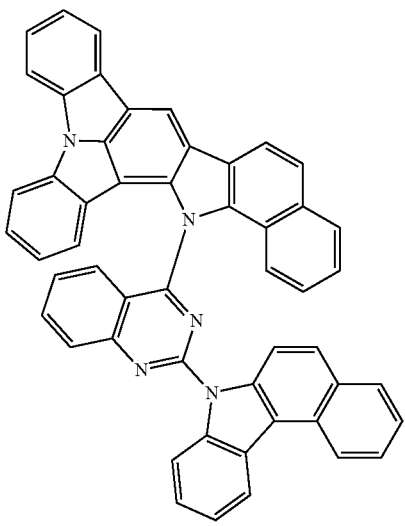
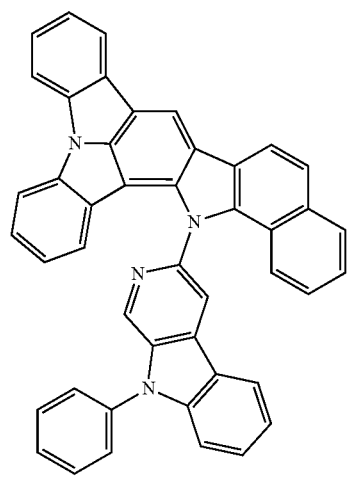
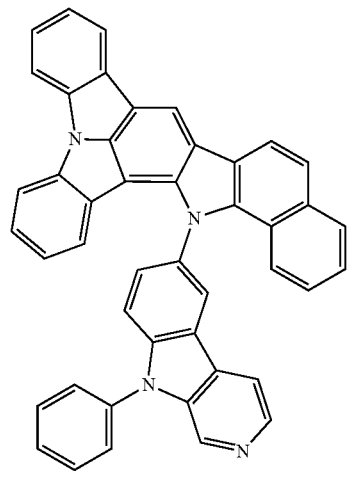
330
-continued
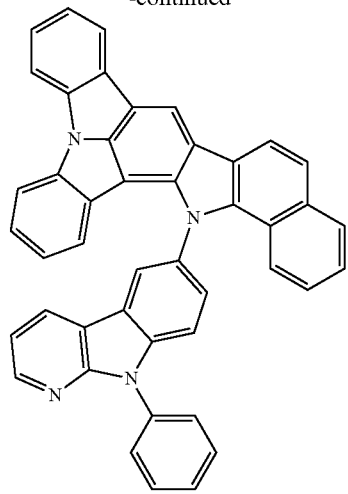
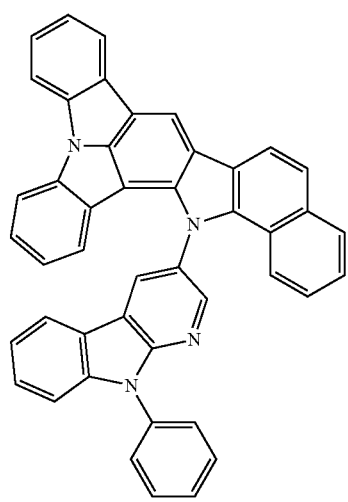
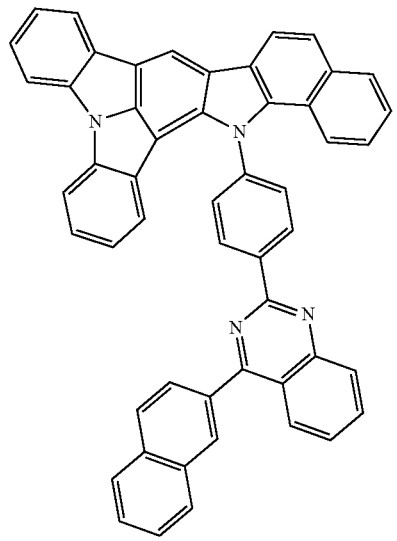

331
-continued
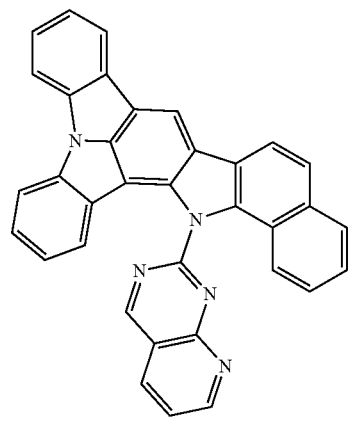
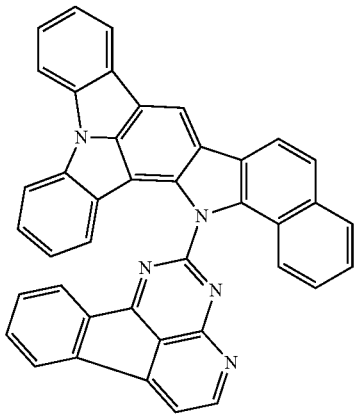
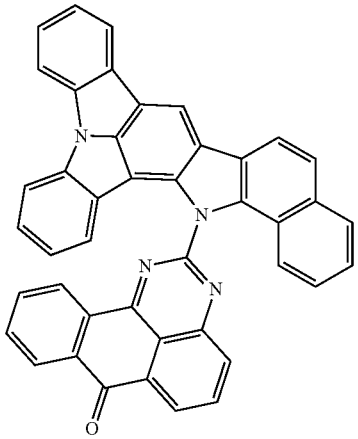
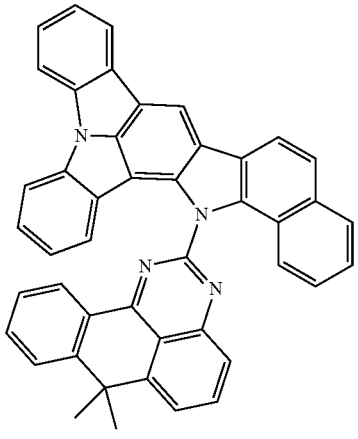
332
-continued
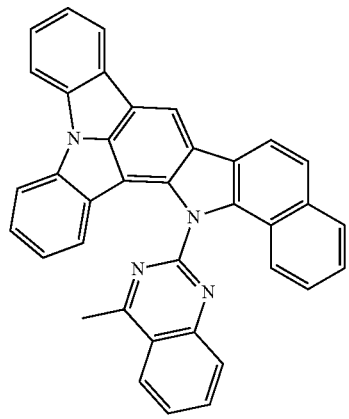
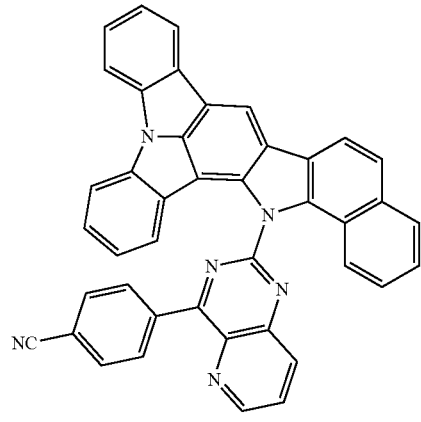
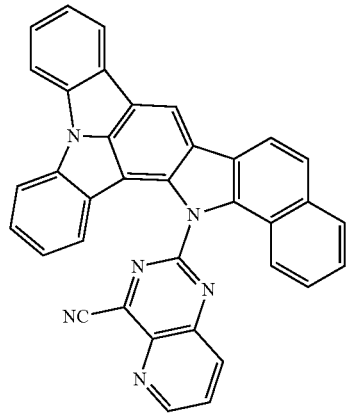
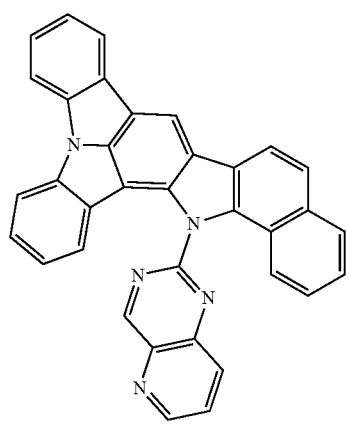

333
-continued
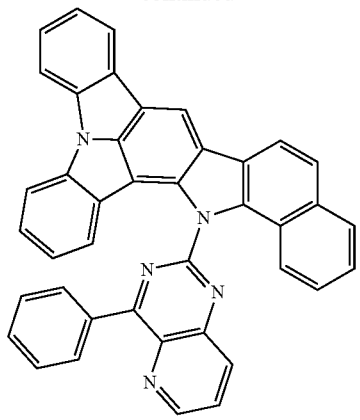
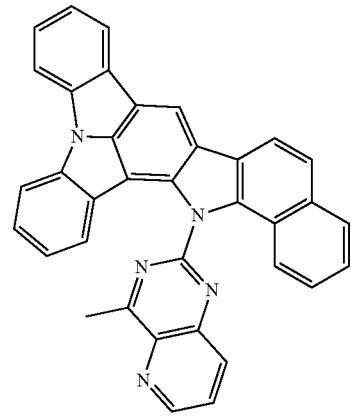
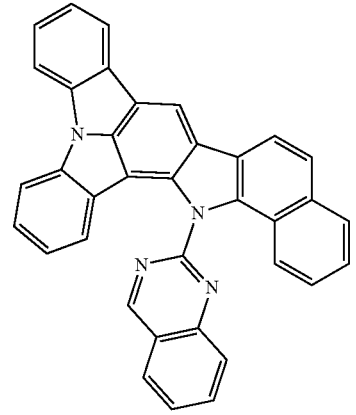
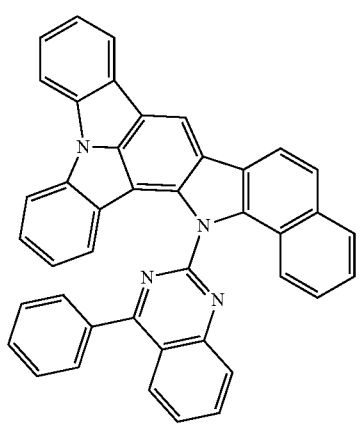
334
-continued
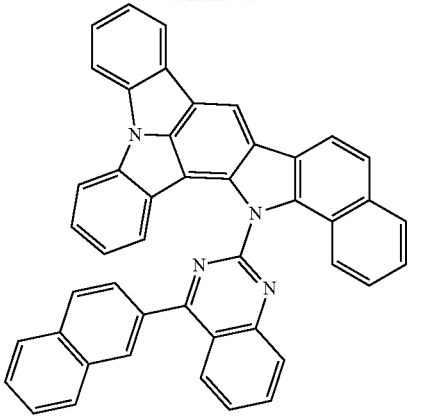
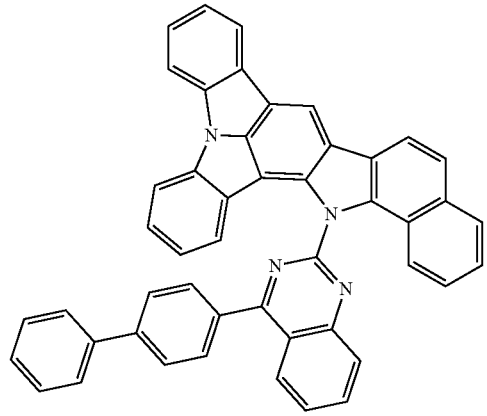
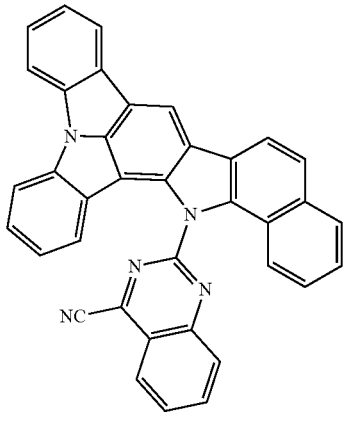
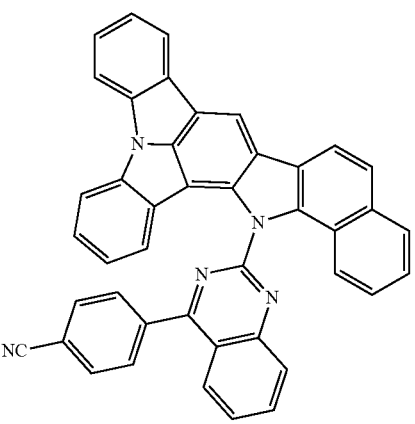

335
-continued
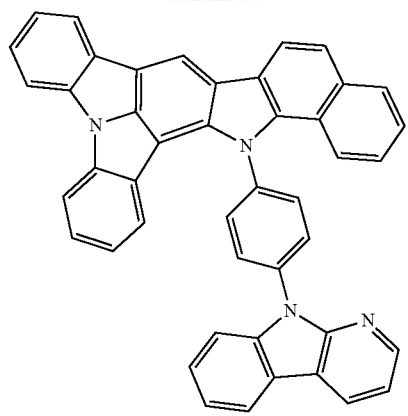
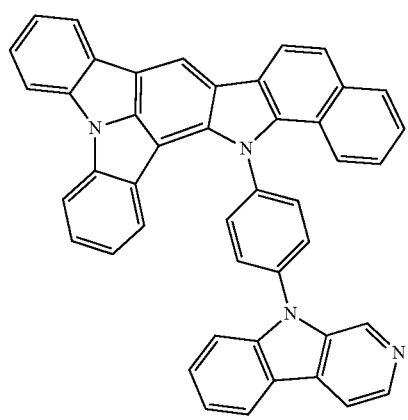
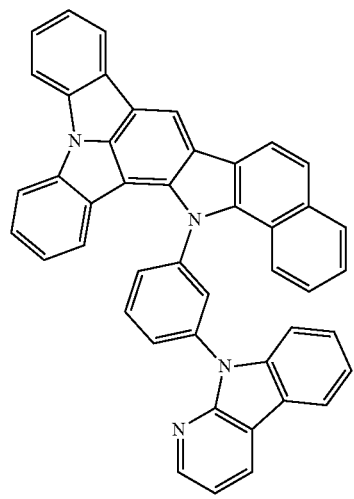
336
-continued
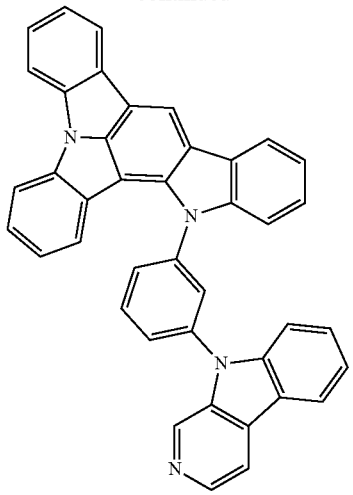
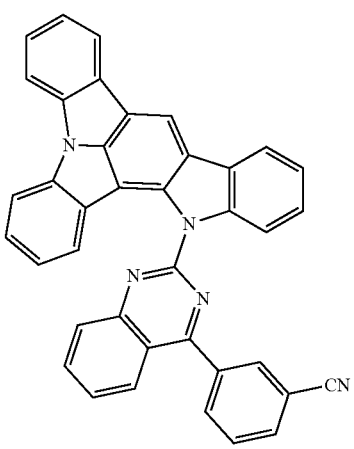
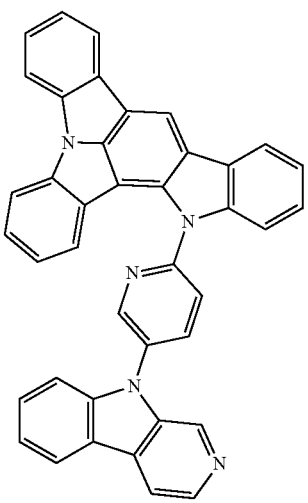

337
-continued
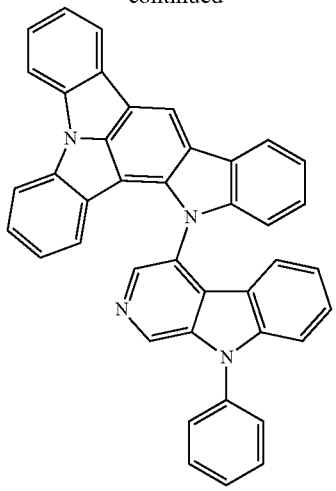
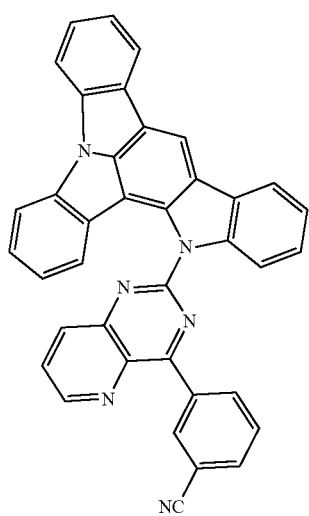 [SMILES: N#Cc1cccc(-c2nc(-n3c4ccccc4c4cc5c6ccccc6n6c7ccccc7c(c43)c56)nc3cccnc23)c1]
338
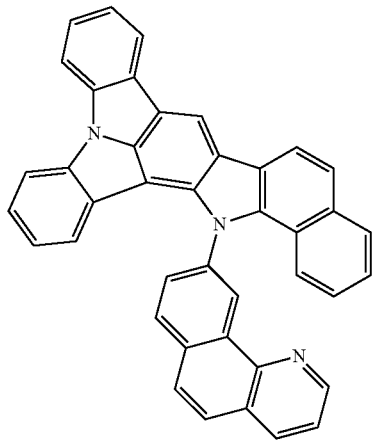
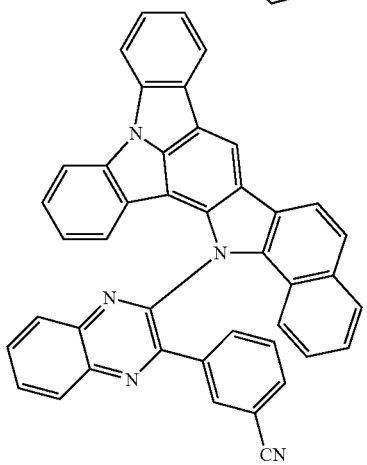
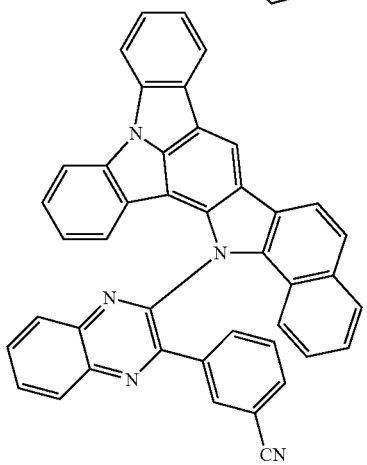

339
-continued
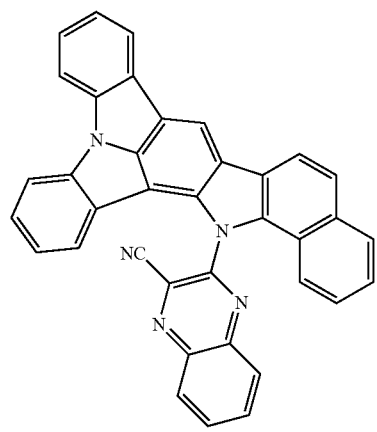
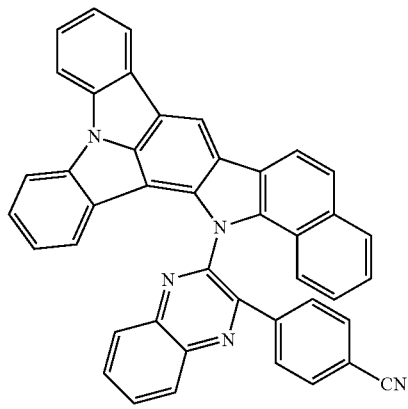

340
-continued
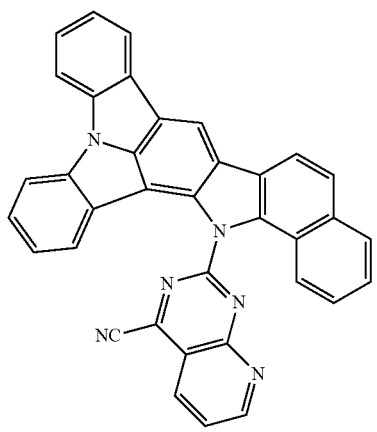
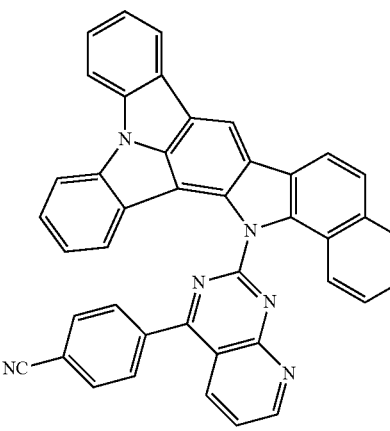
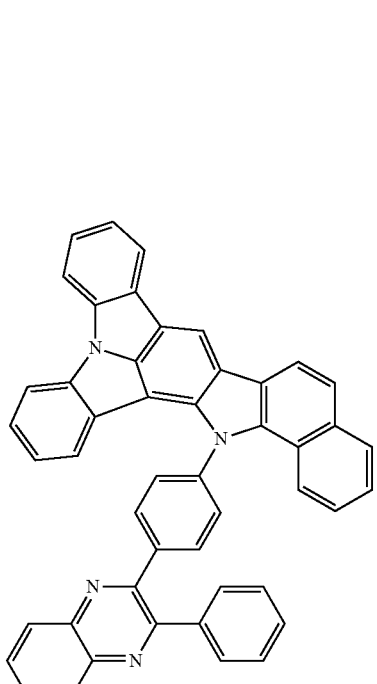

341
-continued
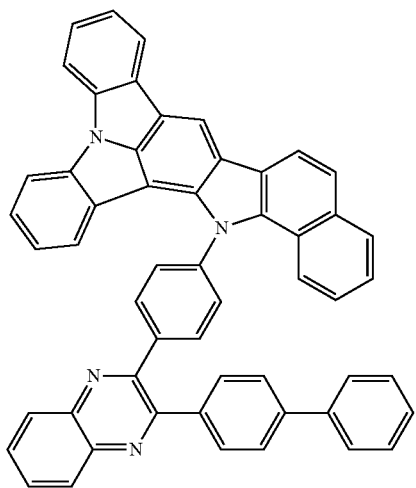
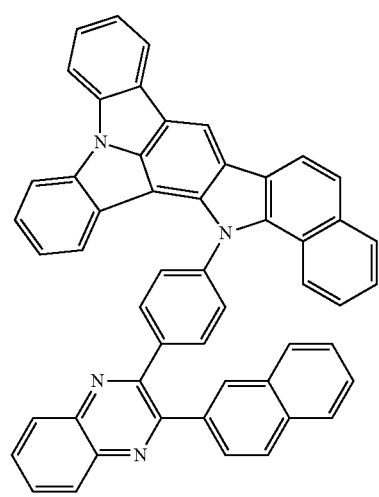
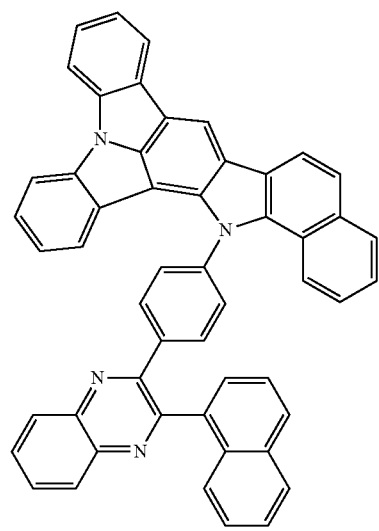
342
-continued
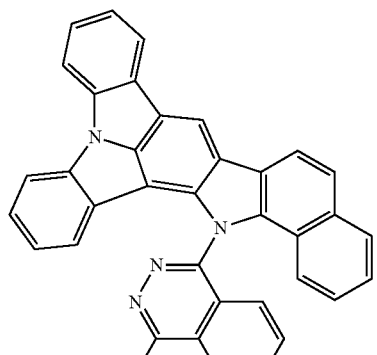
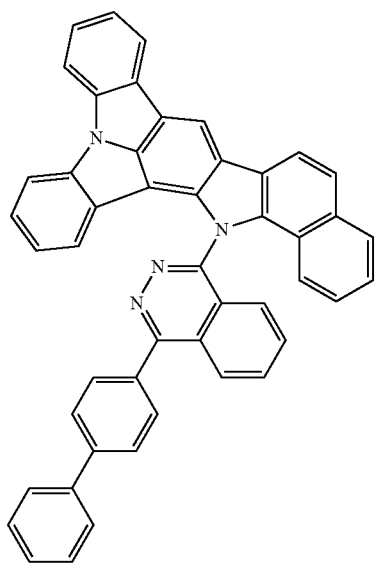 [SMILES: c1ccc(-c2ccc(-c3nnc(-n4c5c6ccccc6ccc5c5cc6c7ccccc7n7c8ccccc8c(c54)c67)c4ccccc34)cc2)cc1]
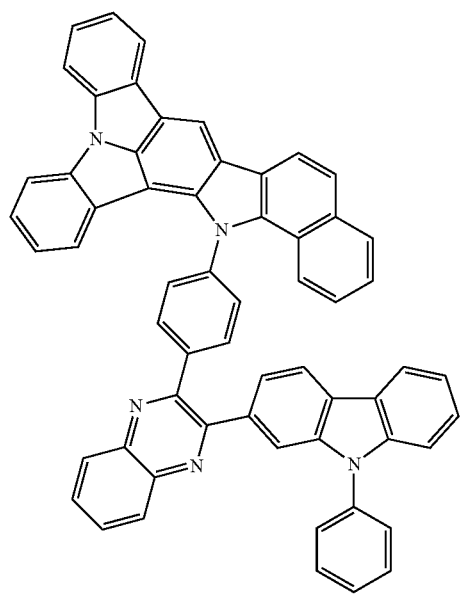

343
-continued
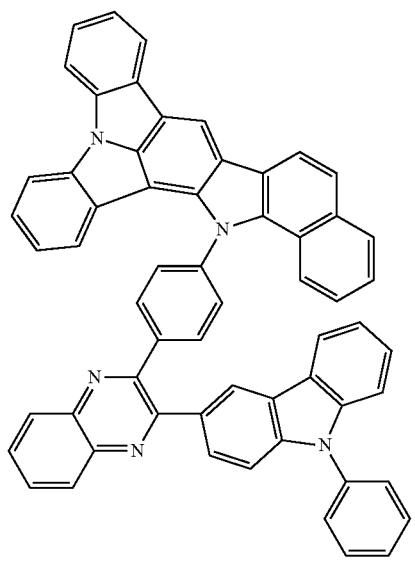
344
-continued
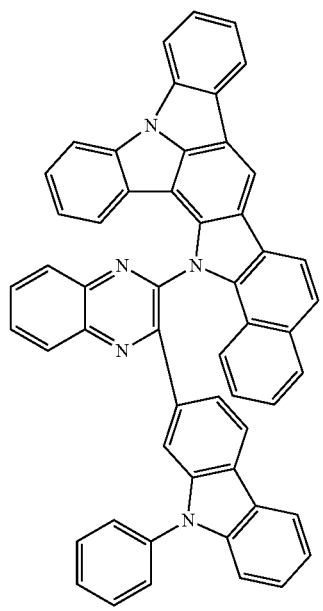
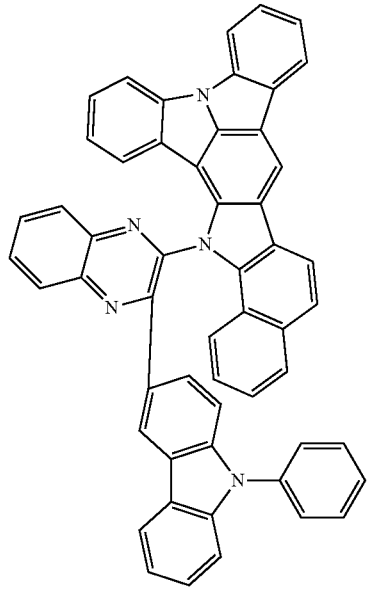
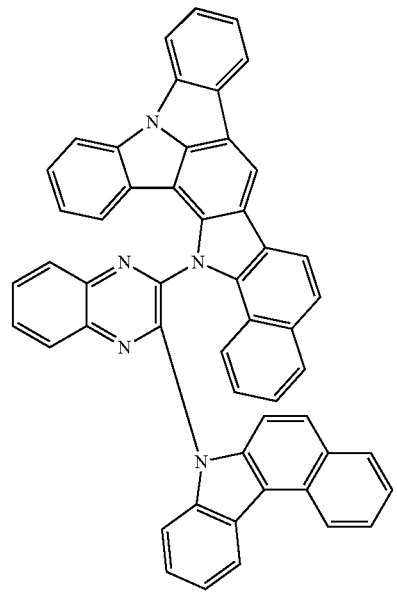

345
-continued
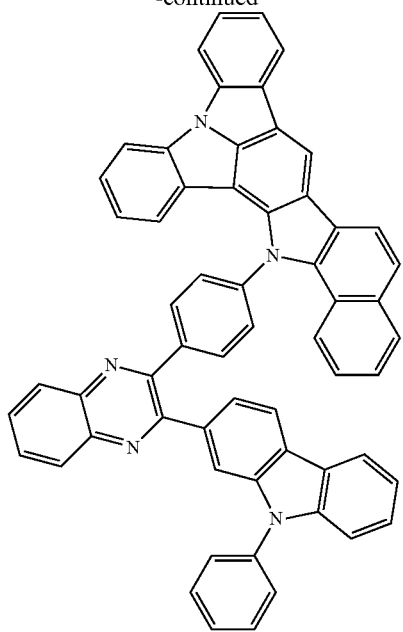
346
-continued
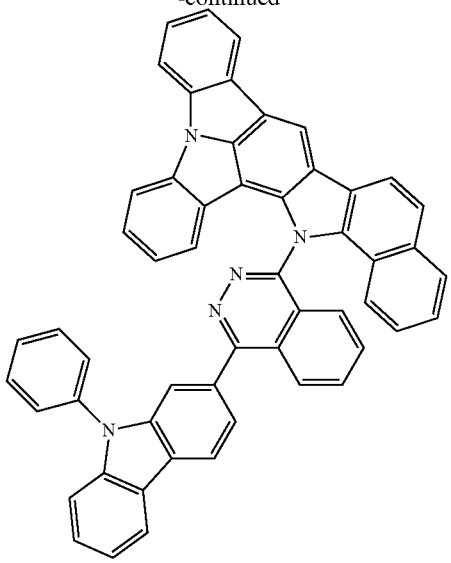
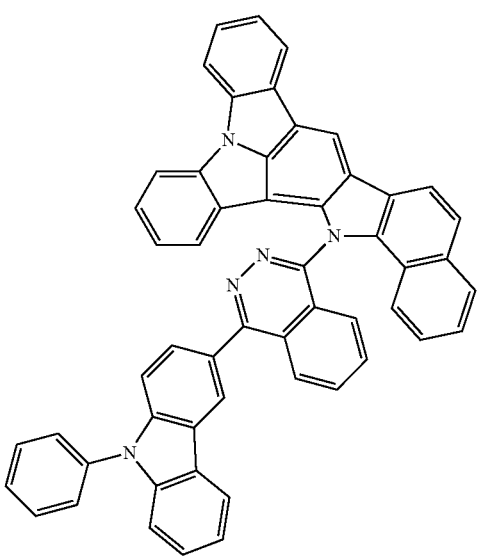
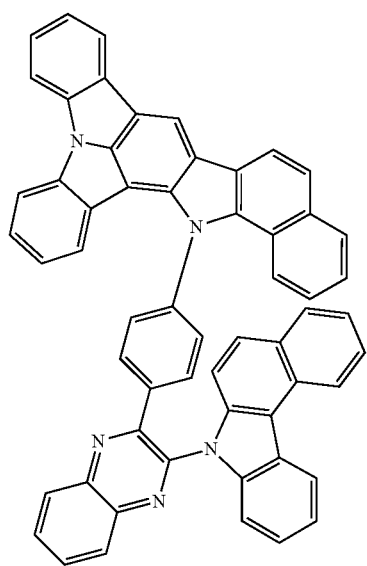

347
-continued
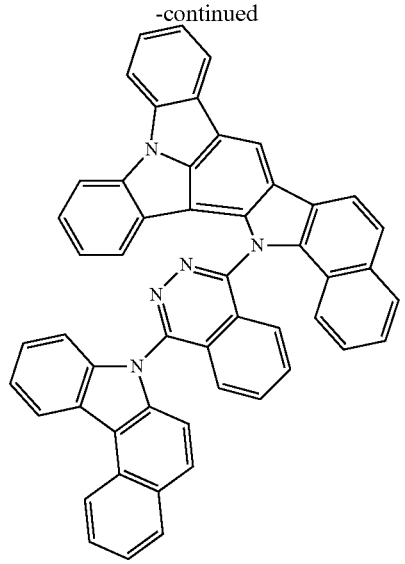
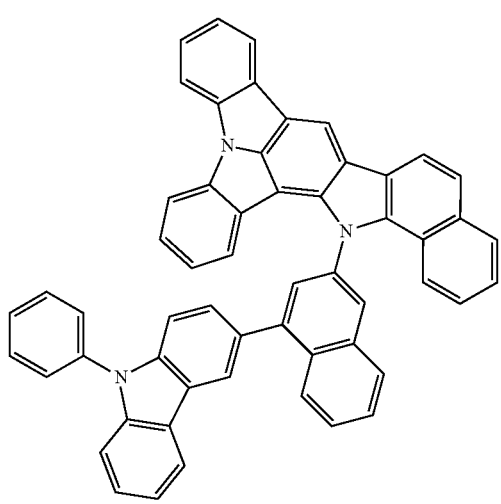
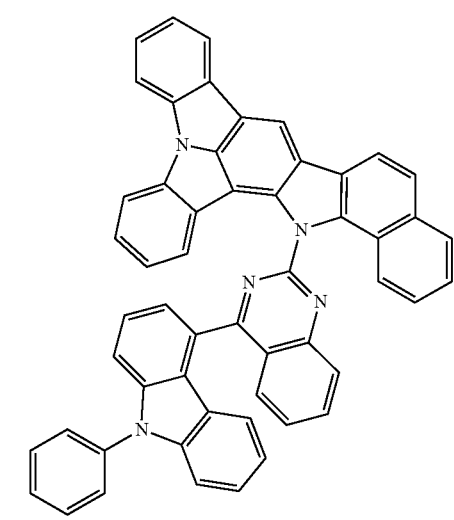
348
-continued
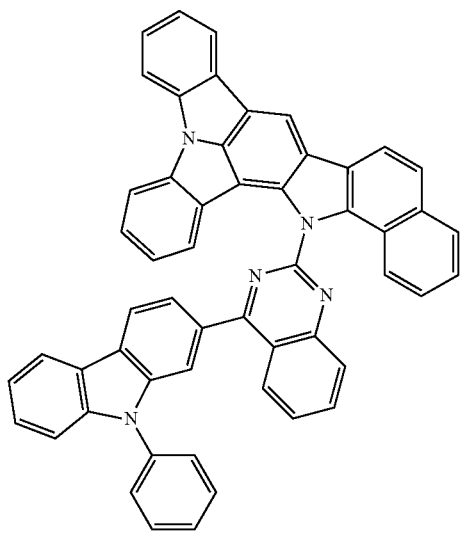
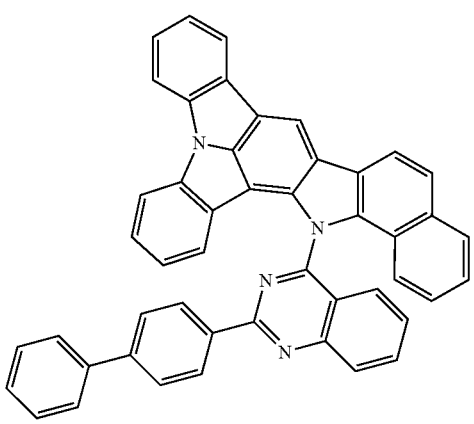
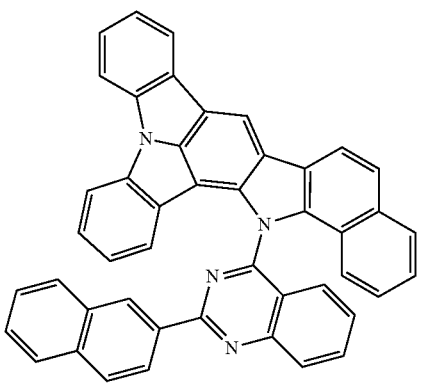

349
-continued
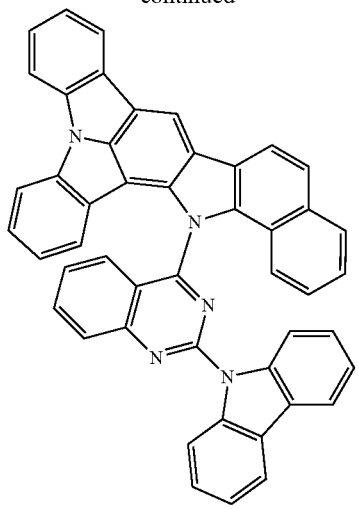
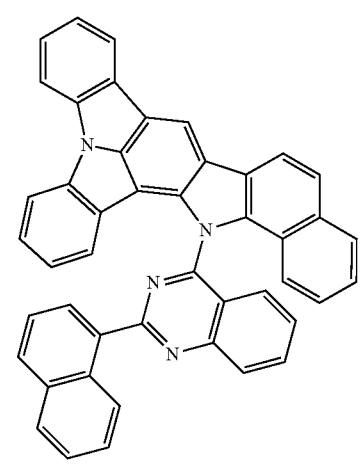
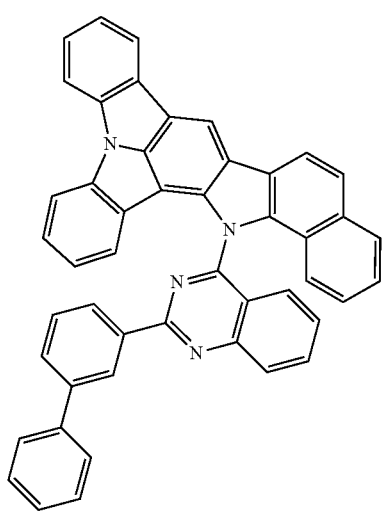
350
-continued
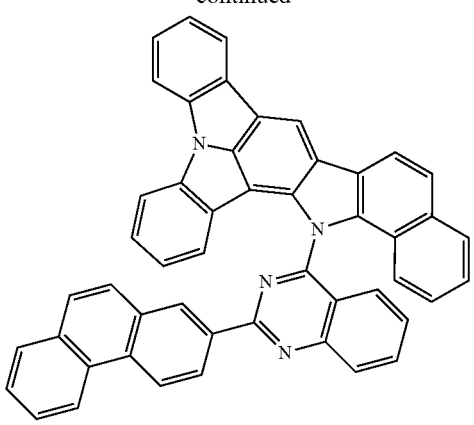
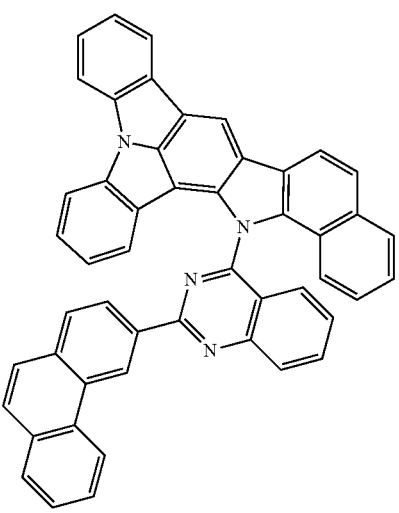
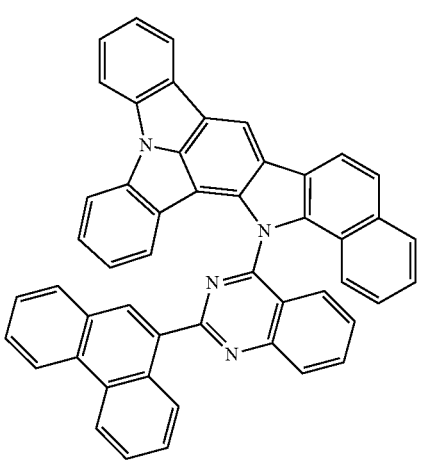

351
-continued
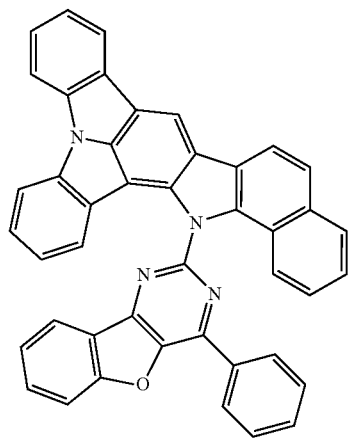
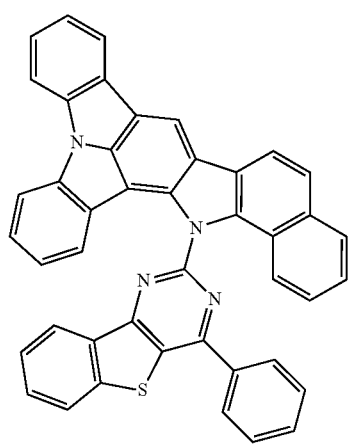
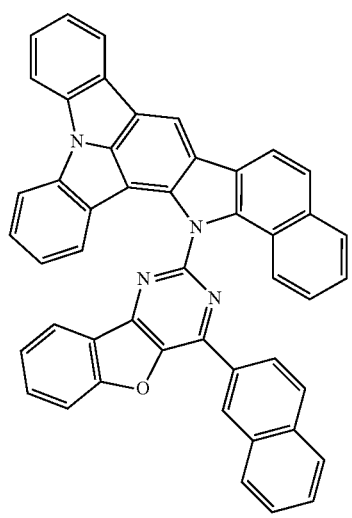
352
-continued
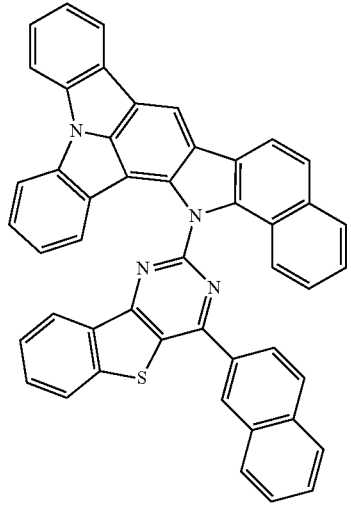
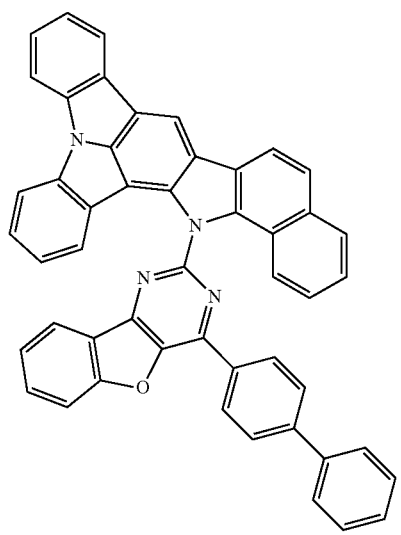
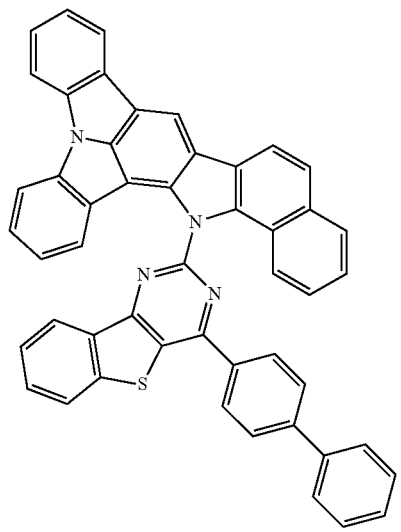

353
-continued
354
-continued
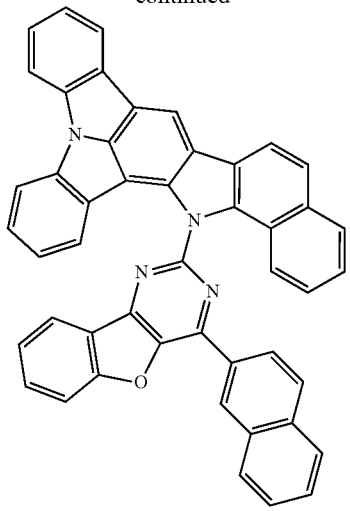
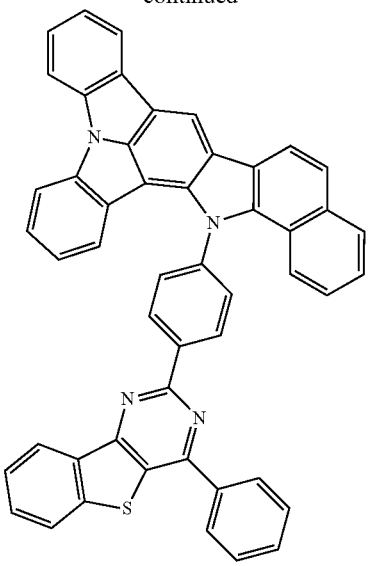
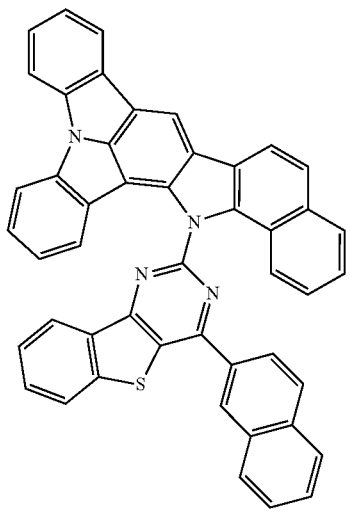
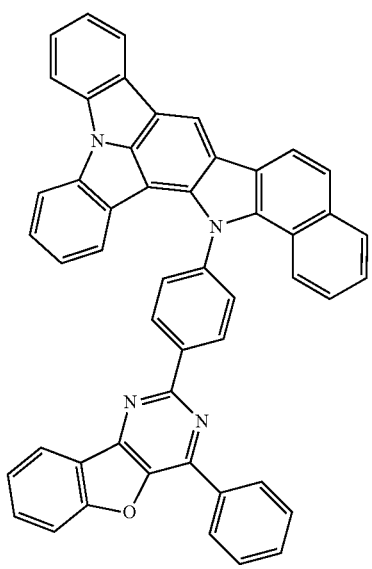
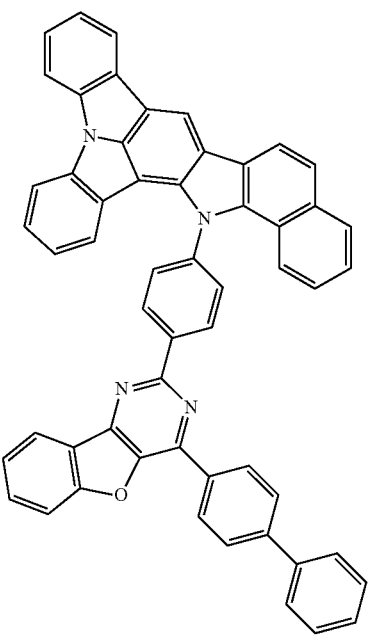

355
-continued
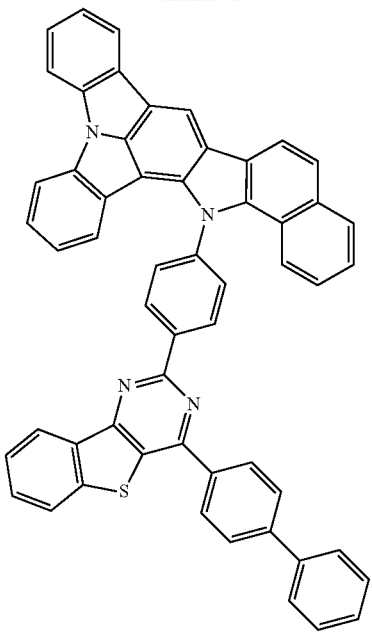
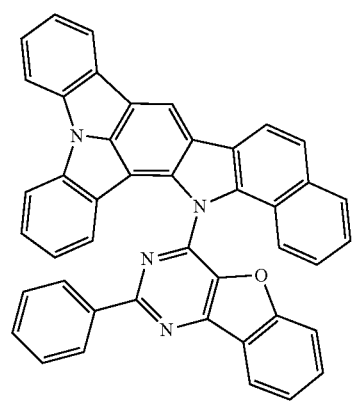
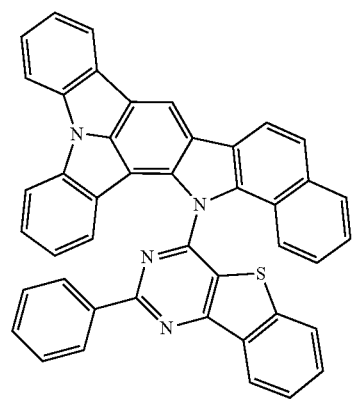
356
-continued
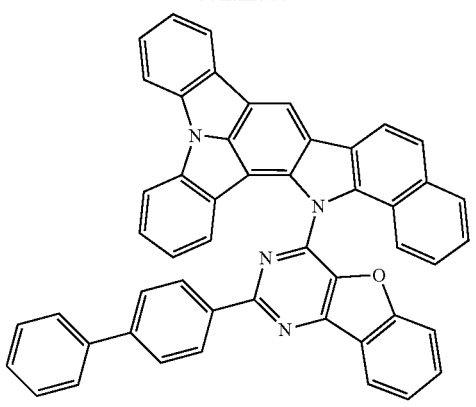
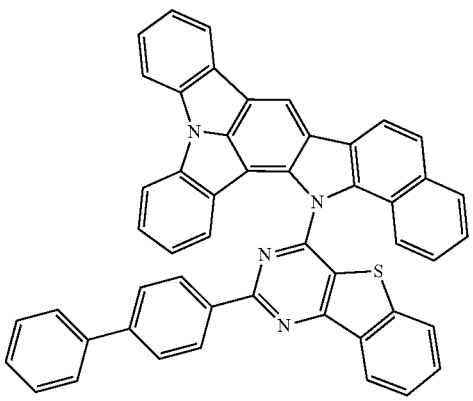
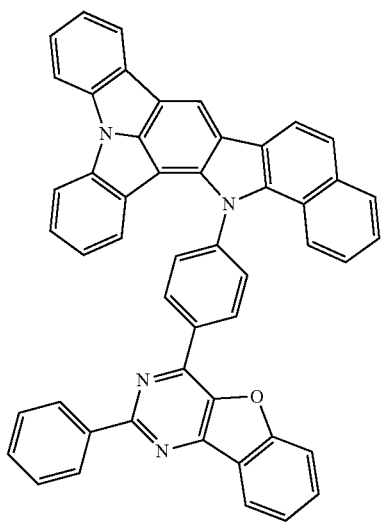

357
-continued
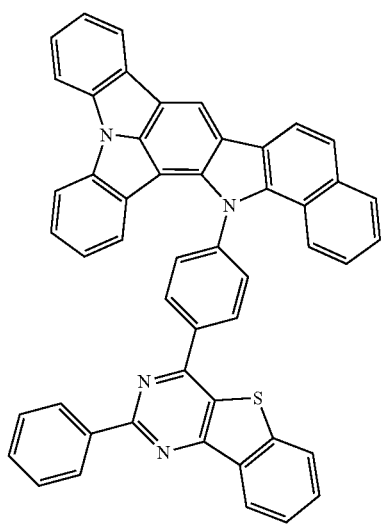
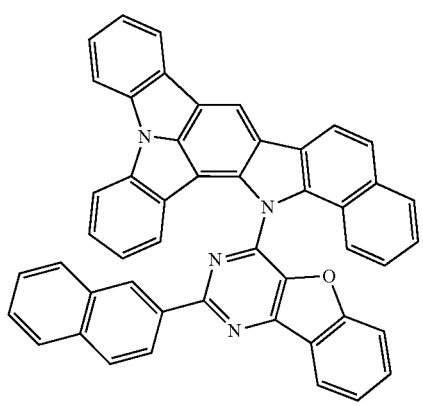
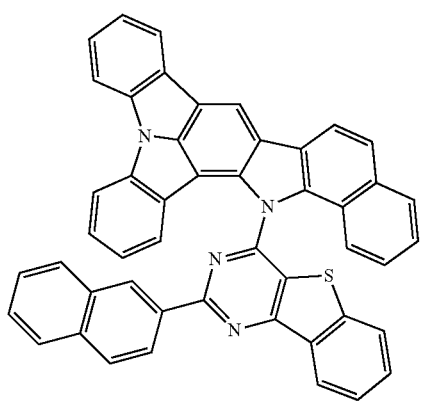
358
-continued
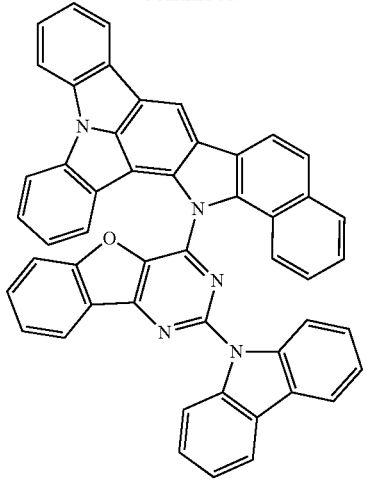
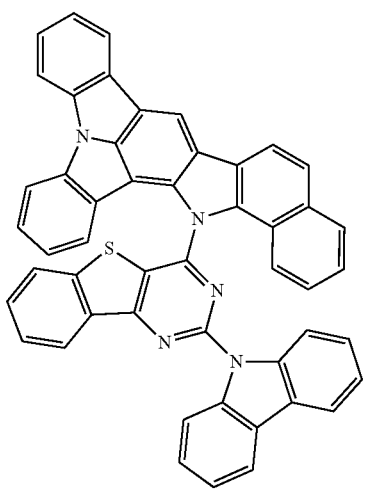
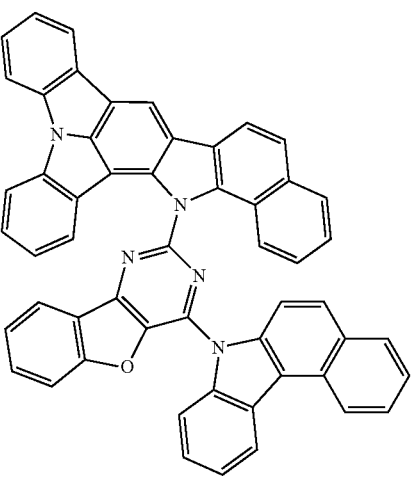

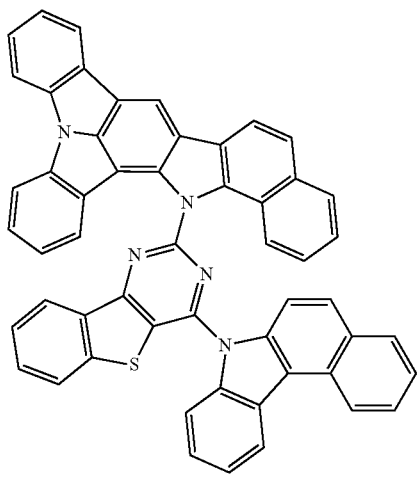
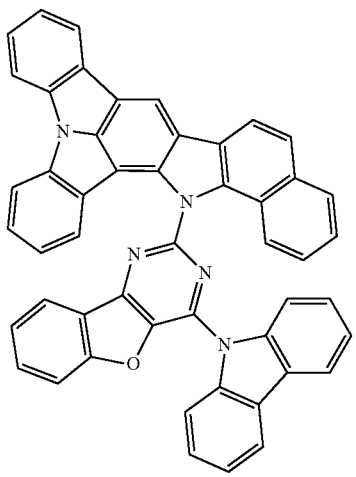
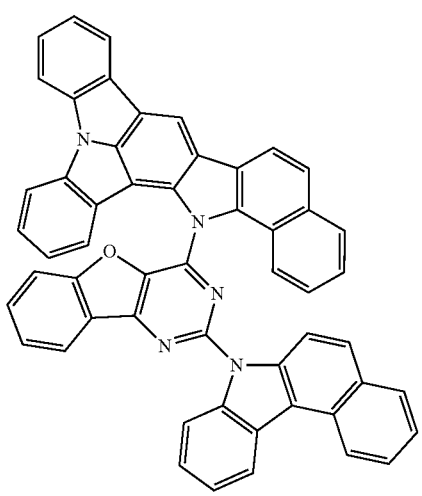
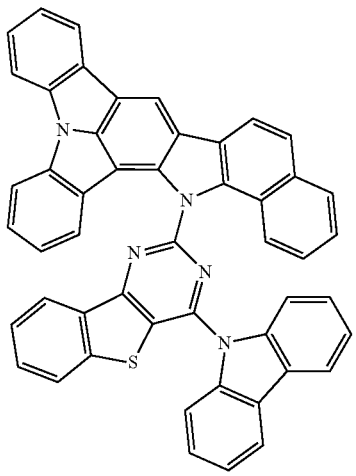
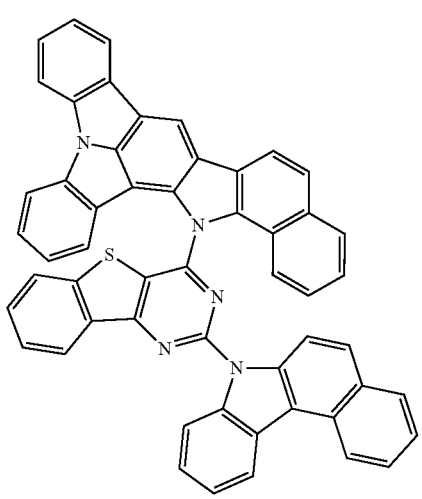
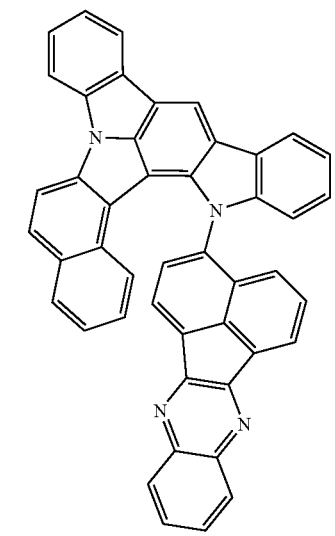

361
-continued
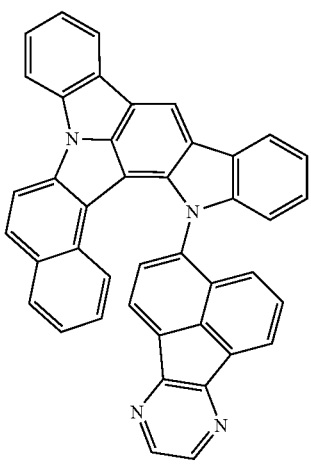
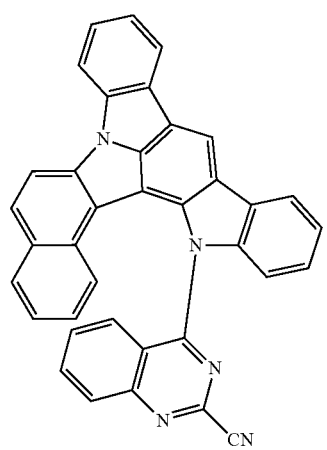
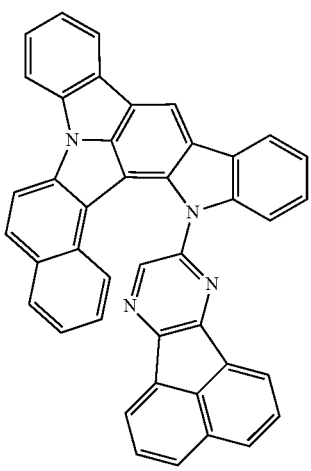
362
-continued
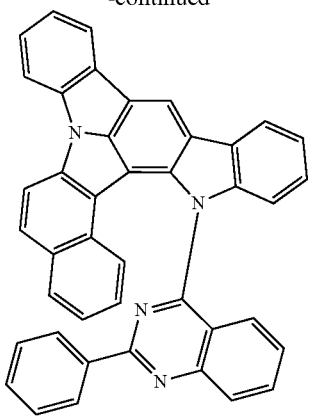
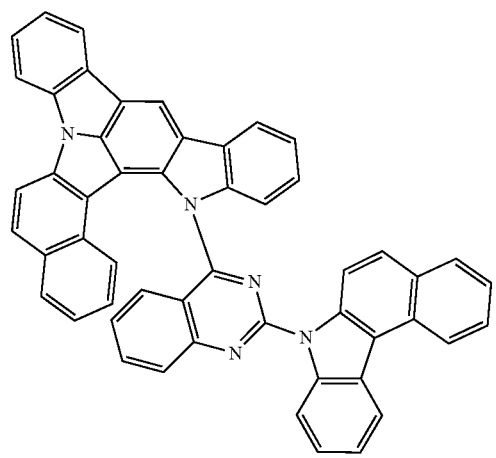
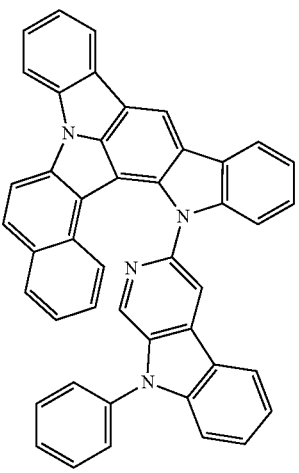

363
-continued
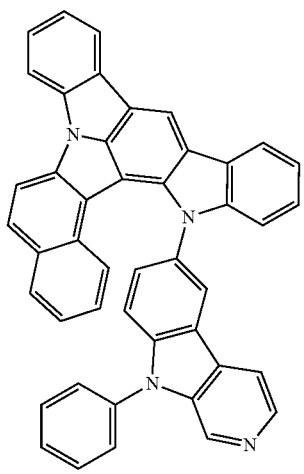
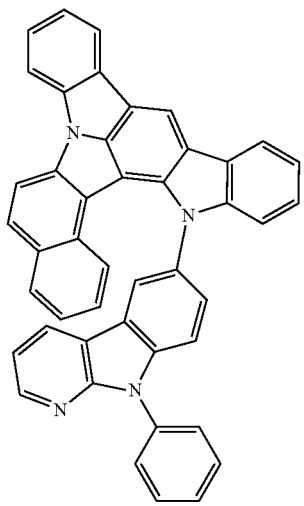
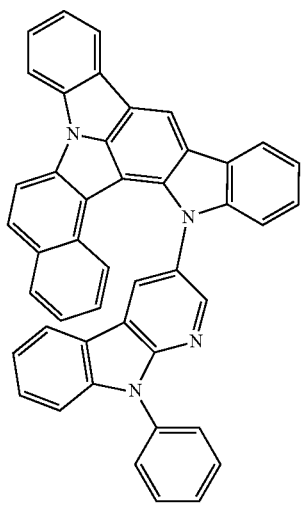
364
-continued
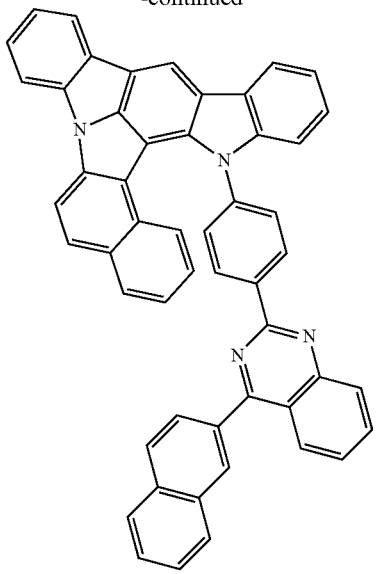
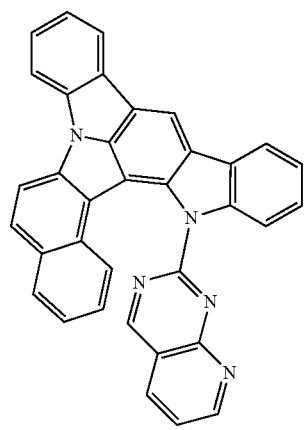
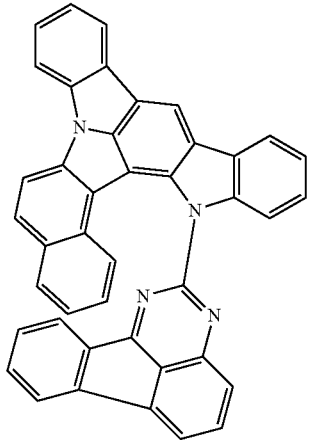

365
-continued
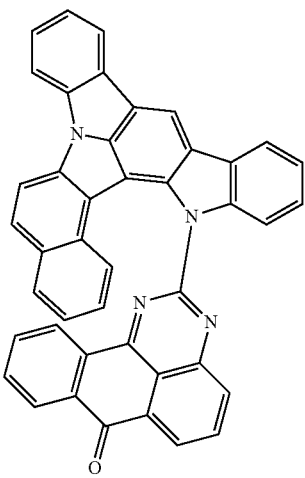
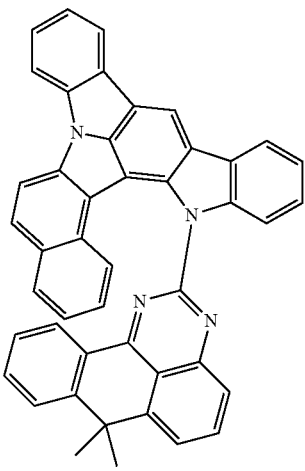
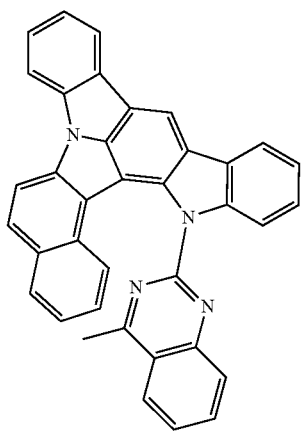 [SMILES: Cc1nc(-n2c3ccccc3c3cc4c5ccccc5n5c6ccc7ccccc7c6c(c32)c45)nc2ccccc12]
366
-continued
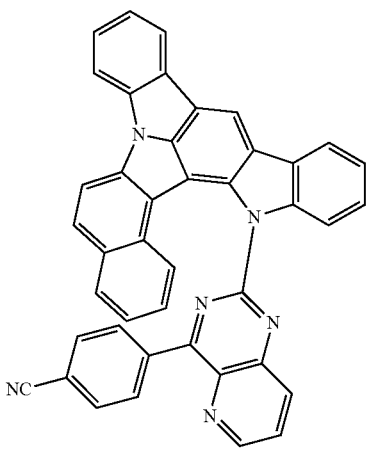
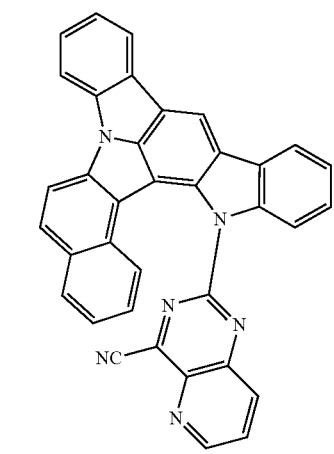
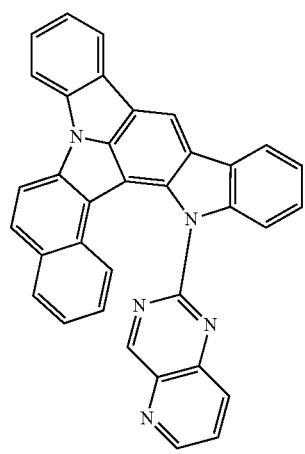

367
-continued
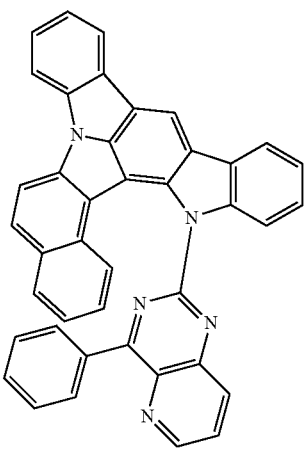
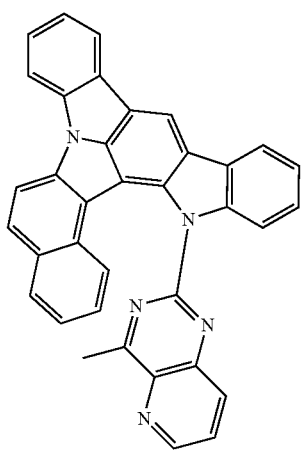
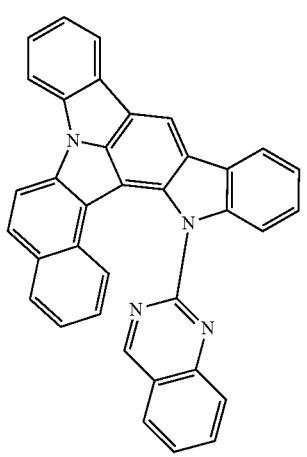
368
-continued
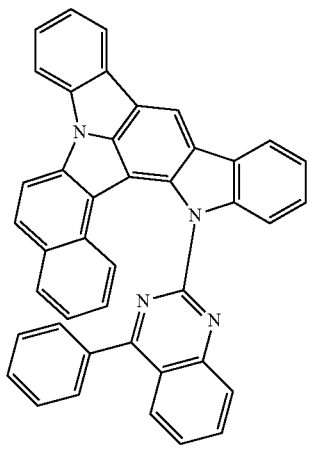
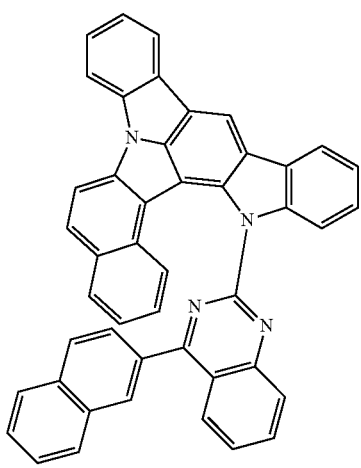
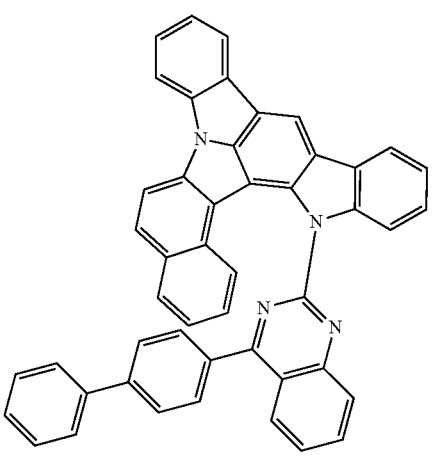

369
-continued
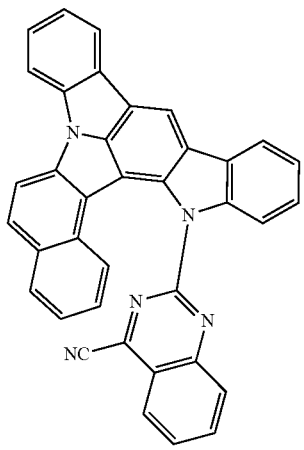
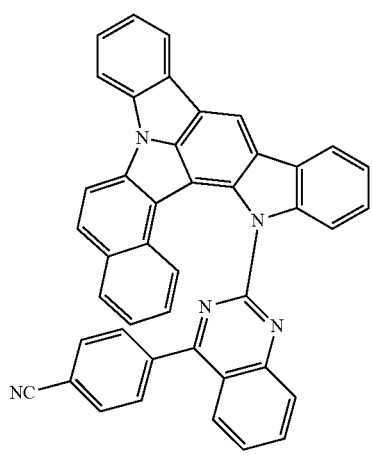
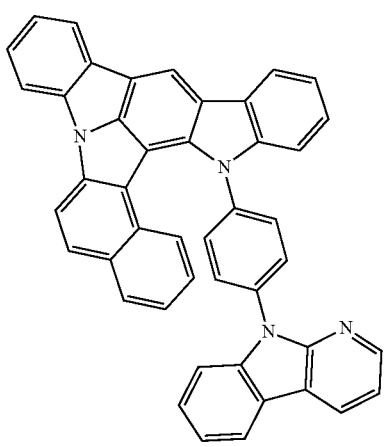
370
-continued
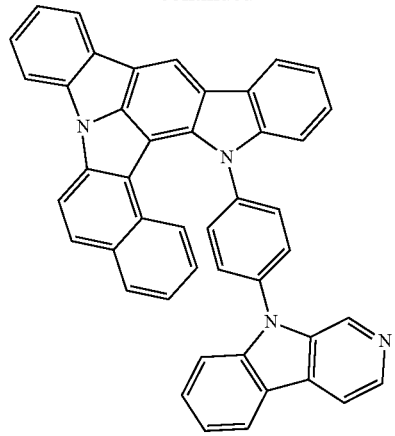
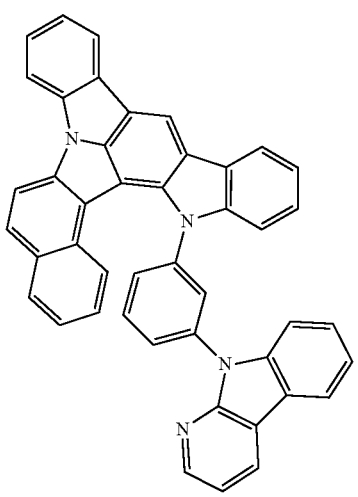
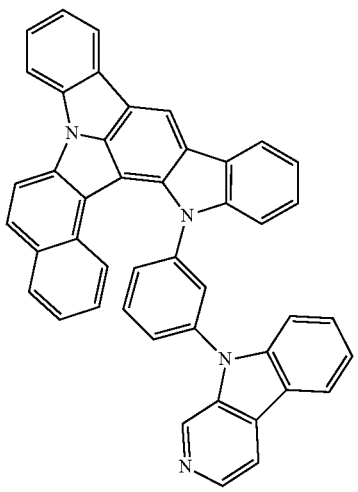

371
-continued
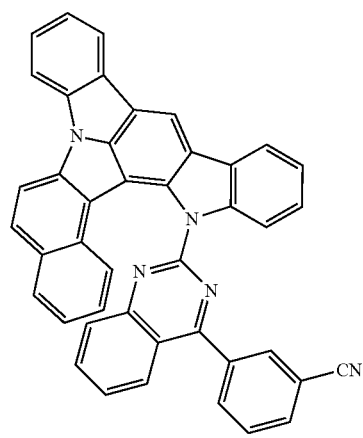
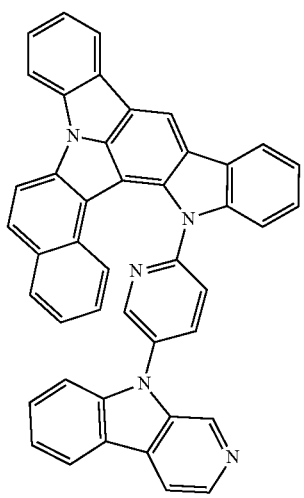
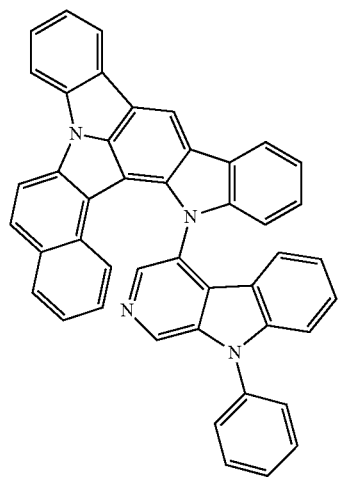
372
-continued
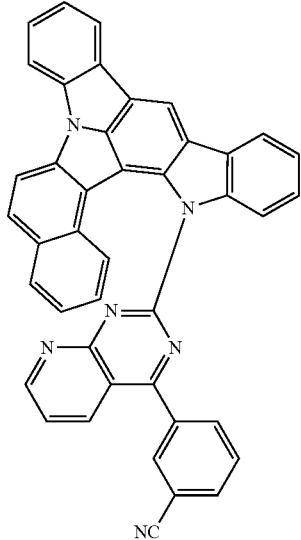
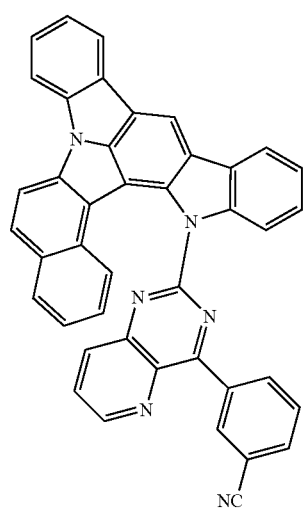
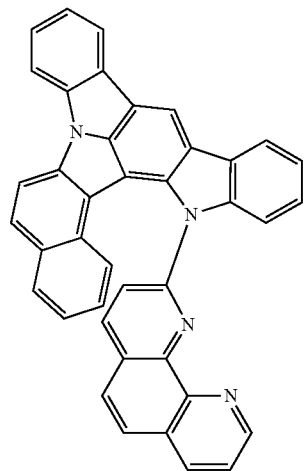

-continued
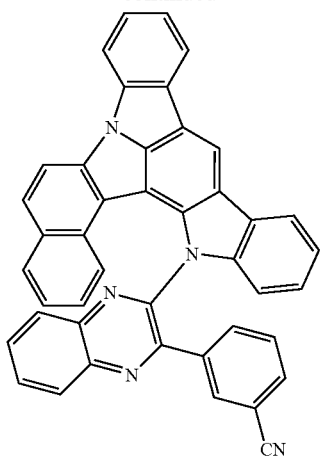
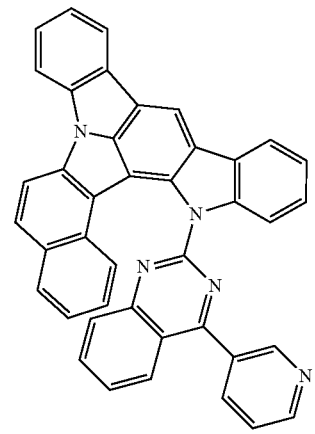
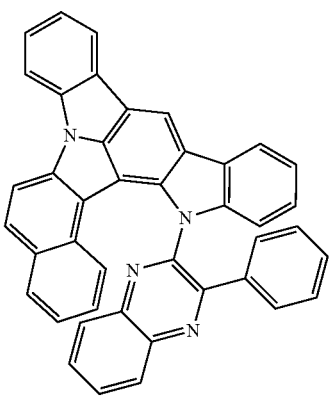
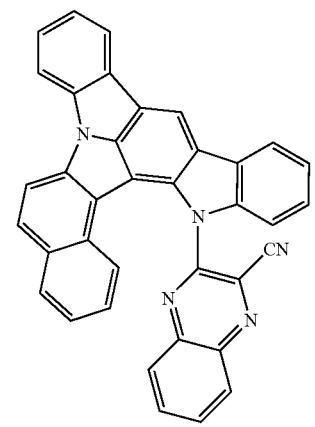
-continued
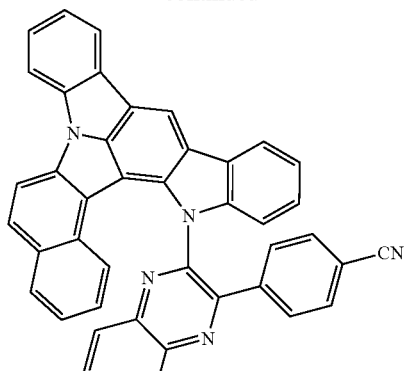
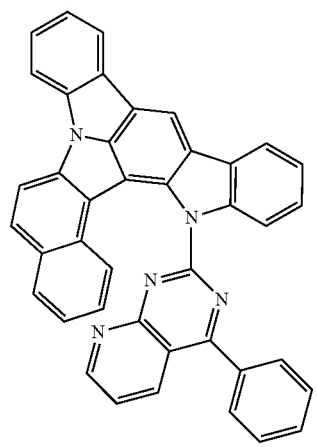
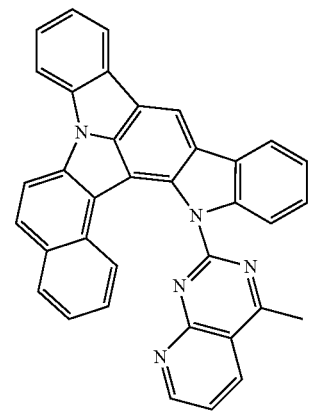
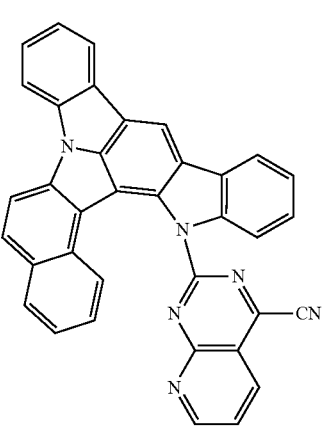

375
-continued
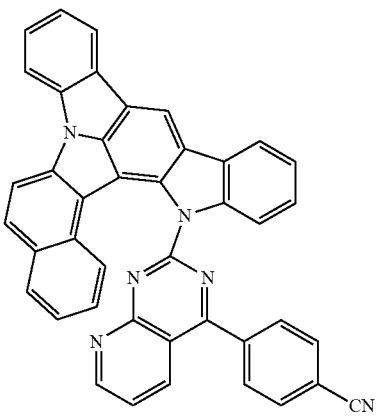
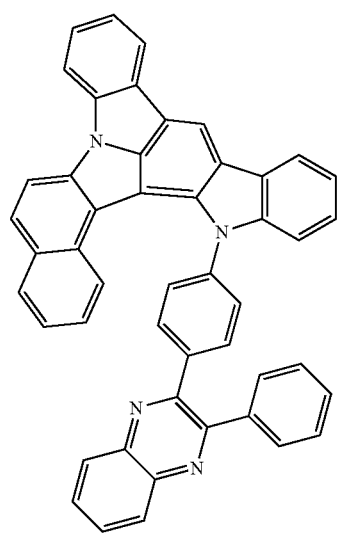
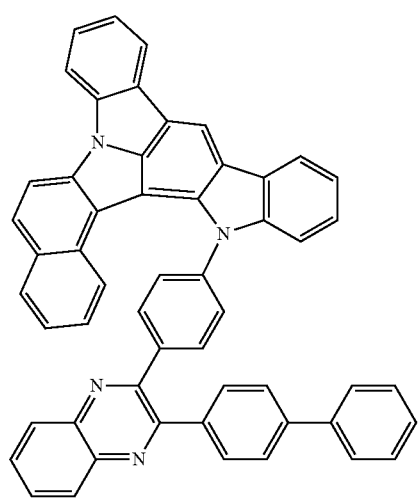
376
-continued
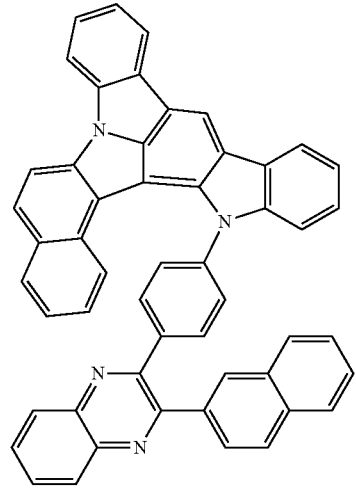
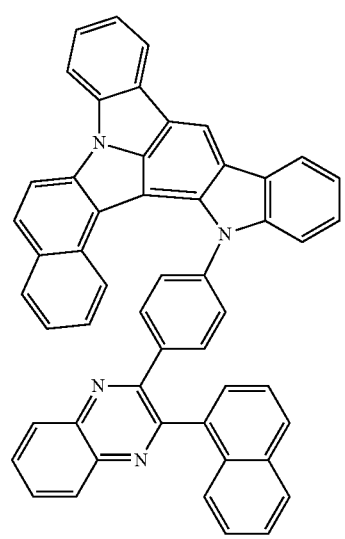
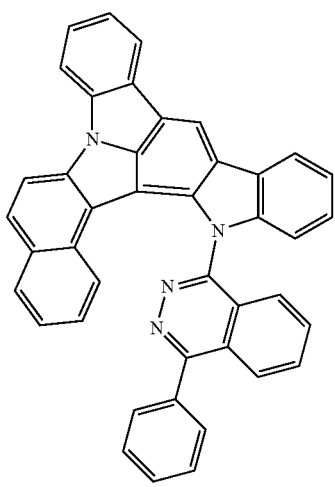

377
-continued
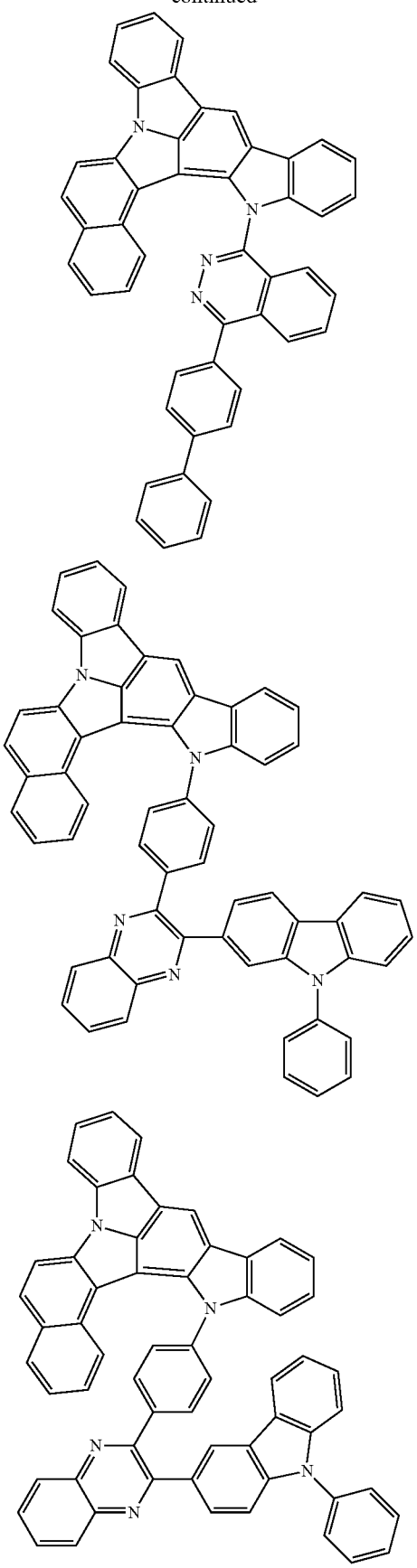
378
-continued
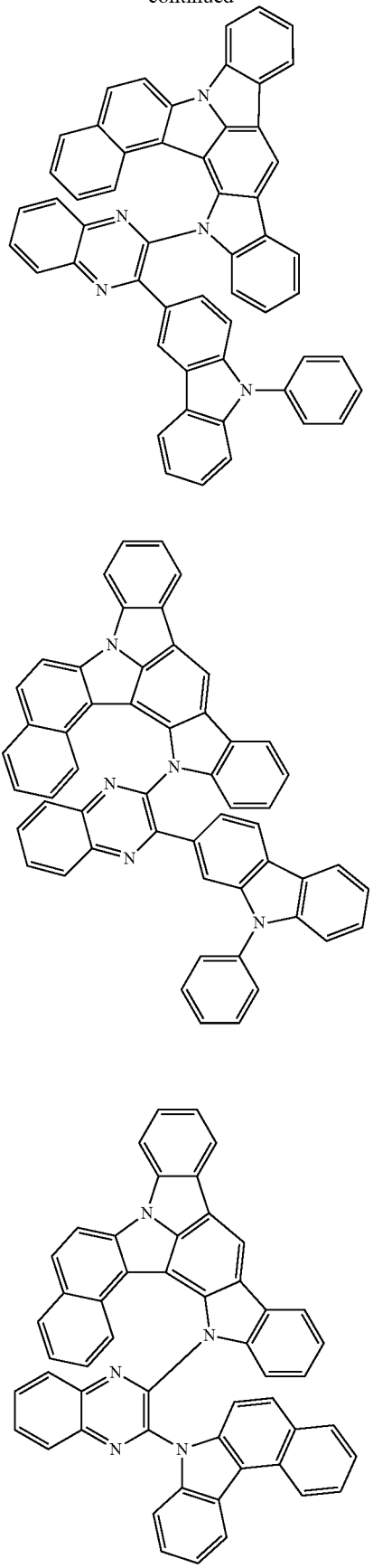

379
-continued
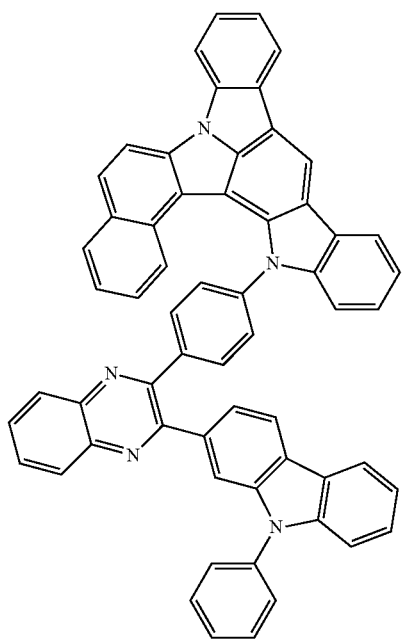
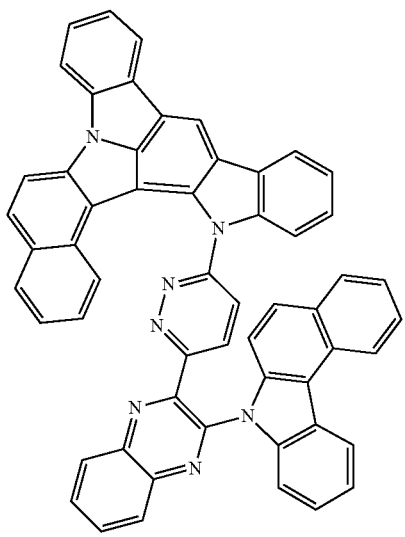
380
-continued
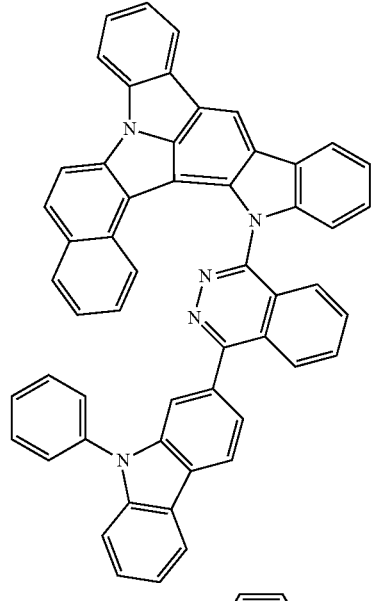
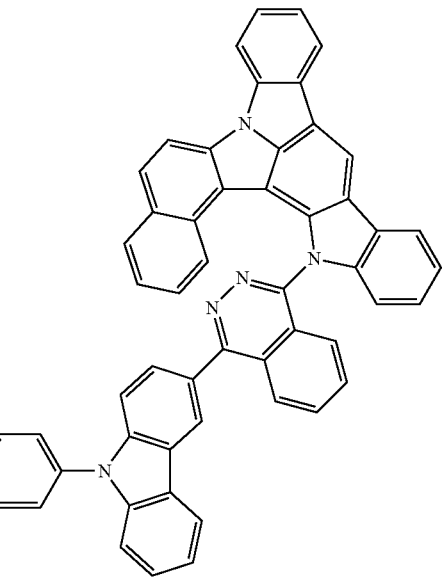
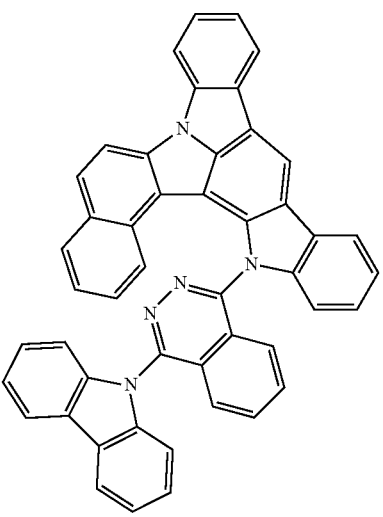

381
-continued
382
-continued
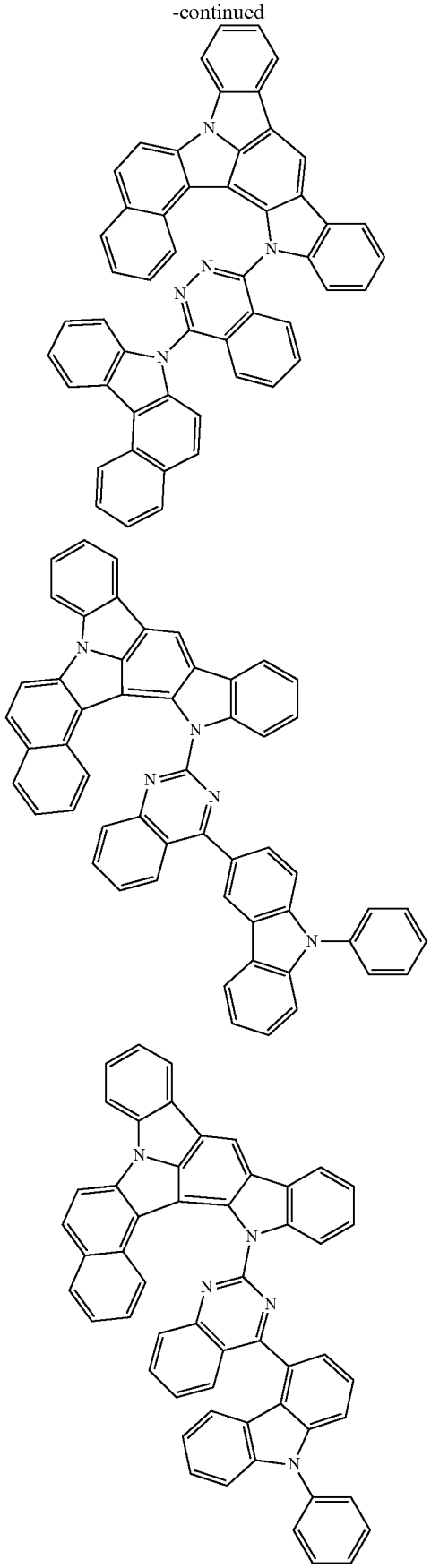
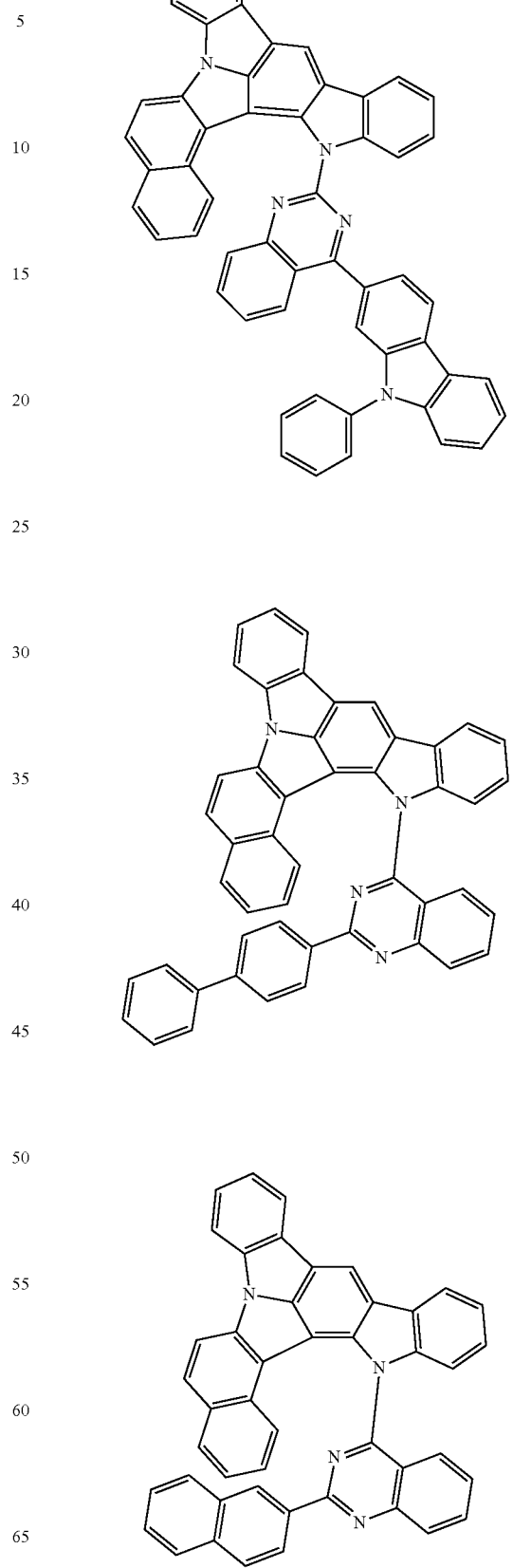

-continued
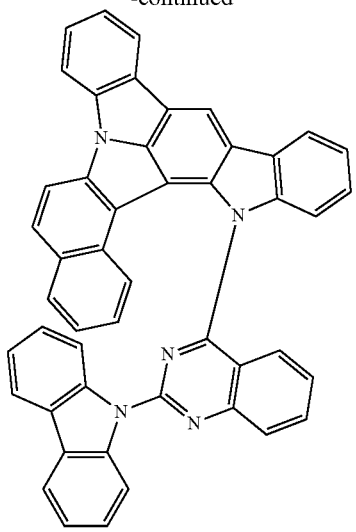
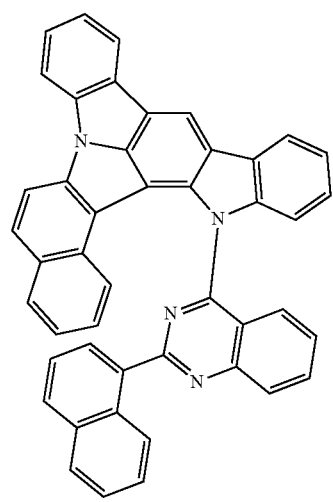
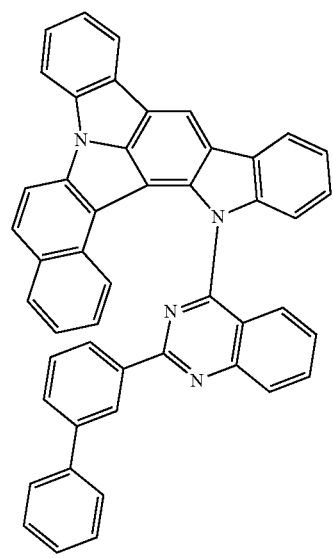
-continued
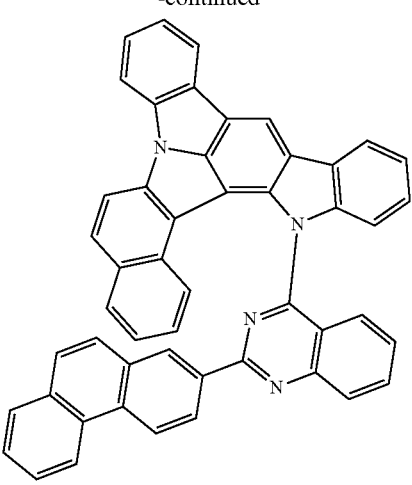
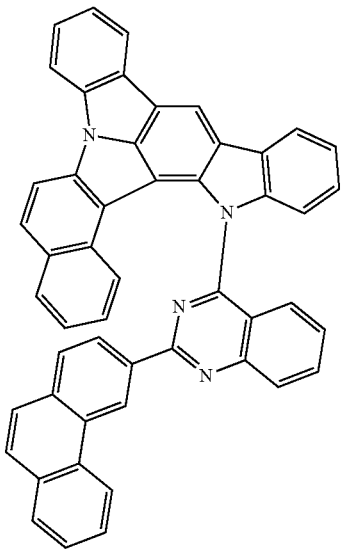
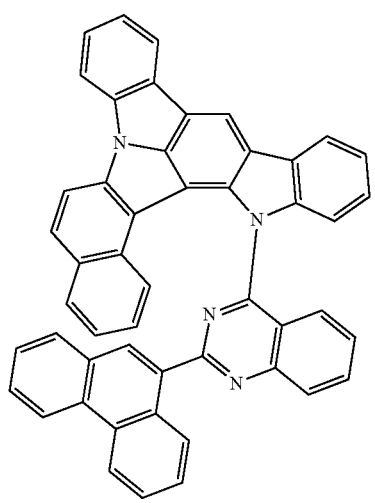

385
-continued
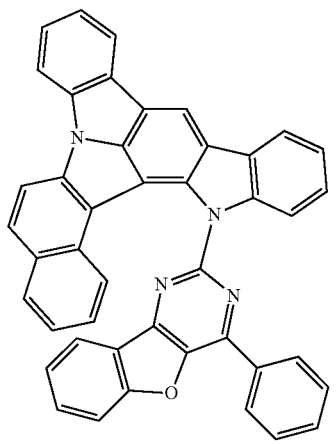
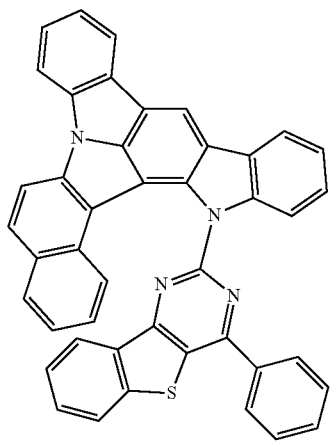
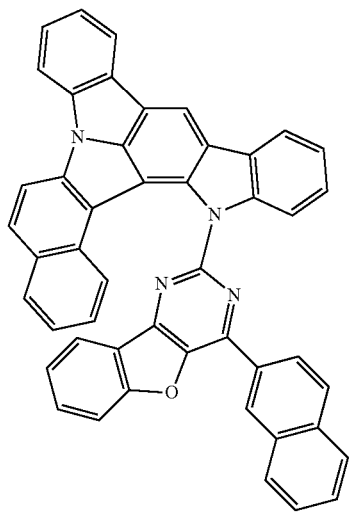
386
-continued
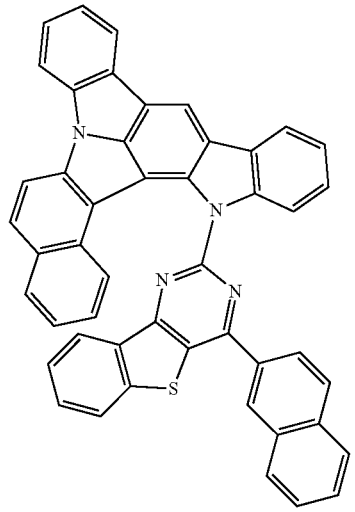
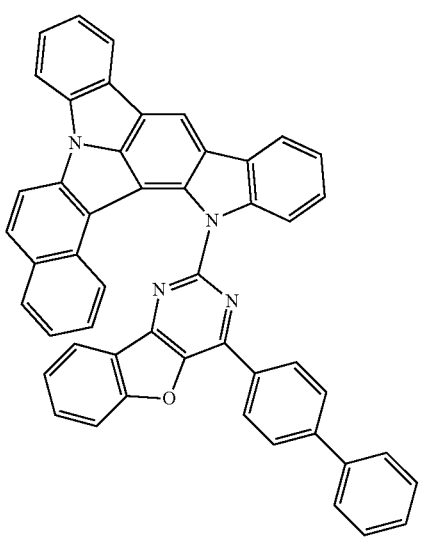
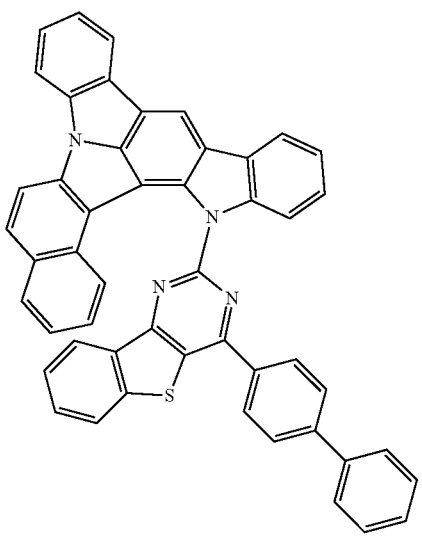

387
-continued
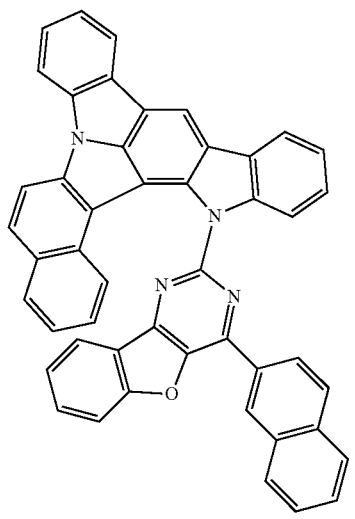
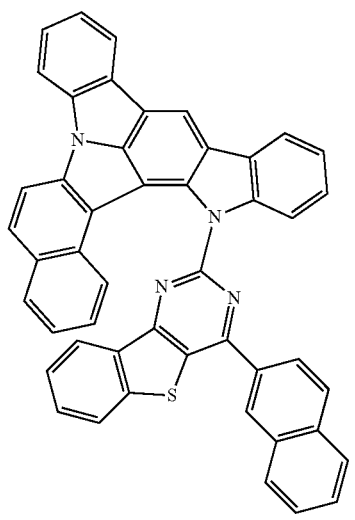
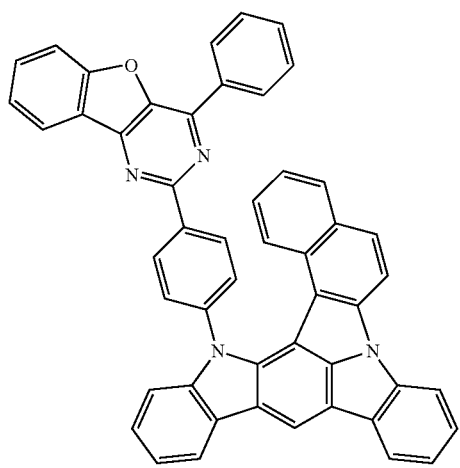
388
-continued
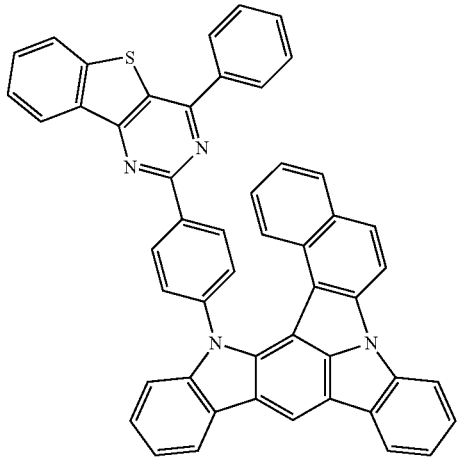
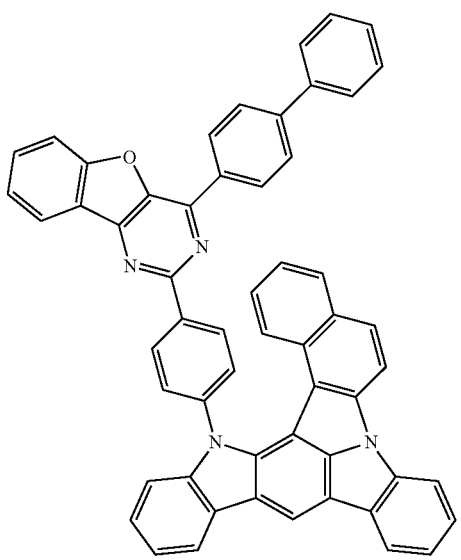
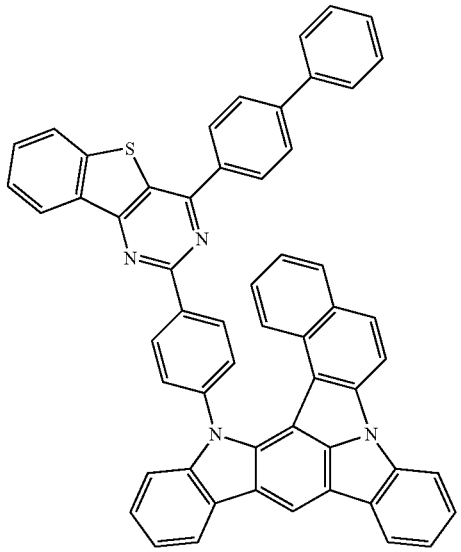

389
-continued
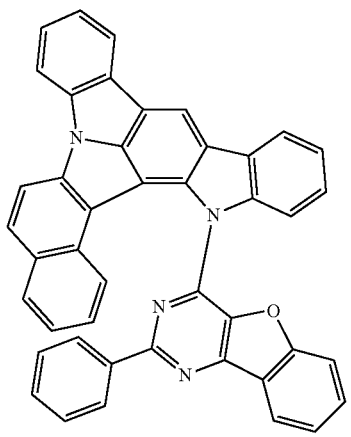
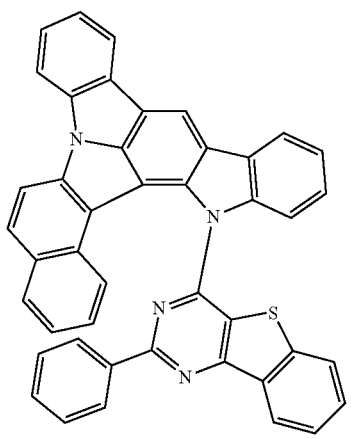
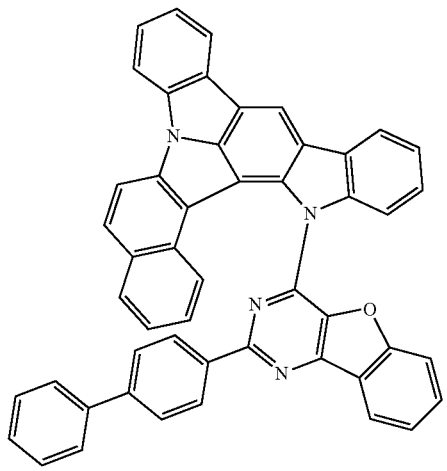
390
-continued
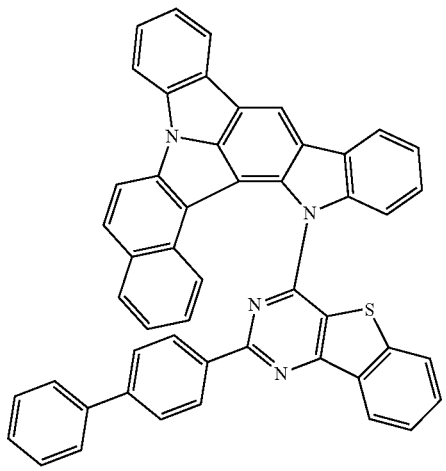
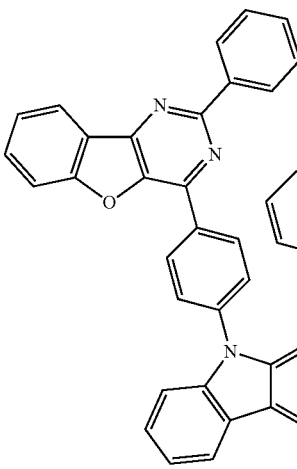
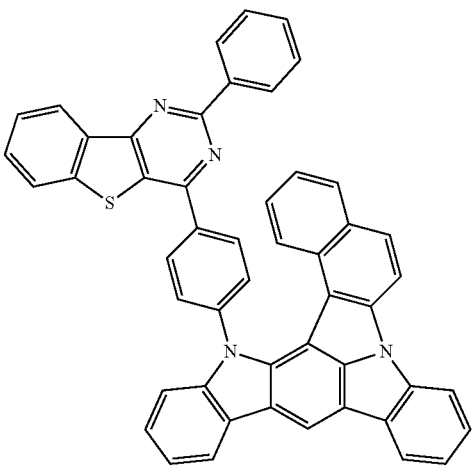

391
-continued
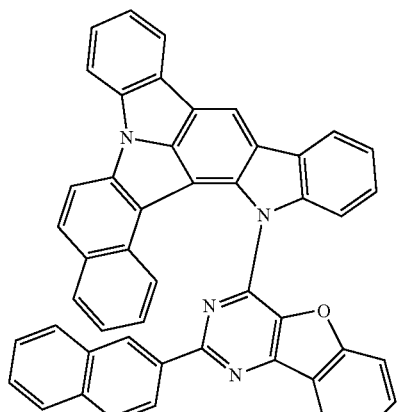
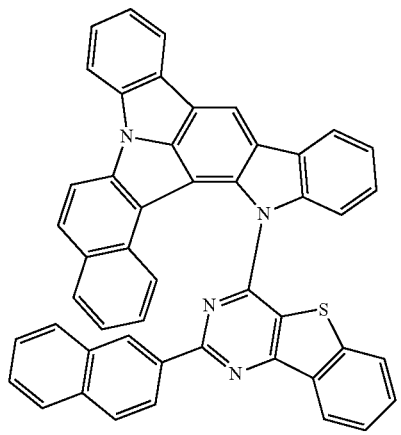
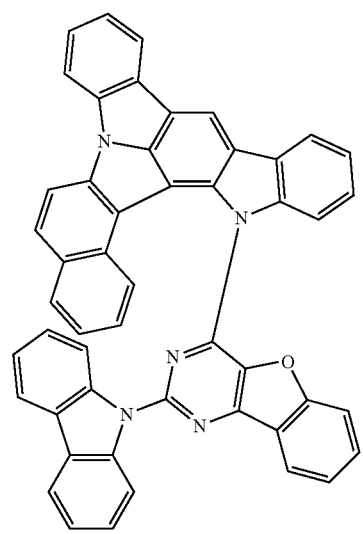
392
-continued
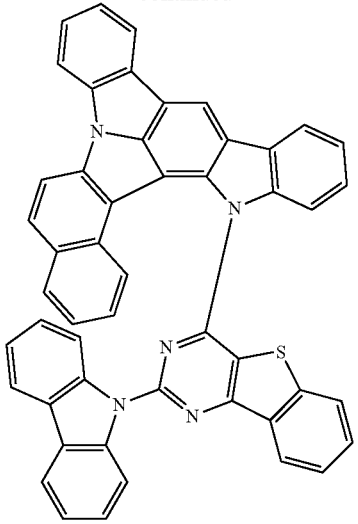
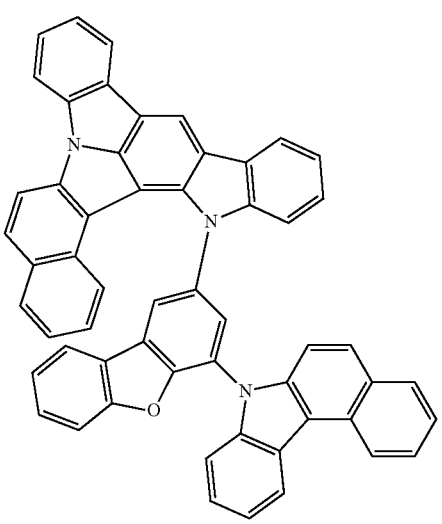
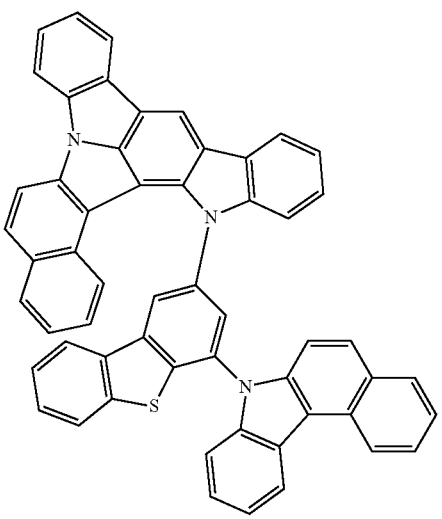

393
-continued
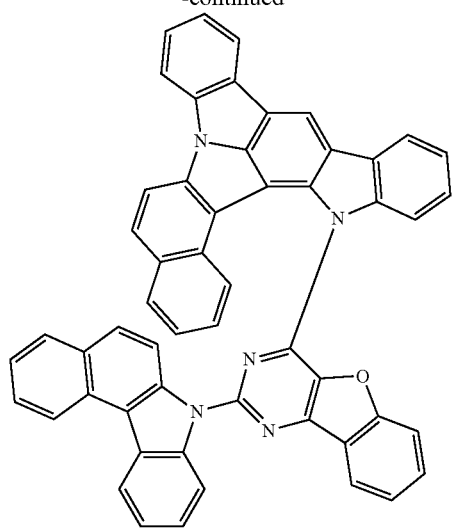
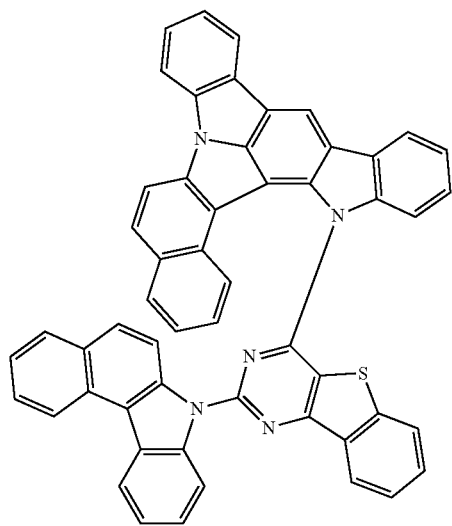
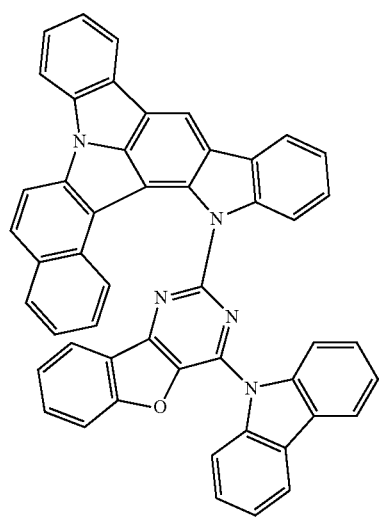
394
-continued
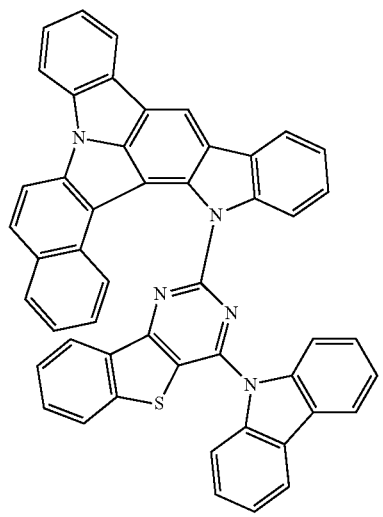
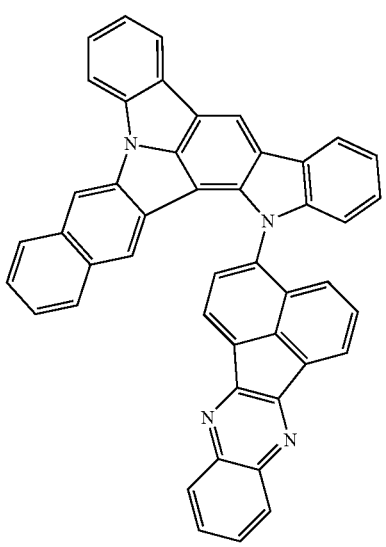
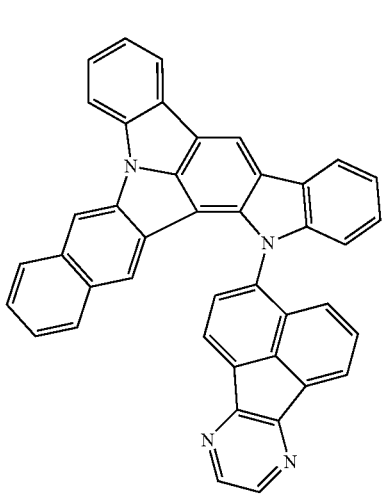 [SMILES: c1ccc2cc3c(cc2c1)c1c2c(cc4c5ccccc5n3c41)c1ccccc1n2-c1ccc2c3c(cccc13)-c1nccnc1-2]

395
-continued
396
-continued
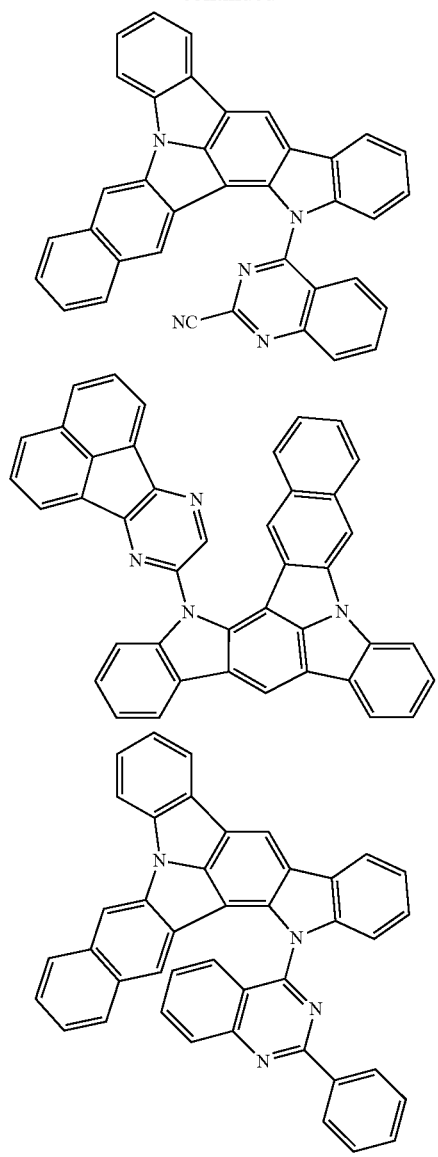
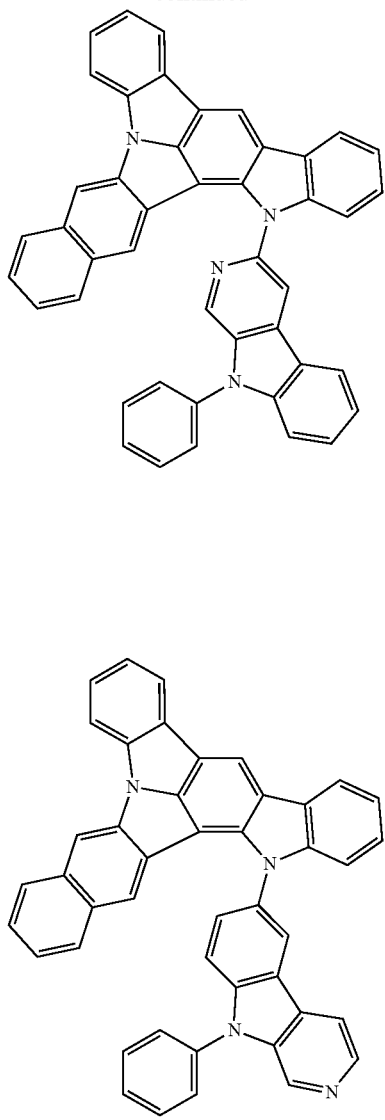
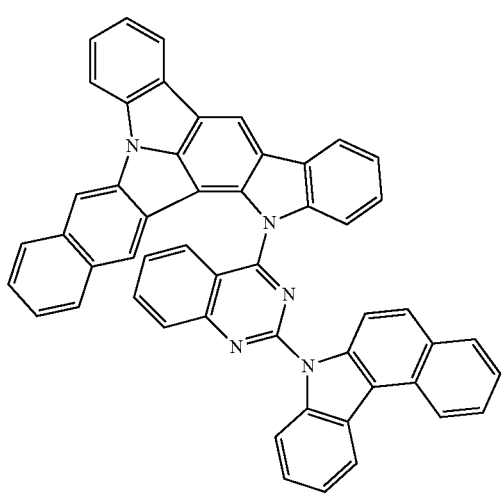
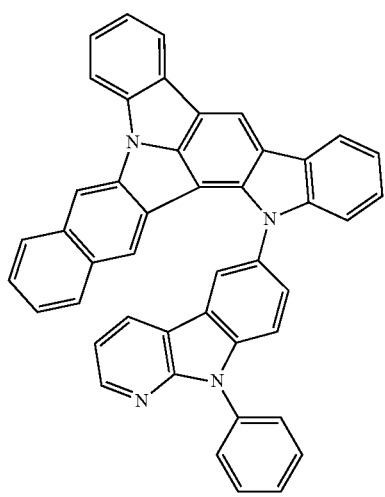

397
-continued
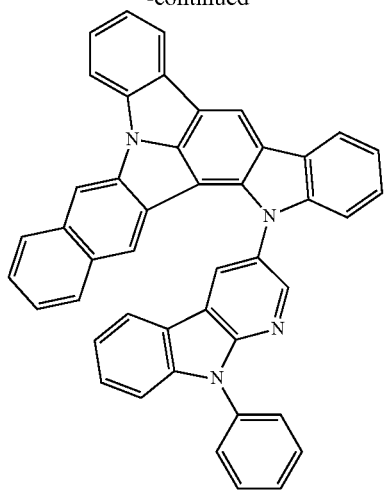
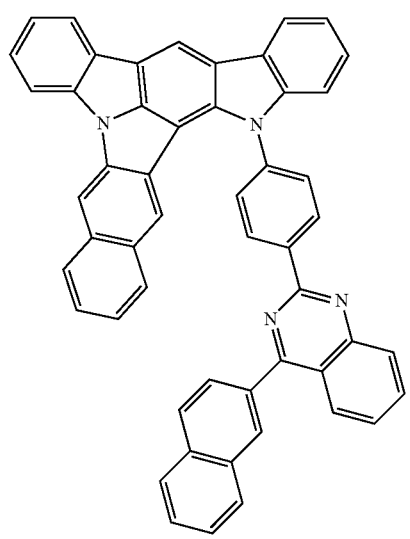
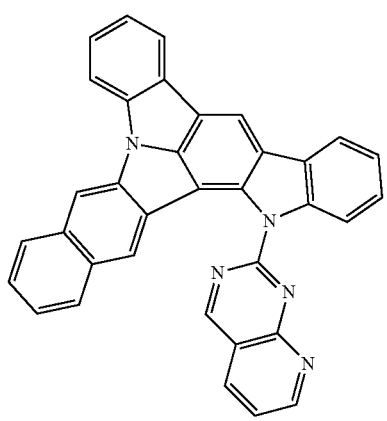
398
-continued
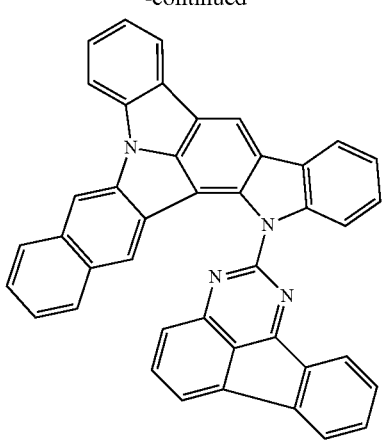
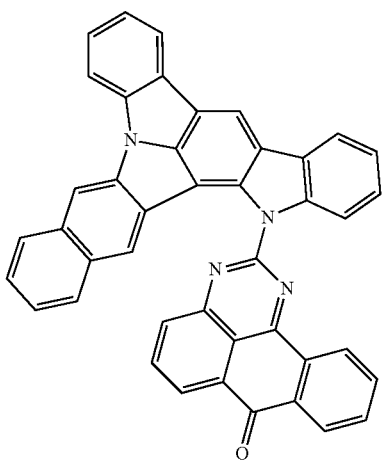
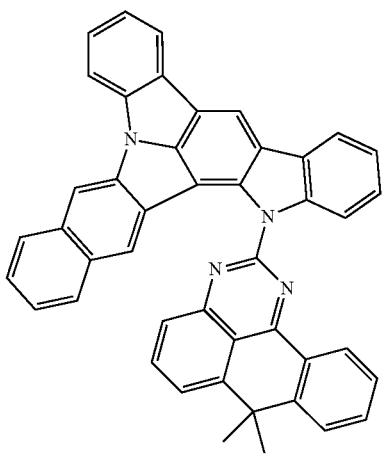

399
-continued
400
-continued
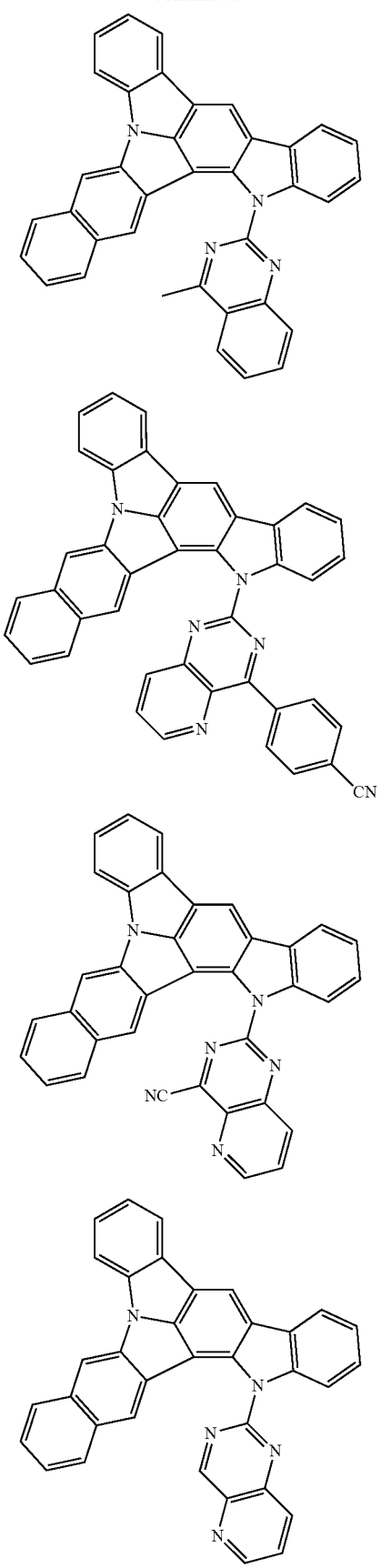
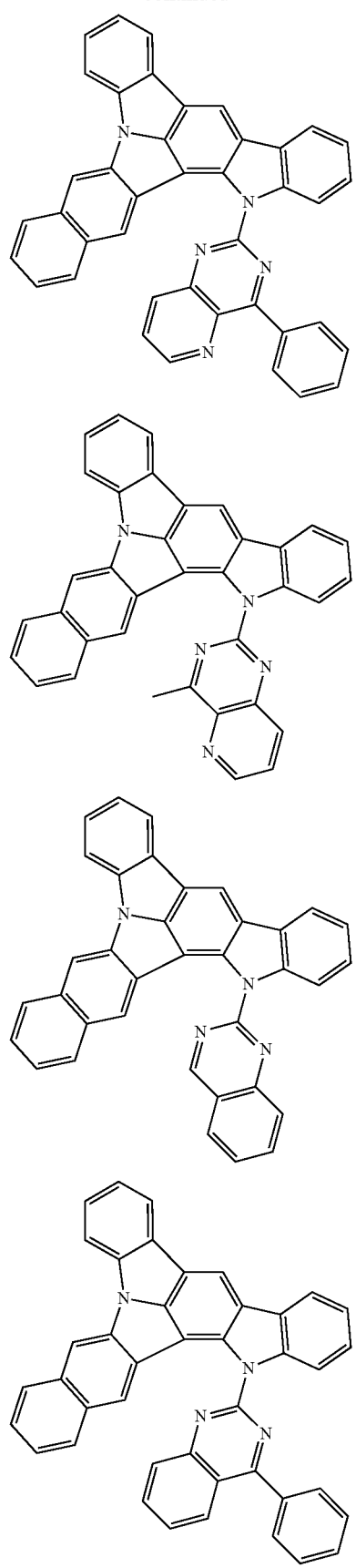

401
-continued
402
-continued
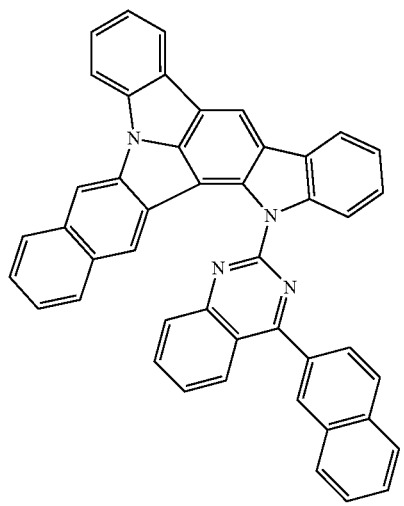
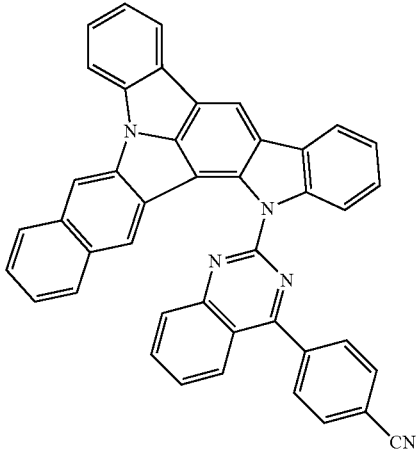
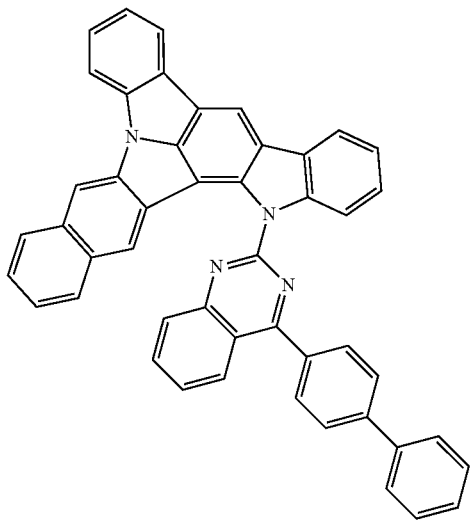
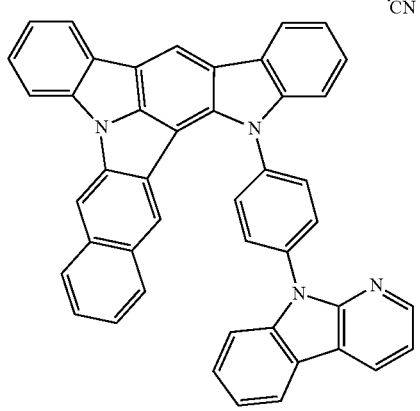
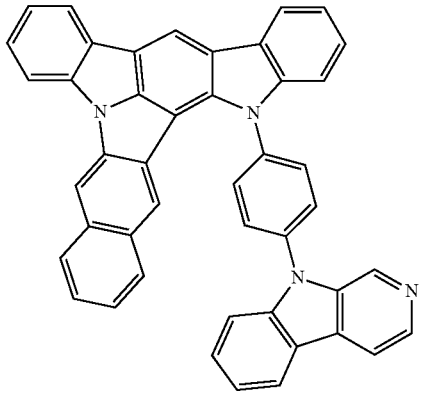
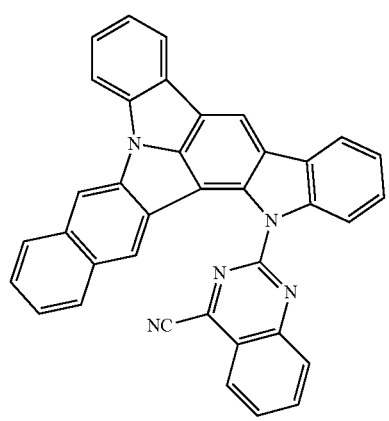
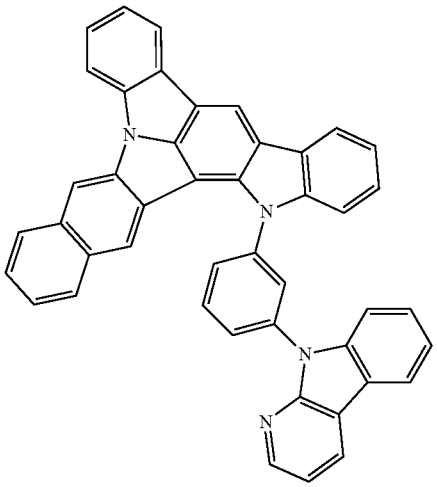

403
-continued
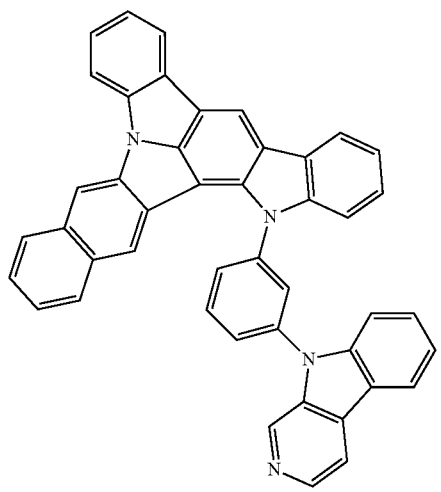
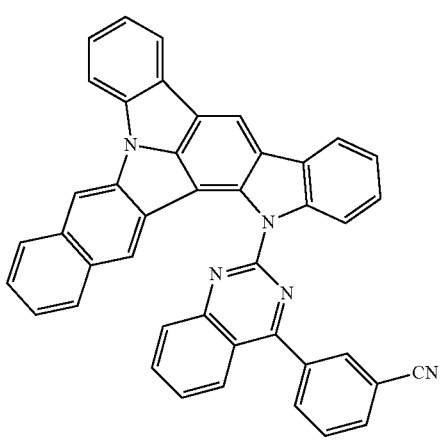
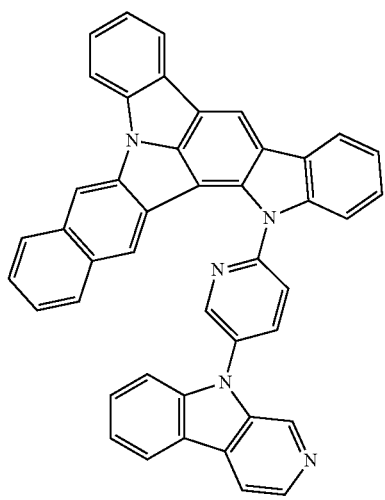
404
-continued
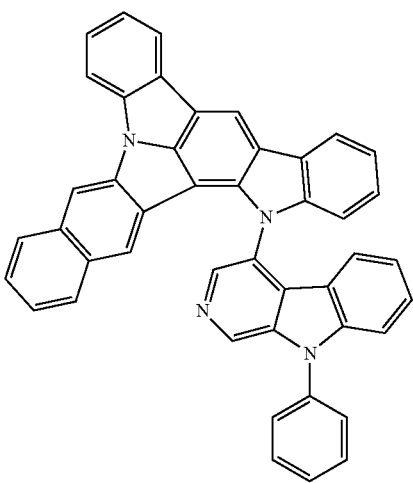
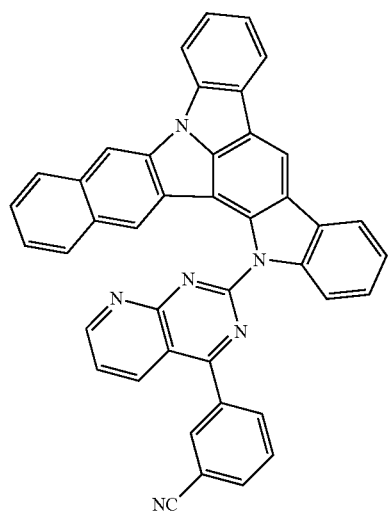
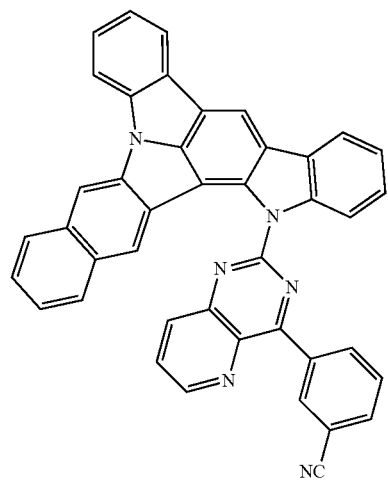

405
-continued
406
-continued
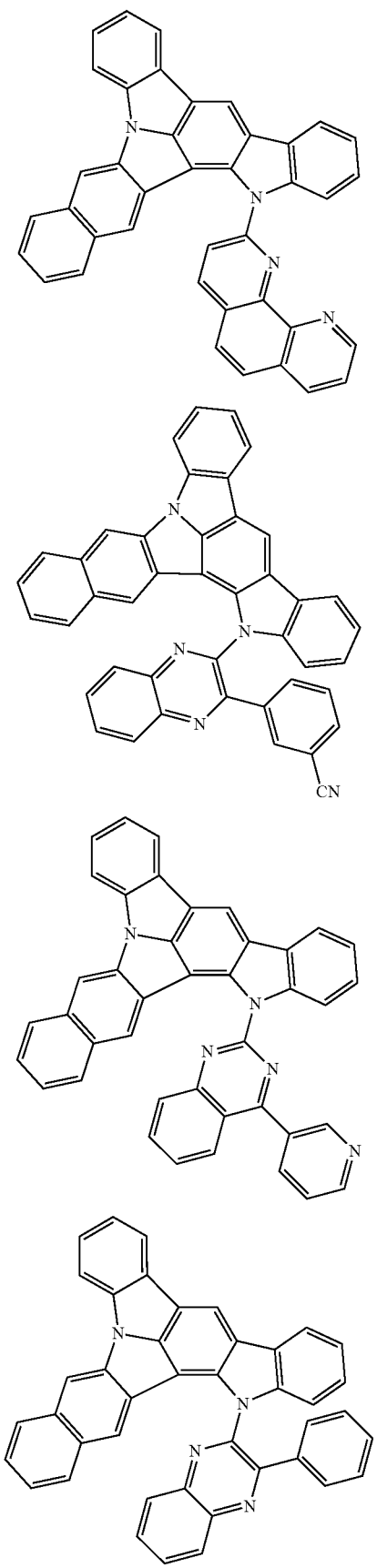
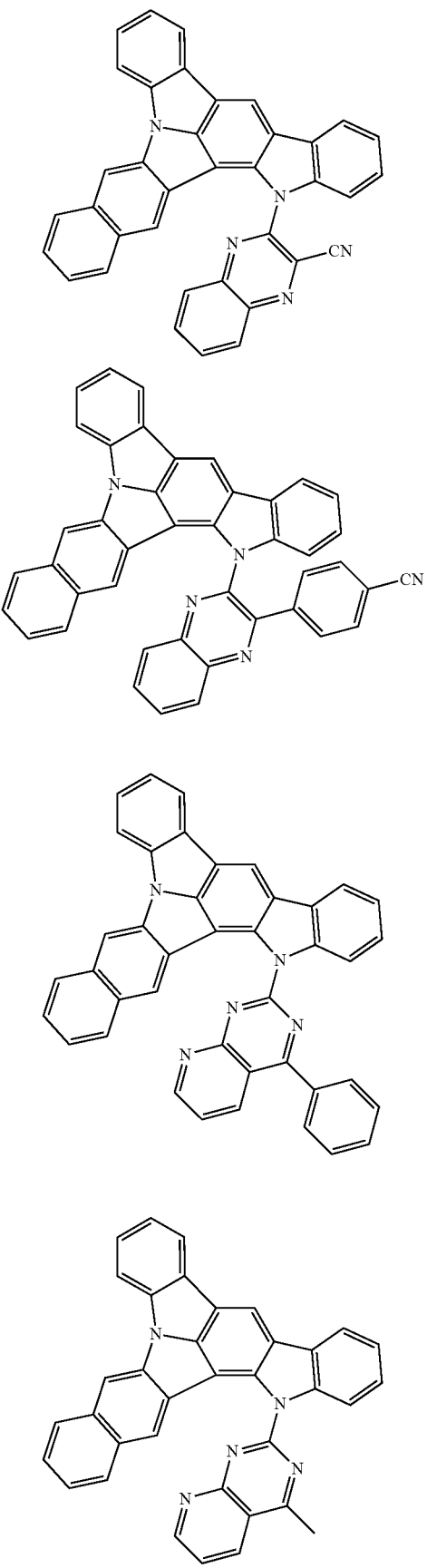

407
-continued
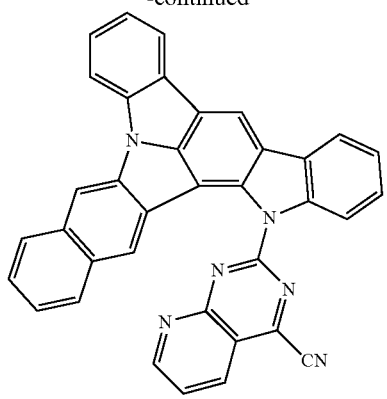
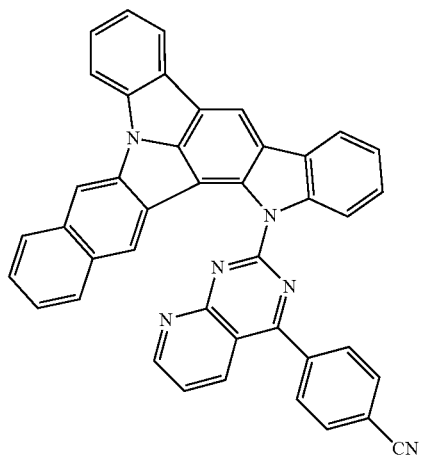
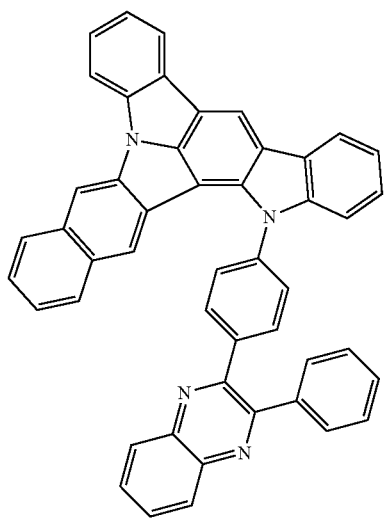
408
-continued
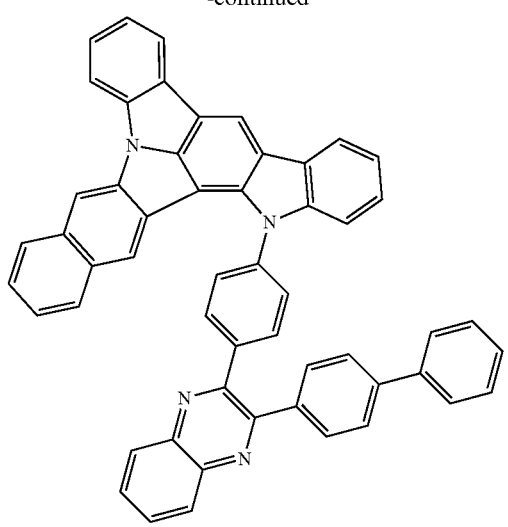
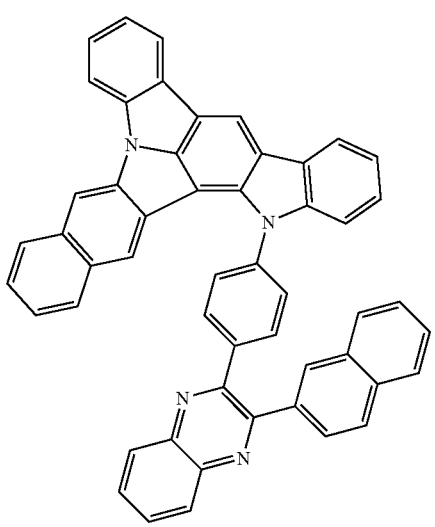
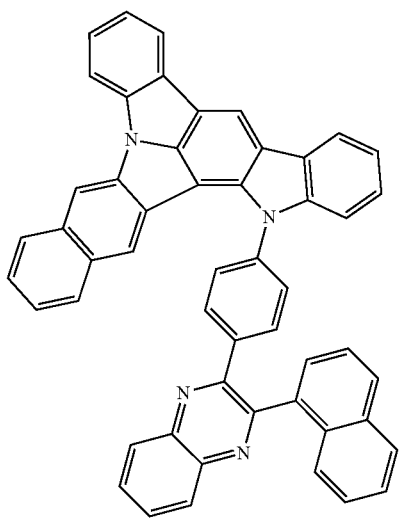

409
-continued
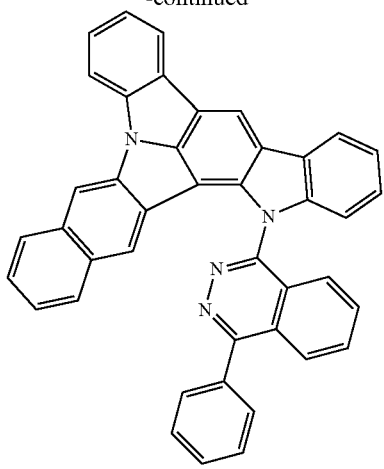
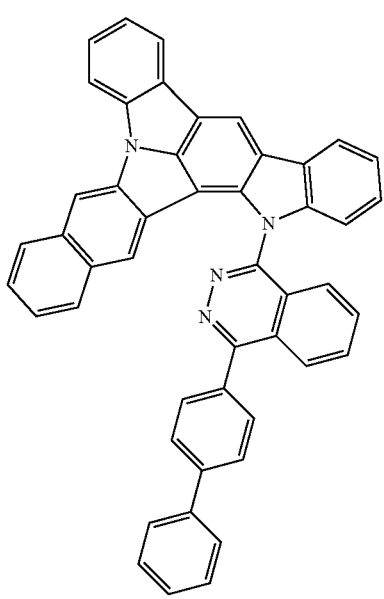
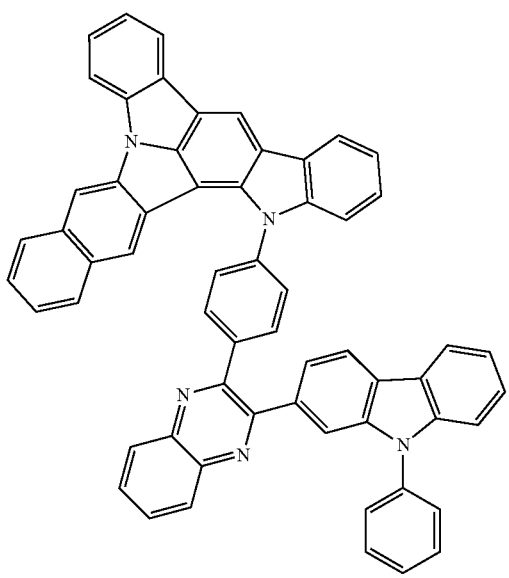
410
-continued
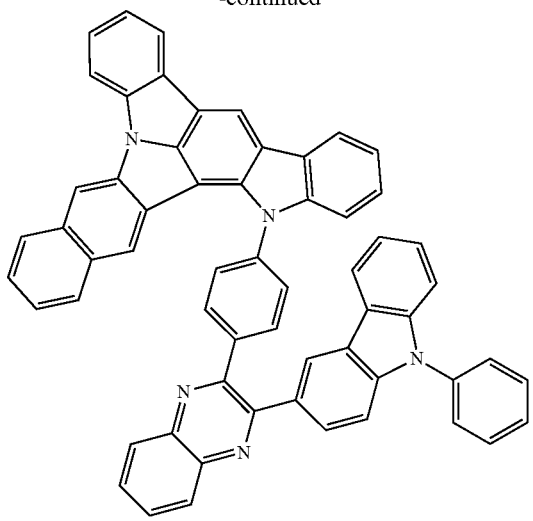
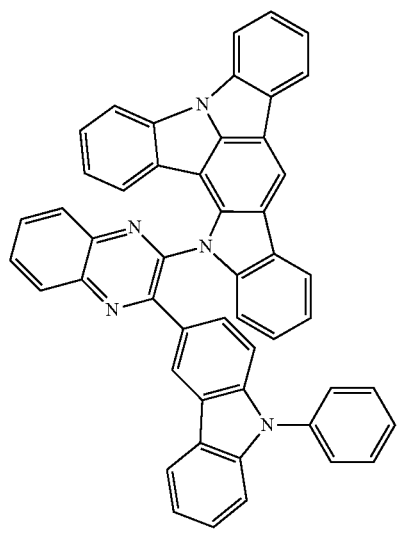
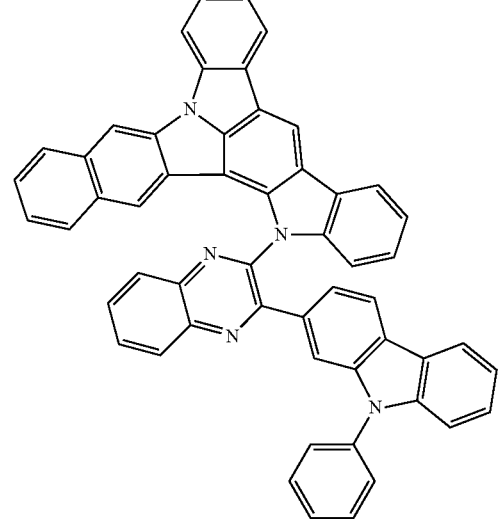

411
-continued
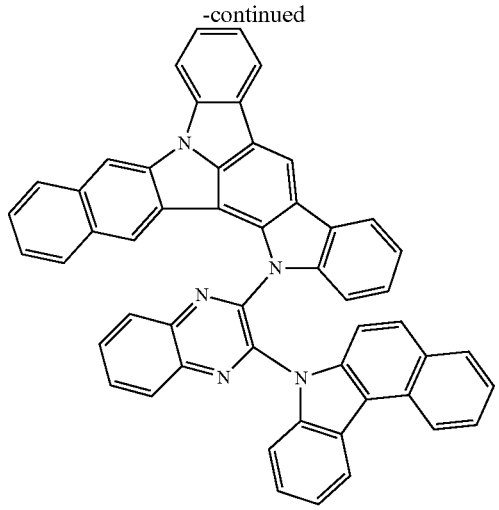
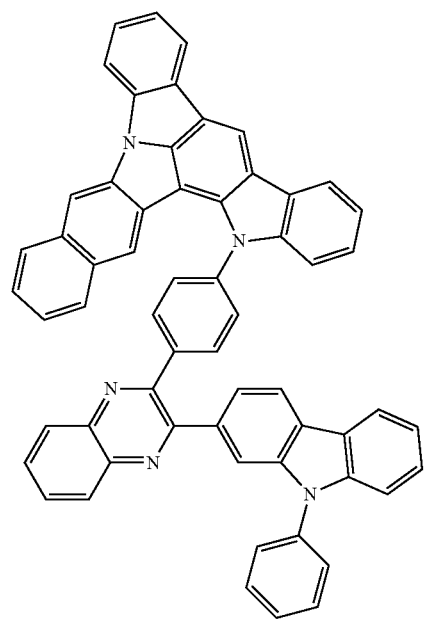
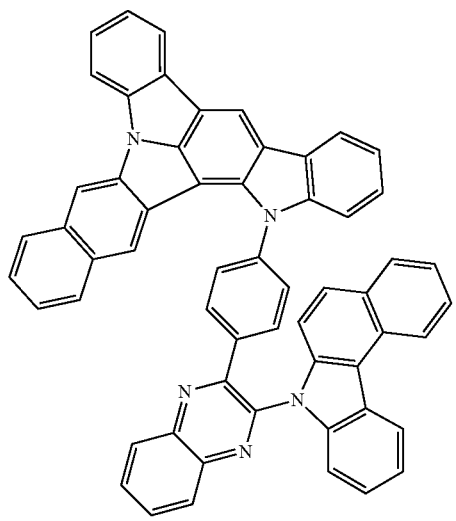
412
-continued
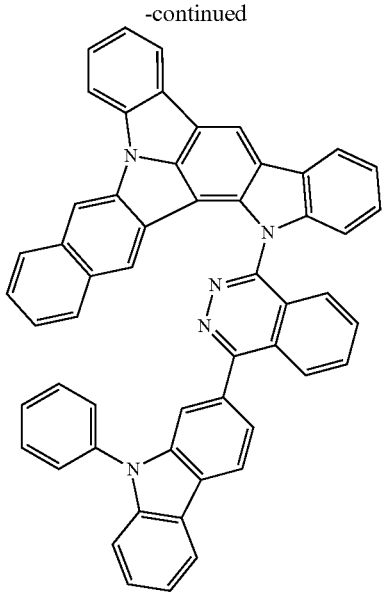
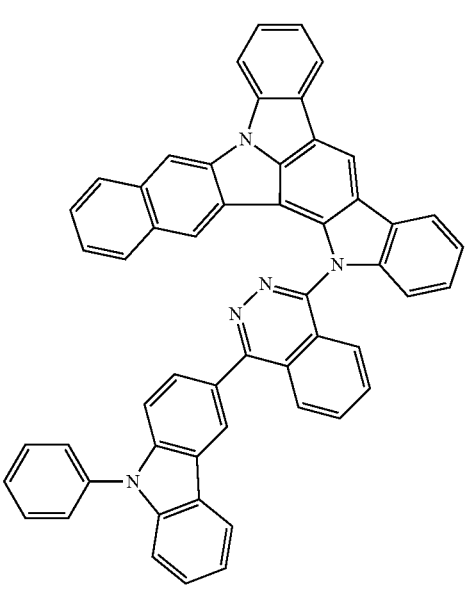
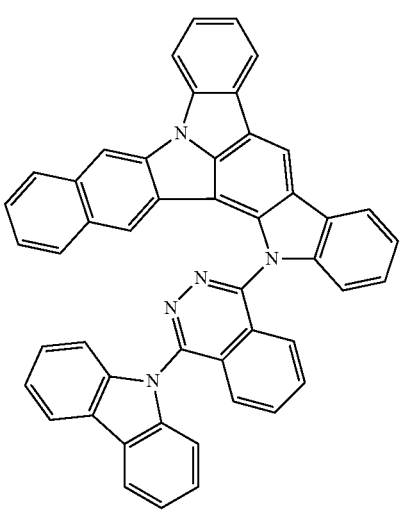

413
-continued
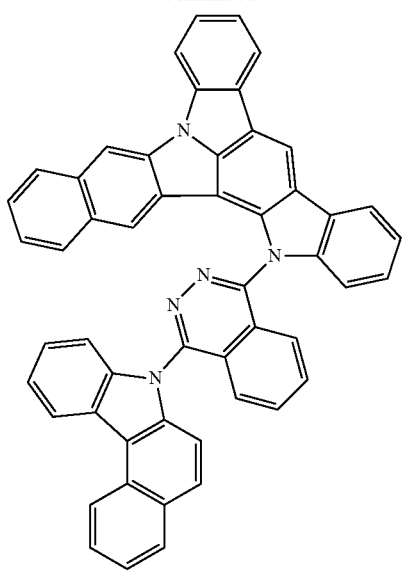
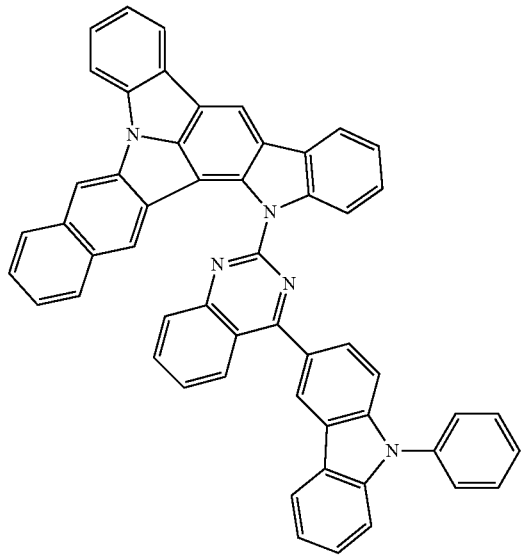
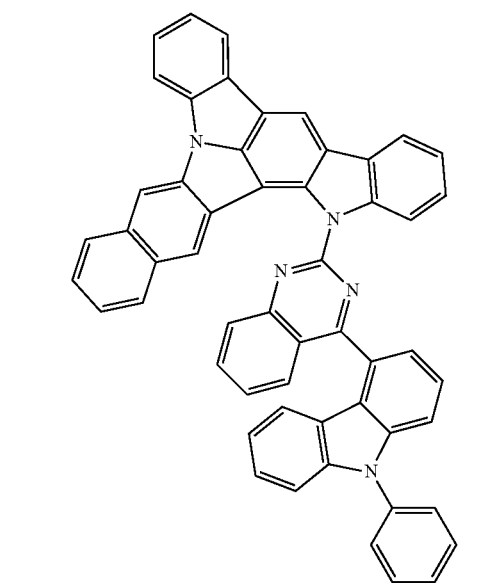
414
-continued
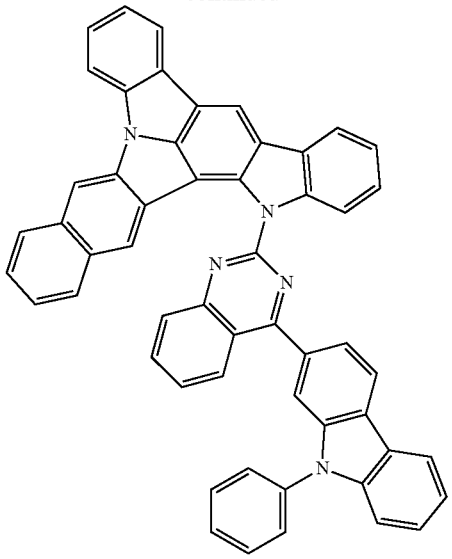
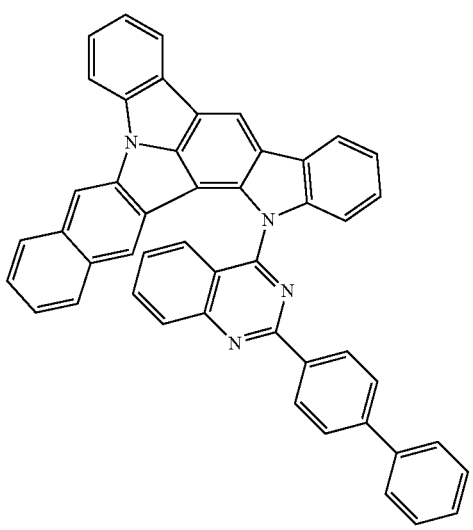
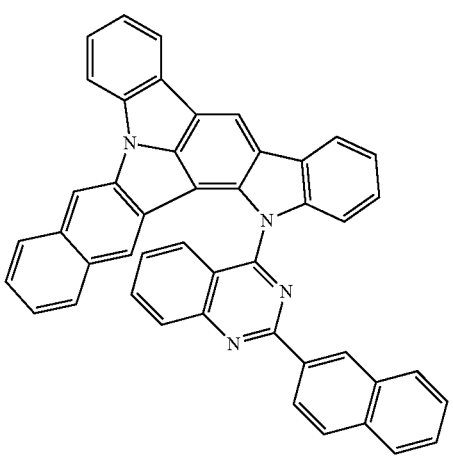

415
-continued
416
-continued
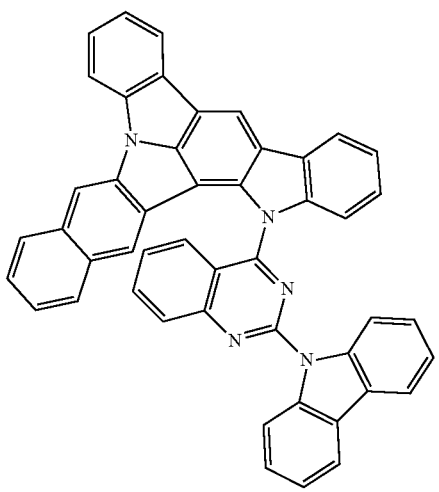
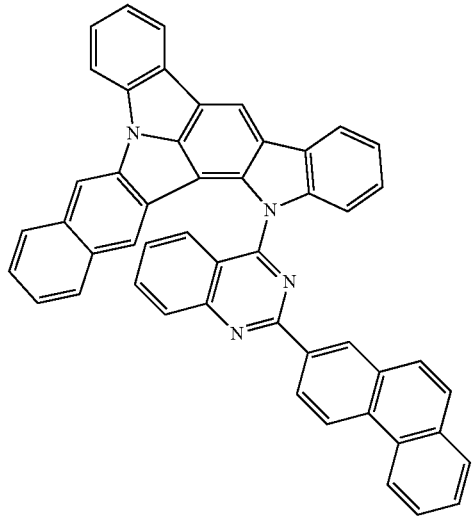
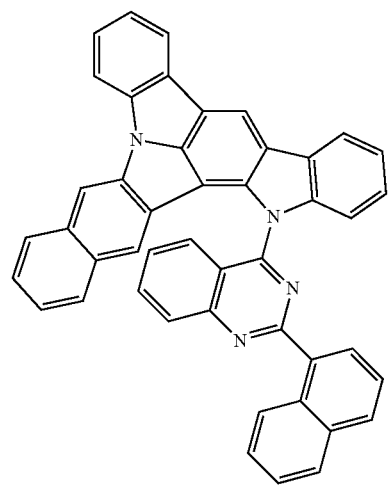
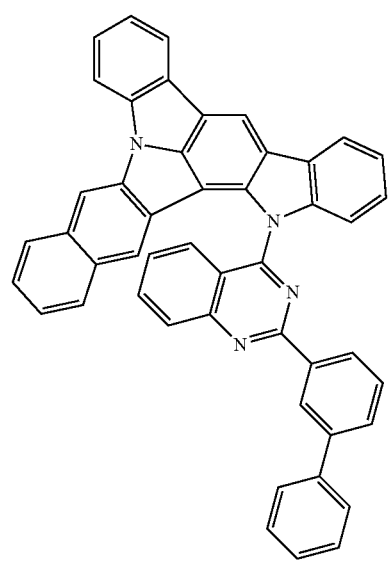

417
-continued
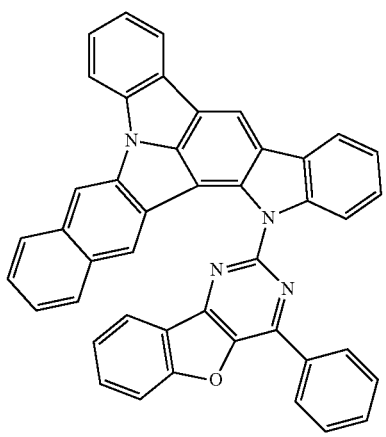
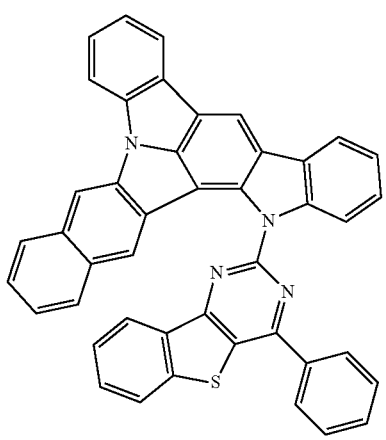
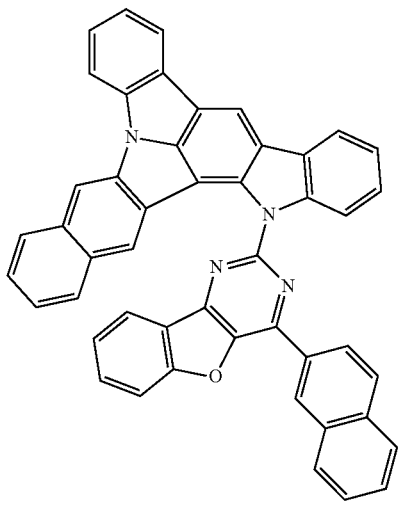
418
-continued
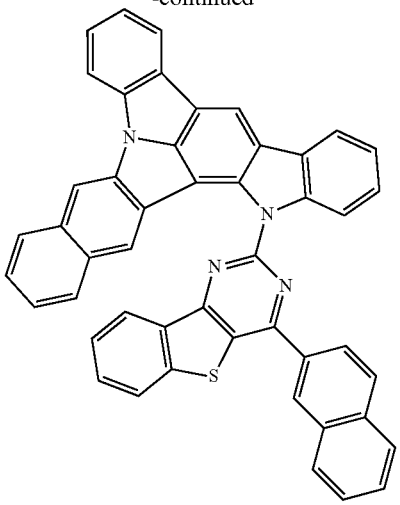
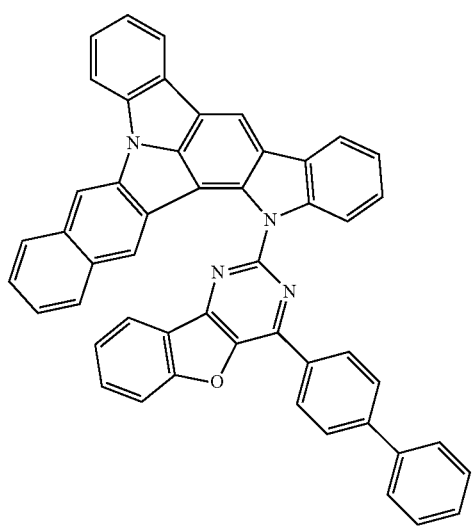
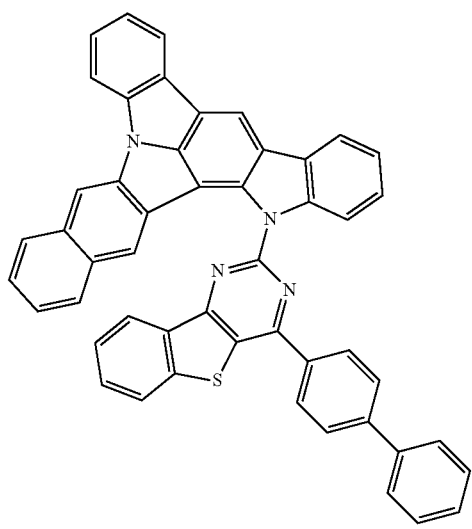

419
-continued
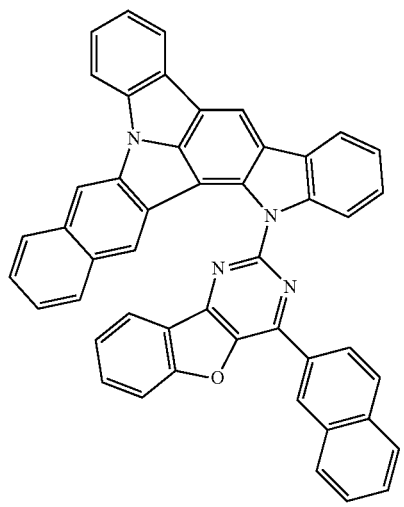
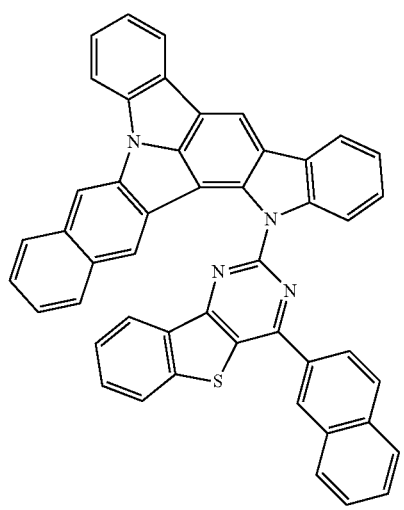
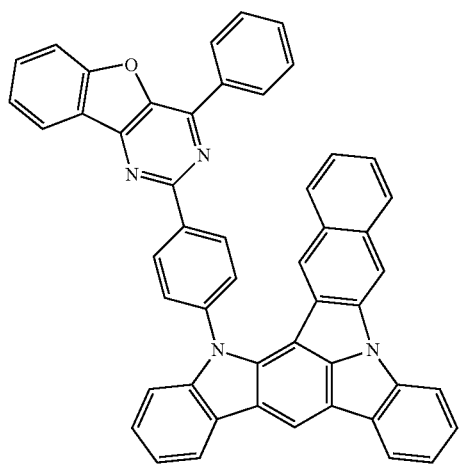
420
-continued
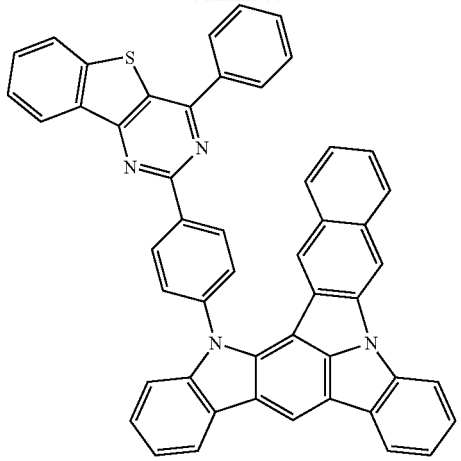
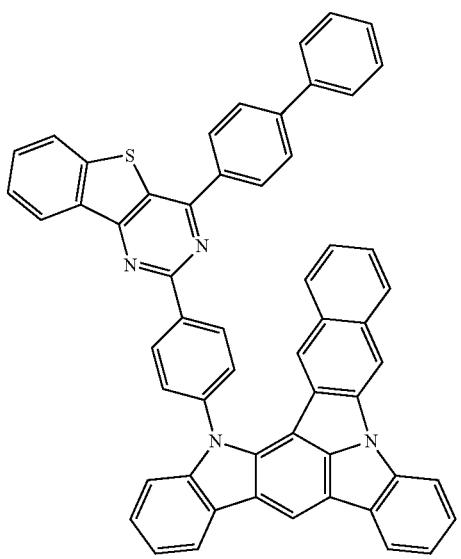

421
-continued
422
-continued
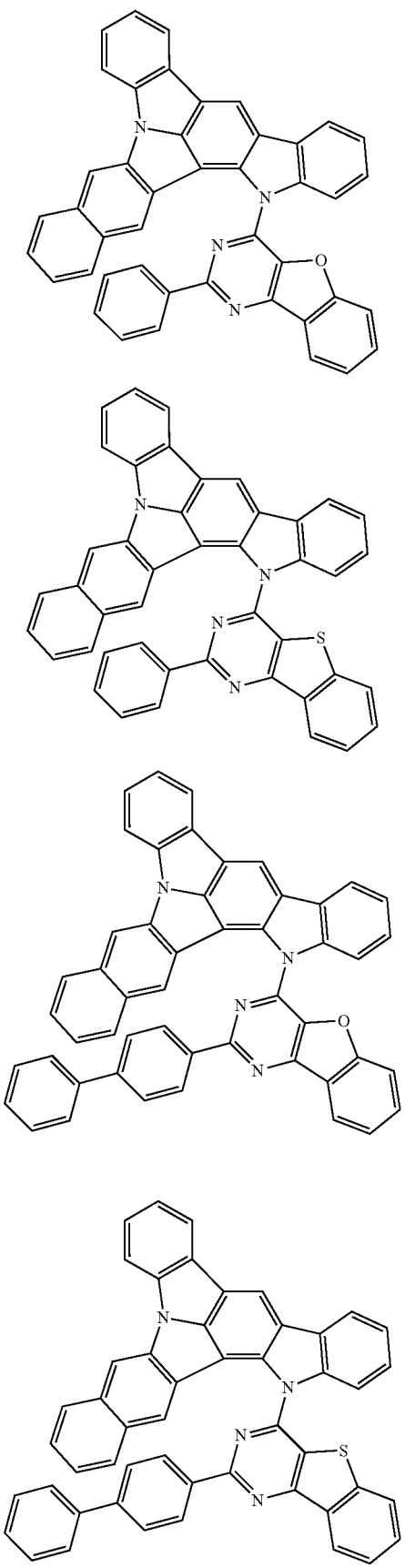

423
-continued
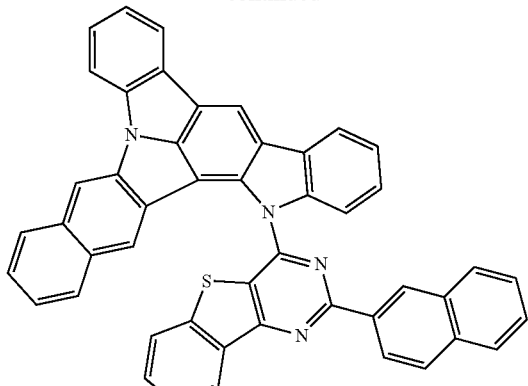
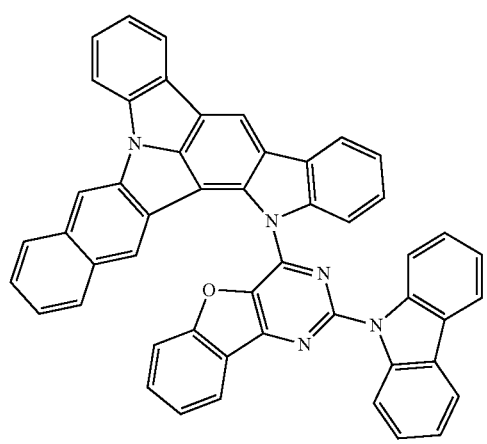
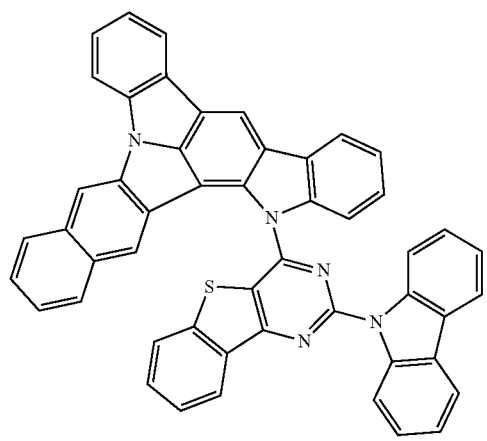
424
-continued
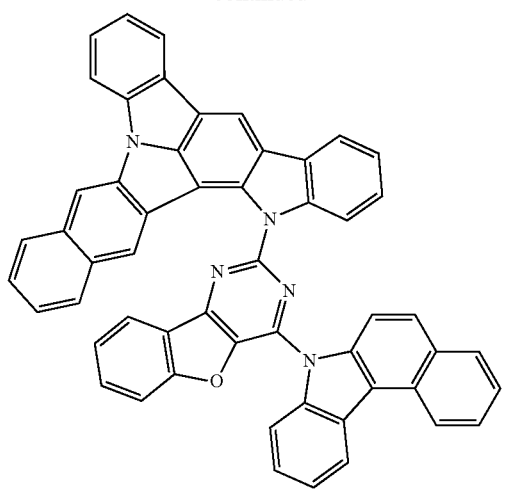
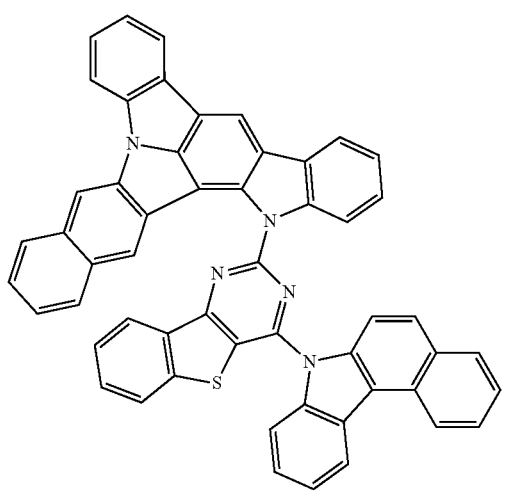
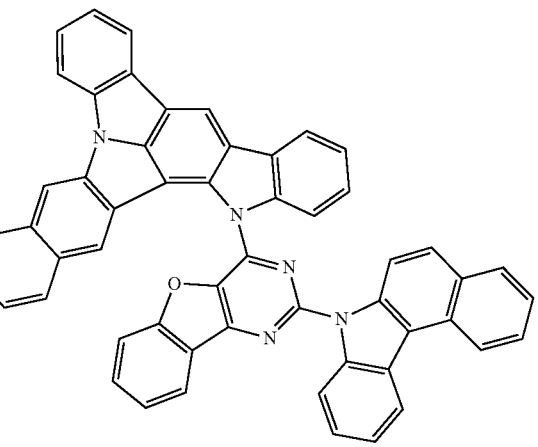

425
-continued
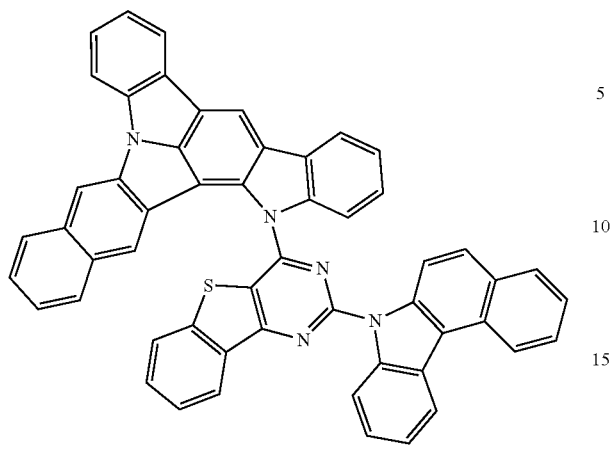
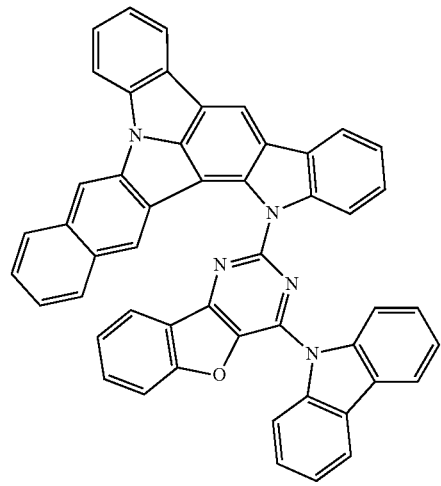
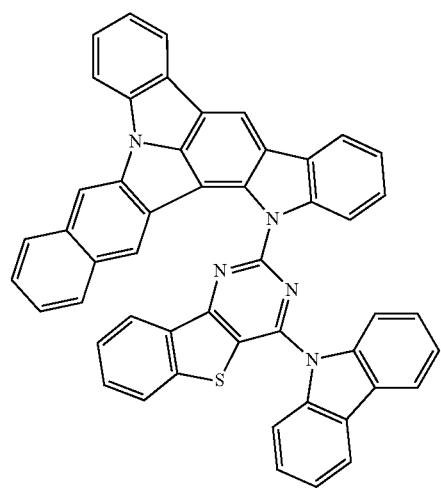
426
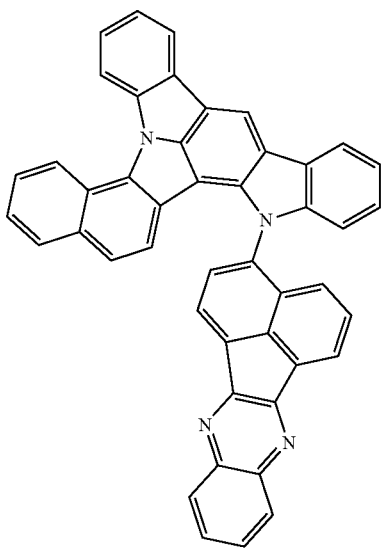
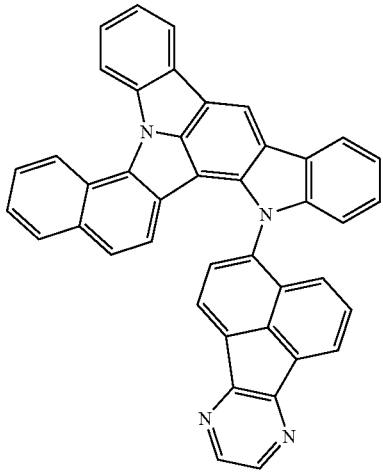
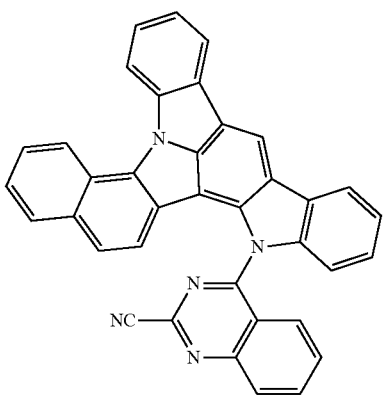

427
-continued
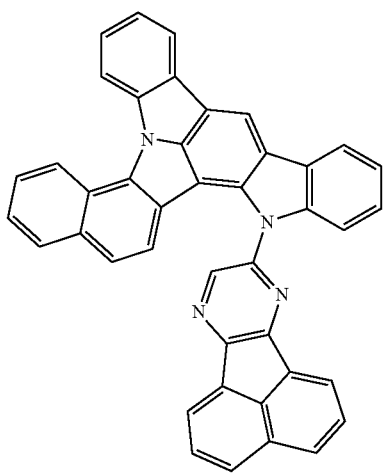
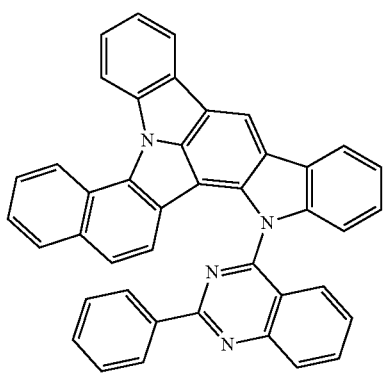
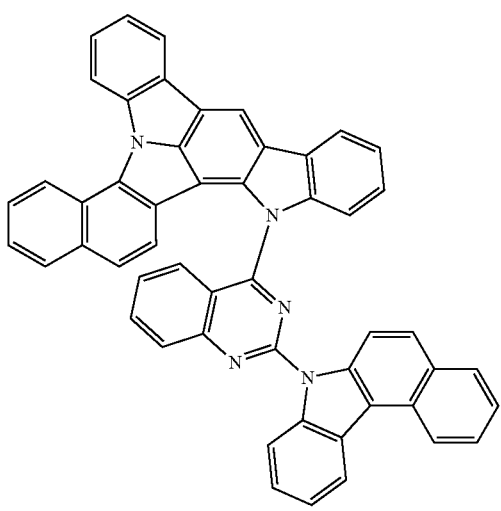
428
-continued
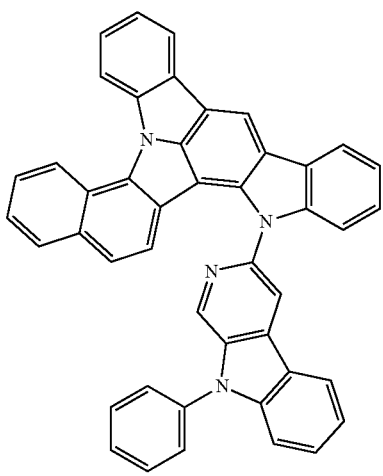
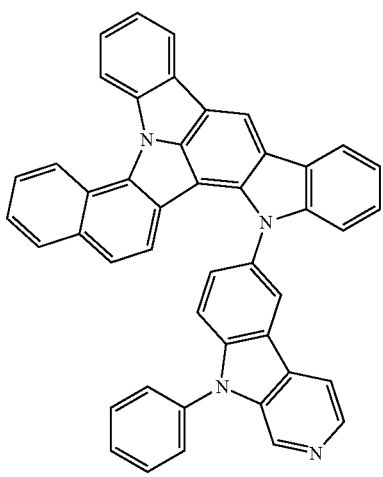
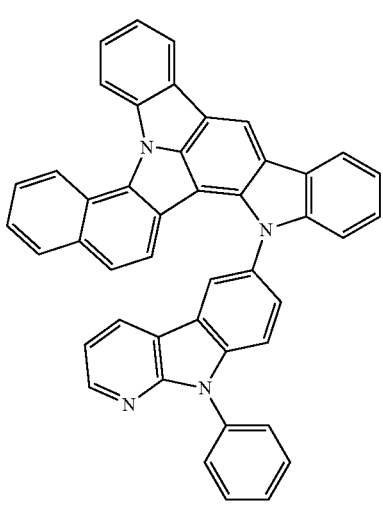

429
-continued
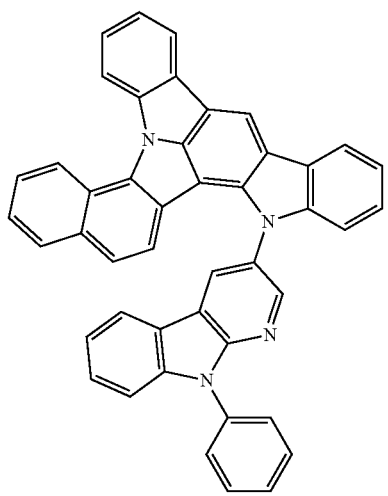
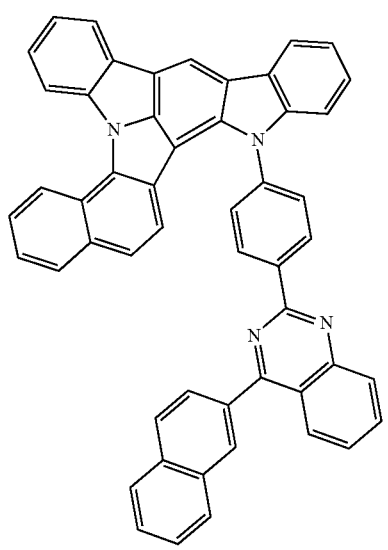
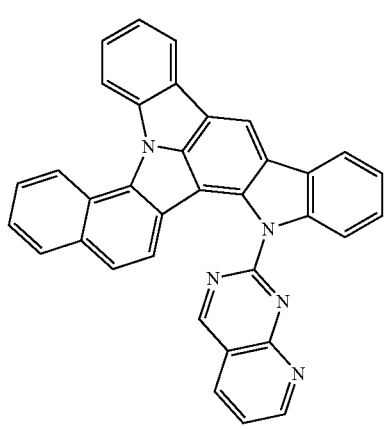
430
-continued
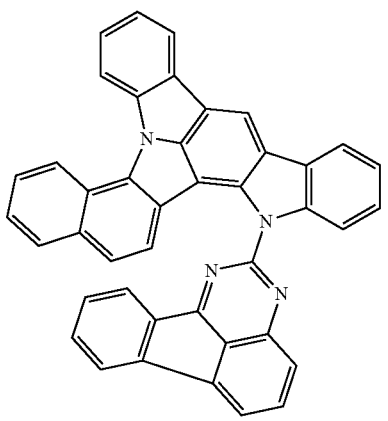
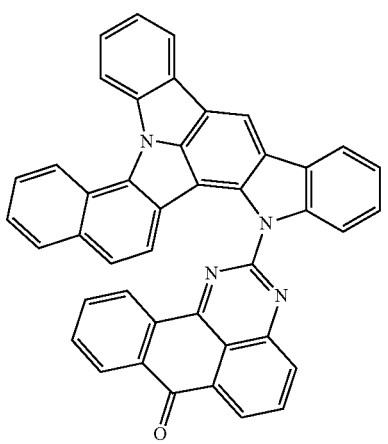
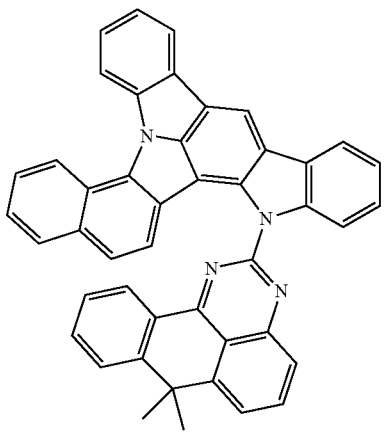
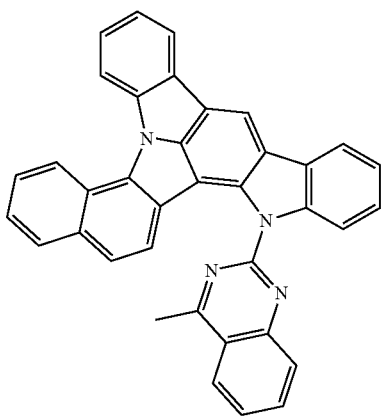

431
-continued
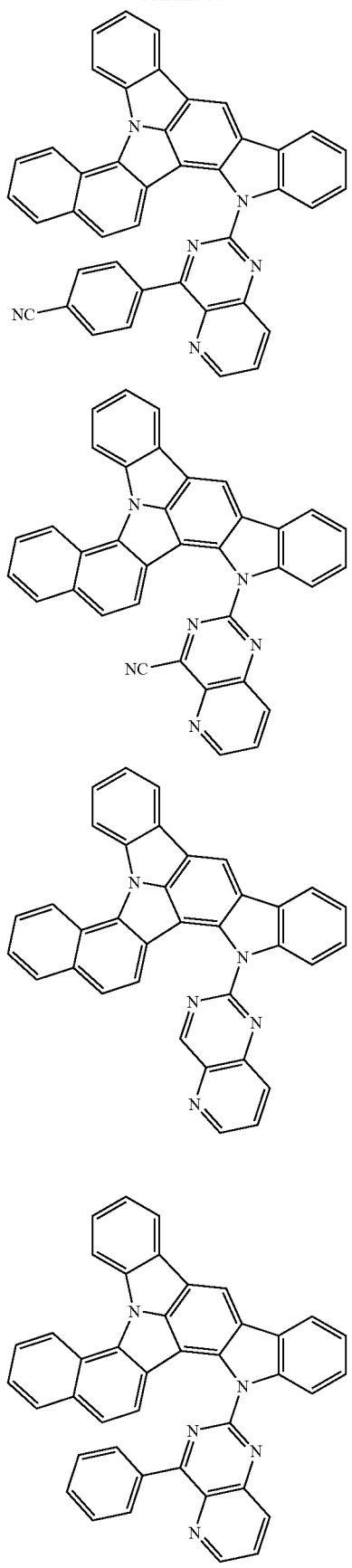
432
-continued

433
-continued
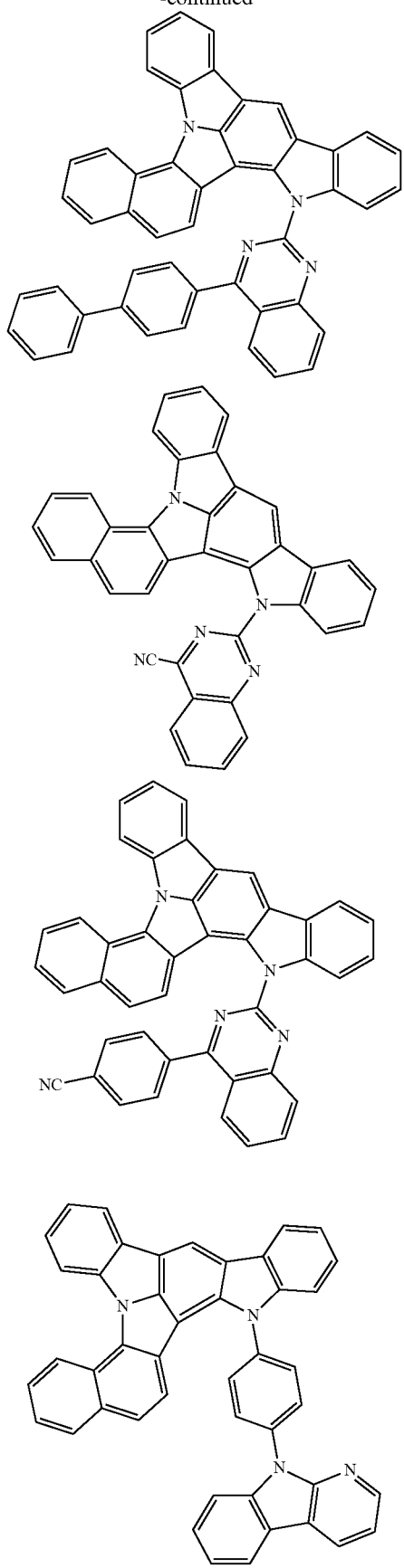
434
-continued
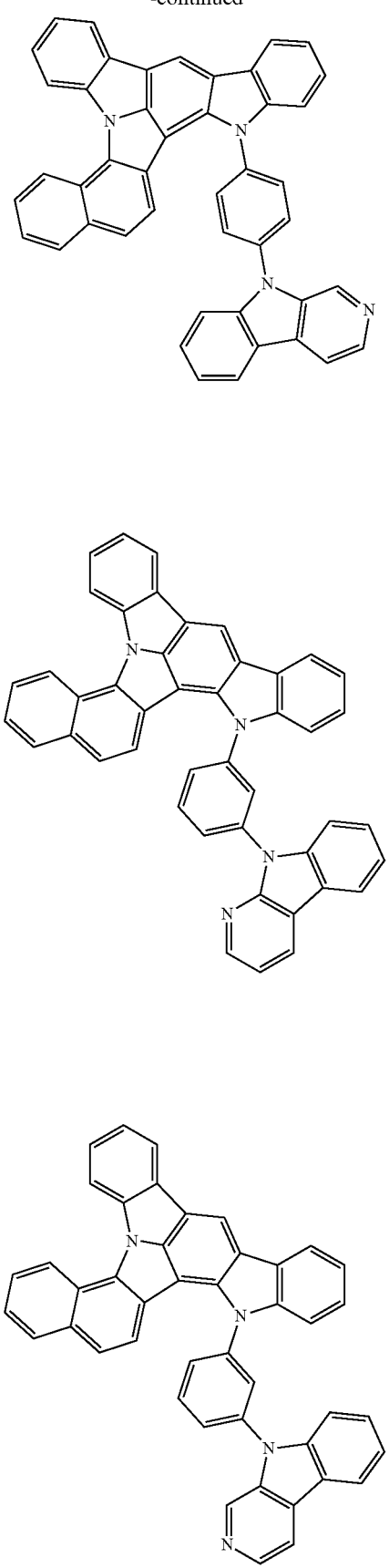

435
-continued
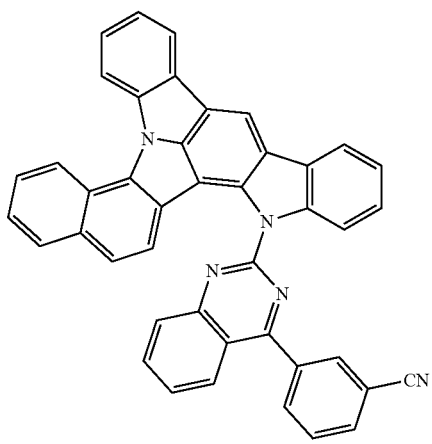
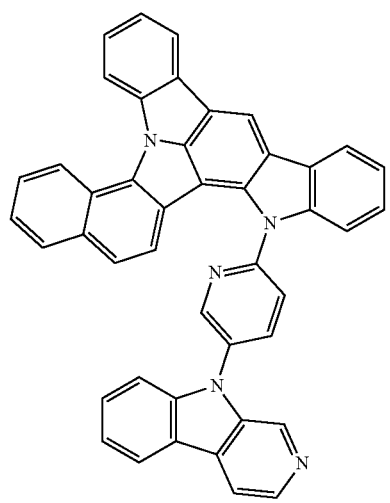
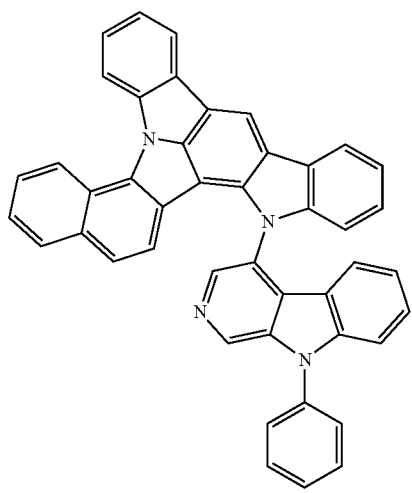
436
-continued
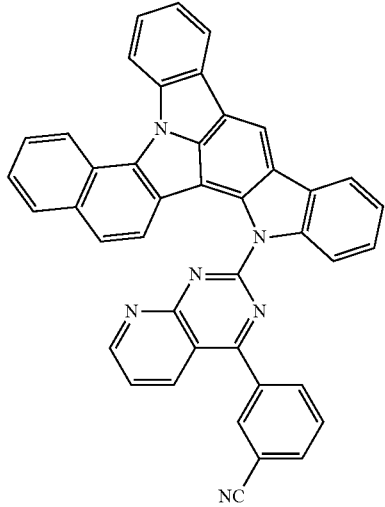
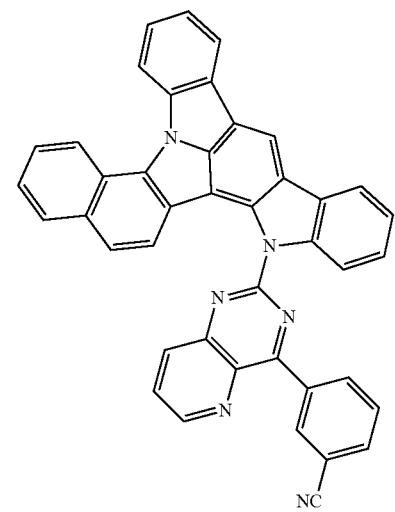
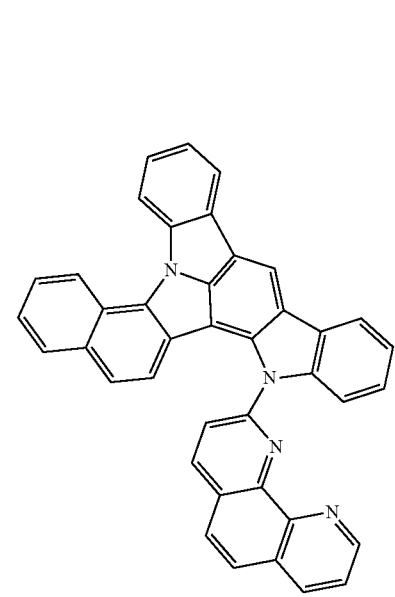

437
-continued
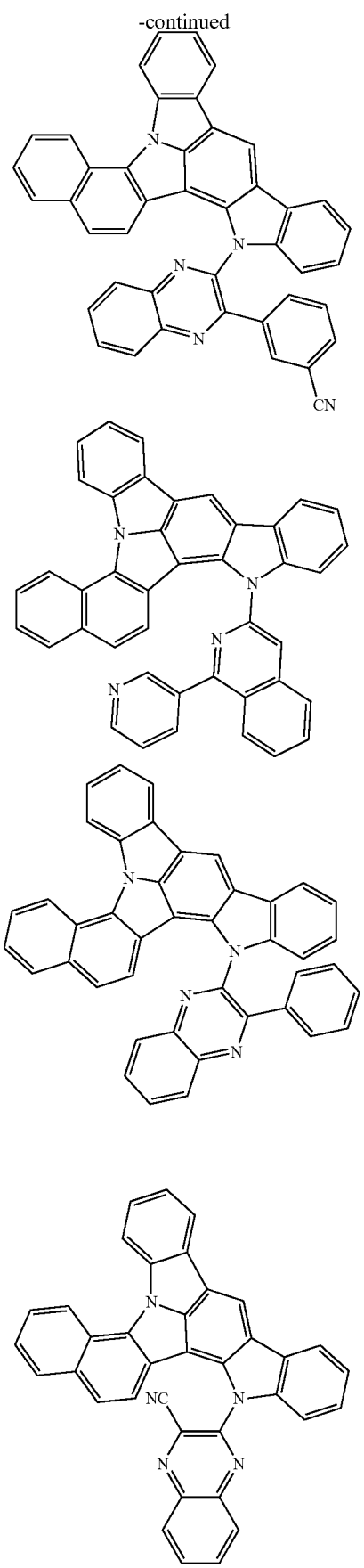
438
-continued
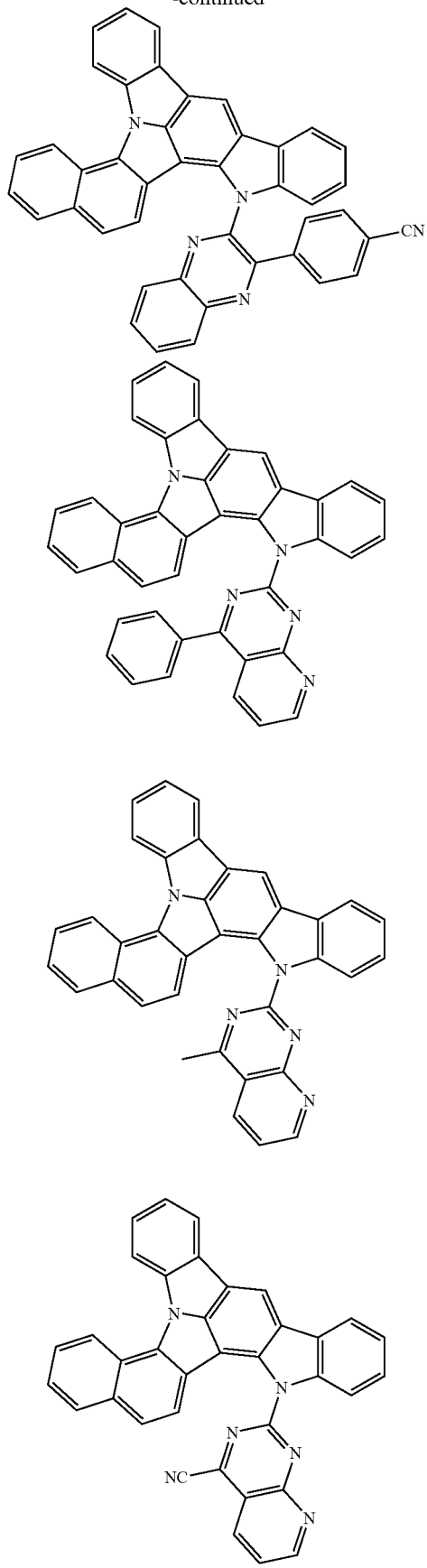

439
-continued
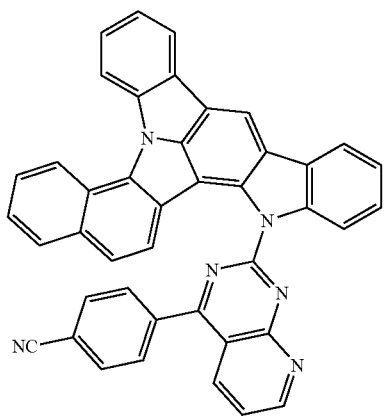
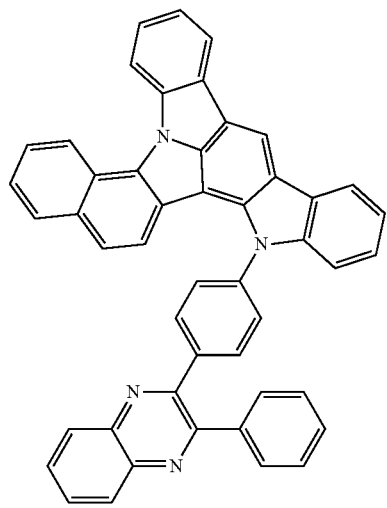
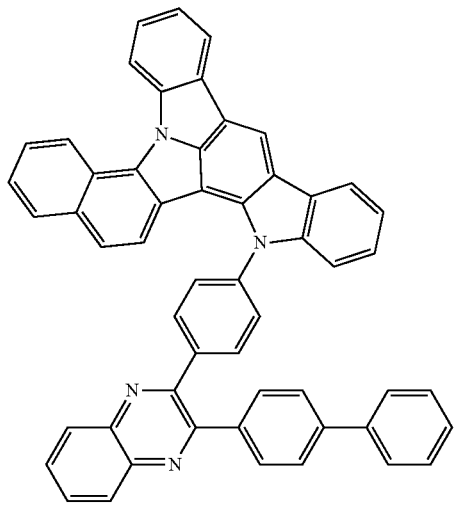
440
-continued
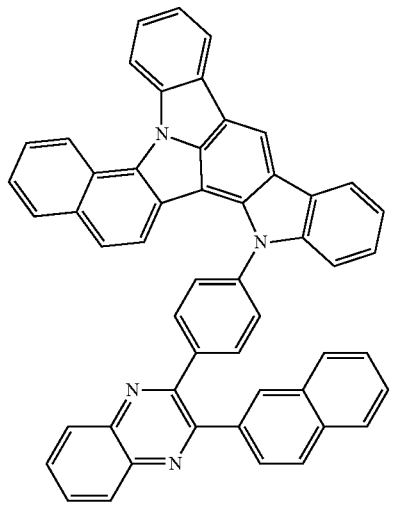
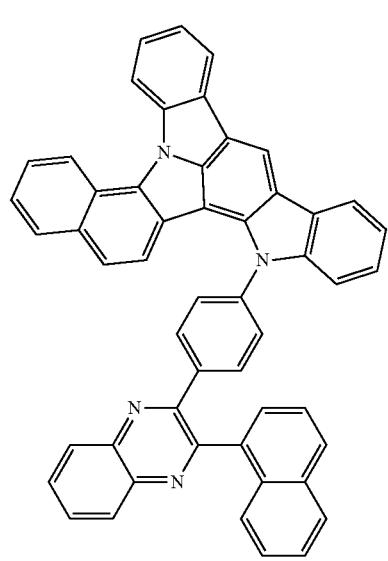
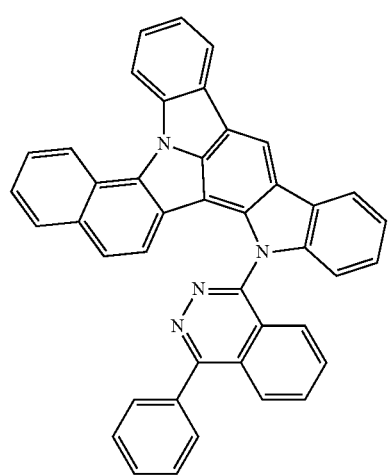

441
-continued
442
-continued
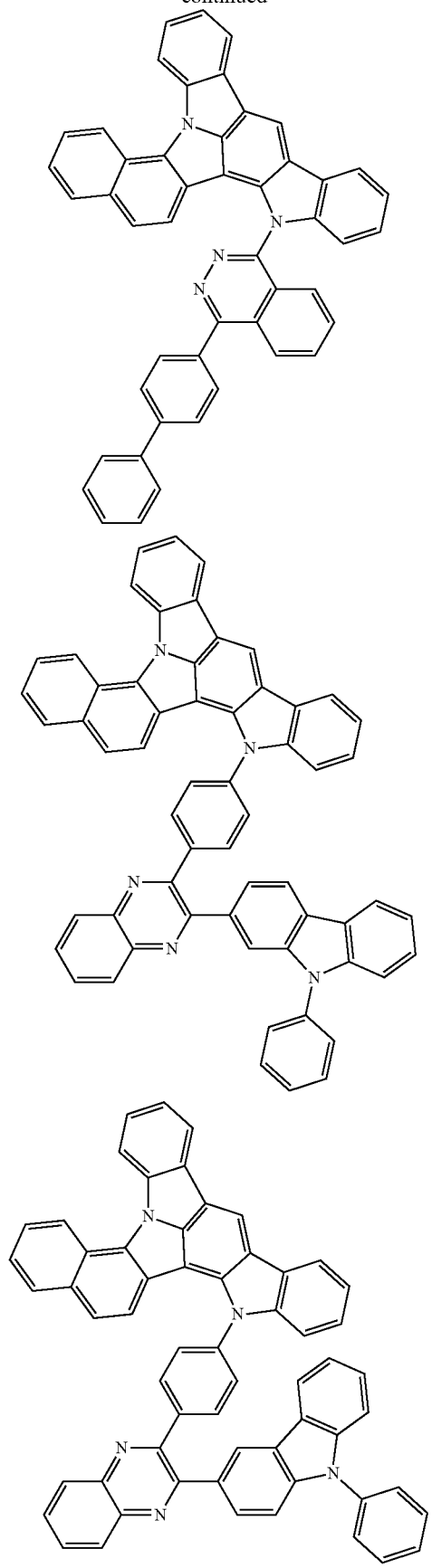
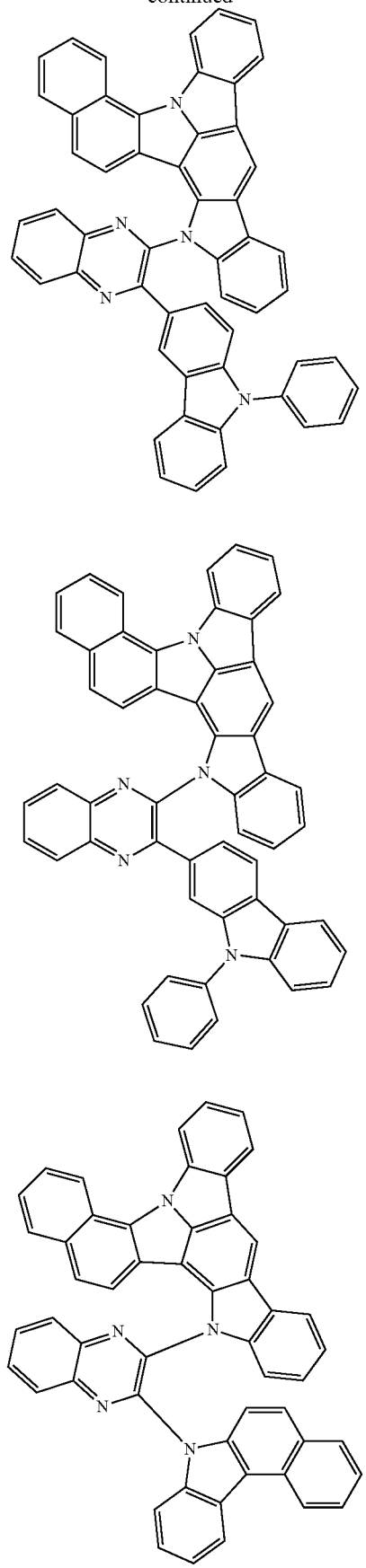

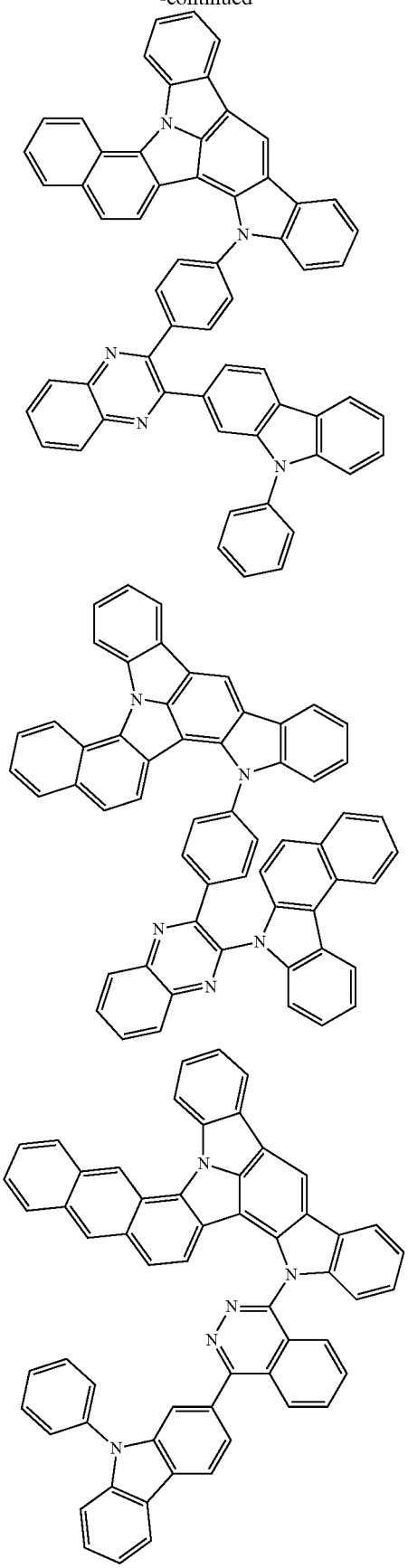
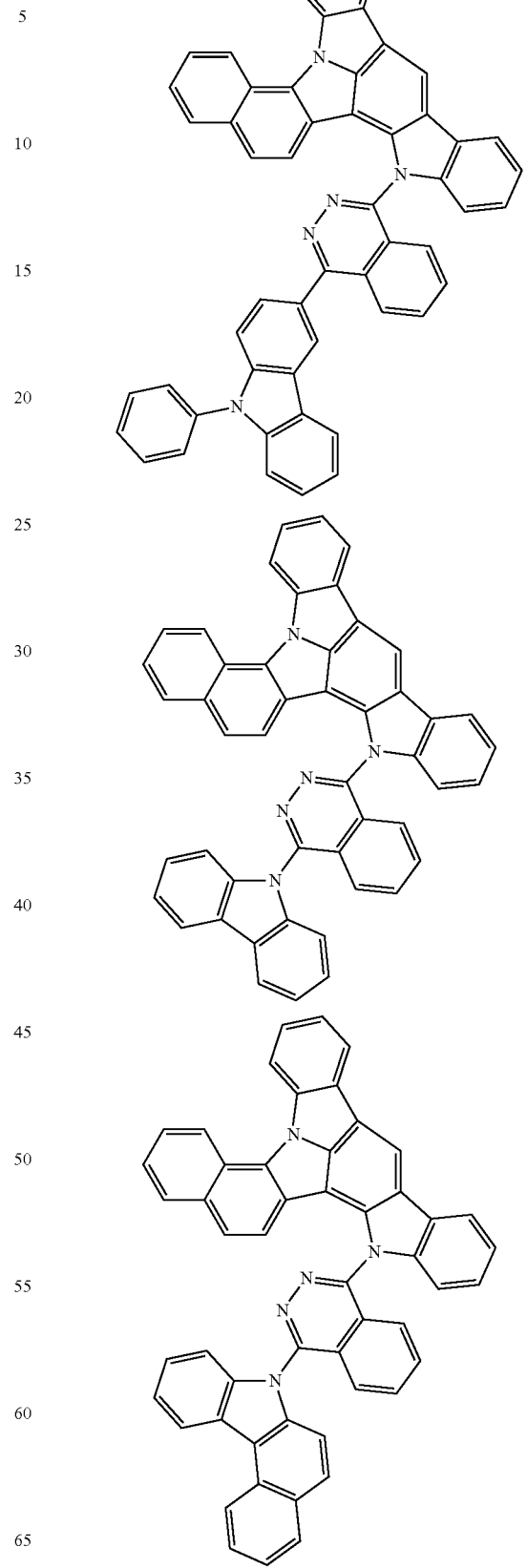

445
-continued
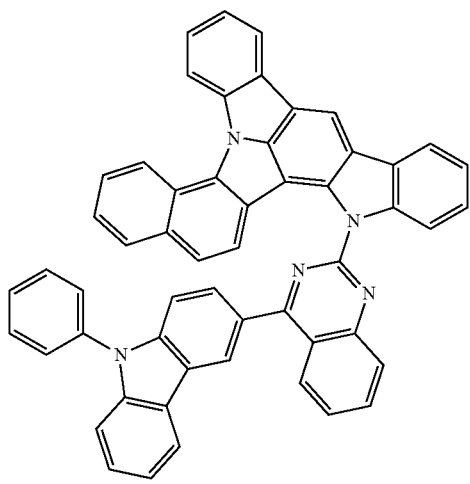
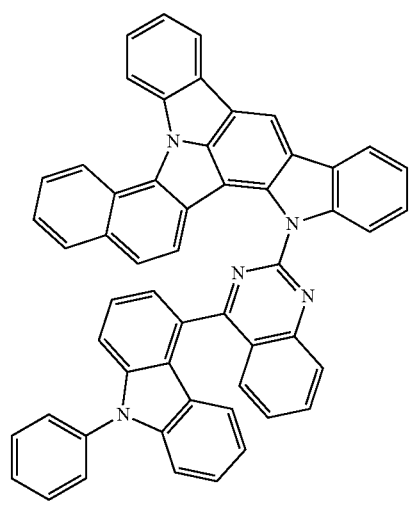
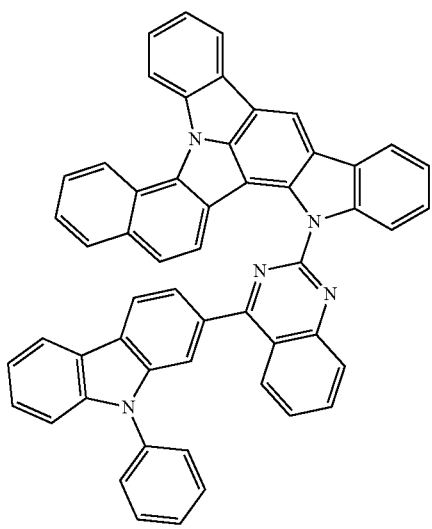
446
-continued
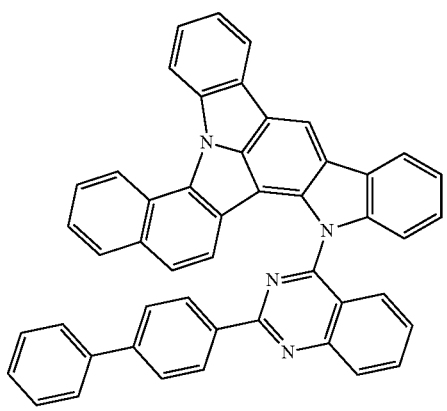
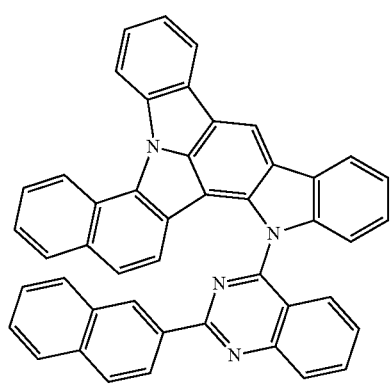
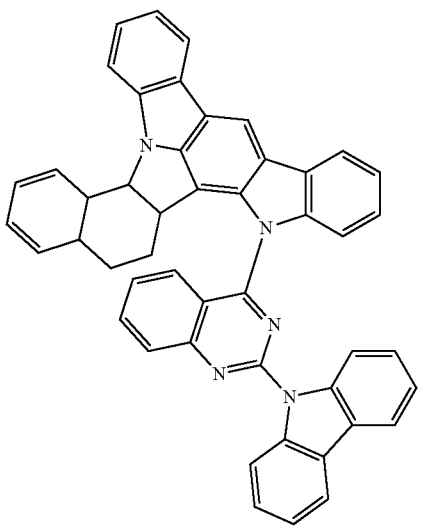

447
-continued
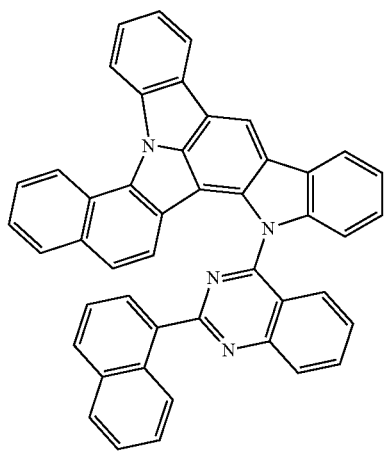
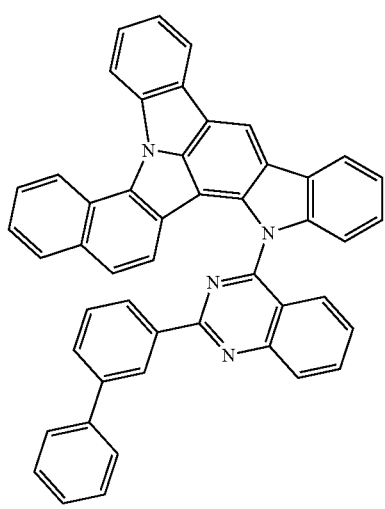
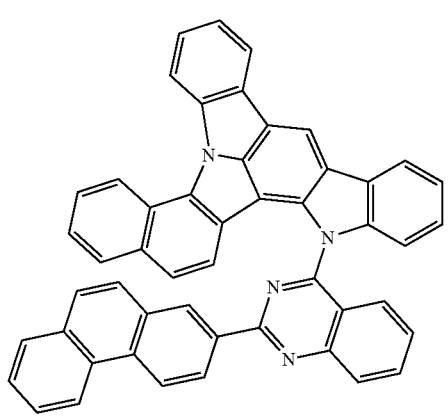
448
-continued
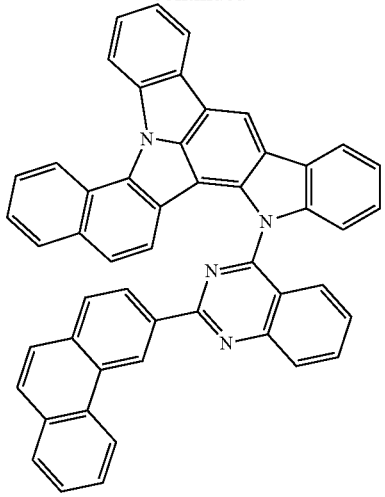
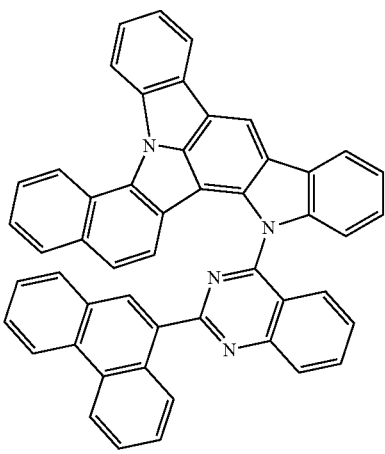
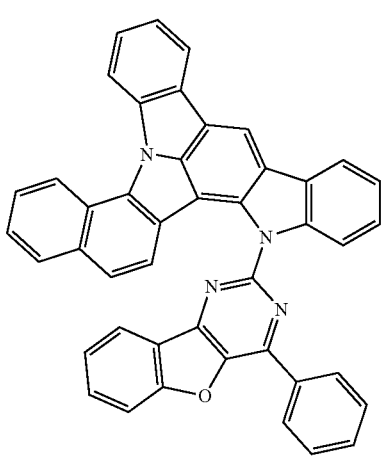

| 449 | 450 |
|---|---|
| -continued | -continued |
| 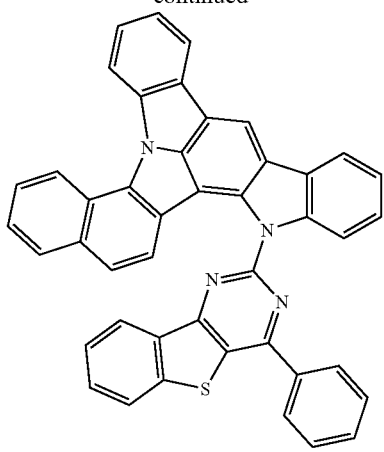 | 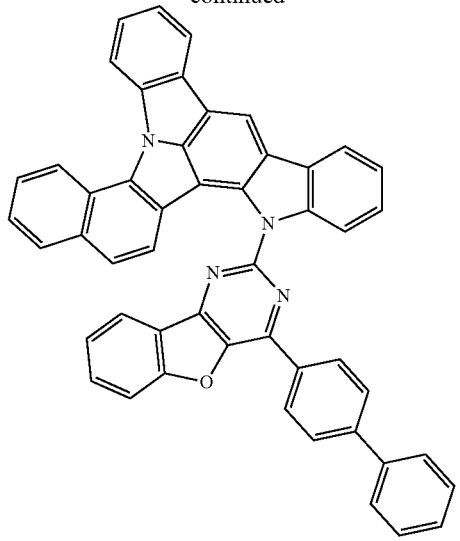 |
| 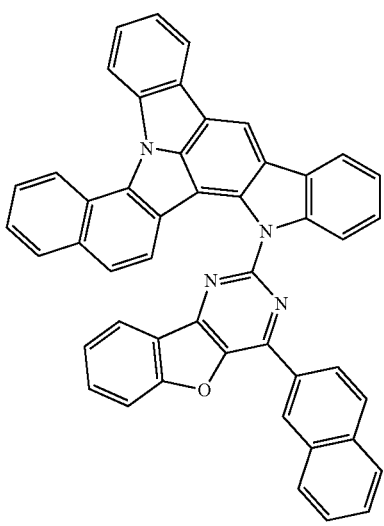 | 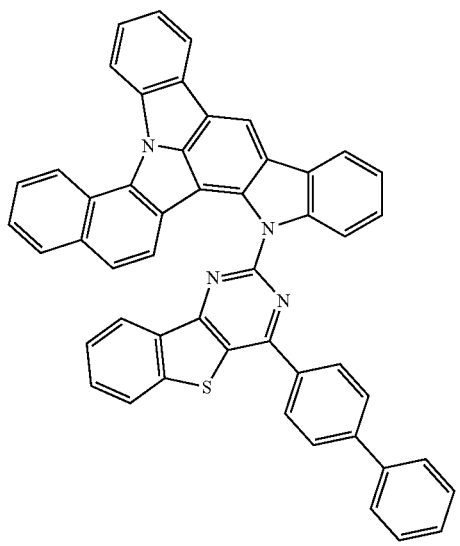 |
| 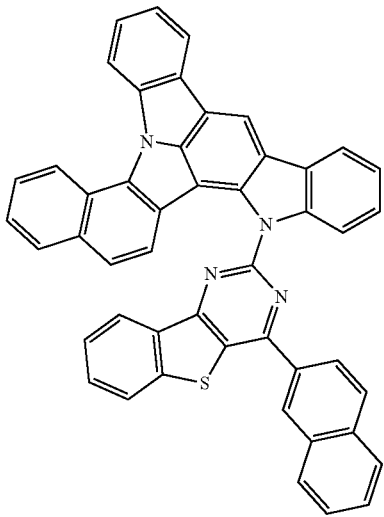 | 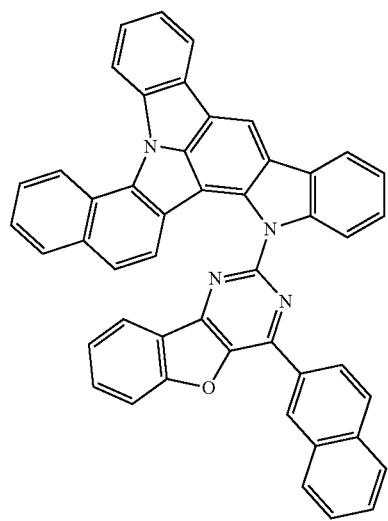 |

451
-continued
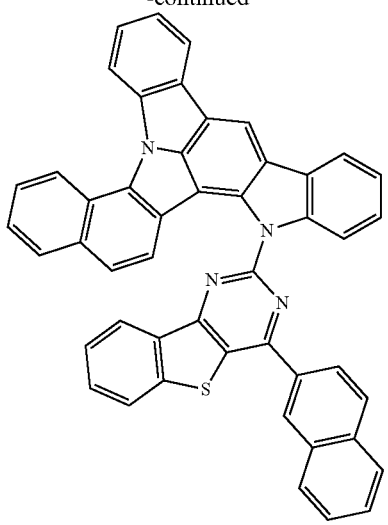
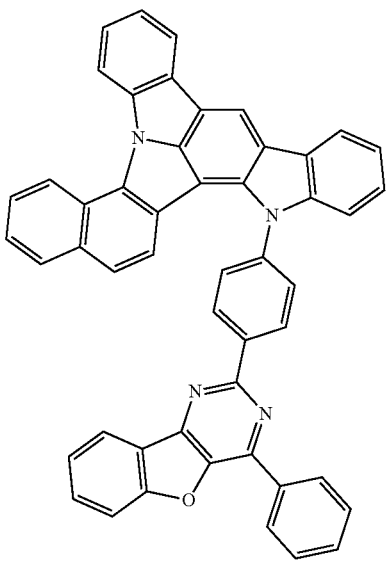
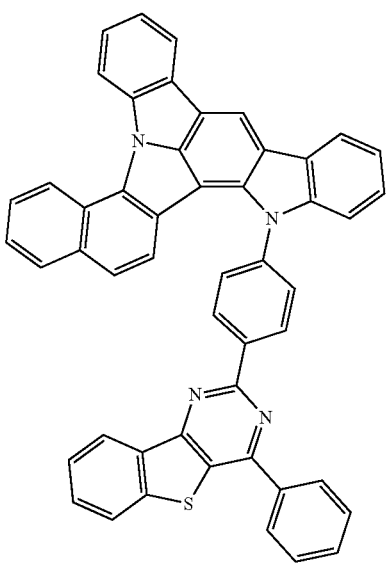
452
-continued
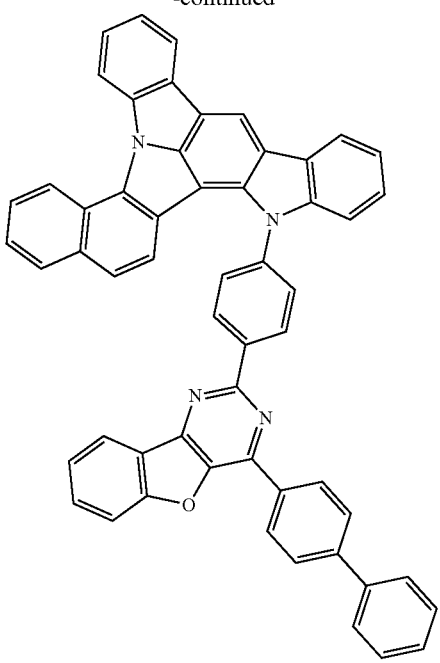
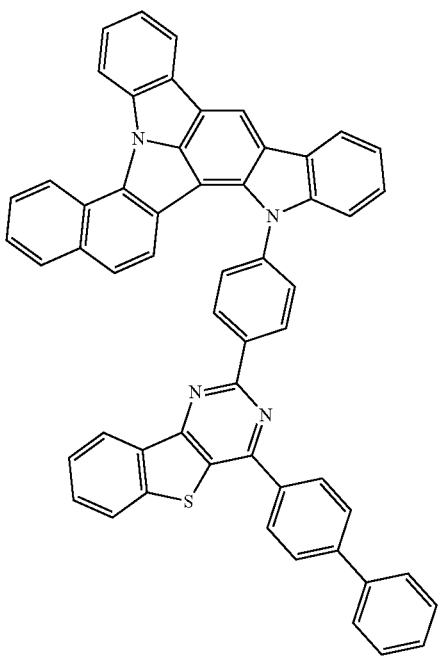
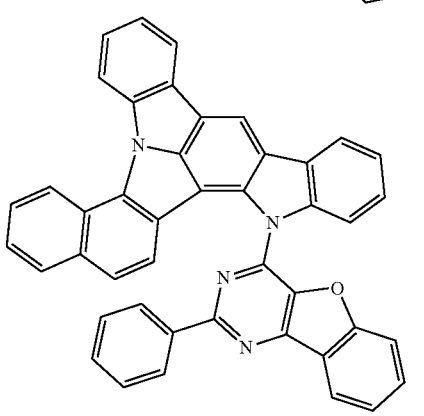

453
-continued
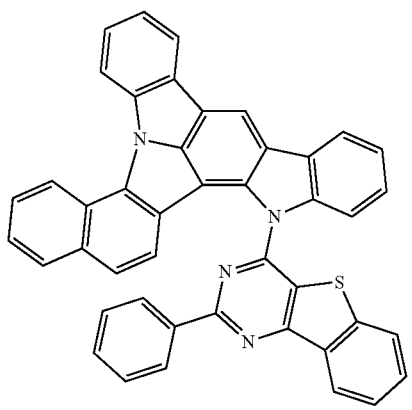
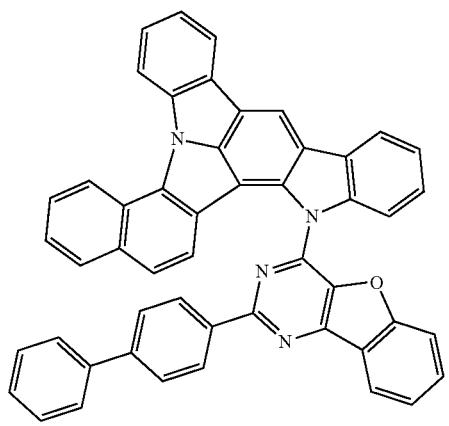
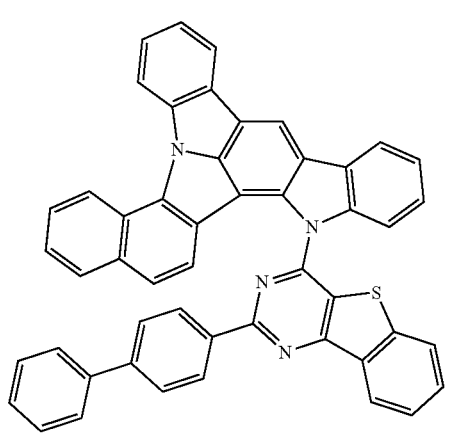
454
-continued
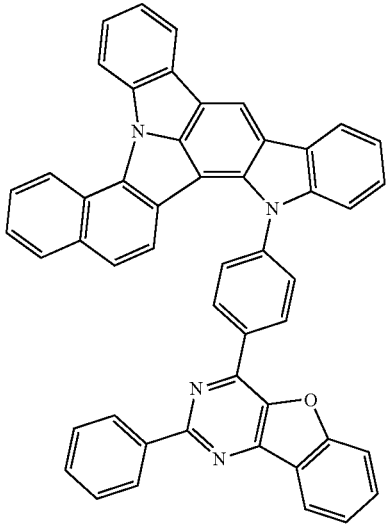
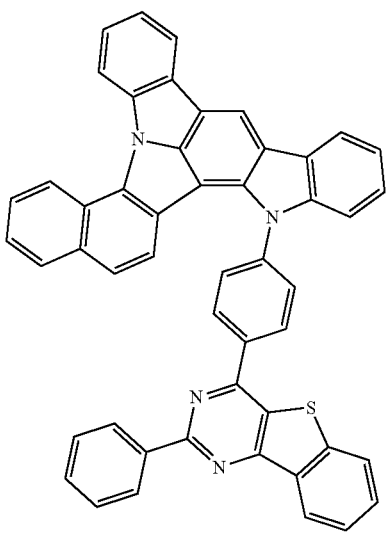
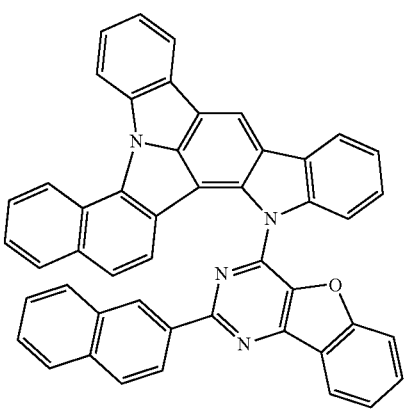

455
-continued
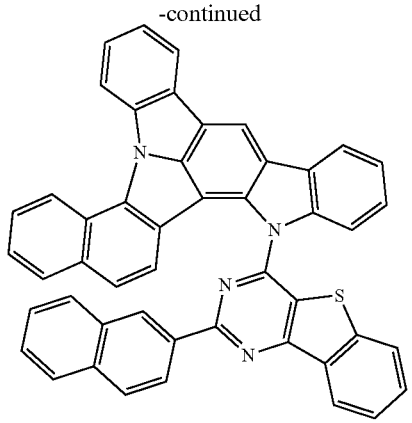
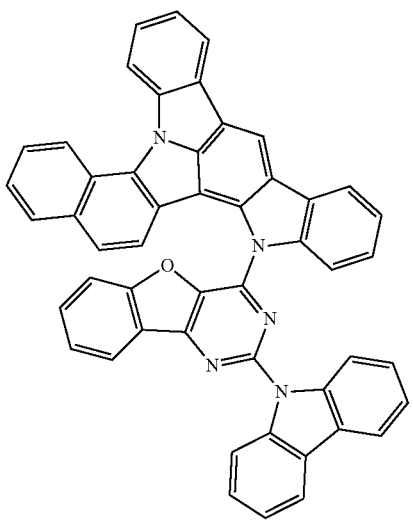
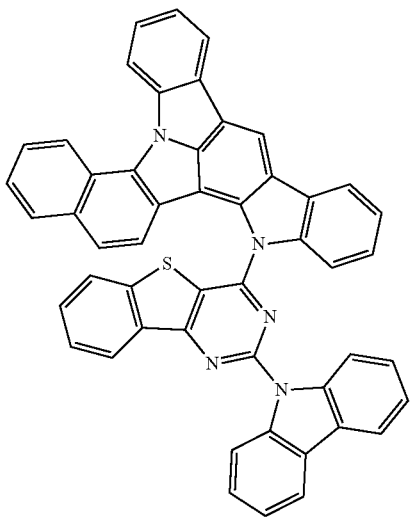
456
-continued
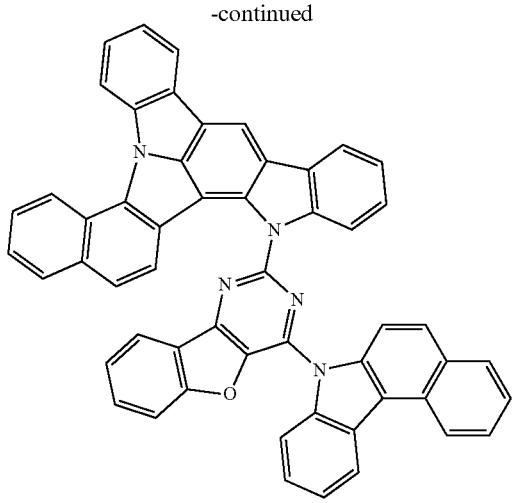
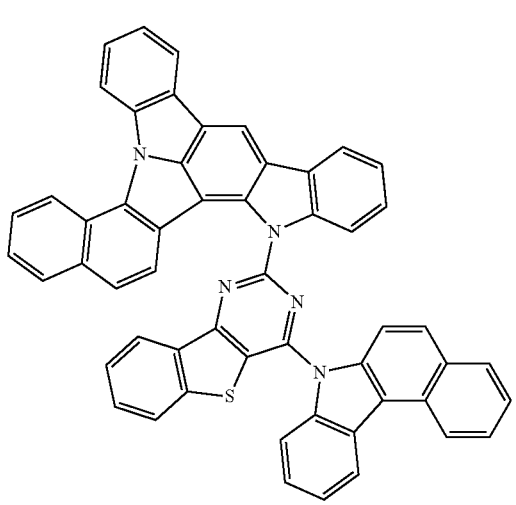
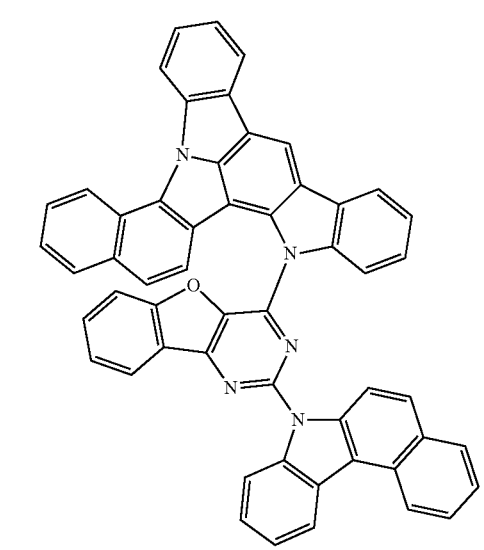

457
-continued
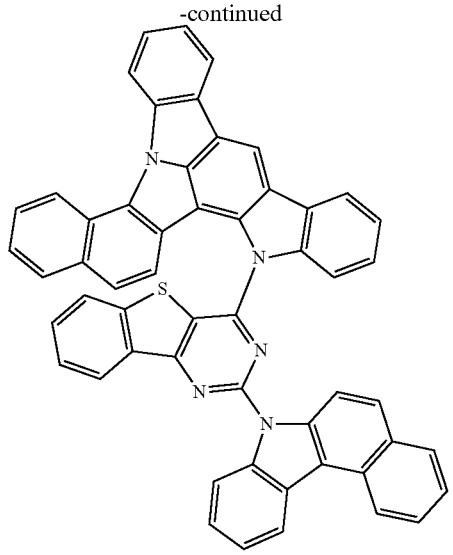
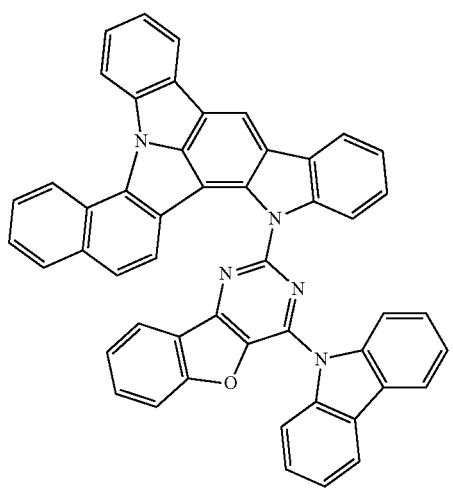 [SMILES: c1ccc2c(c1)ccc1c3c4c(cc5c6ccccc6n(c21)c53)c1ccccc1n4-c1nc(-n2c3ccccc3c3ccccc32)c2oc3ccccc3c2n1]
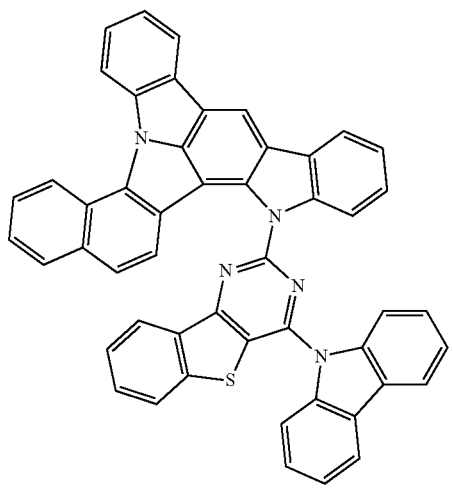
458
-continued
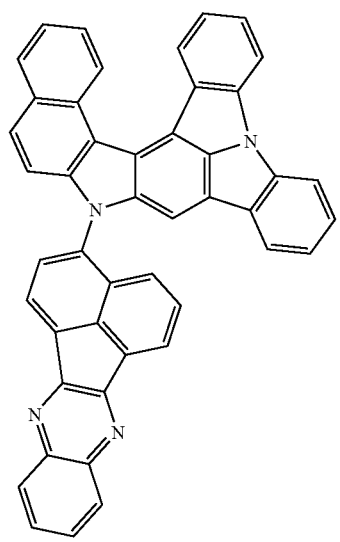
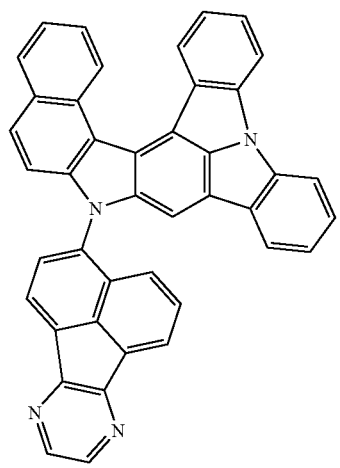
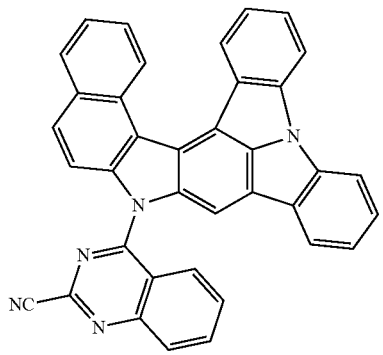

459
-continued
460
-continued
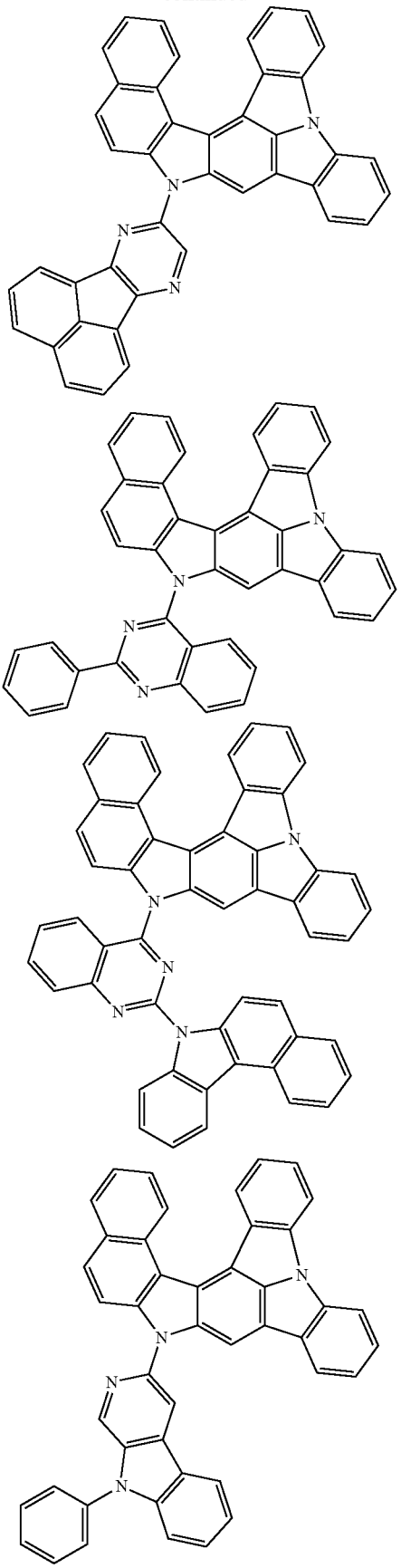
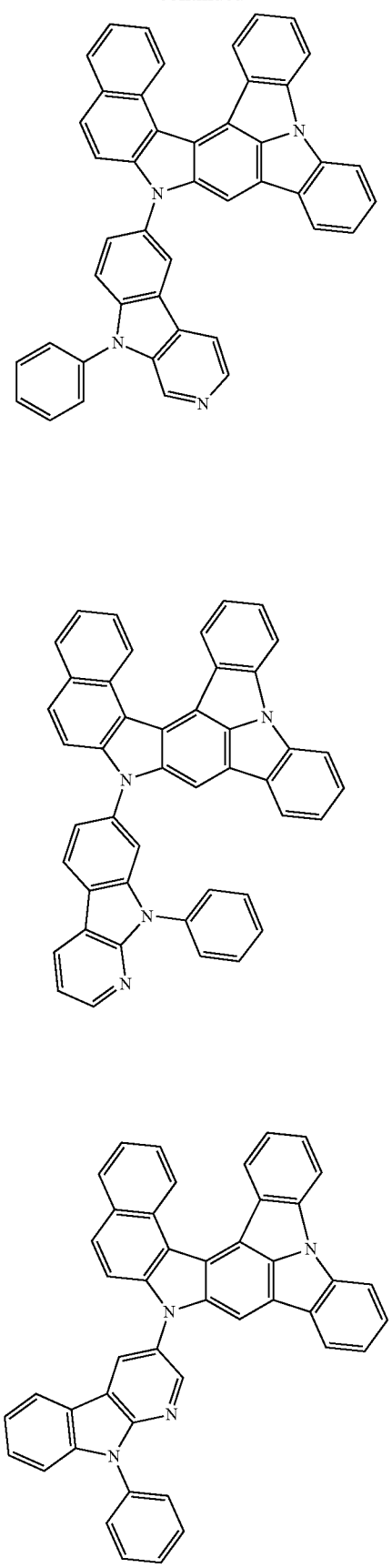

461
-continued
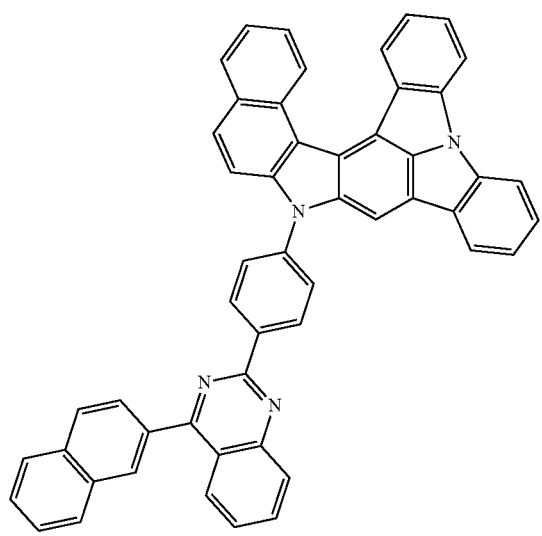
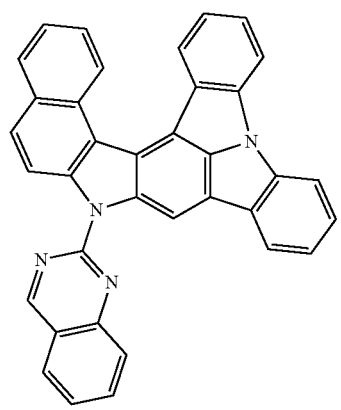
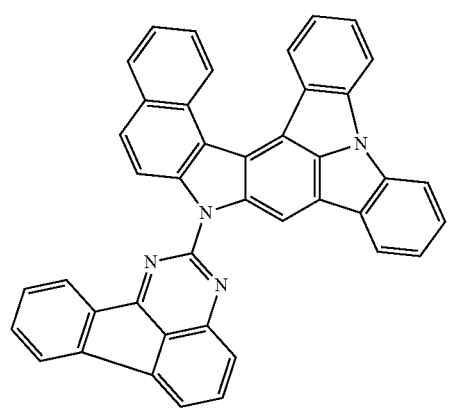
462
-continued
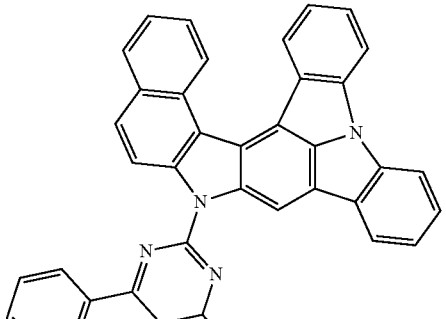
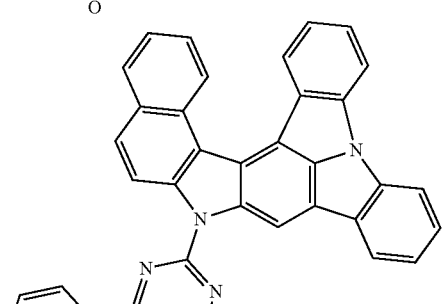
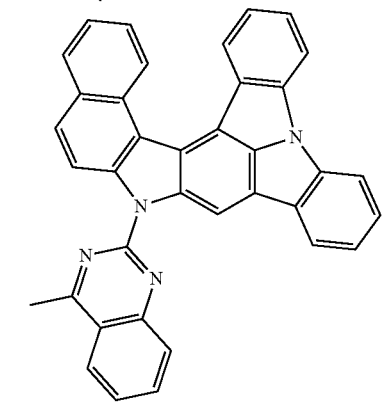
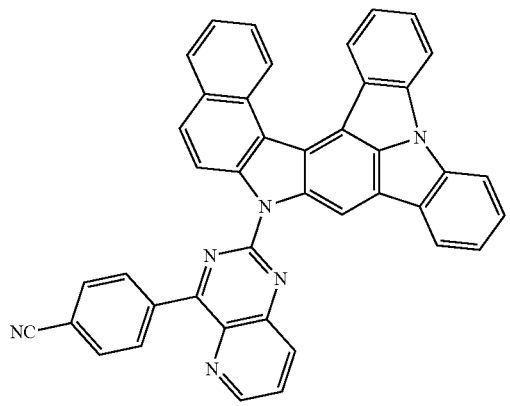

463
-continued
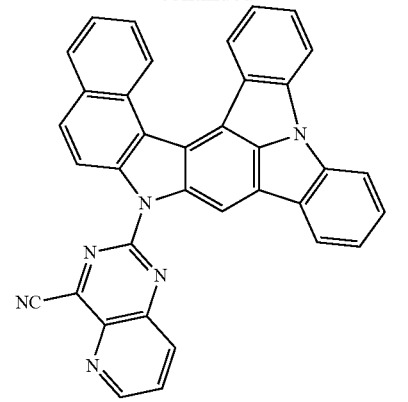
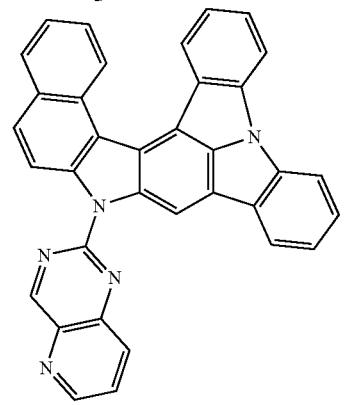
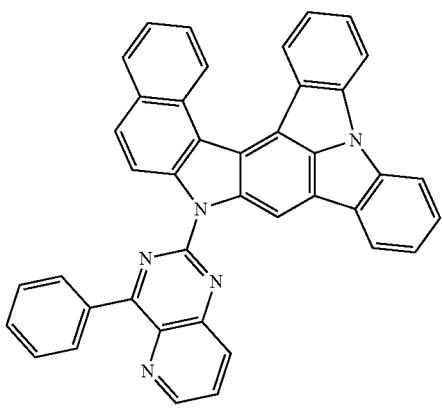
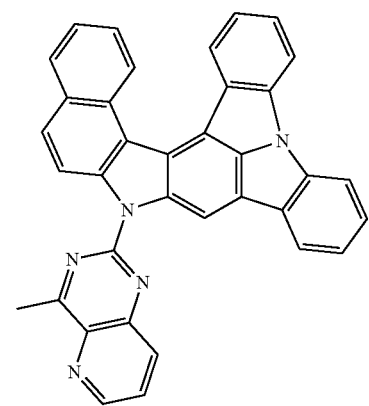
464
-continued
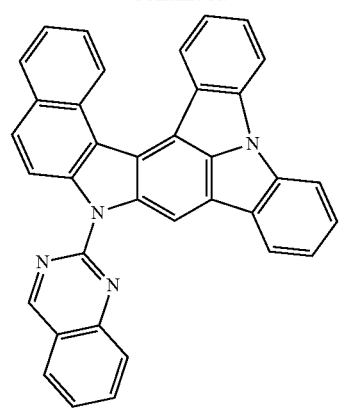
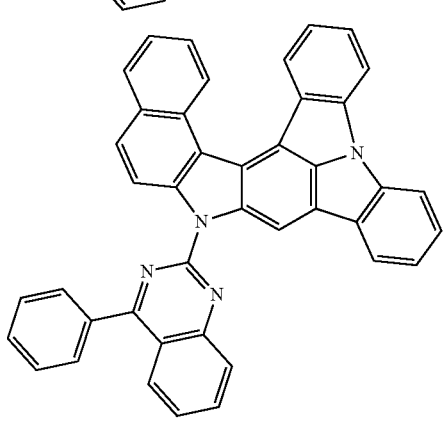
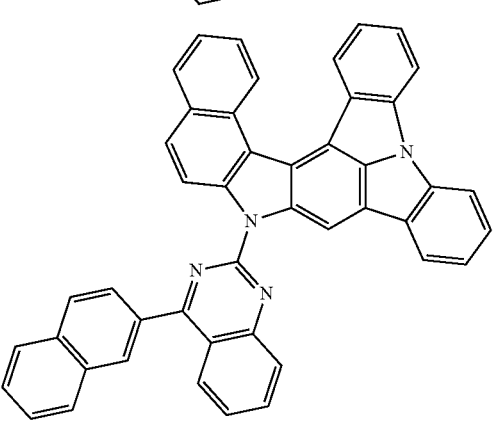
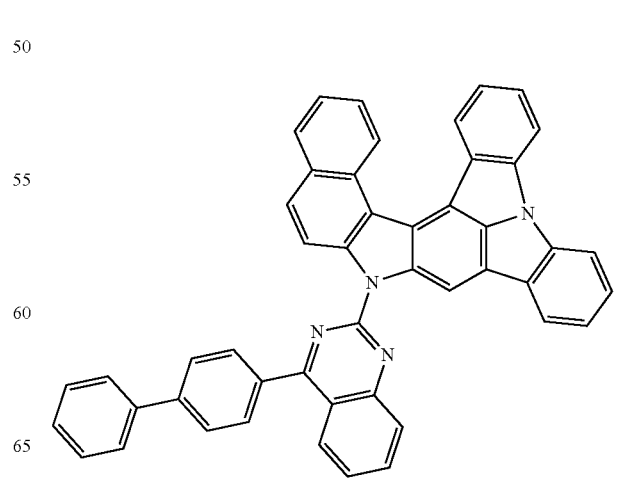

465
-continued
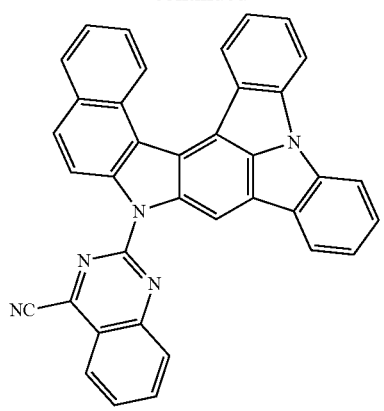
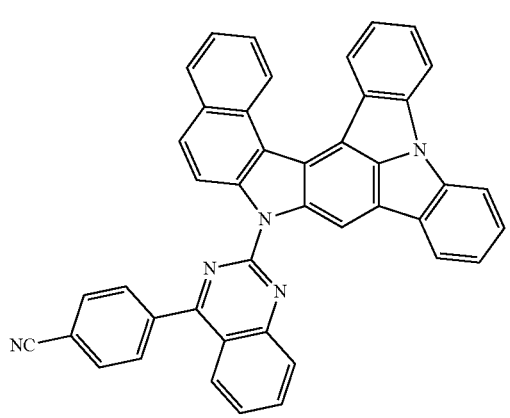
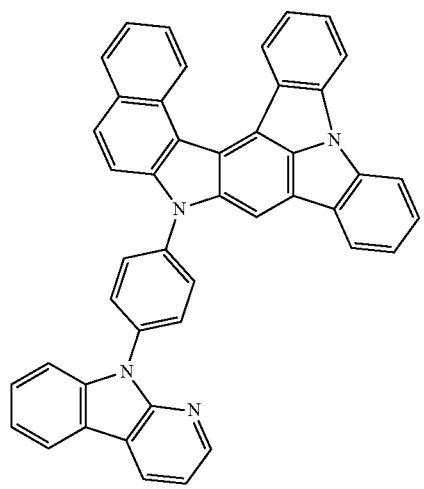
466
-continued
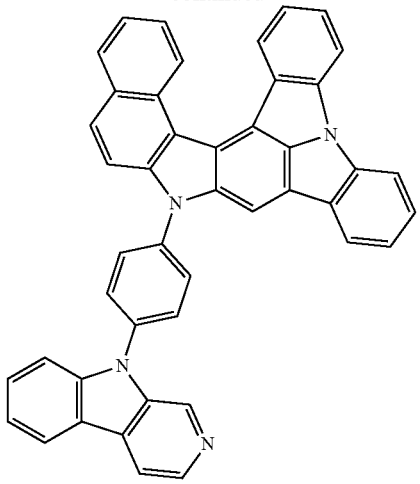
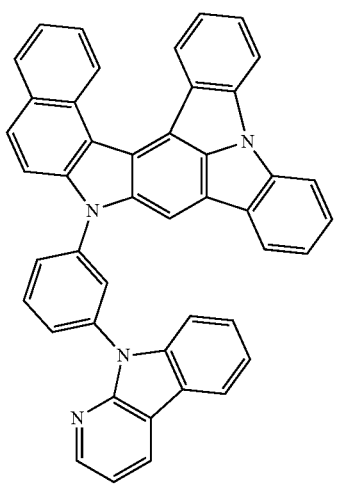
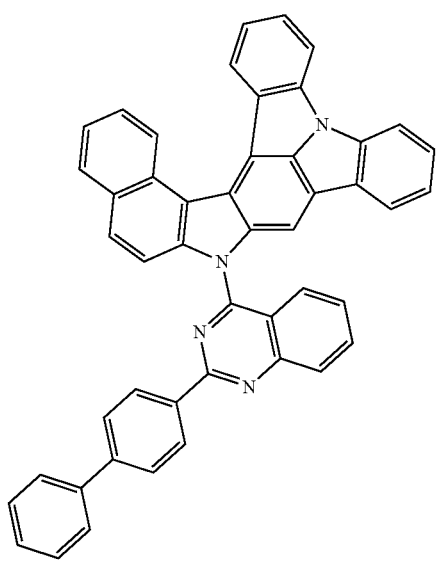

467
-continued
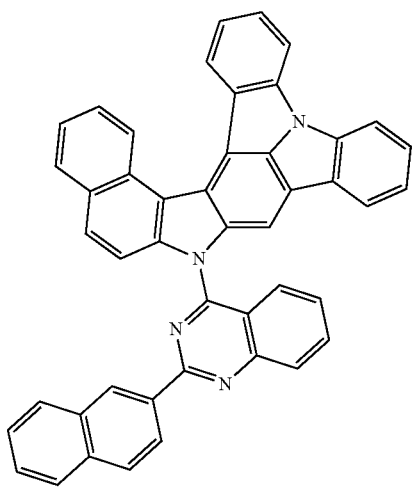
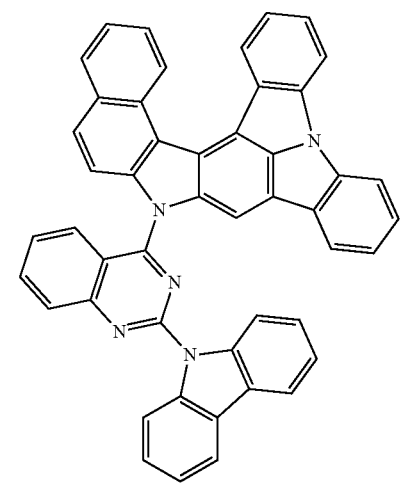
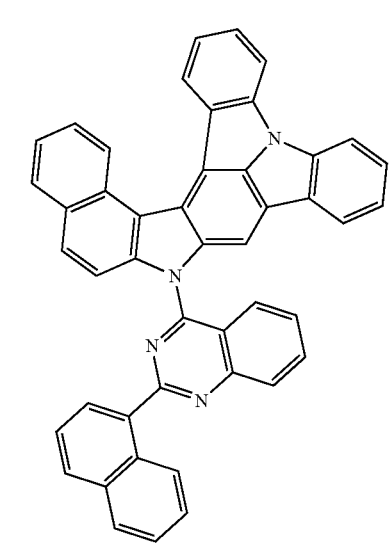
468
-continued
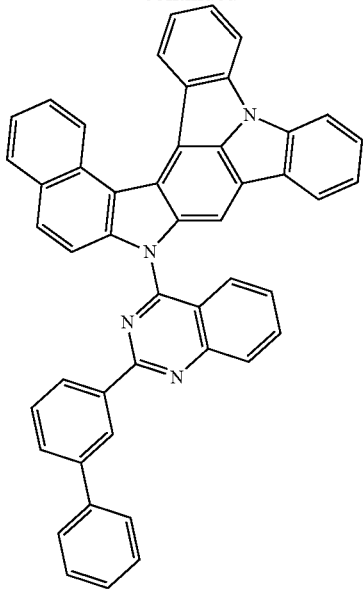
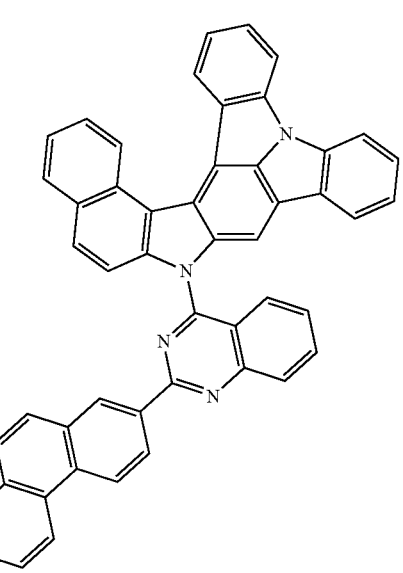

469
-continued
470
-continued
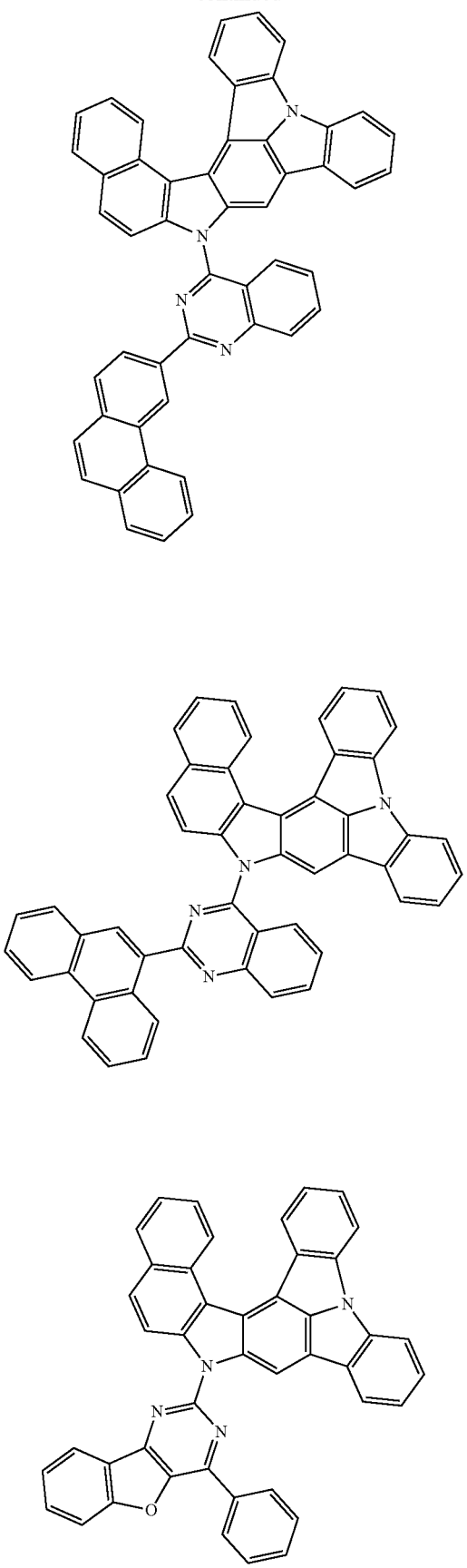
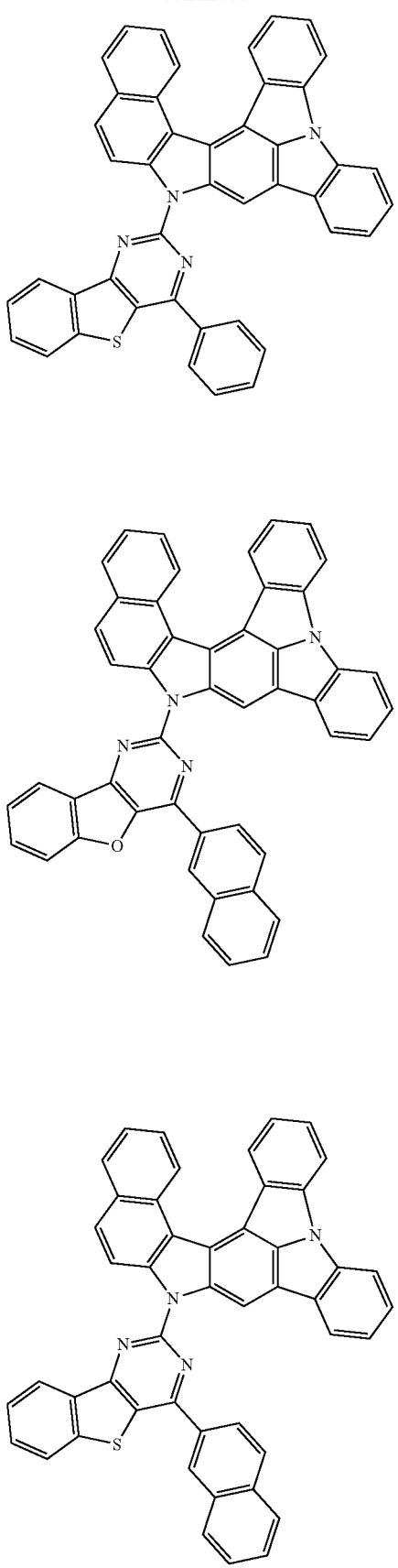

471
-continued
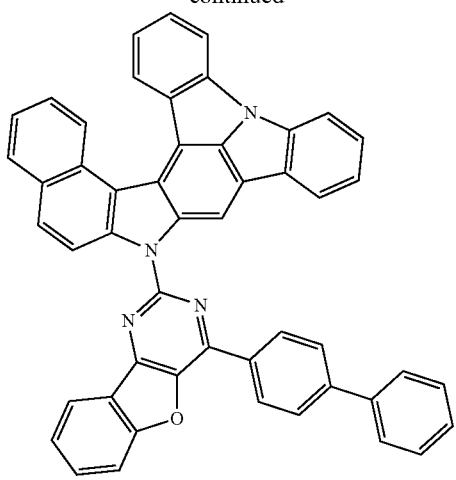
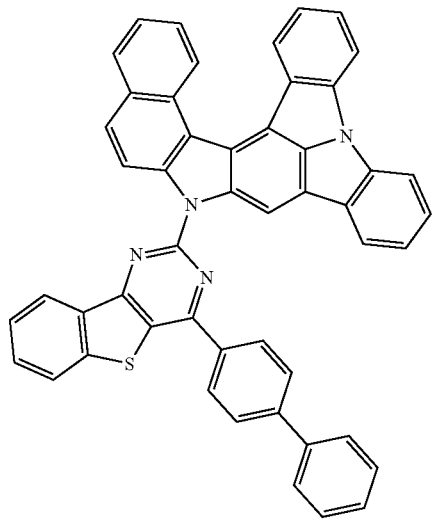
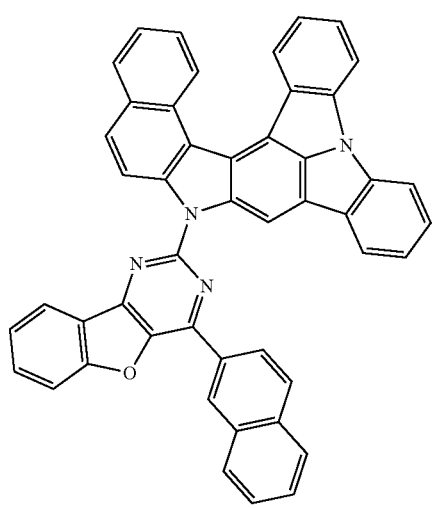
472
-continued
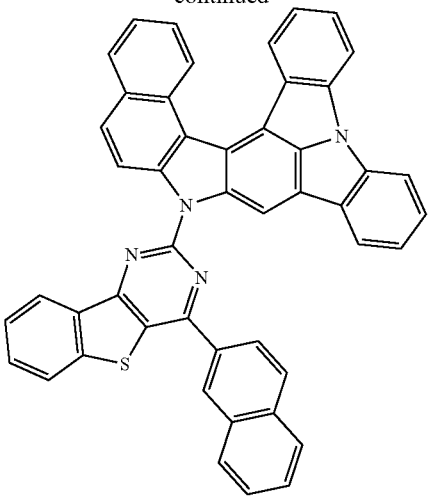
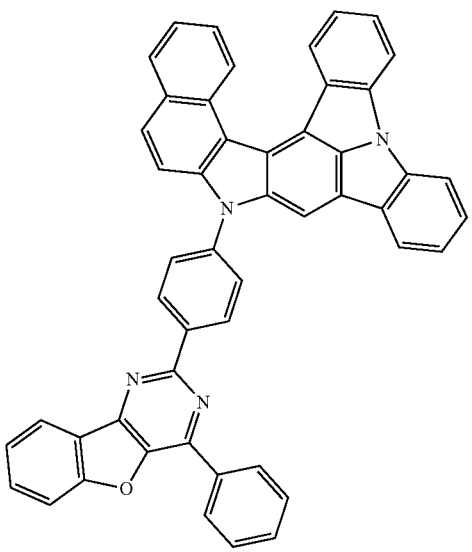
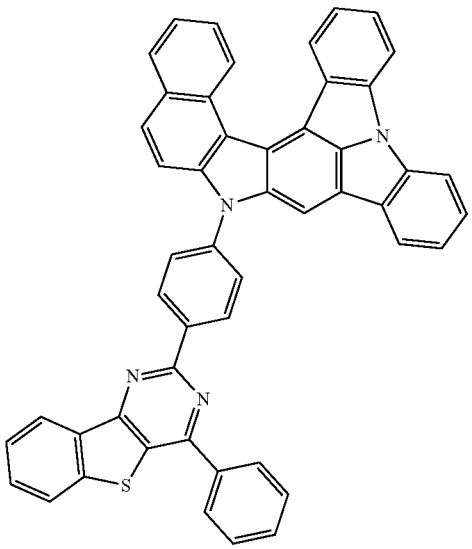

473
-continued
474
-continued
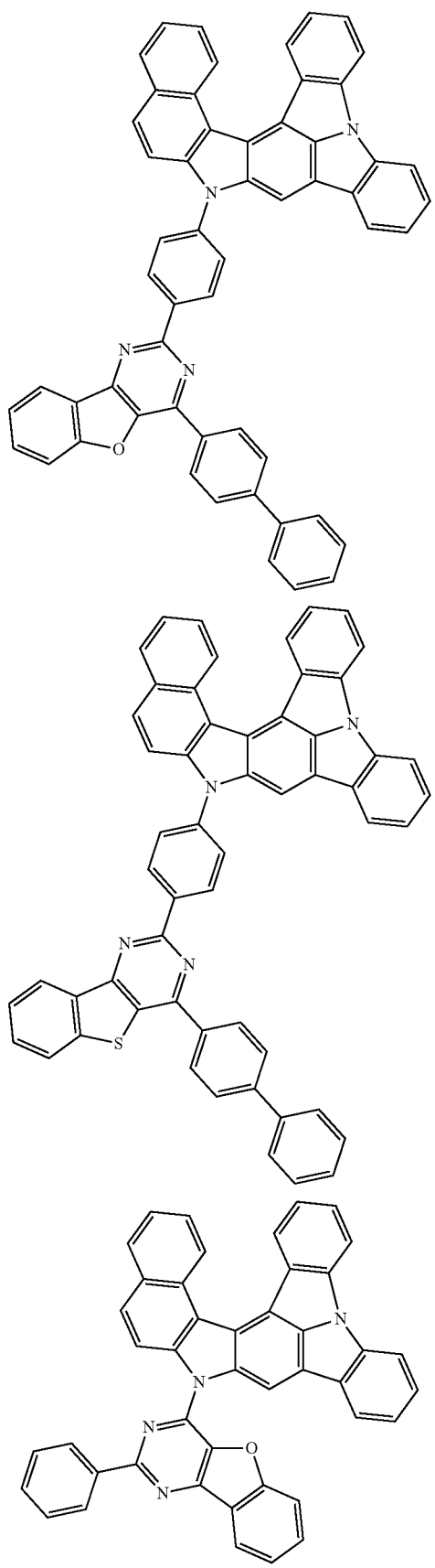
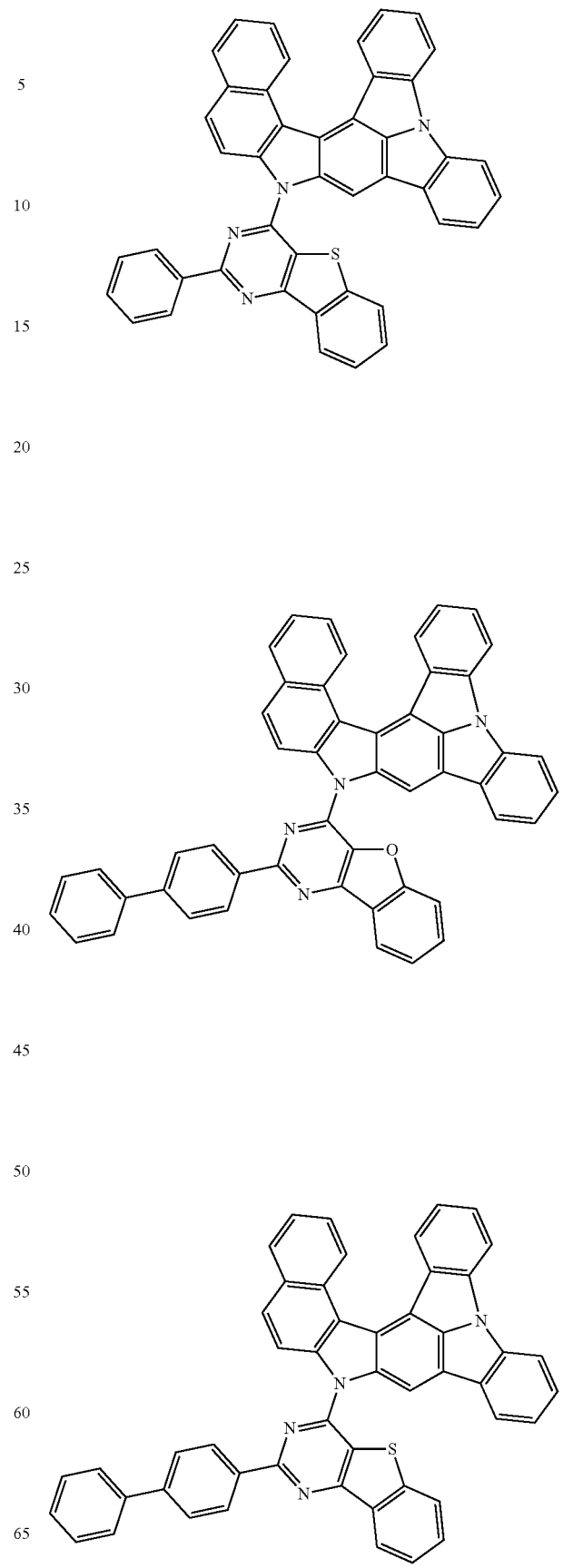

475
-continued
476
-continued
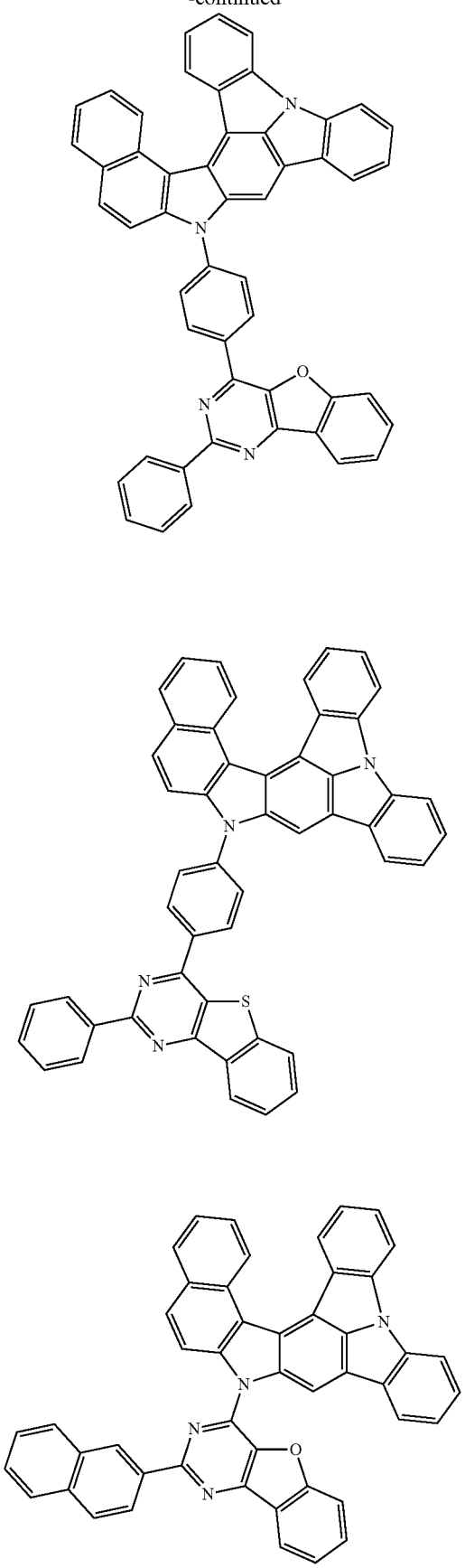
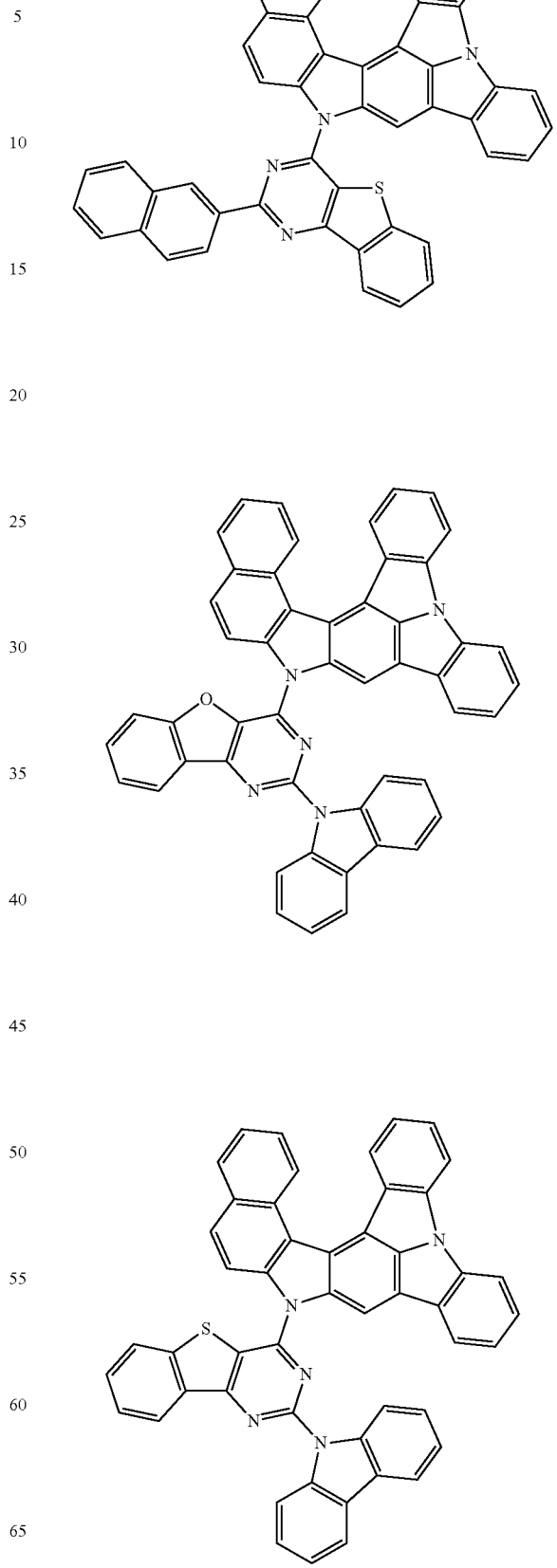

-continued
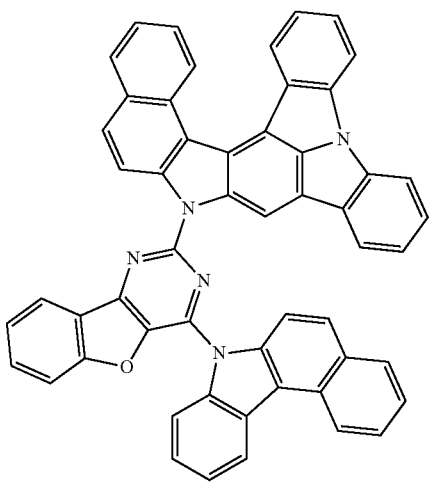
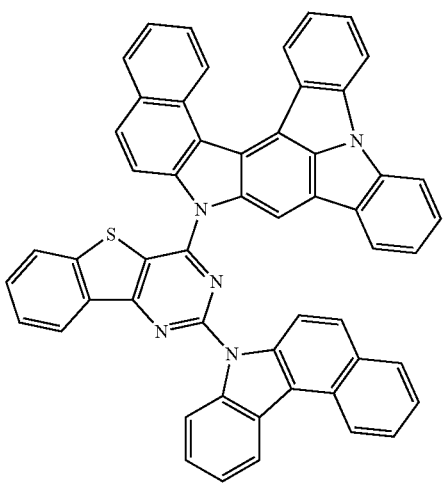
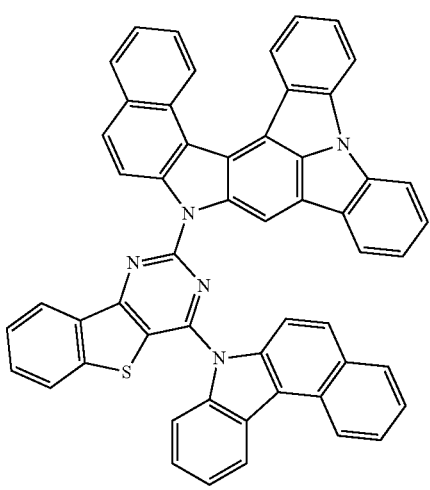
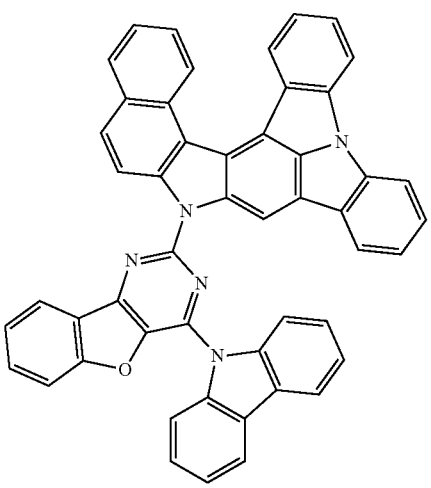
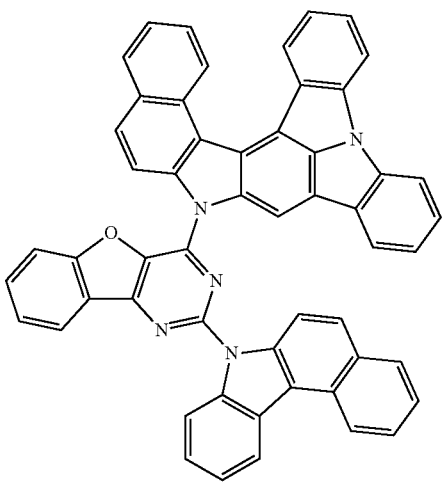

479
-continued
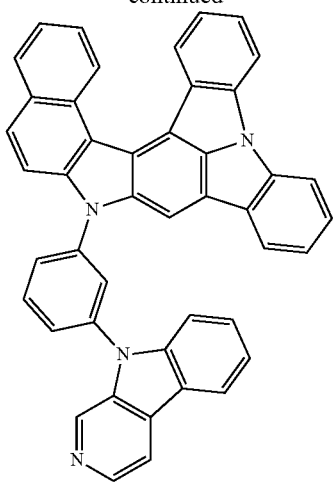
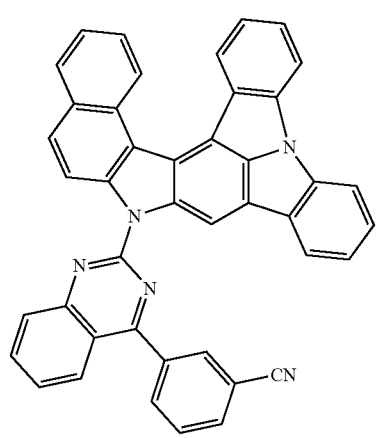
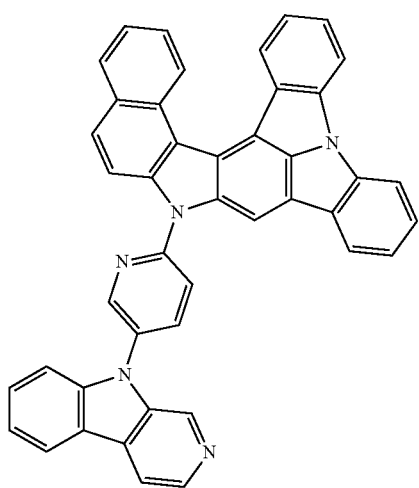
480
-continued
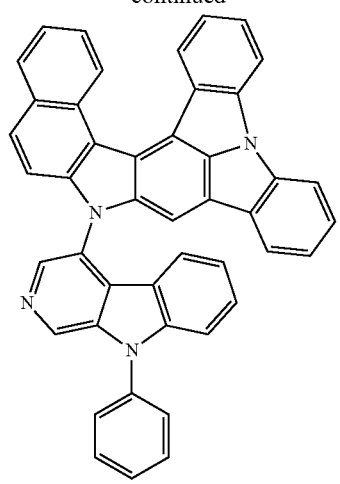
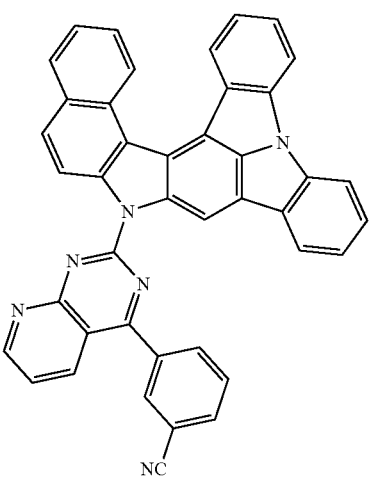
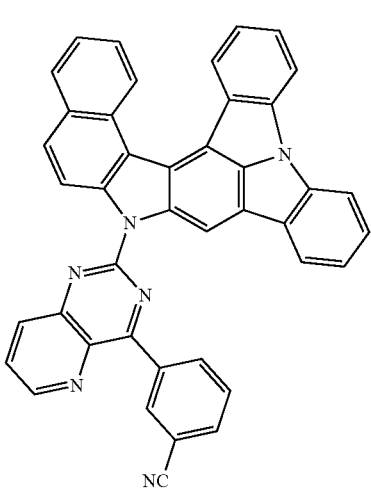

481
-continued
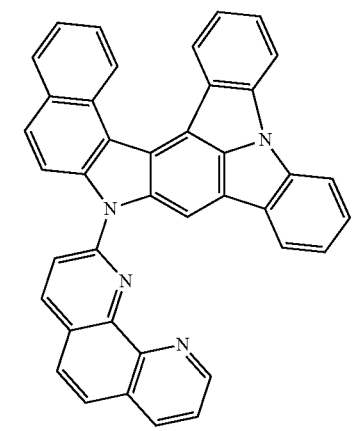
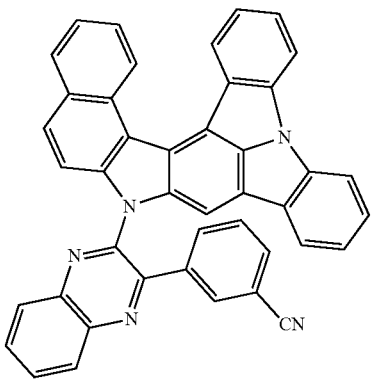
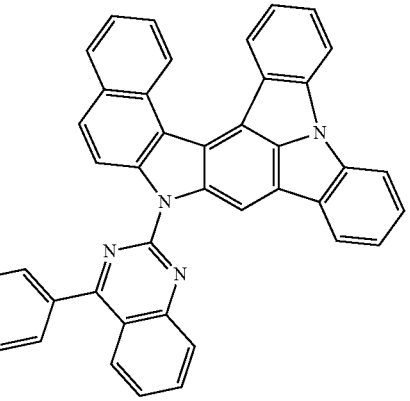
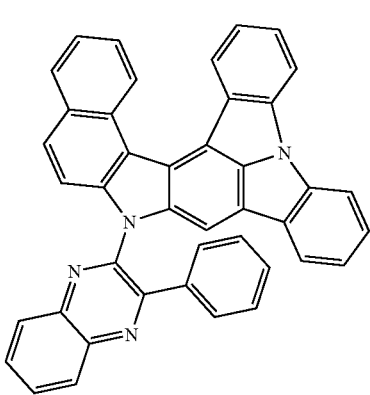
482
-continued
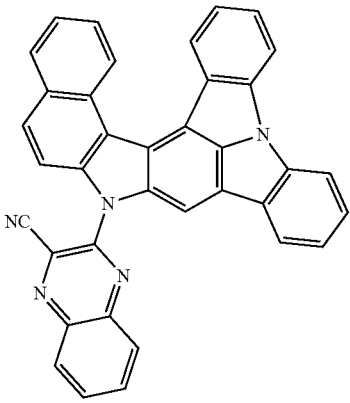
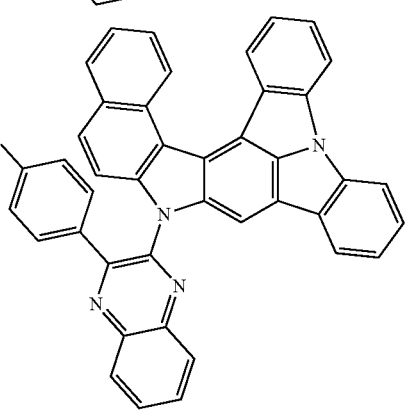

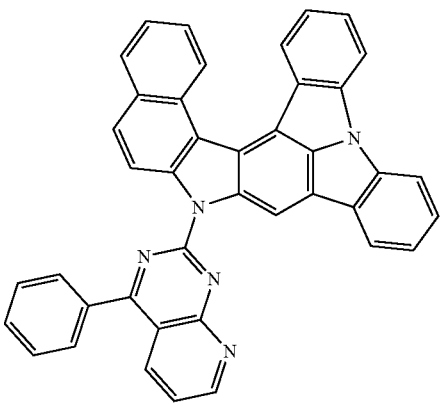

483
-continued
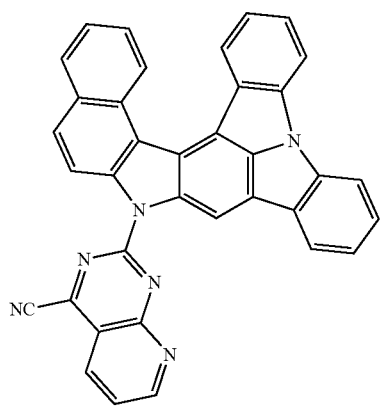
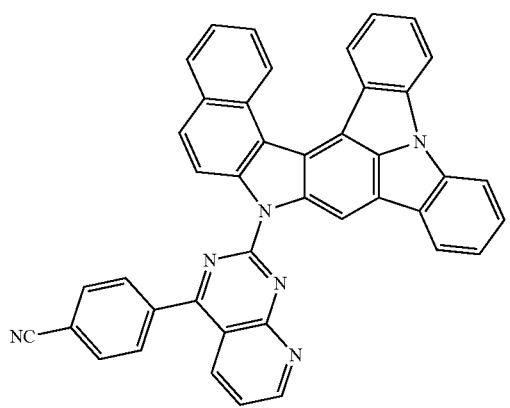
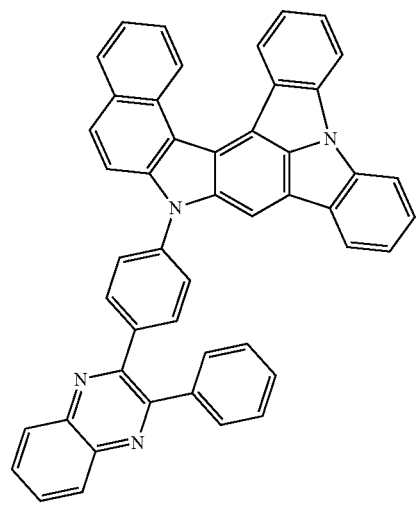
484
-continued
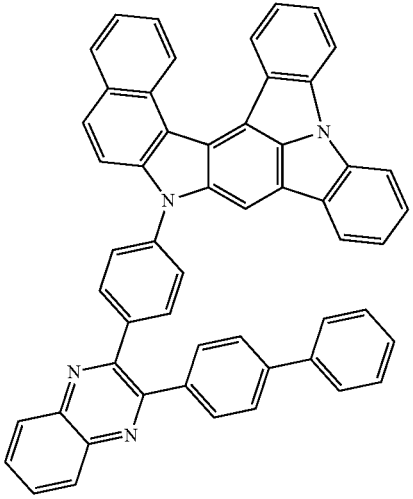
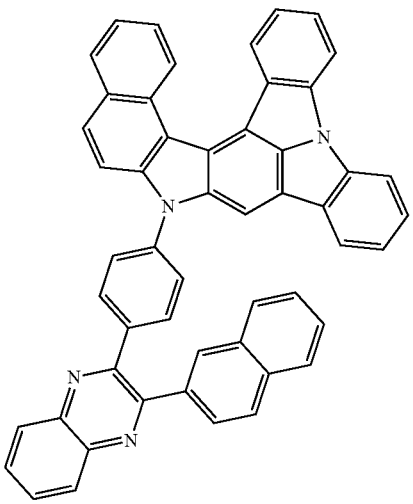
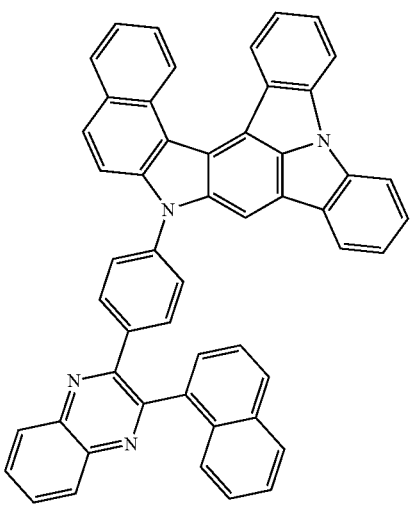

485
-continued
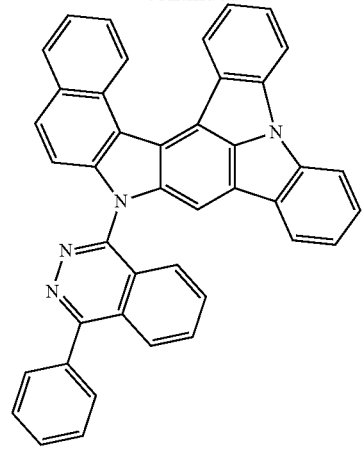
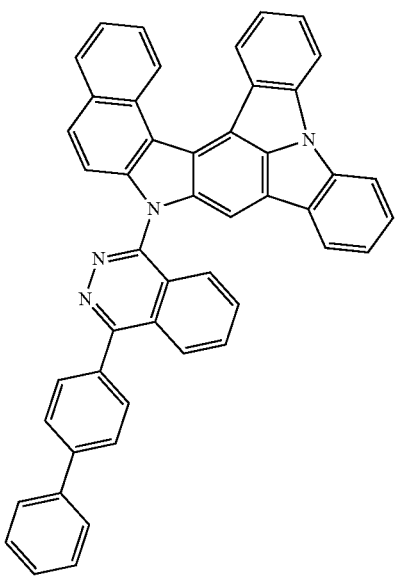
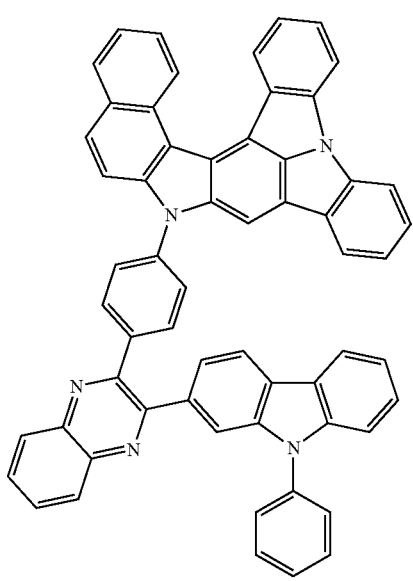
486
-continued
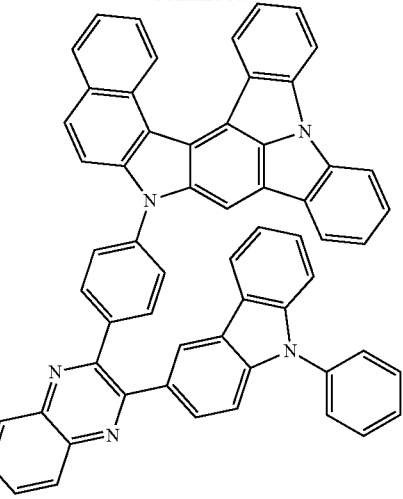
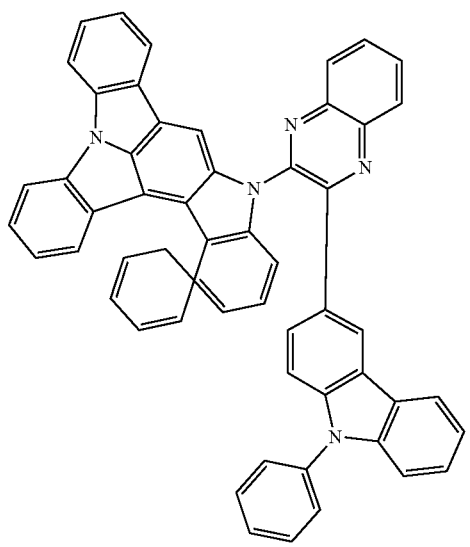
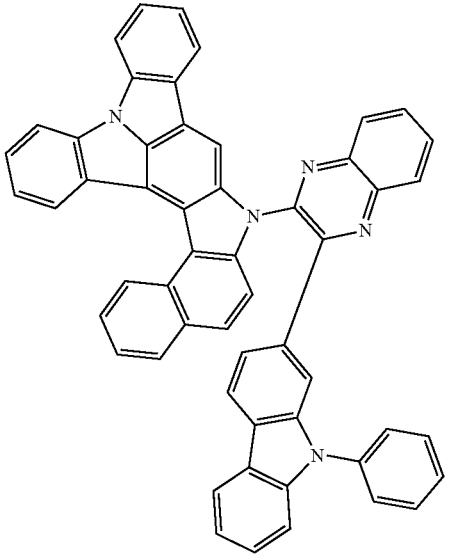

487
-continued
488
-continued
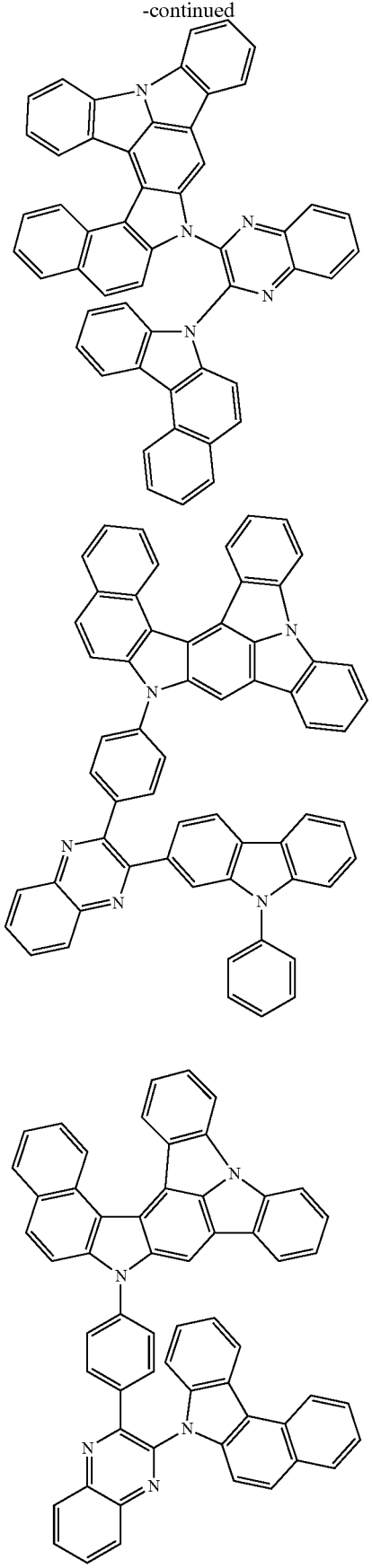
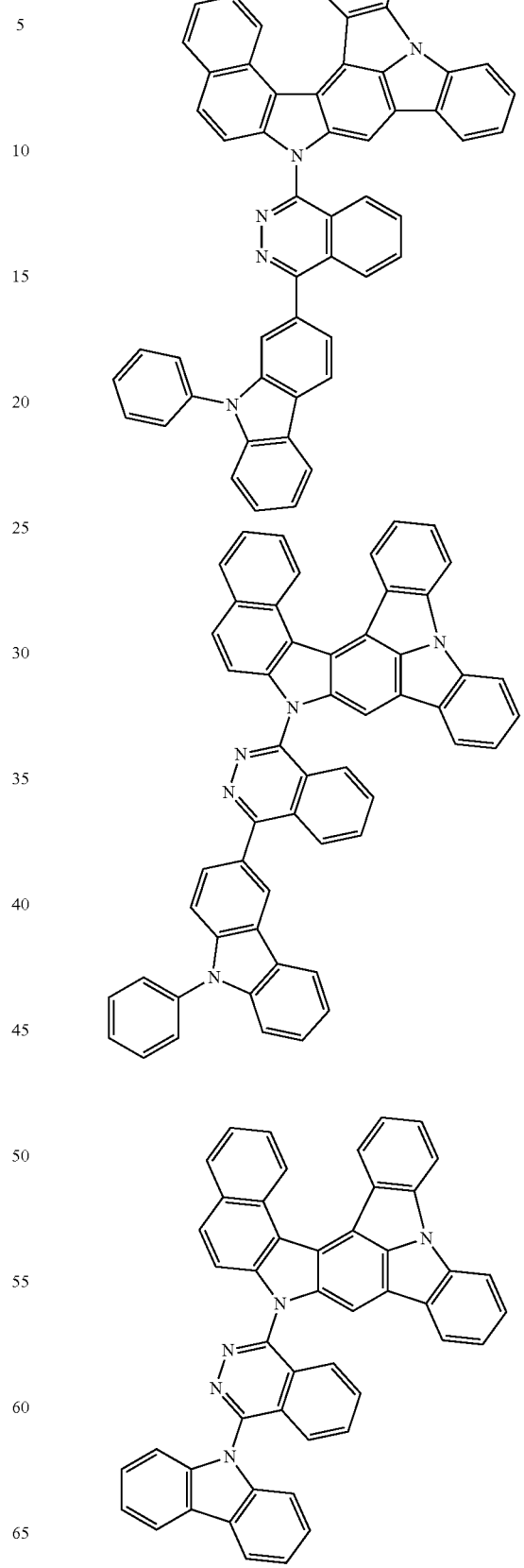

489
-continued
490
-continued
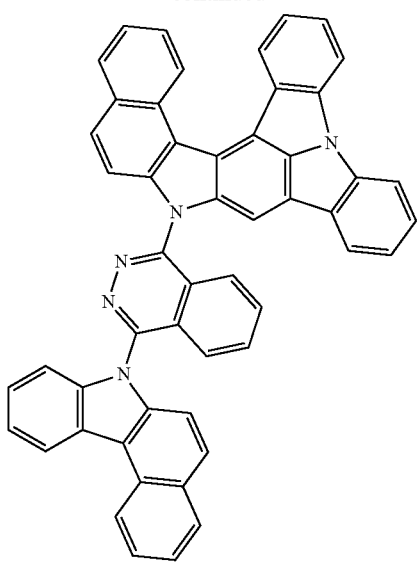
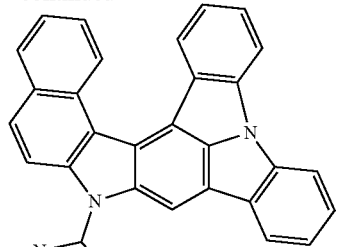
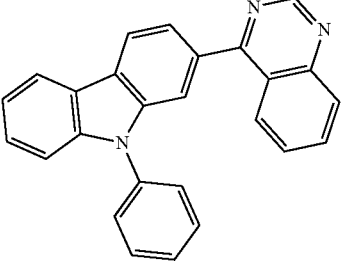
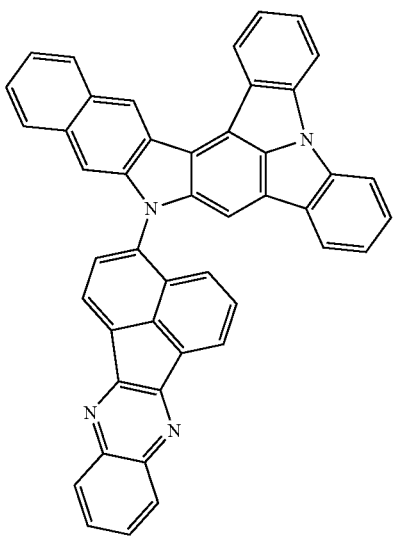
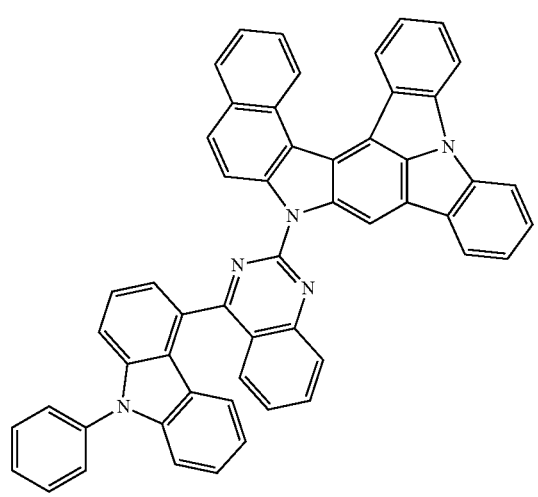
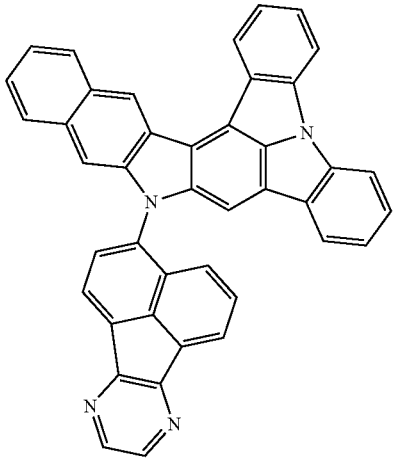

491
-continued
492
-continued
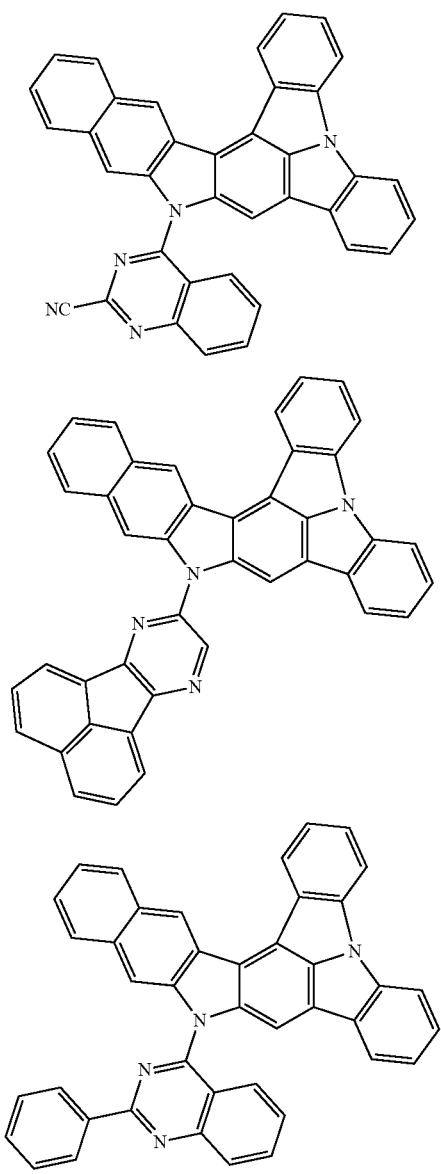
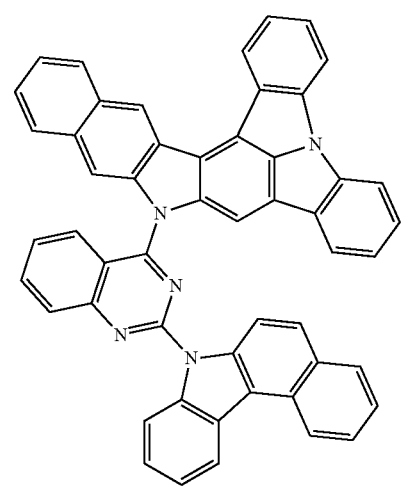
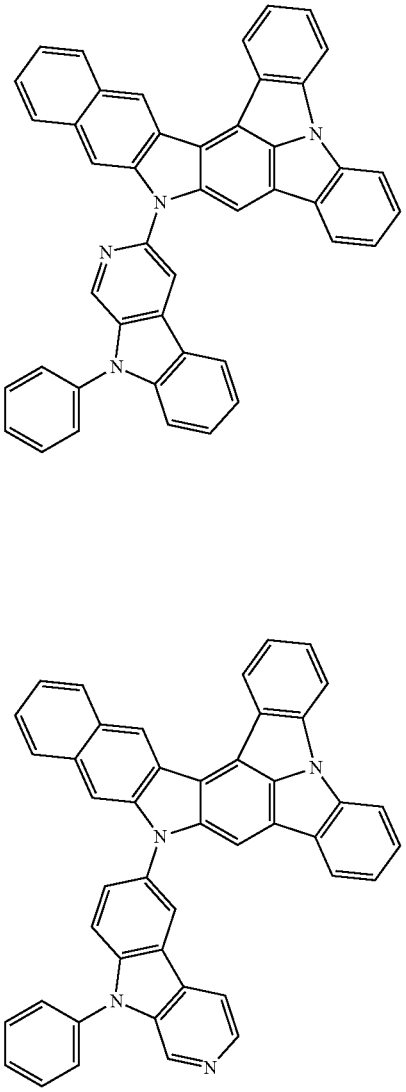
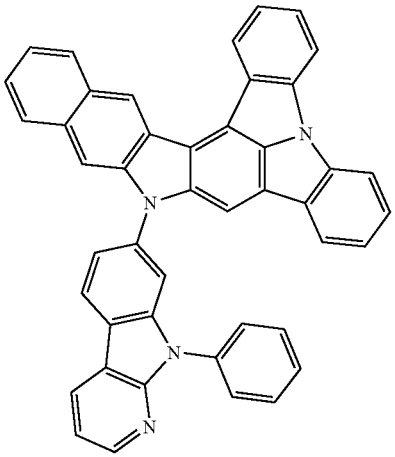

493
-continued
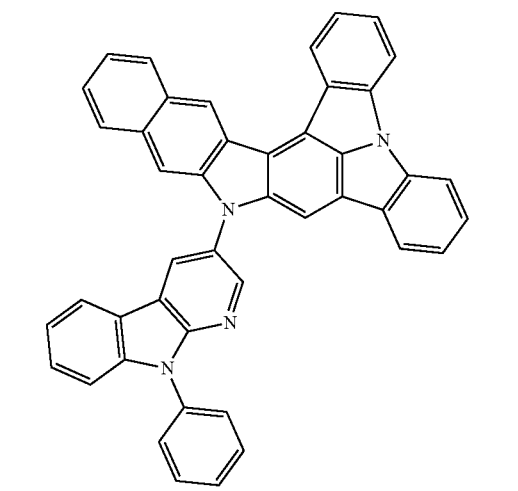 [SMILES: c1ccc(-n2c3ccccc3c3cc(-n4c5cc6ccccc6cc5c5c6c7ccccc7n7c8ccccc8c(cc54)c67)cnc32)cc1]
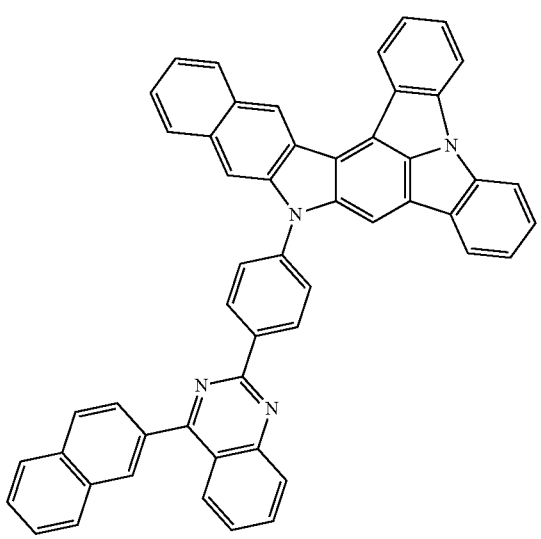
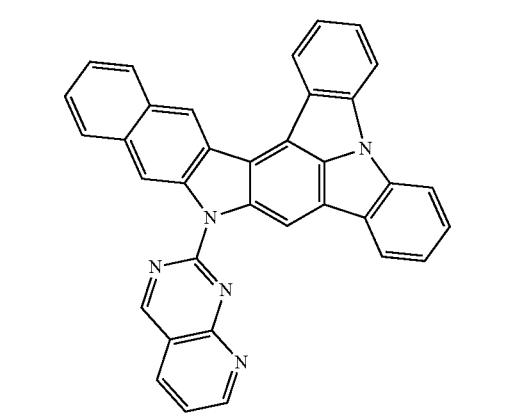
494
-continued
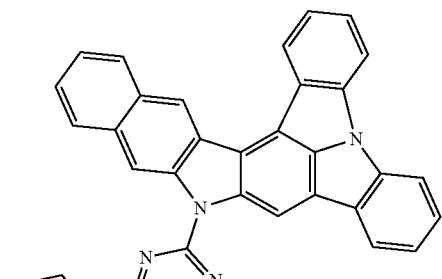
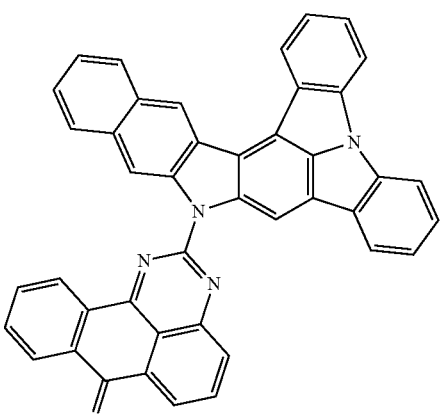
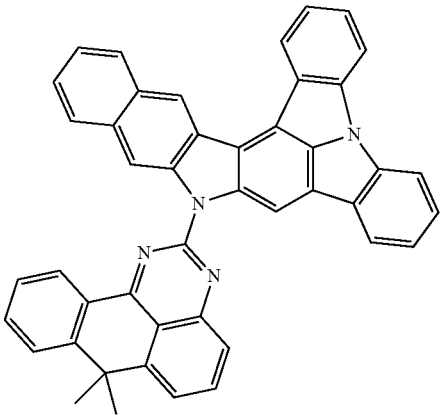
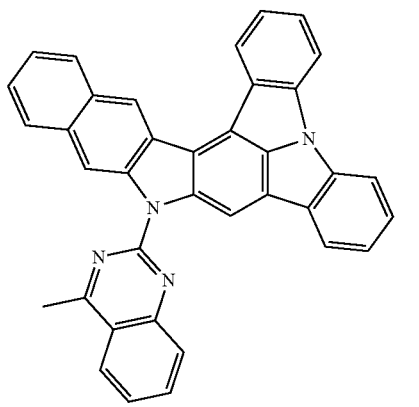

495
-continued
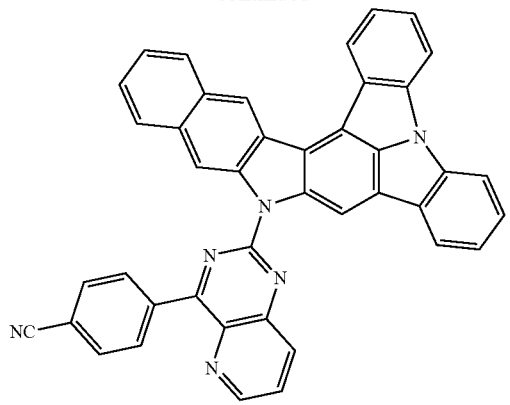
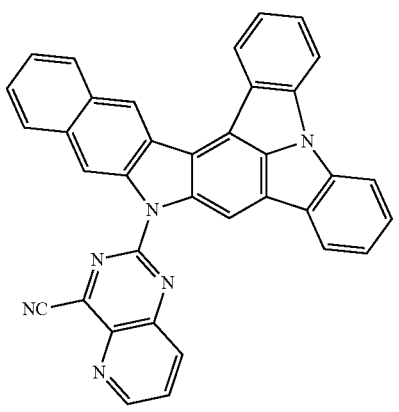
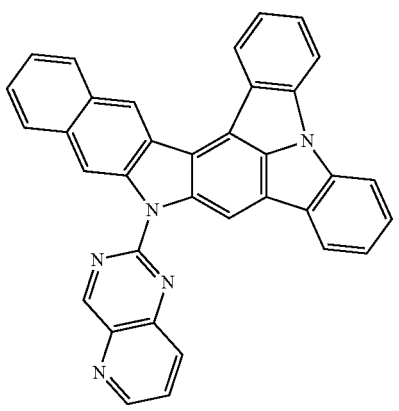
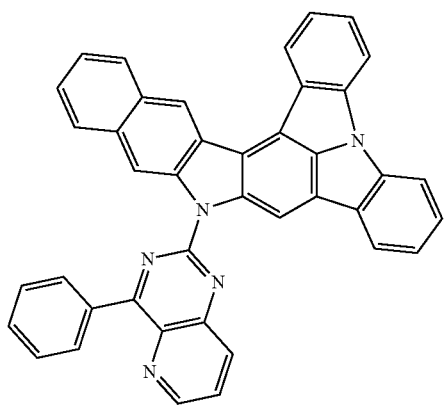
496
-continued
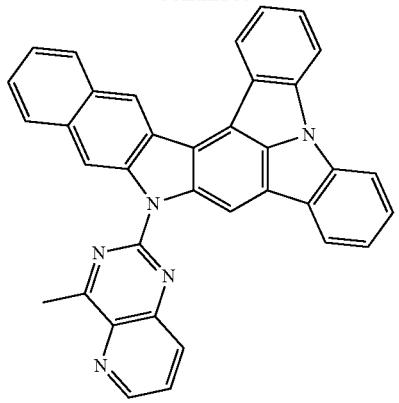
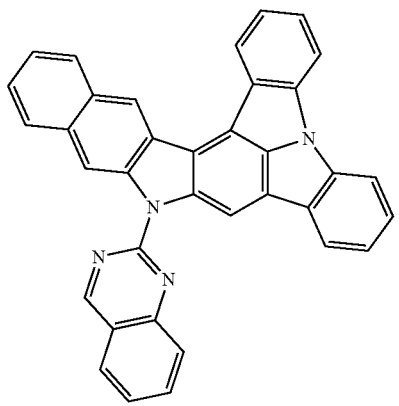
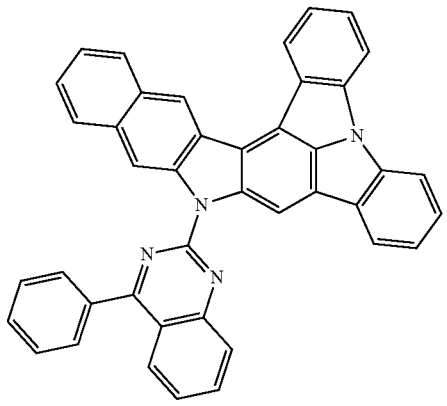
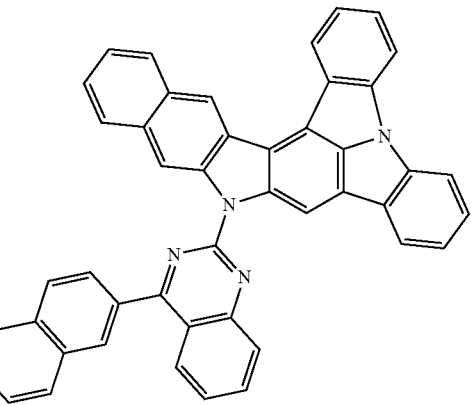

497
-continued
498
-continued
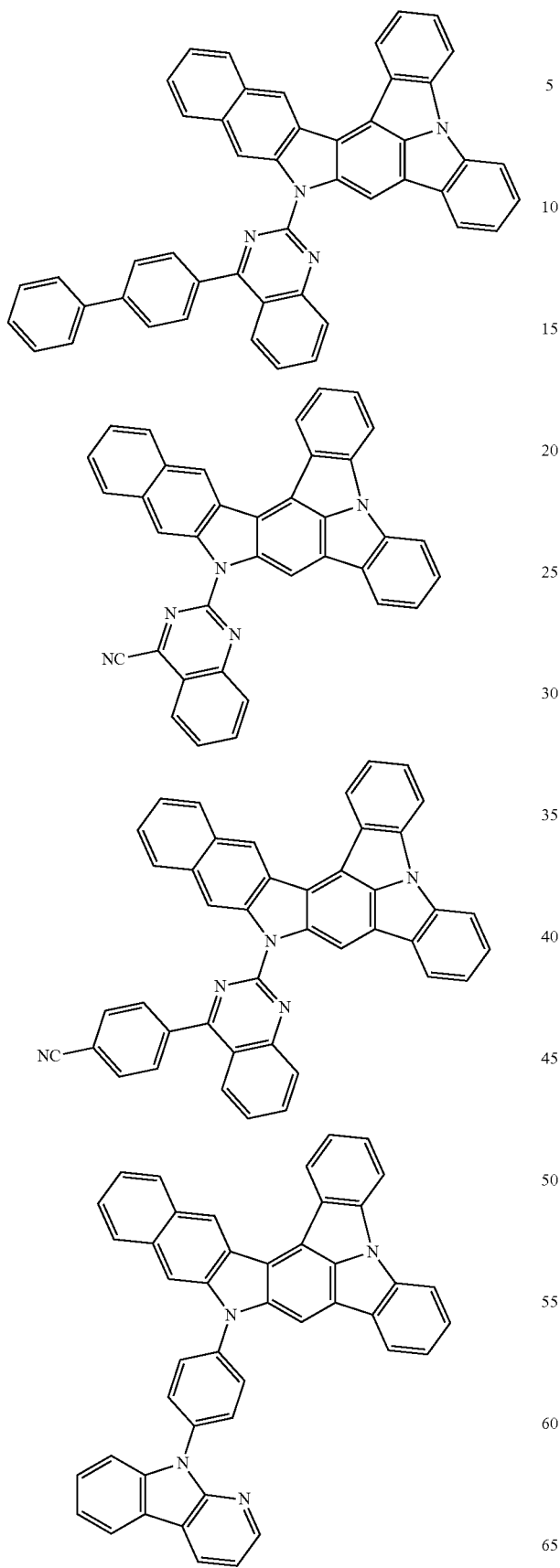
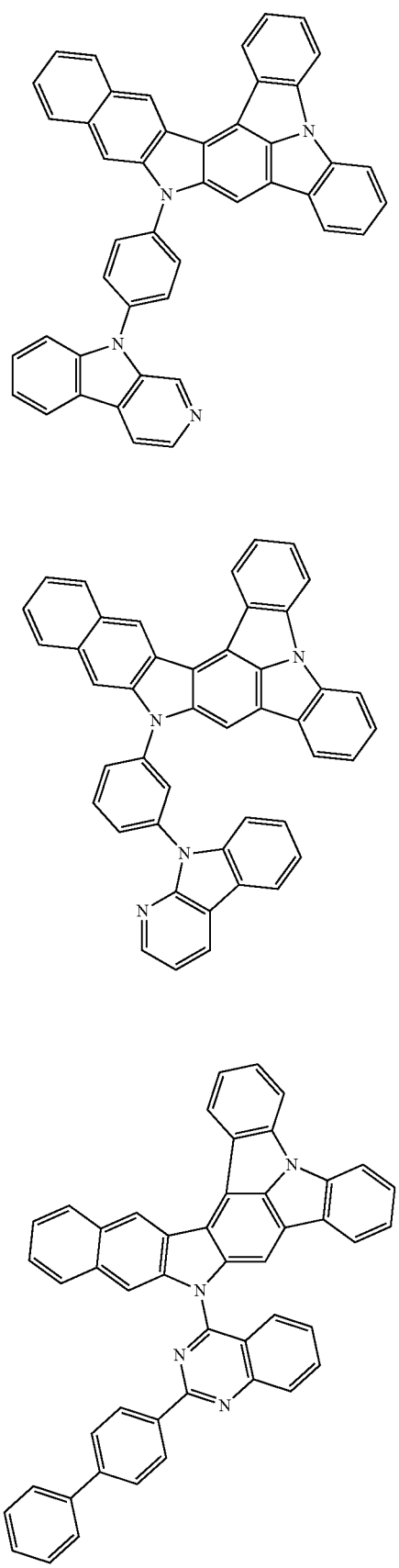

499
-continued
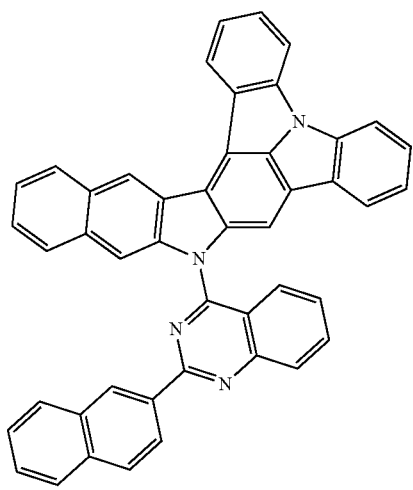
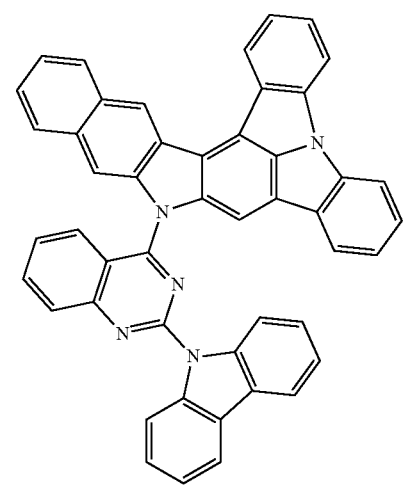
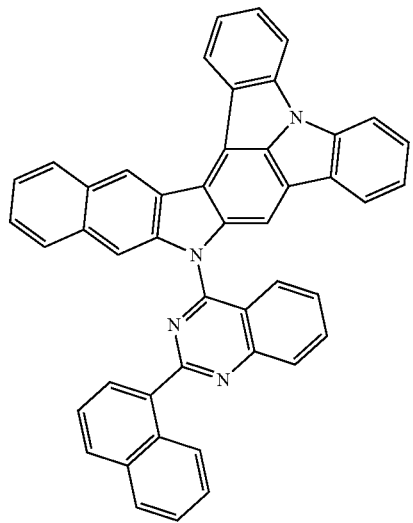
500
-continued
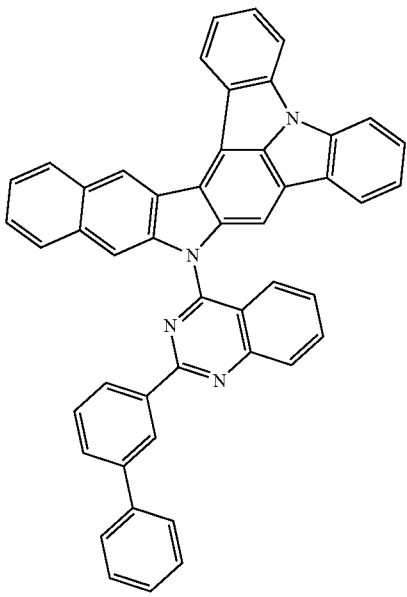
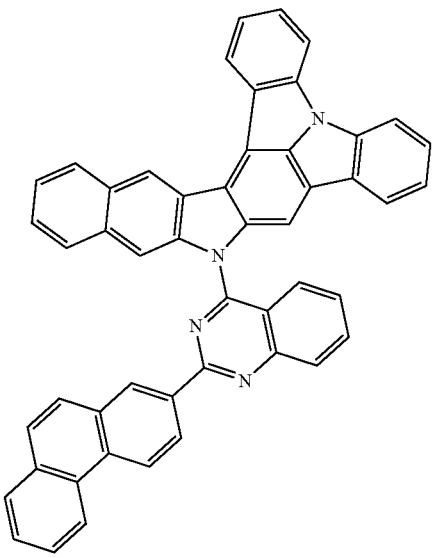

501
-continued
502
-continued
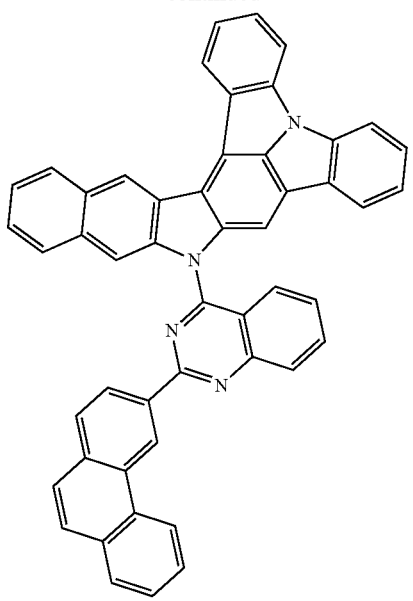
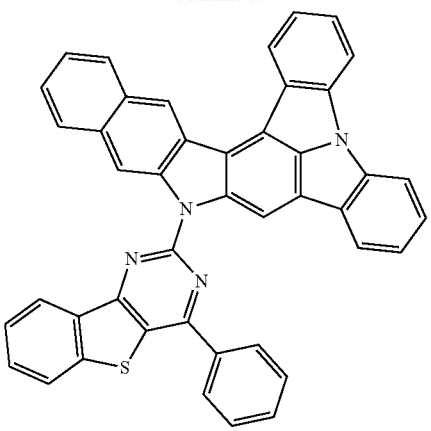
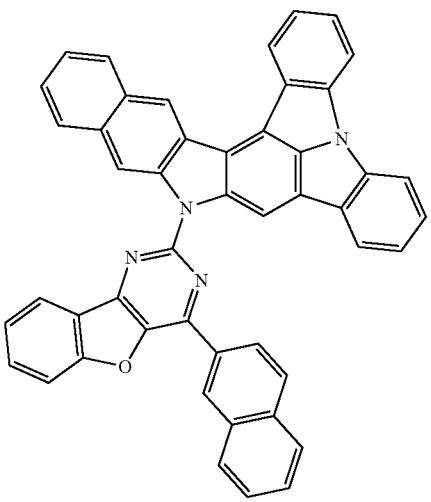
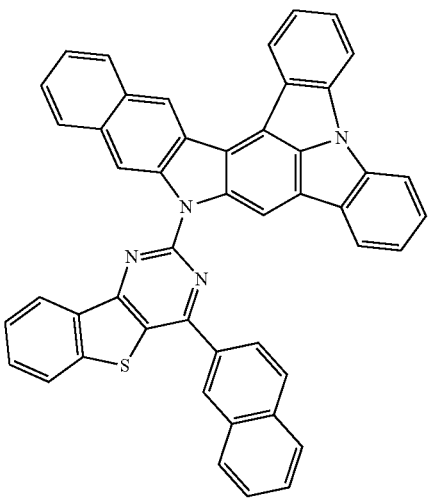

503

504

505
-continued
506
-continued
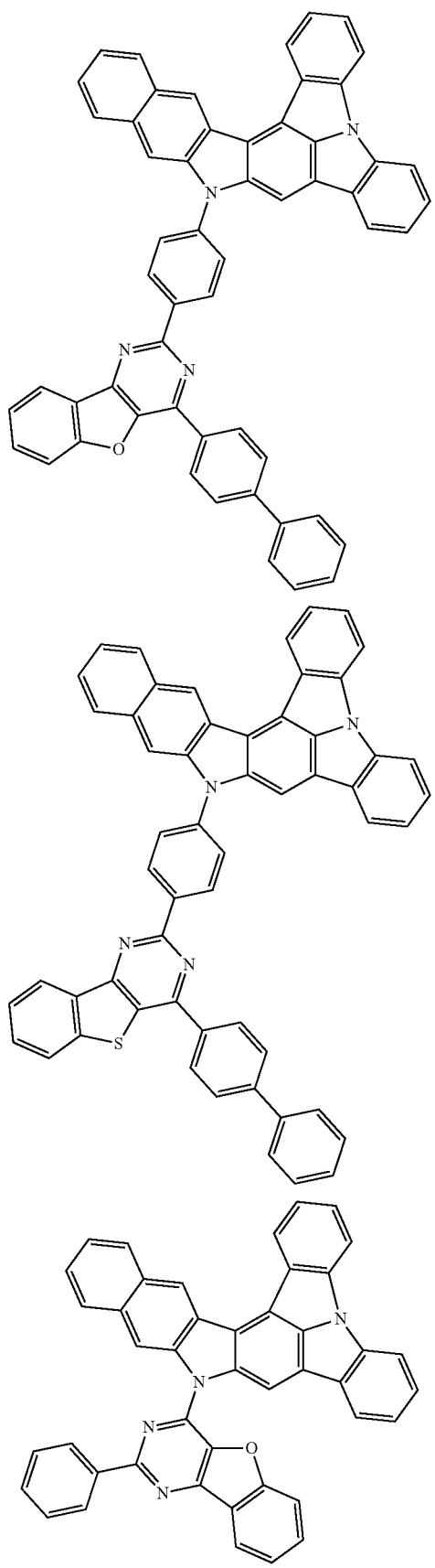
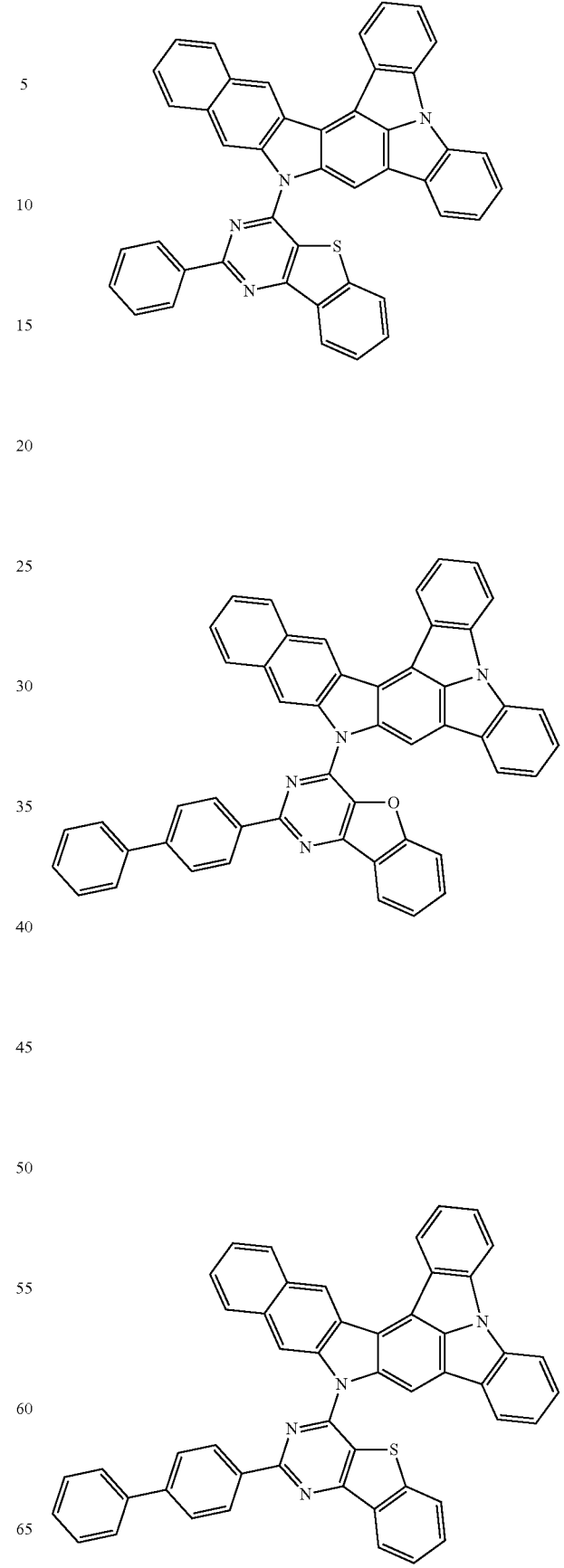

507
-continued
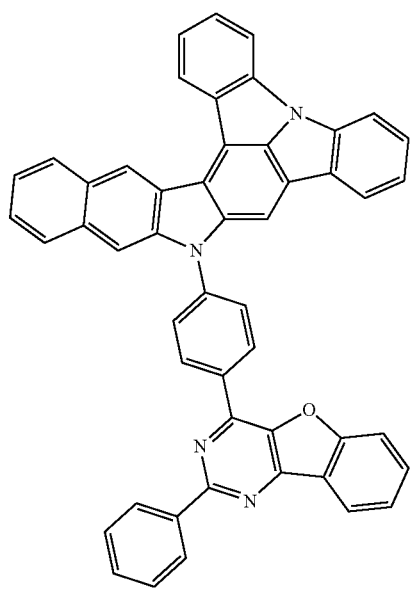
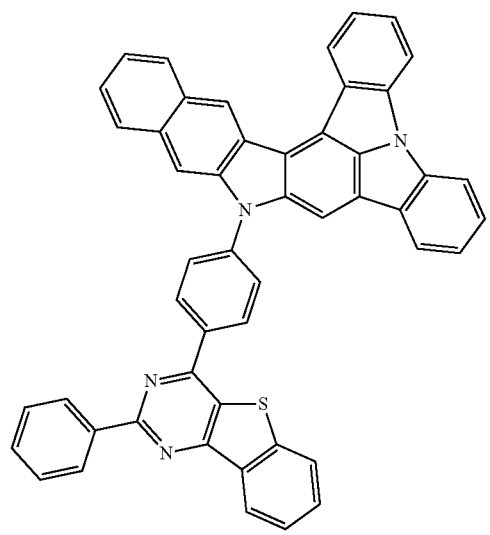
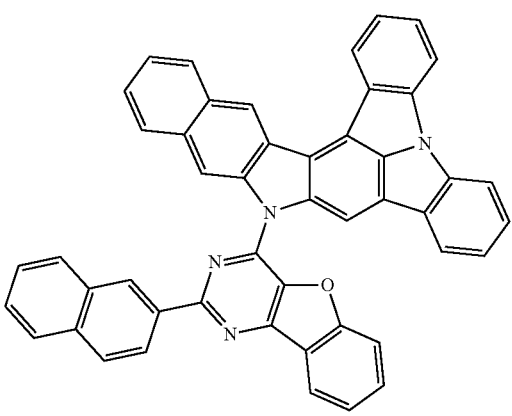
508
-continued
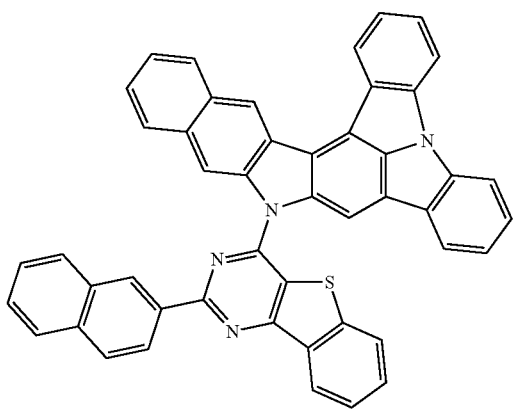
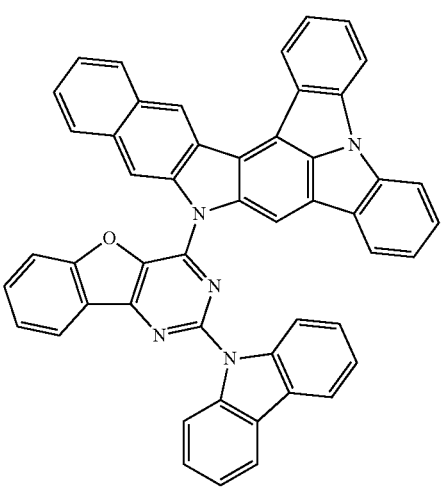
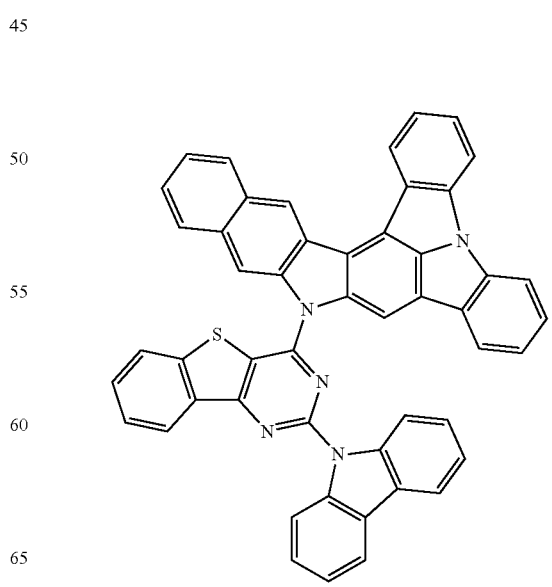

509
-continued
510
-continued
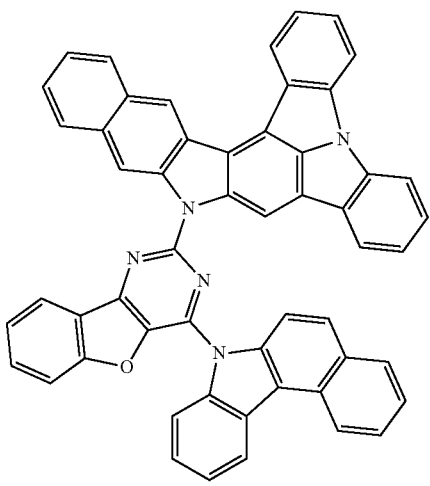
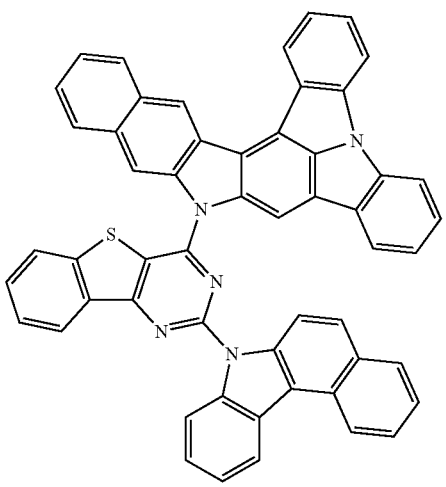
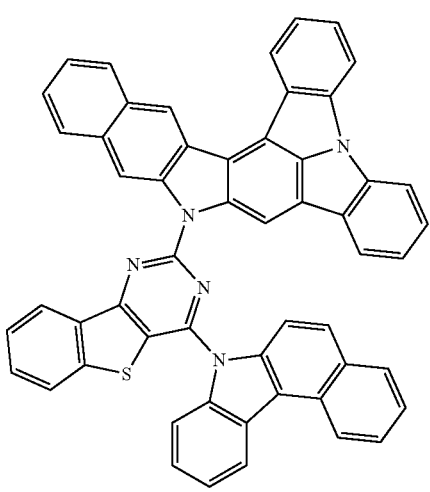
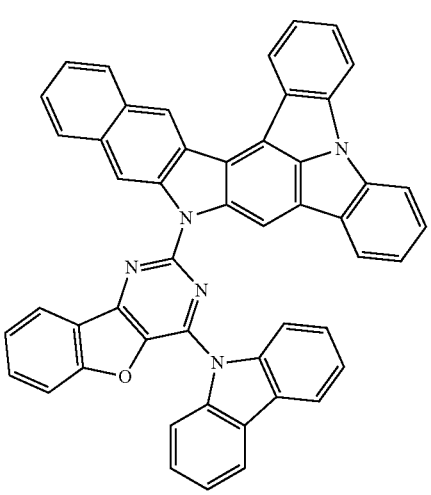
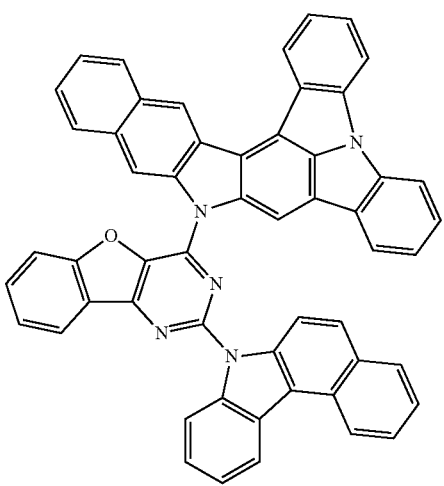
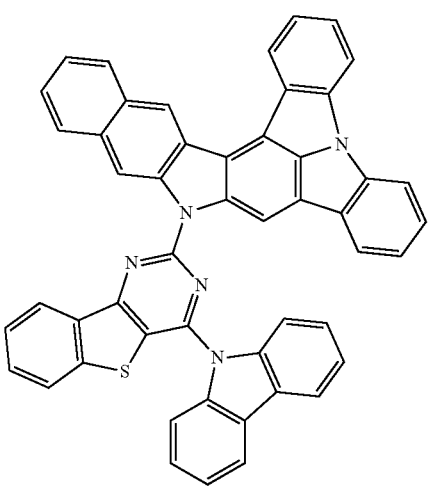

511
-continued
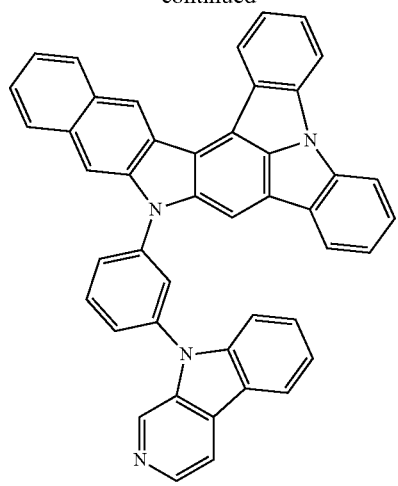
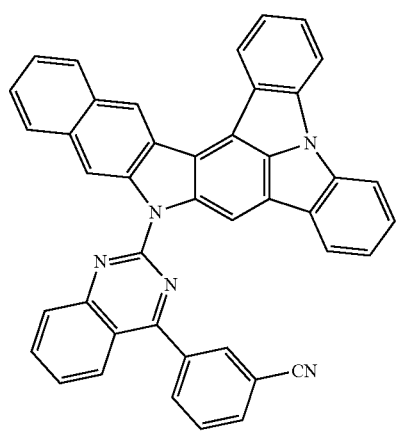
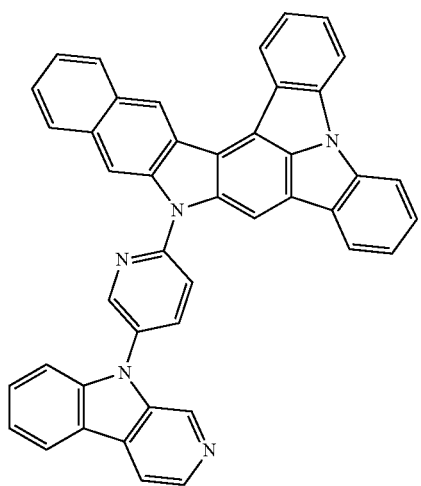
512
-continued
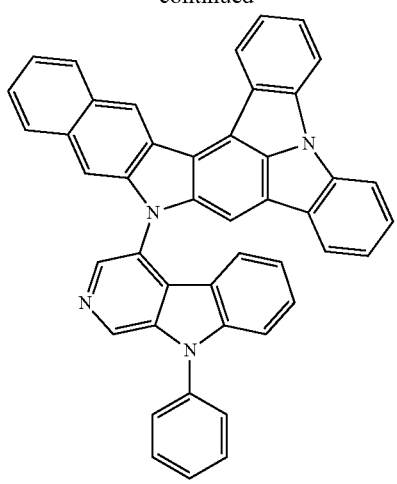
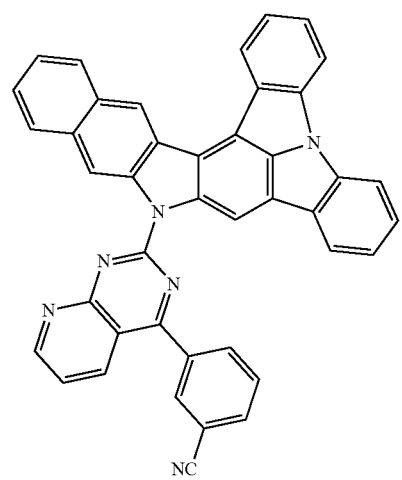
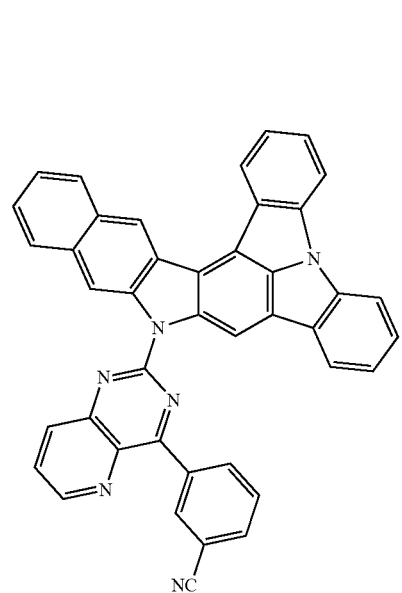

513
-continued
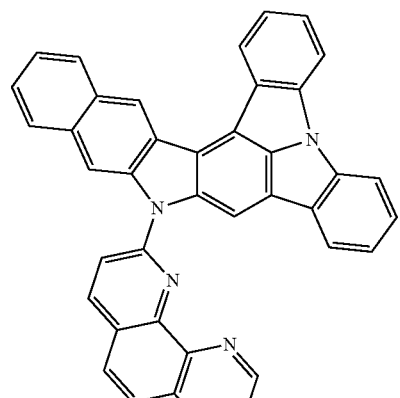
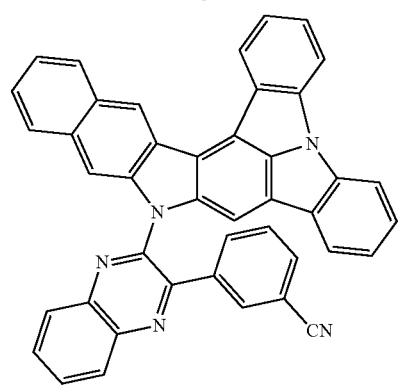
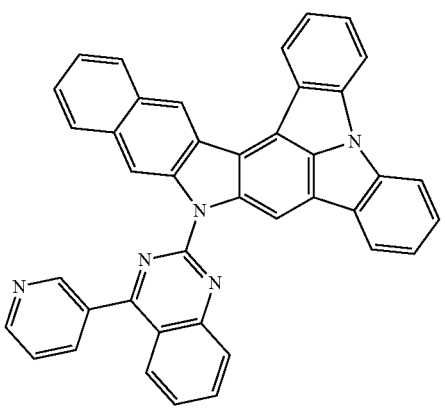
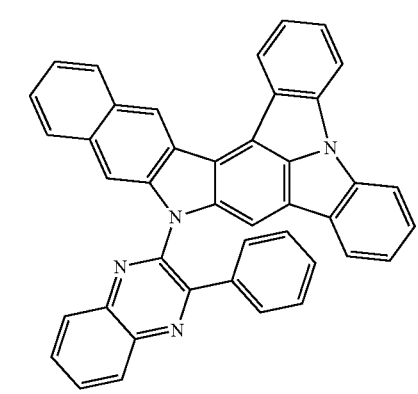
514
-continued
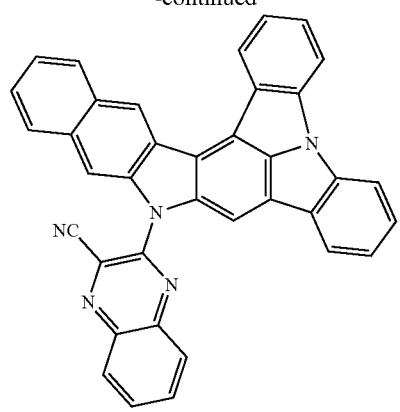
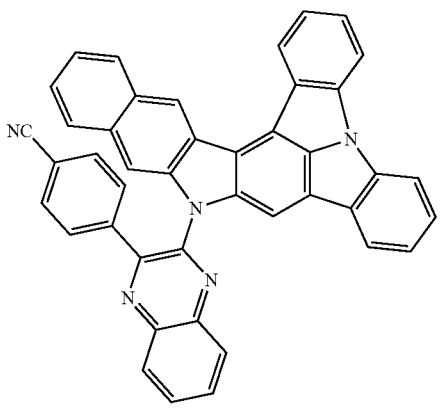
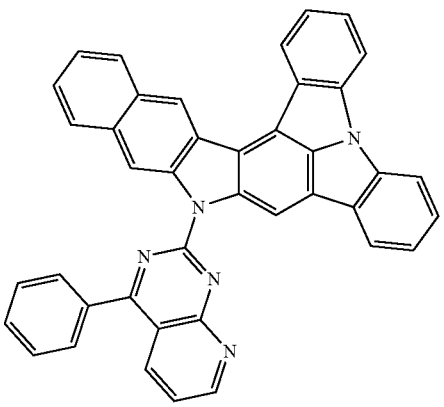
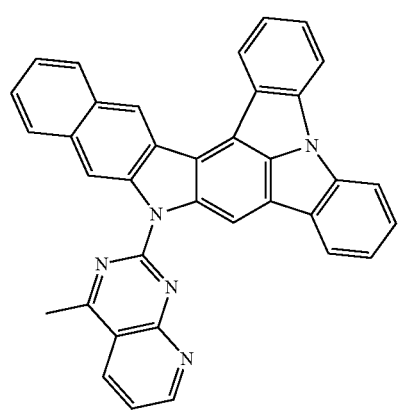

515
-continued

516
-continued

517
-continued
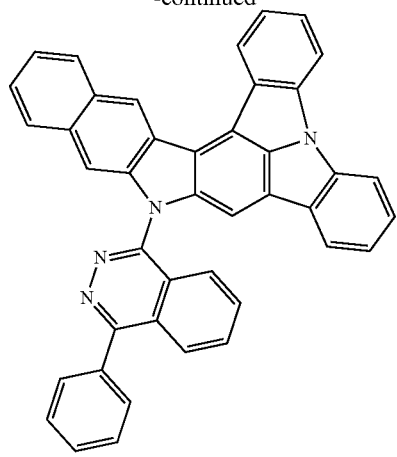
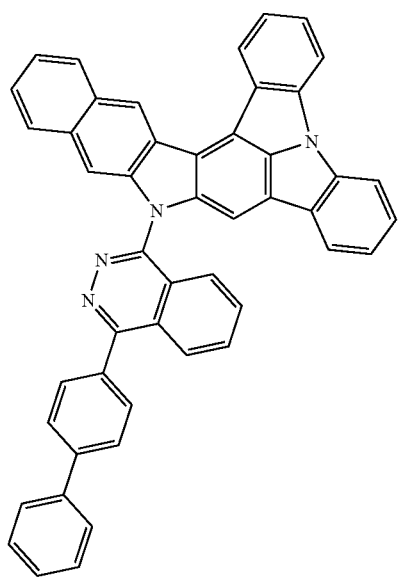
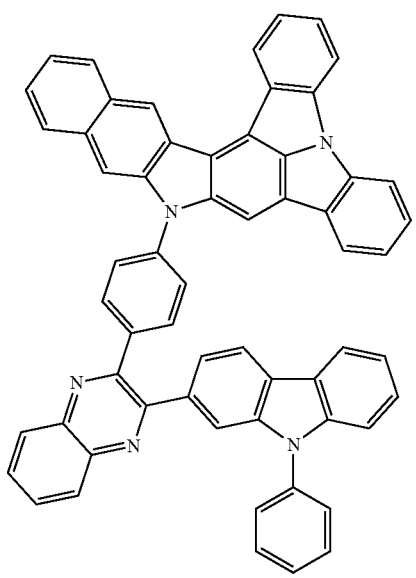
518
-continued
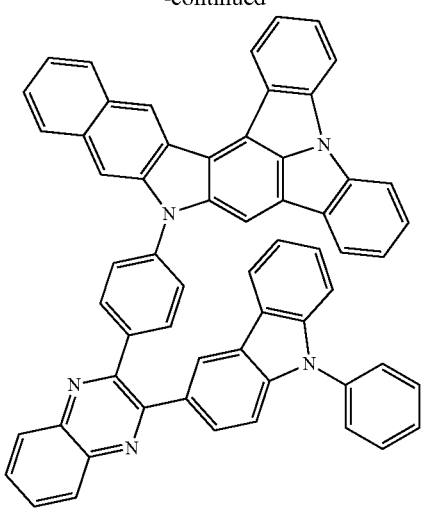
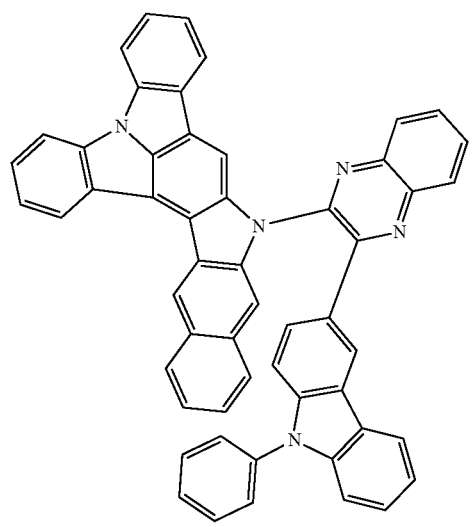
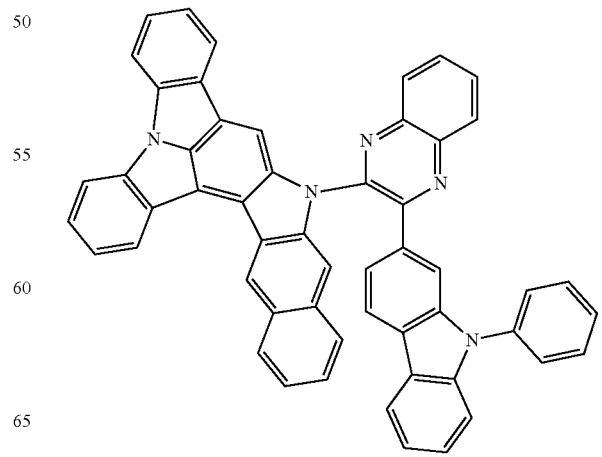

519
-continued
520
-continued
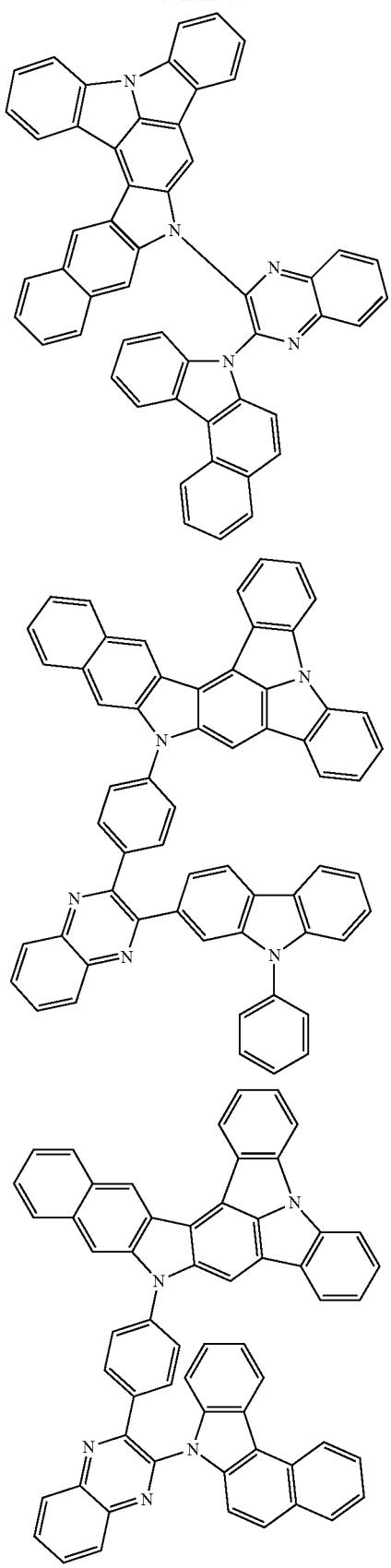
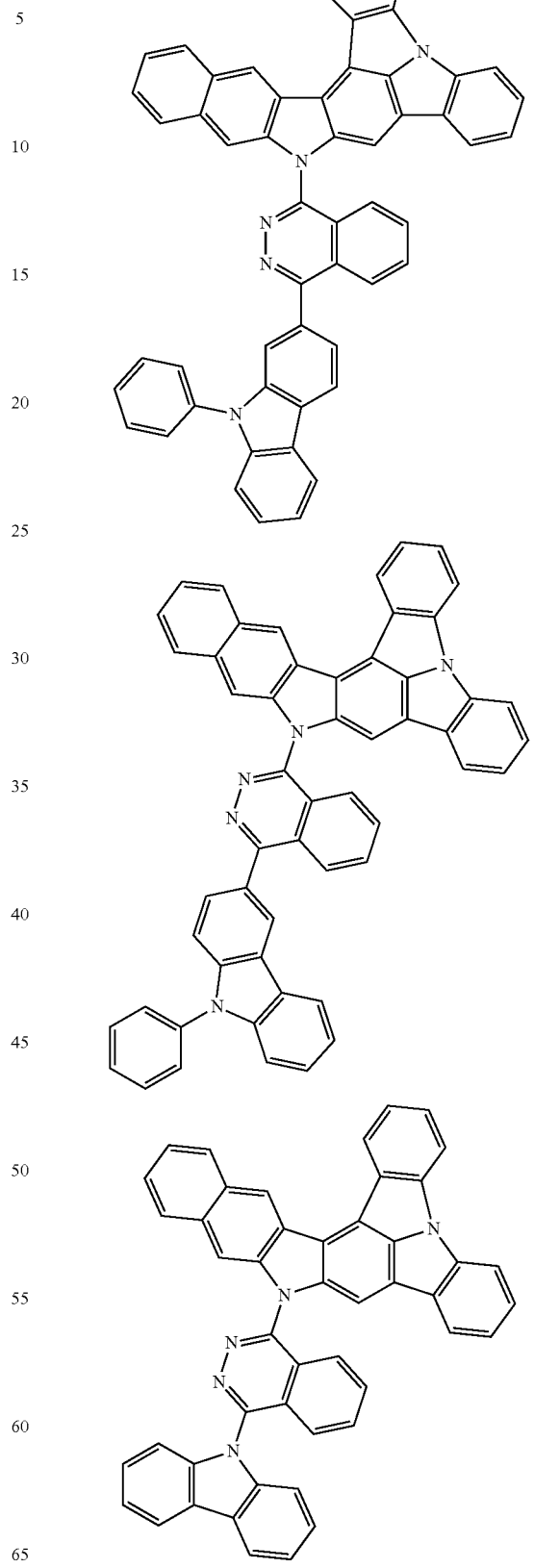

| 521 | 522 |
|---|---|
| -continued | -continued |
| 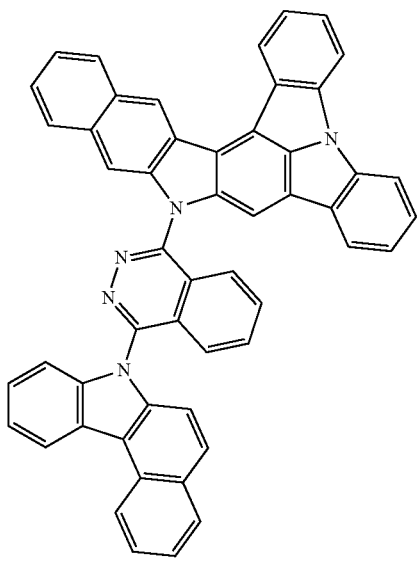 | 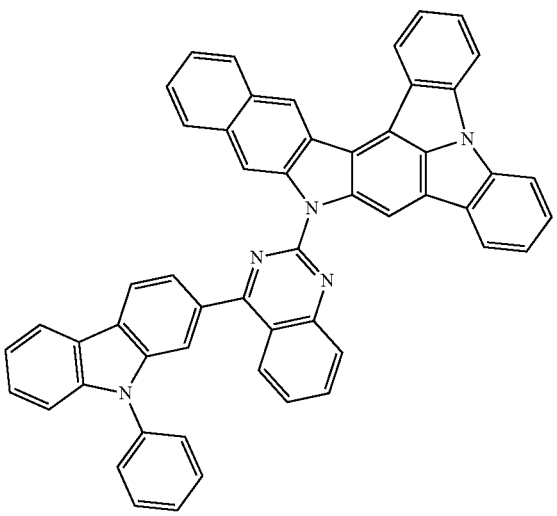 |
| 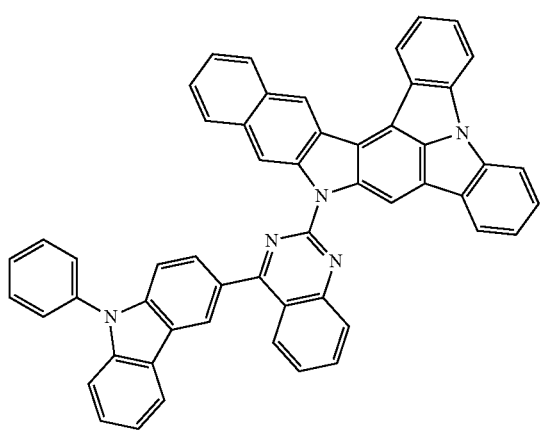 | 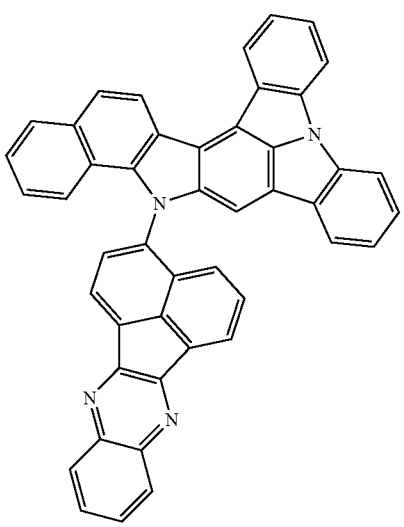 |
| 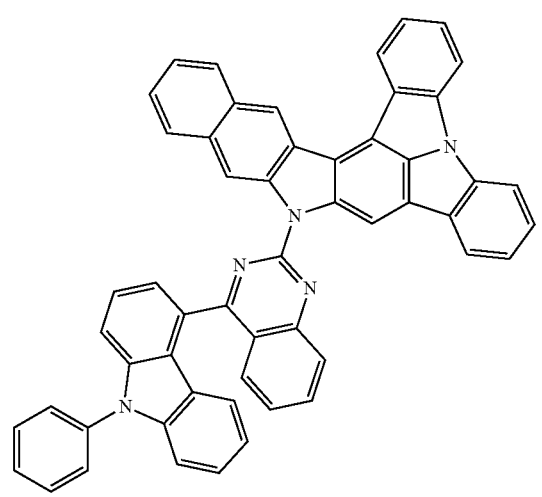 | 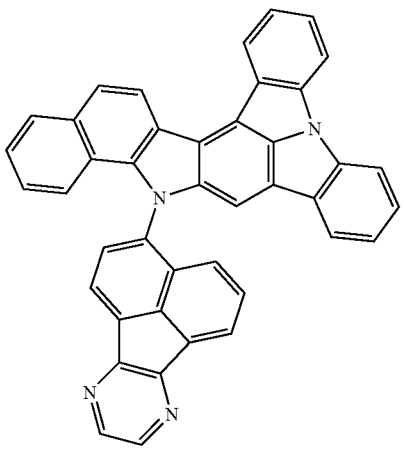 |

523
-continued
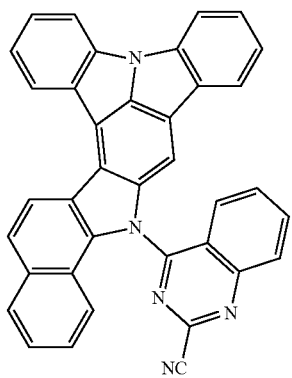
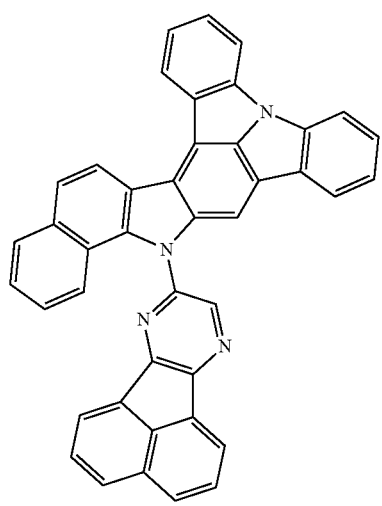
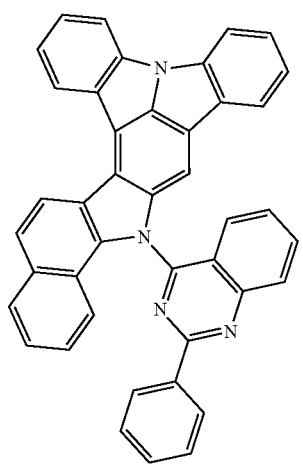
524
-continued
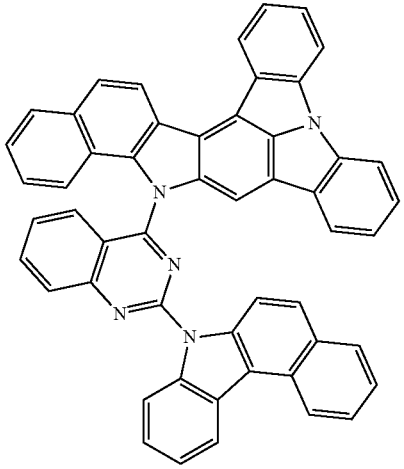
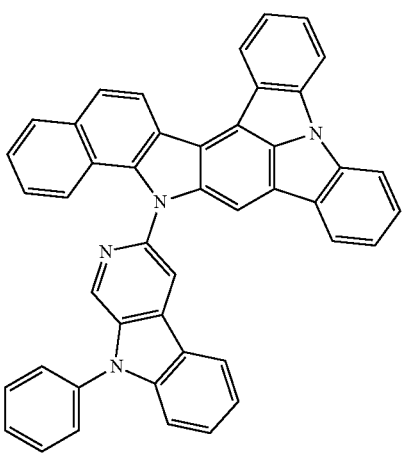
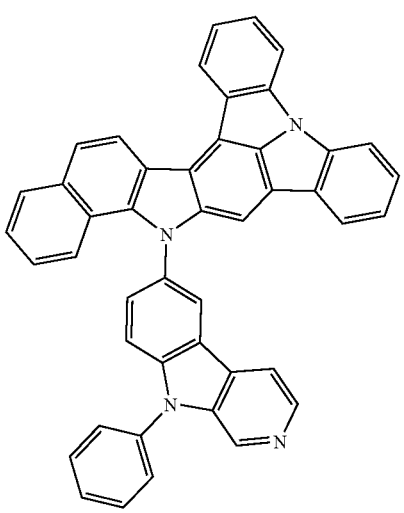

525
-continued
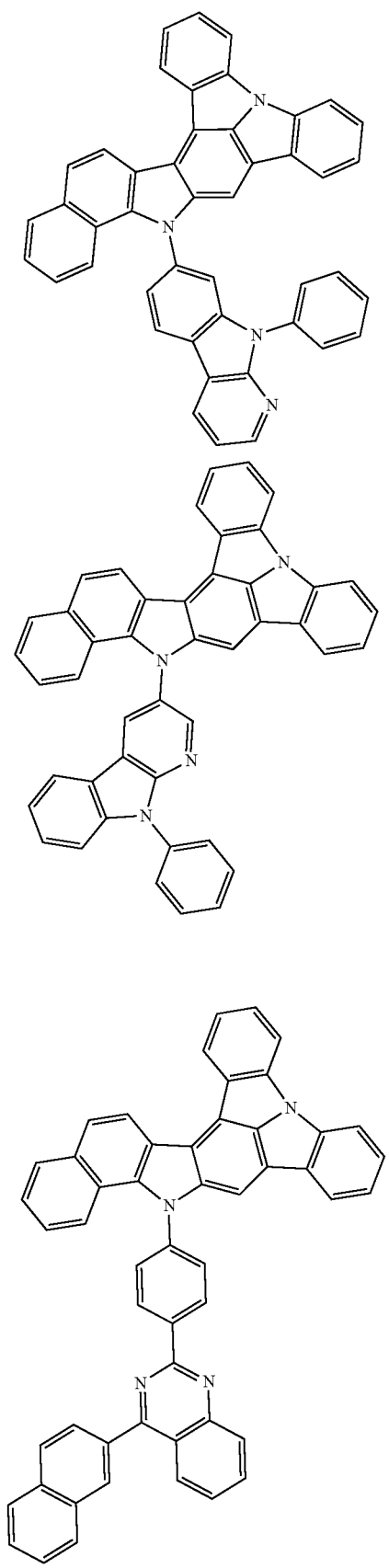
526
-continued
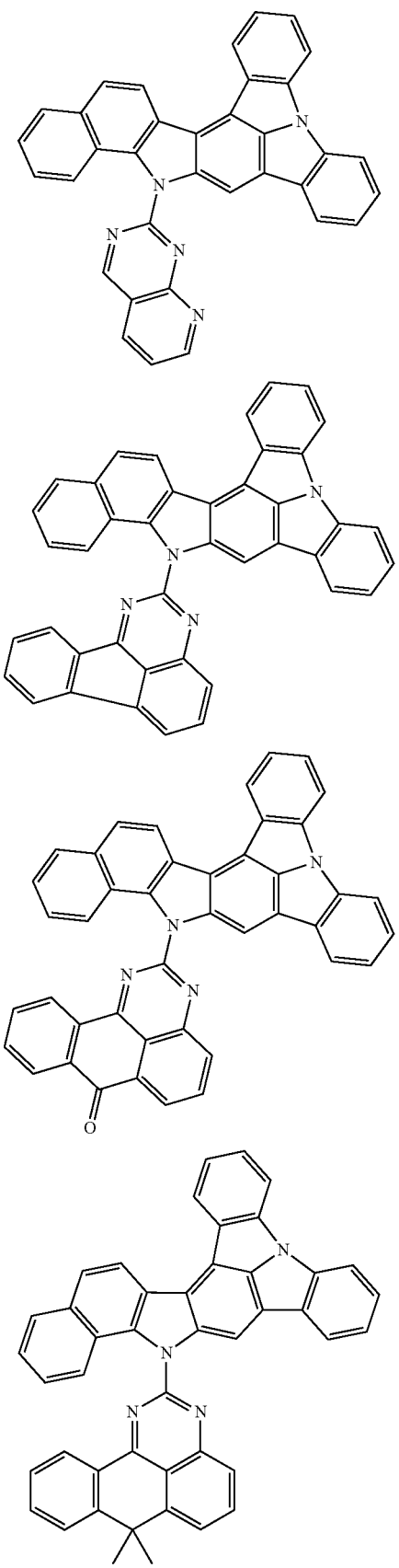 [SMILES: c1cnc2nc(-n3c4cc5c6ccccc6n6c7ccccc7c(c4c4ccc7ccccc7c43)c56)ncc2c1 ; c1ccc2c(c1)-c1cccc3nc(-n4c5cc6c7ccccc7n7c8ccccc8c(c5c5ccc8ccccc8c54)c67)nc-2c13 ; O=C1c2ccccc2-c2nc(-n3c4cc5c6ccccc6n6c7ccccc7c(c4c4ccc7ccccc7c43)c56)nc3cccc1c23 ; CC1(C)c2ccccc2-c2nc(-n3c4cc5c6ccccc6n6c7ccccc7c(c4c4ccc7ccccc7c43)c56)nc3cccc1c23]

527
-continued
528
-continued
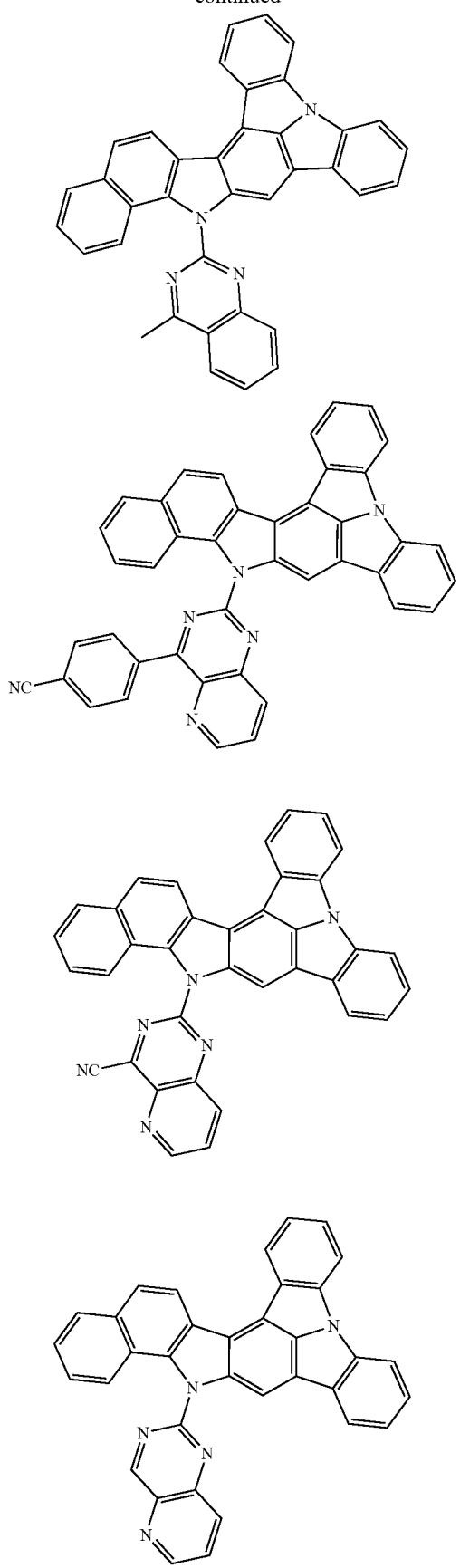
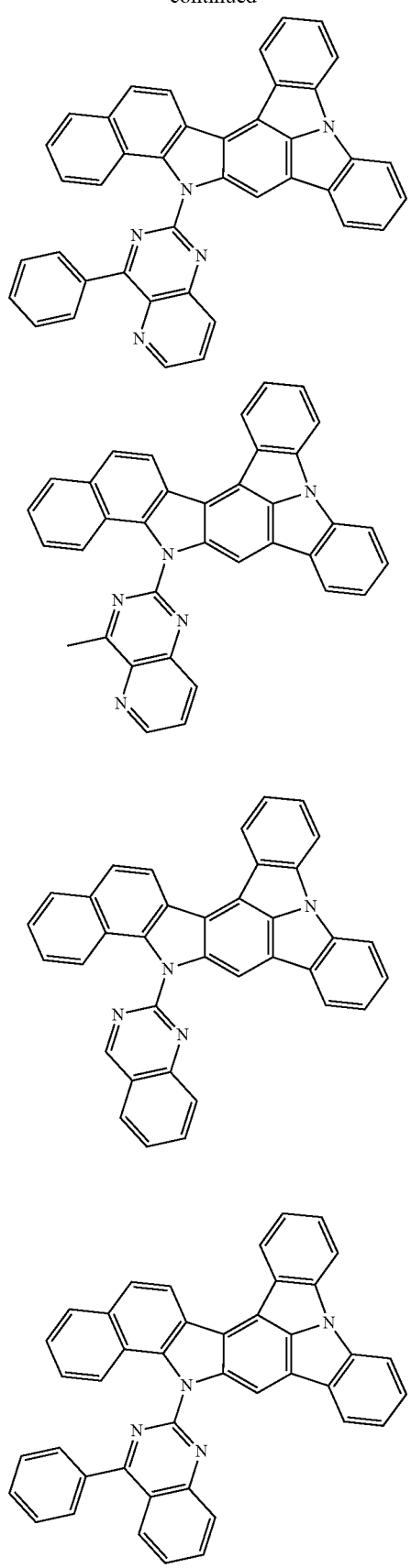

529
-continued
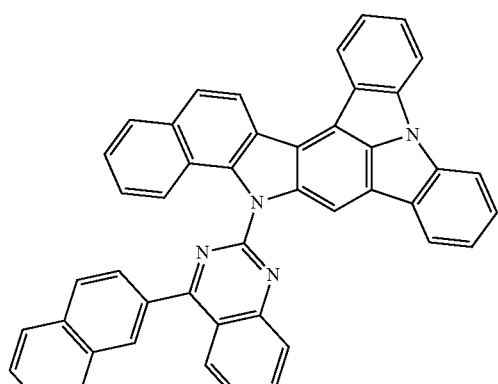
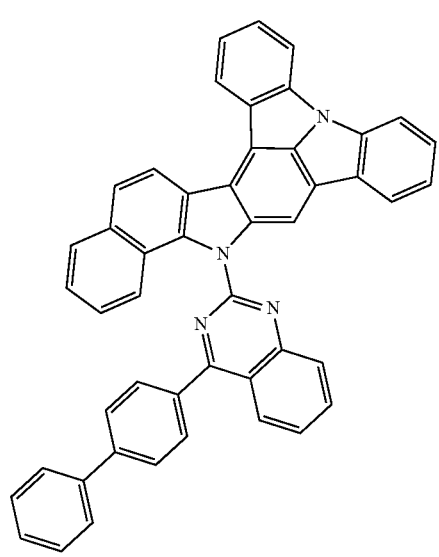
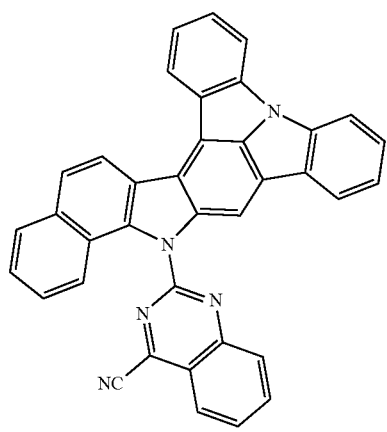
530
-continued
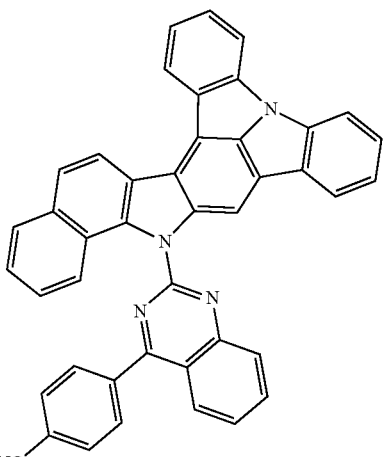
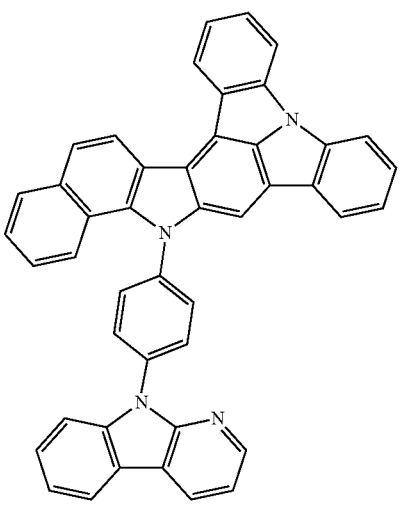
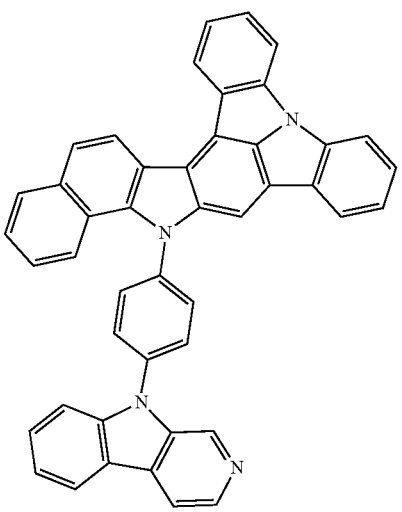

531
-continued
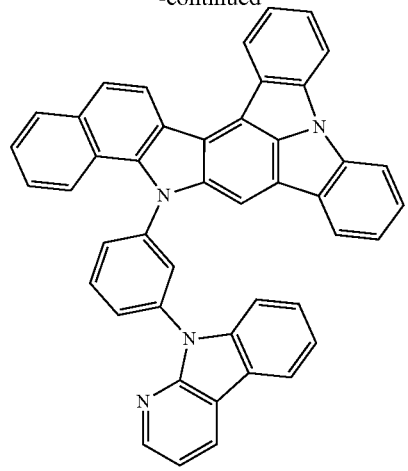
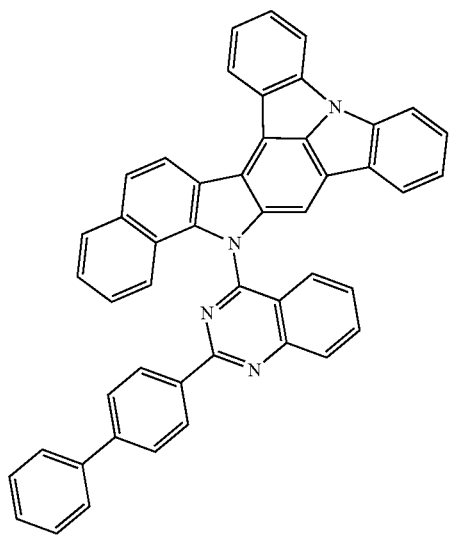
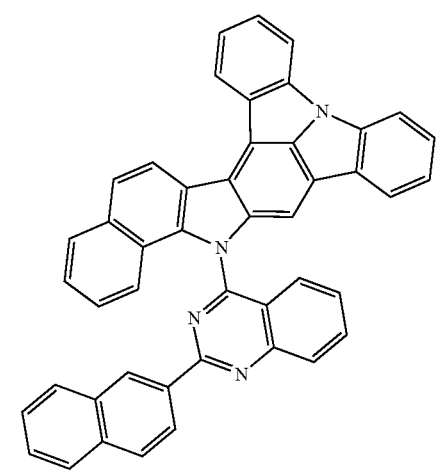
532
-continued
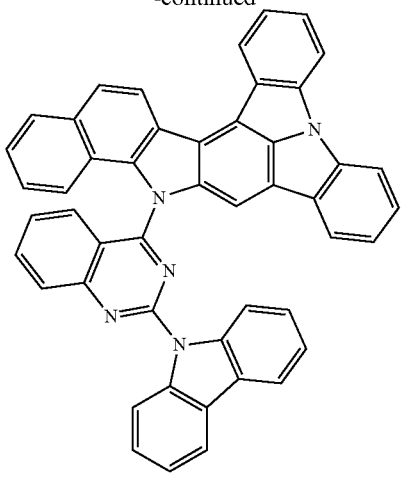
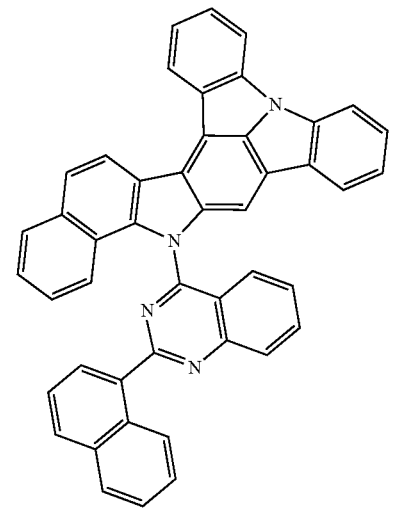
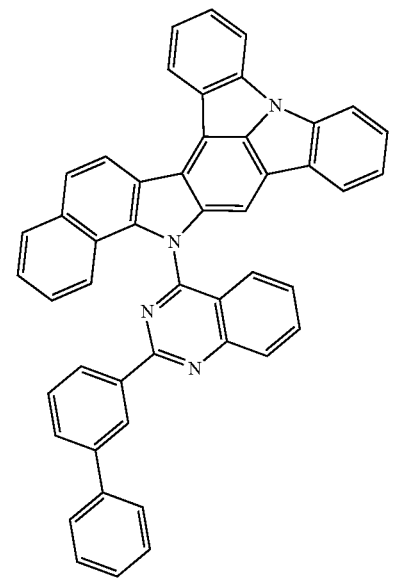

533
-continued
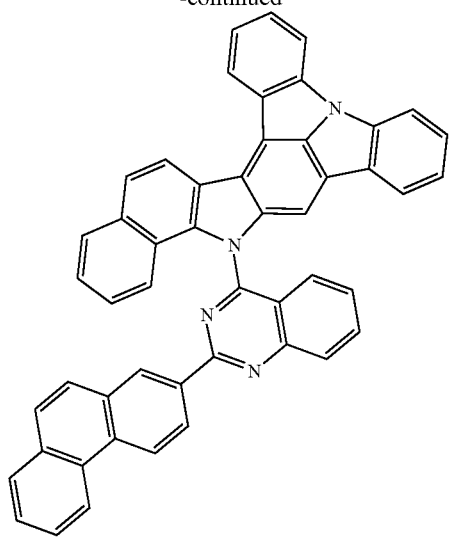
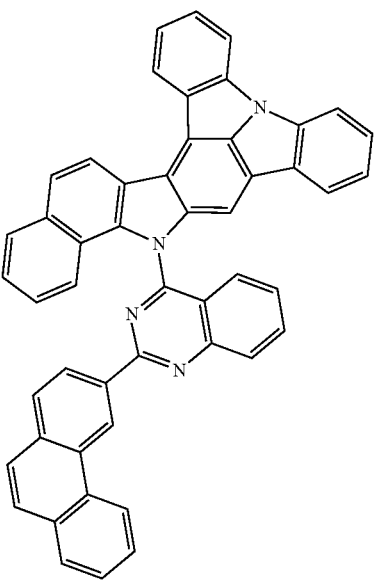
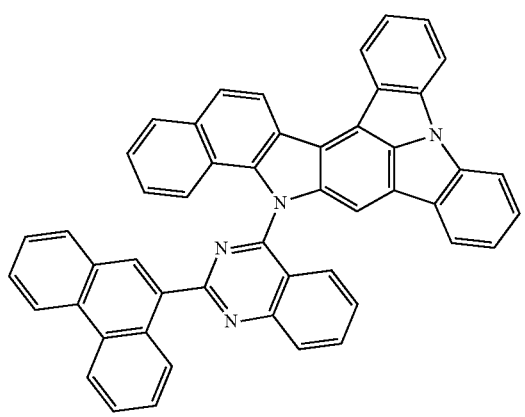
534
-continued
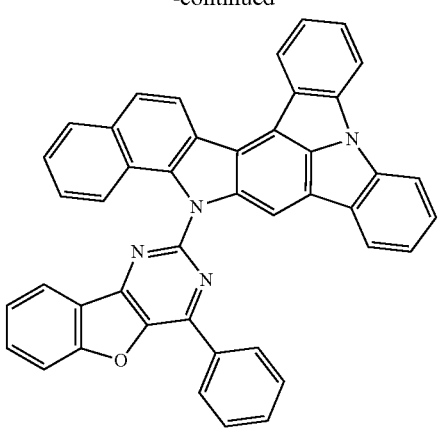
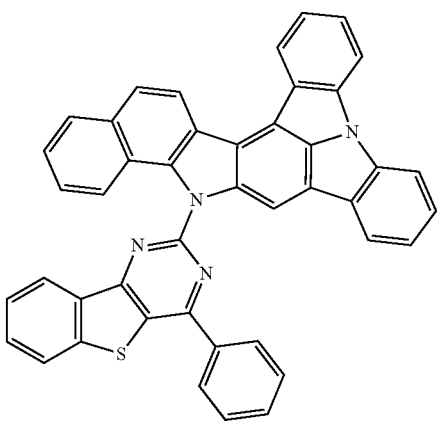
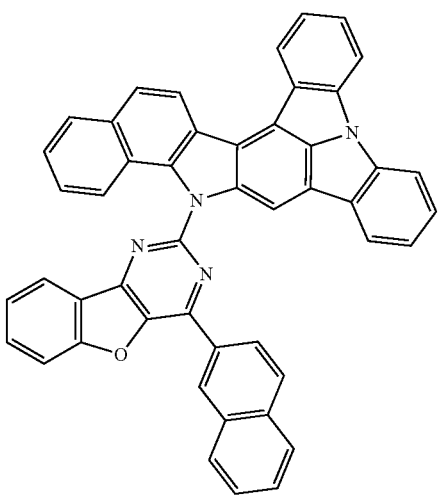

535
-continued
536
-continued
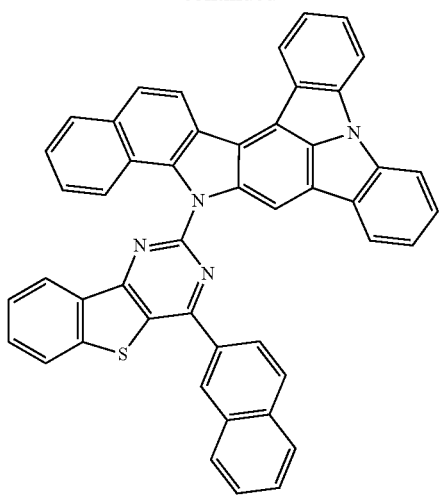
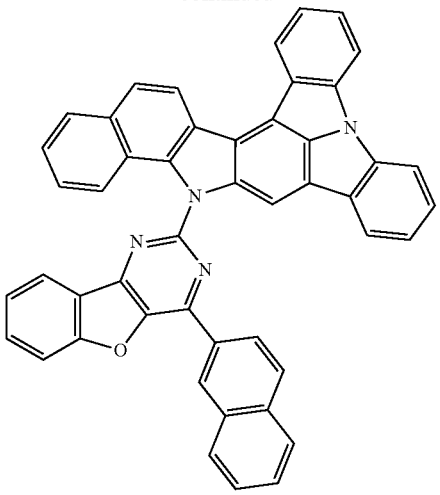
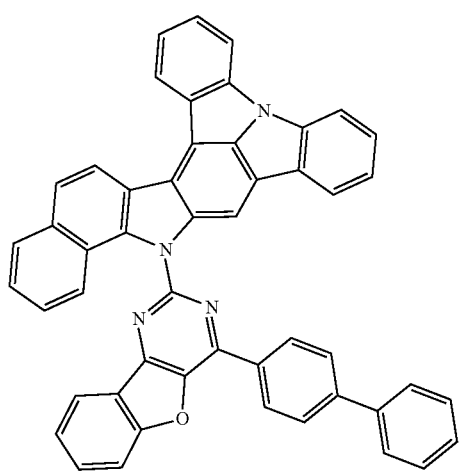
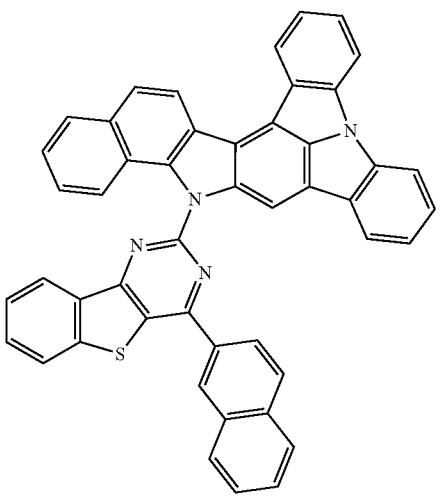
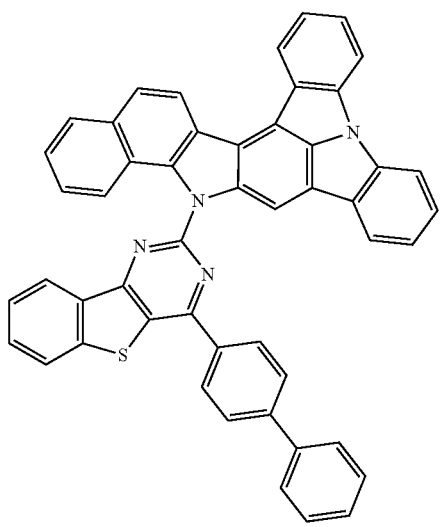
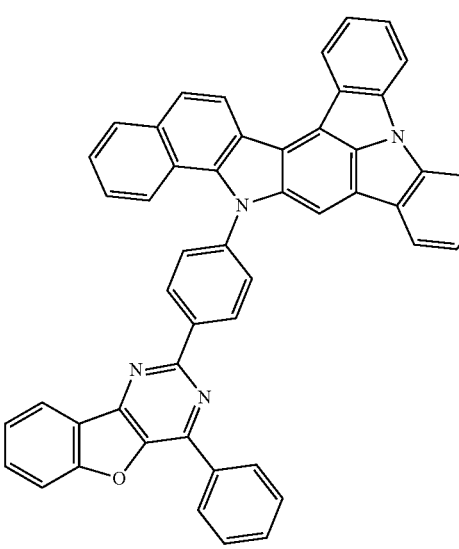

537
-continued
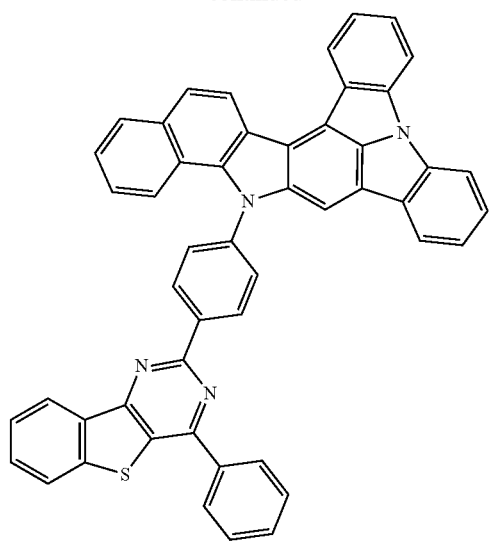
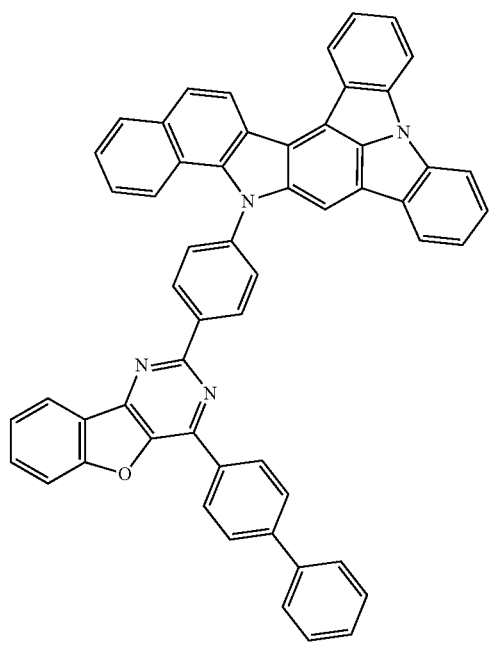
538
-continued
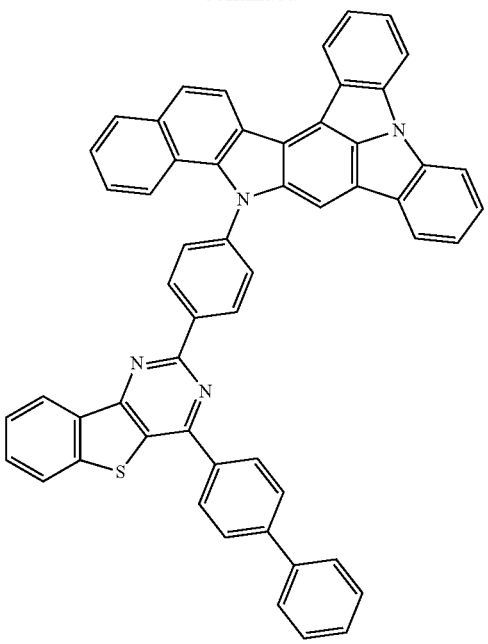
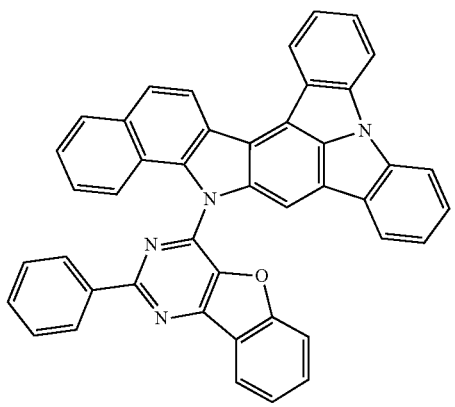
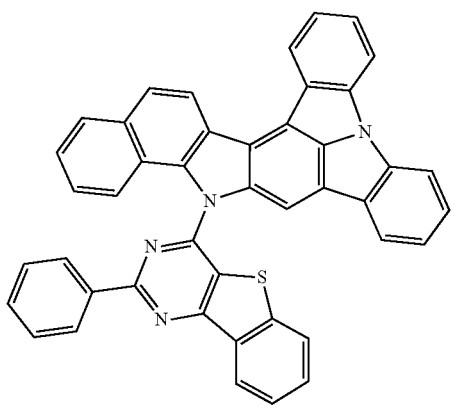

539
-continued
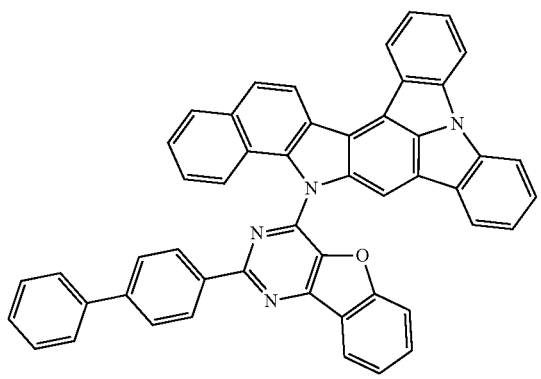
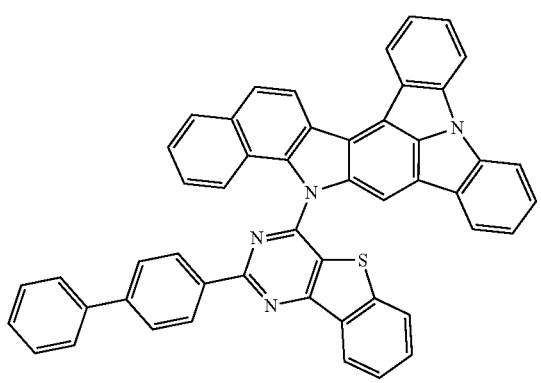
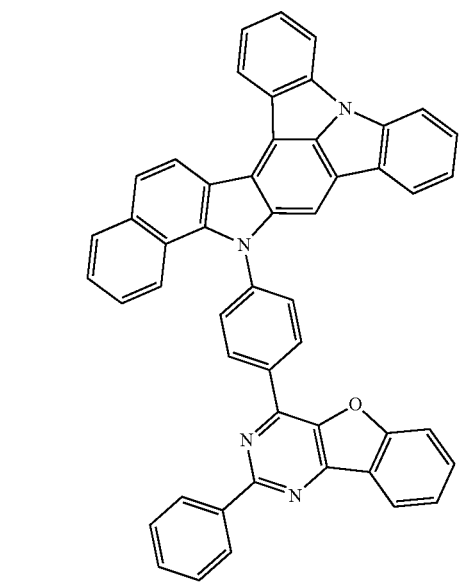
540
-continued
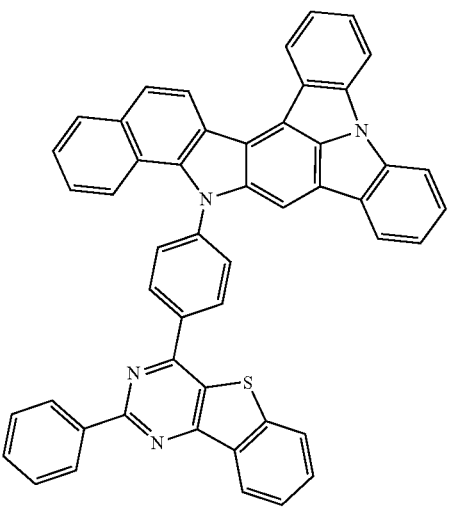
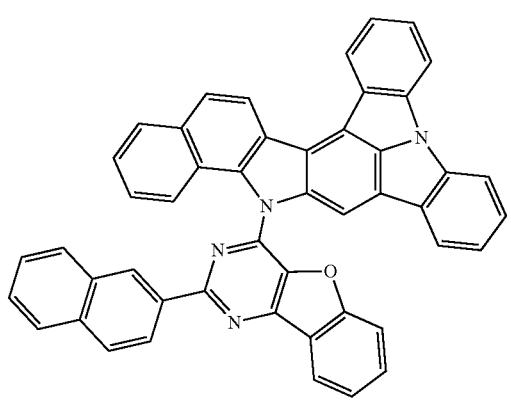
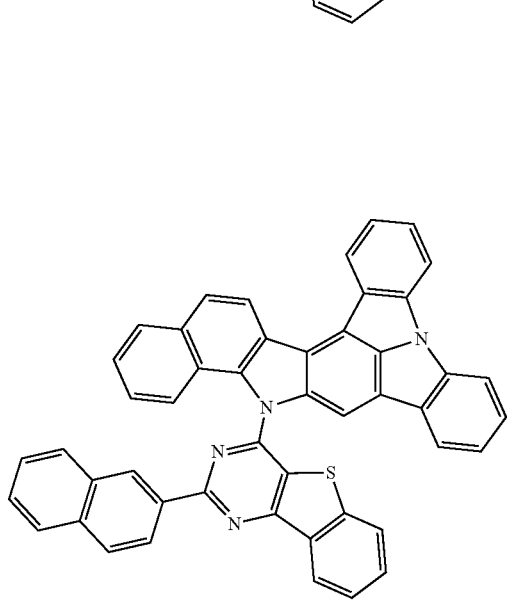

541
-continued
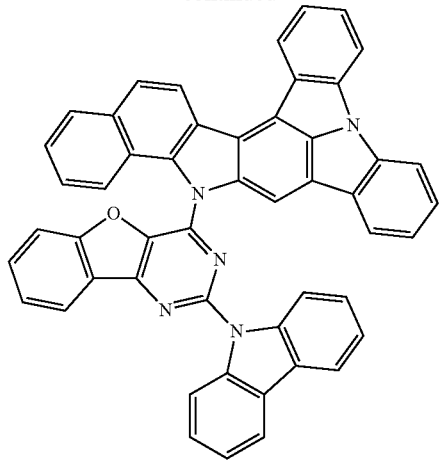
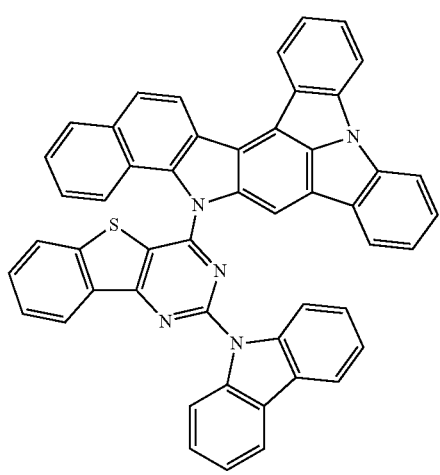
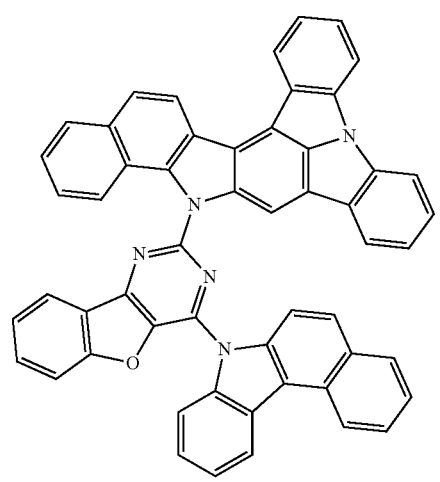
542
-continued
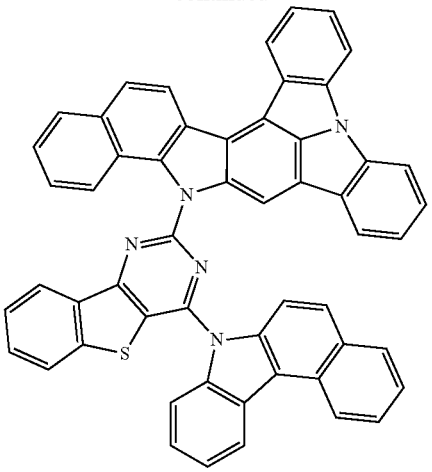
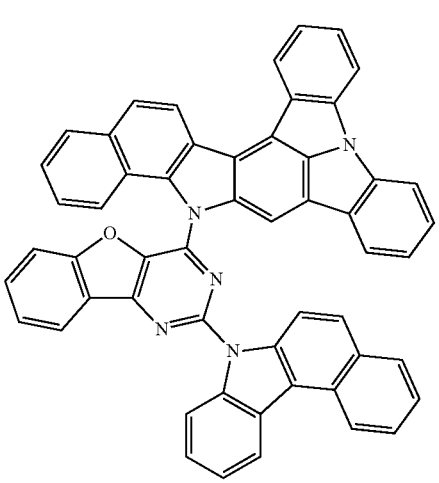
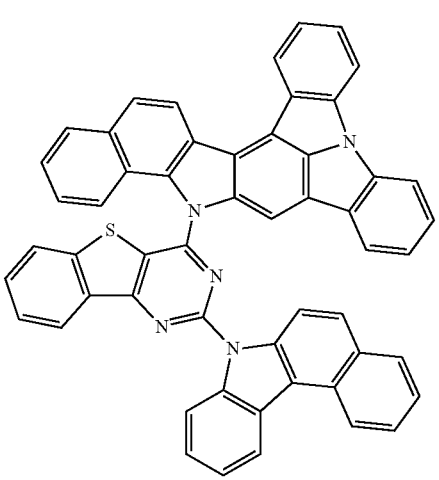

543
-continued
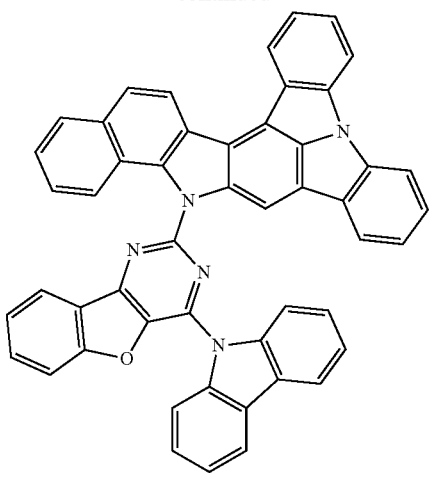
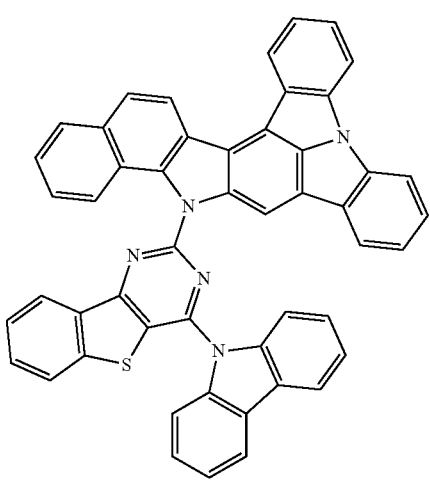
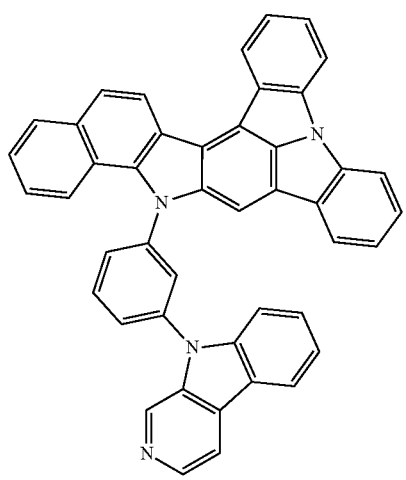
544
-continued
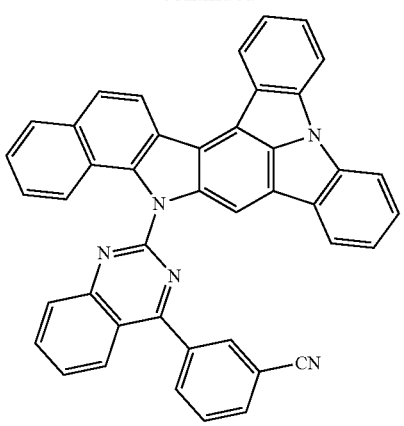
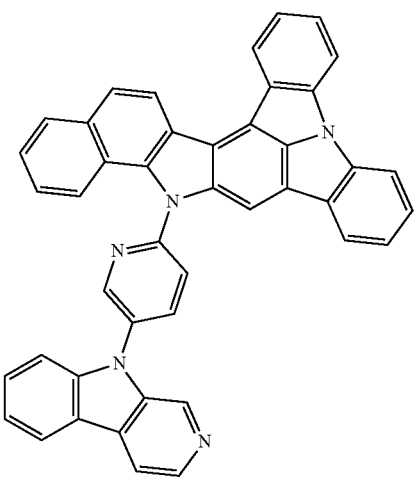
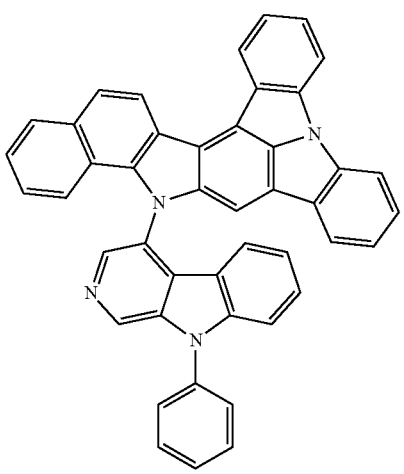

545
-continued
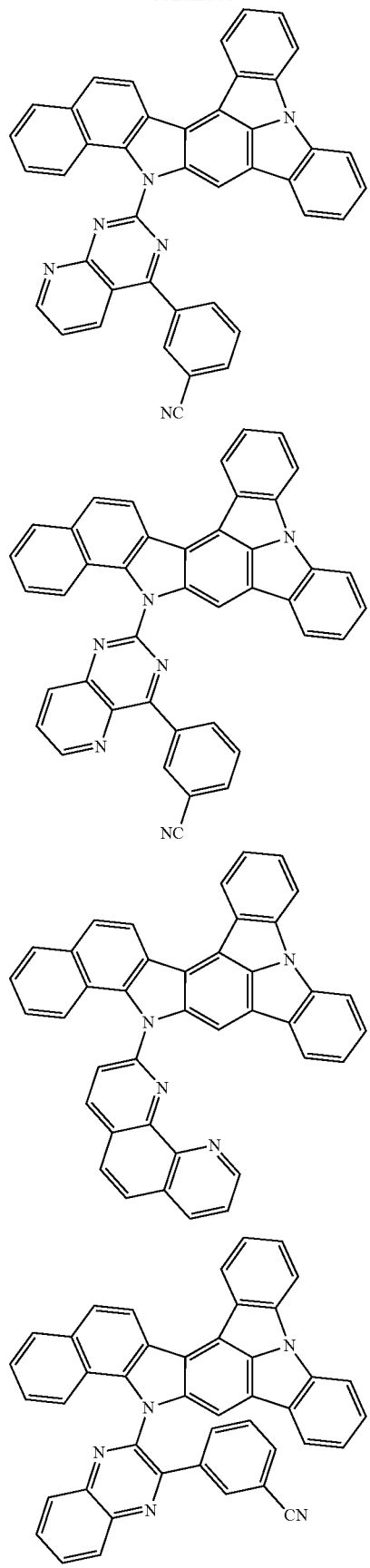
546
-continued
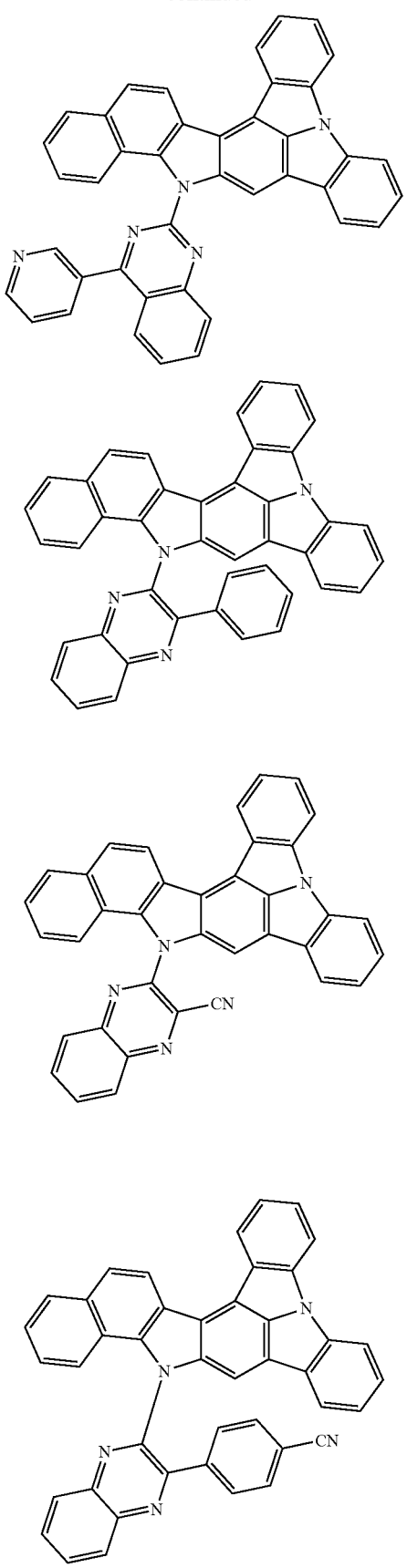

547
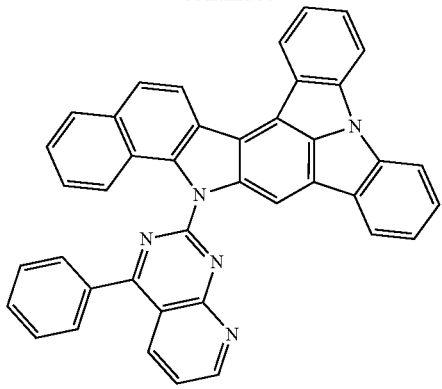
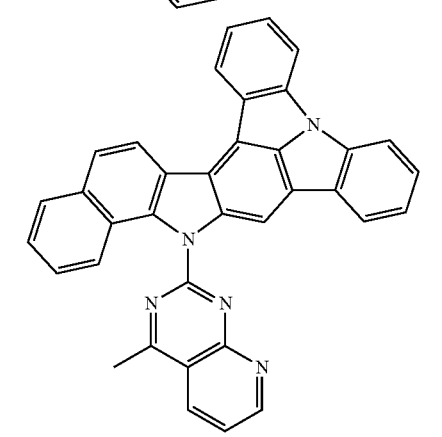
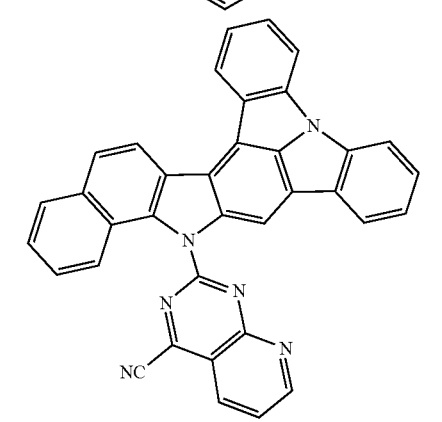
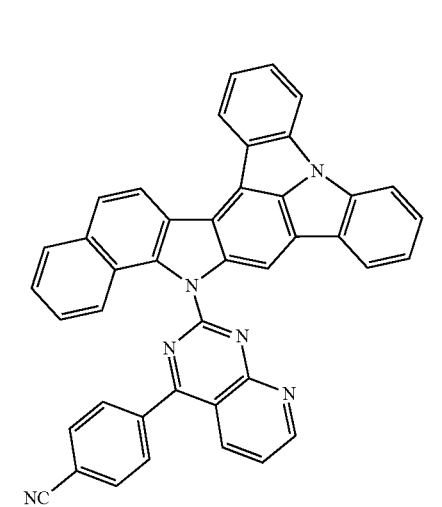
548
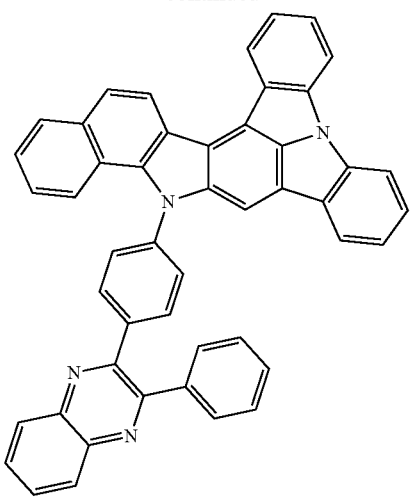

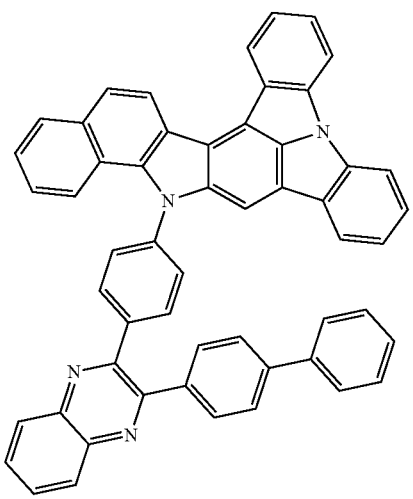
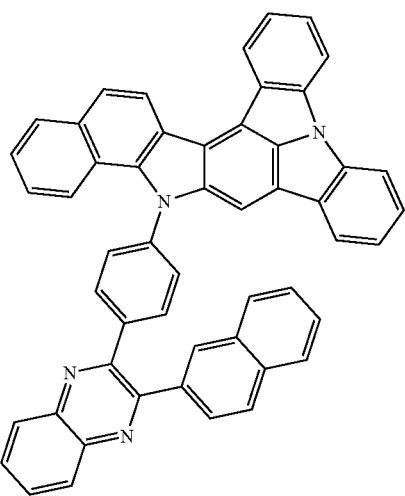

| 549 -continued | 550 -continued |
|---|---|
| 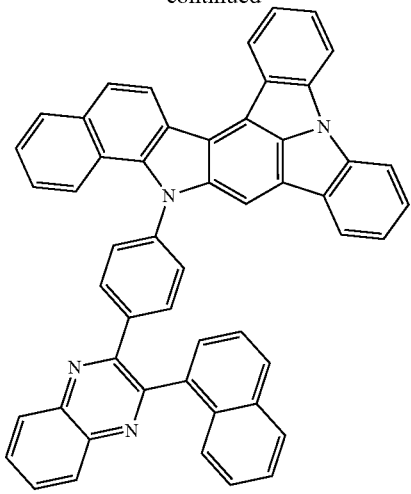 | 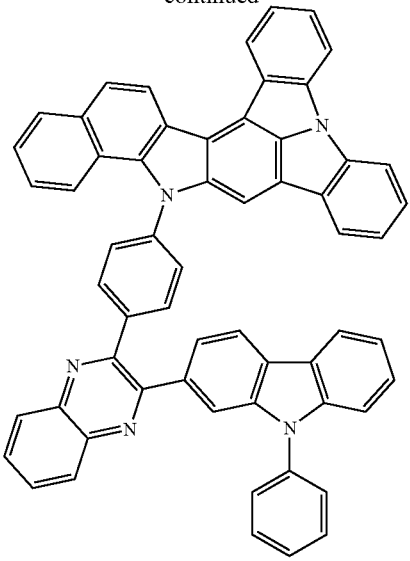 |
| 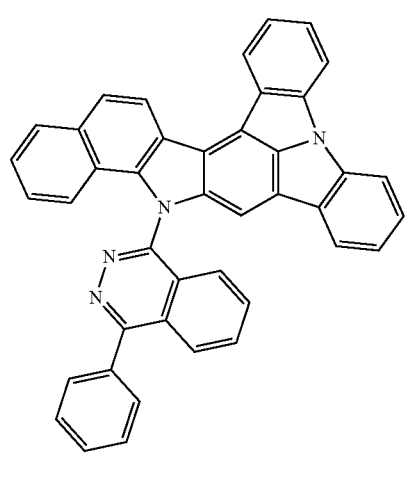 | 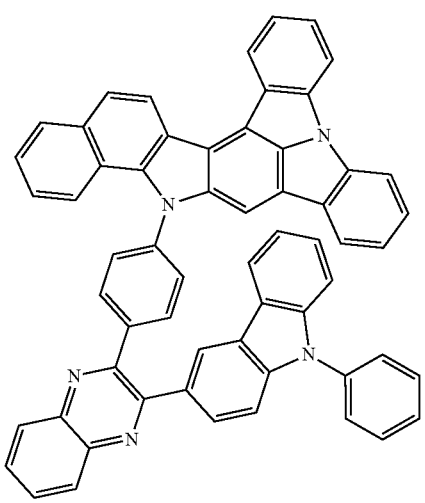 |
| 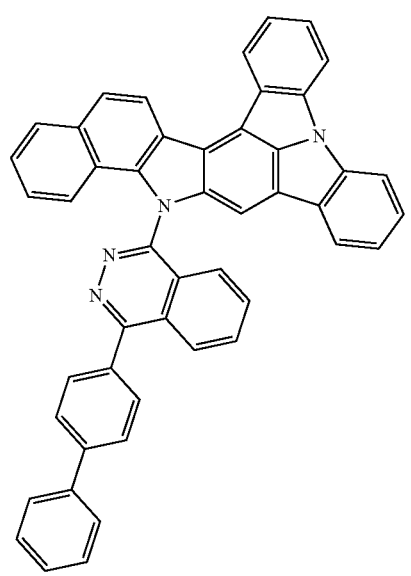 | 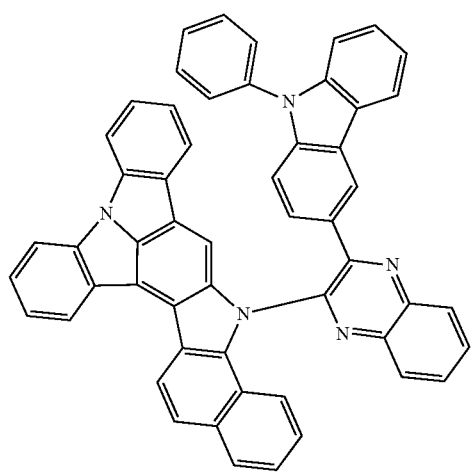 |

551
-continued
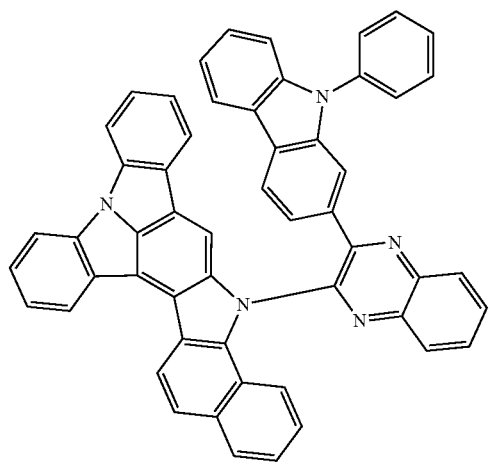
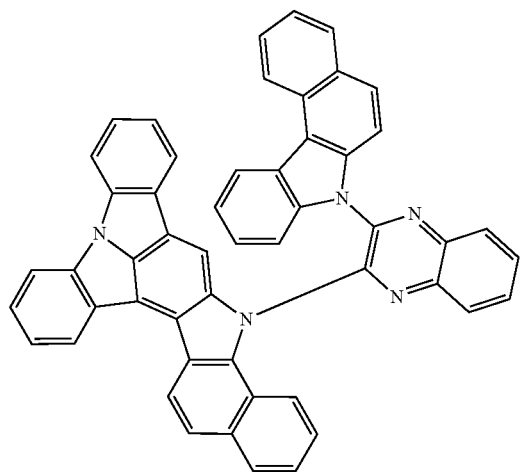
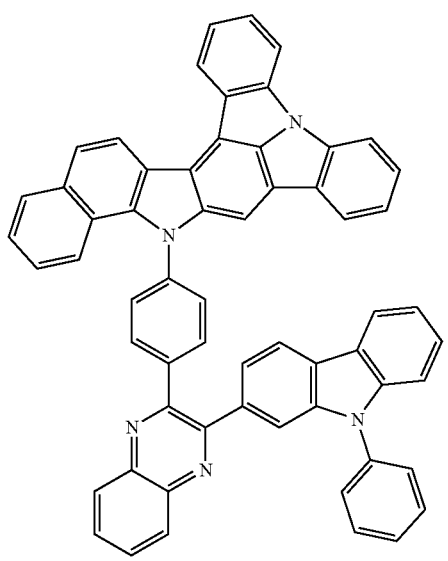
552
-continued
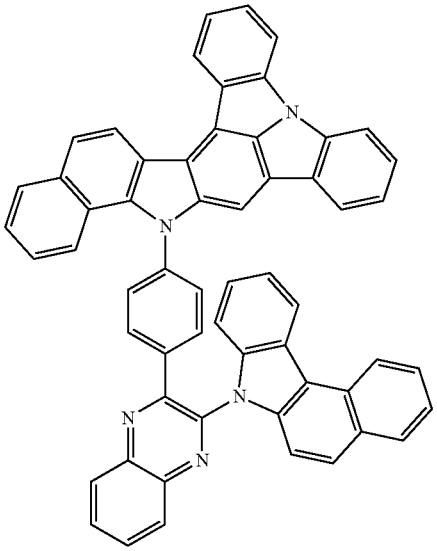
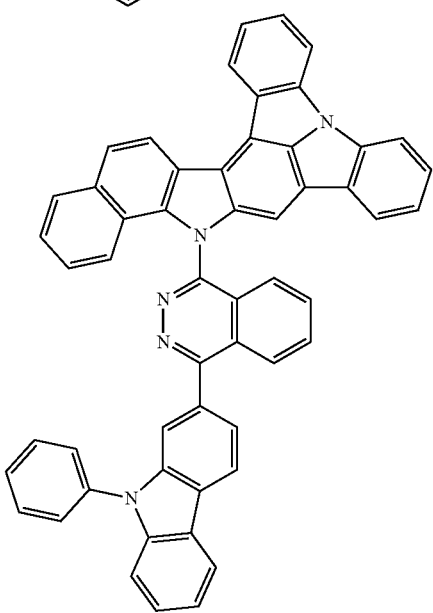
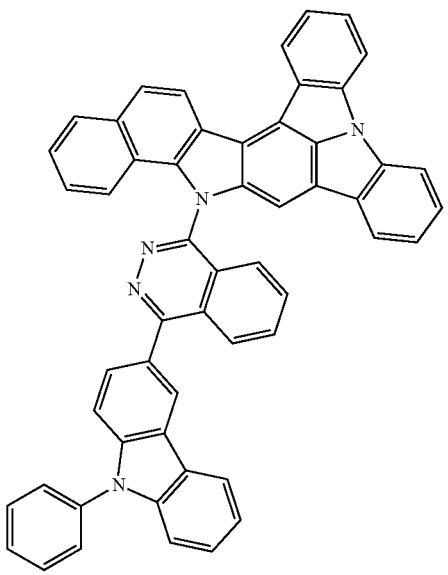

553
-continued
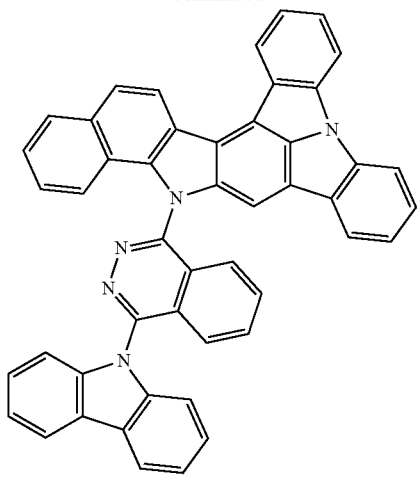
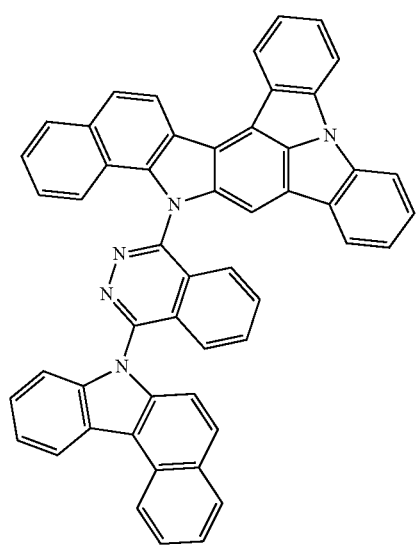
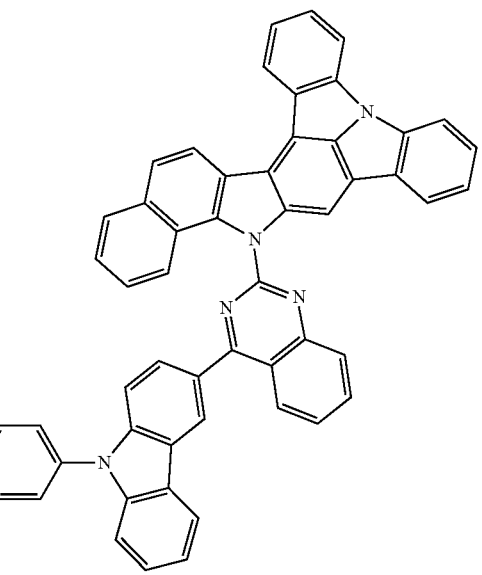
554
-continued
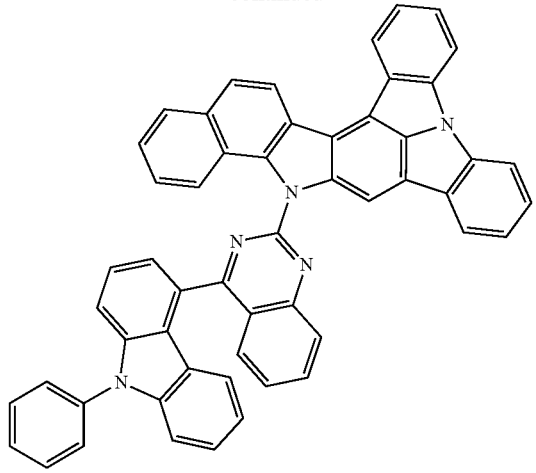
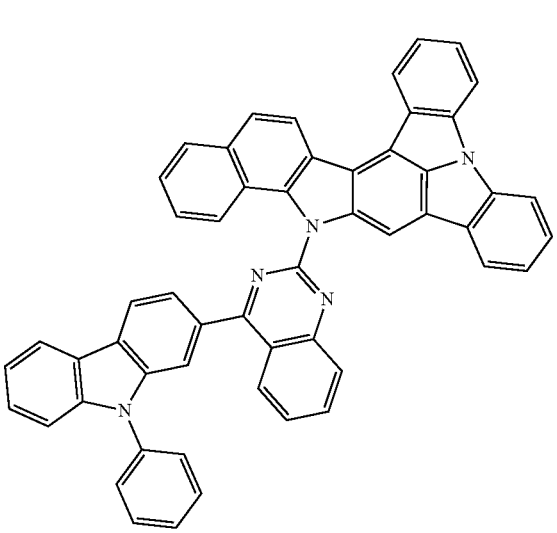
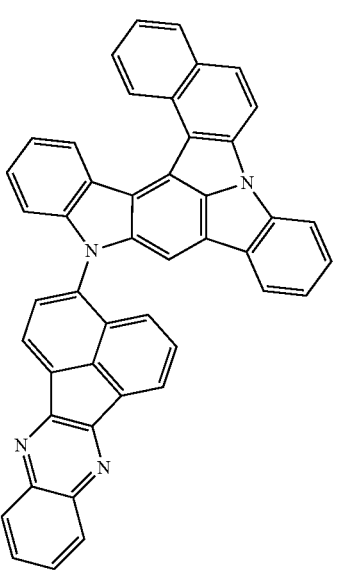 [SMILES: c1ccc2c(c1)ccc1c2c2c3c4ccccc4n(-c4ccc5c6c(cccc46)-c4nc6ccccc6nc4-5)c3cc3c4ccccc4n1c32]

555
-continued
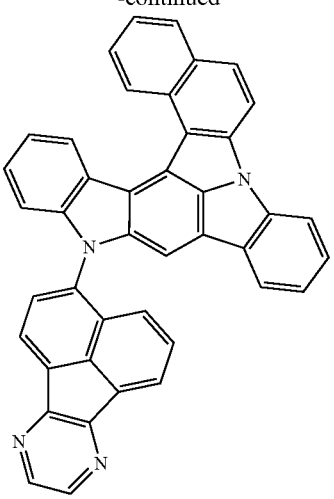
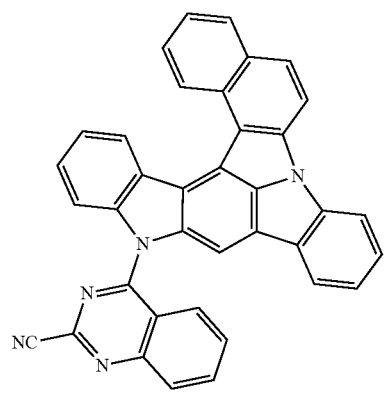
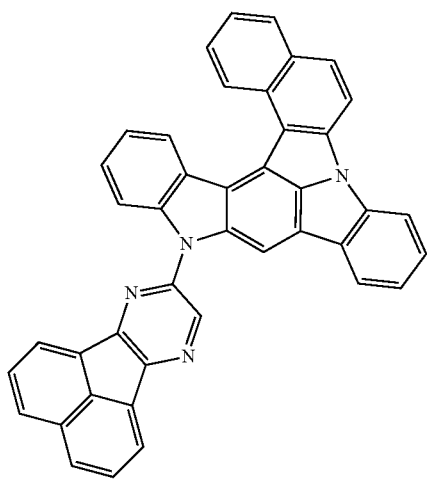
556
-continued
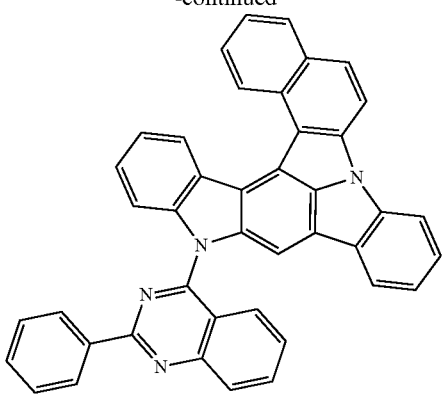
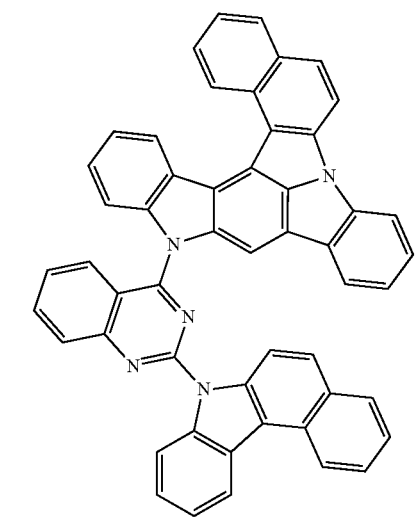
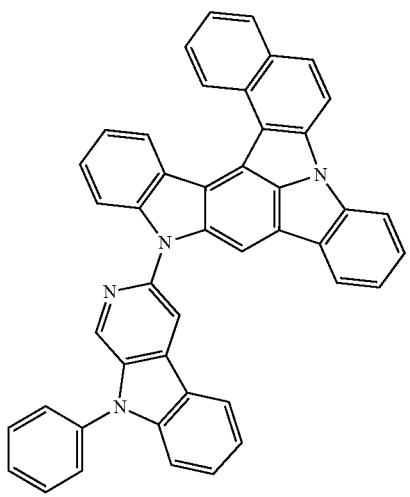

557
-continued
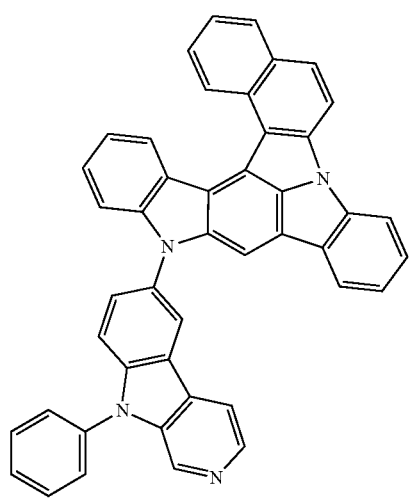
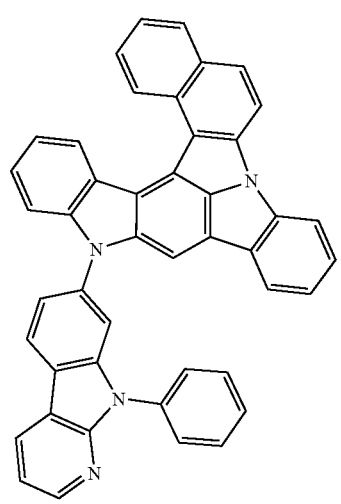
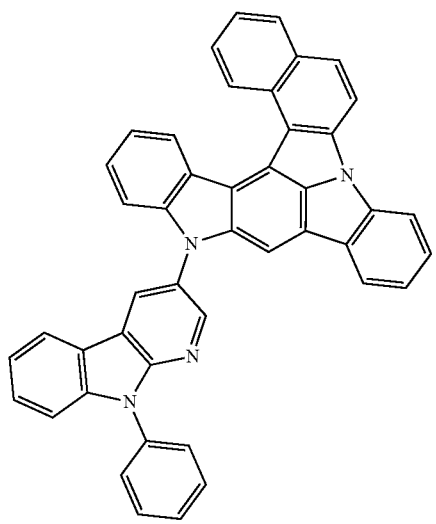
558
-continued
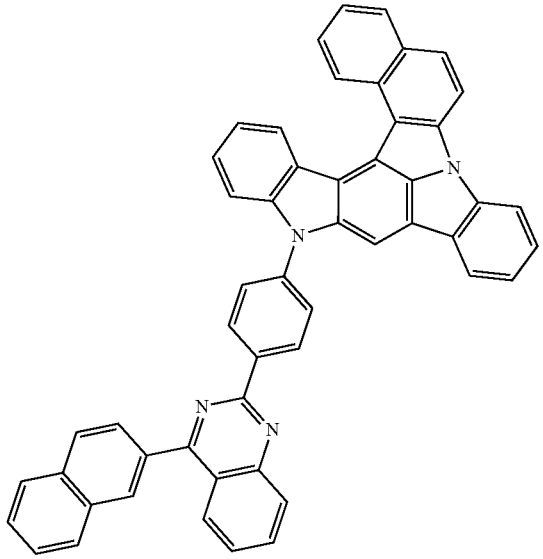
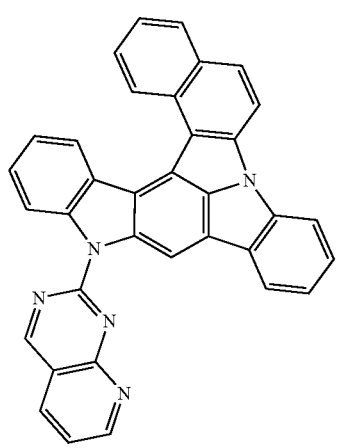
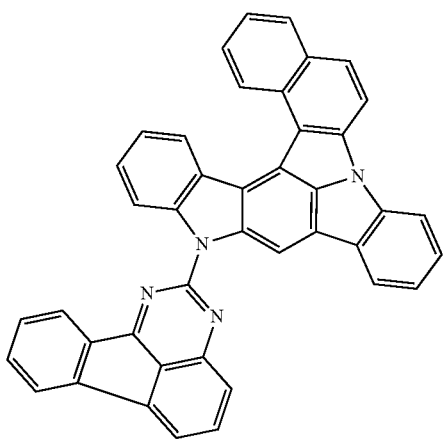

559
-continued
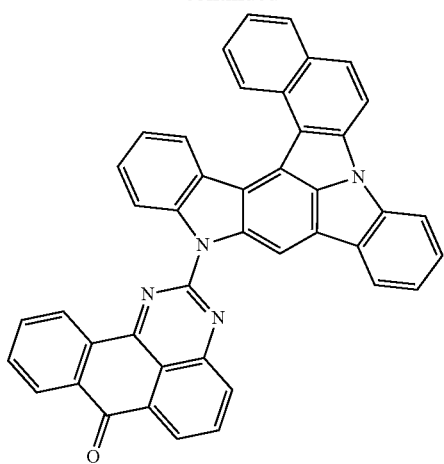
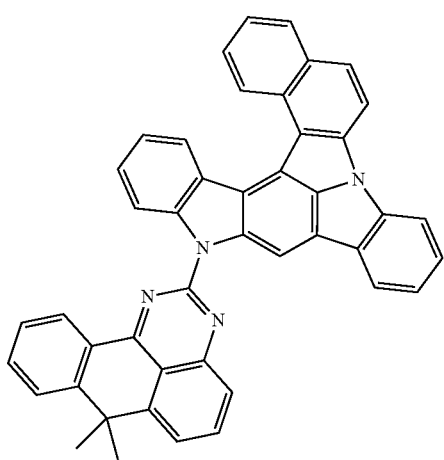
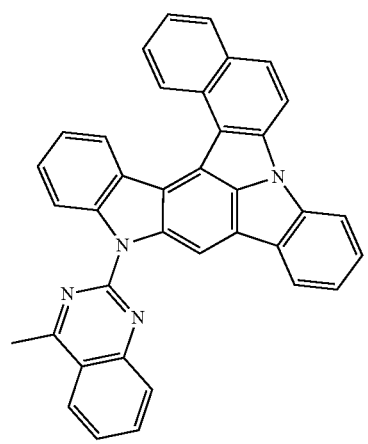
560
-continued
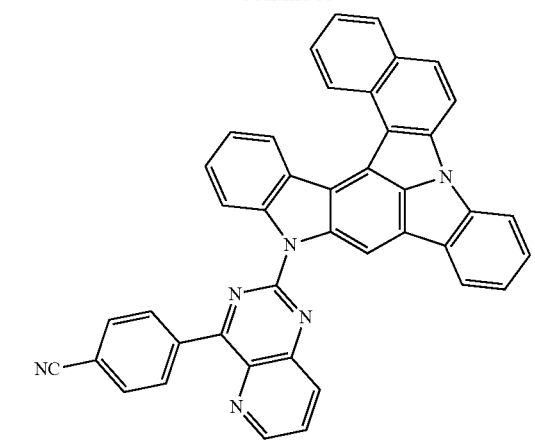
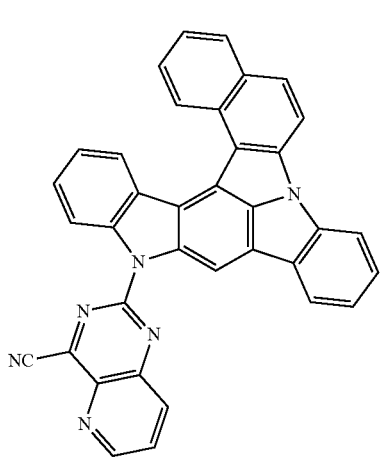
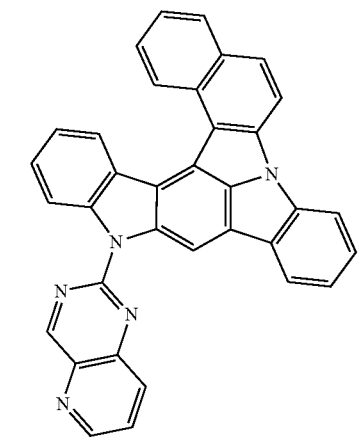

561
-continued
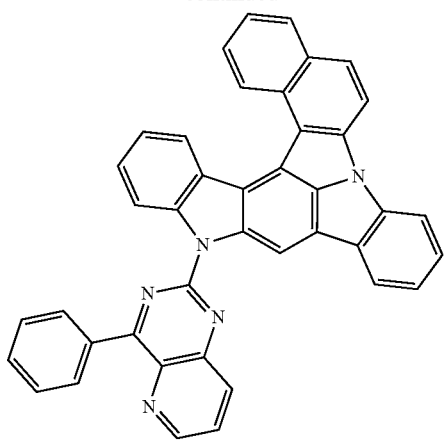
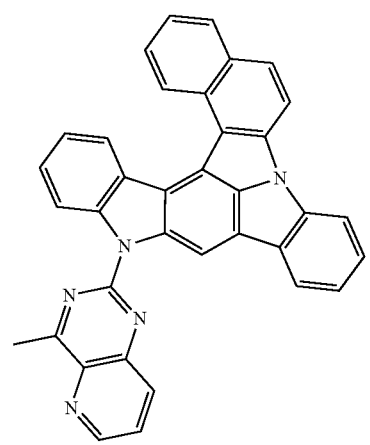
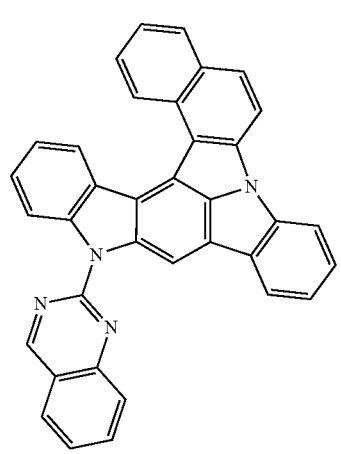
562
-continued
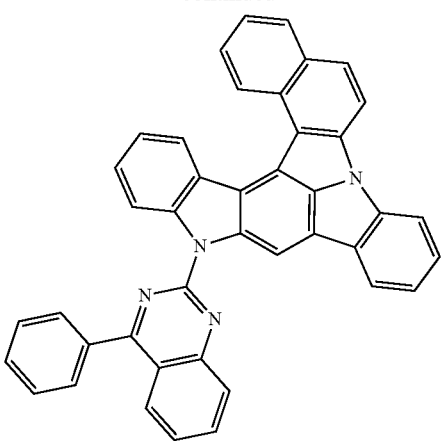
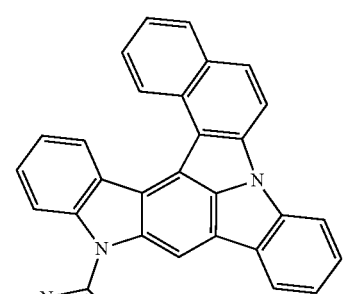
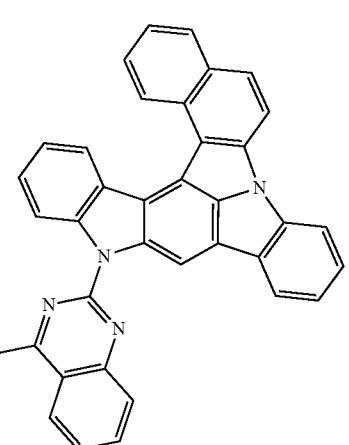

563
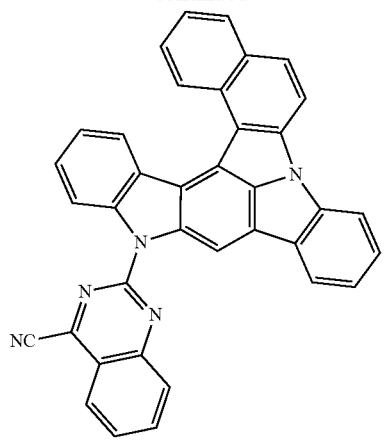
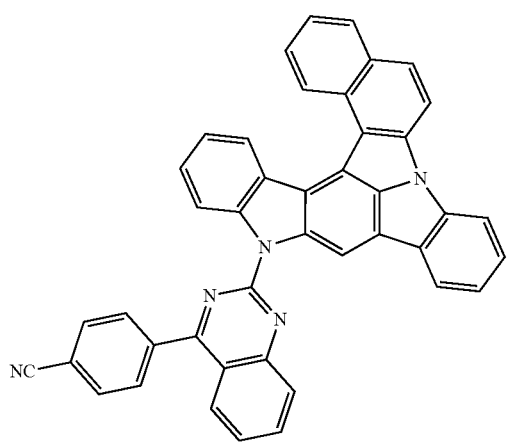
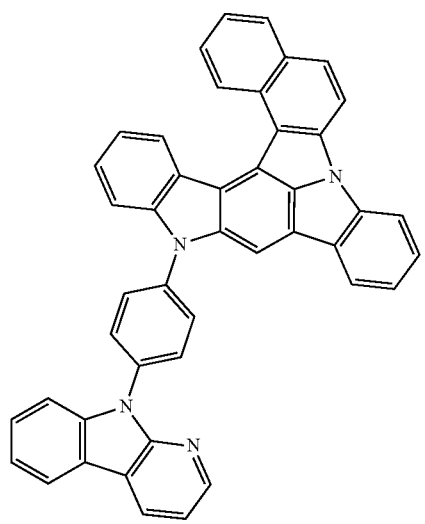
564
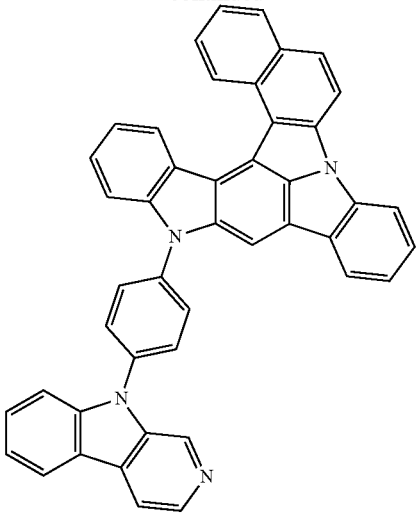
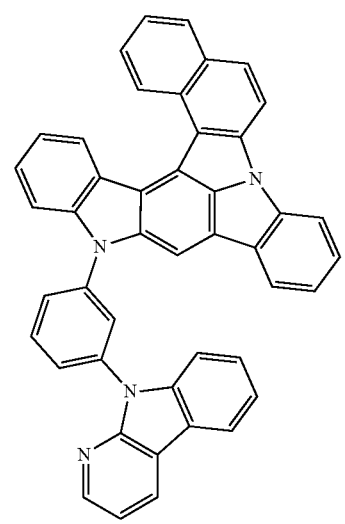
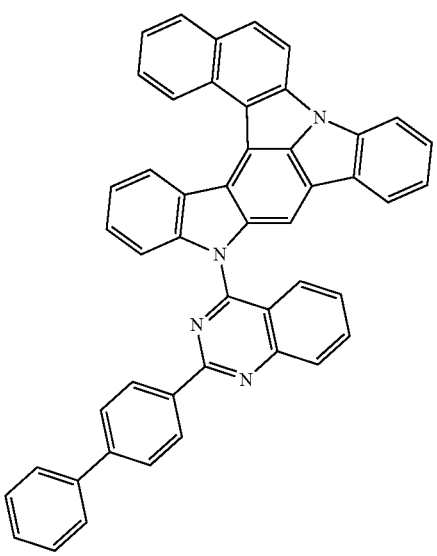

565
-continued

566
-continued

567
-continued
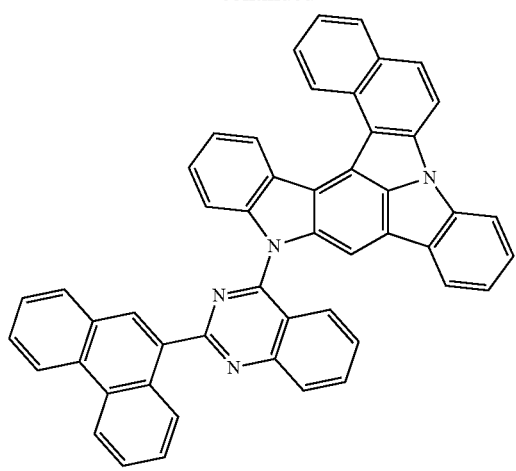
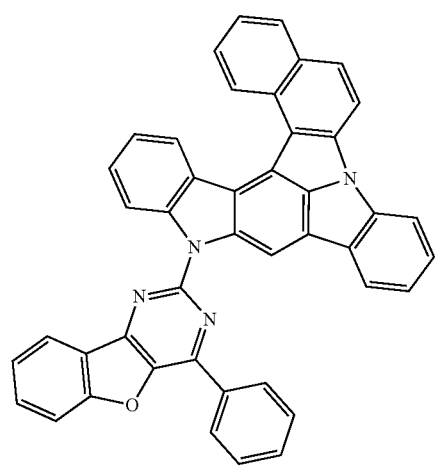
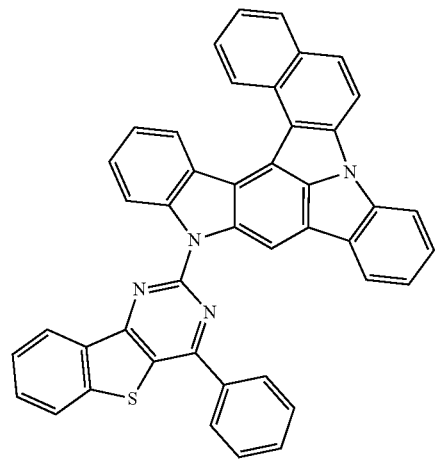
568
-continued
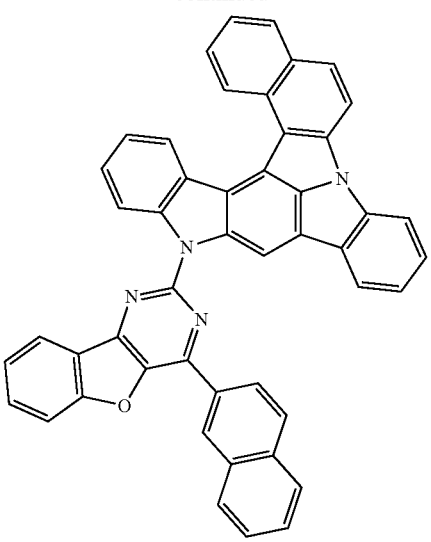
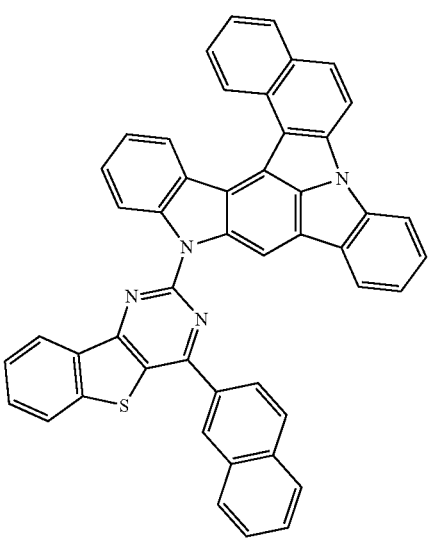
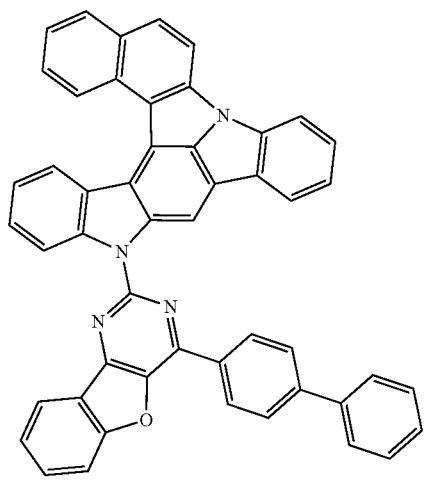

569
-continued
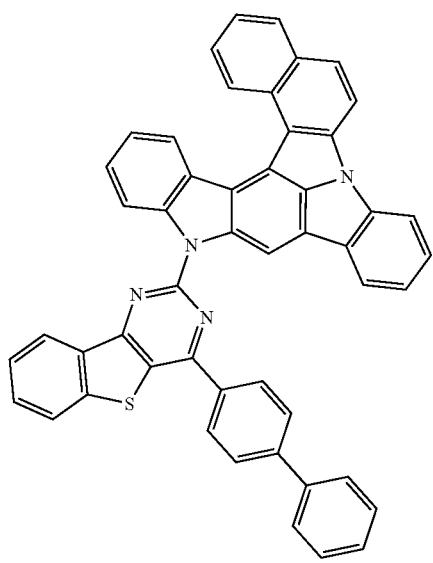
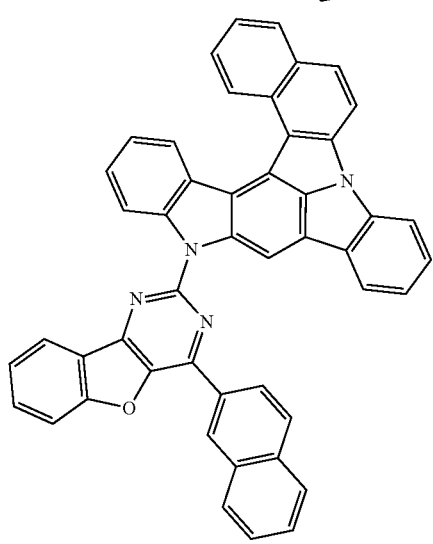
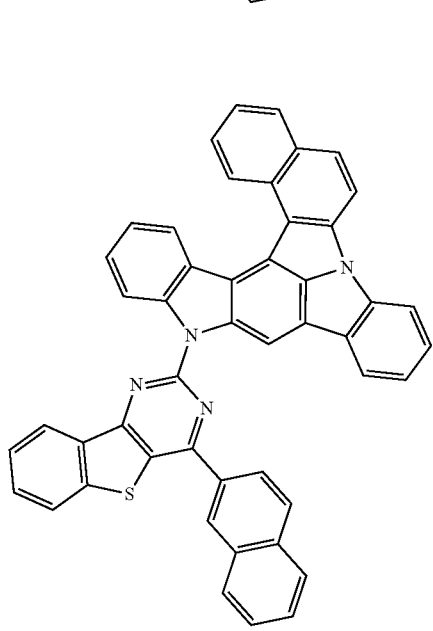
570
-continued
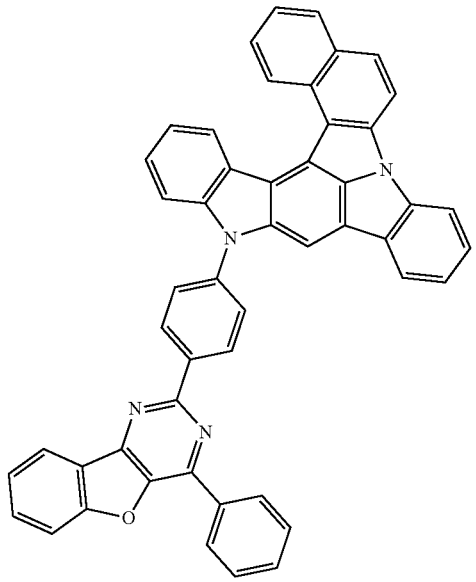
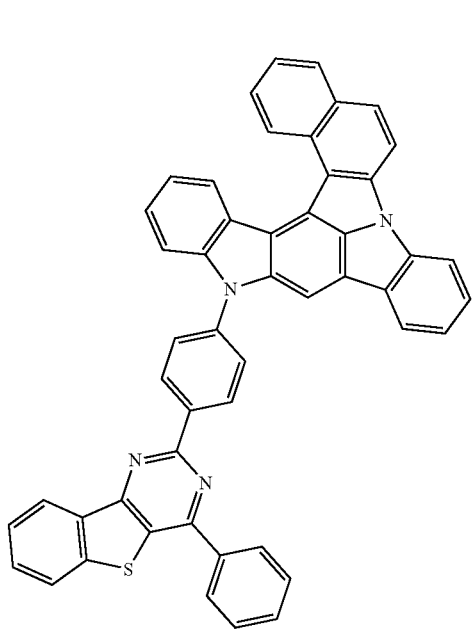

571
-continued
572
-continued
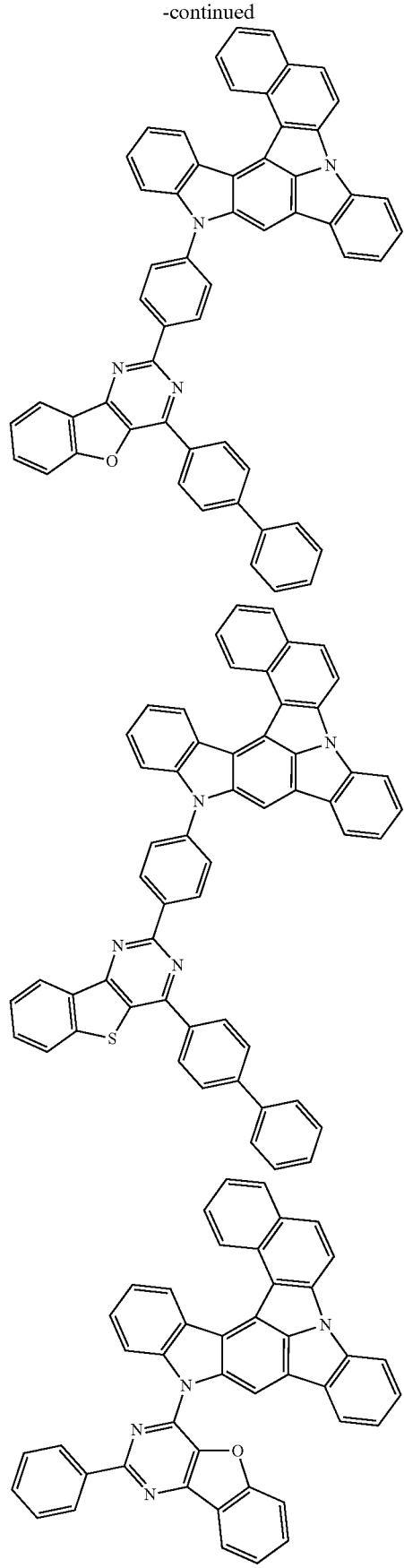
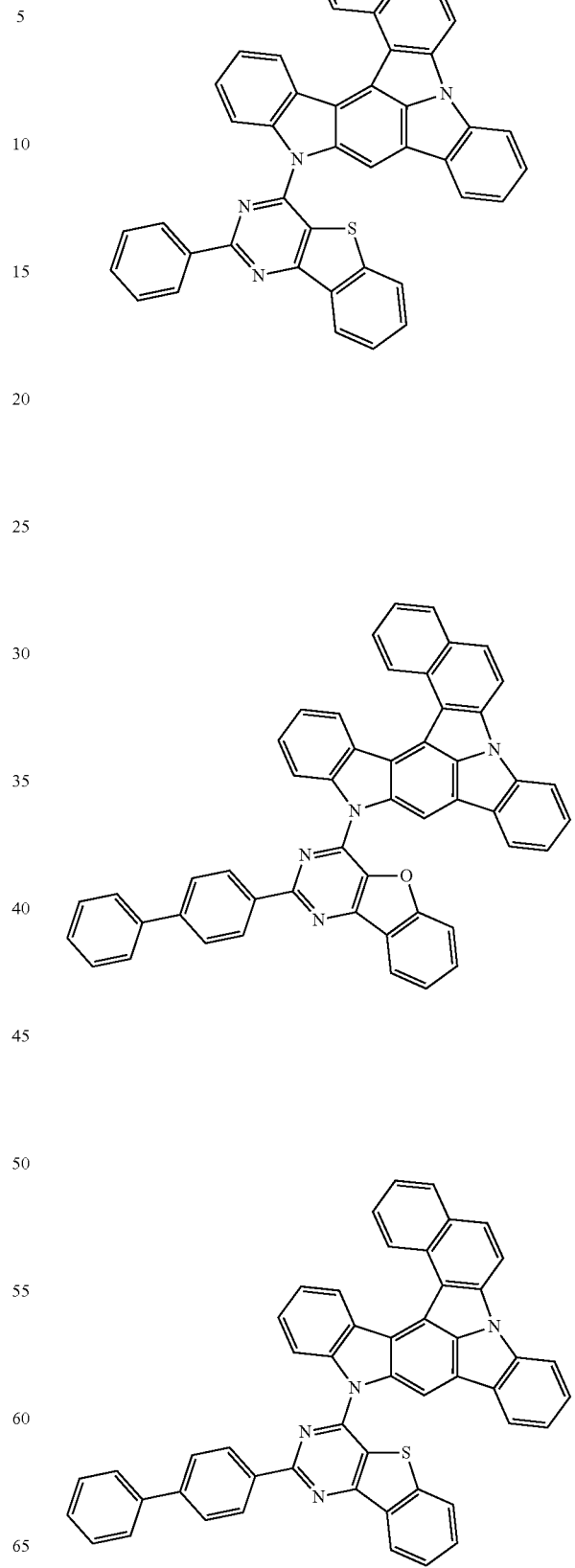

573
-continued
574
-continued
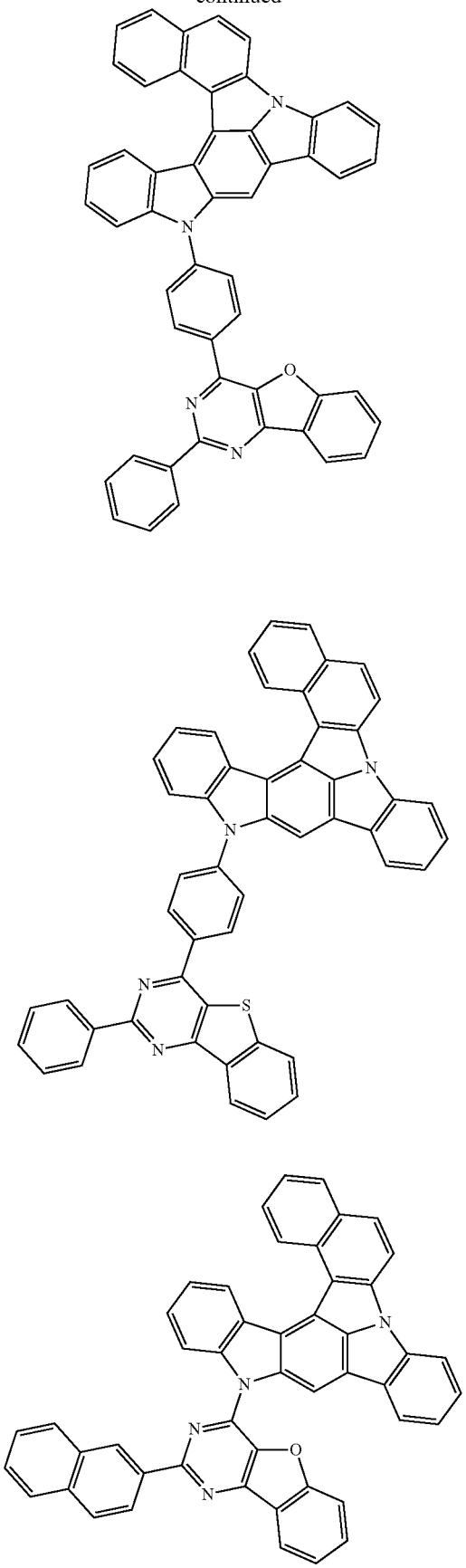

575
-continued
576
-continued
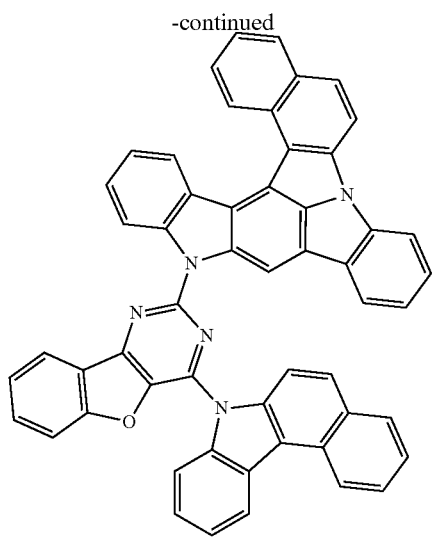
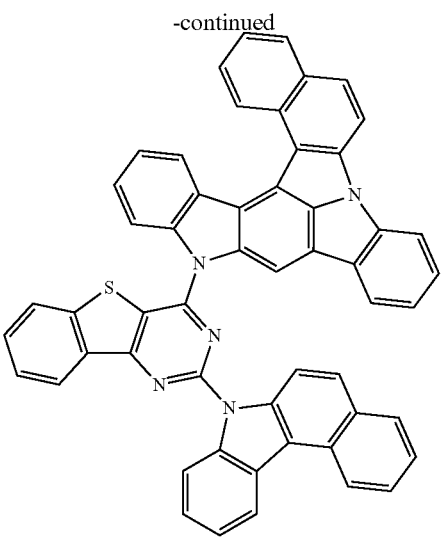
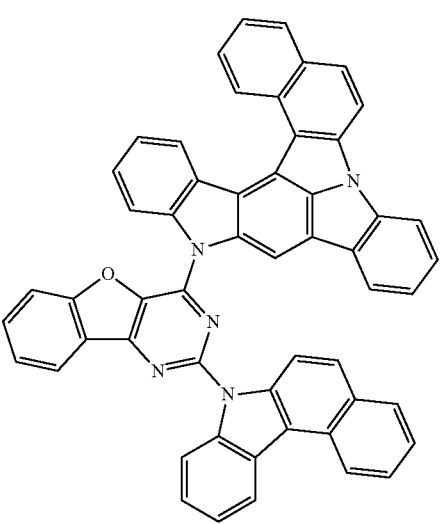

577
-continued
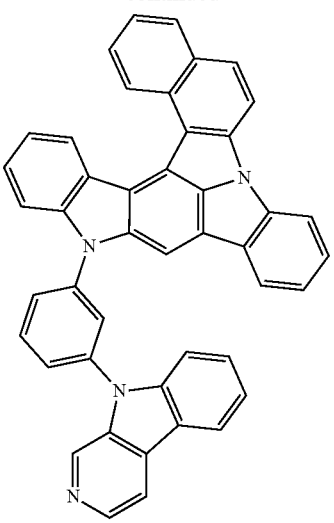
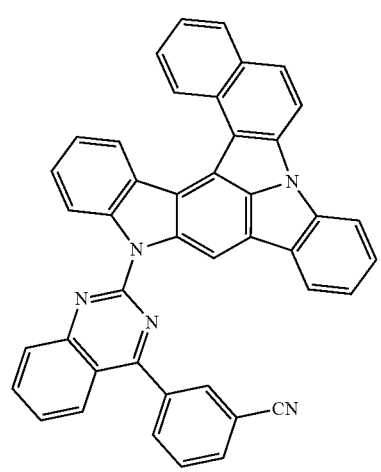
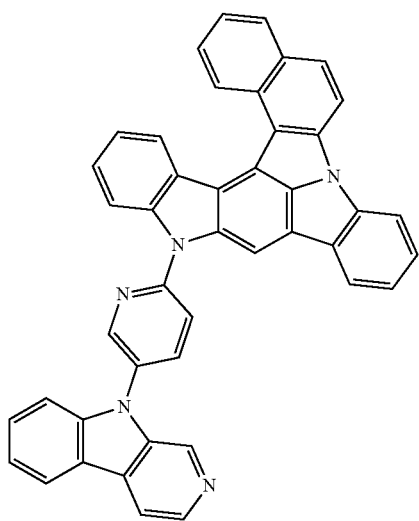
578
-continued
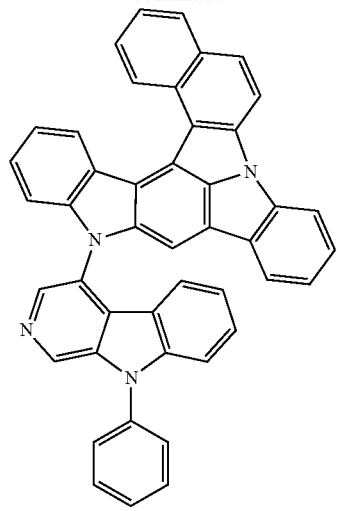
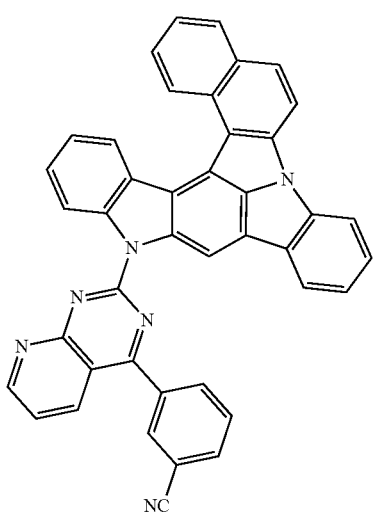
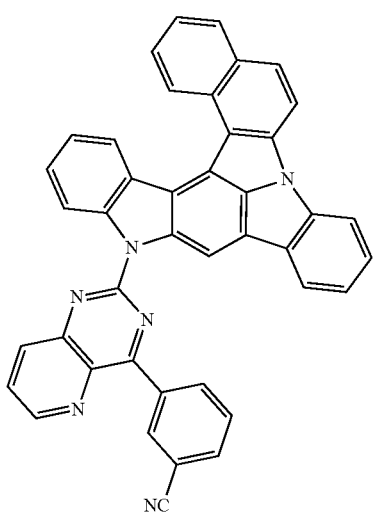

579
-continued
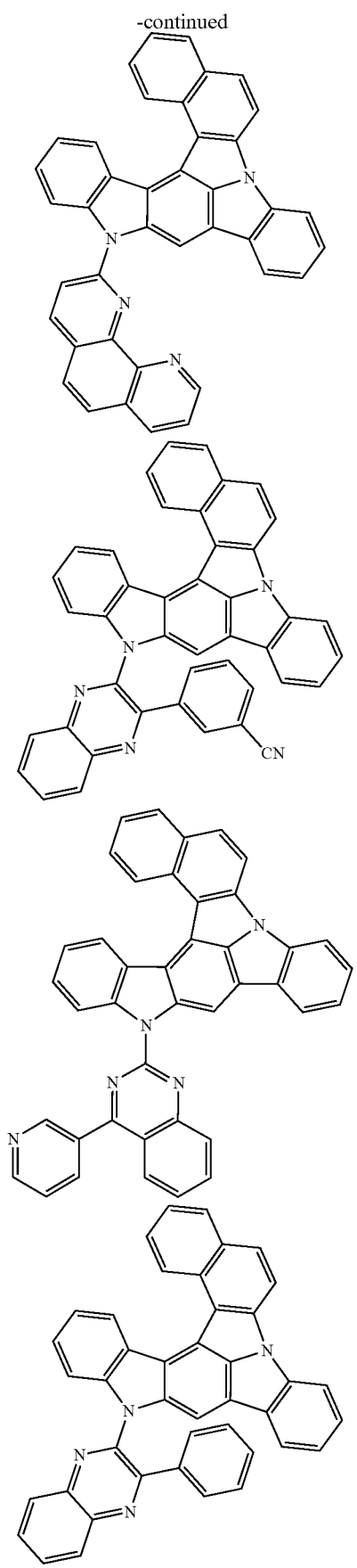
580
-continued
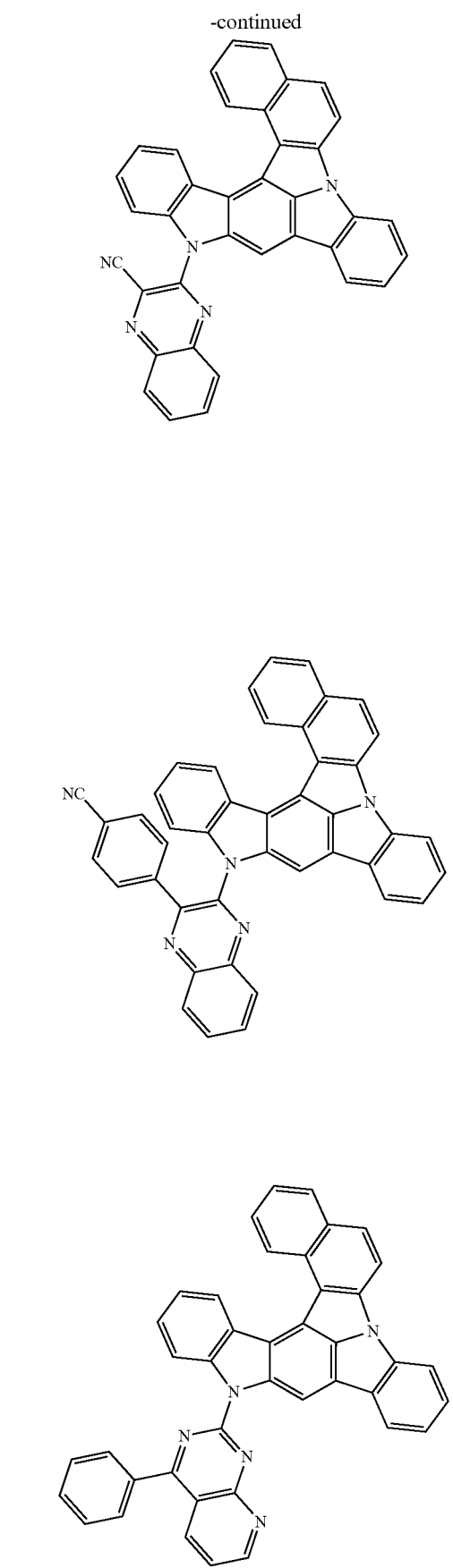

581
-continued
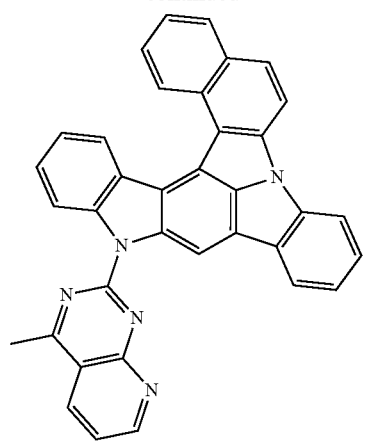
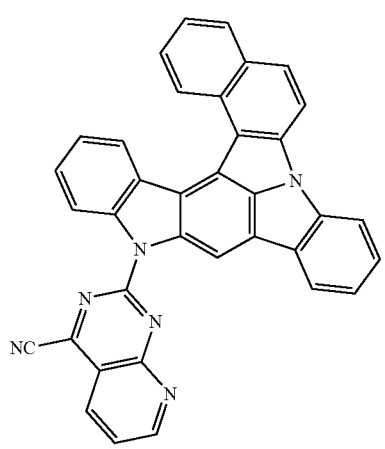
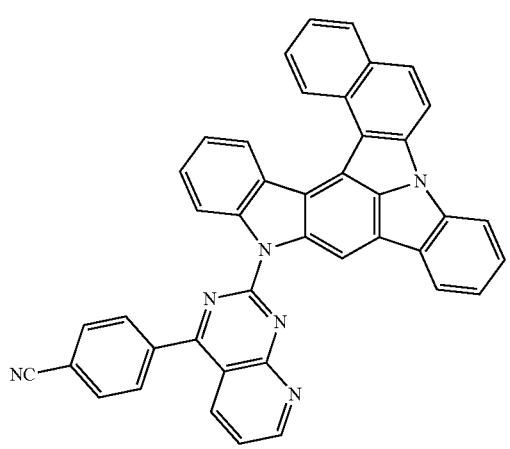
582
-continued
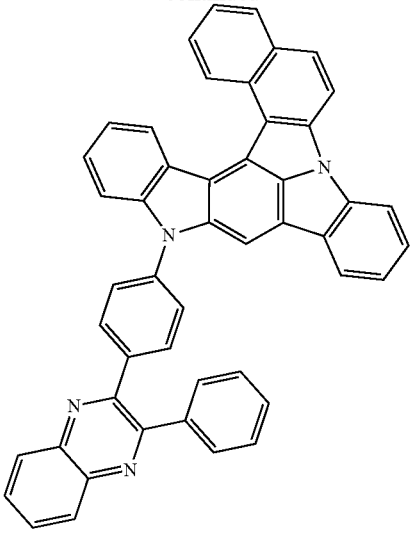
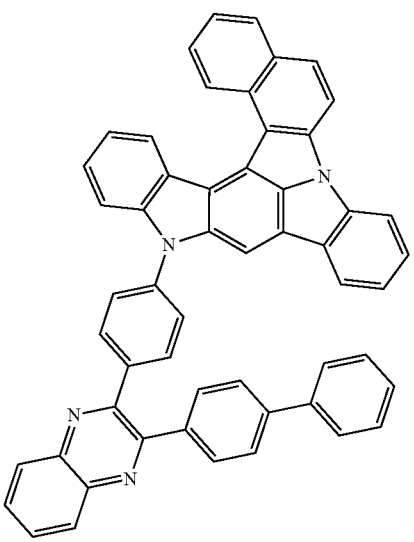
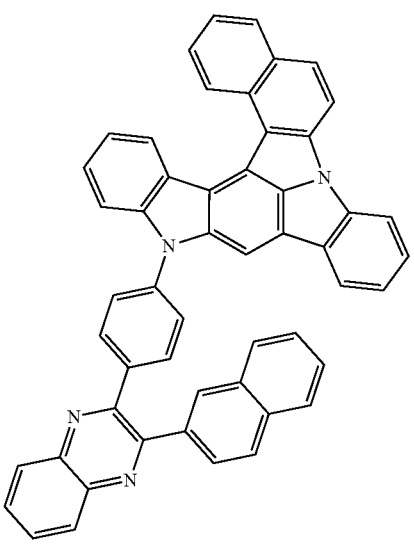

-continued
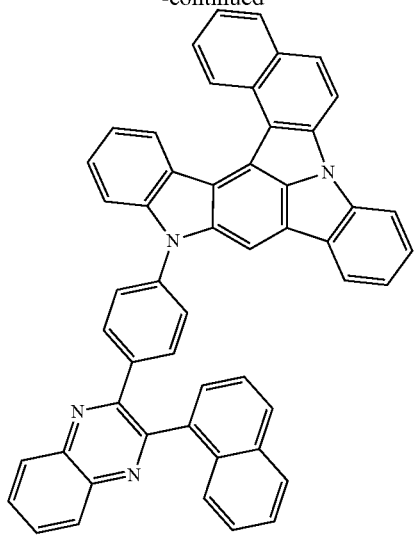
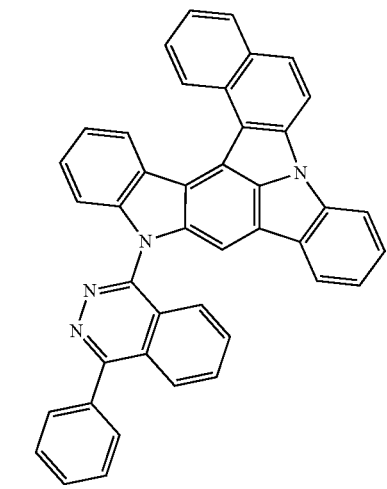
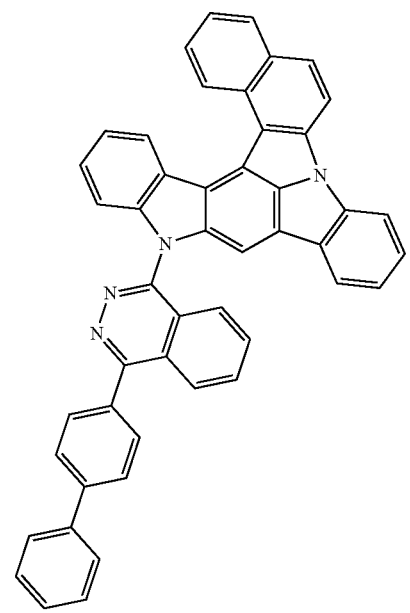
-continued
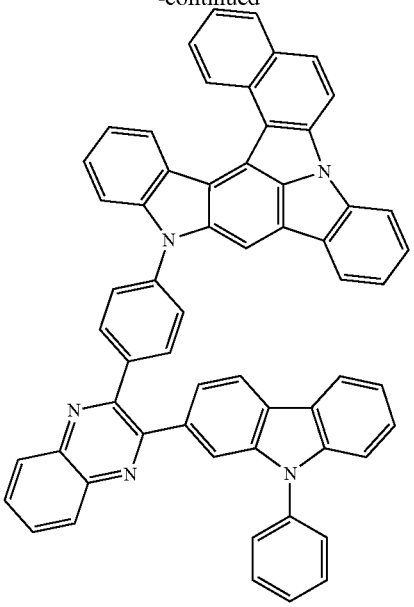
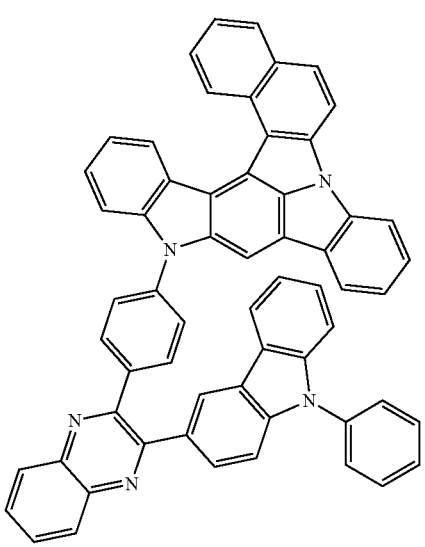
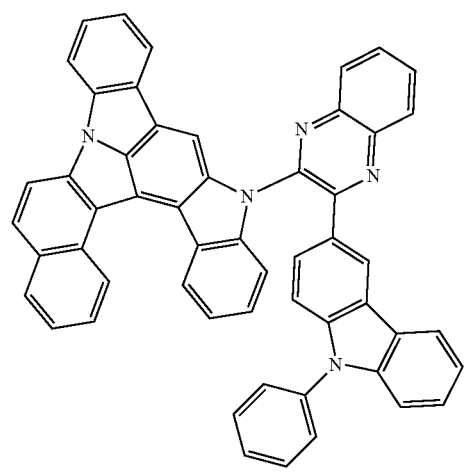

585
-continued
586
-continued
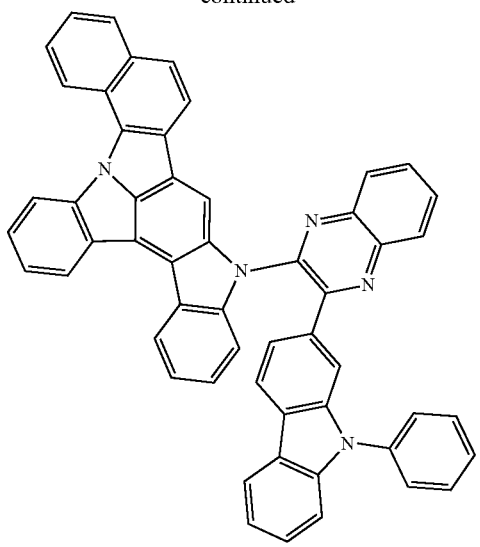
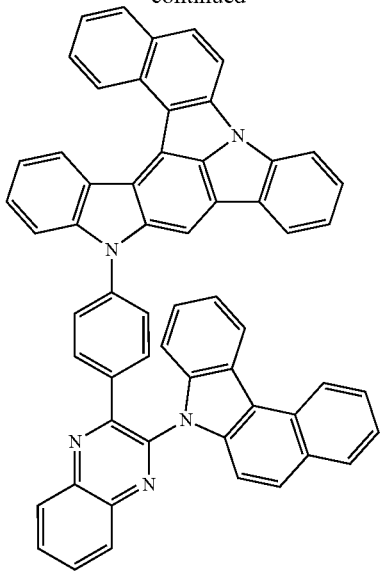
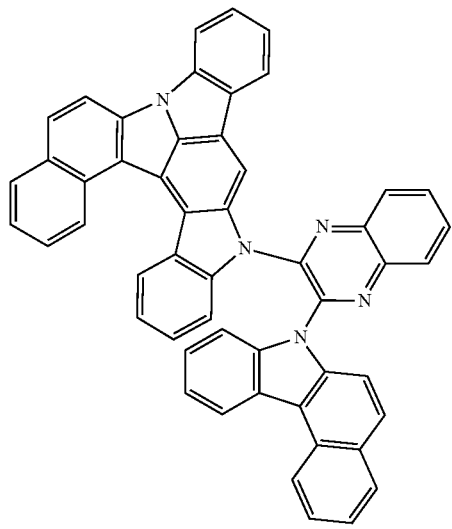
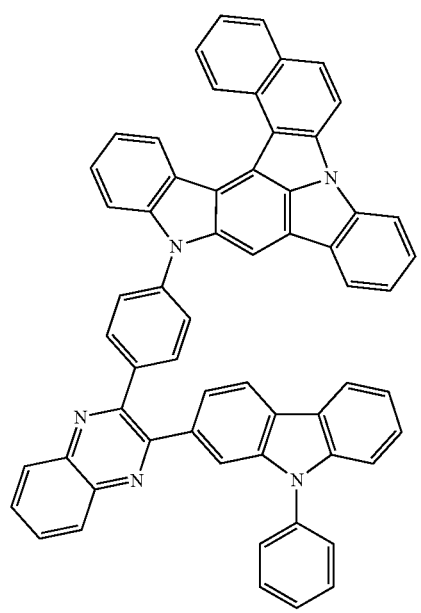
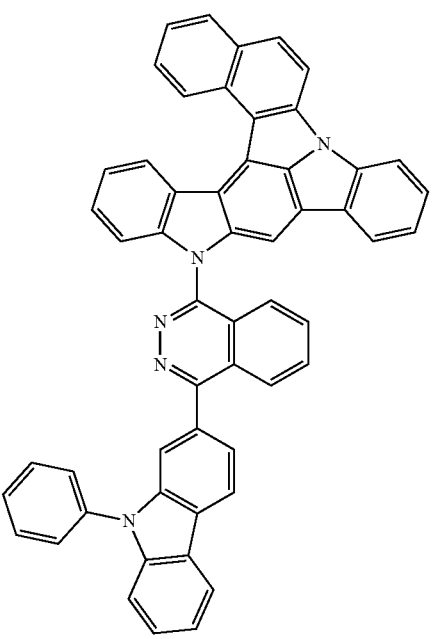

587
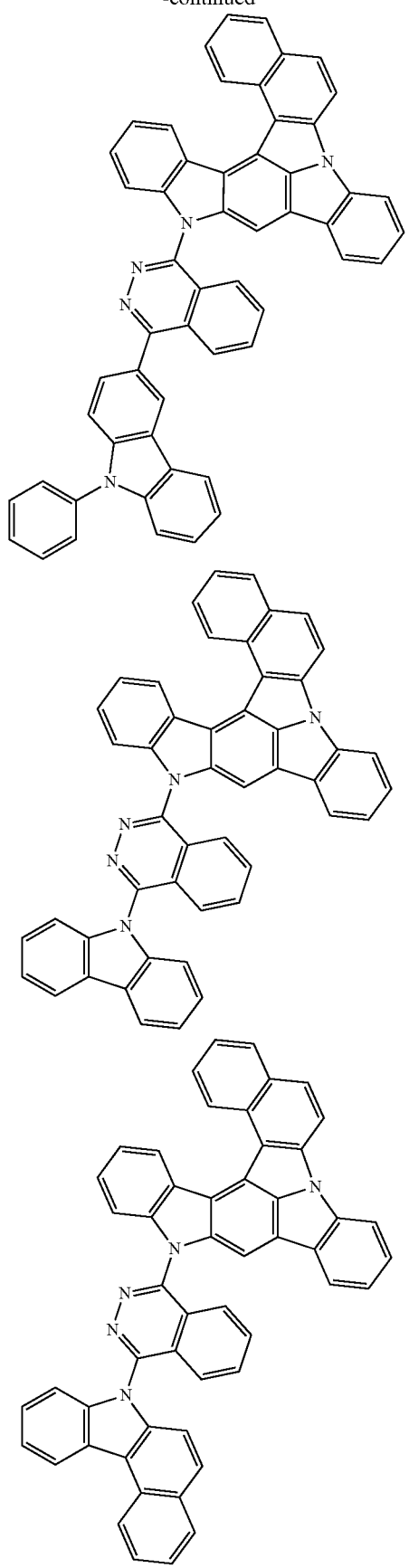
588
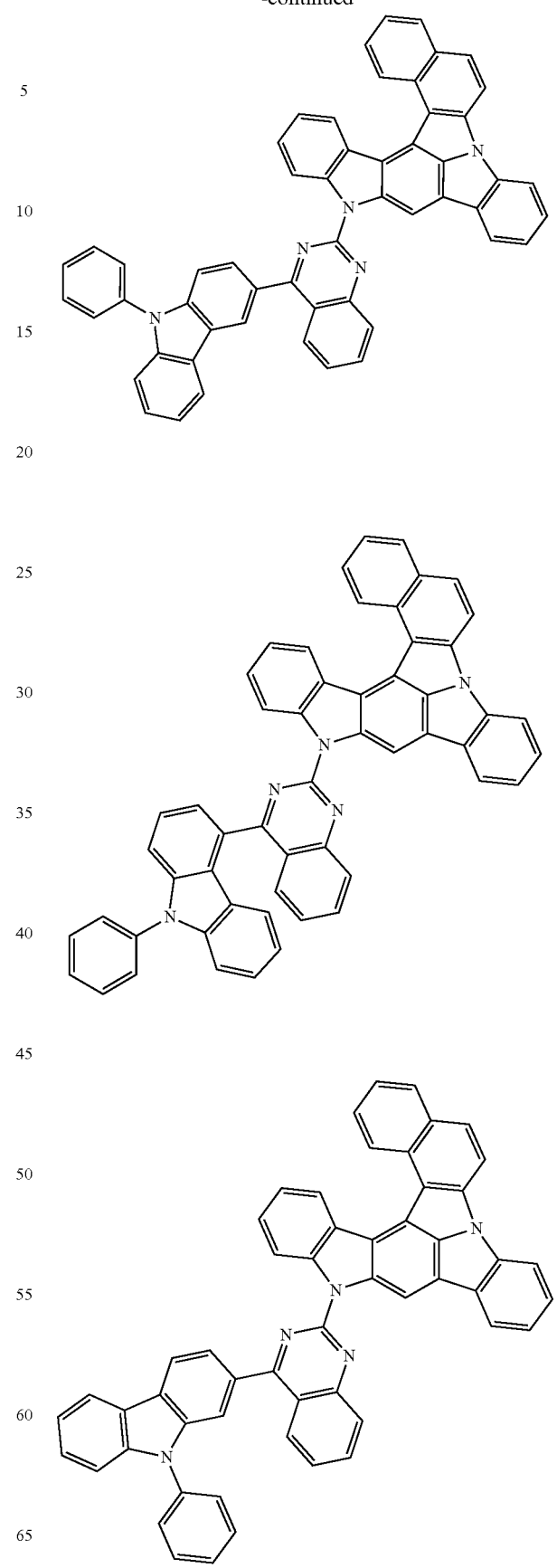

| 589 -continued | 590 -continued |
|---|---|
| 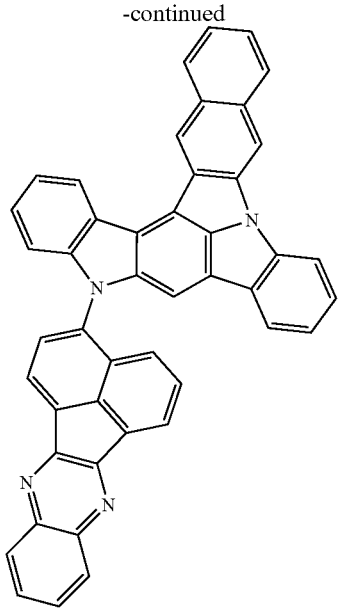 | 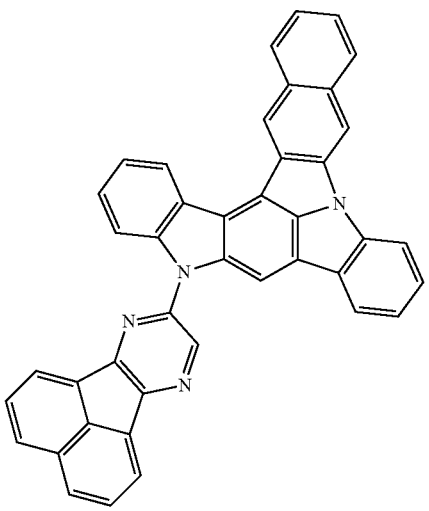 |
| | 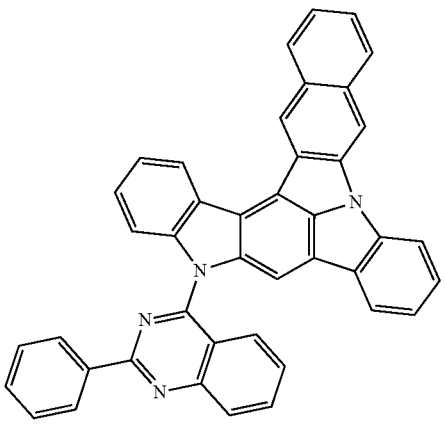 |
| | 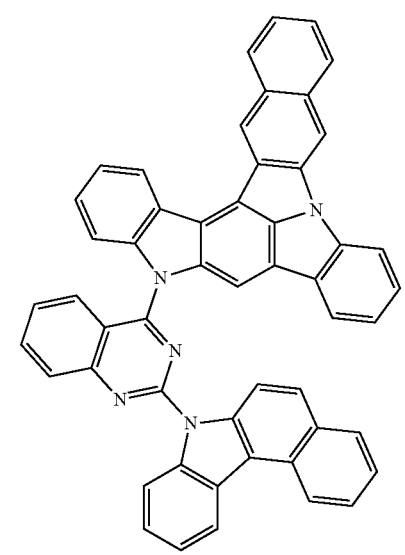 |

591
-continued
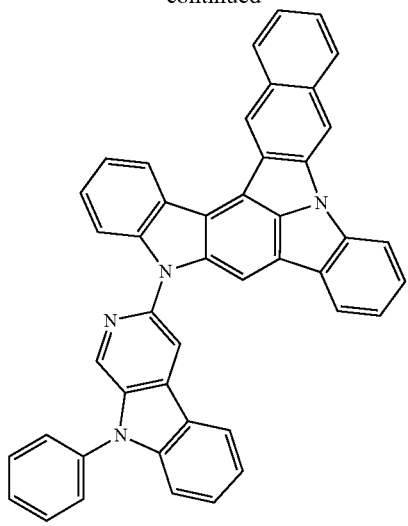
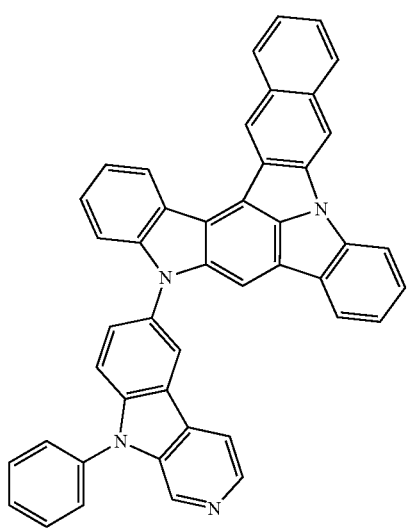
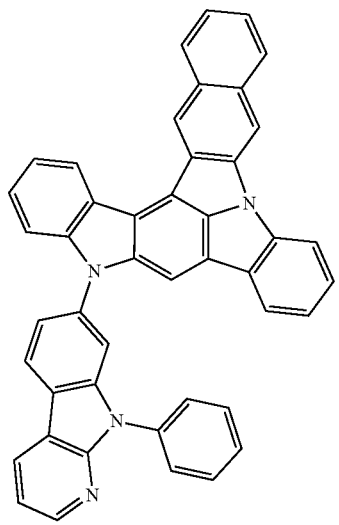
592
-continued
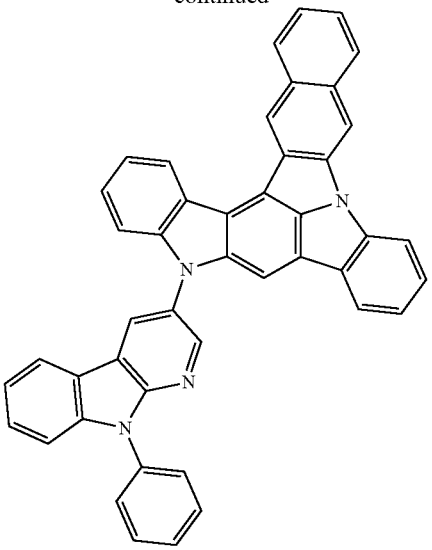
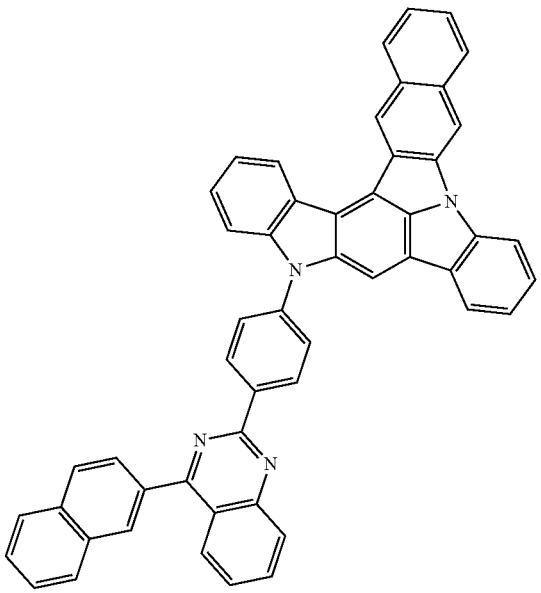
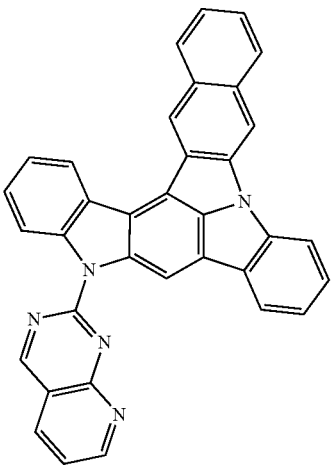

US 10,580,998 B2
593
-continued
594
-continued
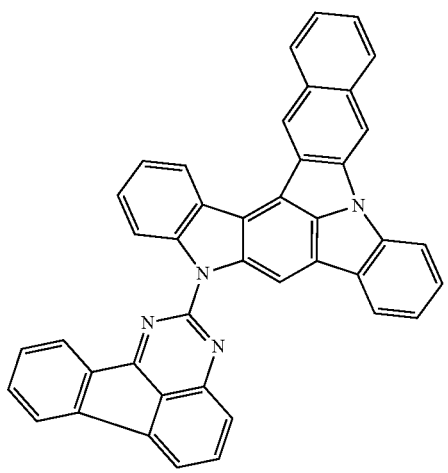
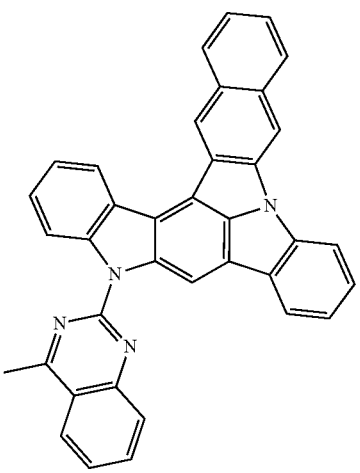
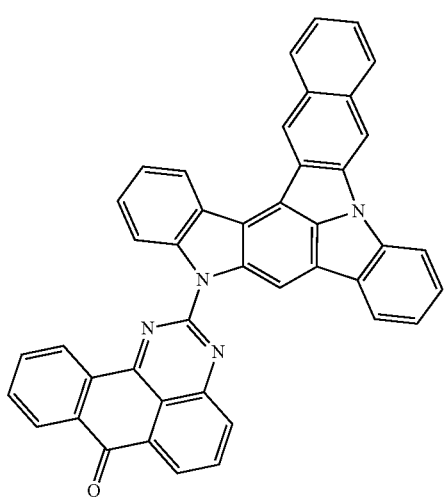
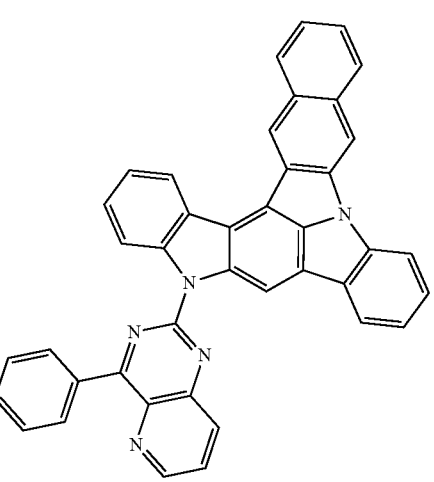
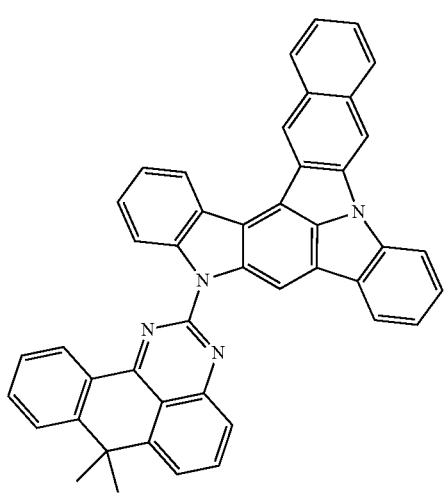
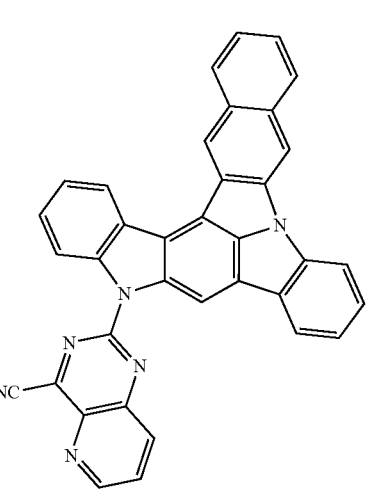

595
-continued
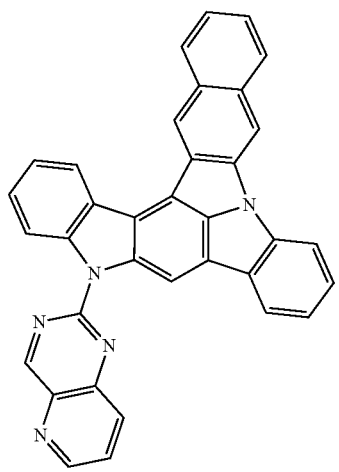
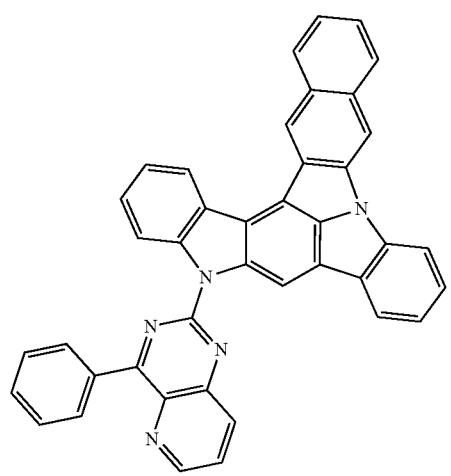
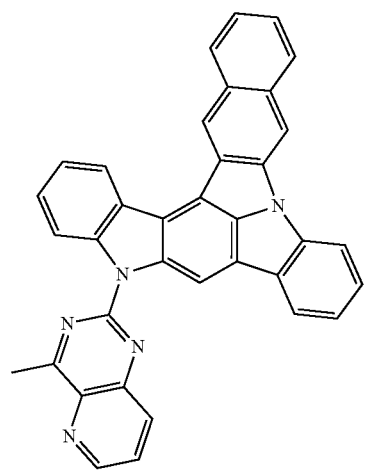
596
-continued
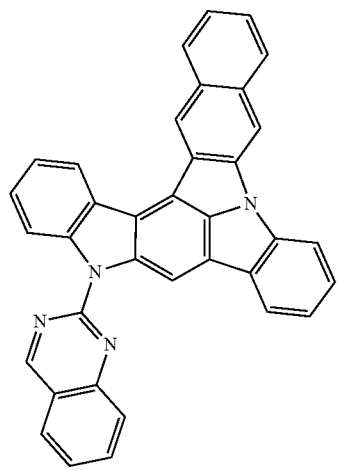
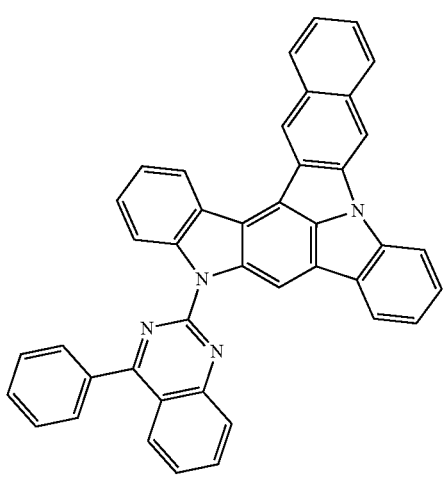
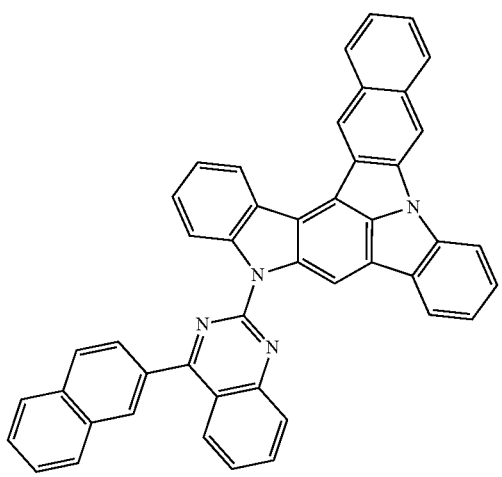

597
-continued
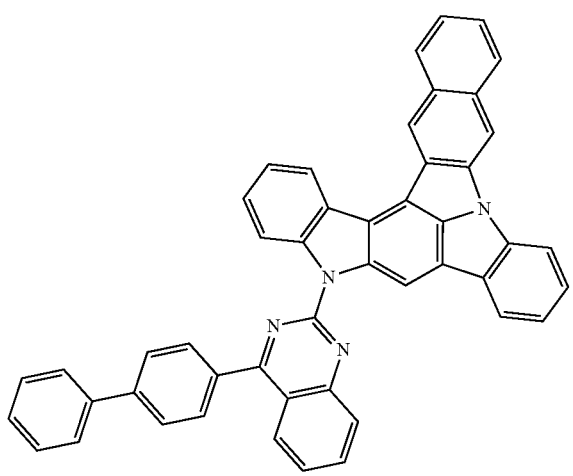
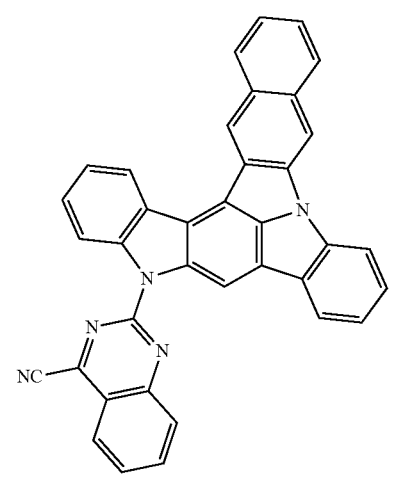
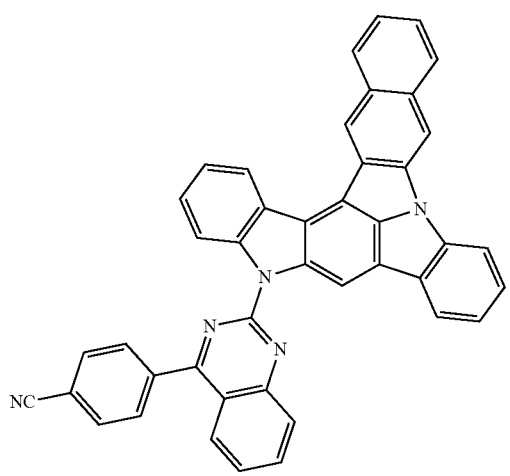
598
-continued
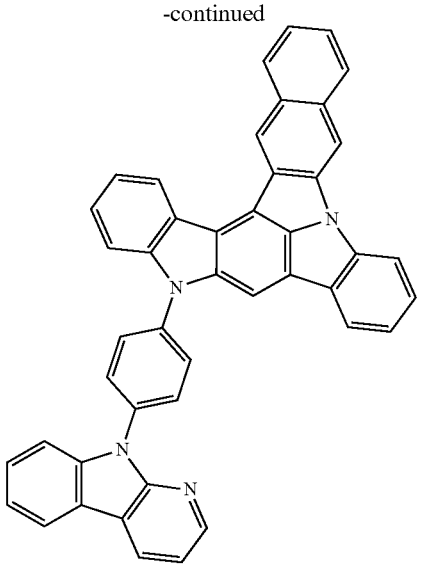
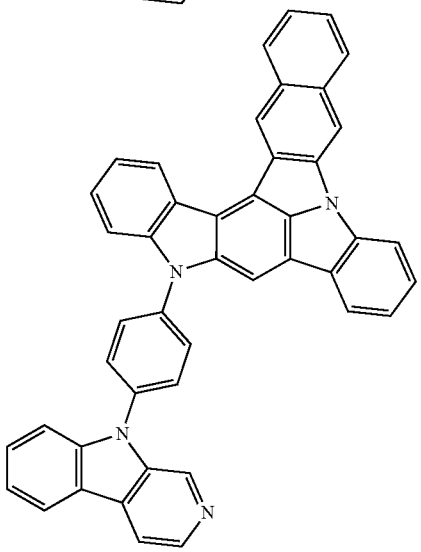
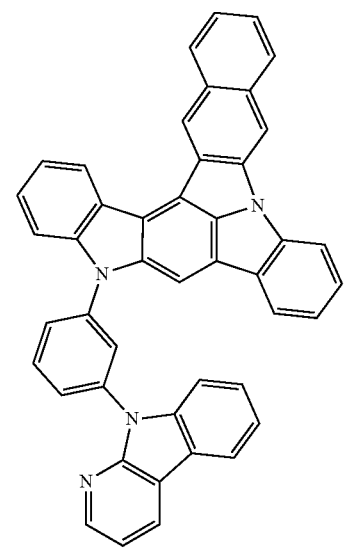

599
-continued
600
-continued
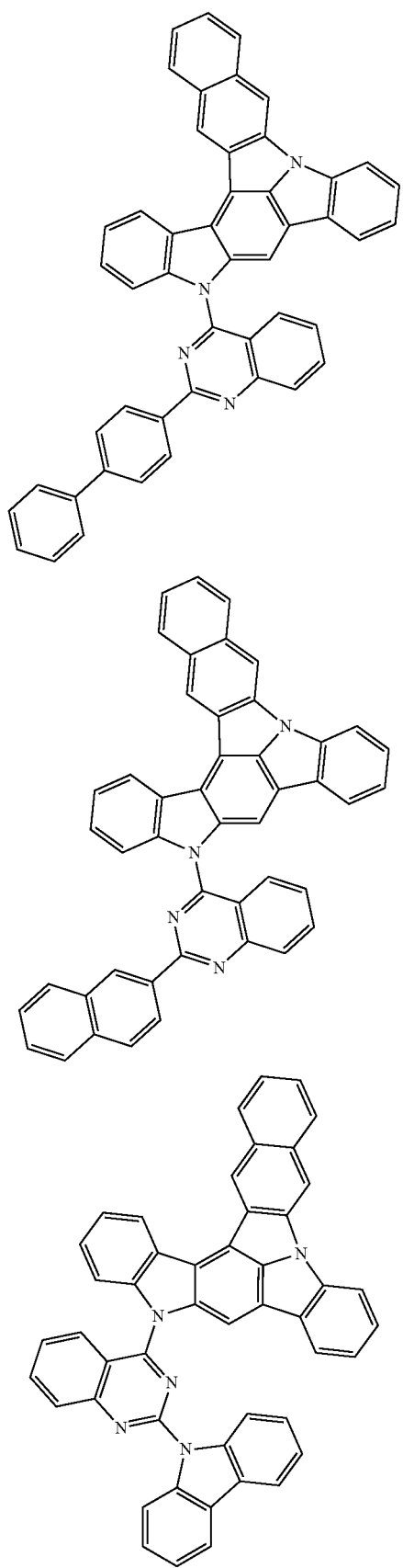

601
-continued
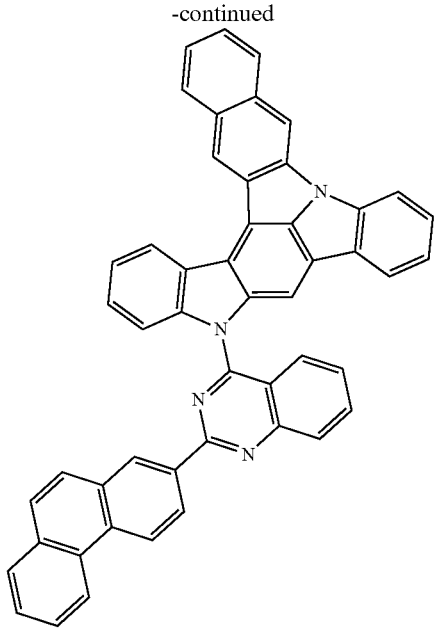
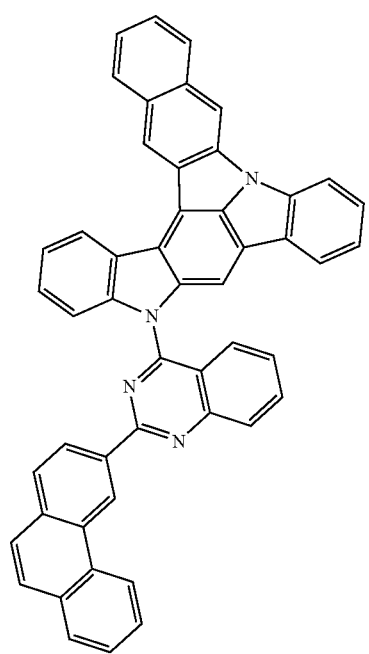
602
-continued
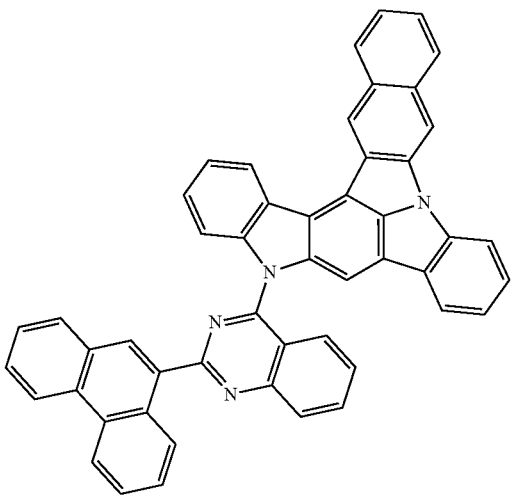
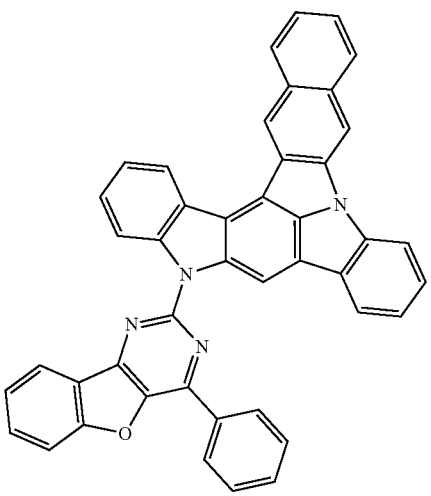
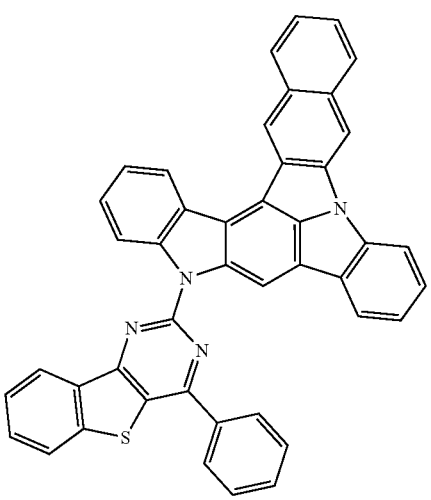

603
-continued
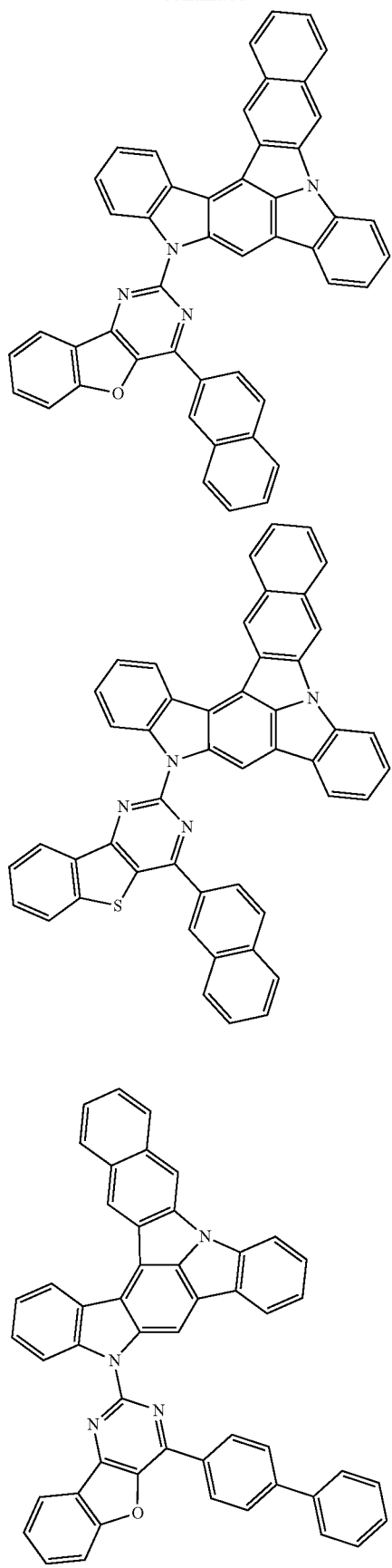
604
-continued
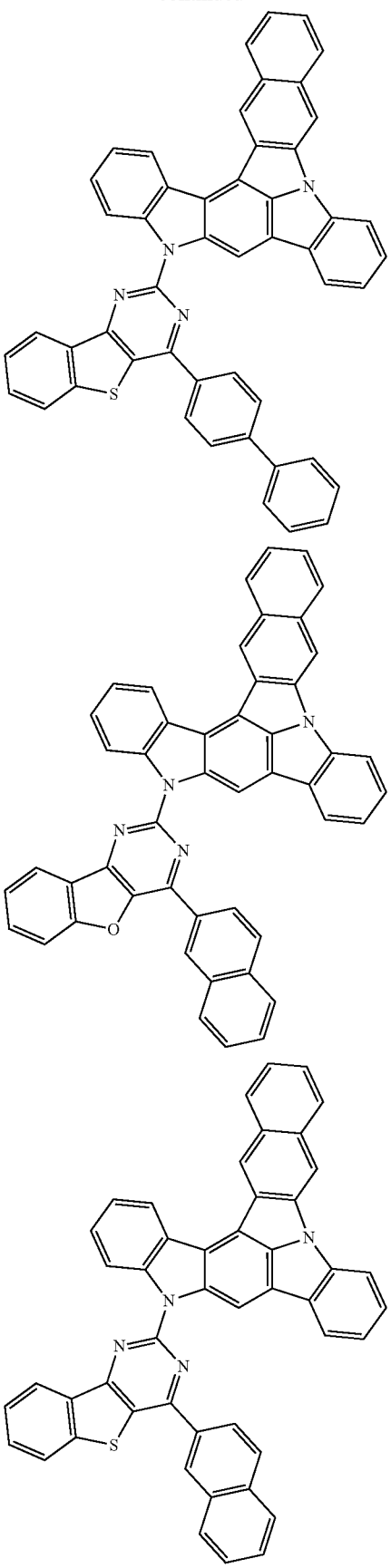

605
-continued
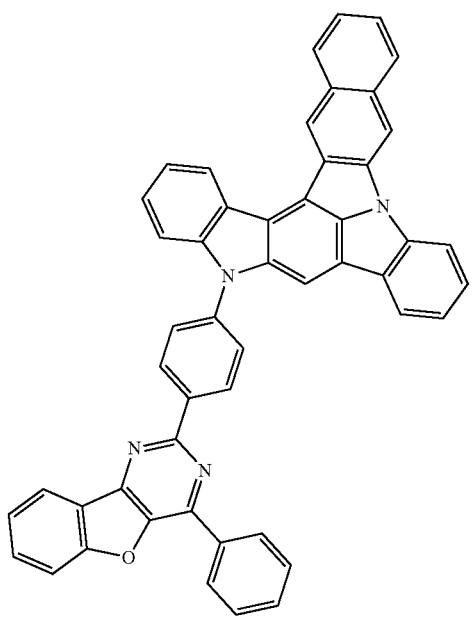
606
-continued
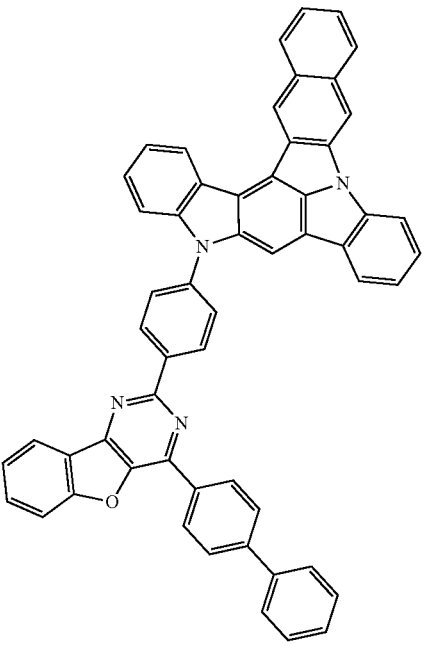
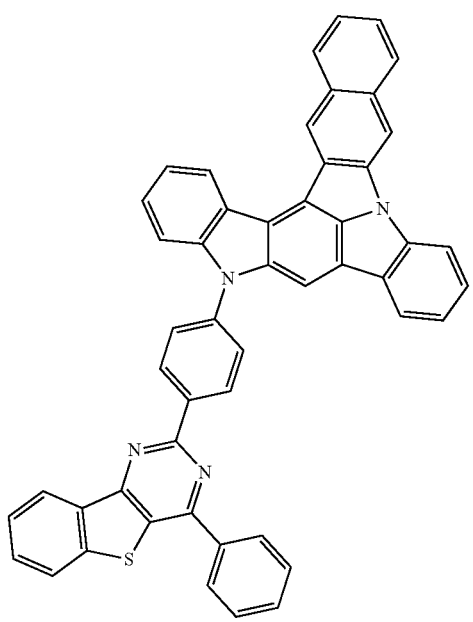
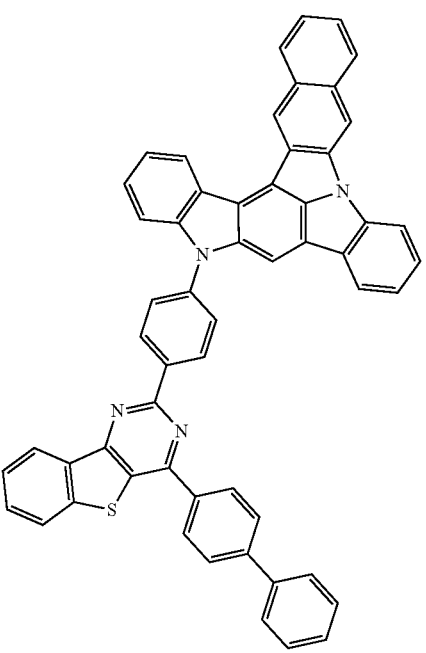

607
-continued
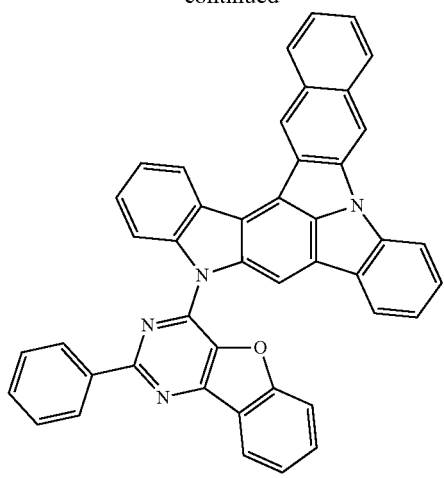
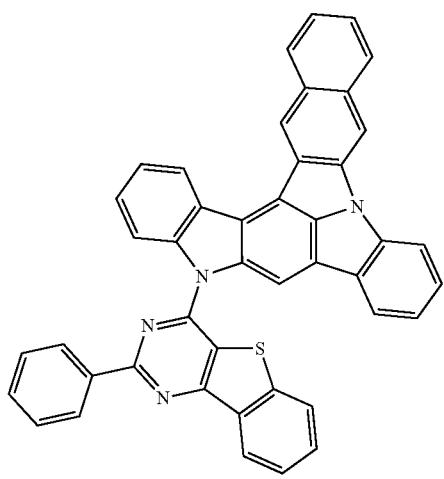
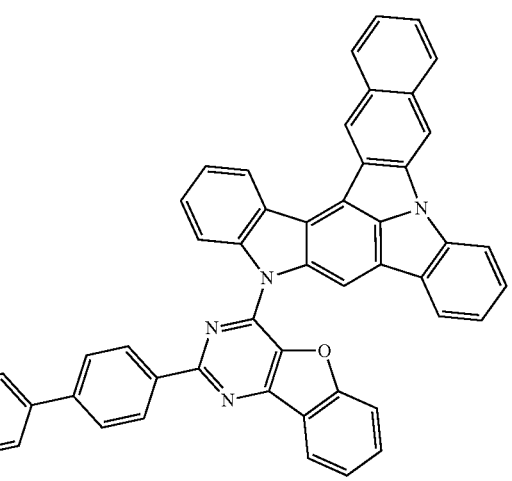
608
-continued
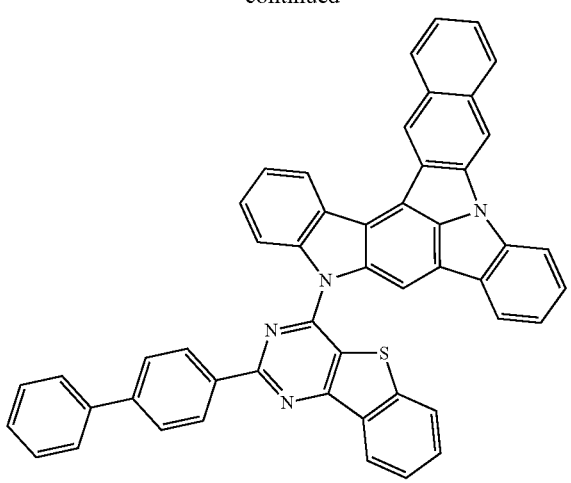
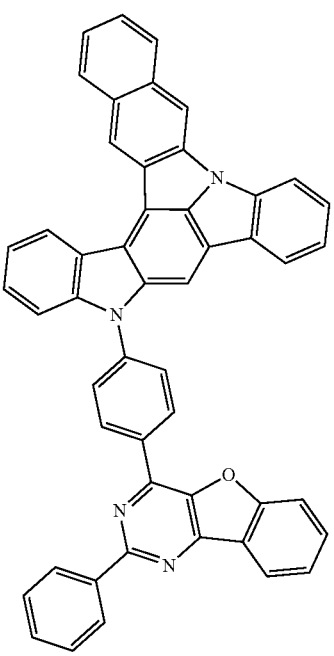
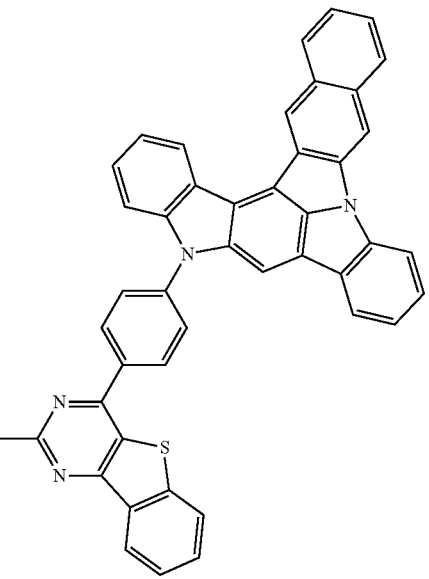

609
-continued
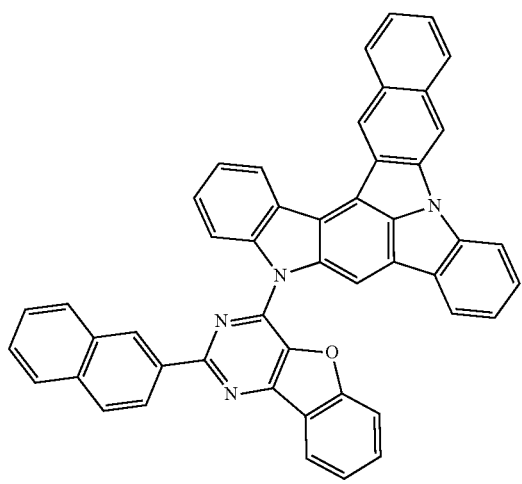
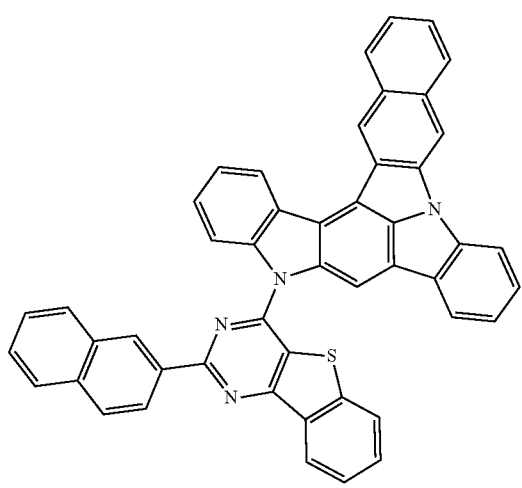
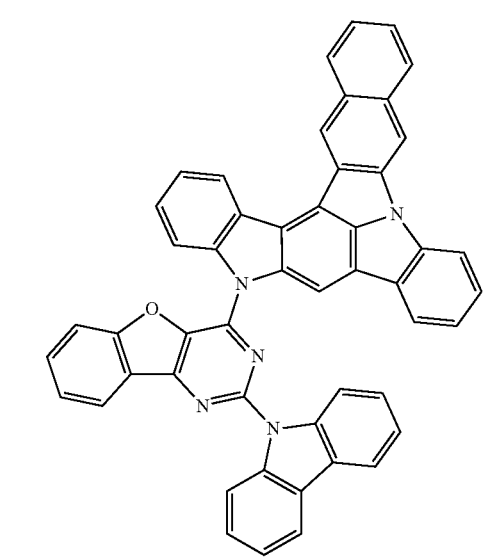
610
-continued
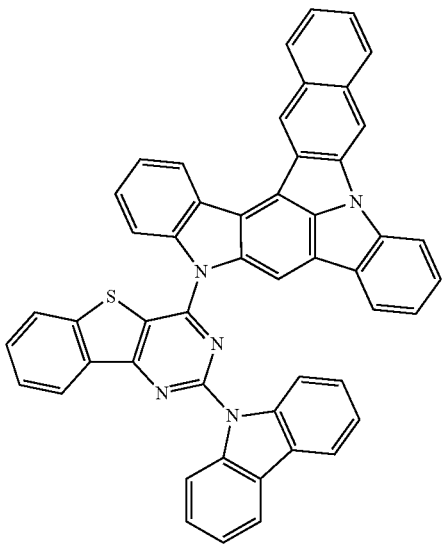
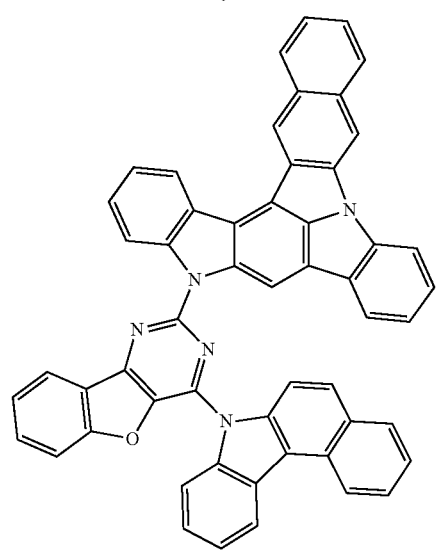
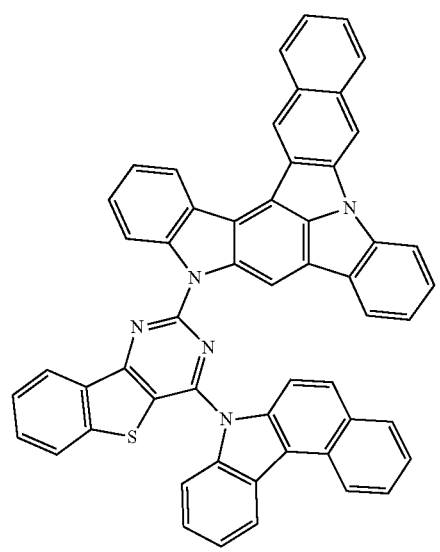

611
-continued
612
-continued
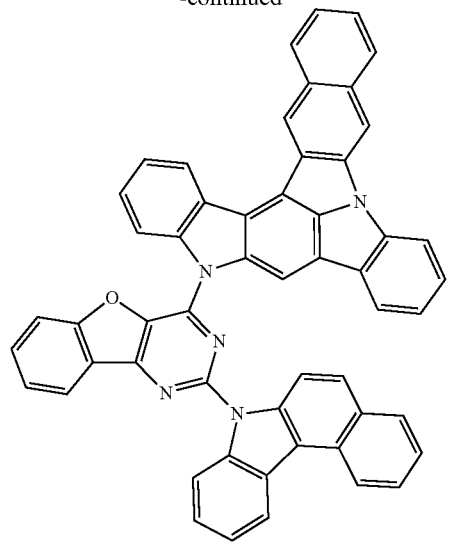
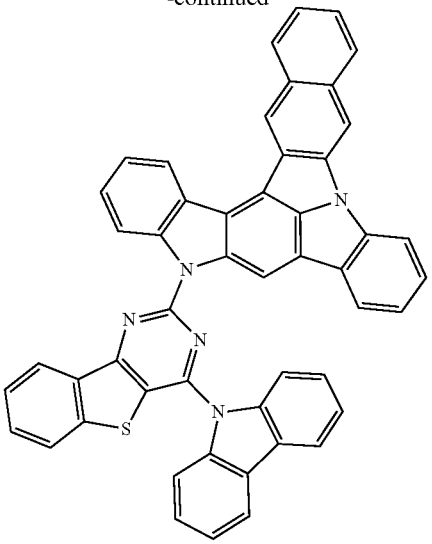
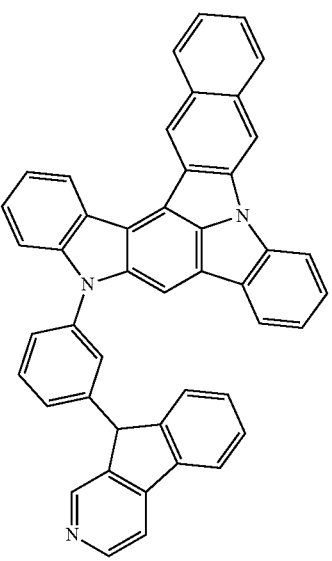

613
-continued

614
-continued

615
-continued
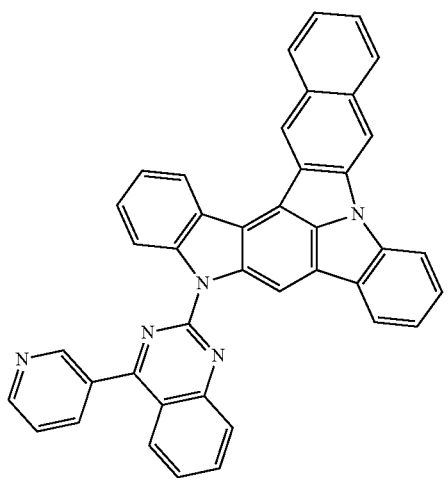
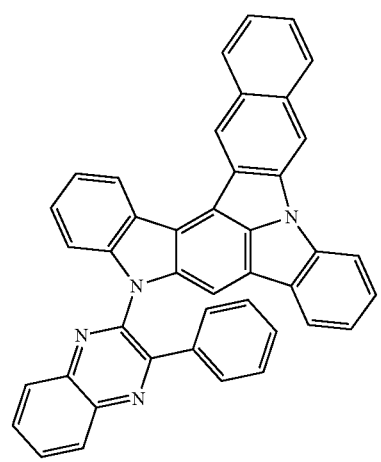
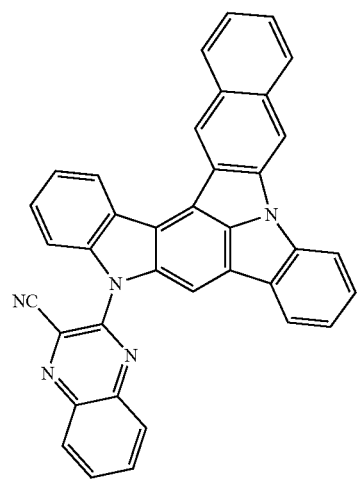
616
-continued
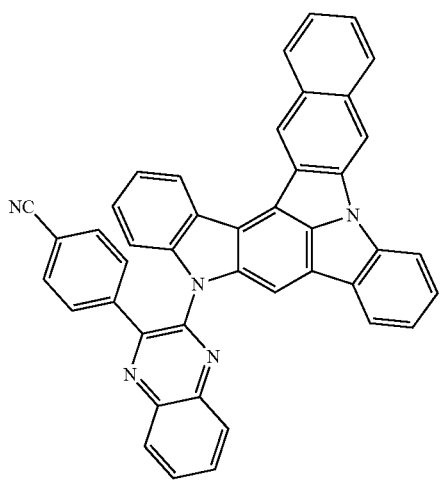
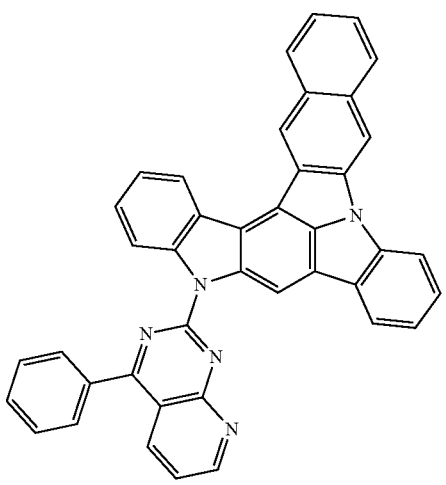
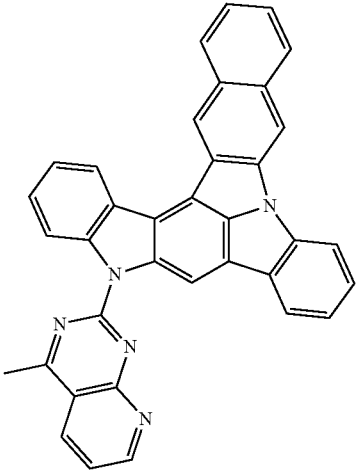

617
-continued
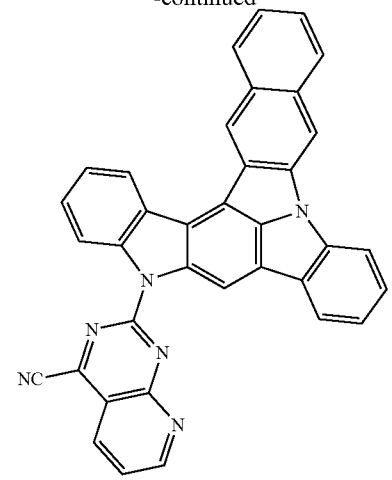
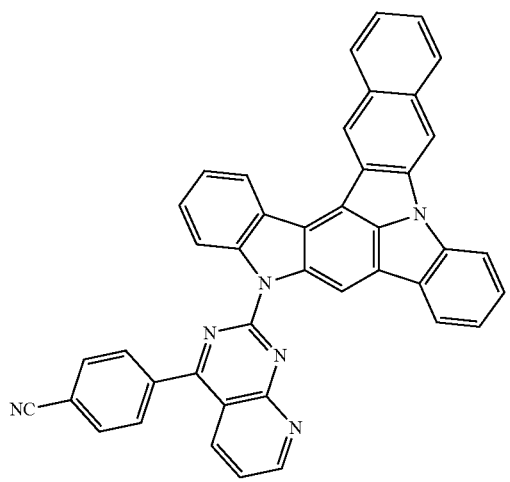
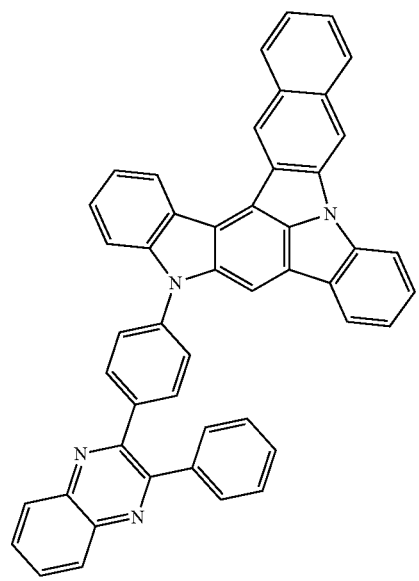
618
-continued
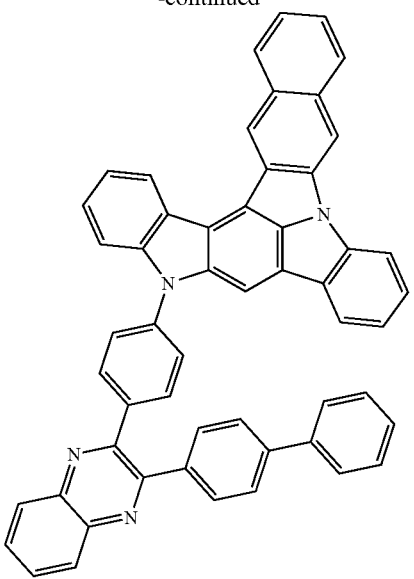
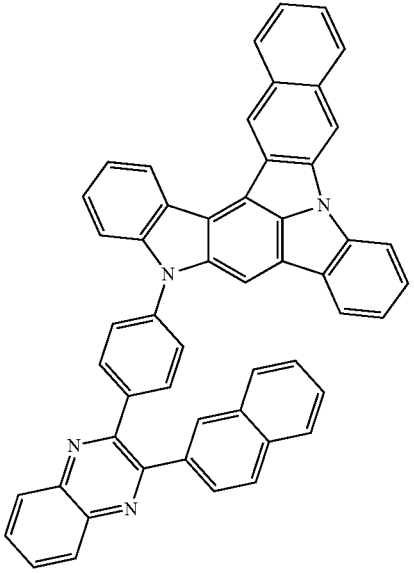
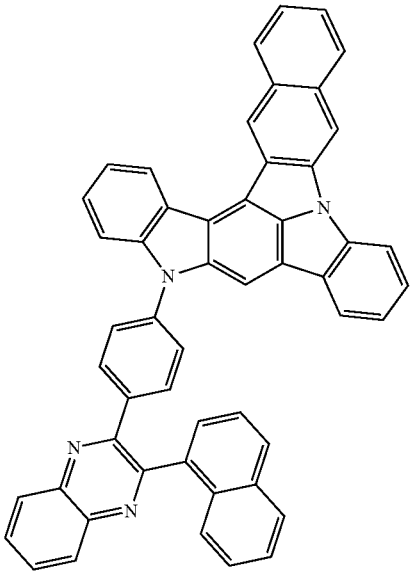

619
-continued
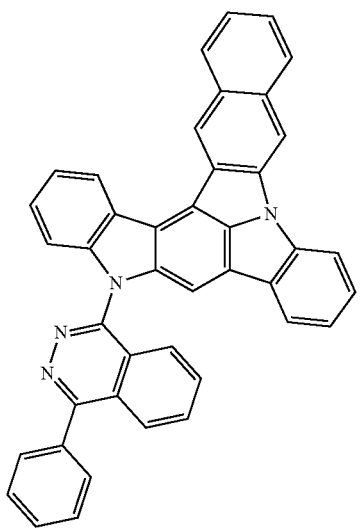
620
-continued
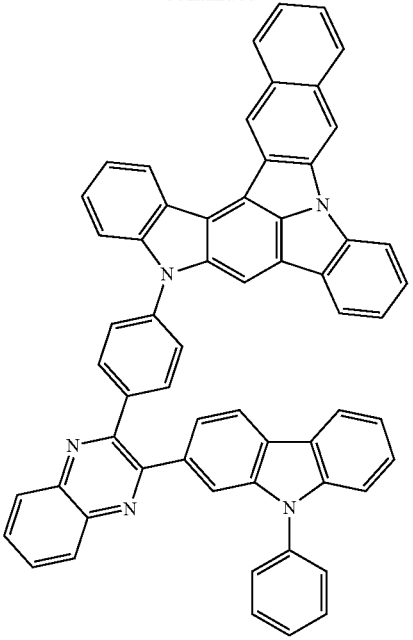
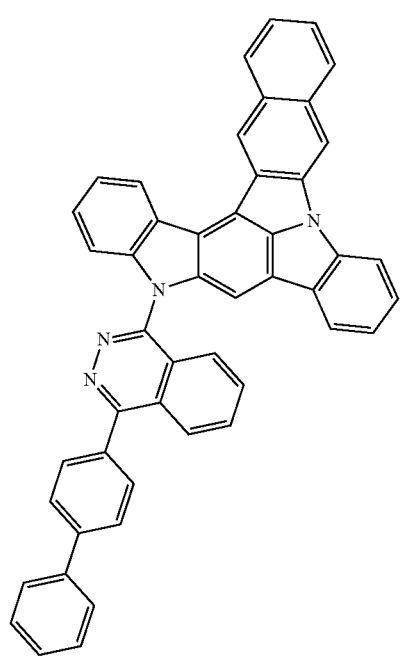
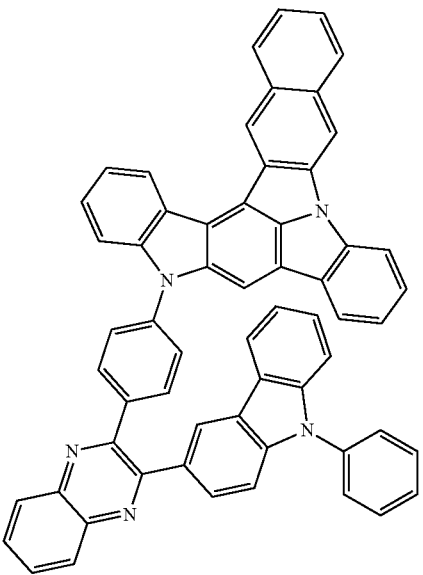

621
-continued
622
-continued
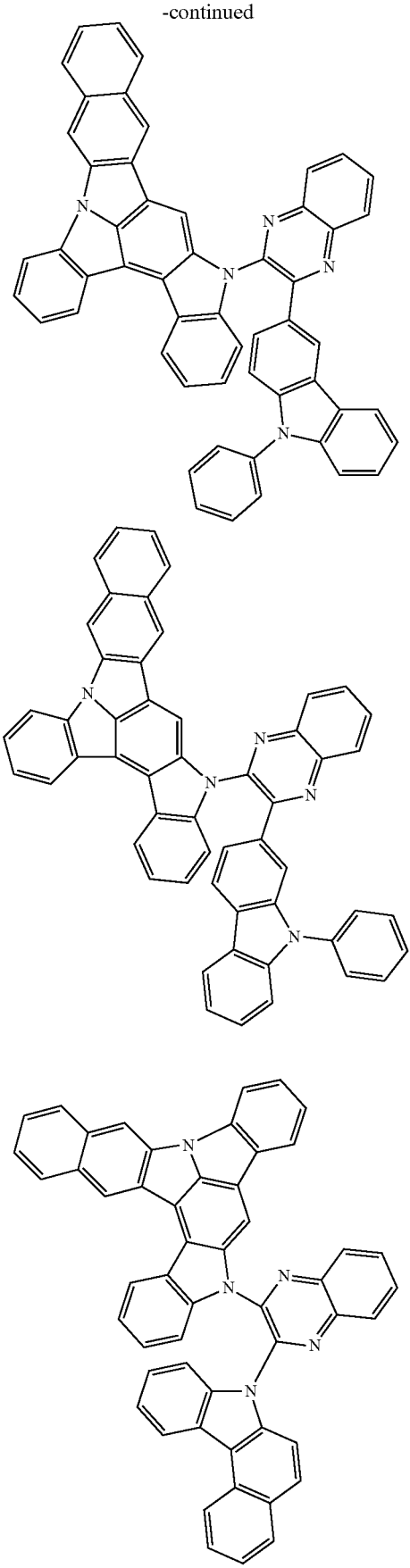

623
-continued
624
-continued
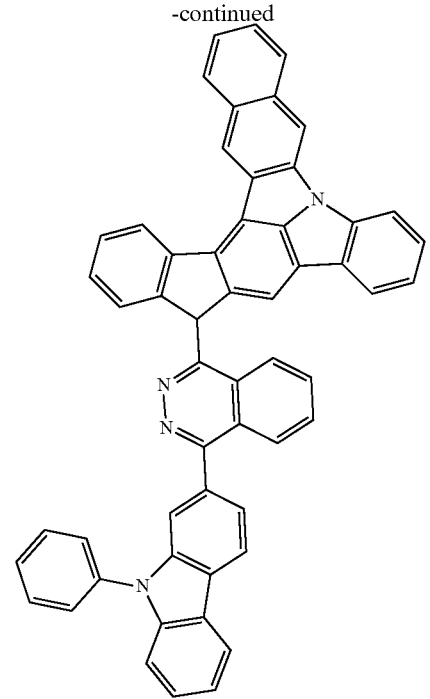
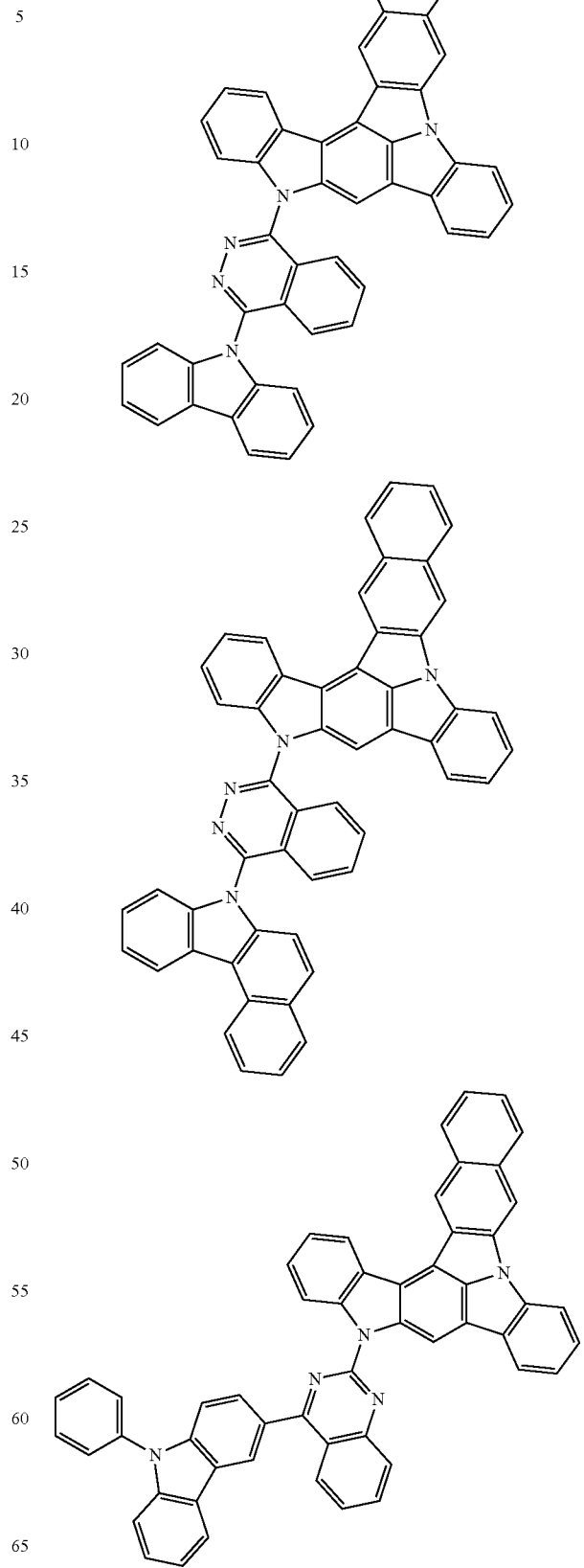

US 10,580,998 B2
625
-continued
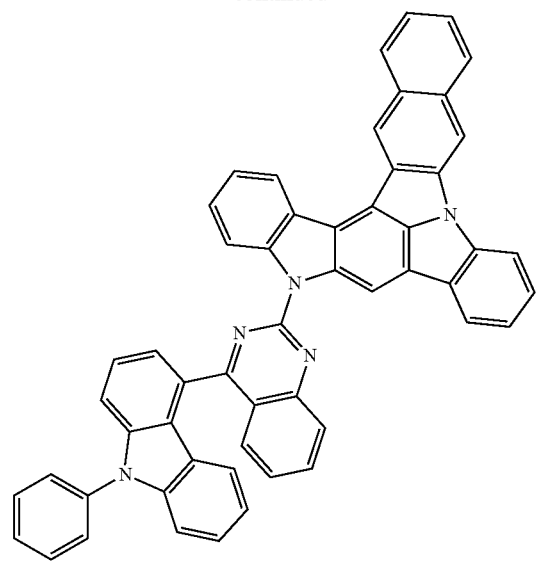
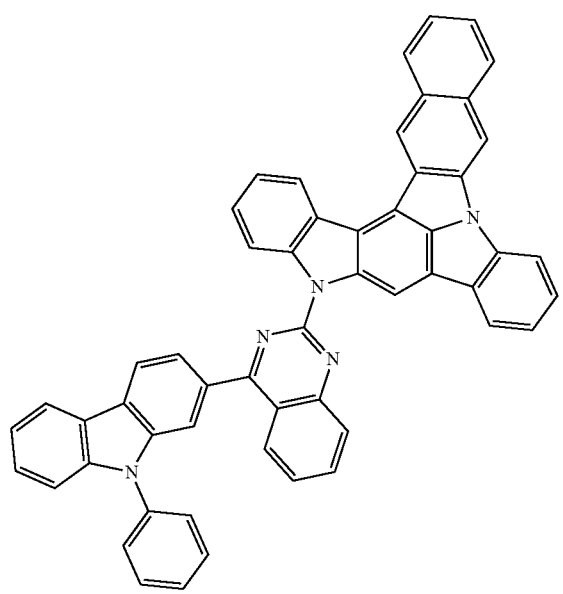
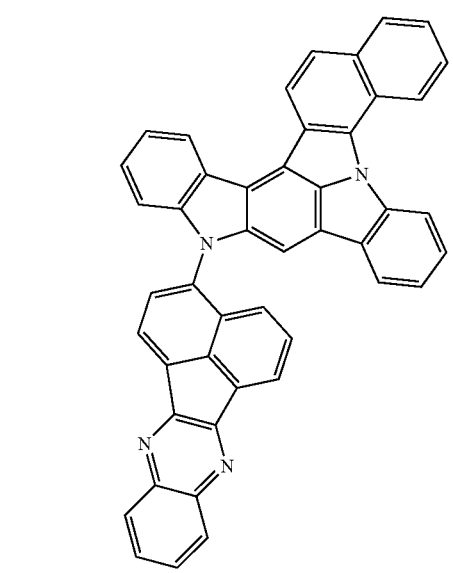
626
-continued
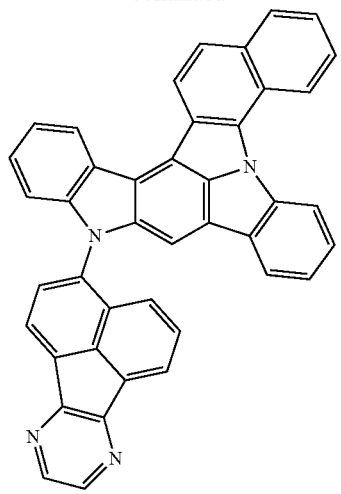
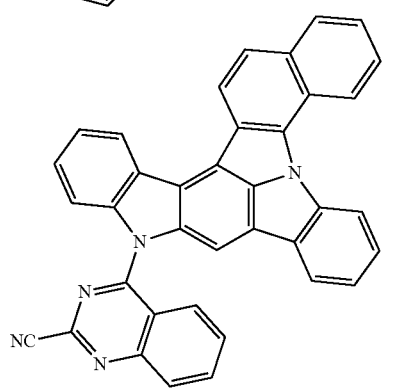
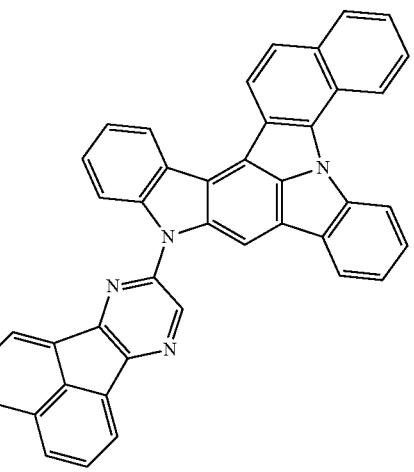
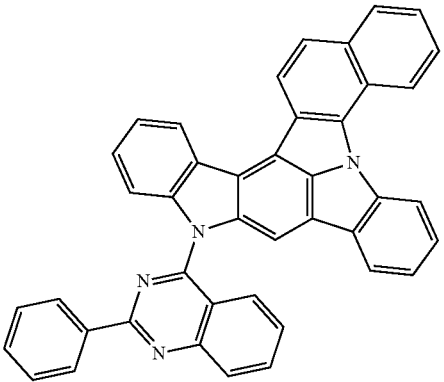

627
-continued
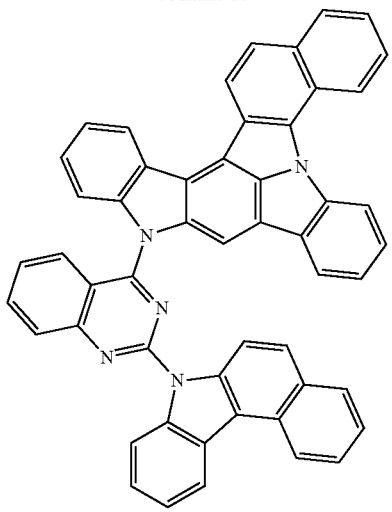
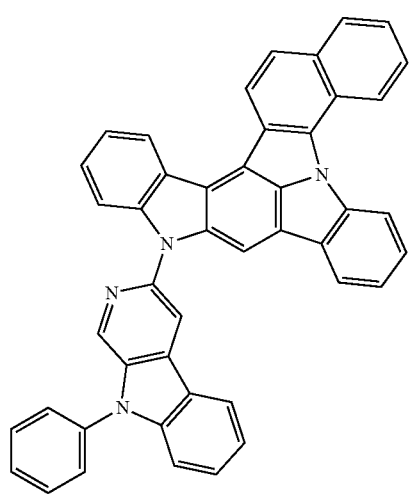
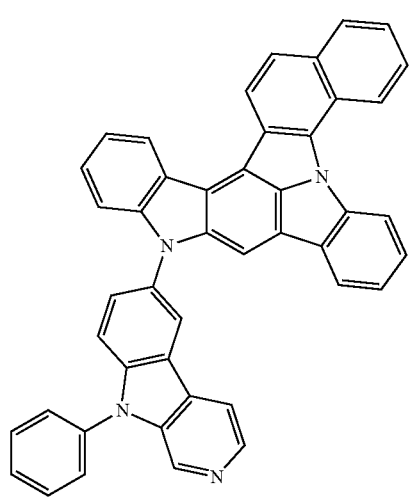
628
-continued
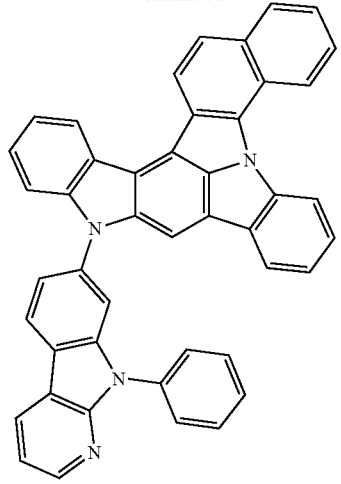
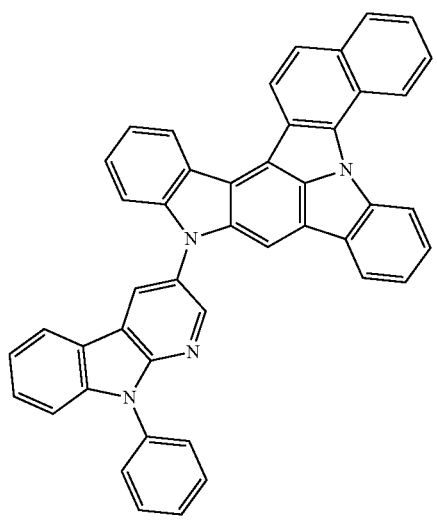
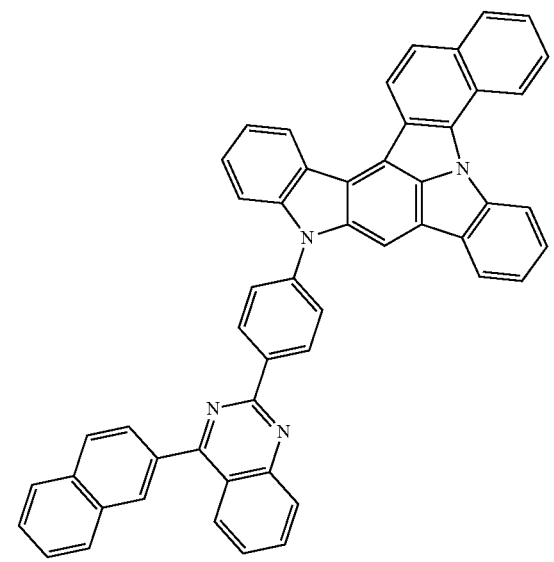

629
-continued
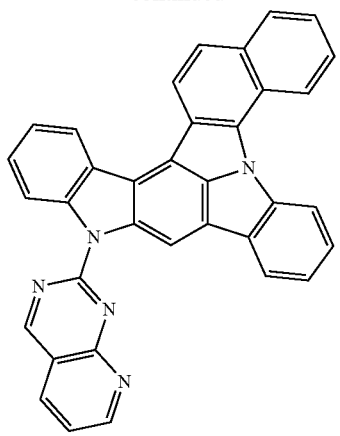
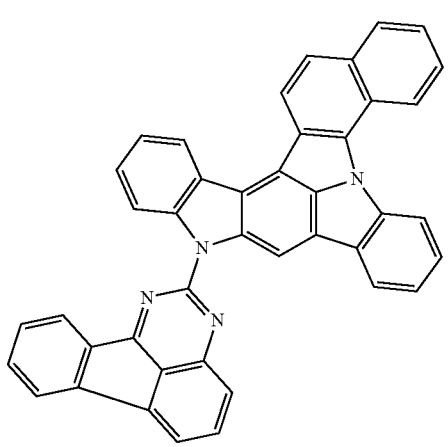
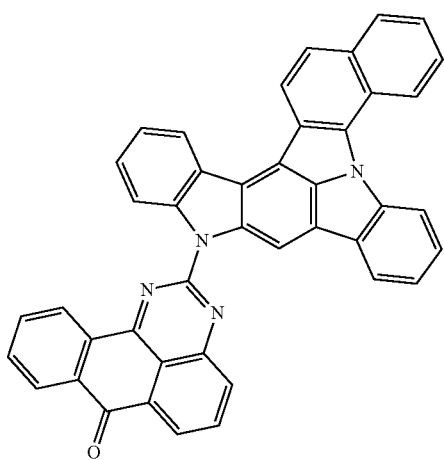
630
-continued
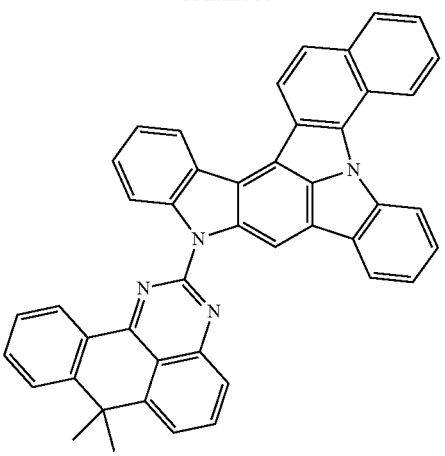
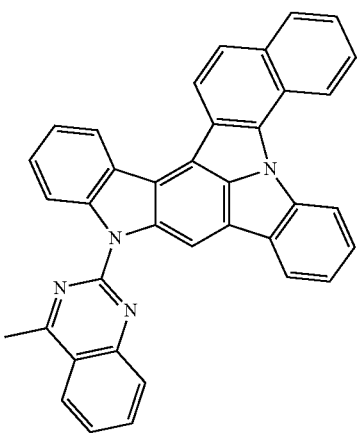
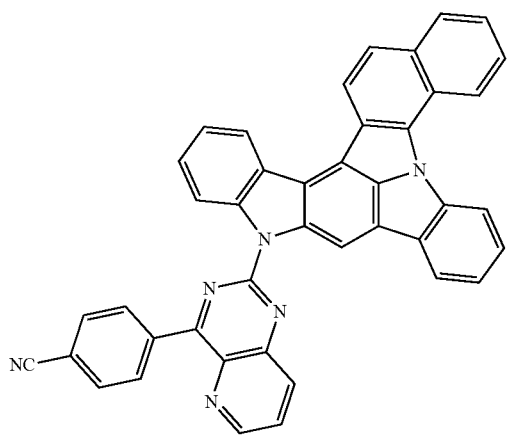

631
-continued
632
-continued
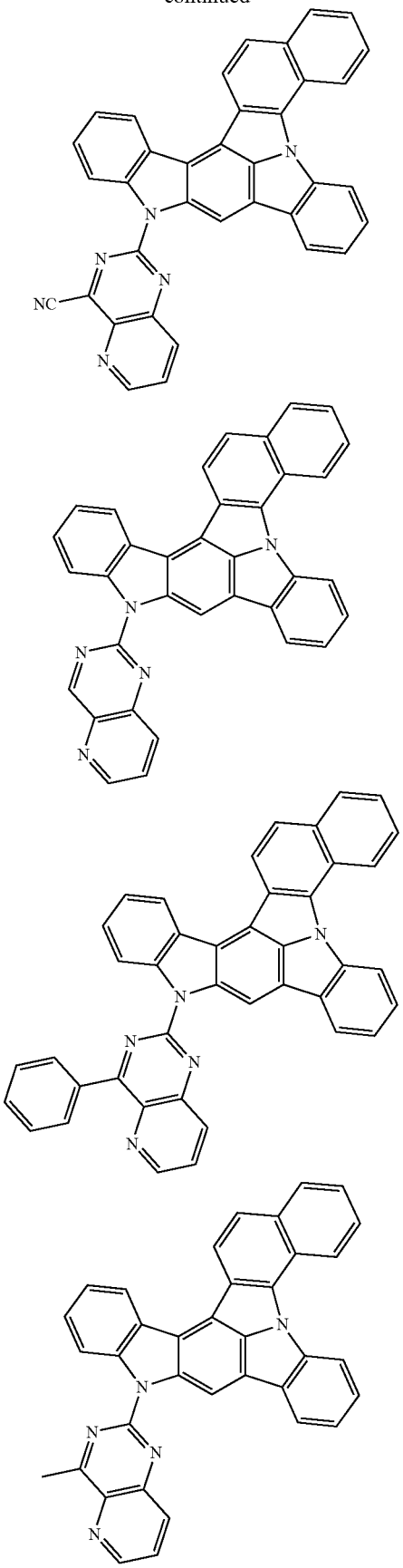
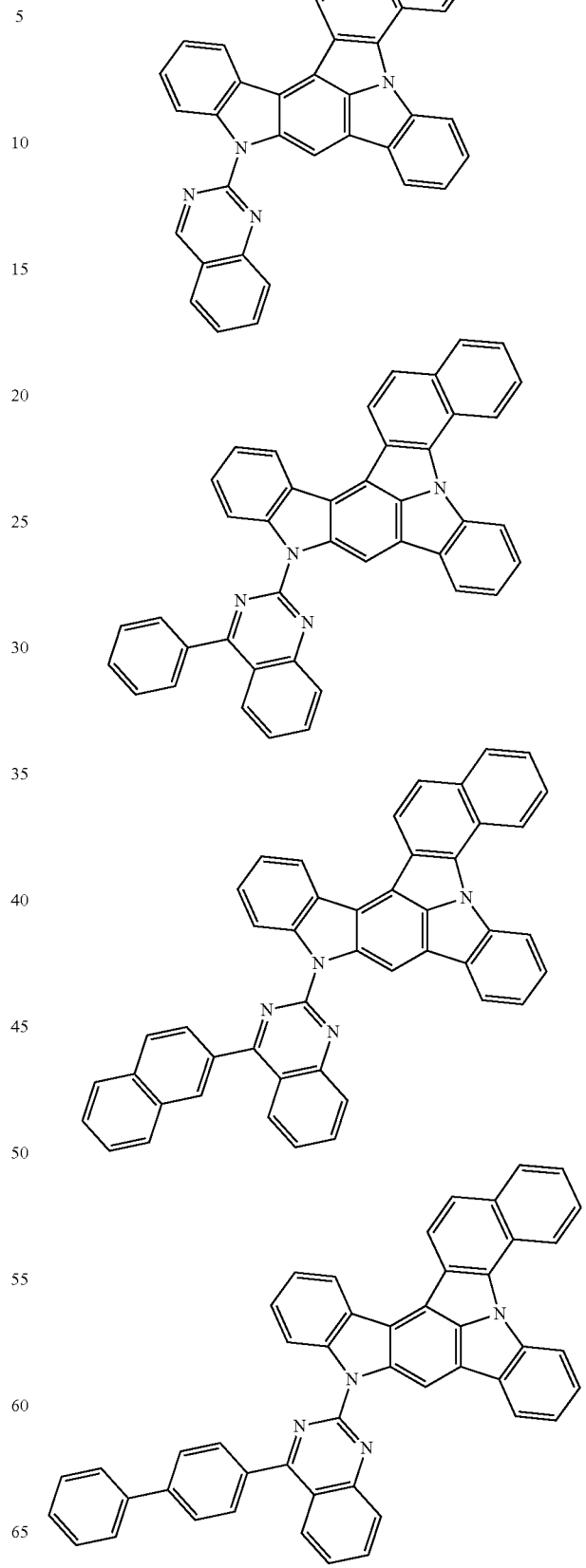

633
-continued
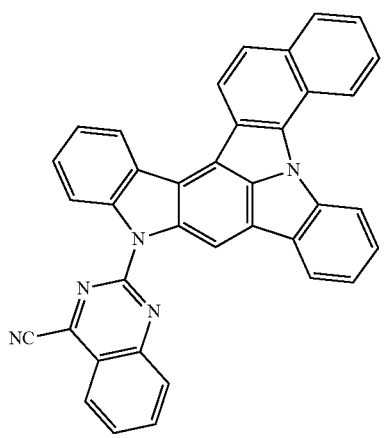
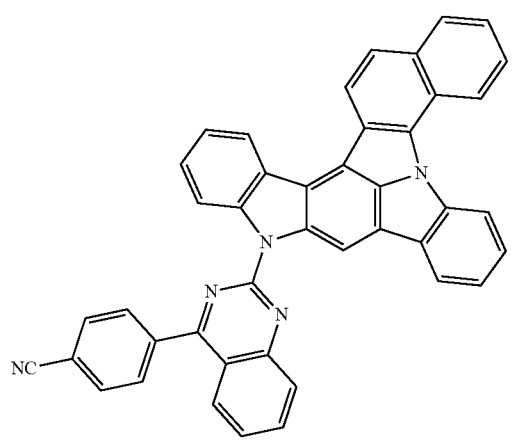
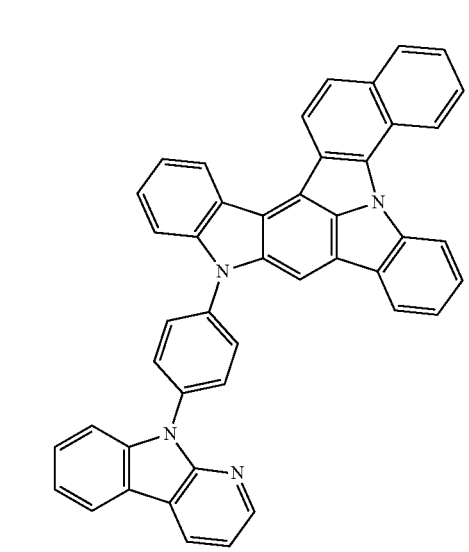
634
-continued
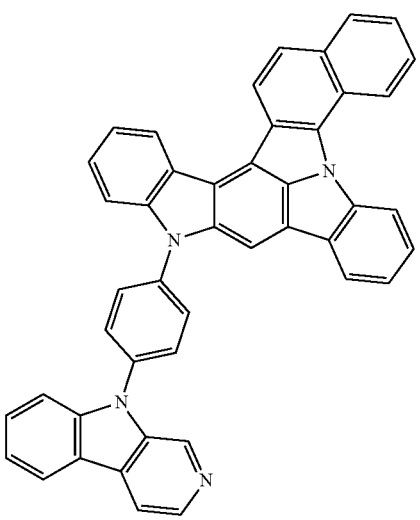
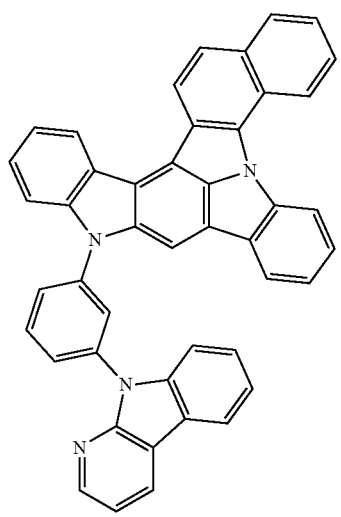
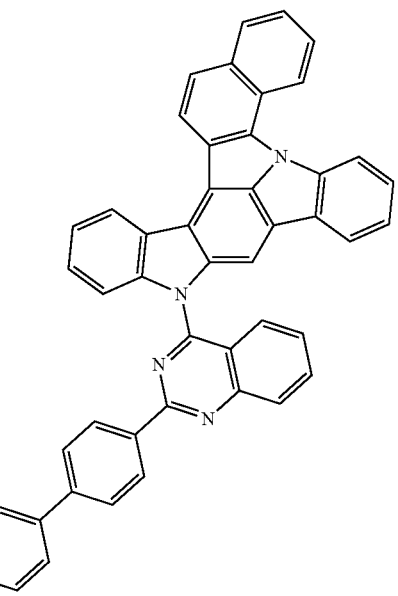

635
-continued
636
-continued
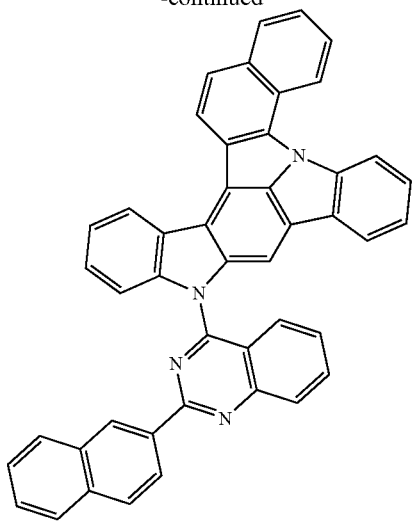
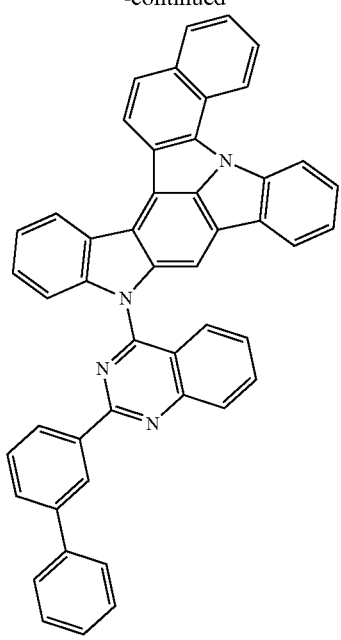
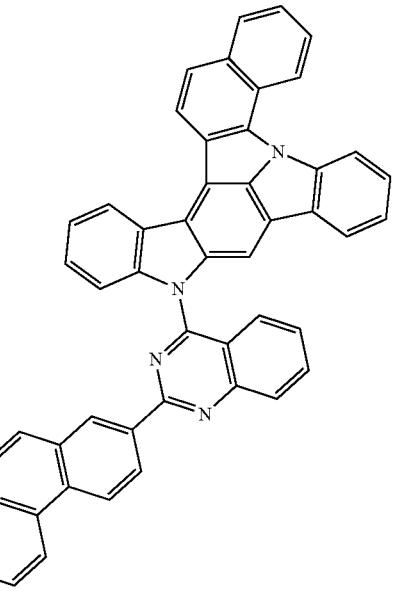

637
-continued
638
-continued
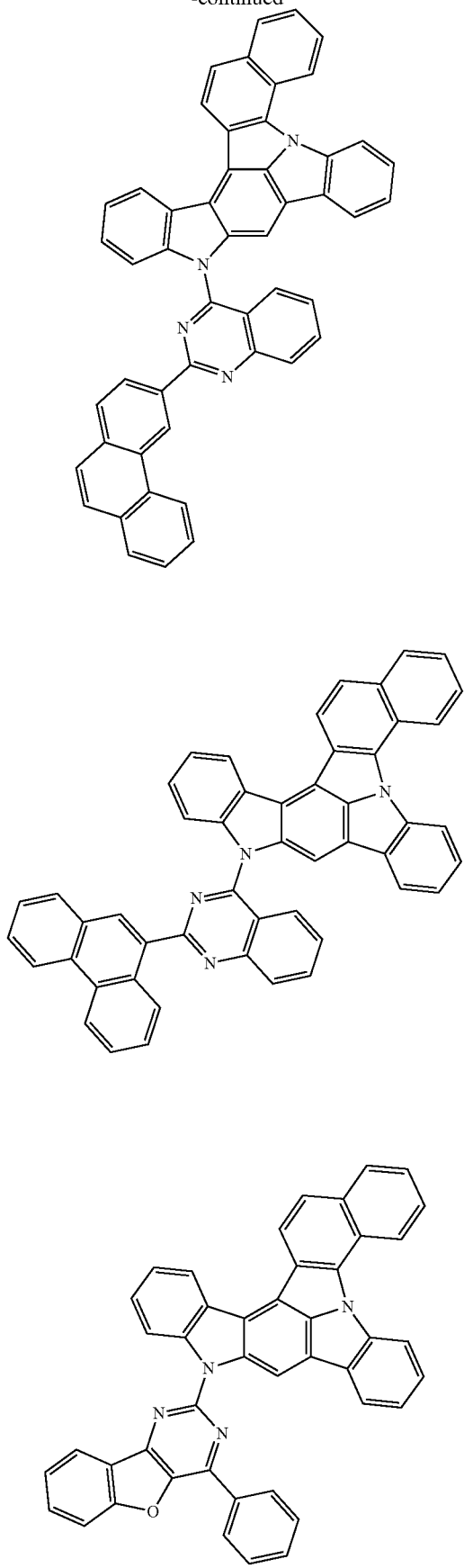
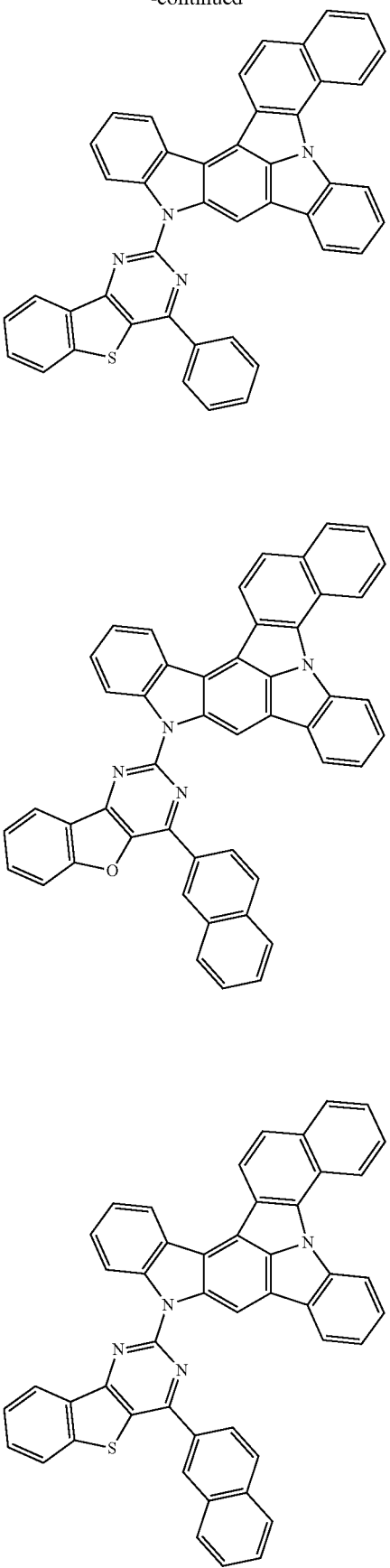

639
-continued
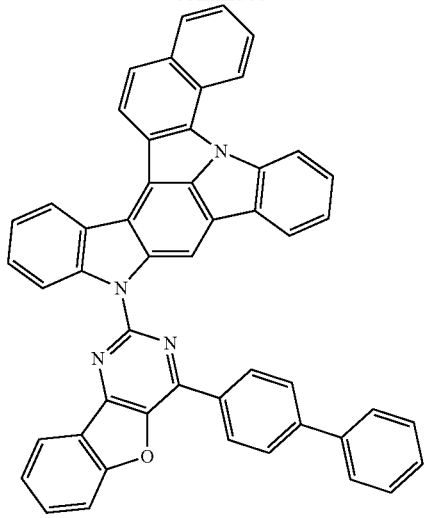
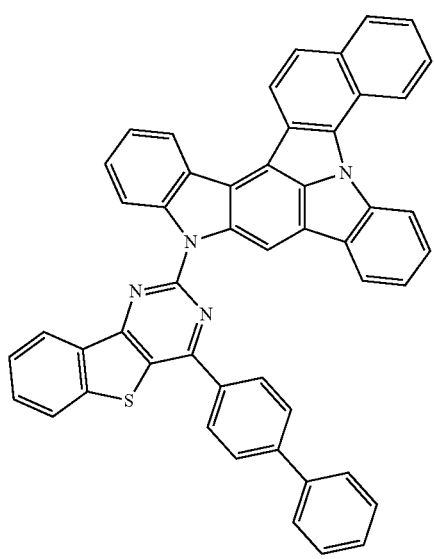
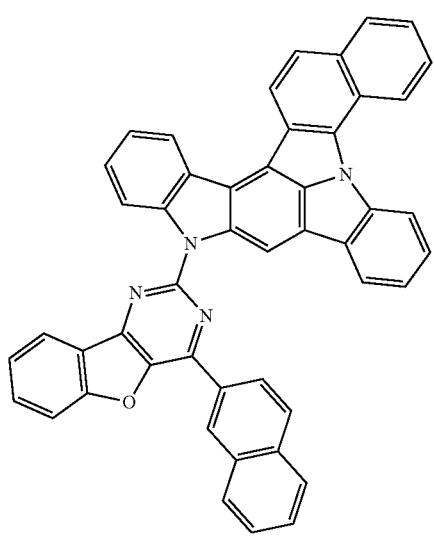
640
-continued
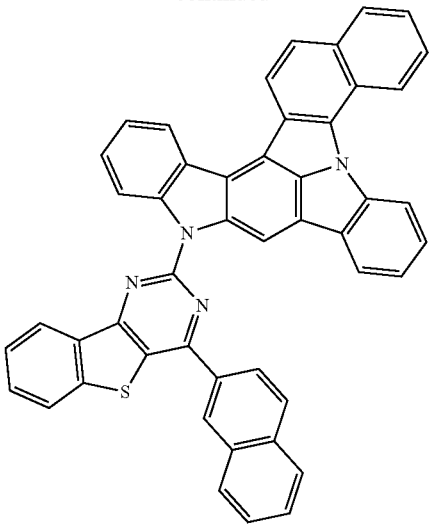
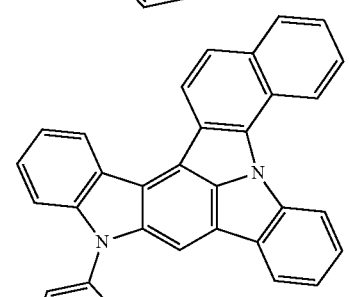
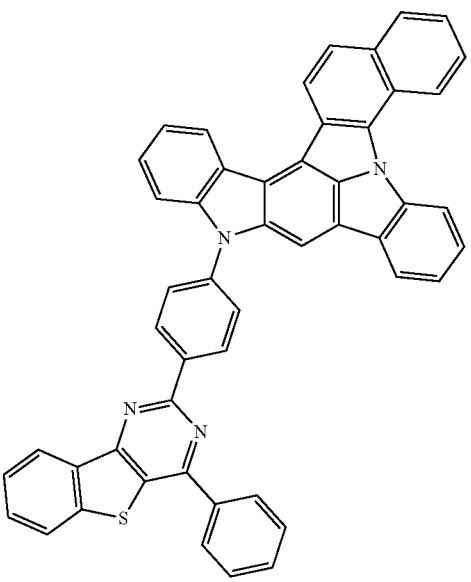

641
-continued
642
-continued
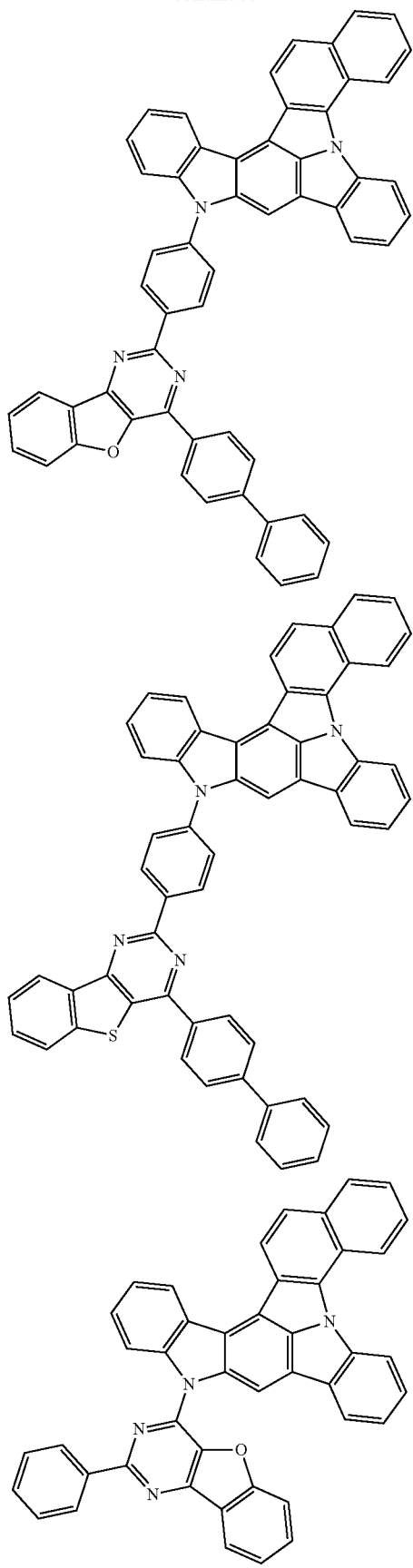
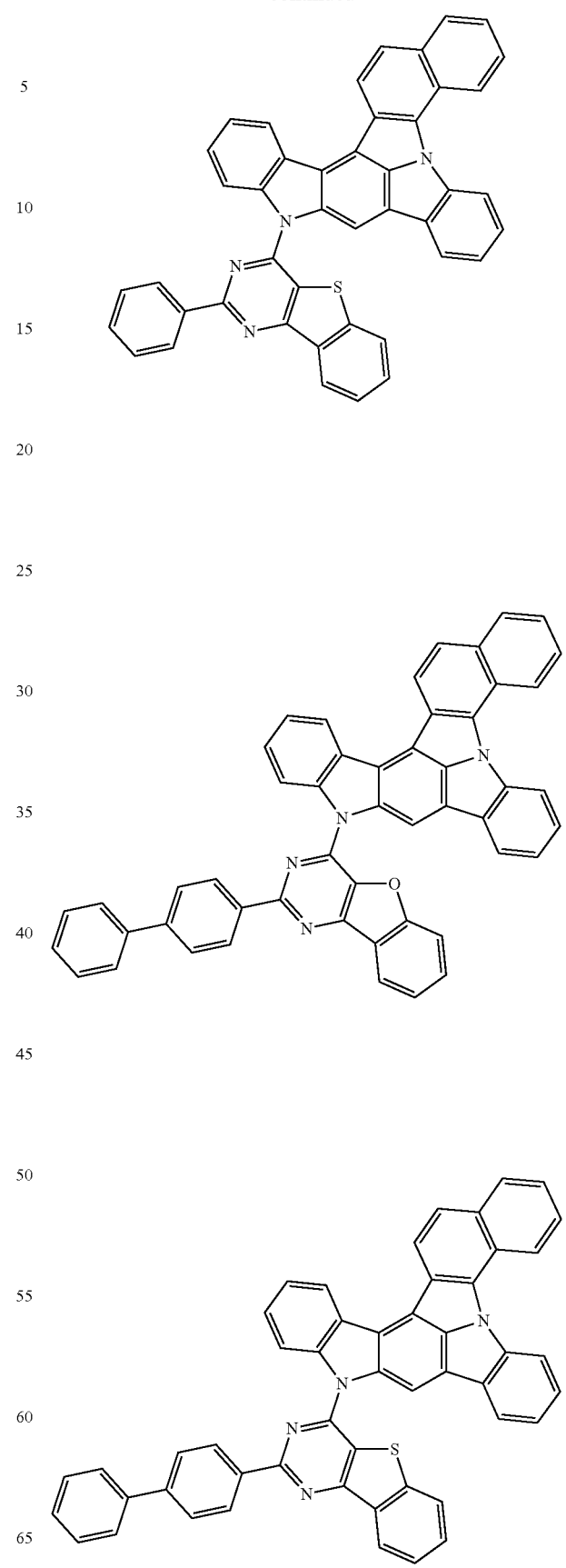

643
-continued
644
-continued
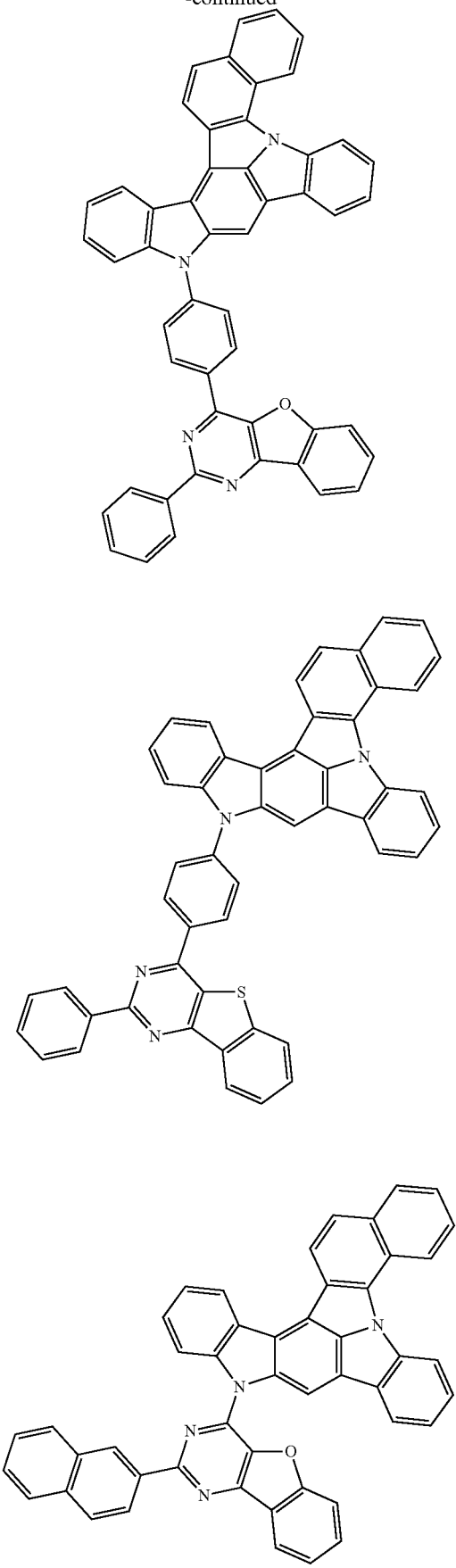
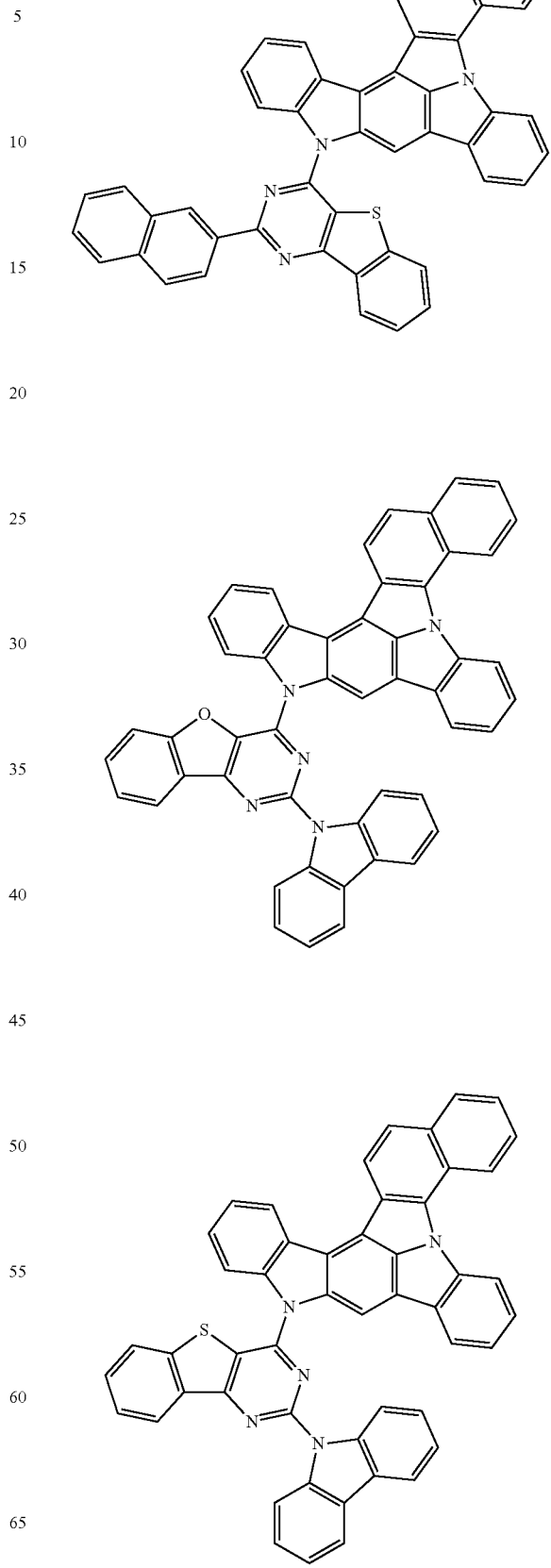

645
-continued
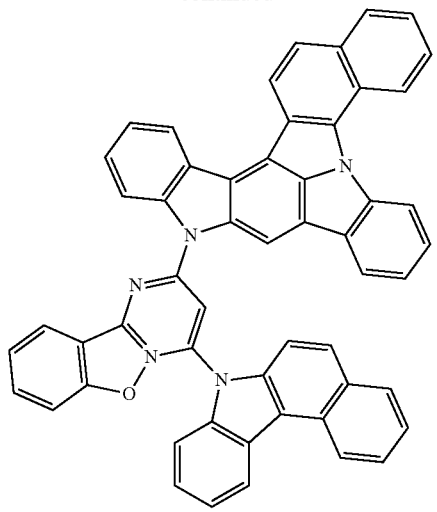
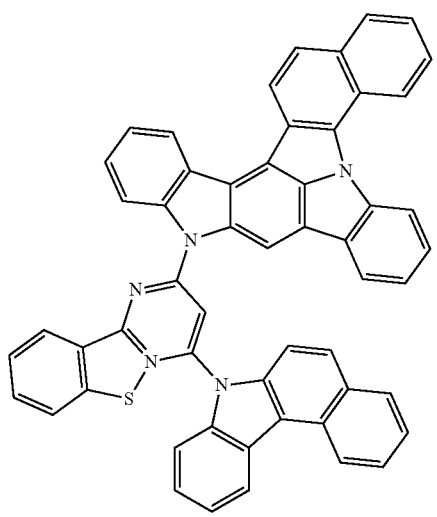
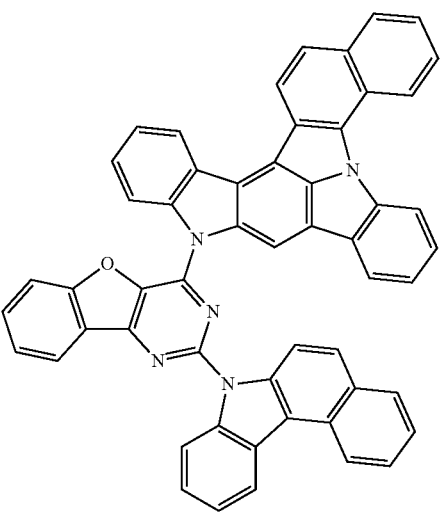
646
-continued
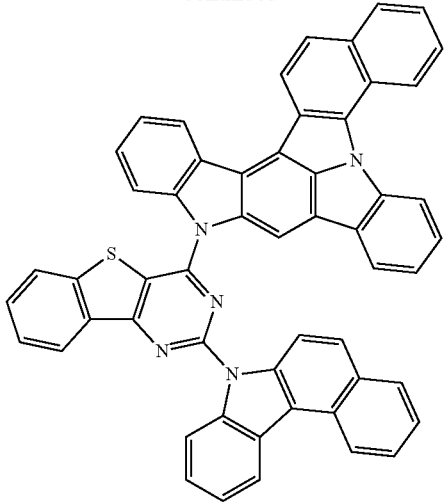
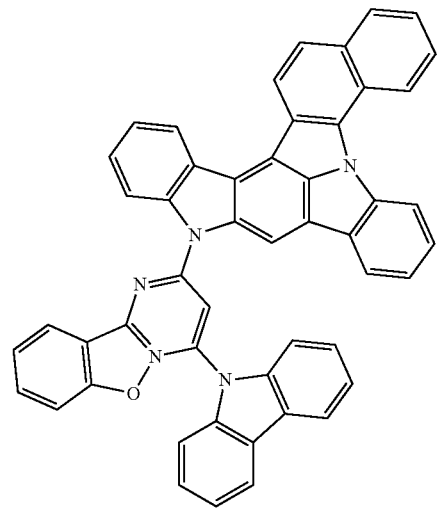
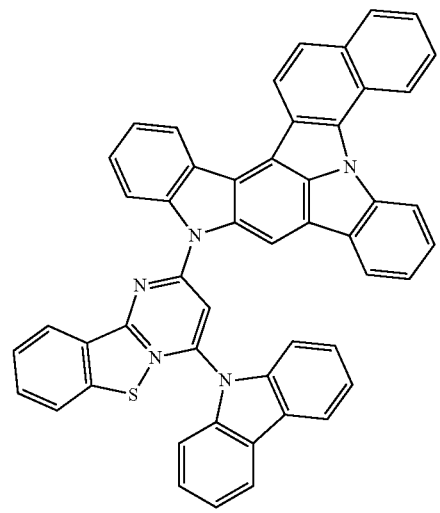

647
-continued
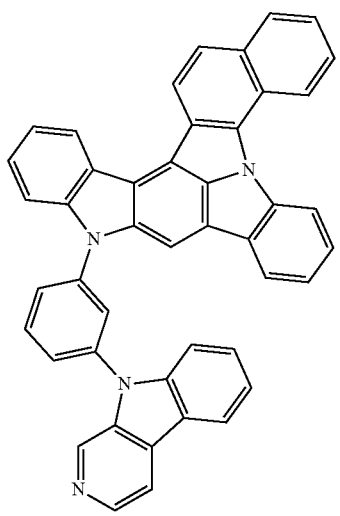
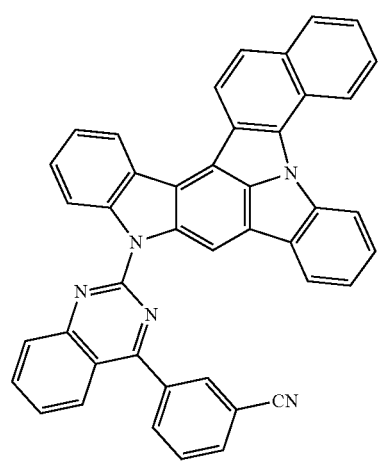
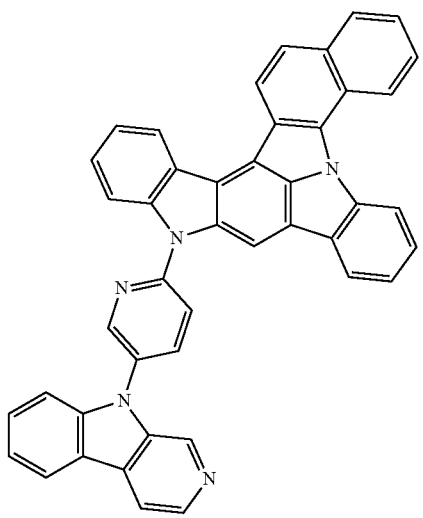
648
-continued
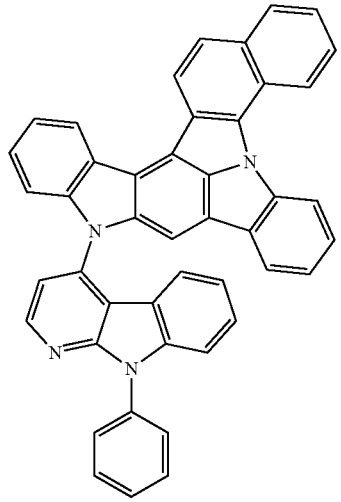
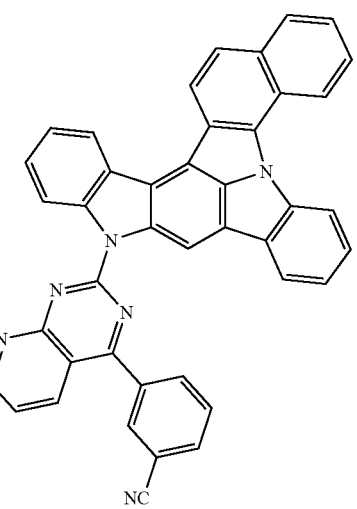
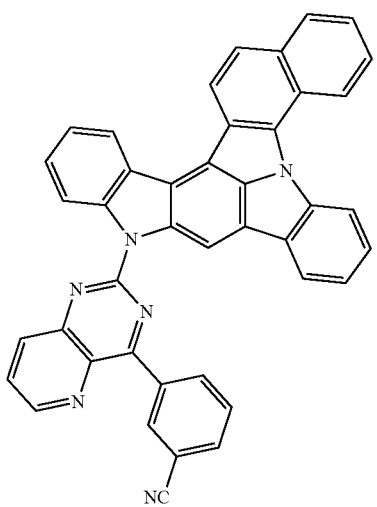

649
-continued
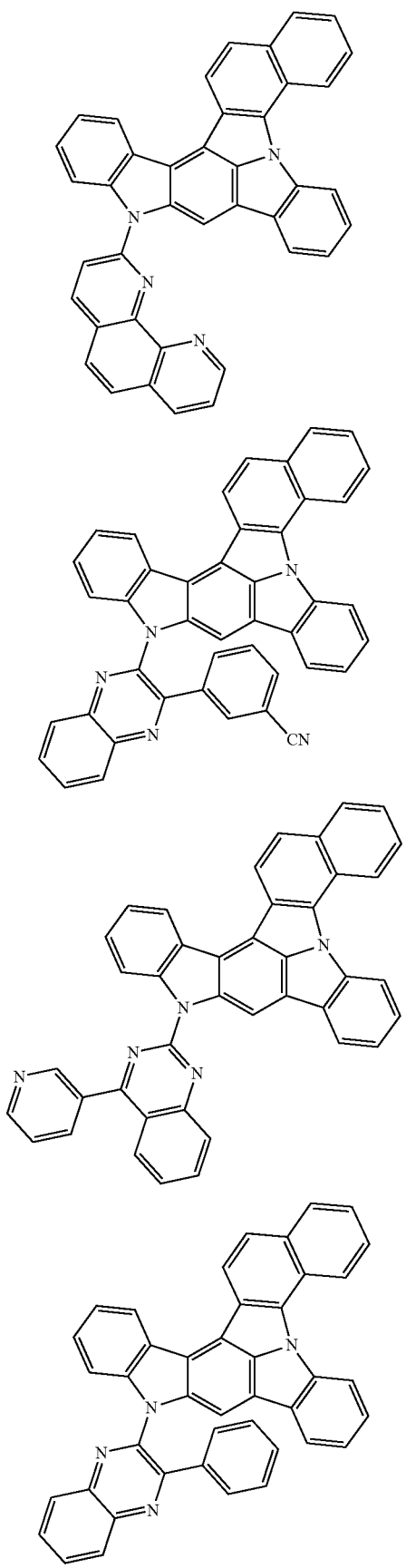
650
-continued
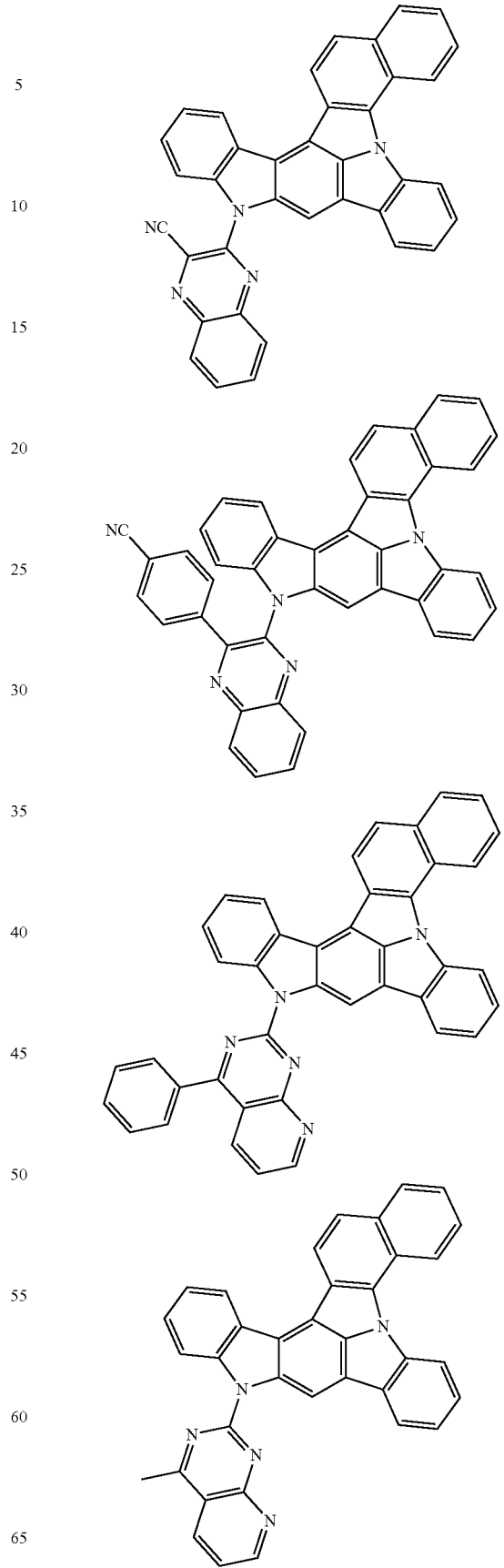

651
-continued
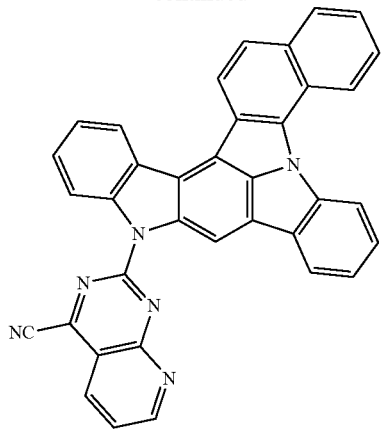
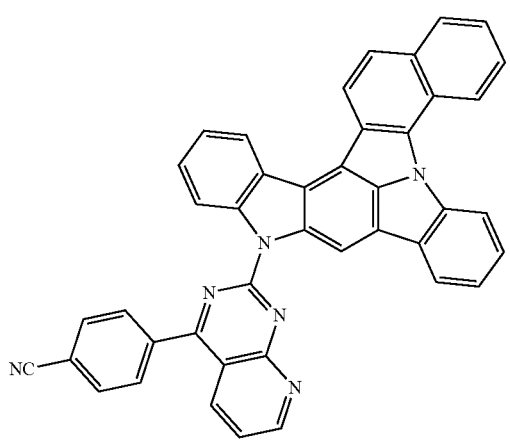
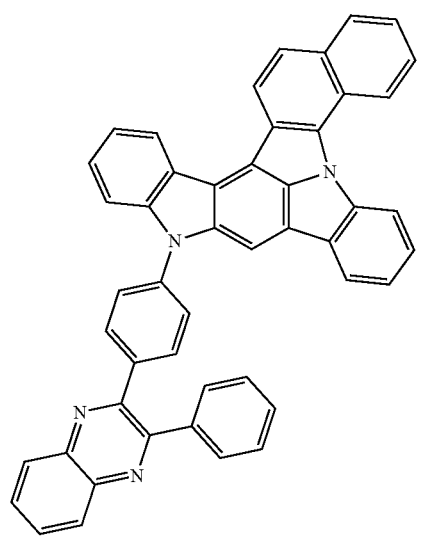
652
-continued
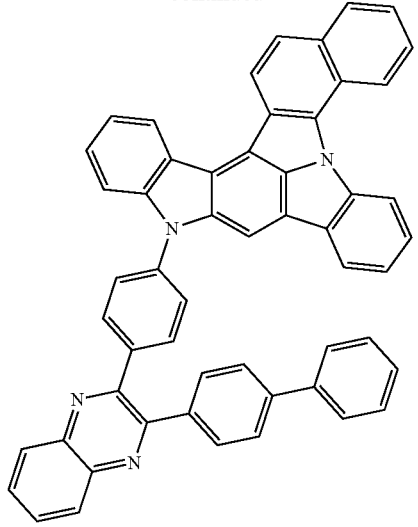
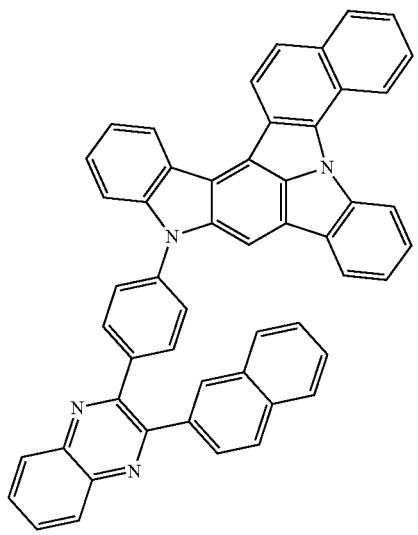
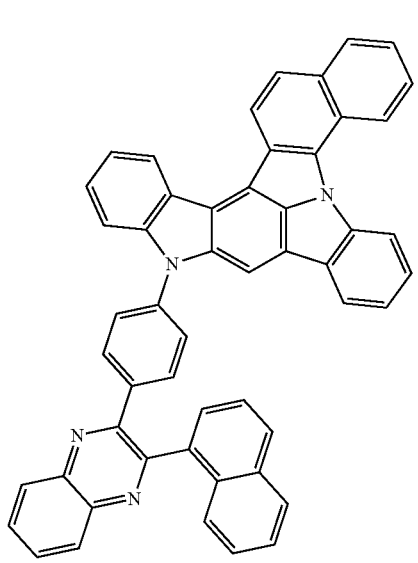

653
-continued
654
-continued
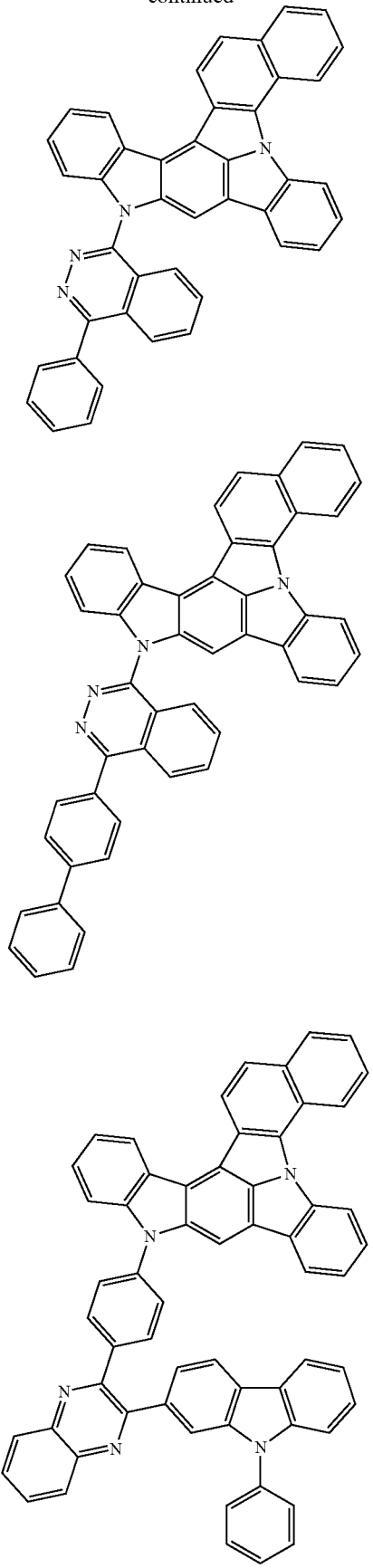

655
-continued
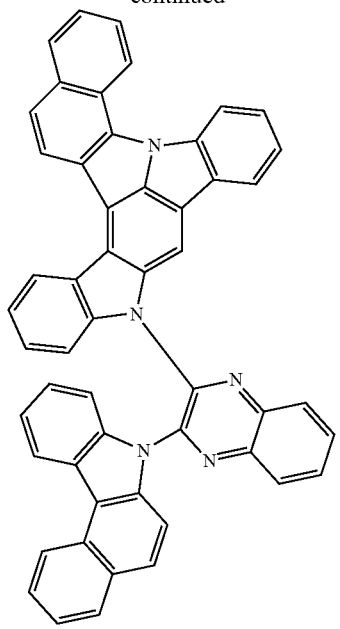
656
-continued
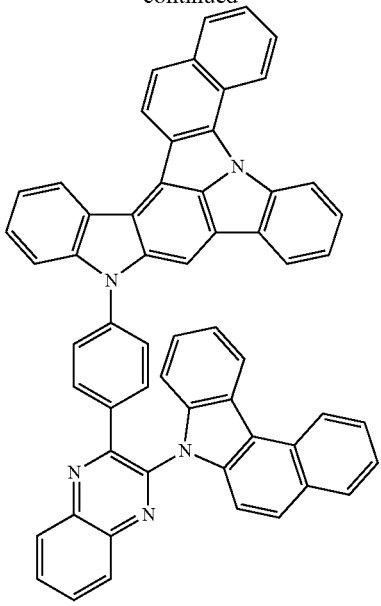
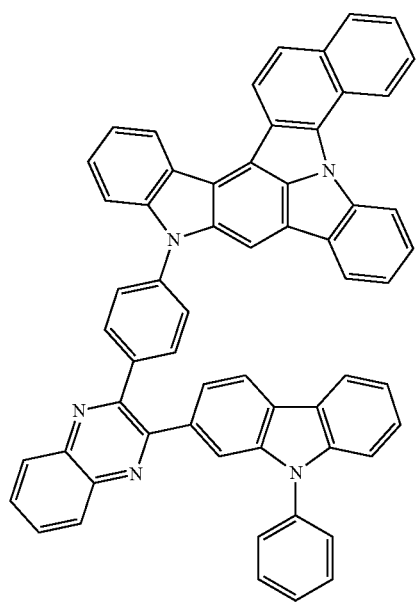
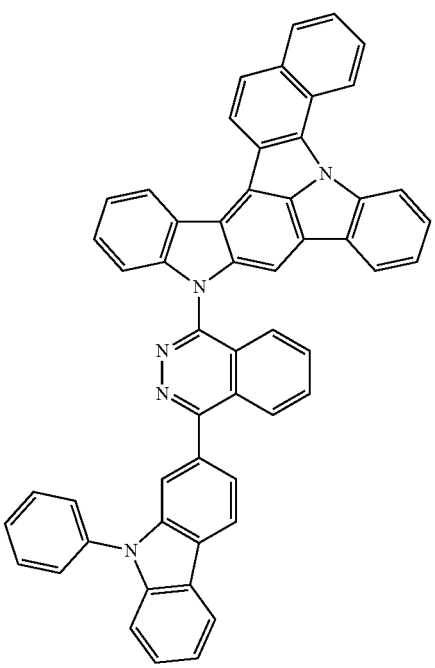

657
-continued
658
-continued
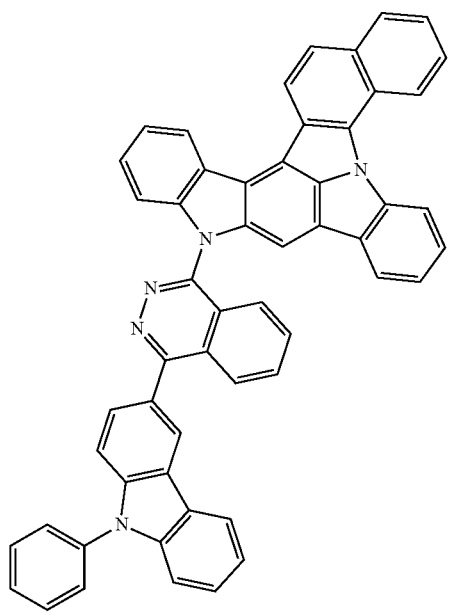
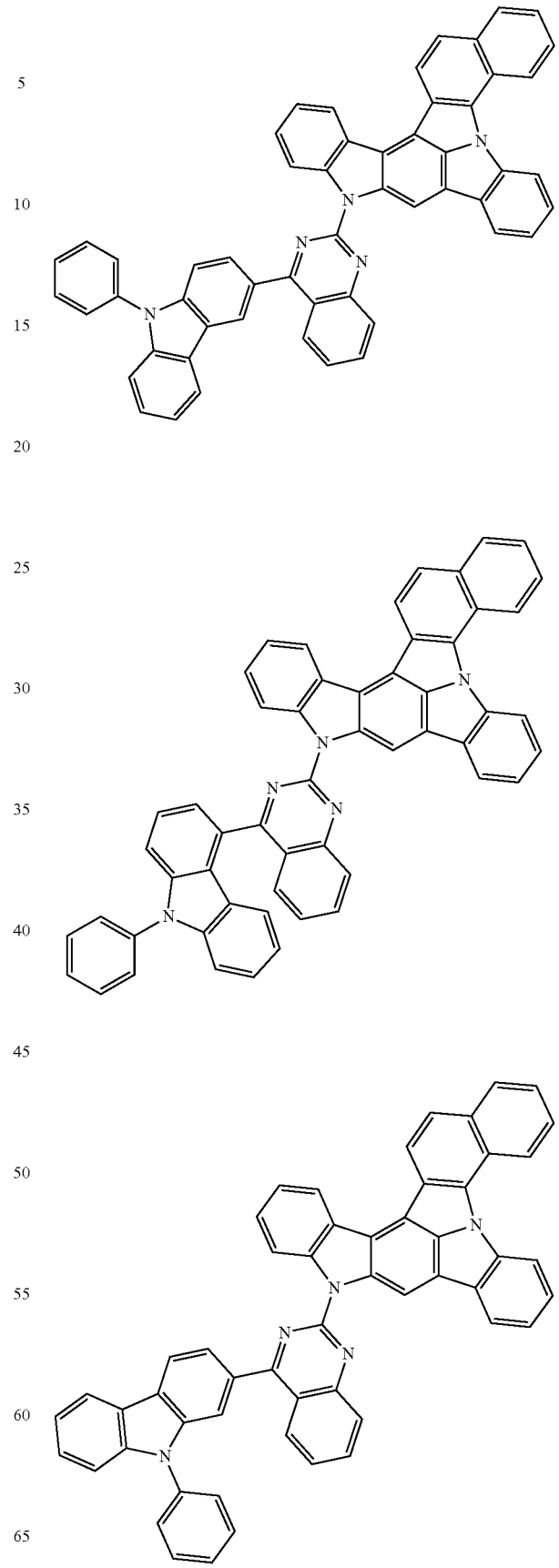

659
-continued
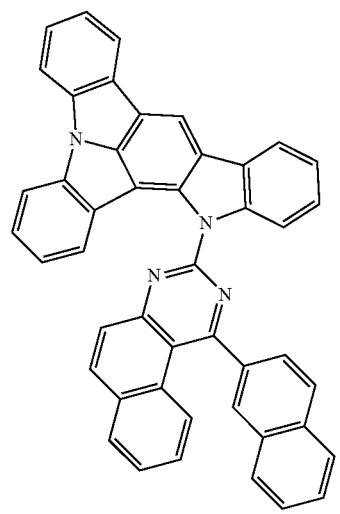
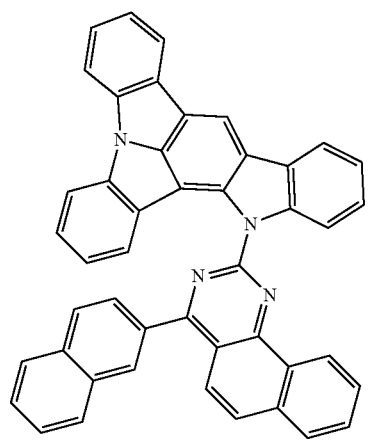
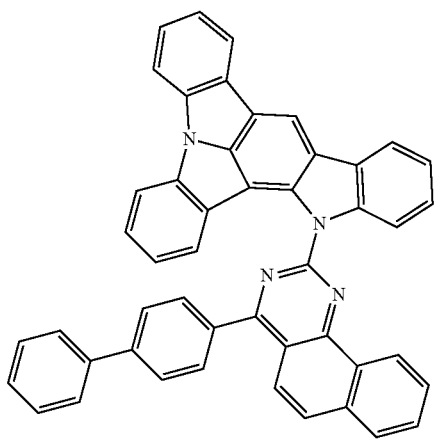
660
-continued
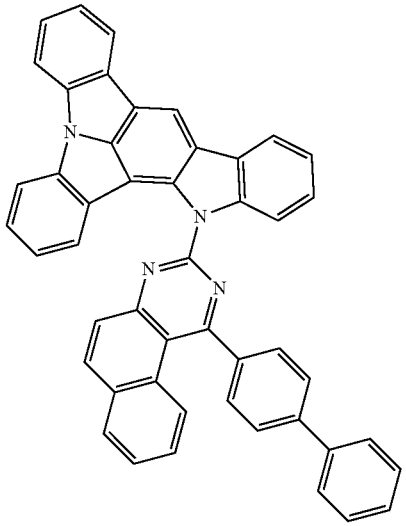
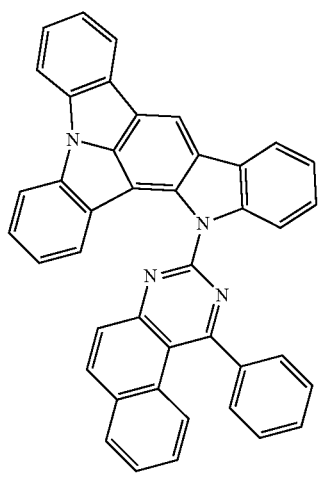
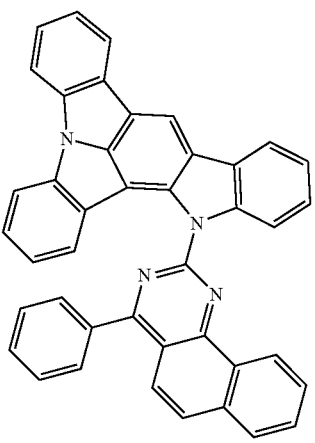

661
-continued
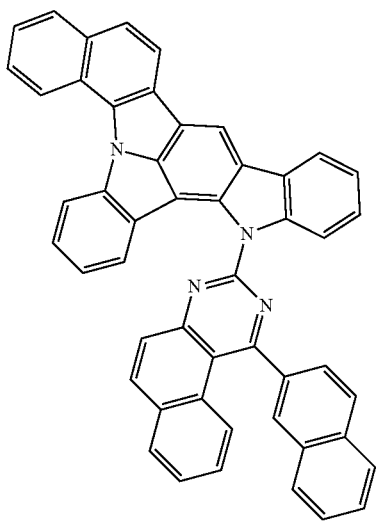
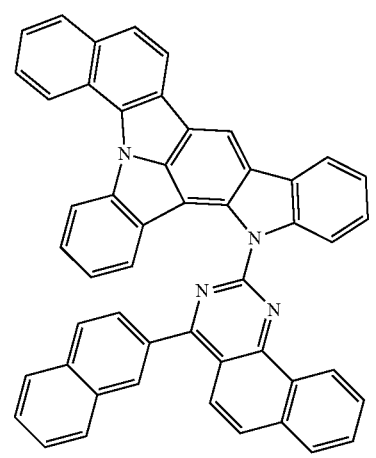
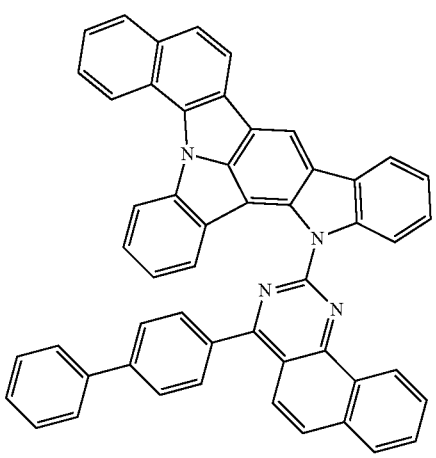
662
-continued
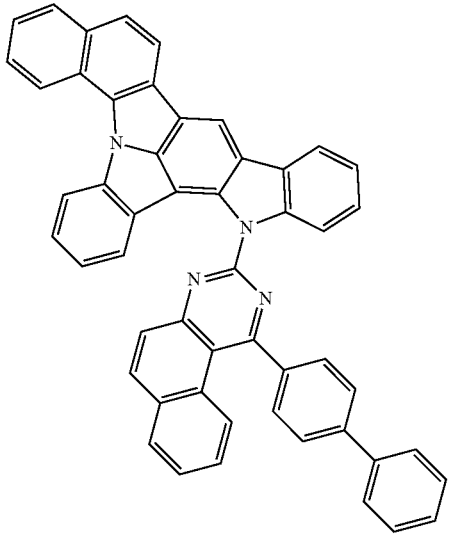
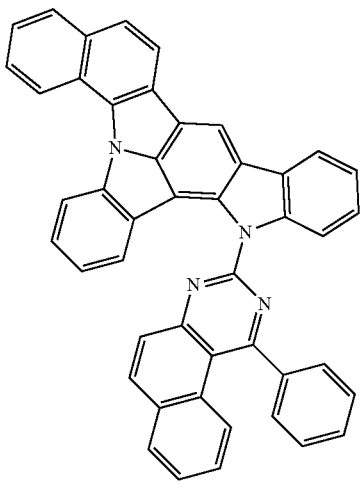
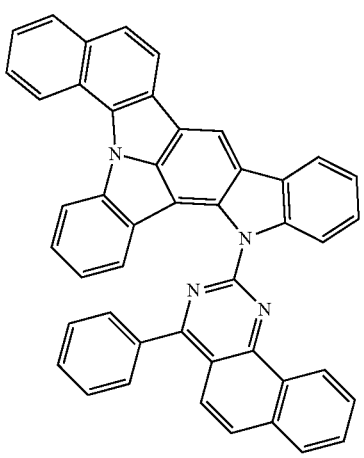

663
-continued
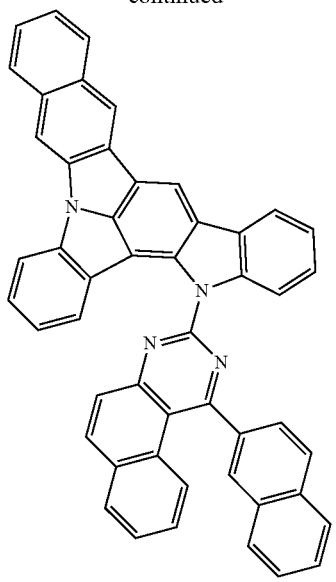
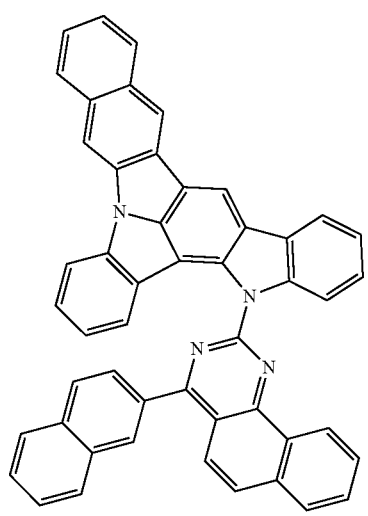
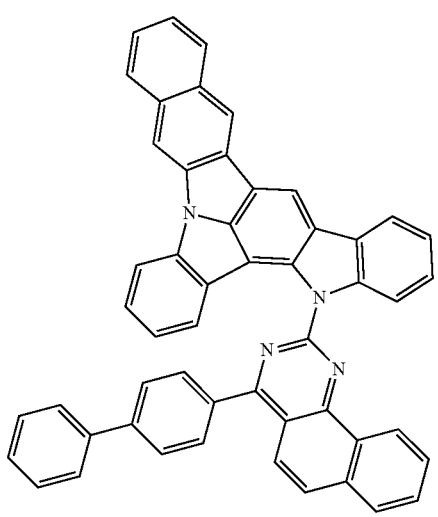
664
-continued
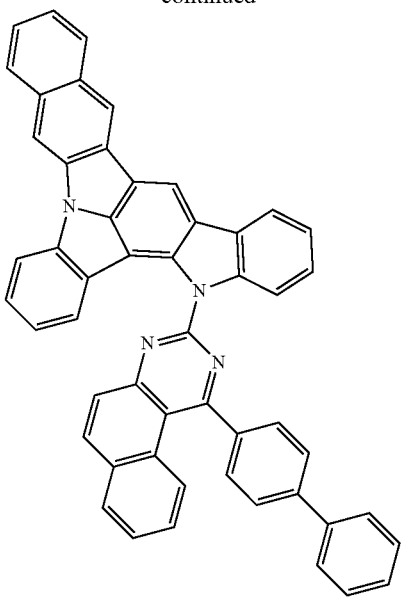
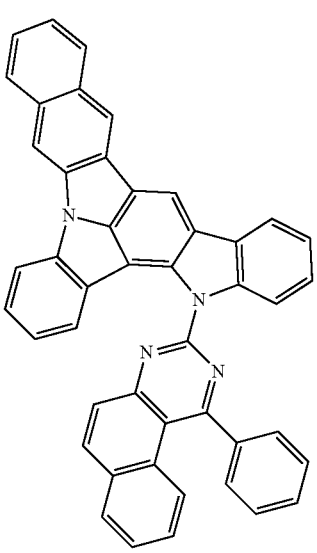
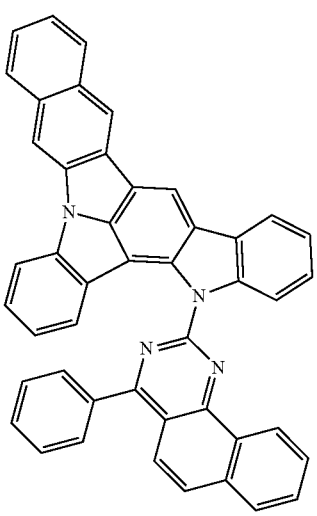

665
-continued
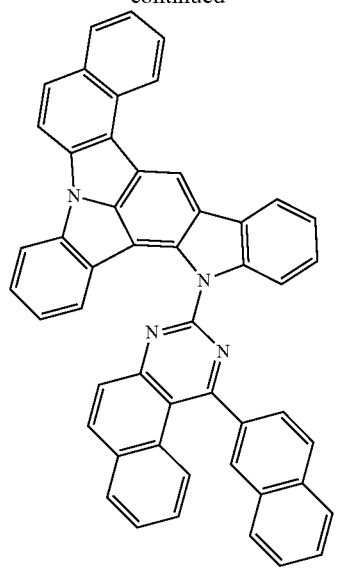
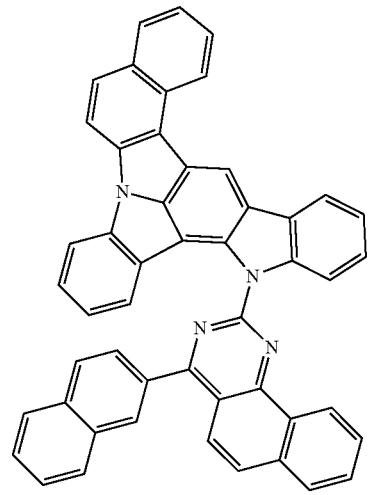
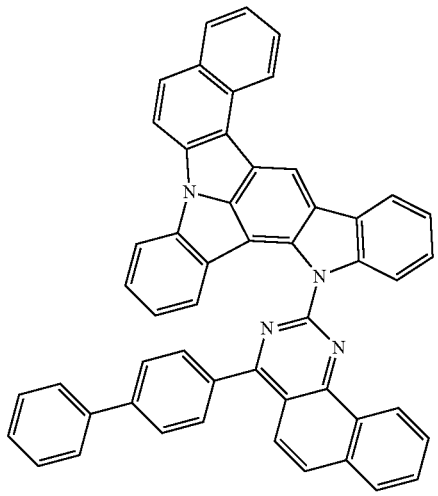
666
-continued
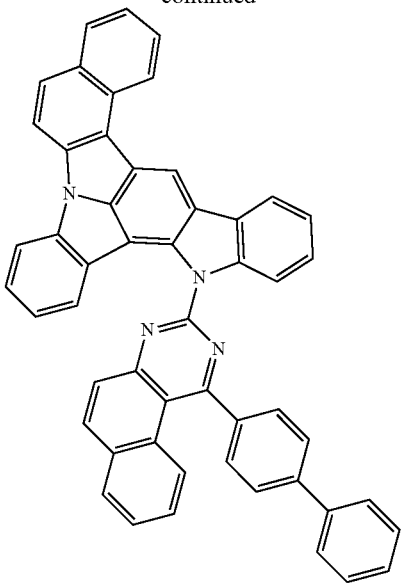
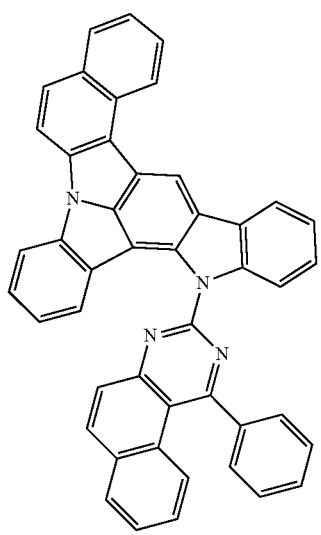
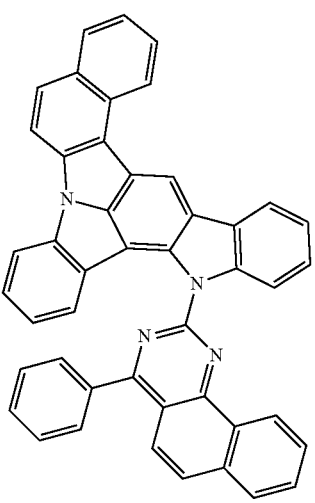

667
-continued
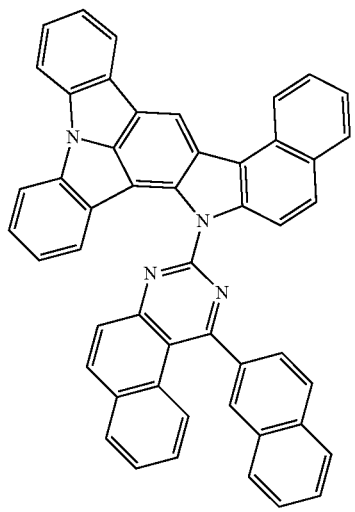
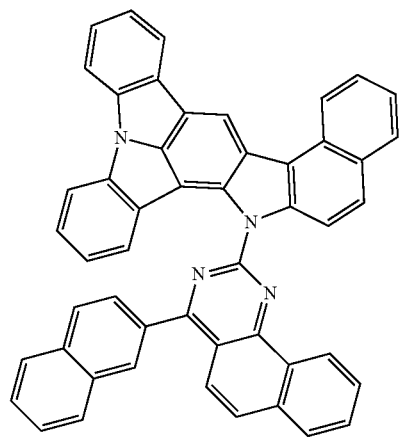
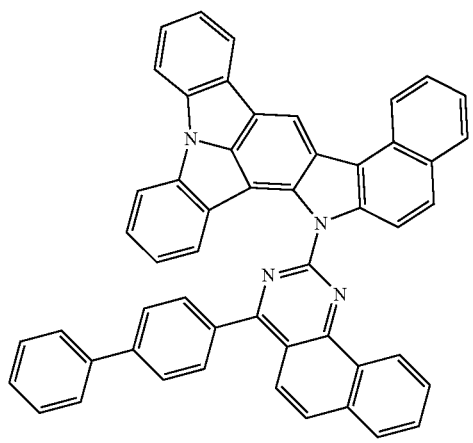
668
-continued
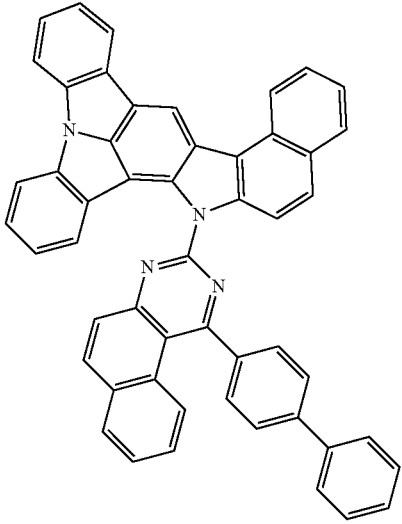
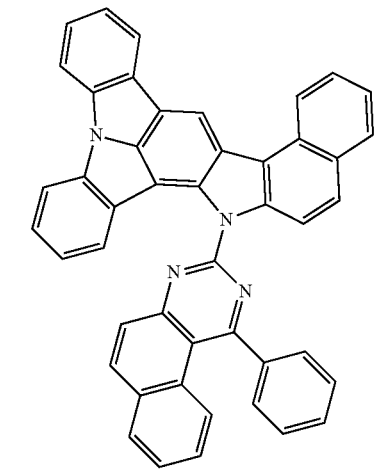
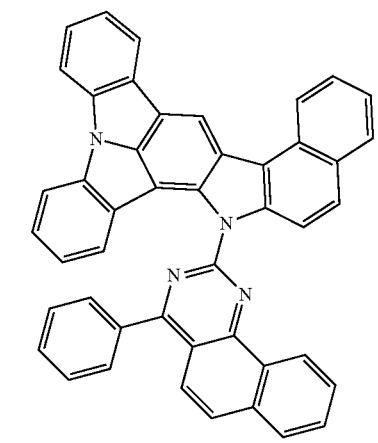

669
-continued
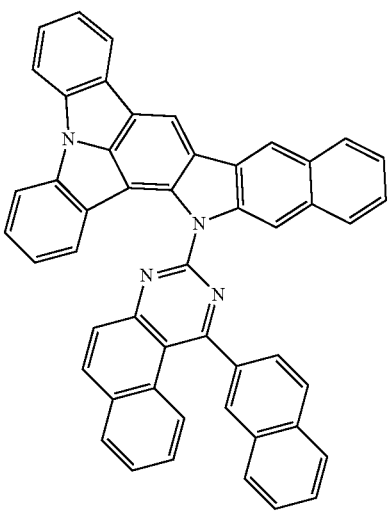
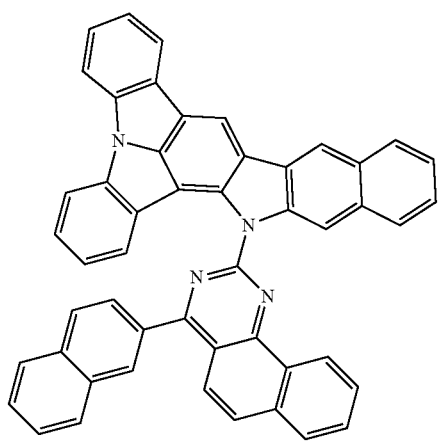
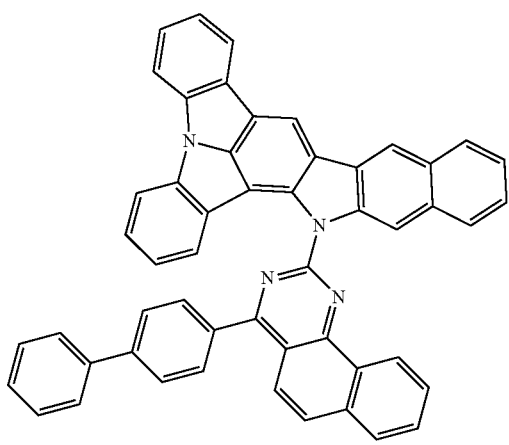
670
-continued
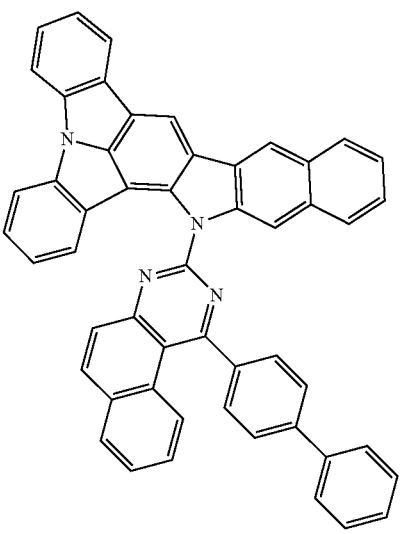
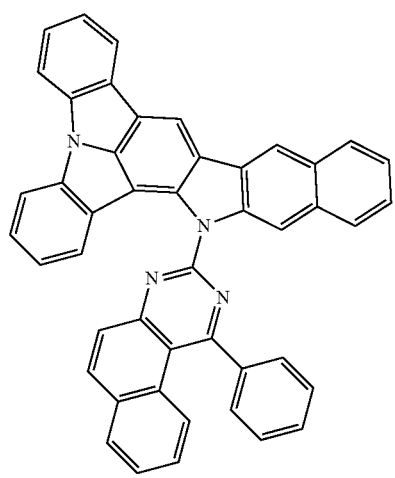
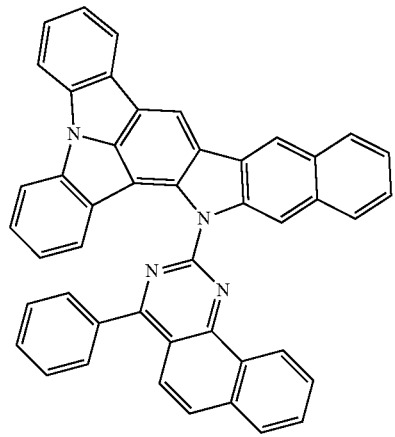

671
-continued
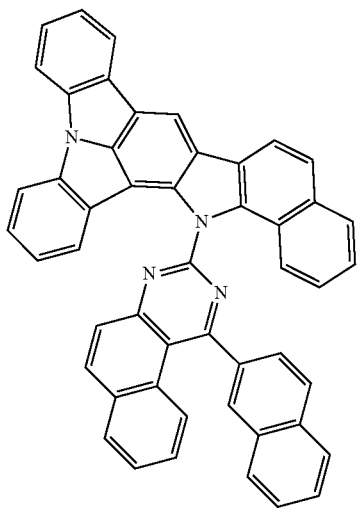
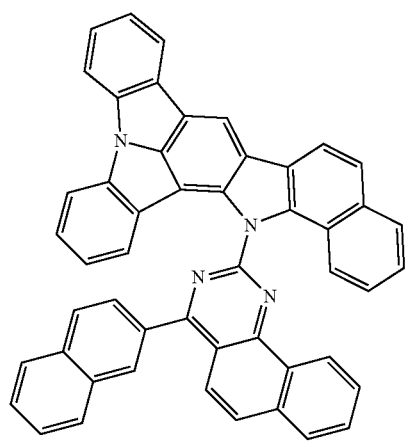
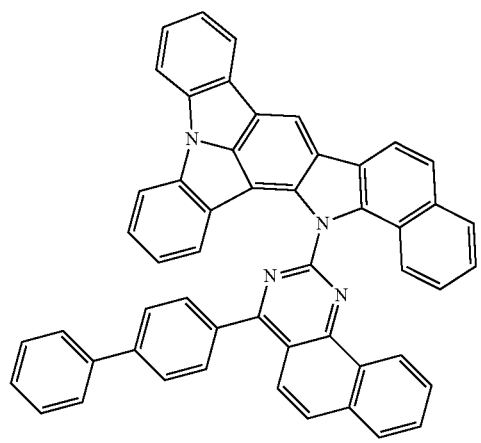
672
-continued
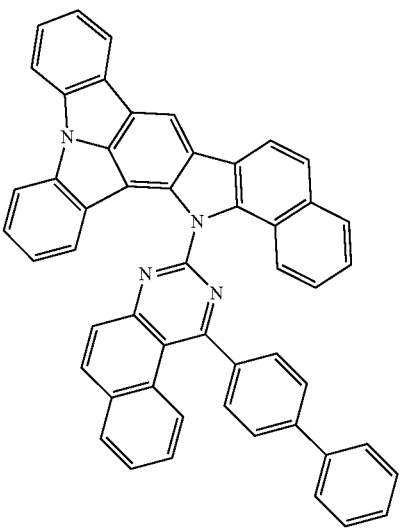
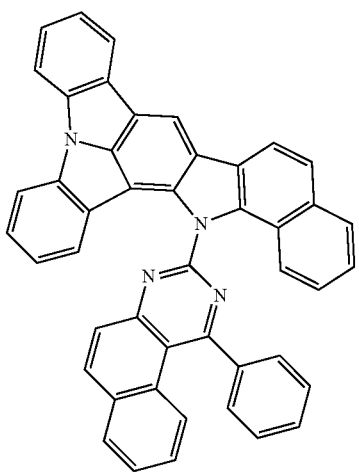
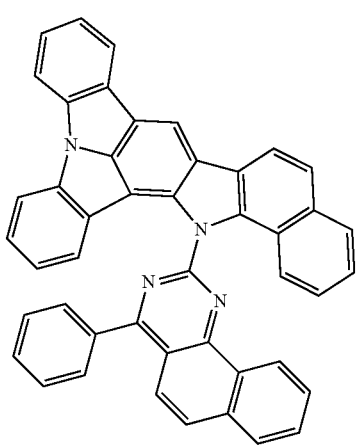

673
-continued
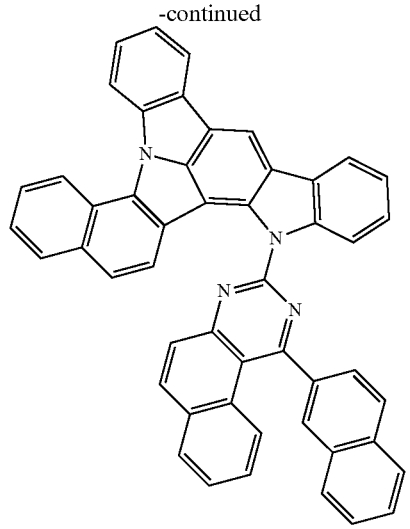
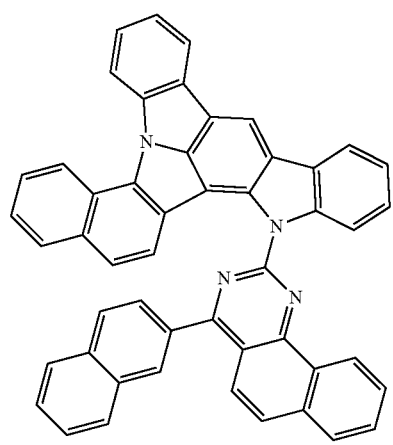
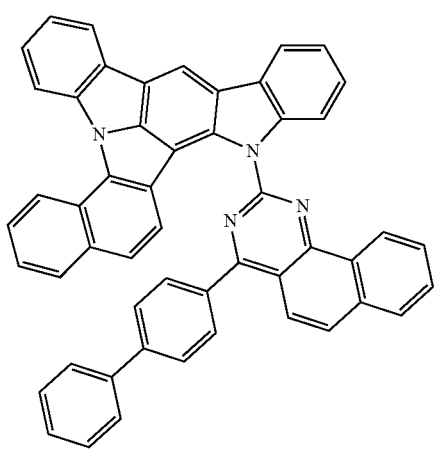
674
-continued
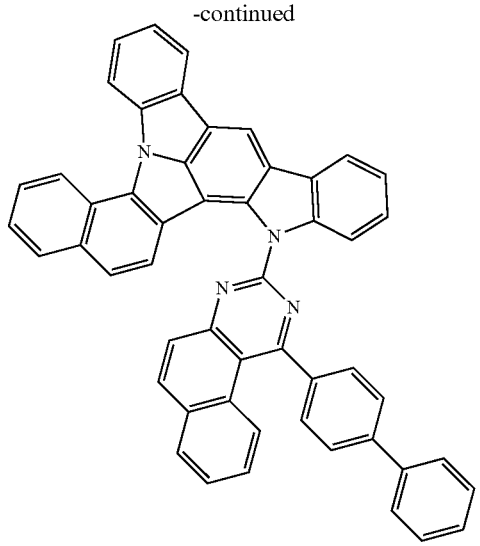
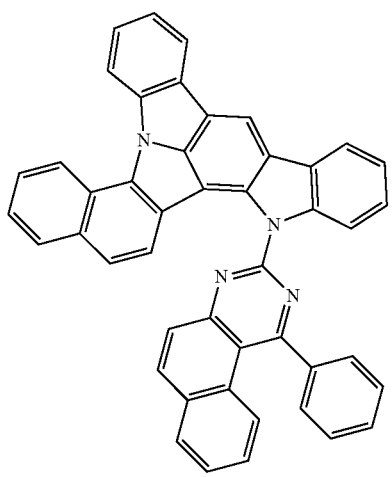
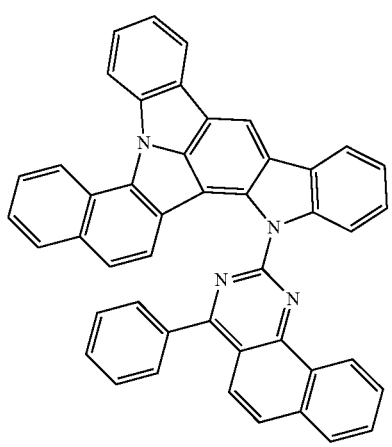

675
-continued
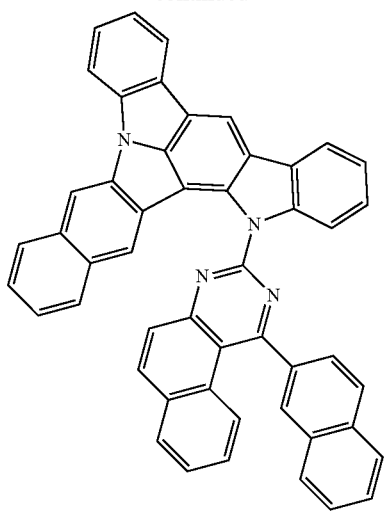
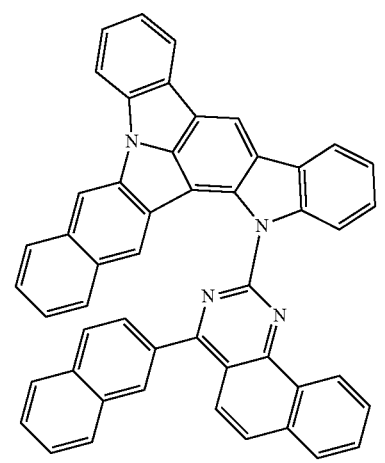
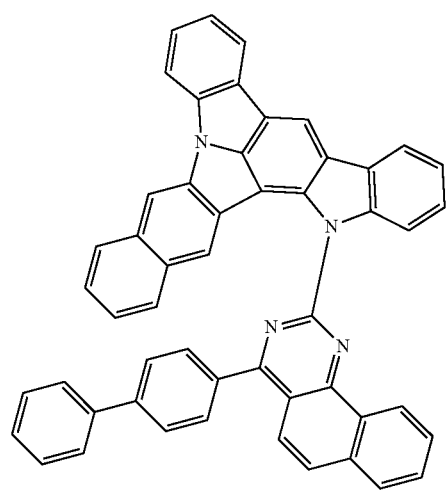
676
-continued
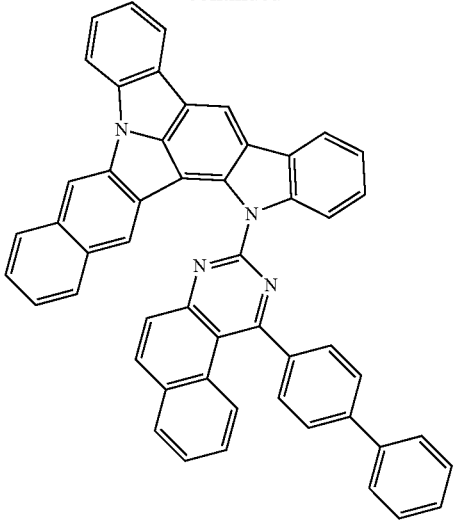
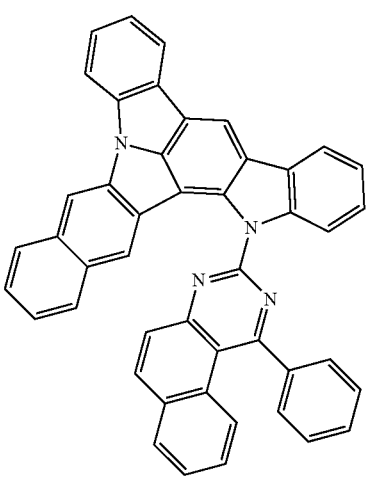
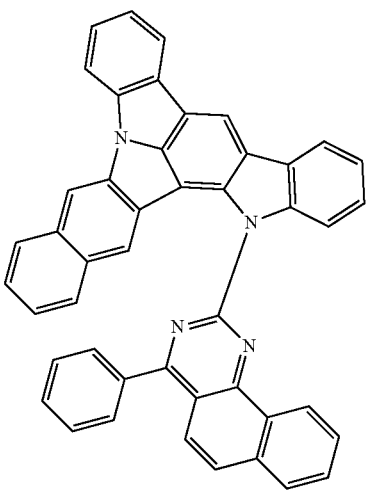

677
-continued
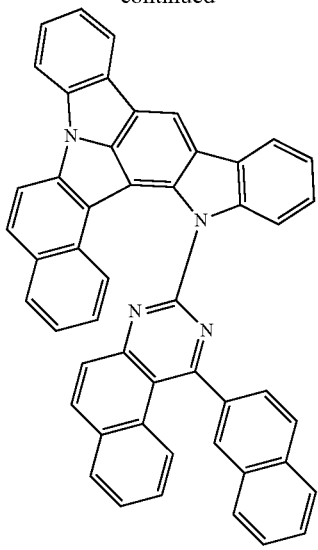
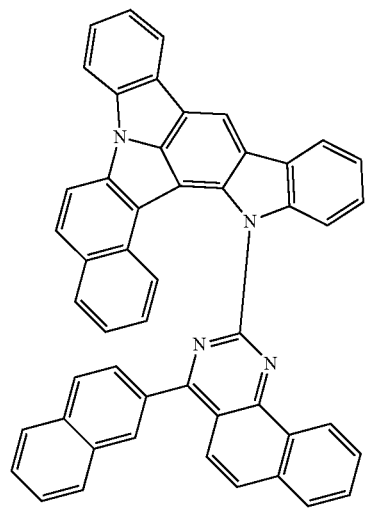
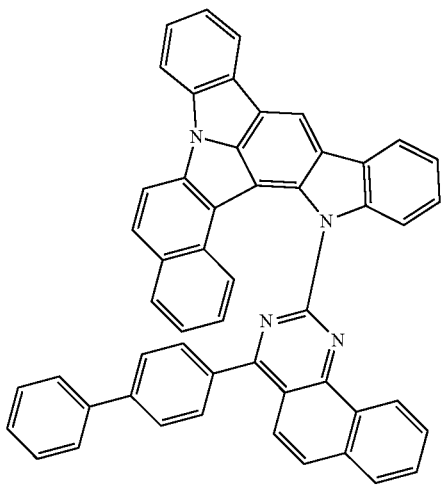
678
-continued
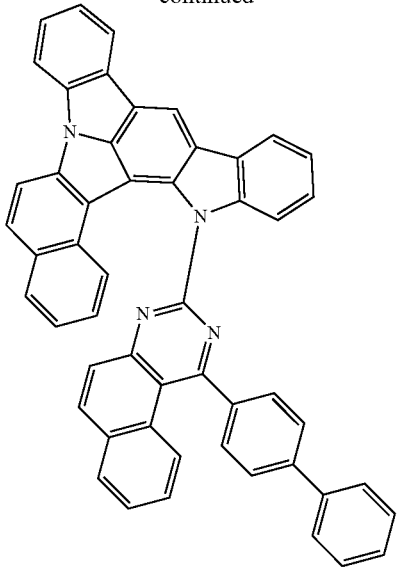
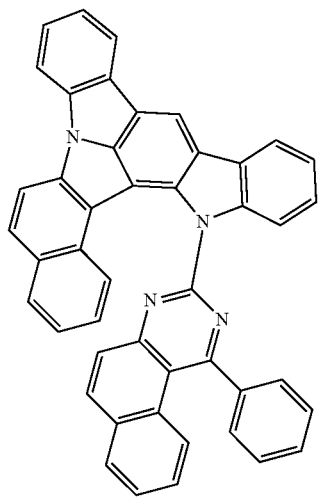
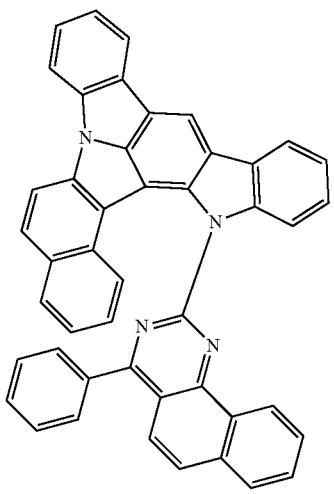

679
-continued
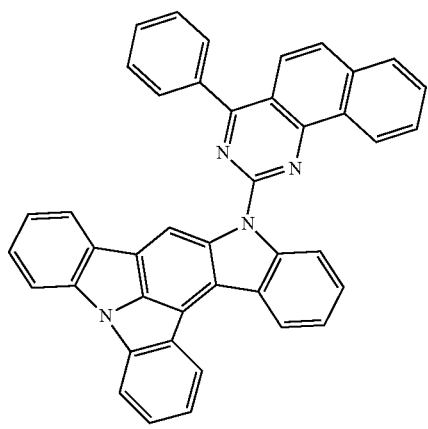
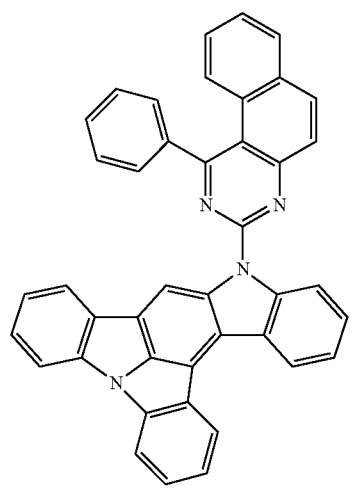
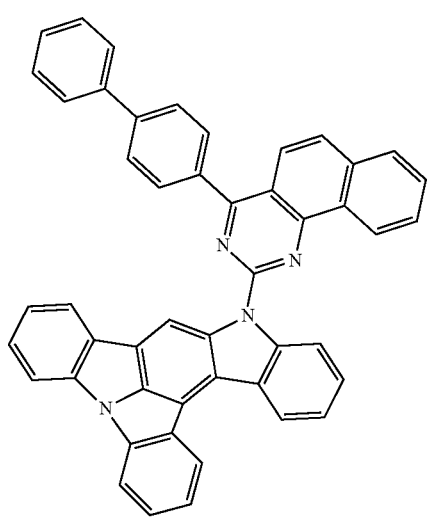
680
-continued
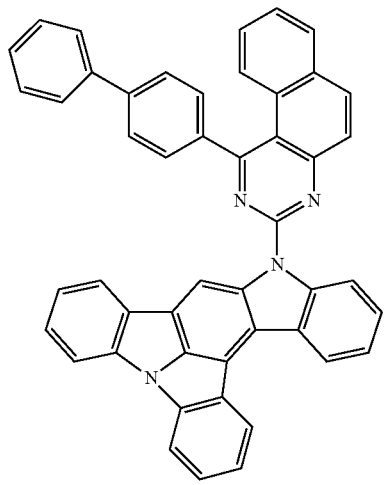
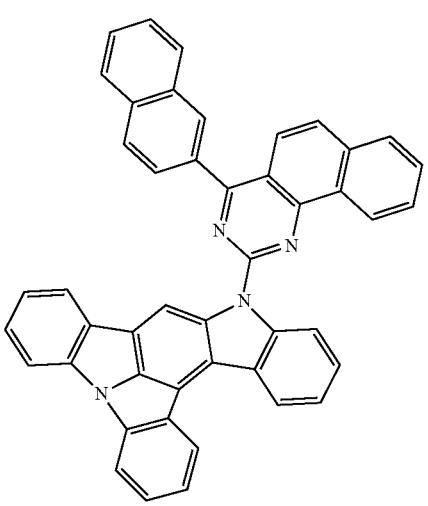
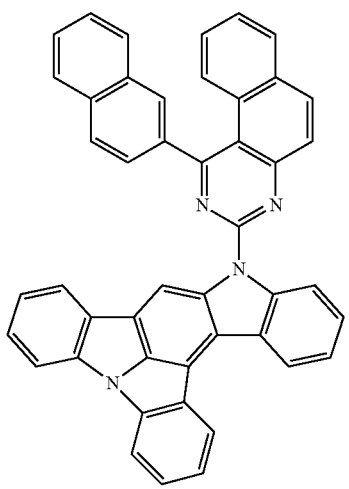

681
-continued
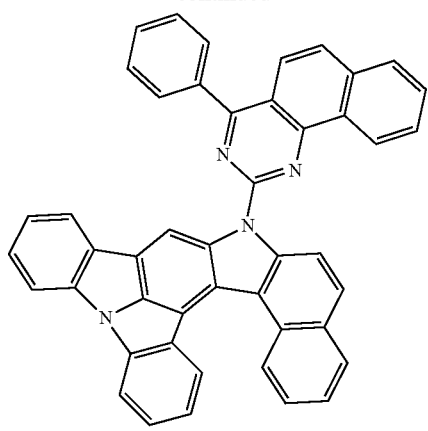
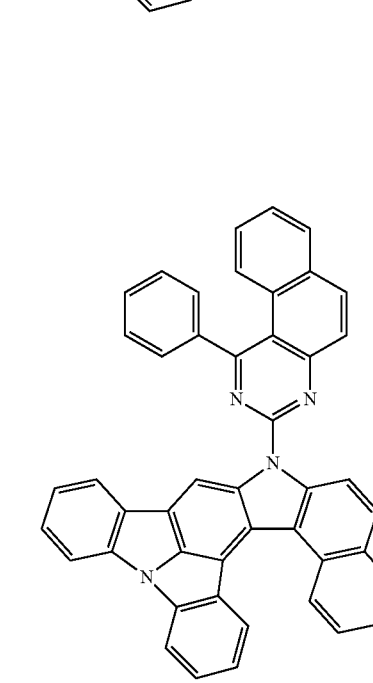
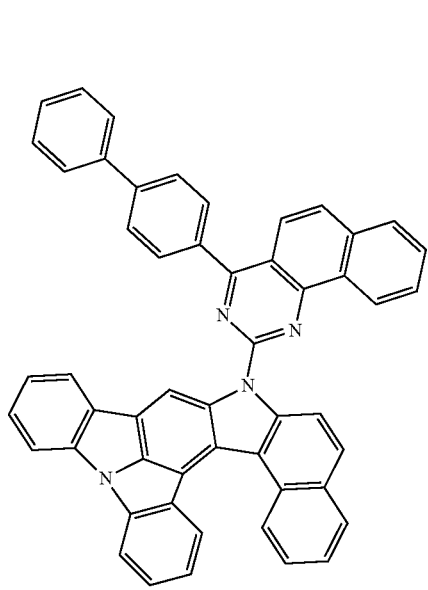
682
-continued
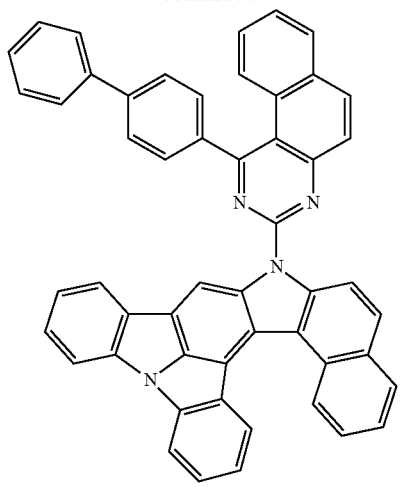
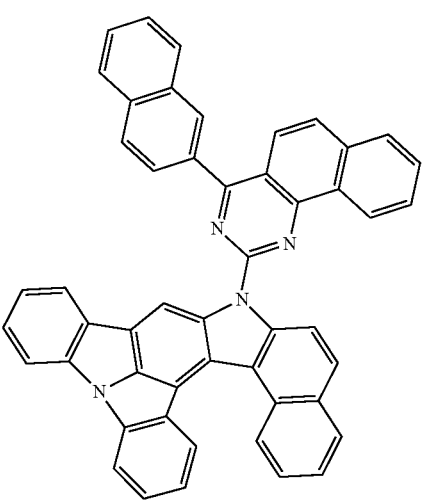
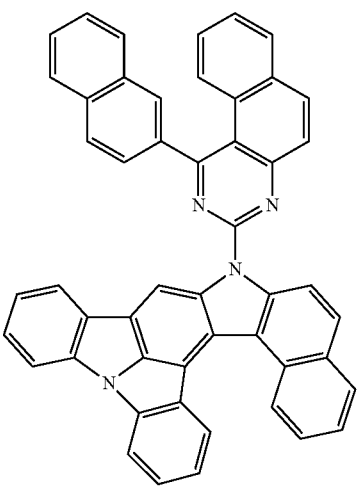

683
-continued
684
-continued
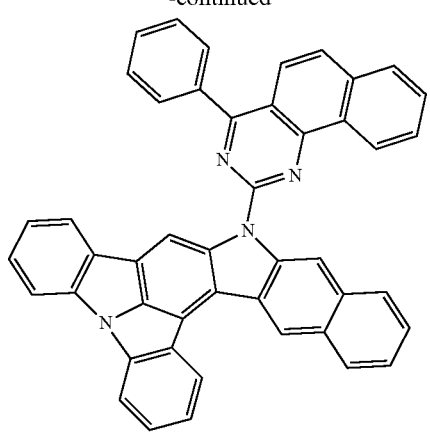
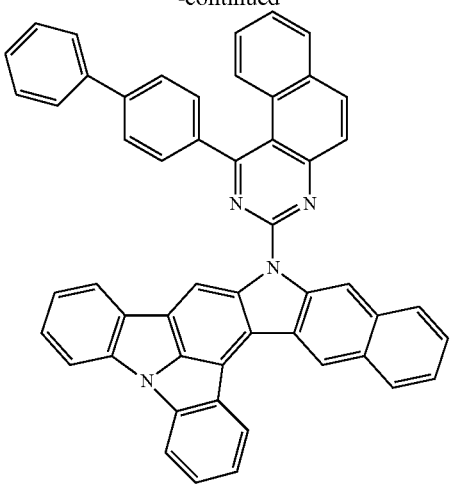
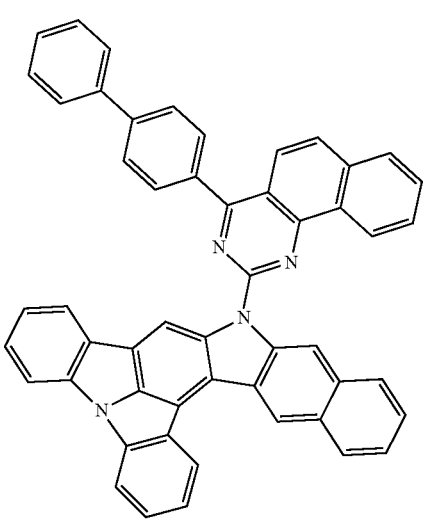

685
-continued
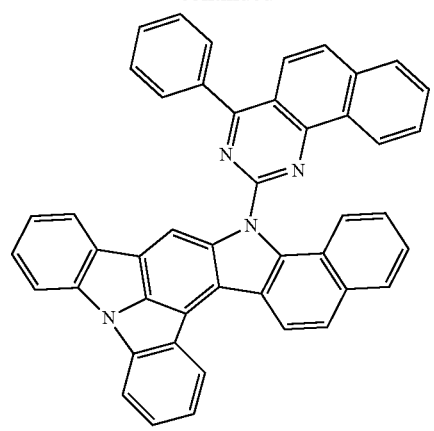
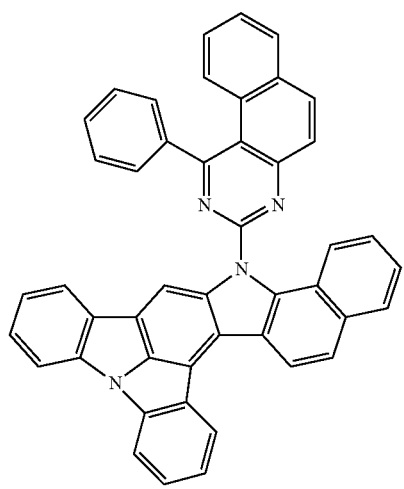
686
-continued
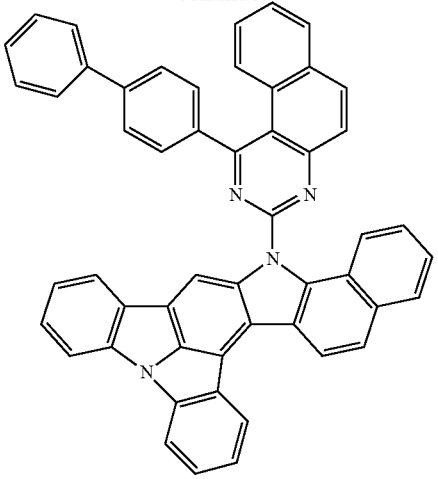
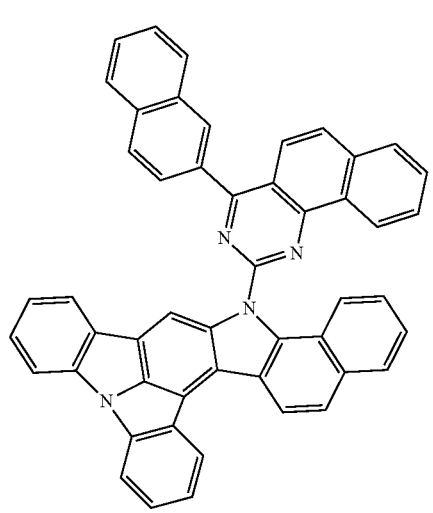
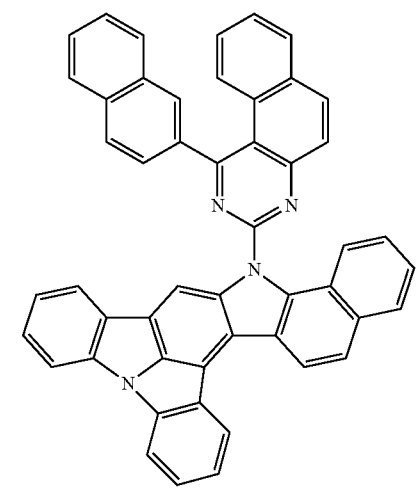

687
-continued
688
-continued
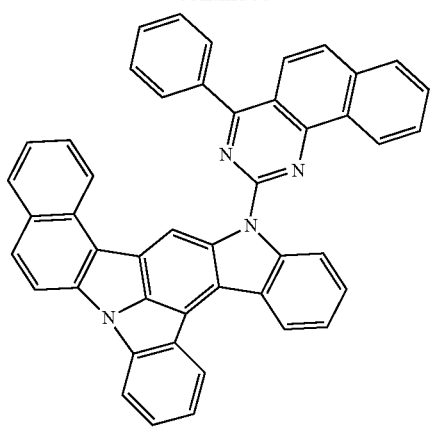
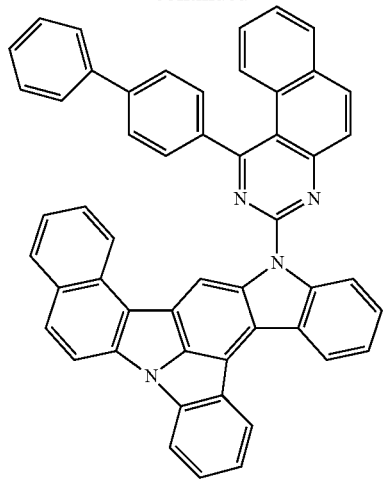
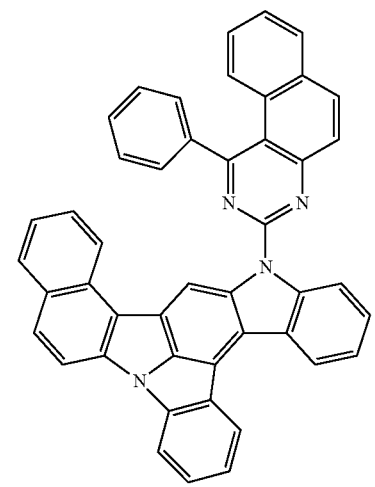
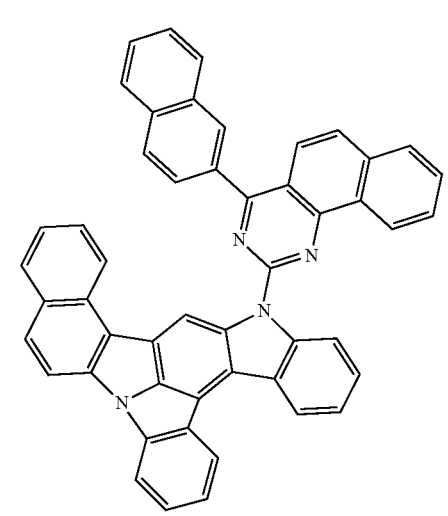
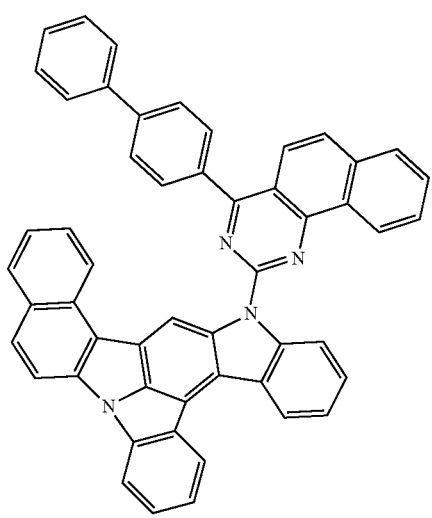
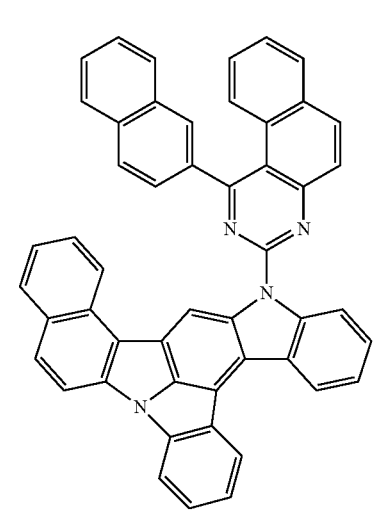

689
-continued
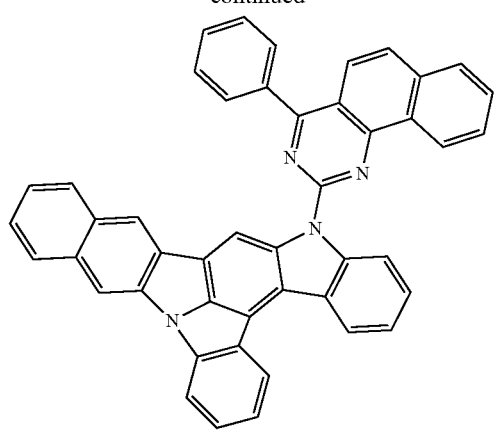
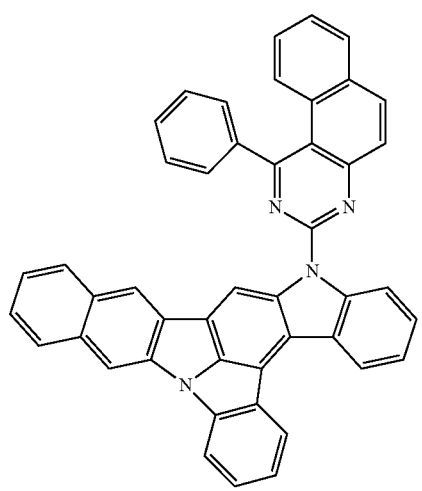
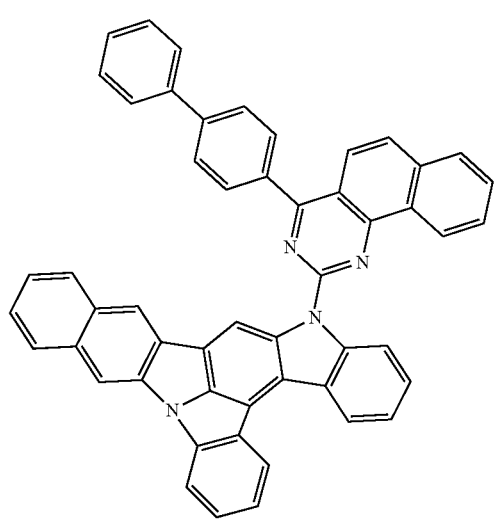
690
-continued
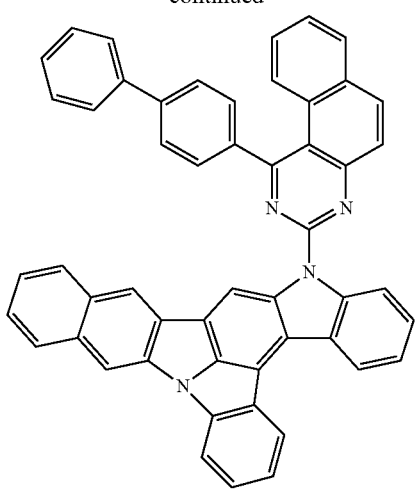
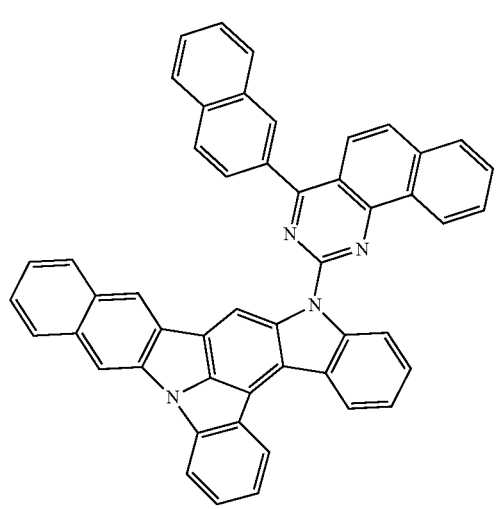
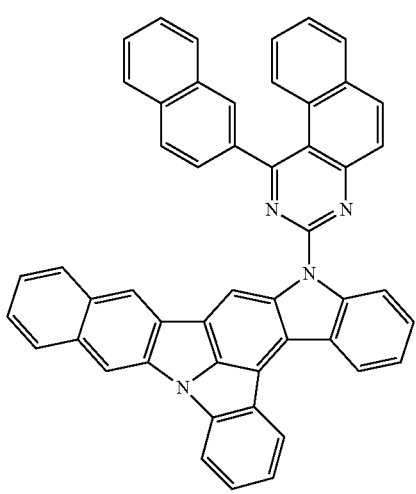

691
-continued
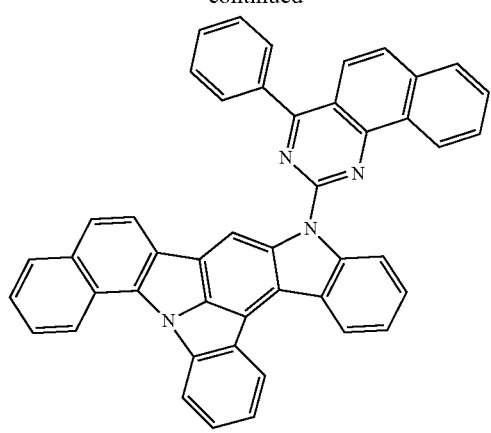
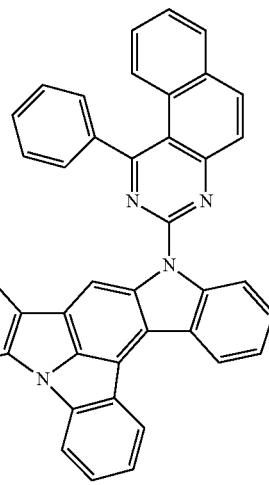
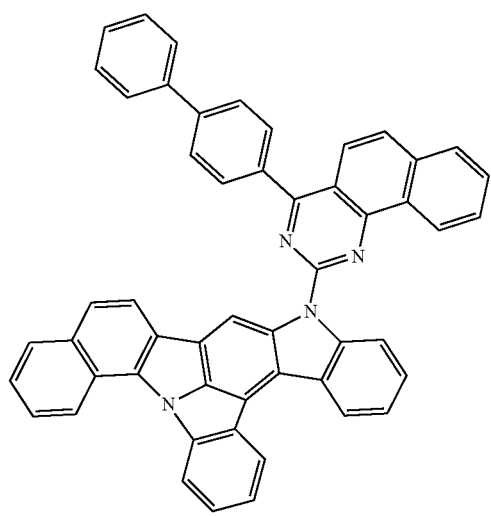
692
-continued
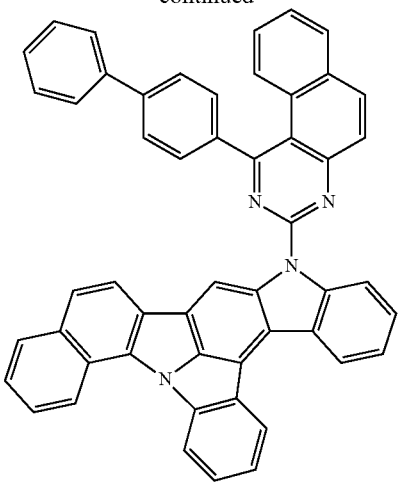
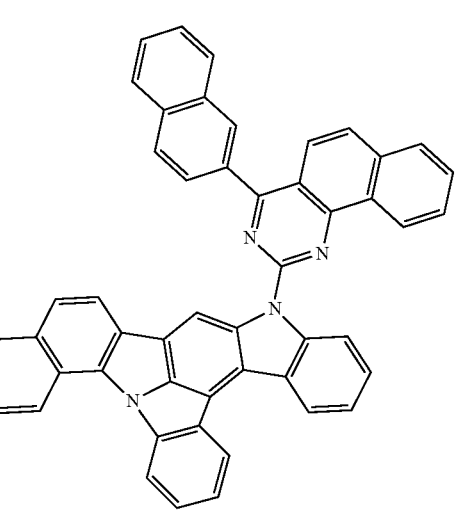
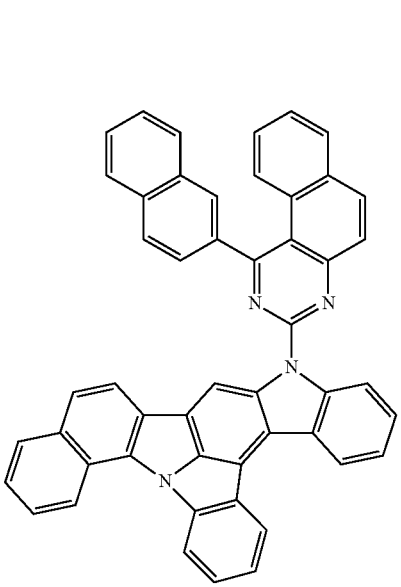

693
-continued
694
-continued
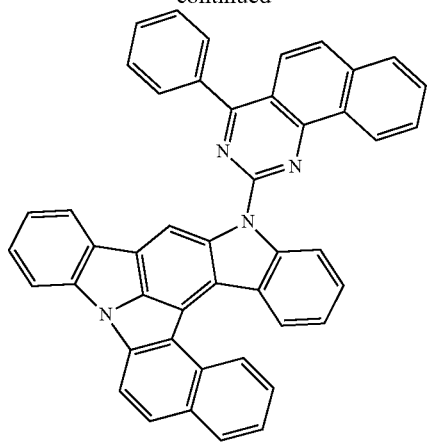
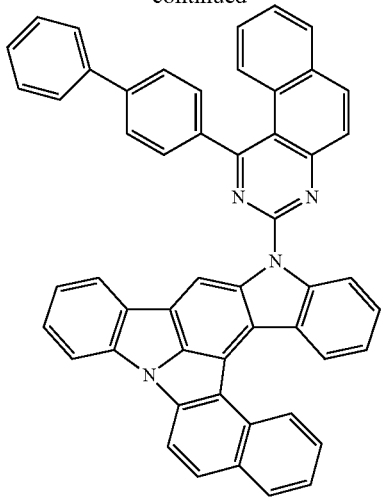
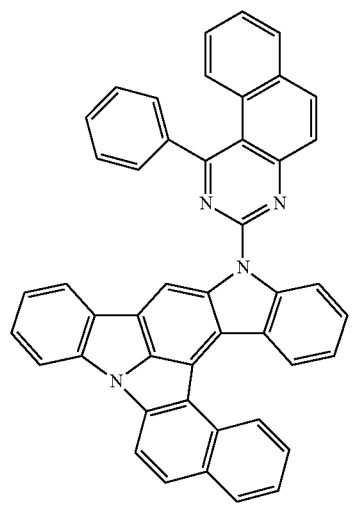
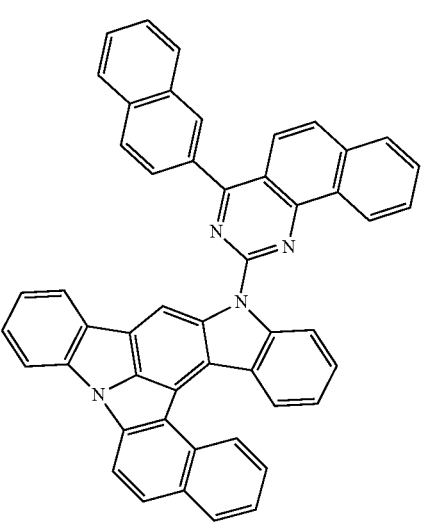
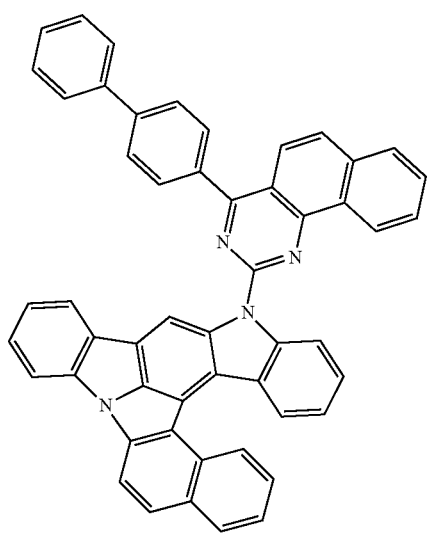
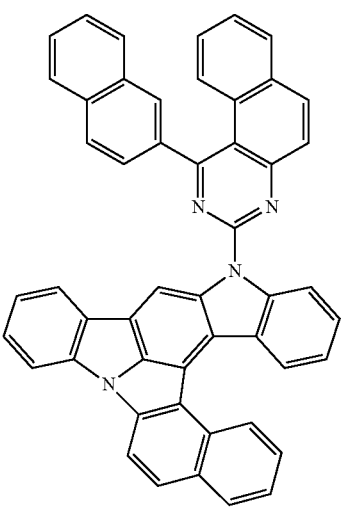

695
-continued
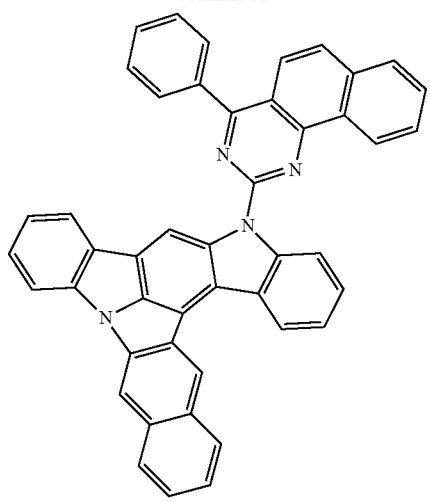
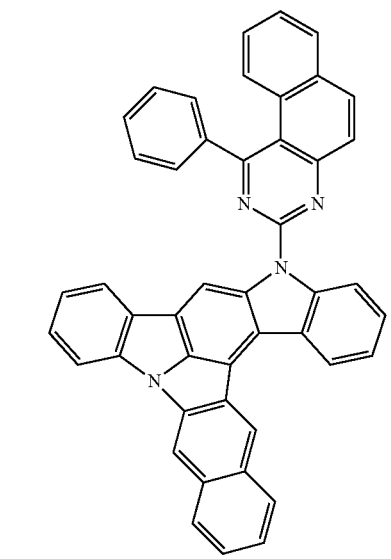
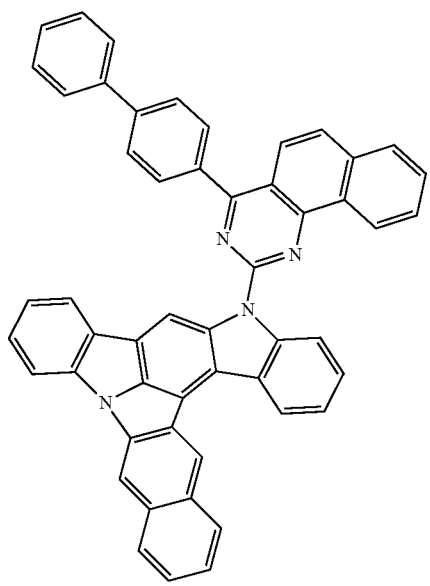
696
-continued
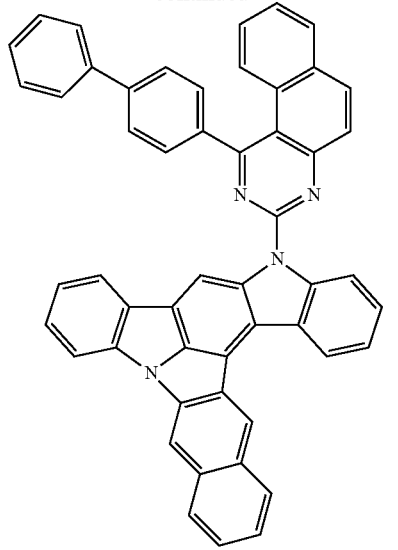
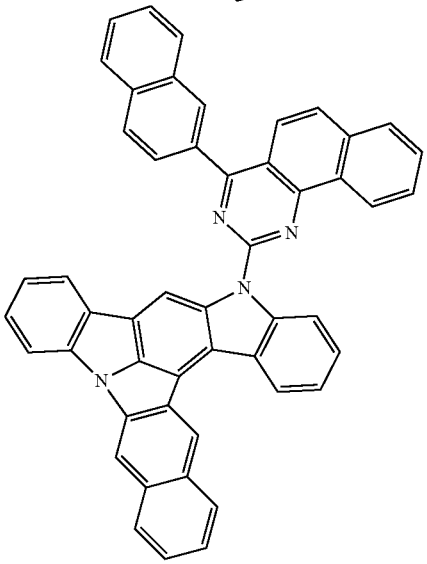
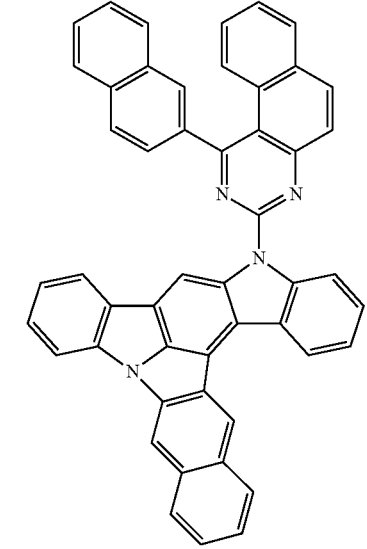

697
-continued
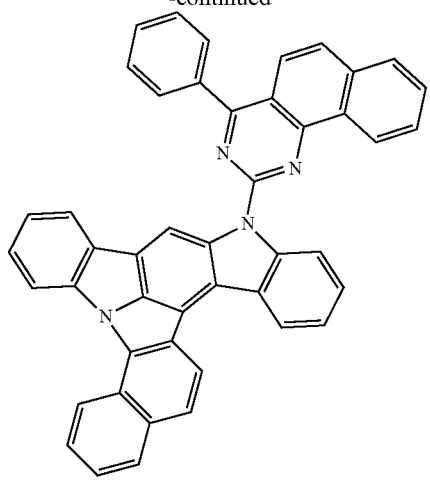
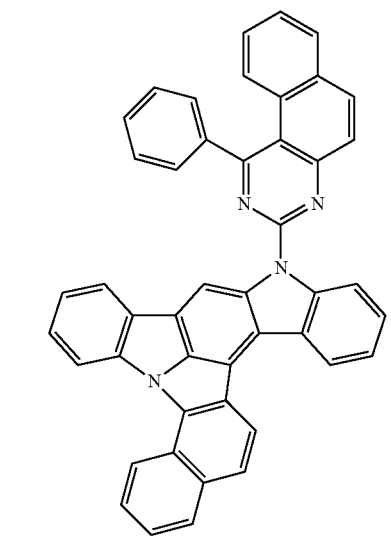
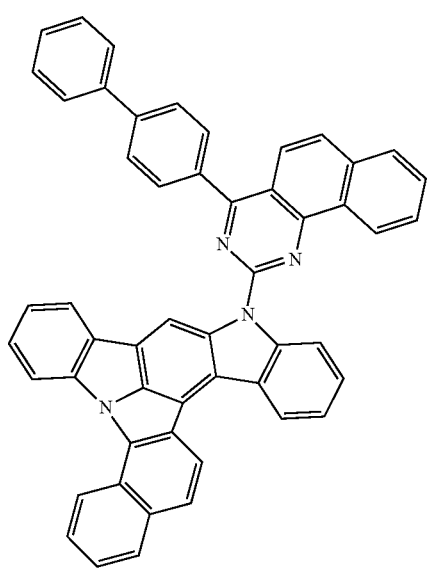
698
-continued
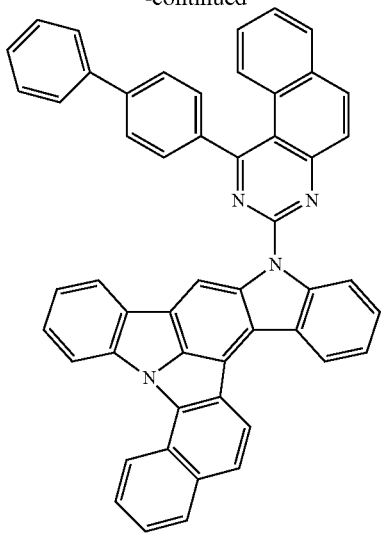
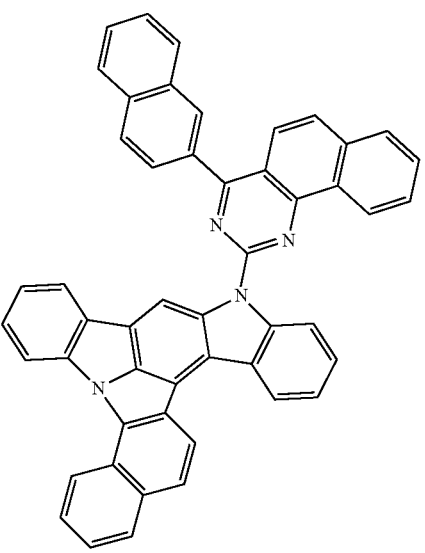
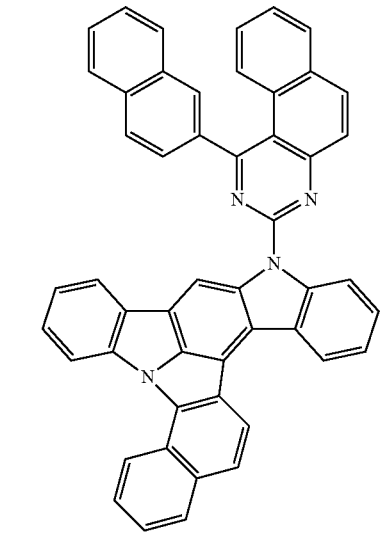

699
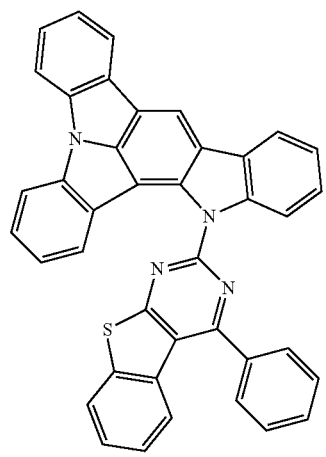
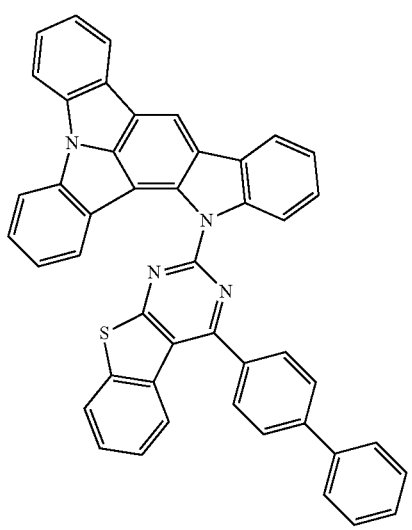
700
-continued
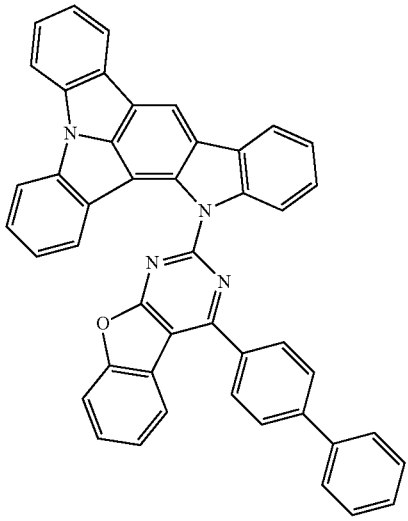
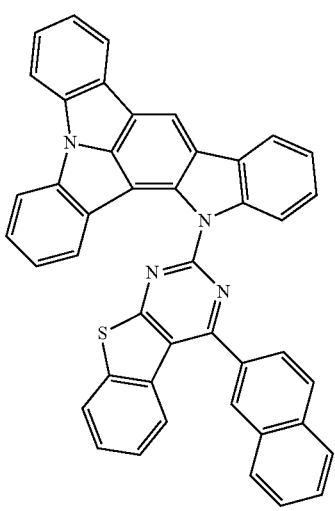
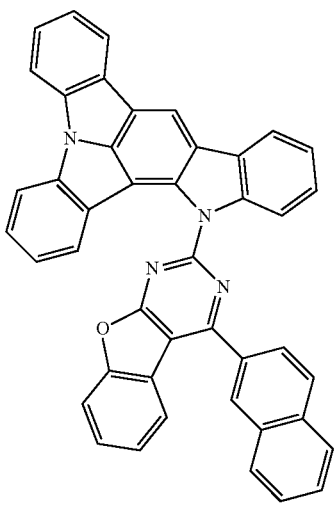

701
-continued
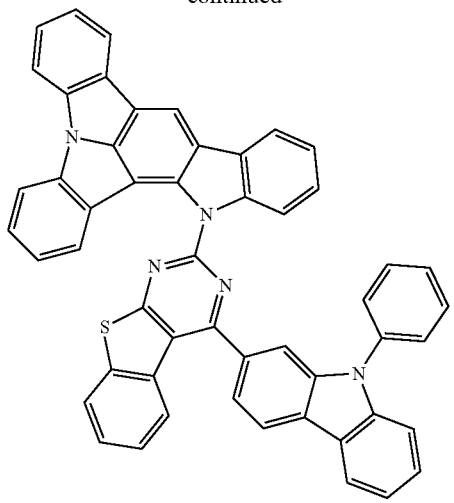
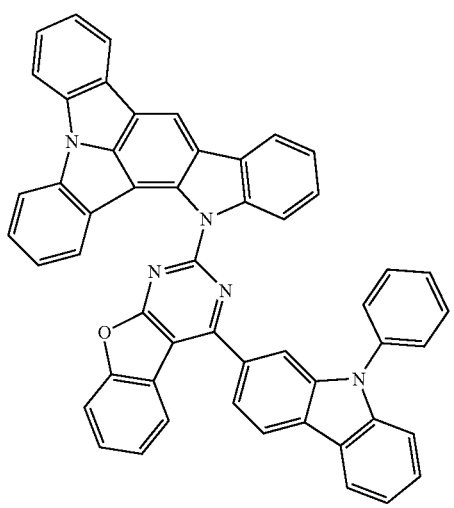
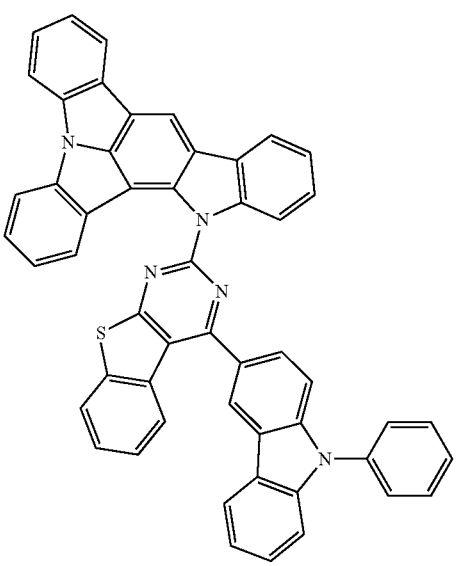
702
-continued
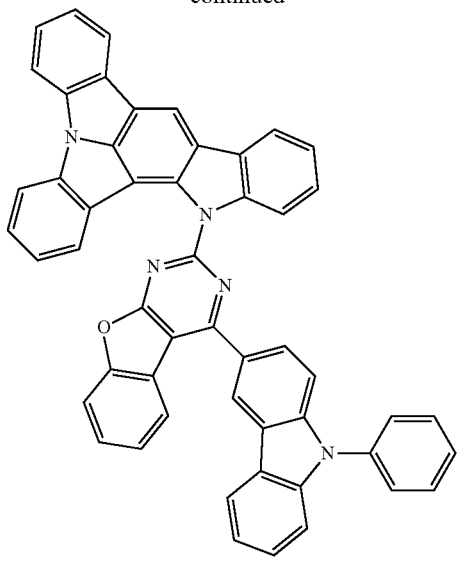
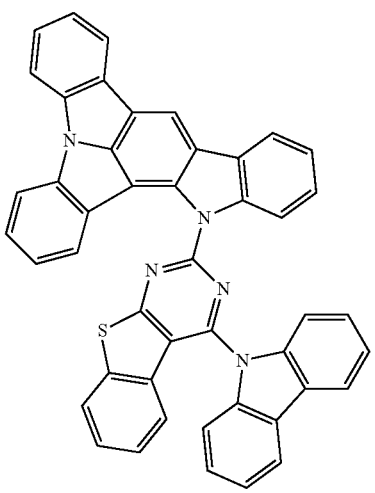
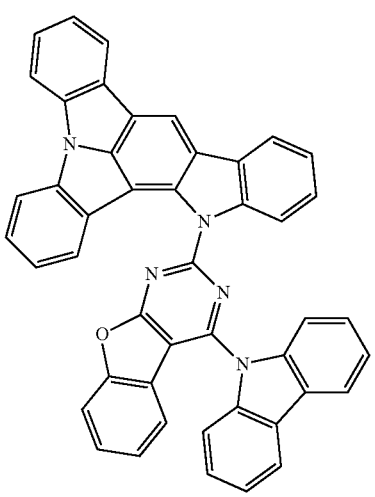

703
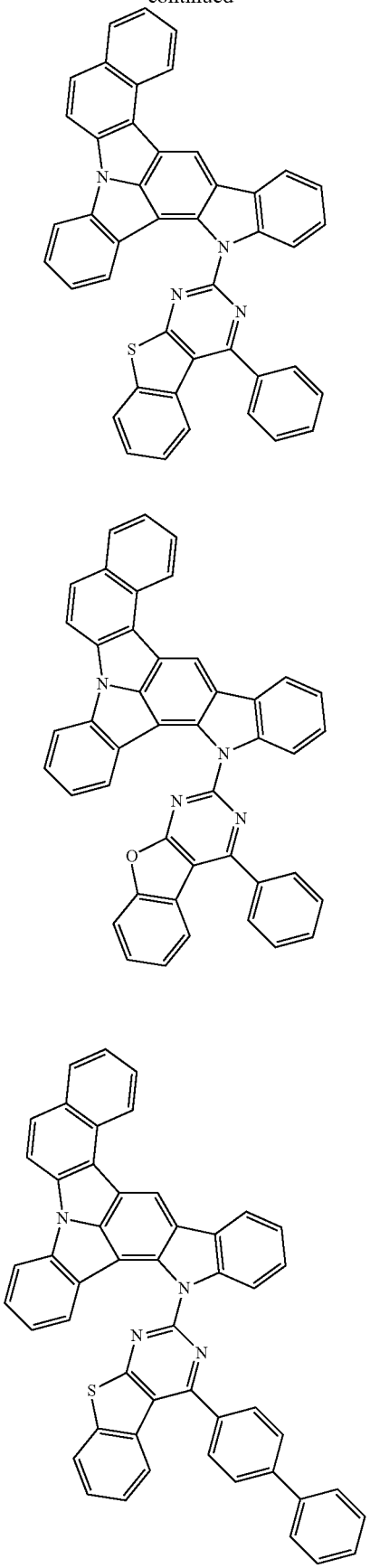
704
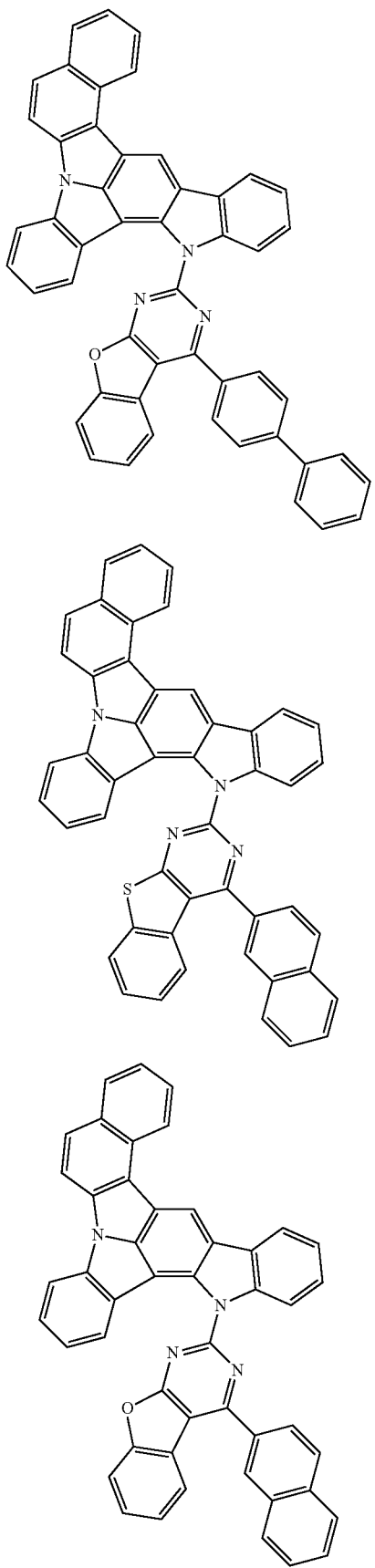

705
-continued
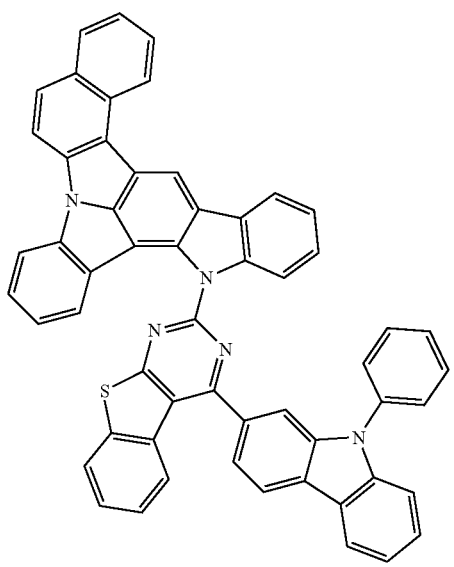
706
-continued
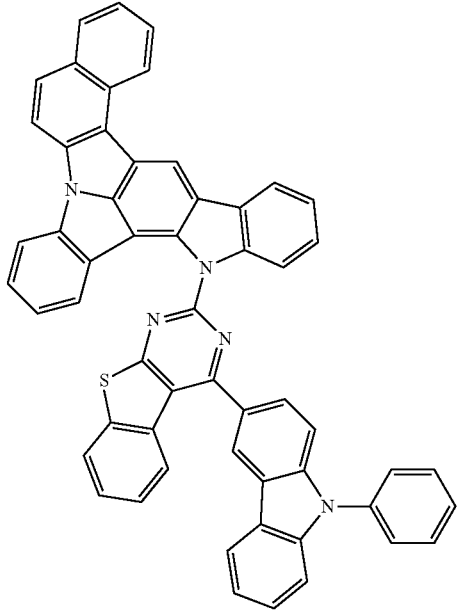
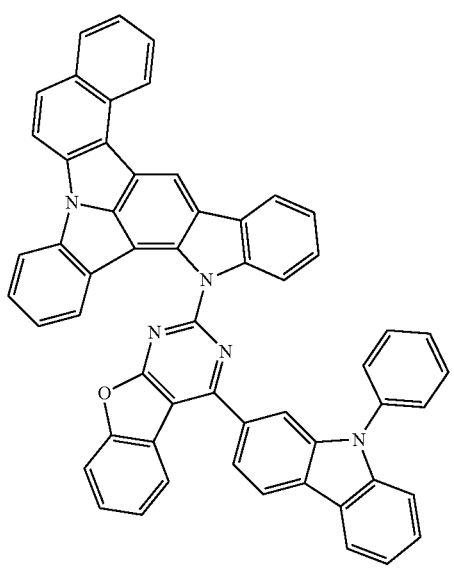
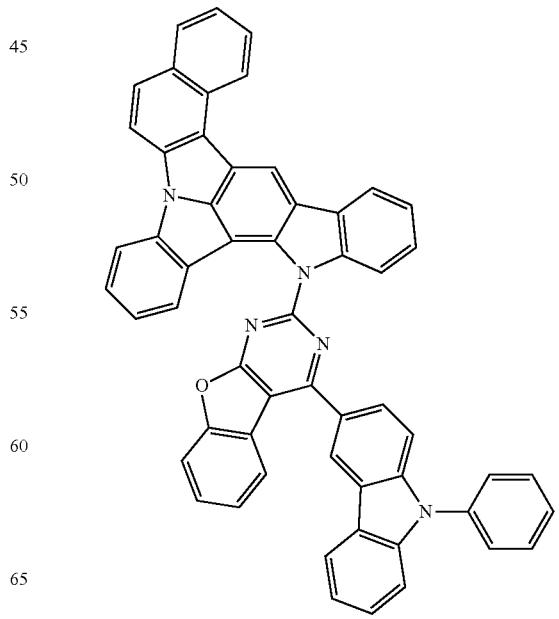

707
-continued
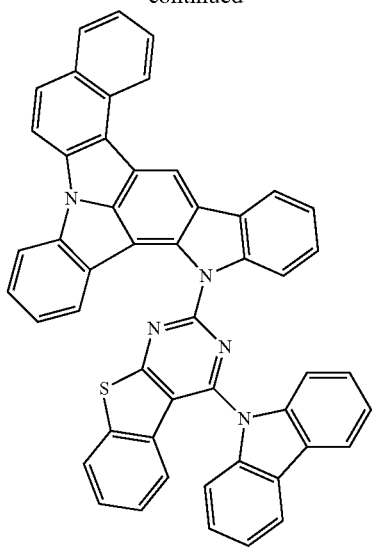
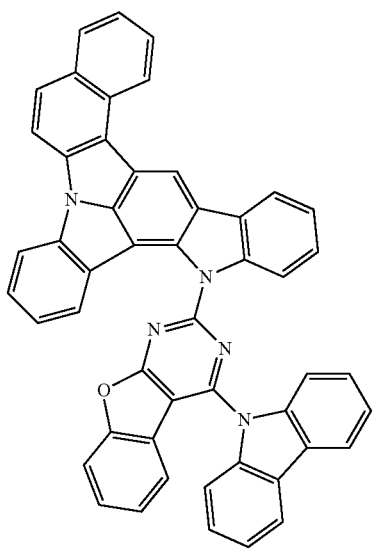
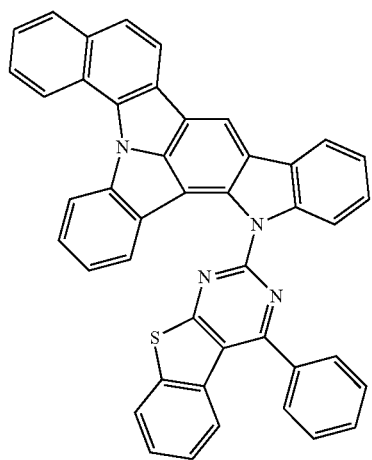
708
-continued
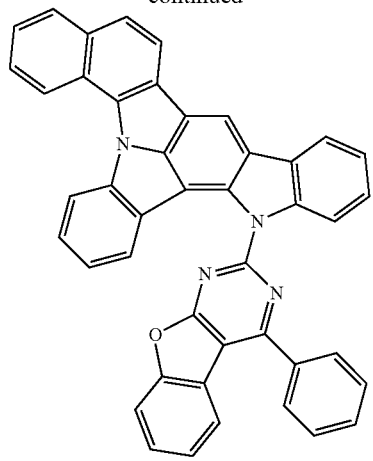
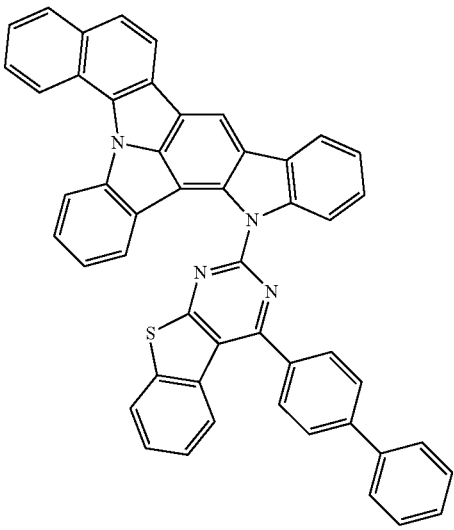
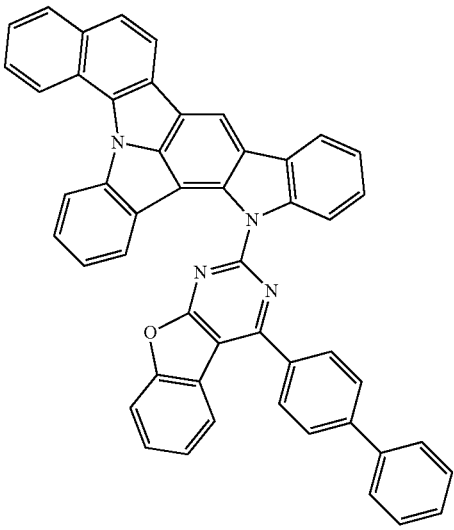

709
-continued
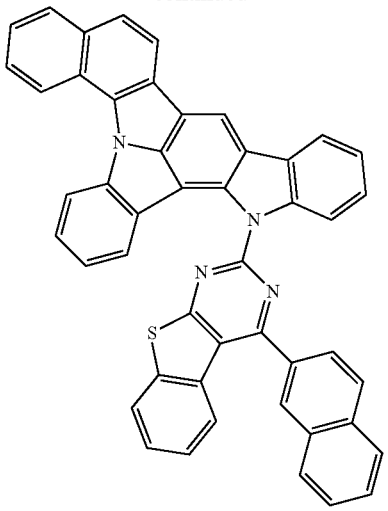
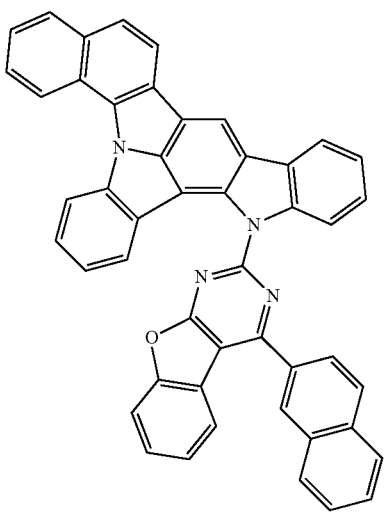
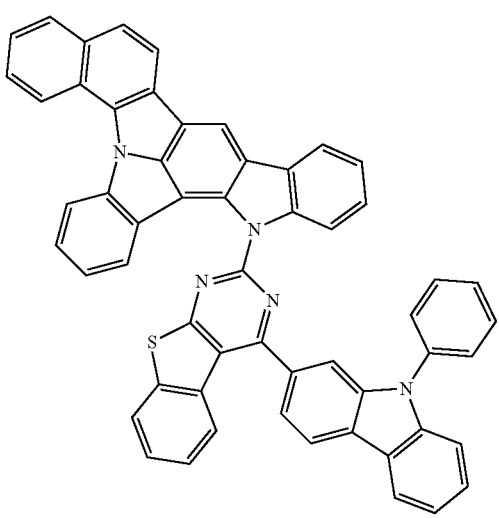
710
-continued
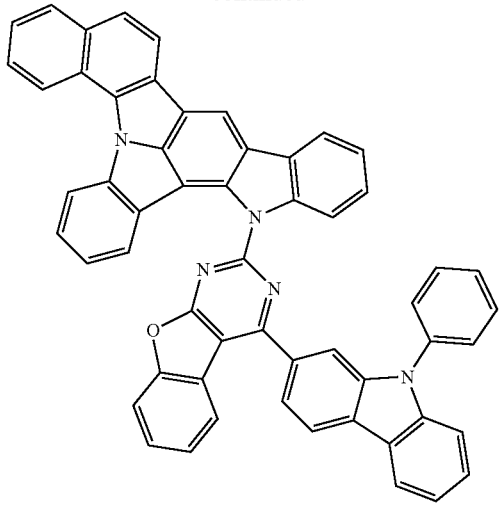
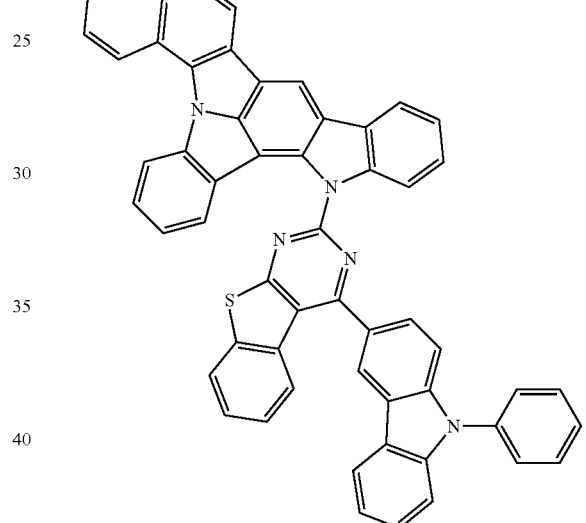
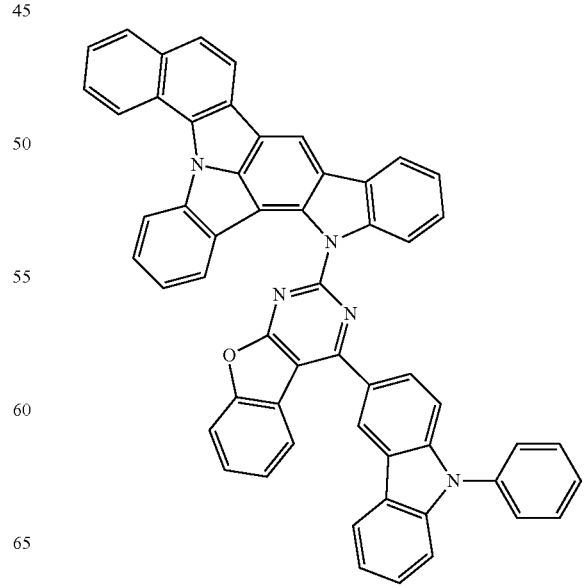

711
-continued
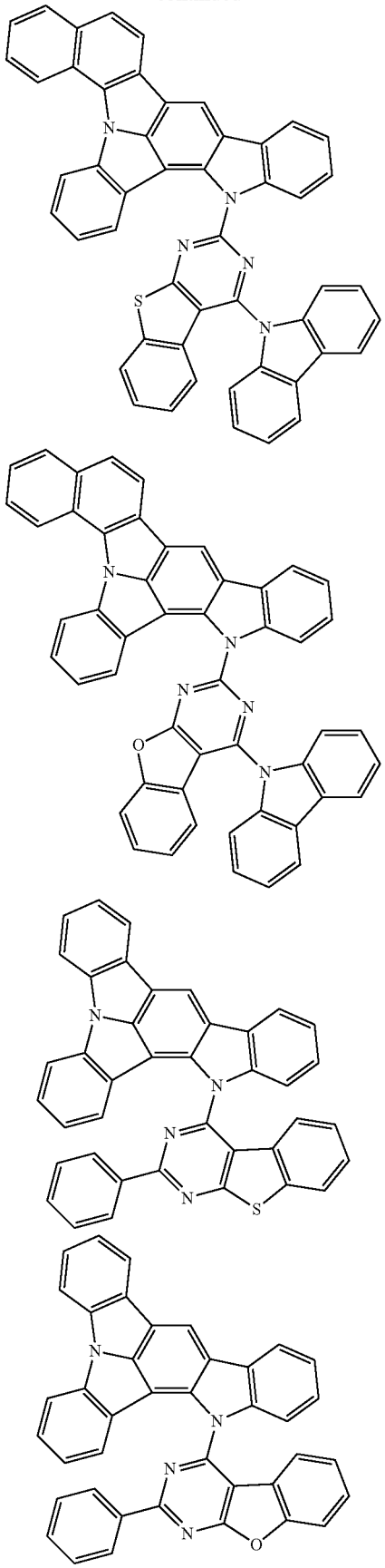
712
-continued
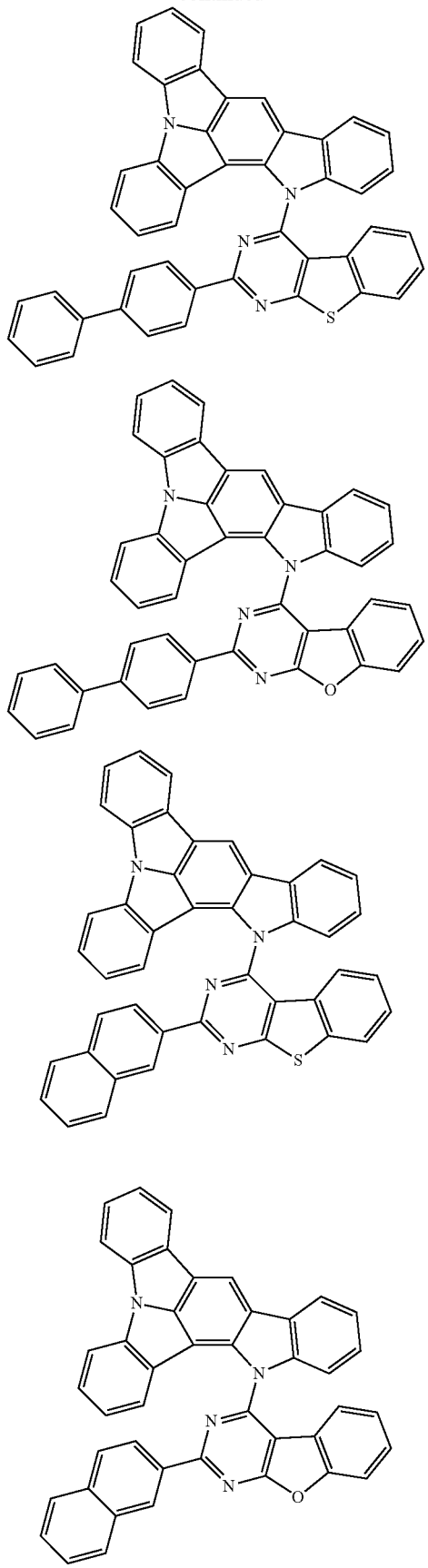

713
-continued
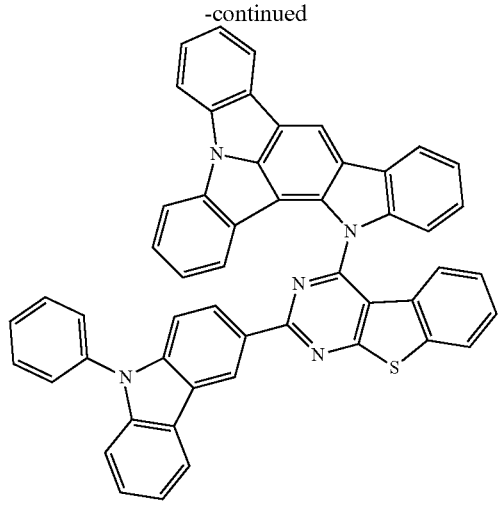
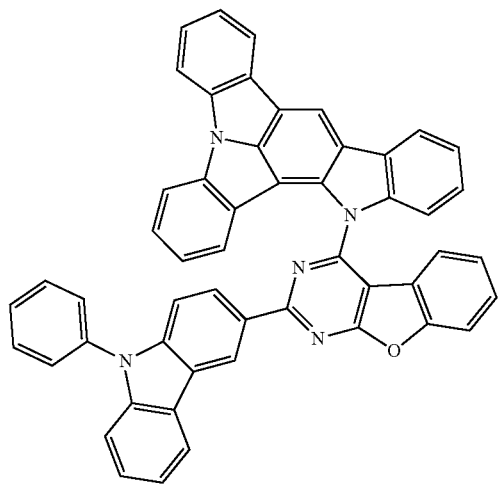
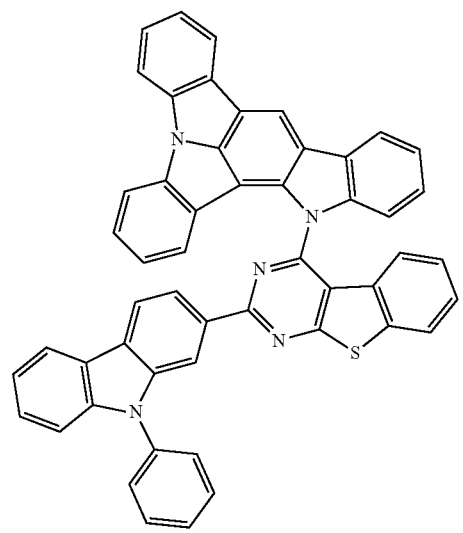
714
-continued
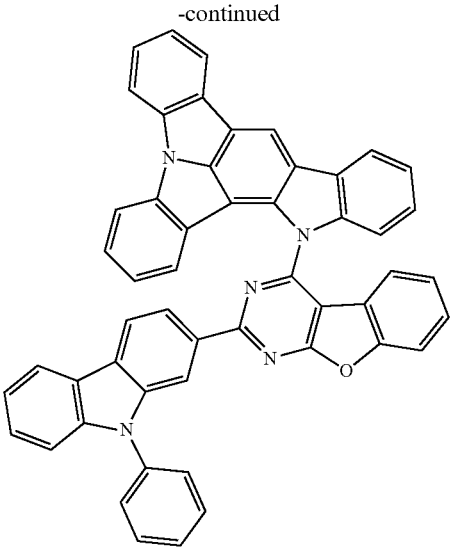
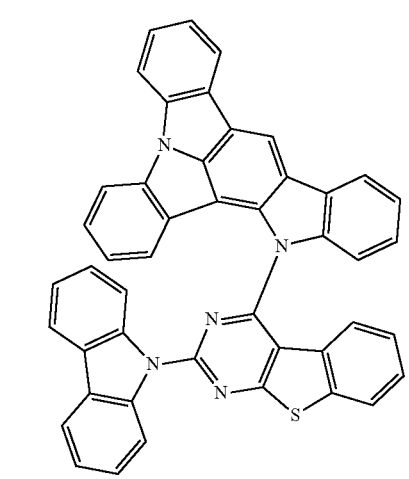
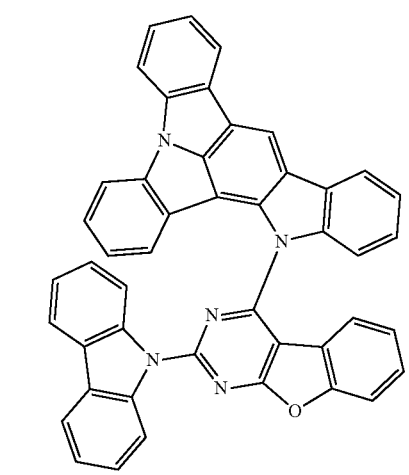

715
-continued
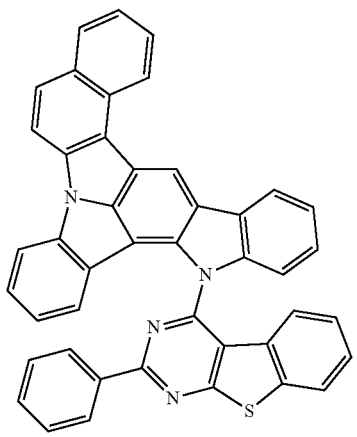
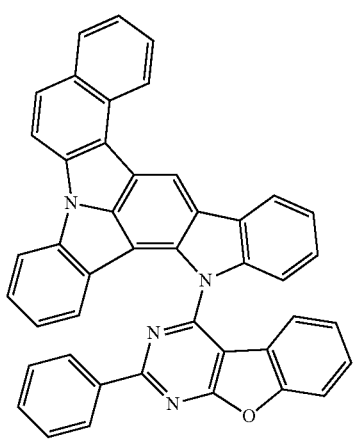
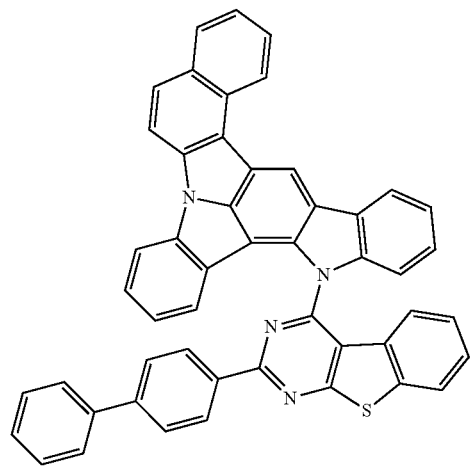
716
-continued
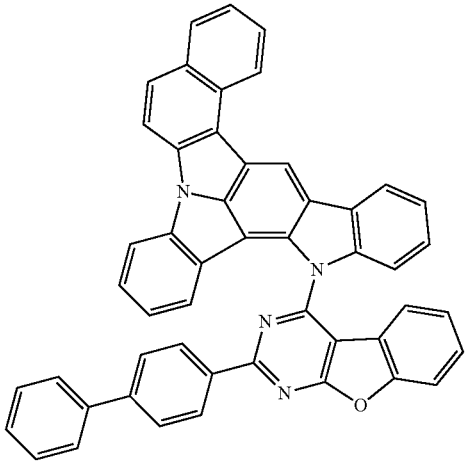
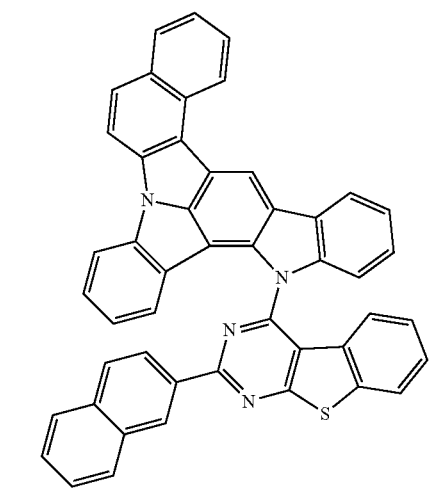
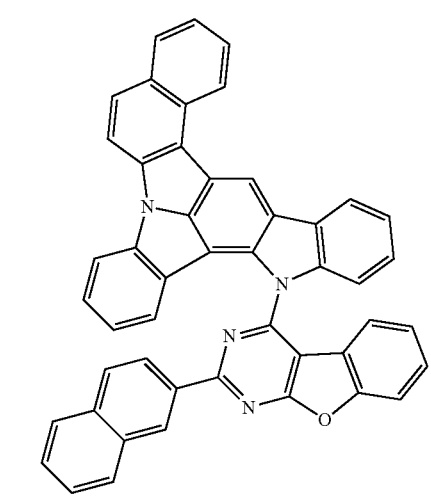

717
-continued
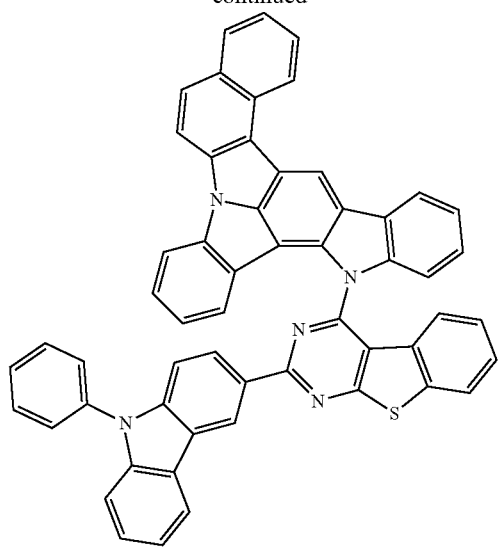
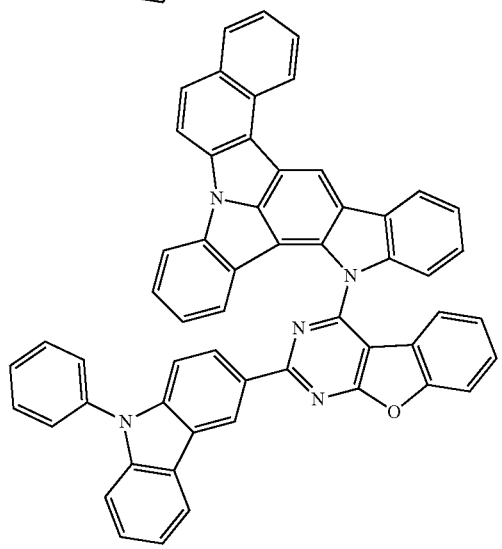
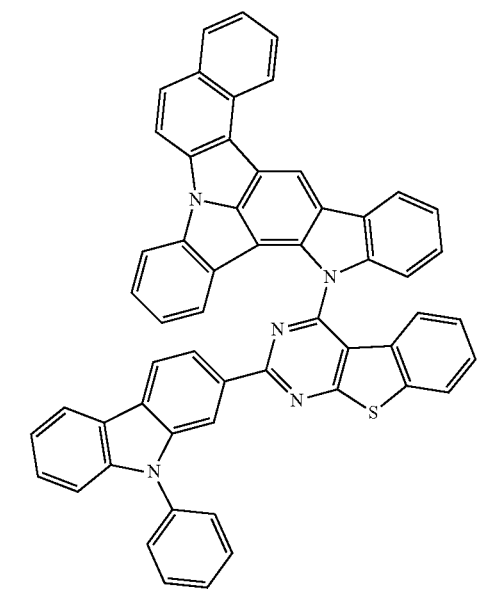
718
-continued
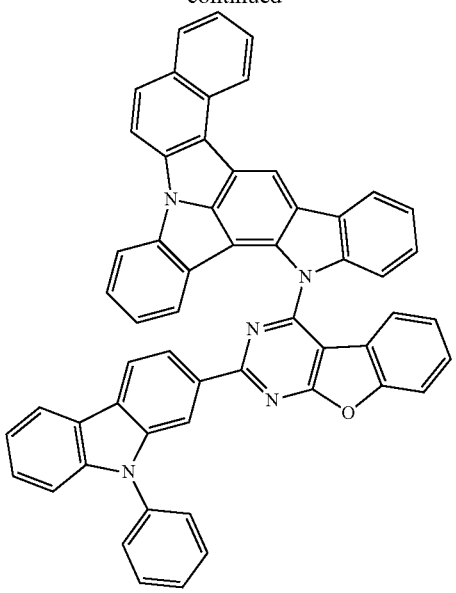
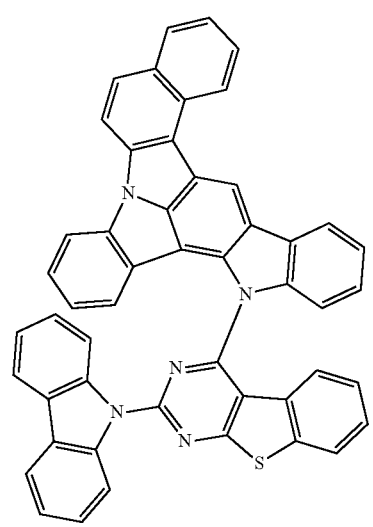
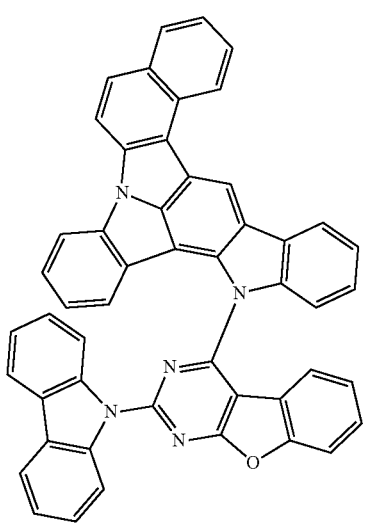

719
-continued
720
-continued
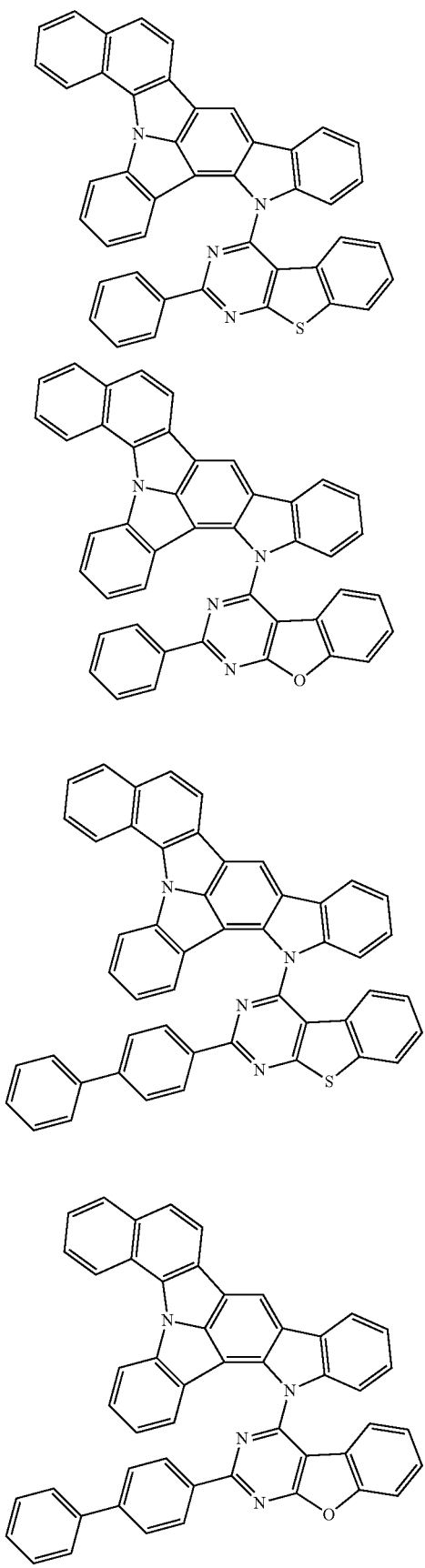
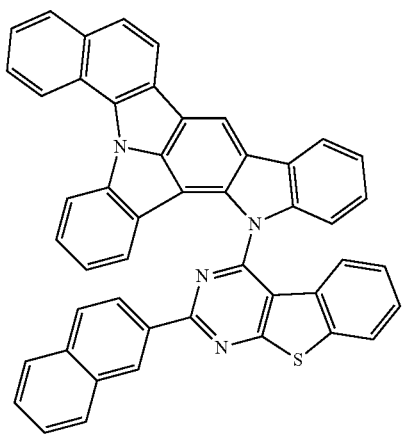
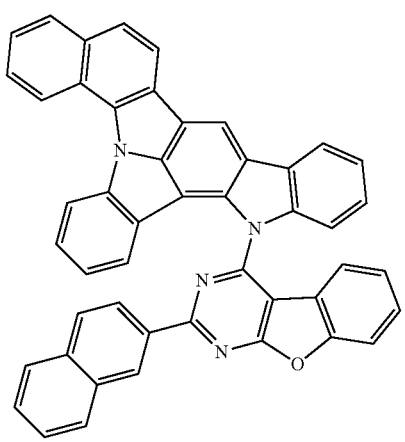
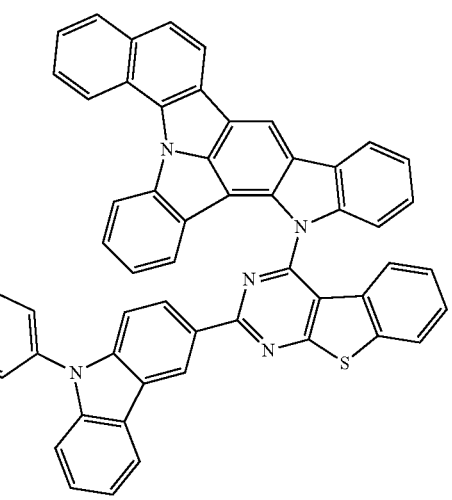

721
-continued
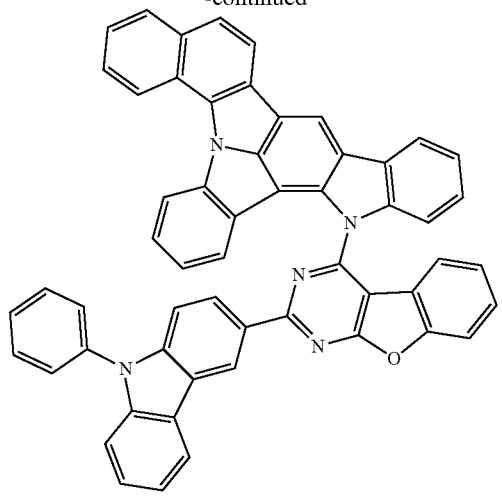
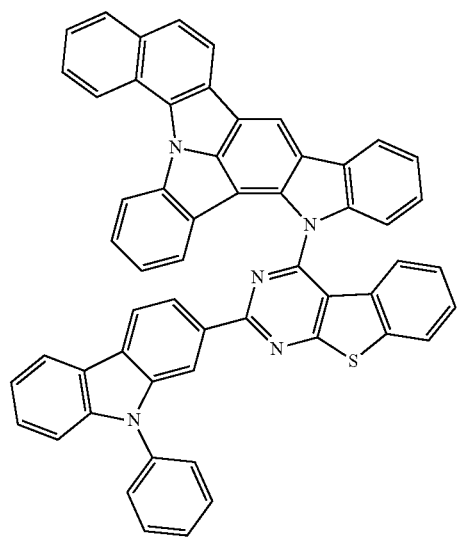
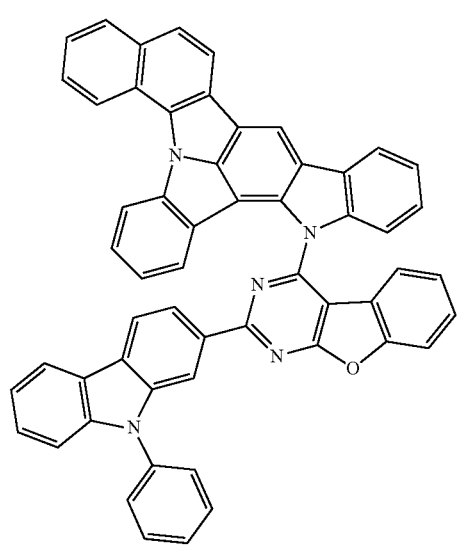
722
-continued
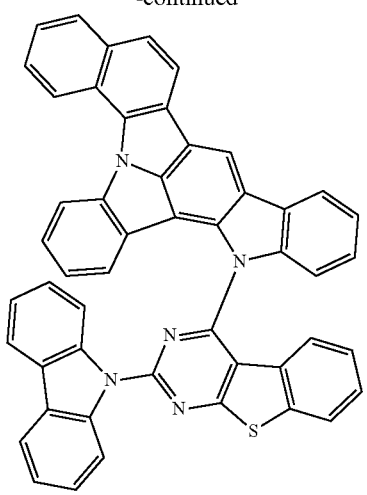
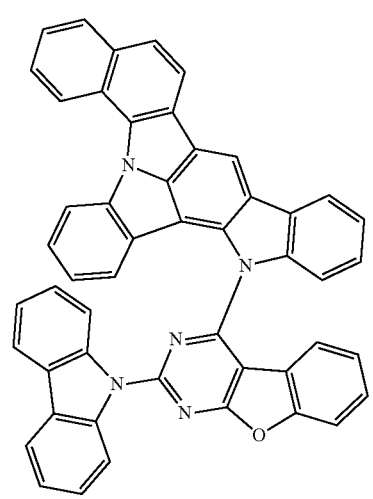
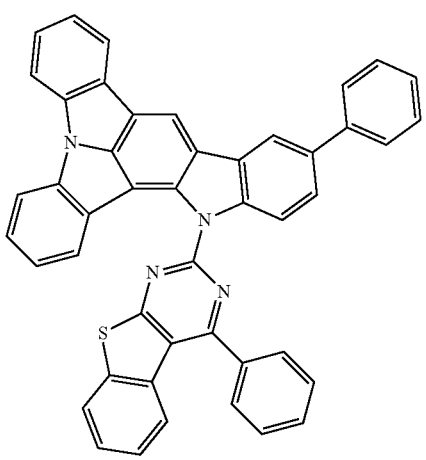

723
-continued
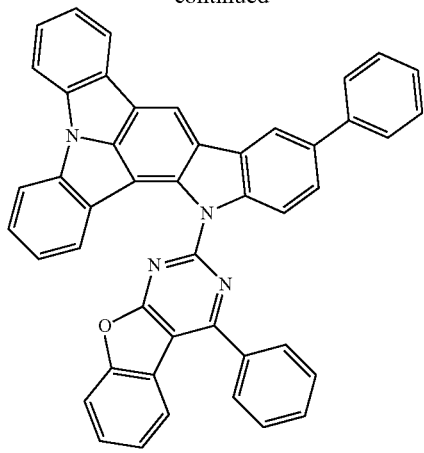
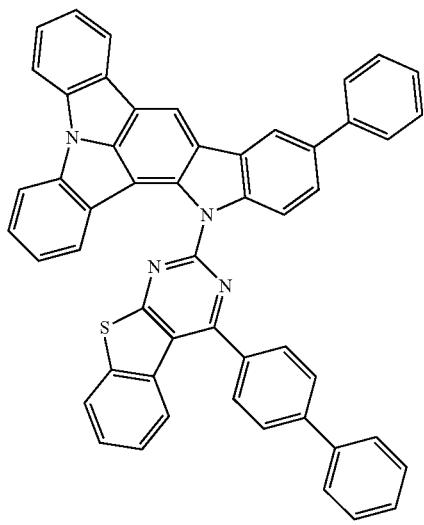
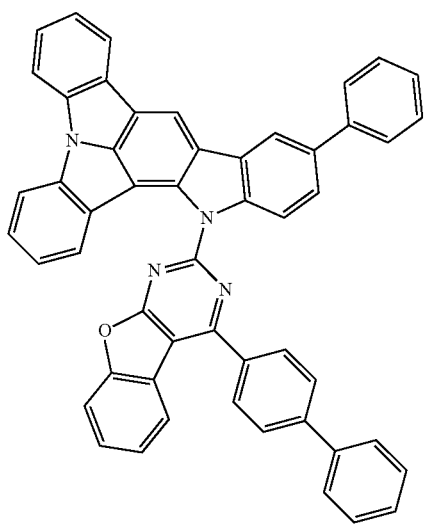
724
-continued
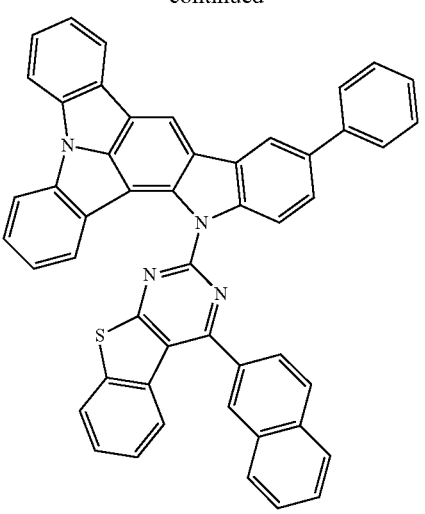
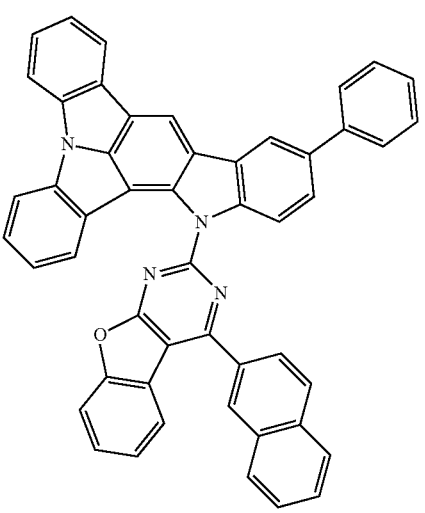
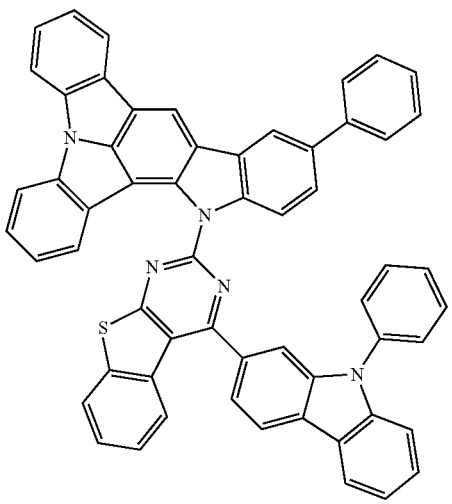

725
-continued
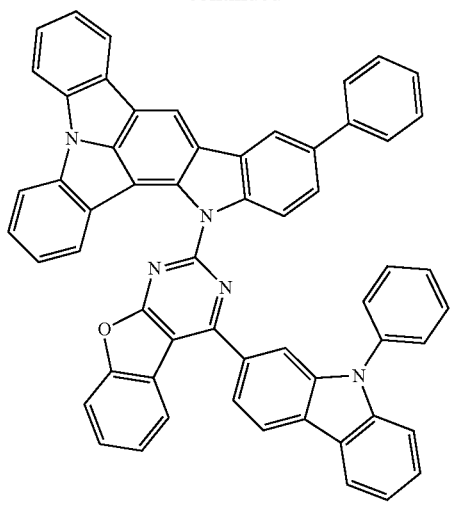
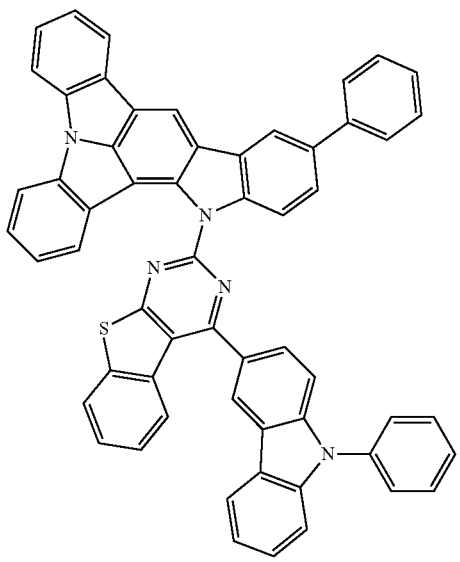
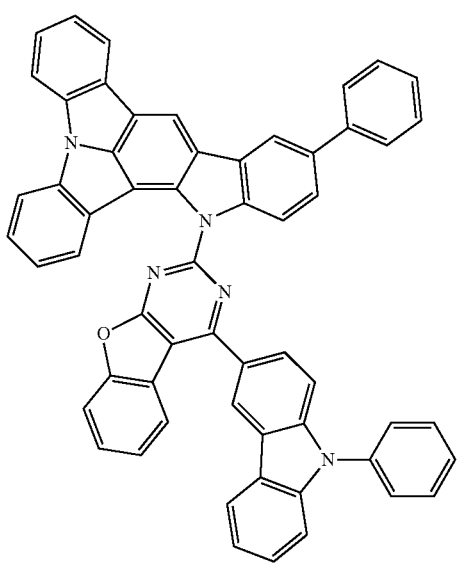
726
-continued
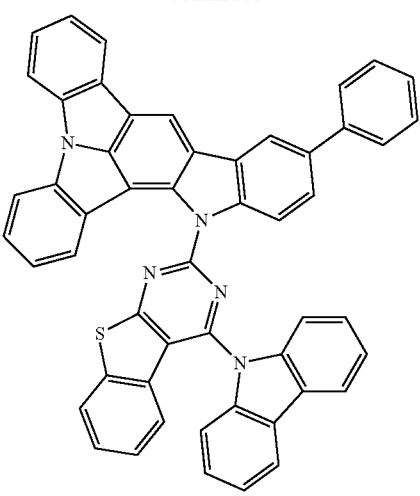
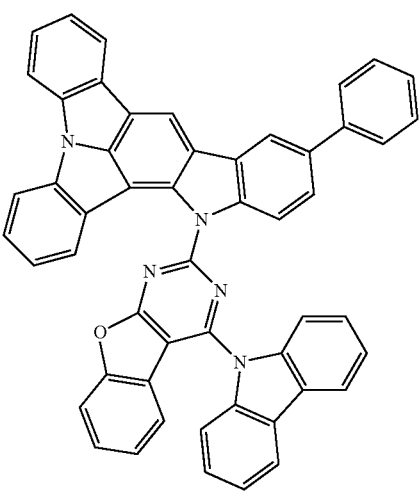
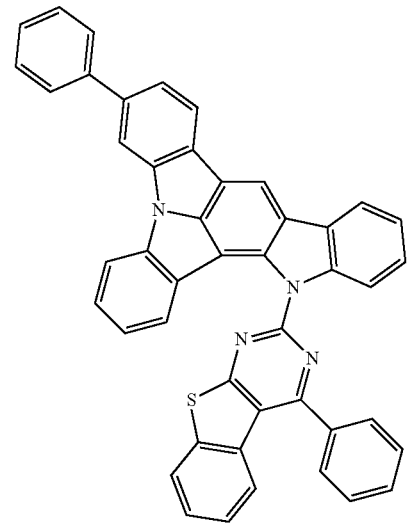

727
-continued
728
-continued
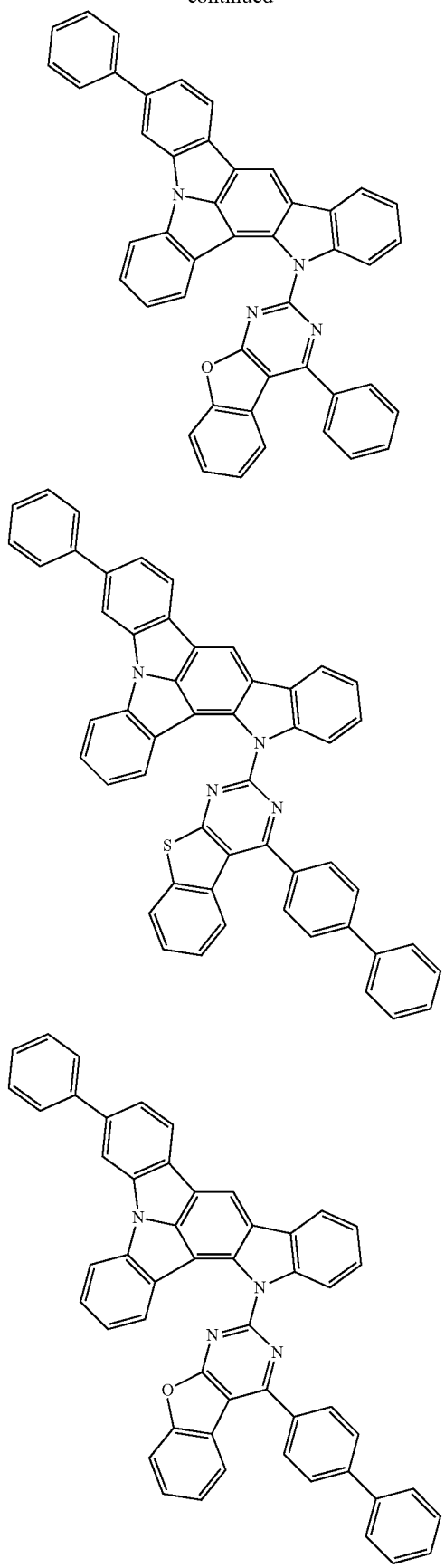
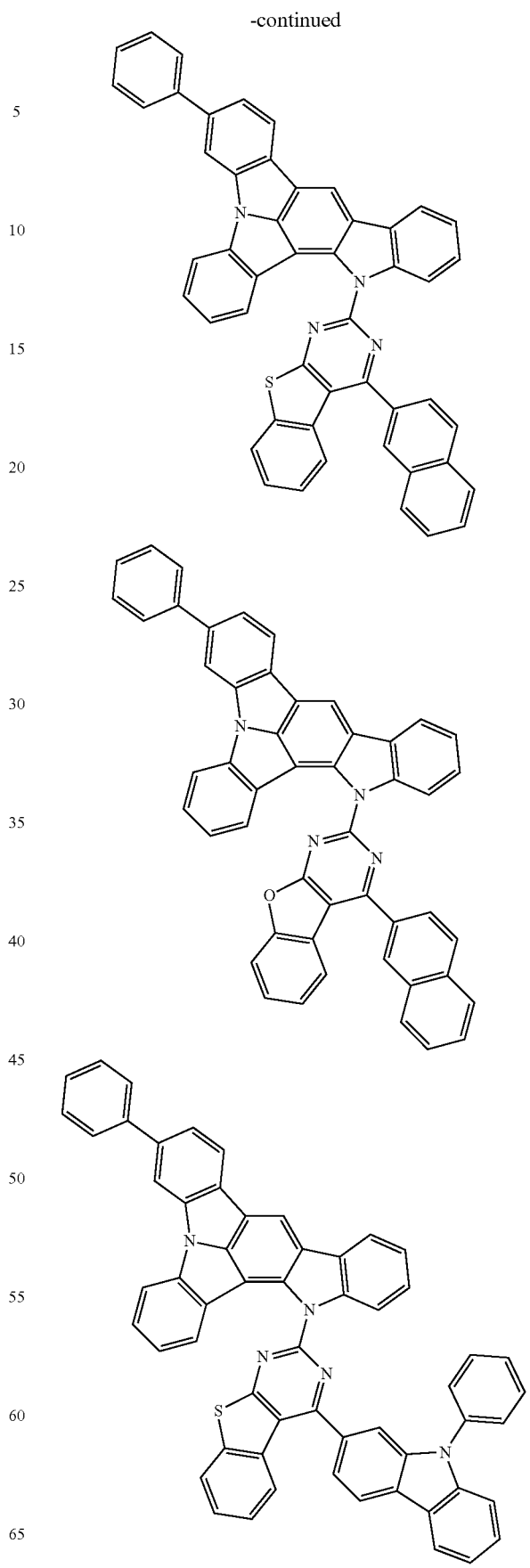

729
-continued
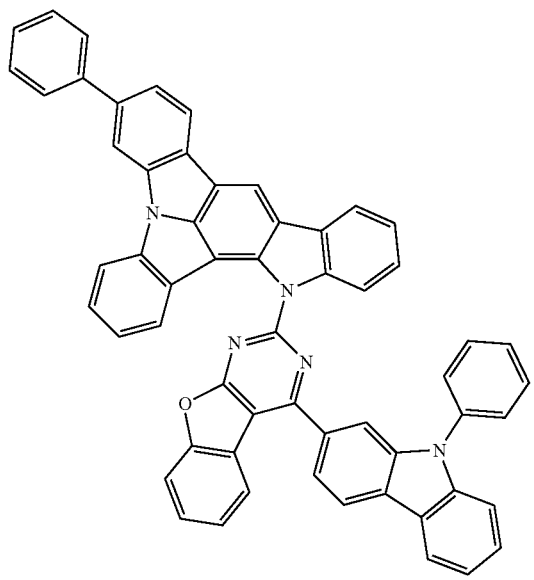
730
-continued
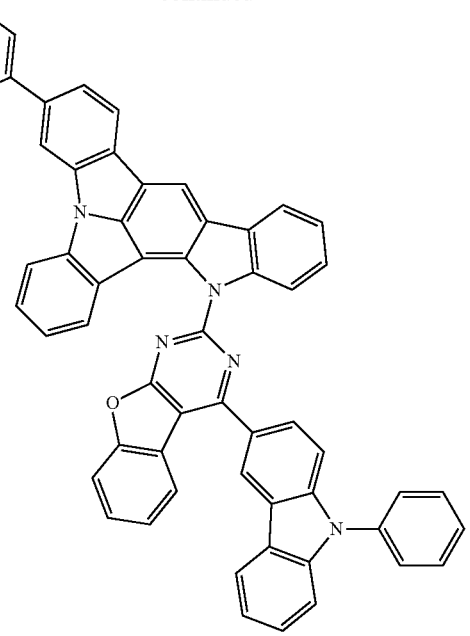
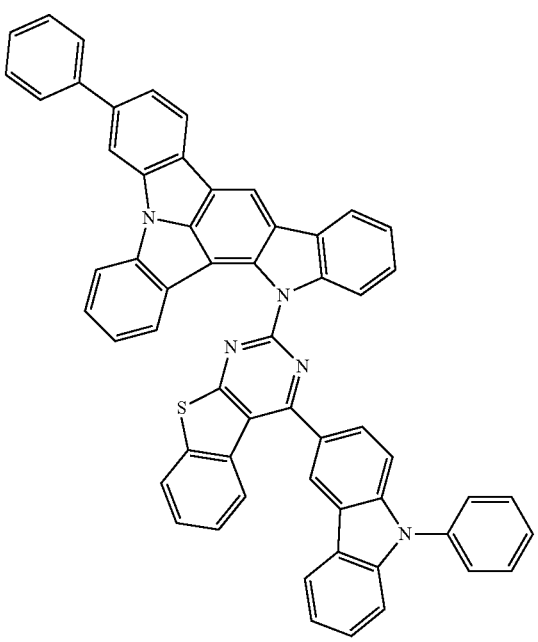
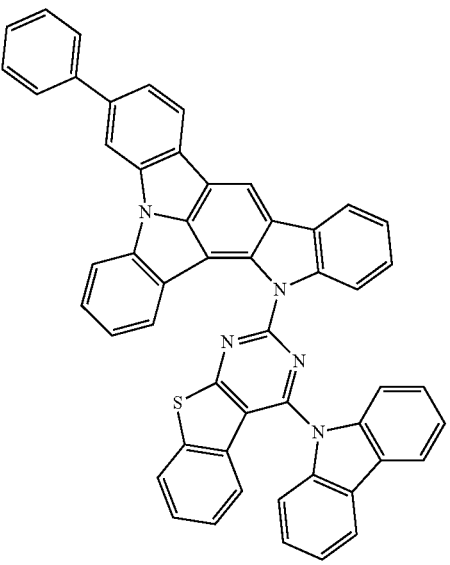

731
-continued
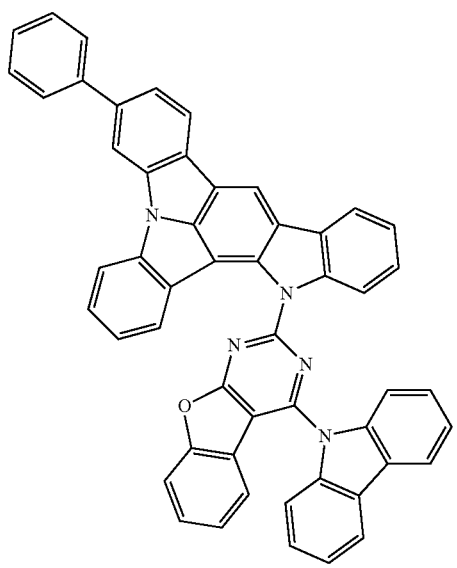
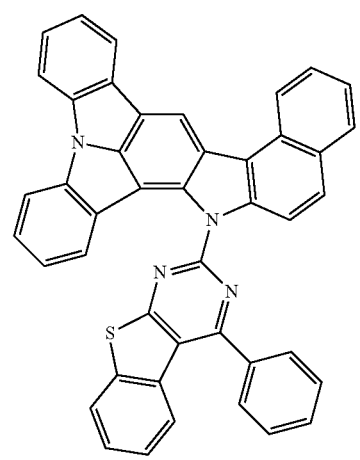
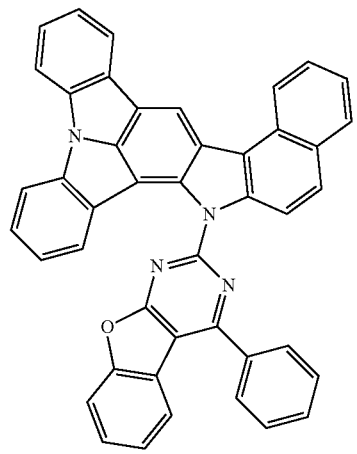
732
-continued
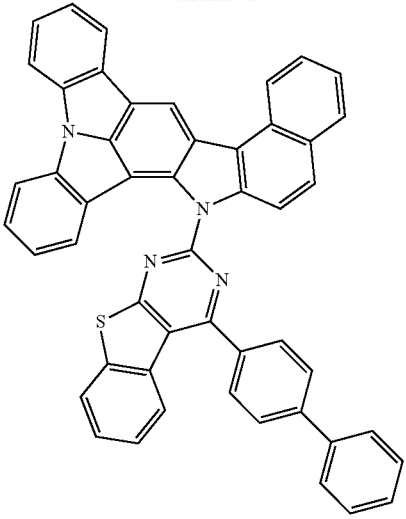
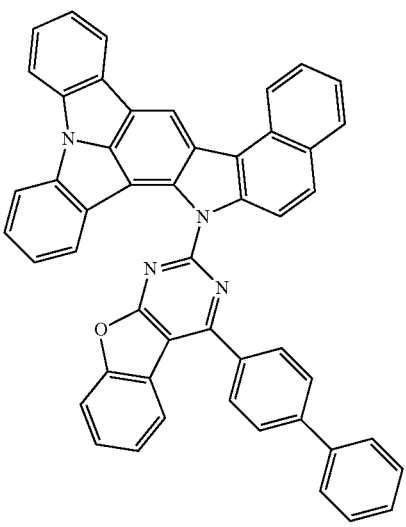
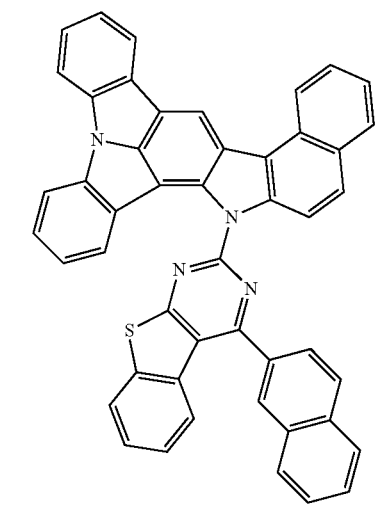

733
-continued
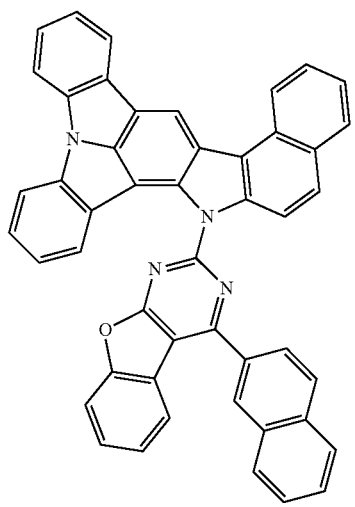
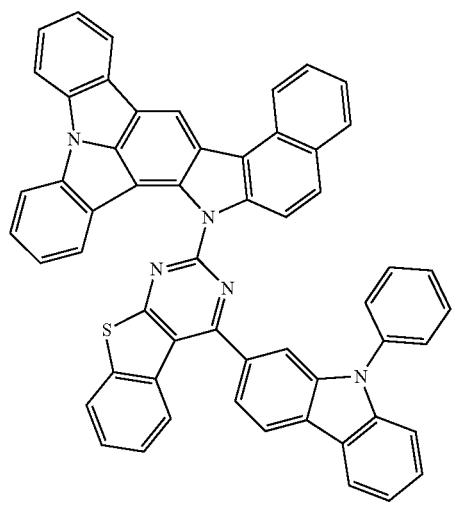
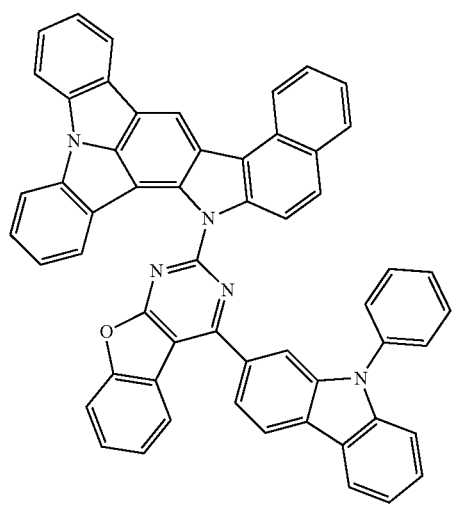
734
-continued
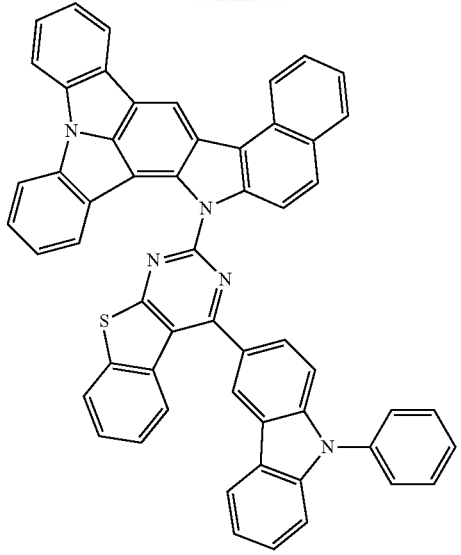
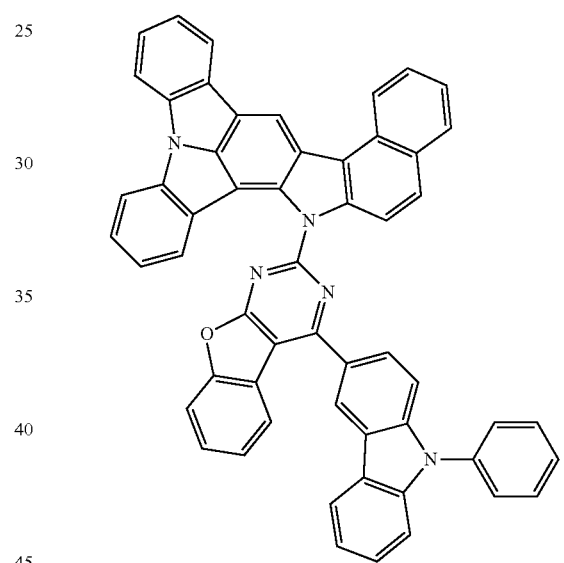
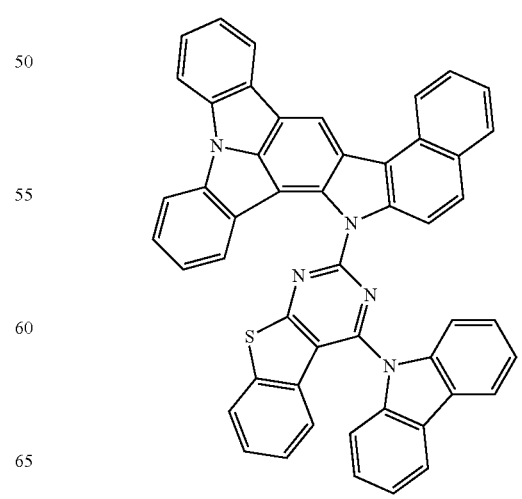

735
-continued
736
-continued
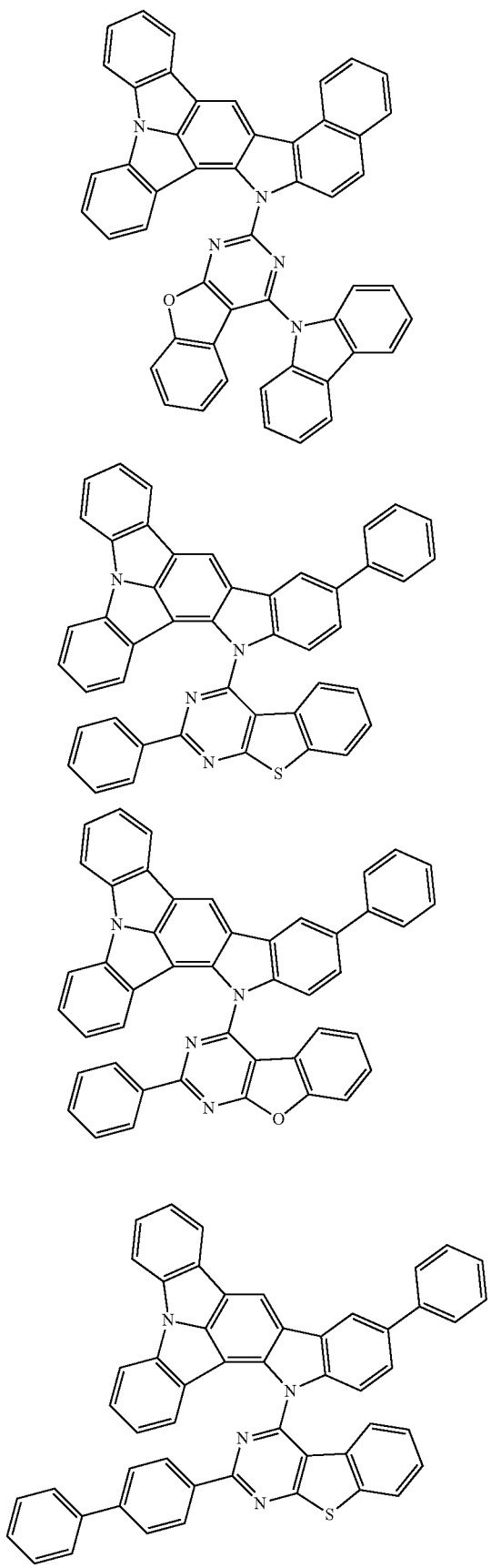
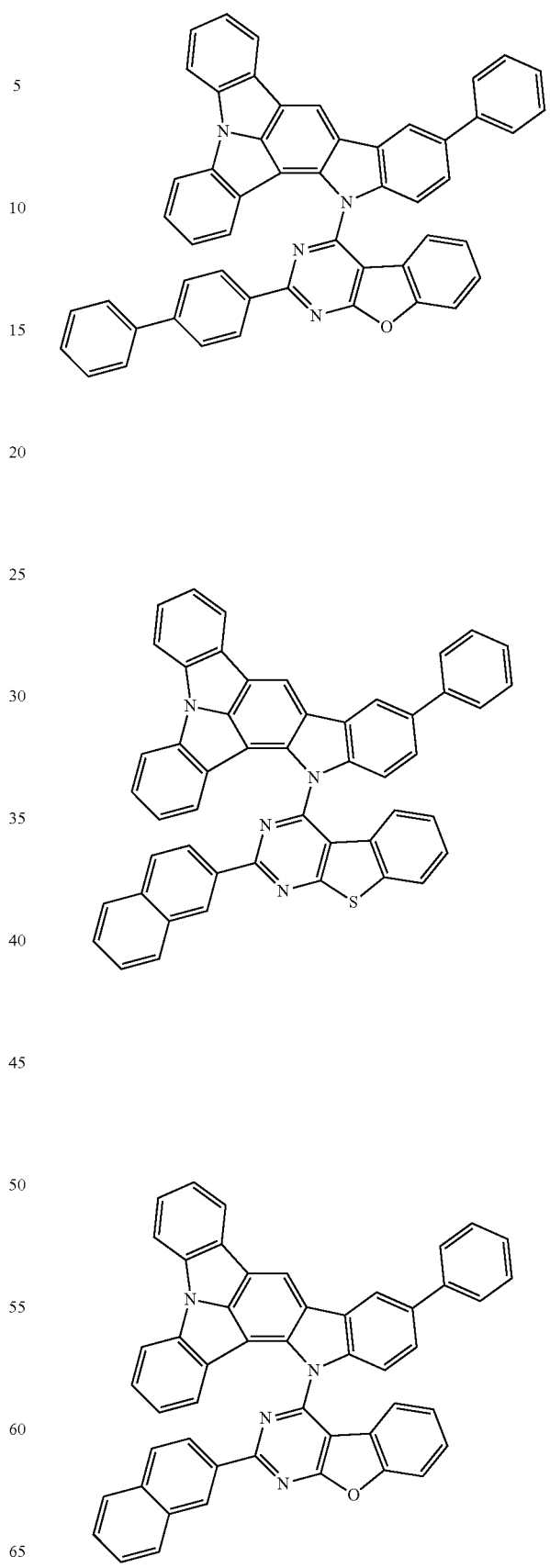

737
-continued
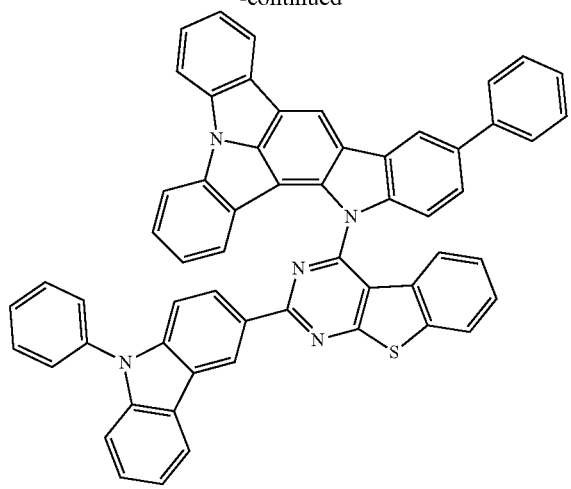
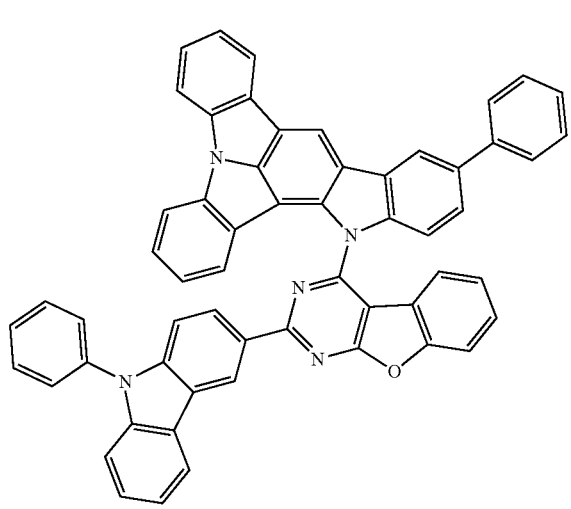
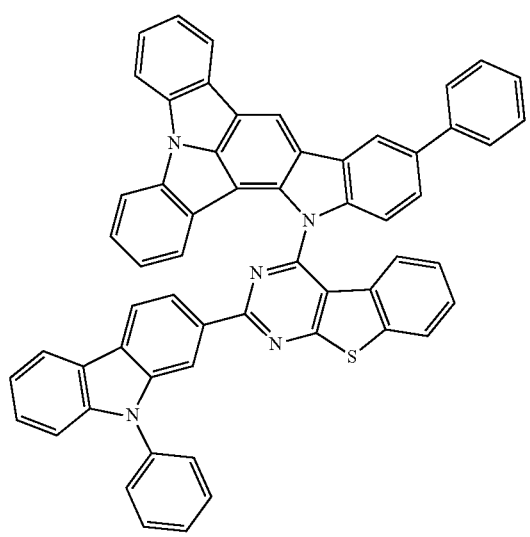
738
-continued
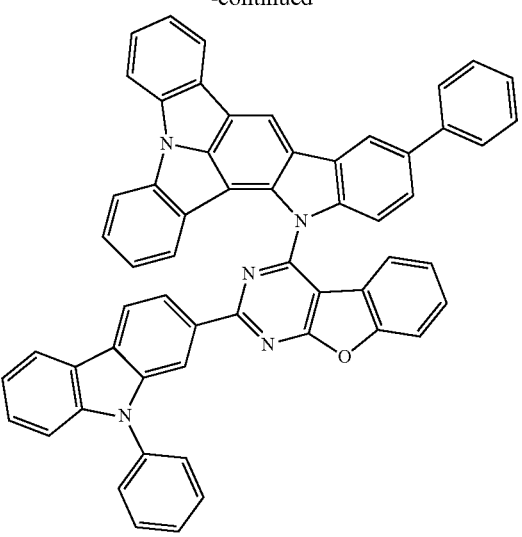
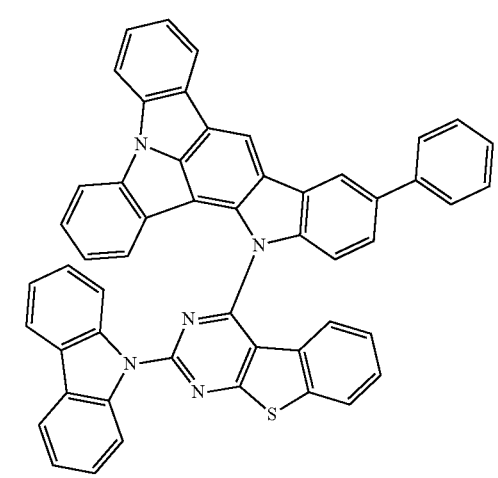
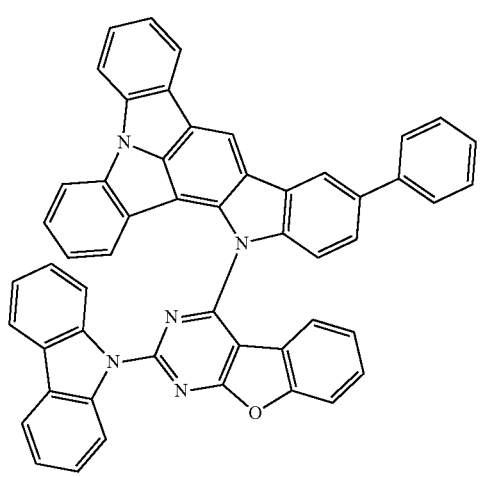

739
-continued
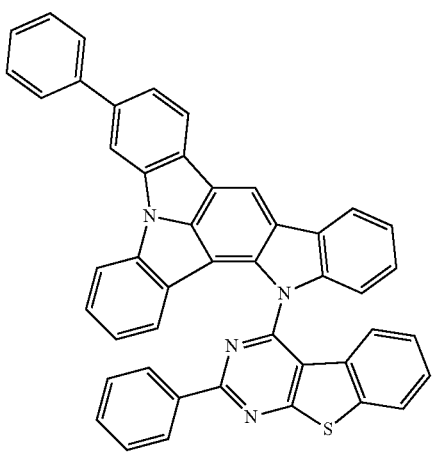
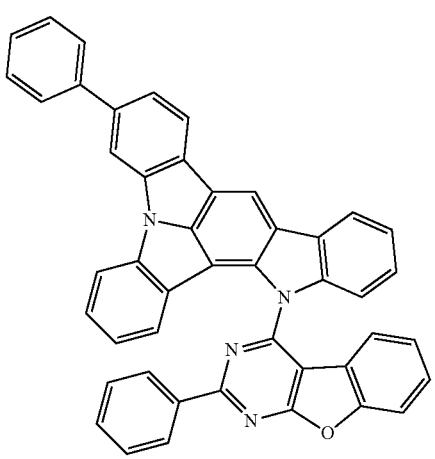
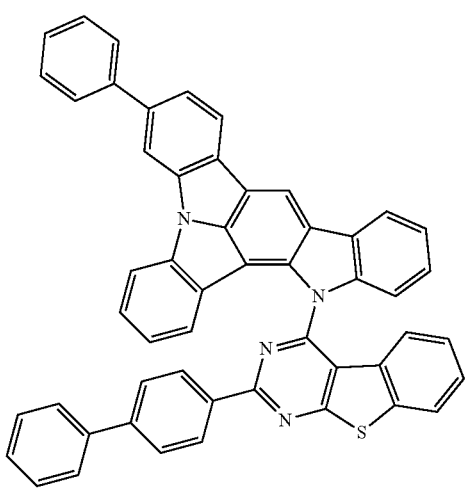
740
-continued
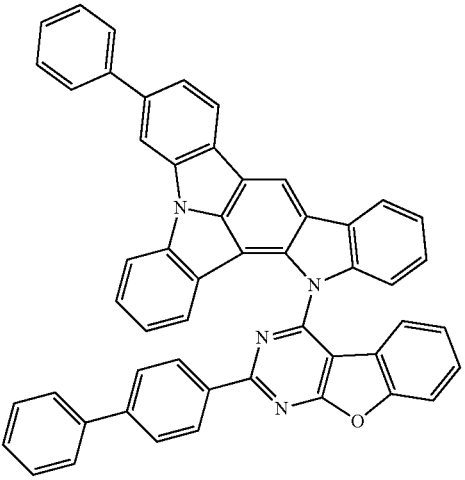
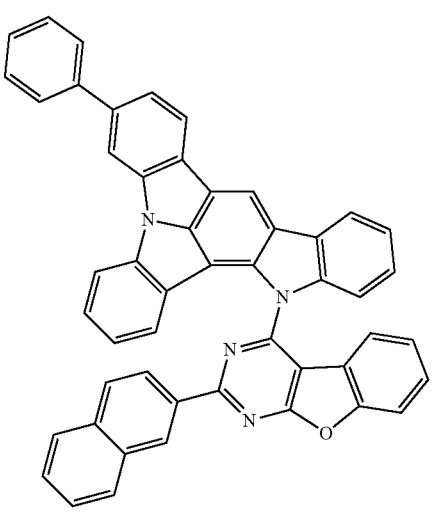

741
-continued
742
-continued
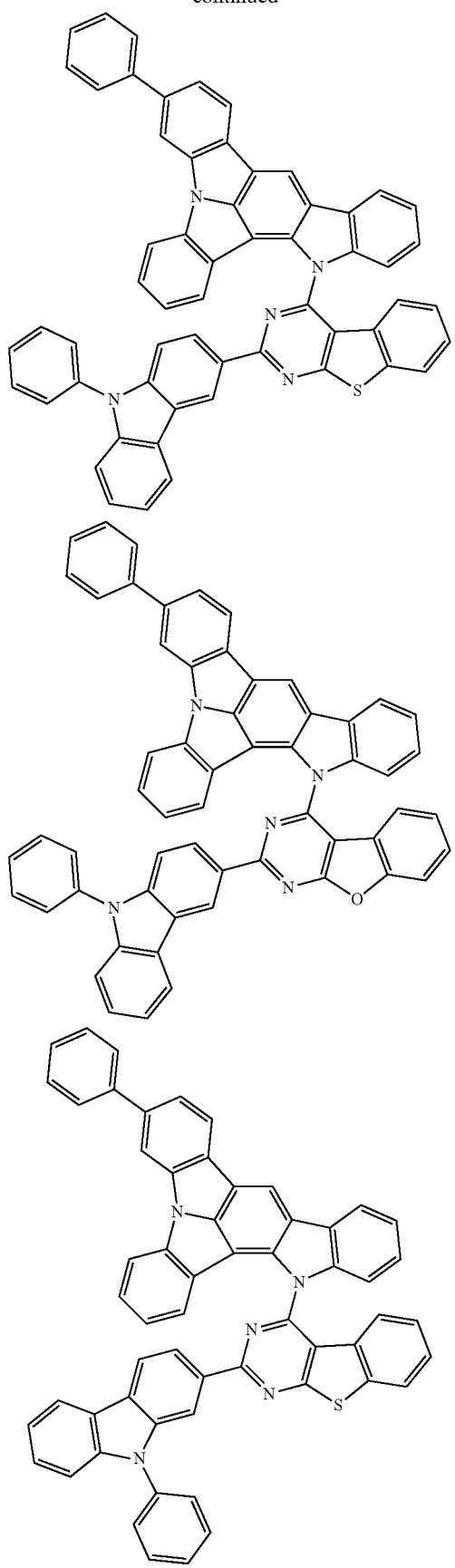
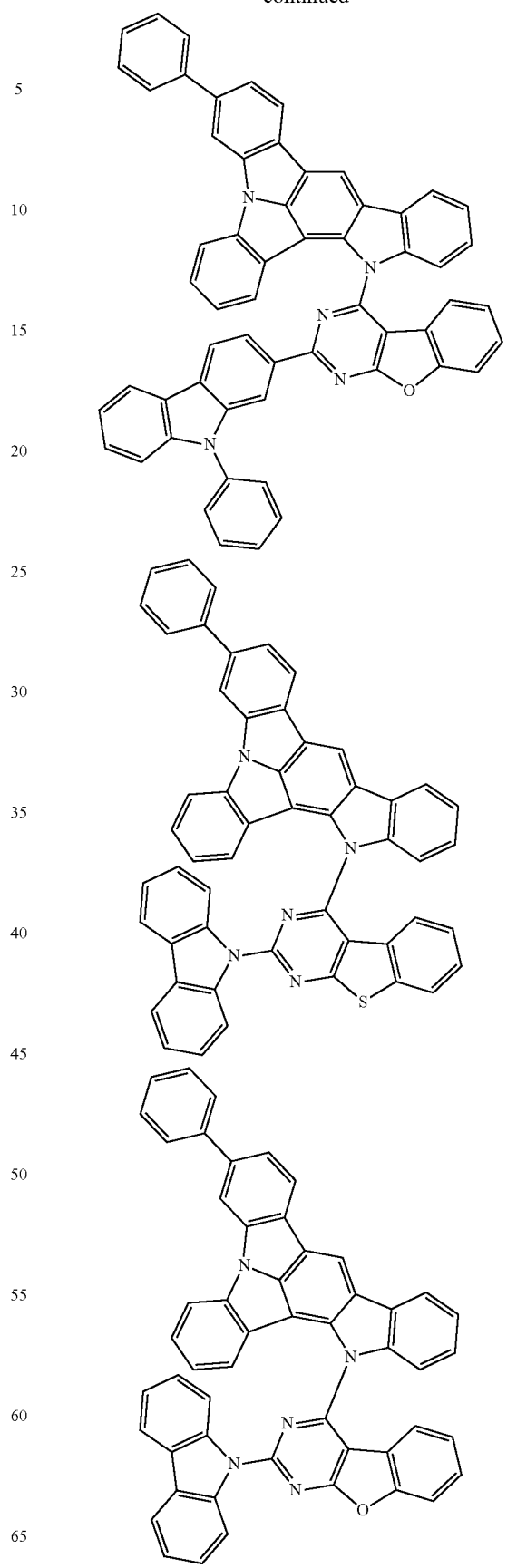

743
-continued
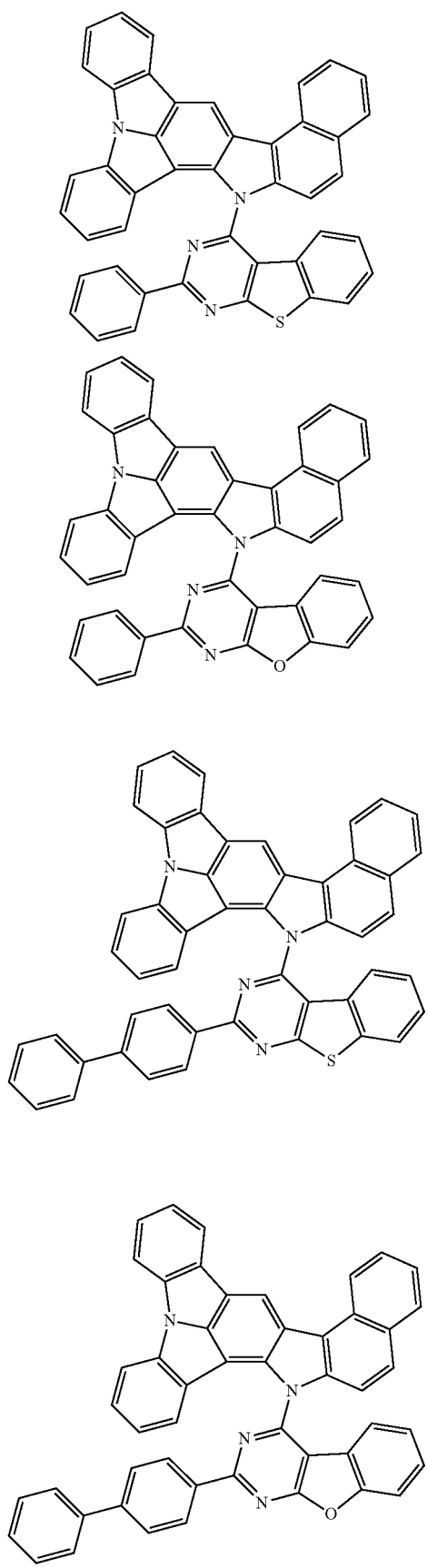
744
-continued
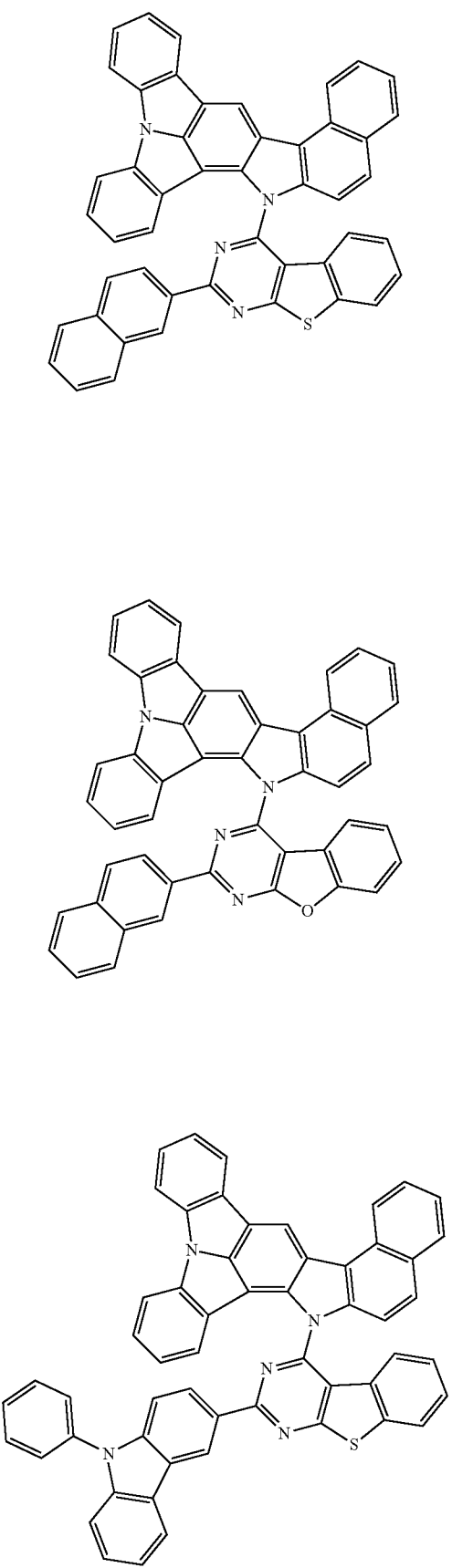

745
-continued
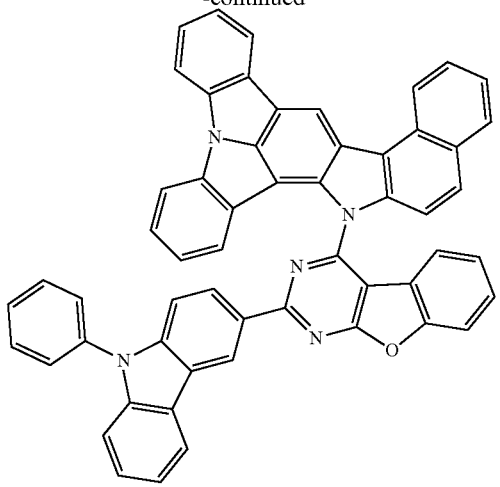
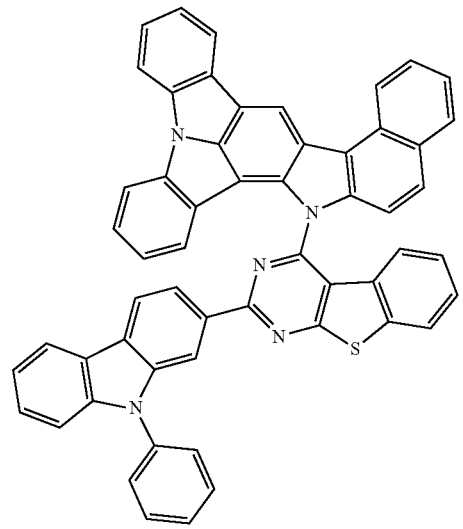
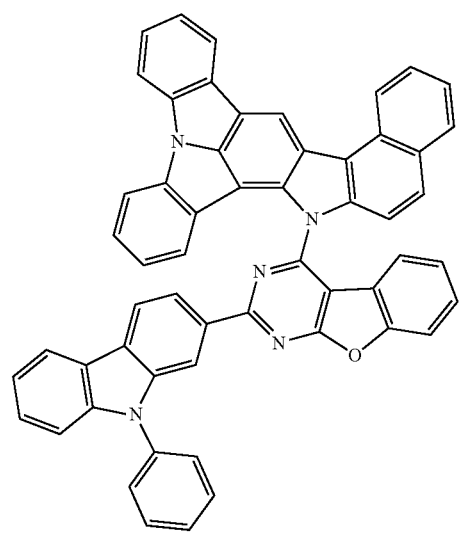
746
-continued
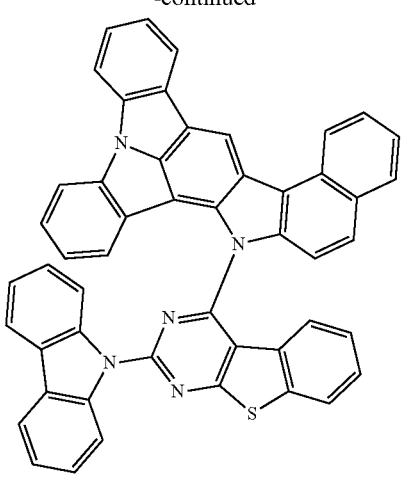
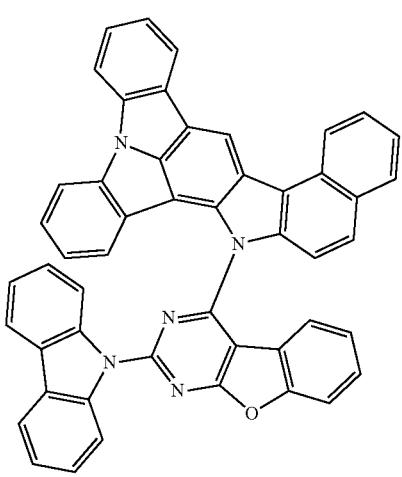
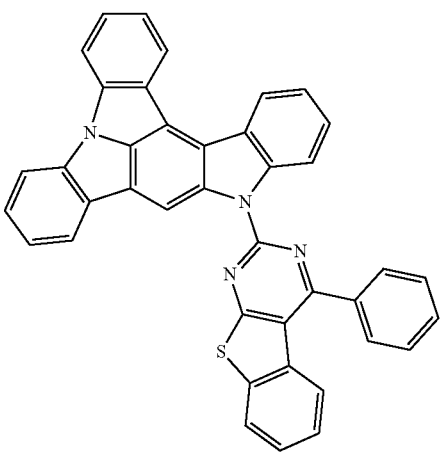

747
-continued
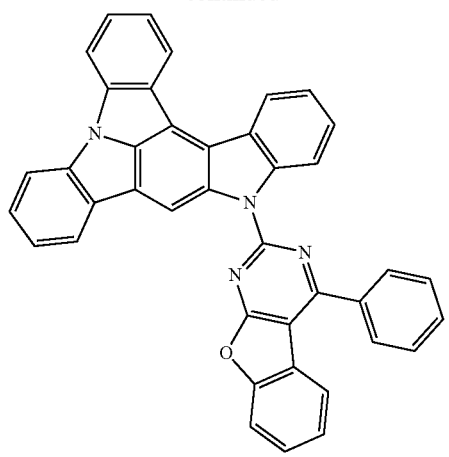
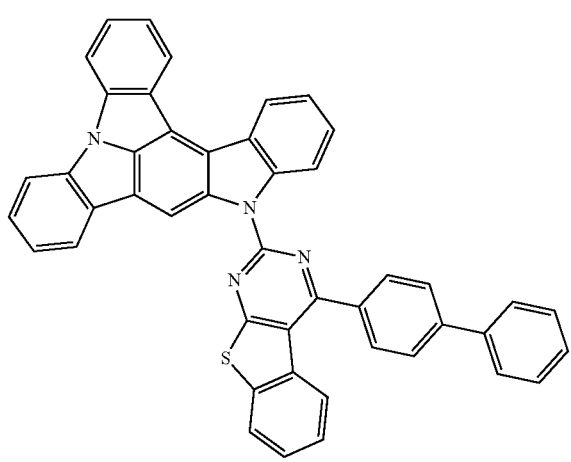
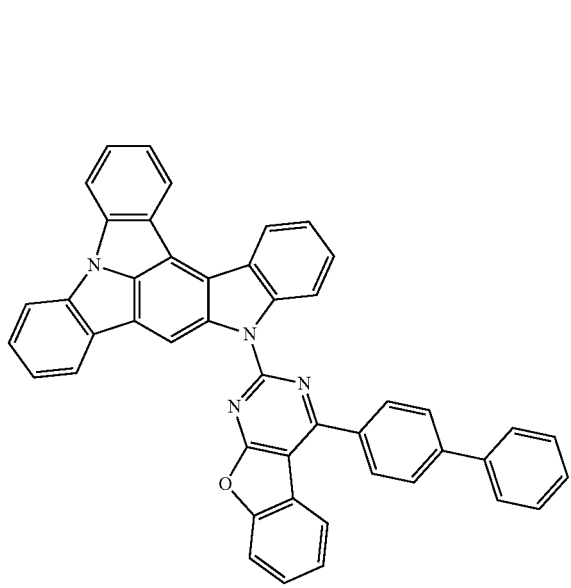
748
-continued
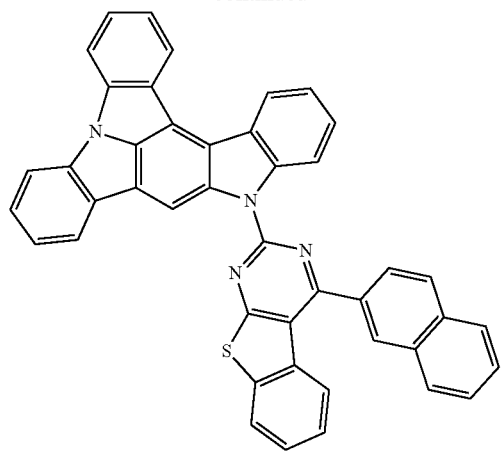
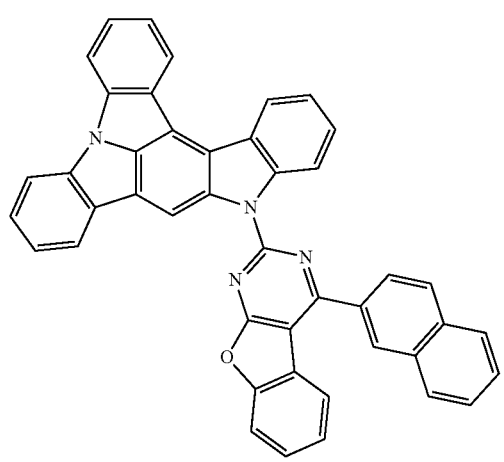
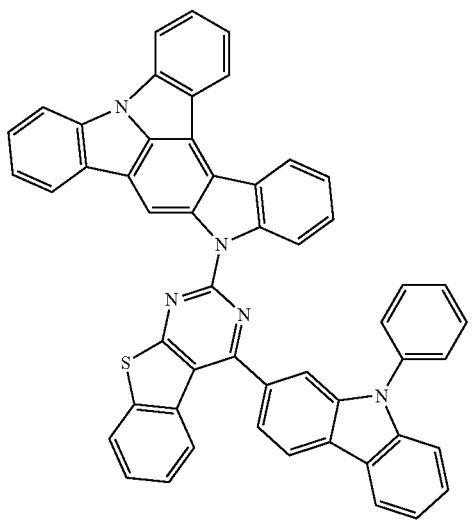

749
-continued
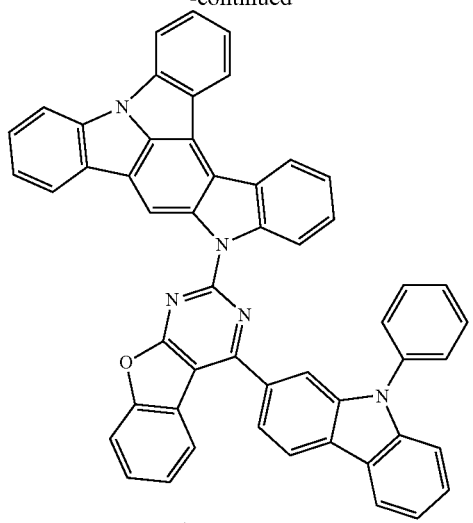
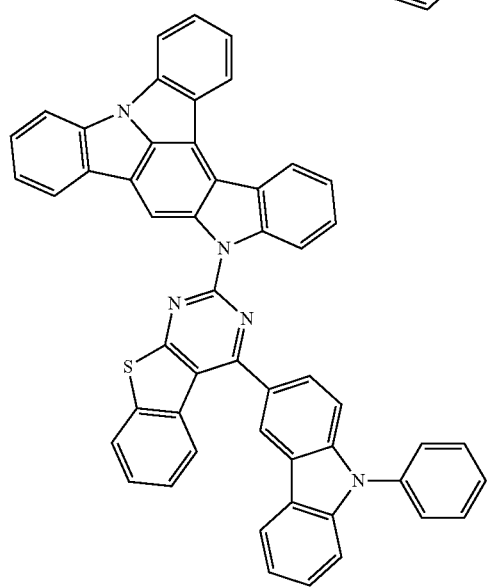
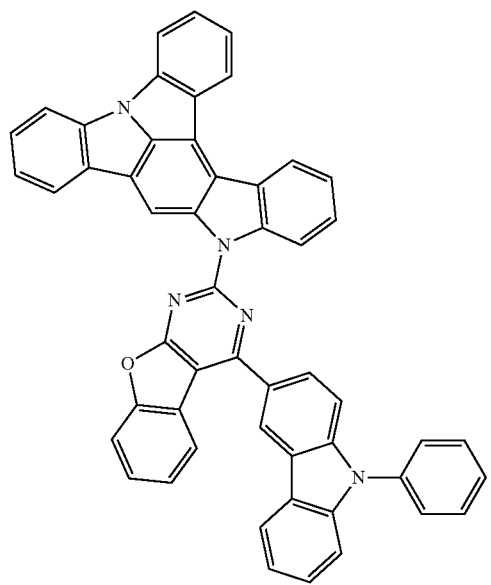
750
-continued
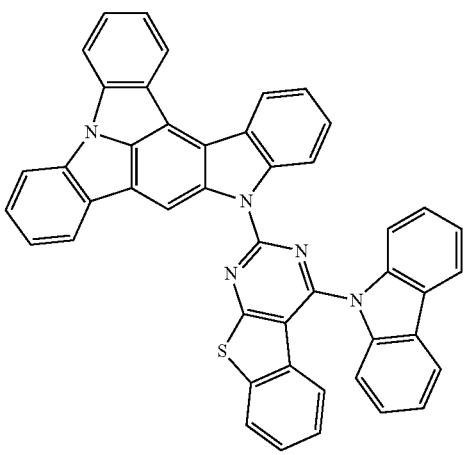
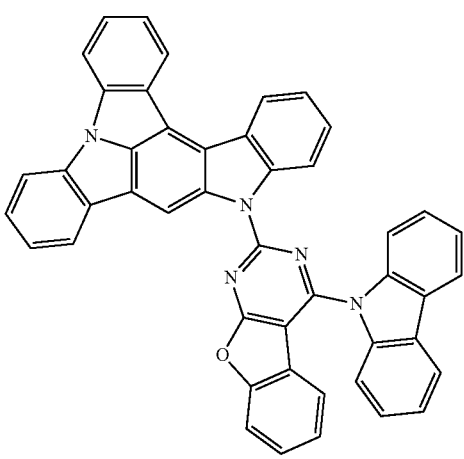
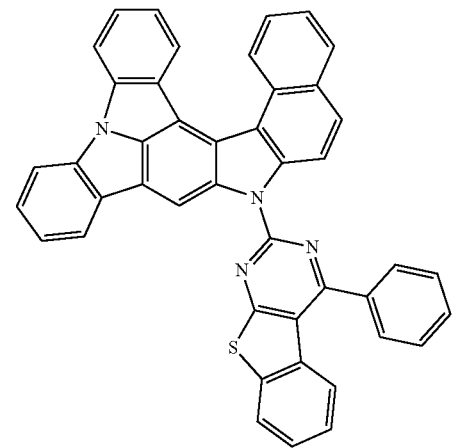

751
-continued
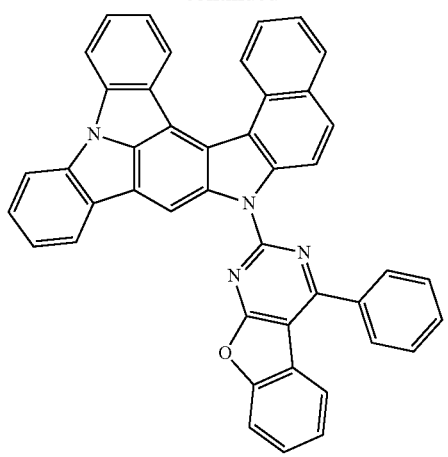
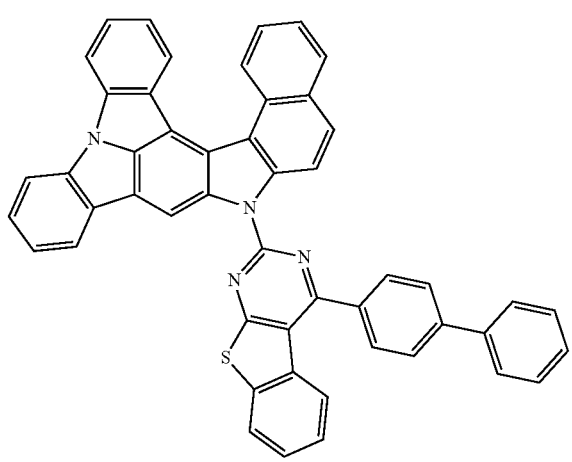
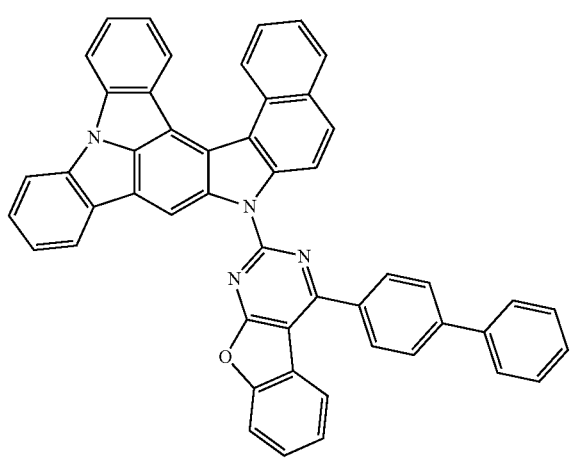
752
-continued
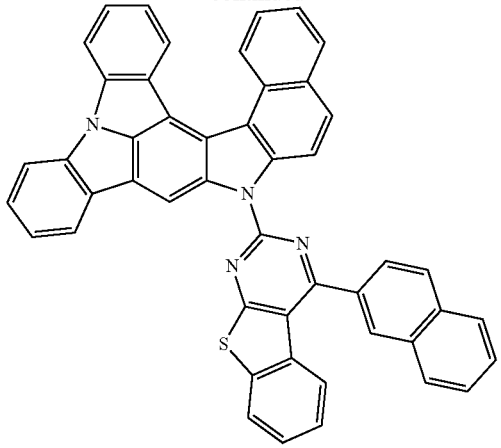
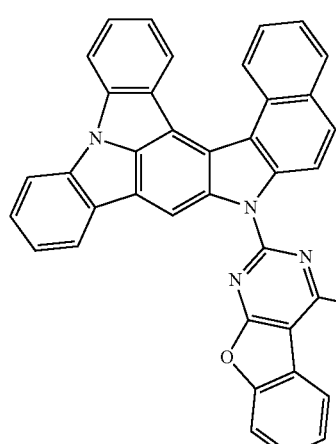
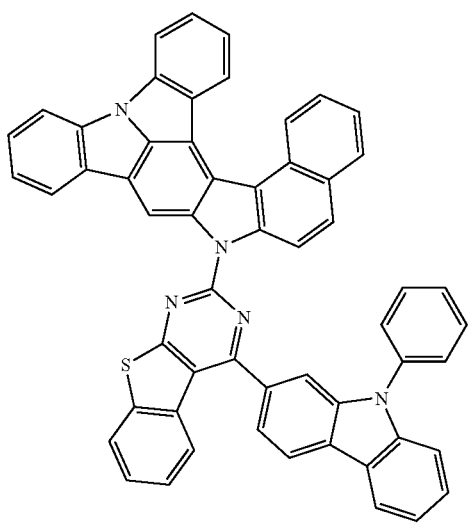

753
-continued
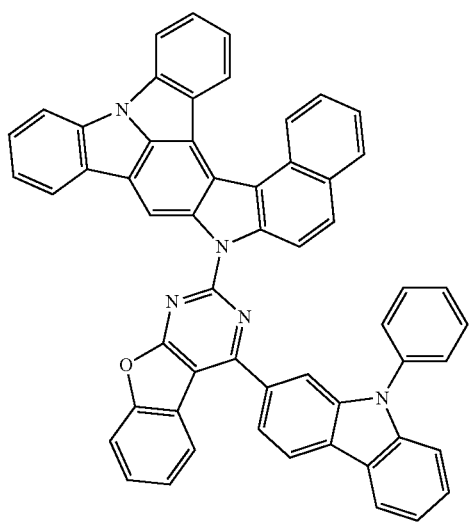
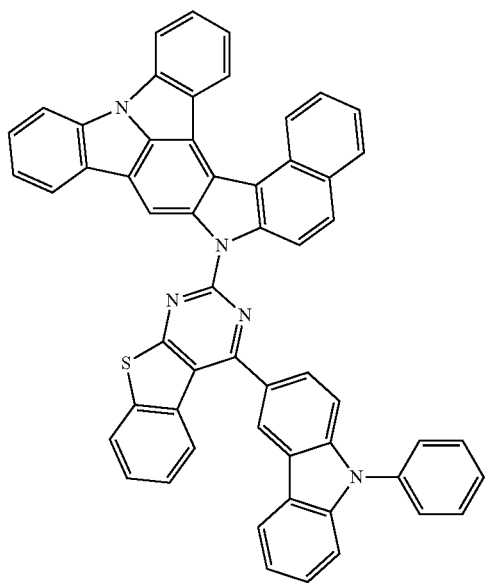
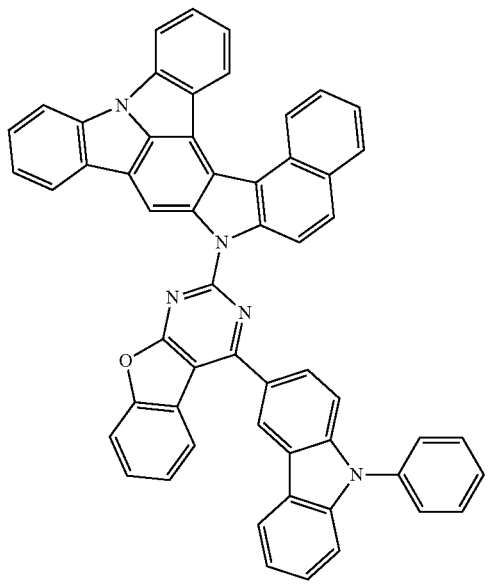
754
-continued
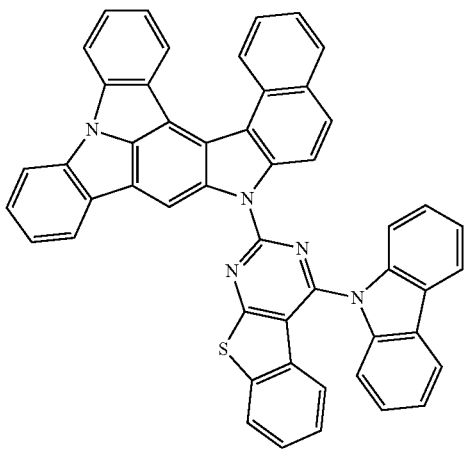
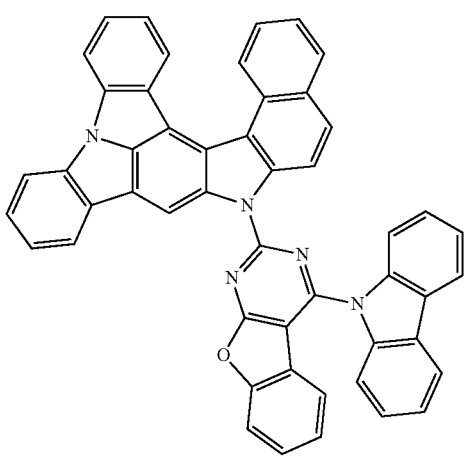
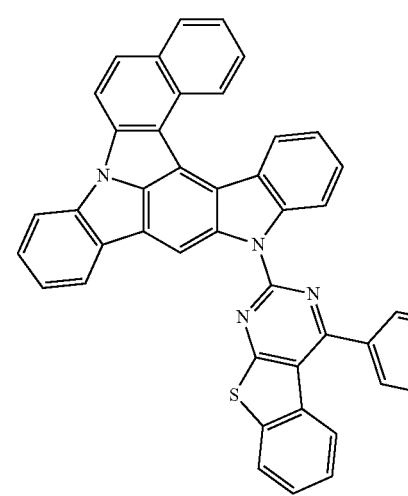

755
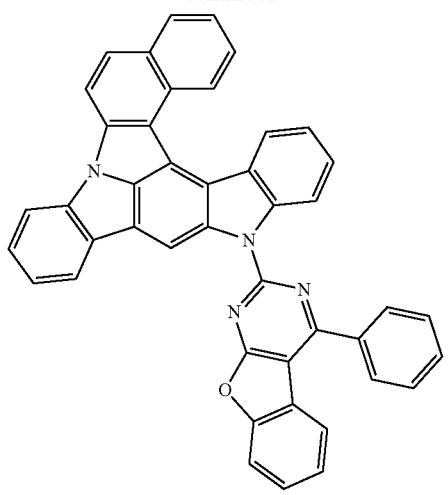
756
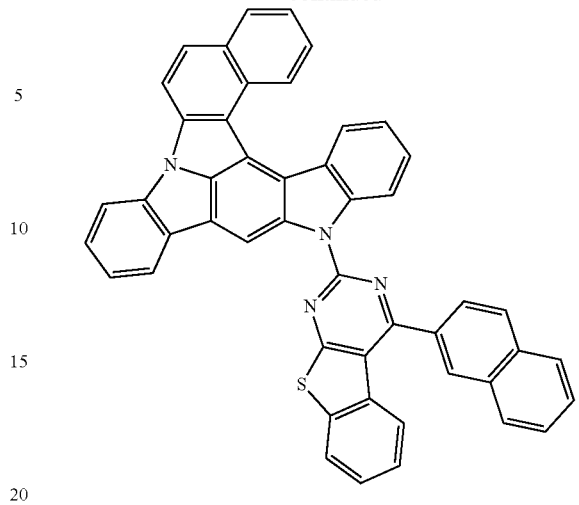
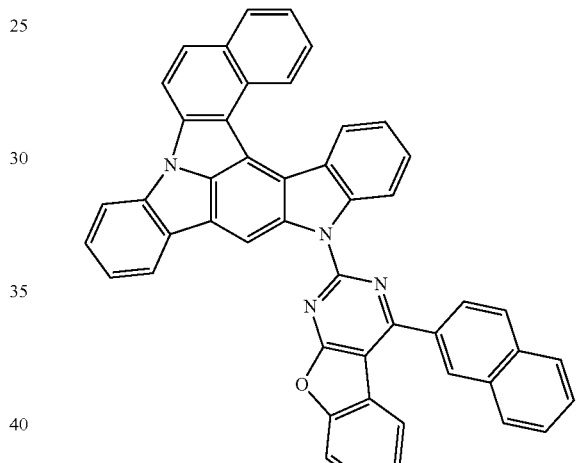
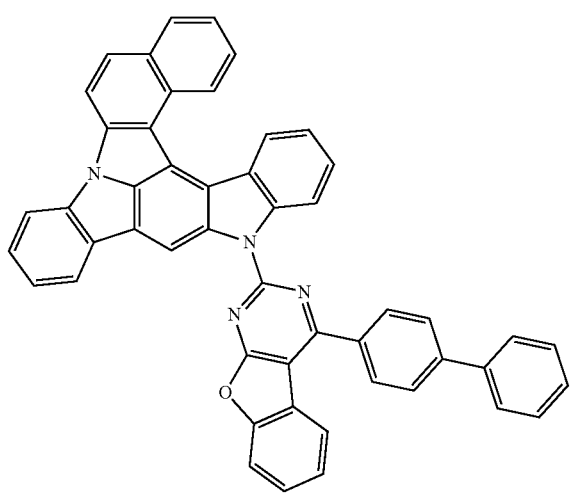
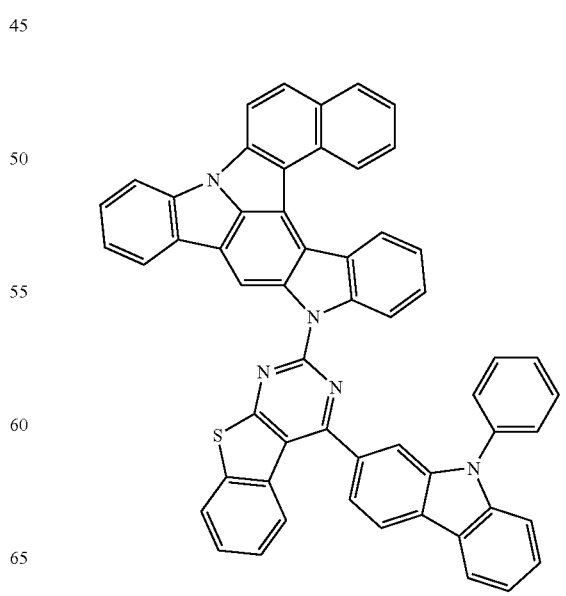

757
-continued
758
-continued
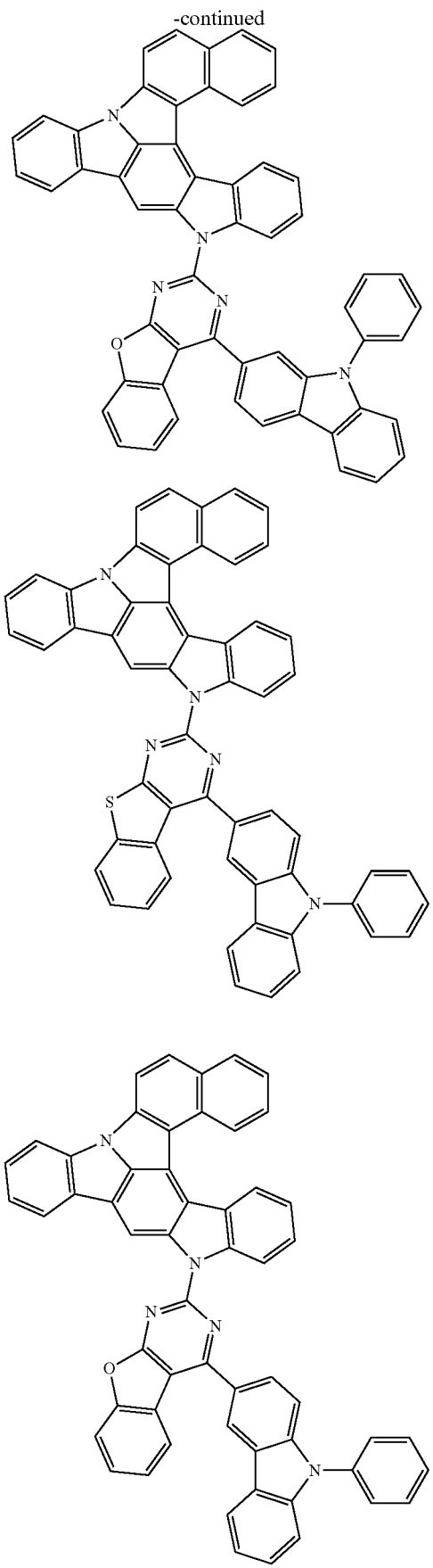
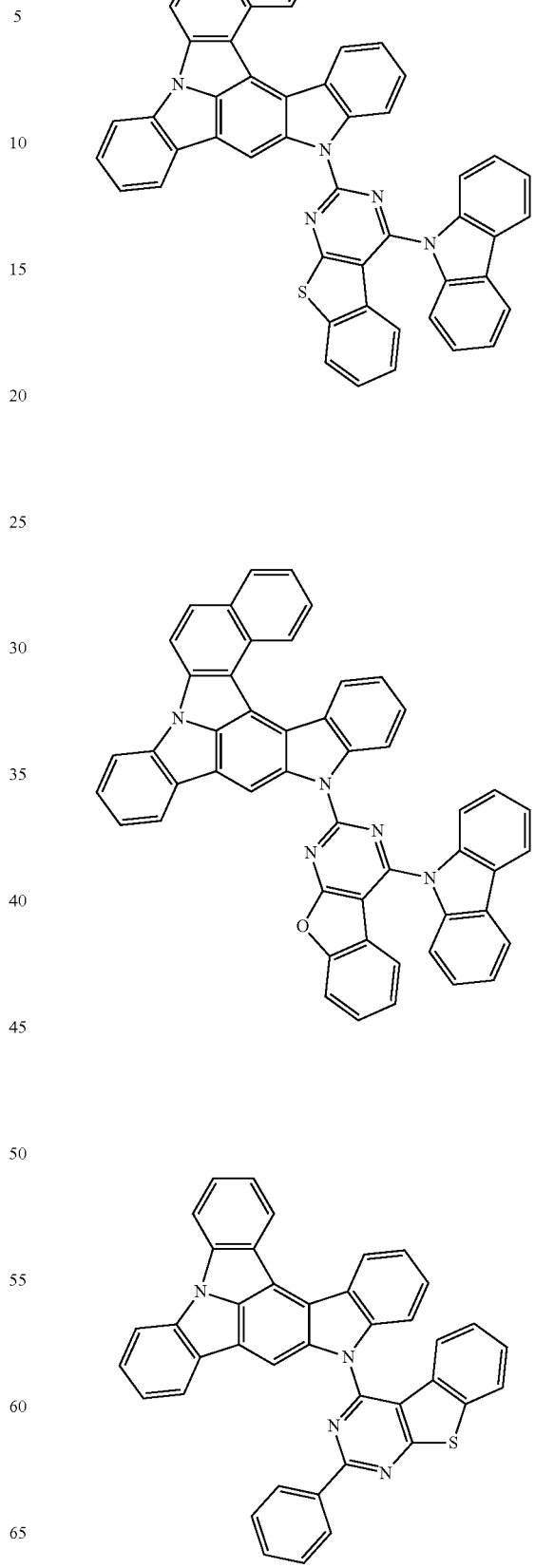

759
-continued
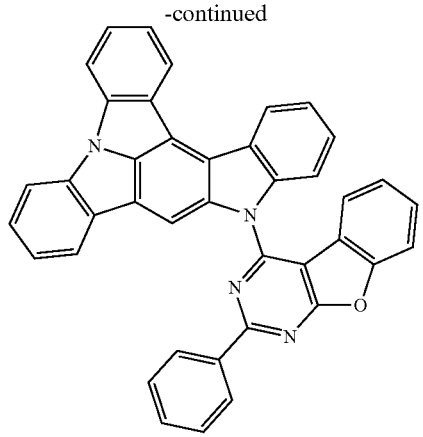
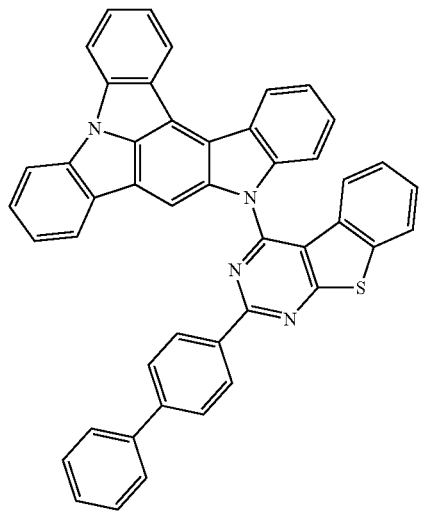
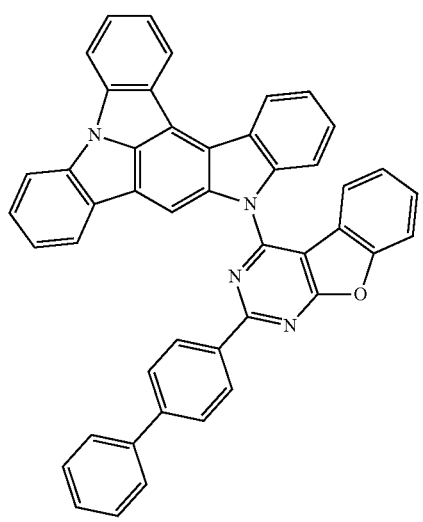
760
-continued
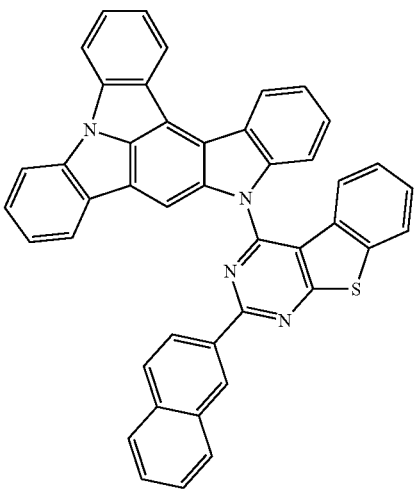
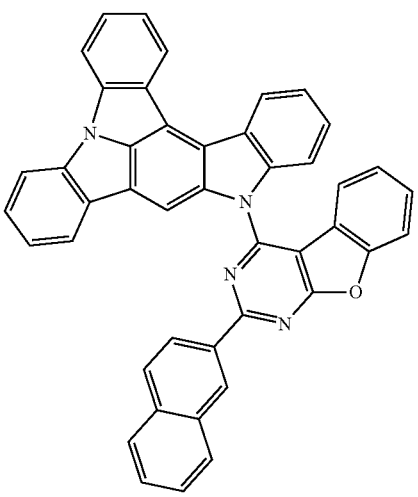
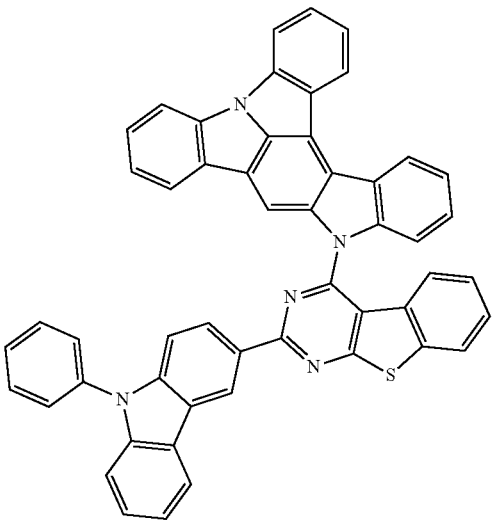

761
-continued
762
-continued
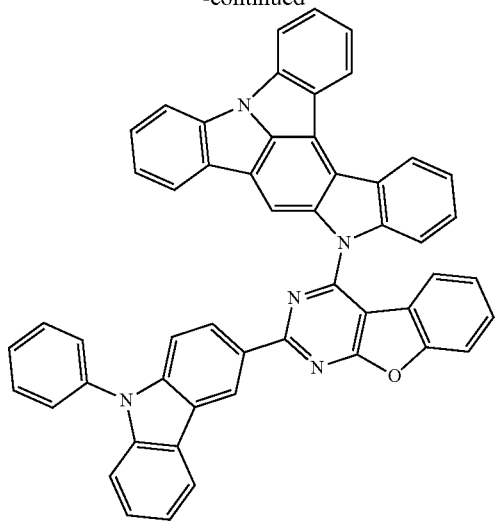
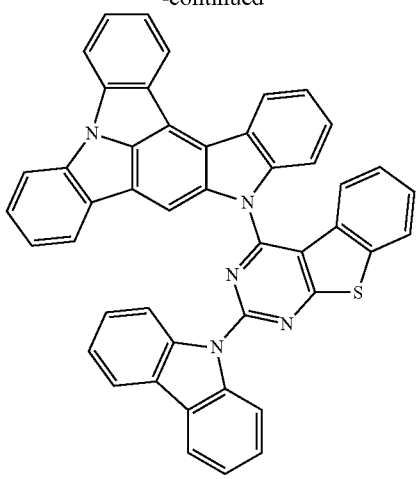
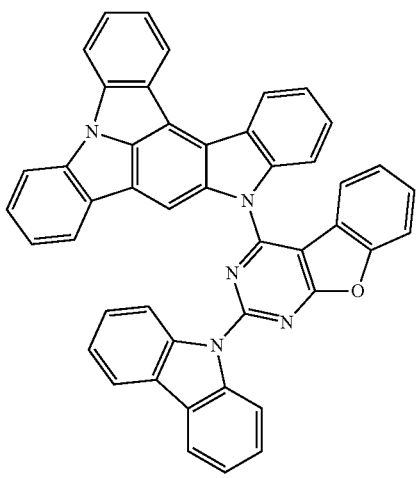
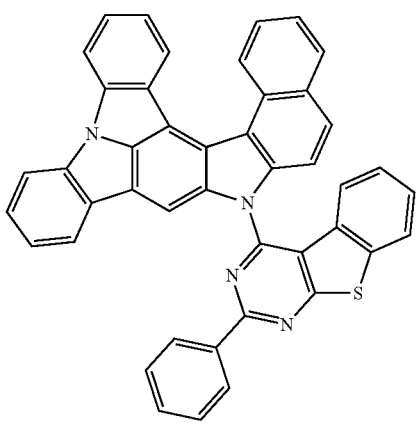

763
-continued
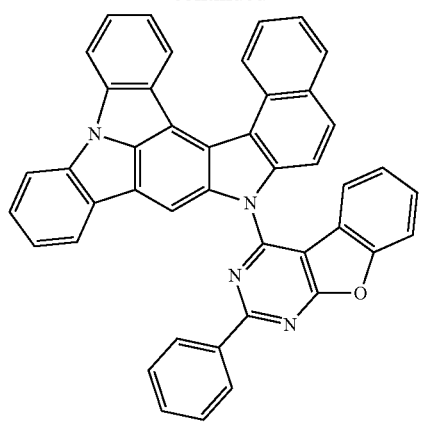
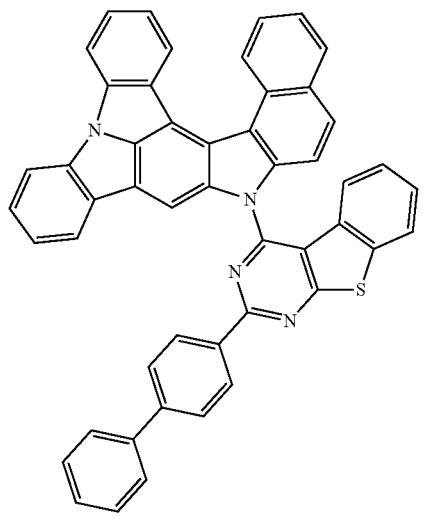
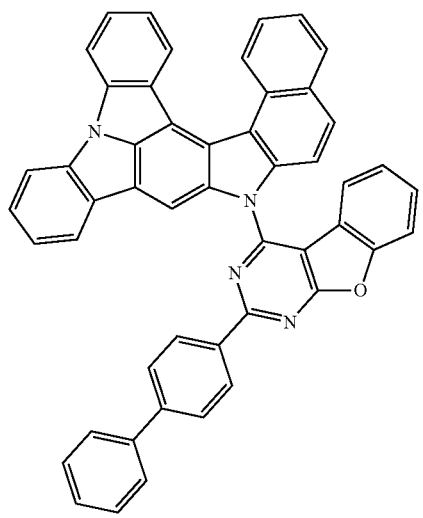
764
-continued
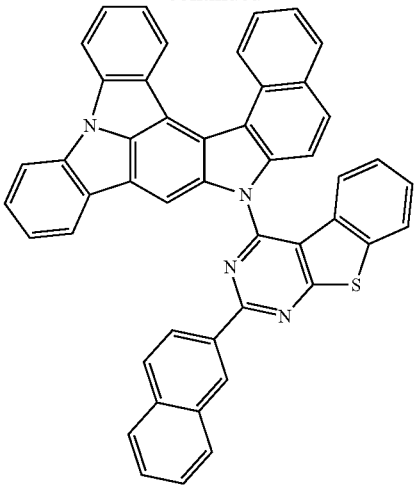
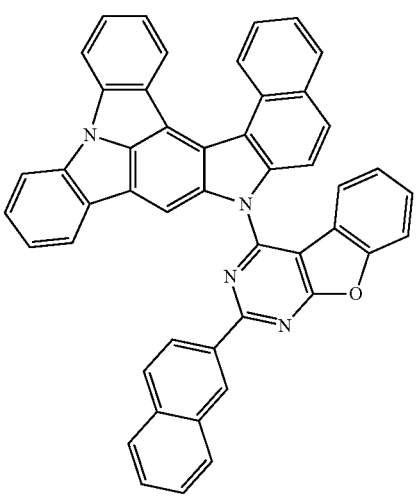
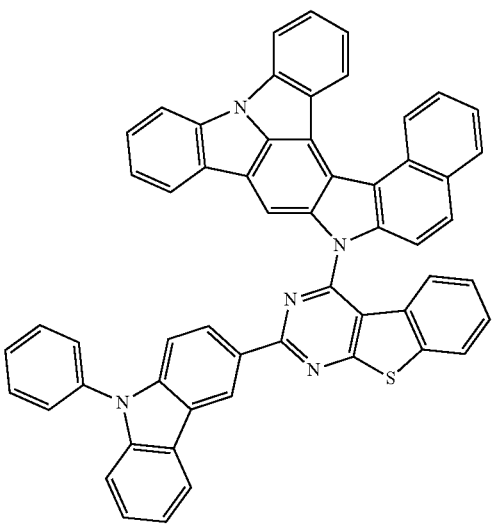

765
-continued
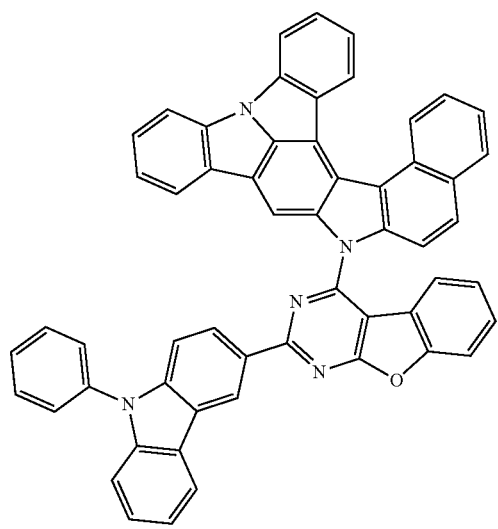
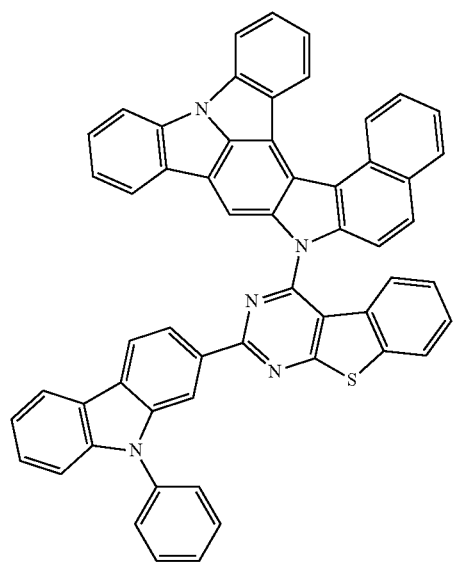
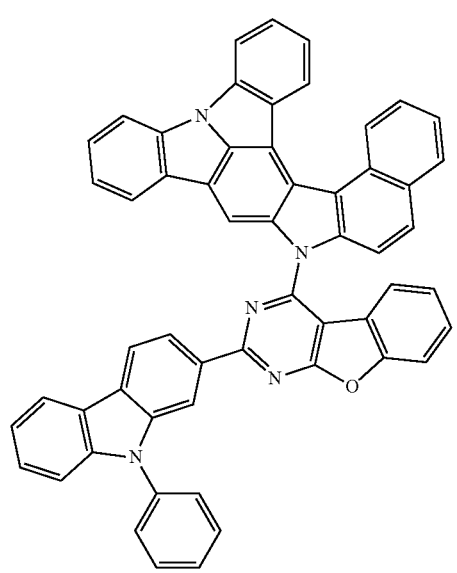
766
-continued
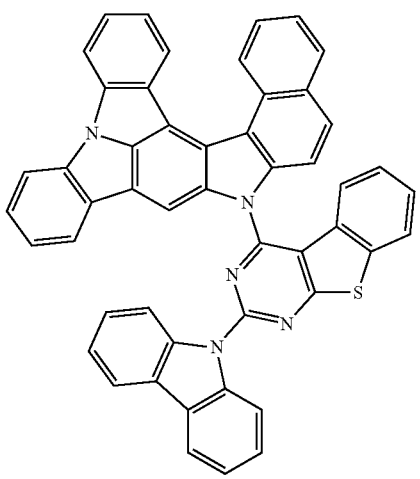
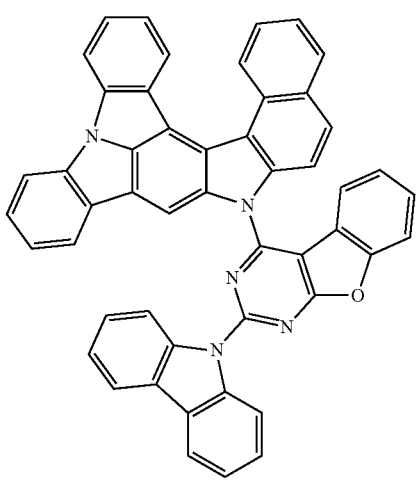
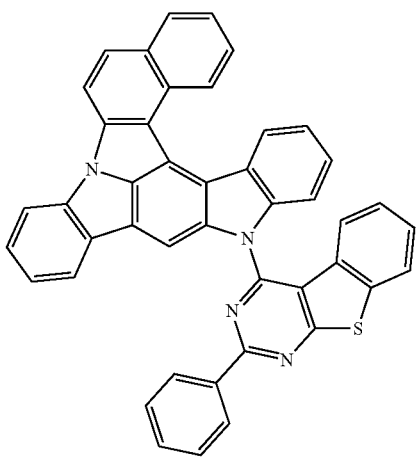

-continued
767
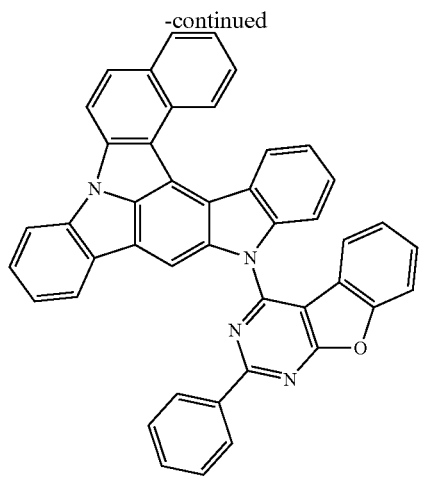
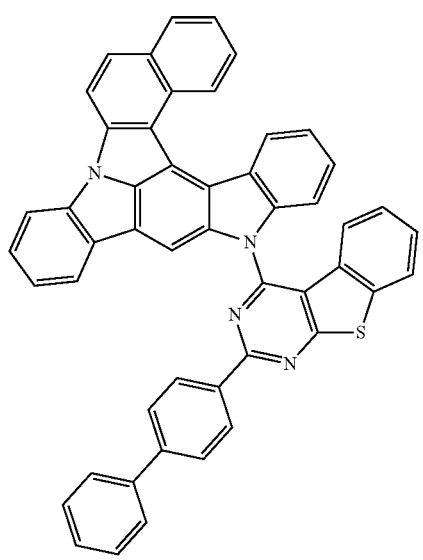
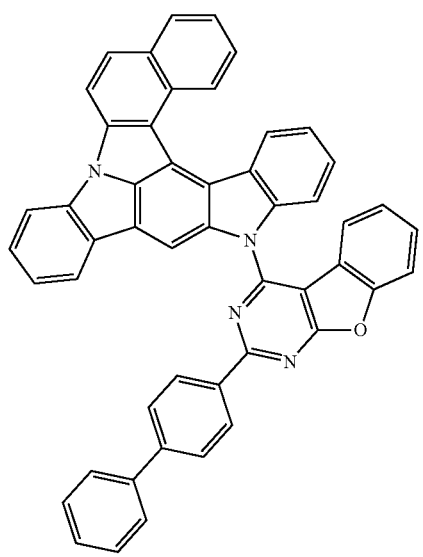
768
-continued
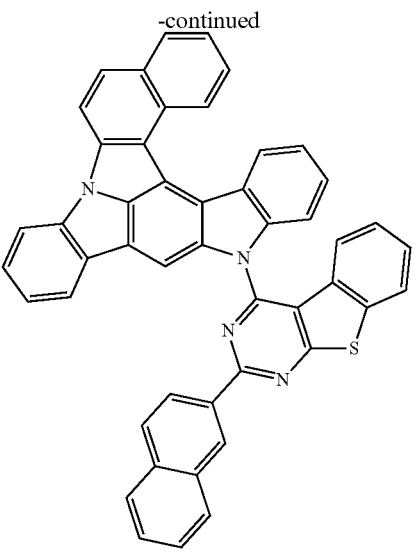
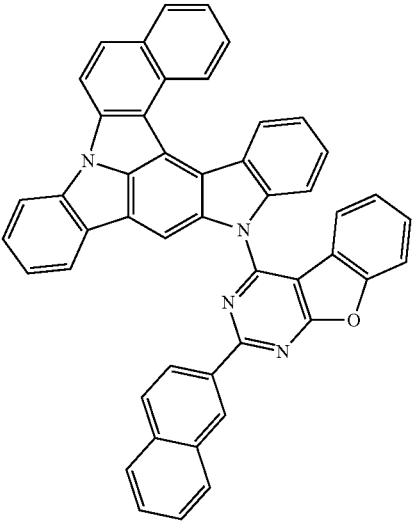
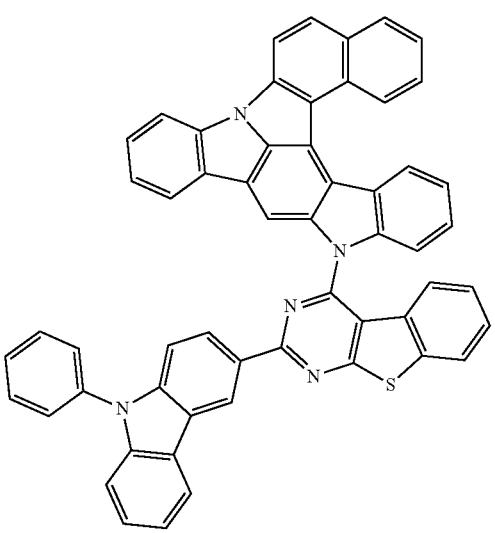

769
-continued
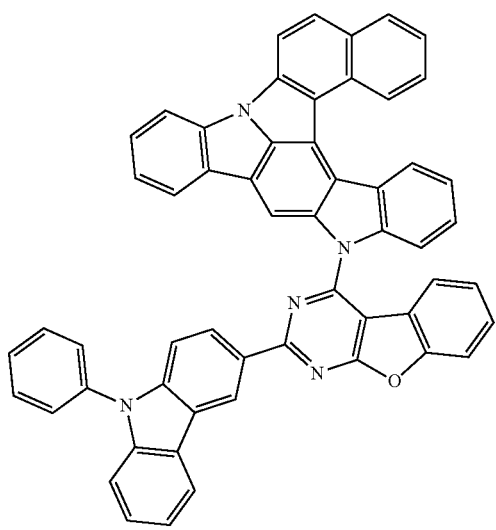
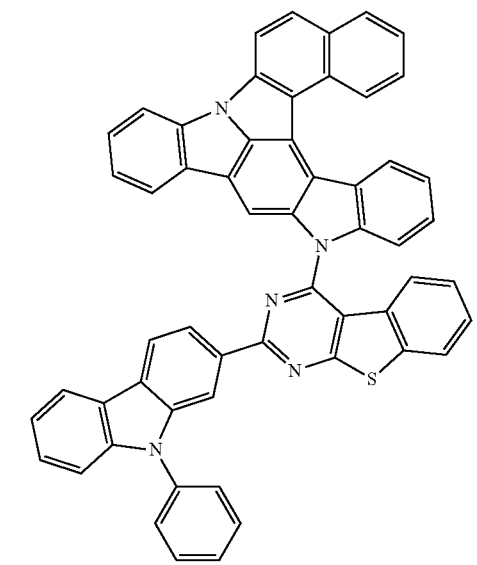
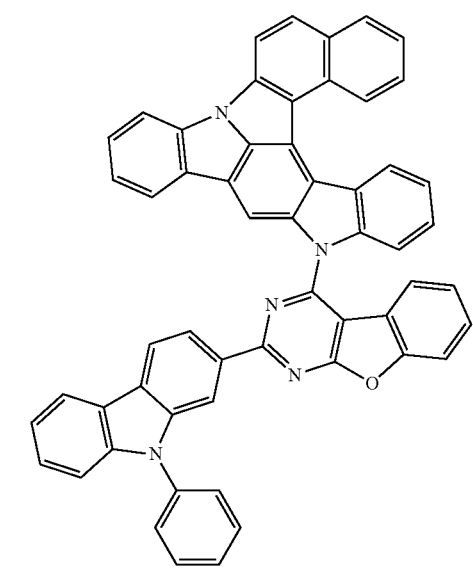
770
-continued
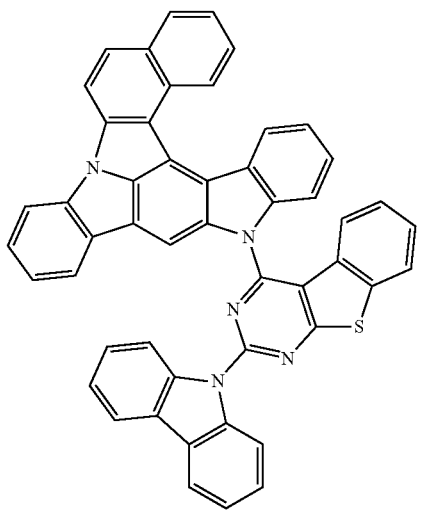
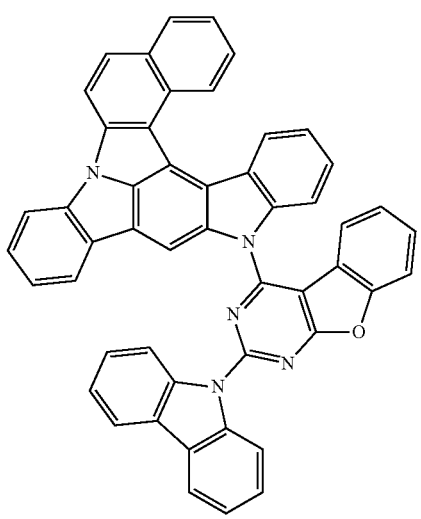
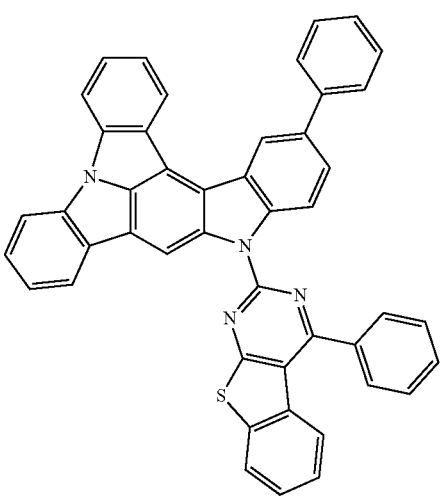

771
-continued
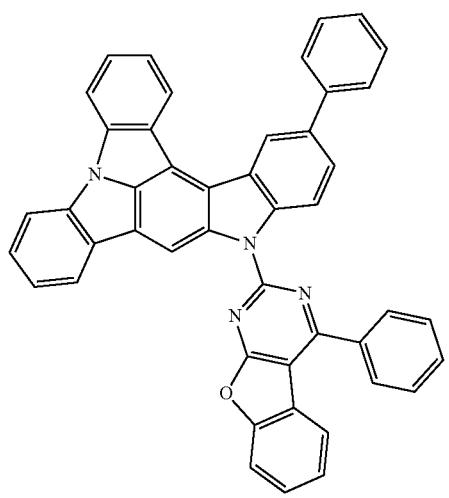
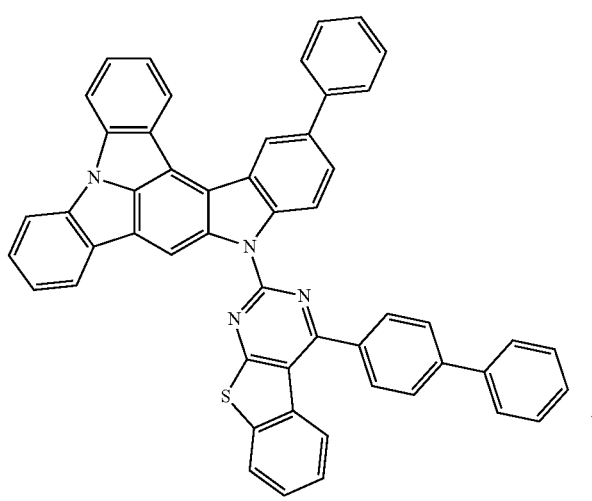
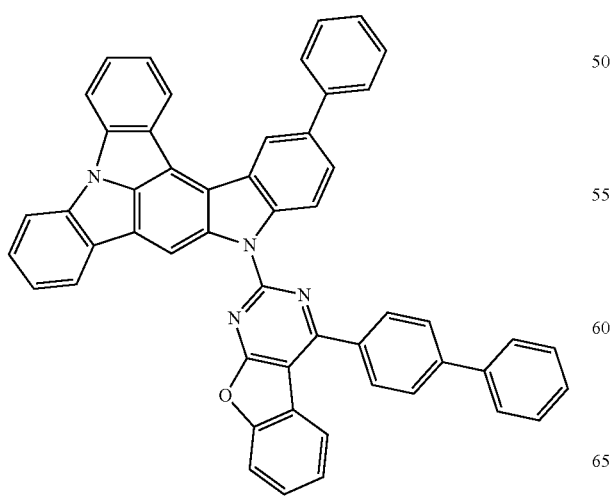
772
-continued
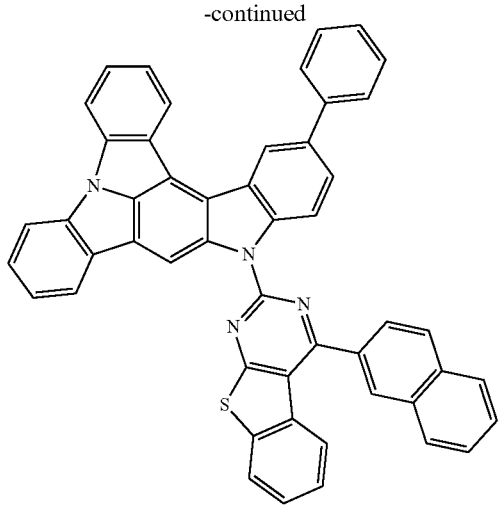
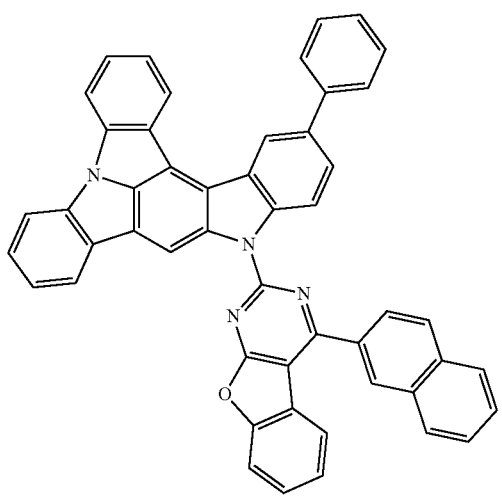
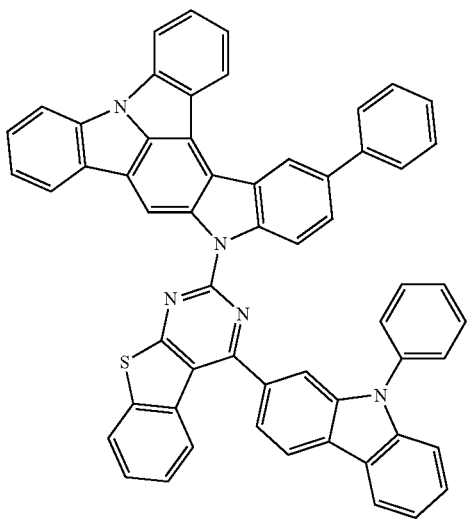

773
-continued
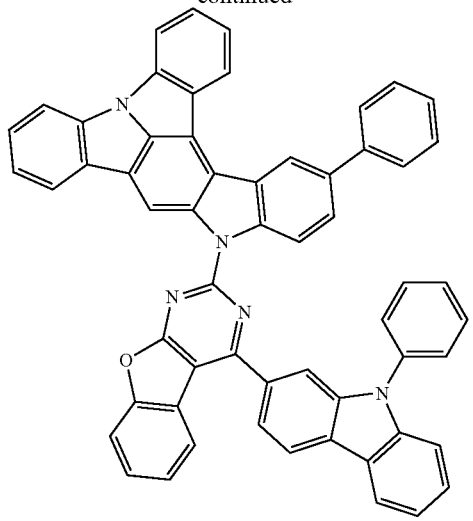
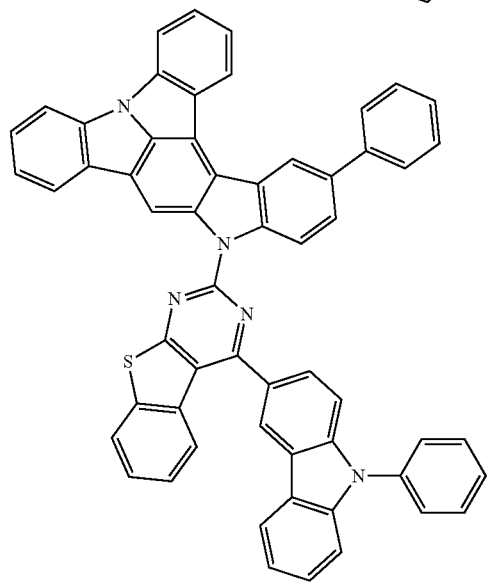
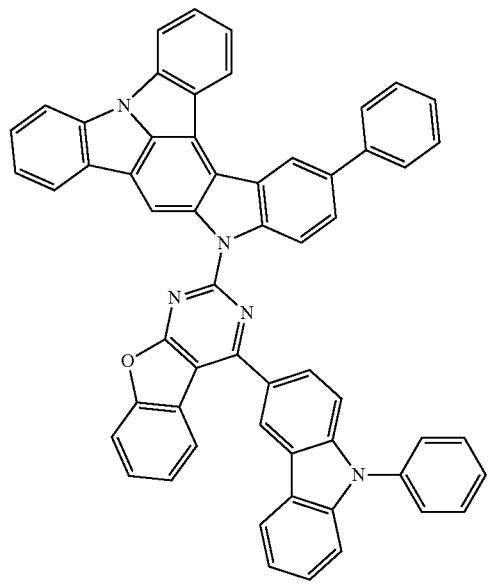
774
-continued
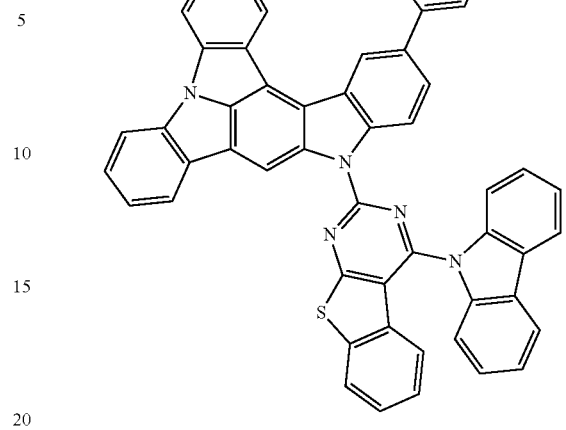
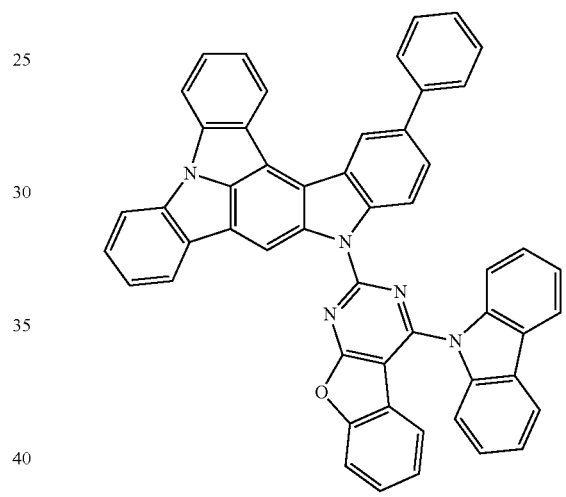
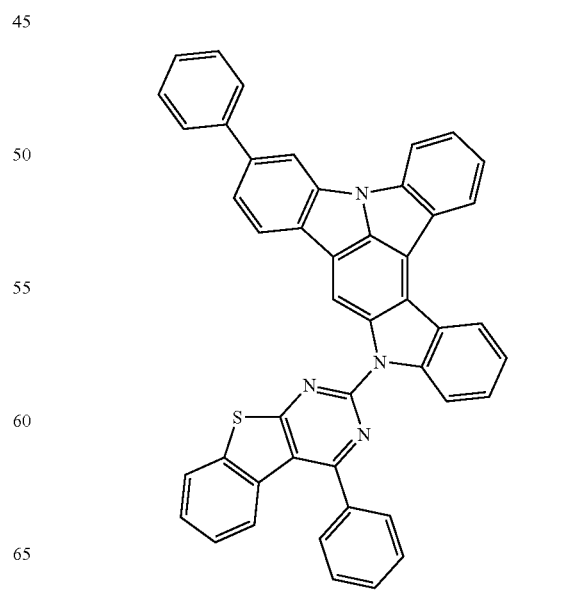

775
-continued
776
-continued
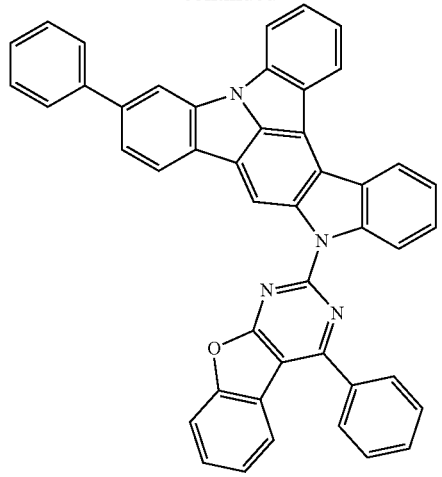
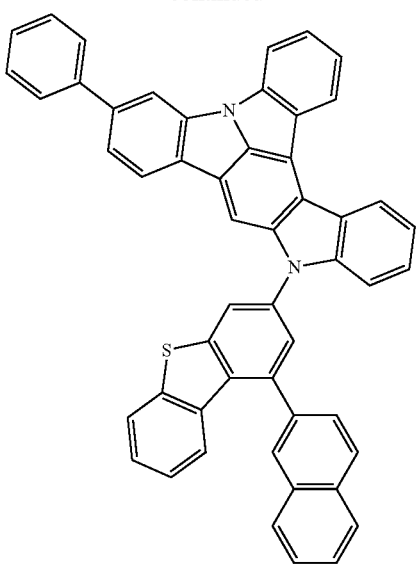
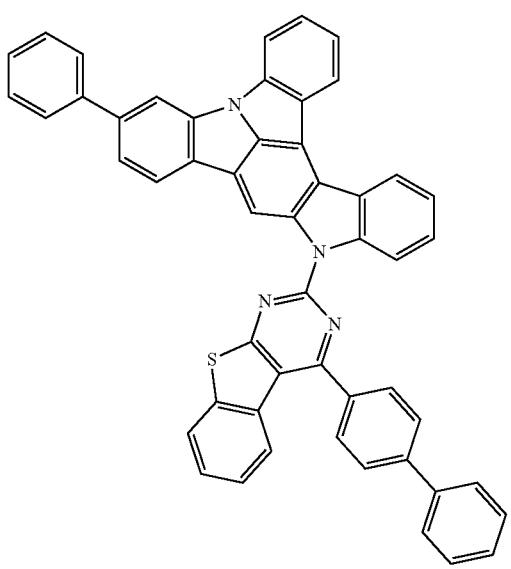
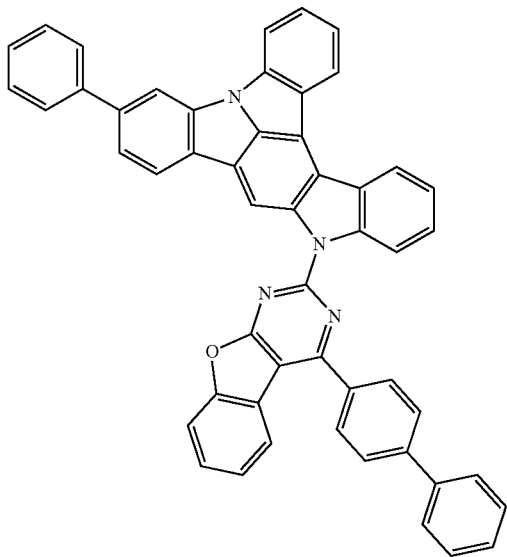
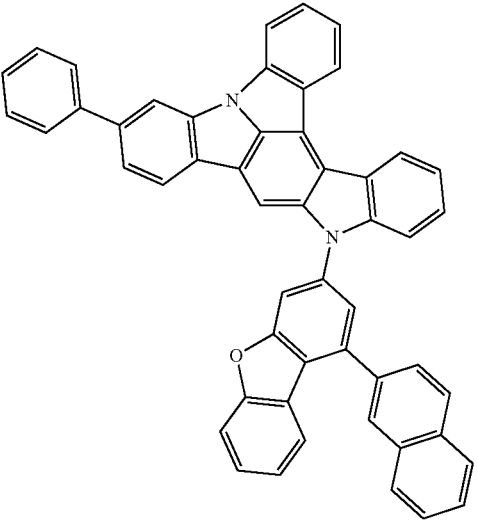

777
-continued
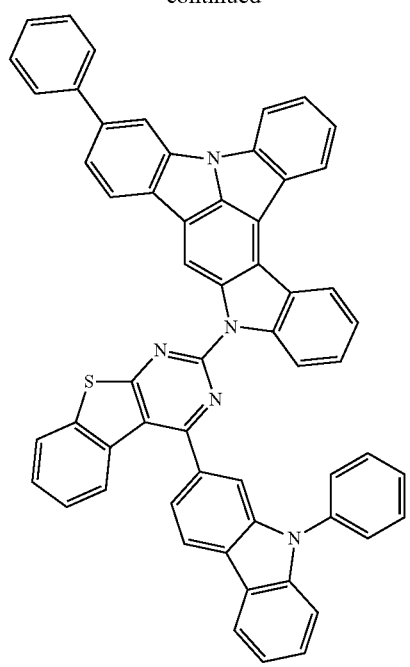
778
-continued
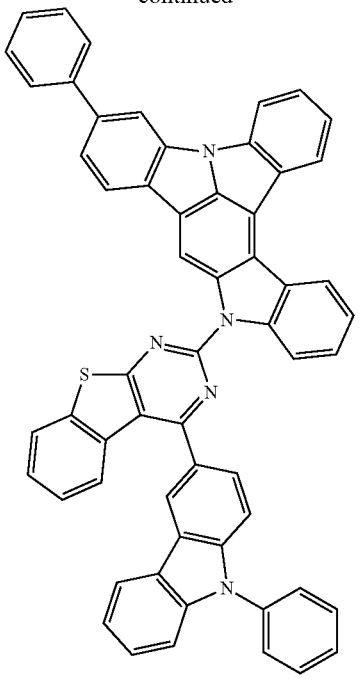
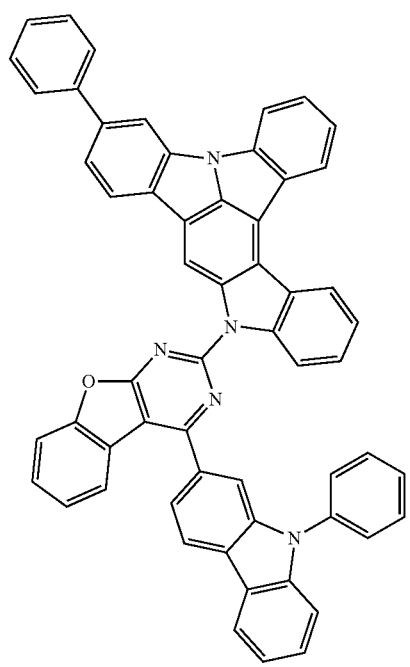
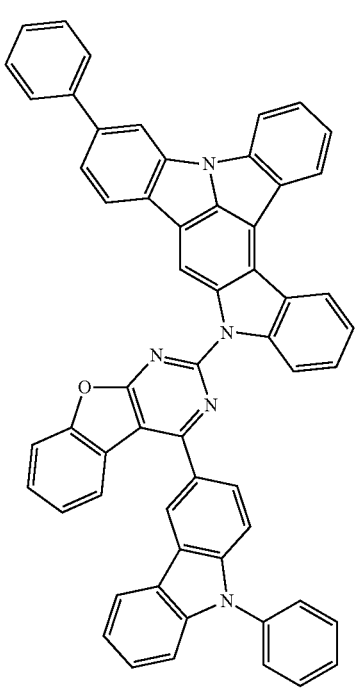

779
-continued
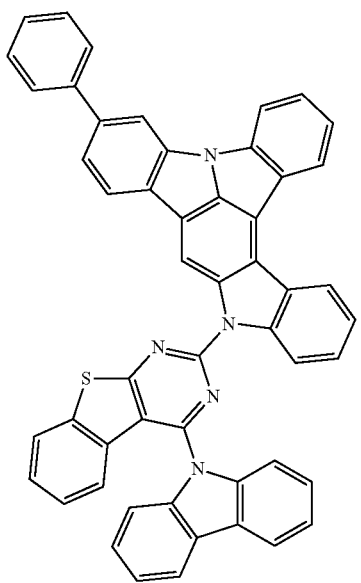
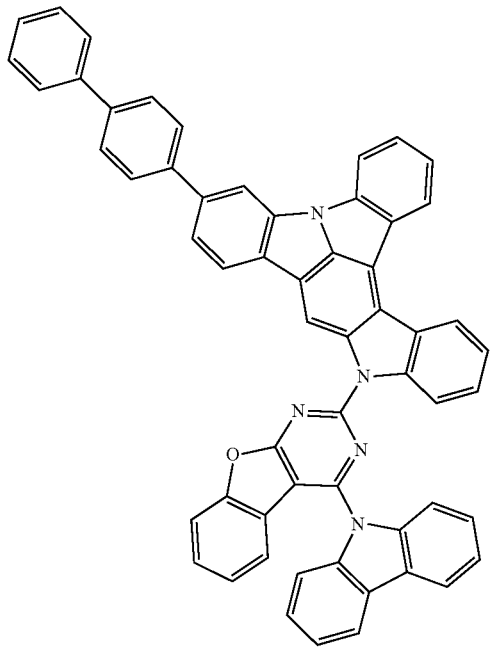
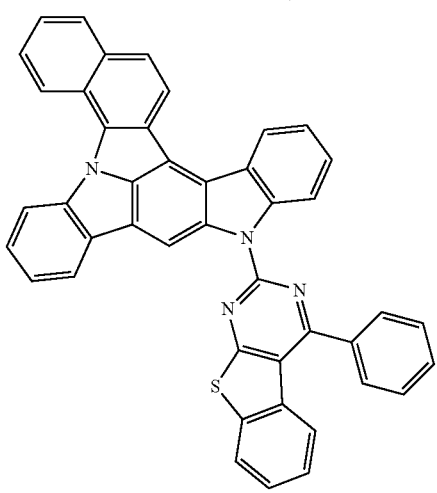
780
-continued
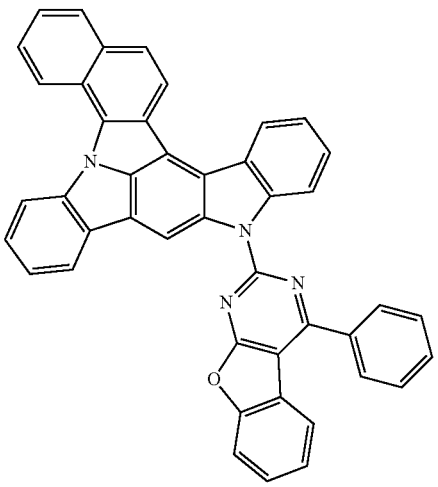
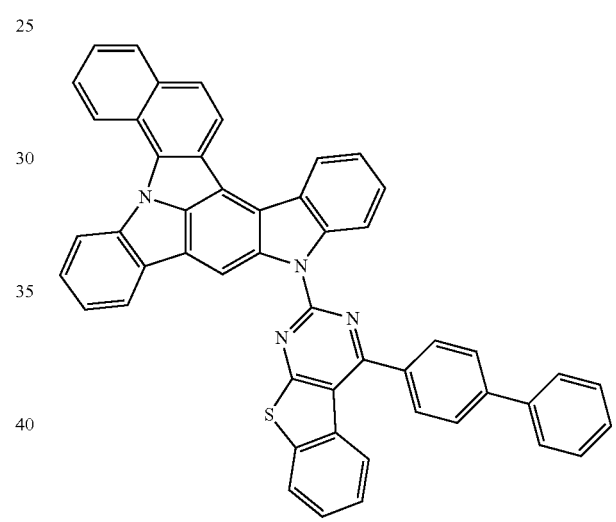
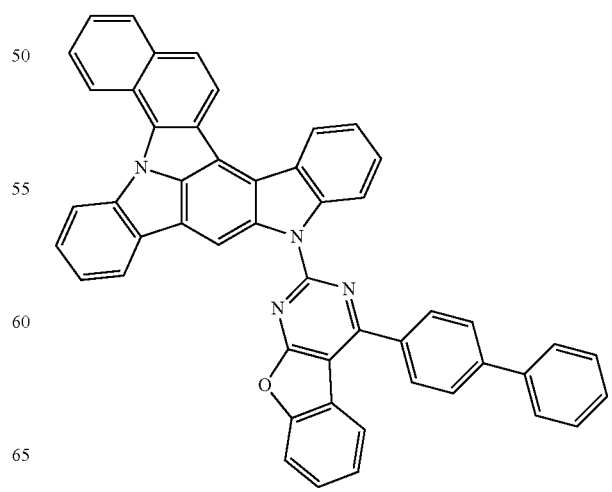

781
-continued
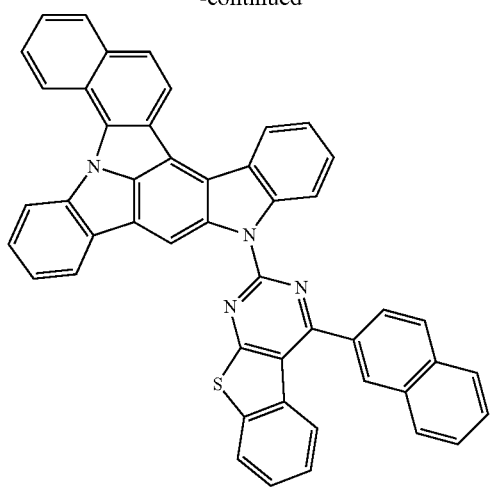
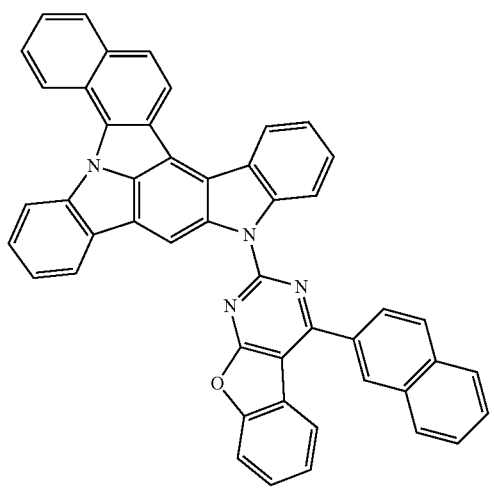
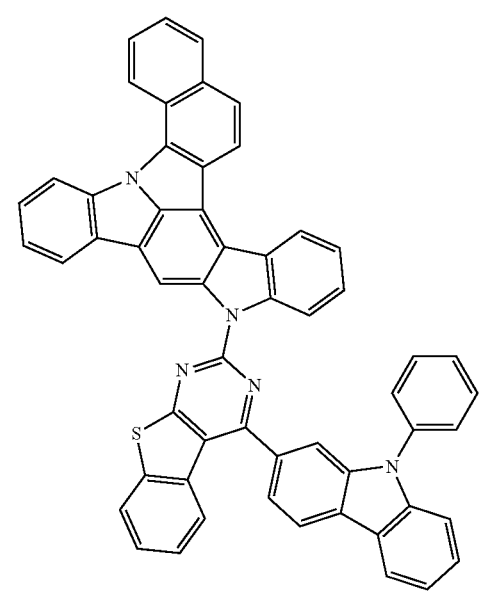
782
-continued
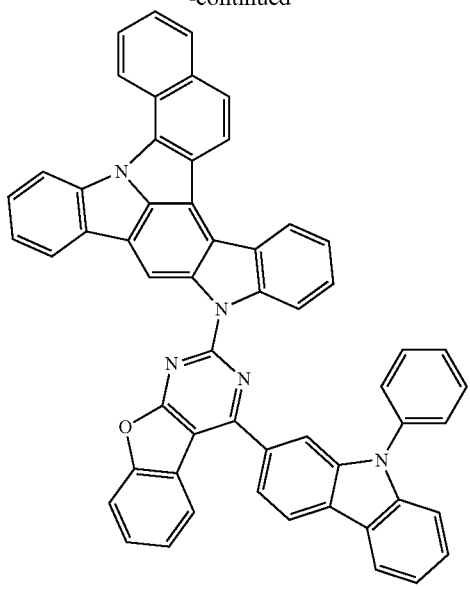
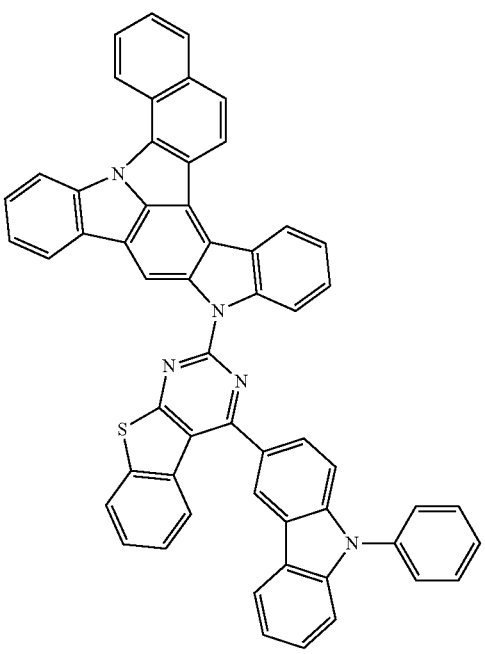

783
-continued
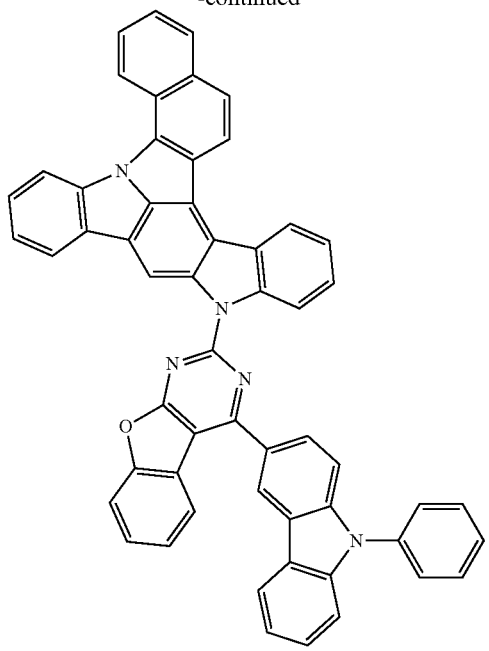
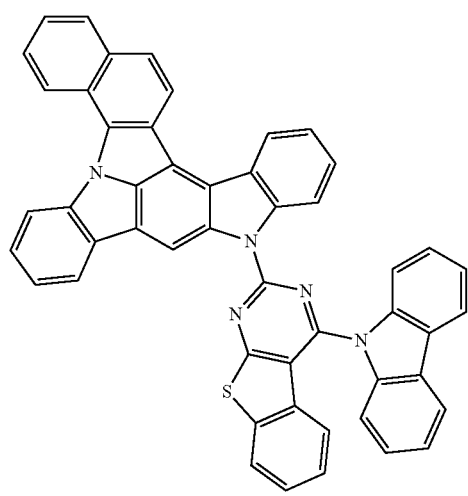
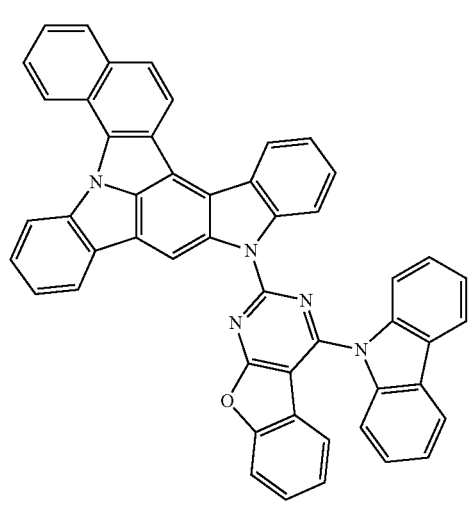
784
-continued
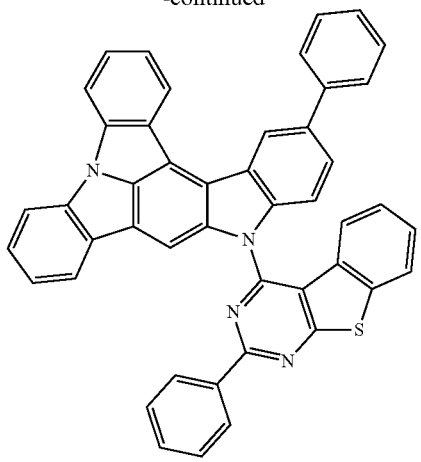
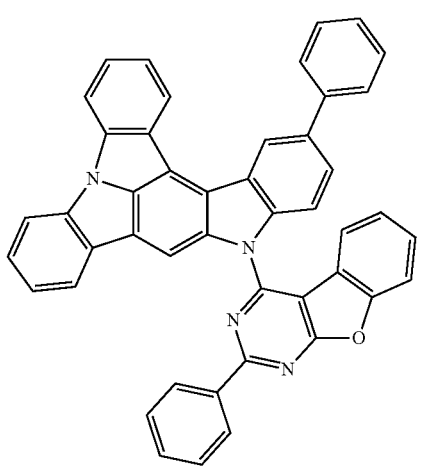
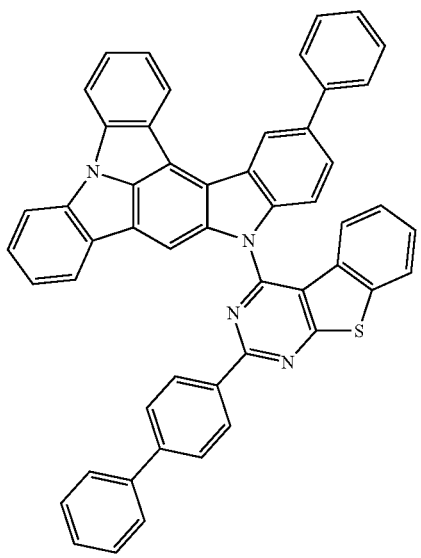

785
-continued
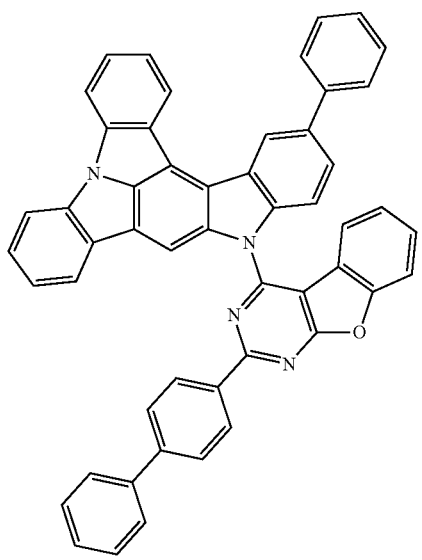
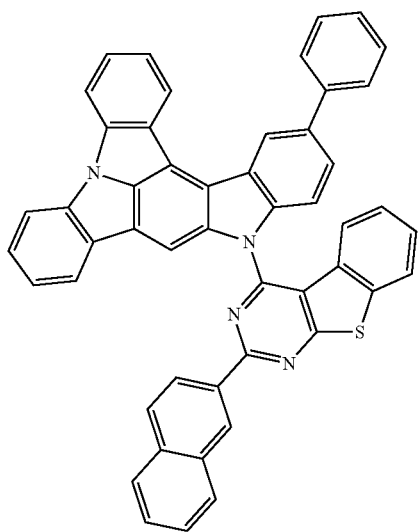
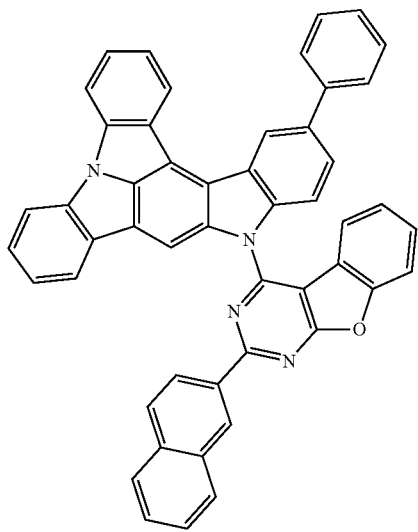
786
-continued
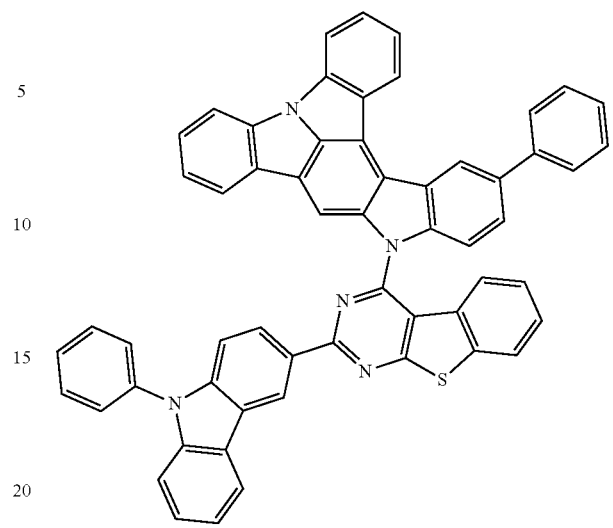
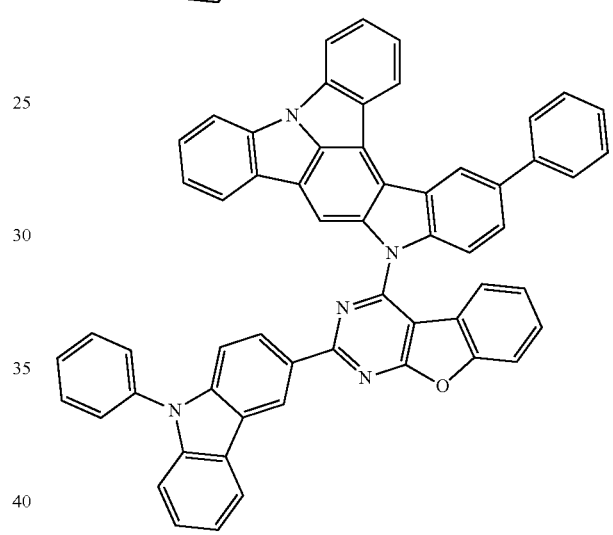

787
-continued
788
-continued
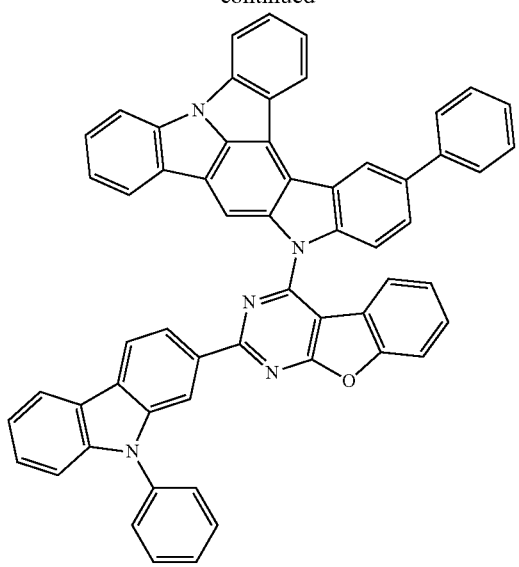
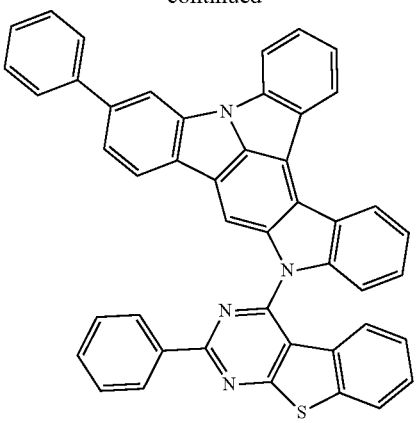
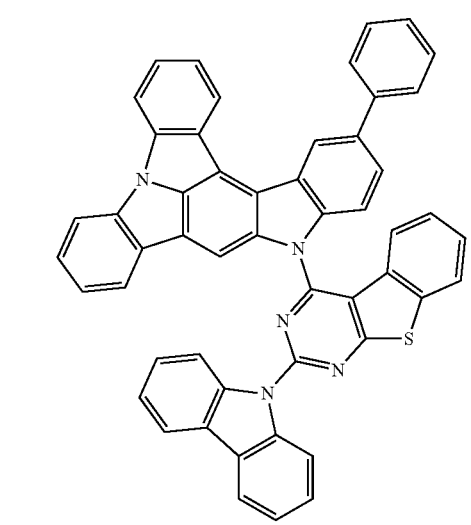
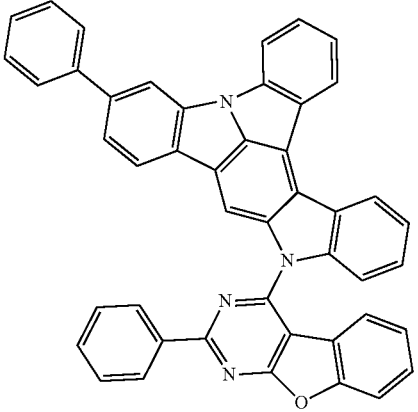
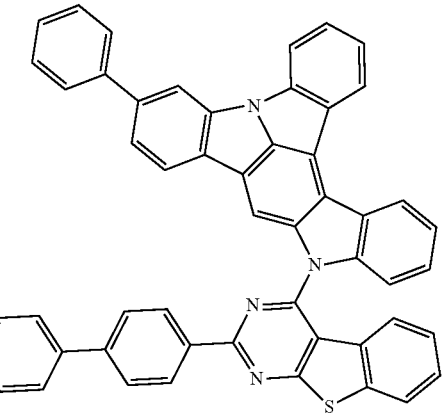
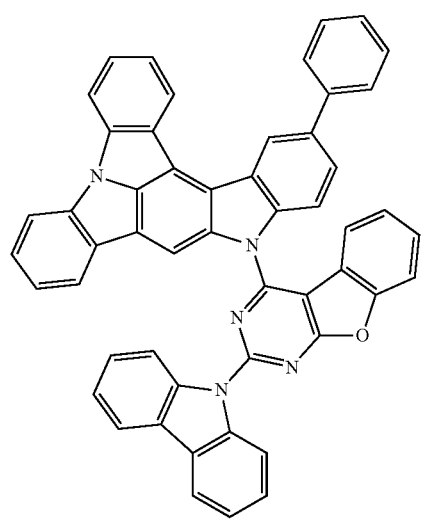
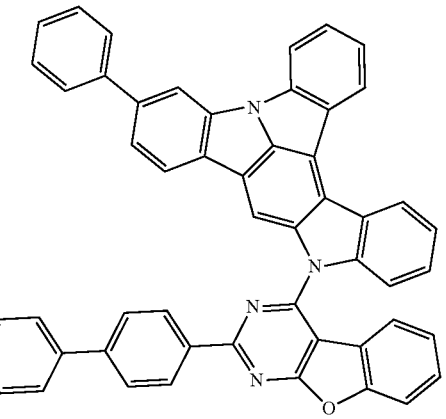

789
-continued
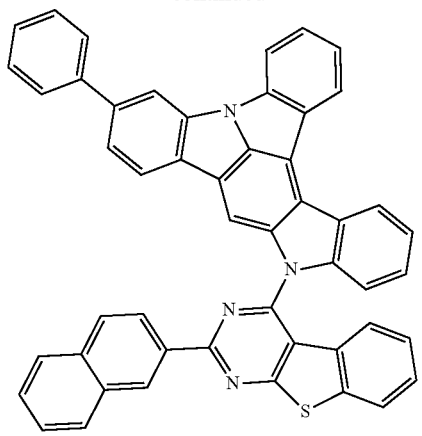
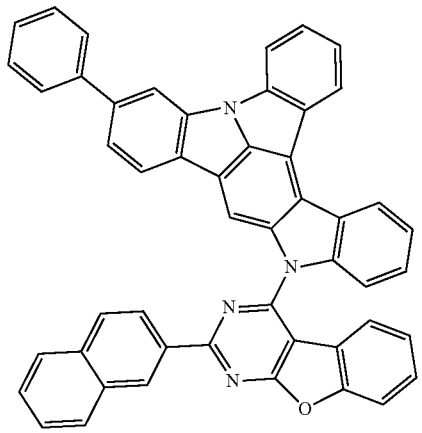
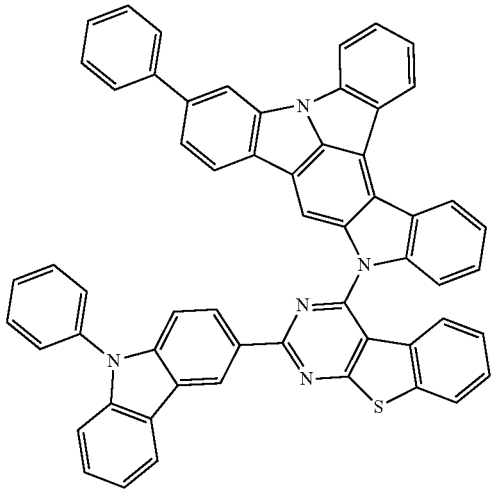
790
-continued
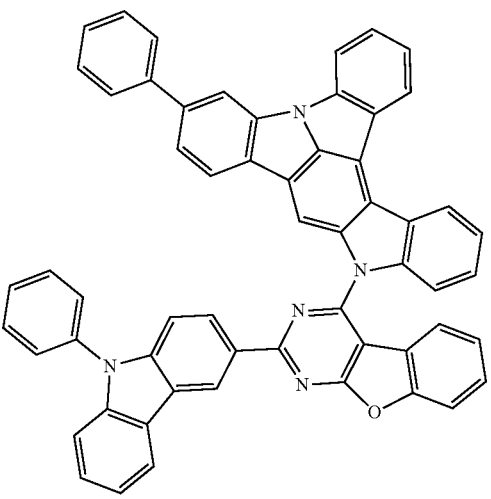
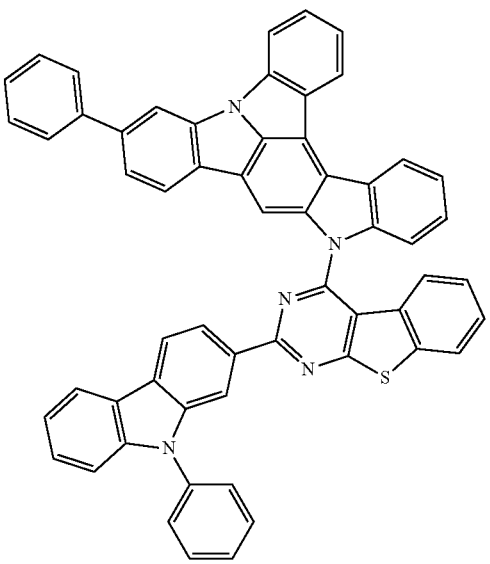
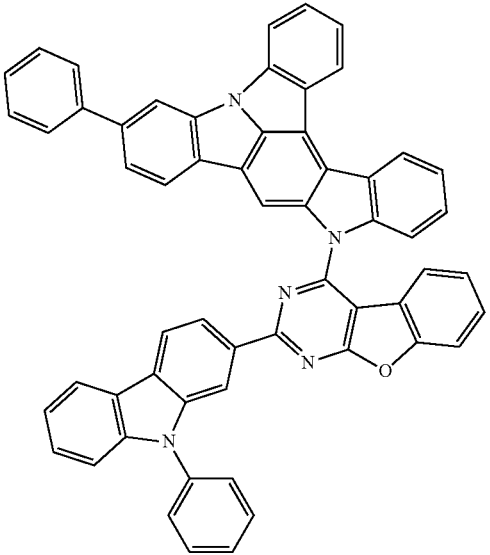

791
-continued
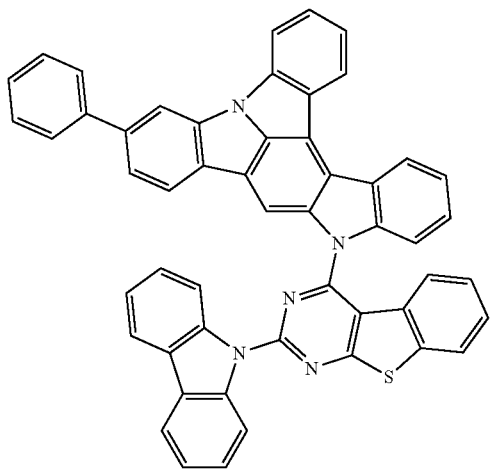
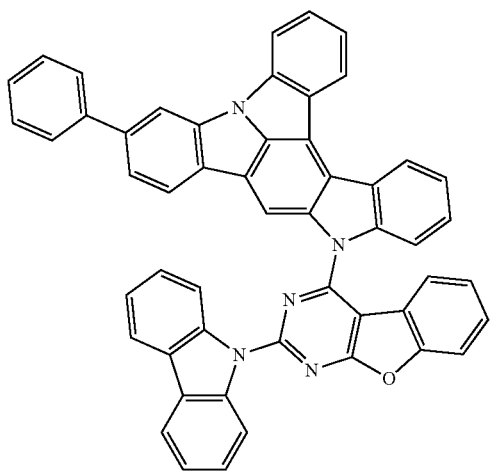
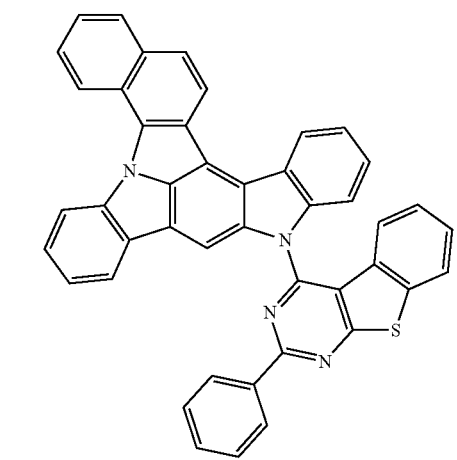
792
-continued
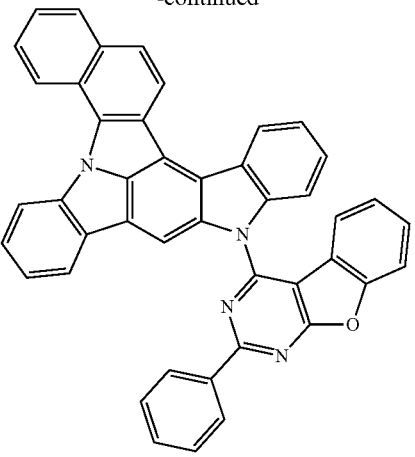
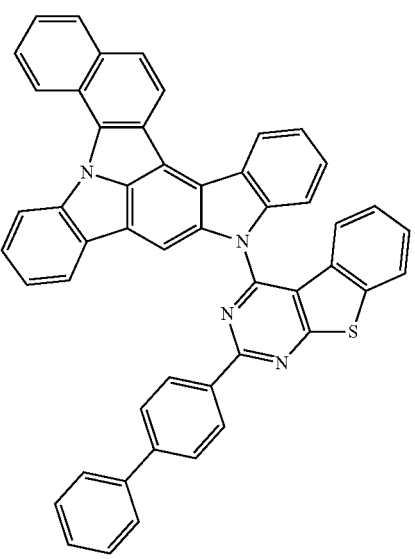
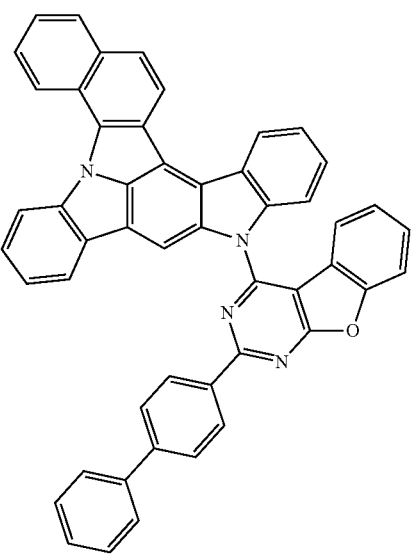

| 793 | 794 |
|---|---|
| -continued | -continued |
| 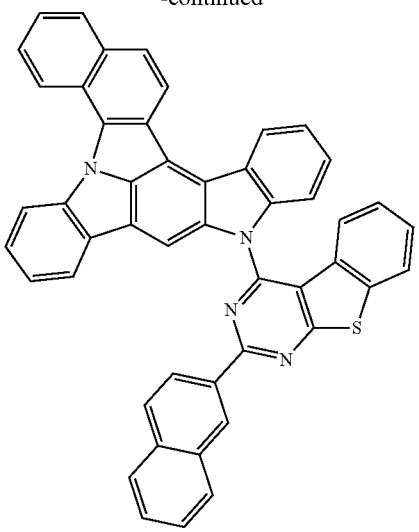 | 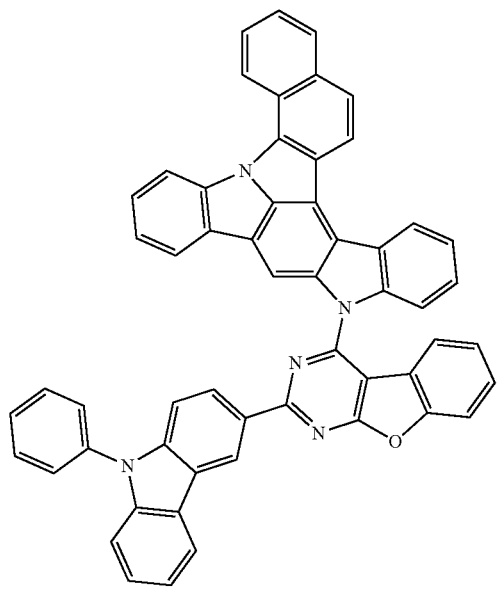 |
| 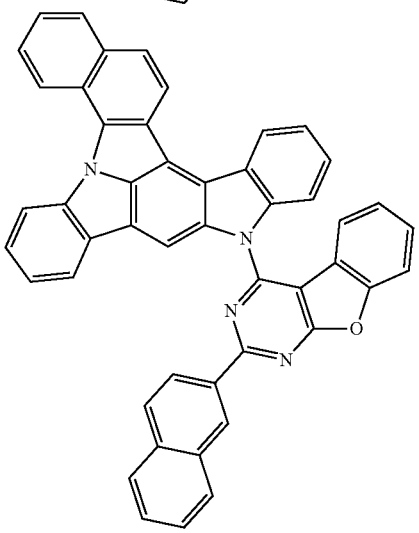 | |
| 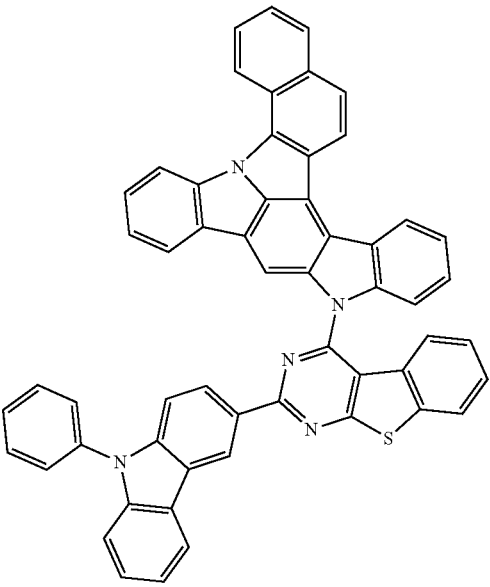 | 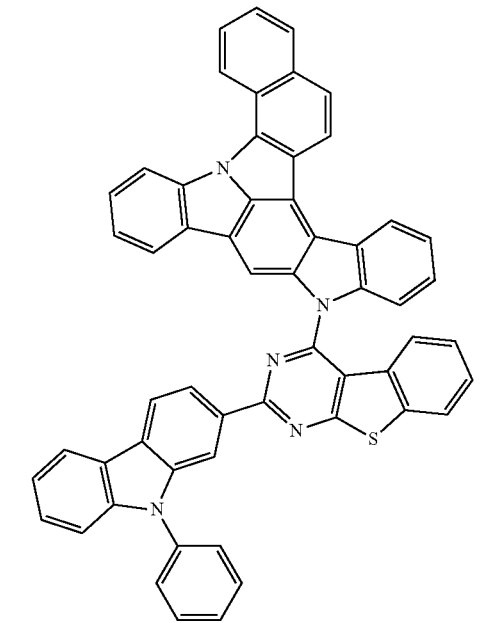 |

-continued

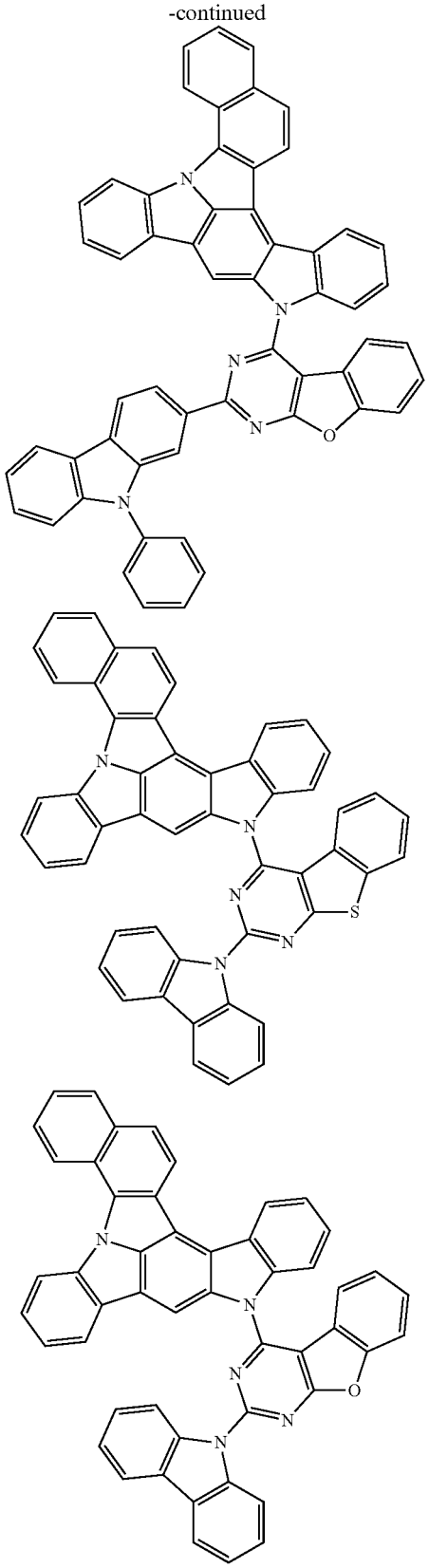

The compound represented by Chemical Formula 1 may undergo an amination reaction by an Ullmann or Buchwald-Hartwig Hartwig coupling reaction, use a Suzuki or Heck coupling reaction, and use a Grignard reagent. In the other chemical formulae, synthesis may also be carried out by the same reactions.

For example, the core of Chemical Formula 2 and the core of Chemical Formula 3 may be prepared by the following Preparation Example 1 and the following Preparation Example 2, respectively, but the preparation method is not limited to the following Preparation Examples. The introduction of the additional substituent may be carried out by using materials and reaction conditions known in the art.

PREPARATION EXAMPLES

Preparation Example 1

Preparation of Core of Chemical Formula 2

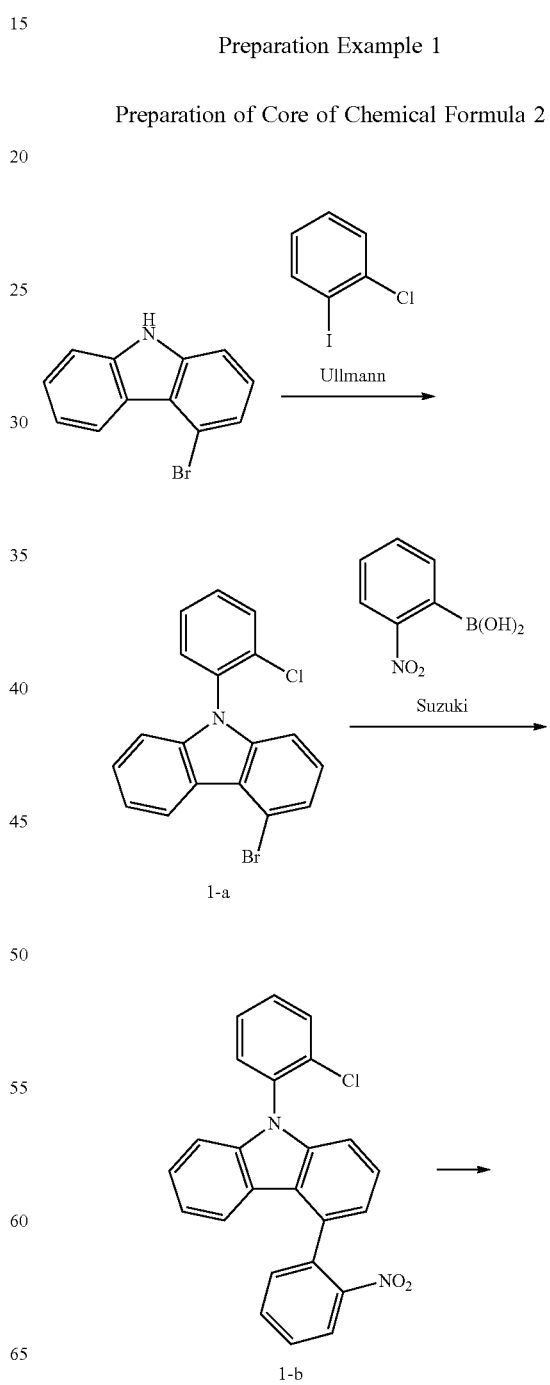

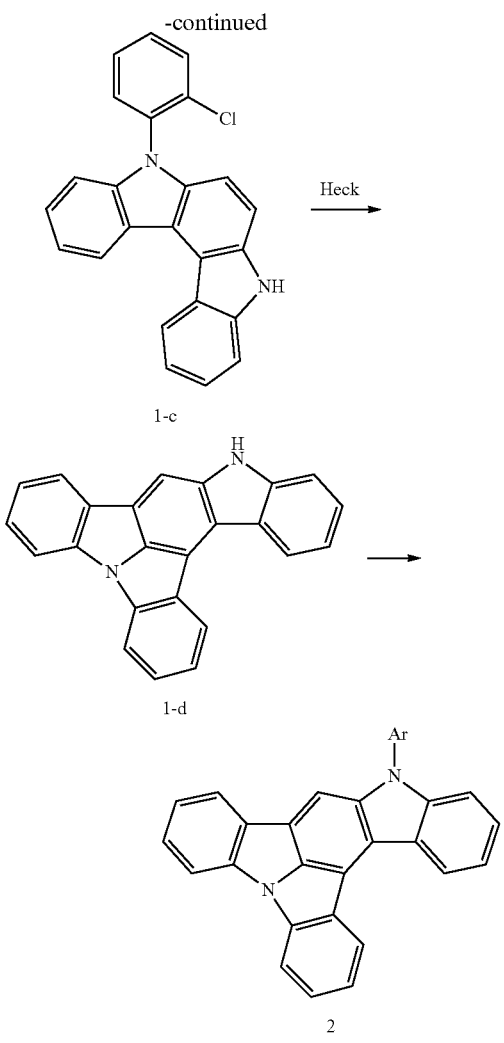

The resulting product was subjected to column chromatography to obtain 121.25 g (304.59 mmol, yield 82%) of Chemical Formula 1-b.

(3) Preparation of Chemical Formula 1-c 121.25 g (304.59 mmol, 1.0 eq) of Chemical Formula 1-b and 151.83 g (913.76 mmol, 3.0 eq) of P(OEt)₃ were put, and stirred under reflux. When the reaction was terminated, a vacuum pump was used to maximally distill P(OEt)₃ and remove the P(OEt)₃. The resulting product was completely dissolved in EA and washed with water, and then the organic layer was separated and placed under reduced pressure to remove all the solvent. The resulting product was subjected to column chromatography to obtain 84.75 g (231.48 mmol, yield 76%) of Chemical Formula 1-c.

(4) Preparation of Chemical Formula 1-d 84.75 g (231.50 mmol, 1.0 eq) of Chemical Formula 1-c, 2.60 g (11.57 mmol, 0.05 eq) of Pd(OAc)₂, 6.07 g (23.15 mmol, 0.1 eq) of PPh₃, 63.98 g (463.00 mmol, 2.0 eq) of K₂CO₃, and 37.31 g (115.75 mmol, 0.5 eq) of tetra-n-butylammonium bromide were put into 550 mL of dimethylacetamide, and reaction was carried out. The reaction solution was stirred at 150° C. for 20 hours, and then the solvent was concentrated under reduced pressure. The concentrated solution was completely dissolved in CHCl₃ and then washed with water, and the solution in which the product was dissolved was concentrated under reduced pressure and purified by using column chromatography. 66.49 g (201.41 mmol, yield 87%) of Chemical Formula 1-d was obtained.

(5) Preparation of Core of Chemical Formula 2

A substituent Ar may be introduced into Chemical Formula 1-d to prepare the core of Chemical Formula 2. The definition of Ar is the same as that described in Chemical Formula 1. Here, L-Ar may be introduced thereinto instead of Ar.

Preparation Example 2

Preparation of Core of Chemical Formula 3

(1) Preparation of Chemical Formula 1-a 100 g (408.20 mmol, 1.0 eq) of 4-bromo-9H-carbazole, 116.53 g (489.83 mmol, 1.2 eq) of 1-chloro-2-iodobenzene, 51.88 g (816.39 mmol, 2.0 eq) of copper powder, and 259.94 g (1,224.59 mmol, 3.0 eq) of K₃PO₄ were put into 1,000 ml of xylene, and stirred under reflux. When the reaction was terminated, the resulting product was cooled to normal temperature, and then the copper powder was first filtered and removed. The solution in which the product was dissolved was placed under reduced pressure to remove all the solvent, and the product was completely dissolved in CHCl₃, washed with water, and again placed under reduced pressure to remove the solvent, and the resulting product was purified by using column chromatography. 131.86 g (371.46 mmol, yield 91%) of Chemical Formula 1-a was obtained.

(2) Preparation of Chemical Formula 1-b 131.86 g (371.46 mmol, 1.0 eq), of Chemical Formula 1-a, 74.46 g (445.75 mmol, 1.2 eq) of 2-(nitrophenyl) boronic acid, and 0.79 g (3.71 mmol, 0.01 eq) of Pd(PPh₃)₄ were dissolved in 900 ml of dioxane and stirred, and then 102.67 g (742.91 mmol, 2.0 eq) of K₂CO₃ was dissolved in 300 ml of water, the resulting solution was added thereto, and the resulting mixture was stirred under reflux. When the reaction was terminated, the organic layer was separated and then placed under reduced pressure to remove the solvent.

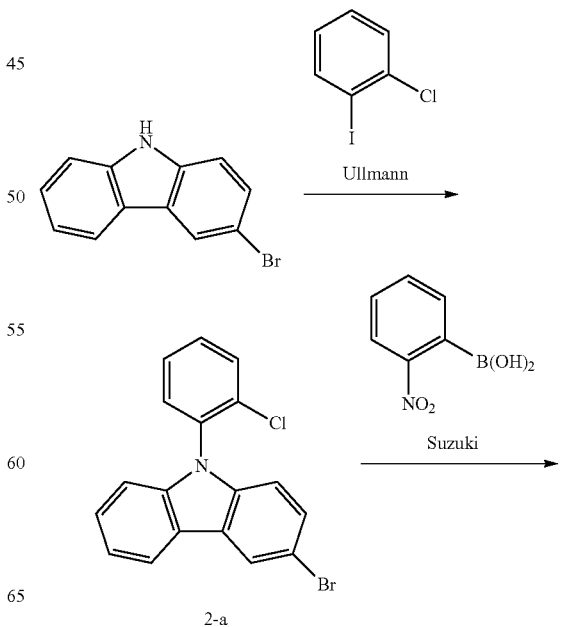

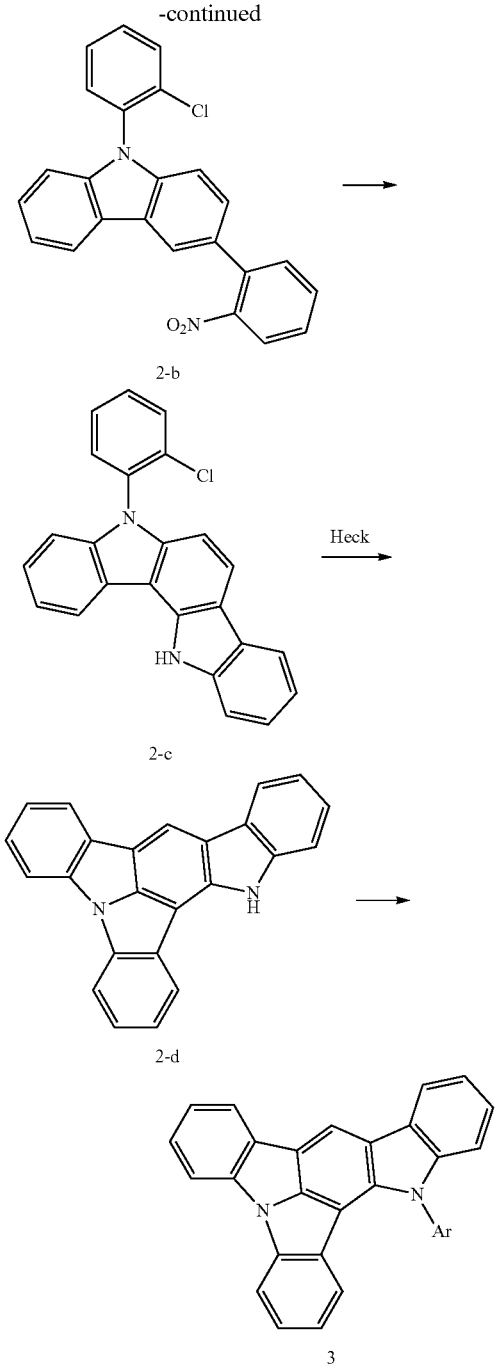

by using column chromatography. 130.41 g (367.38 mmol, yield 90%) of Chemical Formula 2-a was obtained.

(2) Preparation of Chemical Formula 2-b 130.41 g (367.38 mmol, 1.0 eq), of Chemical Formula 2-a, 73.64 g (440.85 mmol, 1.2 eq) of 2-(nitrophenyl)boronic acid, and 0.78 g (3.67 mmol, 0.01 eq) of $Pd(PPh_3)_4$ were dissolved in 900 ml of dioxane and stirred, and then 101.54 g (734.74 mmol, 2.0 eq) of $K_2CO_3$ was dissolved in 300 ml of water, the resulting solution was added thereto, and the resulting mixture was stirred under reflux. When the reaction was terminated, the organic layer was separated and then placed under reduced pressure to remove the solvent. The resulting product was subjected to column chromatography to obtain 121.38 g (304.91 mmol, yield 83%) of Chemical Formula 2-b.

(3) Preparation of Chemical Formula 2-c 121.38 g (304.91 mmol, 1.0 eq) of Chemical Formula 2-b and 151.99 g (914.74 mmol, 3.0 eq) of $P(OEt)_3$ were put, and stirred under reflux. When the reaction was terminated, a vacuum pump was used to maximally distill $P(OEt)_3$ and remove the $P(OEt)_3$. The resulting product was completely dissolved in EA and washed with water, and the organic layer was separated and placed under reduced pressure to remove all the solvent. The resulting product was subjected to column chromatography to obtain 81.49 g (222.58 mmol, yield 73%) of Chemical Formula 2-c.

(4) Preparation of Chemical Formula 2-d 81.49 g (222.58 mmol, 1.0 eq) of Chemical Formula 2-c, 2.50 g (11.13 mmol, 0.05 eq) of $Pd(OAc)_2$, 5.84 g (22.26 mmol, 0.1 eq) of $PPh_3$, 61.53 g (445.19 mmol, 2.0 eq) of $K_2CO_3$, and 35.87 g (111.30 mmol, 0.5 eq) of tetra-n-butylammonium bromide were put into 550 mL of dimethylacetamide, and reaction was carried out. The reaction solution was stirred at 150° C. for 20 hours, and then the solvent was concentrated under reduced pressure. The concentrated solution was completely dissolved in $CHCl_3$ and then washed with water, and the solution in which the product was dissolved was concentrated under reduced pressure and purified by using column chromatography.

65.40 g (198.11 mmol, yield 89%) of Chemical Formula 2-d was obtained.

(5) Preparation of Core of Chemical Formula 3

A substituent Ar may be introduced into Chemical Formula 2-d to prepare the core of Chemical Formula 3. The definition of Ar is the same as that described in Chemical Formula 1. Here, L-Ar may be introduced thereinto instead of Ar.

Preparation Example 3

Preparation of Core of Chemical Formula 26

(1) Preparation of Chemical Formula 2-a 100 g (408.20 mmol, 1.0 eq) of 3-bromo-9H-carbazole, 116.53 g (489.84 mmol, 1.2 eq) of 1-chloro-2-iodobenzene, 51.88 g (816.39 mmol, 2.0 eq) of copper powder, and 259.94 g (1,224.59 mmol, 3.0 eq) of $K_3PO_4$ were put into 1,000 ml of xylene, and stirred under reflux. When the reaction was terminated, the resulting product was cooled to normal temperature, and then the copper powder was first filtered and removed. The solution in which the product was dissolved was placed under reduced pressure to remove all the solvent, and the product was completely dissolved in $CHCl_3$, washed with water, and again placed under reduced pressure to remove the solvent, and the resulting product was purified

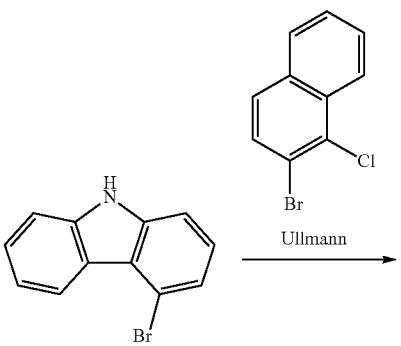

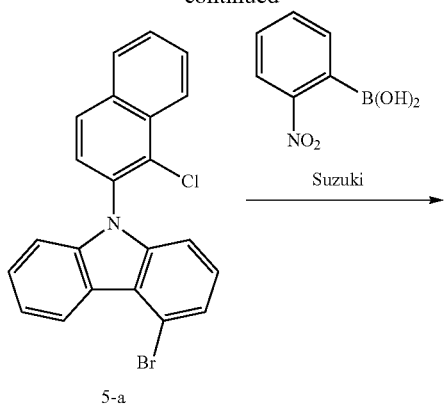
5-a
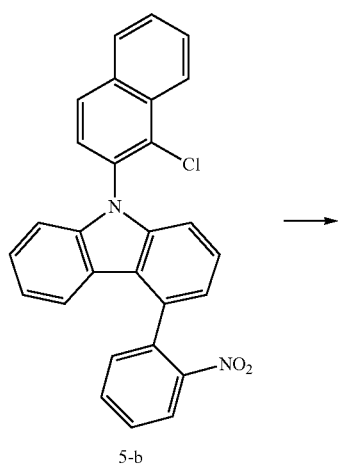
5-b
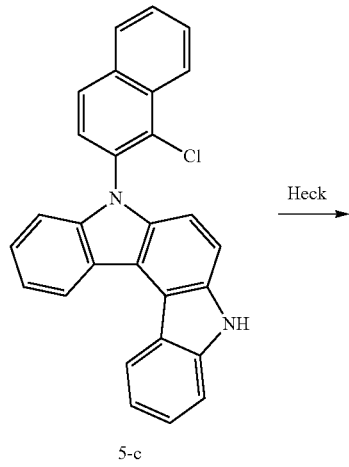
5-c
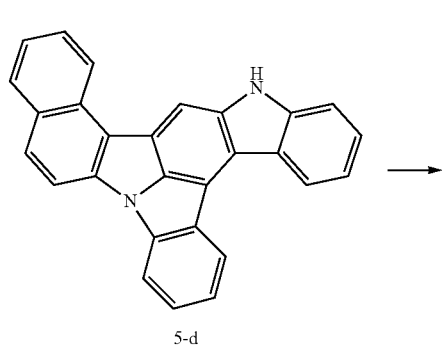
5-d
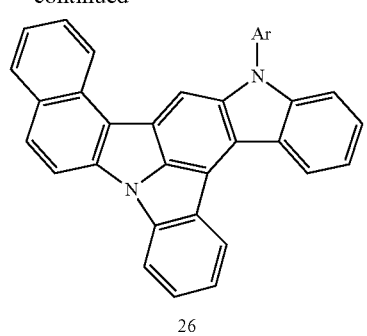
26
A core of Chemical Formula 26 was prepared by performing the preparation in the same manner as in Preparation Example 1, except that 2-bromo-1-chloronaphthalene was used instead of 1-chloro-2-iodobenzene in Preparation Example 1. Here, L-Ar may be introduced thereinto instead of Ar.
Preparation Example 4
Preparation of Core of Chemical Formula 27
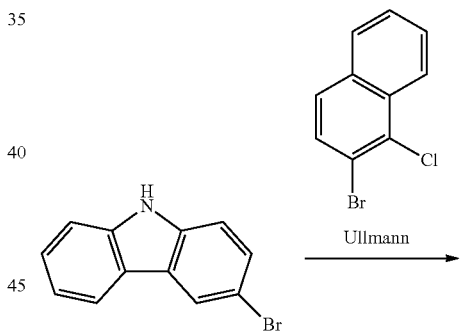
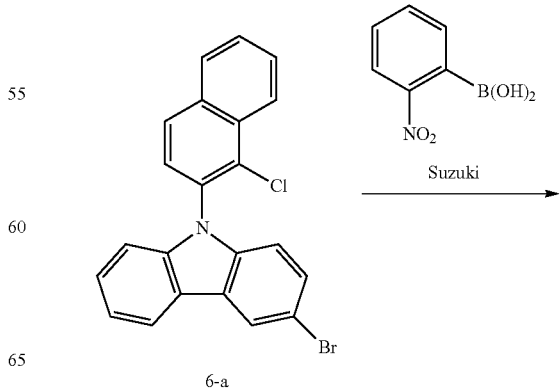
6-a 803
-continued
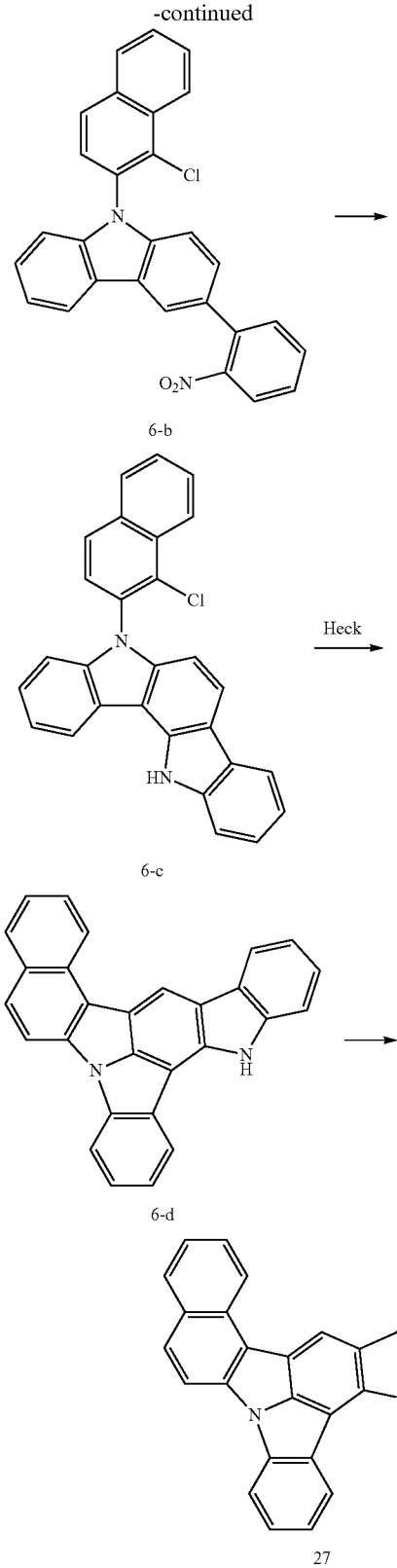
804
was used instead of 1-chloro-2-iodobenzene in Preparation Example 2. Here, L-Ar may be introduced thereinto instead of Ar.
Preparation Example 5
Preparation of Core of Chemical Formula 34
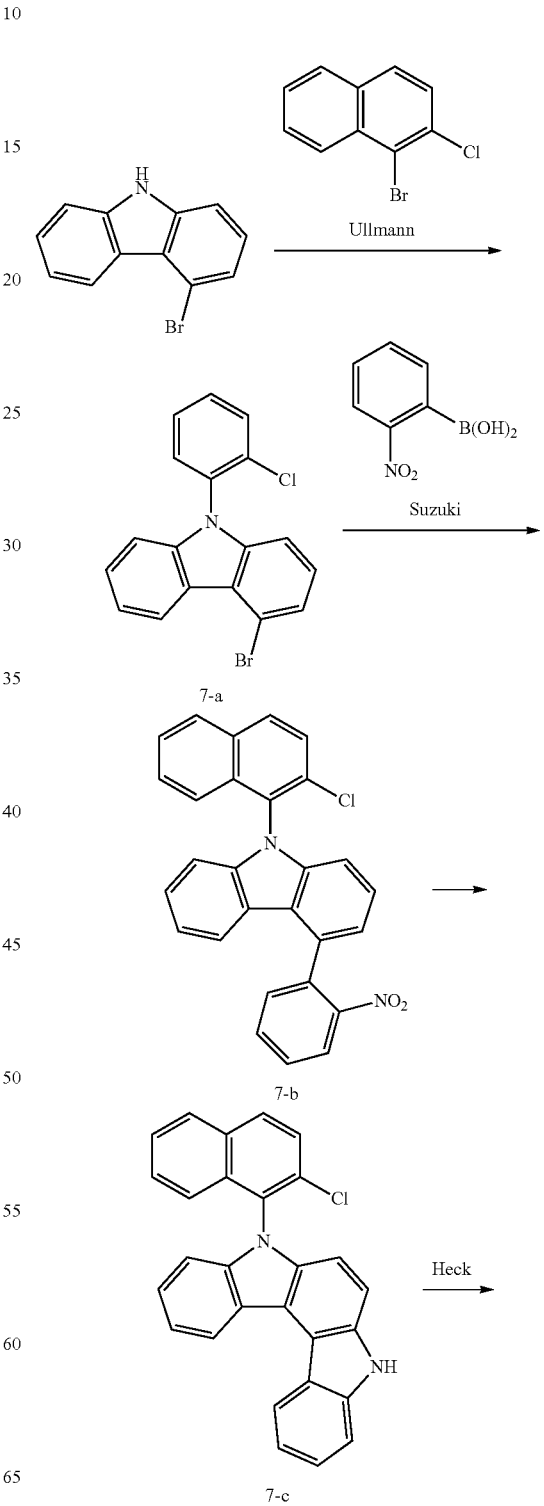
A core of Chemical Formula 27 was prepared by performing the preparation in the same manner as in Preparation Example 2, except that 2-bromo-1-chloronaphthalene

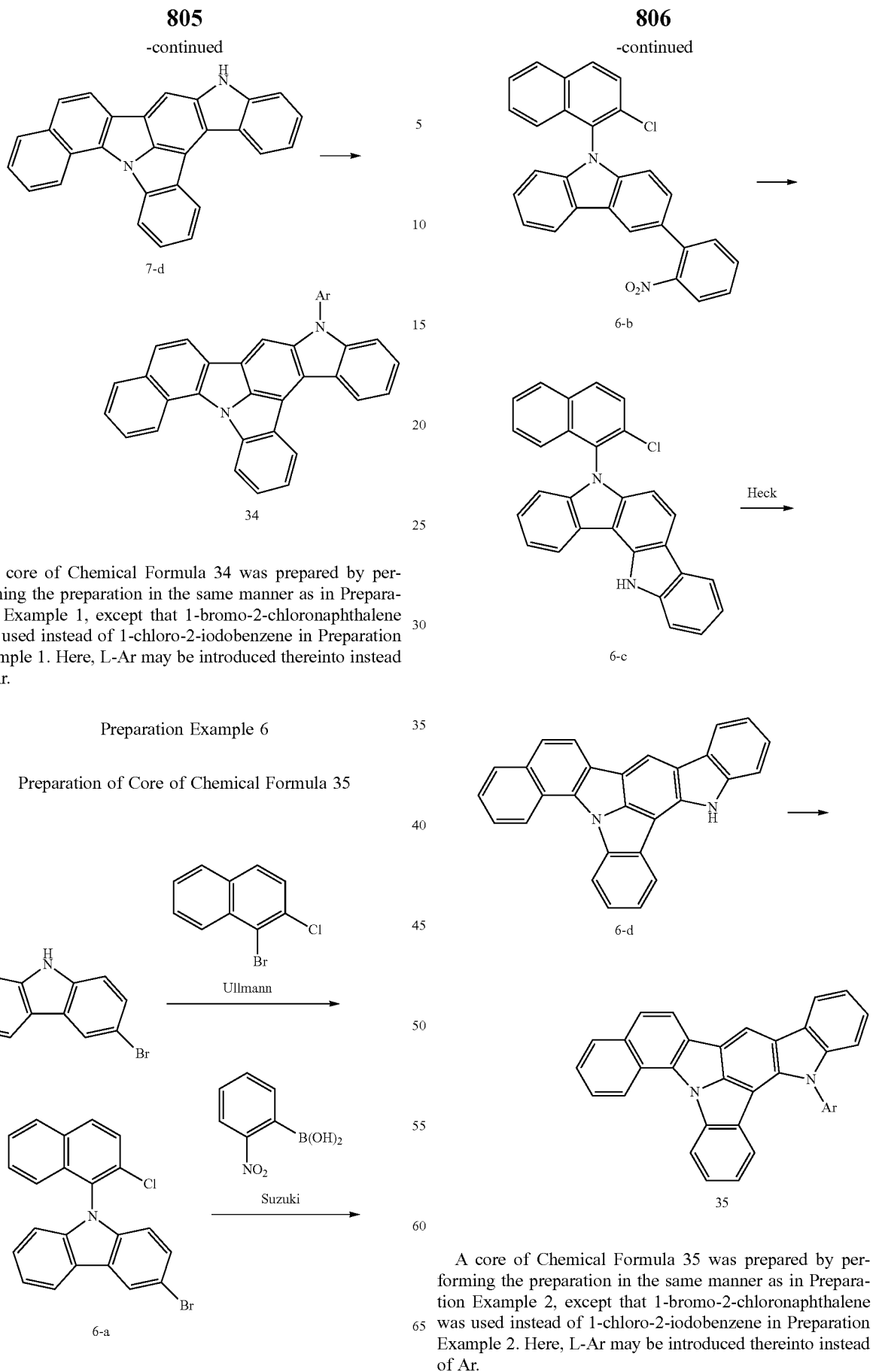

A core of Chemical Formula 34 was prepared by performing the preparation in the same manner as in Preparation Example 1, except that 1-bromo-2-chloronaphthalene was used instead of 1-chloro-2-iodobenzene in Preparation Example 1. Here, L-Ar may be introduced thereinto instead of Ar.

Preparation Example 6

Preparation of Core of Chemical Formula 35

A core of Chemical Formula 35 was prepared by performing the preparation in the same manner as in Preparation Example 2, except that 1-bromo-2-chloronaphthalene was used instead of 1-chloro-2-iodobenzene in Preparation Example 2. Here, L-Ar may be introduced thereinto instead of Ar.

Preparation Example 7

Preparation of Core of Chemical Formula 8

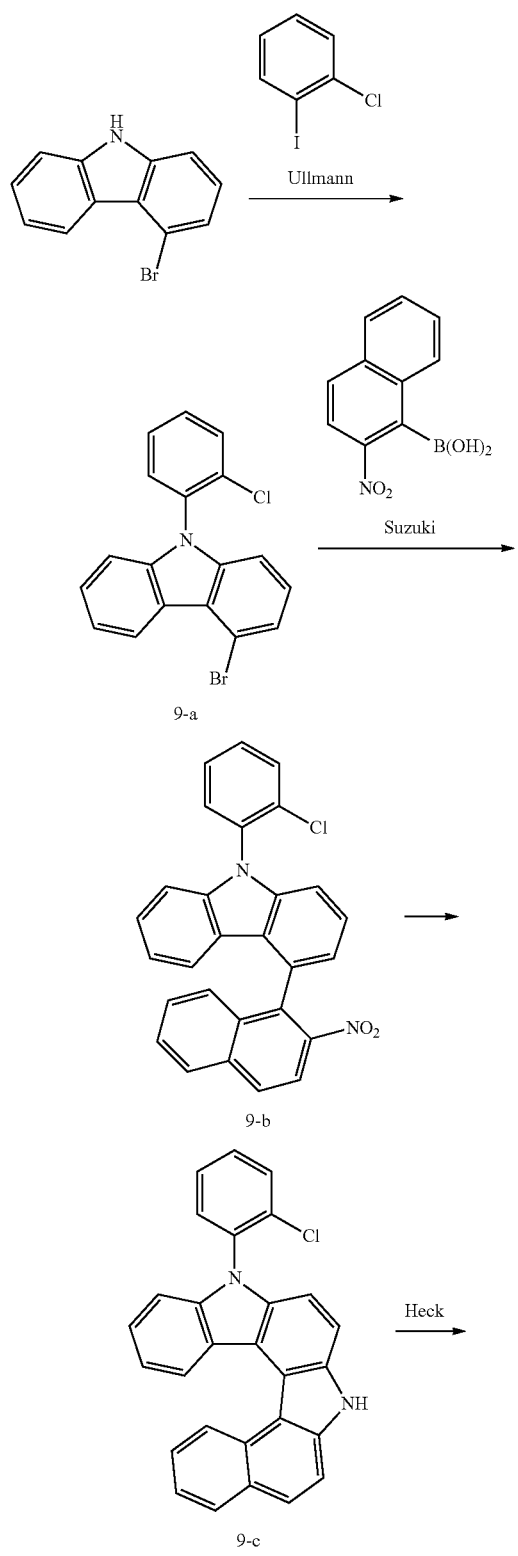

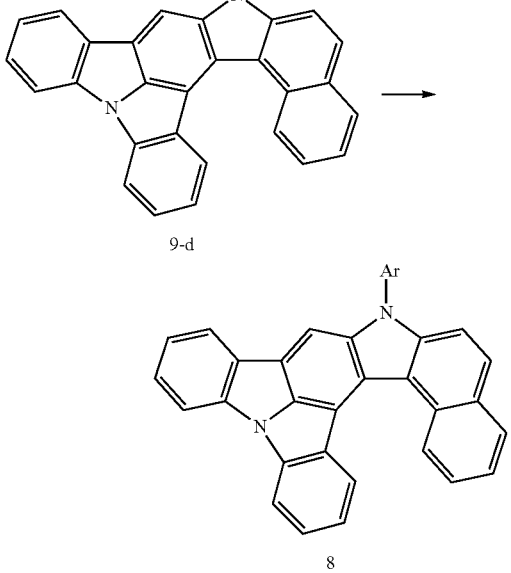

A core of Chemical Formula 8 was prepared by performing the preparation in the same manner as in Preparation Example 1, except that 2-(nitronaphthyl)boronic acid was used instead of 2-(nitrophenyl)boronic acid in Preparation Example 1. Here, L-Ar may be introduced thereinto instead of Ar.

Preparation Example 8

Preparation of Core of Chemical Formula 11

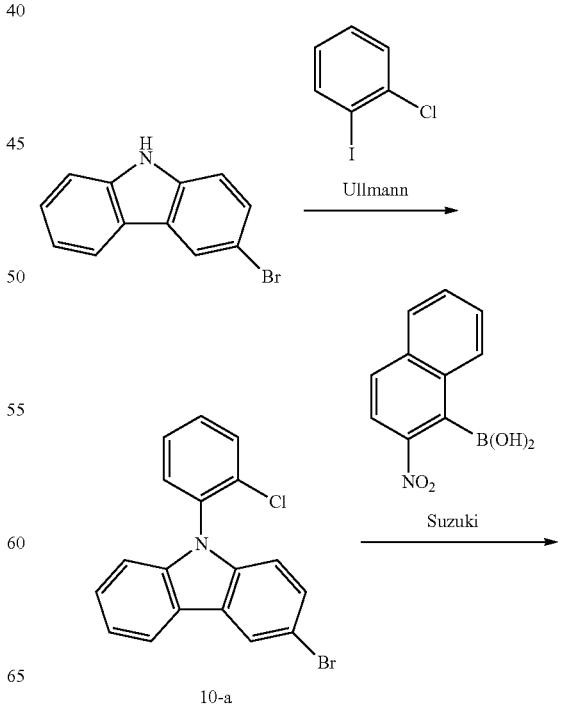

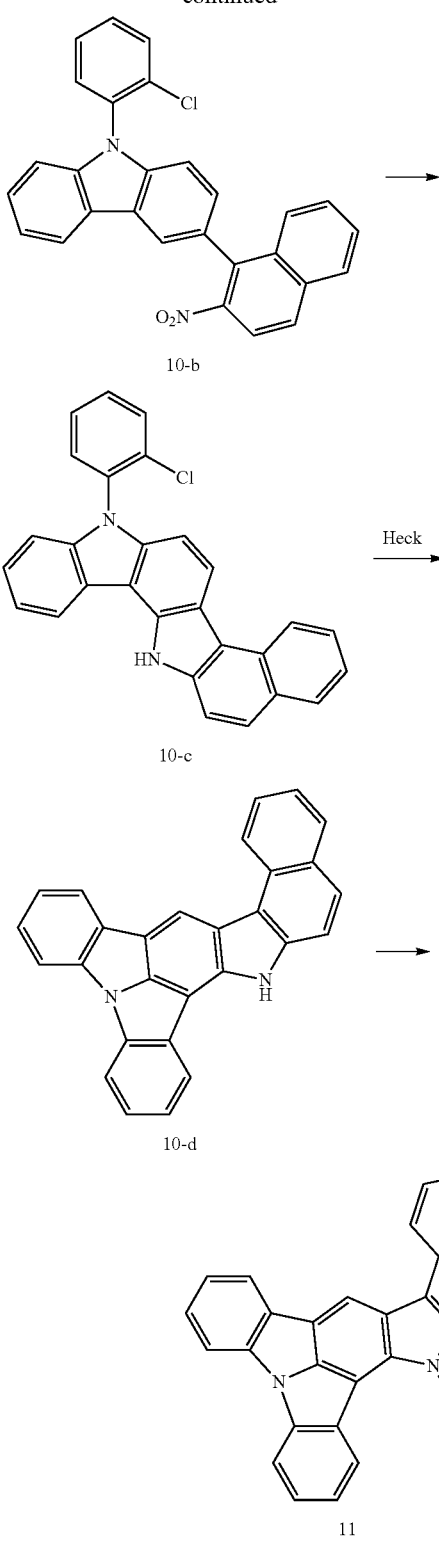

A core of Chemical Formula 11 was prepared by performing the preparation in the same manner as in Preparation Example 2, except that 2-(nitronaphthyl)boronic acid was used instead of 2-(nitrophenyl)boronic acid in Preparation Example 2. Here, L-Ar may be introduced thereinto instead of Ar.

Further, in Chemical Formula 1, the compound in the case where adjacent substituents in R1 to R13 combine with each other and are further fused may be prepared by the following General Preparation Examples 1 and 2, but the preparation method is not limited thereto.

In the following structure,

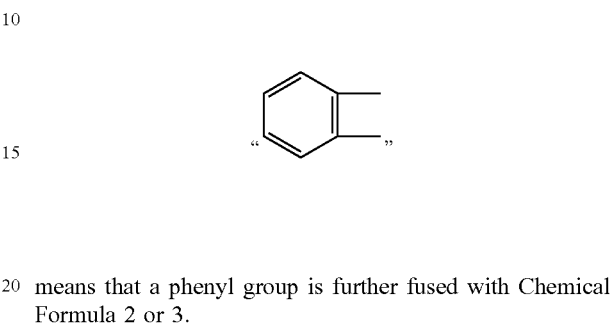

means that a phenyl group is further fused with Chemical Formula 2 or 3.

GENERAL PREPARATION EXAMPLES

General Preparation Example 1

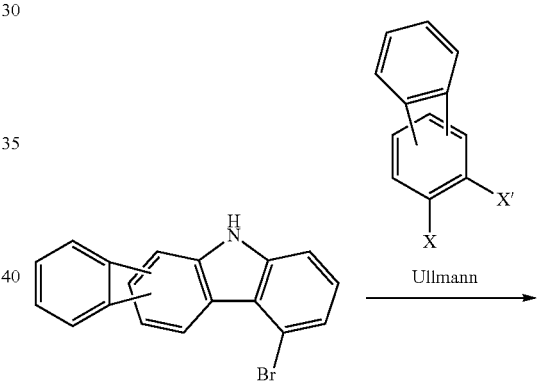

811
-continued
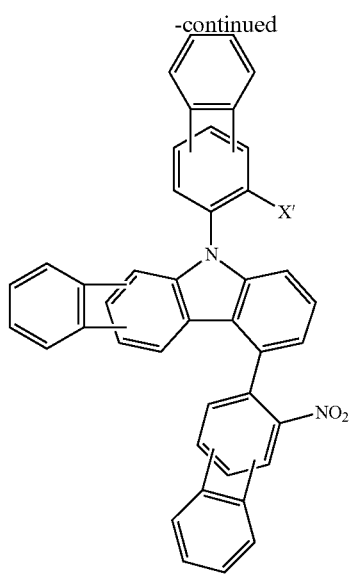
812
-continued
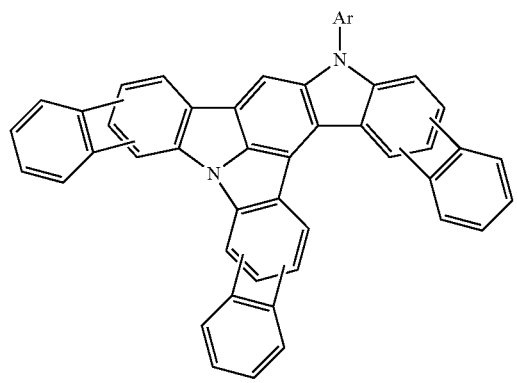
General Preparation Example 2
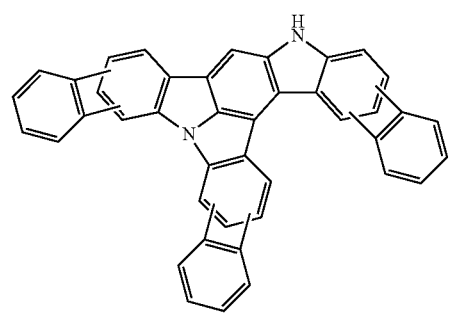
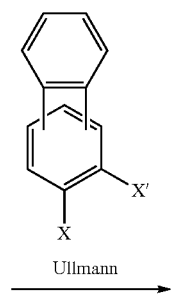
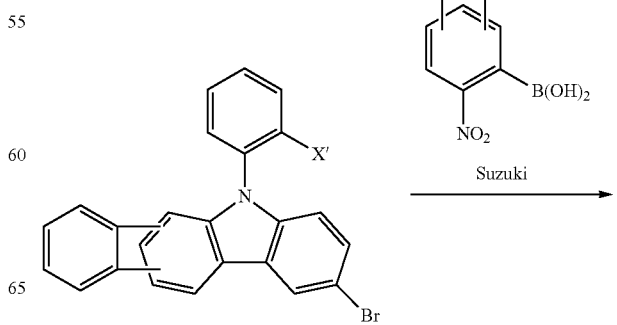

813
-continued

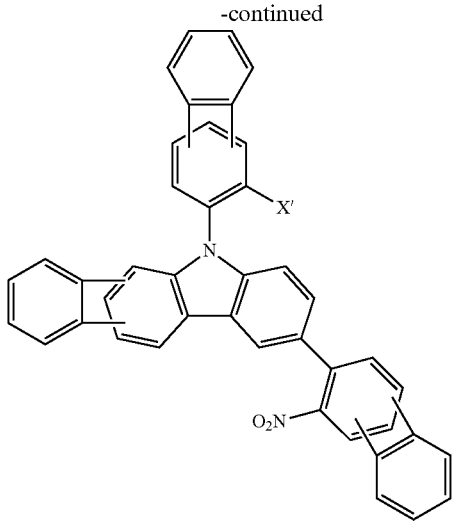

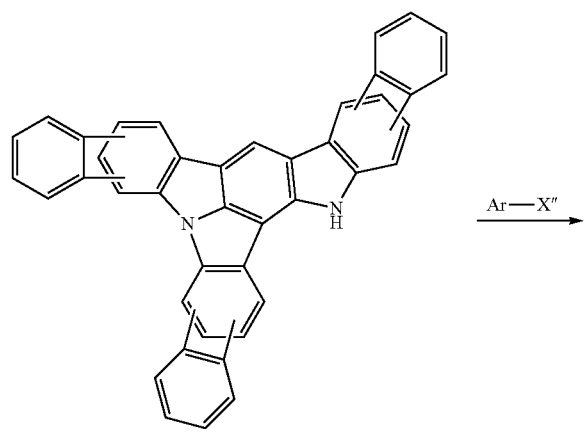

814
-continued

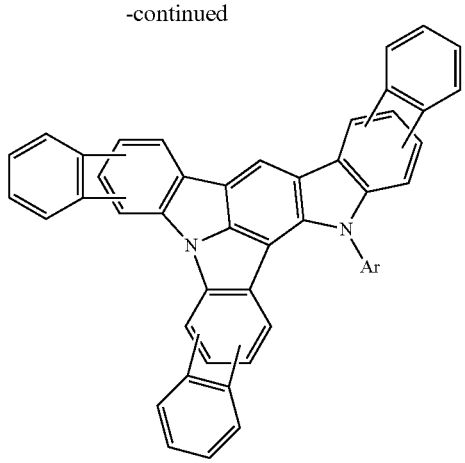

In General Preparation Examples 1 and 2,
X, X', and X" are the same as or different from each other, and each independently a halogen group, and
the definition of Ar is the same as that in Chemical Formula 1. In General Preparation Examples, L-Ar may be introduced thereinto instead of Ar.

Further, another exemplary embodiment of the present specification provides an organic light emitting device including the compound represented by Chemical Formula 1.

The organic light emitting device according to an exemplary embodiment of the present specification includes: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device according to exemplary embodiments of the present specification may be composed of a single-layered structure, but may also be composed of a multi-layered structure in which two or more organic material layers are stacked. For example, the organic light emitting device according to exemplary embodiments of the present specification may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In another exemplary embodiment, the organic material layer includes an electron transporting layer, an electron injection layer, a layer which simultaneously transports and injects electrons, a light emitting layer, a hole transporting layer, a hole injection layer, or a layer which simultaneously transports and injects holes, and the electron transporting layer, the electron injection layer, the layer which simultaneously transports and injects electrons, the light emitting layer, the hole transporting layer, the hole injection layer, or the layer which simultaneously transports and injects holes includes the compound of Chemical Formula 1.

According to an exemplary embodiment of the present specification, the organic material layer includes an electron transporting layer, an electron injection layer, or a layer which simultaneously transports and injects electrons, and the electron transporting layer, the electron injection layer, or the layer which simultaneously transports and injects electrons includes the compound of Chemical Formula 1.

In an exemplary embodiment of the present specification, the light emitting layer includes the compound of Chemical Formula 1.

In an exemplary embodiment of the present specification, the light emitting layer includes the compound of Chemical Formula 1 as a host.

In an exemplary embodiment of the present specification, the light emitting layer including the compound of Chemical Formula 1 may further include a dopant.

As the dopant, those known in the art may be used. For example, a phosphorescent dopant, specifically, an iridium-based complex may be used.

The dopant may be represented by the following compounds, but is not limited thereto.

Dp-1

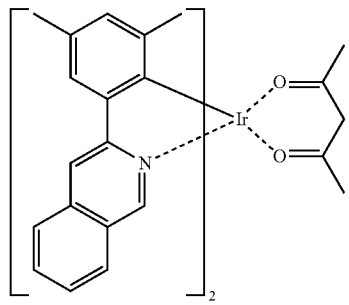

Dp-2

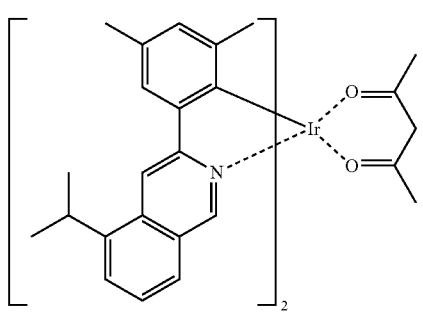

Dp-3

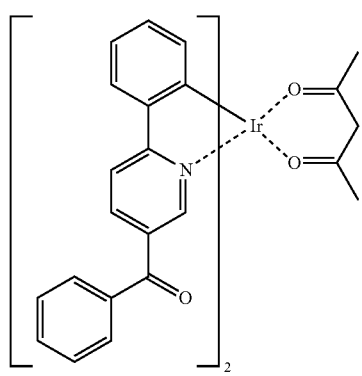

Dp-4

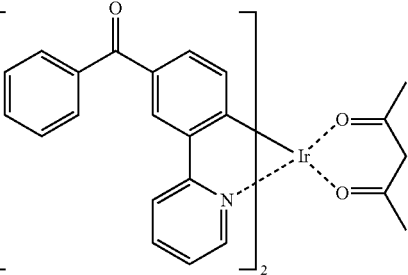

Dp-5

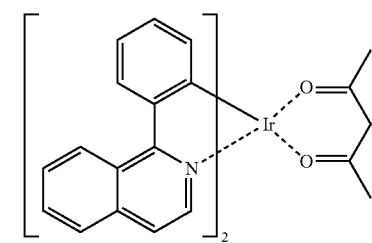

Dp-6

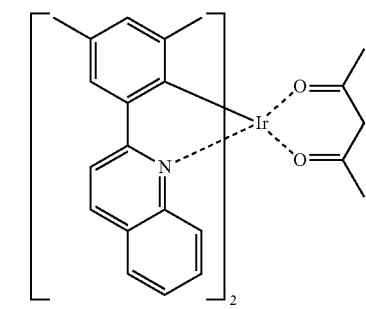

Dp-7

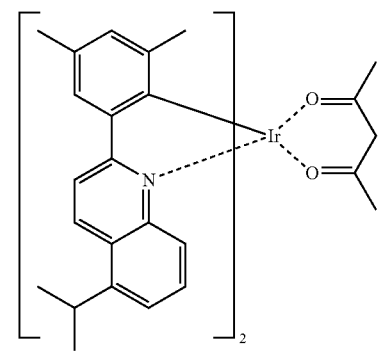

Dp-8

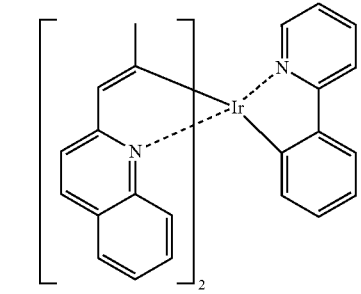

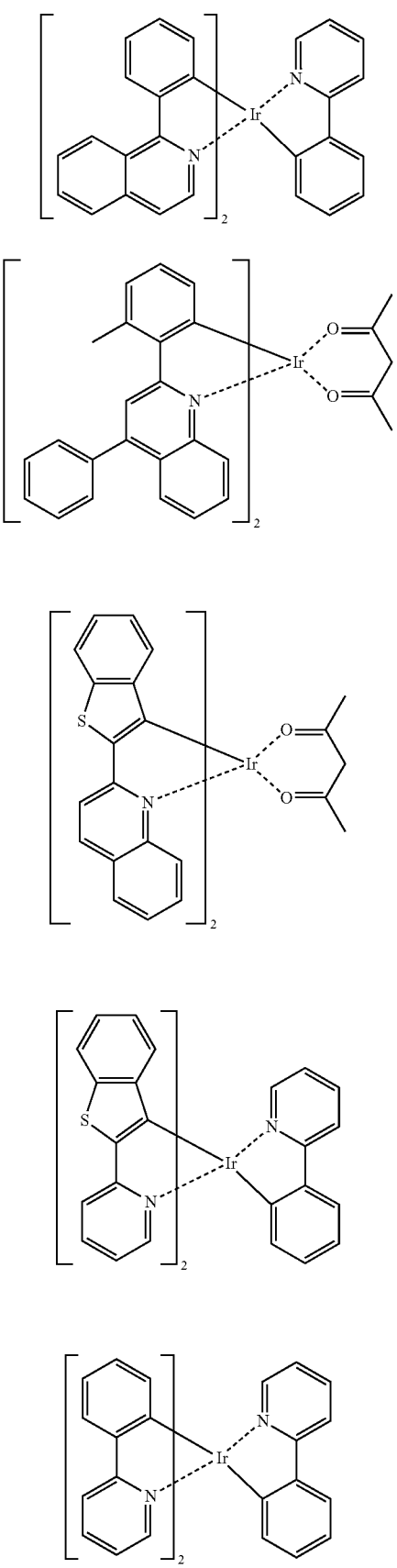
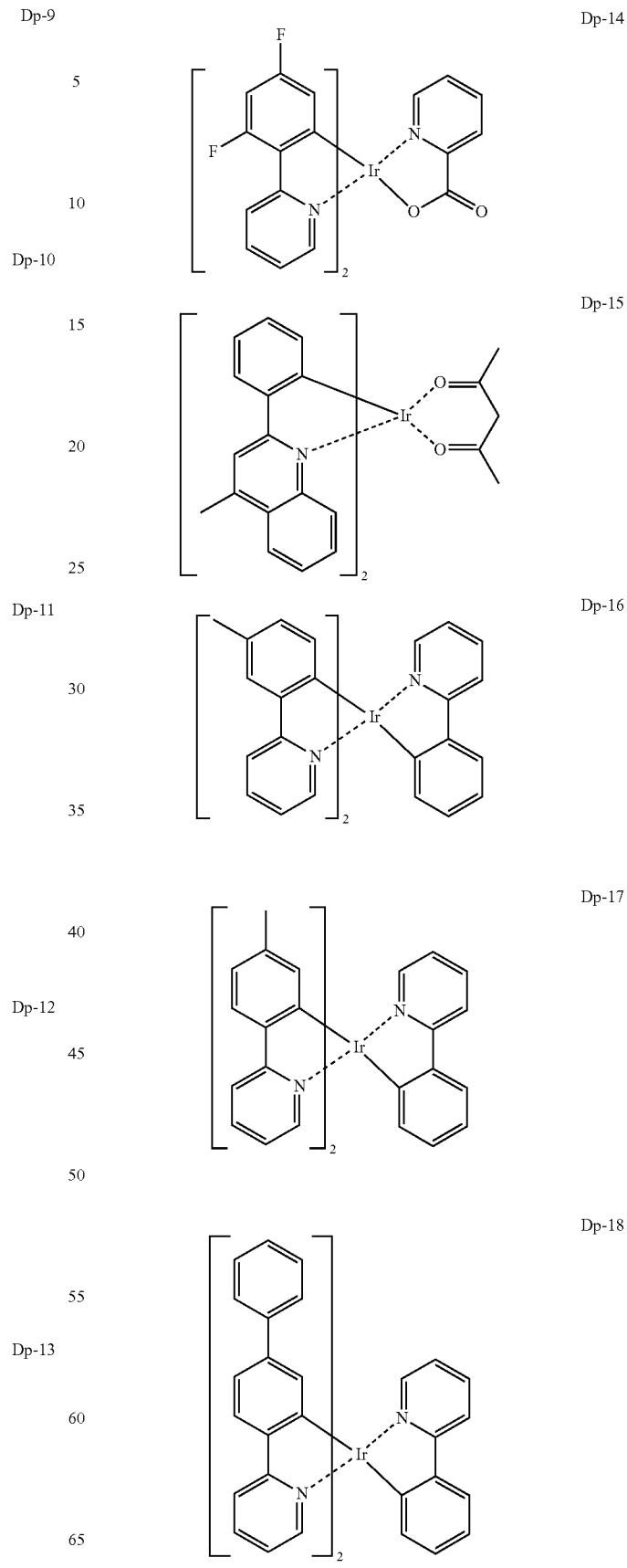

Dp-19 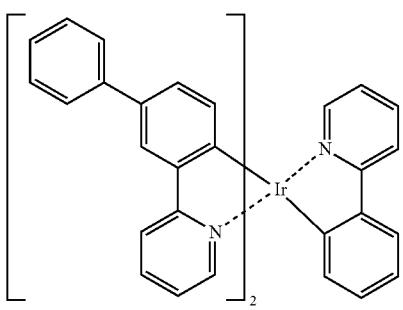

Dp-20 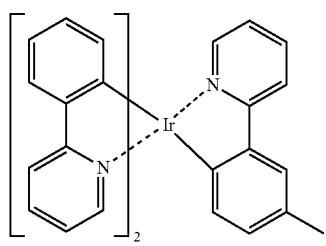

Dp-21 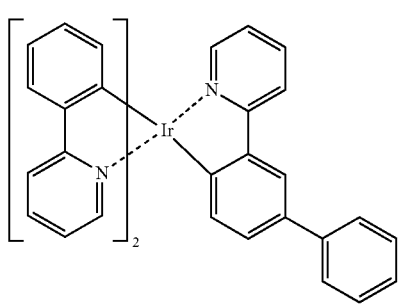

Dp-22 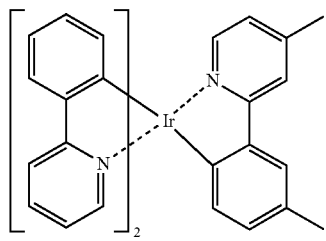

Dp-23 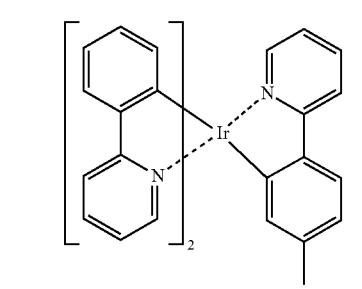

Dp-24 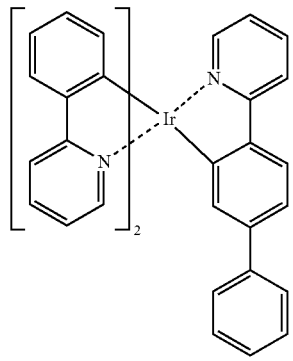

Dp-25 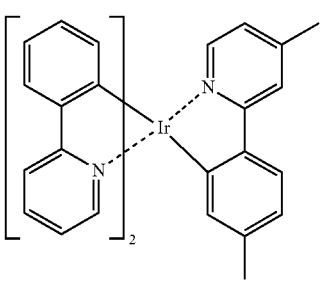

Dp-26 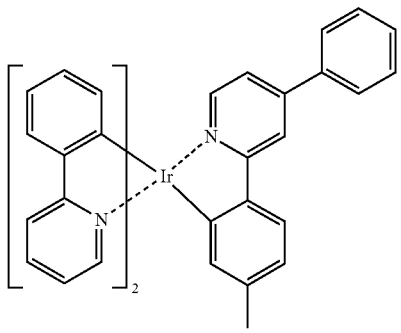

Dp-27 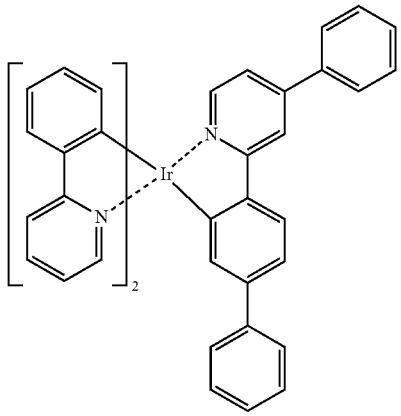

However, the dopant compound is not limited to the examples.

In an exemplary embodiment of the present specification, the organic material layer includes a hole injection layer, a hole transporting layer, or a layer which simultaneously transports and injects holes, and the hole injection layer, the hole transporting layer, or the layer which simultaneously transports and injects holes includes the compound of Chemical Formula 1.

In an exemplary embodiment of the present specification, the organic material layer may further include a hole injection layer or a hole transporting layer, which includes a compound including an arylamino group, a carbazole group, or a benzocarbazole group, in addition to the organic material layer including the compound of Chemical Formula 1.

In an exemplary embodiment of the present specification, the organic material layer including the compound of Chemical Formula 1 may include the compound of Chemical Formula 1 as a host, and may include another organic compound, metal or a metal compound as a dopant.

In another exemplary embodiment, the organic light emitting device may be an organic light emitting device having a structure (normal type) in which a positive electrode, one or more organic material layers, and a negative electrode are sequentially stacked on a substrate.

In still another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to the present invention is illustrated in FIGS. 1 to 5.

FIG. 1 illustrates the structure of an organic light emitting device in which a positive electrode 2, a hole injection layer 3, a hole transporting layer 4, a light emitting layer 5, an electron transporting layer 6, and a negative electrode 7 are sequentially stacked on a substrate 1. In the structure as described above, the compound represented by Chemical Formula 1 may be included in the hole injection layer 3, the hole transporting layer 4, the light emitting layer 5, or the electron transporting layer 6.

FIG. 2 illustrates the structure of an organic light emitting device in which a positive electrode 2, a hole injection layer 3, a hole transporting layer 4, a light emitting layer 5, and a negative electrode 7 are sequentially stacked on a substrate 1. In the structure as described above, the compound represented by Chemical Formula 1 may be included in the hole injection layer 3, the hole transporting layer 4, or the light emitting layer 5.

FIG. 3 illustrates the structure of an organic light emitting device in which a positive electrode 2, a hole transporting layer 4, a light emitting layer 5, an electron transporting layer 6, and a negative electrode 7 are sequentially stacked on a substrate 1. In the structure as described above, the compound represented by Chemical Formula 1 may be included in the hole transporting layer 4, the light emitting layer 5, or the electron transporting layer 6.

FIG. 4 illustrates the structure of an organic light emitting device in which a positive electrode 2, a light emitting layer 5, an electron transporting layer 6, and a negative electrode 7 are sequentially stacked on a substrate 1. In the structure as described above, the compound represented by Chemical Formula 1 may be included in the light emitting layer 5 or the electron transporting layer 6.

FIG. 5 illustrates the structure of an organic light emitting device in which a positive electrode 2, a light emitting layer 5, and a negative electrode 7 are sequentially stacked on a substrate 1. In the structure as described above, the compound represented by Chemical Formula 1 may be included in the light emitting layer 5.

When the organic light emitting device includes a plurality of organic material layers, the organic material layers may be formed of the same material or different materials.

The organic light emitting device of the present specification may be manufactured by the materials and methods known in the art, except that one or more layers of the organic material layers include the compound of the present specification, that is, the compound of Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto. In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a Spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to a light emitting layer, and is suitably a material which has large mobility for the electrons. Specific examples thereof include: an Al complex of 8-hydroxyquinoline; a complex including Alq$_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo [h]quinolinato) beryllium, bis(10-hydroxybenzo [h]quinolinato) zinc, bis(2-methyl-8-quinolinato) chlorogallium, bis (2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

Hereinafter, the present invention will be described in more detail through the Examples. However, the following Examples are only to exemplify the present invention, but do not intend to limit the scope of the present invention.

SYNTHESIS EXAMPLES

Synthesis Example 1

Synthesis of Chemical Formula 1-d-1

Synthesis Example 2

Synthesis of Chemical Formula 1-d-2

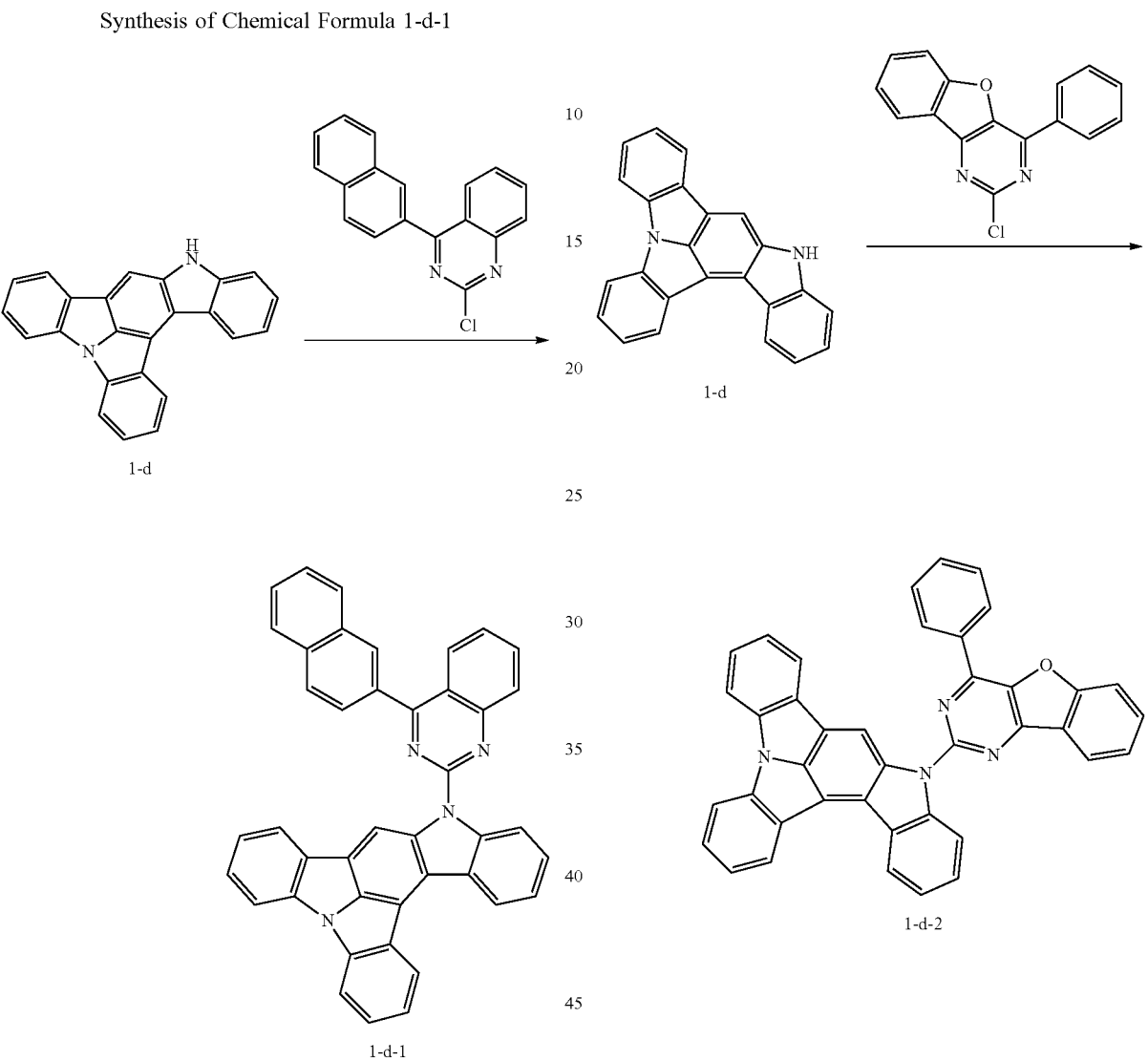

10.00 g (30.29 mmol, 1.0 eq) of Chemical Formula 1-d, 9.66 g (33.32 mmol, 1.1 eq) of 2-chloro-4-(naphthalen-2-yl)quinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.09 g (26.66 mmol, yield 82%) of Chemical Formula 1-d-1.

LC/MS: m/z=584 [(M+1)$^+$]

The 2-chloro-4-(naphthalen-2-yl)quinazoline was synthesized through a Suzuki coupling reaction with naphthalene-2-ylboronic acid by using 2,4-dichloroquinazoline as a starting material.

10.00 g (30.29 mmol, 1.0 eq) of Chemical Formula 1-d, 9.35 g (33.32 mmol, 1.1 eq) of 2-chloro-4-phenylbenzofuro[3,2-d]pyrimidine, 19.29 g (90.88 mmol, 3 eq) of $K_3PO_4$, and 0.07 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.05 g (22.71 mmol, yield 75%) of Chemical Formula 1-d-2.

LC/MS: m/z=574 [(M+1)$^+$]

The 2-chloro-4-phenylbenzofuro[3,2-d]pyrimidine was synthesized through a Suzuki coupling reaction with phenyl boronic acid by using 2,4-dichlorobenzofuro[3,2-d]pyrimidine as a starting material.

Synthesis Example 3

Synthesis of Chemical Formula 1-d-3

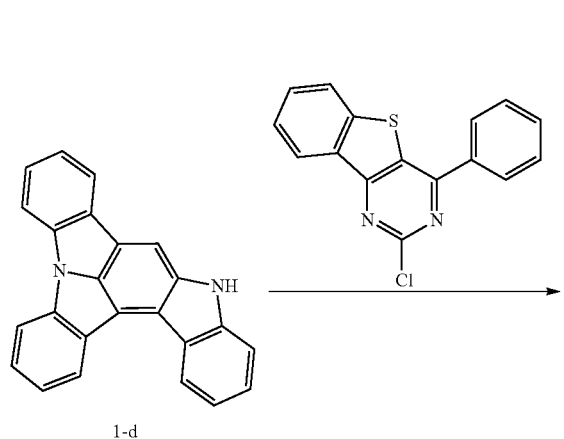

Synthesis Example 4

Synthesis of Chemical Formula 1-d-4

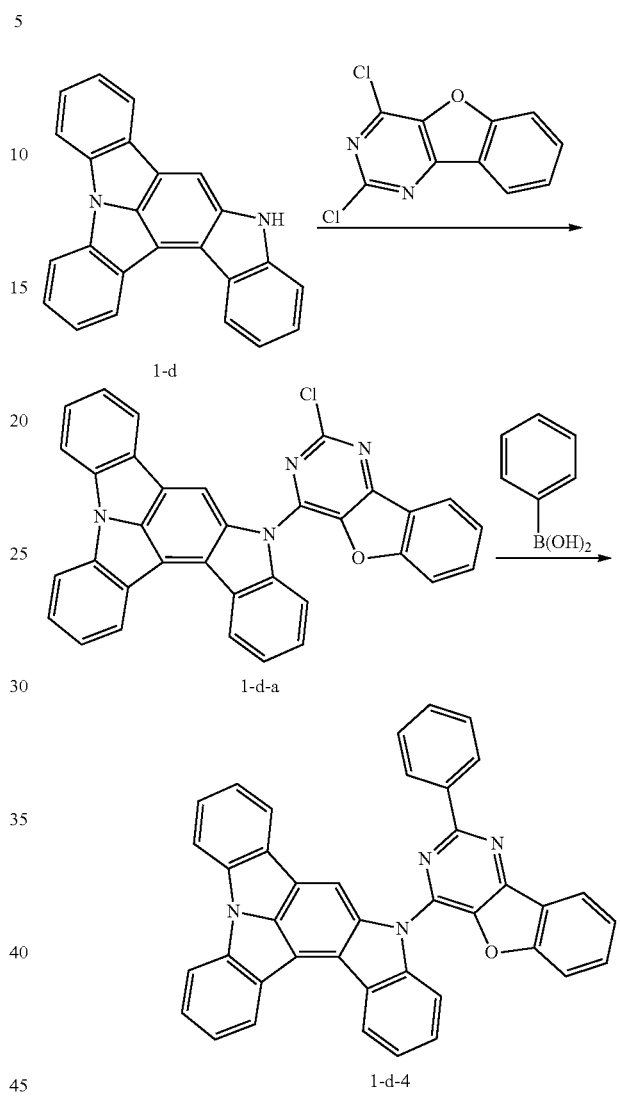

10.00 g (30.29 mmol, 1.0 eq) of Chemical Formula 1-d, 9.88 g (33.32 mmol, 1.1 eq) of 2-chloro-4-phenylbenzo[4,5]thieno[3,2-d]pyrimidine, 19.29 g (90.88 mmol, 3 eq) of $K_3PO_4$, and 0.07 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.77 g (23.32 mmol, yield 77%) of Chemical Formula 1-d-3.

LC/MS:m/z=590 [(M+1)$^+$]

The 2-chloro-4-phenylbenzo[4,5]thieno[3,2-d]pyrimidine was synthesized through a Suzuki coupling reaction with phenyl boronic acid by using 2,4-dichlorobenzothieno[3,2-d]pyrimidine as a starting material.

10.00 g (30.29 mmol, 1.0 eq) of Chemical Formula 1-d, 7.24 g (30.29 mmol, 1.0 eq) of 2,4-dichlorobenzofuro[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.72 g (25.75 mmol, yield 85%) of Chemical Formula 1-d-a.

LC/MS:m/z=532 [(M+1)$^+$]

13.72 g (25.75 mmol, 1.0 eq) of Chemical Formula 1-d-a, 3.76 g (30.88 mmol, 1.2 eq) of phenyl boronic acid, 0.05 g (0.25 mmol, 0.01 eq) of $Pd(PPh_3)_4$, and 7.11 g (51.48 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 13.46 g (23.42 mmol, yield 91%) of Chemical Formula 1-d-4.[+]

LC/MS:m/z=574 [(M+1)[+]]

Synthesis Example 5

Synthesis of Chemical Formula 1-d-5

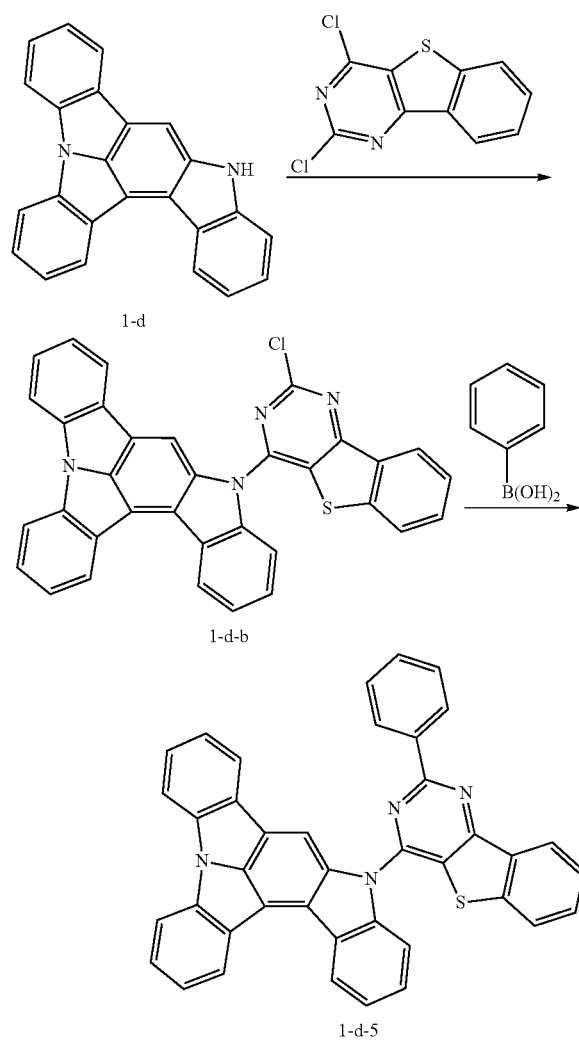

10.00 g (30.29 mmol, 1.0 eq) of Chemical Formula 1-d, 7.72 g (30.29 mmol, 1.0 eq) of dichlorobenzo[4,5]thieno[3,2-d]pyrimidine, and 6.43 g (30.29 mmol, 1.0 eq) of K$_3$PO$_4$ were dissolved in 80 ml of THF, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.80 g (25.14 mmol, yield 83%) of Chemical Formula 1-d-b.

LC/MS:m/z=548 [(M+1)[+]]

13.80 g (25.14 mmol, 1.0 eq) of Chemical Formula 1-d-b, 3.67 g (30.16 mmol, 1.2 eq) of phenyl boronic acid, 0.05 g (0.25 mmol, 0.01 eq) of Pd(PPh$_3$)$_4$, and 6.94 g (50.26 mmol, 2.0 eq) of K$_2$CO$_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 13.51 g (22.87 mmol, yield 88%) of Chemical Formula 1-d-5.

LC/MS:m/z=590 [(M+1)[+]]

Synthesis Example 6

Synthesis of Chemical Formula 1-d-6

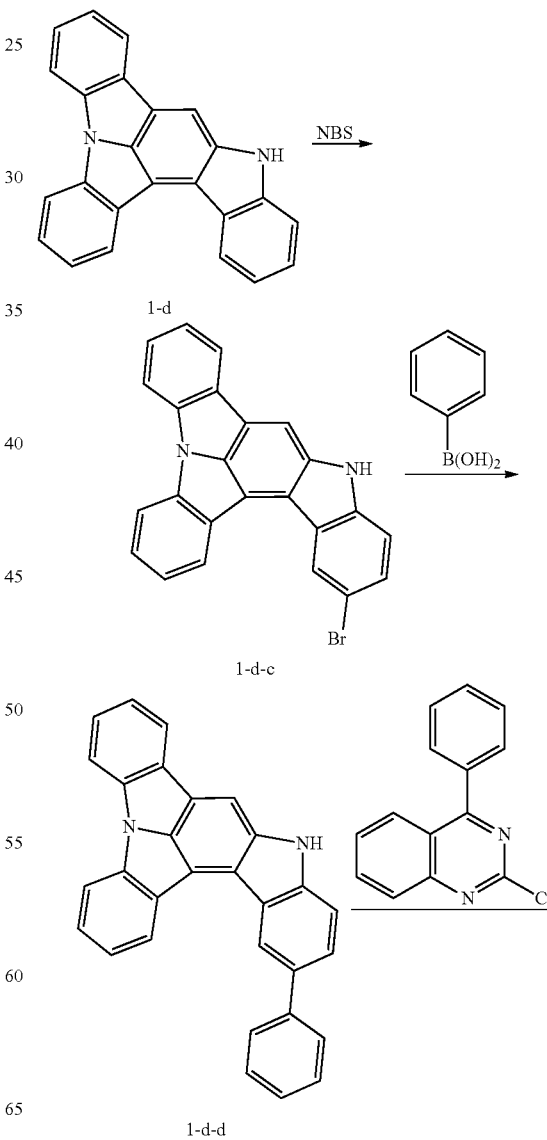

Synthesis Example 7

Synthesis of Chemical Formula 1-d-7

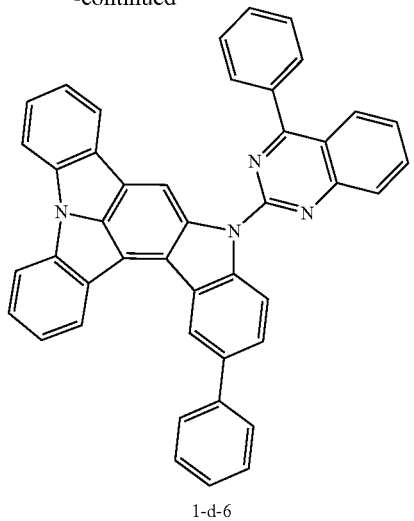

1-d-6

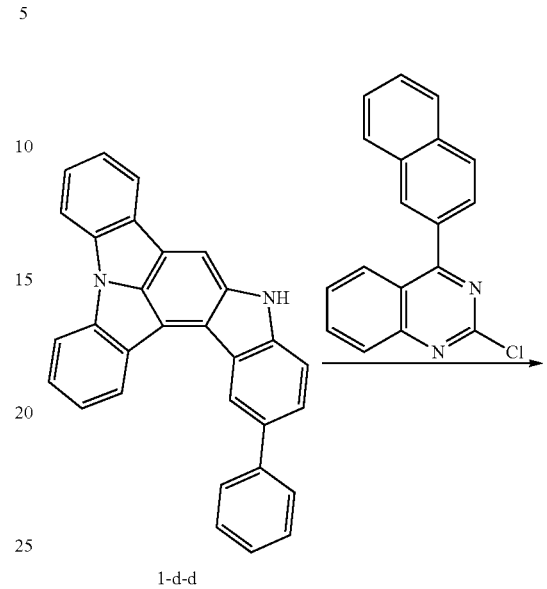

1-d-d

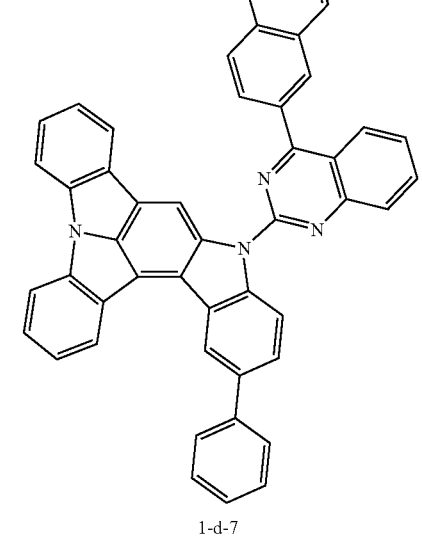

1-d-7

While 50.00 g (151.34 mmol, 1.0 eq) of Chemical Formula 1-d was dissolved in 700 ml of DMF, 26.93 g (151.34 mmol, 1.0 eq) of NBS was slowly added dropwise thereto. After the reaction was terminated, the reaction product was poured into 3 L of water and crystals were dropped thereto to filter the resulting product. The filtered product was completely dissolved in ethyl acetate, washed with water, and again placed under reduced pressure to remove about half of the amount of the solvent, and recrystallization was performed while adding ethanol thereto to obtain 52.64 g (128.64 mmol, yield 85%) of Chemical Formula 1-d-c.

LC/MS:m/z=408 [(M+1)$^+$]

52.64 g (128.64 mmol, 1.0 eq) of Chemical Formula 1-d-c, 18.82 g (154.33 mmol, 1.2 eq) of phenyl boronic acid, 0.27 g (1.28 mmol, 0.01 eq) of Pd(PPh$_3$)$_4$, and 35.54 g (257.22 mmol, 2.0 eq) of K$_2$CO$_3$ were dissolved in 150 ml of water and the resulting solution was added thereto, and the resulting mixture was dissolved in 300 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 47.57 g (117.03 mmol, yield 91%) of Chemical Formula 1-d.

LC/MS:m/z=406 [(M+1)$^+$]

10.00 g (24.60 mmol, 1.0 eq) of Chemical Formula 1-d-d, 7.59 g (27.06 mmol, 1.1 eq) of 2-chloro-4-quinazoline, 17.64 g (17.64 mmol, 3 eq) of K$_3$PO$_4$, and 0.06 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 11.26 g (18.45 mmol, yield 75%) of Chemical Formula 1-d-6.

LC/MS:m/z=610 [(M+1)$^+$]

10.00 g (24.60 mmol, 1.0 eq) of Chemical Formula 1-d-d, 7.86 g (27.06 mmol, 1.1 eq) of 2-chloro-4-(naphthalen-2-yl)quinazoline, 17.64 g (17.64 mmol, 3 eq) of K$_3$PO$_4$, and 0.06 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 12.51 g (18.94 mmol, yield 77%) of Chemical Formula 1-d-10.

LC/MS:m/z=660 [(M+1)$^+$]

Synthesis Example 8

Synthesis of Chemical Formula 1-d-8

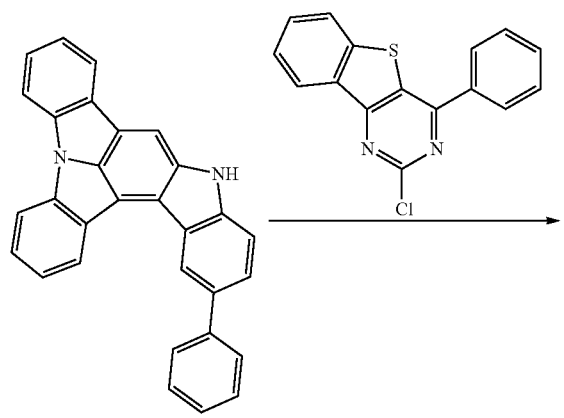

1-d-d

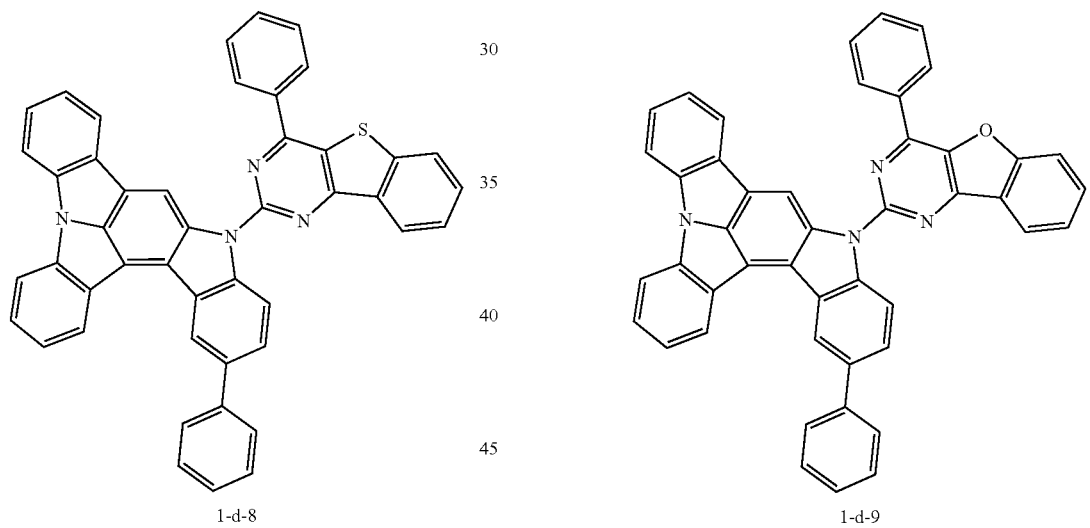

1-d-8

10.00 g (24.60 mmol, 1.0 eq) of Chemical Formula 1-d-d, 8.03 g (27.06 mmol, 1.1 eq) of 2-chloro-4-phenylbenzo[4,5]thieno[3,2-d]pyrimidine, 17.64 g (73.80 mmol, 3 eq) of $K_3PO_4$, and 0.06 g (0.12 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.81 g (17.71 mmol, yield 72%) of Chemical Formula 1-d-8.

LC/MS:m/z=666 [(M+1)$^+$]

Synthesis Example 9

Synthesis of Chemical Formula 1-d-9

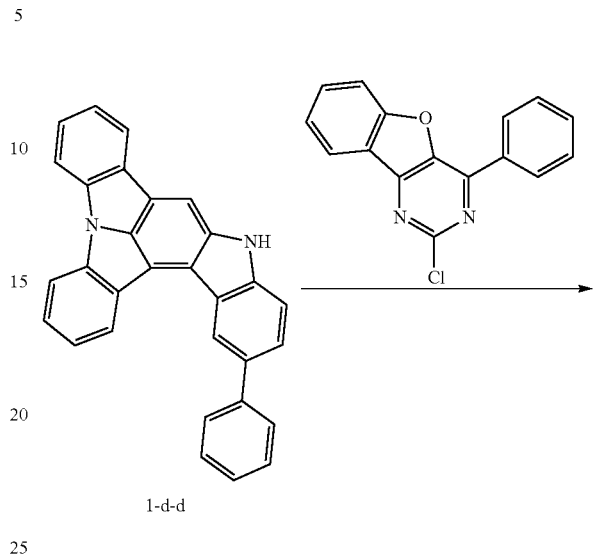

1-d-d 1-d-9

10.00 g (24.60 mmol, 1.0 eq) of Chemical Formula 1-d-d, 7.59 g (27.06 mmol, 1.1 eq) of 2-chloro-4-phenylbenzofuro[3,2-d]pyrimidine, 17.64 g (73.80 mmol, 3 eq) of $K_3PO_4$, and 0.06 g (0.12 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.01 g (18.45 mmol, yield 75%) of Chemical Formula 1-d-9.

LC/MS:m/z=650 [(M+1)$^+$]

Synthesis Example 10

Synthesis of Chemical Formula 2-d-1

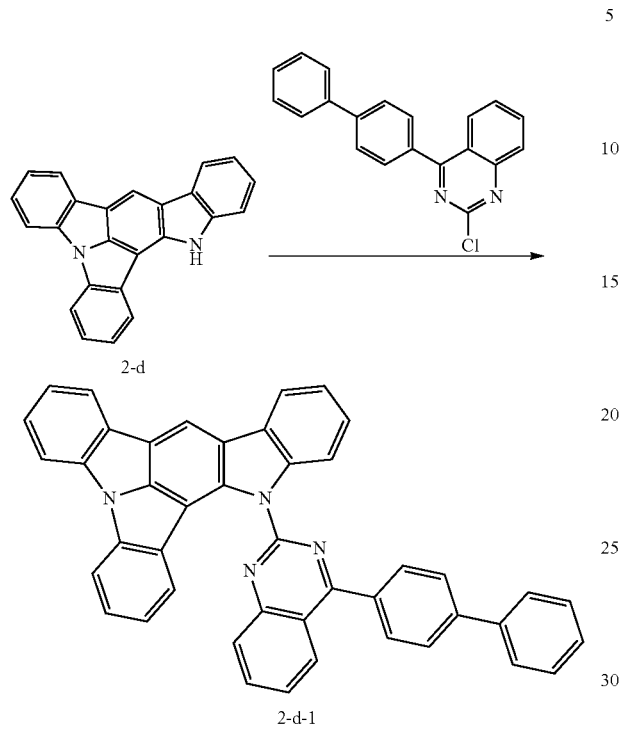

10.00 g (30.29 mmol, 1.0 eq) of Chemical Formula 2-d, 10.53 g (33.32 mmol, 1.1 eq) of 4-([1,1'-biphenyl]-4-yl)-2-chloroquinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 14.88 g (24.23 mmol, yield 80%) of Chemical Formula 2-d-1. 1H NMR spectrum of the compound of Chemical Formula 2-d-1 is illustrated in FIG. 7.

LC/MS:m/z=610 [(M+1)$^+$]

Synthesis Example 11

Synthesis of Chemical Formula 2-d-2

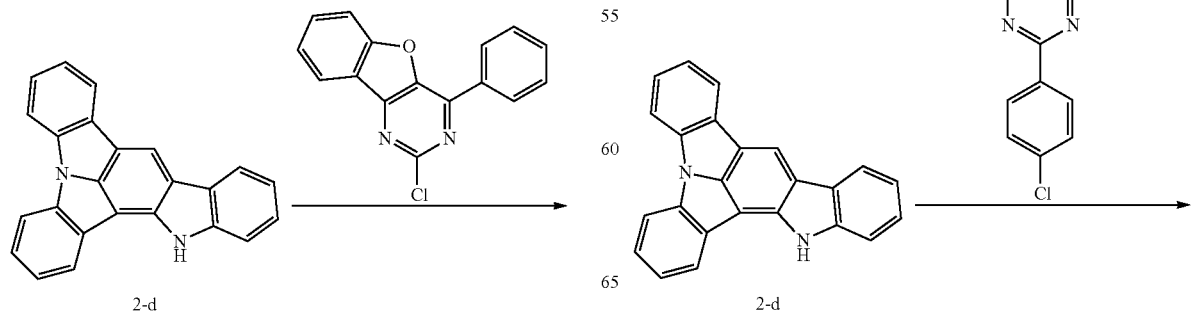

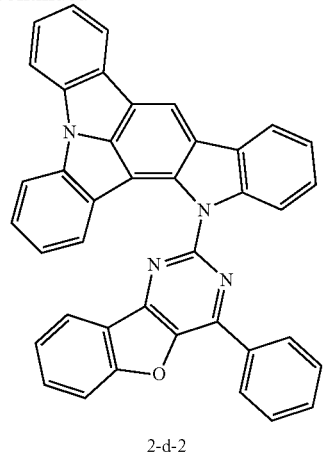

10.00 g (30.29 mmol, 1.0 eq) of Chemical Formula 2-d, 9.35 g (33.32 mmol, 1.1 eq) of 2-chloro-4-phenylbenzofuro[3,2-d]pyrimidine, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.92 g (24.23 mmol, yield 80%) of Chemical Formula 2-d-2.

LC/MS:m/z=574 [(M+1)$^+$]

Synthesis Example 12

Synthesis of Chemical Formula 2-d-3

-continued

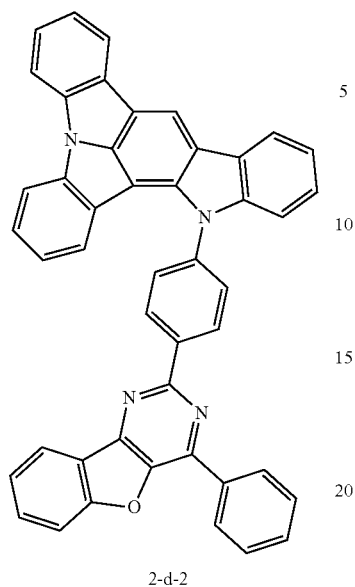

2-d-2

10.00 g (30.29 mmol, 1.0 eq) of Chemical Formula 2-d, 11.88 g (33.32 mmol, 1.1 eq) of 2-(4-chlorophenyl)-4-phenylbenzofuro[3,2-d]pyrimidine, 8.73 g (90.87 mmol, 3 eq) of sodium tert-butoxide, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 15.17 g (23.32 mmol, yield 77%) of Chemical Formula 2-d-3.

LC/MS:m/z=650 [(M+1)$^+$]

Synthesis Example 13

Synthesis of Chemical Formula 2-d-4

-continued

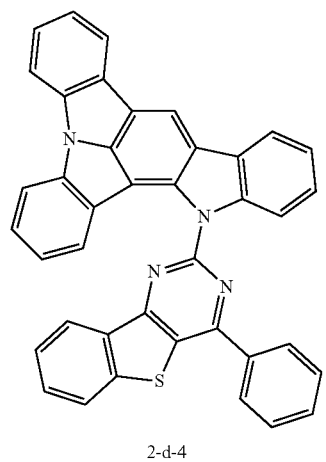

2-d-4

10.00 g (30.29 mmol, 1.0 eq) of Chemical Formula 2-d, 9.89 g (33.32 mmol, 1.1 eq) of 2-chloro-4-phenylbenzo[4,5]thieno[3,2-d]pyrimidine, 19.29 g (90.88 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 14.31 g (24.23 mmol, yield 80%) of Chemical Formula 2-d-4.

LC/MS:m/z=590 [(M+1)$^+$]

Synthesis Example 14

Synthesis of Chemical Formula 2-d-5

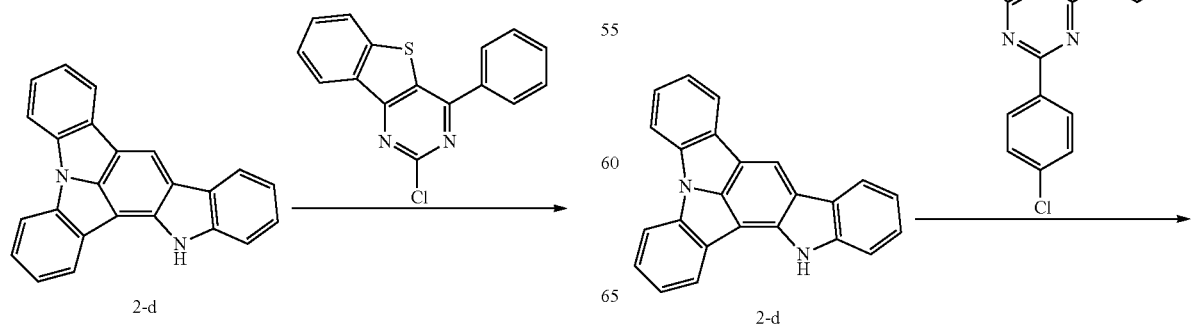

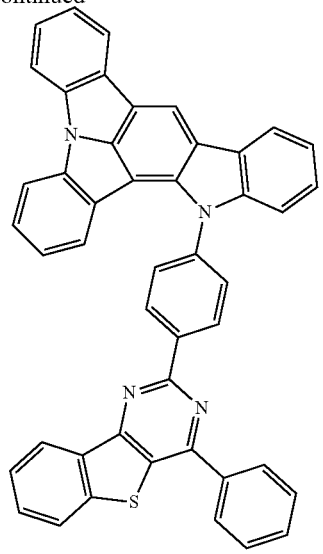

2-d-5

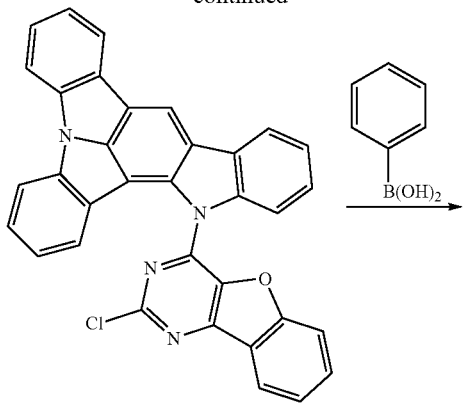

2-d-a

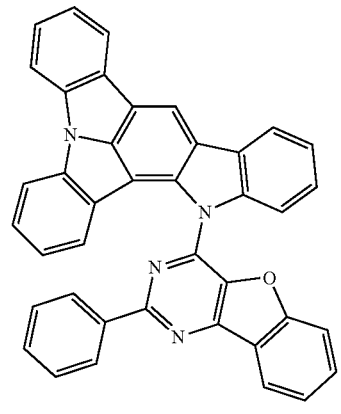

2-d-6

10.00 g (30.29 mmol, 1.0 eq) of Chemical Formula 2-d, 12.42 g (33.32 mmol, 1.1 eq) of 2-(4-chlorophenyl)-4-phenylbenzo[4,5]thieno[3,2-d]pyrimidine, 8.73 g (90.87 mmol, 3 eq) of sodium tert-butoxide, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 14.95 g (22.41 mmol, yield 74%) of Chemical Formula 2-d-5.

LC/MS:m/z=666 [(M+1)$^+$]

Synthesis Example 15

Synthesis of Chemical Formula 2-d-6

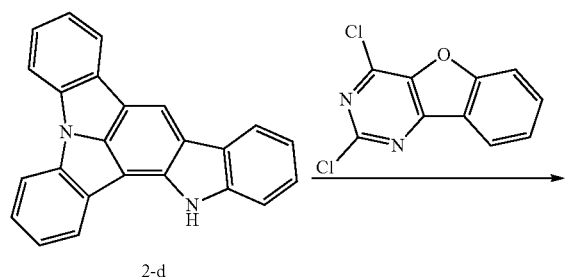

2-d 10.00 g (30.29 mmol, 1.0 eq) of Chemical Formula 2-d, 7.24 g (30.29 mmol, 1.0 eq) of 2,4-dichlorobenzofuro[3,2-d]pyrimidine, and 6.43 g (30.29 mmol, 1.0 eq) of K$_3$PO$_4$ were dissolved in 80 ml of THF, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 14.31 g (26.84 mmol, yield 80%) of Chemical Formula 2-d-a.

LC/MS:m/z=532 [(M+1)$^+$]

14.31 g (26.84 mmol, 1.0 eq) of Chemical Formula 2-d-a, 3.92 g (32.21 mmol, 1.2 eq) of phenyl boronic acid, 0.05 g (0.25 mmol, 0.01 eq) of Pd(PPh$_3$)$_4$, and 7.42 g (51.48 mmol, 2.0 eq) of K$_2$CO$_3$ were dissolved in 30 ml of water and the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 12.80 g (22.28 mmol, yield 83%) of Chemical Formula 2-d-6.

LC/MS:m/z=574 [(M+1)$^+$]

Synthesis Example 16

Synthesis of Chemical Formula 2-d-7

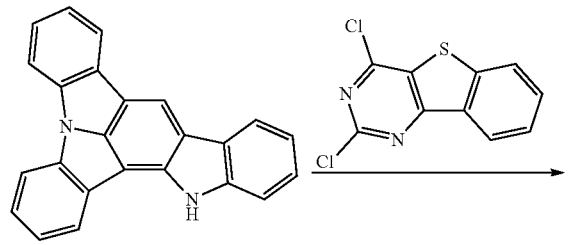

2-d

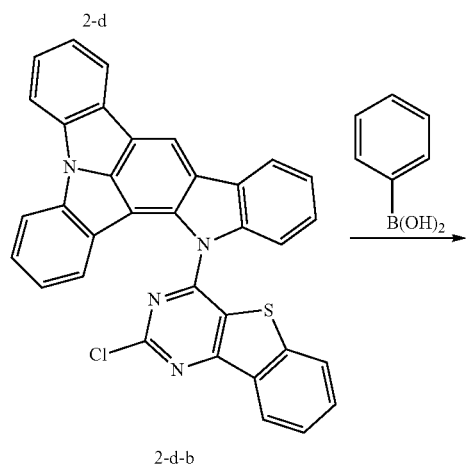

2-d-b

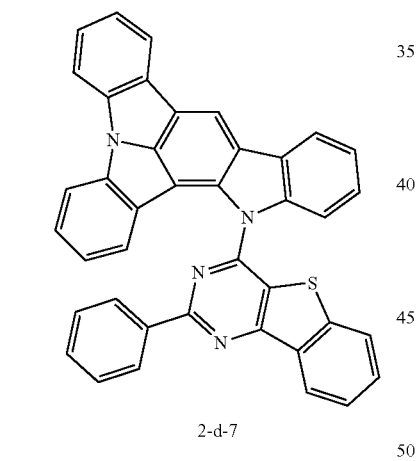

2-d-7

10.00 g (30.29 mmol, 1.0 eq) of Chemical Formula 2-d, 7.73 g (30.29 mmol, 1.0 eq) of 2,4-dichlorobenzo[4,5]thieno[3,2-d]pyrimidine, and 6.43 g (30.29 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.63 g (24.83 mmol, yield 82%) of Chemical Formula 2-d-b.

LC/MS:m/z=578 [(M+1)$^+$]

13.63 g (24.83 mmol, 1.0 eq) of Chemical Formula 2-d-b, 3.81 g (31.27 mmol, 1.2 eq) of phenyl boronic acid, 0.05 g (0.25 mmol, 0.01 eq) of Pd(PPh$_3$)$_4$, and 7.20 g (52.12 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 12.47 g (21.11 mmol, yield 81%) of Chemical Formula 2-d-7.

LC/MS:m/z=590 [(M+1)$^+$]

Synthesis Example 17

Synthesis of Chemical Formula 2-d-8

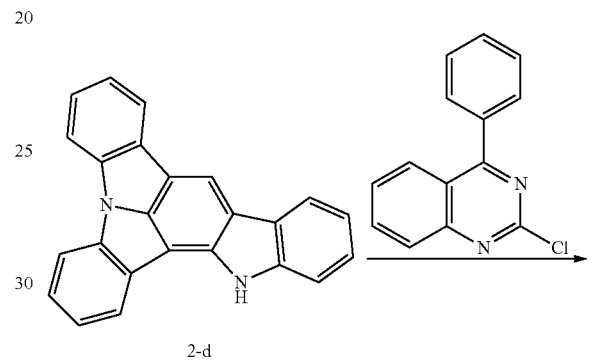

2-d

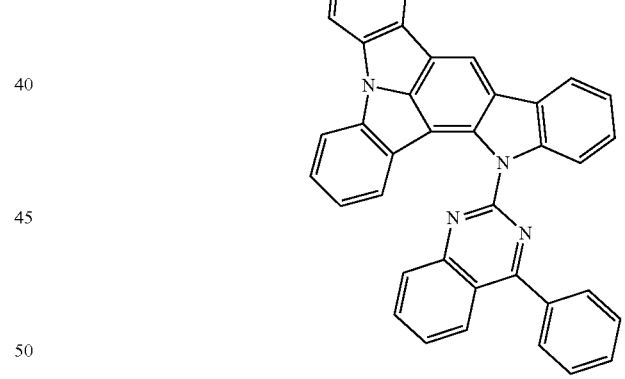

2-d 10.00 g (30.29 mmol, 1.0 eq) of Chemical Formula 2-d, 8.02 g (33.32 mmol, 1.1 eq) of 2-chloro-4-phenylquinazoline, 19.29 g (90.88 mmol, 3 eq) of $K_3PO_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.46 g (23.32 mmol, yield 77%) of Chemical Formula 2-d-8.

LC/MS:m/z=534 [(M+1)$^+$]

Synthesis Example 18

Synthesis of Chemical Formula 2-d-9

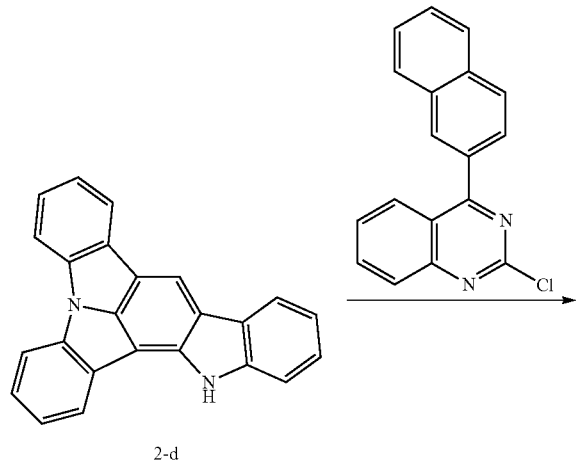

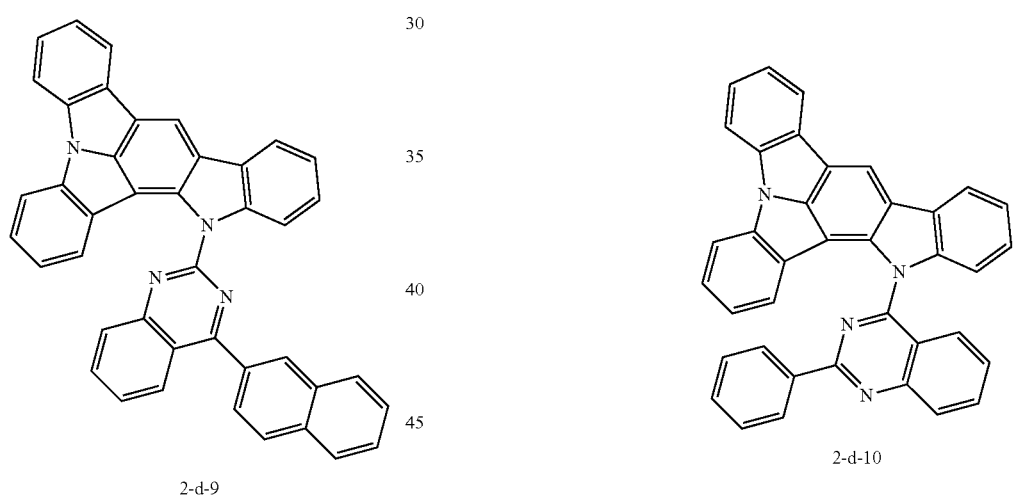

2-d-9

10.00 g (30.29 mmol, 1.0 eq) of Chemical Formula 2-d, 9.68 g (33.32 mmol, 1.1 eq) of 2-chloro-4-(naphthalen-2-yl)quinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.28 g (22.71 mmol, yield 75%) of Chemical Formula 2-d-9.

LC/MS:m/z=584 [(M+1)$^+$]

Synthesis Example 19

Synthesis of Chemical Formula 2-d-10

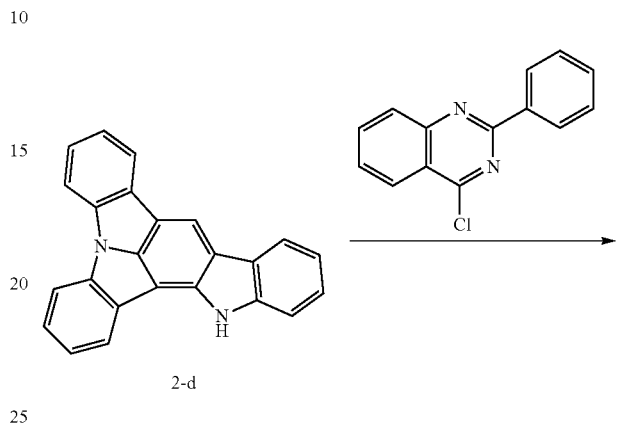

2-d-10

10.00 g (30.29 mmol, 1.0 eq) of Chemical Formula 2-d, 8.02 g (33.32 mmol, 1.1 eq) of 4-chloro-2-phenylquinazoline, 19.29 g (90.88 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.66 g (21.81 mmol, yield 72%) of Chemical Formula 2-d-13.

LC/MS:m/z=534 [(M+1)$^+$]

Synthesis Example 20

Synthesis of Chemical Formula 2-d-11

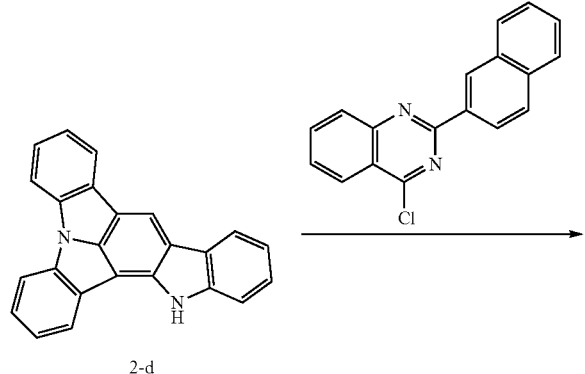
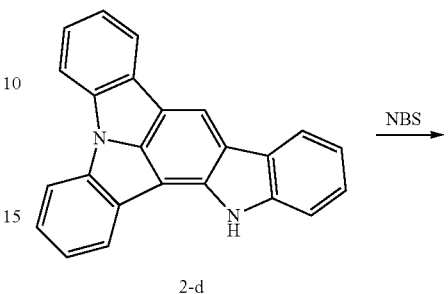

10.00 g (30.29 mmol, 1.0 eq) of Chemical Formula 2-d, 9.68 g (33.32 mmol, 1.1 eq) of 4-chloro-2-(naphthalen-2-yl)quinazoline, 19.29 g (90.88 mmol, 3 eq) of $K_3PO_4$, and 0.08 g (0.15 mmol, 0.005 eq) of $Pd(t-Bu_3P)_4$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.57 g (21.50 mmol, yield 71%) of Chemical Formula 2-d-11.

LC/MS:m/z=584 [(M+1)$^+$]

Synthesis Example 21

Synthesis of Chemical Formula 2-d-12

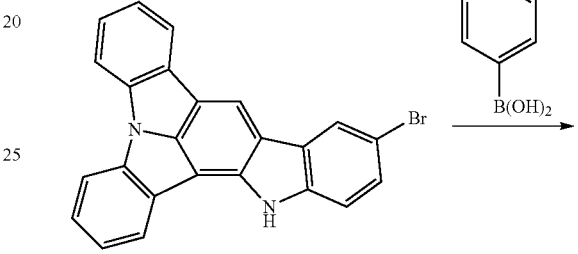
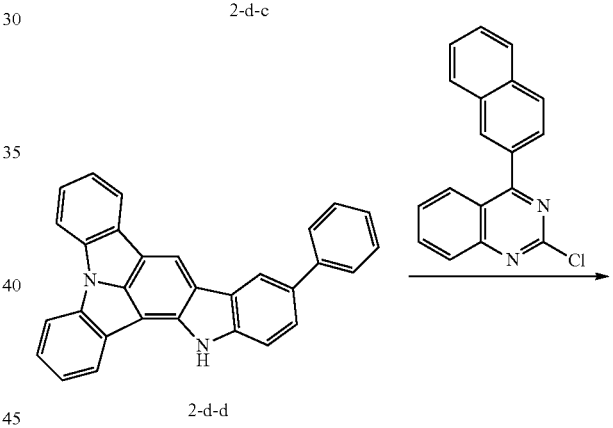
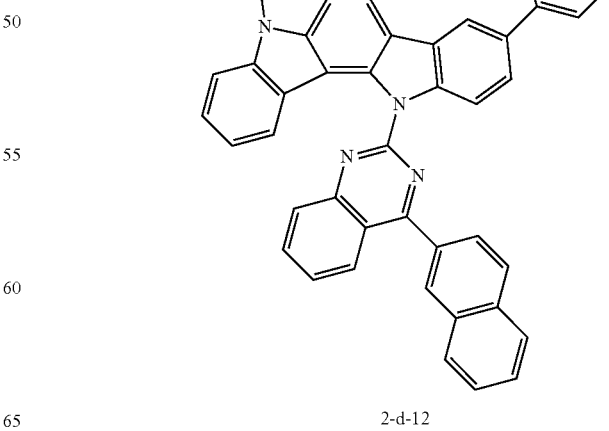

While 50.00 g (151.34 mmol, 1.0 eq) of Chemical Formula 2-d was dissolved in 700 ml of DMF, 26.93 g (151.34 mmol, 1.0 eq) of NBS was slowly added dropwise thereto. After the reaction, the reaction product was poured into 3 L of water and crystals were dropped thereto to filter the resulting product. The filtered product was completely dissolved in ethyl acetate, washed with water, and again placed under reduced pressure to remove about half of the amount of the solvent, and recrystallization was performed while adding ethanol thereto to obtain 53.88 g (131.66 mmol, yield 87%) of Chemical Formula 2-d-c. 1H NMR spectrum of the compound of Chemical Formula 2-d-c is illustrated in FIG. 6.

LC/MS:m/z=408 [(M+1)$^+$]

53.88 g (131.66 mmol, 1.0 eq) of Chemical Formula 2-d-c, 19.26 g (154.33 mmol, 1.2 eq) of phenyl boronic acid, 0.28 g (1.28 mmol, 0.01 eq) of Pd(PPh$_3$)$_4$, and 36.38 g (263.29 mmol, 2.0 eq) of K$_2$CO$_3$ were dissolved in 150 ml of water and the resulting solution was added thereto, and the resulting mixture was dissolved in 300 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 48.69 g (119.79 mmol, yield 90%) of Chemical Formula 2-d-d.

LC/MS:m/z=406 [(M+1)$^+$]

10.00 g (24.60 mmol, 1.0 eq) of Chemical Formula 2-d-d, 7.86 g (27.06 mmol, 1.1 eq) of 2-chloro-4-(naphthalen-2-yl)quinazoline, 17.64 g (17.64 mmol, 3 eq) of K$_3$PO$_4$, and 0.06 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 10.81 g (17.71 mmol, yield 72%) of Chemical Formula 2-d-12.

LC/MS:m/z=660 [(M+1)$^+$]

Synthesis Example 22

Synthesis of Chemical Formula 2-d-13

10.00 g (24.60 mmol, 1.0 eq) of Chemical Formula 2-d-d, 6.51 g (27.06 mmol, 1.1 eq) of 2-chloro-4-phenylquinazoline, 15.66 g (73.80 mmol, 3 eq) of K$_3$PO$_4$, and 0.08 g (0.15 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 10.66 g (17.46 mmol, yield 71%) of Chemical Formula 2-d-13.

LC/MS:m/z=610 [(M+1)$^+$]

Synthesis Example 23

Synthesis of Chemical Formula 2-d-14

849
-continued

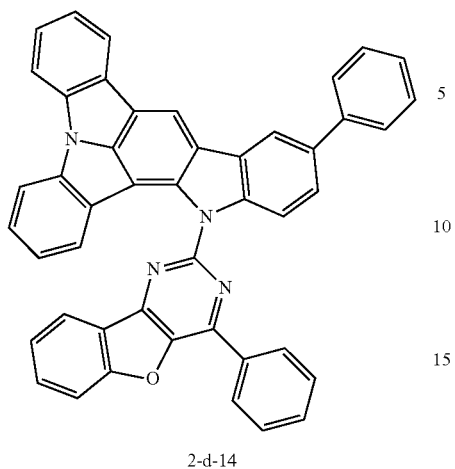

2-d-14

850
-continued

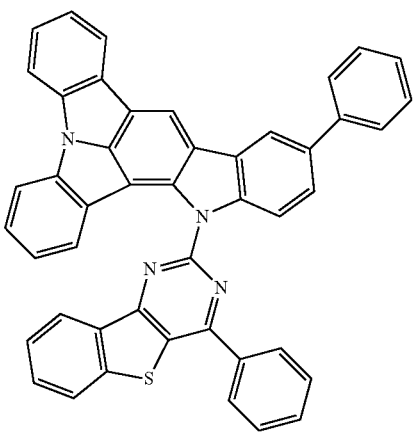

2-d-15

10.00 g (24.60 mmol, 1.0 eq) of Chemical Formula 2-d-d, 7.59 g (27.06 mmol, 1.1 eq) of 2-chloro-4-phenylbenzofuro[3,2-d]pyrimidine, 15.66 g (73.80 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.00 g (18.45 mmol, yield 75%) of Chemical Formula 2-d-14.

LC/MS:m/z=650 [(M+1)$^+$]

Synthesis Example 24

Synthesis of Chemical Formula 2-d-15

10.00 g (24.60 mmol, 1.0 eq) of Chemical Formula 2-d-d, 8.03 g (27.06 mmol, 1.1 eq) of 2-chloro-4-phenylbenzo[4,5]thieno[3,2-d]pyrimidine, 15.66 g (73.80 mmol, 3 eq) of $K_3PO_4$, and 0.08 g (0.15 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.63 g (18.94 mmol, yield 77%) of Chemical Formula 2-d-15.

LC/MS:m/z=666 [(M+1)$^+$]

Synthesis Example 25

Synthesis of Chemical Formula 2-d-16

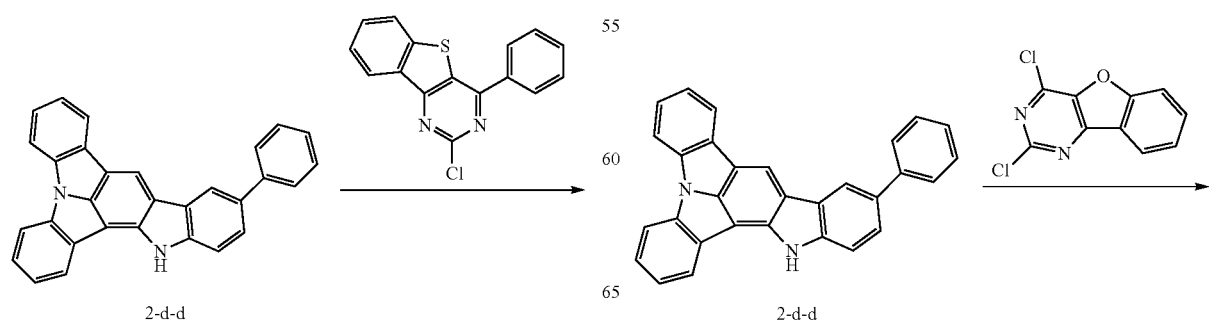

-continued

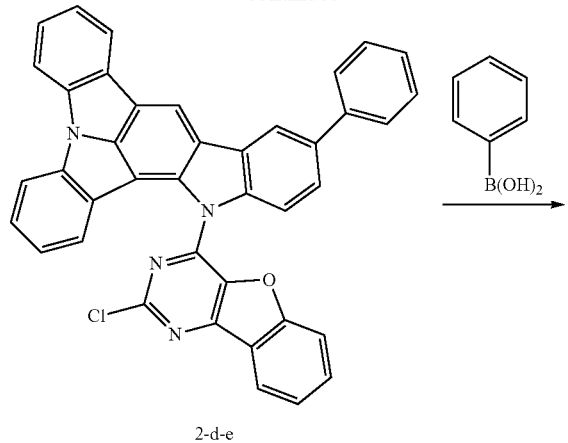

2-d-e

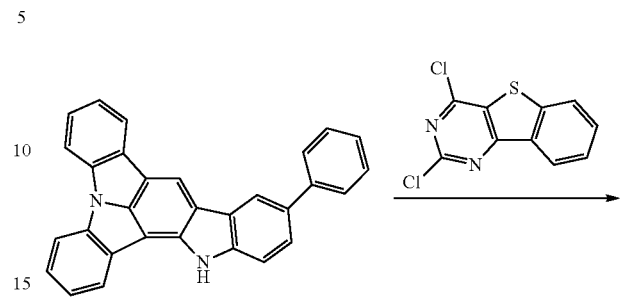

2-d-d

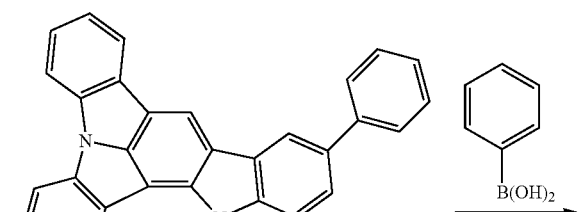

2-d-f 2-d-16

2-d-17

10.00 g (24.60 mmol, 1.0 eq) of Chemical Formula 2-d-d, 5.88 g (24.60 mmol, 1.0 eq) of 2,4-dichlorobenzofuro[3,2-d]pyrimidine, and 5.22 g (24.60 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 12.28 g (20.17 mmol, yield 82%) of Chemical Formula 2-d-e.

LC/MS:m/z=608 [(M+1)$^+$]

12.28 g (20.17 mmol, 1.0 eq) of Chemical Formula 2-d-e, 3.43 g (28.19 mmol, 1.2 eq) of phenyl boronic acid, 0.05 g (0.23 mmol, 0.01 eq) of Pd(PPh$_3$)$_4$, and 6.49 g (46.98 mmol, 2.0 eq) of $K_2CO_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in $CHCl_3$, washed with water, and again placed under reduced pressure to remove the solvent, and the resulting product was subjected to column chromatography to obtain 12.38 g (19.03 mmol, yield 81%) of Chemical Formula 2-d-16.

LC/MS:m/z=650 [(M+1)$^+$]

Synthesis Example 26

Synthesis of Chemical Formula 2-d-17

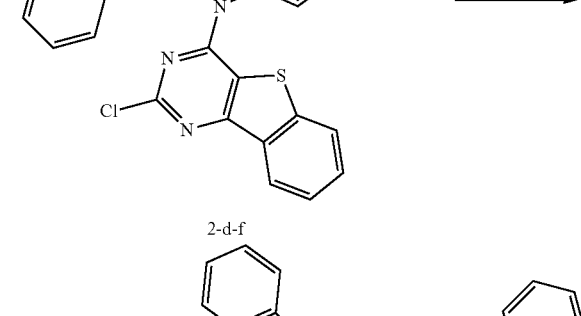

10.00 g (24.60 mmol, 1.0 eq) of Chemical Formula 2-d-d, 6.27 g (24.60 mmol, 1.0 eq) of 2,4-dichlorobenzofuro[3,2-d]pyrimidine, and 5.22 g (24.60 mmol, 1.0 eq) of $K_3PO_4$ were dissolved in 80 ml of THF, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 13.07 g (20.91 mmol, yield 85%) of Chemical Formula 2-d-f.

LC/MS:m/z=624 [(M+1)$^+$]

13.07 g (20.91 mmol, 1.0 eq) of Chemical Formula 2-d-f, 3.35 g (27.46 mmol, 1.2 eq) of phenyl boronic acid, 0.05 g (0.23 mmol, 0.01 eq) of Pd(PPh$_3$)$_4$, and 6.33 g (45.78 mmol, 2.0 eq) of K$_2$CO$_3$ were dissolved in 30 ml of water, the resulting solution was added thereto, and the resulting mixture was dissolved in 70 ml of dioxane and stirred under reflux. When the reaction was terminated, the organic layer was separated and then placed under reduced pressure to remove the solvent. Thereafter, the product was completely dissolved in CHCl$_3$, washed with water, and again placed under reduced pressure to remove the solvent, and the resulting product was subjected to column chromatography to obtain 12.36 g (18.54 mmol, yield 81%) of Chemical Formula 2-d-17.

LC/MS:m/z=650 [(M+1)$^+$]

Synthesis Example 27

Synthesis of Chemical Formula 2-d-18

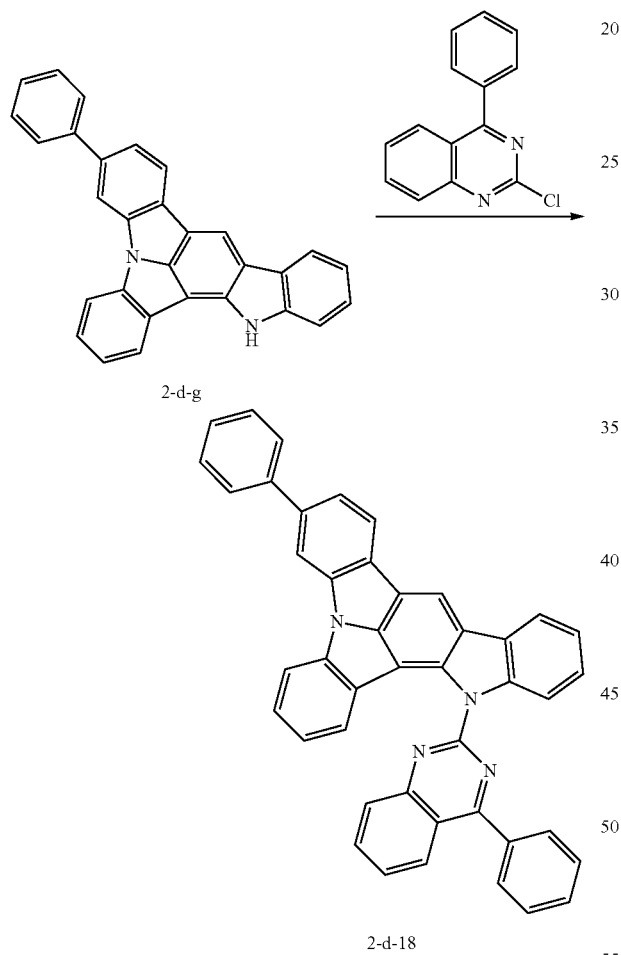

2-d-g 2-d-18

4-chloro-3-iodo-1,1'-biphenyl was used instead of 1-chloro-2-iodobenzene in the preparation of Chemical Formula 2-a to carry out the synthesis, thereby synthesizing Chemical Formula 2-d-g in the same manner as in the method of Chemical Formula 2-d.

LC/MS:m/z=406 [(M+1)$^+$]

10.00 g (24.60 mmol, 1.0 eq) of Chemical Formula 2-d-g, 6.51 g (27.06 mmol, 1.1 eq) of 2-chloro-4-phenylquinazoline, 15.66 g (73.80 mmol, 3 eq) of K$_3$PO$_4$, and 0.08 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 12.77 g (20.91 mmol, yield 85%) of Chemical Formula 2-d-18.

LC/MS:m/z=610 [(M+1)$^+$]

Synthesis Example 28

Synthesis of Chemical Formula 2-d-19

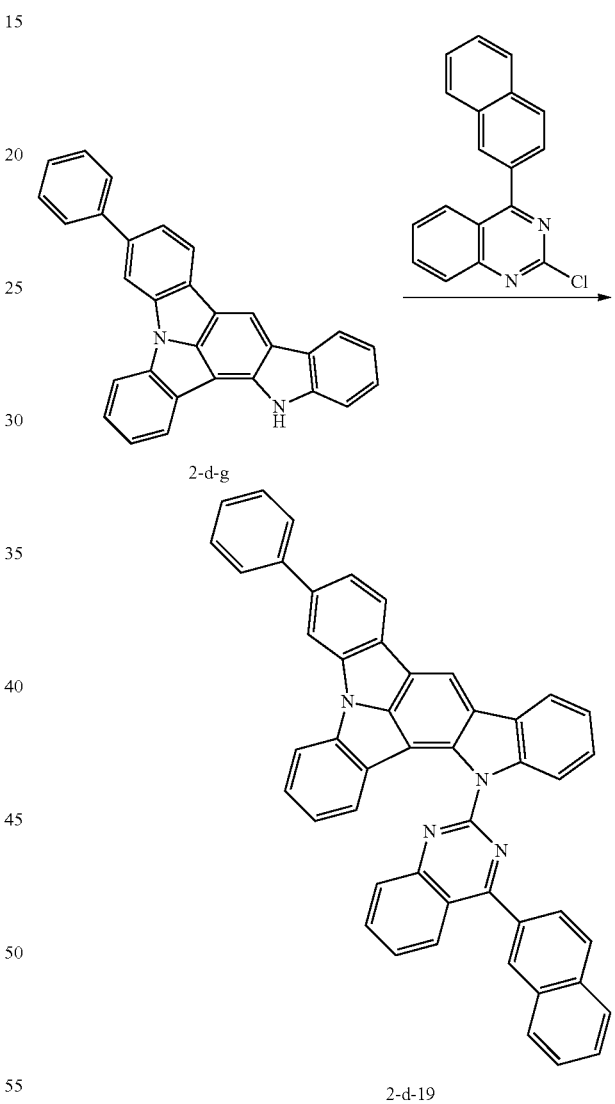

2-d-g 2-d-19

10.00 g (24.60 mmol, 1.0 eq) of Chemical Formula 2-d-g, 7.86 g (27.06 mmol, 1.1 eq) of 2-chloro-4-(naphthalen-2-yl)quinazoline, 15.66 g (73.80 mmol, 3 eq) of K$_3$PO$_4$, and 0.08 g (0.12 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected

Synthesis Example 29

Synthesis of Chemical Formula 6-d-1

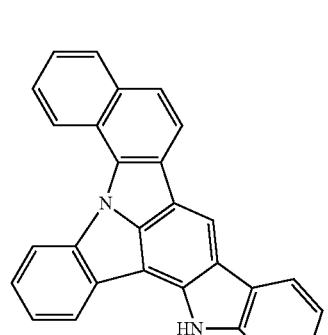 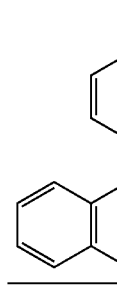

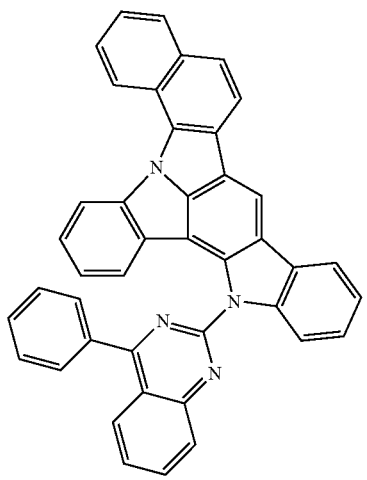

6-d-1

10.00 g (26.28 mmol, 1.0 eq) of Chemical Formula 6-d, 6.95 g (28.91 mmol, 1.1 eq) of 2-chloro-4-phenylquinazoline, 16.73 g (78.85 mmol, 3 eq) of K$_3$PO$_4$, and 0.07 g (0.13 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 11.98 g (20.50 mmol, yield 78%) of Chemical Formula 6-d-1.

LC/MS:m/z=584 [(M+1)$^+$]

to column chromatography to obtain 13.49 g (20.41 mmol, yield 83%) of Chemical Formula 2-d-22.

LC/MS:m/z=660 [(M+1)$^+$]

Synthesis Example 30

Synthesis of Chemical Formula 6-d-2

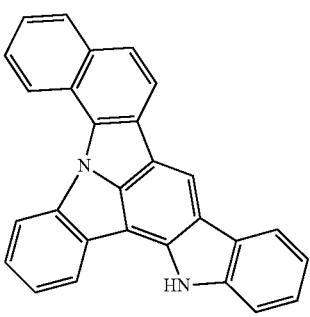 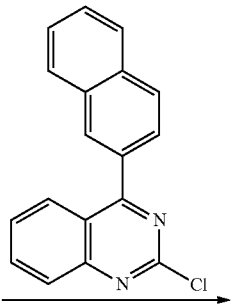

6-d

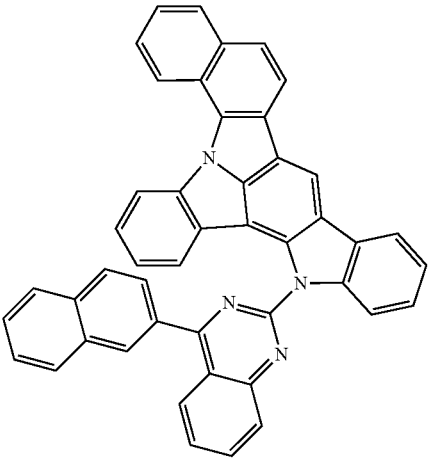

6-d-2

10.00 g (26.28 mmol, 1.0 eq) of Chemical Formula 6-d, 8.40 g (28.91 mmol, 1.1 eq) of 2-chloro-4-(naphthalen-2-yl)quinazoline, 16.73 g (78.85 mmol, 3 eq) of K$_3$PO$_4$, and 0.07 g (0.13 mmol, 0.005 eq) of Pd(t-Bu$_3$P)$_2$ were dissolved in 80 ml of xylene, and stirred under reflux. When the reaction was terminated, the resulting product was placed under reduced pressure to remove the solvent. Thereafter, the product was completely dissolved in CHCl$_3$, washed with water, and again placed under reduced pressure to remove the solvent, and the resulting product was subjected to column chromatography to obtain 13.18 g (20.76 mmol, yield 79%) of Chemical Formula 6-d-2.

LC/MS:m/z=634 [(M+1)$^+$]

Synthesis Example 31

Synthesis of Chemical Formula 6-d-3

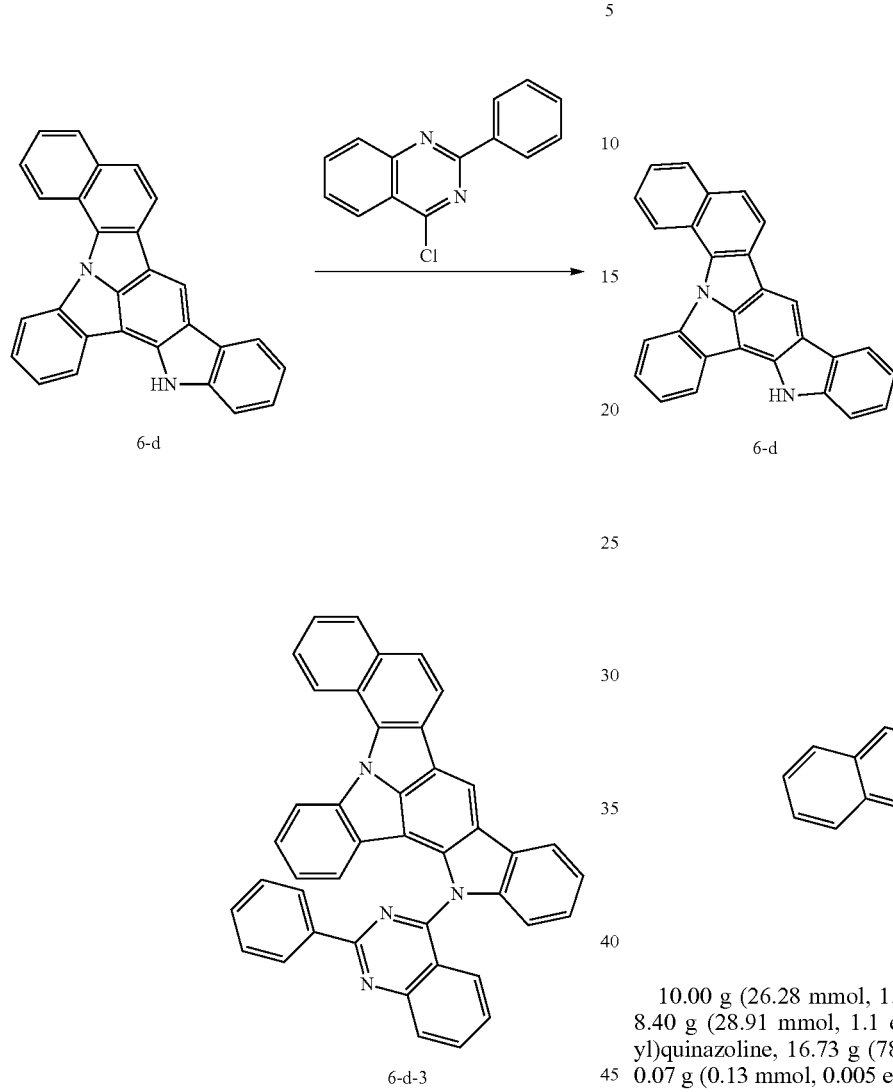

10.00 g (26.28 mmol, 1.0 eq) of Chemical Formula 6-d, 6.95 g (28.91 mmol, 1.1 eq) of 4-chloro-2-phenylquinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.37 g (19.45 mmol, yield 74%) of Chemical Formula 6-d-3.

LC/MS:m/z=584 [(M+1)$^+$]

Synthesis Example 32

Synthesis of Chemical Formula 6-d-4

10.00 g (26.28 mmol, 1.0 eq) of Chemical Formula 6-d, 8.40 g (28.91 mmol, 1.1 eq) of 4-chloro-2-(naphthalen-2-yl)quinazoline, 16.73 g (78.85 mmol, 3 eq) of $K_3PO_4$, and 0.07 g (0.13 mmol, 0.005 eq) of $Pd(t-Bu_3P)_2$ were dissolved in 80 ml of xylene, and stirred under reflux. When the reaction was terminated, the resulting product was placed under reduced pressure to remove the solvent. Thereafter, the product was completely dissolved in $CHCl_3$, washed with water, and again placed under reduced pressure to remove the solvent, and the resulting product was subjected to column chromatography to obtain 11.84 g (18.66 mmol, yield 71%) of Chemical Formula 6-d-4.

LC/MS:m/z=634 [(M+1)$^+$]

Experimental Example 1 to Experimental Example 12

The compounds prepared in the Synthesis Examples were subjected to high-purity sublimation purification by a typically known method, and then red organic light emitting devices were manufactured by the following method.

A glass substrate (Corning 7059 glass) thinly coated with indium tin oxide (ITO) to have a thickness of 1,000 Å was put into distilled water in which a dispersant was dissolved, and ultrasonically washed. A product manufactured by Fischer Co. was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

The substrate was mounted in a vacuum chamber, then the base pressure was maintained at $1 \times 10^{\times 6}$ torr, and then as the organic material, DNTPD (700 Å) was deposited as a hole injection layer on the ITO. α-NPB (300 Å) was deposited as a hole transporting layer thereon, and the compounds in the following Table 1, which had been synthesized in the above-described Synthesis Examples, were subjected to sublimation purification, and then used as a host (95 wt %), and as the dopant, Dp-7 (5 wt %) was co-deposited (300 Å) to deposit a light emitting layer. As a hole blocking layer, BCP (50 Å) was deposited thereon, and ET-1 and ET-2 were evaporated at a rate of 2:1 to deposit an electron transfer layer having a thickness of 300 Å on the light emitting layer. ET-2 (5 Å) as the electron injection layer and an Al negative electrode (1,000 Å) were deposited in this order to manufacture an OLED device.

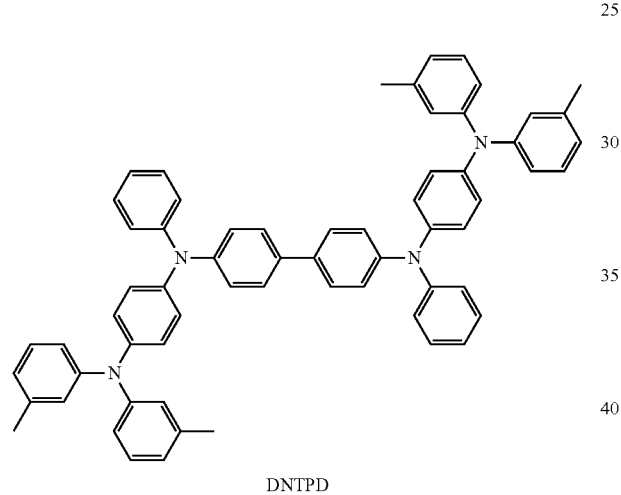

DNTPD

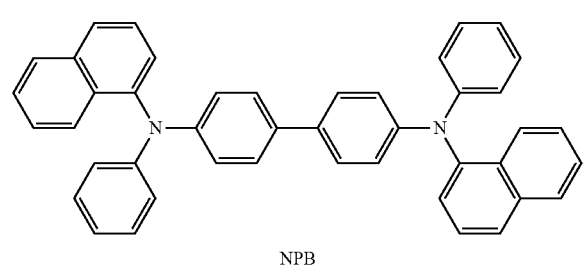

NPB

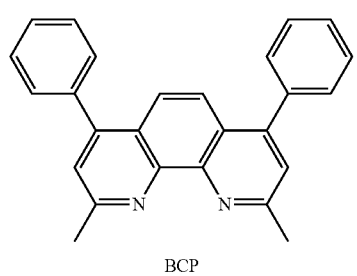

BCP

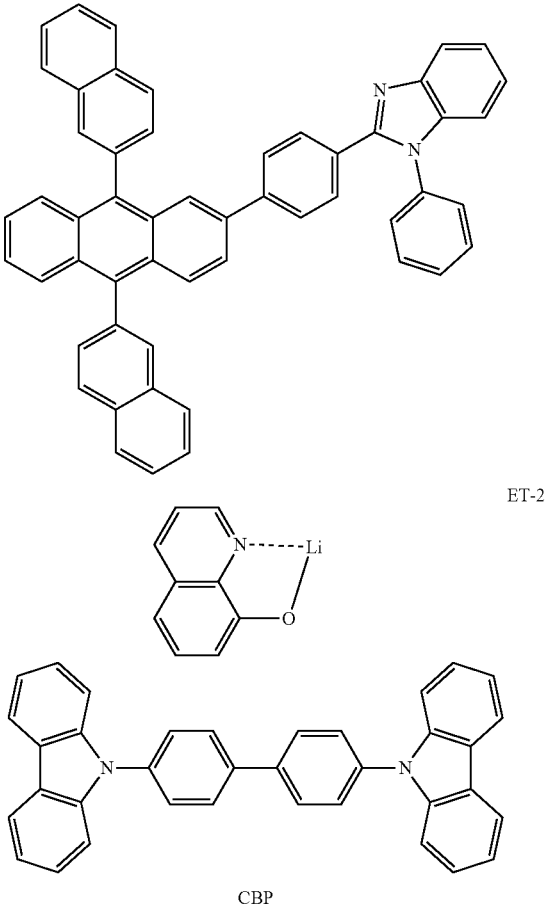

ET-1

ET-2

CBP

Comparative Example 1

The organic light emitting device in Comparative Example 1 was manufactured in the same manner as in Experimental Examples 1 to 12, except that CBP frequently used as a general phosphorescent host material was used instead of the compound of the present invention as the host of the light emitting layer in the structures of the organic light emitting devices in Experimental Examples 1 to 12.

The driving voltage, current efficiency, and service life of the organic light emitting devices manufactured according to the Experimental Examples 1 to 12 and Comparative Example 1 were measured, and the results are shown in the following Table 1.

TABLE 1

|  | Compound | Driving voltage (V) | Current efficiency (cd/A) | Service life (T95) | CIE x | CIE y |
| --- | --- | --- | --- | --- | --- | --- |
| Experimental Example 1 | 1-d-1 | 4.2 | 42.7 | 250 | 0.686 | 0.331 |
| Experimental Example 2 | 1-d-3 | 4.4 | 47.2 | 100 | 0.685 | 0.313 |
| Experimental Example 3 | 1-d-7 | 4.1 | 44.3 | 280 | 0.687 | 0.337 |
| Experimental Example 4 | 2-d-4 | 4.2 | 46.80 | 95 | 0.686 | 0.314 |

TABLE 1-continued

| Compound | Driving voltage (V) | Current efficiency (cd/A) | Service life (T95) | CIE x | CIE y |
|---|---|---|---|---|---|
| Experimental Example 5 | 2-d-8 | 3.8 | 50.8 | 390 | 0.688 | 0.313 |
| Experimental Example 6 | 2-d-9 | 3.9 | 52.3 | 390 | 0.678 | 0.322 |
| Experimental Example 7 | 2-d-11 | 3.7 | 47.0 | 110 | 0.686 | 0.314 |
| Experimental Example 8 | 2-d-12 | 4.0 | 57.5 | 410 | 0.688 | 0.312 |
| Experimental Example 9 | 2-d-13 | 4.1 | 52.2 | 405 | 0.684 | 0.346 |
| Experimental Example 10 | 2-d-15 | 4.3 | 51.6 | 105 | 0.682 | 0.318 |
| Experimental Example 11 | 6-d-1 | 3.5 | 42.0 | 320 | 0.686 | 0.312 |
| Experimental Example 12 | 6-d-4 | 3.6 | 46.6 | 120 | 0.688 | 0.312 |
| Comparative Example 1 | CBP | 6.1 | 20.7 | 57 | 0.675 | 0.330 |

As can be seen from the results in Table 1, it can be seen that the organic light emitting device using the compound of the present invention improves the light emitting efficiency while lowering the driving voltage, and contributes to an effect of increasing the service life. In general, a lower driving voltage and a higher efficiency than CBP used as a comparative host material were exhibited, and excellent results were exhibited even in terms of service life.

EXPLANATION OF REFERENCE NUMERALS AND SYMBOLS

1: Substrate
2: Positive electrode
3: Hole injection layer
4: Hole transporting layer
5: Light emitting layer
6: Electron transporting layer
7: Negative electrode

The invention claimed is:

1. A compound represented by the following Chemical Formula 2 or 3:

[Chemical Formula 2]

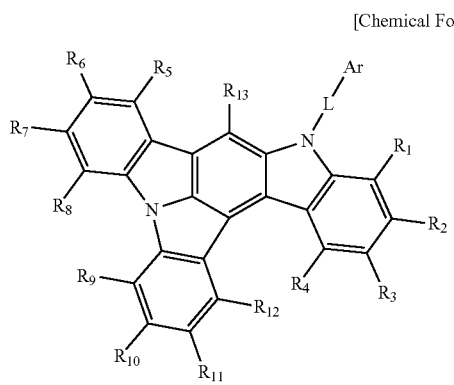

[Chemical Formula 3]

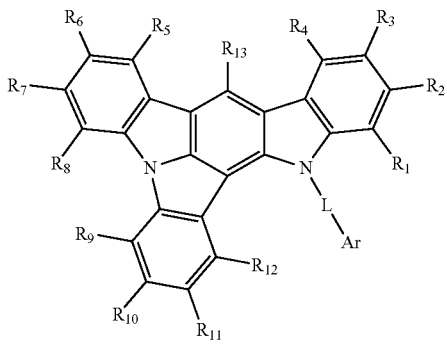

wherein in Chemical Formulae 2 and 3:

Ar is represented by the following Chemical Formula B:

[Chemical Formula B]

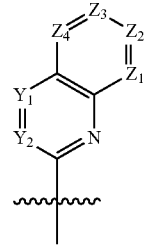

wherein $Y_1$, $Y_2$ and $Z_1$ to $Z_4$ are the same as or different from each other, and each independently N or CRd, Rd is hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group; a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group, or combine with an adjacent group to form a ring, L is a direct bond; or a substituted or unsubstituted arylene group; and $R_1$ to $R_{13}$ are the same as or different from each other, and each independently hydrogen; deuterium; a nitrile group; a substituted or unsubstituted alkyl group; a substituted or unsubstituted alkenyl group; a substituted or unsubstituted cycloalkyl group; a substituted or unsubstituted aryl group; a substituted or unsubstituted aromatic or aliphatic heterocyclic group;

a substituted or unsubstituted alkoxy group; a substituted or unsubstituted aryloxy group; a substituted or unsubstituted alkylamine group; a substituted or unsubstituted arylamine group; a substituted or unsubstituted aralkylamine group; a substituted or unsubstituted alkylarylamine group; or a substituted or unsubstituted heteroarylamine group.

2. The compound of claim 1, wherein the compound of Chemical Formula 2 or 3 is represented by any one of the following compounds:
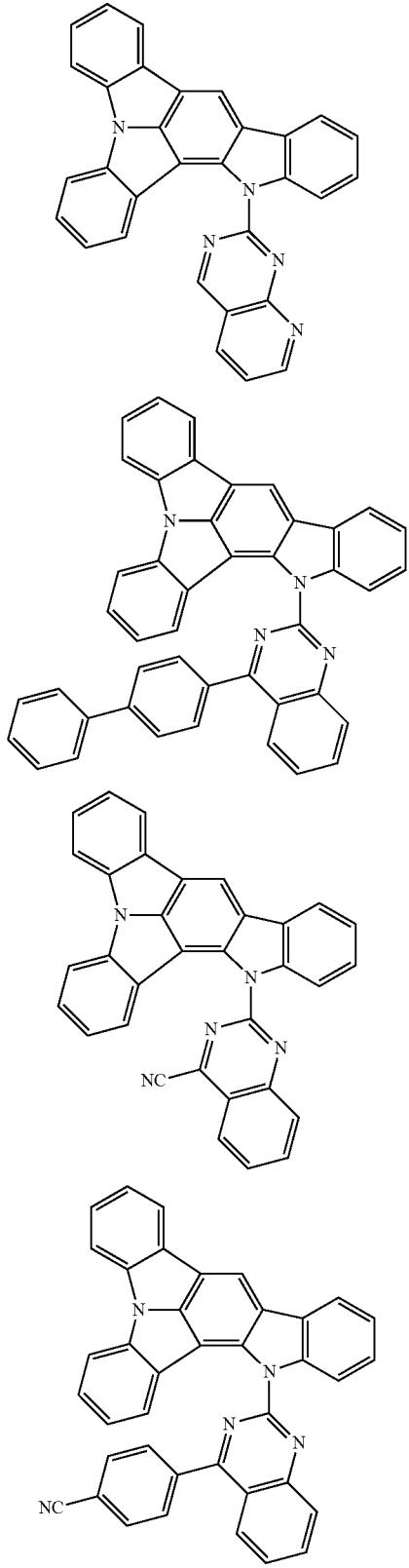
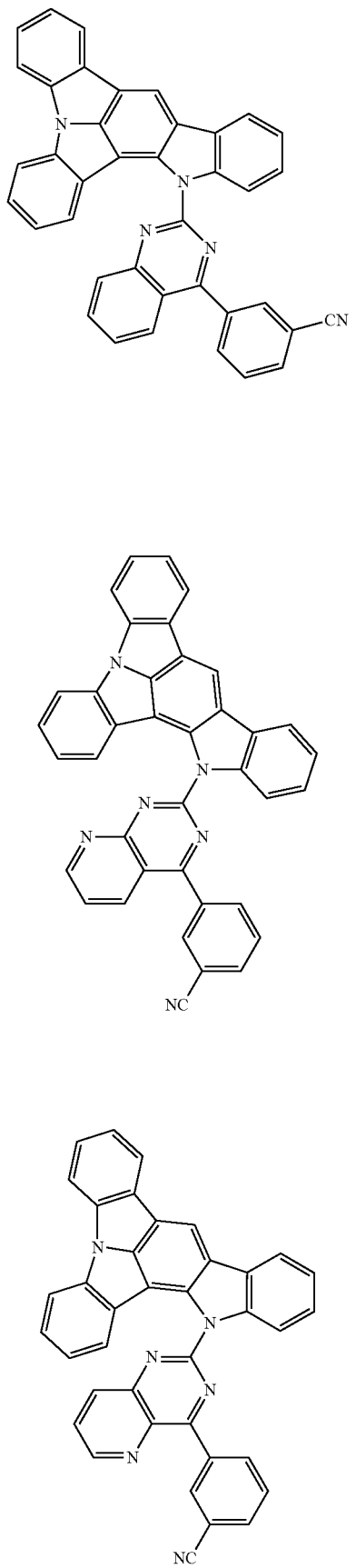

865
-continued
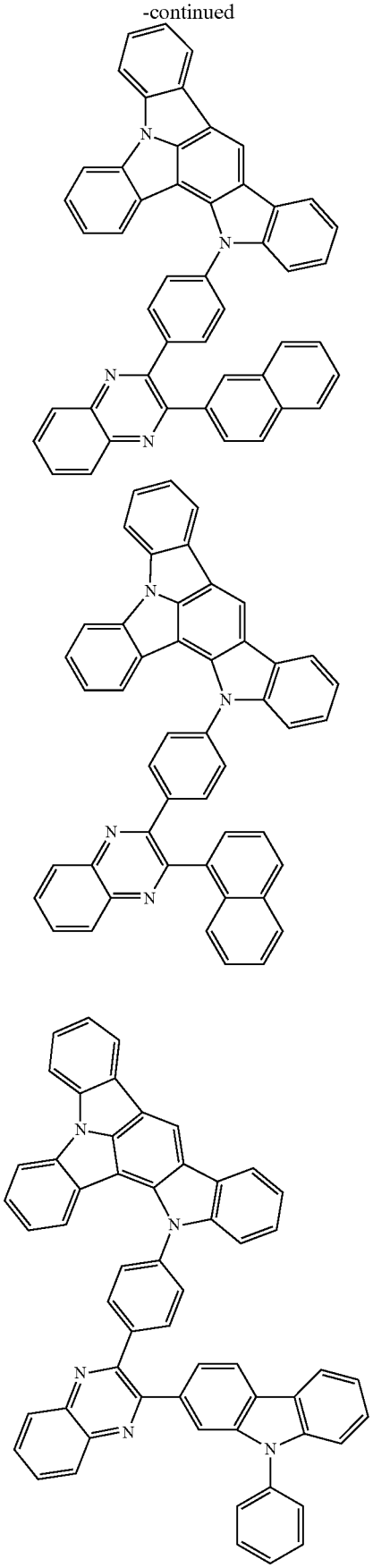
866
-continued
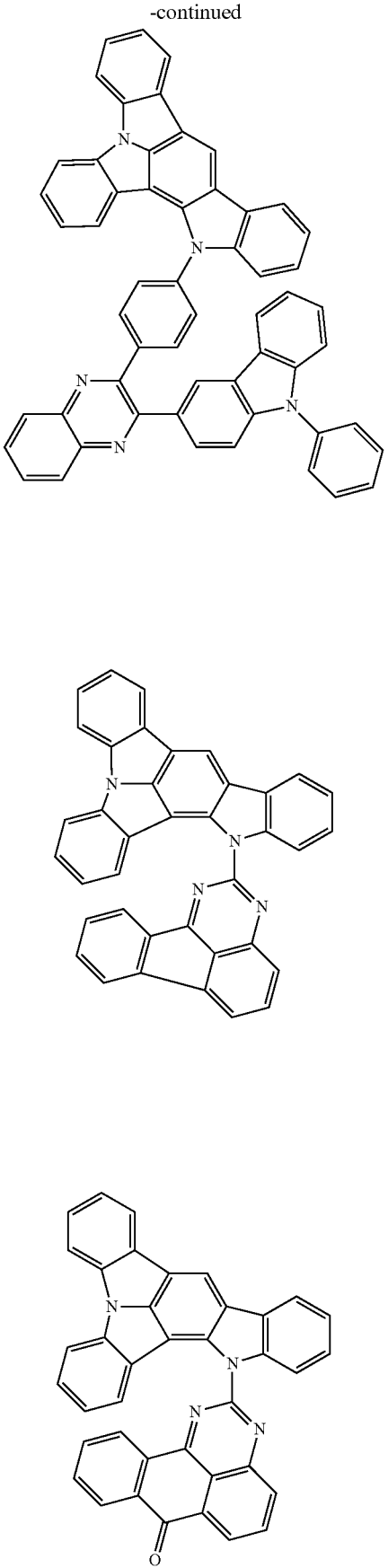

867
-continued
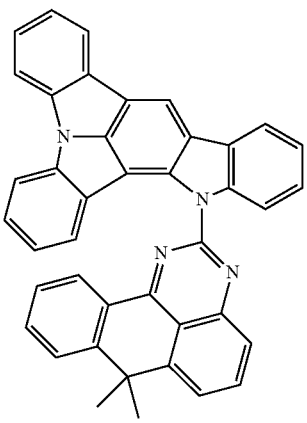
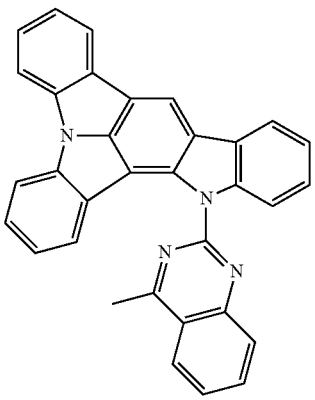
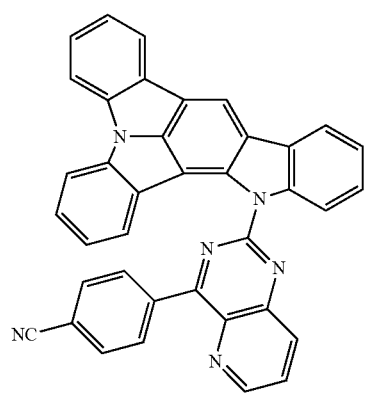
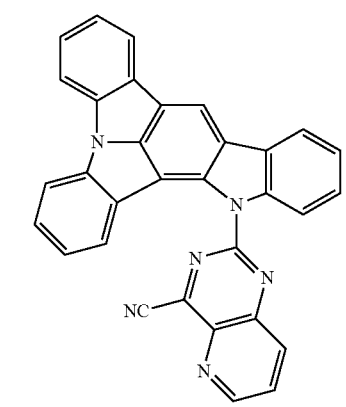
868
-continued
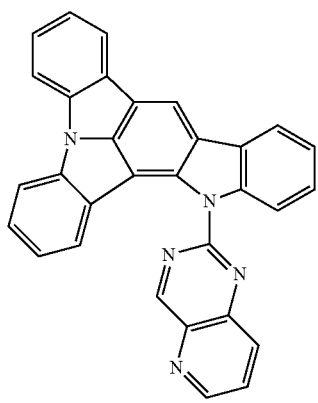
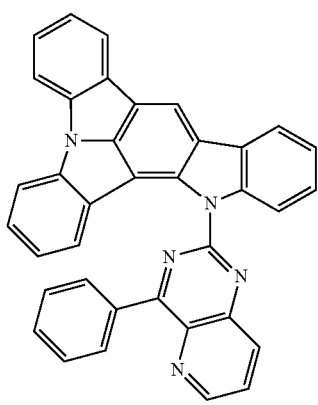
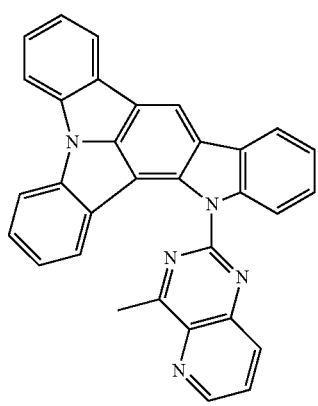
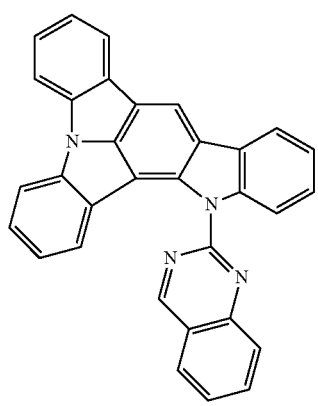

869
-continued
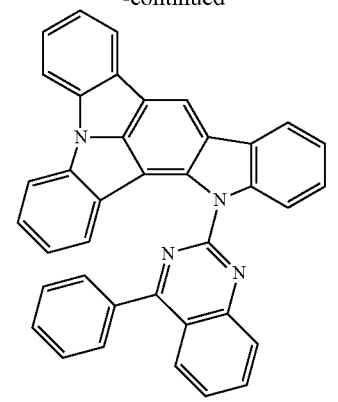
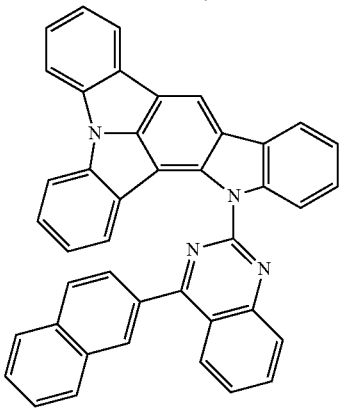
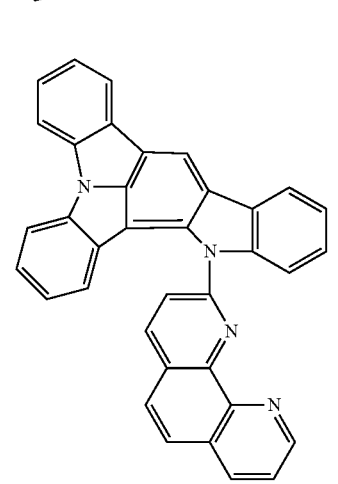
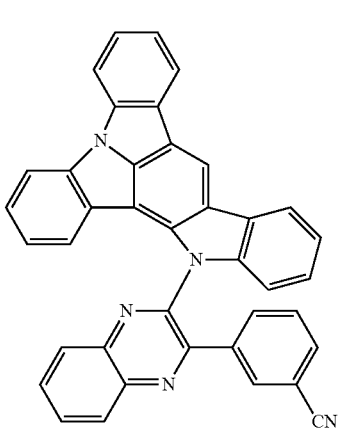
870
-continued
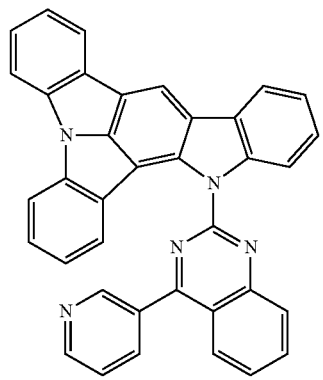
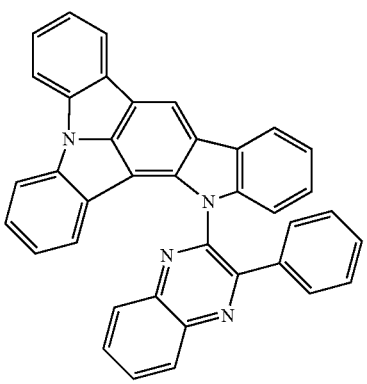
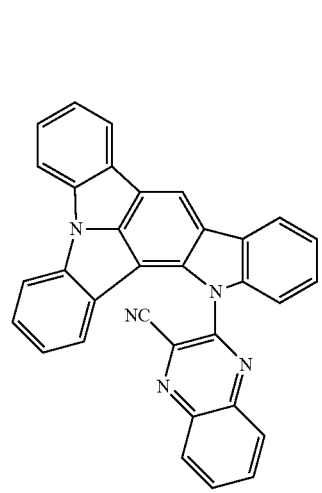

871
-continued
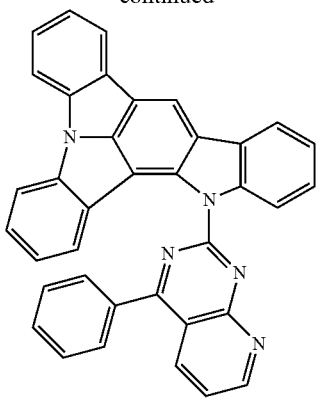
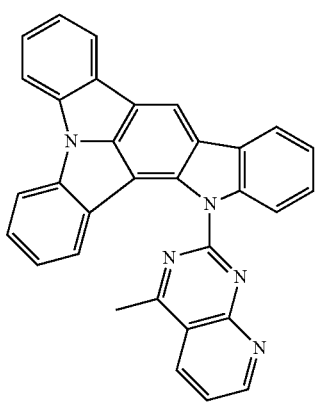
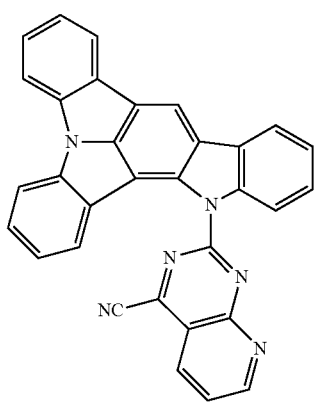
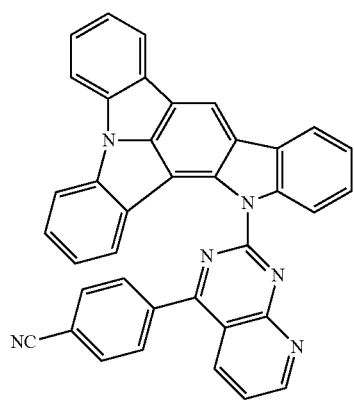
872
-continued
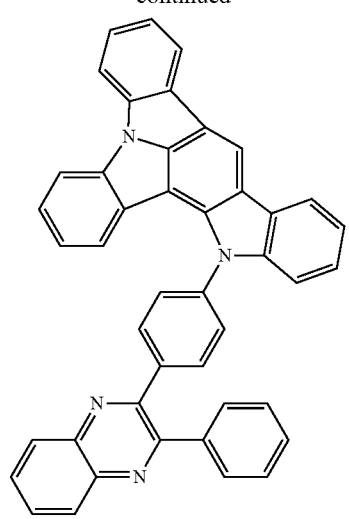
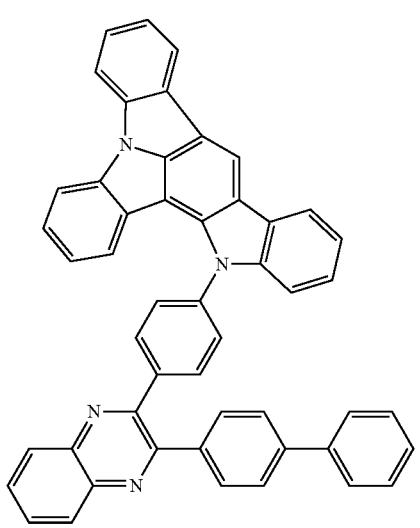
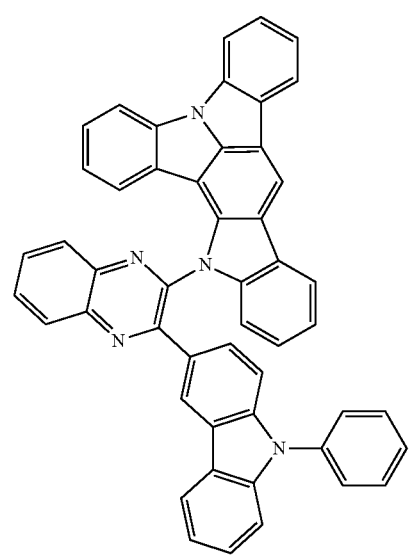

873
-continued
874
-continued
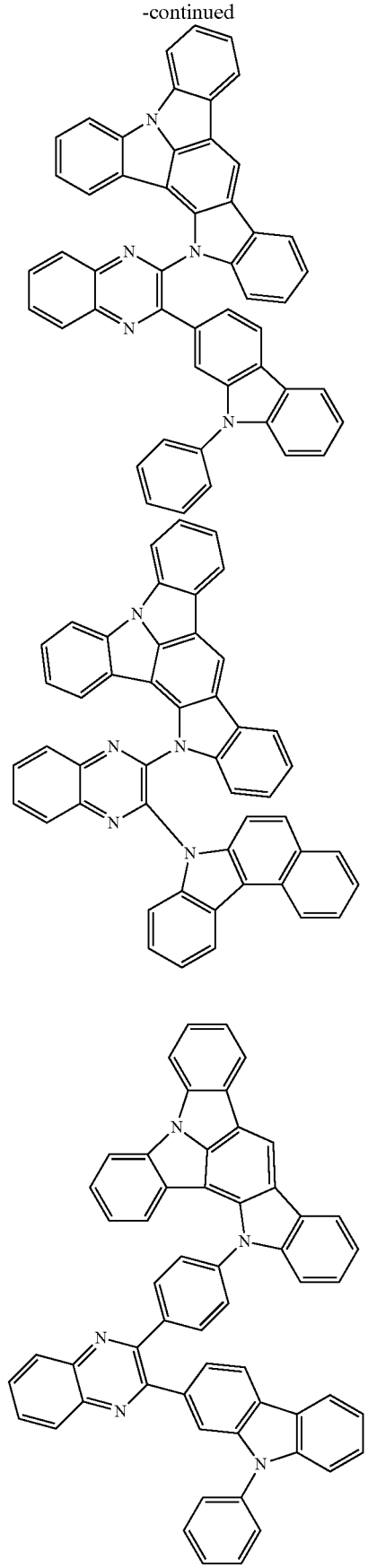
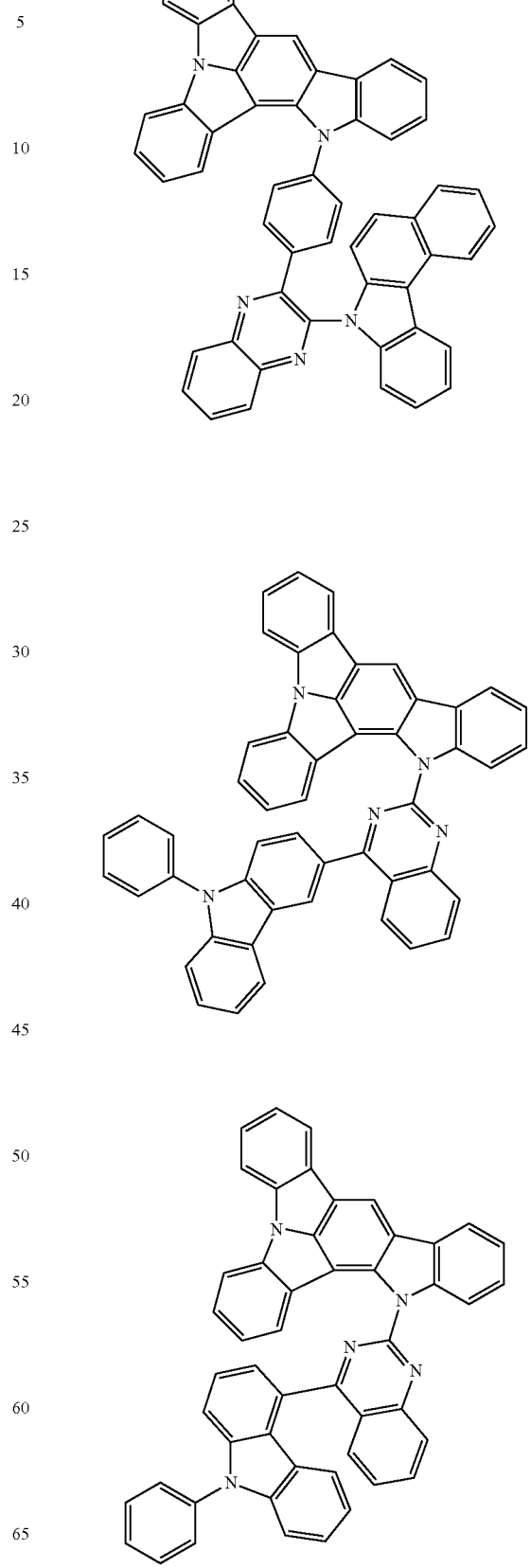

875
-continued
876
-continued
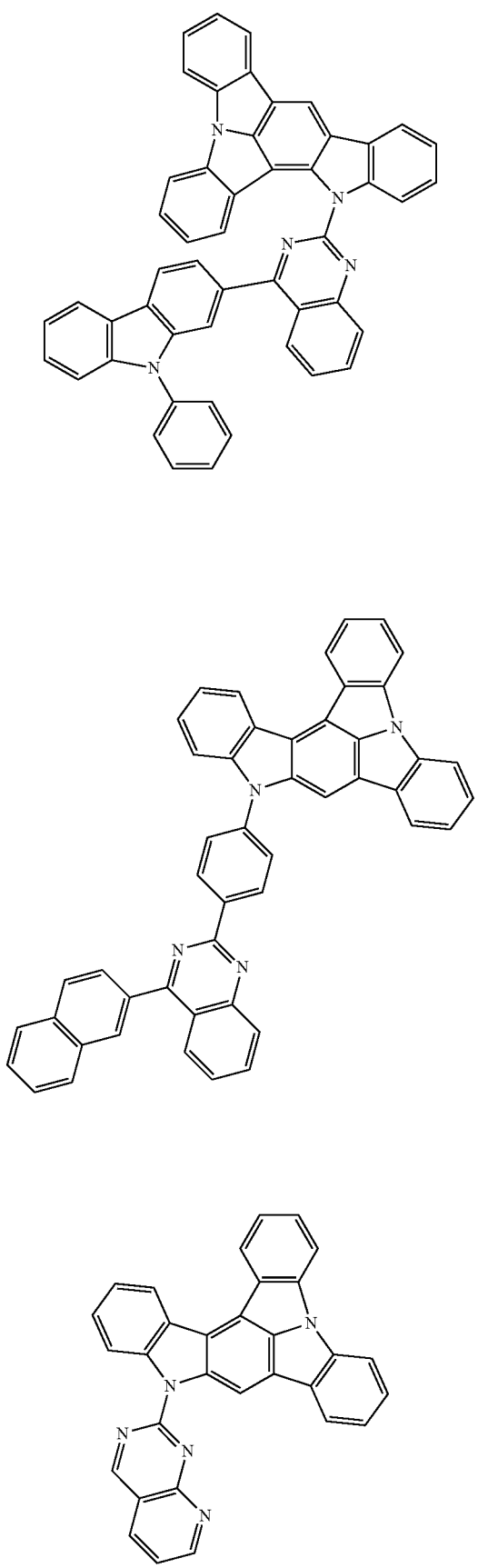
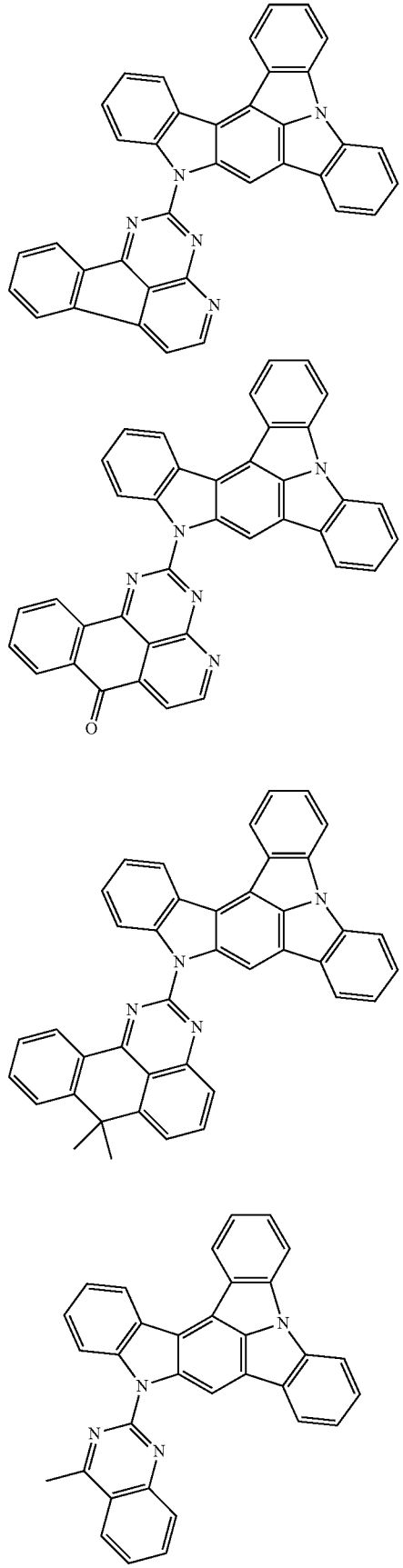

877
-continued
878
-continued
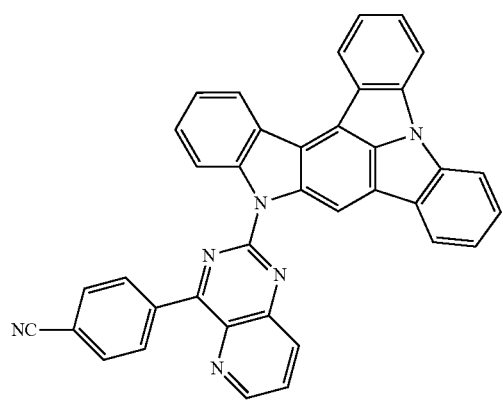
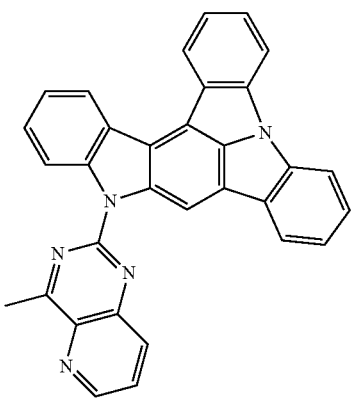
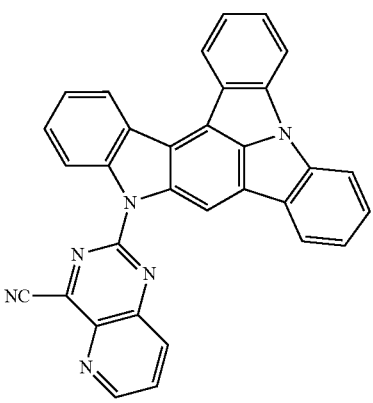
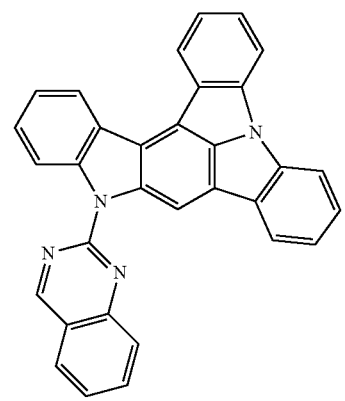
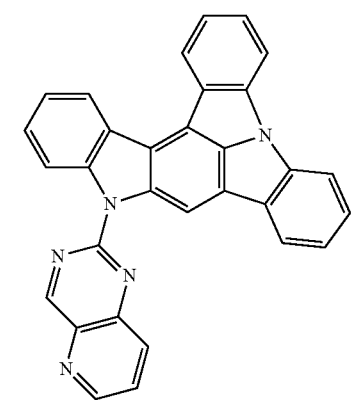
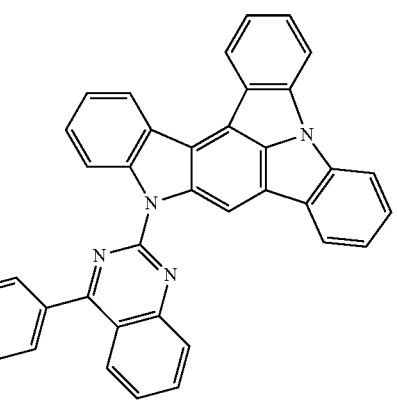
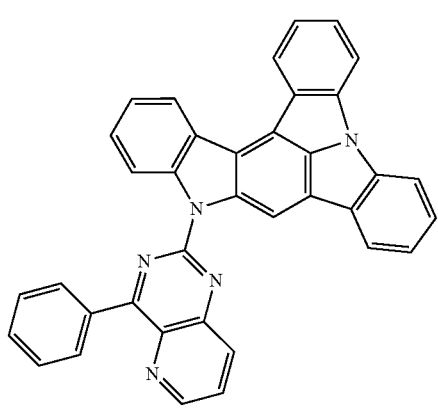
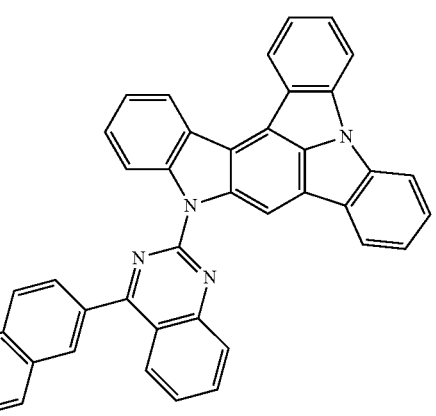

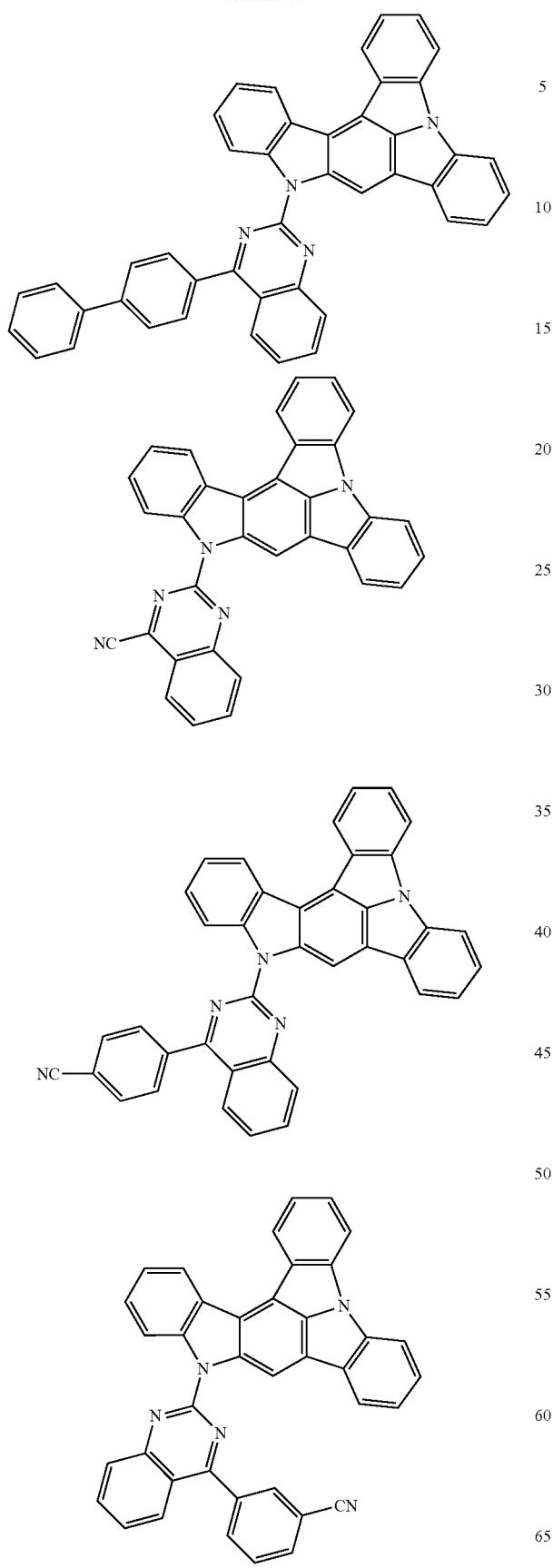
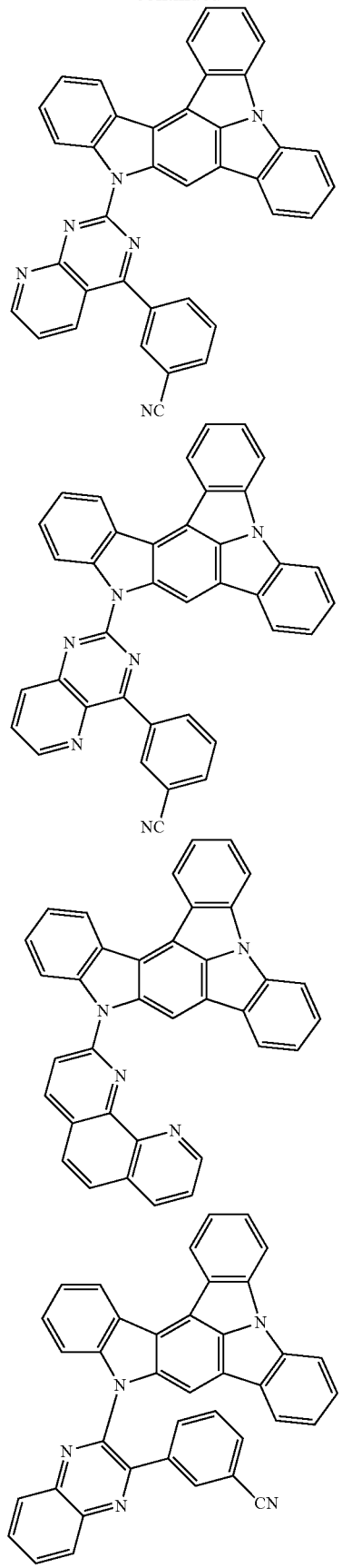

881
-continued
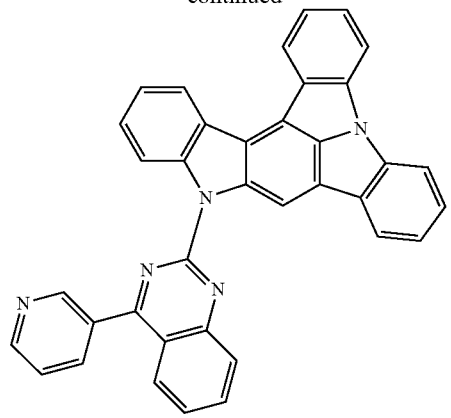
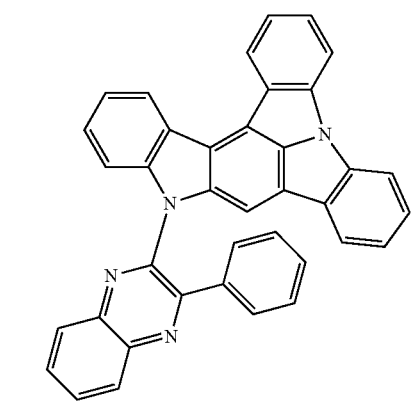
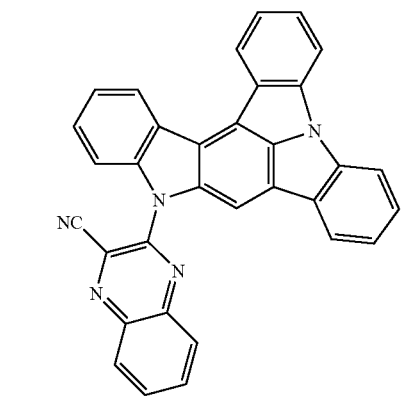
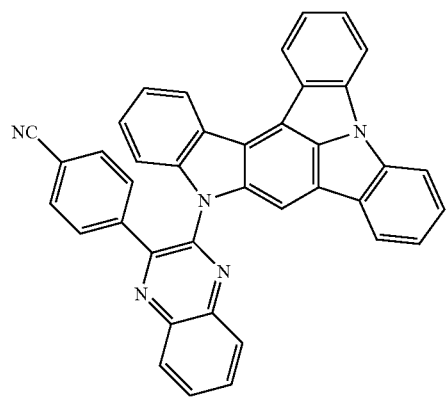
882
-continued
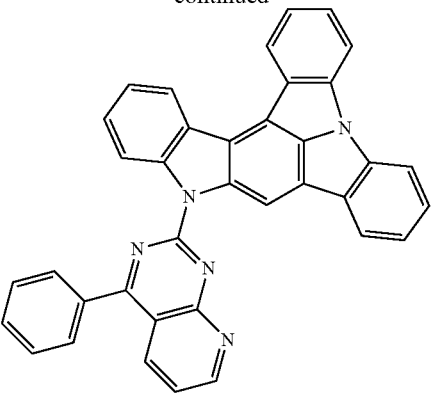
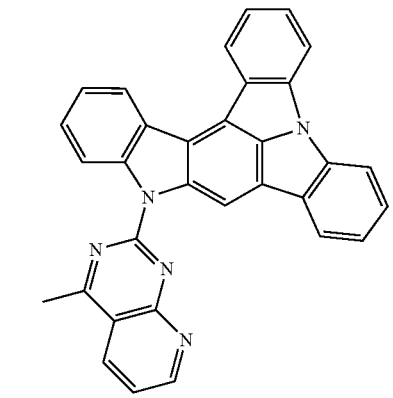
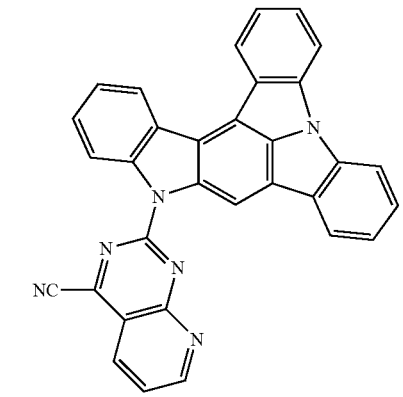
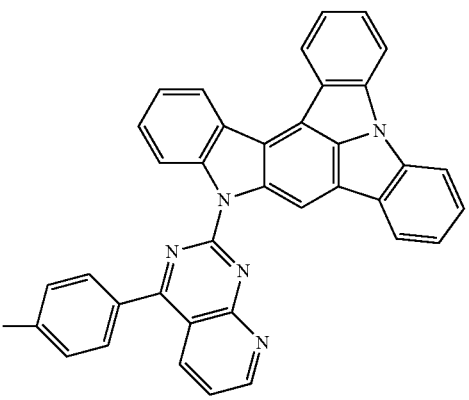

883
-continued
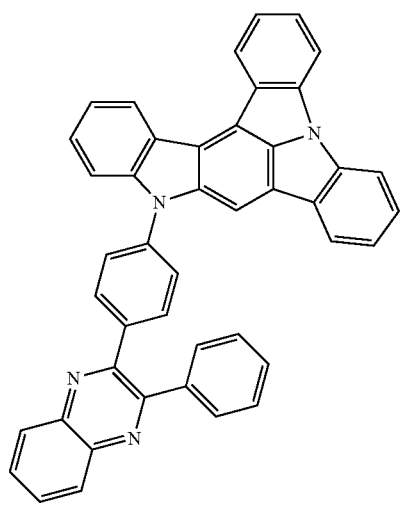
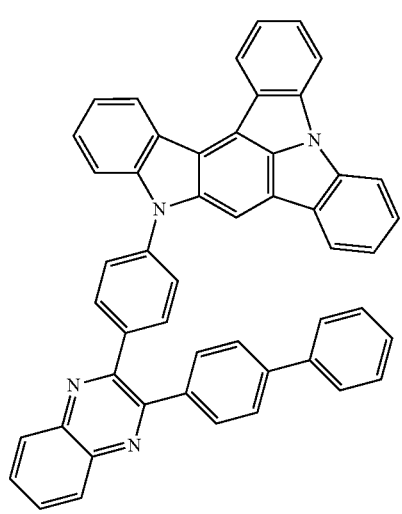
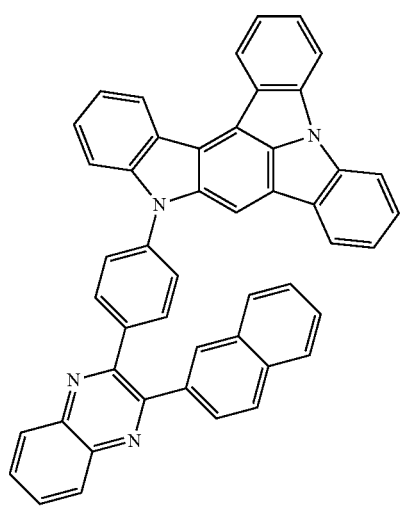
884
-continued
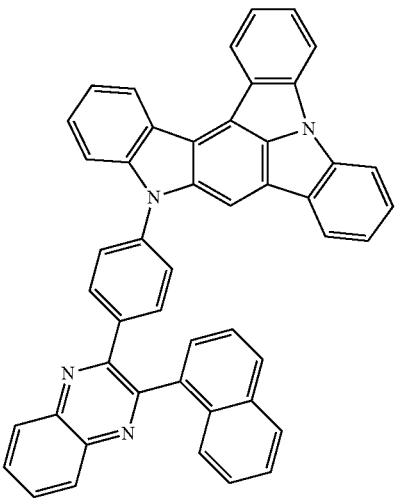
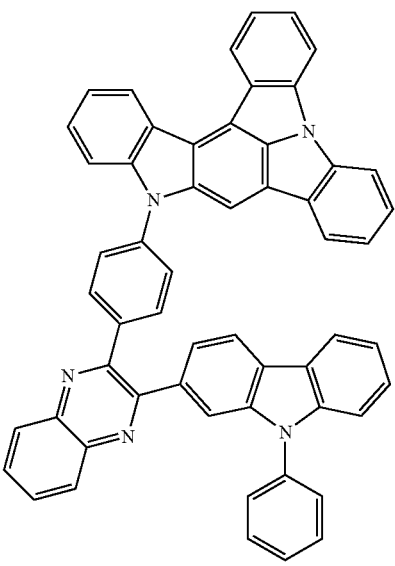
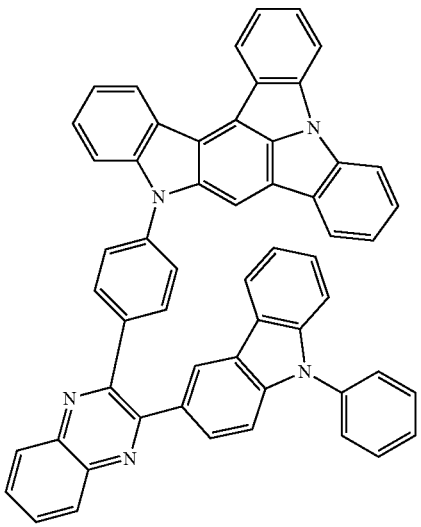

885
-continued
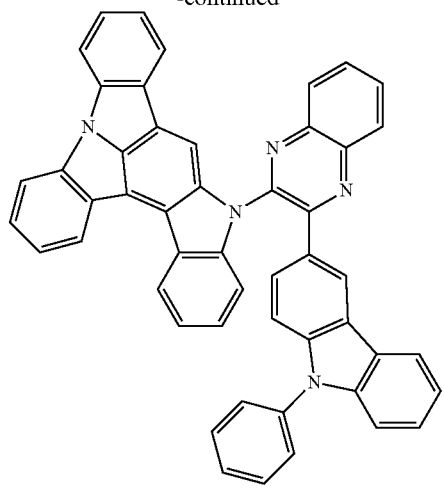
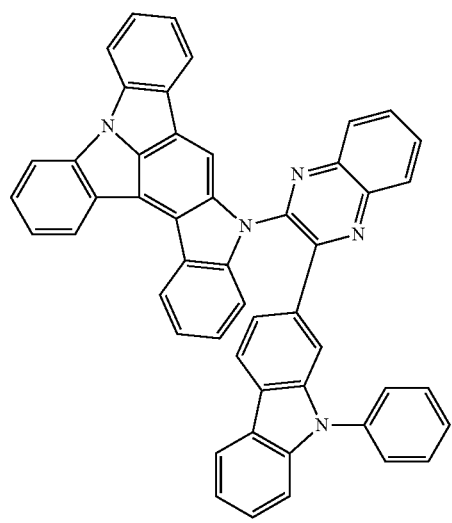
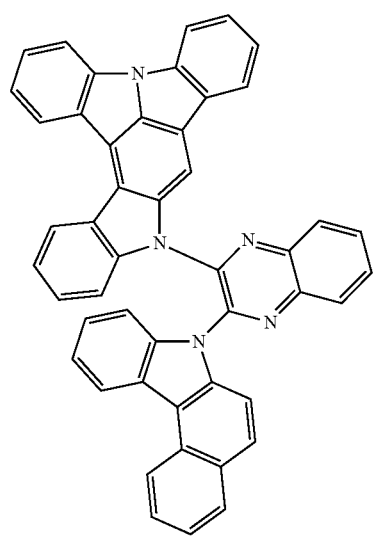
886
-continued
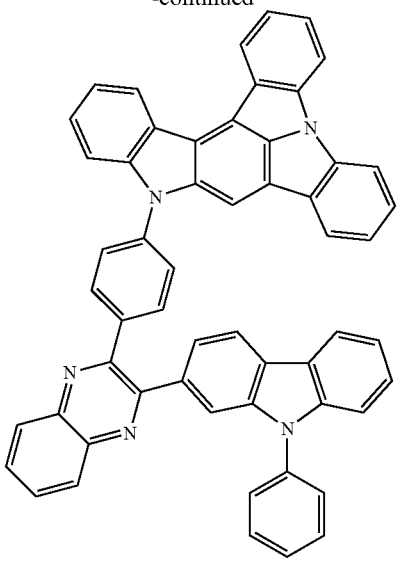
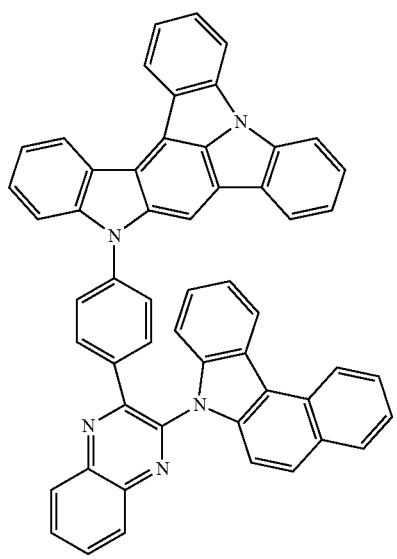

887
-continued
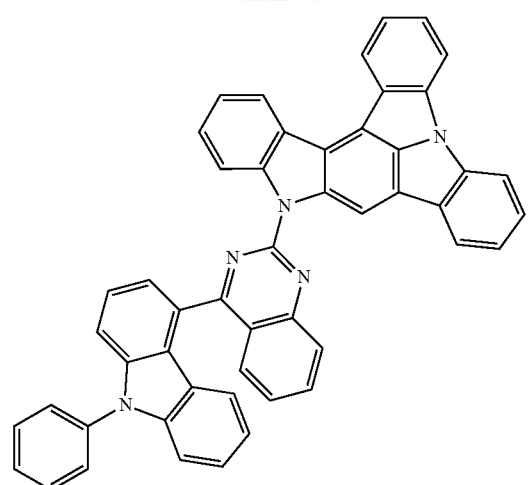
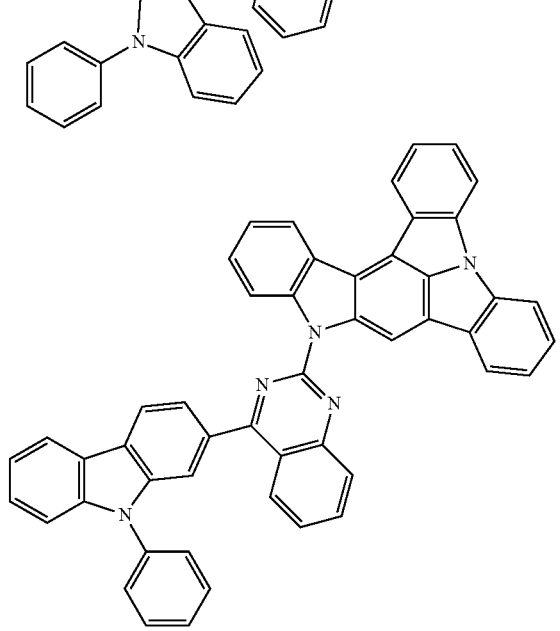
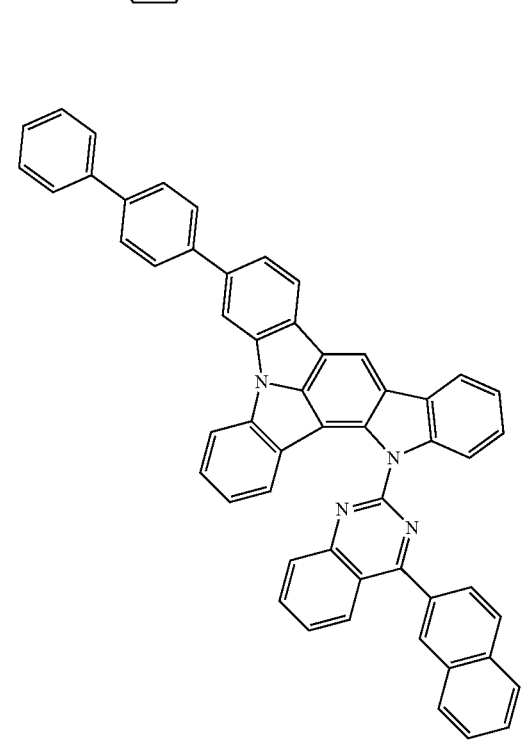
888
-continued
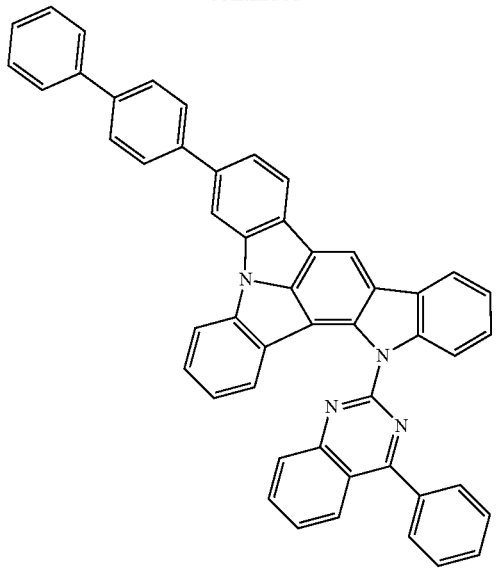
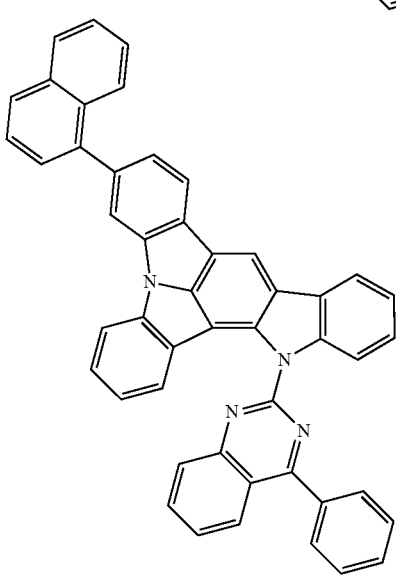

889
-continued
890
-continued
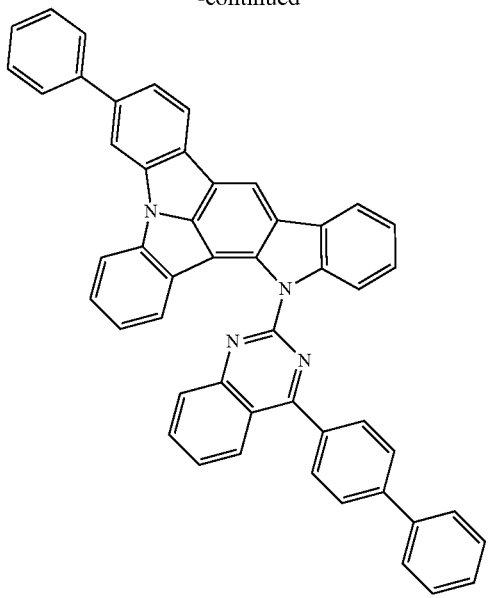
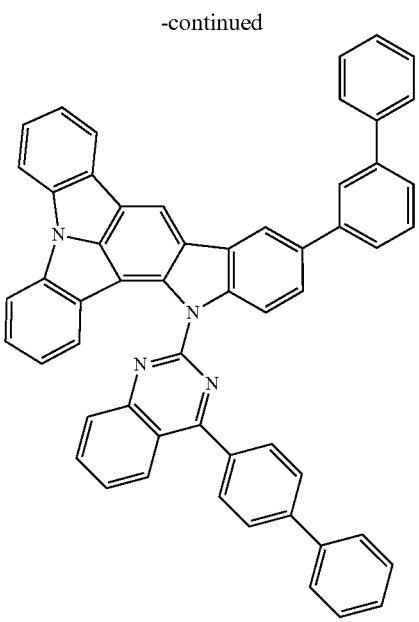
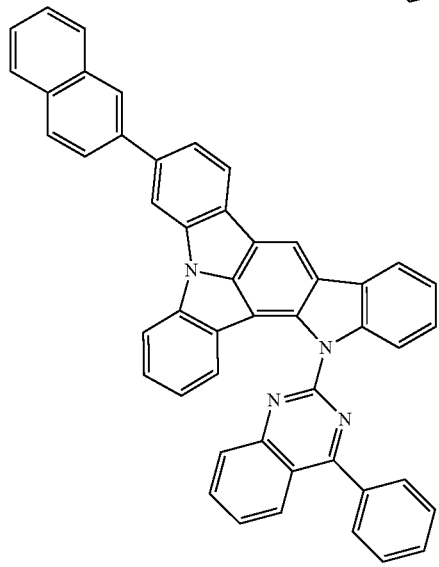
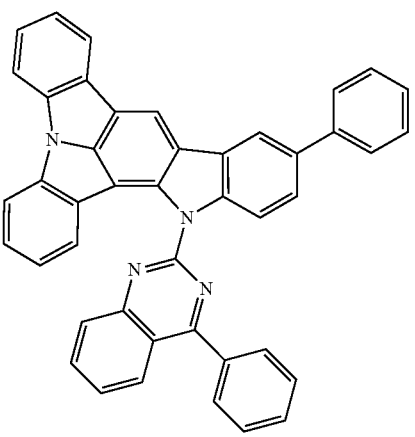
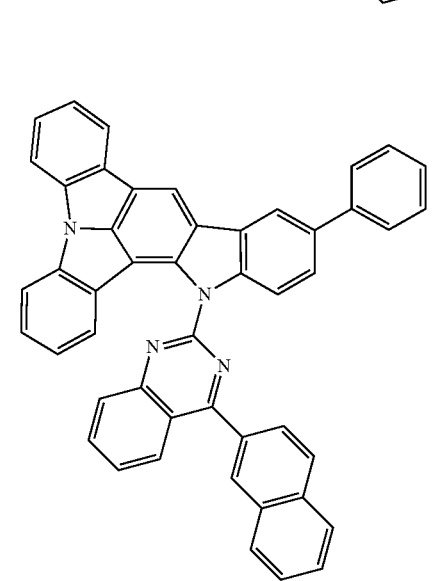
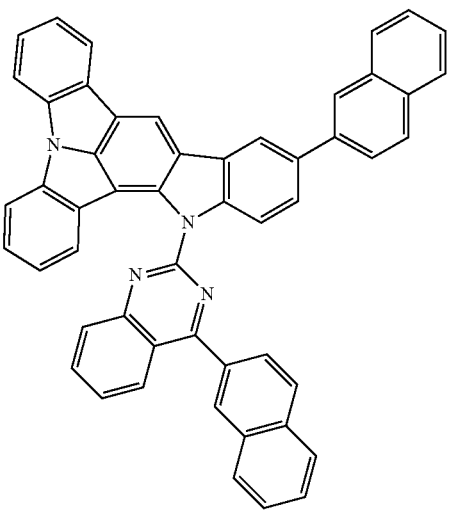

891
-continued
892
-continued
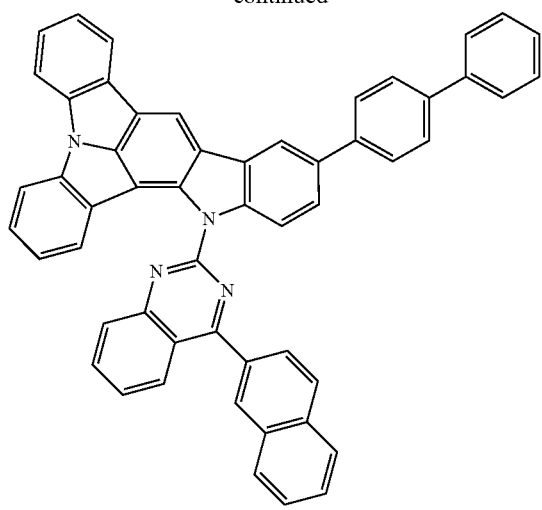
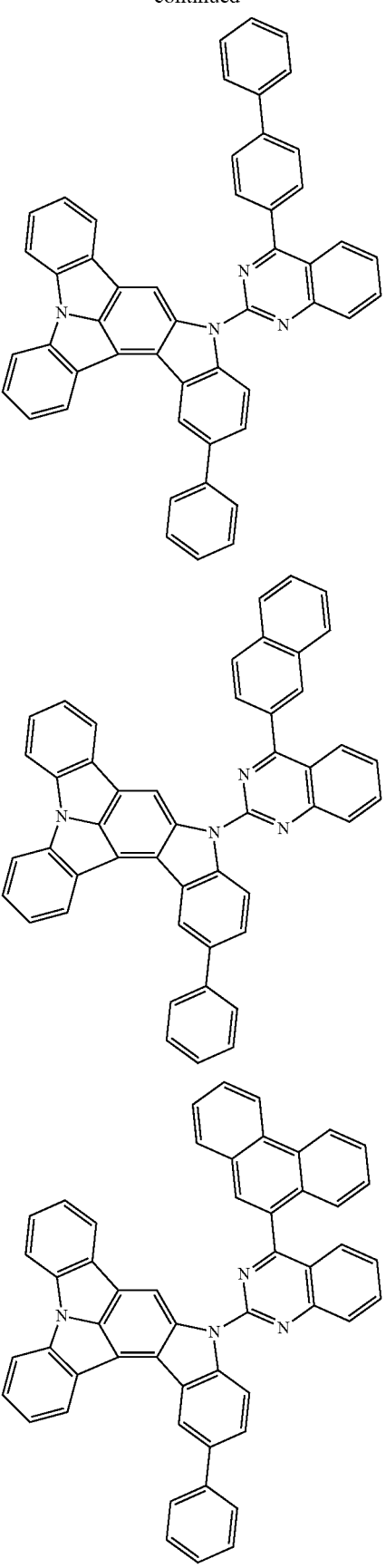

893
-continued
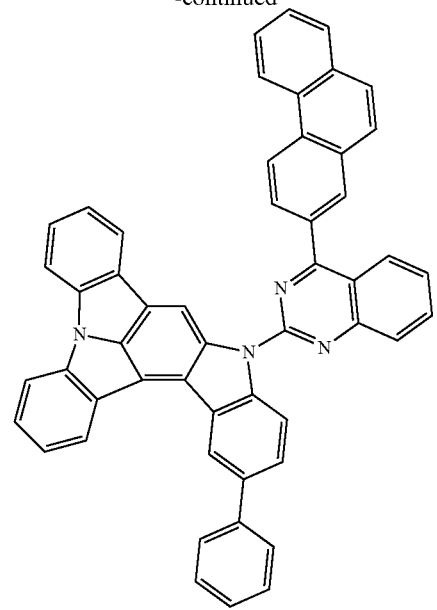
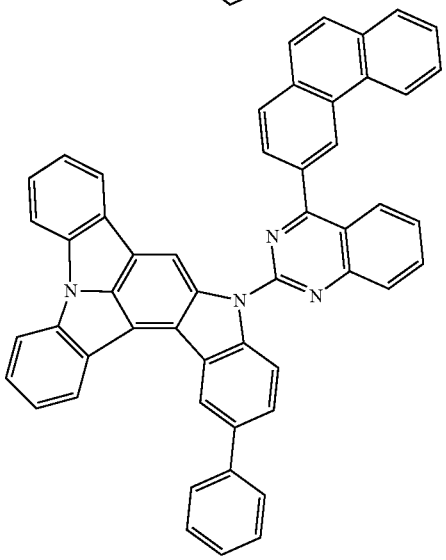
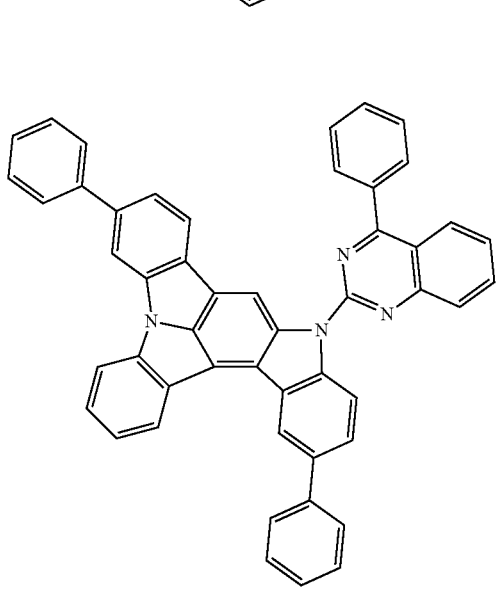
894
-continued
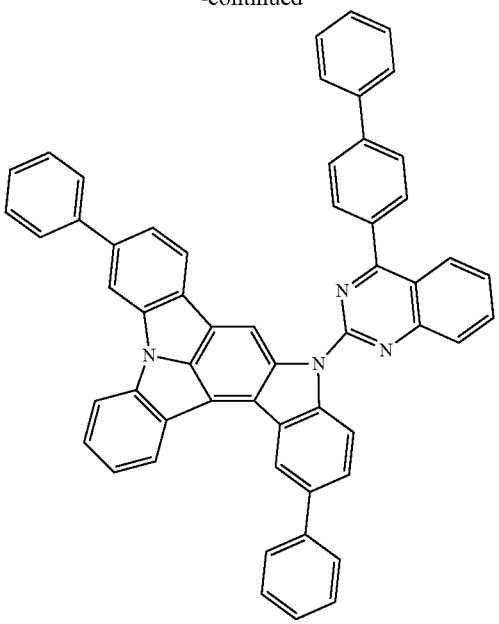
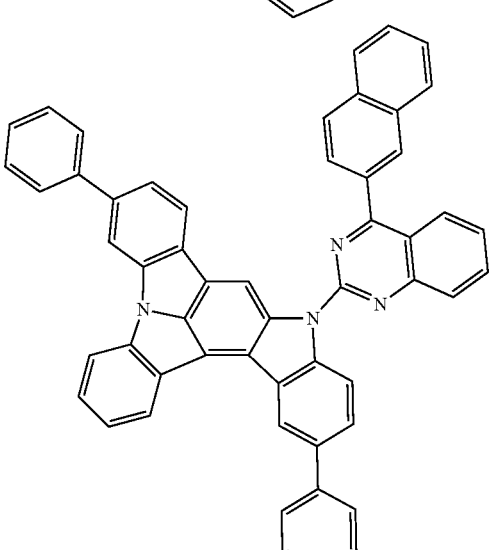
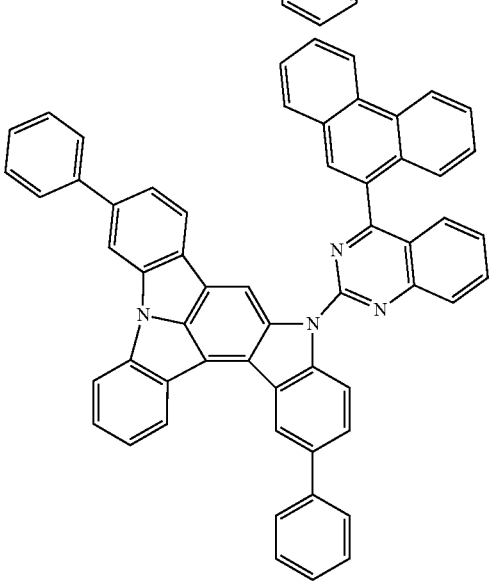

895
-continued
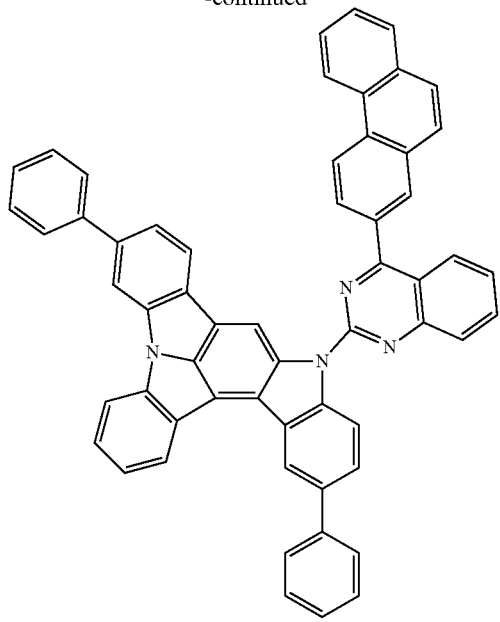
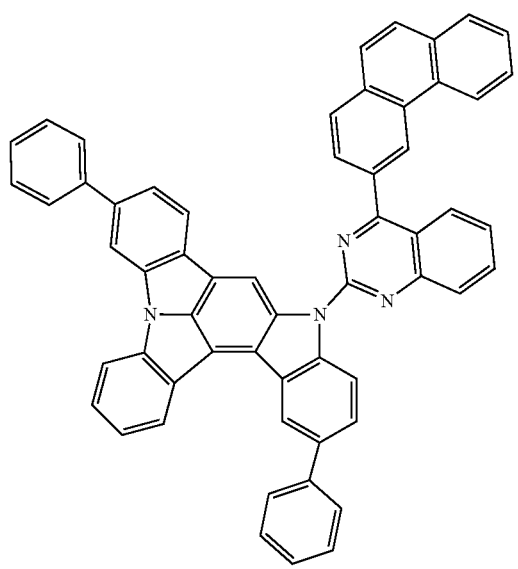
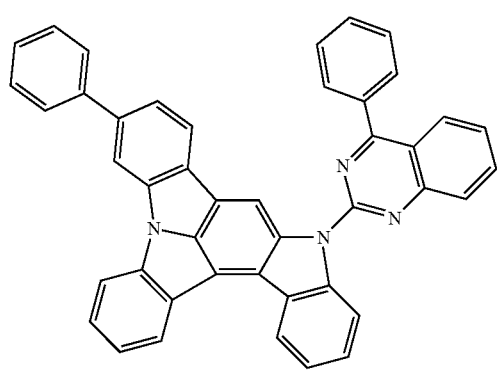
896
-continued
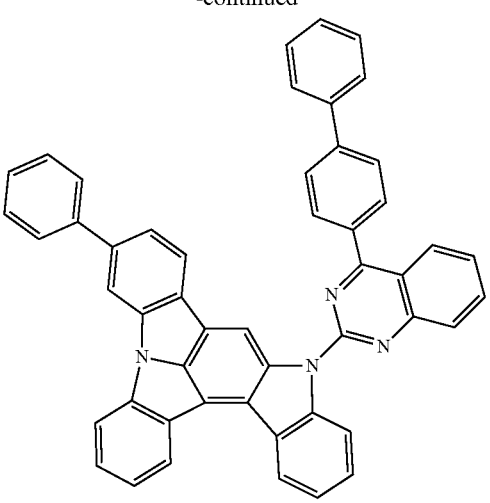
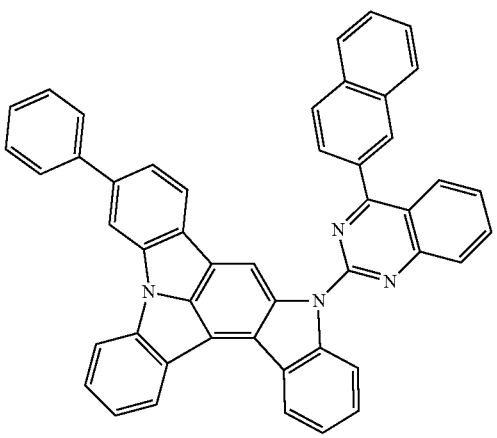
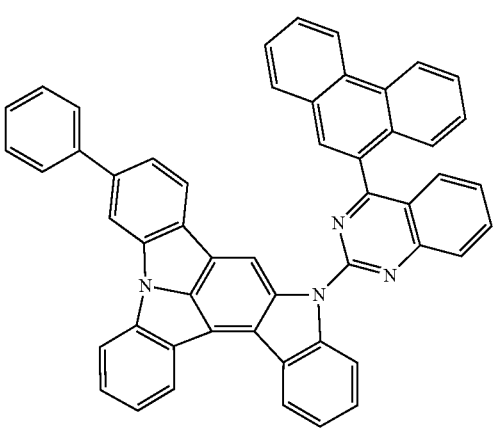

897
-continued
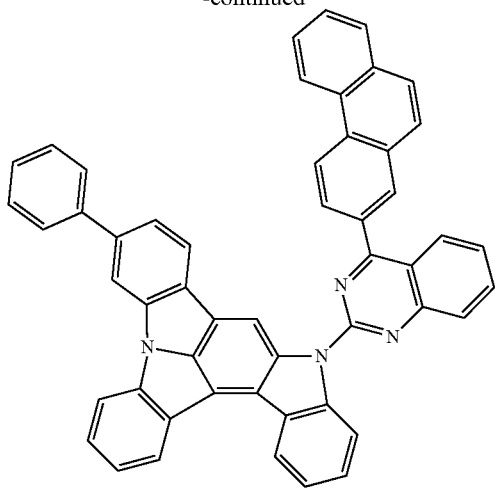
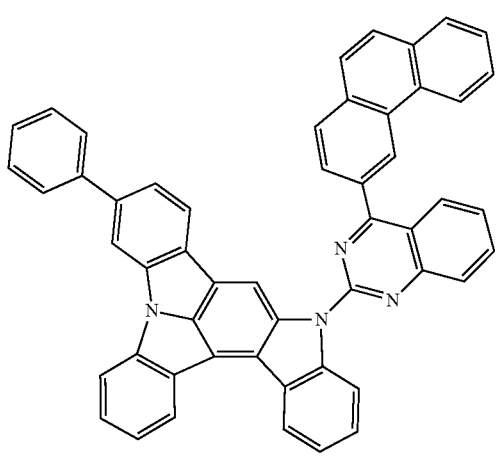
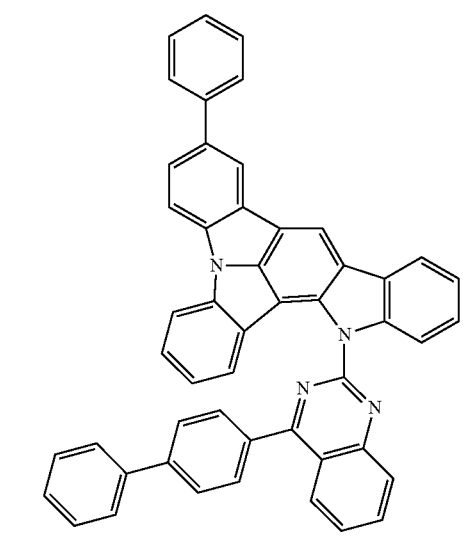
898
-continued
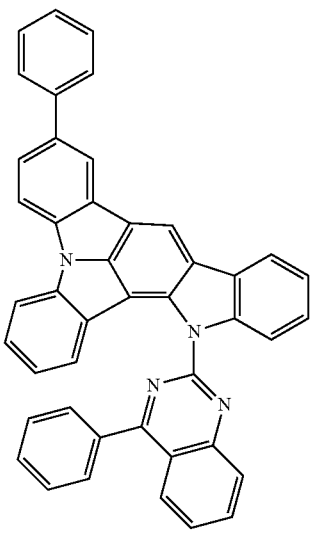
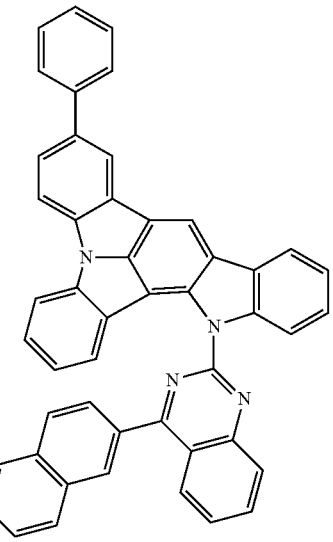
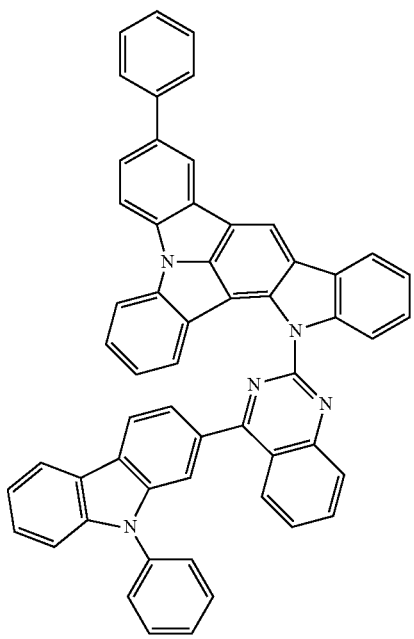

899
-continued
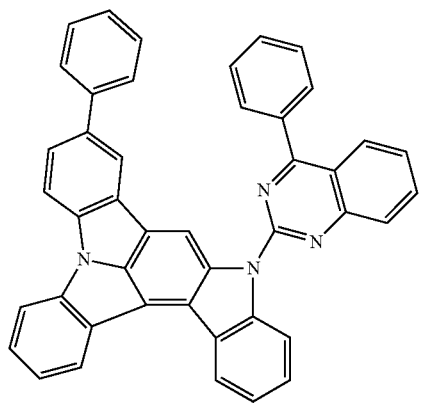
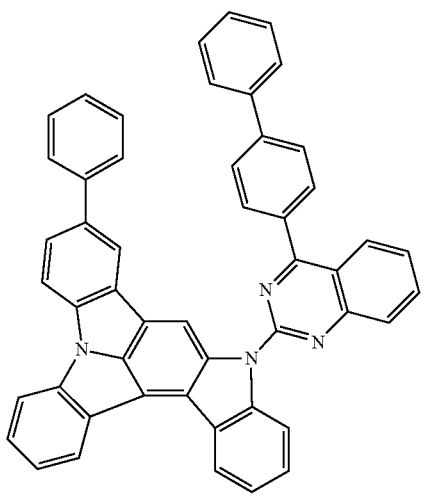
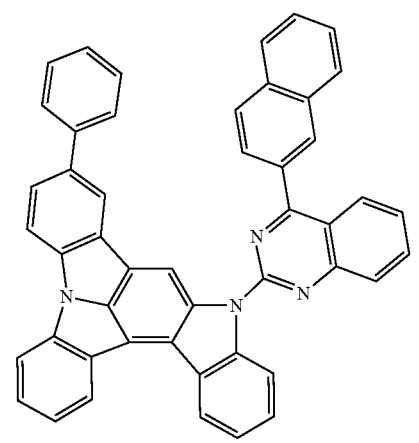
900
-continued
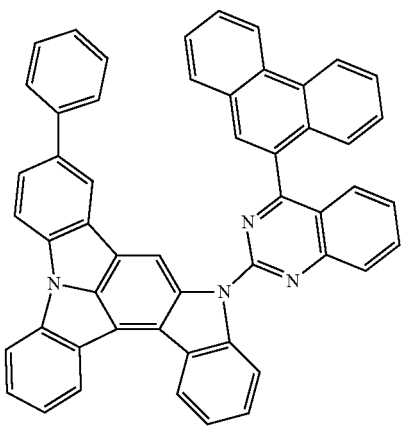
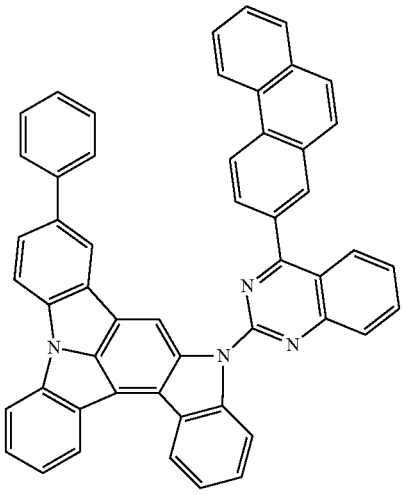
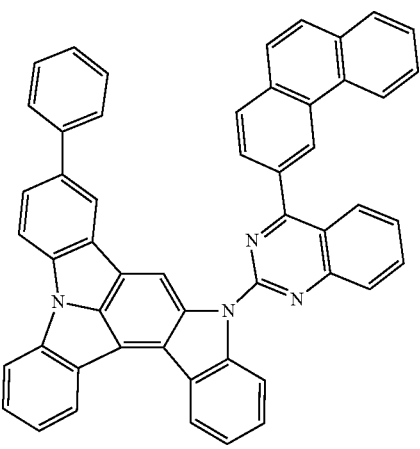

901
-continued

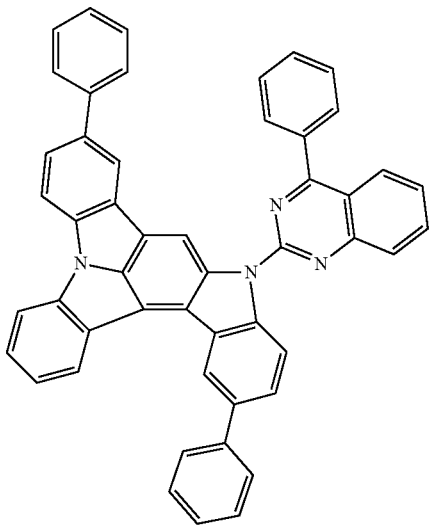

902
-continued

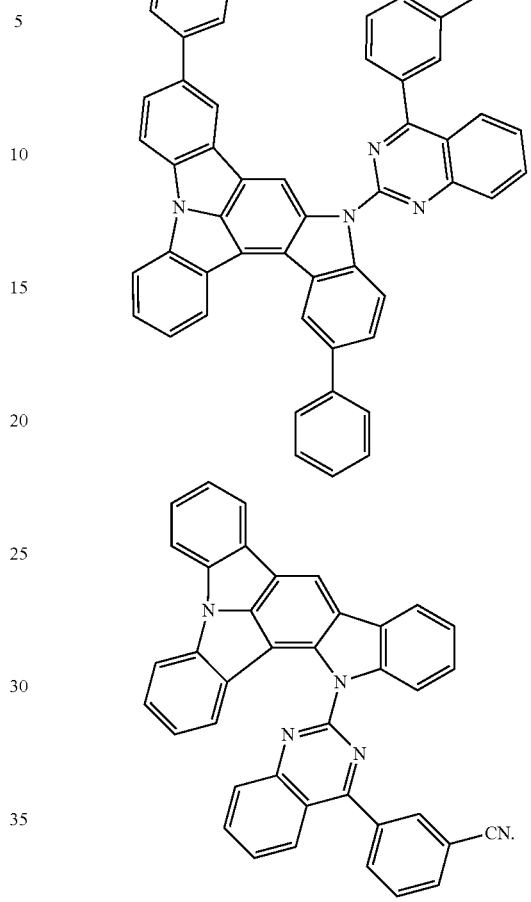

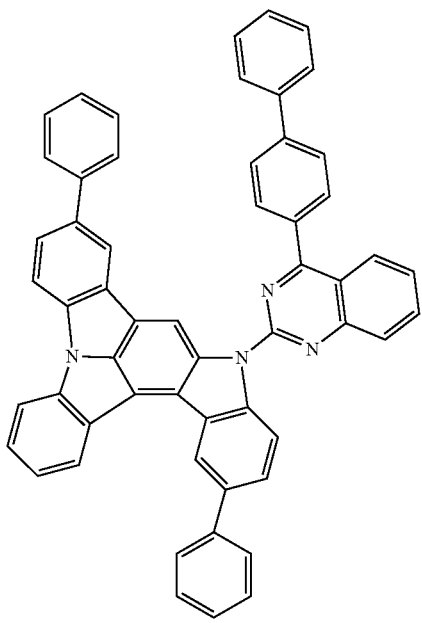

3. An organic light emitting device comprising:
a first electrode;
a second electrode provided to face the first electrode; and
one or more organic material layers provided between the first electrode and the second electrode and comprising a light emitting layer,
wherein one or more layers of the organic material layers comprise the compound of claim 1.

4. The organic light emitting device of claim 3, wherein the organic material layer comprises an electron transporting layer, an electron injection layer, a layer which simultaneously transports and injects electrons, a light emitting layer, a hole transporting layer, a hole injection layer, or a layer which simultaneously transports and injects holes, and the electron transporting layer, the electron injection layer, the layer which simultaneously transports and injects electrons, the light emitting layer, the hole transporting layer, the hole injection layer, or the layer which simultaneously transports and injects holes comprises the compound of Chemical Formula 2 or 3.

5. The organic light emitting device of claim 3, wherein the light emitting layer comprises the compound of Chemical Formula 2 or 3.

* * * * *